United States Patent
Matsuo et al.

(10) Patent No.: US 9,120,749 B2
(45) Date of Patent: Sep. 1, 2015

(54) QUINOLINE DERIVATIVES AND MELK INHIBITORS CONTAINING THE SAME

(75) Inventors: Yo Matsuo, Kanagawa (JP); Shoji Hisada, Kanagawa (JP); Yusuke Nakamura, Tokyo (JP); Feryan Ahmed, Latham, NY (US); Raymond Huntley, Albany, NY (US); Joel R. Walker, Schenectady, NY (US); Helene Decornez, Clifton Park, NY (US)

(73) Assignee: ONCOTHERAPY SCIENCE, INC., Kanagawa (JP)

( * ) Notice: Subject to any disclaimer, the term of this patent is extended or adjusted under 35 U.S.C. 154(b) by 0 days.

(21) Appl. No.: 13/813,134

(22) PCT Filed: Jul. 28, 2011

(86) PCT No.: PCT/US2011/045792
§ 371 (c)(1),
(2), (4) Date: Apr. 22, 2013

(87) PCT Pub. No.: WO2012/016082
PCT Pub. Date: Feb. 2, 2012

(65) Prior Publication Data
US 2013/0217671 A1    Aug. 22, 2013

Related U.S. Application Data

(60) Provisional application No. 61/369,519, filed on Jul. 30, 2010.

(51) Int. Cl.
| | | |
|---|---|---|
| *C07D 215/46* | (2006.01) | |
| *A61K 31/4709* | (2006.01) | |
| *C07D 215/54* | (2006.01) | |
| *C07D 401/04* | (2006.01) | |
| *C07D 401/12* | (2006.01) | |
| *C07D 401/14* | (2006.01) | |
| *C07D 409/04* | (2006.01) | |
| *C07D 409/06* | (2006.01) | |
| *C07D 409/14* | (2006.01) | |
| *C07D 401/10* | (2006.01) | |
| *C07D 413/06* | (2006.01) | |
| *C07D 453/02* | (2006.01) | |
| *C07D 471/04* | (2006.01) | |

(52) U.S. Cl.
CPC ............ *C07D 215/54* (2013.01); *C07D 215/46* (2013.01); *C07D 401/04* (2013.01); *C07D 401/10* (2013.01); *C07D 401/12* (2013.01); *C07D 401/14* (2013.01); *C07D 409/04* (2013.01); *C07D 409/06* (2013.01); *C07D 409/14* (2013.01); *C07D 413/06* (2013.01); *C07D 453/02* (2013.01); *C07D 471/04* (2013.01); *A61K 31/4709* (2013.01)

(58) Field of Classification Search
CPC .. C07D 215/38; C07D 215/18; C07D 215/46; C07D 215/54; C07D 413/06; C07D 453/02; C07D 471/04; C07D 401/04; C07D 401/10; C07D 401/12; C07D 401/14; C07D 409/04; C07D 409/06; C07D 409/14; A61K 31/4709
USPC ......................................... 546/159; 514/312
See application file for complete search history.

(56) References Cited

U.S. PATENT DOCUMENTS

| | | |
|---|---|---|
| 7,998,695 B2 | 8/2011 | Nakamura et al. |
| 2002/0026052 A1 | 2/2002 | Boschelli et al. |
| 2004/0242604 A1 | 12/2004 | Bhattacharya et al. |
| 2006/0024692 A1 | 2/2006 | Nakamura et al. |
| 2008/0242655 A1 | 10/2008 | Goodacre et al. |
| 2009/0175844 A1 | 7/2009 | Nakamura et al. |
| 2009/0263395 A1 | 10/2009 | Nakamura et al. |
| 2009/0317392 A1 | 12/2009 | Nakamura et al. |
| 2012/0014996 A1 | 1/2012 | Nakamura et al. |
| 2013/0011933 A1 | 1/2013 | Nakamura et al. |

FOREIGN PATENT DOCUMENTS

| | | |
|---|---|---|
| CN | 101012224 A | 8/2007 |
| RU | 2005129333 A | 1/2006 |
| RU | 2008/144806 A | 5/2010 |
| SU | 470113 A3 | 5/1975 |
| WO | 02/092571 A1 | 11/2002 |
| WO | WO 2004/031413 A2 | 4/2004 |
| WO | WO 2006/016525 A2 | 2/2006 |
| WO | WO 2006/085684 A2 | 8/2006 |
| WO | WO 2007/013665 A2 | 2/2007 |
| WO | WO 2008/023841 A1 | 2/2008 |
| WO | 2009/122180 A1 | 10/2009 |
| WO | WO 2009/155527 A2 | 12/2009 |
| WO | 2011/022439 A1 | 2/2011 |

OTHER PUBLICATIONS

Smalley, Bioorg & Med Chem Lett, vol. 17, pp. 6257-6260, 2007.*
Carlton, CA145:136522, abstract only of Mag Res in Chem, VOl 44(5), pp. 510-514, 2006.*
Hoglund, J Med Chem, VOl 49, pp. 6351-6363, 2006.*
Scott, Bioorg & Med Chem Lett, VOl 19, pp. 701-705, 2009.*
Atechian, Tetrahedron, vol. 63, pp. 2811-2823, 2007.*
Blot, J., et al., "Cell Cycel Regulation of pEg3, a New *Xenopus* Protein Kinase of the KIN 1/PAR-1/MARK Family," *Developmental Biology*, vol. 241(2), pp. 327-338 (Jan. 15, 2002).
Heyer, B., et al., "Expression a *Melk*, a New Protein Kinase, During Early Mouse Development," *Developmental Dynamics*, vol. 215(4), pp. 344-351 (Aug. 1999).
Lin, M-L, et al., "Involvement of maternal embryonic leucine zipper kinase (MELK) in mammary carcinogenesis through interaction with Bcl-G, a pro-apoptotic member of the Bcl-2 family," *Breast Cancer Research*, vol. 9(1), R17, 13 pgs. (2007).
Nakano, I., et al., "Maternal embryonic leucine zipper kinase (MELK) regulations multipotent neural progenitor proliferation," *The Journal of Cell Biology*, vol. 170(3), pp. 413-427 (Aug. 1, 2005).
Seong, H-A, et al., Phosphorylation of a novel zinc-finger-like protein, ZPR9, by murine protein serine/threonine kinase 38 (MPK38), *Biochem., J.*, vol. 361(Pt 3), p. 597-604 (Feb. 1, 2002).

(Continued)

Primary Examiner — D M Seaman
(74) Attorney, Agent, or Firm — Kilpatrick Townsend & Stockton LLP

(57) ABSTRACT

The present invention directs a compound represented by formula (I).

17 Claims, No Drawings

(56) References Cited

OTHER PUBLICATIONS

Vulsteke, V., "Inhibition of Spliceosome Assembly by the Cell Cycle-regulated Protein Kinase MELK and Involvement of Splicing Factor NIPP1," *The Journal of Biological Chemistry*, vol. 279 (10), pp. 8642-8647 (Mar. 5, 2004, Epub Dec. 29, 2003).

Extended European Search Report issued on Jan. 17, 2014 for European Patent Application No. 11813209.1, 9 pages.

Leach et al., "Reversible Inhibitors of the Gastric (H+/K+)—ATPase.4 Identification of an Inhibitor with an Intermediate Duration of Action", *Journal of Medicinal Chemistry*, vol. 38, No. 14, pp. 2748-2762 (1995).

Boschelli et al., "Synthesis and Src Kinase Inhibitory Activity of a Series of 4-[(2,4-Dichloro-5-methoxyphenyl)amino]-7-furyl-3-quiolinecarbonitriles", *Journal of Medicinal Chemistry*, vol. 49, No. 26, pp. 7868-7876 (2006).

Pannala et al., "Synthesis and structure-activity relationship of 4-(2-aryl-cyclopropylamino)-quinoline-3-carbonitriles as EGFR tyrosine kinase inhibitors", *Bioorganic & Medicinal Chemistry Letters*, Pergamon, GB, vol. 17, No. 21, pp. 5978-5982 (2007).

Boschelli et al., "Inhibition of Src kinase activity by 4-anilino-7-ehieny1-3-quinolinecarbonitriles", *Bioorganic & Medicinal Chemistry Letters*, Pergamon, GB, vol. 12, No. 15, pp. 2011-2014 (2002).

Zhang et al., "4-Anilino-7-pyridyl-3-quinolinecarbonitriles as Src kinase inhibitors", *Bioorganic & Medicinal Chemistry Letters*, Pergamon, GB, vol. 19, No. 17, pp. 5071-5074 (2009).

Eggert et al., "Compounds with Positive Inotropic Activity, III: Synthesis of 4-Aminoquinoline Derivatives as Potential Positive Inotropic Agents", *Arch. Pharm (Weinheim)*, vol. 323, No. 9, pp. 611-618 (1990).

International Preliminary Report on Patentability was issued on Feb. 14, 2013 in PCT Application No. PCT/US2011/045792.

English Translation of Office Action issued on Jan. 13, 2014 for Chinese Patent Application No. 201180047405.5, 4 pages.

\* cited by examiner

QUINOLINE DERIVATIVES AND MELK INHIBITORS CONTAINING THE SAME

PRIORITY

The present application is a U.S. National Phase of PCT/US2011/045792, filed Jul. 28, 2011, which claims the benefit of U.S. Provisional Application No. 61/369,519, filed on Jul. 30, 2010, the entire contents of which are incorporated by reference herein in their entirety.

TECHNICAL FIELD

The present invention relates to a quinoline derivative for inhibiting MELK activity, a method for the preparation thereof, and a pharmaceutical composition containing the compound as an active ingredient.

BACKGROUND ART

MELK, maternal embryonic leucine zipper kinase, was previously identified as a new member of the snf1/AMPK serine-threonine kinase family that is involved in mammalian embryonic development (Heyer B S et al., Dev Dyn. 1999 August 215(4):344-51). The gene was shown to play an important role in stem cell renewal (Nakano I et al., J. Cell Biol. 2005 Aug. 1, 170(3):413-27), cell-cycle progression (Blot J et al., Dev Biol. 2002 Jan. 15, 241(2):327-38; Seong H A et al., Biochem J. 2002 Feb. 1, 361(Pt 3):597-604) and pre-mRNA splicing (Vulsteke V et al., J Biol Chem. 2004 Mar. 5, 279(10):8642-7. Epub 2003 December 29). In addition, through gene expression profile analysis using a genome-wide cDNA microarray containing 23,040 genes, MELK was recently shown to be up-regulated in breast cancer (Lin M L et al., Breast Cancer Res. 2007; 9 (1):R17, WO2006/016525, WO2008/023841). In fact, MELK is up-regulated in several cancer cells, for example lung, bladder, lymphoma and cervical cancer cells (See WO2004/031413, WO2007/013665, and WO2006/085684, the disclosures of which are incorporated by reference herein). Northern blot analysis on multiple human tissues and cancer cell lines demonstrated that MELK was over-expressed at a significantly high level in a great majority of breast cancers and cell lines, but was not expressed in normal vital organs (heart, liver, lung and kidney) (WO2006/016525). Furthermore, suppression of MELK expression by siRNA was shown to significantly inhibit growth of human breast cancer cells. Accordingly, MELK is considered to be a suitable target for cancer therapy in the treatment of a wide array of cancer types. The present inventors have endeavored to develop an effective inhibitor of MELK and have found that a compound can selectively inhibit the activity of MELK.

SUMMARY OF INVENTION

The present invention relates to the following (1) to (33).
(1) A compound represented by the following formula or a pharmaceutically acceptable salt thereof:

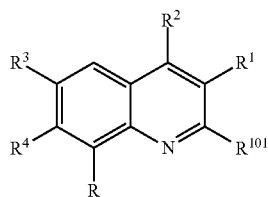

(I)

wherein,
$R^1$ represents
 a hydrogen atom,
 a halogen,
 a cyano,
 an optionally substituted $C_3$-$C_{10}$ cycloalkyl,
 an optionally substituted aromatic heterocyclic group,
 an optionally substituted $C_1$-$C_6$ alkylsulfinyl,
 an optionally substituted $C_1$-$C_6$ alkylsulfonyl, or
 —CO—$R^5$ [wherein,
  $R^5$ is
   an optionally substituted $C_1$-$C_6$ alkyl,
   an optionally substituted aliphatic heterocyclic-($C_1$-$C_6$ alkylenyl),
   an optionally substituted $C_3$-$C_{10}$ cycloalkyl,
   an optionally substituted aryl,
   an optionally substituted aromatic heterocyclic group,
   a hydroxy,
   an optionally substituted $C_1$-$C_6$ alkoxy, or
   —$NR^8R^9$ (wherein,
    $R^8$ and $R^9$ are the same or different and represent
     a hydrogen atom,
     an optionally substituted aryl,
     an optionally substituted $C_1$-$C_6$ alkyl,
     an optionally substituted $C_3$-$C_{10}$ cycloalkyl,
     an optionally substituted aromatic heterocyclic-($C_1$-$C_6$ alkylenyl), or
     an optionally substituted aliphatic heterocyclic-($C_1$-$C_6$ alkylenyl))],
$R^2$ represents
 a hydrogen atom,
 a halogen,
 a hydroxy,
 a di($C_1$-$C_6$ alkyl)amino-($C_1$-$C_6$ alkylenyloxy),
 an optionally substituted aryl,
 an optionally substituted aromatic heterocyclic group,
 an optionally substituted aliphatic heterocyclic group,
 —$NR^6R^7$ [wherein,
  $R^6$ and $R^7$ are the same or different and represent
   a hydrogen atom,
   an optionally substituted $C_1$-$C_6$ alkyl,
   a $C_1$-$C_6$ aminoalkyl,
   an optionally substituted $C_1$-$C_6$ alkylamino-($C_1$-$C_6$ alkylenyl),
   an optionally substituted di($C_1$-$C_6$ alkyl)amino-($C_1$-$C_6$ alkylenyl),
   an optionally substituted $C_2$-$C_7$ alkanoylamino-($C_1$-$C_6$ alkylenyl), or
   —$(CH_2)_n$—$R^{10}$ (wherein,
    n represents an integer of 0 to 6, and
    $R^{10}$ is
     an optionally substituted $C_3$-$C_{10}$ cycloalkyl,
     an optionally substituted aryl,
     an optionally substituted aromatic heterocyclic group, or
     an optionally substituted aliphatic heterocyclic group), or
   $R^6$ and $R^7$ form with an adjacent nitrogen atom an optionally substituted heterocyclic group],
$R^3$ represents
 a hydrogen atom,
 a halogen,
 an optionally substituted $C_1$-$C_6$ alkyl,
 an optionally substituted $C_1$-$C_6$ alkoxy,
 an optionally substituted $C_3$-$C_8$ cycloalkenyl,
 an optionally substituted aryl,
 an optionally substituted aromatic heterocyclic group, or
 an optionally substituted aliphatic heterocyclic group, $R^4$ represents
- a hydrogen atom,
- a halogen
- a cyano,
- a $C_1$-$C_6$ alkyl which may have a halogen as a substituent, or
- an optionally substituted $C_1$-$C_6$ alkoxy, R represents
- a hydrogen atom, or
- a halogen, and $R^{101}$ represents
- a hydrogen atom, or a $C_1$-$C_6$ alkyl.

In particular, the following compounds or pharmaceutically acceptable salts thereof among the compounds represented by the above-mentioned formula (I):
wherein,
$R^1$ is
- a hydrogen atom,
- a halogen,
- a cyano,
- a $C_3$-$C_{10}$ cycloalkyl,
- an aromatic heterocyclic group,
- a $C_1$-$C_6$ alkylsulfinyl,
- a $C_1$-$C_6$ alkylsulfonyl, or
- —CO—$R^5$ [wherein,
    $R^5$ represents
    - an optionally substituted $C_1$-$C_6$ alkyl which may have a substituent group selected from Substituent Group A,
    - an aliphatic heterocyclic-($C_1$-$C_6$ alkylenyl),
    - a $C_3$-$C_{10}$ cycloalkyl,
    - an optionally substituted aryl which may have a substituent group selected from Substituent Group B,
    - an aromatic heterocyclic group,
    - a hydroxy,
    - a $C_1$-$C_6$ alkoxy, or
    - —$NR^8R^9$ (wherein,
        $R^8$ and $R^9$ are the same or different and represent
        - a hydrogen atom,
        - an optionally substituted aryl which may have a substituent group selected from Substituent Group B,
        - a $C_1$-$C_6$ alkyl,
        - an optionally substituted $C_3$-$C_{10}$ cycloalkyl which may have a substituent group selected from Substituent Group B,
        - an aromatic heterocyclic-($C_1$-$C_6$ alkylenyl), or
        - an optionally substituted aliphatic heterocyclic-($C_1$-$C_6$ alkylenyl) which may have a substituent group selected from Substituent Group B)], $R^2$ represents
- a hydrogen atom,
- a halogen,
- a hydroxy,
- a di($C_1$-$C_6$ alkyl)amino-($C_1$-$C_6$ alkylenyloxy),
- an optionally substituted aryl which may have a substituent group selected from Substituent Group B,
- an optionally substituted aromatic heterocyclic group which may have a substituent group selected from Substituent Group B,
- an optionally substituted aliphatic heterocyclic group which may have a substituent group selected from Substituent Group B,
- —$NR^6R^7$ [wherein,
    $R^6$ and $R^7$ are the same or different and represent
    - a hydrogen atom,
    - an optionally substituted $C_1$-$C_6$ alkyl which may have a substituent group selected from Substituent Group A,
    - a $C_1$-$C_6$ aminoalkyl,
    - a $C_1$-$C_6$ alkylamino-($C_1$-$C_6$ alkylenyl),
    - a di($C_1$-$C_6$ alkyl)amino-($C_1$-$C_6$ alkylenyl) which may be substituted with a hydroxy,
    - a $C_2$-$C_7$ alkanoylamino-($C_1$-$C_6$ alkylenyl), or
    - —$(CH_2)_n$—$R^{10}$ (wherein,
        n represents an integer of 0 to 6, and
        $R^{10}$ represents
        - an optionally substituted $C_3$-$C_{10}$ cycloalkyl which may have a substituent group selected from Substituent Group B,
        - an optionally substituted aryl which may have a substituent group selected from Substituent Group B,
        - an optionally substituted aromatic heterocyclic group which may have a substituent group selected from Substituent Group B, or
        - an optionally substituted aliphatic heterocyclic group which may have a substituent group selected from Substituent Group B), or
    $R^6$ and $R^7$ form with an adjacent nitrogen atom an optionally substituted heterocyclic group which may have a substituent group selected from Substituent Group B], $R^3$ represents
- a hydrogen atom,
- a halogen,
- a $C_1$-$C_6$ alkyl,
- an optionally substituted $C_1$-$C_6$ alkoxy which may have a substituent group selected from Substituent Group A,
- an optionally substituted $C_3$-$C_8$ cycloalkenyl which may have a substituent group selected from Substituent Group B,
- an optionally substituted aryl which may have a substituent group selected from Substituent Group B,
- an optionally substituted aromatic heterocyclic group which may have a substituent group selected from Substituent Group B, or
- an optionally substituted aliphatic heterocyclic group which may have a substituent group selected from Substituent Group B, and $R^4$ represents
- a hydrogen atom, or
- a halogen, $R^{101}$ represents
- a hydrogen atom, the above-mentioned substituents are one to three substituents each independently selected from the following Substituent Groups:

Substituent Group A: a halogen, an aliphatic heterocyclic group, an optionally substituted aliphatic heterocyclic-carbonyl which may be substituted with a $C_1$-$C_6$ alkyl (the $C_1$-$C_6$ alkyl has the same meaning as the aforementioned $C_1$-$C_6$ alkyl)

Substituent Group B:
- a halogen,
- a hydroxy,
- a cyano,
- a $C_1$-$C_6$ alkyl,
- a $C_1$-$C_6$ alkoxy,
- a carboxyl,
- a $C_1$-$C_6$ alkoxycarbonyl,
- a trifluoromethoxy,
- a difluoromethoxy, a trifluoromethyl,
a difluoromethyl,
an amino,
a $C_1$-$C_6$ alkylamino (wherein, the $C_1$-$C_6$ alkyl may have a hydroxy as a substituent),
a di($C_1$-$C_6$ alkyl)amino,
a diallylamino,
a $C_1$-$C_6$ alkylsulfonylamino,
a $C_2$-$C_7$ alkanoylamino,
a carbamoyl,
a sulfamoyl,
a benzylureide,
a ($C_1$-$C_6$ alkyl)ureide,
a $C_1$-$C_6$ hydroxyalkyl,
a $C_1$-$C_6$ aminoalkyl,
a $C_1$-$C_6$ aminoalkylenyloxy,
a $C_1$-$C_6$ alkylamino-($C_1$-$C_6$ alkylenyl) (wherein, the $C_1$-$C_6$ alkyl may have a halogen as a substituent),
a di($C_1$-$C_6$ alkyl)amino-($C_1$-$C_6$ alkylenyl) (wherein, either a $C_1$-$C_6$ alkyl or a $C_1$-$C_6$ alkylenyl may have a hydroxy or a cyano as a substituent, and wherein hydrogen atom of $C_1$-$C_6$ alkyl may be substituted with deuterium atom),
a di($C_1$-$C_6$ alkyl)amino-($C_1$-$C_6$ alkylenyl)oxy,
a di($C_1$-$C_6$ alkyl)amino-($C_1$-$C_6$ alkylenyl)amino,
a di($C_1$-$C_6$ alkyl)amino-($C_1$-$C_6$ alkylenyl)carbonyl,
a di($C_1$-$C_6$ alkyl)amino-($C_1$-$C_6$ alkylenyl)carbonylamino,
a di($C_1$-$C_6$ alkyl)amino-($C_1$-$C_6$ alkylenyl)aminocarbonyl,
an aliphatic heterocyclic group (wherein, the aliphatic heterocyclic group may have a $C_1$-$C_6$ alkyl, an amino, a hydroxy, a halogen, a di($C_1$-$C_6$ alkyl)amino, a $C_1$-$C_6$ alkylamino, or a $C_1$-$C_6$ alkoxy as a substituent),
an aliphatic heterocyclic-($C_1$-$C_6$ alkylenyl) (wherein, the aliphatic heterocyclic may have a $C_1$-$C_6$ alkyl, an amino, a hydroxy, a $C_1$-$C_6$ hydroxyalkyl, a $C_1$-$C_6$ alkoxy, a $C_1$-$C_6$ alkylamino, a di($C_1$-$C_6$ alkyl)amino, or a halogen as a substituent),
an aliphatic heterocyclic-carbonyl (wherein, the aliphatic heterocyclic may have a $C_1$-$C_6$ alkyl as a substituent),
an aliphatic heterocyclic-carbonylamino (wherein, the aliphatic heterocyclic may have a $C_1$-$C_6$ alkyl as a substituent),
an aliphatic heterocyclic-amino (wherein, the aliphatic heterocyclic may have a $C_1$-$C_6$ alkyl or an amino as a substituent),
an aliphatic heterocyclic-($C_1$-$C_6$ alkylenyl)amino,
an aliphatic heterocyclic-($C_1$-$C_6$ alkylenyl)oxy,
an aromatic heterocyclic-($C_1$-$C_6$ alkylenyl),
an aliphatic heterocyclic-sulfonyl which may be substituted with a $C_1$-$C_6$ alkyl,
a $C_1$-$C_6$ aminoalkylcarbonylamino,
a hydroxyphenyl,
a dimethylaminocarbonyl,
an aminocyclohexylaminocarbonyl,
a methylpiperazinylphosphonyl,
a $C_3$-$C_8$ cycloalkyl (wherein, the cycloalkyl may have an amino, a $C_1$-$C_6$ alkylamino, or a $C_1$-$C_6$ aminoalkyl as a substituent), and
an oxo.

(2) The compound or a pharmaceutically acceptable salt thereof of the above-mentioned (1), wherein $R^4$ is a hydrogen atom or a halogen and $R^{101}$ is a hydrogen atom.

(3) The compound or a pharmaceutically acceptable salt thereof of the above-mentioned (2), wherein $R^1$ is $R^{1A}$ [$R^{1A}$ represents a cyano, a $C_1$-$C_6$ alkylsulfinyl, a $C_1$-$C_6$ alkylsulfonyl, or —CO—$R^{5A}$ (wherein, $R^{5A}$ represents a $C_1$-$C_6$ alkyl or a $C_3$-$C_{10}$ cycloalkyl)], $R^2$ is $R^{2A}$ {$R^{2A}$ represents an optionally substituted aryl which may have a substituent group selected from Substituent Group C, an optionally substituted aromatic heterocyclic group which may have a substituent group selected from Substituent Group H, or —NR$^{6A}$R$^{7A}$ [wherein, R$^{6A}$ represents a hydrogen atom, and R$^{7A}$ represents —(CH$_2$)$_n$—R$^{10A}$ (wherein, n represents an integer of 0 to 6, and R$^{10A}$ represents an optionally substituted $C_3$-$C_{10}$ cycloalkyl which may have a substituent group selected from Substituent Group D, an optionally substituted aryl which may have a substituent group selected from Substituent Group E, an aliphatic heterocyclic group which may be substituted with a $C_1$-$C_6$ alkyl, or an aromatic heterocyclic group which may have a substituent group selected from Substituent Group I), or R$^{6A}$ and R$^{7A}$ form with an adjacent nitrogen atom an optionally substituted heterocyclic group which may have a substituent group selected from Substituent Group F]}, $R^3$ is $R^{3A}$ ($R^{3A}$ represents an optionally substituted aryl which may have a substituent group selected from Substituent Group G, or an optionally substituted aromatic heterocyclic group which may have a substituent group selected from Substituent Group H), and $R^4$ is a hydrogen atom or a halogen and $R^{101}$ is a hydrogen atom.

More specifically, a compound represented by the following formula (IA) or a pharmaceutically acceptable salt thereof:

(IA)

[Structure with $R^{2A}$, $R^{1A}$, $R^{3A}$, $R^{4A}$ on a quinoline ring]

wherein,
$R^{1A}$ represents
   a cyano,
   a $C_1$-$C_6$ alkylsulfinyl,
   a $C_1$-$C_6$ alkylsulfonyl, or
   a —CO—$R^{5A}$ (wherein, $R^{5A}$ represents a $C_1$-$C_6$ alkyl, or a $C_3$-$C_{10}$ cycloalkyl), $R^{2A}$ represents
   an optionally substituted aryl which may have a substituent group selected from Substituent Group C,
   an optionally substituted aromatic heterocyclic group which may have a substituent group selected from Substituent Group H, or
   —NR$^{6A}$R$^{7A}$ [wherein,
     R$^{6A}$ represents a hydrogen atom, and
     R$^{7A}$ represents
        —(CH$_2$)$_n$—R$^{10A}$ (wherein,
           n represents an integer of 0 to 6, and
           R$^{10A}$ represents
              an optionally substituted $C_3$-$C_{10}$ cycloalkyl which may have a substituent group selected from Substituent Group D,
              an optionally substituted aryl which may have a substituent group selected from Substituent Group E,
              an aliphatic heterocyclic group which may be substituted with a $C_1$-$C_6$ alkyl, or
              an optionally substituted aromatic heterocyclic group which may have a substituent group selected from Substituent Group I), or $R^{6A}$ and $R^{7A}$ form with an adjacent nitrogen atom an optionally substituted heterocyclic group which may have a substituent group selected from Substituent Group F], $R^{3A}$ represents
an optionally substituted aryl which may have a substituent group selected from Substituent Group G, or
an optionally substituted aromatic heterocyclic group which may have a substituent group selected from Substituent Group H, $R^{4A}$ represents a hydrogen atom or a halogen, and
the above-mentioned substituents C to I are one to three substituents each independently selected from the following Substituent Groups:

Substituent Group C: a halogen, a hydroxy, a $C_1$-$C_6$ alkoxy, and a di($C_1$-$C_6$ alkyl)amino;

Substituent Group D: a hydroxy, a $C_1$-$C_6$ alkyl, a $C_1$-$C_6$ aminoalkyl, an aliphatic heterocyclic-($C_1$-$C_6$ alkylenyl) (wherein, the aliphatic heterocyclic may have an amino, a hydroxy, a $C_1$-$C_6$ hydroxyalkyl, a $C_1$-$C_6$ alkoxy, or a halogen as a substituent), a $C_1$-$C_6$ alkylamino-($C_1$-$C_6$ alkylenyl), a di($C_1$-$C_6$ alkyl)amino-($C_1$-$C_6$ alkylenyl) (wherein, either $C_1$-$C_6$ alkyl may have a hydroxy or a cyano as a substituent, and wherein hydrogen atom of $C_1$-$C_6$ alkyl may be substituted with deuterium atom), an amino, a $C_1$-$C_6$ alkylamino, a di($C_1$-$C_6$ alkyl)amino, a $C_1$-$C_6$ aminoalkylcarbonylamino, a di($C_1$-$C_6$ alkyl)amino($C_1$-$C_6$ alkylenyl)carbonylamino, an aliphatic heterocyclic group (wherein, the aliphatic heterocyclic group may have a $C_1$-$C_6$ alkoxy as a substituent), and an aliphatic heterocyclic-carbonylamino;

Substituent Group E: a halogen, a di($C_1$-$C_6$ alkyl)amino-($C_1$-$C_6$ alkylenyl) (wherein, the $C_1$-$C_6$ alkylenyl may have a hydroxy as a substituent), an amino, a $C_2$-$C_7$ alkanoylamino, a di($C_1$-$C_6$ alkyl)amino, a $C_1$-$C_6$ aminoalkyl, and an aliphatic heterocyclic-($C_1$-$C_6$ alkylenyl) (wherein, the aliphatic heterocyclic may have a $C_1$-$C_6$ alkyl as a substituent);

Substituent Group F: a carbamoyl, an amino, a $C_1$-$C_6$ aminoalkyl, a di($C_1$-$C_6$ alkyl)amino-($C_1$-$C_6$ alkylenyl), a $C_1$-$C_6$ alkylamino-($C_1$-$C_6$ alkylenyl), an aliphatic heterocyclic-($C_1$-$C_6$ alkylenyl), and an aliphatic heterocyclic group which may be substituted with a $C_1$-$C_6$ alkyl;

Substituent Group G: a halogen, a hydroxy, a cyano, a $C_1$-$C_6$ alkyl, a $C_1$-$C_6$ alkoxy, a trifluoromethoxy, a $C_1$-$C_6$ aminoalkyl, a $C_1$-$C_6$ alkylamino-($C_1$-$C_6$ alkylenyl), a di($C_1$-$C_6$ alkyl)amino-($C_1$-$C_6$ alkylenyl), an amino, a $C_1$-$C_6$ alkylsulfonylamino, a carbamoyl, a sulfamoyl, a ($C_1$-$C_6$ alkyl)ureide, a benzylureide, and an aliphatic heterocyclic group;

Substituent Group H: a halogen, a cyano, a $C_1$-$C_6$ alkyl, a $C_1$-$C_6$ alkoxy, an amino, a carbamoyl, a dimethylaminopropylaminocarbonyl, and an aminocyclohexylaminocarbonyl;

Substituent Group H: a halogen, a cyano, a $C_1$-$C_6$ alkyl, a $C_1$-$C_6$ alkoxy, an amino, a carbamoyl, a dimethylaminopropylaminocarbonyl, and an aminocyclohexylaminocarbonyl;

Substituent Group I: an aliphatic heterocyclic group (wherein, the aliphatic heterocyclic group may have a $C_1$-$C_6$ alkyl, an amino group, or a $C_1$-$C_6$ alkylamino as a substituent); an aliphatic heterocyclic-($C_1$-$C_6$ alkylenyl); an aliphatic heterocyclic-amino (wherein, the aliphatic heterocyclic may have a $C_1$-$C_6$ alkyl or an amino as a substituent); a di($C_1$-$C_6$ alkyl)amino-($C_1$-$C_6$ alkylenyl); a $C_1$-$C_6$ aminoalkyloxy; a di($C_1$-$C_6$ alkyl)amino-($C_1$-$C_6$ alkylenyl)oxy; a di($C_1$-$C_6$ alkyl)amino-($C_1$-$C_6$ alkylenyl)amino; a cyclohexyl (wherein, the cyclohexyl may have an amino or a $C_1$-$C_6$ aminoalkyl as a substituent).

(4) The compound or a pharmaceutically acceptable salt thereof of any one of the above-mentioned (1) to (3), wherein $R^1$ is —CO—$R^{5A}$ (wherein, $R^{5A}$ has the same meaning as described above).

(5) The compound or a pharmaceutically acceptable salt thereof of the above-mentioned (4), wherein $R^{5A}$ is a $C_1$-$C_6$ alkyl or a $C_3$-$C_{10}$ cycloalkyl.

(6) The compound or a pharmaceutically acceptable salt thereof of the above-mentioned (4), wherein $R^{5A}$ is a methyl, an n-propyl, an isopropyl, an isobutyl, or a cyclopropyl.

(7) The compound or a pharmaceutically acceptable salt thereof of any one of the above-mentioned (1) to (3), wherein $R^1$ is a cyano.

(8) The compound or a pharmaceutically acceptable salt thereof of any one of the above-mentioned (1) to (3), wherein $R^1$ is a $C_1$-$C_6$ alkylsulfonyl.

(9) The compound or a pharmaceutically acceptable salt thereof of any one of the above-mentioned (1) to (3), wherein $R^1$ is a methylsulfonyl.

(10) The compound or a pharmaceutically acceptable salt thereof of any one of the above-mentioned (1) to (9), wherein $R^2$ is —NR$^{6A}$R$^{7A}$ (wherein, $R^{6A}$ and $R^{7A}$ have the same meaning as described above).

Especially, a compound represented by the following formula (IB) or a pharmaceutically acceptable salt thereof:

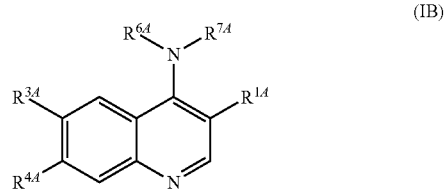

(IB)

wherein, $R^{1A}$, $R^{3A}$, $R^{4A}$, $R^{6A}$, and $R^{7A}$ have the same meaning as described above.

(11) The compound or a pharmaceutically acceptable salt thereof of the above-mentioned (10), wherein $R^{6A}$ is a hydrogen atom, and $R^{7A}$ is —(CH$_2$)$_n$—$R^{10A}$ (wherein, n and $R^{10A}$ have the same meaning as described above).

(12) The compound or a pharmaceutically acceptable salt thereof of the above-mentioned (11), wherein $R^{10A}$ is a three- to eight-membered monocyclic aliphatic heterocyclic group comprising at least one nitrogen atom which may be substituted with a $C_1$-$C_6$ alkyl; a $C_3$-$C_{10}$ cycloalkyl which may have a substituent group selected from Substituent Group D; a phenyl which may have a substituent group selected from Substituent Group E; or an aromatic heterocyclic group which may have a substituent group selected from Substituent Group I, wherein the aromatic heterocyclic group is a pyridyl, a pyrimidinyl, or a pyrazolyl.

Substituent Group D: a hydroxy, a $C_1$-$C_6$ alkyl, a $C_1$-$C_6$ aminoalkyl, an aliphatic heterocyclic-($C_1$-$C_6$ alkylenyl) (wherein, the aliphatic heterocyclic may have an amino, a hydroxy, a $C_1$-$C_6$ hydroxyalkyl, a $C_1$-$C_6$ alkoxy, or a halogen as a substituent), a $C_1$-$C_6$ alkylamino-($C_1$-$C_6$ alkylenyl), a di($C_1$-$C_6$ alkyl)amino-($C_1$-$C_6$ alkylenyl) (wherein, either $C_1$-$C_6$ alkyl may have a hydroxy or a cyano as a substituent, and wherein hydrogen atom of $C_1$-$C_6$ alkyl may be substituted with deuterium atom), an amino, a $C_1$-$C_6$ alkylamino, a di($C_1$-$C_6$ alkyl)amino, a $C_1$-$C_6$ aminoalkylcarbonylamino, a di($C_1$-$C_6$ alkyl)

amino(C₁-C₆ alkylenyl)carbonylamino, an aliphatic heterocyclic group (wherein, the aliphatic heterocyclic group may have a $C_1$-$C_6$ alkoxy as a substituent), and an aliphatic heterocyclic-carbonylamino Substituent Group E: a halogen, a di($C_1$-$C_6$ alkyl)amino-($C_1$-$C_6$ alkylenyl) (wherein, the $C_1$-$C_6$ alkylenyl may have a hydroxy as a substituent), an amino, a $C_2$-$C_7$ alkanoylamino, a di($C_1$-$C_6$ alkyl)amino, a $C_1$-$C_6$ aminoalkyl, and an aliphatic heterocyclic-($C_1$-$C_6$ alkylenyl) (wherein, the aliphatic heterocyclic may have a $C_1$-$C_6$ alkyl as a substituent)

(13) The compound or a pharmaceutically acceptable salt thereof of the above-mentioned (11) or (12), wherein n is an integer of 0 to 2.

(14) The compound or a pharmaceutically acceptable salt thereof of the above-mentioned (10), wherein $R^{6A}$ and $R^{7A}$ form with an adjacent nitrogen atom an optionally substituted heterocyclic group which may have a substituent group selected from Substituent Group F.

(15) The compound or a pharmaceutically acceptable salt thereof of the above-mentioned (10), wherein $R^2$ is a piperidin-4-spiro-3'-pyrrolidin-1-yl, an optionally substituted piperidino which may have a substituent group selected from Substituent Group F, or an optionally substituted 1-piperazinyl which may have a substituent group selected from Substituent Group F.

(16) The compound or a pharmaceutically acceptable salt thereof of the above-mentioned (10), wherein $R^2$ is a piperidin-4-spiro-3'-pyrrolidin-1-yl, a piperidino which may have a substituent group selected from substituent Fa, or a 1-piperazinyl which may have a substituent group selected from substituent Fa, wherein the substituent Fa is a substituent selected from the group consisting of an amino, a di($C_1$-$C_6$ alkyl)amino-($C_1$-$C_6$ alkylenyl), a $C_1$-$C_6$ alkylamino-($C_1$-$C_6$ alkylenyl), a pyrrolidinyl-($C_1$-$C_6$ alkylenyl), a morpholino-($C_1$-$C_6$ alkylenyl), a 1-piperazinyl whose hydrogen atom on the nitrogen of position 4 may be substituted with a $C_1$-$C_6$ alkyl, and a piperazin-1-yl-($C_1$-$C_6$ alkylenyl) whose hydrogen atom on the nitrogen of position 4 may be substituted with a $C_1$-$C_6$ alkyl.

(17) The compound or a pharmaceutically acceptable salt thereof of any one of the above-mentioned (1) to (9), wherein $R^2$ is an optionally substituted aryl which may have a substituent group selected from Substituent Group C.

(18) The compound or a pharmaceutically acceptable salt thereof of the above-mentioned (1) to (9), wherein $R^2$ is an optionally substituted phenyl which may have a substituent group selected from Substituent Group C.

(19) The compound or a pharmaceutically acceptable salt thereof of any one of the above-mentioned (1) to (18), wherein $R^3$ is an optionally substituted aryl which may have a substituent group selected from Substituent Group G, or an optionally substituted aromatic heterocyclic group which may have a substituent group selected from Substituent Group H.

(20) The compound or a pharmaceutically acceptable salt thereof of any one of the above-mentioned (1) to (18), wherein $R^3$ is an optionally substituted phenyl which may have a substituent group selected from Substituent Group G, or an optionally substituted aromatic heterocyclic group which may have a substituent group selected from Substituent Group H, wherein the aromatic heterocyclic group is selected from the group consisting of a thienyl, a pyrrolyl, an imidazolyl, an isoxazolyl, a pyridyl, a pyrimidinyl, a pyrazolyl, a 1H-indazolyl, a benzimidazolyl, a [1,2,4]triazolo[1,5-a]pyridyl, or a pyrrolo[2,3-b]pyridyl.

(21) The compound or a pharmaceutically acceptable salt thereof of any one of the above-mentioned (1) to (18), wherein $R^3$ is an optionally substituted phenyl which may have a substituent group selected from Substituent Group G, or an optionally substituted aromatic heterocyclic group which may have a substituent group selected from Substituent Group H, wherein the aromatic heterocyclic group is selected from the group consisting of a pyridyl, a thienyl, a pyrimidinyl, a benzimidazolyl, and a 1H-indazolyl.

(22) The compound or a pharmaceutically acceptable salt thereof of any one of the above-mentioned (1) to (21), wherein R is a hydrogen atom.

(23) A compound or a pharmaceutically acceptable salt thereof, selected from the following Compound Group:

compound 1: ethyl 4-(3-(dimethylamino)propylamino)-6-methoxyquinoline-3-carboxylate compound 2: ethyl 4-(3-(dimethylamino)propylamino)-6-methylquinoline-3-carboxylate compound 3: ethyl 4-(3-(dimethylamino)propylamino)-6-fluoroquinoline-3-carboxylate compound 4: ethyl 4-(3-(dimethylamino)propylamino)quinoline-3-carboxylate compound 5: ethyl 4-(4-acetamidophenylamino)-6-methylquinoline-3-carboxylate compound 6: ethyl 4-(4-acetamidophenylamino)-6-methoxyquinoline-3-carboxylate compound 7: ethyl 4-(4-acetamidophenylamino)quinoline-3-carboxylate compound 8: ethyl 4-(3-(dimethylamino)propylamino)-6-(trifluoromethoxy)quinoline-3-carboxylate compound 9: N1-(3-bromoquinolin-4-yl)-N3,N3-dimethylpropane-1,3-diamine compound 10: ethyl 4-(4-acetamidophenylamino)-6-fluoroquinoline-3-carboxylate compound 11: N1,N1-dimethyl-N3-(quinolin-4-yl)propane-1,3-diamine compound 12: N-(4-(quinolin-4-ylamino)phenyl)acetamide compound 13: N1,N1-dimethyl-N3-(3-(thiophen-2-yl)quinolin-4-yl)propane-1,3-diamine compound 14: N-(4-(6-chloro-3-(4-chlorobenzoyl)quinolin-4-ylamino)phenyl)acetamide compound 15: (6-chloro-4-(3-(dimethylamino) propylamino)quinolin-3-yl)(4-chlorophenyl)methanone compound 16: 4-(4-acetamidophenylamino)-N-(4-chlorophenyl)quinoline-3-carboxamide compound 17: N-(4-chlorophenyl)-4-(3-(dimethylamino)propylamino)quinoline-3-carboxamide compound 18: N-(4-(6-chloro-3-(cyclopropanecarbonyl)quinolin-4-ylamino)phenyl)acetamide compound 19: (6-chloro-4-(3-(dimethylamino) propylamino)quinolin-3-yl)(cyclopropyl)methanone compound 20: N-(4-chlorophenyl)-4-(4-chlorophenylamino)quinoline-3-carboxamide compound 21: ethyl 4-(4-acetamidophenylamino)-6-(trifluoromethoxy)quinoline-3-carboxylate compound 22: N-(4-chlorophenyl)-4-(piperidin-3-ylmethylamino)quinoline-3-carboxamide compound 23: N-(4-chlorophenyl)-4-((1-ethylpyrrolidin-2-yl)methylamino)quinoline-3-carboxamide compound 24: ethyl 4-(4-acetamidophenylamino)-6-chloroquinoline-3-carboxylate compound 25: ethyl 4-(3-(dimethylamino)propylamino)-6-(4-hydroxyphenyl)quinoline-3-carboxylate compound 26: ethyl 6-bromo-4-(3-(dimethylamino) propylamino)quinoline-3-carboxylate compound 27: ethyl 4-(3-(dimethylamino)propylamino)-6-(thiophen-2-yl)quinoline-3-carboxylate compound 28: ethyl 6-chloro-4-(3-(dimethylamino) propylamino)quinoline-3-carboxylate
compound 29: N-((1-ethylpyrrolidin-2-yl)methyl)-3-(thiophen-2-yl)quinolin-4-amine
compound 30: N-(4-(3-(thiophen-2-yl)quinolin-4-ylamino) phenyl)acetamide
compound 31: ethyl 4-(4-acetamidophenylamino)-6-bromoquinoline-3-carboxylate
compound 32: 4-((trans)-4-aminocyclohexylamino)-N-(4-chlorophenyl)quinoline-3-carboxamide
compound 33: (4-((trans)-4-aminocyclohexylamino)-6-chloroquinolin-3-yl)(cyclopropyl)methanone
compound 34: (4-(3-aminopropylamino) 6-chloroquinolin-3-yl)(cyclopropyl)methanone
compound 35: N-(4-(6-bromo-3-(thiophene-2-carbonyl) quinolin-4-ylamino)phenyl)acetamide
compound 36: (6-bromo-4-(3-(dimethylamino) propylamino)quinolin-3-yl)(thiophen-2-yl)methanone
compound 37: N1,N1-dimethyl-N3-(6-(trifluoromethoxy) quinolin-4-yl)propane-1,3-diamine
compound 38: ethyl 4-(3-(dimethylamino)propylamino)-6-(pyridin-4-yl)quinoline-3-carboxylate
compound 39: ethyl 4-(3-(dimethylamino)propylamino)-6-(3-hydroxyphenyl)quinoline-3-carboxylate
compound 40: (6-chloro-4-(piperidin-3-ylamino)quinolin-3-yl)(cyclopropyl)methanone
compound 41: 4-chloro-1-(6-chloro-4-(piperidin-3-ylamino) quinolin-3-yl) butan-1-one
compound 42: (6-chloro-4-((3-(dimethylamino)propyl)(methyl)amino)quinolin-3-yl)(cyclopropyl)methanone
compound 43: (6-chloro-4-(4-(dimethylamino)phenylamino)quinolin-3-yl)(cyclopropyl)methanone
compound 44: ethyl 4-(4-aminophenylamino)-6-chloroquinoline-3-carboxylate
compound 45: ethyl 6-chloro-4-(4-(dimethylamino)phenylamino)quinoline-3-carboxylate
compound 46: ethyl 4-(4-(dimethylamino)phenylamino)-6-(trifluoromethoxy)quinoline-3-carboxylate
compound 47: (4-(3-(dimethylamino) propylamino)-6-(4-hydroxyphenyl)quinolin-3-yl)(thiophen-2-yl)methanone
compound 48: (6-bromo-4-(3-(dimethylamino) propylamino)quinolin-3-yl)(cyclopropyl)methanone
compound 49: 4,4'-(quinoline-4,6-diyl)diphenol
compound 50: 4-(4-(3-(dimethylamino) propylamino)quinolin-6-yl)phenol
compound 51: N1-(3-(1H-benzo[d]imidazol-2-yl)-6-methoxyquinolin-4-yl)-N3,N3-dimethylpropane-1,3-diamine
compound 52: 4-(4-((trans)-4-aminocyclohexylamino) quinolin-6-yl)phenol
compound 53: (4-((trans)-4-aminocyclohexylamino)-6-(4-hydroxyphenyl)quinolin-3-yl)(thiophen-2-yl)methanone
compound 54: (4-((trans)-4-aminocyclohexylamino)-6-bromoquinolin-3-yl) (thiophen-2-yl)methanone
compound 55: (4-((trans)-4-aminocyclohexylamino)-6-(4-hydroxyphenyl)quinolin-3-yl)(cyclopropyl)methanone
compound 56: (4-((trans)-4-aminocyclohexylamino)-6-bromoquinolin-3-yl)(cyclopropyl)methanone
compound 57: 4-(3-(dimethylamino)propylamino)-6-methoxy-N,N-dimethylquinoline-3-carboxamide
compound 58: 4-(3-(dimethylamino)propylamino)-6-methoxy-N-methylquinoline-3-carboxamide
compound 59: ethyl 6-(4-aminophenyl)-4-(3-(dimethylamino)propylamino)quinoline-3-carboxylate
compound 60: ethyl 6-(4-carbamoylphenyl)-4-(3-(dimethylamino)propylamino)quinoline-3-carboxylate
compound 61: ethyl 6-(6-cyanopyridin-3-yl)-4-(3-(dimethylamino)propylamino)quinoline-3-carboxylate
compound 62: ethyl 6-(6-aminopyridin-3-yl)-4-(3-(dimethylamino)propylamino)quinoline-3-carboxylate
compound 63: ethyl 4-(3-(dimethylamino)propylamino)-6-(4-(methylsulfonamido)phenyl)quinoline-3-carboxylate
compound 64: ethyl 4-(3-(dimethylamino)propylamino)-6-(4-hydroxy-3-methoxyphenyl)quinoline-3-carboxylate
compound 65: ethyl 4-(3-(dimethylamino)propylamino)-6-(4-methoxyphenyl)quinoline-3-carboxylate
compound 66: ethyl 4-(3-(dimethylamino)propylamino)-6-(1H-pyrazol-4-yl)quinoline-3-carboxylate
compound 67: ethyl 4-(3-(dimethylamino)propylamino)-6-(1H-indazol-5-yl)quinoline-3-carboxylate
compound 68: ethyl 4-(3-(dimethylamino)propylamino)-6-(4-sulfamoylphenyl)quinoline-3-carboxylate
compound 69: N-(3-(dimethylamino)propyl)-5-(4-(3-(dimethylamino)propylamino)-3-(thiophen-2-yl)quinolin-6-yl)picolinamide
compound 70: ethyl 4-((trans)-4-aminocyclohexylamino)-6-bromoquinoline-3-carboxylate
compound 71: ethyl 6-bromo-4-((trans)-4-hydroxycyclohexylamino) quinoline-3-carboxylate
compound 72: ethyl 4-(3-aminopropylamino)-6-bromoquinoline-3-carboxylate
compound 73: ethyl 6-bromo-4-(2-(diethylamino) ethylamino)quinoline-3-carboxylate
compound 74: ethyl 6-bromo-4-((1-ethylpyrrolidin-2-yl)methylamino)quinoline-3-carboxylate
compound 75: (6-bromo-4-(3-(dimethylamino) propoxy) quinolin-3-yl)(cyclopropyl)methanone
compound 76: 5-(4-((trans)-4-aminocyclohexylamino)-3-(cyclopropanecarbonyl)quinolin-6-yl)picolinonitrile
compound 77: 5-(4-((trans)-4-aminocyclohexylamino)-3-(thiophene-2-carbonyl)quinolin-6-yl)picolinonitrile
compound 78: 4-(quinolin-6-yl)phenol
compound 79: 4-(4-(3-(dimethylamino) propylamino)-3-(thiophen-2-yl)quinolin-6-yl)phenol
compound 80: 4-(3-(dimethylamino)propylamino)-6-(4-methoxyphenyl)quinoline-3-carboxylic acid dihydrochloride
compound 81: (4-((trans)-4-aminocyclohexylamino)-6-(4-hydroxy-3-methoxyphenyl)quinolin-3-yl)(cyclopropyl)methanone
compound 82: ethyl 6-bromo-4-(1-methylpiperidin-4-ylamino)quinoline-3-carboxylate
compound 83: (4-((trans)-4-aminocyclohexylamino)-6-(6-methoxypyridin-3-yl)quinolin-3-yl)(thiophen-2-yl) methanone
compound 84: N-((trans)-4-aminocyclohexyl)-5-(4-((trans)-4-aminocyclohexylamino)-3-(thiophen-2-yl)quinolin-6-yl)picolinamide
compound 85: ethyl 6-bromo-4-(3-(diethylamino) propylamino)quinoline-3-carboxylate
compound 86: 4-(4-((trans)-4-aminocyclohexylamino)-3-(thiophen-2-yl)quinolin-6-yl)phenol
compound 87: N-((trans)-4-aminocyclohexyl)-5-(4-chloro-3-(thiophen-2-yl)quinolin-6-yl)picolinamide
compound 88: ethyl 4-((trans)-4-(aminomethyl)cyclohexylamino)-6-bromoquinoline-3-carboxylate
compound 89: ethyl 4-(2-(diethylamino)ethylamino)-6-(4-hydroxyphenyl)quinoline-3-carboxylate
compound 90: ethyl 4-((1-ethylpyrrolidin-2-yl)methylamino)-6-(4-hydroxyphenyl)quinoline-3-carboxylate
compound 91: ethyl 6-bromo-4-(piperidin-4-ylmethylamino)quinoline-3-carboxylate
compound 92: ethyl 6-bromo-4-(piperidin-4-ylamino)quinoline-3-carboxylate compound 93: ethyl 4-(3-aminopropylamino)-6-(4-hydroxyphenyl)quinoline-3-carboxylate
compound 94: ethyl 6-bromo-4-(2-(piperazin-1-yl)ethylamino)quinoline-3-carboxylate
compound 95: ethyl 4-(3-(dimethylamino)propylamino)-6-(pyridin-3-yl)quinoline-3-carboxylate
compound 96: 5-(4-((trans)-4-aminocyclohexylamino)-3-(cyclopropanecarbonyl)quinolin-6-yl)pyrimidine-2-carbonitrile
compound 97: 1-(6-bromo-4-(3-(dimethylamino) propylamino)quinolin-3-yl)-4-morpholinobutan-1-one
compound 98: ethyl 6-bromo-4-((trans)-4-(diethylamino)cyclohexylamino)quinoline-3-carboxylate
compound 99: ethyl 4-((cis)-4-aminocyclohexylamino)-6-bromoquinoline-3-carboxylate
compound 100: ethyl 6-bromo-4-(4-((dimethylamino)methyl)piperidin-1-yl)quinoline-3-carboxylate
compound 101: ethyl 4-(3-(1H-imidazol-1-yl)propylamino)-6-bromoquinoline-3-carboxylate
compound 102: 4-(3-cyclopropyl-4-(3-(dimethylamino)propylamino)quinolin-6-yl)-2-methoxyphenol
compound 103: 4-(3-cyclopropyl-4-(3-(dimethylamino)propylamino)quinolin-6-yl)phenol
compound 104: 4-(4-((trans)-4-aminocyclohexylamino)-3-cyclopropylquinolin-6-yl)phenol
compound 105: 4-(3-(1H-benzo[d]imidazol-2-yl)-4-(3-(dimethylamino)propylamino)quinolin-6-yl)phenol
compound 106: ethyl 6-(4-cyanophenyl)-4-(3-(dimethylamino)propylamino)quinoline-3-carboxylate
compound 107: 1-(4-((trans)-4-aminocyclohexylamino)-6-(4-hydroxy-3-methoxyphenyl)quinolin-3-yl)-2-methylpropan-1-one
compound 108: 5-(4-((trans)-4-aminocyclohexylamino)-3-isobutyrylquinolin-6-yl)picolinonitrile
compound 109: 1-(4-((trans)-4-aminocyclohexylamino)-6-bromoquinolin-3-yl)-2-methylpropan-1-one
compound 110: ethyl 6-bromo-4-((1-methylpiperidin-4-yl)methylamino)quinoline-3-carboxylate
compound 111: ethyl 4-((3-(aminomethyl)cyclohexyl)methylamino)-6-bromoquinoline-3-carboxylate
compound 112: ethyl 4-((trans)-4-aminocyclohexylamino)-6-(6-cyanopyridin-3-yl)quinoline-3-carboxylate
compound 113: 4-(3-(dimethylamino)propylamino)-6-(4-hydroxyphenyl)-N,N-dimethylquinoline-3-carboxamide
compound 114: 4-(3-(dimethylamino)propylamino)-N-ethyl-6-(4-hydroxyphenyl)quinoline-3-carboxamide
compound 115: 4-(3-(dimethylamino)propylamino)-N-((trans)-4-hydroxycyclohexyl)-6-(4-hydroxyphenyl)quinoline-3-carboxamide
compound 116: (4-((trans)-4-aminocyclohexylamino)-6-(1H-benzo[d]imidazol-5-yl)quinolin-3-yl)(cyclopropyl)methanone
compound 117: (trans)-N1-(6-bromo-3-(methylsulfonyl)quinolin-4-yl)cyclohexane-1,4-diamine
compound 118: 4-(4-((trans)-4-aminocyclohexylamino)-3-(methylsulfonyl)quinolin-6-yl)-2-methoxyphenol
compound 119: 5-(4-((trans)-4-aminocyclohexylamino)-3-(cyclopropanecarbonyl)quinolin-6-yl)thiophene-2-carbonitrile
compound 120: ethyl 6-bromo-4-(piperidin-3-ylmethylamino)quinoline-3-carboxylate
compound 121: ethyl 4-((trans)-4-aminocyclohexylamino)-6-(4-hydroxyphenyl)quinoline-3-carboxylate
compound 122: 4-(3-(dimethylamino)propylamino)-6-(4-hydroxyphenyl)-N-(2-(piperazin-1-yl)ethyl)quinoline-3-carboxamide
compound 123: 4-(3-(dimethylamino)propylamino)-6-(4-hydroxyphenyl)-N-((1-methylpiperidin-4-yl)methyl)quinoline-3-carboxamide
compound 124: (4-((trans)-4-aminocyclohexylamino)-6-(3-chloro-4-hydroxyphenyl)quinolin-3-yl)(cyclopropyl)methanone
compound 125: 5-(4-((trans)-4-aminocyclohexylamino)-3-(methylsulfonyl)quinolin-6-yl)picolinamide
compound 126: (4-((trans)-4-aminocyclohexylamino)-6-(3-chloro-4-hydroxy-5-methoxyphenyl)quinolin-3-yl)(cyclopropyl)methanone
compound 127: ethyl 6-bromo-4-(3-(2-hydroxyethylamino)propylamino)quinoline-3-carboxylate
compound 128: ethyl 4-(3-aminocyclohexylamino)-6-bromoquinoline-3-carboxylate
compound 129: ethyl 4-(3-acetamido-2-methylpropylamino)-6-bromoquinoline-3-carboxylate
compound 130: ethyl 6-bromo-4-(3-carbamoylpiperidin-1-yl)quinoline-3-carboxylate
compound 131: ethyl 6-bromo-4-(4-carbamoylpiperidin-1-yl)quinoline-3-carboxylate
compound 132: 5-(4-((trans)-4-aminocyclohexylamino)-3-(cyclopropanecarbonyl)quinolin-6-yl)pyridin-2(1H)-one
compound 133: cyclopropyl(4-(4-((dimethylamino)methyl)piperidin-1-yl)-6-(4-hydroxy-3-methoxyphenyl)quinolin-3-yl)methanone
compound 134: N-(2-(1H-imidazol-5-yl)ethyl)-4-(3-(dimethylamino)propylamino)-6-(4-hydroxyphenyl)quinoline-3-carboxamide
compound 135: N-((trans)-4-aminocyclohexyl)-4-(3-(dimethylamino)propylamino)-6-(4-hydroxyphenyl)quinoline-3-carboxamide
compound 136: 5-(3-(cyclopropanecarbonyl)-4-(4-((dimethylamino)methyl)piperidin-1-yl)quinolin-6-yl)pyrimidine-2-carbonitrile
compound 137: (6-bromo-4-(4-((dimethylamino)methyl)piperidin-1-yl)quinolin-3-yl)(cyclopropyl)methanone
compound 138: ethyl 4-(4-aminopiperidin-1-yl)-6-bromoquinoline-3-carboxylate
compound 139: ethyl 6-bromo-4-(3-((dimethylamino)methyl)piperidin-1-yl)quinoline-3-carboxylate
compound 140: ethyl 6-bromo-4-(2,8-diazaspiro[4.5]decan-8-yl)quinoline-3-carboxylate
compound 141: ethyl 6-(4-hydroxyphenyl)-4-(piperidin-3-ylmethylamino)quinoline-3-carboxylate
compound 142: ethyl 6-bromo-4-hydroxyquinoline-3-carboxylate
compound 143: (4-((trans)-4-aminocyclohexylamino)-6-(3,5-dimethylisoxazol-4-yl)quinolin-3-yl)(cyclopropyl)methanone
compound 144: (4-((trans)-4-aminocyclohexylamino)-6-(1H-pyrrol-3-yl)quinolin-3-yl)(cyclopropyl)methanone
compound 145: ethyl 4-(4-(aminomethyl)piperidin-1-yl)-6-bromoquinoline-3-carboxylate
compound 146: ethyl 4-((trans)-4-aminocyclohexylamino)-6-morpholinoquinoline-3-carboxylate
compound 147: (4-((trans)-4-aminocyclohexylamino)-6-(4-(aminomethyl)phenyl)quinolin-3-yl)(cyclopropyl)methanone
compound 148: (6-([1,2,4]triazolo[1,5-a]pyridin-6-yl)-4-((trans)-4-aminocyclohexylamino)quinolin-3-yl)(cyclopropyl)methanone
compound 149: ethyl 6-bromo-4-(pyridin-4-ylmethylamino)quinoline-3-carboxylate
compound 150: ethyl 4-(4-aminobenzylamino)-6-bromoquinoline-3-carboxylate compound 151: ethyl 6-bromo-4-(quinuclidin-3-ylamino)quinoline-3-carboxylate compound 152: ethyl 6-bromo-4-(pyrrolidin-3-ylmethylamino)quinoline-3-carboxylate compound 153: ethyl 4-(azetidin-3-ylmethylamino)-6-bromoquinoline-3-carboxylate compound 154: ethyl 6-bromo-4-(4-((methylamino)methyl)piperidin-1-yl)quinoline-3-carboxylate compound 155: (6-(3-chloro-4-hydroxy-5-methoxyphenyl)-4-(2,8-diazaspiro[4.5]decan-8-yl)quinolin-3-yl)(cyclopropyl)methanone compound 156: (4-((trans)-4-aminocyclohexylamino)-6-(3,5-difluoro-4-hydroxyphenyl)quinolin-3-yl)(cyclopropyl)methanone compound 157(a): (4-((trans)-4-aminocyclohexylamino)-6-(3,5-dichloro-4-hydroxyphenyl)quinolin-3-yl)(cyclopropyl)methanone hydrochloride compound 157(b): (4-((trans)-4-aminocyclohexylamino)-6-(3,5-dichloro-4-hydroxyphenyl)quinolin-3-yl)(cyclopropyl)methanone dihydrochloride compound 158: (4-((trans)-4-aminocyclohexylamino)-6-(3-fluoro-4-hydroxyphenyl)quinolin-3-yl)(cyclopropyl)methanone compound 159: 5-(4-((trans)-4-aminocyclohexylamino)-3-(cyclopropanecarbonyl)quinolin-6-yl)-2-hydroxybenzonitrile compound 160: (4-((trans)-4-aminocyclohexylamino)-6-(2,5-dichloro-4-hydroxyphenyl)quinolin-3-yl)(cyclopropyl)methanone compound 161 (4-((trans)-4-aminocyclohexylamino)-6-(4-hydroxy-3,5-dimethylphenyl)quinolin-3-yl)(cyclopropyl)methanone compound 162: (6-(1H-benzo[d]imidazol-5-yl)-4-(2,8-diazaspiro[4.5]decan-8-yl)quinolin-3-yl)(cyclopropyl)methanone compound 163: (4-((cis)-4-aminocyclohexylamino)-6-(3-chloro-4-hydroxy-5-methoxyphenyl)quinolin-3-yl)(cyclopropyl)methanone compound 164: 5-(4-((cis)-4-aminocyclohexylamino)-3-(cyclopropanecarbonyl)quinolin-6-yl) pyrimidine-2-carbonitrile compound 165: (4-((cis)-4-aminocyclohexylamino)-6-(4-hydroxy-3-methoxyphenyl)quinolin-3-yl)(cyclopropyl)methanone compound 166: (4-((cis)-4-aminocyclohexylamino)-6-(1H-benzo[d]imidazol-5-yl)quinolin-3-yl)(cyclopropyl)methanone compound 167: ethyl 6-bromo-4-(dimethylamino)quinoline-3-carboxylate compound 168: ethyl 6-bromo-4-(ethylamino)quinoline-3-carboxylate compound 169: (4-((trans)-4-aminocyclohexylamino)-6-(3-chloro-4-methoxyphenyl)quinolin-3-yl)(cyclopropyl)methanone compound 170: 5-(3-(cyclopropanecarbonyl)-4-(1-methylpiperidin-4-ylamino)quinolin-6-yl)pyrimidine-2-carbonitrile compound 171: ethyl 6-bromo-4-(4-((dimethylamino)methyl)phenylamino)quinoline-3-carboxylate compound 172: 5-(4-((trans)-4-aminocyclohexylamino)-3-(cyclopropanecarbonyl)quinolin-6-yl)-3-methylpicolinonitrile compound 173: ethyl 6-(3-chloro-4-hydroxy-5-methoxyphenyl)-4-(dimethylamino)quinoline-3-carboxylate compound 174: cyclopropyl(6-(3,5-difluoro-4-hydroxyphenyl)-4-(1-methylpiperidin-4-ylamino)quinolin-3-yl)methanone compound 175: cyclopropyl(6-(3,5-dichloro-4-hydroxyphenyl)-4-(1-methylpiperidin-4-ylamino)quinolin-3-yl)methanone compound 176: (6-(3-chloro-4-hydroxyphenyl)-4-(1-methylpiperidin-4-ylamino)quinolin-3-yl)(cyclopropyl)methanone compound 177: cyclopropyl(6-(4-hydroxy-3-methoxyphenyl)-4-(1-methylpiperidin-4-ylamino)quinolin-3-yl)methanone compound 178: 5-(4-((trans)-4-aminocyclohexylamino)-3-(cyclopropanecarbonyl)quinolin-6-yl)-1H-benzo[d]imidazol-2(3H)-one compound 179: (4-((trans)-4-aminocyclohexylamino)-6-(3-chloro-5-fluoro-4-hydroxyphenyl)quinolin-3-yl)(cyclopropyl)methanone compound 180: (4-((cis)-4-aminocyclohexylamino)-6-(3,5-difluoro-4-hydroxyphenyl)quinolin-3-yl)(cyclopropyl)methanone compound 181: cyclopropyl(6-(3,5-difluoro-4-hydroxyphenyl)-4-(4-(1-(dimethylamino)ethyl)piperidin-1-yl)quinolin-3-yl)methanone compound 182: 4-(4-((trans)-4-aminocyclohexylamino)-3-(cyclopropanecarbonyl)quinolin-6-yl)-1H-pyrrole-2-carbonitrile compound 183: (4-((trans)-4-aminocyclohexylamino)-6-(1H-pyrrolo[2,3-b]pyridin-5-yl)quinolin-3-yl)(cyclopropyl)methanone compound 184: ethyl 6-(3-chloro-4-hydroxy-5-methoxyphenyl)-4-(ethylamino)quinoline-3-carboxylate compound 185(a): (6-(3-chloro-4-hydroxy-5-methoxyphenyl)-4-(4-(diethylamino)cyclohexylamino)quinolin-3-yl)(cyclopropyl)methanone hydrochloride compound 185(b): (6-(3-chloro-4-hydroxy-5-methoxyphenyl)-4-(4-(diethylamino)cyclohexylamino)quinolin-3-yl)(cyclopropyl)methanone dihydrochloride compound 186: 5-(3-(cyclopropanecarbonyl)-4-(4-(diethylamino)cyclohexylamino)quinolin-6-yl)pyrimidine-2-carbonitrile compound 187: cyclopropyl(4-(4-(1-(dimethylamino)ethyl)piperidin-1-yl)-6-(4-hydroxy-3-methoxyphenyl)quinolin-3-yl)methanone compound 188: (4-((trans)-4-aminocyclohexylamino)-6-(4-(hydroxymethyl)phenyl)quinolin-3-yl)(cyclopropyl)methanone compound 189: (4-((trans)-4-aminocyclohexylamino)-6-(2,5-difluoro-4-hydroxyphenyl)quinolin-3-yl)(cyclopropyl)methanone compound 190: (4-((trans)-4-aminocyclohexylamino)-6-(2,3-difluoro-4-hydroxyphenyl)quinolin-3-yl)(cyclopropyl)methanone compound 191: 4-(4-((trans)-4-aminocyclohexylamino)-3-(methylsulfonyl)quinolin-6-yl)-2-chloro-6-fluorophenol compound 192: (6-(3-chloro-4-hydroxyphenyl)-4-(4-(diethylamino)cyclohexylamino)quinolin-3-yl)(cyclopropyl)methanone compound 193: cyclopropyl(4-(4-(diethylamino)cyclohexylamino)-6-(4-hydroxy-3-methoxyphenyl)quinolin-3-yl)methanone compound 194: cyclopropyl(4-(4-(diethylamino)cyclohexylamino)-6-(3,5-difluoro-4-hydroxyphenyl)quinolin-3-yl)methanone compound 195: 4-(4-((trans)-4-aminocyclohexylamino)-3-(methylsulfonyl)quinolin-6-yl)-2-chlorophenol compound 196: cyclopropyl(6-(4-hydroxy-3-methoxyphenyl)-4-((1-methylpiperidin-4-yl)methylamino)quinolin-3-yl)methanone compound 197: (4-((trans)-4-aminocyclohexylamino)-6-(3-chloro-4-hydroxy-5-methylphenyl)quinolin-3-yl)(cyclopropyl)methanone
compound 198: (4-((trans)-4-aminocyclohexylamino)-6-(4-hydroxycyclohex-1-enyl)quinolin-3-yl)(cyclopropyl)methanone
compound 199: (6-(1H-benzo[d]imidazol-5-yl)-4-(4-(diethylamino)cyclohexylamino)quinolin-3-yl)(cyclopropyl)methanone
compound 200: 5-(3-(cyclopropanecarbonyl)-4-((1-methylpiperidin-4-yl)methylamino)quinolin-6-yl) pyrimidine-2-carbonitrile
compound 201: (6-(3-chloro-4-hydroxy-5-methoxyphenyl)-4-((1-methylpiperidin-4-yl)methylamino)quinolin-3-yl)(cyclopropyl)methanone
compound 202: (6-(1H-benzo[d]imidazol-5-yl)-4-((1-methylpiperidin-4-yl)methylamino)quinolin-3-yl)(cyclopropyl)methanone
compound 203: (6-(3-chloro-4-hydroxyphenyl)-4-((1-methylpiperidin-4-yl)methylamino)quinolin-3-yl)(cyclopropyl)methanone
compound 204: cyclopropyl(6-(3,5-difluoro-4-hydroxyphenyl)-4-((1-methylpiperidin-4-yl)methylamino)quinolin-3-yl)methanone
compound 205: 1-(4-((trans)-4-aminocyclohexylamino)-6-(3-chloro-5-fluoro-4-hydroxyphenyl)quinolin-3-yl)-2-methylpropan-1-one
compound 206: (4-((trans)-4-aminocyclohexylamino)-6-(1,2,3,6-tetrahydropyridin-4-yl)quinolin-3-yl)(cyclopropyl)methanone
compound 207: 4-(4-((trans)-4-aminocyclohexylamino)-3-(methylsulfonyl)quinolin-6-yl)-2,6-difluorophenol
compound 208: Cyclopropyl(6-(3,5-difluoro-4-hydroxyphenyl)-4-(2-(piperazin-1-yl)ethylamino)quinolin-3-yl)methanone
compound 209: (4-((cis)-4-aminocyclohexylamino)-6-(2-chlorophenyl)quinolin-3-yl)(cyclopropyl)methanone
compound 210: (6-(3-chloro-4-hydroxy-5-methoxyphenyl)-4-(2-(piperazin-1-yl)ethylamino)quinolin-3-yl)(cyclopropyl)methanone
compound 211: (6-(3-chloro-4-hydroxy-5-methoxyphenyl)-4-(dimethylamino)quinolin-3-yl)(cyclopropyl)methanone
compound 212: (4-((trans)-4-aminocyclohexylamino)-6-(pyridin-4-yl)quinolin-3-yl)(cyclopropyl)methanone
compound 213: (4-((trans)-4-aminocyclohexylamino)-6-(1H-pyrazol-4-yl)quinolin-3-yl)(cyclopropyl)methanone
compound 214: 1-(4-((trans)-4-aminocyclohexylamino)-6-(3,5-difluoro-4-hydroxyphenyl)quinolin-3-yl)-2-methylpropan-1-one
compound 215: (6-(3-chloro-4-hydroxyphenyl)-4-(2-(piperazin-1-yl)ethylamino)quinolin-3-yl)(cyclopropyl)methanone
compound 216: cyclopropyl(6-(4-hydroxy-3-methoxyphenyl)-4-(2-(piperazin-1-yl)ethylamino)quinolin-3-yl)methanone
compound 217: (6-(3-chloro-4-hydroxyphenyl)-4-(dimethylamino)quinolin-3-yl)(cyclopropyl)methanone
compound 218: cyclopropyl(4-(dimethylamino)-6-(4-hydroxy-3-methoxyphenyl)quinolin-3-yl)methanone
compound 219: 1-(4-((trans)-4-aminocyclohexylamino)-6-(3-chloro-4-hydroxyphenyl)quinolin-3-yl)-2-methylpropan-1-one
compound 220: 5-(4-((trans)-4-aminocyclohexylamino)-3-(cyclopropanecarbonyl)quinolin-6-yl)-3-fluoropicolinonitrile
compound 221: (6-(3-chloro-4-hydroxy-5-methoxyphenyl)-4-(diethylamino)quinolin-3-yl)(cyclopropyl)methanone
compound 222: (6-(3-chloro-4-hydroxy-5-methoxyphenyl)-4-(piperidin-1-yl)quinolin-3-yl)(cyclopropyl)methanone
compound 223: 5-(3-(cyclopropanecarbonyl)-4-(diethylamino)quinolin-6-yl) pyrimidine-2-carbonitrile
compound 224: 5-(3-(cyclopropanecarbonyl)-4-(piperidin-1-yl)quinolin-6-yl)pyrimidine-2-carbonitrile
compound 225(a): 1-(4-((trans)-4-aminocyclohexylamino)-6-(3,5-dichloro-4-hydroxyphenyl)quinolin-3-yl)-2-methylpropan-1-one
compound 225(b): 1-(4-((trans)-4-aminocyclohexylamino)-6-(3,5-dichloro-4-hydroxyphenyl)quinolin-3-yl)-2-methylpropan-1-one dihydrochloride
compound 226: 4-(4-((trans)-4-aminocyclohexylamino)-3-(methylsulfonyl)quinolin-6-yl)-2,6-dichlorophenol
compound 227: 4-(4-((trans)-4-aminocyclohexylamino)-3-(methylsulfonyl)quinolin-6-yl)-2-chloro-6-methoxyphenol
compound 228: (4-((trans)-4-aminocyclohexylamino)-6-(2-methoxypyridin-4-yl)quinolin-3-yl)(cyclopropyl)methanone
compound 229: (4-((trans)-4-aminocyclohexylamino)-6-(3-methyl-1H-pyrazol-4-yl)quinolin-3-yl)(cyclopropyl)methanone
compound 230: (4-((trans)-4-aminocyclohexylamino)-6-(3,4-dimethoxyphenyl)quinolin-3-yl)(cyclopropyl)methanone
compound 231: (6-(3-chloro-4-hydroxy-5-methoxyphenyl)-4-(cyclopentylamino)quinolin-3-yl)(cyclopropyl)methanone
compound 232: (6-(3-chloro-4-hydroxy-5-methoxyphenyl)-4-(pentan-3-ylamino)quinolin-3-yl)(cyclopropyl)methanone
compound 233: (6-(3-chloro-4-hydroxyphenyl)-4-(piperidin-1-yl)quinolin-3-yl)(cyclopropyl)methanone
compound 234: (6-(3-chloro-4-hydroxyphenyl)-4-(diethylamino)quinolin-3-yl)(cyclopropyl)methanone
compound 235: N1-(6-bromo-3-(methylsulfonyl)quinolin-4-yl)-N4,N4-diethylcyclohexane-1,4-diamine
compound 236: 2-chloro-4-(4-(4-(diethylamino)cyclohexylamino)-3-(methylsulfonyl)quinolin-6-yl)phenol
compound 237: (4-((trans)-4-aminocyclohexylamino)-6-(2-chloropyridin-4-yl)quinolin-3-yl)(cyclopropyl)methanone
compound 238: 5-(3-(cyclopropanecarbonyl)-4-(pentan-3-ylamino)quinolin-6-yl)pyrimidine-2-carbonitrile
compound 239: 5-(4-(cyclopentylamino)-3-(cyclopropanecarbonyl)quinolin-6-yl)pyrimidine-2-carbonitrile
compound 240: 2-chloro-4-(4-(4-(diethylamino)cyclohexylamino)-3-(methylsulfonyl)quinolin-6-yl)-6-methoxyphenol dihydrochloride
compound 241: cyclopropyl(6-(3,5-difluoro-4-hydroxyphenyl)-4-(piperidin-4-ylmethylamino)quinolin-3-yl)methanone
compound 242: cyclopropyl(6-(4-hydroxy-3-methoxyphenyl)-4-(piperidin-4-ylmethylamino)quinolin-3-yl)methanone
compound 243: (6-(3-chloro-4-hydroxy-5-methoxyphenyl)-4-(piperidin-4-ylmethylamino)quinolin-3-yl)(cyclopropyl)methanone
compound 244: 5-(4-(4-(1-(dimethylamino)ethyl)piperidin-1-yl)-3-(methylsulfonyl)quinolin-6-yl)pyrimidine-2-carbonitrile
compound 245: 2-chloro-4-(4-(4-(1-(dimethylamino)ethyl)piperidin-1-yl)-3-(methylsulfonyl)quinolin-6-yl)-6-methoxyphenol
compound 246: 2-chloro-4-(4-(4-(1-(dimethylamino)ethyl)piperidin-1-yl)-3-(methylsulfonyl)quinolin-6-yl)phenol compound 247: 5-(4-(4-(diethylamino)cyclohexylamino)-3-(methylsulfonyl)quinolin-6-yl)pyrimidine-2-carbonitrile compound 248: 1-(1-(6-bromo-3-(methylsulfonyl)quinolin-4-yl)piperidin-4-yl)-N,N-dimethylethanamine compound 249: (6-(3-chloro-4-hydroxy-5-methoxyphenyl)-4-(1-methylpiperidin-4-ylamino)quinolin-3-yl)(cyclopropyl)methanone compound 250: (6-(3-chloro-4-hydroxy-5-methoxyphenyl)-4-(4-(1-(dimethylamino)ethyl)piperidin-1-yl)quinolin-3-yl)(cyclopropyl)methanone compound 251: 2-chloro-4-(4-(((1-methylpiperidin-4-yl)methylamino)-3-(methylsulfonyl)quinolin-6-yl)phenol compound 252: 2-chloro-6-methoxy-4-(4-(((1-methylpiperidin-4-yl)methylamino)-3-(methylsulfonyl)quinolin-6-yl)phenol compound 253: 6-bromo-N-((1-methylpiperidin-4-yl)methyl)-3-(methylsulfonyl)quinolin-4-amine compound 254: cyclopropyl(6-(3,5-difluoro-4-hydroxyphenyl)-4-((trans)-4-(dimethylamino)cyclohexylamino)quinolin-3-yl)methanone compound 255: (6-(3-chloro-4-hydroxy-5-methoxyphenyl)-4-((trans)-4-(dimethylamino)cyclohexylamino)quinolin-3-yl)(cyclopropyl)methanone compound 256: 1-(4-((trans)-4-aminocyclohexylamino)-6-(3,5-dichloro-4-hydroxyphenyl)quinolin-3-yl)ethanone compound 257: 1-(4-((trans)-4-aminocyclohexylamino)-6-bromoquinolin-3-yl)ethanone compound 258: 1-(4-((trans)-4-aminocyclohexylamino)-6-(3,5-difluoro-4-hydroxyphenyl)quinolin-3-yl)ethanone compound 259: 1-(4-((trans)-4-aminocyclohexylamino)-6-(3-chloro-4-hydroxy-5-methoxyphenyl)quinolin-3-yl)ethanone compound 260: 1-(4-((trans)-4-aminocyclohexylamino)-6-bromoquinolin-3-yl)-3-methylbutan-1-one compound 261: 1-(4-((trans)-4-aminocyclohexylamino)-6-(3,5-difluoro-4-hydroxyphenyl)quinolin-3-yl)-3-methylbutan-1-one compound 262: 1-(4-((trans)-4-aminocyclohexylamino)-6-(3-chloro-4-hydroxy-5-methoxyphenyl)quinolin-3-yl)-3-methylbutan-1-one compound 263: cyclopropyl(6-(3,5-dichloro-4-hydroxyphenyl)-4-((trans)-4-(dimethylamino)cyclohexylamino)quinolin-3-yl)methanone compound 264: (6-(3-chloro-5-fluoro-4-hydroxyphenyl)-4-((trans)-4-(dimethylamino)cyclohexylamino)quinolin-3-yl)(cyclopropyl)methanone compound 265: (6-(3-chloro-4-hydroxyphenyl)-4-((trans)-4-(dimethylamino)cyclohexylamino)quinolin-3-yl)(cyclopropyl)methanone compound 266: cyclopropyl(4-((trans)-4-(dimethylamino)cyclohexylamino)-6-(4-hydroxy-3-methoxyphenyl)quinolin-3-yl)methanone compound 267: 1-(4-((trans)-4-aminocyclohexylamino)-6-(3,5-dichloro-4-hydroxyphenyl)quinolin-3-yl)-3-methylbutan-1-one dihydrochloride compound 268: 5-(3-(cyclopropanecarbonyl)-4-((trans)-4-(dimethylamino)cyclohexylamino)quinolin-6-yl)pyrimidine-2-carbonitrile compound 269: (6-(3-chloro-5-fluoro-4-hydroxyphenyl)-4-(4-(1-(dimethylamino)ethyl)piperidin-1-yl)quinolin-3-yl)(cyclopropyl)methanone compound 270: (6-(3-chloro-5-fluoro-4-hydroxyphenyl)-4-((1-methylpiperidin-4-yl)methylamino)quinolin-3-yl)(cyclopropyl)methanone compound 271: (6-(3-chloro-5-fluoro-4-hydroxyphenyl)-4-(1-methylpiperidin-4-ylamino)quinolin-3-yl)(cyclopropyl)methanone compound 272: 1-(1-(6-bromo-3-(isopropylsulfonyl)quinolin-4-yl)piperidin-4-yl)-N,N-dimethylethanamine compound 273: (4-((trans)-4-aminocyclohexylamino)-6-(2-fluoropyridin-4-yl)quinolin-3-yl)(cyclopropyl)methanone compound 274: 2-chloro-4-(4-(4-(1-(dimethylamino)ethyl)piperidin-1-yl)-3-(isopropylsulfonyl)quinolin-6-yl)-6-methoxyphenol compound 275: 2-chloro-4-(4-(4-(1-(dimethylamino)ethyl)piperidin-1-yl)-3-(isopropylsulfonyl)quinolin-6-yl)phenol compound 276: (6-(3-chloro-4-hydroxy-5-methoxyphenyl)-4-(4-((dimethylamino)methyl)piperidin-1-yl)quinolin-3-yl)(cyclopropyl)methanone compound 277: (6-bromo-4-(4-(pyrrolidin-1-ylmethyl)piperidin-1-yl)quinolin-3-yl)(cyclopropyl)methanone compound 278: cyclopropyl(4-((trans)-4-(dimethylamino)cyclohexylamino)-7-fluoro-6-(4-hydroxy-3-methoxyphenyl)quinolin-3-yl)methanone compound 279: (6-(3-chloro-4-hydroxyphenyl)-4-(4-((dimethylamino)methyl)piperidin-1-yl)quinolin-3-yl)(cyclopropyl)methanone compound 280: (6-(3-chloro-4-hydroxy-5-methoxyphenyl)-4-(4-(pyrrolidin-1-ylmethyl)piperidin-1-yl)quinolin-3-yl)(cyclopropyl)methanone compound 281: (6-(3-chloro-4-hydroxyphenyl)-4-(4-(pyrrolidin-1-ylmethyl)piperidin-1-yl)quinolin-3-yl)(cyclopropyl)methanone compound 282: 5-(3-(cyclopropanecarbonyl)-4-(4-(pyrrolidin-1-ylmethyl)piperidin-1-yl)quinolin-6-yl)pyrimidine-2-carbonitrile compound 283: (6-(3-chloro-5-fluoro-4-hydroxyphenyl)-4-(4-(pyrrolidin-1-ylmethyl)piperidin-1-yl)quinolin-3-yl)(cyclopropyl)methanone compound 284: (4-((trans)-4-aminocyclohexylamino)-6-(3-chloro-4-hydroxy-5-methoxyphenyl)-7-fluoroquinolin-3-yl)(cyclopropyl)methanone compound 285: (4-((trans)-4-aminocyclohexylamino)-6-(3,5-difluoro-4-hydroxyphenyl)-7-fluoroquinolin-3-yl)(cyclopropyl)methanone compound 286: (4-((trans)-4-aminocyclohexylamino)-7-fluoro-6-(4-hydroxy-3-methoxyphenyl)quinolin-3-yl)(cyclopropyl)methanone compound 287: (4-((trans)-4-aminocyclohexylamino)-6-(3-chloro-5-fluoro-4-hydroxyphenyl)-7-fluoroquinolin-3-yl)(cyclopropyl)methanone compound 288: (4-((trans)-4-aminocyclohexylamino)-6-(2-chloro-3-fluoropyridin-4-yl)quinolin-3-yl)(cyclopropyl)methanone compound 289: (6-(3-chloro-4-hydroxy-5-methoxyphenyl)-4-((trans)-4-(dimethylamino)cyclohexylamino)-7-fluoroquinolin-3-yl)(cyclopropyl)methanone compound 290: 5-(3-(cyclopropanecarbonyl)-4-((trans)-4-(dimethylamino)cyclohexylamino)-7-fluoroquinolin-6-yl)pyrimidine-2-carbonitrile compound 291: (6-(3-chloro-4-hydroxy-5-methoxyphenyl)-4-(3-(dimethylamino)propylamino)quinolin-3-yl)(cyclopropyl)methanone compound 292: 5-(3-(cyclopropanecarbonyl)-4-(3-(dimethylamino)propylamino)quinolin-6-yl)pyrimidine-2-carbonitrile compound 293: (6-(3-chloro-5-fluoro-4-hydroxyphenyl)-4-(3-(dimethylamino)propylamino)quinolin-3-yl)(cyclopropyl)methanone compound 294: cyclopropyl(6-(3,5-difluoro-4-hydroxyphenyl)-4-((trans)-4-(dimethylamino)cyclohexylamino)-7-fluoroquinolin-3-yl)methanone compound 295: (6-(3-chloro-5-fluoro-4-hydroxyphenyl)-4-((trans)-4-(dimethylamino)cyclohexylamino)-7-fluoroquinolin-3-yl)(cyclopropyl)methanone compound 296: 1-(6-(3-chloro-4-hydroxy-5-methoxyphenyl)-4-((trans)-4-(dimethylamino)cyclohexylamino)quinolin-3-yl)-2-methylpropan-1-one compound 297: 1-(4-(((trans)-4-(dimethylamino)cyclohexylamino)-6-(3-fluoro-4-hydroxy-5-methoxyphenyl)quinolin-3-yl)-2-methylpropan-1-one compound 298: (6-(3-chloro-4-hydroxy-5-methoxyphenyl)-4-(4-(1-(dimethylamino)ethyl)piperidin-1-yl)-7-fluoroquinolin-3-yl)(cyclopropyl)methanone compound 299: cyclopropyl(4-(4-(1-(dimethylamino)ethyl)piperidin-1-yl)-7-fluoro-6-(4-hydroxy-3-methoxyphenyl)quinolin-3-yl) methanone compound 300: (6-(3-chloro-5-fluoro-4-hydroxyphenyl)-4-(4-(1-(dimethylamino)ethyl)piperidin-1-yl)-7-fluoroquinolin-3-yl)(cyclopropyl)methanone compound 301: cyclopropyl(6-(3,5-dichloro-4-hydroxyphenyl)-4-(4-(1-(dimethylamino)ethyl)piperidin-1-yl)-7-fluoroquinolin-3-yl)methanone compound 302: 1-(6-(3-chloro-4-hydroxy-5-methoxyphenyl)-4-(4-((dimethylamino)methyl)piperidin-1-yl)quinolin-3-yl)-2-methylpropan-1-one compound 303: 1-(6-(3-chloro-4-hydroxy-5-methoxyphenyl)-4-(4-(diethylamino)cyclohexylamino)quinolin-3-yl)ethanone compound 304: (6-(3-chloro-5-fluoro-4-hydroxyphenyl)-4-(piperidin-4-ylmethylamino)quinolin-3-yl)(cyclopropyl)methanone compound 305: 1-(6-(3-chloro-4-hydroxy-5-methoxyphenyl)-4-(4-((dimethylamino)methyl)piperidin-1-yl)quinolin-3-yl)ethanone compound 306: 1-(4-((trans)-4-(dimethylamino)cyclohexylamino)-6-(4-hydroxy-3-(trifluoromethoxy)phenyl)quinolin-3-yl)-2-methylpropan-1-one compound 307: cyclopropyl(6-(3-fluoro-4-hydroxy-5-methoxyphenyl)-4-(4-(pyrrolidin-1-ylmethyl)piperidin-1-yl)quinolin-3-yl)methanone compound 308: {6-(3-Chloro-5-fluoro-4-hydroxyphenyl)-4-[(3-amino)adamantylamino]quinolin-3-yl}(cyclopropyl)methanone compound 309: {6-(3-Chloro-4-hydroxy-5-methoxyphenyl)-4-[(3-amino)adamantylamino]quinolin-3-yl}(cyclopropyl)methanone compound 310: cyclopropyl(6-(3,5-dichloro-4-hydroxyphenyl)-4-(piperidin-4-ylmethylamino)quinolin-3-yl)methanone compound 311: (6-(3-chloro-4-hydroxy-5-methoxyphenyl)-4-((cis)-4-(diethylamino)cyclohexylamino)quinolin-3-yl)(cyclopropyl)methanone compound 312: 1-(4-((trans)-4-aminocyclohexylamino)-6-(3,5-dichlorophenyl)quinolin-3-yl)-2-methylpropan-1-one compound 313: cyclopropyl(6-(4-hydroxy-3-(trifluoromethoxy)phenyl)-4-(4-(pyrrolidin-1-ylmethyl)piperidin-1-yl)quinolin-3-yl)methanone compound 314: (6-(3-chloro-4-hydroxy-5-methoxyphenyl)-4-((trans)-4-(diethylamino)cyclohexylamino)quinolin-3-yl)(cyclopropyl)methanone compound 315: (6-(3-chloro-4-hydroxy-5-methoxyphenyl)-4-(((trans)-4-(dimethylamino)cyclohexyl)methylamino)quinolin-3-yl)(cyclopropyl)methanone compound 316: (6-(3-chloro-4-hydroxy-5-methoxyphenyl)-4-((trans)-4-((dimethylamino)methyl)cyclohexylamino)quinolin-3-yl)(cyclopropyl)methanone compound 317: 1-(4-((trans)-4-(dimethylamino)cyclohexylamino)-6-(3-ethoxy-4-hydroxyphenyl)quinolin-3-yl)-2-methylpropan-1-one compound 318: 1-(6-(3-chloro-4-hydroxyphenyl)-4-(4-(pyrrolidin-1-ylmethyl)piperidin-1-yl)quinolin-3-yl)-2-methylpropan-1-one compound 319: 1-(6-(3-chloro-4-hydroxy-5-methoxyphenyl)-4-(4-(pyrrolidin-1-ylmethyl)piperidin-1-yl)quinolin-3-yl)-2-methylpropan-1-one compound 320: 1-(6-(3-chloro-4-hydroxyphenyl)-4-(4-(pyrrolidin-1-ylmethyl)piperidin-1-yl)quinolin-3-yl)ethanone compound 321: 1-(6-(3-chloro-4-hydroxy-5-methoxyphenyl)-4-(4-(pyrrolidin-1-ylmethyl)piperidin-1-yl)quinolin-3-yl)ethanone compound 322: 1-(6-(3-chloro-5-fluoro-4-hydroxyphenyl)-4-((trans)-4-(dimethylamino)cyclohexylamino)quinolin-3-yl)-2-methylpropan-1-one compound 323: 1-(6-(3-chloro-5-fluoro-4-hydroxyphenyl)-4-(4-(pyrrolidin-1-ylmethyl)piperidin-1-yl)quinolin-3-yl)-2-methylpropan-1-one compound 324: cyclopropyl(6-(3,5-dichloro-4-hydroxyphenyl)-4-((trans)-4-((dimethylamino)methyl)cyclohexylamino)quinolin-3-yl)methanone compound 325: cyclopropyl(6-(3,5-dichloro-4-hydroxyphenyl)-4-(((trans)-4-(dimethylamino)cyclohexyl)methylamino)quinolin-3-yl)methanone compound 326: (6-(3-chloro-5-fluoro-4-hydroxyphenyl)-4-((trans)-4-((dimethylamino)methyl)cyclohexylamino)quinolin-3-yl)(cyclopropyl)methanone compound 327: (6-(3-chloro-5-fluoro-4-hydroxyphenyl)-4-(((trans)-4-(dimethylamino)cyclohexyl)methylamino)quinolin-3-yl)(cyclopropyl)methanone compound 328: (6-(3-chloro-4-hydroxyphenyl)-4-((trans)-4-((dimethylamino)methyl)cyclohexylamino)quinolin-3-yl)(cyclopropyl)methanone compound 329: (6-(3-chloro-4-hydroxyphenyl)-4-(((trans)-4-(dimethylamino)cyclohexyl)methylamino)quinolin-3-yl)(cyclopropyl)methanone compound 330: 1-(4-(4-((trans)-4-aminocyclohexylamino)-3-isobutyrylquinolin-6-yl)phenyl)-3-benzylurea compound 331: 1-(6-(3-chloro-4-hydroxy-5-methoxyphenyl)-4-(4-((dimethylamino)methyl)piperidin-1-yl)quinolin-3-yl)-3-methyl butan-1-one compound 332: (6-(3-chloro-4-hydroxyphenyl)-4-(4-(morpholinomethyl)piperidin-1-yl)quinolin-3-yl)(cyclopropyl)methanone compound 333: 1-(4-(4-((trans)-4-aminocyclohexylamino)-3-isobutyrylquinolin-6-yl)phenyl)-3-methylurea compound 334: (6-(3-chloro-4-hydroxy-5-methoxyphenyl)-4-(4-(morpholinomethyl)piperidin-1-yl)quinolin-3-yl)(cyclopropyl)methanone compound 335: 1-(6-(3-chloro-4-hydroxyphenyl)-4-(4-(diethylamino)cyclohexylamino)quinolin-3-yl)ethanone compound 336: 1-(6-(3-chloro-5-fluoro-4-hydroxyphenyl)-4-(4-(pyrrolidin-1-ylmethyl)piperidin-1-yl)quinolin-3-yl)ethanone compound 337: (6-(3-chloro-5-fluoro-4-hydroxyphenyl)-4-(4-(morpholinomethyl)piperidin-1-yl)quinolin-3-yl)(cyclopropyl)methanone compound 338: (6-(3-chloro-4-hydroxyphenyl)-4-(4-((dimethylamino)methyl)phenylamino)quinolin-3-yl)(cyclopropyl)methanone compound 339: (6-(3-chloro-4-hydroxy-5-methoxyphenyl)-4-((dimethylamino)methyl)phenylamino)quinolin-3-yl)(cyclopropyl)methanone compound 340: cyclopropyl(4-(dimethylamino)-6-(3-(piperazin-1-yl)phenyl)quinolin-3-yl)methanone compound 341: (6-(3-chloro-5-fluoro-4-hydroxyphenyl)-4-((trans)-4-(pyrrolidin-1-yl)cyclohexylamino)quinolin-3-yl)(cyclopropyl)methanone compound 342: (6-(3-chloro-4-hydroxyphenyl)-4-((trans)-4-(pyrrolidin-1-yl)cyclohexylamino)quinolin-3-yl)(cyclopropyl)methanone compound 343: (6-(3-chloro-4-hydroxy-5-methoxyphenyl)-4-((trans)-4-(pyrrolidin-1-yl)cyclohexylamino)quinolin-3-yl)(cyclopropyl)methanone compound 344: 1-(6-(3-chloro-4-hydroxyphenyl)-4-(4-((dimethylamino)methyl)piperidin-1-yl)quinolin-3-yl)-3-methylbutan-1-one compound 345: cyclopropyl(6-(3,5-dichloro-4-hydroxyphenyl)-4-(4-((dimethylamino)methyl)phenylamino)quinolin-3-yl)methanone compound 346: (6-(3-chloro-5-fluoro-4-hydroxyphenyl)-4-(4-((dimethylamino)methyl)phenylamino)quinolin-3-yl)(cyclopropyl)methanone compound 347: (6-(3-chloro-5-fluoro-4-hydroxyphenyl)-4-(4-((dimethylamino)methyl)piperidin-1-yl)quinolin-3-yl)(cyclopropyl)methanone compound 348: 1-(6-(3-chloro-4-hydroxy-5-methoxyphenyl)-4-((trans)-4-(dimethylamino)cyclohexylamino)quinolin-3-yl)-3-methylbutan-1-one compound 349: (6-(3-chloro-5-fluoro-4-hydroxyphenyl)-4-(4-(4-methylpiperazin-1-yl)piperidin-1-yl)quinolin-3-yl)(cyclopropyl)methanone compound 350: (6-(3-chloro-4-hydroxyphenyl)-4-(4-(4-methylpiperazin-1-yl)piperidin-1-yl)quinolin-3-yl)(cyclopropyl)methanone compound 351: (6-(3-chloro-4-hydroxy-5-methoxyphenyl)-4-(4-(4-methylpiperazin-1-yl)piperidin-1-yl)quinolin-3-yl)(cyclopropyl)methanone compound 352: (4,6-bis(3-chloro-4-hydroxy-5-methoxyphenyl)quinolin-3-yl)(cyclopropyl)methanone compound 353: cyclopropyl(4-(4-((dimethylamino)methyl)piperidin-1-yl)-6-(3-ethoxy-4-hydroxyphenyl)quinolin-3-yl)methanone compound 354: 1-(6-(3-chloro-4-hydroxy-5-methoxyphenyl)-4-(4-((dimethylamino)methyl)piperidin-1-yl)quinolin-3-yl)-2,2-dimethylpropan-1-one compound 355: 1-(6-(3-chloro-5-fluoro-4-hydroxyphenyl)-4-(4-((dimethylamino)methyl)piperidin-1-yl)quinolin-3-yl)-2,2-dimethylpropan-1-one compound 356: (6-(3-chloro-4-hydroxy-5-methoxyphenyl)-4-(4-((dimethylamino)methyl)phenyl)quinolin-3-yl)(cyclopropyl)methanone compound 357: (4-(3-chloro-4-hydroxy-5-methoxyphenyl)-6-(4-((dimethylamino)methyl)phenyl)quinolin-3-yl)(cyclopropyl)methanone compound 358: 1-(6-(3-chloro-4-hydroxyphenyl)-4-(4-((dimethylamino)methyl)piperidin-1-yl)quinolin-3-yl)-2,2-dimethylpropan-1-one compound 359: cyclopropyl(4-(4-((dimethylamino)methyl)phenylamino)-6-(4-hydroxy-3-methoxyphenyl)quinolin-3-yl)methanone compound 360: 1-(6-(3-chloro-5-fluoro-4-hydroxyphenyl)-4-((trans)-4-(dimethylamino)cyclohexylamino)quinolin-3-yl)-2,2-dimethylpropan-1-one compound 361: 1-(6-(3-chloro-4-hydroxyphenyl)-4-((trans)-4-(dimethylamino)cyclohexylamino)quinolin-3-yl)-2,2-dimethylpropan-1-one compound 362: 1-(6-(3-chloro-5-fluoro-4-hydroxyphenyl)-4-(4-((dimethylamino)methyl)piperidin-1-yl)quinolin-3-yl)ethanone compound 363: 1-(6-(3-chloro-4-hydroxy-5-methoxyphenyl)-4-((trans)-4-(dimethylamino)cyclohexylamino)quinolin-3-yl)-2,2-dimethylpropan-1-one compound 364: 1-(6-(3-chloro-4-hydroxyphenyl)-4-(4-((dimethylamino)methyl)piperidin-1-yl)quinolin-3-yl)ethanone compound 365: cyclopropyl(6-(4-hydroxy-3-methoxyphenyl)-4-(4-(pyrrolidin-1-ylmethyl)phenylamino)quinolin-3-yl)methanone compound 366: cyclopropyl(6-(3,5-dichloro-4-hydroxyphenyl)-4-(4-(pyrrolidin-1-ylmethyl)phenylamino)quinolin-3-yl)methanone compound 367: (6-(3-chloro-4-hydroxyphenyl)-4-(4-(pyrrolidin-1-ylmethyl)phenylamino)quinolin-3-yl)(cyclopropyl)methanone compound 368: (6-(3-chloro-4-hydroxy-5-methoxyphenyl)-4-(4-(pyrrolidin-1-ylmethyl)phenylamino)quinolin-3-yl)(cyclopropyl)methanone compound 369: 5-(3-acetyl-4-(4-(pyrrolidin-1-ylmethyl)piperidin-1-yl)quinolin-6-yl)pyrimidine-2-carbonitrile compound 370: (6-(3-chloro-4-hydroxy-5-methoxyphenyl)-4-(4-(2-(pyrrolidin-1-yl)ethyl)piperidin-1-yl)quinolin-3-yl)(cyclopropyl)methanone compound 371: (6-(3-chloro-4-hydroxyphenyl)-4-(4-(2-(pyrrolidin-1-yl)ethyl)piperidin-1-yl)quinolin-3-yl)(cyclopropyl)methanone compound 372: (6-(3-chloro-5-fluoro-4-hydroxyphenyl)-4-(4-(2-(pyrrolidin-1-yl)ethyl)piperidin-1-yl)quinolin-3-yl)(cyclopropyl)methanone compound 373: (6-(3-chloro-4-hydroxy-5-methoxyphenyl)-4-(4-(1-methylpiperidin-4-yl)piperazin-1-yl)quinolin-3-yl)(cyclopropyl)methanone compound 374: 1-(6-(3,5-dichloro-4-hydroxyphenyl)-4-(4-((dimethylamino)methyl)phenylamino)quinolin-3-yl)ethanone compound 375: (6-(3-chloro-4-hydroxyphenyl)-4-(4-(1-methylpiperidin-4-yl)piperazin-1-yl)quinolin-3-yl)(cyclopropyl)methanone compound 376: (6-(3-chloro-5-fluoro-4-hydroxyphenyl)-4-(4-(1-methylpiperidin-4-yl)piperazin-1-yl)quinolin-3-yl)(cyclopropyl)methanone compound 377: 1-(6-(3-chloro-5-fluoro-4-hydroxyphenyl)-4-(4-((dimethylamino)methyl)phenylamino)quinolin-3-yl)ethanone compound 378: 1-(6-(3-chloro-5-fluoro-4-hydroxyphenyl)-4-((trans)-4-((dimethylamino)methyl)cyclohexylamino)quinolin-3-yl)ethanone compound 379: 1-(6-(3,5-dichloro-4-hydroxyphenyl)-4-((trans)-4-((dimethylamino)methyl)cyclohexylamino)quinolin-3-yl)ethanone compound 380: 5-(3-(cyclopropanecarbonyl)-4-(4-(pyrrolidin-1-ylmethyl)phenylamino)quinolin-6-yl) pyrimidine-2-carbonitrile compound 381: (6-(3-chloro-4-hydroxy-5-methoxyphenyl)-4-(4-(diethylamino)cyclohexylamino)quinolin-3-yl)(cyclopentyl)methanone compound 382: (6-(3-chloro-4-hydroxy-5-methoxyphenyl)-4-(4-((dimethylamino)methyl)piperidin-1-yl)quinolin-3-yl)(cyclopentyl)methanone compound 383: (6-(3-chloro-4-hydroxy-5-methoxyphenyl)-4-(4-((dimethylamino)methyl)phenylamino)quinolin-3-yl)(cyclopentyl)methanone compound 384: (6-(3-chloro-5-fluoro-4-hydroxyphenyl)-4-(4-((dimethylamino)methyl)piperidin-1-yl)quinolin-3-yl)(cyclopentyl)methanone compound 385: (6-(3-chloro-4-hydroxyphenyl)-4-(4-(diethylamino)cyclohexylamino)quinolin-3-yl)(cyclopentyl)methanone compound 386: (6-(3-chloro-5-fluoro-4-hydroxyphenyl)-4-(4-(diethylamino)cyclohexylamino)quinolin-3-yl)(cyclopentyl)methanone compound 387: (6-(3-chloro-4-hydroxyphenyl)-4-(4-((dimethylamino)methyl)phenylamino)quinolin-3-yl)(cyclopentyl)methanone compound 388: (6-(3-chloro-5-fluoro-4-hydroxyphenyl)-4-(4-((dimethylamino)methyl)phenylamino)quinolin-3-yl)(cyclopentyl)methanone compound 389: (6-(3-chloro-4-hydroxyphenyl)-4-(4-((dimethylamino)methyl)piperidin-1-yl)quinolin-3-yl)(cyclopentyl)methanone compound 390: 2-(6-(3-chloro-5-fluoro-4-hydroxyphenyl)-3-(cyclopropanecarbonyl)quinolin-4-ylamino)-1-(4-methylpiperazin-1-yl)ethanone compound 391: 1-(6-(3-chloro-4-hydroxy-5-methoxyphenyl)-4-(4-((dimethylamino)methyl)phenylamino)quinolin-3-yl)ethanone compound 392: 1-(6-(3-chloro-4-hydroxy-5-methoxyphenyl)-4-(1R,4R)-4-((dimethylamino)methyl)cyclohexylamino)quinolin-3-yl)ethanone compound 393: 2-(6-(3-chloro-4-hydroxyphenyl)-3-(cyclopropanecarbonyl)quinolin-4-ylamino)-1-(4-methylpiperazin-1-yl)ethanone compound 394: (6-(3-chloro-4-hydroxy-5-methoxyphenyl)-4-(4-(2-(pyrrolidin-1-yl)ethyl)piperazin-1-yl)quinolin-3-yl)(cyclopropyl)methanone compound 395: 2-(6-(3-chloro-4-hydroxy-5-methoxyphenyl)-3-(cyclopropanecarbonyl)quinolin-4-ylamino)-1-(4-methylpiperazin-1-yl)ethanone compound 396: (6-(3-chloro-5-fluoro-4-hydroxyphenyl)-4-(4-(pyrrolidin-1-ylmethyl)phenylamino)quinolin-3-yl)(cyclopropyl)methanone compound 397: cyclopropyl(6-(3,5-dichloro-4-hydroxyphenyl)-4-(4-((4-methylpiperazin-1-yl)methyl)phenylamino)quinolin-3-yl)methanone compound 398: (6-(3-chloro-4-hydroxy-5-methoxyphenyl)-4-(4-((4-methylpiperazin-1-yl)methyl)phenylamino)quinolin-3-yl)(cyclopropyl)methanone compound 399: 2-chloro-4-(4-(4-((dimethylamino)methyl)phenylamino)-3-(methylsulfonyl)quinolin-6-yl)-6-fluorophenol compound 400: 2,6-dichloro-4-(4-(4-((dimethylamino)methyl)phenylamino)-3-(methylsulfonyl)quinolin-6-yl)phenol compound 401: 2,6-dichloro-4-(4-(4-((dimethylamino)methyl)phenylamino)-3-(methylsulfonyl)quinolin-6-yl)phenol hydrochloride compound 402: (6-(3-chloro-5-fluoro-4-hydroxyphenyl)-4-(4-(2-(pyrrolidin-1-yl)ethyl)piperazin-1-yl)quinolin-3-yl)(cyclopropyl)methanone compound 403: (6-(3-chloro-4-hydroxyphenyl)-4-(4-(2-(pyrrolidin-1-yl)ethyl)piperazin-1-yl)quinolin-3-yl)(cyclopropyl)methanone compound 404: (6-(3-chloro-4-hydroxy-5-methoxyphenyl)-4-(5-(piperazin-1-yl)pyridin-2-ylamino)quinolin-3-yl)(cyclopropyl)methanone compound 405: cyclopropyl(6-(4-hydroxy-3-methoxyphenyl)-4-(4-((4-methylpiperazin-1-yl)methyl)phenylamino)quinolin-3-yl)methanone compound 406: (6-(3-chloro-4-hydroxyphenyl)-4-(4-((4-methylpiperazin-1-yl)methyl)phenylamino)quinolin-3-yl)(cyclopropyl)methanone compound 407: 2-chloro-6-fluoro-4-(3-(methylsulfonyl)-4-(4-(pyrrolidin-1-ylmethyl)piperidin-1-yl)quinolin-6-yl)phenol compound 408: 2-chloro-4-(3-(methylsulfonyl)-4-(4-(pyrrolidin-1-ylmethyl)piperidin-1-yl)quinolin-6-yl)phenol compound 409: cyclopropyl(6-(3,5-dichloro-4-hydroxyphenyl)-4-(5-(piperazin-1-yl)pyridin-2-ylamino)quinolin-3-yl)methanone compound 410: 2-chloro-4-(4-(4-((dimethylamino)methyl)phenylamino)-3-(methylsulfonyl)quinolin-6-yl)-6-methoxyphenol compound 411: 2-chloro-4-(4-(4-((dimethylamino)methyl)phenylamino)-3-(methylsulfonyl)quinolin-6-yl)phenol compound 412: 2-chloro-6-methoxy-4-(3-(methylsulfonyl)-4-(4-(pyrrolidin-1-ylmethyl)piperidin-1-yl)quinolin-6-yl)phenol compound 413: 5-(3-acetyl-4-(4-(pyrrolidin-1-ylmethyl)phenylamino)quinolin-6-yl)pyrimidine-2-carbonitrile compound 414: 5-(3-acetyl-4-(4-((dimethylamino)methyl)phenylamino)quinolin-6-yl)pyrimidine-2-carbonitrile compound 415: 1-(6-(3,5-dichloro-4-hydroxyphenyl)-4-(4-(pyrrolidin-1-ylmethyl)phenylamino)quinolin-3-yl)ethanone compound 416: 1-(6-(3,5-dichloro-4-hydroxyphenyl)-4-(4-(pyrrolidin-1-ylmethyl)phenylamino)quinolin-3-yl)ethanone dihydrobromide compound 417: cyclopropyl(6-(3,5-dichloro-4-hydroxyphenyl)-4-(5-((dimethylamino)methyl)pyridin-2-ylamino)quinolin-3-yl)methanone compound 418: 5-(3-acetyl-4-(1R,4R)-4-((dimethylamino)methyl)cyclohexylamino)quinolin-6-yl)pyrimidine-2-carbonitrile compound 419: 1-(6-(3-chloro-4-hydroxy-5-methoxyphenyl)-4-(4-(pyrrolidin-1-ylmethyl)phenylamino)quinolin-3-yl)ethanone compound 420: 2,6-dichloro-4-(4-(1R,4R)-4-((dimethylamino)methyl)cyclohexylamino)-3-(methylsulfonyl)quinolin-6-yl)phenol compound 421: 2,6-dichloro-4-(4-((1R,4R)-4-((dimethylamino)methyl)cyclohexylamino)-3-(methylsulfonyl)quinolin-6-yl)phenol compound 422: 2-chloro-4-(4-(1R,4R)-4-((dimethylamino)methyl)cyclohexylamino)-3-(methylsulfonyl)quinolin-6-yl)-6-methoxyphenol compound 423: 2-chloro-4-(4-(1R,4R)-4-((dimethylamino)methyl)cyclohexylamino)-3-(methylsulfonyl)quinolin-6-yl)-6-fluorophenol compound 424: 2-chloro-4-(4-(1R,4R)-4-((dimethylamino)methyl)cyclohexylamino)-3-(methylsulfonyl)quinolin-6-yl)phenol compound 425: (6-(3-chloro-5-fluoro-4-hydroxyphenyl)-4-(6-(piperazin-1-yl)pyridin-3-ylamino)quinolin-3-yl)(cyclopropyl)methanone compound 426: 5-(3-(cyclopropanecarbonyl)-4-(1R,4R)-4-((dimethylamino)methyl)cyclohexylamino)quinolin-6-yl)pyrimidine-2-carbonitrile compound 427: (6-(3-chloro-4-hydroxyphenyl)-4-(5-(piperazin-1-yl)pyridin-2-ylamino)quinolin-3-yl)(cyclopropyl)methanone compound 428: 6-(3-chloro-4-hydroxy-5-methoxyphenyl)-4-(4-(pyrrolidin-1-ylmethyl)piperidin-1-yl)quinoline-3-carbonitrile compound 429: (6-(3-chloro-4-hydroxy-5-methoxyphenyl)-4-(5-((dimethylamino)methyl)pyridin-2-ylamino)quinolin-3-yl)(cyclopropyl)methanone compound 430: cyclopropyl(6-(3,5-dichloro-4-hydroxyphenyl)-4-(4-(4-methylpiperazin-1-yl)phenyl)quinolin-3-yl)methanone
compound 431: cyclopropyl(6-(3,5-dichloro-4-hydroxyphenyl)-4-(4-((dimethylamino)methyl)phenyl)quinolin-3-yl)methanone
compound 432: 6-(3-chloro-5-fluoro-4-hydroxyphenyl)-4-(4-((dimethylamino)methyl)phenylamino)quinoline-3-carbonitrile
compound 433: 6-(3-chloro-4-hydroxyphenyl)-4-(4-(pyrrolidin-1-ylmethyl)piperidin-1-yl)quinoline-3-carbonitrile
compound 434: 6-(3-chloro-5-fluoro-4-hydroxyphenyl)-4-(4-(pyrrolidin-1-ylmethyl)piperidin-1-yl)quinoline-3-carbonitrile
compound 435: (6-(3-chloro-5-fluoro-4-hydroxyphenyl)-4-(5-((dimethylamino)methyl)pyridin-2-ylamino)quinolin-3-yl)(cyclopropyl)methanone
compound 436: (6-(3-chloro-4-hydroxy-5-methoxyphenyl)-4-(4-(pyrrolidin-1-ylmethyl)phenyl)quinolin-3-yl)(cyclopropyl)methanone
compound 437: 1-(4-(6-(3-chloro-4-hydroxy-5-methoxyphenyl)-3-(cyclopropanecarbonyl)quinolin-4-yl)piperazin-1-yl)-2-(dimethylamino)ethanone
compound 438: (6-(3-chloro-4-hydroxy-5-methoxyphenyl)-4-(4-(4-methylpiperazin-1-yl)phenyl)quinolin-3-yl)(cyclopropyl)methanone
compound 439: 5-(3-(cyclopropanecarbonyl)-4-(5-((dimethylamino)methyl)pyridin-2-ylamino)quinolin-6-yl)pyrimidine-2-carbonitrile
compound 440: 4-(6-(3-chloro-5-fluoro-4-hydroxyphenyl)-3-(cyclopropanecarbonyl)quinolin-4-yl)-1-(2-(pyrrolidin-1-yl)ethyl)piperazin-2-one
compound 441: 1-(4-(6-(3-chloro-4-hydroxyphenyl)-3-(cyclopropanecarbonyl)quinolin-4-yl)piperazin-1-yl)-2-(dimethylamino)ethanone
compound 442: 1-(4-(6-(3-chloro-5-fluoro-4-hydroxyphenyl)-3-(cyclopropanecarbonyl)quinolin-4-yl)piperazin-1-yl)-2-(dimethylamino)ethanone
compound 443: (6-(3-chloro-5-fluoro-4-hydroxyphenyl)-4-(5-(1-methylpyrrolidin-2-yl)pyridin-2-ylamino)quinolin-3-yl)(cyclopropyl)methanone
compound 444: (6-(3-chloro-4-hydroxy-5-methoxyphenyl)-4-(5-(1-methylpyrrolidin-2-yl)pyridin-2-ylamino)quinolin-3-yl)(cyclopropyl)methanone
compound 445: cyclopropyl(6-(3,5-dichloro-4-hydroxyphenyl)-4-(5-(1-methylpyrrolidin-2-yl)pyridin-2-ylamino)quinolin-3-yl)methanone
compound 446: 6-(3-chloro-5-fluoro-4-hydroxyphenyl)-4-(1R,4R)-4-(dimethylamino)cyclohexylamino)quinoline-3-carbonitrile
compound 447: 6-(3-chloro-4-hydroxy-5-methoxyphenyl)-4-(1R,4R)-4-(dimethylamino)cyclohexylamino)quinoline-3-carbonitrile
compound 448: (6-(5-chloro-4-hydroxy-2-methylphenyl)-4-(4-((dimethylamino)methyl)piperidin-1-yl)quinolin-3-yl)(cyclopropyl)methanone
compound 449: cyclopropyl(4-(4-((dimethylamino)methyl)piperidin-1-yl)-6-(6-hydroxynaphthalen-2-yl)quinolin-3-yl)methanone
compound 450: cyclopropyl(6-(3,5-dichloro-4-hydroxyphenyl)-4-(6-(2-morpholinoethylamino)pyridin-3-yl)quinolin-3-yl)methanone
compound 451: 4-(3-(cyclopropanecarbonyl)-6-(3,5-dichloro-4-hydroxyphenyl)quinolin-4-yl)-N-(2-(dimethylamino)ethyl)benzamide
compound 452: cyclopropyl(6-(3,5-dichloro-4-hydroxyphenyl)-4-(4-(pyrrolidin-1-ylmethyl)phenyl)quinolin-3-yl)methanone
compound 453: cyclopropyl(4-(4-((dimethylamino)methyl)piperidin-1-yl)-6-(1H-indol-5-yl)quinolin-3-yl)methanone
compound 454: cyclopropyl(4-(4-((dimethylamino)methyl)piperidin-1-yl)-6-(4-hydroxy-3-(trifluoromethyl)phenyl)quinolin-3-yl)methanone
compound 455: 1-((1S,4S)-5-(6-(3-chloro-5-fluoro-4-hydroxyphenyl)-3-(cyclopropanecarbonyl)quinolin-4-yl)-2,5-diazabicyclo[2.2.1]heptan-2-yl)-2-(dimethylamino)ethanone
compound 456: 1-((1S,4S)-5-(6-(3-chloro-4-hydroxy-5-methoxyphenyl)-3-(cyclopropane carbonyl)quinolin-4-yl)-2,5-diazabicyclo[2.2.1]heptan-2-yl)-2-(dimethylamino)ethanone
compound 457: (6-(3-chloro-5-ethoxy-4-hydroxyphenyl)-4-(4-((dimethylamino)methyl)piperidin-1-yl)quinolin-3-yl)(cyclopropyl)methanone
compound 458: cyclopropyl(6-(4-(difluoromethoxy)phenyl)-4-(4-((dimethylamino)methyl)piperidin-1-yl)quinolin-3-yl)methanone
compound 459: cyclopropyl(6-(3,5-dichloro-4-hydroxyphenyl)-4-(6-(piperazin-1-yl)pyridin-3-yl)quinolin-3-yl)methanone
compound 460: (6-(3-chloro-5-fluoro-4-hydroxyphenyl)-4-(4-(morpholinomethyl)phenylamino)quinolin-3-yl)(cyclopropyl)methanone
compound 461: 5-(3-(cyclopropanecarbonyl)-4-(4-(morpholinomethyl)phenylamino)quinolin-6-yl)pyrimidine-2-carbonitrile
compound 462: (6-(3-chloro-4-hydroxy-5-methoxyphenyl)-4-(4-(morpholinomethyl)phenylamino)quinolin-3-yl)(cyclopropyl)methanone
compound 463: cyclopropyl(6-(3,5-dichloro-4-hydroxyphenyl)-4-(4-(morpholinomethyl)phenylamino)quinolin-3-yl)methanone
compound 464: 1-((1S,4S)-5-(6-(3-chloro-4-hydroxyphenyl)-3-(cyclopropanecarbonyl)quinolin-4-yl)-2,5-diazabicyclo[2.2.1]heptan-2-yl)-2-(dimethylamino)ethanone
compound 465: cyclopropyl(6-(4-(difluoromethyl)phenyl)-4-(4-((dimethylamino)methyl)piperidin-1-yl)quinolin-3-yl)methanone
compound 466: 2-chloro-4-(4-(4-((dimethylamino)methyl)piperidin-1-yl)-3-(methylsulfinyl)quinolin-6-yl)phenol
compound 467: 2-chloro-4-(4-(4-((dimethylamino)methyl)piperidin-1-yl)-3-(methylsulfinyl)quinolin-6-yl)-6-fluorophenol
compound 468: 2-chloro-4-(4-(4-((dimethylamino)methyl)piperidin-1-yl)-3-(methylsulfinyl)quinolin-6-yl)-6-methoxyphenol
compound 469: 5-(3-(cyclopropanecarbonyl)-4-(6-(4-methylpiperazin-1-yl)pyridin-3-ylamino)quinolin-6-yl)pyrimidine-2-carbonitrile
compound 470: (6-(3-chloro-4-hydroxy-5-methoxyphenyl)-4-(6-(4-methylpiperazin-1-yl)pyridin-3-ylamino)quinolin-3-yl)(cyclopropyl)methanone
compound 471: (6-(3-chloro-5-fluoro-4-hydroxyphenyl)-4-(6-(4-methylpiperazin-1-yl)pyridin-3-ylamino)quinolin-3-yl)(cyclopropyl)methanone
compound 472: cyclopropyl(6-(3,5-dichloro-4-hydroxyphenyl)-4-(6-(4-methylpiperazin-1-yl)pyridin-3-ylamino)quinolin-3-yl)methanone
compound 473: 2,6-dichloro-4-(4-(4-((dimethylamino)methyl)phenylamino)-3-(methylsulfinyl)quinolin-6-yl)phenol compound 474: 5-(3-(cyclopropanecarbonyl)-4-(4-((dimethylamino)methyl)piperidin-1-yl)quinolin-6-yl)indolin-2-one compound 475: (6-(3-chloro-4-hydroxy-5-methoxyphenyl)-4-(2-(4-methylpiperazin-1-yl)pyrimidin-5-yl)quinolin-3-yl)(cyclopropyl)methanone compound 476: (4-(6-(3-chloro-4-hydroxy-5-methoxyphenyl)-3-(cyclopropanecarbonyl)quinolin-4-yl)phenyl)(4-methylpiperazin-1-yl)methanone compound 477: 1-(4-(3-acetyl-6-(3-chloro-4-hydroxy-5-methoxyphenyl)quinolin-4-yl)piperazin-1-yl)-2-(dimethylamino)ethanone compound 478: cyclopropyl(6-(3,5-dichloro-4-hydroxyphenyl)-4-(3-((4-methylpiperazin-1-yl)methyl)phenyl)quinolin-3-yl)methanone compound 479: cyclopropyl(6-(3,5-dichloro-4-hydroxyphenyl)-4-(2-(4-methylpiperazin-1-yl)pyrimidin-5-yl)quinolin-3-yl)methanone compound 480: 1-(4-((1R,4R)-4-aminocyclohexylamino)-6-(5-hydroxy-1H-indol-2-yl)quinolin-3-yl)-2-methylpropan-1-one compound 481: methyl 4-(3-(cyclopropanecarbonyl)-4-(4-((dimethylamino)methyl)piperidin-1-yl)quinolin-6-yl)benzoate compound 482: cyclopropyl(6-(3,5-dichloro-4-hydroxyphenyl)-4-(4-((4-methylpiperazin-1-yl)methyl)phenyl)quinolin-3-yl)methanone compound 483: 1-(6-(3-chloro-4-hydroxy-5-methoxyphenyl)-4-(6-(4-methylpiperazin-1-yl)pyridin-3-ylamino)quinolin-3-yl)ethanone compound 484: 1-(4-(3-acetyl-6-(3-chloro-5-fluoro-4-hydroxyphenyl)quinolin-4-yl)piperazin-1-yl)-2-(dimethylamino)ethanone compound 485: cyclopropyl(6-(3,5-dichloro-4-hydroxyphenyl)-4-(4-(2-(pyrrolidin-1-yl)ethoxy)phenyl)quinolin-3-yl)methanone compound 486: 1-(4-((1R,4R)-4-aminocyclohexylamino)-6-(3-chloro-5-ethoxy-4-hydroxyphenyl)quinolin-3-yl)ethanone compound 487: 1-(6-(3-chloro-5-fluoro-4-hydroxyphenyl)-4-(6-(4-methylpiperazin-1-yl)pyridin-3-ylamino)quinolin-3-yl)ethanone compound 488: 14643-chloro-5-fluoro-4-hydroxyphenyl)-4-(6-(4-methylpiperazin-1-yl)pyridin-3-ylamino)quinolin-3-yl)ethanone compound 489: (4-(4-((1H-imidazol-1-yl)methyl)phenylamino)-6-(3-chloro-5-fluoro-4-hydroxyphenyl)quinolin-3-yl)(cyclopropyl)methanone compound 490: (4-(4-((1H-imidazol-1-yl)methyl)phenylamino)-6-(3-chloro-4-hydroxy-5-methoxyphenyl)quinolin-3-yl)(cyclopropyl)methanone compound 491: 4-(4-((1R,4R)-4-aminocyclohexylamino)-3-(methylsulfinyl)quinolin-6-yl)-2,6-dichlorophenol compound 492: 4-(3-(cyclopropanecarbonyl)-4-(4-((dimethylamino)methyl)piperidin-1-yl)quinolin-6-yl)benzoic acid compound 493: (4-(1R,4R)-4-(aminomethyl)cyclohexylamino)-6-(3-chloro-4-hydroxy-5-methoxyphenyl)quinolin-3-yl)(cyclopropyl)methanone compound 494: (4-(1R,4R)-4-(aminomethyl)cyclohexylamino)-6-(3-chloro-4-hydroxy-5-methoxyphenyl)quinolin-3-yl)(cyclopropyl)methanone hydrochloride compound 495: (4-(1R,4R)-4-(aminomethyl)cyclohexylamino)-6-(3,5-dichloro-4-hydroxyphenyl)quinolin-3-yl)(cyclopropyl)methanone compound 496: (6-(3-chloro-5-fluoro-4-hydroxyphenyl)-4-(2-(piperazin-1-yl)pyrimidin-5-ylamino)quinolin-3-yl)(cyclopropyl)methanone compound 497: cyclopropyl(6-(3,5-dichloro-4-hydroxyphenyl)-4-(2-(piperazin-1-yl)pyrimidin-5-ylamino)quinolin-3-yl)methanone compound 498: 4-(4-((1R,4R)-4-aminocyclohexylamino)-3-(methylsulfinyl)quinolin-6-yl)-2-chloro-6-fluorophenol compound 499: 4-(4-((1R,4R)-4-aminocyclohexylamino)-3-(methylsulfinyl)quinolin-6-yl)-2-chlorophenol compound 500: 4-(4-((1R,4R)-4-aminocyclohexylamino)-3-(methylsulfinyl)quinolin-6-yl)-2-chloro-6-methoxyphenol compound 501: (4-((1R,4R)-4-(aminomethyl)cyclohexylamino)-6-(3-chloro-5-fluoro-4-hydroxyphenyl)quinolin-3-yl)(cyclopropyl)methanone compound 502: 1-(4-((1R,4R)-4-aminocyclohexylamino)-6-(3-chloro-4-hydroxy-5-methoxyphenyl)quinolin-3-yl)-2-methylpropan-1-one compound 503: (6-(3-chloro-4-hydroxy-5-methoxyphenyl)-4-(2-(piperazin-1-yl)pyrimidin-5-ylamino)quinolin-3-yl)(cyclopropyl)methanone compound 504: (4-(4-(aminomethyl)phenylamino)-6-(3-chloro-5-fluoro-4-hydroxyphenyl)quinolin-3-yl)(cyclopropyl)methanone compound 505: (4-(4-(aminomethyl)phenylamino)-6-(3-chloro-5-fluoro-4-hydroxyphenyl)quinolin-3-yl)(cyclopropyl)methanone hydrochloride compound 506: (4-(4-(aminomethyl)phenylamino)-6-(3-chloro-4-hydroxy-5-methoxyphenyl)quinolin-3-yl)(cyclopropyl)methanone compound 507: (4-(4-(aminomethyl)phenylamino)-6-(3,5-dichloro-4-hydroxyphenyl)quinolin-3-yl)(cyclopropyl)methanone compound 508: (4-(4-(aminomethyl)phenylamino)-6-(3,5-dichloro-4-hydroxyphenyl)quinolin-3-yl)(cyclopropyl)methanone hydrochloride compound 509: 5-(4-(4-(aminomethyl)phenylamino)-3-(cyclopropanecarbonyl)quinolin-6-yl)pyrimidine-2-carbonitrile compound 510: cyclopropyl(6-(3,5-dichloro-4-hydroxyphenyl)-4-((1R,4R)-4-(methylamino)cyclohexylamino)quinolin-3-yl)methanone compound 511: cyclopropyl(6-(3,5-dichloro-4-hydroxyphenyl)-4-(1-(piperidin-4-yl)-1H-pyrazol-4-ylamino)quinolin-3-yl)methanone compound 512: (6-(3-chloro-4-hydroxy-5-methoxyphenyl)-4-(1-(piperidin-4-yl)-1H-pyrazol-4-ylamino)quinolin-3-yl)(cyclopropyl)methanone compound 513: (6-(3-chloro-4-hydroxy-5-methoxyphenyl)-4-((1s,4s)-4-((dimethylamino)methyl)cyclohexylamino)quinolin-3-yl)(cyclopropyl)methanone compound 514: (6-(3-chloro-5-fluoro-4-hydroxyphenyl)-4-((1s,4s)-4-((dimethylamino)methyl)cyclohexylamino)quinolin-3-yl)(cyclopropyl)methanone compound 515: (4-((1s,4s)-4-(aminomethyl)cyclohexylamino)-6-(3-chloro-5-fluoro-4-hydroxyphenyl)quinolin-3-yl)(cyclopropyl)methanone compound 516: (6-(3-chloro-4-hydroxy-5-methoxyphenyl)-4-(1,2,3,6-tetrahydropyridin-4-yl)quinolin-3-yl)(cyclopropyl)methanone compound 517: (6-(3-chloro-4-hydroxy-5-methoxyphenyl)-4-((1R,4R)-4-(methylamino)cyclohexyl)amino)quinolin-3-yl)(cyclopropyl)methanone compound 518: 2-(((((1s,4s)-4-(6-(3-chloro-4-hydroxy-5-methoxyphenyl)-3-(cyclopropanecarbonyl)quinolin-4-ylamino)cyclohexyl)methyl)(methyl)amino)acetonitrile compound 519: (6-(3-chloro-4-hydroxyphenyl)-4-(1-(piperidin-4-yl)-1H-pyrazol-4-ylamino)quinolin-3-yl)(cyclopropyl)methanone compound 520: (6-(3-chloro-5-fluoro-4-hydroxyphenyl)-4-(1-(piperidin-4-yl)-1H-pyrazol-4-ylamino)quinolin-3-yl)(cyclopropyl)methanone compound 521: 1-(4-(6-(3-chloro-4-hydroxy-5-methoxyphenyl)-3-(cyclopropanecarbonyl)quinolin-4-yl)-5,6-dihydropyridin-1(2H)-yl)-2-(dimethylamino)ethanone compound 522: 5-(3-(cyclopropanecarbonyl)-4-(1R,4R)-4-(methylamino)cyclohexylamino)quinolin-6-yl)pyrimidine-2-carbonitrile compound 523: (6-(3-chloro-5-fluoro-4-hydroxyphenyl)-4-(1R,4R)-4-(methylamino)cyclohexylamino)quinolin-3-yl)(cyclopropyl)methanone compound 524: 2-(((((1s,4s)-4-(6-(3-chloro-5-fluoro-4-hydroxyphenyl)-3-(cyclopropanecarbonyl)quinolin-4-ylamino)cyclohexyl)methyl)(methyl)amino)acetonitrile compound 525: (6-(3-chloro-5-fluoro-4-hydroxyphenyl)-4-(5-(piperazin-1-yl)pyridin-2-ylamino)quinolin-3-yl)(cyclopropyl)methanone compound 526: cyclopropyl(6-(3,5-dichloro-4-hydroxyphenyl)-4-((1s,4s)-4-((dimethylamino)methyl)cyclohexylamino)quinolin-3-yl)methanone compound 527: 1-(4-(1R,4R)-4-aminocyclohexylamino)-6-(3-chloro-5-fluoro-4-hydroxyphenyl)quinolin-3-yl)ethanone compound 528: (6-(3-chloro-4-hydroxy-5-methoxyphenyl)-4-(5-(piperazin-1-yl)pyridin-2-ylamino)quinolin-3-yl)(cyclopropyl)methanone hydrochloride compound 529: 1-(4-(1R,4R)-4-aminocyclohexylamino)-6-(3-chloro-4-hydroxy-5-methoxyphenyl)quinolin-3-yl)butan-1-one compound 530: 1-(6-(3,5-dichloro-4-hydroxyphenyl)-4-(4-((dimethylamino)methyl)phenylamino)quinolin-3-yl)butan-1-one compound 531: 1-(6-(3,5-dichloro-4-hydroxyphenyl)-4-(4-((dimethylamino)methyl)phenylamino)quinolin-3-yl)butan-1-one dihydrochloride compound 532: 1-(4-(1R,4R)-4-aminocyclohexylamino)-6-(3-chloro-5-fluoro-4-hydroxyphenyl)quinolin-3-yl)butan-1-one compound 533: (6-(3-chloro-4-hydroxy-5-methoxyphenyl)-4-(4-methylpiperazin-1-yl)quinolin-3-yl)(cyclopropyl)methanone compound 534: (6-(3-chloro-5-fluoro-4-hydroxyphenyl)-4-(4-methylpiperazin-1-yl)quinolin-3-yl)(cyclopropyl)methanone compound 535: 1-(4-(1R,4R)-4-aminocyclohexylamino)-6-(3,5-dichloro-4-hydroxyphenyl)quinolin-3-yl)butan-1-one compound 536: (6-(3-chloro-4-hydroxy-5-methoxyphenyl)-4-(1H-pyrazol-4-yl)quinolin-3-yl)(cyclopropyl)methanone compound 537: 1-(6-(3-chloro-5-fluoro-4-hydroxyphenyl)-4-(4-((dimethylamino)methyl)phenylamino)quinolin-3-yl)butan-1-one compound 538: 1-(6-(3-chloro-4-hydroxy-5-methoxyphenyl)-4-(4-((dimethylamino)methyl)phenylamino)quinolin-3-yl)butan-1-one compound 539: 5-(3-butyryl-4-(4-((dimethylamino)methyl)phenylamino)quinolin-6-yl)pyrimidine-2-carbonitrile compound 540: (6-(3-chloro-4-hydroxy-5-methoxyphenyl)-4-(4-((dimethylamino)methyl)phenylamino)-7-fluoroquinolin-3-yl)(cyclopropyl)methanone compound 541: (6-(3-chloro-5-fluoro-4-hydroxyphenyl)-4-(4-((dimethylamino)methyl)phenylamino)-7-fluoroquinolin-3-yl)(cyclopropyl)methanone compound 542: 1-(6-(3-chloro-4-hydroxy-5-methoxyphenyl)-4-(1R,4R)-4-(methylamino)cyclohexylamino)quinolin-3-yl)ethanone compound 543: 1-(6-(3-chloro-4-hydroxy-5-methoxyphenyl)-4-(1R,4R)-4-(methylamino)cyclohexylamino)quinolin-3-yl)ethanone dihydrochloride compound 544: 4-(3-acetyl-6-(3-chloro-4-hydroxy-5-methoxyphenyl)quinolin-4-ylamino)benzamide compound 545: 4-(3-acetyl-6-(3,5-dichloro-4-hydroxyphenyl)quinolin-4-ylamino)benzamide compound 546: 4-(6-(3-chloro-4-hydroxy-5-methoxyphenyl)-3-(cyclopropanecarbonyl)quinolin-4-ylamino)benzamide compound 547: cyclopropyl(6-(3,5-dichloro-4-hydroxyphenyl)-4-(4-((dimethylamino)methyl)phenylamino)-7-fluoroquinolin-3-yl)methanone compound 548: (4-(6-(4-aminopiperidin-1-yl)pyridin-3-ylamino)-6-(3,5-dichloro-4-hydroxyphenyl)quinolin-3-yl)(cyclopropyl)methanone compound 549: (4-(6-(4-aminopiperidin-1-yl)pyridin-3-ylamino)-6-(3,5-dichloro-4-hydroxyphenyl)quinolin-3-yl)(cyclopropyl)methanone hydrochloride compound 550: (4-(6-(4-aminopiperidin-1-yl)pyridin-3-ylamino)-6-(3-chloro-4-hydroxy-5-methoxyphenyl)quinolin-3-yl)(cyclopropyl)methanone compound 551: (6-(3-chloro-4-hydroxy-5-methoxyphenyl)-4-(4-((dimethylamino)methyl)phenylamino)-8-fluoroquinolin-3-yl)(cyclopropyl)methanone compound 552: cyclopropyl(6-(3,5-dichloro-4-hydroxyphenyl)-4-(4-((dimethylamino)methyl)phenylamino)-8-fluoroquinolin-3-yl)methanone compound 553: (4-(2-(4-aminopiperidin-1-yl)pyrimidin-5-ylamino)-6-(3-chloro-4-hydroxy-5-methoxyphenyl)quinolin-3-yl)(cyclopropyl)methanone compound 554: (4-(6-(3-aminopiperidin-1-yl)pyridin-3-ylamino)-6-(3-chloro-4-hydroxy-5-methoxyphenyl)quinolin-3-yl)(cyclopropyl)methanone compound 555: (4-(1R,4R)-4-aminocyclohexylamino)-6-(3-chloro-5-fluoro-4-hydroxyphenyl)-8-fluoroquinolin-3-yl)(cyclopropyl)methanone compound 556: (4-(6-(3-aminopiperidin-1-yl)pyridin-3-ylamino)-6-(3,5-dichloro-4-hydroxyphenyl)quinolin-3-yl)(cyclopropyl)methanone compound 557: (4-(6-(4-aminopiperidin-1-yl)pyridin-3-ylamino)-6-(3-chloro-5-fluoro-4-hydroxyphenyl)quinolin-3-yl)(cyclopropyl)methanone compound 558: 1-(6-(3,5-dichloro-4-hydroxyphenyl)-4-(1R,4R)-4-(methylamino)cyclohexylamino)quinolin-3-yl)ethanone compound 559: cyclopropyl(6-(3,5-dichloro-4-hydroxyphenyl)-7-fluoro-4-(6-(piperazin-1-yl)pyridin-3-ylamino)quinolin-3-yl)methanone compound 560: 1-(6-(3-chloro-5-fluoro-4-hydroxyphenyl)-4-(1R,4R)-4-(methylamino)cyclohexylamino)quinolin-3-yl)ethanone compound 561: (4-(6-(3-aminopiperidin-1-yl)pyridin-3-ylamino)-6-(3-chloro-5-fluoro-4-hydroxyphenyl)quinolin-3-yl)(cyclopropyl)methanone compound 562: (4-(6-(3-aminopiperidin-1-yl)pyridin-3-ylamino)-6-(3-chloro-5-fluoro-4-hydroxyphenyl)quinolin-3-yl)(cyclopropyl)methanone hydrochloride compound 563: (6-(3-chloro-5-fluoro-4-hydroxyphenyl)-4-(4-((dimethylamino)methyl)phenylamino)-8-fluoroquinolin-3-yl)(cyclopropyl)methanone compound 564: (4-(1R,4R)-4-aminocyclohexylamino)-6-(3-chloro-4-hydroxy-5-methoxyphenyl)-8-fluoroquinolin-3-yl)(cyclopropyl)methanone compound 565: (4-(1R,4R)-4-aminocyclohexylamino)-6-(3,5-dichloro-4-hydroxyphenyl)-8-fluoroquinolin-3-yl)(cyclopropyl)methanone compound 566: (4-(2-(4-aminopiperidin-1-yl)pyrimidin-5-ylamino)-6-(3,5-dichloro-4-hydroxyphenyl)quinolin-3-yl)(cyclopropyl)methanone compound 567: (4-(2-(4-aminopiperidin-1-yl)pyrimidin-5-ylamino)-6-(3-chloro-5-fluoro-4-hydroxyphenyl)quinolin-3-yl)(cyclopropyl)methanone compound 568: (4-(6-(3-aminopyrrolidin-1-yl)pyridin-3-ylamino)-6-(3-chloro-4-hydroxy-5-methoxyphenyl)quinolin-3-yl)(cyclopropyl)methanone compound 569: (6-(3-chloro-4-hydroxy-5-methoxyphenyl)-4-(1R,4R)-4-(((R)-3-fluoropyrrolidin-1-yl)methyl)cyclohexylamino)quinolin-3-yl)(cyclopropyl)methanone compound 570: (6-(3-chloro-5-fluoro-4-hydroxyphenyl)-4-(1R,4R)-4-(R)-3-fluoropyrrolidin-1-yl)methyl)cyclohexylamino)quinolin-3-yl)(cyclopropyl)methanone compound 571: cyclopropyl(6-(3,5-dichloro-4-hydroxyphenyl)-4-(1R,4R)-4-(((R)-3-fluoropyrrolidin-1-yl)methyl)cyclohexylamino)quinolin-3-yl)methanone compound 572: (4-(2-(3-aminopyrrolidin-1-yl)pyrimidin-5-ylamino)-6-(3-chloro-5-fluoro-4-hydroxyphenyl)quinolin-3-yl)(cyclopropyl)methanone compound 573: (4-(2-(3-aminopyrrolidin-1-yl)pyrimidin-5-ylamino)-6-(3-chloro-5-fluoro-4-hydroxyphenyl)quinolin-3-yl)(cyclopropyl)methanone hydrochloride compound 574: (4-(2-(3-aminopyrrolidin-1-yl)pyrimidin-5-ylamino)-6-(3,5-dichloro-4-hydroxyphenyl)quinolin-3-yl)(cyclopropyl)methanone compound 575: (4-(6-(3-aminopyrrolidin-1-yl)pyridin-3-ylamino)-6-(3,5-dichloro-4-hydroxyphenyl)quinolin-3-yl)(cyclopropyl)methanone compound 576: (4-(6-(3-aminopyrrolidin-1-yl)pyridin-3-ylamino)-6-(3-chloro-5-fluoro-4-hydroxyphenyl)quinolin-3-yl)(cyclopropyl)methanone compound 577: (4-(6-(3-aminopyrrolidin-1-yl)pyridin-3-ylamino)-6-(3-chloro-5-fluoro-4-hydroxyphenyl)quinolin-3-yl)(cyclopropyl)methanone hydrochloride)

compound 578: (6-(3-chloro-4-hydroxy-5-methoxyphenyl)-7-fluoro-4-(6-(piperazin-1-yl)pyridin-3-ylamino)quinolin-3-yl)(cyclopropyl)methanone compound 579: (4-((1R,3r,5S)-8-azabicyclo[3.2.1]octan-3-ylamino)-6-(3-chloro-4-hydroxy-5-methoxyphenyl)quinolin-3-yl)(cyclopropyl)methanone compound 580: (4-((1R,3r,5S)-8-azabicyclo[3.2.1]octan-3-ylamino)-6-(3,5-dichloro-4-hydroxyphenyl)quinolin-3-yl)(cyclopropyl)methanone compound 581: cyclopropyl(6-(3,5-dichloro-4-hydroxyphenyl)-4-(4-((3,3-difluoropyrrolidin-1-yl)methyl)phenylamino)quinolin-3-yl)methanone compound 582: (4-(2-(3-aminopyrrolidin-1-yl)pyrimidin-5-ylamino)-6-(3-chloro-4-hydroxy-5-methoxyphenyl)quinolin-3-yl)(cyclopropyl)methanone compound 583: cyclopropyl(4-(4-(diallylamino)-4-methylcyclohexylamino)-6-(3,5-dichloro-4-hydroxyphenyl)quinolin-3-yl)methanone compound 584: cyclopropyl(6-(3,5-dichloro-4-hydroxyphenyl)-4-(1R,4R)-4-(pyrrolidin-1-ylmethyl)cyclohexylamino)quinolin-3-yl)methanone compound 585: cyclopropyl(6-(3,5-dichloro-4-hydroxyphenyl)-4-(1R,4R)-4-(pyrrolidin-1-ylmethyl)cyclohexylamino)quinolin-3-yl)methanone hydrochloride compound 586: (6-(3-chloro-4-hydroxy-5-methoxyphenyl)-4-(1R,4R)-4-(pyrrolidin-1-yl methyl)cyclohexylamino)quinolin-3-yl)(cyclopropyl)methanone compound 587: (6-(3-chloro-5-fluoro-4-hydroxyphenyl)-4-(1R,4R)-4-(pyrrolidin-1-ylmethyl)cyclohexylamino)quinolin-3-yl)(cyclopropyl)methanone compound 588: (6-(3-chloro-5-fluoro-4-hydroxyphenyl)-4-(1R,4R)-4-(pyrrolidin-1-ylmethyl)cyclohexylamino)quinolin-3-yl)(cyclopropyl)methanone hydrochloride compound 589: (4-(6-aminopyridin-3-ylamino)-6-(3-chloro-4-hydroxy-5-methoxyphenyl)quinolin-3-yl)(cyclopropyl)methanone compound 590: (4-(6-aminopyridin-3-ylamino)-6-(3,5-dichloro-4-hydroxyphenyl)quinolin-3-yl)(cyclopropyl)methanone compound 591: (4-(6-aminopyridin-3-ylamino)-6-(3-chloro-5-fluoro-4-hydroxyphenyl)quinolin-3-yl)(cyclopropyl)methanone compound 592: (6-(3-chloro-5-fluoro-4-hydroxyphenyl)-4-(1-(1-methylpiperidin-4-yl)-1H-pyrazol-4-ylamino)quinolin-3-yl)(cyclopropyl)methanone compound 593: cyclopropyl(6-(3,5-dichloro-4-hydroxyphenyl)-4-(1-(1-methylpiperidin-4-yl)-1H-pyrazol-4-ylamino)quinolin-3-yl)methanone compound 594: 1-(6-(3-chloro-5-fluoro-4-hydroxyphenyl)-4-(2-(piperazin-1-yl)pyrimidin-5-ylamino)quinolin-3-yl)ethanone compound 595: (4-(4,4'-bipiperidin-1-yl)-6-(3-chloro-4-hydroxy-5-methoxyphenyl)quinolin-3-yl)(cyclopropyl)methanone compound 596: (4-(4,4'-bipiperidin-1-yl)-6-(3,5-dichloro-4-hydroxyphenyl)quinolin-3-yl)(cyclopropyl)methanone compound 597: 1-(6-(3-chloro-5-fluoro-4-hydroxyphenyl)-4-(1R,4R)-4-((dimethylamino)methyl)cyclohexylamino)quinolin-3-yl)butan-1-one compound 598: cyclopropyl(6-(3,5-dichloro-4-hydroxyphenyl)-4-(1R,4R)-4-((3-methoxy pyrrolidin-1-yl)methyl)cyclohexylamino)quinolin-3-yl)methanone compound 599: (6-(3-chloro-4-hydroxy-5-methoxyphenyl)-4-(1R,4R)-4-((3-methoxypyrrolidin-1-yl)methyl)cyclohexylamino)quinolin-3-yl)(cyclopropyl)methanone compound 600: cyclopropyl(6-(3,5-dichloro-4-hydroxyphenyl)-4-(1R,4R)-4-(3-hydroxypyrrolidin-1-yl)methyl)cyclohexylamino)quinolin-3-yl)methanone compound 601: (4-(4-(2-aminopropan-2-yl)phenylamino)-6-(3,5-dichloro-4-hydroxyphenyl)quinolin-3-yl)(cyclopropyl)methanone hydrochloride compound 602: (4-(4-(2-aminopropan-2-yl)phenylamino)-6-(3,5-dichloro-4-hydroxyphenyl)quinolin-3-yl)(cyclopropyl)methanone compound 603: (4-(4-(2-aminopropan-2-yl)phenylamino)-6-(3-chloro-4-hydroxy-5-methoxyphenyl)quinolin-3-yl)(cyclopropyl)methanone compound 604: (4-(4-(2-aminopropan-2-yl)phenylamino)-6-(3-chloro-5-fluoro-4-hydroxyphenyl)quinolin-3-yl)(cyclopropyl)methanone compound 605: 1-(6-(3,5-dichloro-4-hydroxyphenyl)-4-(1R,4R)-4-((dimethylamino)methyl)cyclohexylamino)quinolin-3-yl)butan-1-one compound 606: 1-(6-(3-chloro-4-hydroxy-5-methoxyphenyl)-4-(1R,4R)-4-((dimethylamino)methyl)cyclohexylamino)quinolin-3-yl)-2-methylpropan-1-one compound 607: 1-(6-(3-chloro-4-hydroxy-5-methoxyphenyl)-4-(1R,4R)-4-((dimethylamino)methyl)cyclohexylamino)quinolin-3-yl)butan-1-one compound 608: 1-(6-(3,5-dichloro-4-hydroxyphenyl)-4-(1R,4R)-4-((dimethylamino)methyl)cyclohexylamino)quinolin-3-yl)-2-methylpropan-1-one
compound 609: (6-(3-chloro-4-hydroxy-5-methoxyphenyl)-4-(6-(piperidin-3-ylamino)pyridin-3-ylamino)quinolin-3-yl)(cyclopropyl)methanone
compound 610: cyclopropyl(6-(3,5-dichloro-4-hydroxyphenyl)-4-(6-(piperidin-3-ylamino)pyridin-3-ylamino)quinolin-3-yl)methanone
compound 611: (6-(3-chloro-5-fluoro-4-hydroxyphenyl)-4-(6-(piperidin-3-ylamino)pyridin-3-ylamino)quinolin-3-yl)(cyclopropyl)methanone
compound 612: (6-(3-chloro-4-hydroxy-5-methoxyphenyl)-4-(4-(2-(dimethylamino)ethyl)phenylamino)quinolin-3-yl)(cyclopropyl)methanone
compound 613: cyclopropyl(6-(3,5-dichloro-4-hydroxyphenyl)-4-(4-(2-(dimethylamino)ethyl)phenylamino)quinolin-3-yl)methanone
compound 614: cyclopropyl(6-(3,5-dichloro-4-hydroxyphenyl)-4-(4-(2-(dimethylamino)ethyl)phenylamino)quinolin-3-yl)methanone hydrochloride
compound 615: (6-(3-chloro-5-fluoro-4-hydroxyphenyl)-4-(4-(2-(dimethylamino)ethyl)phenylamino)quinolin-3-yl)(cyclopropyl)methanone
compound 616: 1-(6-(3-chloro-4-hydroxy-5-methoxyphenyl)-4-(2-(piperazin-1-yl)pyrimidin-5-ylamino)quinolin-3-yl)ethanone
compound 617: 1-(6-(3-chloro-4-hydroxy-5-methoxyphenyl)-4-(6-(piperazin-1-yl)pyridin-3-ylamino)quinolin-3-yl)butan-1-one
compound 618: cyclopropyl(6-(3,5-dichloro-4-hydroxyphenyl)-4-(1R,4R)-4-((4-methylpiperazin-1-yl)methyl)cyclohexylamino)quinolin-3-yl)methanone
compound 619: cyclopropyl(6-(3,5-dichloro-4-hydroxyphenyl)-4-(1R,4R)-4-((4-methylpiperazin-1-yl)methyl)cyclohexylamino)quinolin-3-yl)methanone hydrochloride
compound 620: 1-(6-(3-chloro-5-fluoro-4-hydroxyphenyl)-4-(1R,4R)-4-((dimethylamino)methyl)cyclohexylamino)quinolin-3-yl)-2-methylpropan-1-one
compound 621: (4-((1R,3r,5S)-8-azabicyclo[3.2.1]octan-3-ylamino)-6-(3-chloro-5-fluoro-4-hydroxyphenyl)quinolin-3-yl)(cyclopropyl)methanone
compound 622: (6-(3-chloro-4-hydroxy-5-methoxyphenyl)-4-(3-((dimethylamino)methyl)phenylamino)quinolin-3-yl)(cyclopropyl)methanone
compound 623: 1-(6-(3-chloro-5-fluoro-4-hydroxyphenyl)-4-(6-(piperazin-1-yl)pyridin-3-ylamino)quinolin-3-yl)butan-1-one
compound 624: cyclopropyl(6-(3,5-dichloro-4-hydroxyphenyl)-4-(3-((dimethylamino)methyl)phenylamino)quinolin-3-yl)methanone
compound 625: 1-(6-(3,5-dichloro-4-hydroxyphenyl)-4-(6-(piperazin-1-yl)pyridin-3-ylamino)quinolin-3-yl)butan-1-one
compound 626: (4-(2-(3-aminopiperidin-1-yl)pyrimidin-5-ylamino)-6-(3-chloro-5-fluoro-4-hydroxyphenyl)quinolin-3-yl)(cyclopropyl)methanone
compound 627: (6-(3-chloro-5-fluoro-4-hydroxyphenyl)-4-(1R,4R)-4-((3-methoxypyrrolidin-1-yl)methyl)cyclohexylamino)quinolin-3-yl)(cyclopropyl)methanone
compound 628: (4-(2-(3-aminopiperidin-1-yl)pyrimidin-5-ylamino)-6-(3,5-dichloro-4-hydroxyphenyl)quinolin-3-yl)(cyclopropyl)methanone
compound 629: (6-(3-chloro-5-fluoro-4-hydroxyphenyl)-4-(3-((dimethylamino)methyl)phenylamino)quinolin-3-yl)(cyclopropyl)methanone
compound 630: (6-(3-chloro-4-hydroxy-5-methoxyphenyl)-4-(1R,4R)-4-(3-hydroxypyrrolidin-1-yl)methyl)cyclohexylamino)quinolin-3-yl)(cyclopropyl)methanone
compound 631: (6-(3-chloro-5-fluoro-4-hydroxyphenyl)-4-(1R,4R)-4-((3-hydroxypyrrolidin-1-yl)methyl)cyclohexylamino)quinolin-3-yl)(cyclopropyl)methanone
compound 632: (6-(3-chloro-5-fluoro-4-hydroxyphenyl)-4-(1R,4R)-4-(((2-hydroxyethyl)(methyl)amino)methyl)cyclohexylamino)quinolin-3-yl)(cyclopropyl)methanone
compound 633: (6-(3-chloro-4-hydroxy-5-methoxyphenyl)-4-(1R,4R)-4-(((2-hydroxyethyl)(methyl)amino)methyl)cyclohexylamino)quinolin-3-yl)(cyclopropyl)methanone
compound 634: cyclopropyl(6-(3,5-dichloro-4-hydroxyphenyl)-4-(1R,4R)-4-(((2-hydroxyethyl)(methyl)amino)methyl)cyclohexylamino)quinolin-3-yl)methanone
compound 635: cyclopropyl(6-(3,5-dichloro-4-hydroxyphenyl)-4-(1R,4R)-4-(((2-hydroxyethyl)(methyl)amino)methyl)cyclohexylamino)quinolin-3-yl)methanone hydrochloride
compound 636: (6-(3-chloro-5-fluoro-4-hydroxyphenyl)-4-(1R,4R)-4-((4-methylpiperazin-1-yl)methyl)cyclohexylamino)quinolin-3-yl)(cyclopropyl)methanone
compound 637: (6-(3-chloro-4-hydroxy-5-methoxyphenyl)-4-(1R,4R)-4-((4-methylpiperazin-1-yl)methyl)cyclohexylamino)quinolin-3-yl)(cyclopropyl)methanone
compound 638: (4-(4-amino-4-methylcyclohexylamino)-6-(3,5-dichloro-4-hydroxyphenyl)quinolin-3-yl)(cyclopropyl)methanone
compound 639: (4-(4-amino-4-methylcyclohexylamino)-6-(3-chloro-4-hydroxy-5-methoxyphenyl)quinolin-3-yl)(cyclopropyl)methanone
compound 640: 1-(6-(3-chloro-4-hydroxy-5-methoxyphenyl)-4-(4-((dimethylamino)methyl)phenylamino)quinolin-3-yl)-2-methylpropan-1-one
compound 641: 1-(6-(3,5-dichloro-4-hydroxyphenyl)-4-(4-((dimethylamino)methyl)phenylamino)quinolin-3-yl)-2-methylpropan-1-one
compound 642: (R)-(6-(3-chloro-5-fluoro-4-hydroxyphenyl)-4-(4-(3-fluoropyrrolidin-1-yl)cyclohexylamino)quinolin-3-yl)(cyclopropyl)methanone
compound 643: (R)-cyclopropyl(6-(3,5-dichloro-4-hydroxyphenyl)-4-(4-(3-fluoropyrrolidin-1-yl)cyclohexylamino)quinolin-3-yl)methanone
compound 644: (4-(2-(3-aminopiperidin-1-yl)pyrimidin-5-ylamino)-6-(3-chloro-4-hydroxy-5-methoxyphenyl)quinolin-3-yl)(cyclopropyl)methanone
compound 645: (R)-(6-(3-chloro-4-hydroxy-5-methoxyphenyl)-4-(4-(3-fluoropyrrolidin-1-yl)cyclohexylamino)quinolin-3-yl)(cyclopropyl)methanone
compound 646: (S)-(4-(6-(3-aminopiperidin-1-yl)pyridin-3-ylamino)-6-(3,5-dichloro-4-hydroxyphenyl)quinolin-3-yl)(cyclopropyl)methanone
compound 647: (S)-(4-(6-(3-aminopiperidin-1-yl)pyridin-3-ylamino)-6-(3,5-dichloro-4-hydroxyphenyl)quinolin-3-yl)(cyclopropyl)methanone hydrochloride
compound 648: (S)-(4-(6-(3-aminopiperidin-1-yl)pyridin-3-ylamino)-6-(3-chloro-5-fluoro-4-hydroxyphenyl)quinolin-3-yl)(cyclopropyl)methanone
compound 649: (R)-(4-(6-(3-aminopiperidin-1-yl)pyridin-3-ylamino)-6-(3-chloro-4-hydroxy-5-methoxyphenyl)quinolin-3-yl)(cyclopropyl)methanone
compound 650: (R)-(4-(6-(3-aminopiperidin-1-yl)pyridin-3-ylamino)-6-(3,5-dichloro-4-hydroxyphenyl)quinolin-3-yl)(cyclopropyl)methanone
compound 651: (R)-(4-(6-(3-aminopiperidin-1-yl)pyridin-3-ylamino)-6-(3-chloro-5-fluoro-4-hydroxyphenyl)quinolin-3-yl)(cyclopropyl)methanone compound 652: cyclopropyl(6-(3,5-dichloro-4-hydroxyphenyl)-4-((1s,4s)-4-((dimethylamino)methyl)-4-hydroxycyclohexylamino)quinolin-3-yl)methanone compound 653: 1-(6-(3-chloro-4-hydroxy-5-methoxyphenyl)-4-(4-((4-methylpiperazin-1-yl)methyl)phenylamino)quinolin-3-yl)ethanone compound 654: 1-(6-(3,5-dichloro-4-hydroxyphenyl)-4-(4-((4-methylpiperazin-1-yl)methyl)phenylamino)quinolin-3-yl)ethanone compound 655: 1-(6-(3,5-dichloro-4-hydroxyphenyl)-4-((4-((4-methylpiperazin-1-yl)methyl)phenyl)amino)quinolin-3-yl)ethanone compound 656: 1-(6-(3-chloro-5-fluoro-4-hydroxyphenyl)-4-(4-((4-methylpiperazin-1-yl)methyl)phenylamino)quinolin-3-yl)ethanone compound 657: cyclopropyl(6-(3,5-dichloro-4-hydroxyphenyl)-4-(6-((dimethylamino)methyl)pyridin-3-ylamino)quinolin-3-yl)methanone compound 658: cyclopropyl(6-(3,5-dichloro-4-hydroxyphenyl)-4-(6-(pyrrolidin-1-ylmethyl)pyridin-3-ylamino)quinolin-3-yl)methanone compound 659: (6-(3-chloro-4-hydroxy-5-methoxyphenyl)-4-(6-(pyrrolidin-1-ylmethyl)pyridin-3-ylamino)quinolin-3-yl)methanone compound 660: (S)-(4-(6-(3-aminopiperidin-1-yl)pyridin-3-ylamino)-6-(3-chloro-4-hydroxy-5-methoxyphenyl)quinolin-3-yl)(cyclopropyl)methanone compound 661: cyclopropyl(6-(3,5-dichloro-4-hydroxyphenyl)-4-(4-(3-methoxypyrrolidin-1-yl)cyclohexylamino)quinolin-3-yl)methanone compound 662: (6-(3-chloro-5-fluoro-4-hydroxyphenyl)-4-(1R,4R)-4-(3-(dimethylamino)pyrrolidin-1-yl)methyl)cyclohexylamino)quinolin-3-yl)(cyclopropyl)methanone compound 663: cyclopropyl(6-(3,5-dichloro-4-hydroxyphenyl)-4-(1R,4R)-4-(3-(dimethylamino)pyrrolidin-1-yl)methyl)cyclohexylamino)quinolin-3-yl)methanone compound 664: cyclopropyl(6-(3,5-dichloro-4-hydroxyphenyl)-4-(4-(3,3-difluoropyrrolidin-1-yl)cyclohexylamino)quinolin-3-yl)methanone compound 665: (6-(3-chloro-4-hydroxy-5-methoxyphenyl)-4-(6-(pyrrolidin-3-ylamino)pyridin-3-ylamino)quinolin-3-yl)(cyclopropyl)methanone compound 666: cyclopropyl(6-(3,5-dichloro-4-hydroxyphenyl)-4-(6-(pyrrolidin-3-ylamino)pyridin-3-ylamino)quinolin-3-yl)methanone compound 667: (6-(3-chloro-5-fluoro-4-hydroxyphenyl)-4-(6-(pyrrolidin-3-ylamino)pyridin-3-ylamino)quinolin-3-yl)(cyclopropyl)methanone compound 668: (6-(3-chloro-4-hydroxy-5-methoxyphenyl)-4-(1R,4R)-4-((3-(dimethylamino)pyrrolidin-1-yl)methyl)cyclohexylamino)quinolin-3-yl)(cyclopropyl)methanone compound 669: (6-(3-chloro-4-hydroxy-5-methoxyphenyl)-4-(6-(3-hydroxypyrrolidin-1-yl)pyridin-3-ylamino)quinolin-3-yl)(cyclopropyl)methanone compound 670: cyclopropyl(6-(3,5-dichloro-4-hydroxyphenyl)-4-(6-(3-hydroxypyrrolidin-1-yl)pyridin-3-ylamino)quinolin-3-yl)methanone compound 671: (6-(3-chloro-5-fluoro-4-hydroxyphenyl)-4-(6-(3-hydroxypyrrolidin-1-yl)pyridin-3-ylamino)quinolin-3-yl)(cyclopropyl)methanone compound 672: (6-(3-chloro-5-fluoro-4-hydroxyphenyl)-4-(6-(pyrrolidin-1-ylmethyl)pyridin-3-ylamino)quinolin-3-yl)(cyclopropyl)methanone compound 673: (6-(3-chloro-5-fluoro-4-hydroxyphenyl)-4-((1s,4s)-4-((dimethylamino)methyl)-4-hydroxycyclohexylamino)quinolin-3-yl)(cyclopropyl)methanone compound 674: 1-(6-(3-chloro-5-fluoro-4-hydroxyphenyl)-4-(6-(piperazin-1-yl)pyridin-3-ylamino)quinolin-3-yl)-2-methylpropan-1-one compound 675: (6-(3-chloro-5-fluoro-4-hydroxyphenyl)-4-(4-(3,3-difluoropyrrolidin-1-yl)cyclohexylamino)quinolin-3-yl)(cyclopropyl)methanone compound 676: (6-(3-chloro-4-hydroxy-5-methoxyphenyl)-4-(4-(3,3-difluoropyrrolidin-1-yl)cyclohexylamino)quinolin-3-yl)(cyclopropyl)methanone compound 677: (6-(3-chloro-4-hydroxy-5-methoxyphenyl)-4-(6-(2-hydroxyethylamino)pyridin-3-ylamino)quinolin-3-yl)(cyclopropyl)methanone compound 678: cyclopropyl(6-(3,5-dichloro-4-hydroxyphenyl)-4-(6-(2-hydroxyethylamino)pyridin-3-ylamino)quinolin-3-yl)methanone compound 679: (6-(3-chloro-5-fluoro-4-hydroxyphenyl)-4-(6-(2-hydroxyethylamino)pyridin-3-ylamino)quinolin-3-yl)(cyclopropyl)methanone compound 680: 1-(6-(3-chloro-4-hydroxy-5-methoxyphenyl)-4-(6-(piperazin-1-yl)pyridin-3-ylamino)quinolin-3-yl)-2-methylpropan-1-one compound 681: 1-(4-(6-(3-aminopiperidin-1-yl)pyridin-3-ylamino)-6-(3,5-dichloro-4-hydroxyphenyl)quinolin-3-yl)ethanone compound 682: cyclopropyl(6-(3,5-dichloro-4-hydroxyphenyl)-4-(6-((4-methylpiperazin-1-yl)methyl)pyridin-3-ylamino)quinolin-3-yl)methanone compound 683: (6-(3-chloro-4-hydroxy-5-methoxyphenyl)-4-(6-((4-methylpiperazin-1-yl)methyl)pyridin-3-ylamino)quinolin-3-yl)(cyclopropyl)methanone compound 684: (6-(3-chloro-5-fluoro-4-hydroxyphenyl)-4-(6-((4-methylpiperazin-1-yl)methyl)pyridin-3-ylamino)quinolin-3-yl)(cyclopropyl)methanone compound 685: cyclopropyl(6-(3,5-dichloro-4-hydroxyphenyl)-4-(1R,4R)-4-((methylamino)methyl)cyclohexylamino)quinolin-3-yl)methanone compound 686: (6-(3-chloro-5-fluoro-4-hydroxyphenyl)-4-(4-(3-methoxypyrrolidin-1-yl)cyclohexylamino)quinolin-3-yl)(cyclopropyl)methanone compound 687: (6-(3-chloro-4-hydroxy-5-methoxyphenyl)-4-(4-(3-methoxypyrrolidin-1-yl)cyclohexylamino)quinolin-3-yl)(cyclopropyl)methanone compound 688: 1-(4-(6-(3-aminopiperidin-1-yl)pyridin-3-ylamino)-6-(3-chloro-4-hydroxy-5-methoxyphenyl)quinolin-3-yl)ethanone compound 689: (6-(3-chloro-4-hydroxy-5-methoxyphenyl)-4-(6-(3-(dimethylamino)pyrrolidin-1-yl)pyridin-3-ylamino)quinolin-3-yl)(cyclopropyl)methanone compound 690: cyclopropyl(6-(3,5-dichloro-4-hydroxyphenyl)-4-(6-(3-(dimethylamino)pyrrolidin-1-yl)pyridin-3-ylamino)quinolin-3-yl)methanone compound 691: (6-(3-chloro-5-fluoro-4-hydroxyphenyl)-4-(6-(3-(dimethylamino)pyrrolidin-1-yl)pyridin-3-ylamino)quinolin-3-yl)(cyclopropyl)methanone compound 692: (6-(3-chloro-4-hydroxy-5-methoxyphenyl)-4-(3-(2-(dimethylamino)ethyl)phenylamino)quinolin-3-yl)(cyclopropyl)methanone compound 693: (6-(3-chloro-5-fluoro-4-hydroxyphenyl)-4-(3-(2-(dimethylamino)ethyl)phenylamino)quinolin-3-yl)(cyclopropyl)methanone compound 694: cyclopropyl(6-(3,5-dichloro-4-hydroxyphenyl)-4-(4-((3-(dimethylamino)pyrrolidin-1-yl)methyl)phenylamino)quinolin-3-yl)methanone compound 695: cyclopropyl(6-(3,5-dichloro-4-hydroxyphenyl)-4-(4-((3-(dimethylamino) pyrrolidin-1-yl)methyl)phenylamino)quinolin-3-yl)methanone hydrochloride compound 696: (6-(3-chloro-5-fluoro-4-hydroxyphenyl)-4-(4-((3-(dimethylamino)pyrrolidin-1-yl)methyl)phenylamino)quinolin-3-yl)(cyclopropyl)methanone
compound 697: (6-(3-chloro-4-hydroxy-5-methoxyphenyl)-4-(4-((3-(dimethylamino)pyrrolidin-1-yl)methyl)phenylamino)quinolin-3-yl)(cyclopropyl)methanone
compound 698: cyclopropyl(6-(3,5-dichloro-4-hydroxyphenyl)-4-(3-(2-(dimethylamino)ethyl)phenylamino)quinolin-3-yl)methanone
compound 699: (6-(3-chloro-5-fluoro-4-hydroxyphenyl)-4-(1-(1-methylpiperidin-3-yl)-1H-pyrazol-4-ylamino)quinolin-3-yl)(cyclopropyl)methanone
compound 700: cyclopropyl(6-(3,5-dichloro-4-hydroxyphenyl)-4-(1R,4R)-4-((2-fluoroethylamino)methyl)cyclohexylamino)quinolin-3-yl)methanone
compound 701: (6-(3-chloro-5-fluoro-4-hydroxyphenyl)-4-(1R,4R)-4-((2-fluoroethylamino)methyl)cyclohexylamino)quinolin-3-yl)(cyclopropyl)methanone
compound 702: 1-(6-(3,5-dichloro-4-hydroxyphenyl)-4-(6-(piperazin-1-yl)pyridin-3-ylamino)quinolin-3-yl)ethanone hydrochloride
compound 703: cyclopropyl(6-(3,5-dichloro-4-hydroxyphenyl)-4-(1-(1-methylpiperidin-3-yl)-1H-pyrazol-4-ylamino)quinolin-3-yl)methanone
compound 704: 1-(6-(3-chloro-4-hydroxy-5-methoxyphenyl)-4-(6-(piperazin-1-yl)pyridin-3-ylamino)quinolin-3-yl)ethanone hydrochloride
compound 705: cyclopropyl(6-(3,5-dichloro-4-hydroxyphenyl)-4-(1-(1R,4R)-4-(methylamino)cyclohexyl)-1H-pyrazol-4-ylamino)quinolin-3-yl)methanone
compound 706: (4-(1-(1R,4R)-4-aminocyclohexyl)-1H-pyrazol-4-ylamino)-6-(3,5-dichloro-4-hydroxyphenyl)quinolin-3-yl)(cyclopropyl)methanone hydrochloride
compound 707: (6-(3-chloro-5-fluoro-4-hydroxyphenyl)-4-(4-(2-(dimethylamino)-1-hydroxyethyl)phenylamino)quinolin-3-yl)(cyclopropyl)methanone
compound 708: (6-(3-chloro-4-hydroxy-5-methoxyphenyl)-4-(4-(2-(dimethylamino)-1-hydroxyethyl)phenylamino)quinolin-3-yl)(cyclopropyl)methanone
compound 709: cyclopropyl(6-(3,5-dichloro-4-hydroxyphenyl)-4-(4-(2-(dimethylamino)-1-hydroxyethyl)phenylamino)quinolin-3-yl)methanone
compound 710: (6-(3-chloro-5-fluoro-4-hydroxyphenyl)-4-(6-(2-(dimethylamino)ethoxy)pyridin-3-ylamino)quinolin-3-yl)(cyclopropyl)methanone
compound 711: cyclopropyl(6-(3,5-dichloro-4-hydroxyphenyl)-4-(6-(2-(dimethylamino)ethoxy)pyridin-3-ylamino)quinolin-3-yl)methanone
compound 712: (6-(3-chloro-4-hydroxy-5-methoxyphenyl)-4-(6-(2-(dimethylamino)ethoxy)pyridin-3-ylamino)quinolin-3-yl)(cyclopropyl)methanone
compound 713: 1-(6-(3-chloro-4-hydroxy-5-methoxyphenyl)-4-(1R,4R)-4-((dimethylamino)methyl)cyclohexylamino)quinolin-3-yl)propan-1-one
compound 714: 1-(6-(3-chloro-5-fluoro-4-hydroxyphenyl)-4-(1R,4R)-4-((dimethylamino)methyl)cyclohexylamino)quinolin-3-yl)propan-1-one
compound 715: 1-(6-(3,5-dichloro-4-hydroxyphenyl)-4-(1R,4R)-4-((dimethylamino)methyl)cyclohexylamino)quinolin-3-yl)propan-1-one
compound 716: 1-(6-(3,5-dichloro-4-hydroxyphenyl)-4-((1R,4R)-4-((dimethylamino)methyl)cyclohexyl)amino)quinolin-3-yl)propan-1-one dihydrochloride
compound 717: 1-(6-(3-chloro-5-fluoro-4-hydroxyphenyl)-4-((1R,3R)-3-((dimethylamino)methyl)cyclopentylamino)quinolin-3-yl)ethanone
compound 718: 1-(6-(3,5-dichloro-4-hydroxyphenyl)-4-(1R,3R)-3-((dimethylamino)methyl)cyclopentylamino)quinolin-3-yl)ethanone
compound 719: (6-(3-chloro-5-fluoro-4-hydroxyphenyl)-4-(piperidin-4-ylamino)quinolin-3-yl)(cyclopropyl)methanone
compound 720: 1-(6-(3,5-dichloro-4-hydroxyphenyl)-4-(1-(dimethylamino)-2,3-dihydro-1H-inden-5-ylamino)quinolin-3-yl)ethanone
compound 721: 1-(6-(3,5-difluoro-4-hydroxyphenyl)-4-(1R,4R)-4-((dimethylamino)methyl)cyclohexylamino)quinolin-3-yl)ethanone
compound 722: (4-(6-(2-aminoethoxy)pyridin-3-ylamino)-6-(3-chloro-4-hydroxy-5-methoxyphenyl)quinolin-3-yl)(cyclopropyl)methanone
compound 723: (4-(6-(2-aminoethoxy)pyridin-3-ylamino)-6-(3,5-dichloro-4-hydroxyphenyl)quinolin-3-yl)(cyclopropyl)methanone
compound 724: (4-(6-(2-aminoethoxy)pyridin-3-ylamino)-6-(3-chloro-5-fluoro-4-hydroxyphenyl)quinolin-3-yl)(cyclopropyl)methanone
compound 725: (4-(6-(3-aminopiperidin-1-yl)pyridin-3-ylamino)-6-(3,5-difluoro-4-hydroxyphenyl)quinolin-3-yl)(cyclopropyl)methanone
compound 726: cyclopropyl(6-(3,5-dichloro-4-hydroxyphenyl)-4-(piperidin-4-ylamino)quinolin-3-yl)methanone
compound 727: (6-(3-chloro-4-hydroxy-5-methoxyphenyl)-4-(piperidin-4-ylamino)quinolin-3-yl)(cyclopropyl)methanone
compound 728: 1-(6-(3,5-dichloro-4-hydroxyphenyl)-4-(1R,3R)-3-((4-methylpiperazin-1-yl)methyl)cyclopentylamino)quinolin-3-yl)ethanone
compound 729: 1-(6-(3,5-dichloro-4-hydroxyphenyl)-4-(3-(2-(dimethylamino)ethyl)phenylamino)quinolin-3-yl)ethanone
compound 730: 1-(6-(3-chloro-4-hydroxy-5-methoxyphenyl)-4-(3-(2-(dimethylamino)ethyl)phenylamino)quinolin-3-yl)ethanone
compound 731: 1-(6-(3-chloro-5-fluoro-4-hydroxyphenyl)-4-(1R,4R)-4-(pyrrolidin-1-ylmethyl)cyclohexylamino)quinolin-3-yl)ethanone
compound 732: 1-(4-(6-(3-aminopiperidin-1-yl)pyridin-3-ylamino)-6-(3-chloro-5-fluoro-4-hydroxyphenyl)quinolin-3-yl)ethanone
compound 733: 1-(4-((6-(3-aminopiperidin-1-yl)pyridin-3-yl)amino)-6-(3-chloro-5-fluoro-4-hydroxyphenyl)quinolin-3-yl)ethanone
compound 734: 1-(6-(3-chloro-4-hydroxy-5-methoxyphenyl)-4-(1R,4R)-4-(pyrrolidin-1-ylmethyl)cyclohexylamino)quinolin-3-yl)ethanone
compound 735: (4-(2-(4-aminopiperidin-1-yl)pyridin-4-ylamino)-6-(3,5-dichloro-4-hydroxyphenyl)quinolin-3-yl)(cyclopropyl)methanone
compound 736: 1-(6-(3-chloro-5-fluoro-4-hydroxyphenyl)-4-(6-(4-methylpiperazin-1-yl)pyridin-3-ylamino)quinolin-3-yl)propan-1-one
compound 737: 1-(6-(3,5-dichloro-4-hydroxyphenyl)-4-(6-(4-methylpiperazin-1-yl)pyridin-3-ylamino)quinolin-3-yl)propan-1-one
compound 738: 1-(6-(3-chloro-4-hydroxy-5-methoxyphenyl)-4-(1R,4R)-4-(2-(dimethylamino)ethyl)cyclohexylamino)quinolin-3-yl)ethanone
compound 739: 1-(6-(3,5-dichloro-4-hydroxyphenyl)-4-(1R,4R)-4-(2-(dimethylamino)ethyl)cyclohexylamino)quinolin-3-yl)ethanone compound 740: 1-(6-(3,5-dichloro-4-hydroxyphenyl)-4-(1R,4R)-4-(2-(dimethylamino)ethyl)cyclohexyl)amino)quinolin-3-yl)ethanone hydrochloride
compound 741: 1-(6-(3-chloro-5-fluoro-4-hydroxyphenyl)-4-(1R,4R)-4-(2-(dimethylamino)ethyl)cyclohexylamino)quinolin-3-yl)ethanone
compound 742: 1-(6-(3-chloro-5-fluoro-4-hydroxyphenyl)-4-(1R,4R)-4-(2-(dimethylamino)ethyl)cyclohexylamino)quinolin-3-yl)ethanone dihydrochloride
compound 743: 1-(6-(3-chloro-4-hydroxy-5-methoxyphenyl)-4-(4-(2-(dimethylamino)ethyl)phenylamino)quinolin-3-yl)ethanone
compound 744: 1-(6-(3,5-dichloro-4-hydroxyphenyl)-4-(4-(2-(dimethylamino)ethyl)phenylamino)quinolin-3-yl)ethanone
compound 745: 1-(6-(3-chloro-5-fluoro-4-hydroxyphenyl)-4-(4-(2-(dimethylamino)ethyl)phenylamino)quinolin-3-yl)ethanone
compound 746: (6-(3-chloro-4-hydroxy-5-methoxyphenyl)-4-(6-(2-(dimethylamino)ethylamino)pyridin-3-ylamino)quinolin-3-yl)(cyclopropyl)methanone
compound 747: cyclopropyl(6-(3,5-dichloro-4-hydroxyphenyl)-4-(6-(2-(dimethylamino)ethylamino)pyridin-3-ylamino)quinolin-3-yl)methanone
compound 748: cyclopropyl(6-(3,5-dichloro-4-hydroxyphenyl)-4-(6-(2-(dimethylamino)ethylamino)pyridin-3-ylamino)quinolin-3-yl)methanone hydrochloride
compound 749: 1-(6-(3-chloro-4-hydroxy-5-methoxyphenyl)-4-(1R,4R)-4-((3-hydroxypyrrolidin-1-yl)methyl)cyclohexylamino)quinolin-3-yl)ethanone
compound 750: 1-(6-(3,5-dichloro-4-hydroxyphenyl)-4-((1R,3R)-3-((dimethylamino)methyl)cyclohexylamino)quinolin-3-yl)ethanone
compound 751: 1-(6-(3-chloro-5-fluoro-4-hydroxyphenyl)-4-(1R,3R)-3-((dimethylamino)methyl)cyclohexylamino)quinolin-3-yl)ethanone
compound 752: 1-(6-(3-chloro-4-hydroxy-5-methoxyphenyl)-4-((1R,3R)-3-((dimethylamino)methyl)cyclohexylamino)quinolin-3-yl)ethanone
compound 753: 1-(6-(3,5-dichloro-4-hydroxyphenyl)-4-(1R,4R)-4-((3-hydroxypyrrolidin-1-yl)methyl)cyclohexylamino)quinolin-3-yl)ethanone
compound 754: 1-(6-(3,5-dichloro-4-hydroxyphenyl)-4-(1R,4R)-4-(dimethylamino)cyclohexylamino)quinolin-3-yl)propan-1-one
compound 755: 1-(6-(3-chloro-4-hydroxy-5-methoxyphenyl)-4-(1R,4R)-4-(dimethylamino)cyclohexylamino)quinolin-3-yl)propan-1-one
compound 756: cyclopropyl(6-(3,5-dichloro-4-hydroxyphenyl)-4-(4-(2-(pyrrolidin-1-yl)ethyl)piperidin-1-yl)quinolin-3-yl)methanone
compound 757: 1-(6-(3-chloro-5-fluoro-4-hydroxyphenyl)-4-(1R,4R)-4-(dimethylamino)cyclohexylamino)quinolin-3-yl)propan-1-one
compound 758: 1-(6-(3,5-dichloro-4-hydroxyphenyl)-4-(6-(2-(dimethylamino)ethylamino)pyridin-3-ylamino)quinolin-3-yl)ethanone
compound 759: 1-(6-(3-chloro-5-fluoro-4-hydroxyphenyl)-4-(3-(2-(dimethylamino)ethyl)phenylamino)quinolin-3-yl)ethanone
compound 760: 1-(4-(6-(3-aminopyrrolidin-1-yl)pyridin-3-ylamino)-6-(3-chloro-5-fluoro-4-hydroxyphenyl)quinolin-3-yl)propan-1-one
compound 761: 1-(4-(6-(3-aminopyrrolidin-1-yl)pyridin-3-ylamino)-6-(3,5-dichloro-4-hydroxyphenyl)quinolin-3-yl)propan-1-one
compound 762: 1-(6-(3-chloro-5-fluoro-4-hydroxyphenyl)-4-(6-(2-(dimethylamino)ethylamino)pyridin-3-ylamino)quinolin-3-yl)ethanone
compound 763: 1-(6-(3-chloro-5-fluoro-4-hydroxyphenyl)-4-(1R,4R)-4-(dimethylamino)cyclohexylamino)quinolin-3-yl)ethanone
compound 764: (6-(3-chloro-4-hydroxy-5-methoxyphenyl)-4-(1-(pyrrolidin-3-yl)piperidin-4-ylamino)quinolin-3-yl)(cyclopropyl)methanone
compound 765: 1-(6-(3,5-dichloro-4-hydroxyphenyl)-4-(1R,4R)-4-(dimethylamino)cyclohexylamino)quinolin-3-yl)ethanone
compound 766: 1-(6-(3,5-dichloro-4-hydroxyphenyl)-4-((1R,4R)-4-(dimethylamino)cyclohexyl)amino)quinolin-3-yl)ethanone hydrochloride
compound 767: 1-(6-(3,5-dichloro-4-hydroxyphenyl)-4-(1R,4R)-4-(pyrrolidin-1-ylmethyl)cyclohexylamino)quinolin-3-yl)ethanone
compound 768: 1-(6-(3,5-dichloro-4-hydroxyphenyl)-4-((1R,4R)-4-(pyrrolidin-1-ylmethyl)cyclohexyl)amino)quinolin-3-yl)ethanone hydrochloride
compound 769: 1-(6-(3-chloro-4-hydroxy-5-methoxyphenyl)-4-(4-((dimethylamino)methyl)phenylamino)quinolin-3-yl)propan-1-one
compound 770: 1-(6-(3-chloro-5-fluoro-4-hydroxyphenyl)-4-(4-((dimethylamino)methyl)phenylamino)quinolin-3-yl)propan-1-one
compound 771: 1-(6-(3,5-dichloro-4-hydroxyphenyl)-4-(4-((dimethylamino)methyl)phenylamino)quinolin-3-yl)propan-1-one
compound 772: 1-(6-(3,5-dichloro-4-hydroxyphenyl)-4-(1R,4R)-4-(piperazin-1-ylmethyl)cyclohexylamino)quinolin-3-yl)ethanone dihydrochloride
compound 773: 1-(4-(6-(3-aminopyrrolidin-1-yl)pyridin-3-ylamino)-6-(3-chloro-5-fluoro-4-hydroxyphenyl)quinolin-3-yl)ethanone
compound 774: 1-(4-(6-(3-aminopyrrolidin-1-yl)pyridin-3-ylamino)-6-(3-chloro-4-hydroxy-5-methoxyphenyl)quinolin-3-yl)ethanone
compound 775: 1-(4-(6-(3-aminopyrrolidin-1-yl)pyridin-3-ylamino)-6-(3-chloro-4-hydroxy-5-methoxyphenyl)quinolin-3-yl)propan-1-one
compound 776: (6-(3-chloro-5-fluoro-4-hydroxyphenyl)-4-(6-(2-(dimethylamino)ethylamino)pyridin-3-ylamino)quinolin-3-yl)(cyclopropyl)methanone
compound 777: (6-(3-chloro-5-fluoro-4-hydroxyphenyl)-4-(6-(2-(dimethylamino)ethylamino)pyridin-3-ylamino)quinolin-3-yl)(cyclopropyl)methanone trihydrochloride
compound 778: cyclopropyl(6-(3,5-difluoro-4-hydroxyphenyl)-4-(6-(4-methylpiperazin-1-yl)pyridin-3-ylamino)quinolin-3-yl)methanone
compound 779: 1-(4-(1R,4R)-4-((3-aminopyrrolidin-1-yl)methyl)cyclohexylamino)-6-(3,5-dichloro-4-hydroxyphenyl)quinolin-3-yl)ethanone hydrochloride
compound 780: 1-(4-(1R,4R)-4-((3-aminopyrrolidin-1-yl)methyl)cyclohexylamino)-6-(3-chloro-4-hydroxy-5-methoxyphenyl)quinolin-3-yl)ethanone hydrochloride
compound 781: 1-(6-(3-chloro-5-fluoro-4-hydroxyphenyl)-4-(1R,4R)-4-((4-methylpiperazin-1-yl)methyl)cyclohexylamino)quinolin-3-yl)ethanone hydrochloride
compound 782: 1-(6-(3,5-dichloro-4-hydroxyphenyl)-4-(1R,4R)-4-((4-methylpiperazin-1-yl)methyl)cyclohexylamino)quinolin-3-yl)ethanone hydrochloride
compound 783: 1-(6-(3-chloro-5-fluoro-4-hydroxyphenyl)-4-(1R,4R)-4-(piperazin-1-ylmethyl)cyclohexylamino)quinolin-3-yl)ethanone dihydrochloride

- compound 784: 1-(6-(3,5-dichloro-4-hydroxyphenyl)-4-((1r,3r)-3-((dimethylamino)methyl)cyclobutylamino)quinolin-3-yl)ethanone
- compound 785: 1-(6-(3-chloro-5-fluoro-4-hydroxyphenyl)-4-(6-(3-(methylamino)pyrrolidin-1-yl)pyridin-3-ylamino)quinolin-3-yl)ethanone trihydrochloride
- compound 786: 1-(4-(1R,4R)-4-((3-aminopyrrolidin-1-yl)methyl)cyclohexylamino)-6-(3-chloro-5-fluoro-4-hydroxyphenyl)quinolin-3-yl)ethanone hydrochloride
- compound 787: 1-(6-(3-chloro-4-hydroxy-5-methoxyphenyl)-4-(1R,4R)-4-((4-methylpiperazin-1-yl)methyl)cyclohexylamino)quinolin-3-yl)ethanone hydrochloride
- compound 788: 1-(6-(3,5-dichloro-4-hydroxyphenyl)-4-(6-(3-(methylamino)pyrrolidin-1-yl)pyridin-3-ylamino)quinolin-3-yl)ethanone trihydrochloride
- compound 789: (6-(3-chloro-5-fluoro-4-hydroxyphenyl)-4-(6-(3-(methylamino)pyrrolidin-1-yl)pyridin-3-ylamino)quinolin-3-yl)(cyclopropyl)methanone trihydrochloride
- compound 790: 1-(6-(3,5-dichloro-4-hydroxyphenyl)-4-(1R,4R)-4-((diethylamino)methyl)cyclohexylamino)quinolin-3-yl)ethanone dihydrochloride
- compound 791: 1-(6-(3-chloro-4-hydroxy-5-methoxyphenyl)-4-(1R,4R)-4-((diethylamino)methyl)cyclohexylamino)quinolin-3-yl)ethanone hydrochloride
- compound 792: 1-(6-(3,5-dichloro-4-hydroxyphenyl)-4-((1S,4r)-4-(((S)-2-(hydroxymethyl)pyrrolidin-1-yl)methyl)cyclohexylamino)quinolin-3-yl)ethanone
- compound 793: 1-(6-(3-chloro-4-hydroxy-5-methoxyphenyl)-4-((1S,4r)-4-(((S)-2-(hydroxymethyl)pyrrolidin-1-yl)methyl)cyclohexylamino)quinolin-3-yl)ethanone
- compound 794: 1-(6-(3-chloro-5-fluoro-4-hydroxyphenyl)-4-(1R,4R)-4-((diethylamino)methyl)cyclohexylamino)quinolin-3-yl)ethanone dihydrochloride
- compound 795: cyclopropyl(6-(3,5-difluoro-4-hydroxyphenyl)-4-(6-(pyrrolidin-1-ylmethyl)pyridin-3-ylamino)quinolin-3-yl)methanone
- compound 796: cyclopropyl(6-(3,5-difluoro-4-hydroxyphenyl)-4-(3-(2-(dimethylamino)ethyl)phenylamino)quinolin-3-yl)methanone
- compound 797: cyclopropyl(6-(3,5-dichloro-4-hydroxyphenyl)-4-(3-(2-(pyrrolidin-1-yl)ethyl)phenylamino)quinolin-3-yl)methanone
- compound 798: cyclopropyl(6-(3,5-dichloro-4-hydroxyphenyl)-4-(3-(2-(pyrrolidin-1-yl)ethyl)phenylamino)quinolin-3-yl)methanone hydrochloride
- compound 799: (6-(3-chloro-5-fluoro-4-hydroxyphenyl)-4-(3-(2-(pyrrolidin-1-yl)ethyl)phenylamino)quinolin-3-yl)(cyclopropyl)methanone
- compound 800: (6-(3-chloro-5-fluoro-4-hydroxyphenyl)-4-(3-(2-(pyrrolidin-1-yl)ethyl)phenylamino)quinolin-3-yl)(cyclopropyl)methanone hydrochloride
- compound 801: 1-(6-(3,5-dichloro-4-hydroxyphenyl)-4-(3-(2-(pyrrolidin-1-yl)ethyl)phenylamino)quinolin-3-yl)ethanone
- compound 802: 1-(6-(3,5-dichloro-4-hydroxyphenyl)-4-((3-(2-(pyrrolidin-1-yl)ethyl)phenyl)amino)quinolin-3-yl)ethanone hydrochloride
- compound 803: 1-(6-(3-chloro-5-fluoro-4-hydroxyphenyl)-4-(3-(2-(pyrrolidin-1-yl)ethyl)phenylamino)quinolin-3-yl)ethanone
- compound 804: cyclopropyl(6-(3,5-dichloro-4-hydroxyphenyl)-4-(6-(3-(methylamino)pyrrolidin-1-yl)pyridin-3-ylamino)quinolin-3-yl)methanone trihydrochloride
- compound 805: 1-(6-(3-chloro-5-fluoro-4-hydroxyphenyl)-4-(1-(1-methylpiperidin-4-yl)-1H-pyrazol-4-ylamino)quinolin-3-yl)ethanone hydrochloride
- compound 806: 1-(6-(3,5-dichloro-4-hydroxyphenyl)-4-(6-(3-(methylamino)piperidin-1-yl)pyridin-3-ylamino)quinolin-3-yl)ethanone trihydrochloride
- compound 807: cyclopropyl(6-(3,5-dichloro-4-hydroxyphenyl)-4-(6-(3-(methylamino)piperidin-1-yl)pyridin-3-ylamino)quinolin-3-yl)methanone trihydrochloride
- compound 808: 1-(6-(3-chloro-5-fluoro-4-hydroxyphenyl)-4-(1R,4R)-4-(((R)-2-(hydroxymethyl)pyrrolidin-1-yl)methyl)cyclohexylamino)quinolin-3-yl)ethanone hydrochloride
- compound 809: 1-(4-(1R,4R)-4-((3-aminopiperidin-1-yl)methyl)cyclohexylamino)-6-(3-chloro-4-hydroxy-5-methoxyphenyl)quinolin-3-yl)ethanone hydrochloride
- compound 810: 1-(4-(1R,4R)-4-((3-aminopiperidin-1-yl)methyl)cyclohexylamino)-6-(3,5-dichloro-4-hydroxyphenyl)quinolin-3-yl)ethanone trihydrochloride
- compound 811: 1-(6-(3-chloro-4-hydroxy-5-methoxyphenyl)-4-(1R,4R)-4-(((R)-2-(hydroxymethyl)pyrrolidin-1-yl)methyl)cyclohexylamino)quinolin-3-yl)ethanone
- compound 812: 1-(6-(3,5-dichloro-4-hydroxyphenyl)-4-(1R,4R)-4-(((R)-2-(hydroxymethyl)pyrrolidin-1-yl)methyl)cyclohexylamino)quinolin-3-yl)ethanone
- compound 813: 1-(6-(3-chloro-5-fluoro-4-hydroxyphenyl)-4-(1-(1-methylpyrrolidin-3-yl)-1H-pyrazol-4-ylamino)quinolin-3-yl)ethanone dihydrochloride
- compound 814: 1-(6-(3,5-dichloro-4-hydroxyphenyl)-4-(1-(1-methylpyrrolidin-3-yl)-1H-pyrazol-4-ylamino)quinolin-3-yl)ethanone dihydrochloride
- compound 815: 1-(6-(3-chloro-5-fluoro-4-hydroxyphenyl)-4-(6-(3-(methylamino)piperidin-1-yl)pyridin-3-ylamino)quinolin-3-yl)ethanone trihydrochloride
- compound 816: 1-(6-(3-chloro-4-hydroxy-5-methoxyphenyl)-4-(1R,4R)-4-((ethyl(methyl)amino)methyl)cyclohexylamino)quinolin-3-yl)ethanone hydrochloride
- compound 817: 1-(6-(3,5-dichloro-4-hydroxyphenyl)-4-(1R,4R)-4-((ethyl(methyl)amino)methyl)cyclohexylamino)quinolin-3-yl)ethanone dihydrochloride
- compound 818: 1-(4-(1R,4R)-4-((3-aminopiperidin-1-yl)methyl)cyclohexylamino)-6-(3-chloro-5-fluoro-4-hydroxyphenyl)quinolin-3-yl)ethanone trihydrochloride
- compound 819: cyclopropyl(6-(3,5-dichloro-4-hydroxyphenyl)-4-(1-(2-(dimethylamino)ethyl)piperidin-4-ylamino)quinolin-3-yl)methanone
- compound 820: cyclopropyl(6-(3,5-dichloro-4-hydroxyphenyl)-4-(1-(2-(dimethylamino)ethyl)piperidin-4-ylamino)quinolin-3-yl)methanone
- compound 821: 1-(6-(3-chloro-5-fluoro-4-hydroxyphenyl)-4-(1-(2-(dimethylamino)ethyl)piperidin-4-ylamino)quinolin-3-yl)ethanone
- compound 822: (6-(3-chloro-5-fluoro-4-hydroxyphenyl)-4-(1-(2-(dimethylamino)ethyl)piperidin-4-ylamino)quinolin-3-yl)(cyclopropyl)methanone
- compound 823: 1-(6-(3,5-dichloro-4-hydroxyphenyl)-4-(1-(2-(dimethylamino)ethyl)piperidin-4-ylamino)quinolin-3-yl)ethanone
- compound 824: 1-(4-(6-(3-aminopiperidin-1-yl)pyridin-3-ylamino)-6-(3,5-dichloro-4-hydroxyphenyl)quinolin-3-yl)propan-1-one trihydrochloride
- compound 825: 1-(4-(6-(3-aminopiperidin-1-yl)pyridin-3-ylamino)-6-(3-chloro-5-fluoro-4-hydroxyphenyl)quinolin-3-yl)propan-1-one trihydrochloride
- compound 826: 1-(6-(3-chloro-5-fluoro-4-hydroxyphenyl)-4-((1S,3R)-3-((dimethylamino)methyl)cyclohexylamino)quinolin-3-yl)ethanone hydrochloride
- compound 827: 1-(6-(3,5-dichloro-4-hydroxyphenyl)-4-(1S,3R)-3-((dimethylamino)methyl)cyclohexylamino)quinolin-3-yl)ethanone hydrochloride compound 828: (6-(3-chloro-5-fluoro-4-hydroxyphenyl)-4-(3-(2-(4-methylpiperazin-1-yl)ethyl)phenylamino)quinolin-3-yl)(cyclopropyl)methanone compound 829: cyclopropyl(6-(3,5-dichloro-4-hydroxyphenyl)-4-(3-(2-(4-methylpiperazin-1-yl)ethyl)phenylamino)quinolin-3-yl)methanone compound 830: 1-(6-(3-chloro-5-fluoro-4-hydroxyphenyl)-4-(3-(2-(4-methylpiperazin-1-yl)ethyl)phenylamino)quinolin-3-yl)ethanone compound 831: 1-(6-(3,5-dichloro-4-hydroxyphenyl)-4-(3-(2-(4-methylpiperazin-1-yl)ethyl)phenylamino)quinolin-3-yl)ethanone compound 832: 1-(6-(3-chloro-5-fluoro-4-hydroxyphenyl)-4-((1S,3R)-3-((4-methylpiperazin-1-yl)methyl)cyclohexylamino)quinolin-3-yl)ethanone hydrochloride compound 833: 1-(6-(3,5-dichloro-4-hydroxyphenyl)-4-(1R,4R)-4-((dimethylamino)methyl)cyclohexylamino)-2-methylquinolin-3-yl)ethanone hydrochloride compound 834: 1-(6-(3-chloro-5-fluoro-4-hydroxyphenyl)-4-(1R,4R)-4-((dimethylamino)methyl)cyclohexylamino)-2-methylquinolin-3-yl)ethanone hydrochloride compound 835: 1-(6-(3,5-dichloro-4-hydroxyphenyl)-4-(1S,3R)-3-((4-methylpiperazin-1-yl)methyl)cyclohexylamino)quinolin-3-yl)ethanone hydrochloride compound 836: 1-(6-(3,5-dichloro-4-hydroxyphenyl)-4-(1-(1-methylpiperidin-4-yl)-1H-pyrazol-4-ylamino)quinolin-3-yl)ethanone dihydrochloride compound 837: 1-(6-(3-chloro-5-fluoro-4-hydroxyphenyl)-2-methyl-4-(6-(4-methylpiperazin-1-yl)pyridin-3-ylamino)quinolin-3-yl)ethanone hydrochloride compound 838: 1-(6-(3,5-dichloro-4-hydroxyphenyl)-2-methyl-4-(6-(4-methylpiperazin-1-yl)pyridin-3-ylamino)quinolin-3-yl)ethanone hydrochloride compound 839: cyclopropyl(6-(3,5-dichloro-4-hydroxyphenyl)-4-(6-(4-methylpiperazin-1-yl)pyridin-3-ylamino)-7-(trifluoromethyl)quinolin-3-yl)methanone compound 840: (6-(3-chloro-5-fluoro-4-hydroxyphenyl)-4-(6-(4-methylpiperazin-1-yl)pyridin-3-ylamino)-7-(trifluoromethyl)quinolin-3-yl)(cyclopropyl)methanone compound 841: (6-(3-chloro-5-fluoro-4-hydroxyphenyl)-4-(1R,4R)-4-((dimethylamino)methyl)cyclohexylamino)-7-(trifluoromethyl)quinolin-3-yl)(cyclopropyl)methanone compound 842: cyclopropyl(6-(3,5-dichloro-4-hydroxyphenyl)-4-(1R,4R)-4-((dimethylamino)methyl)cyclohexylamino)-7-(trifluoromethyl)quinolin-3-yl)methanone compound 843: 1-(6-(3,5-dichloro-4-hydroxyphenyl)-4-(1R,4R)-4-(pyrrolidin-1-ylmethyl)cyclohexylamino)quinolin-3-yl)propan-1-one dihydrochloride compound 844: 14643-chloro-5-fluoro-4-hydroxyphenyl)-4-((1S,4r)-4-(((S)-2-(hydroxymethyl)pyrrolidin-1-yl)methyl)cyclohexylamino)quinolin-3-yl)ethanone compound 845: 1-(6-(3-chloro-5-fluoro-4-hydroxyphenyl)-4-(1R,4R)-4-((ethyl(methyl)amino)methyl)cyclohexylamino)quinolin-3-yl)ethanone dihydrochloride compound 846: 1-(6-(3-chloro-5-fluoro-4-hydroxyphenyl)-4-(1R,4R)-4-(pyrrolidin-1-ylmethyl)cyclohexylamino)quinolin-3-yl)propan-1-one dihydrochloride compound 847: 1-(6-(3,5-dichloro-4-hydroxyphenyl)-4-(4-((dimethylamino)methyl)phenylamino)-7-methylquinolin-3-yl)ethanone hydrochloride compound 848: 1-(6-(3-chloro-5-fluoro-4-hydroxyphenyl)-4-(6-(2-(dimethylamino)ethoxy)pyridin-3-ylamino)quinolin-3-yl)ethanone hydrochloride compound 849: 1-(6-(3-chloro-5-fluoro-4-hydroxyphenyl)-4-(4-(4-methylpiperazine-1-carbonyl)cyclohexylamino)quinolin-3-yl)ethanone hydrochloride compound 850: 1-(6-(3,5-dichloro-4-hydroxyphenyl)-4-(1-(2-(dimethylamino)ethyl)piperidin-3-ylamino)quinolin-3-yl)ethanone compound 851: 1-(6-(3-chloro-5-fluoro-4-hydroxyphenyl)-4-(1-(2-(dimethylamino)ethyl)piperidin-3-ylamino)quinolin-3-yl)ethanone compound 852: 1-(6-(3,5-dichloro-4-hydroxyphenyl)-4-(6-(2-(dimethylamino)ethoxy)pyridin-3-ylamino)quinolin-3-yl)ethanone dihydrochloride compound 853: 1-(6-(3-chloro-5-fluoro-4-hydroxyphenyl)-4-((6-(3-(dimethylamino)pyrrolidin-1-yl)pyridin-3-yl)amino)quinolin-3-yl)ethanone compound 854: 1-(6-(3,5-dichloro-4-hydroxyphenyl)-4-((6-(3-(dimethylamino)pyrrolidin-1-yl)pyridin-3-yl)amino)quinolin-3-yl)ethanone compound 855: 1-(6-(3,5-dichloro-4-hydroxyphenyl)-4-((6-(3-(dimethylamino)pyrrolidin-1-yl)pyridin-3-yl)amino)quinolin-3-yl)ethanone hydrochloride compound 856: 1-(6-(3-chloro-5-fluoro-4-hydroxyphenyl)-7-methyl-4-((6-(4-methylpiperazin-1-yl)pyridin-3-yl)amino)quinolin-3-yl)ethanone hydrochloride compound 857: 1-(6-(3,5-dichloro-4-hydroxyphenyl)-4-((1R,4R)-4-((dimethylamino)methyl)cyclohexyl)amino)-7-methylquinolin-3-yl)ethanone compound 858: 1-(6-(3-chloro-5-fluoro-4-hydroxyphenyl)-4-((4-((dimethylamino)methyl)phenyl)amino)-7-methylquinolin-3-yl)ethanone hydrochloride compound 859: 1-(6-(3-chloro-5-fluoro-4-hydroxyphenyl)-4-(1R,4R)-4-((dimethylamino)methyl)cyclohexyl)amino)-7-methylquinolin-3-yl)ethanone hydrochloride compound 860: 1-(6-(3-chloro-5-fluoro-4-hydroxyphenyl)-4-((6-(3-(dimethylamino)pyrrolidin-1-yl)pyridin-3-yl)amino)quinolin-3-yl)propan-1-one compound 861: 1-(6-(3,5-dichloro-4-hydroxyphenyl)-4-(((1S,3R)-3-(2-(dimethylamino)ethyl)cyclohexyl)amino)quinolin-3-yl)ethanone hydrochloride compound 862: 1-(6-(3-chloro-5-fluoro-4-hydroxyphenyl)-4-(((1S,3R)-3-(2-(dimethylamino)ethyl)cyclohexyl)amino)quinolin-3-yl)ethanone hydrochloride compound 863: 1-(6-(3,5-dichloro-4-hydroxyphenyl)-4-((6-(3-(dimethylamino)pyrrolidin-1-yl)pyridin-3-yl)amino)quinolin-3-yl)propan-1-one compound 864: 1-(6-(3,5-dichloro-4-hydroxyphenyl)-4-((1R,4R)-4-((bis-(trideuteromethyl)amino)methyl)cyclohexyl)amino)quinolin-3-yl)ethanone dihydrochloride compound 865: (1r,4r)-4-((3-acetyl-6-(3,5-dichloro-4-hydroxyphenyl)quinolin-4-yl)amino)-N,N-dimethylcyclohexanecarboxamide hydrochloride compound 866: 1-(6-(3,5-dichloro-4-hydroxyphenyl)-7-methyl-4-((6-(4-methylpiperazin-1-yl)pyridin-3-yl)amino)quinolin-3-yl)ethanone hydrochloride compound 867: 1-(6-(3-chloro-5-fluoro-4-hydroxyphenyl)-4-(6-methyl-5-(2-(pyrrolidin-1-yl)ethyl)pyridin-3-yl)amino)quinolin-3-yl)ethanone compound 868: 1-(6-(3,5-dichloro-4-hydroxyphenyl)-4-((1R,4R)-4-(2-(diethylamino)ethoxy)cyclohexyl)amino)quinolin-3-yl)ethanone hydrochloride compound 869: 1-(6-(3-chloro-5-fluoro-4-hydroxyphenyl)-4-((1R,4R)-4-(2-(diethylamino)ethoxy)cyclohexyl)amino)quinolin-3-yl)ethanone hydrochloride compound 870: (1r,4r)-4-((3-acetyl-6-(3-chloro-5-fluoro-4-hydroxyphenyl)quinolin-4-yl)amino)-N,N-dimethylcyclohexanecarboxamide hydrochloride compound 871: 1-(6-(3,5-dichloro-4-hydroxyphenyl)-4-((6-methyl-5-(2-(pyrrolidin-1-yl)ethyl)pyridin-3-yl)amino)quinolin-3-yl)ethanone compound 872: 1-(4-(((1R,4R)-4-((3-aminopyrrolidin-1-yl)methyl)cyclohexyl)amino)-6-(3,5-dichloro-4-hydroxyphenyl)-7-methylquinolin-3-yl)ethanone hydrochloride
compound 873: 1-(6-(3,5-dichloro-4-hydroxyphenyl)-4-((5-(2-(pyrrolidin-1-yl)ethyl)pyridin-3-yl)amino)quinolin-3-yl)ethanone hydrochloride
compound 874: N-(1R,4R)-4-((3-acetyl-6-(3-chloro-5-fluoro-4-hydroxyphenyl)quinolin-4-yl)amino)cyclohexyl)-1-methylpyrrolidine-2-carboxamide hydrochloride
compound 875: N-(1R,4R)-4-((3-acetyl-6-(3,5-dichloro-4-hydroxyphenyl)quinolin-4-yl)amino)cyclohexyl)-1-methylpyrrolidine-2-carboxamide hydrochloride
compound 876: N-(1R,4R)-4-((3-acetyl-6-(3-chloro-5-fluoro-4-hydroxyphenyl)quinolin-4-yl)amino)cyclohexyl)-2-(dimethylamino)acetamide dihydrochloride
compound 877: N-(1R,4R)-4-((3-acetyl-6-(3,5-dichloro-4-hydroxyphenyl)quinolin-4-yl)amino)cyclohexyl)-2-(dimethylamino)acetamide hydrochloride
compound 878: (S)—N-((1r,4S)-4-((3-acetyl-6-(3-chloro-5-fluoro-4-hydroxyphenyl)quinolin-4-yl)amino)cyclohexyl)-2-aminopropanamide dihydrochloride
compound 879: 2-chloro-6-fluoro-4-(3-(methylsulfonyl)-4-((3-(2-(pyrrolidin-1-yl)ethyl)phenyl)amino)quinolin-6-yl)phenol hydrochloride
compound 880: 1-(6-(3-chloro-5-fluoro-4-hydroxyphenyl)-4-((5-(2-(pyrrolidin-1-yl)ethyl)pyridin-3-yl)amino)quinolin-3-yl)ethanone hydrochloride
compound 881: cyclopropyl(6-(3,5-dichloro-4-hydroxyphenyl)-4-(5-(2-(pyrrolidin-1-yl)ethyl)pyridin-3-yl)amino)quinolin-3-yl)methanone
compound 882: (6-(3-chloro-5-fluoro-4-hydroxyphenyl)-4-((5-(2-(pyrrolidin-1-yl)ethyl)pyridin-3-yl)amino)quinolin-3-yl)(cyclopropyl)methanone
compound 883: 2,6-dichloro-4-(3-(methylsulfonyl)-4-((3-(2-(pyrrolidin-1-yl)ethyl)phenyl)amino)quinolin-6-yl)phenol hydrochloride
compound 884: 2,6-dichloro-4-(4-((6-(2-(dimethylamino)ethoxy)pyridin-3-yl)amino)-3-(methylsulfonyl)quinolin-6-yl)phenol hydrochloride
compound 885: 2-chloro-4-(4-((6-(2-(dimethylamino)ethoxy)pyridin-3-yl)amino)-3-(methylsulfonyl)quinolin-6-yl)-6-fluorophenol hydrochloride
compound 886: (S)—N-((1r,4S)-4-((3-acetyl-6-(3,5-dichloro-4-hydroxyphenyl)quinolin-4-yl)amino)cyclohexyl)-2-aminopropanamide dihydrochloride
compound 887: 1-(6-(3,5-dichloro-4-hydroxyphenyl)-4-((4-((4-methylpiperazin-1-yl)sulfonyl)phenyl)amino)quinolin-3-yl)ethanone hydrochloride
compound 888: 1-(6-(4'-hydroxy-[1,1'-biphenyl]-4-yl)-4-((3-(2-(pyrrolidin-1-yl)ethyl)phenyl)amino)quinolin-3-yl)ethanone hydrochloride
compound 889: 2-chloro-4-(4-((6-(3-(dimethylamino)pyrrolidin-1-yl)pyridin-3-yl)amino)-3-(methylsulfonyl)quinolin-6-yl)-6-fluorophenol hydrochloride
compound 890: 2,6-dichloro-4-(3-(methylsulfonyl)-4-(1R,4R)-4-(pyrrolidin-1-ylmethyl)cyclohexyl)amino)quinolin-6-yl)phenol hydrochloride
compound 891: 2-chloro-6-fluoro-4-(3-(methylsulfonyl)-4-((1R,4R)-4-(pyrrolidin-1-ylmethyl)cyclohexyl)amino)quinolin-6-yl)phenol hydrochloride
compound 892: (1r,4r)-4-((3-acetyl-6-(3,5-dichloro-4-hydroxyphenyl)quinolin-4-yl)amino)-N-(2-(dimethylamino)ethyl)cyclohexanecarboxamide hydrochloride
compound 893: (1r,4r)-4-((3-acetyl-6-(3-chloro-5-fluoro-4-hydroxyphenyl)quinolin-4-yl)amino)-N-(2-(dimethylamino)ethyl)cyclohexanecarboxamide hydrochloride
compound 894: 1-(6-(3-chloro-5-fluoro-4-hydroxyphenyl)-4-((4-((4-methylpiperazin-1-yl)sulfonyl)phenyl)amino)quinolin-3-yl)ethanone hydrochloride
compound 895: 1-(6-(1H-benzo[d]imidazol-6-yl)-4-((1-(1-methylpiperidin-4-yl)-1H-pyrazol-4-yl)amino)quinolin-3-yl)ethanone hydrochloride
compound 896: 1-(6-(1H-benzo[d]imidazol-6-yl)-4-((3-(2-(pyrrolidin-1-yl)ethyl)phenyl)amino)quinolin-3-yl)ethanone hydrochloride
compound 897: 1-(6-(3,5-dichloro-4-hydroxyphenyl)-4-(2-methyl-5-(2-(pyrrolidin-1-yl)ethyl)pyridin-3-yl)amino)quinolin-3-yl)ethanone
compound 898: 1-(6-(3,5-dichloro-4-hydroxyphenyl)-4-((1R,4R)-4-(4-methylpiperazine-1-carbonyl)cyclohexyl)amino)quinolin-3-yl)ethanone hydrochloride
compound 899: 2,6-dichloro-4-(4-((1-(1-methylpiperidin-4-yl)-1H-pyrazol-4-yl)amino)-3-(methylsulfonyl)quinolin-6-yl)phenol hydrochloride
compound 900: 2-chloro-6-fluoro-4-(4-((1-(1-methylpiperidin-4-yl)-1H-pyrazol-4-yl)amino)-3-(methylsulfonyl)quinolin-6-yl)phenol hydrochloride
compound 901: 1-(6-(1H-benzo[d]imidazol-6-yl)-4-((6-(4-methylpiperazin-1-yl)pyridin-3-yl)amino)quinolin-3-yl)ethanone hydrochloride
compound 902: 1-(6-(1H-benzo[d]imidazol-6-yl)-4-((6-(2-(dimethylamino)ethoxy)pyridin-3-yl)amino)quinolin-3-yl)ethanone hydrochloride
compound 903: 1-(6-(3,5-dichloro-4-hydroxyphenyl)-4-((1R,4R)-4-((dimethylamino)methyl)cyclohexyl)amino)-7-fluoroquinolin-3-yl)ethanone hydrochloride
compound 904: 1-(6-(3-chloro-5-fluoro-4-hydroxyphenyl)-4-((1R,4R)-4-((dimethylamino)methyl)cyclohexyl)amino)-7-fluoroquinolin-3-yl)ethanone hydrochloride
compound 905: 146-(1H-benzo[d]imidazol-6-yl)-4-((6-(3-(dimethylamino)pyrrolidin-1-yl)pyridin-3-yl)amino)quinolin-3-yl)ethanone hydrochloride
compound 906: 2,6-dichloro-4-(4-((6-(3-(dimethylamino)pyrrolidin-1-yl)pyridin-3-yl)amino)-3-(methylsulfonyl)quinolin-6-yl)phenol hydrochloride
compound 907: N-(1R,4R)-4-((3-acetyl-6-(3-chloro-5-fluoro-4-hydroxyphenyl)quinolin-4-yl)amino)cyclohexyl)-2-amino-3-methylbutanamide dihydrochloride
compound 908: 1-(4-(((1R,4R)-4-((dimethylamino)methyl)cyclohexyl)amino)-6-(pyridin-4-yl)quinolin-3-yl)ethanone hydrochloride
compound 909: 4-(4-((6-(3-aminopiperidin-1-yl)pyridin-3-yl)amino)-3-(methylsulfonyl)quinolin-6-yl)-2-chloro-6-fluorophenol trihydrochloride
compound 910: 1-(4-(((1R,4R)-4-((dimethylamino)methyl)cyclohexyl)amino)-6-(1H-indazol-5-yl)quinolin-3-yl)ethanone hydrochloride
compound 911: 1-(6-(1H-benzo[d]imidazol-6-yl)-4-((1R,4R)-4-((dimethylamino)methyl)cyclohexyl)amino)quinolin-3-yl)ethanone hydrochloride
compound 912: 1-(4-(((1R,4R)-4-((dimethylamino)methyl)cyclohexyl)amino)-6-(1H-pyrazol-4-yl)quinolin-3-yl)ethanone hydrochloride
compound 913: 4-(4-((6-(3-aminopiperidin-1-yl)pyridin-3-yl)amino)-3-(methylsulfonyl)quinolin-6-yl)-2,6-dichlorophenol trihydrochloride
compound 914: (S)—N-((1r,4S)-4-(3-acetyl-6-(3-chloro-5-fluoro-4-hydroxyphenyl)quinolin-4-yl)amino)cyclohexyl)-2-amino-3,3-dimethylbutanamide hydrochloride
compound 915: N-(1R,4R)-4-((3-acetyl-6-(3,5-dichloro-4-hydroxyphenyl)quinolin-4-yl)amino)cyclohexyl)-2-amino-3-methylbutanamide dihydrochloride compound 916: (6-(3-chloro-4-hydroxy-5-methoxyphenyl)-4-((1R,4R)-4-((dimethylamino)methyl)cyclohexyl)amino)quinolin-3-yl)(cyclopentyl)methanone hydrochloride compound 917: cyclopentyl(6-(3,5-dichloro-4-hydroxyphenyl)-4-((1R,4R)-4-((dimethylamino)methyl)cyclohexyl)amino)quinolin-3-yl)methanone hydrochloride compound 918: 1-(6-(3,5-dichloro-4-hydroxyphenyl)-4-((1R,4R)-4-((dimethylamino)methyl)cyclohexyl)amino)quinolin-3-yl)-2,2-dimethylpropan-1-one hydrochloride compound 919: 1-(6-(3-chloro-5-fluoro-4-hydroxyphenyl)-4-((1R,4R)-4-((dimethylamino)methyl)cyclohexyl)amino)quinolin-3-yl)-2,2-dimethylpropan-1-one hydrochloride compound 920: (S)—N-((1 r,4S)-4-((3-acetyl-6-(3,5-dichloro-4-hydroxyphenyl)quinolin-4-yl)amino)cyclohexyl)pyrrolidine-2-carboxamide dihydrochloride compound 921: (S)—N-((1r,4S)-4-((3-acetyl-6-(3-chloro-5-fluoro-4-hydroxyphenyl)quinolin-4-yl)amino)cyclohexyl)pyrrolidine-2-carboxamide dihydrochloride compound 922: (S)—N-((1 r,4S)-4-((3-acetyl-6-(3,5-dichloro-4-hydroxyphenyl)quinolin-4-yl)amino)cyclohexyl)-2-amino-3,3-dimethylbutanamide hydrochloride compound 923: 1-(6-(3,5-dichloro-4-hydroxyphenyl)-7-fluoro-4-((1R,4R)-4-(pyrrolidin-1-ylmethyl)cyclohexyl)amino)quinolin-3-yl)ethanone hydrochloride compound 924: (6-(3-chloro-4-hydroxy-5-methoxyphenyl)-4-((3-(2-(pyrrolidin-1-yl)ethyl)phenyl)amino)quinolin-3-yl)(cyclopentyl)methanone hydrochloride compound 925: 1-(6-(3-chloro-5-fluoro-4-hydroxyphenyl)-7-fluoro-4-((1R,4R)-4-(pyrrolidin-1-ylmethyl)cyclohexyl)amino)quinolin-3-yl)ethanone hydrochloride compound 926: 1-(6-(3-chloro-4-hydroxy-5-methoxyphenyl)-7-fluoro-4-((1R,4R)-4-(pyrrolidin-1-ylmethyl)cyclohexyl)amino)quinolin-3-yl)ethanone hydrochloride compound 927: cyclopentyl(6-(3,5-dichloro-4-hydroxyphenyl)-4-((3-(2-(pyrrolidin-1-yl)ethyl)phenyl)amino)quinolin-3-yl)methanone hydrochloride compound 928: 2-amino-N-(1R,4R)-4-((6-(3,5-dichloro-4-hydroxyphenyl)-3-pivaloylquinolin-4-yl)amino)cyclohexyl)propanamide hydrochloride compound 929: 1-(4-((1R,4R)-4-((dimethylamino)methyl)cyclohexyl)amino)-6-(6-hydroxynaphthalen-2-yl)quinolin-3-yl)ethanone hydrochloride compound 930: 1-(6-(3-chloro-5-fluoro-4-hydroxyphenyl)-4-((1-(1-methylpiperidin-4-yl)-1H-pyrazol-4-yl)amino)quinolin-3-yl)-2,2-dimethylpropan-1-one hydrochloride compound 931: 1-(6-(3,5-dichloro-4-hydroxyphenyl)-4-((1-(1-methylpiperidin-4-yl)-1H-pyrazol-4-yl)amino)quinolin-3-yl)-2,2-dimethylpropan-1-one hydrochloride compound 932: 2-amino-N-(1R,4R)-4-(6-(3-chloro-5-fluoro-4-hydroxyphenyl)-3-pivaloylquinolin-4-yl)amino)cyclohexyl)propanamide hydrochloride compound 933: 2-(3-acetyl-4-(1R,4R)-4-((dimethylamino)methyl)cyclohexylamino)quinolin-6-yl)-5-methoxyisoindolin-1-one compound 934: (S)-1-(4-(6-(3-aminopiperidin-1-yl)pyridin-3-ylamino)-6-(3,5-dichloro-4-hydroxy phenyl)quinolin-3-yl)propan-1-one trihydrochloride compound 935: 1-(4-(1R,4R)-4-((dimethylamino)methyl)cyclohexylamino)-6-(4-hydroxyphenyl)quinolin-3-yl)ethanone dihydrochloride compound 936: (4-((trans)-4-aminocyclohexylamino)-6-(3-chloro-5-fluoro-4-hydroxyphenyl)quinolin-3-yl)(cyclopropyl)methanone hydrochloride compound 937: 1-(4-((trans)-4-aminocyclohexylamino)-6-(3-chloro-5-fluoro-4-hydroxyphenyl)quinolin-3-yl)-2-methylpropan-1-one dihydrochloride compound 938: 1-(4-((trans)-4-aminocyclohexylamino)-6-(3,5-difluoro-4-hydroxyphenyl)quinolin-3-yl)-2-methylpropan-1-one hydrochloride compound 939: 1-(4-((trans)-4-aminocyclohexylamino)-6-(3,5-dichloro-4-hydroxyphenyl)quinolin-3-yl)ethanone hydrochloride compound 940: 1-(4-((trans)-4-aminocyclohexylamino)-6-(3-chloro-4-hydroxy-5-methoxyphenyl)quinolin-3-yl)ethanone hydrochloride compound 941: cyclopropyl(6-(3,5-dichloro-4-hydroxyphenyl)-4-((trans)-4-(dimethylamino)cyclohexylamino)quinolin-3-yl)methanone dihydrobromide compound 942: 1-(6-(3,5-dichloro-4-hydroxyphenyl)-4-(4-((dimethylamino)methyl)phenylamino)quinolin-3-yl)ethanone dihydrobromide compound 943: 1-(6-(3-chloro-5-fluoro-4-hydroxyphenyl)-4-((trans)-4-((dimethylamino)methyl)cyclohexylamino)quinolin-3-yl)ethanone dihydrochloride compound 944: 1-(6-(3,5-dichloro-4-hydroxyphenyl)-4-((trans)-4-((dimethylamino)methyl)cyclohexylamino)quinolin-3-yl)ethanone dihydrochloride compound 945: 5-(3-acetyl-4-((1R,4R)-4-((dimethylamino)methyl)cyclohexyl)amino)quinolin-6-yl)pyridin-2(1H)-one hydrochloride Of these, preferable compounds are as follow;

Compound Nos:
55, 81, 96, 108, 116, 119, 133, 155, 156, 157(a), 157(b), 160, 165, 177, 179, 180, 181, 185(a), 185(b), 187, 192, 193, 201, 205, 212, 213, 214, 215, 219, 225(a), 225(b), 240, 243, 245, 246, 249, 250, 255, 256, 258, 259, 262, 263, 264, 266, 267, 269, 270, 276, 279, 280, 283, 284, 294, 295, 303, 305, 307, 309, 311, 313, 314, 315, 316, 318, 321, 323, 324, 325, 327, 332, 334, 335, 336, 339, 342, 343, 345, 347, 348, 349, 350, 351, 353, 356, 366, 374, 378, 379, 396, 397, 400, 409, 415, 416, 421, 425, 425, 447, 487, 493, 494, 495, 496, 497, 501, 502, 504, 505, 507, 508, 510, 511, 513, 517, 518, 519, 520, 523, 524, 527, 529, 530, 531, 532, 535, 537, 541, 542, 543, 548, 549, 554, 556, 558, 561, 562, 568, 570, 570, 571, 572, 573, 574, 575, 576, 577, 582, 584, 585, 587, 588, 592, 593, 594, 597, 598, 600, 601, 602, 604, 605, 608, 610, 613, 614, 615, 620, 623, 624, 626, 627, 628, 629, 631, 632, 634, 638, 639, 641, 644, 646, 647, 648, 649, 650, 651, 652, 655, 657, 658, 660, 661, 666, 667, 673, 681, 685, 693, 698, 699, 702, 703, 705, 706, 707, 709, 710, 711, 714, 715, 716, 720, 723, 724, 725, 729, 732, 733, 739, 740, 741, 742, 744, 745, 747, 748, 753, 754, 757, 758, 760, 761, 762, 763, 765, 766, 767, 768, 770, 771, 772, 773, 774, 775, 776, 777, 783, 785, 788, 789, 790, 792, 794, 797, 798, 799, 800, 801, 802, 804, 806, 807, 810, 812, 813, 814, 815, 817, 818, 824, 825, 829, 836, 843, 845, 846, 852, 864, 876, 878, 881, 886, 907, 909, 913, 915, 920, 921, 934, 936, 937, 938, 939, 940, 941, 942, 943 and 944.

(24) A pharmaceutical composition comprising as an active ingredient a compound or a pharmaceutically acceptable salt thereof of any one of the above-mentioned (1) to (23).

(25) An MELK inhibitor comprising as an active ingredient a compound or a pharmaceutically acceptable salt thereof of any one of the above-mentioned (1) to (23).

(26) An MELK-expression modulating agent comprising as an active ingredient a compound or a pharmaceutically acceptable salt thereof of any one of the above-mentioned (1) to (23).

(27) An antitumor agent comprising as an active ingredient a compound or a pharmaceutically acceptable salt thereof of any one of the above-mentioned (1) to (23).

(28) A therapeutic and/or preventive agent for a disease that involves overexpression of MELK, comprising as an active ingredient a compound or a pharmaceutically acceptable salt thereof of any one of the above-mentioned (1) to (23).

(29) The therapeutic and/or preventive agent of the above-mentioned (28), wherein the disease is cancer.

(30) The therapeutic and/or preventive agent of the above-mentioned (29), wherein the cancer is selected from the group consisting of breast cancer, lung cancer, bladder cancer, lymphoma, and uterine cancer.

(31) A method for treating and/or preventing a disease that involves overexpression of MELK, wherein an effective amount of a compound or a pharmaceutically acceptable salt thereof of the above-mentioned (1) to (23) is administered to a subject in need thereof.

(32) A compound or a pharmaceutically acceptable salt thereof any one of the above-mentioned (1) to (23) for use in a treatment and/or prevention of a disease that involves overexpression of MELK.

(33) Use of a compound or a pharmaceutically acceptable salt thereof of any one of the above-mentioned (1) to (23) in the manufacture of a therapeutic and/or preventive agent for a disease that involves overexpression of MELK.

Accordingly, it is an object of the present invention to provide a compound for inhibiting MELK activity.

It is another object of the present invention to provide an inhibitor having high inhibitory activity against MELK.

It is still another object of the present invention to provide a method for preparing the compound.

It is a further object of the present invention to provide a pharmaceutical composition including the compound, a pharmaceutically acceptable salt, hydrate, solvate, or isomer thereof.

DESCRIPTION OF EMBODIMENTS

Definition

Hereinafter, a compound represented by formula (I) will be referred to as compound (I). The same applies to the compounds represented by the other formula numbers. It must be noted that as used herein and in the appended claims, the singular forms "a", "an", and "the" include plural reference unless the context clearly dictates otherwise. Thus, for example, reference to a "group" is a reference to one or more groups.

In the definitions of each of the groups of formulas (I), (IA), and (IB),

The "$C_1$-$C_6$ alkyl", and the "$C_1$-$C_6$ alkyl portion" of "$C_1$-$C_6$ alkoxy", "$C_1$-$C_6$ alkylsulfinyl", and "$C_1$-$C_6$ alkylsulfonyl" mean a straight-chain or branched-chain "monovalent alkyl group (a group formed by removing one hydrogen atom from an alkane)" having one to six carbon atoms. Specifically, examples of the "$C_1$-$C_6$ alkyl" and the "$C_1$-$C_6$ alkyl portion" include methyl, ethyl, propyl, isopropyl, butyl, isobutyl, sec-butyl, tert-butyl, pentyl, 1-methylbutyl, 1-ethylpropyl, 2-methylbutyl, isopentyl, tert-pentyl, 1,2-dimethylpropyl, neopentyl, hexyl, 1-methylpentyl, 1-ethylbutyl, 2-methylpentyl, 3-methylpentyl, 4-methylpentyl, isohexyl, 1,1-dimethylbutyl, 1,2-dimethylbutyl, 1,3-dimethylbutyl, 1-isopropylpropyl, 1-ethyl-1-methylpropyl, 2,3-dimethylbutyl, 3,3-dimethylbutyl, 2,2-dimethylbutyl, 2-ethylbutyl, and 3-ethylbutyl, but are not limited thereto. In particular, for $R^5$ or $R^{5A}$, methyl, ethyl, propyl, isopropyl, isobutyl, or tert-butyl is preferred, and methyl, ethyl, propyl, isopropyl, or isobutyl is most preferred.

Hereinbelow, in this specification, the $C_1$-$C_6$ alkyl portion in each group has the same definition as the aforementioned "$C_1$-$C_6$ alkyl portion" unless otherwise noted.

Specific examples of "$C_1$-$C_6$ alkoxy" include methoxy, ethoxy, propoxy, isopropoxy, isobutyloxy, tert-butyloxy, butoxy, pentyloxy, and hexyloxy, but are not limited thereto. In particular, for $R^5$, ethoxy is preferred. In particular, for $R^4$, methoxy is preferred.

"$C_1$-$C_6$ alkoxycarbonyl" refers to a monovalent group in which the "$C_1$-$C_6$ alkoxy" binds to a carbonyl.

Preferred examples of "$C_1$-$C_6$ alkylsulfonyl" include methylsulfonyl, ethylsulfonyl, isopropylsulfonyl, and such, but are not limited thereto. In particular, methylsulfonyl is most preferred.

Preferred examples of "$C_1$-$C_6$ alkylsulfinyl" include methylsulfinyl, ethylsulfinyl, isopropylsulfinyl, and such, but are not limited thereto. In particular, methylsulfinyl is most preferred.

The term "halogen" means each of the fluorine, chlorine, bromine, and iodine atoms.

The term "halogenated $C_1$-$C_6$ alkyl" refers to "$C_1$-$C_6$ alkyl" substituted by the above-defined "halogen", wherein the $C_1$-$C_6$ alkyl has the same meaning as defined above. Preferred examples of "halogenated $C_1$-$C_6$ alkyl" trifluoromethyl and such, but are not limited thereto.

The term "$C_3$-$C_{10}$ cycloalkyl" refers to a saturated monocyclic hydrocarbon group having three to eight carbon atoms, and a bridged cyclic hydrocarbon group having four to ten carbon atoms which is formed when two or more saturated monocyclic hydrocarbons share two or more carbon atoms. Specifically, examples of "$C_3$-$C_{10}$ cycloalkyl" include saturated monocyclic hydrocarbon groups such as cyclopropyl, cyclobutyl, cyclopentyl, cyclohexyl, cycloheptyl, and cyclooctyl, and bridged cyclic hydrocarbon groups such as adamantyl, but are not limited thereto. In particular, for $R^5$ or $R^{5A}$, cyclopropyl or cyclopentyl is preferred, and cyclopropyl is most preferred. In particular, for $R^{10}$ or $R^{10A}$, cyclohexyl or adamantyl is preferred.

The term "$C_3$-$C_8$ cycloalkenyl" refers to an unsaturated monocyclic hydrocarbon group having three to eight carbon atoms. Specific examples include cyclopropenyl, cyclobutenyl, cyclopentenyl, cyclohexenyl, cycloheptenyl, and cyclooctenyl, but are not limited thereto. In particular, cyclohexenyl is preferred.

The term "aryl" refers to an aromatic hydrocarbon group having six to 14 carbon atoms, and a bicyclic or tricyclic group in which an aromatic hydrocarbon group and a three- to eight-membered cyclic hydrocarbon are condensed. Specific examples include phenyl, 1-naphthyl, 2-naphthyl, 1-anthryl, 2-anthryl, 9-anthryl, and 2,3-dihydro-1H-indenyl but are not limited thereto. In particular, phenyl or 2,3-dihydro-1H-indenyl is preferred.

The term "heterocyclic group" refers to an aromatic heterocyclic group and/or an aliphatic heterocyclic group.

The term "aromatic heterocyclic group" refers to a five-membered or six-membered monocyclic aromatic heterocyclic group comprising at least one heteroatom, preferably one to three heteroatoms, selected from a nitrogen atom, an oxygen atom, or a sulfur atom; and a bicyclic or tricyclic condensed aromatic heterocyclic group comprising at least one atom, preferably one to three atoms, selected from a nitrogen atom, an oxygen atom, or a sulfur atom formed by fusion of four- to eight-membered rings. Specific examples include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzooxazolyl, benzothiazolyl, isoindolyl, indolyl, 1H-indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, pyridopyrimidinyl, [1,2,4]triazolo[1,5-a]pyridyl, and pyrrolo[2,3-b]pyridyl, but are not limited thereto. Particularly, thienyl, pyrrolyl, imidazolyl, isoxazolyl, pyridyl, pyrimidinyl, pyrazolyl, 1H-indazolyl, benzimidazolyl, [1,2,4]triazolo[1,5-a]pyridyl, or pyrrolo[2,3-b]pyridyl is preferred. In particular, for $R^1$, pyridyl or benzimidazolyl is most preferable. In particular, for $R^3$ or $R^{3A}$, thienyl, pyridyl, pyrimidinyl, 1H-indazolyl, or benzimidazolyl is most preferred. In particular, for $R^5$ or $R^{5A}$, thienyl is most preferred. In particular, for $R^{10}$ or $R^{10A}$, pyridyl, pyrimidinyl, pyrazolyl, thienyl or imidazolyl is more preferred and pyridyl, pyrazolyl, or thienyl is most preferred.

The term "aliphatic heterocyclic group" refers to a three- to eight-membered monocyclic aliphatic heterocyclic group comprising at least one heteroatom, preferably one to three atoms, selected from a nitrogen atom, an oxygen atom, and a sulfur atom; a bicyclic or tricyclic condensed aliphatic heterocyclic group comprising at least one atom, preferably one to three atoms, selected from a nitrogen atom, an oxygen atom, and a sulfur atom formed by fusion of three- to eight-membered rings; and a spiro-cyclic or bridged-cyclic aliphatic heterocyclic group comprising at least one heteroatom, preferably one to three atoms, selected from a nitrogen atom, an oxygen atom, and a sulfur atom. A group of an aliphatic heterocyclic condensed with an aryl group or an aromatic heterocyclic is also included in the definition of "aliphatic heterocyclic group".

Specific examples include aziridinyl, azetidinyl, pyrrolidinyl, piperidino, piperidyl, azepanyl, 1,2,5,6-tetrahydropyridyl, 1,2,3,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, tetrahydrothiophenyl, tetrahydro-2H-thiopyranyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, 2,3-dihydrobenzimidazolyl, 2,3-dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, oxetanyl, 1,2-dihydropyridyl, 1-azabicyclo[2.2.2]octan-3-yl, 2,5-azabicyclo[2.2.1]heptyl, 8-azabicyclo[3.2.1]octyl, piperidin-4-spiro-3'-pyrrolidin-1-yl, and isoindolyl, but are not limited thereto. In particular, azetidinyl, pyrrolidinyl, piperidino, piperidyl, piperazinyl, morpholino, morpholinyl, 1,2-dihydropyridyl, 1,2,5,6-tetrahydropyridyl, 1-azabicyclo[2.2.2]octan-3-yl, 2,5-azabicyclo[2.2.1]heptyl, 8-azabicyclo[3.2.1]octyl, 2,3-dihydrobenzimidazolyl, or piperidin-4-Spiro-3'-pyrrolidin-1-yl is preferred. In particular, for $R^3$ or $R^{3A}$, morpholino, morpholinyl, 1,2-dihydropyridyl, 1-azabicyclo[2.2.2]octan-3-yl, 1,2,5,6-tetrahydropyridyl, or 2,3-dihydrobenzimidazolyl is most preferred. In particular, for $R^{10}$ or $R^{10A}$, piperidyl, pyrrolidinyl, or piperazinyl is more preferred, and piperidyl or piperazinyl is most preferred.

"Heterocyclic group formed with an adjacent nitrogen atom" refers to a group formed by removing a hydrogen atom on a nitrogen atom in heterocycles of a three- to eight-membered monocyclic heterocyclic group comprising at least one nitrogen atom, preferably one to two atoms (the monocyclic heterocyclic group may contain other nitrogen atoms, oxygen atoms, or sulfur atoms); a bicyclic or tricyclic condensed heterocyclic group comprising at least one nitrogen atom, preferably one to two atoms, formed by fusion of three- to eight-membered rings (the condensed heterocyclic group may contain other nitrogen atoms, oxygen atoms, or sulfur atoms); and a spiro-cyclic heterocyclic group comprising at least one nitrogen atom, preferably one to two atoms (the monocyclic heterocyclic group may contain other nitrogen atoms, oxygen atoms, or sulfur atoms). Specific examples include 1-aziridinyl, 1-azetidinyl, 1-pyrrolidinyl, piperidino, 1-azepanyl, 1-perhydroazepinyl, 1-perhydroazocinyl, 1-pyrrolyl, 1-imidazolidinyl, 1-imidazolyl, 1-pyrazolidinyl, 1-pyrazolinyl, 1-pyrazolyl, 1-piperadinyl, 1-homopiperadinyl, 1-oxazolidinyl, morpholino, thiomorpholino, 1-dihydroindolyl, 2-dihydroisoindolyl, 1-indolyl, 2-isoindolyl, 1-tetrahydroquinolyl, 2-tetrahydroisoquinolyl, and piperidin-4-spiro-3'-pyrrolidin-1-yl, but are not limited thereto. In particular, piperidino, 1-piperazinyl, and piperidin-4-spiro-3'-pyrrolidin-1-yl are preferred.

"Aromatic heterocyclic-($C_1$-$C_6$ alkylenyl)" and "aliphatic heterocyclic-($C_1$-$C_6$ alkylenyl)" refer to a monovalent group in which an aromatic heterocyclic or an aliphatic heterocyclic binds to a $C_1$-$C_6$ alkylene portion. The "$C_1$-$C_6$ alkylene portion" of "aromatic heterocyclic-($C_1$-$C_6$ alkylenyl)" and "aliphatic heterocyclic-($C_1$-$C_6$ alkylenyl)" means a straight-chain or branched-chain "divalent alkyl group (a group formed by removing two hydrogen atoms from an alkane)" having one to six carbon atoms. Specific examples include groups formed by removing a single hydrogen atom from each of the groups indicated as examples for the aforementioned "$C_1$-$C_6$ alkyl". The "aromatic heterocyclic group portion" of aromatic heterocyclic-($C_1$-$C_6$ alkylenyl) has the same meaning as the aforementioned aromatic heterocyclic group, and specific examples include groups indicated as examples for the aforementioned aromatic heterocyclic group. The "aliphatic heterocyclic group portion" of aliphatic heterocyclic-($C_1$-$C_6$ alkylenyl) has the same meaning as the aforementioned aliphatic heterocyclic group, and specific examples include groups indicated as examples for the aforementioned aliphatic heterocyclic group.

Hereinbelow, in this specification, the "—($C_1$-$C_6$ alkylenyl)" in each group has the same definition as the aforementioned "—($C_1$-$C_6$ alkylenyl)" unless otherwise noted.

Preferred examples of "aromatic heterocyclic-($C_1$-$C_6$ alkylenyl)" include aromatic heterocyclic methyl, aromatic heterocyclic ethyl, and aromatic heterocyclic propyl, and more preferred examples include imidazolylmethyl, imidazolylethyl, and imidazolylpropyl, and most preferred examples include imidazolylethyl, but are not limited thereto.

Preferred examples of "aliphatic heterocyclic-($C_1$-$C_6$ alkylenyl)" include aliphatic heterocyclic methyl, aliphatic heterocyclic ethyl, and aliphatic heterocyclic propyl, and more preferred examples include morpholinomethyl, morpholinoethyl, morpholinopropyl, piperadinylmethyl, piperadinylethyl, piperadinylpropyl, piperidylmethyl, piperidylethyl, piperidylpropyl, pyrrolidinylmethyl, pyrrolidinylethyl, and pyrrolidinylpropyl and most preferred examples include morpholinopropyl, pyrrolidinylmethyl, piperadinylmethyl, piperadinylethyl, and piperidylmethyl, but are not limited thereto.

"Aromatic heterocyclic-($C_1$-$C_6$ alkylenyl)amino" and "aliphatic heterocyclic-($C_1$-$C_6$ alkylenyl)amino" refer to a group in which a hydrogen atom of an amino group is replaced with the aforementioned "aromatic heterocyclic-($C_1$-$C_6$ alkylenyl)" or "aliphatic heterocyclic-($C_1$-$C_6$ alkylenyl)".

"Aliphatic heterocyclic-amino" refers to a group in which a hydrogen atom of an amino group is replaced with the aforementioned aliphatic heterocyclic group.

"$C_1$-$C_6$ aminoalkyl" refers to a group in which any hydrogen atom of the aforementioned alkyl group is replaced with an amino group.

"$C_1$-$C_6$ alkylamino" and "di($C_1$-$C_6$ alkyl)amino" refer to a group in which one and two hydrogen atoms, respectively of an amino group is/are replaced with the aforementioned $C_1$-$C_6$ alkyl. Herein, a hydrogen atom in the $C_1$-$C_6$ alkyl portion of the "$C_1$-$C_6$ alkylamino" and "di($C_1$-$C_6$ alkyl)amino" can be a deuterium.

"$C_2$-$C_7$ alkanoylamino" and "$C_1$-$C_6$ alkylsulfonylamino" refer to a group in which one hydrogen atom of an amino group is replaced with "$C_2$-$C_7$ alkanoyl" and "$C_1$-$C_6$ alkylsulfonyl", respectively.

"$C_1$-$C_6$ alkylamino-($C_1$-$C_6$ alkylenyl)", "di($C_1$-$C_6$ alkyl)amino-($C_1$-$C_6$ alkylenyl)", and "$C_2$-$C_7$ alkanoylamino-($C_1$-$C_6$ alkylenyl)" refer to a group in which "$C_1$-$C_6$ alkylamino", "di($C_1$-$C_6$ alkyl)amino", and "$C_2$-$C_7$ alkanoylamino", respectively bind to "($C_1$-$C_6$ alkylenyl)".

"Di($C_1$-$C_6$ alkyl)amino-($C_1$-$C_6$ alkylenyloxy)" refers to a group in which "di($C_1$-$C_6$ alkyl)amino" binds to "($C_1$-$C_6$ alkylenyloxy)".

The "$C_1$-$C_6$ alkylene portion" of "$C_1$-$C_6$ alkylamino-($C_1$-$C_6$ alkylenyl)", "di($C_1$-$C_6$ alkyl)amino-($C_1$-$C_6$ alkylenyl)", "$C_2$-$C_7$ alkanoylamino-($C_1$-$C_6$ alkylenyl)", and "di($C_1$-$C_6$ alkyl)amino-($C_1$-$C_6$ alkylenyloxy)" means a straight-chain or branched-chain "divalent alkyl group (a group formed by removing two hydrogen atoms from an alkane)" having one to six carbon atoms. Specific examples include groups produced by removing a single hydrogen atom from each of the groups indicated as examples for the aforementioned "$C_1$-$C_6$ alkyl".

The "$C_1$-$C_6$ alkyl portion" of "$C_1$-$C_6$ aminoalkyl", "$C_1$-$C_6$ alkylamino", "di($C_1$-$C_6$ alkyl)amino", "$C_1$-$C_6$ alkylamino-($C_1$-$C_6$ alkylenyl)", "di($C_1$-$C_6$ alkyl)amino-($C_1$-$C_6$ alkylenyl)", "$C_2$-$C_7$ alkanoylamino-($C_1$-$C_6$ alkylenyl)", and "di($C_1$-$C_6$ alkyl)amino-($C_1$-$C_6$ alkylenyloxy)" has the same meaning as the aforementioned $C_1$-$C_6$ alkyl portion, and specific examples include groups indicated as examples for the aforementioned $C_1$-$C_6$ alkyl portion. The two alkyl portions of di($C_1$-$C_6$ alkyl)amino may be the same or different.

"Di($C_1$-$C_6$ alkyl)amino-($C_1$-$C_6$ alkylenyl)carbonyl" refers to a monovalent group in which the aforementioned "di($C_1$-$C_6$ alkyl)amino-($C_1$-$C_6$ alkylenyl)" binds to a carbonyl.

"Di($C_1$-$C_6$ alkyl)amino-($C_1$-$C_6$ alkylenyl)aminocarbonyl" refers to a monovalent group in which a group in which one hydrogen atom of an amino is replaced with the aforementioned "di($C_1$-$C_6$ alkyl)amino-($C_1$-$C_6$ alkylenyl)" binds to a carbonyl.

"$C_1$-$C_6$ aminoalkylcarbonyl" refers to a monovalent group in which the aforementioned "$C_1$-$C_6$ aminoalkyl" binds to a carbonyl.

"$C_1$-$C_6$ aminoalkylcarbonylamino" refers to a monovalent group in which one hydrogen atom of an amino is replaced with the aforementioned "$C_1$-$C_6$ aminoalkylcarbonyl".

"Di($C_1$-$C_6$ alkyl)amino-($C_1$-$C_6$ alkylenyl)carbonyl" refers to a monovalent group in which the aforementioned "di($C_1$-$C_6$ alkyl)amino-($C_1$-$C_6$ alkylenyl)" binds to a carbonyl.

"Di($C_1$-$C_6$ alkyl)amino-($C_1$-$C_6$ alkylenyl)carbonylamino" refers to a monovalent group in which one hydrogen atom of an amino group is replaced with the aforementioned "di($C_1$-$C_6$ alkyl)amino-($C_1$-$C_6$ alkylenyl)carbonyl".

"Aliphatic heterocyclic group-carbonyl" refers to a monovalent group in which the aforementioned "aliphatic heterocyclic group" binds to a carbonyl.

"Aliphatic heterocyclic group-carbonylamino" refers to a monovalent group in which one hydrogen atom of an amino group is replaced with the aforementioned "aliphatic heterocyclic group-carbonyl".

"Di($C_1$-$C_6$ alkyl)amino-($C_1$-$C_6$ alkylenyl)amino" refers to a monovalent group in which one hydrogen atom of an amino group is replaced with the aforementioned "di($C_1$-$C_6$ alkyl)amino-($C_1$-$C_6$ alkylenyl)".

"$C_1$-$C_6$ hydroxyalkyl" refers to a group in which any hydrogen atom of an alkyl group is replaced with a hydroxy group.

"$C_1$-$C_6$ aminoalkyloxy" refers to a monovalent group in which a hydrogen atom of a hydroxy group is replaced with the aforementioned "$C_1$-$C_6$ aminoalkyl".

Preferred examples of "$C_1$-$C_6$ aminoalkyl" include aminomethyl, aminoethyl, aminopropyl, 1-amino-1-methylethyl, and 3-amino-2-methylpropyl.

Preferred examples of "$C_1$-$C_6$ alkylamino-($C_1$-$C_6$ alkylenyl)" include methylaminomethyl, methylaminoethyl, ethylaminoethyl, and ethylaminopropyl.

Preferred examples of "di($C_1$-$C_6$ alkyl)amino-($C_1$-$C_6$ alkylenyl)" include dimethylaminomethyl, (methyl)(ethyl)aminomethyl, diethylaminomethyl, de(t-butyl)aminomethyl, dimethylaminoethyl, diethylaminoethyl, dimethylaminopropyl, and diethylaminopropyl.

Preferred examples of "$C_2$-$C_7$ alkanoylamino-($C_1$-$C_6$ alkylenyl)" include acetylaminomethyl, acetylaminoethyl, acetylaminopropyl, and 3-(acetylamino)-2-methylpropyl.

Preferred examples of "di($C_1$-$C_6$ alkyl)amino-($C_1$-$C_6$ alkylenyloxy)" include di($C_1$-$C_6$ alkyl)aminomethyloxy, di($C_1$-$C_6$ alkyl)aminoethyloxy, and di($C_1$-$C_6$ alkyl)aminopropyloxy, and more preferred examples include dimethylaminoethyloxy and dimethylaminopropyloxy.

Substituents of the optionally substituted $C_1$-$C_6$ alkyl, the optionally substituted $C_1$-$C_6$ alkoxy, the optionally substituted $C_1$-$C_6$ alkylsulfinyl, the optionally substituted $C_1$-$C_6$ alkylsulfonyl, the optionally substituted $C_2$-$C_7$ alkanoylamino-($C_1$-$C_6$ alkylenyl), the optionally substituted $C_1$-$C_6$ alkylamino-($C_1$-$C_6$ alkylenyl), and the optionally substituted di($C_1$-$C_6$ alkyl)amino-($C_1$-$C_6$ alkylenyl) may be the same or different, and may be one to an allowable number of substituents for example, preferably one to three substituents. Specific examples include halogen, hydroxy, cyano, $C_1$-$C_6$ alkoxy, trifluoromethoxy, amino, $C_1$-$C_6$ alkylamino, di($C_1$-$C_6$ alkyl)amino, $C_1$-$C_6$ alkylsulfonylamino, carbamoyl, sulfamoyl, benzylureide, ($C_1$-$C_6$ alkyl)ureide, $C_2$-$C_7$ alkanoylamino, aliphatic heterocyclic group which may be substituted with $C_1$-$C_6$ alkyl (the $C_1$-$C_6$ alkyl has the same meaning as the aforementioned $C_1$-$C_6$ alkyl), dimethylaminopropylaminocarbonyl, aminocyclohexylaminocarbonyl, oxo, and aliphatic heterocyclic-carbonyl which may be substituted with $C_1$-$C_6$ alkyl (the $C_1$-$C_6$ alkyl has the same meaning as the aforementioned $C_1$-$C_6$ alkyl) but are not limited thereto.

Substituents of the optionally substituted $C_3$-$C_{10}$ cycloalkyl, the optionally substituted $C_3$-$C_8$ cycloalkenyl, the optionally substituted aryl, the optionally substituted aromatic heterocyclic group, the optionally substituted aliphatic heterocyclic group, the optionally substituted aromatic heterocyclic-($C_1$-$C_6$ alkylenyl), the optionally substituted aliphatic heterocyclic-($C_1$-$C_6$ alkylenyl), the optionally substituted heterocyclic group formed with an adjacent nitrogen atom, and the optionally substituted di($C_1$-$C_6$ alkyl)amino-($C_1$-$C_6$ alkylenyloxy) may be the same or different, and may be one to an allowable number of substituents for example, preferably one to three substituents. Specific examples include halogen,
hydroxy,
cyano,
$C_1$-$C_6$ alkyl,
$C_1$-$C_6$ alkoxy,
carboxyl,
$C_1$-$C_6$ alkoxycarbonyl,
trifluoromethoxy,
difluoromethoxy,
trifluoromethyl,
difluoromethyl,
amino,
$C_1$-$C_6$ alkylamino (wherein, $C_1$-$C_6$ alkyl may have hydroxy as a substituent),
di($C_1$-$C_6$ alkyl)amino,
diallylamino,
$C_1$-$C_6$ alkylsulfonylamino,
$C_2$-$C_7$ alkanoylamino,
carbamoyl,
sulfamoyl,
benzylureide,
($C_1$-$C_6$ alkyl)ureide,
$C_1$-$C_6$ hydroxyalkyl,
$C_1$-$C_6$ aminoalkyl,
$C_1$-$C_6$ aminoalkylenyloxy,
$C_1$-$C_6$ alkylamino-($C_1$-$C_6$ alkylenyl)(wherein, $C_1$-$C_6$ alkyl may have halogen as a substituent),
di($C_1$-$C_6$ alkyl)amino-($C_1$-$C_6$ alkylenyl)(wherein, either $C_1$-$C_6$ alkyl or $C_1$-$C_6$ alkylenyl may have hydroxy or cyano as a substituent, and wherein hydrogen atom of $C_1$-$C_6$ alkyl may be substituted with deuterium atom),
di($C_1$-$C_6$ alkyl)amino-($C_1$-$C_6$ alkylenyl)oxy,
di($C_1$-$C_6$ alkyl)amino-($C_1$-$C_6$ alkylenyl)amino,
di($C_1$-$C_6$ alkyl)amino-($C_1$-$C_6$ alkylenyl)carbonyl,
di($C_1$-$C_6$ alkyl)amino-($C_1$-$C_6$ alkylenyl)carbonylamino,
di($C_1$-$C_6$ alkyl)amino-($C_1$-$C_6$ alkylenyl)aminocarbonyl,
aliphatic heterocyclic group (wherein, the aliphatic heterocyclic group may have $C_1$-$C_6$ alkyl, amino, hydroxy, halogen, di($C_1$-$C_6$ alkyl)amino, $C_1$-$C_6$ alkylamino, or $C_1$-$C_6$ alkoxy as a substituent),
aliphatic heterocyclic-($C_1$-$C_6$ alkylenyl)(wherein, the aliphatic heterocyclic group may have $C_1$-$C_6$ alkyl, amino, hydroxy, $C_1$-$C_6$ hydroxyalkyl, $C_1$-$C_6$ alkoxy, $C_1$-$C_6$ alkylamino, di($C_1$-$C_6$ alkyl)amino, or halogen as a substituent),
an aliphatic heterocyclic-carbonyl (wherein, the aliphatic heterocyclic may have $C_1$-$C_6$ alkyl as a substituent),
an aliphatic heterocyclic-carbonylamino (wherein, the aliphatic heterocyclic may have $C_1$-$C_6$ alkyl as a substituent),
an aliphatic heterocyclic-amino (wherein, the aliphatic heterocyclic may have $C_1$-$C_6$ alkyl or amino as a substituent),
aliphatic heterocyclic-($C_1$-$C_6$ alkylenyl)amino,
aliphatic heterocyclic-($C_1$-$C_6$ alkylenyl)oxy,
aromatic heterocyclic-($C_1$-$C_6$ alkylenyl),
aliphatic heterocyclic-sulfonyl which may be substituted with $C_1$-$C_6$ alkyl,
$C_1$-$C_6$ aminoalkylcarbonylamino,
hydroxyphenyl,
dimethylaminocarbonyl,
aminocyclohexylaminocarbonyl,
methylpiperazinylphosphonyl,
$C_3$-$C_8$ cycloalkyl (wherein, the cycloalkyl may have amino, $C_1$-$C_6$ alkylamino, or $C_1$-$C_6$ aminoalkyl as a substituent), and
oxo, but are not limited thereto.

In particular, substituents selected from Substituent Group A or B as more preferred substituents in formula (I) are the following.

Substituent Group A: a halogen;
Substituent Group B:
a halogen,
a hydroxy,
a cyano,
a $C_1$-$C_6$ alkyl,
a $C_1$-$C_6$ alkoxy,
a trifluoromethoxy,
an amino,
a $C_1$-$C_6$ alkylamino,
a di($C_1$-$C_6$ alkyl)amino,
a $C_1$-$C_6$ alkylsulfonylamino,
a $C_1$-$C_6$ aminoalkyl,
an aliphatic heterocyclic group (wherein, the aliphatic heterocyclic group may have a $C_1$-$C_6$ alkyl, an amino, a $C_1$-$C_6$ alkylamino, or a $C_1$-$C_6$ alkoxy as a substituent),
an aliphatic heterocyclic-($C_1$-$C_6$ alkylenyl)(wherein, the aliphatic heterocyclic may have a $C_1$-$C_6$ alkyl, an amino, a hydroxy, a $C_1$-$C_6$ hydroxyalkyl, a $C_1$-$C_6$ alkoxy, or a halogen as a substituent),
an aliphatic heterocyclic-amino (wherein, the aliphatic heterocyclic may have a $C_1$-$C_6$ alkyl or an amino as a substituent),
a $C_1$-$C_6$ alkylamino-($C_1$-$C_6$ alkylenyl),
a di($C_1$-$C_6$ alkyl)amino-($C_1$-$C_6$ alkylenyl)(wherein, either $C_1$-$C_6$ alkyl or $C_1$-$C_6$ alkylenyl may have hydroxy or cyano as a substituent, and wherein hydrogen atom of $C_1$-$C_6$ alkyl may be substituted with deuterium atom),
a carbamoyl,
a sulfamoyl,
a ($C_1$-$C_6$ alkyl)ureide,
a benzylureide,
a dimethylaminopropylaminocarbonyl,
an aminocyclohexylaminocarbonyl,
a $C_1$-$C_6$ aminoalkylcarbonylamino,
a di($C_1$-$C_6$ alkyl)amino-($C_1$-$C_6$ alkylenyl)carbonylamino,
a di($C_1$-$C_6$ alkyl)amino-($C_1$-$C_6$ alkylenyl)oxy,
a di($C_1$-$C_6$ alkyl)amino-($C_1$-$C_6$ alkylenyl)amino,
an aliphatic heterocyclic-carbonylamino,
a $C_2$-$C_7$ alkanoylamino,
a $C_1$-$C_6$ aminoalkylenyloxy,
a cyclohexyl (wherein, the cyclohexyl may have an amino or a $C_1$-$C_6$ aminoalkyl as a substituent),
and an oxo.

Furthermore, substituents selected from Substituent Groups C to I as more preferred substituents in formulas (IA) and (IB) are the following.

Substituent Group C: a halogen, a hydroxy, a $C_1$-$C_6$ alkoxy, and a di($C_1$-$C_6$ alkyl) amino;

Substituent Group D: a hydroxy, a $C_1$-$C_6$ alkyl, a $C_1$-$C_6$ aminoalkyl, an aliphatic heterocyclic-($C_1$-$C_6$ alkylenyl)(wherein, the aliphatic heterocyclic may have an amino, a hydroxy, a $C_1$-$C_6$ hydroxyalkyl, a $C_1$-$C_6$ alkoxy, or a halogen as a substituent), a $C_1$-$C_6$ alkylamino-($C_1$-$C_6$ alkylenyl), a di($C_1$-$C_6$ alkyl)amino-($C_1$-$C_6$ alkylenyl)(wherein, either $C_1$-$C_6$ alkyl may have a hydroxy or a cyano as a substituent, and wherein hydrogen atom of $C_1$-$C_6$ alkyl may be substituted with deuterium atom), an amino, a $C_1$-$C_6$ alkylamino, a di($C_1$-$C_6$ alkyl)amino, a $C_1$-$C_6$ aminoalkylcarbonylamino, a di($C_1$-$C_6$ alkyl)amino($C_1$-$C_6$ alkylenyl)carbonylamino, an aliphatic heterocyclic group (wherein, the aliphatic heterocyclic group may have a $C_1$-$C_6$ alkoxy as a substituent), and an aliphatic heterocyclic-carbonylamino;

Substituent Group E: a halogen, a di($C_1$-$C_6$ alkyl)amino-($C_1$-$C_6$ alkylenyl)(wherein, the $C_1$-$C_6$ alkylenyl may have a hydroxy as a substituent), an amino, a $C_2$-$C_7$ alkanoylamino, a di($C_1$-$C_6$ alkyl)amino, a $C_1$-$C_6$ aminoalkyl, and an aliphatic heterocyclic-($C_1$-$C_6$ alkylenyl) (wherein, the aliphatic heterocyclic may have a $C_1$-$C_6$ alkyl as a substituent);

Substituent Group F: a carbamoyl, an amino, a $C_1$-$C_6$ aminoalkyl, a di($C_1$-$C_6$ alkyl)amino-($C_1$-$C_6$ alkylenyl), a $C_1$-$C_6$ alkylamino-($C_1$-$C_6$ alkylenyl), an aliphatic heterocyclic-($C_1$-$C_6$ alkylenyl), and an aliphatic heterocyclic group which may be substituted with a $C_1$-$C_6$ alkyl;

Substituent Group G: a halogen, a hydroxy, a cyano, a $C_1$-$C_6$ alkyl, a $C_1$-$C_6$ alkoxy, a trifluoromethoxy, a $C_1$-$C_6$ aminoalkyl, a $C_1$-$C_6$ alkylamino-($C_1$-$C_6$ alkylenyl), a di($C_1$-$C_6$ alkyl)amino-($C_1$-$C_6$ alkylenyl), an amino, a $C_1$-$C_6$ alkylsulfonylamino, a carbamoyl, a sulfamoyl, a ($C_1$-$C_6$ alkyl) ureide, a benzylureide, and an aliphatic heterocyclic group;

Substituent Group H: a halogen, a cyano, a $C_1$-$C_6$ alkyl, a $C_1$-$C_6$ alkoxy, an amino, a carbamoyl, a dimethylaminopropylaminocarbonyl, and an aminocyclohexylaminocarbonyl;

Substituent Group I: an aliphatic heterocyclic group (wherein, the aliphatic heterocyclic group may have a $C_1$-$C_6$ alkyl, an amino group, or a $C_1$-$C_6$ alkylamino as a substituent); an aliphatic heterocyclic-($C_1$-$C_6$ alkylenyl); an aliphatic heterocyclic-amino (wherein, the aliphatic heterocyclic may have a $C_1$-$C_6$ alkyl or an amino as a substituent); a di($C_1$-$C_6$ alkyl)amino-($C_1$-$C_6$ alkylenyl); a $C_1$-$C_6$ aminoalkylenyloxy; a di($C_1$-$C_6$ alkyl)amino-($C_1$-$C_6$ alkylenyl)oxy; a di($C_1$-$C_6$ alkyl)amino-($C_1$-$C_6$ alkylenyl)amino; a cyclohexyl (wherein, the cyclohexyl may have an amino or a $C_1$-$C_6$ aminoalkyl as a substituent).

The "$C_1$-$C_6$ alkyl portion" of a ($C_1$-$C_6$ alkyl)ureide, a $C_1$-$C_6$ hydroxyalkyl, a $C_1$-$C_6$ alkylamino, a di($C_1$-$C_6$ alkyl)amino, a $C_2$-$C_7$ alkanoylamino, and a $C_1$-$C_6$ alkylsulfonylamino of each substituent exemplified herein has the same meaning as the aforementioned $C_1$-$C_6$ alkyl portion, and specific examples include the groups and such indicated as examples for the aforementioned $C_1$-$C_6$ alkyl portion. The two alkyl portions of di($C_1$-$C_6$ alkyl)amino may be the same or different.

Preferred examples of "($C_1$-$C_6$ alkyl)ureide" include methylureide and ethylureide, but are not limited thereto.

Preferred examples of "$C_1$-$C_6$ hydroxyalkyl" include hydroxymethyl and hydroxyethyl, but are not limited thereto.

Preferred examples of "$C_1$-$C_6$ alkylsulfonylamino" include methylsulfonylamino, ethylsulfonylamino, and isopropylsulfonylamino, but are not limited thereto.

Preferred examples of "$C_1$-$C_6$ alkylamino" include methylamino and ethylamino, but are not limited thereto.

Preferred examples of "di($C_1$-$C_6$ alkyl)amino" include dimethylamino and diethylamino, but are not limited thereto.

Specific examples of "$C_2$-$C_7$ alkanoylamino" include acetylamino, propionylamino, butyrylamino, isobutyrylamino, valerylamino, isovalerylamino, and hexanoylamino, but are not limited thereto. In particular, acetylamino is preferred.

In addition, more preferred examples among each of the Substituent Groups are shown below.

As Substituent C, a dimethylamino is most preferred.

As Substituent D, a methyl, hydroxy, an aminomethyl, a dimethylaminomethyl, $(CD_3)_2NCH_2$— (wherein D means deuterium atom), an ethylmethylaminomethyl, a diethylaminomethyl, a di-tert-butylaminomethyl, a dimethylaminoethyl, an amino, a methylamino, a dimethylamino, a diethylamino, a methylaminomethyl, a cyanomethyl(methyl)aminomethyl, a 2-hydroxyethyl(methyl)aminomethyl, a pyrrolidinyl, a methoxypyrrolidinyl, a pyrrolidinylmethyl, a pyrrolidinylethyl, a piperazinylmethyl, a fluoropyrrolidinylmethyl, a hydroxypyrrolidinylmethyl, a hydroxymethylpyrrolidinylmethyl, a methoxypyrrolidinylmethyl, an aminopiperidinylmethyl, a dimethylaminomethylcarbonylamino, a 1-aminoethylcarbonylamino, a 1-aminoisobutylcarbonylamino, or a pyrrolidinylcarbonylamino is most preferred.

As Substituent E, a halogen, an aminomethyl, a 1-amino-1-methylethyl, a 2-(dimethylamino)-1-hydroxyethyl, a dimethylaminomethyl, a dimethylaminoethyl, an acetylamino, a dimethylamino, a methylpiperazinylmethyl, a pyrrolidinylmethyl, a pyrrolidinylethyl, or a methylpiperazinylethyl is more preferred, and a dimethylaminomethyl is most preferred.

As Substituent F, a carbamoyl, an amino, an aminomethyl, a methylaminomethyl, a dimethylaminomethyl, a 1-(dimethylamino)ethyl, a pyrrolidinylmethyl, a pyrrolidinylethyl, a morpholino, a morpholinomethyl, or a 4-methylpiperazinyl is preferred, and a dimethylaminomethyl, a 1-(dimethylamino)ethyl, a pyrrolidinylmethyl, a morpholinomethyl, or a 4-methylpiperazinyl is most preferred.

As Substituent G, a halogen, a hydroxy, a cyano, a methyl, a methoxy, an ethoxy, a trifluoromethoxy, an amino, a methylsulfonylamino, a carbamoyl, a sulfamoyl, a dimethylaminomethyl, a methylureide, a benzylureide, or a piperazinyl is more preferred, and a halogen, a hydroxy, a methoxy, an ethoxy, or a trifluoromethoxy is most preferred.

As Substituent H, a halogen, a cyano, a methyl, a methoxy, an amino, a carbamoyl, or a dimethylaminopropylaminocarbonyl, or an aminocyclohexylaminocarbonyl is preferred, and a cyano is most preferred.

As Substituent I, a dimethylaminomethyl, a piperazinyl, a methylpiperazinyl, a piperidyl, methylpiperidyl, an aminopiperidyl, a methylaminopiperidyl, a methylpyrrolidinyl, a pyrrolidinylmethyl, an aminopyrrolidinyl, a methylaminopyrrolidinyl, a dimethylaminopyrrolidinyl, a piperidylamino, a pyrrolidinylamino, an aminocyclohexyl, a methylaminocyclohexyl, a 2-aminoethoxy, a 2-(dimethylamino)ethoxy, 2-(dimethylamino)ethylamino, a 2-pyrrolidinylethyl, or a dimethylaminoethyloxy is most preferred.

Pharmaceutically acceptable salts of compound (I) mean, for example, pharmaceutically acceptable acid-added salts, amino acid-added salts, or such. Specific examples of the pharmaceutically acceptable acid-added salts of compound (I) include inorganic acid salts such as hydrochloride, sulfate, and phosphate, organic acid salts such as acetate, maleate, fumarate, citrate, and such, and examples of pharmaceutically acceptable amino acid-added salts include addition salts such as of lysine, glycine, phenylalanine, asparagine acid, or glutamic acid.

Examples of diseases involving overexpression of MELK, which may be treated and/or prevented by pharmaceutical compositions comprising as an active ingredient a compound or a pharmaceutically acceptable salt thereof of the present invention, include cancer, breast cancer, bladder cancer, cervical cancer, cholangiocellular carcinoma, chronic myeloid leukemia (CML), colorectal cancer, endometriosis, esophagus cancer, gastric cancer, liver cancer, non-small cell lung cancer (NSCLC), lymphoma, osteosarcoma, ovarian cancer, pancreatic cancer, prostate cancer, renal carcinoma and small cell lung cancer (SCC), but are not limited thereto. Examples of the cancer which may be treated and/or prevented include breast cancer, bladder cancer, cervical cancer, cholangiocellular carcinoma, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC, but are not limited thereto.

Compound (I) includes compounds which may have stereoisomers such as regioisomers, geometrical isomers, optical isomers, and tautomers, and all possible isomers including them and mixtures thereof are included in the present invention.

When a salt of compound (I) is to be obtained, if compound (I) is obtained in the form of a salt, it may be purified as it is, and if it is obtained in a free form, compound (I) can be isolated and purified by dissolving or suspending it in an appropriate solvent, and adding an acid or amino acid to form a salt.

Furthermore, compound (I) and pharmaceutically acceptable salts thereof may exist in a form of adducts with water or various other solvents, and these adducts are also included in the present invention.

Specific examples of Compound (I) of the present invention are shown in Table 1. However, compounds of the present invention are not limited thereto. (Example No. corresponds to above mentioned compound number.)

TABLE 1

| No. | Structure | Compound Name | ESI MS (m/z) |
|---|---|---|---|
| 1 | 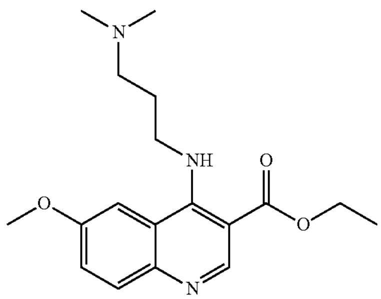 [SMILES: CCOC(=O)c1cnc2ccc(OC)cc2c1NCCCN(C)C] | ethyl 4-(3-(dimethylamino)propylamino)-6-methoxyquinoline-3-carboxylate | 331 |
| 2 | 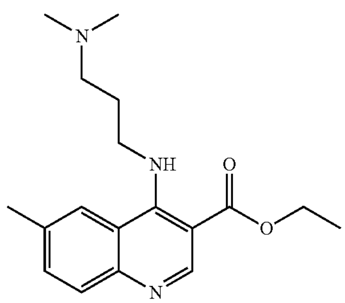 [SMILES: CCOC(=O)c1cnc2ccc(C)cc2c1NCCCN(C)C] | ethyl 4-(3-(dimethylamino)propylamino)-6-methylquinoline-3-carboxylate | 315 |
| 3 | 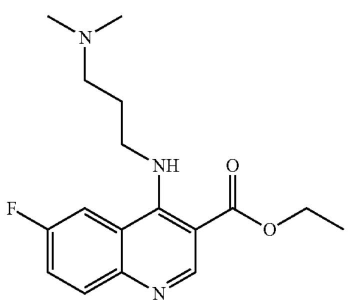 [SMILES: CCOC(=O)c1cnc2ccc(F)cc2c1NCCCN(C)C] | ethyl 4-(3-(dimethylamino)propylamino)-6-fluoroquinoline-3-carboxylate | 319 |
| 4 | 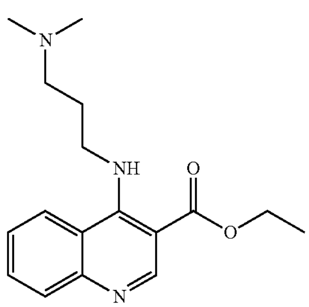 [SMILES: CCOC(=O)c1cnc2ccccc2c1NCCCN(C)C] | ethyl 4-(3-(dimethylamino)propylamino)quinoline-3-carboxylate | 301 |

TABLE 1-continued

| No. | Structure | Compound Name | ESI MS (m/z) |
|---|---|---|---|
| 5 | 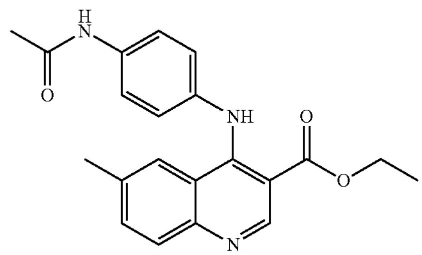 [SMILES: CCOC(=O)c1cnc2ccc(C)cc2c1Nc1ccc(NC(C)=O)cc1] | ethyl 4-(4-acetamidophenylamino)-6-methylquinoline-3-carboxylate | 363 |
| 6 | 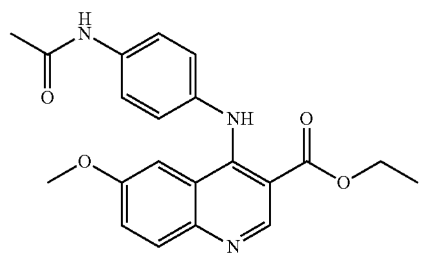 [SMILES: CCOC(=O)c1cnc2ccc(OC)cc2c1Nc1ccc(NC(C)=O)cc1] | ethyl 4-(4-acetamidophenylamino)-6-methoxyquinoline-3-carboxylate | 379 |
| 7 | 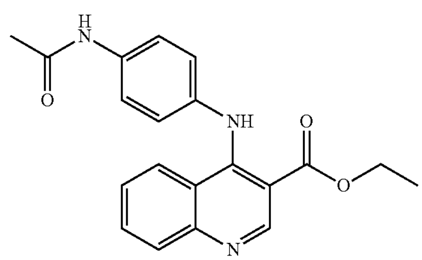 [SMILES: CCOC(=O)c1cnc2ccccc2c1Nc1ccc(NC(C)=O)cc1] | ethyl 4-(4-acetamidophenylamino)quinoline-3-carboxylate | 349 |
| 8 | 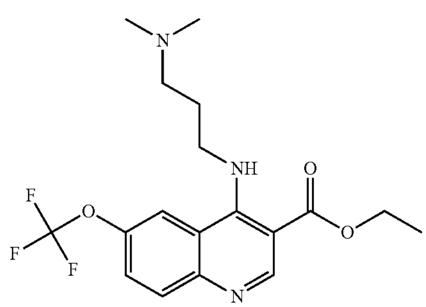 [SMILES: CCOC(=O)c1cnc2ccc(OC(F)(F)F)cc2c1NCCCN(C)C] | ethyl 4-(3-(dimethylamino)propylamino)-6-(trifluoromethoxy)quinoline-3-carboxylate | 385 |
| 9 | 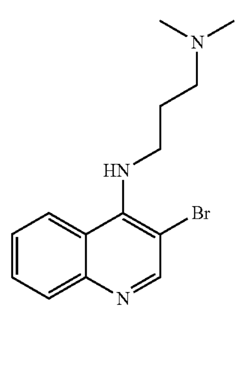 [SMILES: CN(C)CCCNc1c(Br)cnc2ccccc12] | N1-(3-bromoquinolin-4-yl)-N3,N3-dimethylpropane-1,3-diamine | 308 |

TABLE 1-continued

| No. | Structure | Compound Name | ESI MS (m/z) |
|---|---|---|---|
| 10 | 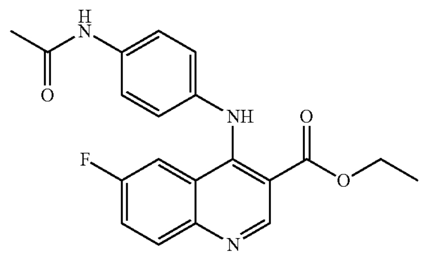 [SMILES: CCOC(=O)c1cnc2ccc(F)cc2c1Nc1ccc(NC(C)=O)cc1] | ethyl 4-(4-acetamidophenylamino)-6-fluoroquinoline-3-carboxylate | 367 |
| 11 | 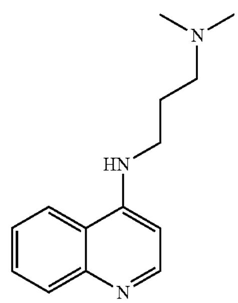 [SMILES: CN(C)CCCNc1ccnc2ccccc12] | N1,N1-dimethyl-N3-(quinolin-4-yl)propane-1,3-diamine | 229 |
| 12 | 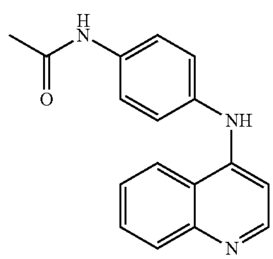 [SMILES: CC(=O)Nc1ccc(Nc2ccnc3ccccc23)cc1] | N-(4-(quinolin-4-ylamino)phenyl)acetamide | 277 |
| 13 | 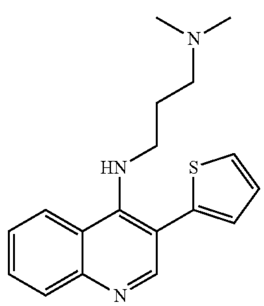 [SMILES: CN(C)CCCNc1c(-c2cccs2)cnc2ccccc12] | N1,N1-dimethyl-N3-(3-(thiophen-2-yl)quinolin-4-yl)propane-1,3-diamine | 311 |
| 14 | 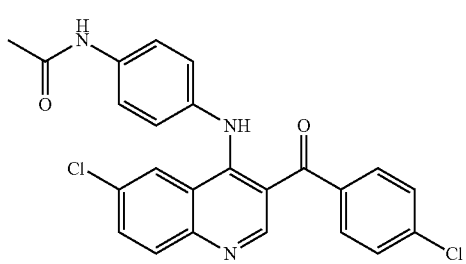 [SMILES: CC(=O)Nc1ccc(Nc2c(C(=O)c3ccc(Cl)cc3)cnc3ccc(Cl)cc23)cc1] | N-(4-(6-chloro-3-(4-chlorobenzoyl)quinolin-4-ylamino)phenyl)acetamide | 450 |

TABLE 1-continued

| No. | Structure | Compound Name | ESI MS (m/z) |
|---|---|---|---|
| 15 | 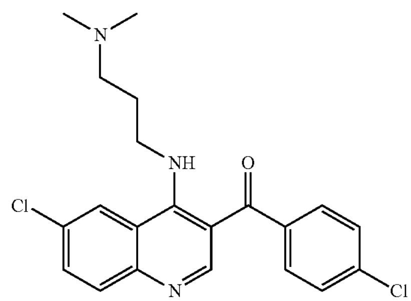 [SMILES: CN(C)CCCNc1c(C(=O)c2ccc(Cl)cc2)cnc2ccc(Cl)cc12] | (6-chloro-4-(3-(dimethylamino)propylamino)quinolin-3-yl)(4-chlorophenyl)methanone | 402 |
| 16 | 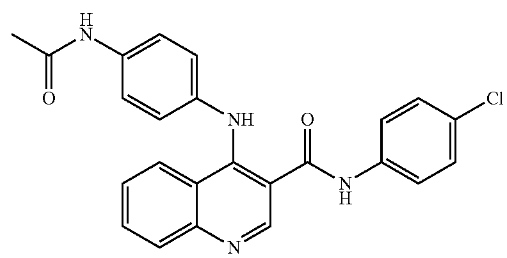 [SMILES: CC(=O)Nc1ccc(Nc2c(C(=O)Nc3ccc(Cl)cc3)cnc3ccccc23)cc1] | 4-(4-acetamidophenylamino)-N-(4-chlorophenyl)quinoline-3-carboxamide | 431 |
| 17 | 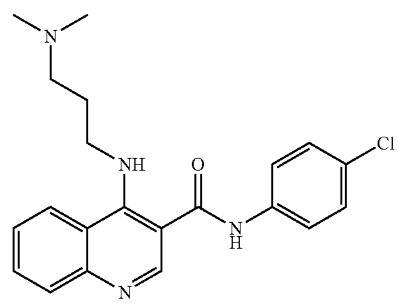 [SMILES: CN(C)CCCNc1c(C(=O)Nc2ccc(Cl)cc2)cnc2ccccc12] | N-(4-chlorophenyl)-4-(3-(dimethylamino)propylamino)quinoline-3-carboxamide | 383 |
| 18 | 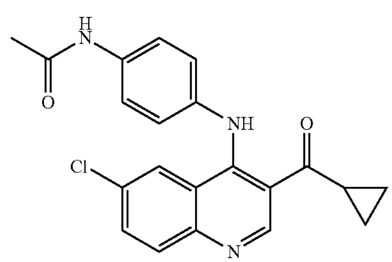 [SMILES: CC(=O)Nc1ccc(Nc2c(C(=O)C3CC3)cnc3ccc(Cl)cc23)cc1] | N-(4-(6-chloro-3-(cyclopropanecarbonyl)quinolin-4-ylamino)phenyl)acetamide | 380 |
| 19 | 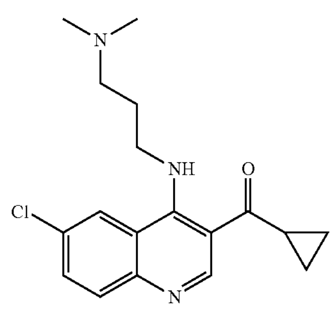 [SMILES: CN(C)CCCNc1c(C(=O)C2CC2)cnc2ccc(Cl)cc12] | (6-chloro-4-(3-(dimethylamino)propylamino)quinolin-3-yl)(cyclopropyl)methanone | 332 |

TABLE 1-continued

| No. | Structure | Compound Name | ESI MS (m/z) |
|---|---|---|---|
| 20 | 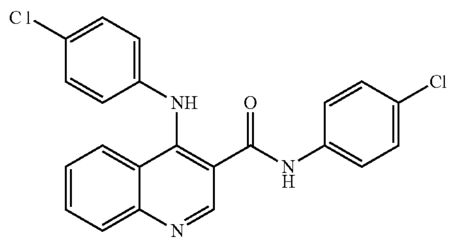 | N-(4-chlorophenyl)-4-(4-chlorophenylamino)quinoline-3-carboxamide | 408 |
| 21 | 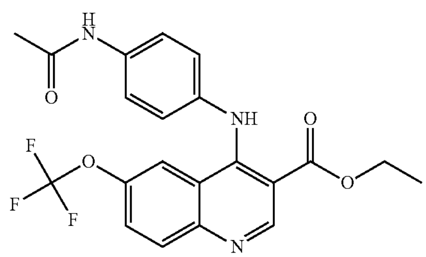 [SMILES: CCOC(=O)c1cnc2ccc(OC(F)(F)F)cc2c1Nc1ccc(NC(C)=O)cc1] | ethyl 4-(4-acetamidophenylamino)-6-(trifluoromethoxy)quinoline-3-carboxylate | 433 |
| 22 | 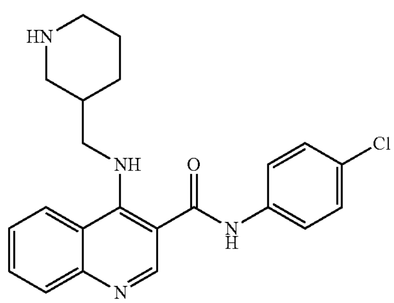 [SMILES: O=C(Nc1ccc(Cl)cc1)c1cnc2ccccc2c1NCC1CCCNC1] | N-(4-chlorophenyl)-4-(piperidin-3-ylmethylamino)quinoline-3-carboxamide | 395 |
| 23 | 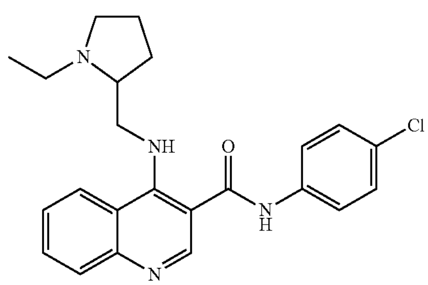 [SMILES: CCN1CCCC1CNc1c(C(=O)Nc2ccc(Cl)cc2)cnc2ccccc12] | N-(4-chlorophenyl)-4-((1-ethylpyrrolidin-2-yl)methylamino)quinoline-3-carboxamide | 409 |
| 24 | 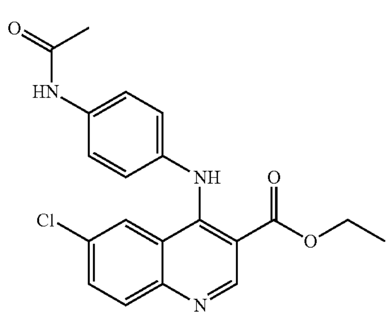 [SMILES: CCOC(=O)c1cnc2ccc(Cl)cc2c1Nc1ccc(NC(C)=O)cc1] | ethyl 4-(4-acetamidophenylamino)-6-chloroquinoline-3-carboxylate | 384 |

TABLE 1-continued

| No. | Structure | Compound Name | ESI MS (m/z) |
|---|---|---|---|
| 25 | 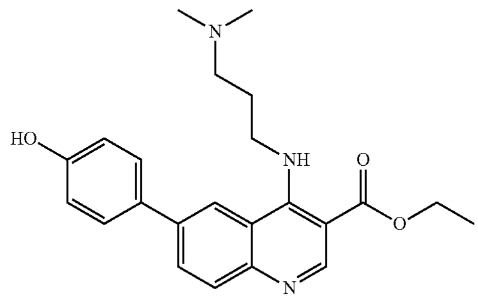 [SMILES: CCOC(=O)c1cnc2ccc(-c3ccc(O)cc3)cc2c1NCCCN(C)C] | ethyl 4-(3-(dimethylamino)propylamino)-6-(4-hydroxyphenyl)quinoline-3-carboxylate | 393 |
| 26 | 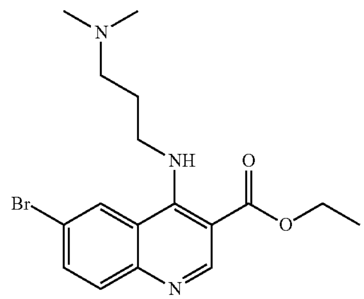 [SMILES: CCOC(=O)c1cnc2ccc(Br)cc2c1NCCCN(C)C] | ethyl 6-bromo-4-(3-(dimethylamino)propylamino)quinoline-3-carboxylate | 380 |
| 27 | 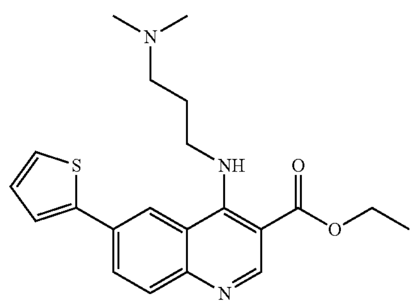 [SMILES: CCOC(=O)c1cnc2ccc(-c3cccs3)cc2c1NCCCN(C)C] | ethyl 4-(3-(dimethylamino)propylamino)-6-(thiophen-2-yl)quinoline-3-carboxylate | 384 |
| 28 | 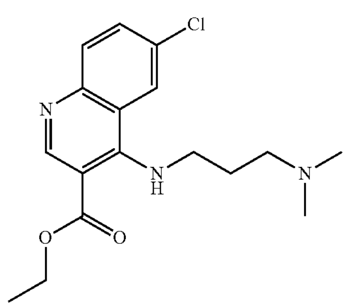 [SMILES: CCOC(=O)c1cnc2ccc(Cl)cc2c1NCCCN(C)C] | ethyl 6-chloro-4-(3-(dimethylamino)propylamino)quinoline-3-carboxylate | 336 |
| 29 | 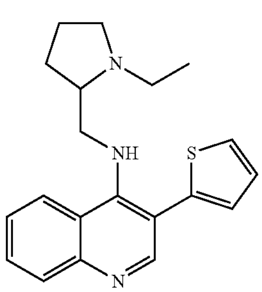 [SMILES: CCN1CCCC1CNc1c(-c2cccs2)cnc2ccccc12] | N-((1-ethylpyrrolidin-2-yl)methyl)-3-(thiophen-2-yl)quinolin-4-amine | 337 |

TABLE 1-continued

| No. | Structure | Compound Name | ESI MS (m/z) |
|---|---|---|---|
| 30 | 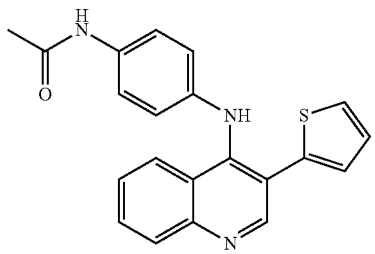 [SMILES: CC(=O)Nc1ccc(Nc2c(-c3cccs3)cnc3ccccc23)cc1] | N-(4-(3-(thiophen-2-yl)quinolin-4-ylamino)phenyl)acetamide | 359 |
| 31 | 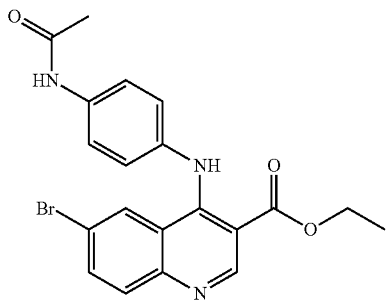 [SMILES: CCOC(=O)c1cnc2ccc(Br)cc2c1Nc1ccc(NC(C)=O)cc1] | ethyl 4-(4-acetamidophenylamino)-6-bromoquinoline-3-carboxylate | 438 |
| 32 | 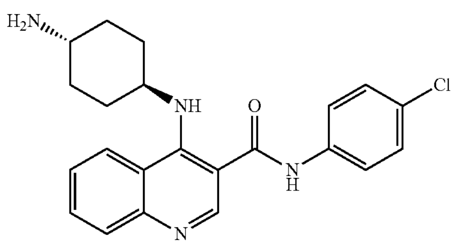 [SMILES: N[C@H]1CC[C@H](Nc2c(C(=O)Nc3ccc(Cl)cc3)cnc3ccccc23)CC1] | 4-((trans)-4-aminocyclohexylamino)-N-(4-chlorophenyl)quinoline-3-carboxamide | 395 |
| 33 | 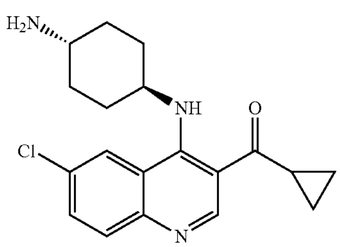 [SMILES: N[C@H]1CC[C@H](Nc2c(C(=O)C3CC3)cnc3ccc(Cl)cc23)CC1] | (4-((trans)-4-aminocyclohexylamino)-6-chloroquinolin-3-yl)(cyclopropyl)methanone | 344 |
| 34 | 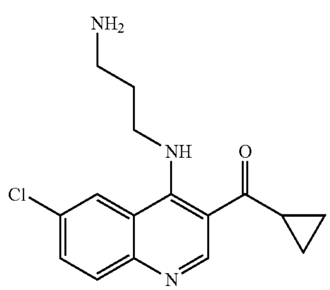 [SMILES: NCCCNc1c(C(=O)C2CC2)cnc2ccc(Cl)cc12] | (4-(3-aminopropylamino)6-chloroquinolin-3-yl)(cyclopropyl)methanone | 304 |

TABLE 1-continued

| No. | Structure | Compound Name | ESI MS (m/z) |
|---|---|---|---|
| 35 | 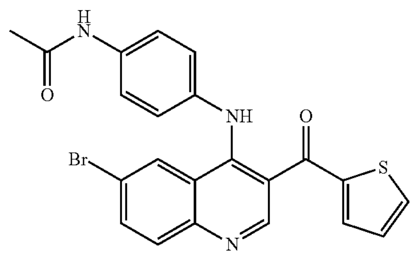 [SMILES: CC(=O)Nc1ccc(Nc2c(C(=O)c3cccs3)cnc3ccc(Br)cc23)cc1] | N-(4-(6-bromo-3-(thiophene-2-carbonyl)quinolin-4-ylamino)phenyl)acetamide | 466 |
| 36 | 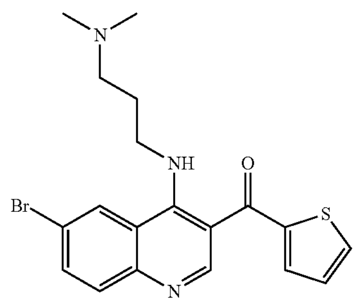 [SMILES: CN(C)CCCNc1c(C(=O)c2cccs2)cnc2ccc(Br)cc12] | (6-bromo-4-(3-(dimethylamino)propylamino)quinolin-3-yl)(thiophen-2-yl)methanone | 418 |
| 37 | 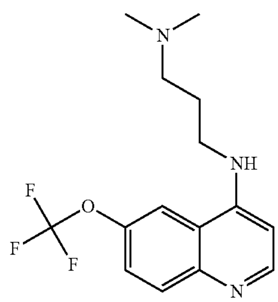 [SMILES: CN(C)CCCNc1ccnc2ccc(OC(F)(F)F)cc12] | N1,N1-dimethyl-N3-(6-(trifluoromethoxy)quinolin-4-yl)propane-1,3-diamine | 313 |
| 38 | 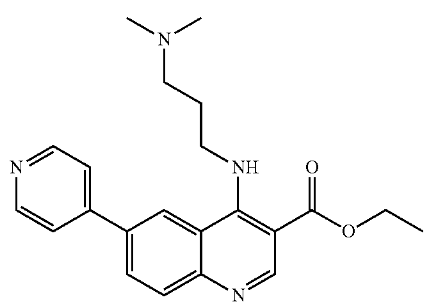 [SMILES: CCOC(=O)c1cnc2ccc(-c3ccncc3)cc2c1NCCCN(C)C] | ethyl 4-(3-(dimethylamino)propylamino)-6-(pyridin-4-yl)quinoline-3-carboxylate | 378 |
| 39 | 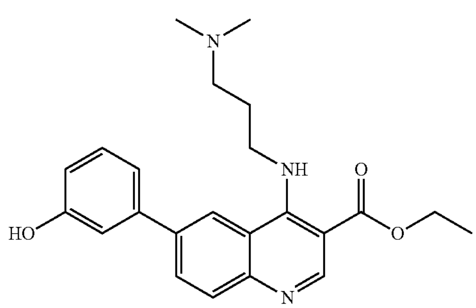 [SMILES: CCOC(=O)c1cnc2ccc(-c3cccc(O)c3)cc2c1NCCCN(C)C] | ethyl 4-(3-(dimethylamino)propylamino)-6-(3-hydroxyphenyl)quinoline-3-carboxylate | 393 |

TABLE 1-continued

| No. | Structure | Compound Name | ESI MS (m/z) |
|---|---|---|---|
| 40 | 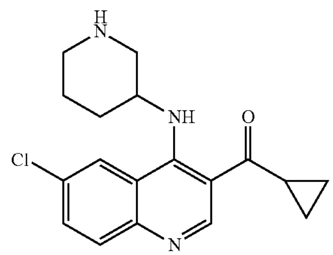 [SMILES: O=C(c1cnc2ccc(Cl)cc2c1NC1CCCNC1)C1CC1] | (6-chloro-4-(piperidin-3-ylamino) quinolin-3-yl)(cyclopropyl) methanone | 330 |
| 41 | 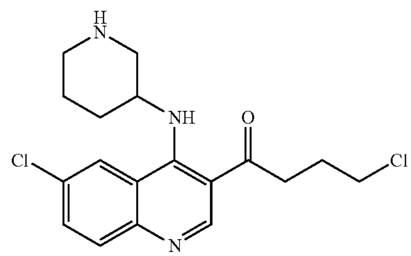 [SMILES: O=C(CCCCl)c1cnc2ccc(Cl)cc2c1NC1CCCNC1] | 4-chloro-1-(6-chloro-4-(piperidin-3-ylamino)quinolin-3-yl) butan-1-one | 366 |
| 42 | 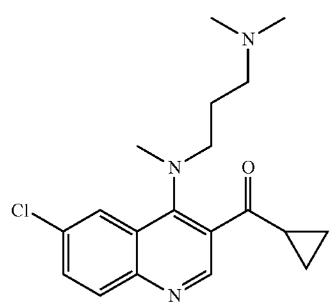 [SMILES: CN(C)CCCN(C)c1c(C(=O)C2CC2)cnc2ccc(Cl)cc12] | (6-chloro-4-((3-(dimethylamino) propyl)(methyl)amino)quinolin-3-yl)(cyclopropyl)methanone | 346 |
| 43 | 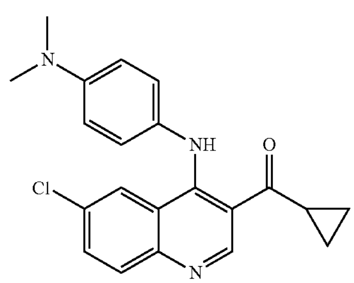 [SMILES: CN(C)c1ccc(Nc2c(C(=O)C3CC3)cnc3ccc(Cl)cc23)cc1] | (6-chloro-4-(4-(dimethylamino) phenylamino)quinolin-3-yl) (cyclopropyl)methanone | 366 |
| 44 | 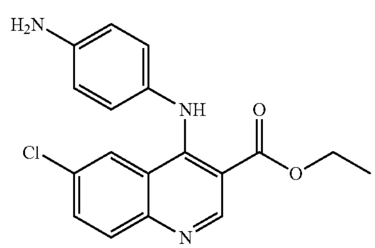 [SMILES: CCOC(=O)c1cnc2ccc(Cl)cc2c1Nc1ccc(N)cc1] | ethyl 4-(4-aminophenylamino)-6-chloroquinoline-3-carboxylate | 342 |

TABLE 1-continued

| No. | Structure | Compound Name | ESI MS (m/z) |
|---|---|---|---|
| 45 | 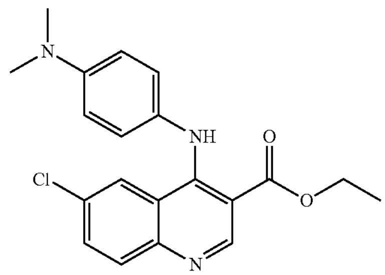 [SMILES: CCOC(=O)c1cnc2ccc(Cl)cc2c1Nc1ccc(N(C)C)cc1] | ethyl 6-chloro-4-(4-(dimethylamino) phenylamino)quinoline-3-carboxylate | 370 |
| 46 | 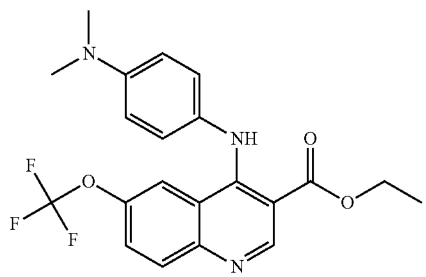 [SMILES: CCOC(=O)c1cnc2ccc(OC(F)(F)F)cc2c1Nc1ccc(N(C)C)cc1] | ethyl 4-(4-(dimethylamino) phenylamino)-6-(trifluoromethoxy) quinoline-3-carboxylate | 419 |
| 47 | 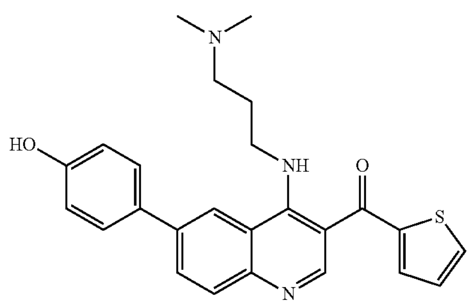 [SMILES: CN(C)CCCNc1c(C(=O)c2cccs2)cnc2ccc(-c3ccc(O)cc3)cc12] | (4-(3-(dimethylamino) propylamino)-6-(4-hydroxyphenyl) quinolin-3-yl)(thiophen-2-yl) methanone | 432 |
| 48 | 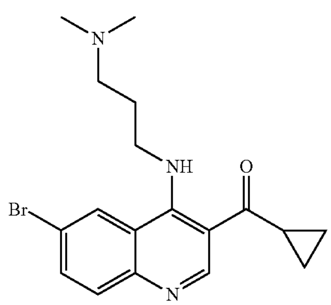 | (6-bromo-4-(3-(dimethylamino) propylamino)quinolin-3-yl) (cyclopropyl)methanone | 376 |
| 49 | 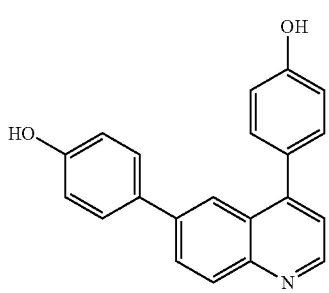 [SMILES: Oc1ccc(-c2ccc3nccc(-c4ccc(O)cc4)c3c2)cc1] | 4,4'-(quinoline-4,6-diyl)diphenol | 313 |

TABLE 1-continued

| No. | Structure | Compound Name | ESI MS (m/z) |
|---|---|---|---|
| 50 | 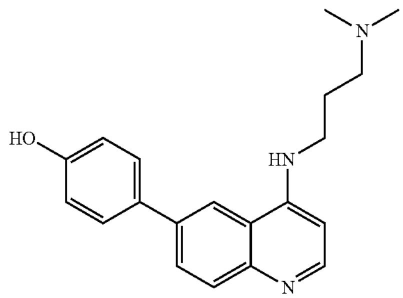 [SMILES: CN(C)CCCNc1ccnc2ccc(-c3ccc(O)cc3)cc12] | 4-(4-(3-(dimethylamino) propylamino)quinolin-6-yl)phenol | 321 |
| 51 | 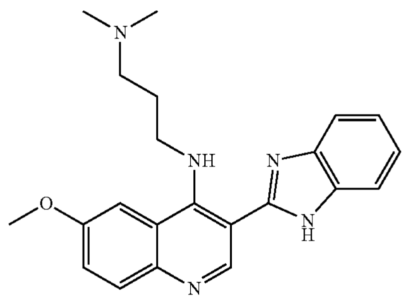 [SMILES: COc1ccc2ncc(-c3nc4ccccc4[nH]3)c(NCCCN(C)C)c2c1] | N1-(3-(1H-benzo[d]imidazol-2-yl)-6-methoxyquinolin-4-yl)-N3,N3-dimethylpropane-1,3-diamine | 375 |
| 52 | 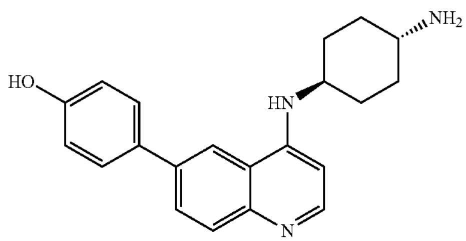 [SMILES: N[C@H]1CC[C@H](Nc2ccnc3ccc(-c4ccc(O)cc4)cc23)CC1] | 4-(4-((trans)-4-aminocyclohexyl-amino)quinolin-6-yl)phenol | 333 |
| 53 | 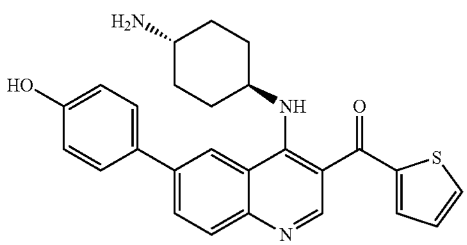 [SMILES: N[C@H]1CC[C@H](Nc2c(C(=O)c3cccs3)cnc3ccc(-c4ccc(O)cc4)cc23)CC1] | (4-((trans)-4-aminocyclohexylamino)-6-(4-hydroxyphenyl)quinolin-3-yl)(thiophen-2-yl)methanone | 444 |
| 54 | 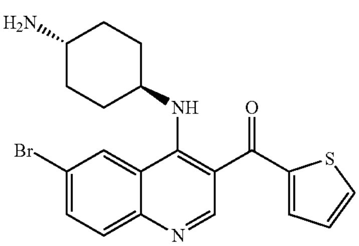 [SMILES: N[C@H]1CC[C@H](Nc2c(C(=O)c3cccs3)cnc3ccc(Br)cc23)CC1] | (4-((trans)-4-aminocyclohexylamino)-6-bromoquinolin-3-yl)(thiophen-2-yl)methanone | 430 |
| 55 | 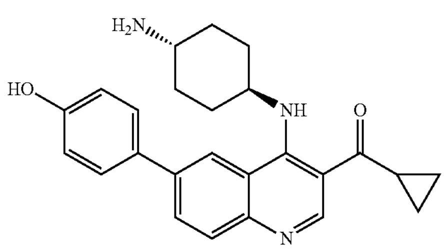 [SMILES: N[C@H]1CC[C@H](Nc2c(C(=O)C3CC3)cnc3ccc(-c4ccc(O)cc4)cc23)CC1] | (4-((trans)-4-aminocyclohexylamino)-6-(4-hydroxyphenyl)quinolin-3-yl)(cyclopropyl)methanone | 402 |

TABLE 1-continued

| No. | Structure | Compound Name | ESI MS (m/z) |
|---|---|---|---|
| 56 | 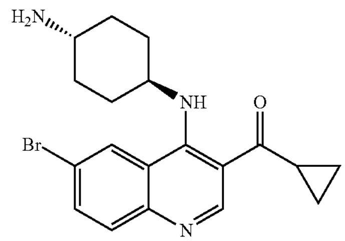 | (4-((trans)-4-aminocyclohexylamino)-6-bromoquinolin-3-yl)(cyclopropyl)methanone | 388 |
| 57 | 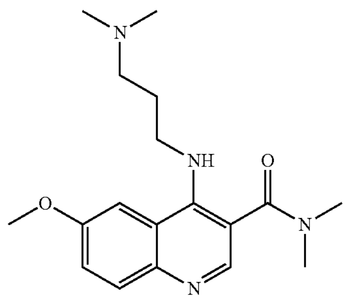 | 4-(3-(dimethylamino)propylamino)-6-methoxy-N,N-dimethylquinoline-3-carboxamide | 330 |
| 58 | 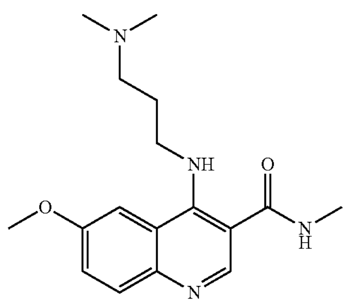 | 4-(3-(dimethylamino)propylamino)-6-methoxy-N-methylquinoline-3-carboxamide | 316 |
| 59 | 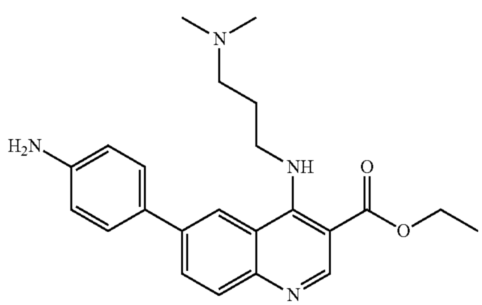 [SMILES: CCOC(=O)c1cnc2ccc(-c3ccc(N)cc3)cc2c1NCCCN(C)C] | ethyl 6-(4-aminophenyl)-4-(3-(dimethylamino)propylamino)quinoline-3-carboxylate | 392 |
| 60 | 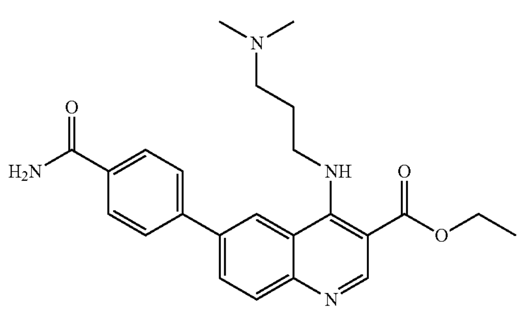 [SMILES: CCOC(=O)c1cnc2ccc(-c3ccc(C(N)=O)cc3)cc2c1NCCCN(C)C] | ethyl 6-(4-carbamoylphenyl)-4-(3-(dimethylamino)propylamino)quinoline-3-carboxylate | 421 |

TABLE 1-continued

| No. | Structure | Compound Name | ESI MS (m/z) |
|---|---|---|---|
| 61 | 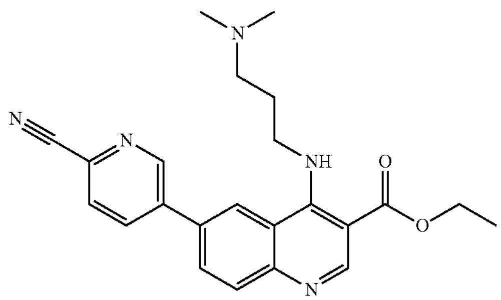 [SMILES: CCOC(=O)c1cnc2ccc(-c3ccc(C#N)nc3)cc2c1NCCCN(C)C] | ethyl 6-(6-cyanopyridin-3-yl)-4-(3-(dimethylamino)propylamino)quinoline-3-carboxylate | 403 |
| 62 | 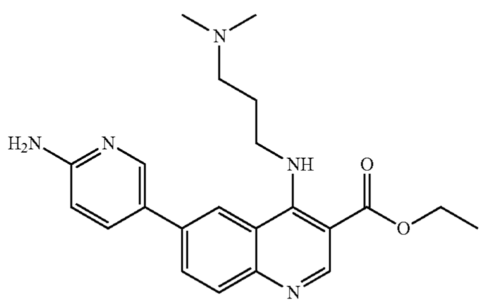 [SMILES: CCOC(=O)c1cnc2ccc(-c3ccc(N)nc3)cc2c1NCCCN(C)C] | ethyl 6-(6-aminopyridin-3-yl)-4-(3-(dimethylamino)propylamino)quinoline-3-carboxylate | 393 |
| 63 | 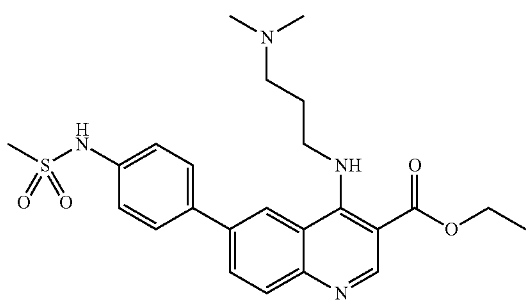 [SMILES: CCOC(=O)c1cnc2ccc(-c3ccc(NS(C)(=O)=O)cc3)cc2c1NCCCN(C)C] | ethyl 4-(3-(dimethylamino)propylamino)-6-(4-(methylsulfonamido)phenyl)quinoline-3-carboxylate | 471 |
| 64 | 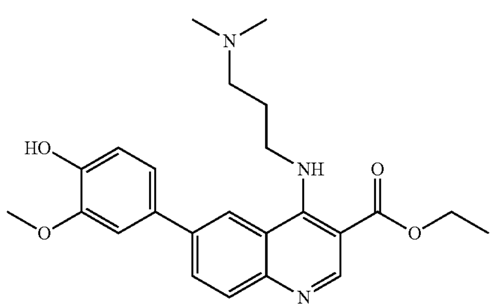 [SMILES: CCOC(=O)c1cnc2ccc(-c3ccc(O)c(OC)c3)cc2c1NCCCN(C)C] | ethyl 4-(3-(dimethylamino)propylamino)-6-(4-hydroxy-3-methoxyphenyl)quinoline-3-carboxylate | 424 |
| 65 | 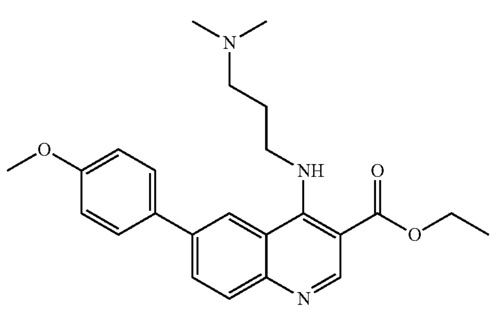 [SMILES: CCOC(=O)c1cnc2ccc(-c3ccc(OC)cc3)cc2c1NCCCN(C)C] | ethyl 4-(3-(dimethylamino)propylamino)-6-(4-methoxyphenyl)quinoline-3-carboxylate | 408 |

TABLE 1-continued

| No. | Structure | Compound Name | ESI MS (m/z) |
|---|---|---|---|
| 66 | 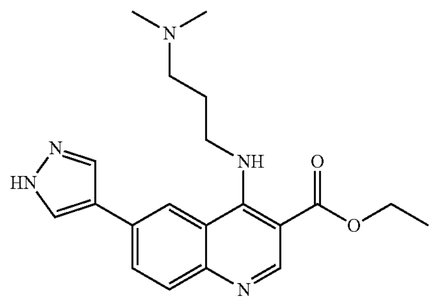 [SMILES: CCOC(=O)c1cnc2ccc(-c3cn[nH]c3)cc2c1NCCCN(C)C] | ethyl 4-(3-(dimethylamino)propylamino)-6-(1H-pyrazol-4-yl)quinoline-3-carboxylate | 367 |
| 67 | 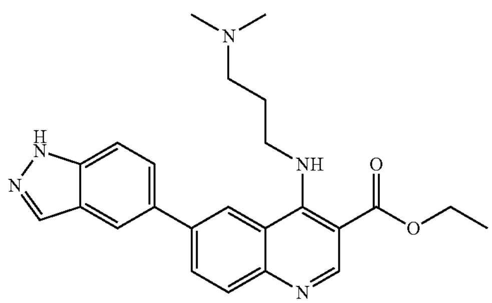 [SMILES: CCOC(=O)c1cnc2ccc(-c3ccc4[nH]ncc4c3)cc2c1NCCCN(C)C] | ethyl 4-(3-(dimethylamino)propylamino)-6-(1H-indazol-5-yl)quinoline-3-carboxylate | 418 |
| 68 | 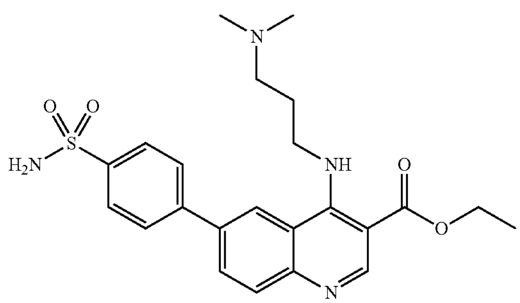 [SMILES: CCOC(=O)c1cnc2ccc(-c3ccc(S(N)(=O)=O)cc3)cc2c1NCCCN(C)C] | ethyl 4-(3-(dimethylamino)propylamino)-6-(4-sulfamoylphenyl)quinoline-3-carboxylate | 457 |
| 69 | 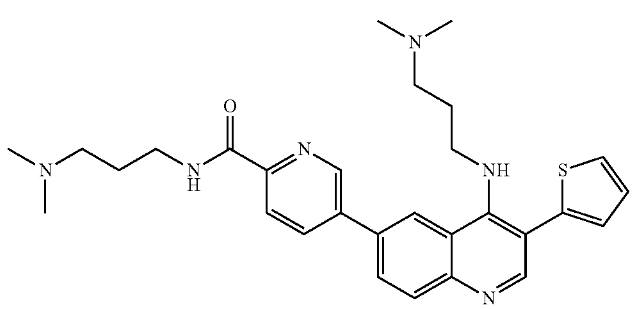 [SMILES: CN(C)CCCNC(=O)c1ccc(-c2ccc3ncc(-c4cccs4)c(NCCCN(C)C)c3c2)cn1] | N-(3-(dimethylamino)propyl)-5-(4-(3-(dimethylamino)propylamino)-3-(thiophen-2-yl)quinolin-6-yl)picolinamide | 517 |
| 70 | 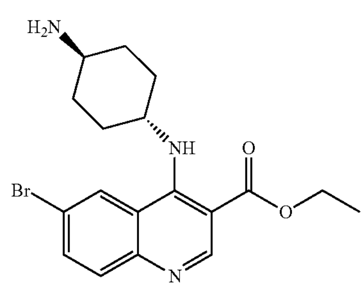 [SMILES: CCOC(=O)c1cnc2ccc(Br)cc2c1N[C@H]1CC[C@H](N)CC1] | ethyl 4-((trans)-4-aminocyclohexylamino)-6-bromoquinoline-3-carboxylate | 392 |

TABLE 1-continued

| No. | Structure | Compound Name | ESI MS (m/z) |
|---|---|---|---|
| 71 | 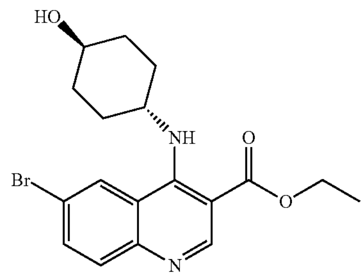 [SMILES: CCOC(=O)c1cnc2ccc(Br)cc2c1N[C@H]1CC[C@H](O)CC1] | ethyl 6-bromo-4-((trans)-4-hydroxycyclohexylamino) quinoline-3-carboxylate | 393 |
| 72 | 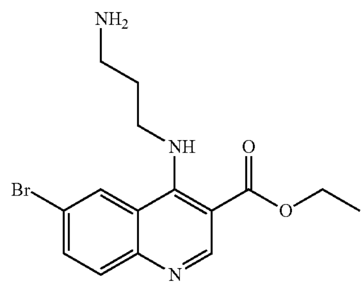 [SMILES: CCOC(=O)c1cnc2ccc(Br)cc2c1NCCCN] | ethyl 4-(3-aminopropylamino)-6-bromoquinoline-3-carboxylate | 352 |
| 73 | 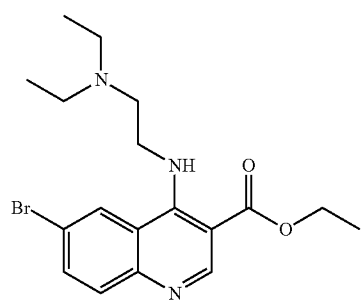 [SMILES: CCOC(=O)c1cnc2ccc(Br)cc2c1NCCN(CC)CC] | ethyl 6-bromo-4-(2-(diethylamino) ethylamino)quinoline-3-carboxylate | 394 |
| 74 | 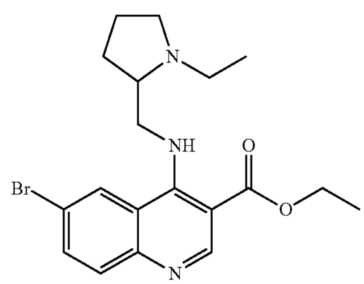 [SMILES: CCOC(=O)c1cnc2ccc(Br)cc2c1NCC1CCCN1CC] | ethyl 6-bromo-4-((1-ethylpyrrolidin-2-yl)methylamino)quinoline-3-carboxylate | 406 |
| 75 | 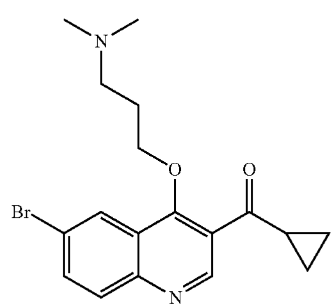 [SMILES: CN(C)CCCOc1c(C(=O)C2CC2)cnc2ccc(Br)cc12] | (6-bromo-4-(3-(dimethylamino)propoxy)quinolin-3-yl)(cyclopropyl)methanone | 377 |

TABLE 1-continued

| No. | Structure | Compound Name | ESI MS (m/z) |
|---|---|---|---|
| 76 | 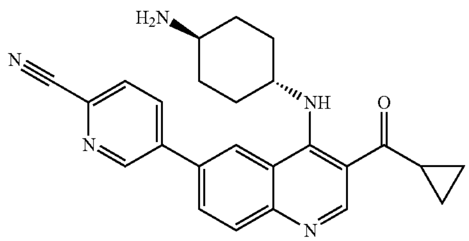 [SMILES: N#Cc1ccc(-c2ccc3ncc(C(=O)C4CC4)c(N[C@H]4CC[C@H](N)CC4)c3c2)cn1] | 5-(4-((trans)-4-aminocyclohexyl-amino)-3-(cyclopropanecarbonyl)quinolin-6-yl)picolinonitrile | 411 |
| 77 | 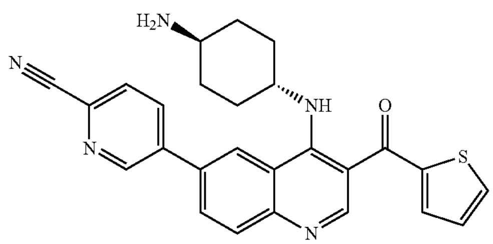 [SMILES: N#Cc1ccc(-c2ccc3ncc(C(=O)c4cccs4)c(N[C@H]4CC[C@H](N)CC4)c3c2)cn1] | 5-(4-((trans)-4-aminocyclohexyl-amino)-3-(thiophene-2-carbonyl)quinolin-6-yl)picolinonitrile | 454 |
| 78 | 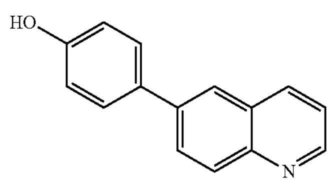 [SMILES: Oc1ccc(-c2ccc3ncccc3c2)cc1] | 4-(quinolin-6-yl)phenol | 221 |
| 79 | 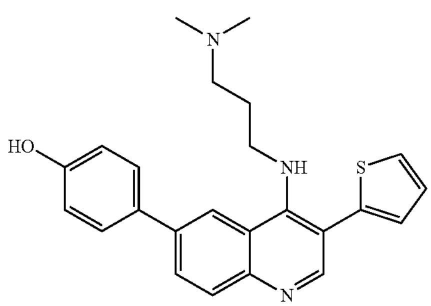 [SMILES: CN(C)CCCNc1c(-c2cccs2)cnc2ccc(-c3ccc(O)cc3)cc12] | 4-(4-(3-(dimethylamino)propylamino)-3-(thiophen-2-yl)quinolin-6-yl)phenol | 404 |
| 80 | 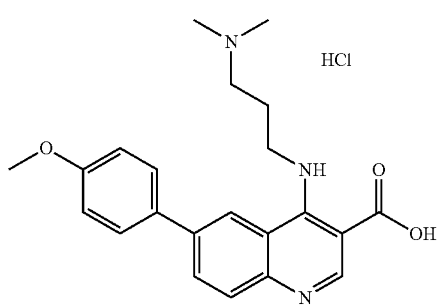 [SMILES: COc1ccc(-c2ccc3ncc(C(=O)O)c(NCCCN(C)C)c3c2)cc1 ; Cl] | 4-(3-(dimethylamino)propylamino)-6-(4-methoxyphenyl)quinoline-3-carboxylic acid dihydrochloride | 379 |
| 81 | 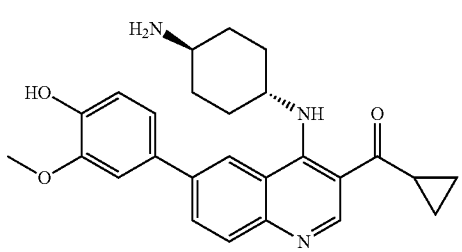 [SMILES: COc1cc(-c2ccc3ncc(C(=O)C4CC4)c(N[C@H]4CC[C@H](N)CC4)c3c2)ccc1O] | (4-((trans)-4-aminocyclohexylamino)-6-(4-hydroxy-3-methoxyphenyl)quinolin-3-yl)(cyclopropyl)methanone | 432 |

TABLE 1-continued

| No. | Structure | Compound Name | ESI MS (m/z) |
|---|---|---|---|
| 82 | 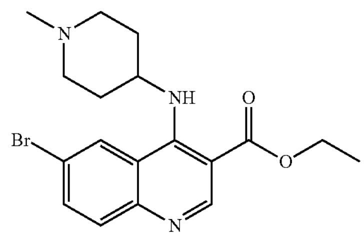 [SMILES: CCOC(=O)c1cnc2ccc(Br)cc2c1NC1CCN(C)CC1] | ethyl 6-bromo-4-(1-methylpiperidin-4-ylamino)quinoline-3-carboxylate | 392 |
| 83 | 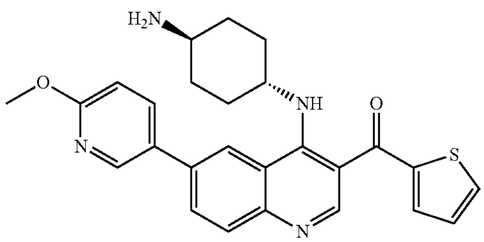 [SMILES: COc1ccc(-c2ccc3ncc(C(=O)c4cccs4)c(N[C@H]4CC[C@H](N)CC4)c3c2)cn1] | (4-((trans)-4-aminocyclohexylamino)-6-(6-methoxypyridin-3-yl)quinolin-3-yl)(thiophen-2-yl)methanone | 459 |
| 84 | 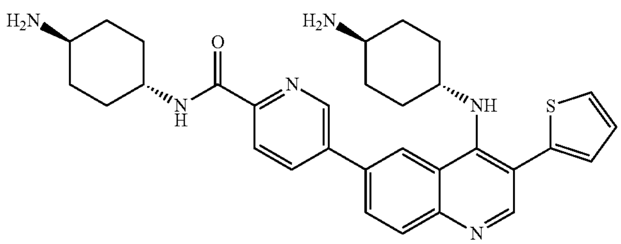 [SMILES: N[C@H]1CC[C@H](NC(=O)c2ccc(-c3ccc4ncc(-c5cccs5)c(N[C@H]5CC[C@H](N)CC5)c4c3)cn2)CC1] | N-((trans)-4-aminocyclohexyl)-5-(4-((trans)-4-aminocyclohexylamino)-3-(thiophen-2-yl)quinolin-6-yl)picolinamide | 540 |
| 85 | 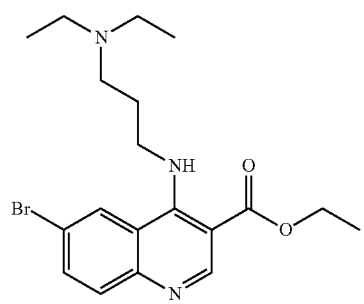 [SMILES: CCOC(=O)c1cnc2ccc(Br)cc2c1NCCCN(CC)CC] | ethyl 6-bromo-4-(3-(diethylamino)propylamino)quinoline-3-carboxylate | 408 |
| 86 | 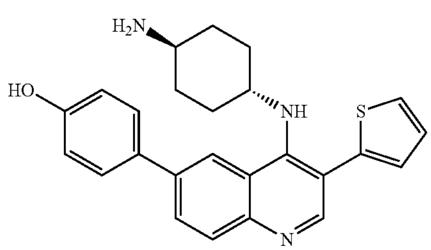 [SMILES: N[C@H]1CC[C@H](Nc2c(-c3cccs3)cnc3ccc(-c4ccc(O)cc4)cc23)CC1] | 4-(4-((trans)-4-aminocyclohexylamino)-3-(thiophen-2-yl)quinolin-6-yl)phenol | 416 |
| 87 | 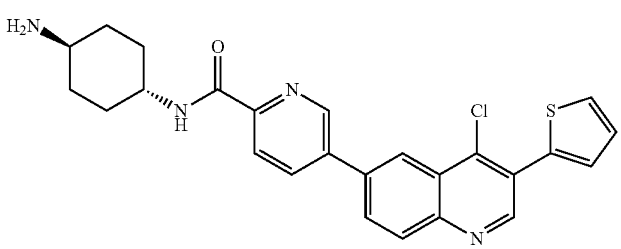 [SMILES: N[C@H]1CC[C@H](NC(=O)c2ccc(-c3ccc4ncc(-c5cccs5)c(Cl)c4c3)cn2)CC1] | N-((trans)-4-aminocyclohexyl)-5-(4-chloro-3-(thiophen-2-yl)quinolin-6-yl)picolinamide | 463 |

TABLE 1-continued

| No. | Structure | Compound Name | ESI MS (m/z) |
|---|---|---|---|
| 88 | 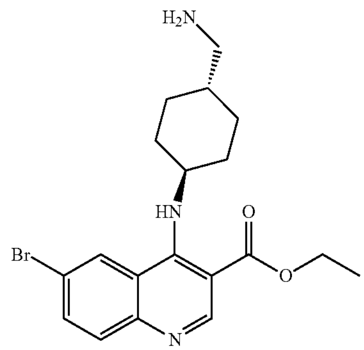 [SMILES: CCOC(=O)c1cnc2ccc(Br)cc2c1N[C@H]1CC[C@H](CN)CC1] | ethyl 4-((trans)-4-(aminomethyl) cyclohexylamino)-6-bromoquinoline-3-carboxylate | 406 |
| 89 | 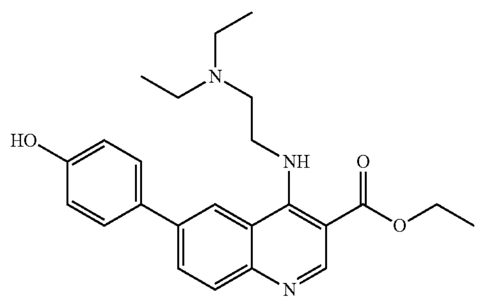 [SMILES: CCOC(=O)c1cnc2ccc(-c3ccc(O)cc3)cc2c1NCCN(CC)CC] | ethyl 4-(2-(diethylamino)ethylamino)-6-(4-hydroxyphenyl)quinoline-3-carboxylate | 408 |
| 90 | 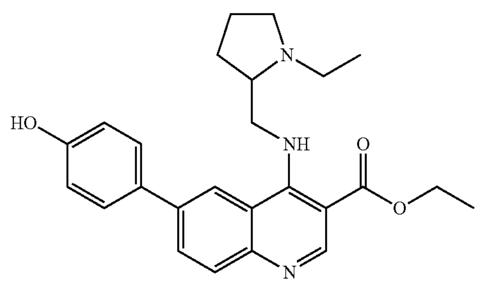 [SMILES: CCOC(=O)c1cnc2ccc(-c3ccc(O)cc3)cc2c1NCC1CCCN1CC] | ethyl 4-((1-ethylpyrrolidin-2-yl)methylamino)-6-(4-hydroxyphenyl)quinoline-3-carboxylate | 420 |
| 91 | 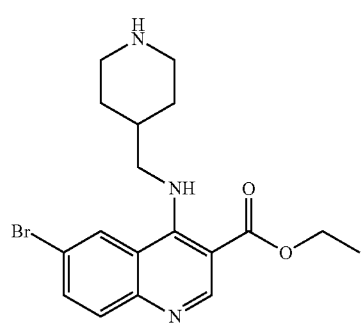 [SMILES: CCOC(=O)c1cnc2ccc(Br)cc2c1NCC1CCNCC1] | ethyl 6-bromo-4-(piperidin-4-ylmethylamino)quinoline-3-carboxylate | 392 |
| 92 | 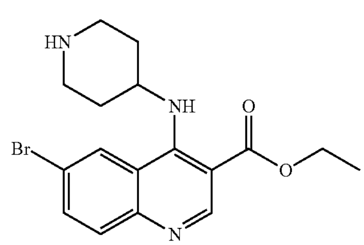 [SMILES: CCOC(=O)c1cnc2ccc(Br)cc2c1NC1CCNCC1] | ethyl 6-bromo-4-(piperidin-4-ylamino)quinoline-3-carboxylate | 378 |

TABLE 1-continued

| No. | Structure | Compound Name | ESI MS (m/z) |
|---|---|---|---|
| 93 | 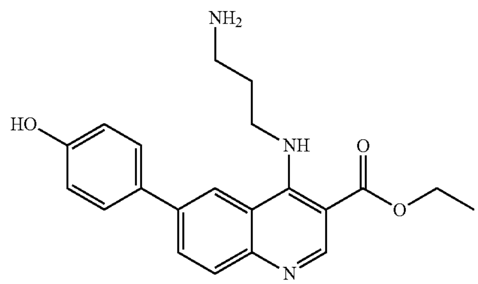 [SMILES: CCOC(=O)c1cnc2ccc(-c3ccc(O)cc3)cc2c1NCCCN] | ethyl 4-(3-aminopropylamino)-6-(4-hydroxyphenyl)quinoline-3-carboxylate | 365 |
| 94 | 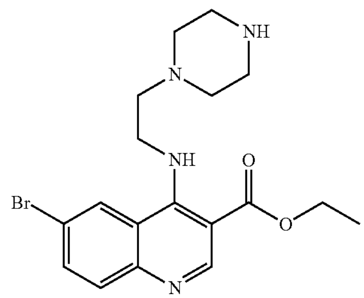 [SMILES: CCOC(=O)c1cnc2ccc(Br)cc2c1NCCN1CCNCC1] | ethyl 6-bromo-4-(2-(piperazin-1-yl)ethylamino)quinoline-3-carboxylate | 407 |
| 95 | 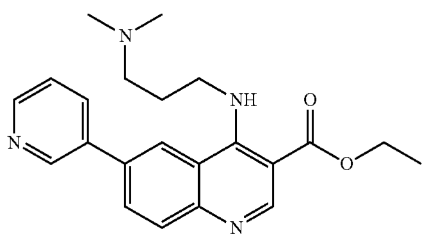 [SMILES: CCOC(=O)c1cnc2ccc(-c3cccnc3)cc2c1NCCCN(C)C] | ethyl 4-(3-(dimethylamino)propylamino)-6-(pyridin-3-yl)quinoline-3-carboxylate | 378 |
| 96 | 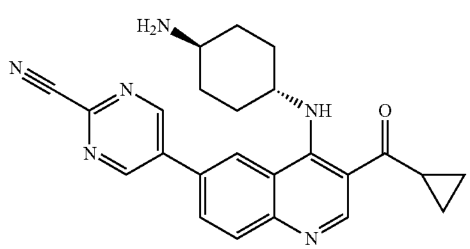 [SMILES: N#Cc1ncc(-c2ccc3ncc(C(=O)C4CC4)c(N[C@H]4CC[C@H](N)CC4)c3c2)cn1] | 5-(4-((trans)-4-aminocyclohexylamino)-3-(cyclopropanecarbonyl)quinolin-6-yl)pyrimidine-2-carbonitrile | 412 |
| 97 | 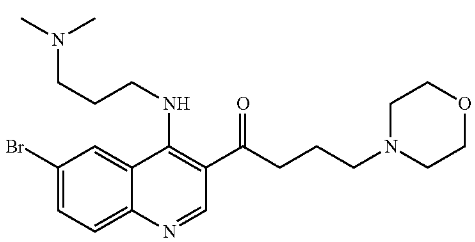 [SMILES: CN(C)CCCNc1c(C(=O)CCCN2CCOCC2)cnc2ccc(Br)cc12] | 1-(6-bromo-4-(3-(dimethylamino)propylamino)quinolin-3-yl)-4-morpholinobutan-1-one | 463 |

TABLE 1-continued

| No. | Structure | Compound Name | ESI MS (m/z) |
|---|---|---|---|
| 98 | 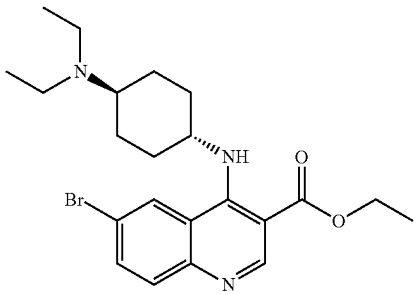 [SMILES: CCOC(=O)c1cnc2ccc(Br)cc2c1N[C@H]1CC[C@H](N(CC)CC)CC1] | ethyl 6-bromo-4-((trans)-4-(diethylamino)cyclohexylamino)quinoline-3-carboxylate | 448 |
| 99 | 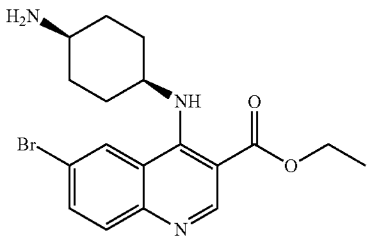 [SMILES: CCOC(=O)c1cnc2ccc(Br)cc2c1N[C@H]1CC[C@@H](N)CC1] | ethyl 4-((cis)-4-aminocyclohexylamino)-6-bromoquinoline-3-carboxylate | 392 |
| 100 | 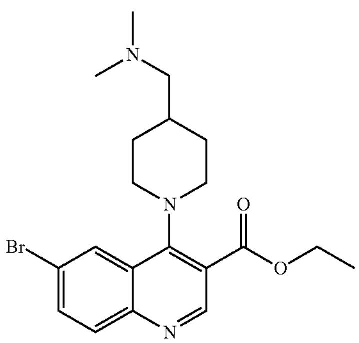 [SMILES: CCOC(=O)c1cnc2ccc(Br)cc2c1N1CCC(CN(C)C)CC1] | ethyl 6-bromo-4-(4-((dimethylamino)methyl)piperidin-1-yl)quinoline-3-carboxylate | 420 |
| 101 | 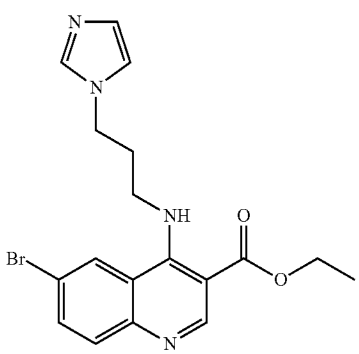 [SMILES: CCOC(=O)c1cnc2ccc(Br)cc2c1NCCCn1ccnc1] | ethyl 4-(3-(1H-imidazol-1-yl)propylamino)-6-bromoquinoline-3-carboxylate | 403 |
| 102 | 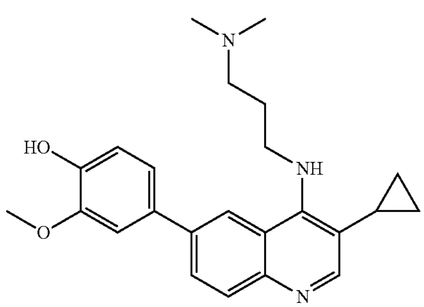 [SMILES: COc1cc(-c2ccc3ncc(C4CC4)c(NCCCN(C)C)c3c2)ccc1O] | 4-(3-cyclopropyl-4-(3-(dimethylamino)propylamino)quinolin-6-yl)-2-methoxyphenol | 392 |

TABLE 1-continued

| No. | Structure | Compound Name | ESI MS (m/z) |
|---|---|---|---|
| 103 | 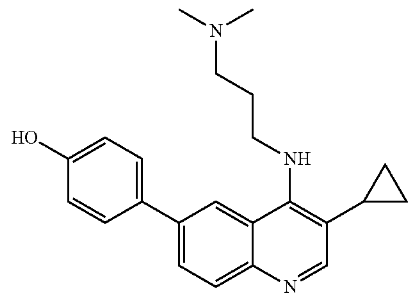 [SMILES: CN(C)CCCNc1c(C2CC2)cnc2ccc(-c3ccc(O)cc3)cc12] | 4-(3-cyclopropyl-4-(3-(dimethylamino)propylamino)quinolin-6-yl)phenol | 361 |
| 104 | 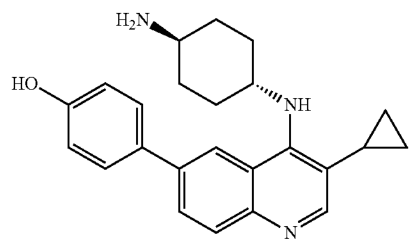 [SMILES: N[C@H]1CC[C@H](Nc2c(C3CC3)cnc3ccc(-c4ccc(O)cc4)cc23)CC1] | 4-(4-((trans)-4-aminocyclohexyl-amino)-3-cyclopropylquinolin-6-yl)phenol | 373 |
| 105 | 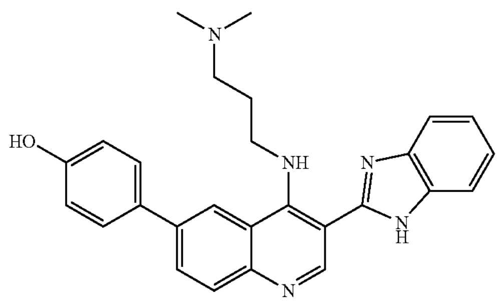 [SMILES: CN(C)CCCNc1c(-c2nc3ccccc3[nH]2)cnc2ccc(-c3ccc(O)cc3)cc12] | 4-(3-(1H-benzo[d]imidazol-2-yl)-4-(3-(dimethylamino)propylamino)quinolin-6-yl)phenol | 438 |
| 106 | 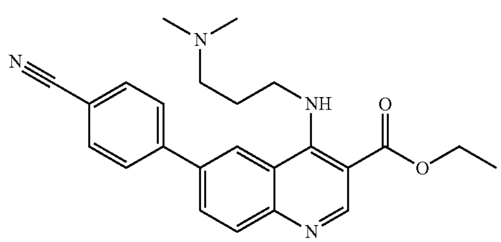 [SMILES: CCOC(=O)c1cnc2ccc(-c3ccc(C#N)cc3)cc2c1NCCCN(C)C] | ethyl 6-(4-cyanophenyl)-4-(3-(dimethylamino)propylamino)quinoline-3-carboxylate | 402 |
| 107 | 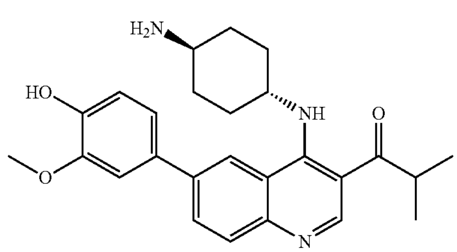 [SMILES: COc1cc(-c2ccc3ncc(C(=O)C(C)C)c(N[C@H]4CC[C@H](N)CC4)c3c2)ccc1O] | 1-(4-((trans)-4-aminocyclohexyl-amino)-6-(4-hydroxy-3-methoxyphenyl)quinolin-3-yl)-2-methylpropan-1-one | 434 |
| 108 | 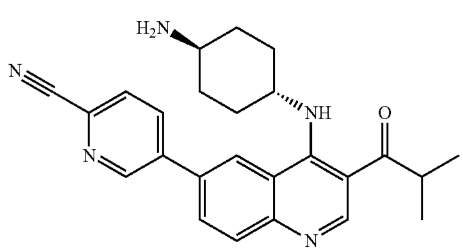 [SMILES: CC(C)C(=O)c1cnc2ccc(-c3ccc(C#N)nc3)cc2c1N[C@H]1CC[C@H](N)CC1] | 5-(4-((trans)-4-aminocyclohexyl-amino)-3-isobutyrylquinolin-6-yl)picolinonitrile | 414 |

TABLE 1-continued

| No. | Structure | Compound Name | ESI MS (m/z) |
|---|---|---|---|
| 109 | 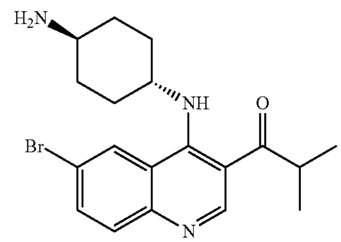 [SMILES: CC(C)C(=O)c1cnc2ccc(Br)cc2c1N[C@H]1CC[C@H](N)CC1] | 1-(4-((trans)-4-aminocyclohexyl-amino)-6-bromoquinolin-3-yl)-2-methylpropan-1-one | 390 |
| 110 | 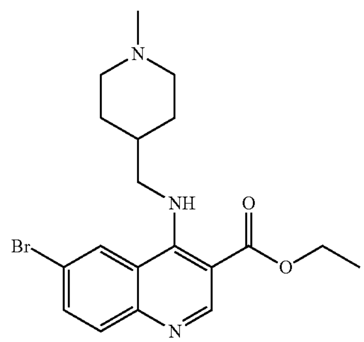 [SMILES: CCOC(=O)c1cnc2ccc(Br)cc2c1NCC1CCN(C)CC1] | ethyl 6-bromo-4-((1-methylpiperidin-4-yl)methylamino)quinoline-3-carboxylate | 406 |
| 111 | 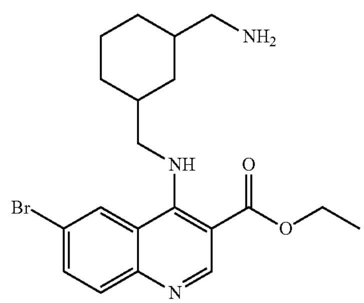 [SMILES: CCOC(=O)c1cnc2ccc(Br)cc2c1NCC1CCCC(CN)C1] | ethyl 4-((3-(aminomethyl)cyclohexyl)methylamino)-6-bromoquinoline-3-carboxylate | 420 |
| 112 | 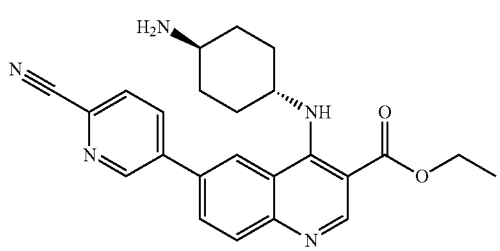 [SMILES: CCOC(=O)c1cnc2ccc(-c3ccc(C#N)nc3)cc2c1N[C@H]1CC[C@H](N)CC1] | ethyl 4-((trans)-4-aminocyclohexylamino)-6-(6-cyanopyridin-3-yl)quinoline-3-carboxylate | 415 |
| 113 | 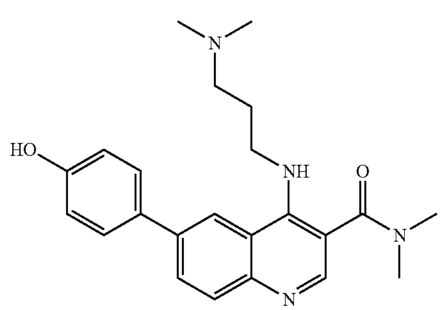 [SMILES: CN(C)CCCNc1c(C(=O)N(C)C)cnc2ccc(-c3ccc(O)cc3)cc12] | 4-(3-(dimethylamino)propylamino)-6-(4-hydroxyphenyl)-N,N-dimethylquinoline-3-carboxamide | 392 |

TABLE 1-continued

| No. | Structure | Compound Name | ESI MS (m/z) |
|---|---|---|---|
| 114 | 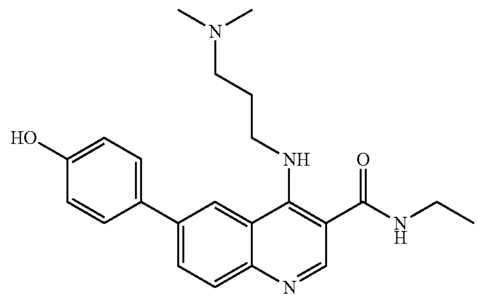 [SMILES: CCNC(=O)c1cnc2ccc(-c3ccc(O)cc3)cc2c1NCCCN(C)C] | 4-(3-(dimethylamino)propylamino)-N-ethyl-6-(4-hydroxyphenyl)quinoline-3-carboxamide | 392 |
| 115 | 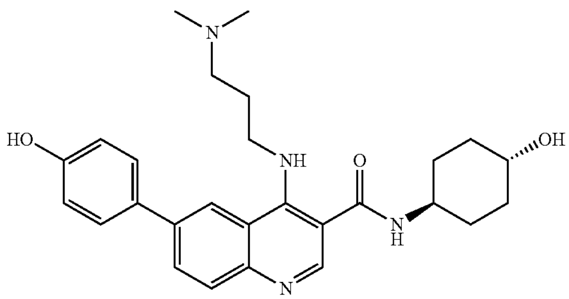 [SMILES: CN(C)CCCNc1c(C(=O)N[C@H]2CC[C@H](O)CC2)cnc2ccc(-c3ccc(O)cc3)cc12] | 4-(3-(dimethylamino)propylamino)-N-((trans)-4-hydroxycyclohexyl)-6-(4-hydroxyphenyl)quinoline-3-carboxamide | 463 |
| 116 | 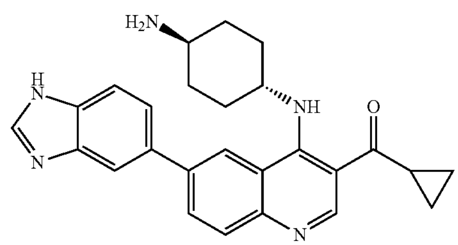 [SMILES: N[C@H]1CC[C@H](Nc2c(C(=O)C3CC3)cnc3ccc(-c4ccc5[nH]cnc5c4)cc23)CC1] | (4-((trans)-4-aminocyclohexylamino)-6-(1H-benzo[d]imidazol-5-yl)quinolin-3-yl)(cyclopropyl)methanone | 426 |
| 117 | 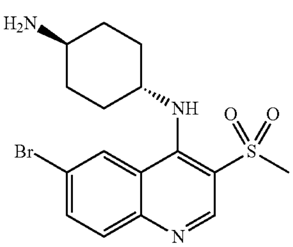 [SMILES: CS(=O)(=O)c1cnc2ccc(Br)cc2c1N[C@H]1CC[C@H](N)CC1] | (trans)-N1-(6-bromo-3-(methylsulfonyl)quinolin-4-yl)cyclohexane-1,4-diamine | 398 |
| 118 | 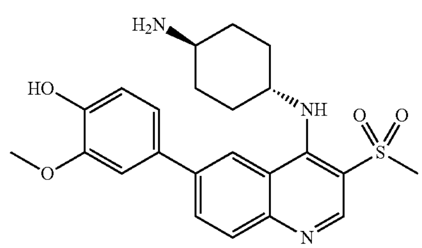 | 4-(4-((trans)-4-aminocyclohexyl-amino)-3-(methylsulfonyl)quinolin-6-yl)-2-methoxyphenol | 442 |
| 119 | 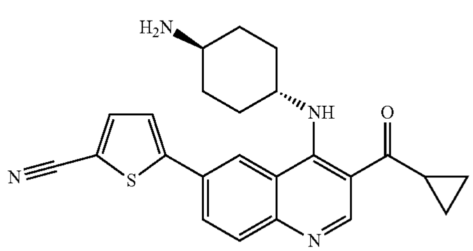 [SMILES: N#Cc1ccc(-c2ccc3ncc(C(=O)C4CC4)c(N[C@H]4CC[C@H](N)CC4)c3c2)s1] | 5-(4-((trans)-4-aminocyclohexyl-amino)-3-(cyclopropanecarbonyl)quinolin-6-yl)thiophene-2-carbonitrile | 417 |

TABLE 1-continued

| No. | Structure | Compound Name | ESI MS (m/z) |
|---|---|---|---|
| 120 | 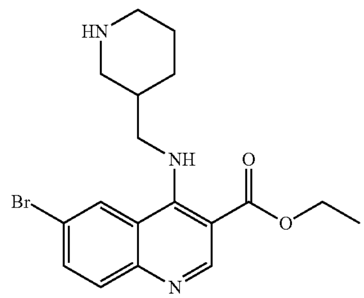 [SMILES: CCOC(=O)c1cnc2ccc(Br)cc2c1NCC1CCCNC1] | ethyl 6-bromo-4-(piperidin-3-ylmethylamino)quinoline-3-carboxylate | 392 |
| 121 | 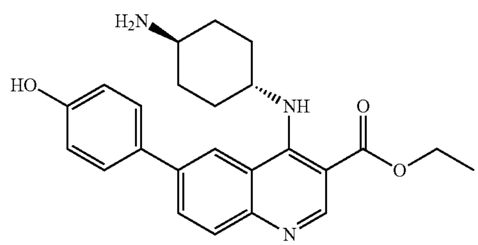 [SMILES: CCOC(=O)c1cnc2ccc(-c3ccc(O)cc3)cc2c1N[C@H]1CC[C@H](N)CC1] | ethyl 4-((trans)-4-aminocyclohexylamino)-6-(4-hydroxyphenyl)quinoline-3-carboxylate | 405 |
| 122 | 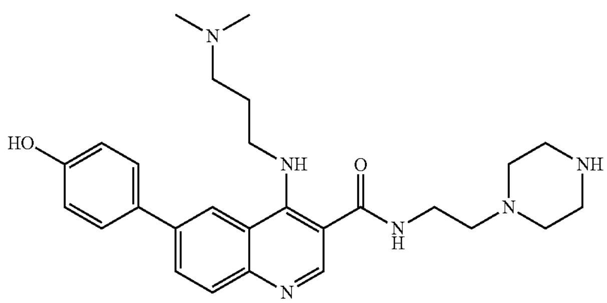 [SMILES: CN(C)CCCNc1c(C(=O)NCCN2CCNCC2)cnc2ccc(-c3ccc(O)cc3)cc12] | 4-(3-(dimethylamino)propylamino)-6-(4-hydroxyphenyl)-N-(2-(piperazin-1-yl)ethyl)quinoline-3-carboxamide | 477 |
| 123 | 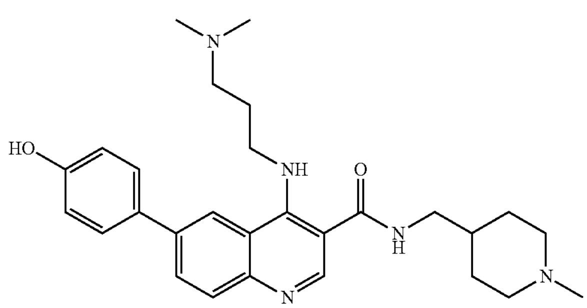 [SMILES: CN(C)CCCNc1c(C(=O)NCC2CCN(C)CC2)cnc2ccc(-c3ccc(O)cc3)cc12] | 4-(3-(dimethylamino)propylamino)-6-(4-hydroxyphenyl)-N-((1-methylpiperidin-4-yl)methyl)quinoline-3-carboxamide | 476 |
| 124 | 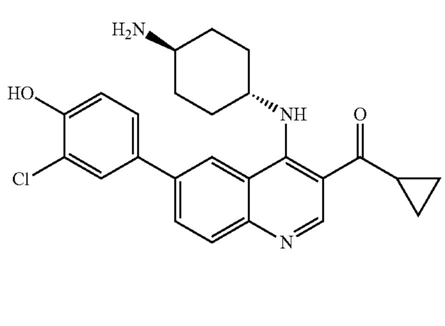 [SMILES: N[C@H]1CC[C@H](Nc2c(C(=O)C3CC3)cnc3ccc(-c4ccc(O)c(Cl)c4)cc23)CC1] | (4-((trans)-4-aminocyclohexylamino)-6-(3-chloro-4-hydroxyphenyl)quinolin-3-yl)(cyclopropyl)methanone | 436 |

TABLE 1-continued

| No. | Structure | Compound Name | ESI MS (m/z) |
|---|---|---|---|
| 125 | 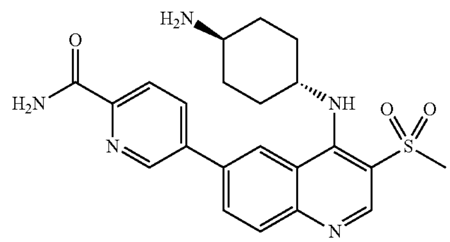 [SMILES: CS(=O)(=O)c1cnc2ccc(-c3ccc(C(N)=O)nc3)cc2c1N[C@H]1CC[C@H](N)CC1] | 5-(4-((trans)-4-aminocyclohexyl-amino)-3-(methylsulfonyl)quinolin-6-yl)picolinamide | 440 |
| 126 | 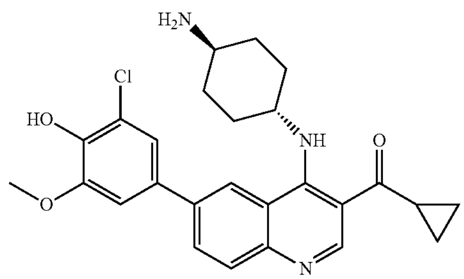 [SMILES: COc1cc(-c2ccc3ncc(C(=O)C4CC4)c(N[C@H]4CC[C@H](N)CC4)c3c2)cc(Cl)c1O] | (4-((trans)-4-aminocyclohexylamino)-6-(3-chloro-4-hydroxy-5-methoxyphenyl)quinolin-3-yl)(cyclopropyl)methanone | 466 |
| 127 | 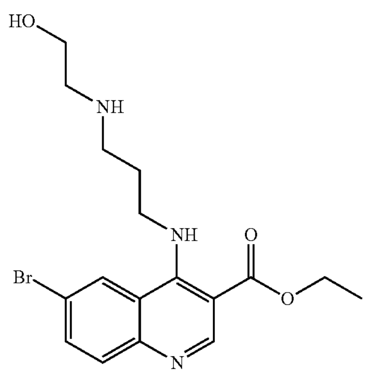 [SMILES: CCOC(=O)c1cnc2ccc(Br)cc2c1NCCCNCCO] | ethyl 6-bromo-4-(3-(2-hydroxyethylamino)propylamino)quinoline-3-carboxylate | 396 |
| 128 | 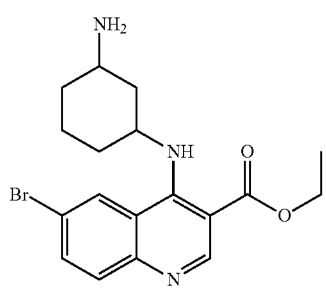 [SMILES: CCOC(=O)c1cnc2ccc(Br)cc2c1NC1CCCC(N)C1] | ethyl 4-(3-aminocyclohexylamino)-6-bromoquinoline-3-carboxylate | 392 |
| 129 | 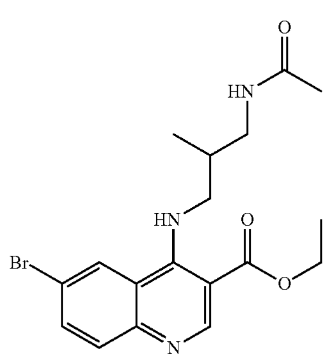 [SMILES: CCOC(=O)c1cnc2ccc(Br)cc2c1NCC(C)CNC(C)=O] | ethyl 4-(3-acetamido-2-methylpropylamino)-6-bromoquinoline-3-carboxylate | 408 |

TABLE 1-continued

| No. | Structure | Compound Name | ESI MS (m/z) |
|---|---|---|---|
| 130 | 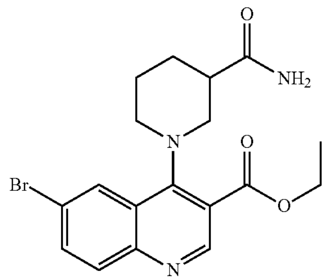 [SMILES: CCOC(=O)c1cnc2ccc(Br)cc2c1N1CCCC(C(N)=O)C1] | ethyl 6-bromo-4-(3-carbamoylpiperidin-1-yl)quinoline-3-carboxylate | 406 |
| 131 | 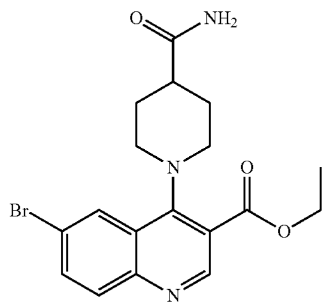 [SMILES: CCOC(=O)c1cnc2ccc(Br)cc2c1N1CCC(C(N)=O)CC1] | ethyl 6-bromo-4-(4-carbamoylpiperidin-1-yl)quinoline-3-carboxylate | 406 |
| 132 | 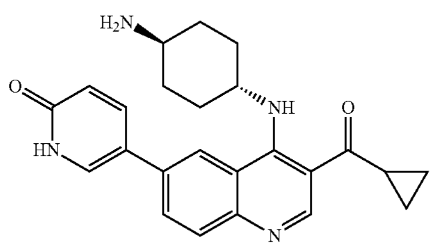 [SMILES: N[C@H]1CC[C@H](Nc2c(C(=O)C3CC3)cnc3ccc(-c4ccc(=O)[nH]c4)cc23)CC1] | 5-(4-((trans)-4-aminocyclohexyl-amino)-3-(cyclopropanecarbonyl)quinolin-6-yl)pyridin-2(1H)-one | 402 |
| 133 | 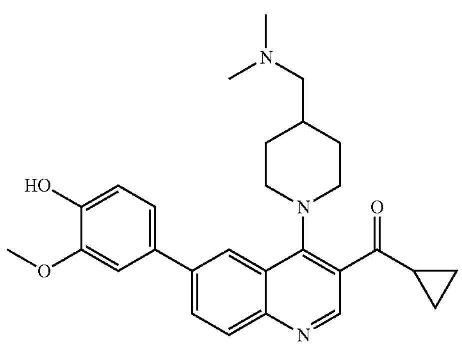 [SMILES: COc1cc(-c2ccc3ncc(C(=O)C4CC4)c(N4CCC(CN(C)C)CC4)c3c2)ccc1O] | cyclopropyl(4-(4-((dimethylamino)methyl)piperidin-1-yl)-6-(4-hydroxy-3-methoxyphenyl)quinolin-3-yl)methanone | 460 |
| 134 | 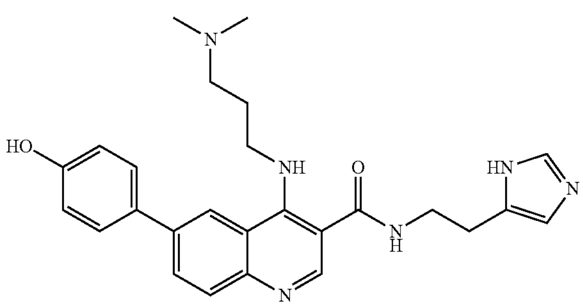 [SMILES: CN(C)CCCNc1c(C(=O)NCCc2cnc[nH]2)cnc2ccc(-c3ccc(O)cc3)cc12] | N-(2-(1H-imidazol-5-yl)ethyl)-4-(3-(dimethylamino)propylamino)-6-(4-hydroxyphenyl)quinoline-3-carboxamide | 459 |

TABLE 1-continued

| No. | Structure | Compound Name | ESI MS (m/z) |
|---|---|---|---|
| 135 | 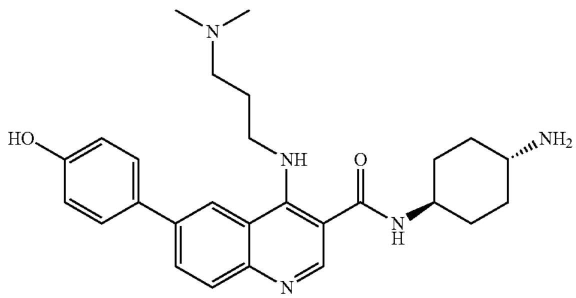 [SMILES: CN(C)CCCNc1c(C(=O)N[C@H]2CC[C@H](N)CC2)cnc2ccc(-c3ccc(O)cc3)cc12] | N-((trans)-4-aminocyclohexyl)-4-(3-(dimethylamino)propylamino)-6-(4-hydroxyphenyl)quinoline-3-carboxamide | 462 |
| 136 | 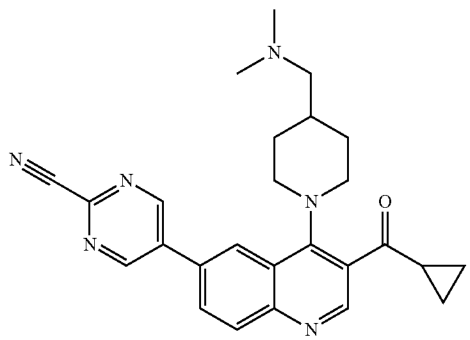 [SMILES: CN(C)CC1CCN(c2c(C(=O)C3CC3)cnc3ccc(-c4cnc(C#N)nc4)cc23)CC1] | 5-(3-(cyclopropanecarbonyl)-4-(4-((dimethylamino)methyl)piperidin-1-yl)quinolin-6-yl)pyrimidine-2-carbonitrile | 441 |
| 137 | 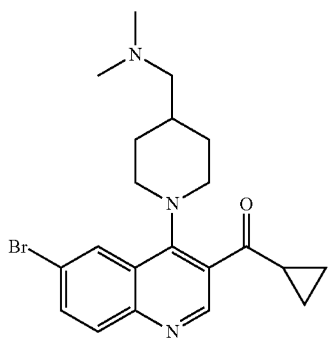 [SMILES: CN(C)CC1CCN(c2c(C(=O)C3CC3)cnc3ccc(Br)cc23)CC1] | (6-bromo-4-(4-((dimethylamino)methyl)piperidin-1-yl)quinolin-3-yl)(cyclopropyl)methanone | 416 |
| 138 | 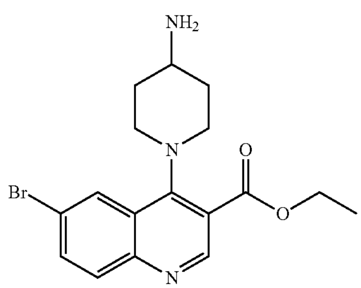 [SMILES: CCOC(=O)c1cnc2ccc(Br)cc2c1N1CCC(N)CC1] | ethyl 4-(4-aminopiperidin-1-yl)-6-bromoquinoline-3-carboxylate | 378 |
| 139 | 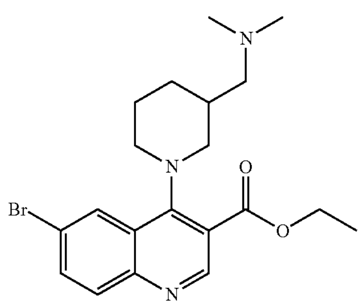 [SMILES: CCOC(=O)c1cnc2ccc(Br)cc2c1N1CCCC(CN(C)C)C1] | ethyl 6-bromo-4-(3-((dimethylamino)methyl)piperidin-1-yl)quinoline-3-carboxylate | 420 |

TABLE 1-continued

| No. | Structure | Compound Name | ESI MS (m/z) |
|---|---|---|---|
| 140 | 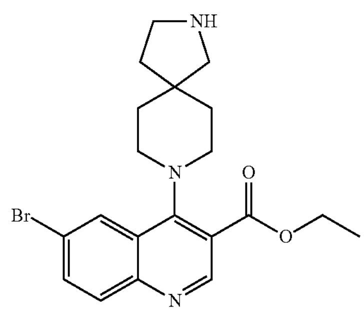 [SMILES: CCOC(=O)c1cnc2ccc(Br)cc2c1N1CCC2(CCNC2)CC1] | ethyl 6-bromo-4-(2,8-diazaspiro[4.5]decan-8-yl)quinoline-3-carboxylate | 418 |
| 141 | 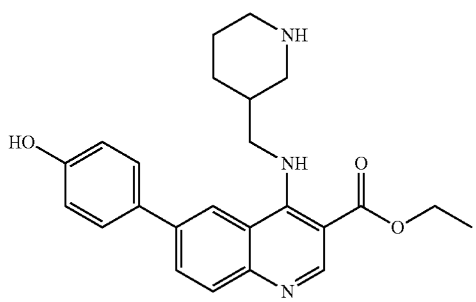 [SMILES: CCOC(=O)c1cnc2ccc(-c3ccc(O)cc3)cc2c1NCC1CCCNC1] | ethyl 6-(4-hydroxyphenyl)-4-(piperidin-3-ylmethylamino)quinoline-3-carboxylate | 405 |
| 142 | 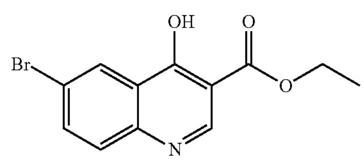 [SMILES: CCOC(=O)c1cnc2ccc(Br)cc2c1O] | ethyl 6-bromo-4-hydroxyquinoline-3-carboxylate | 296 |
| 143 | 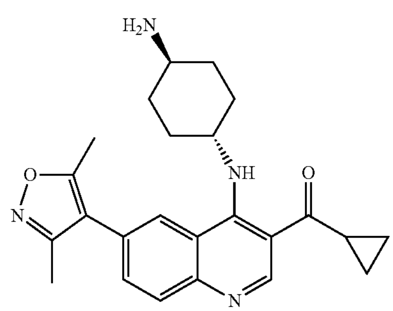 [SMILES: Cc1noc(C)c1-c1ccc2ncc(C(=O)C3CC3)c(N[C@H]3CC[C@H](N)CC3)c2c1] | (4-((trans)-4-aminocyclohexylamino)-6-(3,5-dimethylisoxazol-4-yl)quinolin-3-yl)(cyclopropyl)methanone | 405 |
| 144 | 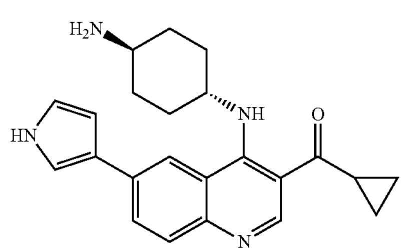 [SMILES: N[C@H]1CC[C@H](Nc2c(C(=O)C3CC3)cnc3ccc(-c4cc[nH]c4)cc23)CC1] | (4-((trans)-4-aminocyclohexylamino)-6-(1H-pyrrol-3-yl)quinolin-3-yl)(cyclopropyl)methanone | 374 |

TABLE 1-continued

| No. | Structure | Compound Name | ESI MS (m/z) |
| --- | --- | --- | --- |
| 145 | 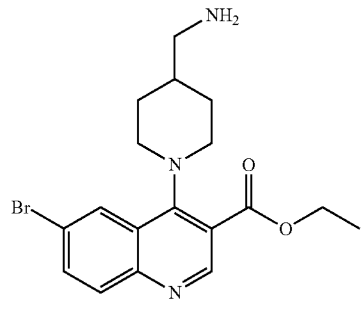 [SMILES: CCOC(=O)c1cnc2ccc(Br)cc2c1N1CCC(CN)CC1] | ethyl 4-(4-(aminomethyl)piperidin-1-yl)-6-bromoquinoline-3-carboxylate | 392 |
| 146 | 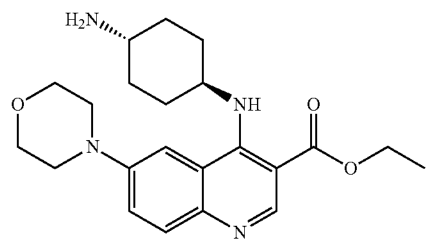 [SMILES: CCOC(=O)c1cnc2ccc(N3CCOCC3)cc2c1N[C@H]1CC[C@H](N)CC1] | ethyl 4-((trans)-4-aminocyclohexylamino)-6-morpholinoquinoline-3-carboxylate | 398 |
| 147 | 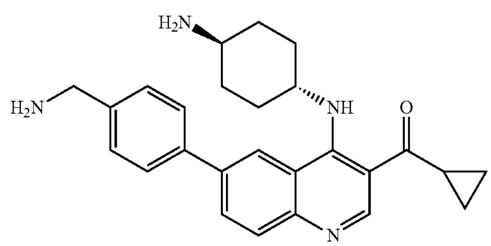 [SMILES: NCc1ccc(-c2ccc3ncc(C(=O)C4CC4)c(N[C@H]4CC[C@H](N)CC4)c3c2)cc1] | (4-((trans)-4-aminocyclohexylamino)-6-(4-(aminomethyl)phenyl)quinolin-3-yl)(cyclopropyl)methanone | 415 |
| 148 | 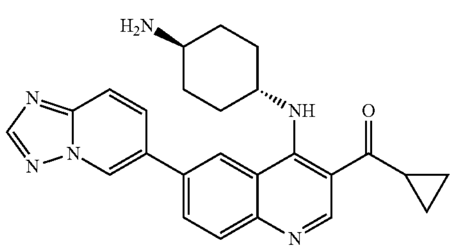 [SMILES: N[C@H]1CC[C@H](Nc2c(C(=O)C3CC3)cnc3ccc(-c4ccc5ncnn5c4)cc23)CC1] | (6-([1,2,4]triazolo[1,5-a]pyridin-6-yl)-4-((trans)-4-aminocyclohexylamino)quinolin-3-yl)(cyclopropyl)methanone | 427 |
| 149 | 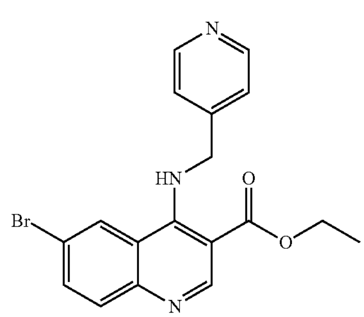 [SMILES: CCOC(=O)c1cnc2ccc(Br)cc2c1NCc1ccncc1] | ethyl 6-bromo-4-(pyridin-4-ylmethylamino)quinoline-3-carboxylate | 386 |

TABLE 1-continued

| No. | Structure | Compound Name | ESI MS (m/z) |
|---|---|---|---|
| 150 | 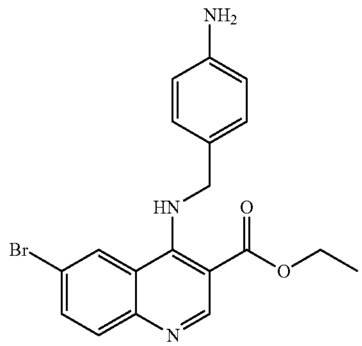 [SMILES: CCOC(=O)c1cnc2ccc(Br)cc2c1NCc1ccc(N)cc1] | ethyl 4-(4-aminobenzylamino)-6-bromoquinoline-3-carboxylate | 400 |
| 151 | 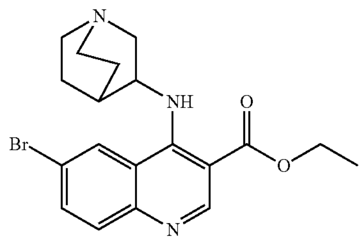 [SMILES: CCOC(=O)c1cnc2ccc(Br)cc2c1NC1CN2CCC1CC2] | ethyl 6-bromo-4-(quinuclidin-3-ylamino)quinoline-3-carboxylate | 404 |
| 152 | 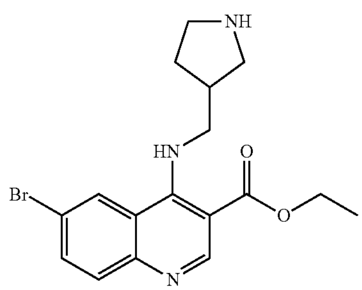 [SMILES: CCOC(=O)c1cnc2ccc(Br)cc2c1NCC1CCNC1] | ethyl 6-bromo-4-(pyrrolidin-3-ylmethylamino)quinoline-3-carboxylate | 378 |
| 153 | 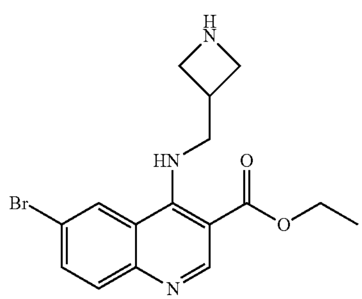 [SMILES: CCOC(=O)c1cnc2ccc(Br)cc2c1NCC1CNC1] | ethyl 4-(azetidin-3-ylmethylamino)-6-bromoquinoline-3-carboxylate | 364 |
| 154 | 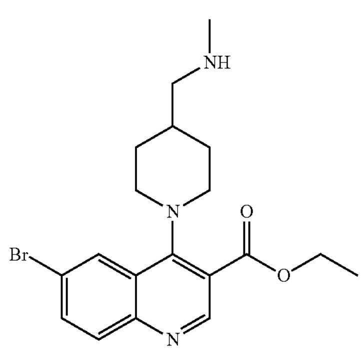 [SMILES: CCOC(=O)c1cnc2ccc(Br)cc2c1N1CCC(CNC)CC1] | ethyl 6-bromo-4-(4-((methylamino)methyl)piperidin-1-yl)quinoline-3-carboxylate | 406 |

TABLE 1-continued

| No. | Structure | Compound Name | ESI MS (m/z) |
|---|---|---|---|
| 155 | 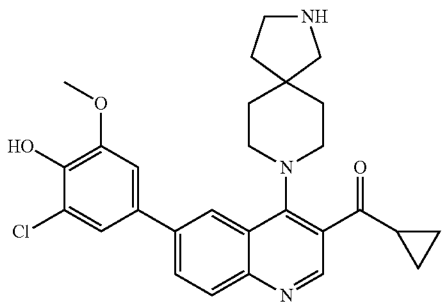 [SMILES: COc1cc(-c2ccc3ncc(C(=O)C4CC4)c(N4CCC5(CCNC5)CC4)c3c2)cc(Cl)c1O] | (6-(3-chloro-4-hydroxy-5-methoxyphenyl)-4-(2,8-diazaspiro[4.5]decan-8-yl)quinolin-3-yl)(cyclopropyl)methanone | 492 |
| 156 | 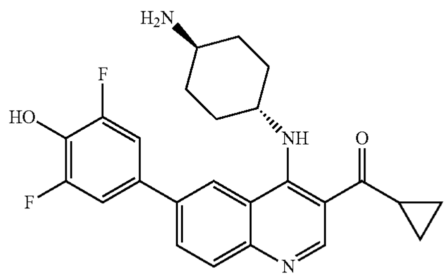 | (4-((trans)-4-aminocyclohexylamino)-6-(3,5-difluoro-4-hydroxyphenyl)quinolin-3-yl)(cyclopropyl)methanone | 437 |
| 157(a) | 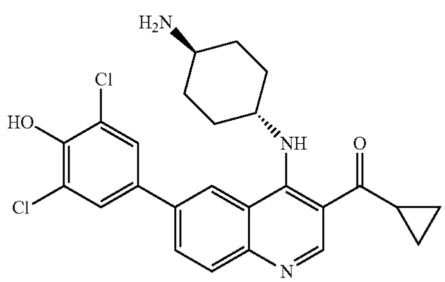 | (4-((trans)-4-aminocyclohexylamino)-6-(3,5-dichloro-4-hydroxyphenyl)quinolin-3-yl)(cyclopropyl)methanone hydrochloride | 470 |
| 157(b) | 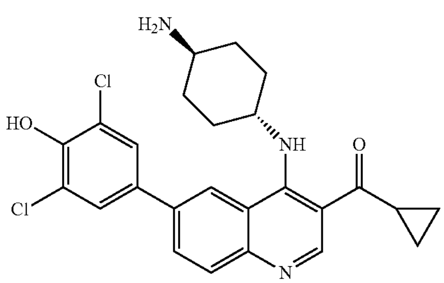 | (4-((trans)-4-aminocyclohexylamino)-6-(3,5-dichloro-4-hydroxyphenyl)quinolin-3-yl)(cyclopropyl)methanone dihydrochloride | 470 |
| 158 | 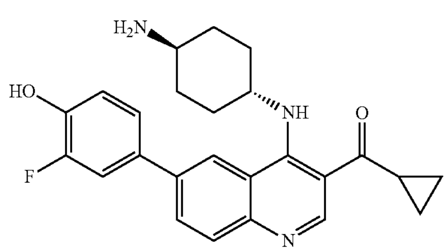 [SMILES: N[C@H]1CC[C@H](Nc2c(C(=O)C3CC3)cnc3ccc(-c4ccc(O)c(F)c4)cc23)CC1] | (4-((trans)-4-aminocyclohexylamino)-6-(3-fluoro-4-hydroxyphenyl)quinolin-3-yl)(cyclopropyl)methanone | 419 |

TABLE 1-continued

| No. | Structure | Compound Name | ESI MS (m/z) |
|---|---|---|---|
| 159 | 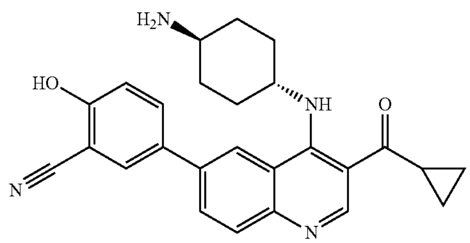 [SMILES: N#Cc1cc(-c2ccc3ncc(C(=O)C4CC4)c(N[C@H]4CC[C@H](N)CC4)c3c2)ccc1O] | 5-(4-((trans)-4-aminocyclohexyl-amino)-3-(cyclopropanecarbonyl)quinolin-6-yl)-2-hydroxybenzonitrile | 427 |
| 160 | 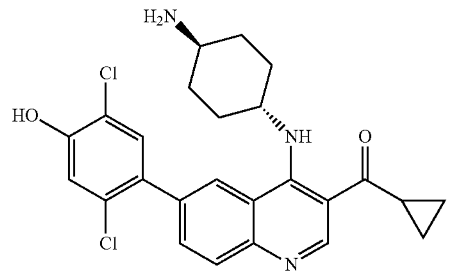 [SMILES: N[C@H]1CC[C@H](Nc2c(C(=O)C3CC3)cnc3ccc(-c4cc(Cl)c(O)cc4Cl)cc23)CC1] | (4-((trans)-4-aminocyclohexylamino)-6-(2,5-dichloro-4-hydroxyphenyl)quinolin-3-yl)(cyclopropyl)methanone | 470 |
| 161 | 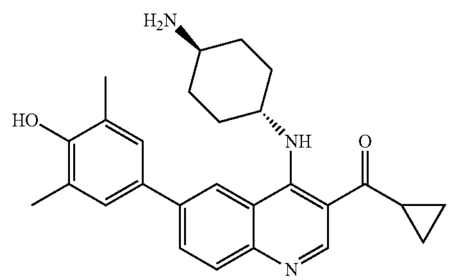 | (4-((trans)-4-aminocyclohexylamino)-6-(4-hydroxy-3,5-dimethylphenyl)quinolin-3-yl)(cyclopropyl)methanone | 430 |
| 162 | 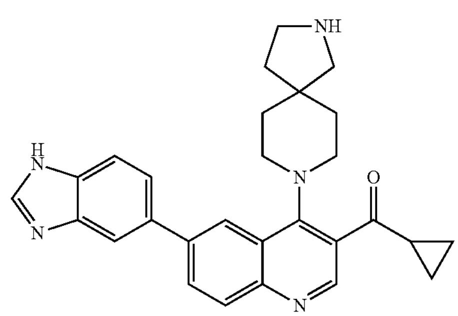 [SMILES: O=C(c1cnc2ccc(-c3ccc4[nH]cnc4c3)cc2c1N1CCC2(CCNC2)CC1)C1CC1] | (6-(1H-benzo[d]imidazol-5-yl)-4-(2,8-diazaspiro[4.5]decan-8-yl)quinolin-3-yl)(cyclopropyl)methanone | 452 |
| 163 | 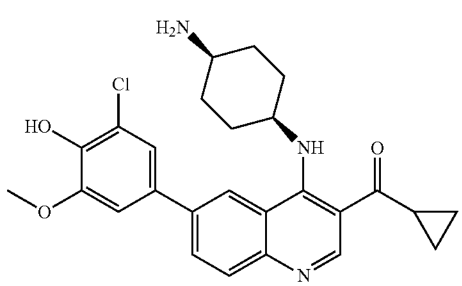 [SMILES: COc1cc(-c2ccc3ncc(C(=O)C4CC4)c(N[C@H]4CC[C@@H](N)CC4)c3c2)cc(Cl)c1O] | (4-((cis)-4-aminocyclohexylamino)-6-(3-chloro-4-hydroxy-5-methoxyphenyl)quinolin-3-yl)(cyclopropyl)methanone | 466 |

TABLE 1-continued

| No. | Structure | Compound Name | ESI MS (m/z) |
|---|---|---|---|
| 164 | 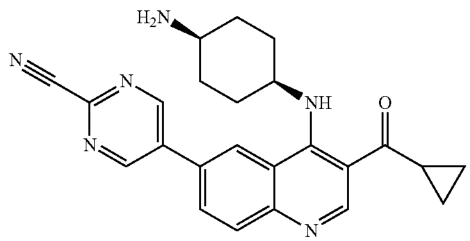 [SMILES: N#Cc1ncc(-c2ccc3ncc(C(=O)C4CC4)c(N[C@H]4CC[C@@H](N)CC4)c3c2)cn1] | 5-(4-((cis)-4-aminocyclohexylamino)-3-(cyclopropanecarbonyl)quinolin-6-yl) pyrimidine-2-carbonitrile | 412 |
| 165 | 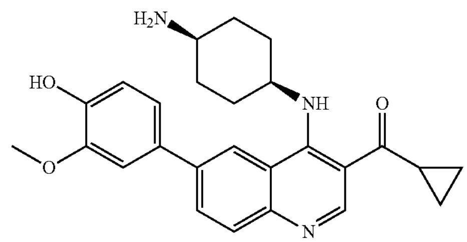 [SMILES: COc1cc(-c2ccc3ncc(C(=O)C4CC4)c(N[C@H]4CC[C@@H](N)CC4)c3c2)ccc1O] | (4-((cis)-4-aminocyclohexylamino)-6-(4-hydroxy-3-methoxyphenyl)quinolin-3-yl)(cyclopropyl)methanone | 432 |
| 166 | 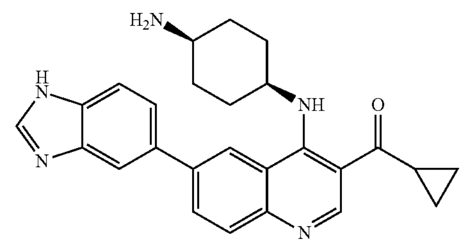 [SMILES: N[C@H]1CC[C@@H](Nc2c(C(=O)C3CC3)cnc3ccc(-c4ccc5[nH]cnc5c4)cc23)CC1] | (4-((cis)-4-aminocyclohexylamino)-6-(1H-benzo[d]imidazol-5-yl)quinolin-3-yl)(cyclopropyl)methanone | 426 |
| 167 | 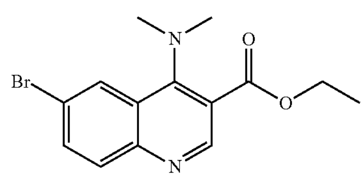 [SMILES: CCOC(=O)c1cnc2ccc(Br)cc2c1N(C)C] | ethyl 6-bromo-4-(dimethylamino)quinoline-3-carboxylate | 323 |
| 168 | 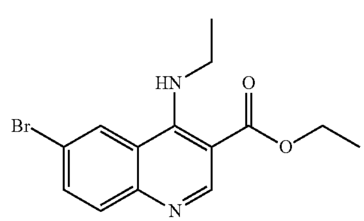 [SMILES: CCNc1c(C(=O)OCC)cnc2ccc(Br)cc12] | ethyl 6-bromo-4-(ethylamino)quinoline-3-carboxylate | 323 |
| 169 | 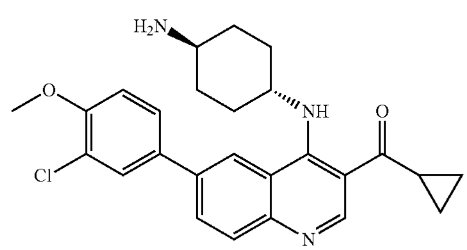 [SMILES: COc1ccc(-c2ccc3ncc(C(=O)C4CC4)c(N[C@H]4CC[C@H](N)CC4)c3c2)cc1Cl] | (4-((trans)-4-aminocyclohexylamino)-6-(3-chloro-4-methoxyphenyl)quinolin-3-yl)(cyclopropyl)methanone | 450 |

TABLE 1-continued

| No. | Structure | Compound Name | ESI MS (m/z) |
|---|---|---|---|
| 170 | 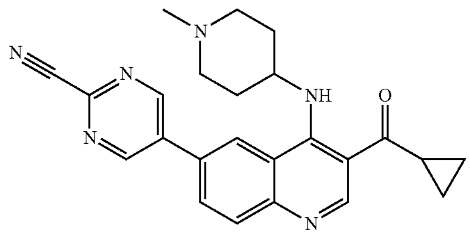 [SMILES: CN1CCC(Nc2c(C(=O)C3CC3)cnc3ccc(-c4cnc(C#N)nc4)cc23)CC1] | 5-(3-(cyclopropanecarbonyl)-4-(1-methylpiperidin-4-ylamino)quinolin-6-yl)pyrimidine-2-carbonitrile | 412 |
| 171 | 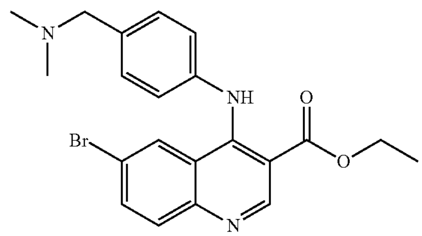 [SMILES: CCOC(=O)c1cnc2ccc(Br)cc2c1Nc1ccc(CN(C)C)cc1] | ethyl 6-bromo-4-(4-((dimethylamino)methyl)phenylamino)quinoline-3-carboxylate | 428 |
| 172 | 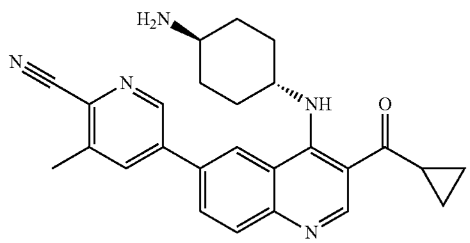 | 5-(4-((trans-4-aminocyclohexyl-amino)-3-(cyclopropanecarbonyl)quinolin-6-yl)-3-methylpicolinonitrile | 426 |
| 173 | 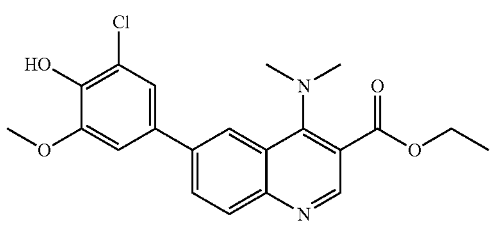 [SMILES: CCOC(=O)c1cnc2ccc(-c3cc(Cl)c(O)c(OC)c3)cc2c1N(C)C] | ethyl 6-(3-chloro-4-hydroxy-5-methoxyphenyl)-4-(dimethylamino)quinoline-3-carboxylate | 401 |
| 174 | 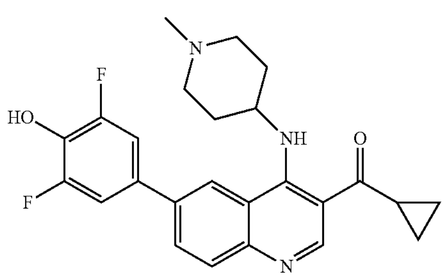 [SMILES: CN1CCC(Nc2c(C(=O)C3CC3)cnc3ccc(-c4cc(F)c(O)c(F)c4)cc23)CC1] | cyclopropyl(6-(3,5-difluoro-4-hydroxyphenyl)-4-(1-methylpiperidin-4-ylamino)quinolin-3-yl)methanone | 437 |
| 175 | 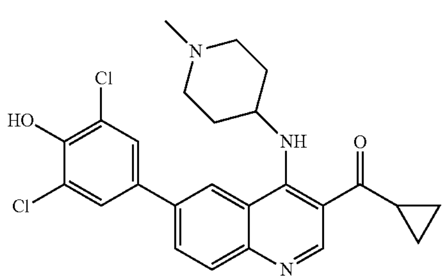 [SMILES: CN1CCC(Nc2c(C(=O)C3CC3)cnc3ccc(-c4cc(Cl)c(O)c(Cl)c4)cc23)CC1] | cyclopropyl(6-(3,5-dichloro-4-hydroxyphenyl)-4-(1-methylpiperidin-4-ylamino)quinolin-3-yl)methanone | 470 |

TABLE 1-continued

| No. | Structure | Compound Name | ESI MS (m/z) |
|---|---|---|---|
| 176 | 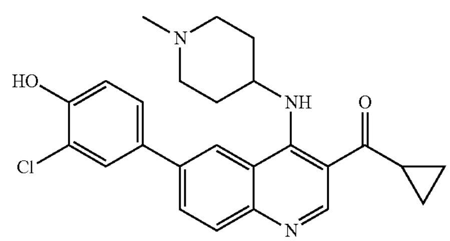 [SMILES: CN1CCC(Nc2c(C(=O)C3CC3)cnc3ccc(-c4ccc(O)c(Cl)c4)cc23)CC1] | (6-(3-chloro-4-hydroxyphenyl)-4-(1-methylpiperidin-4-ylamino)quinolin-3-yl)(cyclopropyl)methanone | 436 |
| 177 | 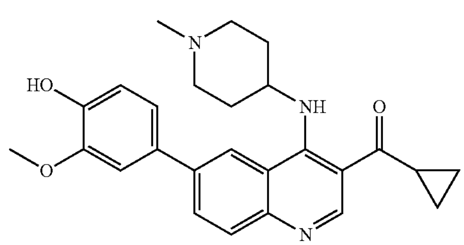 [SMILES: COc1cc(-c2ccc3ncc(C(=O)C4CC4)c(NC4CCN(C)CC4)c3c2)ccc1O] | cyclopropyl(6-(4-hydroxy-3-methoxyphenyl)-4-(1-methylpiperidin-4-ylamino)quinolin-3-yl)methanone | 432 |
| 178 | 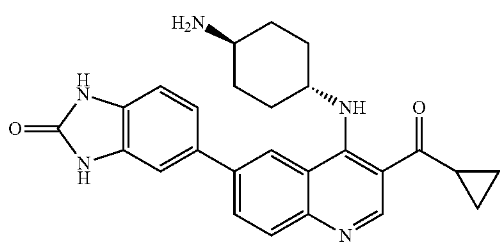 [SMILES: N[C@H]1CC[C@H](Nc2c(C(=O)C3CC3)cnc3ccc(-c4ccc5[nH]c(=O)[nH]c5c4)cc23)CC1] | 5-(4-((trans)-4-aminocyclohexyl-amino)-3-(cyclopropanecarbonyl)quinolin-6-yl)-1H-benzo[d]imidazol-2(3H)-one | 442 |
| 179 | 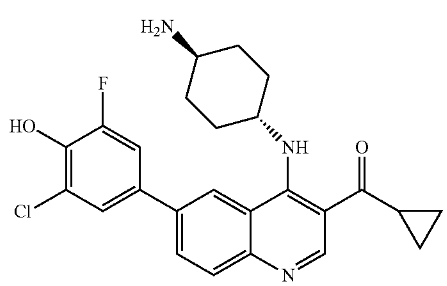 | (4-((trans)-4-aminocyclohexylamino)-6-(3-chloro-5-fluoro-4-hydroxyphenyl)quinolin-3-yl)(cyclopropyl)methanone | 454 |
| 180 | 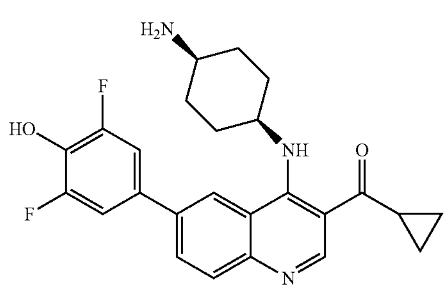 [SMILES: N[C@H]1CC[C@@H](Nc2c(C(=O)C3CC3)cnc3ccc(-c4cc(F)c(O)c(F)c4)cc23)CC1] | (4-((cis)-4-aminocyclohexylamino)-6-(3,5-difluoro-4-hydroxyphenyl)quinolin-3-yl)(cyclopropyl)methanone | 437 |

TABLE 1-continued

| No. | Structure | Compound Name | ESI MS (m/z) |
|---|---|---|---|
| 181 | 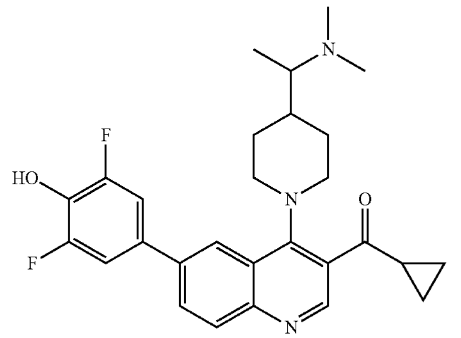 [SMILES: CC(C1CCN(c2c(C(=O)C3CC3)cnc3ccc(-c4cc(F)c(O)c(F)c4)cc23)CC1)N(C)C] | cyclopropyl(6-(3,5-difluoro-4-hydroxyphenyl)-4-(4-(1-(dimethylamino)ethyl)piperidin-1-yl)quinolin-3-yl)methanone | 480 |
| 182 | 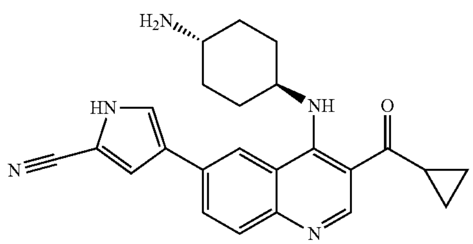 [SMILES: N#Cc1cc(-c2ccc3ncc(C(=O)C4CC4)c(N[C@H]4CC[C@H](N)CC4)c3c2)c[nH]1] | 4-(4-((trans)-4-aminocyclohexyl-amino)-3-(cyclopropanecarbonyl)quinolin-6-yl)-1H-pyrrole-2-carbonitrile | 399 |
| 183 | 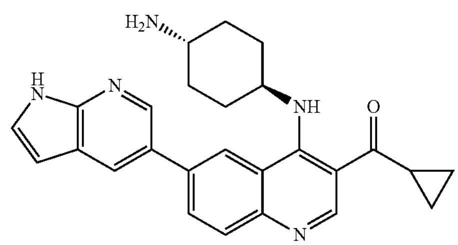 [SMILES: N[C@H]1CC[C@H](Nc2c(C(=O)C3CC3)cnc3ccc(-c4cnc5[nH]ccc5c4)cc23)CC1] | (4-((trans)-4-aminocyclohexylamino)-6-(1H-pyrrolo[2,3-b]pyridin-5-yl)quinolin-3-yl)(cyclopropyl)methanone | 426 |
| 184 | 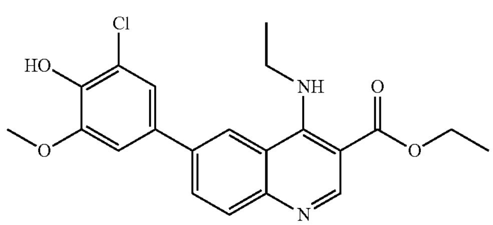 [SMILES: CCNc1c(C(=O)OCC)cnc2ccc(-c3cc(Cl)c(O)c(OC)c3)cc12] | ethyl 6-(3-chloro-4-hydroxy-5-methoxyphenyl)-4-(ethylamino)quinoline-3-carboxylate | 401 |
| 185(a) | 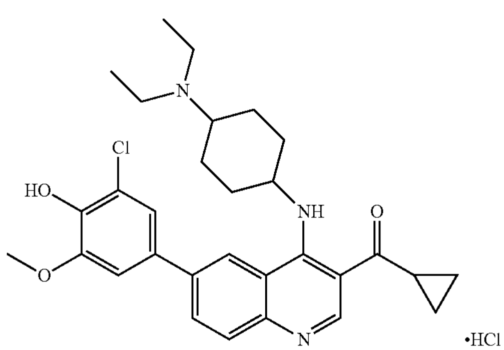 [SMILES: CCN(CC)C1CCC(Nc2c(C(=O)C3CC3)cnc3ccc(-c4cc(Cl)c(O)c(OC)c4)cc23)CC1 ; Cl] | (6-(3-chloro-4-hydroxy-5-methoxyphenyl)-4-(4-(diethylamino)cyclohexylamino)quinolin-3-yl)(cyclopropyl)methanone hydrochloride | 522 |

TABLE 1-continued

| No. | Structure | Compound Name | ESI MS (m/z) |
|---|---|---|---|
| 185(b) | 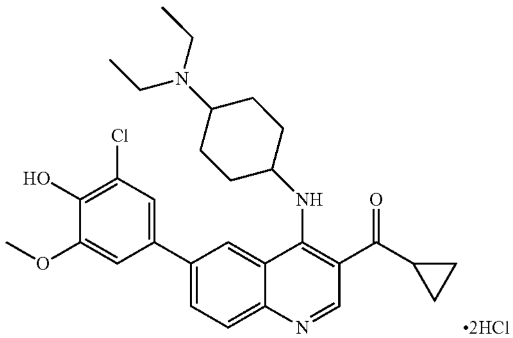 [SMILES: CCN(CC)C1CCC(Nc2c(C(=O)C3CC3)cnc3ccc(-c4cc(Cl)c(O)c(OC)c4)cc23)CC1 ; "·2HCl"] | (6-(3-chloro-4-hydroxy-5-methoxyphenyl)-4-(4-(diethylamino)cyclohexylamino)quinolin-3-yl)(cyclopropyl)methanone dihydrochloride | 522 |
| 186 | 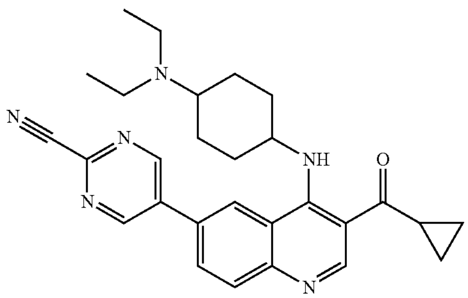 [SMILES: CCN(CC)C1CCC(Nc2c(C(=O)C3CC3)cnc3ccc(-c4cnc(C#N)nc4)cc23)CC1] | 5-(3-(cyclopropanecarbonyl)-4-(4-(diethylamino)cyclohexylamino)quinolin-6-yl)pyrimidine-2-carbonitrile | 469 |
| 187 | 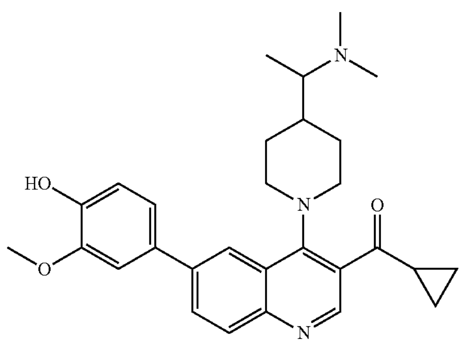 [SMILES: COc1cc(-c2ccc3ncc(C(=O)C4CC4)c(N4CCC(C(C)N(C)C)CC4)c3c2)ccc1O] | cyclopropyl(4-(4-(1-(dimethylamino)ethyl)piperidin-1-yl)-6-(4-hydroxy-3-methoxyphenyl)quinolin-3-yl)methanone | 474 |
| 188 | 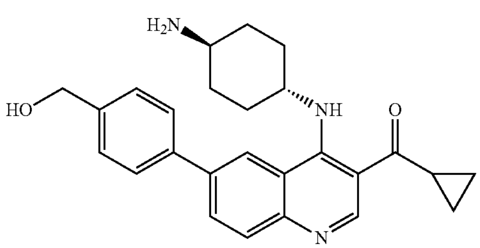 [SMILES: N[C@H]1CC[C@H](Nc2c(C(=O)C3CC3)cnc3ccc(-c4ccc(CO)cc4)cc23)CC1] | (4-((trans)-4-aminocyclohexylamino)-6-(4-(hydroxymethyl)phenyl)quinolin-3-yl)(cyclopropyl)methanone | 416 |
| 189 | 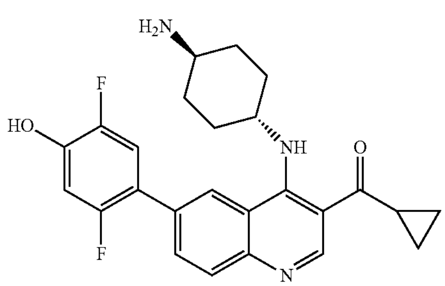 [SMILES: N[C@H]1CC[C@H](Nc2c(C(=O)C3CC3)cnc3ccc(-c4cc(F)c(O)cc4F)cc23)CC1] | (4-((trans)-4-aminocyclohexylamino)-6-(2,5-difluoro-4-hydroxyphenyl)quinolin-3-yl)(cyclopropyl)methanone | 437 |

TABLE 1-continued

| No. | Structure | Compound Name | ESI MS (m/z) |
|---|---|---|---|
| 190 | 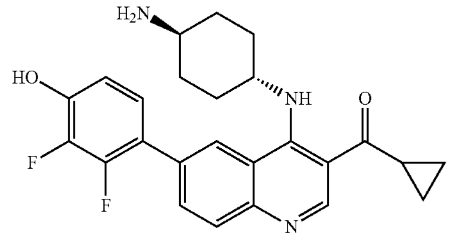 [SMILES: N[C@H]1CC[C@H](Nc2c(C(=O)C3CC3)cnc3ccc(-c4ccc(O)c(F)c4F)cc23)CC1] | (4-((trans)-4-aminocyclohexylamino)-6-(2,3-difluoro-4-hydroxyphenyl)quinolin-3-yl)(cyclopropyl)methanone | 437 |
| 191 | 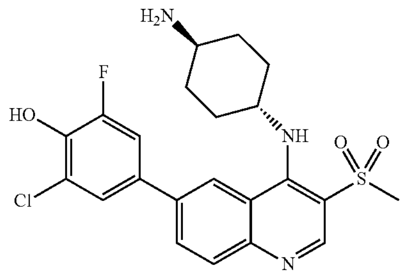 [SMILES: CS(=O)(=O)c1cnc2ccc(-c3cc(F)c(O)c(Cl)c3)cc2c1N[C@H]1CC[C@H](N)CC1] | 4-(4-((trans)-4-aminocyclohexylamino)-3-(methylsulfonyl)quinolin-6-yl)-2-chloro-6-fluorophenol | 464 |
| 192 | 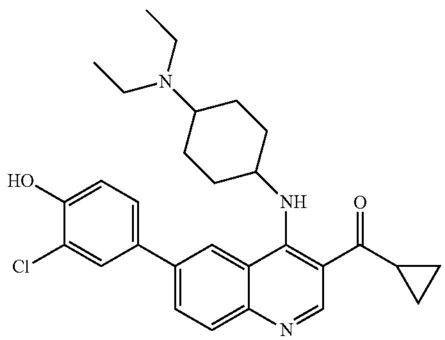 [SMILES: CCN(CC)C1CCC(Nc2c(C(=O)C3CC3)cnc3ccc(-c4ccc(O)c(Cl)c4)cc23)CC1] | (6-(3-chloro-4-hydroxyphenyl)-4-(4-(diethylamino)cyclohexylamino)quinolin-3-yl)(cyclopropyl)methanone | 492 |
| 193 | 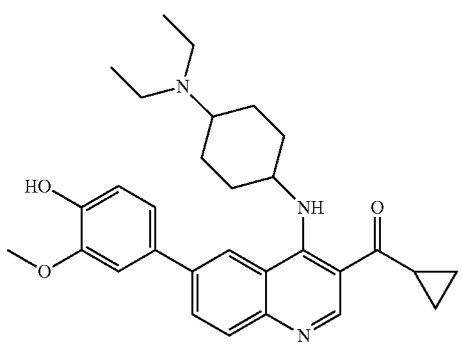 [SMILES: CCN(CC)C1CCC(Nc2c(C(=O)C3CC3)cnc3ccc(-c4ccc(O)c(OC)c4)cc23)CC1] | cyclopropyl(4-(4-(diethylamino)cyclohexylamino)-6-(4-hydroxy-3-methoxyphenyl)quinolin-3-yl)methanone | 488 |
| 194 | 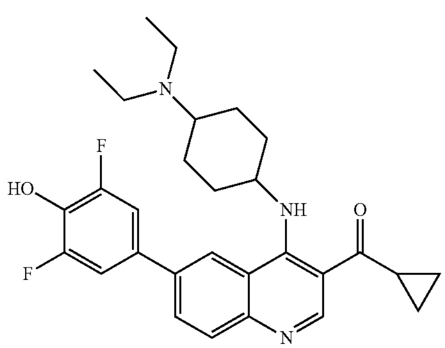 [SMILES: CCN(CC)C1CCC(Nc2c(C(=O)C3CC3)cnc3ccc(-c4cc(F)c(O)c(F)c4)cc23)CC1] | cyclopropyl(4-(4-(diethylamino)cyclohexylamino)-6-(3,5-difluoro-4-hydroxyphenyl)quinolin-3-yl)methanone | 494 |

TABLE 1-continued

| No. | Structure | Compound Name | ESI MS (m/z) |
|---|---|---|---|
| 195 | 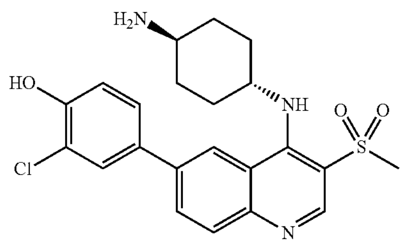 [SMILES: CS(=O)(=O)c1cnc2ccc(-c3ccc(O)c(Cl)c3)cc2c1N[C@H]1CC[C@H](N)CC1] | 4-(4-((trans)-4-aminocyclohexyl-amino)-3-(methylsulfonyl)quinolin-6-yl)-2-chlorophenol | 446 |
| 196 | 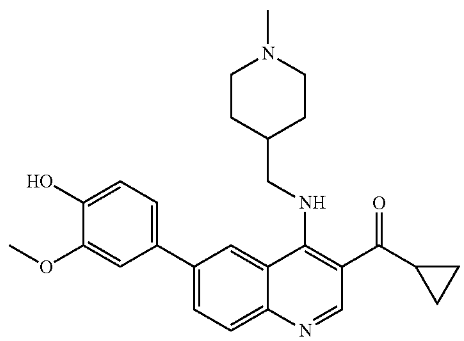 [SMILES: COc1cc(-c2ccc3ncc(C(=O)C4CC4)c(NCC4CCN(C)CC4)c3c2)ccc1O] | cyclopropyl(6-(4-hydroxy-3-methoxyphenyl)-4-((1-methylpiperidin-4-yl)methylamino)quinolin-3-yl)methanone | 446 |
| 197 | 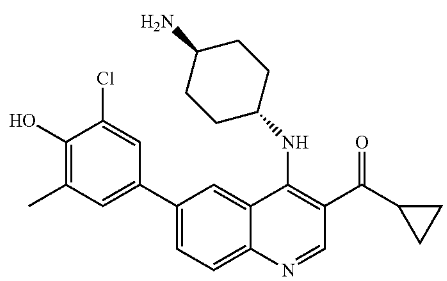 [SMILES: Cc1cc(-c2ccc3ncc(C(=O)C4CC4)c(N[C@H]4CC[C@H](N)CC4)c3c2)cc(Cl)c1O] | (4-((trans)-4-aminocyclohexylamino)-6-(3-chloro-4-hydroxy-5-methylphenyl)quinolin-3-yl)(cyclopropyl)methanone | 450 |
| 198 | 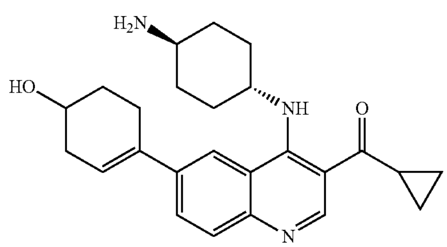 [SMILES: N[C@H]1CC[C@H](Nc2c(C(=O)C3CC3)cnc3ccc(C4=CCC(O)CC4)cc23)CC1] | (4-((trans)-4-aminocyclohexylamino)-6-(4-hydroxycyclohex-1-enyl)quinolin-3-yl)(cyclopropyl)methanone | 406 |
| 199 | 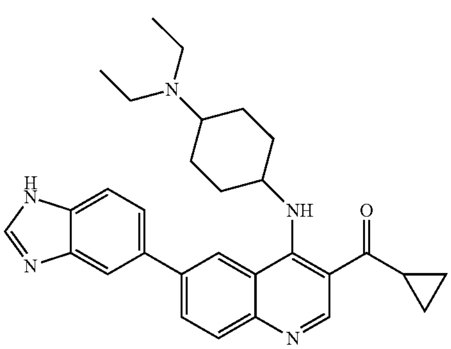 [SMILES: CCN(CC)C1CCC(Nc2c(C(=O)C3CC3)cnc3ccc(-c4ccc5[nH]cnc5c4)cc23)CC1] | (6-(1H-benzo[d]imidazol-5-yl)-4-(4-(diethylamino)cyclohexylamino)quinolin-3-yl)(cyclopropyl)methanone | 482 |

TABLE 1-continued

| No. | Structure | Compound Name | ESI MS (m/z) |
|---|---|---|---|
| 200 | 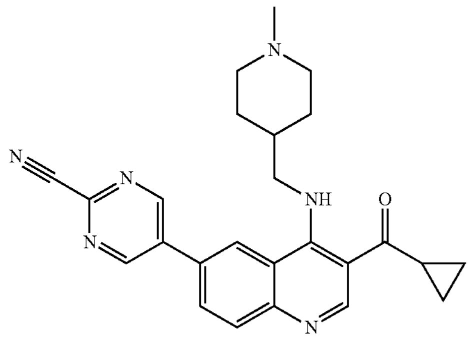 [SMILES: CN1CCC(CNc2c(C(=O)C3CC3)cnc3ccc(-c4cnc(C#N)nc4)cc23)CC1] | 5-(3-(cyclopropanecarbonyl)-4-((1-methylpiperidin-4-yl)methylamino)quinolin-6-yl)pyrimidine-2-carbonitrile | 427 |
| 201 | 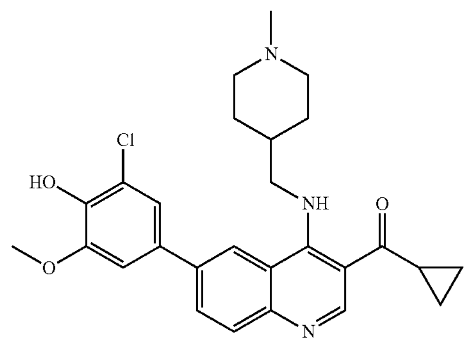 [SMILES: COc1cc(-c2ccc3ncc(C(=O)C4CC4)c(NCC4CCN(C)CC4)c3c2)cc(Cl)c1O] | (6-(3-chloro-4-hydroxy-5-methoxyphenyl)-4-((1-methylpiperidin-4-yl)methylamino)quinolin-3-yl)(cyclopropyl)methanone | 480 |
| 202 | 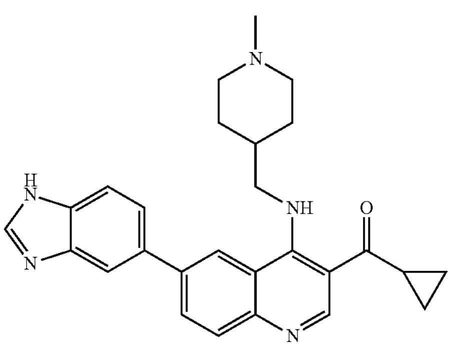 [SMILES: CN1CCC(CNc2c(C(=O)C3CC3)cnc3ccc(-c4ccc5[nH]cnc5c4)cc23)CC1] | (6-(1H-benzo[d]imidazol-5-yl)-4-((1-methylpiperidin-4-yl)methylamino)quinolin-3-yl)(cyclopropyl)methanone | 440 |
| 203 | 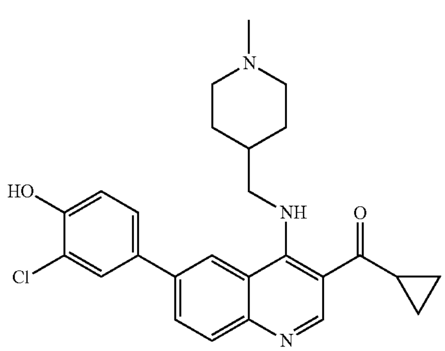 [SMILES: CN1CCC(CNc2c(C(=O)C3CC3)cnc3ccc(-c4ccc(O)c(Cl)c4)cc23)CC1] | (6-(3-chloro-4-hydroxyphenyl)-4-((1-methylpiperidin-4-yl)methylamino)quinolin-3-yl)(cyclopropyl)methanone | 450 |

TABLE 1-continued

| No. | Structure | Compound Name | ESI MS (m/z) |
|---|---|---|---|
| 204 | 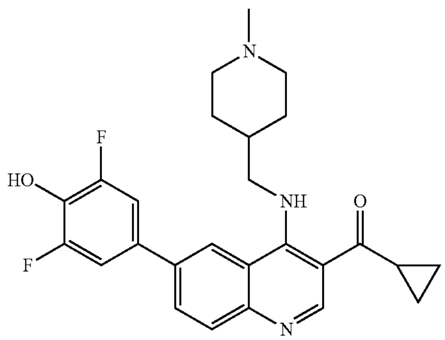 [SMILES: CN1CCC(CNc2c(C(=O)C3CC3)cnc3ccc(-c4cc(F)c(O)c(F)c4)cc23)CC1] | cyclopropyl(6-(3,5-difluoro-4-hydroxyphenyl)-4-((1-methylpiperidin-4-yl)methylamino)quinolin-3-yl)methanone | 452 |
| 205 | 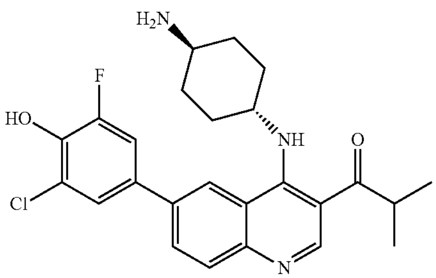 [SMILES: CC(C)C(=O)c1cnc2ccc(-c3cc(F)c(O)c(Cl)c3)cc2c1N[C@H]1CC[C@H](N)CC1] | 1-(4-((trans)-4-aminocyclohexylamino)-6-(3-chloro-5-fluoro-4-hydroxyphenyl)quinolin-3-yl)-2-methylpropan-1-one | 456 |
| 206 | 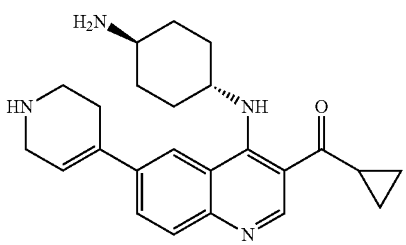 [SMILES: N[C@H]1CC[C@H](Nc2c(C(=O)C3CC3)cnc3ccc(C4=CCNCC4)cc23)CC1] | (4-((trans)-4-aminocyclohexylamino)-6-(1,2,3,6-tetrahydropyridin-4-yl)quinolin-3-yl)(cyclopropyl)methanone | 391 |
| 207 | 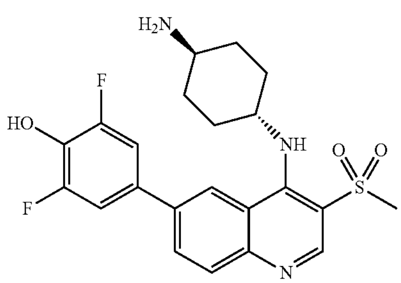 [SMILES: CS(=O)(=O)c1cnc2ccc(-c3cc(F)c(O)c(F)c3)cc2c1N[C@H]1CC[C@H](N)CC1] | 4-(4-((trans)-4-aminocyclohexylamino)-3-(methylsulfonyl)quinolin-6-yl)-2,6-difluorophenol | 447 |
| 208 | 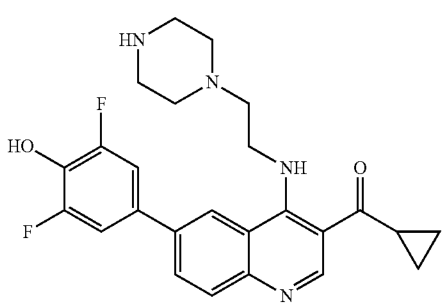 [SMILES: O=C(c1cnc2ccc(-c3cc(F)c(O)c(F)c3)cc2c1NCCN1CCNCC1)C1CC1] | Cyclopropyl(6-(3,5-difluoro-4-hydroxyphenyl)-4-(2-(piperazin-1-yl)ethylamino)quinolin-3-yl)methanone | 452 |

TABLE 1-continued

| No. | Structure | Compound Name | ESI MS (m/z) |
|---|---|---|---|
| 209 | 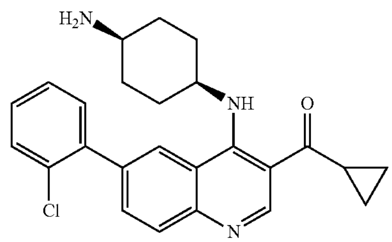 [SMILES: N[C@H]1CC[C@@H](Nc2c(C(=O)C3CC3)cnc3ccc(-c4ccccc4Cl)cc23)CC1] | (4-((cis)-4-aminocyclohexylamino)-6-(2-chlorophenyl)quinolin-3-yl)(cyclopropyl)methanone | 420 |
| 210 | 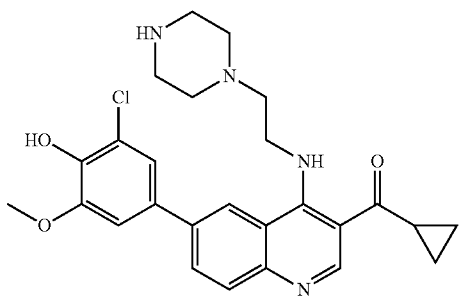 [SMILES: COc1cc(-c2ccc3ncc(C(=O)C4CC4)c(NCCN4CCNCC4)c3c2)cc(Cl)c1O] | (6-(3-chloro-4-hydroxy-5-methoxyphenyl)-4-(2-(piperazin-1-yl)ethylamino)quinolin-3-yl)(cyclopropyl)methanone | 481 |
| 211 | 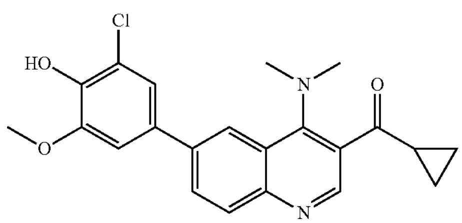 [SMILES: COc1cc(-c2ccc3ncc(C(=O)C4CC4)c(N(C)C)c3c2)cc(Cl)c1O] | (6-(3-chloro-4-hydroxy-5-methoxyphenyl)-4-(dimethylamino)quinolin-3-yl)(cyclopropyl)methanone | 397 |
| 212 | 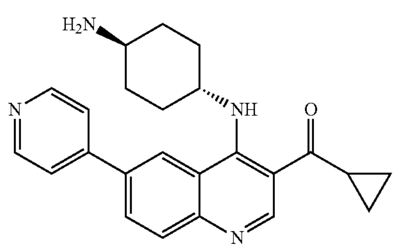 [SMILES: N[C@H]1CC[C@H](Nc2c(C(=O)C3CC3)cnc3ccc(-c4ccncc4)cc23)CC1] | (4-((trans)-4-aminocyclohexylamino)-6-(pyridin-4-yl)quinolin-3-yl)(cyclopropyl)methanone | 386 |
| 213 | 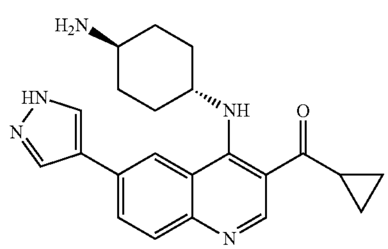 [SMILES: N[C@H]1CC[C@H](Nc2c(C(=O)C3CC3)cnc3ccc(-c4cn[nH]c4)cc23)CC1] | (4-((trans)-4-aminocyclohexylamino)-6-(1H-pyrazol-4-yl)quinolin-3-yl)(cyclopropyl)methanone | 375 |
| 214 | 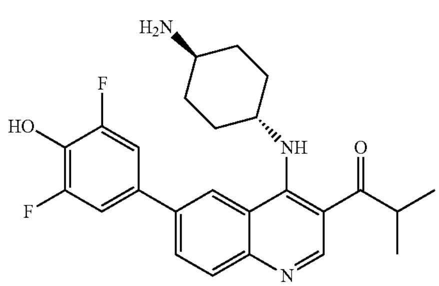 [SMILES: CC(C)C(=O)c1cnc2ccc(-c3cc(F)c(O)c(F)c3)cc2c1N[C@H]1CC[C@H](N)CC1] | 1-(4-((trans)-4-aminocyclohexylamino)-6-(3,5-difluoro-4-hydroxyphenyl)quinolin-3-yl)-2-methylpropan-1-one | 439 |

TABLE 1-continued

| No. | Structure | Compound Name | ESI MS (m/z) |
|---|---|---|---|
| 215 | 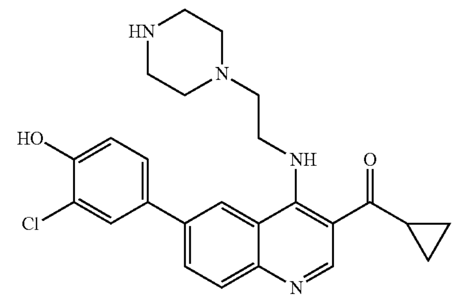 [SMILES: O=C(c1cnc2ccc(-c3ccc(O)c(Cl)c3)cc2c1NCCN1CCNCC1)C1CC1] | (6-(3-chloro-4-hydroxyphenyl)-4-(2-(piperazin-1-yl)ethylamino)quinolin-3-yl)(cyclopropyl)methanone | 451 |
| 216 | 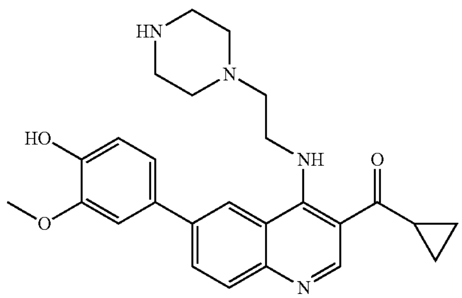 [SMILES: COc1cc(-c2ccc3ncc(C(=O)C4CC4)c(NCCN4CCNCC4)c3c2)ccc1O] | cyclopropyl(6-(4-hydroxy-3-methoxyphenyl)-4-(2-(piperazin-1-yl)ethylamino)quinolin-3-yl)methanone | 447 |
| 217 | 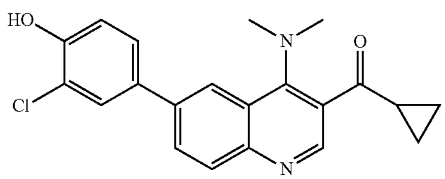 [SMILES: CN(C)c1c(C(=O)C2CC2)cnc2ccc(-c3ccc(O)c(Cl)c3)cc12] | (6-(3-chloro-4-hydroxyphenyl)-4-(dimethylamino)quinolin-3-yl)(cyclopropyl)methanone | 367 |
| 218 | 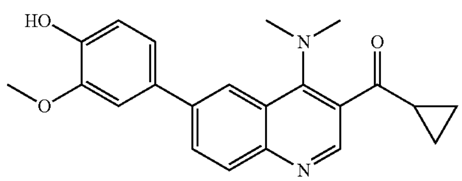 [SMILES: COc1cc(-c2ccc3ncc(C(=O)C4CC4)c(N(C)C)c3c2)ccc1O] | cyclopropyl(4-(dimethylamino)-6-(4-hydroxy-3-methoxyphenyl)quinolin-3-yl)methanone | 362 |
| 219 | 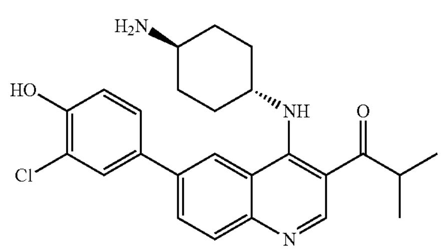 [SMILES: CC(C)C(=O)c1cnc2ccc(-c3ccc(O)c(Cl)c3)cc2c1N[C@H]1CC[C@H](N)CC1] | 1-(4-((trans)-4-aminocyclohexylamino)-6-(3-chloro-4-hydroxyphenyl)quinolin-3-yl)-2-methylpropan-1-one | 438 |
| 220 | 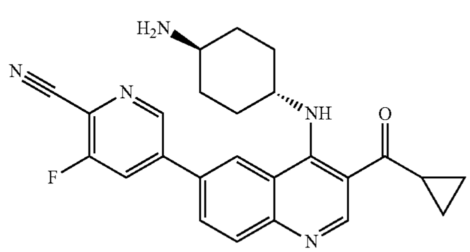 [SMILES: N#Cc1ncc(-c2ccc3ncc(C(=O)C4CC4)c(N[C@H]4CC[C@H](N)CC4)c3c2)cc1F] | 5-(4-((trans)-4-aminocyclohexylamino)-3-(cyclopropanecarbonyl)quinolin-6-yl)-3-fluoropicolinonitrile | 429 |

TABLE 1-continued

| No. | Structure | Compound Name | ESI MS (m/z) |
|---|---|---|---|
| 221 | 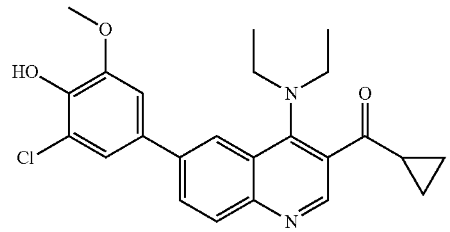 [SMILES: CCN(CC)c1c(C(=O)C2CC2)cnc2ccc(-c3cc(Cl)c(O)c(OC)c3)cc12] | (6-(3-chloro-4-hydroxy-5-methoxyphenyl)-4-(diethylamino)quinolin-3-yl)(cyclopropyl)methanone | 425 |
| 222 | 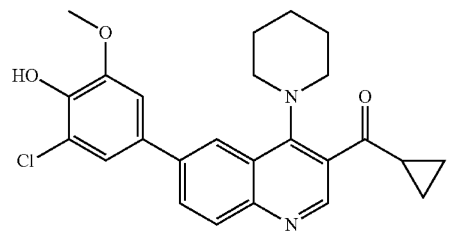 [SMILES: COc1cc(-c2ccc3ncc(C(=O)C4CC4)c(N4CCCCC4)c3c2)cc(Cl)c1O] | (6-(3-chloro-4-hydroxy-5-methoxyphenyl)-4-(piperidin-1-yl)quinolin-3-yl)(cyclopropyl)methanone | 437 |
| 223 | 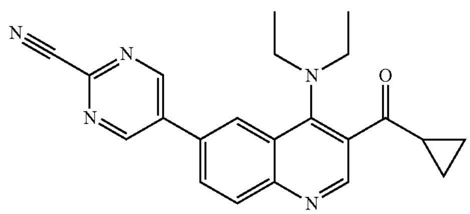 [SMILES: CCN(CC)c1c(C(=O)C2CC2)cnc2ccc(-c3cnc(C#N)nc3)cc12] | 5-(3-(cyclopropanecarbonyl)-4-(diethylamino)quinolin-6-yl)pyrimidine-2-carbonitrile | 371 |
| 224 | 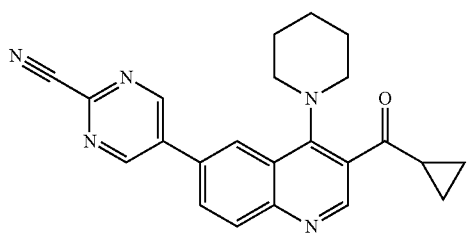 [SMILES: N#Cc1ncc(-c2ccc3ncc(C(=O)C4CC4)c(N4CCCCC4)c3c2)cn1] | 5-(3-(cyclopropanecarbonyl)-4-(piperidin-1-yl)quinolin-6-yl)pyrimidine-2-carbonitrile | 383 |
| 225(a) | 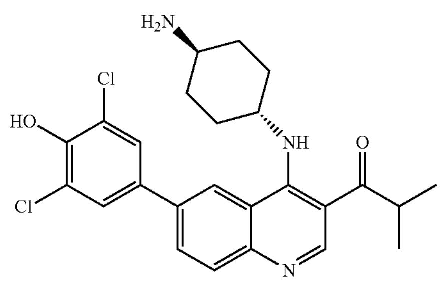 | 1-(4-((trans)-4-aminocyclohexyl-amino)-6-(3,5-dichloro-4-hydroxyphenyl)quinolin-3-yl)-2-methylpropan-1-one | 472 |
| 225(b) | 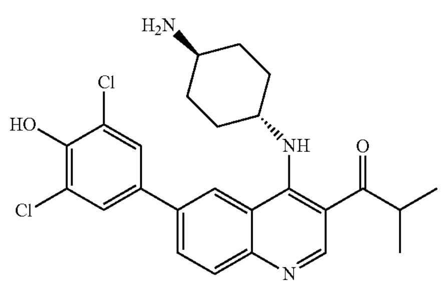 | 1-(4-((trans)-4-aminocyclohexyl-amino)-6-(3,5-dichloro-4-hydroxyphenyl)quinolin-3-yl)-2-methylpropan-1-one dihydrochloride | 472 |

TABLE 1-continued

| No. | Structure | Compound Name | ESI MS (m/z) |
|---|---|---|---|
| 226 | 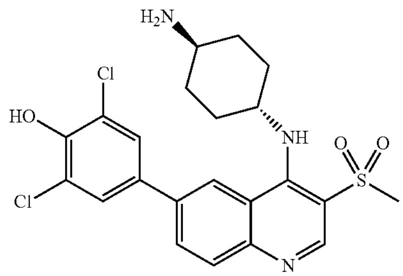 | 4-(4-((trans)-4-aminocyclohexyl-amino)-3-(methylsulfonyl)quinolin-6-yl)-2,6-dichlorophenol | 480 |
| 227 | 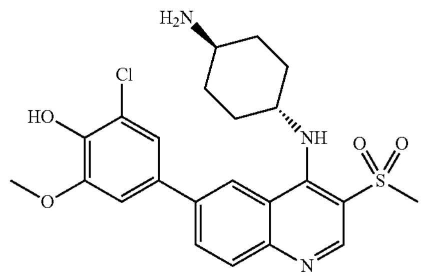 | 4-(4-((trans)-4-aminocyclohexyl-amino)-3-(methylsulfonyl)quinolin-6-yl)-2-chloro-6-methoxyphenol | 476 |
| 228 | 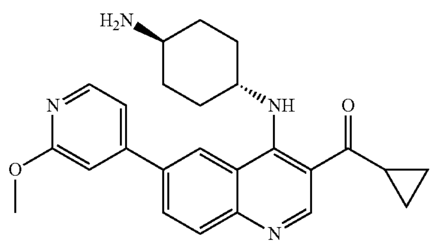 [SMILES: COc1cc(-c2ccc3ncc(C(=O)C4CC4)c(N[C@H]4CC[C@H](N)CC4)c3c2)ccn1] | (4-((trans)-4-aminocyclohexyl-amino)-6-(2-methoxypyridin-4-yl)quinolin-3-yl)(cyclopropyl)methanone | 417 |
| 229 | 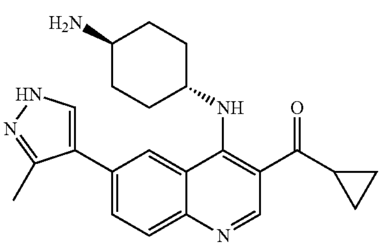 [SMILES: Cc1n[nH]cc1-c1ccc2ncc(C(=O)C3CC3)c(N[C@H]3CC[C@H](N)CC3)c2c1] | (4-((trans)-4-aminocyclohexylamino)-6-(3-methyl-1H-pyrazol-4-yl)quinolin-3-yl)(cyclopropyl)methanone | 389 |
| 230 | 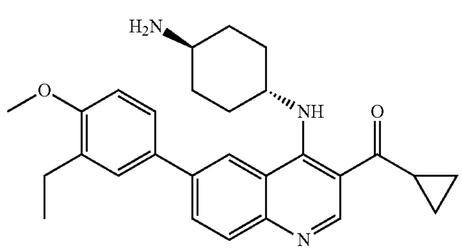 [SMILES: CCc1cc(-c2ccc3ncc(C(=O)C4CC4)c(N[C@H]4CC[C@H](N)CC4)c3c2)ccc1OC] | (4-((trans)-4-aminocyclohexylamino)-6-(3,4-dimethoxyphenyl)quinolin-3-yl)(cyclopropyl)methanone | 446 |
| 231 | 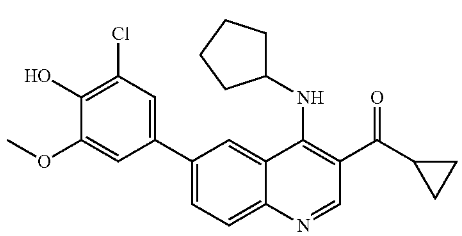 [SMILES: COc1cc(-c2ccc3ncc(C(=O)C4CC4)c(NC4CCCC4)c3c2)cc(Cl)c1O] | (6-(3-chloro-4-hydroxy-5-methoxyphenyl)-4-(cyclopentylamino)quinolin-3-yl)(cyclopropyl)methanone | 437 |

TABLE 1-continued

| No. | Structure | Compound Name | ESI MS (m/z) |
|---|---|---|---|
| 232 | 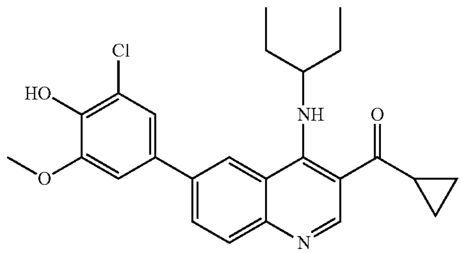 [SMILES: CCC(CC)Nc1c(C(=O)C2CC2)cnc2ccc(-c3cc(Cl)c(O)c(OC)c3)cc12] | (6-(3-chloro-4-hydroxy-5-methoxyphenyl)-4-(pentan-3-ylamino)quinolin-3-yl)(cyclopropyl)methanone | 439 |
| 233 | 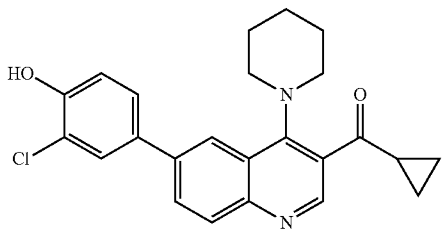 [SMILES: O=C(c1cnc2ccc(-c3ccc(O)c(Cl)c3)cc2c1N1CCCCC1)C1CC1] | (6-(3-chloro-4-hydroxyphenyl)-4-(piperidin-1-yl)quinolin-3-yl)(cyclopropyl)methanone | 407 |
| 234 | 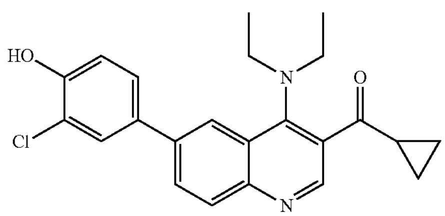 [SMILES: CCN(CC)c1c(C(=O)C2CC2)cnc2ccc(-c3ccc(O)c(Cl)c3)cc12] | (6-(3-chloro-4-hydroxyphenyl)-4-(diethylamino)quinolin-3-yl)(cyclopropyl)methanone | 395 |
| 235 | 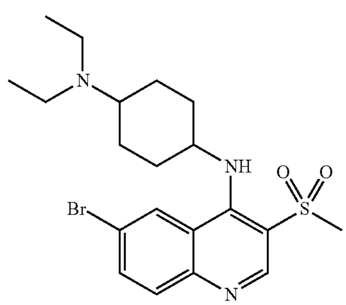 [SMILES: CCN(CC)C1CCC(Nc2c(S(C)(=O)=O)cnc3ccc(Br)cc23)CC1] | N1-(6-bromo-3-(methylsulfonyl)quinolin-4-yl)-N4,N4-diethylcyclohexane-1,4-diamine | 454 |
| 236 | 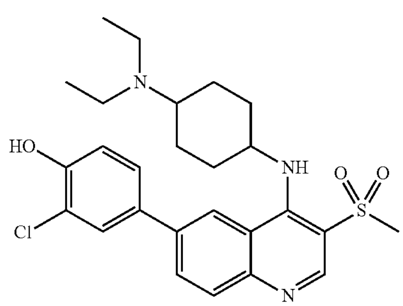 [SMILES: CCN(CC)C1CCC(Nc2c(S(C)(=O)=O)cnc3ccc(-c4ccc(O)c(Cl)c4)cc23)CC1] | 2-chloro-4-(4-(4-(diethylamino)cyclohexylamino)-3-(methylsulfonyl)quinolin-6-yl)phenol | 502 |
| 237 | 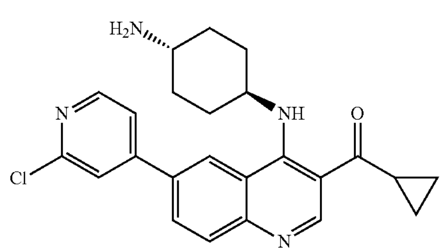 [SMILES: N[C@H]1CC[C@H](Nc2c(C(=O)C3CC3)cnc3ccc(-c4ccnc(Cl)c4)cc23)CC1] | (4-((trans)-4-aminocyclohexylamino)-6-(2-chloropyridin-4-yl)quinolin-3-yl)(cyclopropyl)methanone | 421 |

TABLE 1-continued

| No. | Structure | Compound Name | ESI MS (m/z) |
|---|---|---|---|
| 238 | 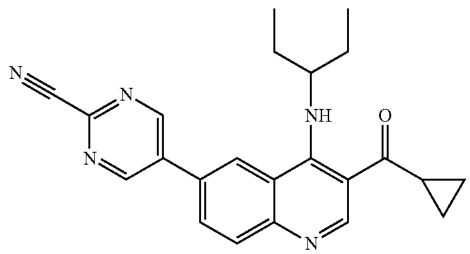 [SMILES: CCC(CC)Nc1c(C(=O)C2CC2)cnc2ccc(-c3cnc(C#N)nc3)cc12] | 5-(3-(cyclopropanecarbonyl)-4-(pentan-3-ylamino)quinolin-6-yl)pyrimidine-2-carbonitrile | 385 |
| 239 | 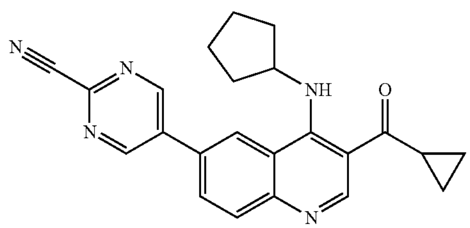 [SMILES: N#Cc1ncc(-c2ccc3ncc(C(=O)C4CC4)c(NC4CCCC4)c3c2)cn1] | 5-(4-(cyclopentylamino)-3-(cyclopropanecarbonyl)quinolin-6-yl)pyrimidine-2-carbonitrile | 383 |
| 240 | 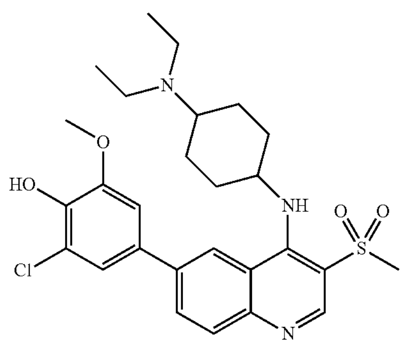 [SMILES: CCN(CC)C1CCC(Nc2c(S(C)(=O)=O)cnc3ccc(-c4cc(Cl)c(O)c(OC)c4)cc23)CC1] | 2-chloro-4-(4-(4-(diethylamino)cyclohexylamino)-3-(methylsulfonyl)quinolin-6-yl)-6-methoxyphenol dihydrochloride | 532 |
| 241 | 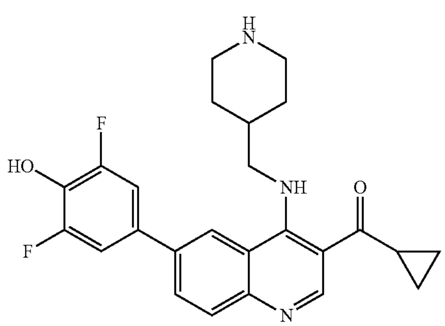 [SMILES: O=C(c1cnc2ccc(-c3cc(F)c(O)c(F)c3)cc2c1NCC1CCNCC1)C1CC1] | cyclopropyl(6-(3,5-difluoro-4-hydroxyphenyl)-4-(piperidin-4-ylmethylamino)quinolin-3-yl)methanone | 437 |
| 242 | 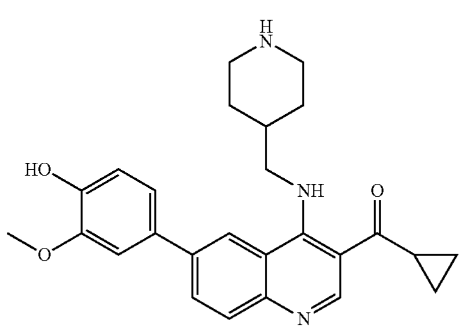 [SMILES: COc1cc(-c2ccc3ncc(C(=O)C4CC4)c(NCC4CCNCC4)c3c2)ccc1O] | cyclopropyl(6-(4-hydroxy-3-methoxyphenyl)-4-(piperidin-4-ylmethylamino)quinolin-3-yl)methanone | 432 |

TABLE 1-continued

| No. | Structure | Compound Name | ESI MS (m/z) |
|---|---|---|---|
| 243 | 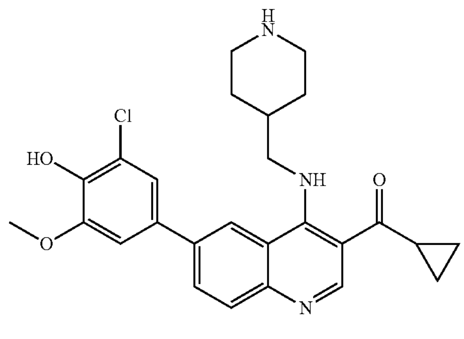 [SMILES: COc1cc(-c2ccc3ncc(C(=O)C4CC4)c(NCC4CCNCC4)c3c2)cc(Cl)c1O] | (6-(3-chloro-4-hydroxy-5-methoxyphenyl)-4-(piperidin-4-ylmethylamino)quinolin-3-yl)(cyclopropyl)methanone | 466 |
| 244 | 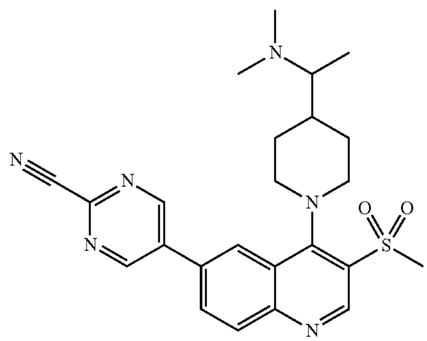 [SMILES: CC(C1CCN(c2c(S(C)(=O)=O)cnc3ccc(-c4cnc(C#N)nc4)cc23)CC1)N(C)C] | 5-(4-(4-(1-(dimethylamino)ethyl)piperidin-1-yl)-3-(methylsulfonyl)quinolin-6-yl)pyrimidine-2-carbonitrile | 465 |
| 245 | 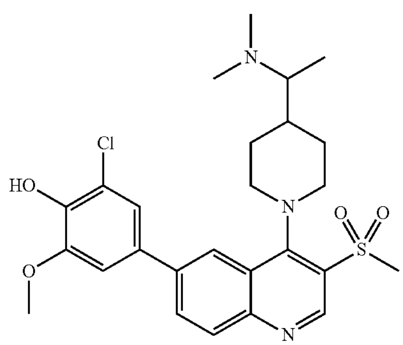 [SMILES: COc1cc(-c2ccc3ncc(S(C)(=O)=O)c(N4CCC(C(C)N(C)C)CC4)c3c2)cc(Cl)c1O] | 2-chloro-4-(4-(4-(1-(dimethylamino)ethyl)piperidin-1-yl)-3-(methylsulfonyl)quinolin-6-yl)-6-methoxyphenol | 518 |
| 246 | 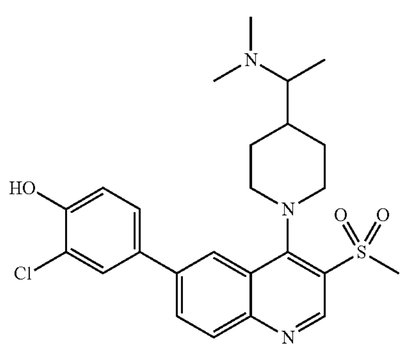 [SMILES: CC(C1CCN(c2c(S(C)(=O)=O)cnc3ccc(-c4ccc(O)c(Cl)c4)cc23)CC1)N(C)C] | 2-chloro-4-(4-(4-(1-(dimethylamino)ethyl)piperidin-1-yl)-3-(methylsulfonyl)quinolin-6-yl)phenol | 488 |

| No. | Structure | Compound Name | ESI MS (m/z) |
|---|---|---|---|
| 247 | 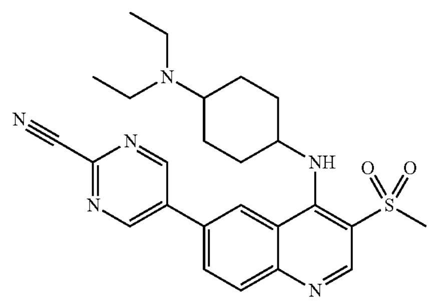 [SMILES: CCN(CC)C1CCC(Nc2c(S(C)(=O)=O)cnc3ccc(-c4cnc(C#N)nc4)cc23)CC1] | 5-(4-(4-(diethylamino) cyclohexylamino)-3-(methylsulfonyl)quinolin-6-yl) pyrimidine-2-carbonitrile | 479 |
| 248 | 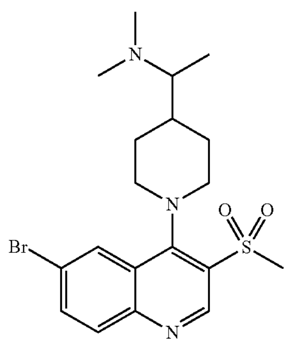 [SMILES: CC(C1CCN(c2c(S(C)(=O)=O)cnc3ccc(Br)cc23)CC1)N(C)C] | 1-(1-(6-bromo-3-(methylsulfonyl) quinolin-4-yl)piperidin-4-yl)-N,N-dimethylethanamine | 440 |
| 249 | 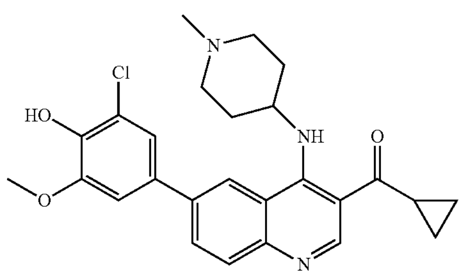 [SMILES: COc1cc(-c2ccc3ncc(C(=O)C4CC4)c(NC4CCN(C)CC4)c3c2)cc(Cl)c1O] | (6-(3-chloro-4-hydroxy-5-methoxyphenyl)-4-(1-methylpiperidin-4-ylamino) quinolin-3-yl)(cyclopropyl) methanone | 466 |
| 250 | 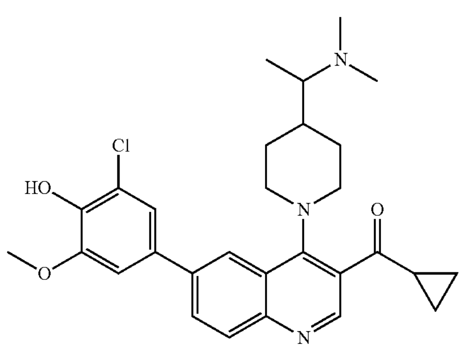 [SMILES: COc1cc(-c2ccc3ncc(C(=O)C4CC4)c(N4CCC(C(C)N(C)C)CC4)c3c2)cc(Cl)c1O] | (6-(3-chloro-4-hydroxy-5-methoxyphenyl)-4-(4-(1-(dimethylamino)ethyl)piperidin-1-yl)quinolin-3-yl)(cyclopropyl) methanone | 508 |

TABLE 1-continued

| No. | Structure | Compound Name | ESI MS (m/z) |
|---|---|---|---|
| 251 | 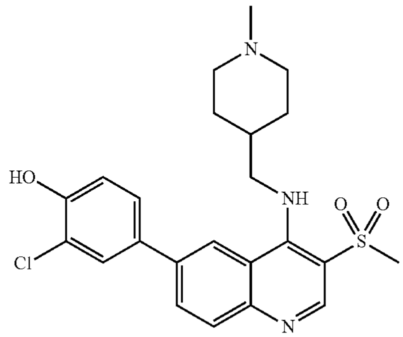 [SMILES: CN1CCC(CNc2c(S(C)(=O)=O)cnc3ccc(-c4ccc(O)c(Cl)c4)cc23)CC1] | 2-chloro-4-(4-((1-methylpiperidin-4-yl)methylamino)-3-(methylsulfonyl)quinolin-6-yl)phenol | 460 |
| 252 | 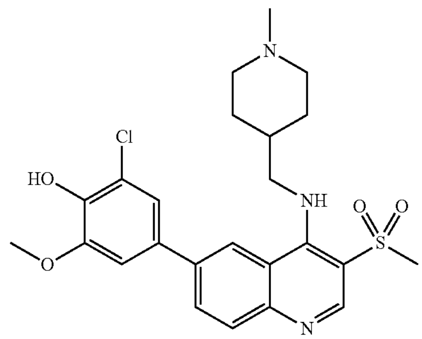 | 2-chloro-6-methoxy-4-(4-((1-methylpiperidin-4-yl)methylamino)-3-(methylsulfonyl)quinolin-6-yl)phenol | 490 |
| 253 | 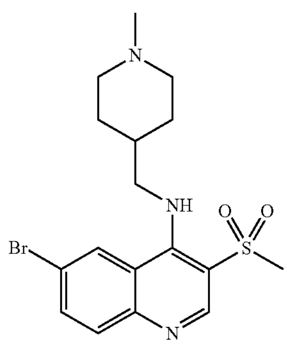 [SMILES: CN1CCC(CNc2c(S(C)(=O)=O)cnc3ccc(Br)cc23)CC1] | 6-bromo-N-((1-methylpiperidin-4-yl)methyl)-3-(methylsulfonyl)quinolin-4-amine | 412 |
| 254 | 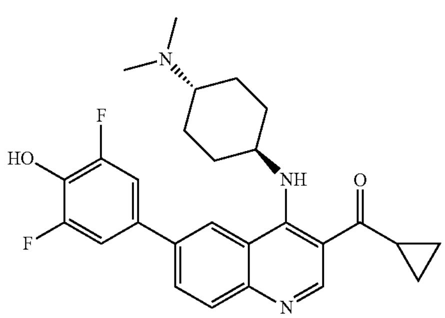 | cyclopropyl(6-(3,5-difluoro-4-hydroxyphenyl)-4-((trans)-4-(dimethylamino)cyclohexylamino)quinolin-3-yl)methanone | 466 |

TABLE 1-continued

| No. | Structure | Compound Name | ESI MS (m/z) |
|---|---|---|---|
| 255 | 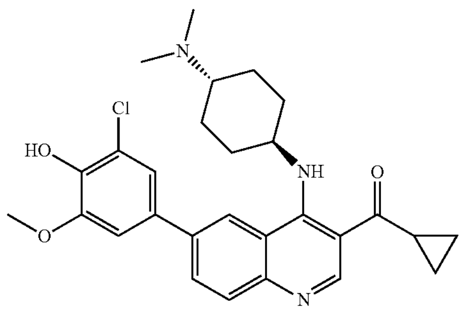 [SMILES: COc1cc(-c2ccc3ncc(C(=O)C4CC4)c(N[C@H]4CC[C@H](N(C)C)CC4)c3c2)cc(Cl)c1O] | (6-(3-chloro-4-hydroxy-5-methoxyphenyl)-4-((trans)-4-(dimethylamino)cyclohexylamino)quinolin-3-yl)(cyclopropyl)methanone | 494 |
| 256 | 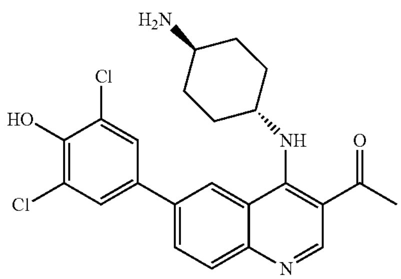 [SMILES: CC(=O)c1cnc2ccc(-c3cc(Cl)c(O)c(Cl)c3)cc2c1N[C@H]1CC[C@H](N)CC1] | 1-(4-((trans)-4-aminocyclohexyl-amino)-6-(3,5-dichloro-4-hydroxyphenyl)quinolin-3-yl)ethanone | 444 |
| 257 | 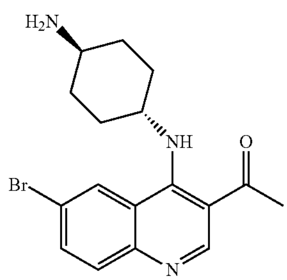 [SMILES: CC(=O)c1cnc2ccc(Br)cc2c1N[C@H]1CC[C@H](N)CC1] | 1-(4-((trans)-4-aminocyclohexyl-amino)-6-bromoquinolin-3-yl)ethanone | 362 |
| 258 | 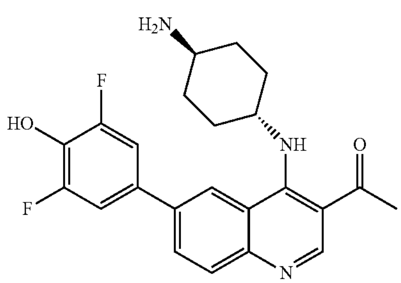 [SMILES: CC(=O)c1cnc2ccc(-c3cc(F)c(O)c(F)c3)cc2c1N[C@H]1CC[C@H](N)CC1] | 1-(4-((trans)-4-aminocyclohexyl-amino)-6-(3,5-difluoro-4-hydroxyphenyl)quinolin-3-yl)ethanone | 411 |
| 259 | 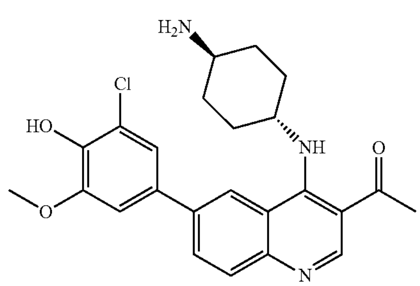 [SMILES: COc1cc(-c2ccc3ncc(C(C)=O)c(N[C@H]4CC[C@H](N)CC4)c3c2)cc(Cl)c1O] | 1-(4-((trans)-4-aminocyclohexyl-amino)-6-(3-chloro-4-hydroxy-5-methoxyphenyl)quinolin-3-yl)ethanone | 440 |

TABLE 1-continued

| No. | Structure | Compound Name | ESI MS (m/z) |
|---|---|---|---|
| 260 | 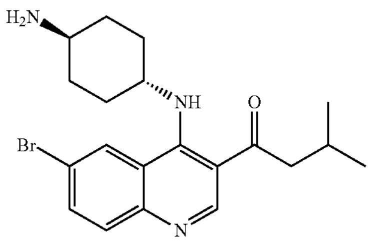 [SMILES: CC(C)CC(=O)c1cnc2ccc(Br)cc2c1N[C@H]1CC[C@H](N)CC1] | 1-(4-((trans)-4-aminocyclohexyl-amino)-6-bromoquinolin-3-yl)-3-methylbutan-1-one | 404 |
| 261 | 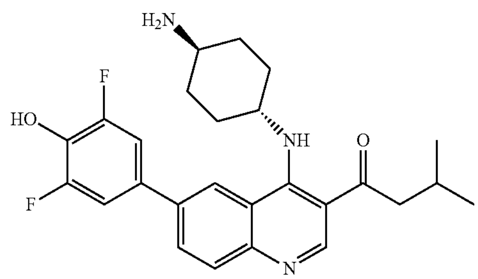 [SMILES: CC(C)CC(=O)c1cnc2ccc(-c3cc(F)c(O)c(F)c3)cc2c1N[C@H]1CC[C@H](N)CC1] | 1-(4-((trans)-4-aminocyclohexyl-amino)-6-(3,5-difluoro-4-hydroxyphenyl)quinolin-3-yl)-3-methylbutan-1-one | 454 |
| 262 | 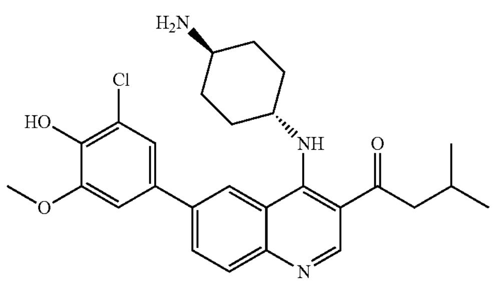 [SMILES: COc1cc(-c2ccc3ncc(C(=O)CC(C)C)c(N[C@H]4CC[C@H](N)CC4)c3c2)cc(Cl)c1O] | 1-(4-((trans)-4-aminocyclohexyl-amino)-6-(3-chloro-4-hydroxy-5-methoxyphenyl)quinolin-3-yl)-3-methylbutan-1-one | 482 |
| 263 | 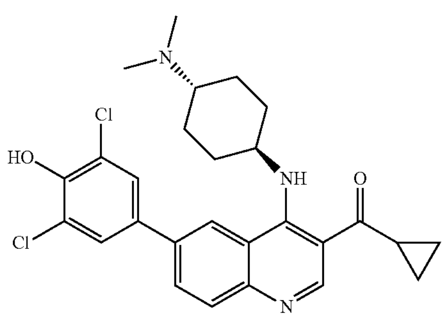 [SMILES: CN(C)[C@H]1CC[C@H](Nc2c(C(=O)C3CC3)cnc3ccc(-c4cc(Cl)c(O)c(Cl)c4)cc23)CC1] | cyclopropyl(6-(3,5-dichloro-4-hydroxyphenyl)-4-((trans)-4-(dimethylamino)cyclohexylamino)quinolin-3-yl)methanone | 498 |
| 264 | 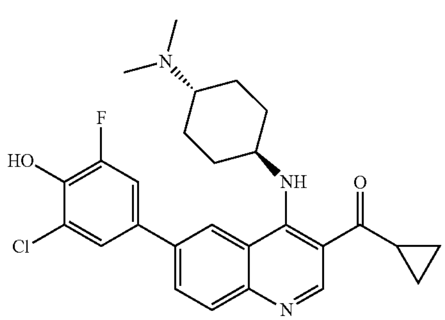 [SMILES: CN(C)[C@H]1CC[C@H](Nc2c(C(=O)C3CC3)cnc3ccc(-c4cc(F)c(O)c(Cl)c4)cc23)CC1] | (6-(3-chloro-5-fluoro-4-hydroxyphenyl)-4-((trans)-4-(dimethylamino)cyclohexylamino)quinolin-3-yl)(cyclopropyl)methanone | 482 |

TABLE 1-continued

| No. | Structure | Compound Name | ESI MS (m/z) |
|---|---|---|---|
| 265 | 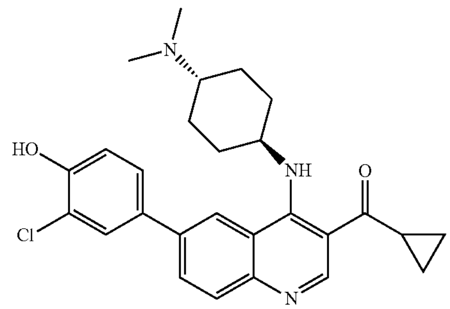 [SMILES: CN(C)[C@H]1CC[C@H](Nc2c(C(=O)C3CC3)cnc3ccc(-c4ccc(O)c(Cl)c4)cc23)CC1] | (6-(3-chloro-4-hydroxyphenyl)-4-((trans)-4-(dimethylamino)cyclohexylamino)quinolin-3-yl)(cyclopropyl)methanone | 464 |
| 266 | 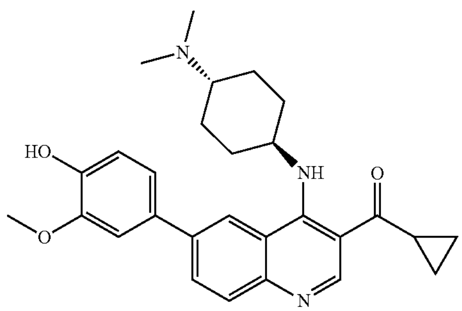 [SMILES: COc1cc(-c2ccc3ncc(C(=O)C4CC4)c(N[C@H]4CC[C@H](N(C)C)CC4)c3c2)ccc1O] | cyclopropyl(4-((trans)-4-(dimethylamino)cyclohexylamino)-6-(4-hydroxy-3-methoxyphenyl)quinolin-3-yl)methanone | 460 |
| 267 | 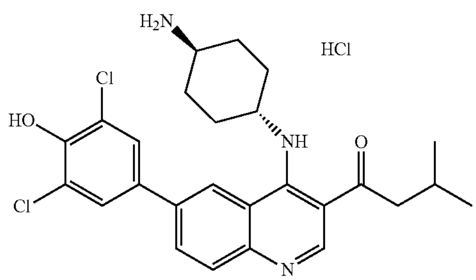 [SMILES: CC(C)CC(=O)c1cnc2ccc(-c3cc(Cl)c(O)c(Cl)c3)cc2c1N[C@H]1CC[C@H](N)CC1 ; Cl] | 1-(4-((trans)-4-aminocyclohexyl-amino)-6-(3,5-dichloro-4-hydroxyphenyl)quinolin-3-yl)-3-methylbutan-1-one dihydrochloride | 486 |
| 268 | 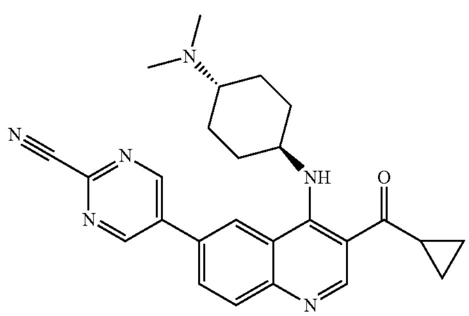 [SMILES: CN(C)[C@H]1CC[C@H](Nc2c(C(=O)C3CC3)cnc3ccc(-c4cnc(C#N)nc4)cc23)CC1] | 5-(3-(cyclopropanecarbonyl)-4-((trans)-4-(dimethylamino)cyclohexylamino)quinolin-6-yl)pyrimidine-2-carbonitrile | 441 |
| 269 | 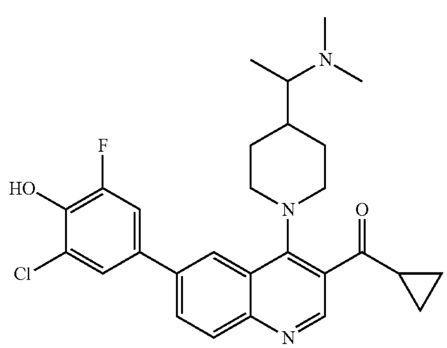 | (6-(3-chloro-5-fluoro-4-hydroxyphenyl)-4-(4-(1-(dimethylamino)ethyl)piperidin-1-yl)quinolin-3-yl)(cyclopropyl)methanone | 496 |

TABLE 1-continued

| No. | Structure | Compound Name | ESI MS (m/z) |
|---|---|---|---|
| 270 | 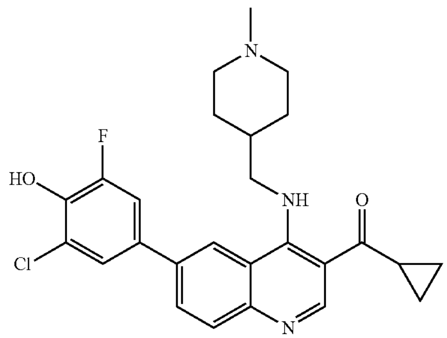 | (6-(3-chloro-5-fluoro-4-hydroxyphenyl)-4-((1-methylpiperidin-4-yl)methylamino)quinolin-3-yl)(cyclopropyl)methanone | 468 |
| 271 | 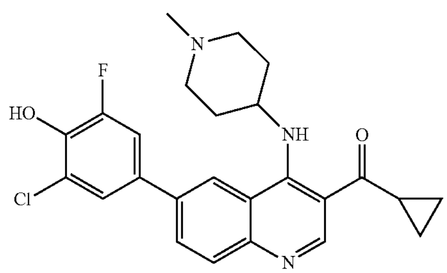 | (6-(3-chloro-5-fluoro-4-hydroxyphenyl)-4-(1-methylpiperidin-4-ylamino)quinolin-3-yl)(cyclopropyl)methanone | 454 |
| 272 | 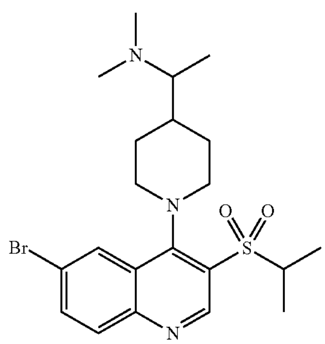 [SMILES: CC(C1CCN(c2c(S(=O)(=O)C(C)C)cnc3ccc(Br)cc23)CC1)N(C)C] | 1-(1-(6-bromo-3-(isopropylsulfonyl)quinolin-4-yl)piperidin-4-yl)-N,N-dimethylethanamine | 468 |
| 273 | 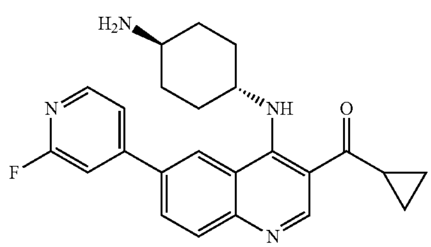 [SMILES: N[C@H]1CC[C@H](Nc2c(C(=O)C3CC3)cnc3ccc(-c4ccnc(F)c4)cc23)CC1] | (4-((trans)-4-aminocyclohexylamino)-6-(2-fluoropyridin-4-yl)quinolin-3-yl)(cyclopropyl)methanone | 404 |
| 274 | 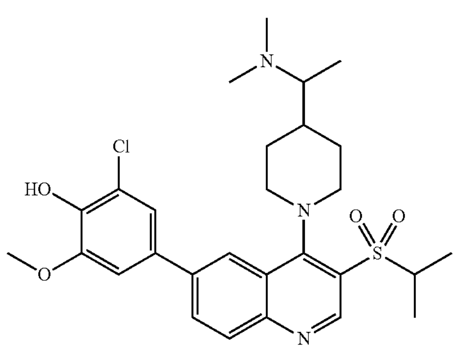 [SMILES: COc1cc(-c2ccc3ncc(S(=O)(=O)C(C)C)c(N4CCC(C(C)N(C)C)CC4)c3c2)cc(Cl)c1O] | 2-chloro-4-(4-(4-(1-(dimethylamino)ethyl)piperidin-1-yl)-3-(isopropylsulfonyl)quinolin-6-yl)-6-methoxyphenol | 546 |

TABLE 1-continued

| No. | Structure | Compound Name | ESI MS (m/z) |
|---|---|---|---|
| 275 | 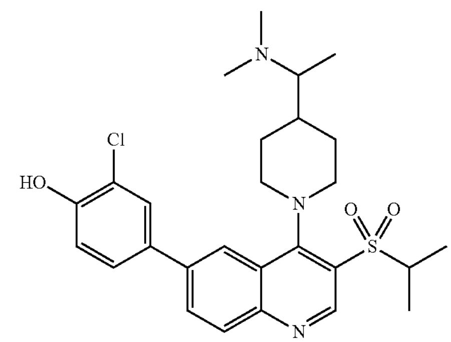 [SMILES: CC(C1CCN(c2c(S(=O)(=O)C(C)C)cnc3ccc(-c4ccc(O)c(Cl)c4)cc23)CC1)N(C)C] | 2-chloro-4-(4-(4-(1-(dimethylamino)ethyl)piperidin-1-yl)-3-(isopropylsulfonyl)quinolin-6-yl)phenol | 516 |
| 276 | 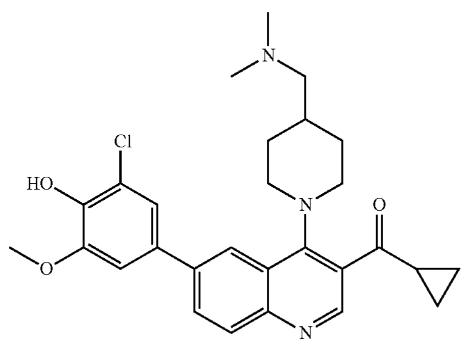 [SMILES: COc1cc(-c2ccc3ncc(C(=O)C4CC4)c(N4CCC(CN(C)C)CC4)c3c2)cc(Cl)c1O] | (6-(3-chloro-4-hydroxy-5-methoxyphenyl)-4-(4-((dimethylamino)methyl)piperidin-1-yl)quinolin-3-yl)(cyclopropyl)methanone | 494 |
| 277 | 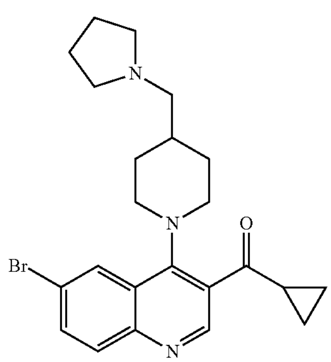 [SMILES: O=C(c1cnc2ccc(Br)cc2c1N1CCC(CN2CCCC2)CC1)C1CC1] | (6-bromo-4-(4-(pyrrolidin-1-ylmethyl)piperidin-1-yl)quinolin-3-yl)(cyclopropyl)methanone | 442 |
| 278 | 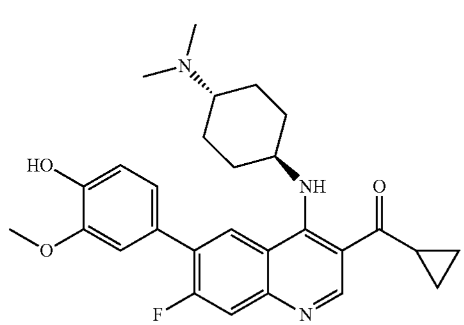 [SMILES: COc1cc(-c2cc3c(N[C@H]4CC[C@H](N(C)C)CC4)c(C(=O)C4CC4)cnc3cc2F)ccc1O] | cyclopropyl(4-((trans)-4-(dimethylamino)cyclohexylamino)-7-fluoro-6-(4-hydroxy-3-methoxyphenyl)quinolin-3-yl)methanone | 478 |

TABLE 1-continued

| No. | Structure | Compound Name | ESI MS (m/z) |
|---|---|---|---|
| 279 | 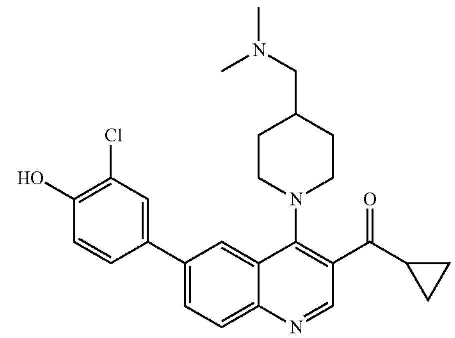 [SMILES: CN(C)CC1CCN(c2c(C(=O)C3CC3)cnc3ccc(-c4ccc(O)c(Cl)c4)cc23)CC1] | (6-(3-chloro-4-hydroxyphenyl)-4-(4-((dimethylamino)methyl)piperidin-1-yl)quinolin-3-yl)(cyclopropyl)methanone | 464 |
| 280 | 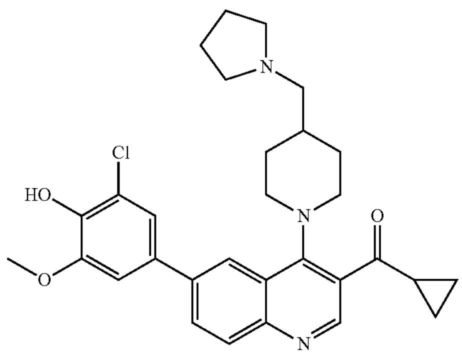 [SMILES: COc1cc(-c2ccc3ncc(C(=O)C4CC4)c(N4CCC(CN5CCCC5)CC4)c3c2)cc(Cl)c1O] | (6-(3-chloro-4-hydroxy-5-methoxyphenyl)-4-(4-(pyrrolidin-1-ylmethyl)piperidin-1-yl)quinolin-3-yl)(cyclopropyl)methanone | 520 |
| 281 | 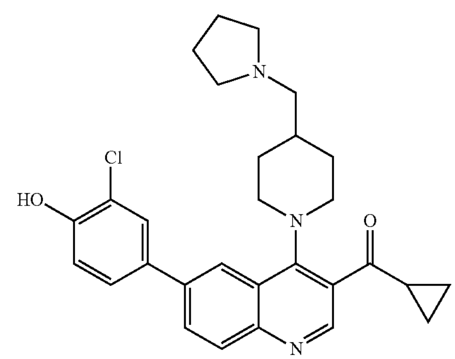 [SMILES: O=C(c1cnc2ccc(-c3ccc(O)c(Cl)c3)cc2c1N1CCC(CN2CCCC2)CC1)C1CC1] | (6-(3-chloro-4-hydroxyphenyl)-4-(4-(pyrrolidin-1-ylmethyl)piperidin-1-yl)quinolin-3-yl)(cyclopropyl)methanone | 490 |
| 282 | 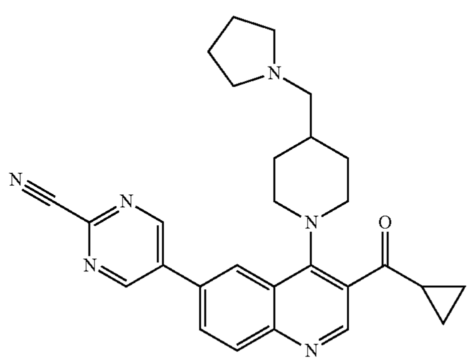 [SMILES: N#Cc1ncc(-c2ccc3ncc(C(=O)C4CC4)c(N4CCC(CN5CCCC5)CC4)c3c2)cn1] | 5-(3-(cyclopropanecarbonyl)-4-(4-(pyrrolidin-1-ylmethyl)piperidin-1-yl)quinolin-6-yl)pyrimidine-2-carbonitrile | 467 |

TABLE 1-continued

| No. | Structure | Compound Name | ESI MS (m/z) |
|---|---|---|---|
| 283 | 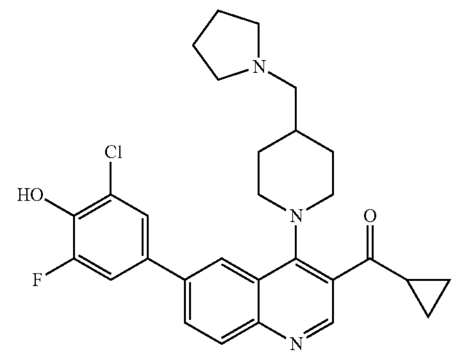 [SMILES: O=C(c1cnc2ccc(-c3cc(F)c(O)c(Cl)c3)cc2c1N1CCC(CN2CCCC2)CC1)C1CC1] | (6-(3-chloro-5-fluoro-4-hydroxyphenyl)-4-(4-(pyrrolidin-1-ylmethyl)piperidin-1-yl)quinolin-3-yl)(cyclopropyl)methanone | 508 |
| 284 | 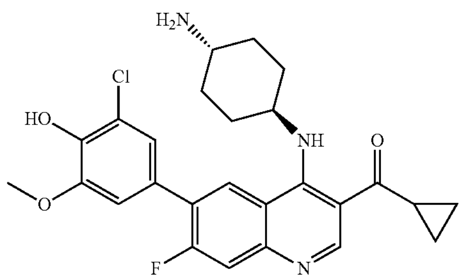 [SMILES: COc1cc(-c2cc3c(N[C@H]4CC[C@H](N)CC4)c(C(=O)C4CC4)cnc3cc2F)cc(Cl)c1O] | (4-((trans)-4-aminocyclohexylamino)-6-(3-chloro-4-hydroxy-5-methoxyphenyl)-7-fluoroquinolin-3-yl)(cyclopropyl)methanone | 484 |
| 285 | 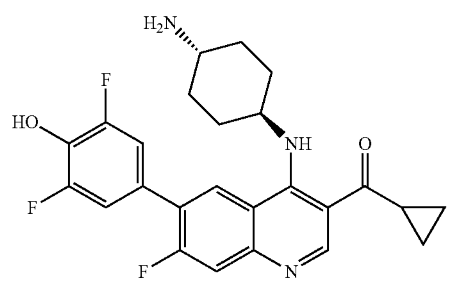 [SMILES: N[C@H]1CC[C@H](Nc2c(C(=O)C3CC3)cnc3cc(F)c(-c4cc(F)c(O)c(F)c4)cc23)CC1] | (4-((trans)-4-aminocyclohexylamino)-6-(3,5-difluoro-4-hydroxyphenyl)-7-fluoroquinolin-3-yl)(cyclopropyl) methanone | 455 |
| 286 | 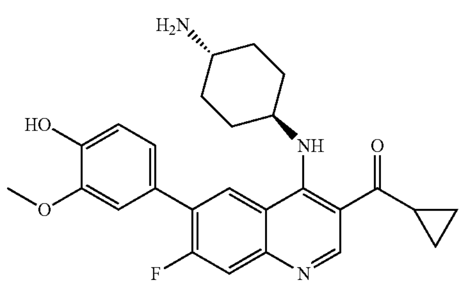 [SMILES: COc1cc(-c2cc3c(N[C@H]4CC[C@H](N)CC4)c(C(=O)C4CC4)cnc3cc2F)ccc1O] | (4-((trans)-4-aminocyclohexylamino)-7-fluoro-6-(4-hydroxy-3-methoxyphenyl)quinolin-3-yl)(cyclopropyl)methanone | 450 |
| 287 | 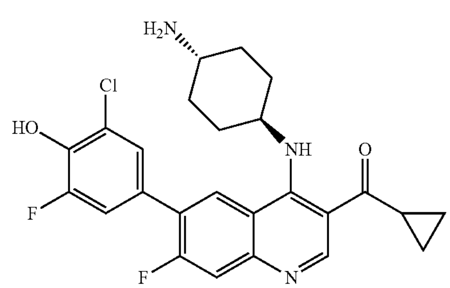 | (4-((trans)-4-aminocyclohexylamino)-6-(3-chloro-5-fluoro-4-hydroxyphenyl)-7-fluoroquinolin-3-yl)(cyclopropyl)methanone | 472 |

TABLE 1-continued

| No. | Structure | Compound Name | ESI MS (m/z) |
|---|---|---|---|
| 288 | 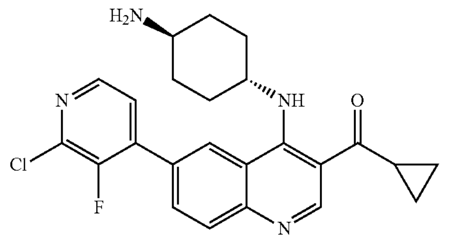 [SMILES: N[C@H]1CC[C@H](Nc2c(C(=O)C3CC3)cnc3ccc(-c4ccnc(Cl)c4F)cc23)CC1] | (4-((trans)-4-aminocyclohexylamino)-6-(2-chloro-3-fluoropyridin-4-yl)quinolin-3-yl)(cyclopropyl)methanone | 439 |
| 289 | 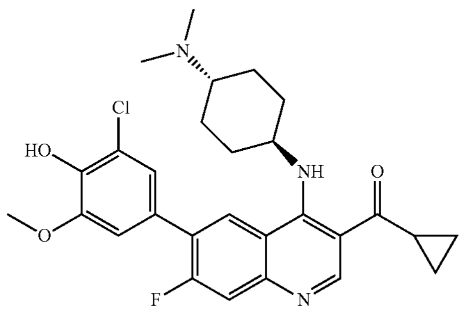 [SMILES: COc1cc(-c2cc3c(N[C@H]4CC[C@H](N(C)C)CC4)c(C(=O)C4CC4)cnc3cc2F)cc(Cl)c1O] | (6-(3-chloro-4-hydroxy-5-methoxyphenyl)-4-((trans)-4-(dimethylamino)cyclohexylamino)-7-fluoroquinolin-3-yl)(cyclopropyl)methanone | 512 |
| 290 | 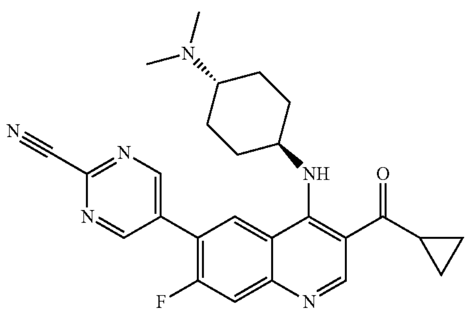 [SMILES: CN(C)[C@H]1CC[C@H](Nc2c(C(=O)C3CC3)cnc3cc(F)c(-c4cnc(C#N)nc4)cc23)CC1] | 5-(3-(cyclopropanecarbonyl)-4-((trans)-4-(dimethylamino)cyclohexylamino)-7-fluoroquinolin-6-yl)pyrimidine-2-carbonitrile | 459 |
| 291 | 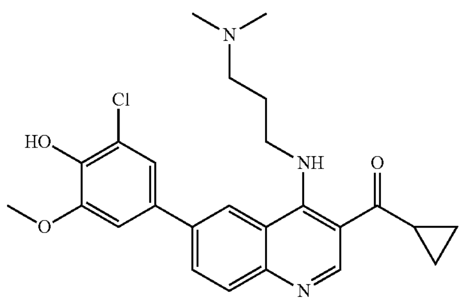 [SMILES: COc1cc(-c2ccc3ncc(C(=O)C4CC4)c(NCCCN(C)C)c3c2)cc(Cl)c1O] | (6-(3-chloro-4-hydroxy-5-methoxyphenyl)-4-(3-(dimethylamino)propylamino)quinolin-3-yl)(cyclopropyl)methanone | 454 |
| 292 | 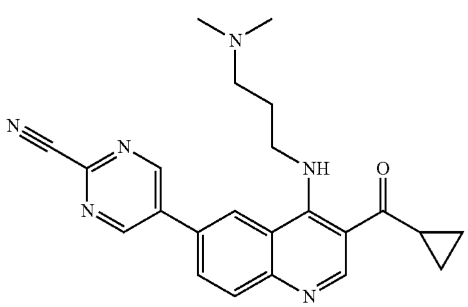 [SMILES: CN(C)CCCNc1c(C(=O)C2CC2)cnc2ccc(-c3cnc(C#N)nc3)cc12] | 5-(3-(cyclopropanecarbonyl)-4-(3-(dimethylamino)propylamino)quinolin-6-yl)pyrimidine-2-carbonitrile | 400 |

TABLE 1-continued

| No. | Structure | Compound Name | ESI MS (m/z) |
|---|---|---|---|
| 293 | 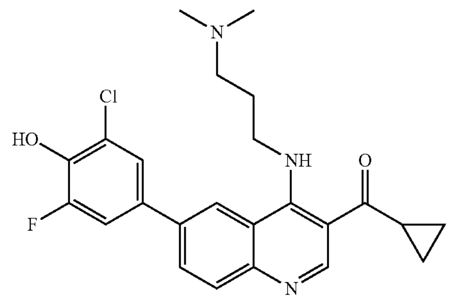 [SMILES: CN(C)CCCNc1c(C(=O)C2CC2)cnc2ccc(-c3cc(F)c(O)c(Cl)c3)cc12] | (6-(3-chloro-5-fluoro-4-hydroxyphenyl)-4-(3-(dimethylamino)propylamino)quinolin-3-yl)(cyclopropyl)methanone | 442 |
| 294 | 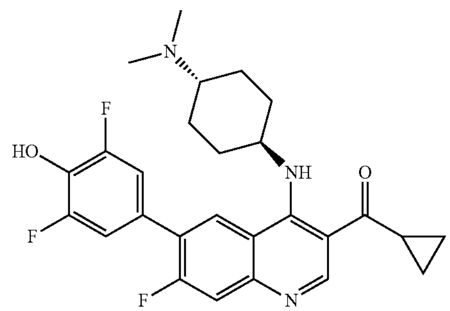 [SMILES: CN(C)[C@H]1CC[C@H](Nc2c(C(=O)C3CC3)cnc3cc(F)c(-c4cc(F)c(O)c(F)c4)cc23)CC1] | cyclopropyl(6-(3,5-difluoro-4-hydroxyphenyl)-4-((trans)-4-(dimethylamino)cyclohexylamino)-7-fluoroquinolin-3-yl)methanone | 484 |
| 295 | 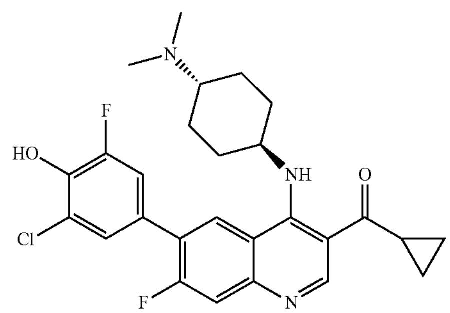 [SMILES: CN(C)[C@H]1CC[C@H](Nc2c(C(=O)C3CC3)cnc3cc(F)c(-c4cc(F)c(O)c(Cl)c4)cc23)CC1] | (6-(3-chloro-5-fluoro-4-hydroxyphenyl)-4-((trans)-4-(dimethylamino)cyclohexylamino)-7-fluoroquinolin-3-yl)(cyclopropyl)methanone | 500 |
| 296 | 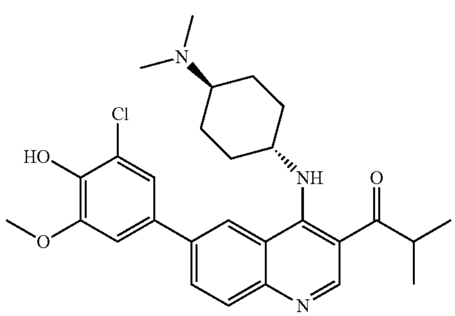 [SMILES: COc1cc(-c2ccc3ncc(C(=O)C(C)C)c(N[C@H]4CC[C@H](N(C)C)CC4)c3c2)cc(Cl)c1O] | 1-(6-(3-chloro-4-hydroxy-5-methoxyphenyl)-4-((trans)-4-(dimethylamino)cyclohexylamino)quinolin-3-yl)-2-methylpropan-1-one | 496 |
| 297 | 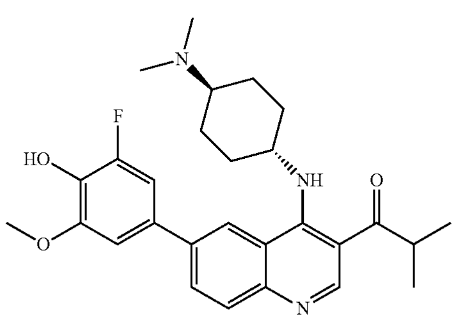 [SMILES: COc1cc(-c2ccc3ncc(C(=O)C(C)C)c(N[C@H]4CC[C@H](N(C)C)CC4)c3c2)cc(F)c1O] | 1-(4-((trans)-4-(dimethylamino)cyclohexylamino)-6-(3-fluoro-4-hydroxy-5-methoxyphenyl)quinolin-3-yl)-2-methylpropan-1-one | 480 |

TABLE 1-continued

| No. | Structure | Compound Name | ESI MS (m/z) |
|---|---|---|---|
| 298 | 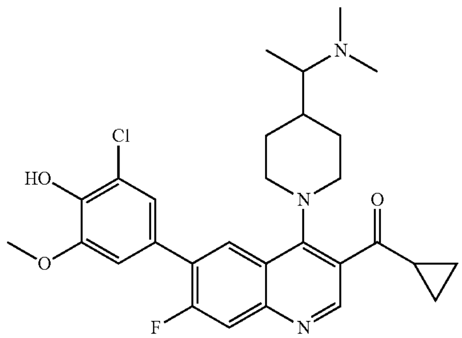 [SMILES: COc1cc(-c2cc3c(N4CCC(C(C)N(C)C)CC4)c(C(=O)C4CC4)cnc3cc2F)cc(Cl)c1O] | (6-(3-chloro-4-hydroxy-5-methoxyphenyl)-4-(4-(1-(dimethylamino)ethyl)piperidin-1-yl)-7-fluoroquinolin-3-yl)(cyclopropyl)methanone | 526 |
| 299 | 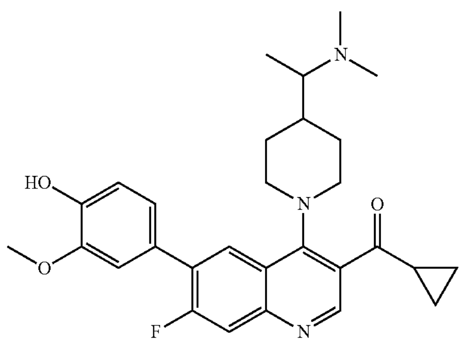 [SMILES: COc1cc(-c2cc3c(N4CCC(C(C)N(C)C)CC4)c(C(=O)C4CC4)cnc3cc2F)ccc1O] | cyclopropyl(4-(4-(1-(dimethylamino)ethyl)piperidin-1-yl)-7-fluoro-6-(4-hydroxy-3-methoxyphenyl)quinolin-3-yl)methanone | 492 |
| 300 | 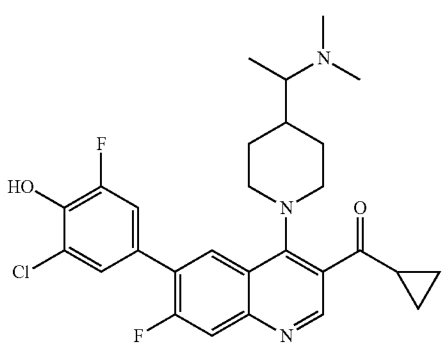 [SMILES: CC(C1CCN(c2c(C(=O)C3CC3)cnc3cc(F)c(-c4cc(F)c(O)c(Cl)c4)cc23)CC1)N(C)C] | (6-(3-chloro-5-fluoro-4-hydroxyphenyl)-4-(4-(1-(dimethylamino)ethyl)piperidin-1-yl)-7-fluoroquinolin-3-yl)(cyclopropyl)methanone | 514 |
| 301 | 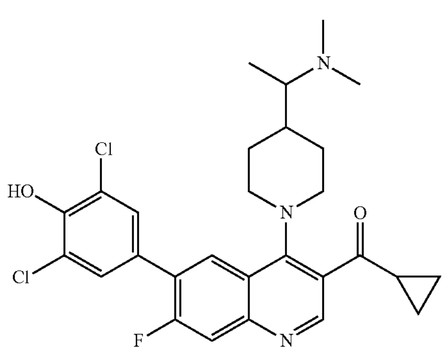 [SMILES: CC(C1CCN(c2c(C(=O)C3CC3)cnc3cc(F)c(-c4cc(Cl)c(O)c(Cl)c4)cc23)CC1)N(C)C] | cyclopropyl(6-(3,5-dichloro-4-hydroxyphenyl)-4-(4-(1-(dimethylamino)ethyl)piperidin-1-yl)-7-fluoroquinolin-3-yl)methanone | 530 |

TABLE 1-continued

| No. | Structure | Compound Name | ESI MS (m/z) |
|---|---|---|---|
| 302 | 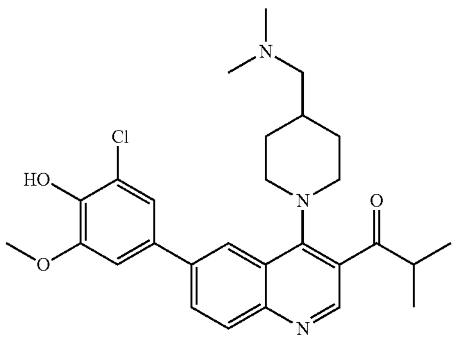 [SMILES: COc1cc(-c2ccc3ncc(C(=O)C(C)C)c(N4CCC(CN(C)C)CC4)c3c2)cc(Cl)c1O] | 1-(6-(3-chloro-4-hydroxy-5-methoxyphenyl)-4-(4-((dimethylamino)methyl)piperidin-1-yl)quinolin-3-yl)-2-methylpropan-1-one | 496 |
| 303 | 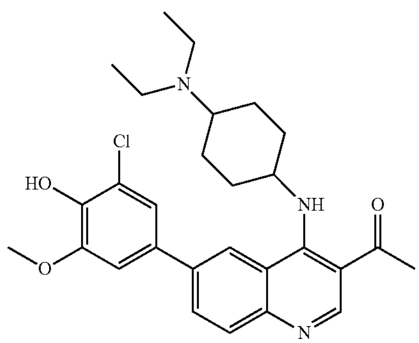 [SMILES: CCN(CC)C1CCC(Nc2c(C(C)=O)cnc3ccc(-c4cc(Cl)c(O)c(OC)c4)cc23)CC1] | 1-(6-(3-chloro-4-hydroxy-5-methoxyphenyl)-4-(4-(diethylamino)cyclohexylamino)quinolin-3-yl)ethanone | 496 |
| 304 | 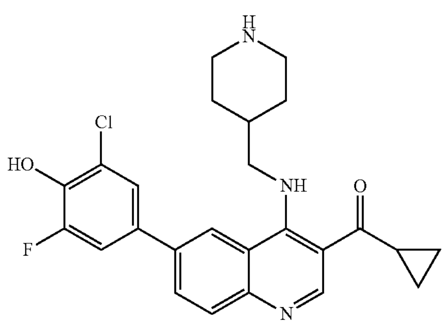 | (6-(3-chloro-5-fluoro-4-hydroxyphenyl)-4-(piperidin-4-ylmethylamino)quinolin-3-yl)(cyclopropyl)methanone | 454 |
| 305 | 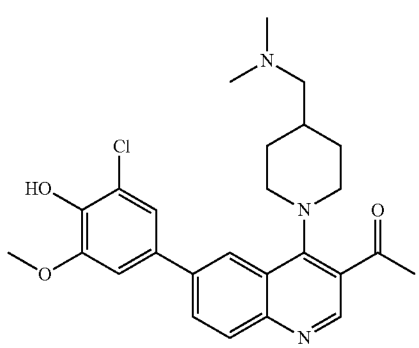 [SMILES: COc1cc(-c2ccc3ncc(C(C)=O)c(N4CCC(CN(C)C)CC4)c3c2)cc(Cl)c1O] | 1-(6-(3-chloro-4-hydroxy-5-methoxyphenyl)-4-(4-((dimethylamino)methyl)piperidin-1-yl)quinolin-3-yl)ethanone | 468 |

TABLE 1-continued

| No. | Structure | Compound Name | ESI MS (m/z) |
|---|---|---|---|
| 306 | 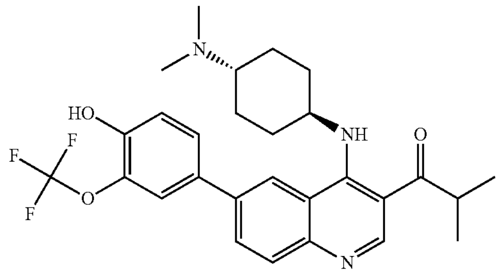 [SMILES: CC(C)C(=O)c1cnc2ccc(-c3ccc(O)c(OC(F)(F)F)c3)cc2c1N[C@H]1CC[C@H](N(C)C)CC1] | 1-(4-((trans)-4-(dimethylamino)cyclohexylamino)-6-(4-hydroxy-3-(trifluoromethoxy)phenyl)quinolin-3-yl)-2-methylpropan-1-one | 516 |
| 307 | 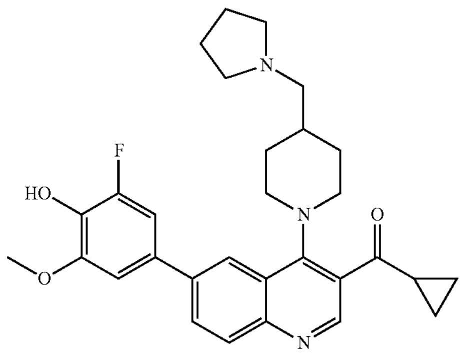 [SMILES: COc1cc(-c2ccc3ncc(C(=O)C4CC4)c(N4CCC(CN5CCCC5)CC4)c3c2)cc(F)c1O] | cyclopropyl(6-(3-fluoro-4-hydroxy-5-methoxyphenyl)-4-(4-(pyrrolidin-1-ylmethyl)piperidin-1-yl)quinolin-3-yl)methanone | 504 |
| 308 | 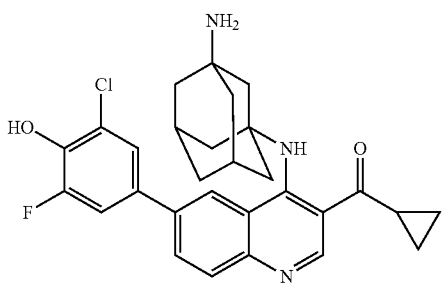 [SMILES: NC12CC3CC(C1)CC(Nc1c(C(=O)C4CC4)cnc4ccc(-c5cc(F)c(O)c(Cl)c5)cc14)(C3)C2] | {6-(3-Chloro-5-fluoro-4-hydroxyphenyl)-4-[(3-amino)adamantylamino]quinolin-3-yl}(cyclopropyl)methanone | 506 |
| 309 | 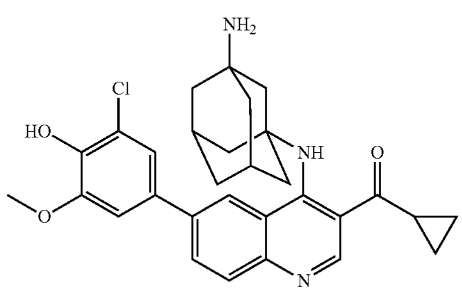 [SMILES: COc1cc(-c2ccc3ncc(C(=O)C4CC4)c(NC45CC6CC(CC(N)(C6)C4)C5)c3c2)cc(Cl)c1O] | {6-(3-Chloro-4-hydroxy-5-methoxyphenyl)-4-[(3-amino)adamantylamino]quinolin-3-yl}(cyclopropyl)methanone | 518 |
| 310 | 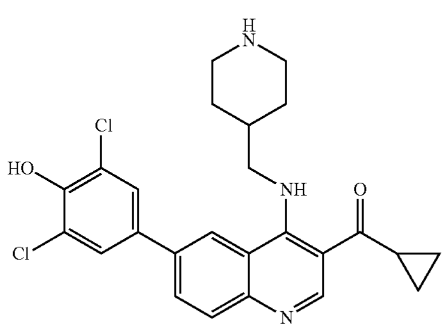 [SMILES: O=C(c1cnc2ccc(-c3cc(Cl)c(O)c(Cl)c3)cc2c1NCC1CCNCC1)C1CC1] | cyclopropyl(6-(3,5-dichloro-4-hydroxyphenyl)-4-(piperidin-4-ylmethylamino)quinolin-3-yl)methanone | 470 |

TABLE 1-continued

| No. | Structure | Compound Name | ESI MS (m/z) |
|---|---|---|---|
| 311 | 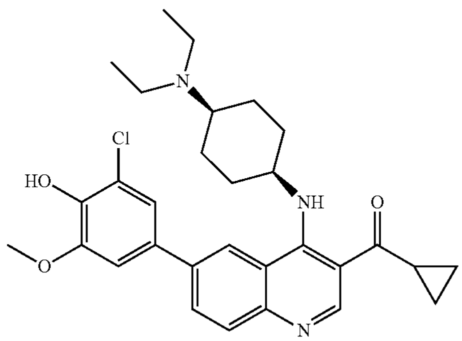 [SMILES: CCN(CC)[C@H]1CC[C@@H](Nc2c(C(=O)C3CC3)cnc3ccc(-c4cc(Cl)c(O)c(OC)c4)cc23)CC1] | (6-(3-chloro-4-hydroxy-5-methoxyphenyl)-4-((cis)-4-(diethylamino)cyclohexylamino)quinolin-3-yl)(cyclopropyl)methanone | 522 |
| 312 | 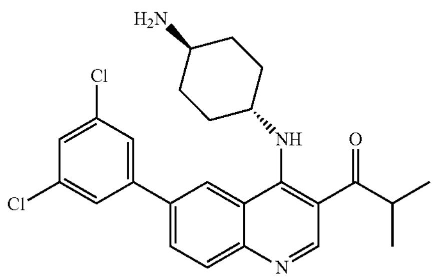 [SMILES: CC(C)C(=O)c1cnc2ccc(-c3cc(Cl)cc(Cl)c3)cc2c1N[C@H]1CC[C@H](N)CC1] | 1-(4-((trans)-4-aminocyclohexyl-amino)-6-(3,5-dichloro-phenyl)quinolin-3-yl)-2-methylpropan-1-one | 456 |
| 313 | 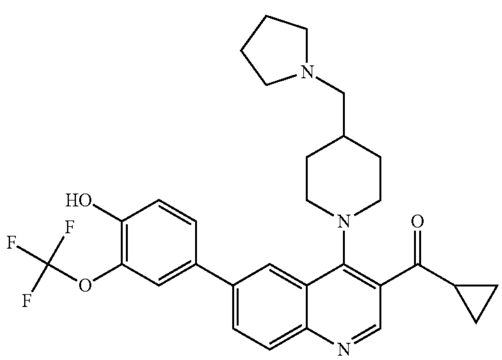 [SMILES: O=C(c1cnc2ccc(-c3ccc(O)c(OC(F)(F)F)c3)cc2c1N1CCC(CN2CCCC2)CC1)C1CC1] | cyclopropyl(6-(4-hydroxy-3-(trifluoromethoxy)phenyl)-4-(4-(pyrrolidin-1-ylmethyl)piperidin-1-yl)quinolin-3-yl)methanone | 540 |
| 314 | 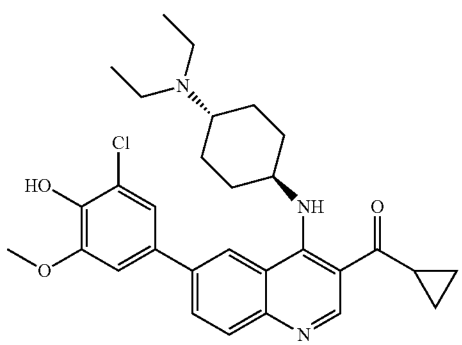 [SMILES: CCN(CC)[C@H]1CC[C@H](Nc2c(C(=O)C3CC3)cnc3ccc(-c4cc(Cl)c(O)c(OC)c4)cc23)CC1] | (6-(3-chloro-4-hydroxy-5-methoxyphenyl)-4-((trans)-4-(diethylamino)cyclohexylamino)quinolin-3-yl)(cyclopropyl)methanone | 522 |

TABLE 1-continued

| No. | Structure | Compound Name | ESI MS (m/z) |
|---|---|---|---|
| 315 | 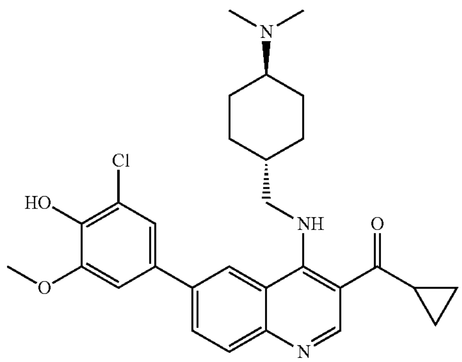 [SMILES: COc1cc(-c2ccc3ncc(C(=O)C4CC4)c(NC[C@H]4CC[C@H](N(C)C)CC4)c3c2)cc(Cl)c1O] | (6-(3-chloro-4-hydroxy-5-methoxyphenyl)-4-(((trans)-4-(dimethylamino)cyclohexyl) methylamino)quinolin-3-yl) (cyclopropyl)methanone | 508 |
| 316 | 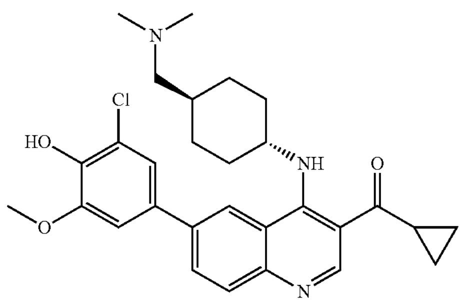 [SMILES: COc1cc(-c2ccc3ncc(C(=O)C4CC4)c(N[C@H]4CC[C@H](CN(C)C)CC4)c3c2)cc(Cl)c1O] | (6-(3-chloro-4-hydroxy-5-methoxyphenyl)-4-((trans)-4-((dimethylamino)methyl) cyclohexylamino)quinolin-3-yl) (cyclopropyl)methanone | 508 |
| 317 | 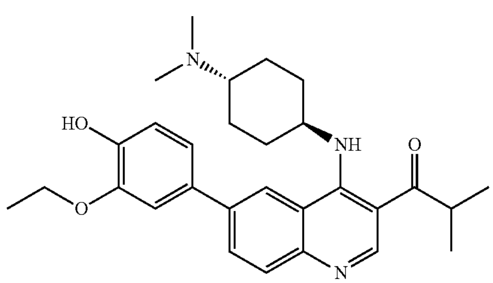 [SMILES: CCOc1cc(-c2ccc3ncc(C(=O)C(C)C)c(N[C@H]4CC[C@H](N(C)C)CC4)c3c2)ccc1O] | 1-(4-((trans)-4-(dimethylamino) cyclohexylamino)-6-(3-ethoxy-4-hydroxyphenyl)quinolin-3-yl)-2-methylpropan-1-one | 476 |
| 318 | 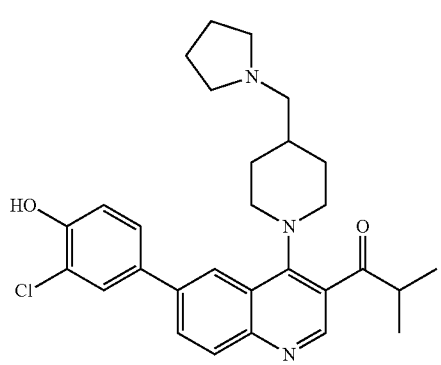 [SMILES: CC(C)C(=O)c1cnc2ccc(-c3ccc(O)c(Cl)c3)cc2c1N1CCC(CN2CCCC2)CC1] | 1-(6-(3-chloro-4-hydroxyphenyl)-4-(4-(pyrrolidin-1-ylmethyl) piperidin-1-yl)quinolin-3-yl)-2-methylpropan-1-one | 492 |

TABLE 1-continued

| No. | Structure | Compound Name | ESI MS (m/z) |
|---|---|---|---|
| 319 | 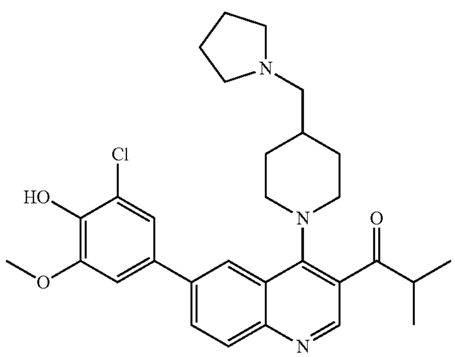 [SMILES: COc1cc(-c2ccc3ncc(C(=O)C(C)C)c(N4CCC(CN5CCCC5)CC4)c3c2)cc(Cl)c1O] | 1-(6-(3-chloro-4-hydroxy-5-methoxyphenyl)-4-(4-(pyrrolidin-1-ylmethyl)piperidin-1-yl)quinolin-3-yl)-2-methylpropan-1-one | 522 |
| 320 | 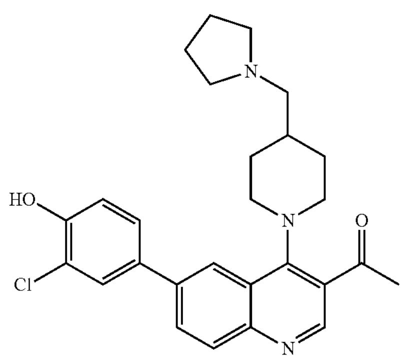 [SMILES: CC(=O)c1cnc2ccc(-c3ccc(O)c(Cl)c3)cc2c1N1CCC(CN2CCCC2)CC1] | 1-(6-(3-chloro-4-hydroxyphenyl)-4-(4-(pyrrolidin-1-ylmethyl)piperidin-1-yl)quinolin-3-yl)ethanone | 464 |
| 321 | 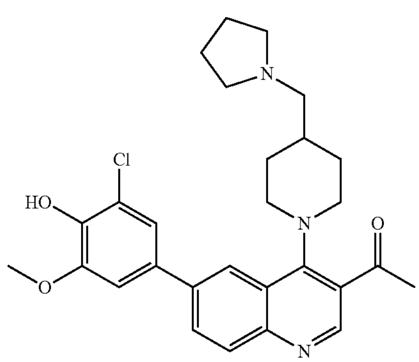 [SMILES: COc1cc(-c2ccc3ncc(C(C)=O)c(N4CCC(CN5CCCC5)CC4)c3c2)cc(Cl)c1O] | 1-(6-(3-chloro-4-hydroxy-5-methoxyphenyl)-4-(4-(pyrrolidin-1-ylmethyl)piperidin-1-yl)quinolin-3-yl)ethanone | 494 |
| 322 | 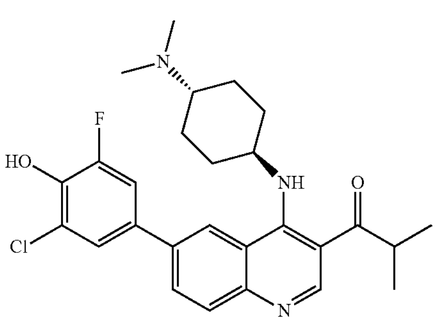 [SMILES: CC(C)C(=O)c1cnc2ccc(-c3cc(F)c(O)c(Cl)c3)cc2c1N[C@H]1CC[C@H](N(C)C)CC1] | 1-(6-(3-chloro-5-fluoro-4-hydroxyphenyl)-4-((trans)-4-(dimethylamino)cyclohexylamino)quinolin-3-yl)-2-methylpropan-1-one | 484 |

TABLE 1-continued

| No. | Structure | Compound Name | ESI MS (m/z) |
|---|---|---|---|
| 323 | 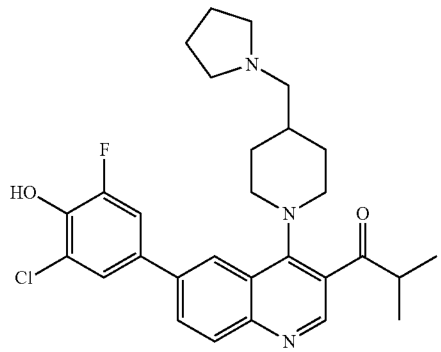 | 1-(6-(3-chloro-5-fluoro-4-hydroxyphenyl)-4-(4-(pyrrolidin-1-ylmethyl)piperidin-1-yl)quinolin-3-yl)-2-methylpropan-1-one | 510 |
| 324 | 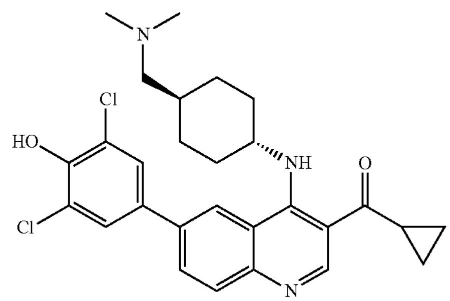 [SMILES: CN(C)C[C@H]1CC[C@H](Nc2c(C(=O)C3CC3)cnc3ccc(-c4cc(Cl)c(O)c(Cl)c4)cc23)CC1] | cyclopropyl(6-(3,5-dichloro-4-hydroxyphenyl)-4-((trans)-4-((dimethylamino)methyl)cyclohexylamino)quinolin-3-yl)methanone | 512 |
| 325 | 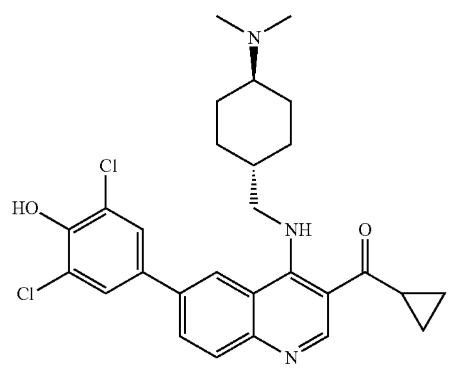 [SMILES: CN(C)[C@H]1CC[C@H](CNc2c(C(=O)C3CC3)cnc3ccc(-c4cc(Cl)c(O)c(Cl)c4)cc23)CC1] | cyclopropyl(6-(3,5-dichloro-4-hydroxyphenyl)-4-(((trans)-4-(dimethylamino)cyclohexyl)methylamino)quinolin-3-yl)methanone | 512 |
| 326 | 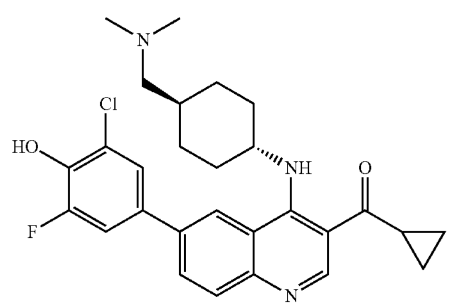 [SMILES: CN(C)C[C@H]1CC[C@H](Nc2c(C(=O)C3CC3)cnc3ccc(-c4cc(F)c(O)c(Cl)c4)cc23)CC1] | (6-(3-chloro-5-fluoro-4-hydroxyphenyl)-4-((trans)-4-((dimethylamino)methyl)cyclohexylamino)quinolin-3-yl)(cyclopropyl)methanone | 496 |

TABLE 1-continued

| No. | Structure | Compound Name | ESI MS (m/z) |
|---|---|---|---|
| 327 | 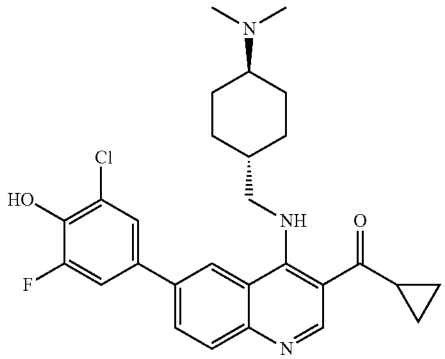 [SMILES: CN(C)[C@H]1CC[C@H](CNc2c(C(=O)C3CC3)cnc3ccc(-c4cc(F)c(O)c(Cl)c4)cc23)CC1] | (6-(3-chloro-5-fluoro-4-hydroxyphenyl)-4-(((trans)-4-(dimethylamino)cyclohexyl)methylamino)quinolin-3-yl)(cyclopropyl)methanone | 496 |
| 328 | 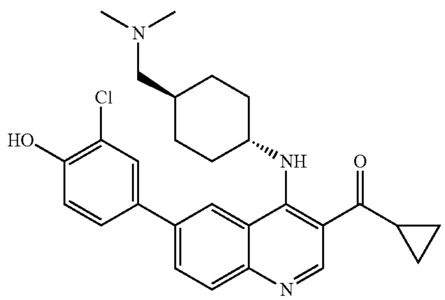 [SMILES: CN(C)C[C@H]1CC[C@H](Nc2c(C(=O)C3CC3)cnc3ccc(-c4ccc(O)c(Cl)c4)cc23)CC1] | (6-(3-chloro-4-hydroxyphenyl)-4-((trans)-4-((dimethylamino)methyl)cyclohexylamino)quinolin-3-yl)(cyclopropyl)methanone | 478 |
| 329 | 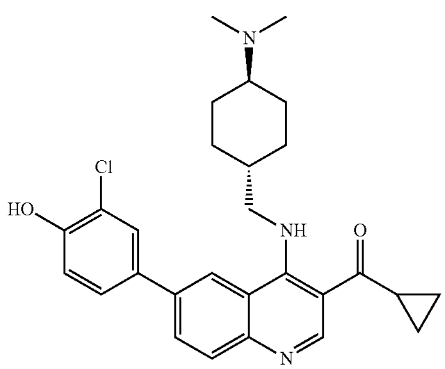 [SMILES: CN(C)[C@H]1CC[C@H](CNc2c(C(=O)C3CC3)cnc3ccc(-c4ccc(O)c(Cl)c4)cc23)CC1] | (6-(3-chloro-4-hydroxyphenyl)-4-(((trans)-4-(dimethylamino)cyclohexyl)methylamino)quinolin-3-yl)(cyclopropyl)methanone | 478 |
| 330 | 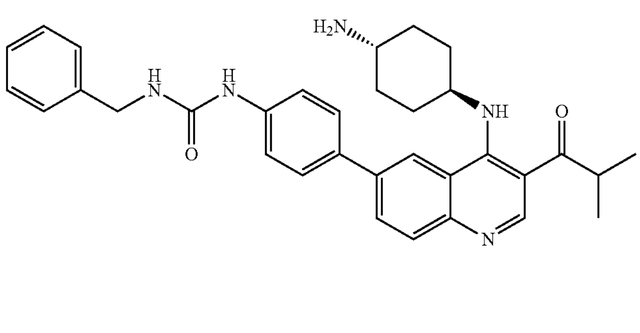 [SMILES: CC(C)C(=O)c1cnc2ccc(-c3ccc(NC(=O)NCc4ccccc4)cc3)cc2c1N[C@H]1CC[C@H](N)CC1] | 1-(4-(4-((trans)-4-aminocyclohexylamino)-3-isobutyrylquinolin-6-yl)phenyl)-3-benzylurea | 536 |

TABLE 1-continued

| No. | Structure | Compound Name | ESI MS (m/z) |
|---|---|---|---|
| 331 | 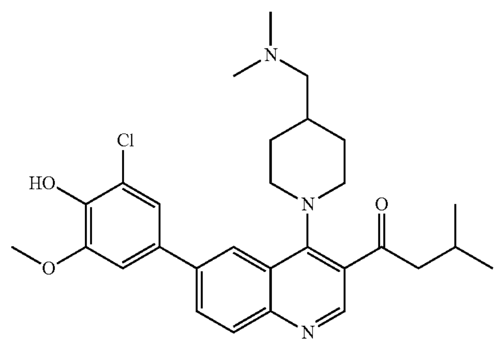 [SMILES: COc1cc(-c2ccc3ncc(C(=O)CC(C)C)c(N4CCC(CN(C)C)CC4)c3c2)cc(Cl)c1O] | 1-(6-(3-chloro-4-hydroxy-5-methoxyphenyl)-4-(4-((dimethylamino)methyl)piperidin-1-yl)quinolin-3-yl)-3-methylbutan-1-one | 510 |
| 332 | 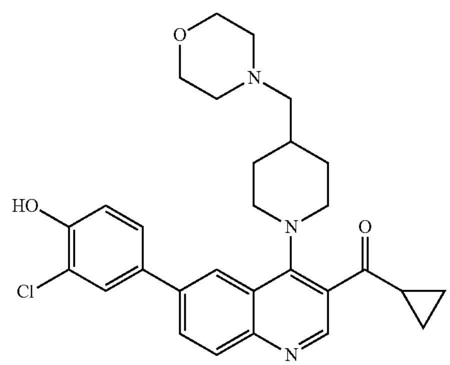 [SMILES: O=C(c1cnc2ccc(-c3ccc(O)c(Cl)c3)cc2c1N1CCC(CN2CCOCC2)CC1)C1CC1] | (6-(3-chloro-4-hydroxyphenyl)-4-(4-(morpholinomethyl)piperidin-1-yl)quinolin-3-yl)(cyclopropyl)methanone | 506 |
| 333 | 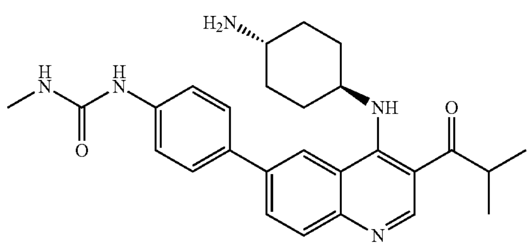 [SMILES: CNC(=O)Nc1ccc(-c2ccc3ncc(C(=O)C(C)C)c(N[C@H]4CC[C@H](N)CC4)c3c2)cc1] | 1-(4-(4-((trans)-4-aminocyclohexylamino)-3-isobutyrylquinolin-6-yl)phenyl)-3-methylurea | 460 |
| 334 | 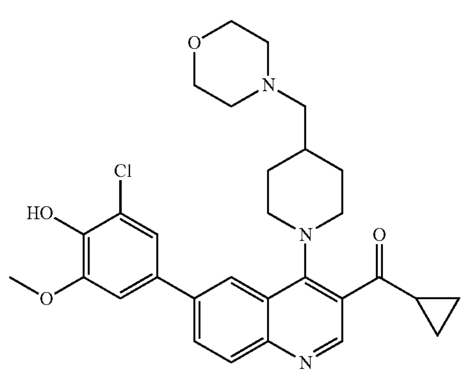 [SMILES: COc1cc(-c2ccc3ncc(C(=O)C4CC4)c(N4CCC(CN5CCOCC5)CC4)c3c2)cc(Cl)c1O] | (6-(3-chloro-4-hydroxy-5-methoxyphenyl)-4-(4-(morpholinomethyl)piperidin-1-yl)quinolin-3-yl)(cyclopropyl)methanone | 536 |

TABLE 1-continued

| No. | Structure | Compound Name | ESI MS (m/z) |
|---|---|---|---|
| 335 | 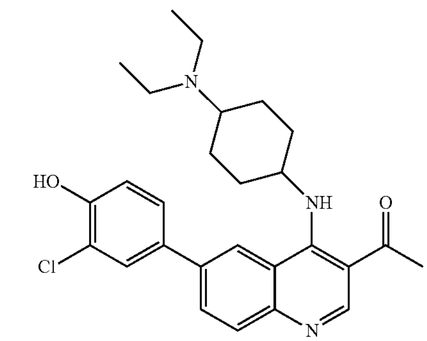 [SMILES: CCN(CC)C1CCC(Nc2c(C(C)=O)cnc3ccc(-c4ccc(O)c(Cl)c4)cc23)CC1] | 1-(6-(3-chloro-4-hydroxyphenyl)-4-(4-(diethylamino)cyclohexyl-amino)quinolin-3-yl)ethanone | 466 |
| 336 | 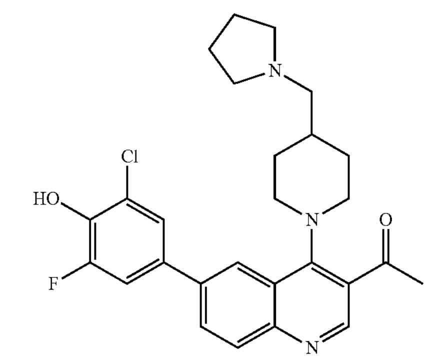 [SMILES: CC(=O)c1cnc2ccc(-c3cc(F)c(O)c(Cl)c3)cc2c1N1CCC(CN2CCCC2)CC1] | 1-(6-(3-chloro-5-fluoro-4-hydroxyphenyl)-4-(4-(pyrrolidin-1-ylmethyl)piperidin-1-yl)quinolin-3-yl)ethanone | 482 |
| 337 | 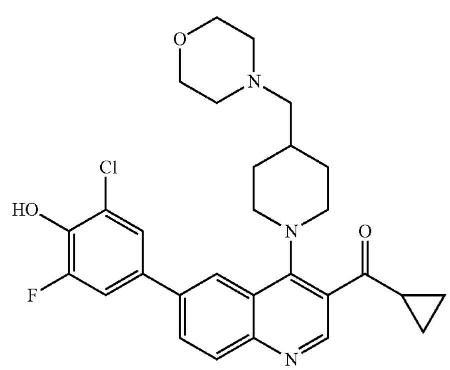 [SMILES: O=C(c1cnc2ccc(-c3cc(F)c(O)c(Cl)c3)cc2c1N1CCC(CN2CCOCC2)CC1)C1CC1] | (6-(3-chloro-5-fluoro-4-hydroxyl-phenyl)-4-(4-(morpholinomethyl)piperidin-1-yl)quinolin-3-yl)(cyclopropyl)methanone | 524 |
| 338 | 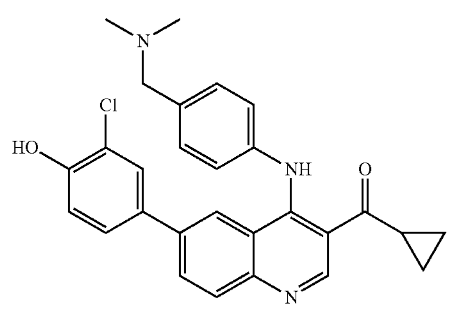 | (6-(3-chloro-4-hydroxyphenyl)-4-(4-((dimethylamino)methyl)phenylamino)quinolin-3-yl)(cyclopropyl)methanone | 472 |

TABLE 1-continued

| No. | Structure | Compound Name | ESI MS (m/z) |
|---|---|---|---|
| 339 | 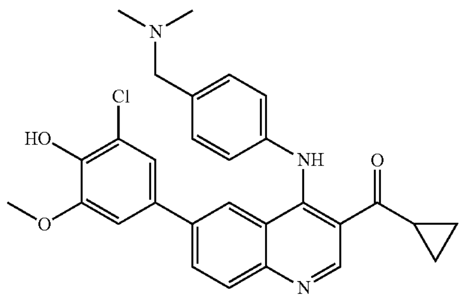 [SMILES: COc1cc(-c2ccc3ncc(C(=O)C4CC4)c(Nc4ccc(CN(C)C)cc4)c3c2)cc(Cl)c1O] | (6-(3-chloro-4-hydroxy-5-methoxyphenyl)-4-(4-((dimethylamino)methyl)phenylamino)quinolin-3-yl)(cyclopropyl)methanone | 502 |
| 340 | 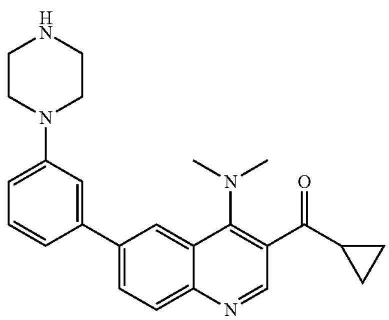 [SMILES: CN(C)c1c(C(=O)C2CC2)cnc2ccc(-c3cccc(N4CCNCC4)c3)cc12] | cyclopropyl(4-(dimethylamino)-6-(3-(piperazin-1-yl)phenyl)quinolin-3-yl)methanone | 401 |
| 341 | 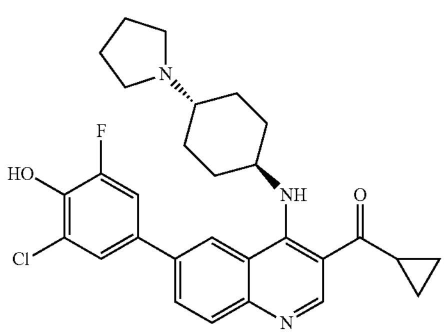 [SMILES: O=C(c1cnc2ccc(-c3cc(F)c(O)c(Cl)c3)cc2c1N[C@H]1CC[C@H](N2CCCC2)CC1)C1CC1] | (6-(3-chloro-5-fluoro-4-hydroxyphenyl)-4-((trans)-4-(pyrrolidin-1-yl)cyclohexylamino)quinolin-3-yl)(cyclopropyl)methanone | 508 |
| 342 | 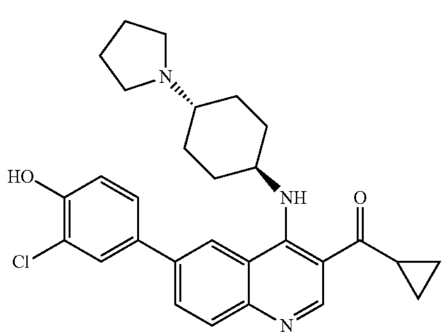 [SMILES: O=C(c1cnc2ccc(-c3ccc(O)c(Cl)c3)cc2c1N[C@H]1CC[C@H](N2CCCC2)CC1)C1CC1] | (6-(3-chloro-4-hydroxyphenyl)-4-((trans)-4-(pyrrolidin-1-yl)cyclohexylamino)quinolin-3-yl)(cyclopropyl)methanone | 490 |

TABLE 1-continued

| No. | Structure | Compound Name | ESI MS (m/z) |
|---|---|---|---|
| 343 | 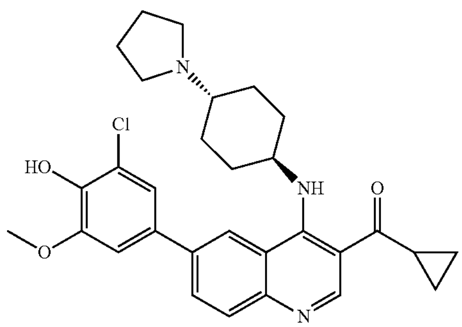 [SMILES: COc1cc(-c2ccc3ncc(C(=O)C4CC4)c(N[C@H]4CC[C@H](N5CCCC5)CC4)c3c2)cc(Cl)c1O] | (6-(3-chloro-4-hydroxy-5-methoxyphenyl)-4-((trans)-4-(pyrrolidin-1-yl)cyclohexylamino)quinolin-3-yl)(cyclopropyl)methanone | 520 |
| 344 | 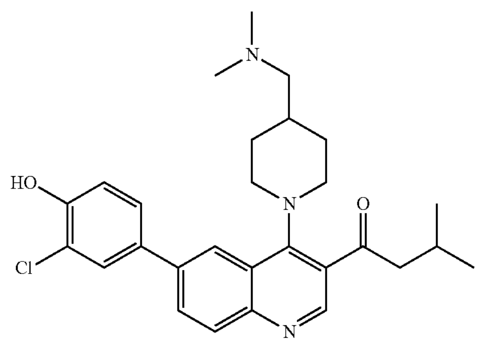 [SMILES: CC(C)CC(=O)c1cnc2ccc(-c3ccc(O)c(Cl)c3)cc2c1N1CCC(CN(C)C)CC1] | 1-(6-(3-chloro-4-hydroxyphenyl)-4-(4-((dimethylamino)methyl)piperidin-1-yl)quinolin-3-yl)-3-methylbutan-1-one | 480 |
| 345 | 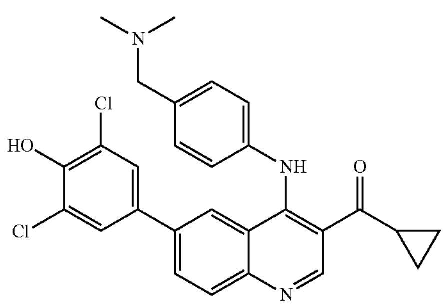 [SMILES: CN(C)Cc1ccc(Nc2c(C(=O)C3CC3)cnc3ccc(-c4cc(Cl)c(O)c(Cl)c4)cc23)cc1] | cyclopropyl(6-(3,5-dichloro-4-hydroxyphenyl)-4-(4-((dimethylamino)methyl)phenylamino)quinolin-3-yl)methanone | 506 |
| 346 | 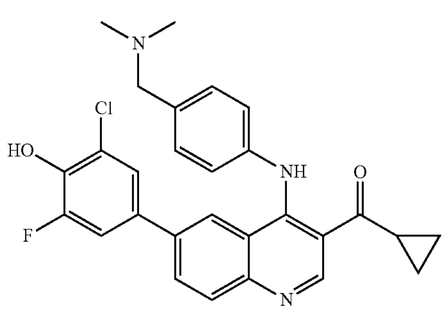 [SMILES: CN(C)Cc1ccc(Nc2c(C(=O)C3CC3)cnc3ccc(-c4cc(F)c(O)c(Cl)c4)cc23)cc1] | (6-(3-chloro-5-fluoro-4-hydroxyphenyl)-4-(4-((dimethylamino)methyl)phenylamino)quinolin-3-yl)(cyclopropyl)methanone | 490 |

TABLE 1-continued

| No. | Structure | Compound Name | ESI MS (m/z) |
|---|---|---|---|
| 347 | 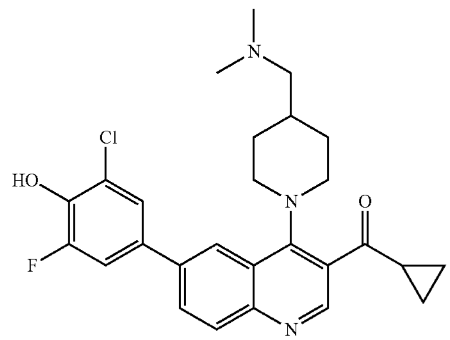 [SMILES: CN(C)CC1CCN(c2c(C(=O)C3CC3)cnc3ccc(-c4cc(F)c(O)c(Cl)c4)cc23)CC1] | (6-(3-chloro-5-fluoro-4-hydroxyphenyl)-4-(4-((dimethylamino)methyl)piperidin-1-yl)quinolin-3-yl)(cyclopropyl)methanone | 482 |
| 348 | 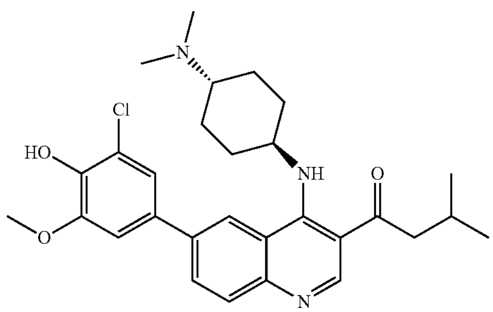 [SMILES: COc1cc(-c2ccc3ncc(C(=O)CC(C)C)c(N[C@H]4CC[C@H](N(C)C)CC4)c3c2)cc(Cl)c1O] | 1-(6-(3-chloro-4-hydroxy-5-methoxyphenyl)-4-((trans)-4-(dimethylamino)cyclohexylamino)quinolin-3-yl)-3-methylbutan-1-one | 510 |
| 349 | 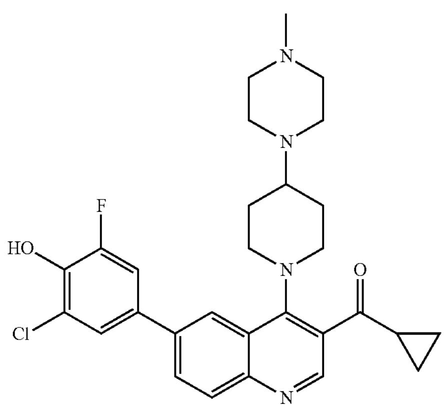 [SMILES: CN1CCN(C2CCN(c3c(C(=O)C4CC4)cnc4ccc(-c5cc(F)c(O)c(Cl)c5)cc34)CC2)CC1] | (6-(3-chloro-5-fluoro-4-hydroxyphenyl)-4-(4-(4-methylpiperazin-1-yl)piperidin-1-yl)quinolin-3-yl)(cyclopropyl)methanone | 523 |
| 350 | 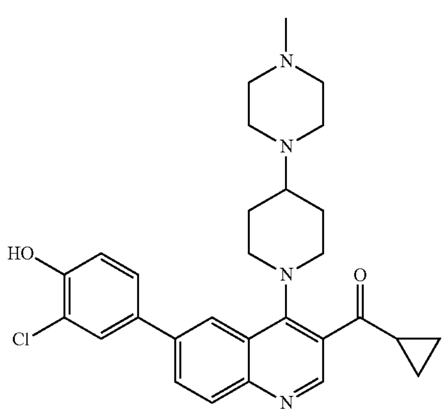 [SMILES: CN1CCN(C2CCN(c3c(C(=O)C4CC4)cnc4ccc(-c5ccc(O)c(Cl)c5)cc34)CC2)CC1] | (6-(3-chloro-4-hydroxyphenyl)-4-(4-(4-methylpiperazin-1-yl)piperidin-1-yl)quinolin-3-yl)(cyclopropyl)methanone | 505 |

TABLE 1-continued

| No. | Structure | Compound Name | ESI MS (m/z) |
|---|---|---|---|
| 351 | 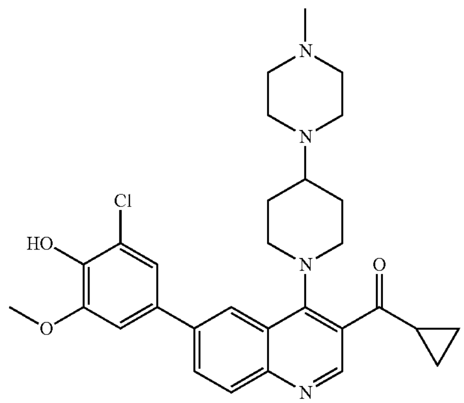 [SMILES: COc1cc(-c2ccc3ncc(C(=O)C4CC4)c(N4CCC(N5CCN(C)CC5)CC4)c3c2)cc(Cl)c1O] | (6-(3-chloro-4-hydroxy-5-methoxyphenyl)-4-(4-(4-methylpiperazin-1-yl)piperidin-1-yl)quinolin-3-yl)(cyclopropyl)methanone | 535 |
| 352 | 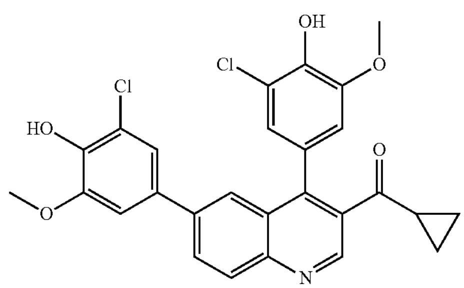 [SMILES: COc1cc(-c2ccc3ncc(C(=O)C4CC4)c(-c4cc(Cl)c(O)c(OC)c4)c3c2)cc(Cl)c1O] | (4,6-bis(3-chloro-4-hydroxy-5-methoxyphenyl)quinolin-3-yl)(cyclopropyl)methanone | 510 |
| 353 | 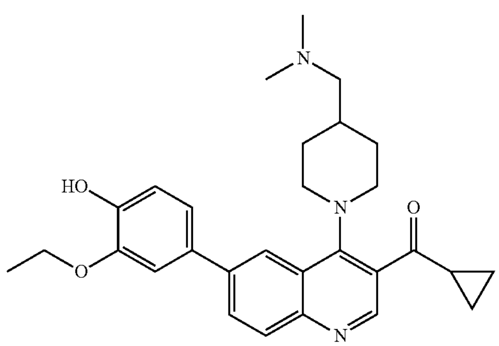 [SMILES: CCOc1cc(-c2ccc3ncc(C(=O)C4CC4)c(N4CCC(CN(C)C)CC4)c3c2)ccc1O] | cyclopropyl(4-(4-((dimethylamino)methyl)piperidin-1-yl)-6-(3-ethoxy-4-hydroxyphenyl)quinolin-3-yl)methanone | 474 |
| 354 | 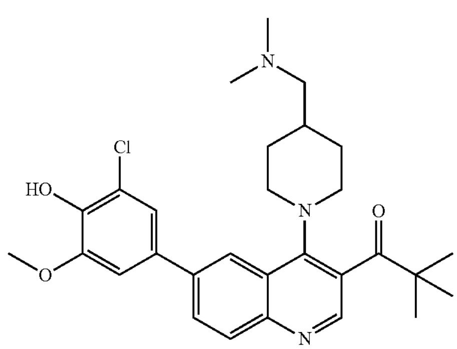 [SMILES: COc1cc(-c2ccc3ncc(C(=O)C(C)(C)C)c(N4CCC(CN(C)C)CC4)c3c2)cc(Cl)c1O] | 1-(6-(3-chloro-4-hydroxy-5-methoxyphenyl)-4-(4-((dimethylamino)methyl)piperidin-1-yl)quinolin-3-yl)-2,2-dimethylpropan-1-one | 510 |

TABLE 1-continued

| No. | Structure | Compound Name | ESI MS (m/z) |
|---|---|---|---|
| 355 | 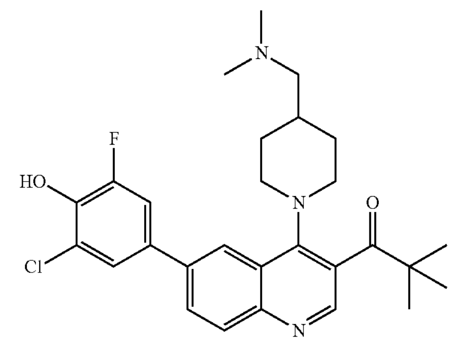 [SMILES: CN(C)CC1CCN(c2c(C(=O)C(C)(C)C)cnc3ccc(-c4cc(F)c(O)c(Cl)c4)cc23)CC1] | 1-(6-(3-chloro-5-fluoro-4-hydroxyphenyl)-4-(4-((dimethylamino)methyl)piperidin-1-yl)quinolin-3-yl)-2,2-dimethylpropan-1-one | 498 |
| 356 | 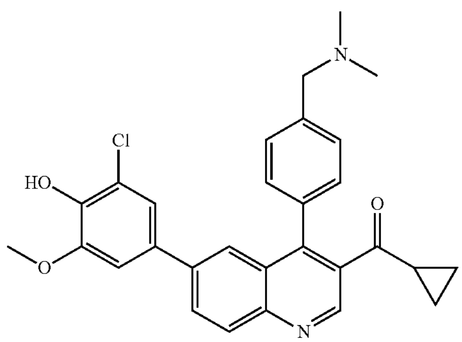 [SMILES: COc1cc(-c2ccc3ncc(C(=O)C4CC4)c(-c4ccc(CN(C)C)cc4)c3c2)cc(Cl)c1O] | (6-(3-chloro-4-hydroxy-5-methoxyphenyl)-4-(4-((dimethylamino)methyl)phenyl)quinolin-3-yl)(cyclopropyl)methanone | 487 |
| 357 | 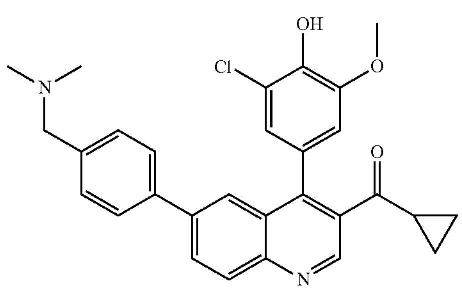 [SMILES: COc1cc(-c2c(C(=O)C3CC3)cnc3ccc(-c4ccc(CN(C)C)cc4)cc23)cc(Cl)c1O] | (4-(3-chloro-4-hydroxy-5-methoxyphenyl)-6-(4-((dimethylamino)methyl)phenyl)quinolin-3-yl)(cyclopropyl)methanone | 487 |
| 358 | 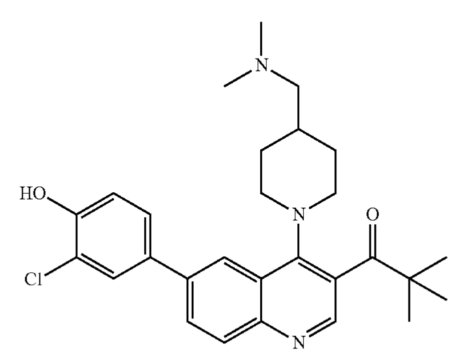 [SMILES: CN(C)CC1CCN(c2c(C(=O)C(C)(C)C)cnc3ccc(-c4ccc(O)c(Cl)c4)cc23)CC1] | 1-(6-(3-chloro-4-hydroxyphenyl)-4-(4-((dimethylamino)methyl)piperidin-1-yl)quinolin-3-yl)-2,2-dimethylpropan-1-one | 480 |

TABLE 1-continued

| No. | Structure | Compound Name | ESI MS (m/z) |
|---|---|---|---|
| 359 | 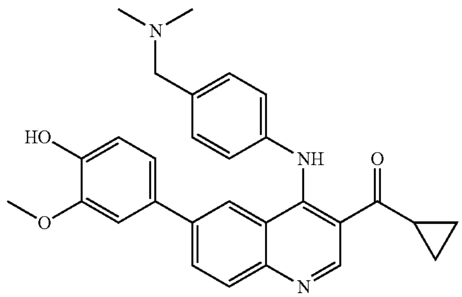 [SMILES: COc1cc(-c2ccc3ncc(C(=O)C4CC4)c(Nc4ccc(CN(C)C)cc4)c3c2)ccc1O] | cyclopropyl(4-(4-((dimethylamino)methyl)phenylamino)-6-(4-hydroxy-3-methoxyphenyl)quinolin-3-yl)methanone | 468 |
| 360 | 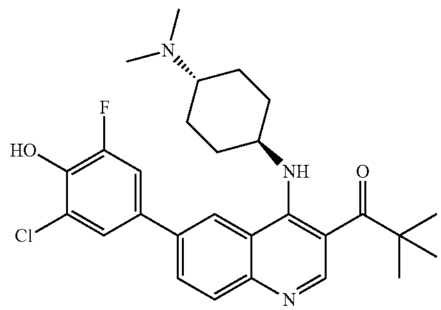 [SMILES: CN(C)[C@H]1CC[C@H](Nc2c(C(=O)C(C)(C)C)cnc3ccc(-c4cc(F)c(O)c(Cl)c4)cc23)CC1] | 1-(6-(3-chloro-5-fluoro-4-hydroxyphenyl)-4-((trans)-4-(dimethylamino)cyclohexylamino)quinolin-3-yl)-2,2-dimethylpropan-1-one | 498 |
| 361 | 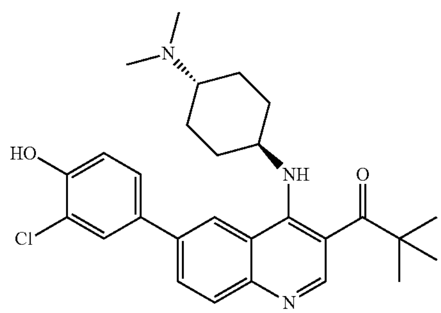 [SMILES: CN(C)[C@H]1CC[C@H](Nc2c(C(=O)C(C)(C)C)cnc3ccc(-c4ccc(O)c(Cl)c4)cc23)CC1] | 1-(6-(3-chloro-4-hydroxyphenyl)-4-((trans)-4-(dimethylamino)cyclohexylamino)quinolin-3-yl)-2,2-dimethylpropan-1-one | 480 |
| 362 | 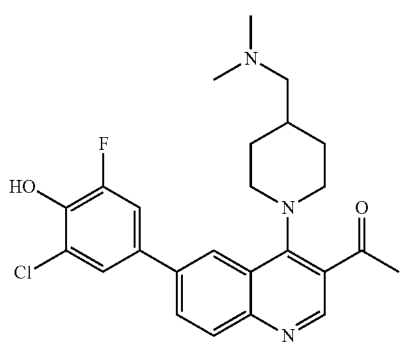 [SMILES: CC(=O)c1cnc2ccc(-c3cc(F)c(O)c(Cl)c3)cc2c1N1CCC(CN(C)C)CC1] | 1-(6-(3-chloro-5-fluoro-4-hydroxyphenyl)-4-(4-((dimethylamino)methyl)piperidin-1-yl)quinolin-3-yl)ethanone | 456 |
| 363 | 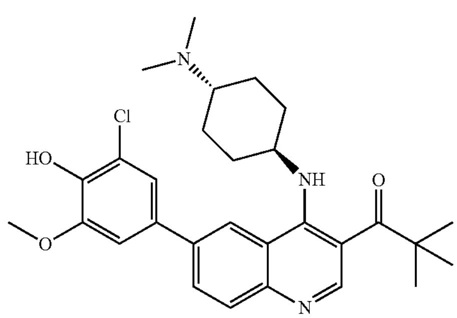 [SMILES: COc1cc(-c2ccc3ncc(C(=O)C(C)(C)C)c(N[C@H]4CC[C@H](N(C)C)CC4)c3c2)cc(Cl)c1O] | 1-(6-(3-chloro-4-hydroxy-5-methoxyphenyl)-4-((trans)-4-(dimethylamino)cyclohexylamino)quinolin-3-yl)-2,2-dimethylpropan-1-one | 510 |

TABLE 1-continued

| No. | Structure | Compound Name | ESI MS (m/z) |
|---|---|---|---|
| 364 | 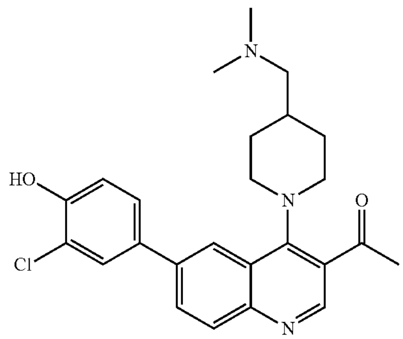 [SMILES: CC(=O)c1cnc2ccc(-c3ccc(O)c(Cl)c3)cc2c1N1CCC(CN(C)C)CC1] | 1-(6-(3-chloro-4-hydroxyphenyl)-4-(4-((dimethylamino)methyl)piperidin-1-yl)quinolin-3-yl)ethanone | 438 |
| 365 | 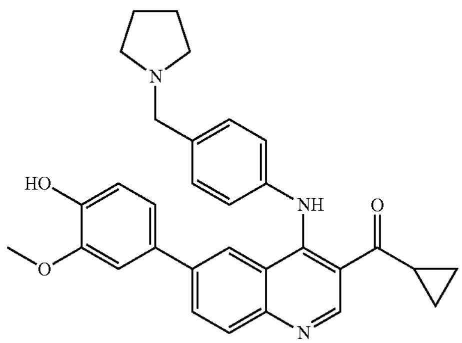 [SMILES: COc1cc(-c2ccc3ncc(C(=O)C4CC4)c(Nc4ccc(CN5CCCC5)cc4)c3c2)ccc1O] | cyclopropyl(6-(4-hydroxy-3-methoxyphenyl)-4-(4-(pyrrolidin-1-ylmethyl)phenylamino)quinolin-3-yl)methanone | 494 |
| 366 | 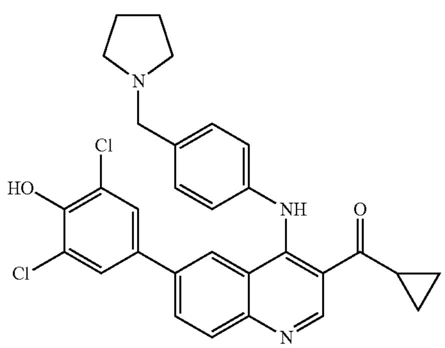 [SMILES: O=C(c1cnc2ccc(-c3cc(Cl)c(O)c(Cl)c3)cc2c1Nc1ccc(CN2CCCC2)cc1)C1CC1] | cyclopropyl(6-(3,5-dichloro-4-hydroxyphenyl)-4-(4-(pyrrolidin-1-ylmethyl)phenylamino)quinolin-3-yl)methanone | 532 |
| 367 | 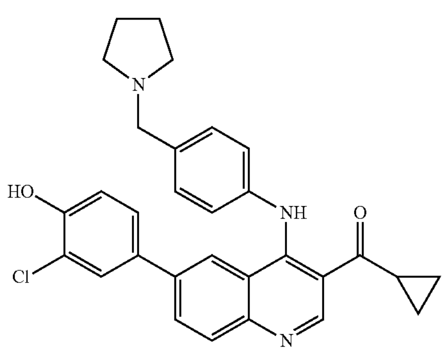 [SMILES: O=C(c1cnc2ccc(-c3ccc(O)c(Cl)c3)cc2c1Nc1ccc(CN2CCCC2)cc1)C1CC1] | (6-(3-chloro-4-hydroxyphenyl)-4-(4-(pyrrolidin-1-ylmethyl)phenylamino)quinolin-3-yl)(cyclopropyl)methanone | 498 |

TABLE 1-continued

| No. | Structure | Compound Name | ESI MS (m/z) |
|---|---|---|---|
| 368 | 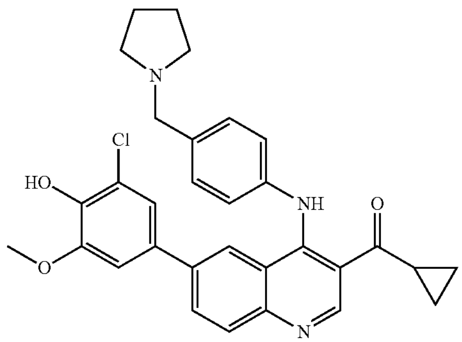 [SMILES: COc1cc(-c2ccc3ncc(C(=O)C4CC4)c(Nc4ccc(CN5CCCC5)cc4)c3c2)cc(Cl)c1O] | (6-(3-chloro-4-hydroxy-5-methoxyphenyl)-4-(4-(pyrrolidin-1-ylmethyl)phenylamino)quinolin-3-yl)(cyclopropyl)methanone | 528 |
| 369 | 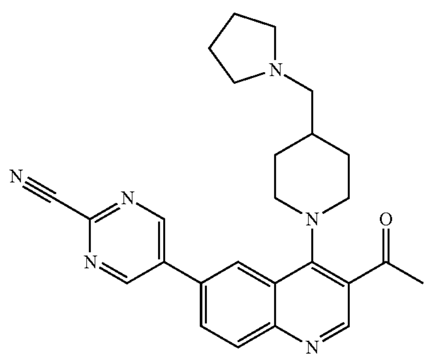 [SMILES: CC(=O)c1cnc2ccc(-c3cnc(C#N)nc3)cc2c1N1CCC(CN2CCCC2)CC1] | 5-(3-acetyl-4-(4-(pyrrolidin-1-ylmethyl)piperidin-1-yl)quinolin-6-yl)pyrimidine-2-carbonitrile | 441 |
| 370 | 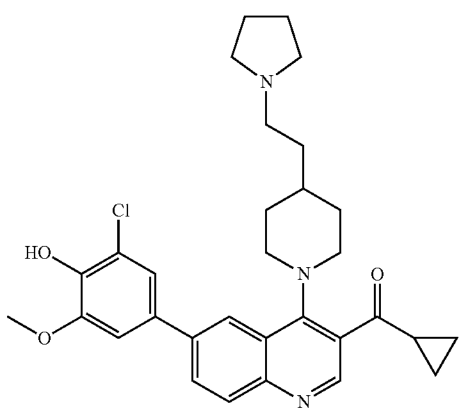 [SMILES: COc1cc(-c2ccc3ncc(C(=O)C4CC4)c(N4CCC(CCN5CCCC5)CC4)c3c2)cc(Cl)c1O] | (6-(3-chloro-4-hydroxy-5-methoxyphenyl)-4-(4-(2-(pyrrolidin-1-yl)ethyl)piperidin-1-yl)quinolin-3-yl)(cyclopropyl)methanone | 534 |
| 371 | 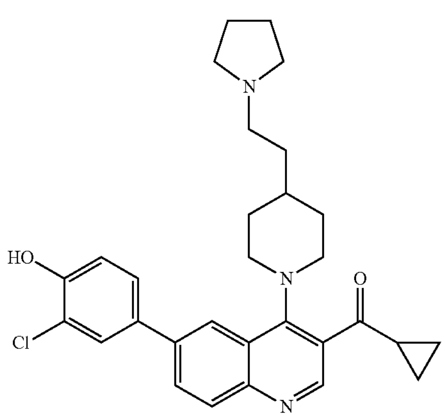 | (6-(3-chloro-4-hydroxyphenyl)-4-(4-(2-(pyrrolidin-1-yl)ethyl)piperidin-1-yl)quinolin-3-yl)(cyclopropyl)methanone | 504 |

TABLE 1-continued

| No. | Structure | Compound Name | ESI MS (m/z) |
|---|---|---|---|
| 372 | 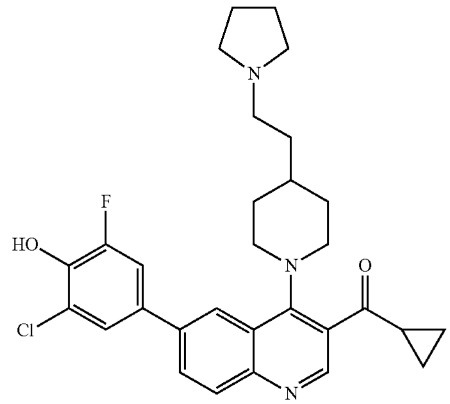 | (6-(3-chloro-5-fluoro-4-hydroxyphenyl)-4-(4-(2-(pyrrolidin-1-yl)ethyl)piperidin-1-yl)quinolin-3-yl)(cyclopropyl)methanone | 522 |
| 373 | 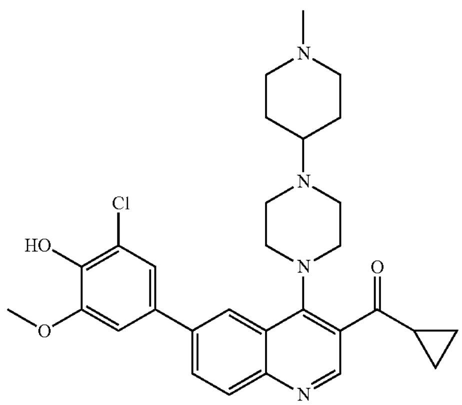 [SMILES: COc1cc(-c2ccc3ncc(C(=O)C4CC4)c(N4CCN(C5CCN(C)CC5)CC4)c3c2)cc(Cl)c1O] | (6-(3-chloro-4-hydroxy-5-methoxyphenyl)-4-(4-(1-methylpiperidin-4-yl)piperazin-1-yl)quinolin-3-yl)(cyclopropyl)methanone | 535 |
| 374 | 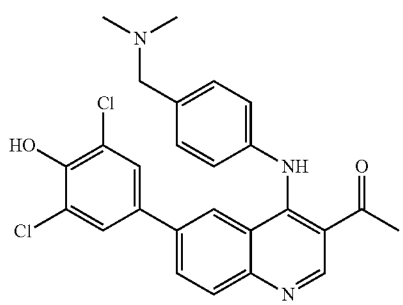 [SMILES: CC(=O)c1cnc2ccc(-c3cc(Cl)c(O)c(Cl)c3)cc2c1Nc1ccc(CN(C)C)cc1] | 1-(6-(3,5-dichloro-4-hydroxyphenyl)-4-(4-((dimethylamino)methyl)phenylamino)quinolin-3-yl)ethanone | 480 |
| 375 | 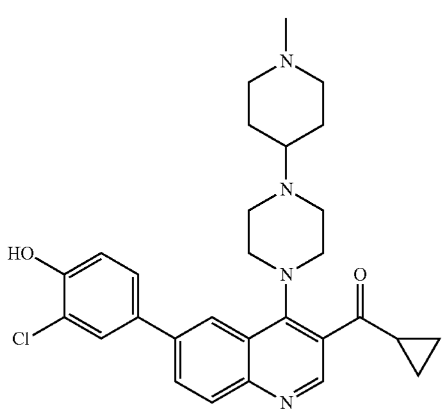 [SMILES: CN1CCC(N2CCN(c3c(C(=O)C4CC4)cnc4ccc(-c5ccc(O)c(Cl)c5)cc34)CC2)CC1] | (6-(3-chloro-4-hydroxyphenyl)-4-(4-(1-methylpiperidin-4-yl)piperazin-1-yl)quinolin-3-yl)(cyclopropyl)methanone | 505 |

TABLE 1-continued

| No. | Structure | Compound Name | ESI MS (m/z) |
|---|---|---|---|
| 376 | 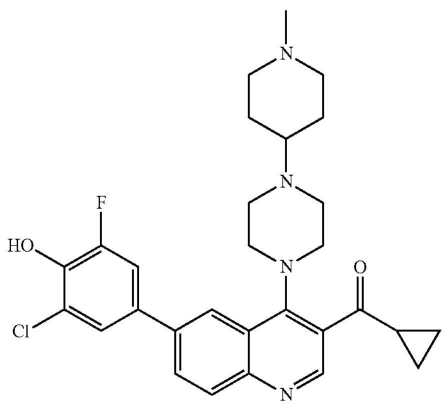 [SMILES: CN1CCC(N2CCN(c3c(C(=O)C4CC4)cnc4ccc(-c5cc(F)c(O)c(Cl)c5)cc34)CC2)CC1] | (6-(3-chloro-5-fluoro-4-hydroxyphenyl)-4-(4-(1-methylpiperidin-4-yl)piperazin-1-yl)quinolin-3-yl)(cyclopropyl)methanone | 523 |
| 377 | 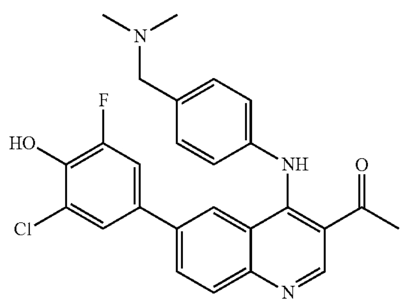 [SMILES: CC(=O)c1cnc2ccc(-c3cc(F)c(O)c(Cl)c3)cc2c1Nc1ccc(CN(C)C)cc1] | 1-(6-(3-chloro-5-fluoro-4-hydroxyphenyl)-4-(4-((dimethylamino)methyl)phenylamino)quinolin-3-yl)ethanone | 464 |
| 378 | 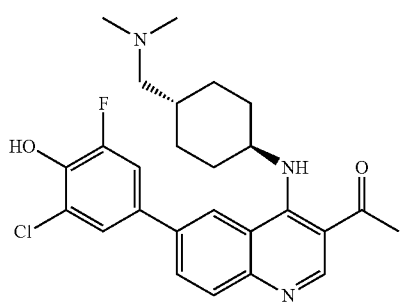 [SMILES: CC(=O)c1cnc2ccc(-c3cc(F)c(O)c(Cl)c3)cc2c1N[C@H]1CC[C@H](CN(C)C)CC1] | 1-(6-(3-chloro-5-fluoro-4-hydroxyphenyl)-4-((trans)-4-((dimethylamino)methyl)cyclohexylamino)quinolin-3-yl)ethanone | 470 |
| 379 | 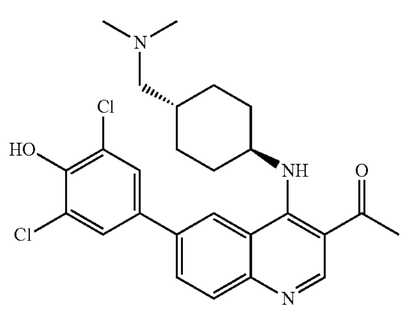 [SMILES: CC(=O)c1cnc2ccc(-c3cc(Cl)c(O)c(Cl)c3)cc2c1N[C@H]1CC[C@H](CN(C)C)CC1] | 1-(6-(3,5-dichloro-4-hydroxyphenyl)-4-((trans)-4-((dimethylamino)methyl)cyclohexylamino)quinolin-3-yl)ethanone | 486 |

TABLE 1-continued

| No. | Structure | Compound Name | ESI MS (m/z) |
|---|---|---|---|
| 380 | 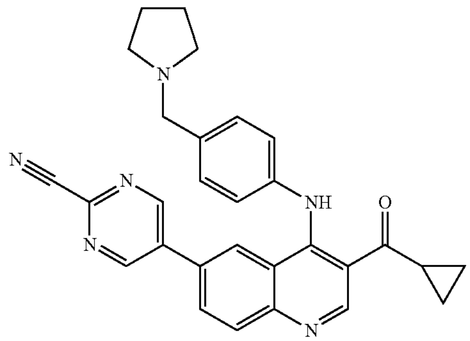 [SMILES: N#Cc1ncc(-c2ccc3ncc(C(=O)C4CC4)c(Nc4ccc(CN5CCCC5)cc4)c3c2)cn1] | 5-(3-(cyclopropanecarbonyl)-4-(4-(pyrrolidin-1-ylmethyl)phenylamino)quinolin-6-yl)pyrimidine-2-carbonitrile | 475 |
| 381 | 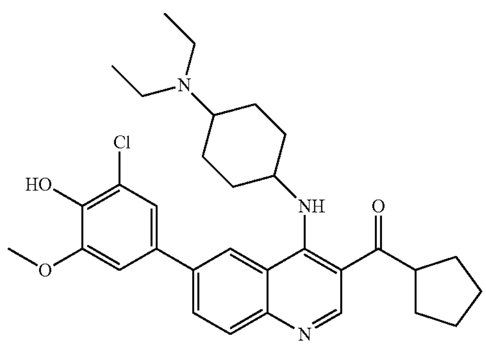 [SMILES: CCN(CC)C1CCC(Nc2c(C(=O)C3CCCC3)cnc3ccc(-c4cc(Cl)c(O)c(OC)c4)cc23)CC1] | (6-(3-chloro-4-hydroxy-5-methoxyphenyl)-4-(4-(diethylamino)cyclohexylamino)quinolin-3-yl)(cyclopentyl)methanone | 550 |
| 382 | 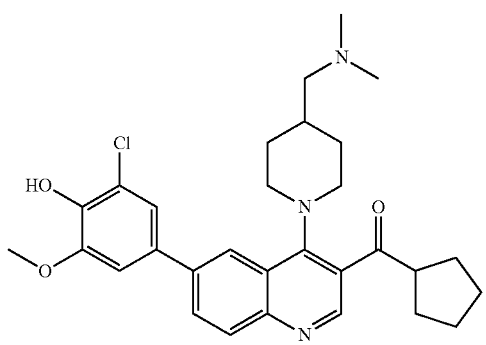 [SMILES: COc1cc(-c2ccc3ncc(C(=O)C4CCCC4)c(N4CCC(CN(C)C)CC4)c3c2)cc(Cl)c1O] | (6-(3-chloro-4-hydroxy-5-methoxyphenyl)-4-(4-((dimethylamino)methyl)piperidin-1-yl)quinolin-3-yl)(cyclopentyl)methanone | 522 |
| 383 | 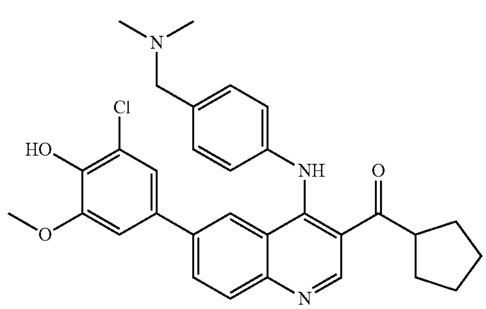 [SMILES: COc1cc(-c2ccc3ncc(C(=O)C4CCCC4)c(Nc4ccc(CN(C)C)cc4)c3c2)cc(Cl)c1O] | (6-(3-chloro-4-hydroxy-5-methoxyphenyl)-4-(4-((dimethylamino)methyl)phenylamino)quinolin-3-yl)(cyclopentyl)methanone | 530 |

TABLE 1-continued

| No. | Structure | Compound Name | ESI MS (m/z) |
|---|---|---|---|
| 384 | 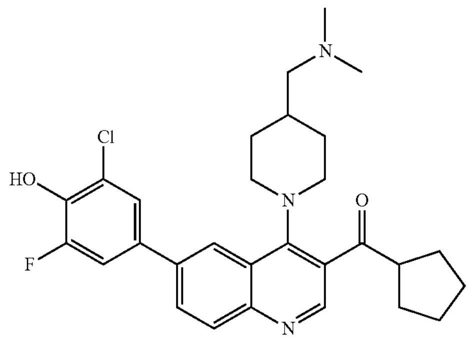 [SMILES: CN(C)CC1CCN(c2c(C(=O)C3CCCC3)cnc3ccc(-c4cc(F)c(O)c(Cl)c4)cc23)CC1] | (6-(3-chloro-5-fluoro-4-hydroxy-phenyl)-4-(4-((dimethylamino)methyl)piperidin-1-yl)quinolin-3-yl)(cyclopentyl)methanone | 510 |
| 385 | 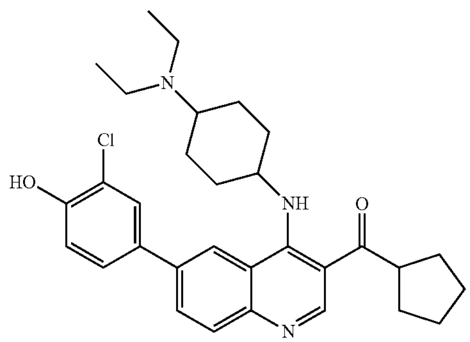 [SMILES: CCN(CC)C1CCC(Nc2c(C(=O)C3CCCC3)cnc3ccc(-c4ccc(O)c(Cl)c4)cc23)CC1] | (6-(3-chloro-4-hydroxyphenyl)-4-(4-(diethylamino)cyclohexylamino)quinolin-3-yl)(cyclopentyl)methanone | 520 |
| 386 | 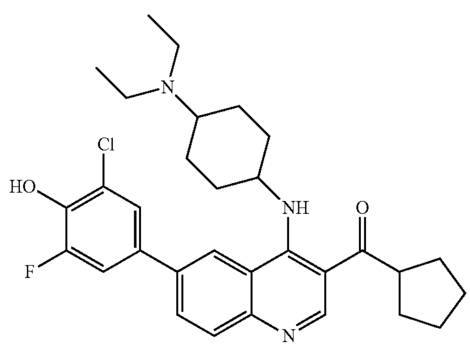 [SMILES: CCN(CC)C1CCC(Nc2c(C(=O)C3CCCC3)cnc3ccc(-c4cc(F)c(O)c(Cl)c4)cc23)CC1] | (6-(3-chloro-5-fluoro-4-hydroxy-phenyl)-4-(4-(diethylamino)cyclo-hexylamino)quinolin-3-yl)(cyclopentyl)methanone | 538 |
| 387 | 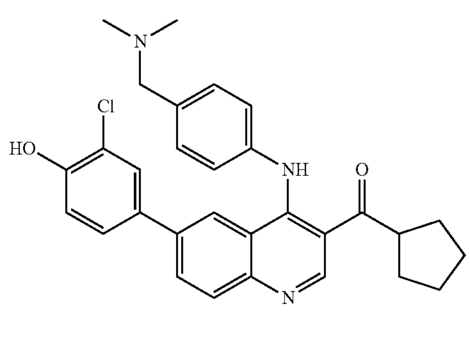 [SMILES: CN(C)Cc1ccc(Nc2c(C(=O)C3CCCC3)cnc3ccc(-c4ccc(O)c(Cl)c4)cc23)cc1] | (6-(3-chloro-4-hydroxyphenyl)-4-(4-((dimethylamino)methyl)phenyl-amino)quinolin-3-yl)(cyclopentyl)methanone | 500 |

TABLE 1-continued

| No. | Structure | Compound Name | ESI MS (m/z) |
|---|---|---|---|
| 388 | 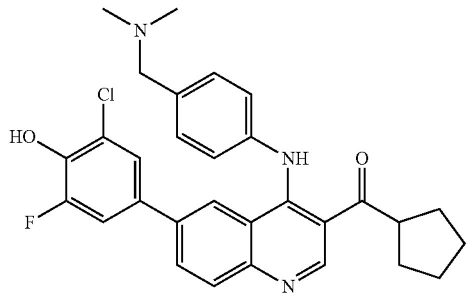 [SMILES: CN(C)Cc1ccc(Nc2c(C(=O)C3CCCC3)cnc3ccc(-c4cc(F)c(O)c(Cl)c4)cc23)cc1] | (6-(3-chloro-5-fluoro-4-hydroxy-phenyl)-4-(4-((dimethylamino)methyl)phenylamino)quinolin-3-yl)(cyclopentyl)methanone | 518 |
| 389 | 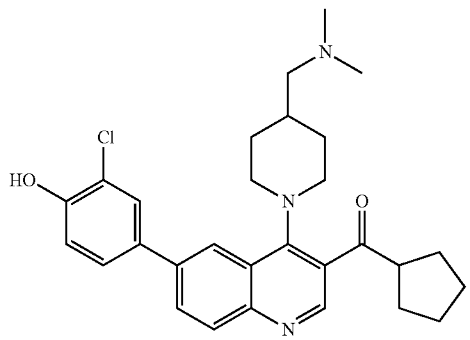 [SMILES: CN(C)CC1CCN(c2c(C(=O)C3CCCC3)cnc3ccc(-c4ccc(O)c(Cl)c4)cc23)CC1] | (6-(3-chloro-4-hydroxyphenyl)-4-(4-((dimethylamino)methyl)piperidin-1-yl)quinolin-3-yl)(cyclopentyl)methanone | 492 |
| 390 | 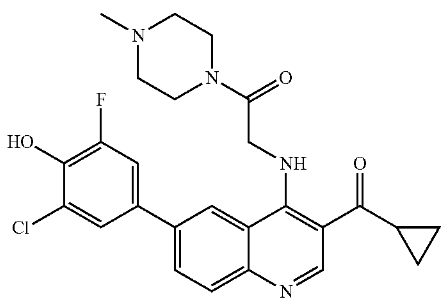 [SMILES: CN1CCN(C(=O)CNc2c(C(=O)C3CC3)cnc3ccc(-c4cc(F)c(O)c(Cl)c4)cc23)CC1] | 2-(6-(3-chloro-5-fluoro-4-hydroxy-phenyl)-3-(cyclopropanecarbonyl)quinolin-4-ylamino)-1-(4-methyl-piperazin-1-yl)ethanone | 497 |
| 391 | 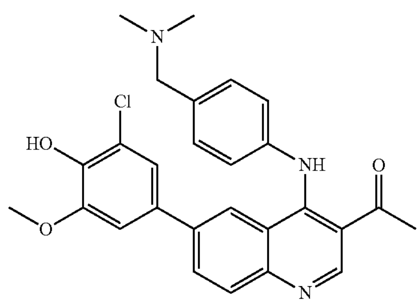 [SMILES: COc1cc(-c2ccc3ncc(C(C)=O)c(Nc4ccc(CN(C)C)cc4)c3c2)cc(Cl)c1O] | 1-(6-(3-chloro-4-hydroxy-5-methoxy-phenyl)-4-(4-((dimethylamino)methyl)phenylamino)quinolin-3-yl)ethanone | 476 |
| 392 | 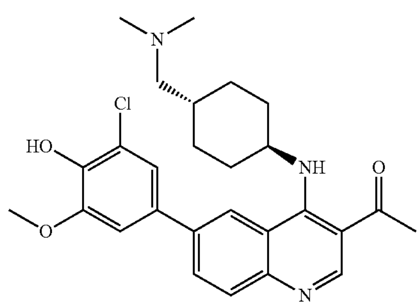 [SMILES: COc1cc(-c2ccc3ncc(C(C)=O)c(N[C@H]4CC[C@H](CN(C)C)CC4)c3c2)cc(Cl)c1O] | 1-(6-(3-chloro-4-hydroxy-5-methoxy-phenyl)-4-(1R,4R)-4-((dimethyl-amino)methyl)cyclohexylamino)quinolin-3-yl)ethanone | 482 |

TABLE 1-continued

| No. | Structure | Compound Name | ESI MS (m/z) |
|---|---|---|---|
| 393 | 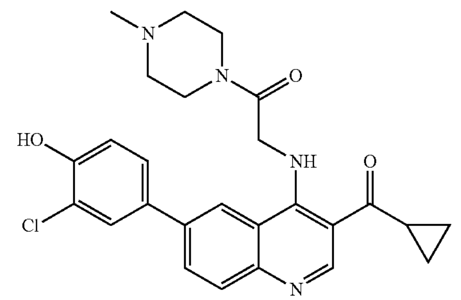 [SMILES: CN1CCN(C(=O)CNc2c(C(=O)C3CC3)cnc3ccc(-c4ccc(O)c(Cl)c4)cc23)CC1] | 2-(6-(3-chloro-4-hydroxyphenyl)-3-(cyclopropanecarbonyl)quinolin-4-ylamino)-1-(4-methylpiperazin-1-yl)ethanone | 479 |
| 394 | 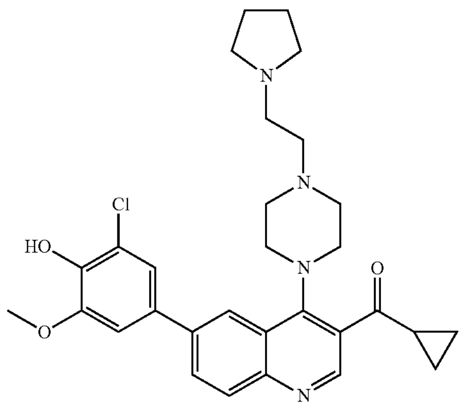 [SMILES: COc1cc(-c2ccc3ncc(C(=O)C4CC4)c(N4CCN(CCN5CCCC5)CC4)c3c2)cc(Cl)c1O] | (6-(3-chloro-4-hydroxy-5-methoxyphenyl)-4-(4-(2-(pyrrolidin-1-yl)ethyl)piperazin-1-yl)quinolin-3-yl)(cyclopropyl)methanone | 535 |
| 395 | 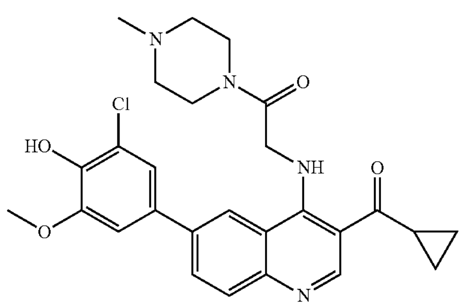 [SMILES: COc1cc(-c2ccc3ncc(C(=O)C4CC4)c(NCC(=O)N4CCN(C)CC4)c3c2)cc(Cl)c1O] | 2-(6-(3-chloro-4-hydroxy-5-methoxyphenyl)-3-(cyclopropanecarbonyl)quinolin-4-ylamino)-1-(4-methylpiperazin-1-yl)ethanone | 509 |
| 396 | 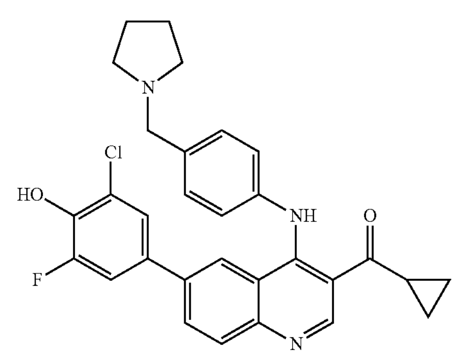 | (6-(3-chloro-5-fluoro-4-hydroxyphenyl)-4-(4-(pyrrolidin-1-ylmethyl)phenylamino)quinolin-3-yl)(cyclopropyl)methanone | 516 |

TABLE 1-continued

| No. | Structure | Compound Name | ESI MS (m/z) |
|---|---|---|---|
| 397 | 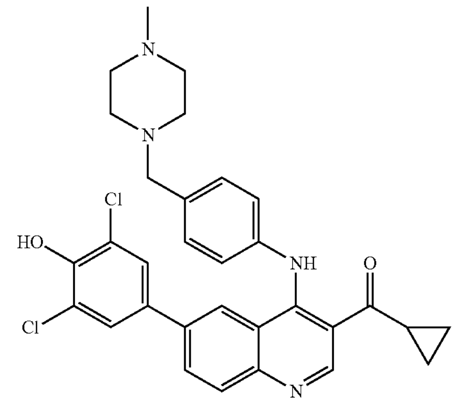 [SMILES: CN1CCN(Cc2ccc(Nc3c(C(=O)C4CC4)cnc4ccc(-c5cc(Cl)c(O)c(Cl)c5)cc34)cc2)CC1] | cyclopropyl(6-(3,5-dichloro-4-hydroxyphenyl)-4-(4-((4-methyl-piperazin-1-yl)methyl)phenyl-amino)quinolin-3-yl)methanone | 562 |
| 398 | 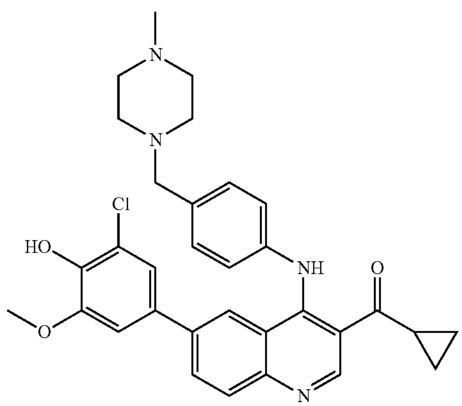 [SMILES: COc1cc(-c2ccc3ncc(C(=O)C4CC4)c(Nc4ccc(CN5CCN(C)CC5)cc4)c3c2)cc(Cl)c1O] | (6-(3-chloro-4-hydroxy-5-methoxy-phenyl)-4-(4-((4-methylpiperazin-1-yl)methyl)phenylamino)quinolin-3-yl)(cyclopropyl)methanone | 557 |
| 399 | 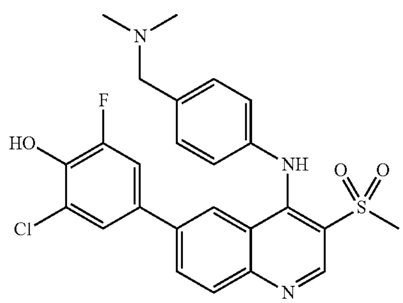 [SMILES: CN(C)Cc1ccc(Nc2c(S(C)(=O)=O)cnc3ccc(-c4cc(F)c(O)c(Cl)c4)cc23)cc1] | 2-chloro-4-(4-(4-((dimethylamino)methyl)phenylamino)-3-(methyl-sulfonyl)quinolin-6-yl)-6-fluoro-phenol | 500 |
| 400 | 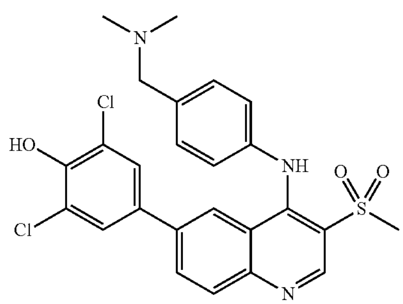 [SMILES: CN(C)Cc1ccc(Nc2c(S(C)(=O)=O)cnc3ccc(-c4cc(Cl)c(O)c(Cl)c4)cc23)cc1] | 2,6-dichloro-4-(4-(4-((dimethyl-amino)methyl)phenylamino)-3-(methylsulfonyl)quinolin-6-yl)phenol | 516 |

TABLE 1-continued

| No. | Structure | Compound Name | ESI MS (m/z) |
|---|---|---|---|
| 401 | 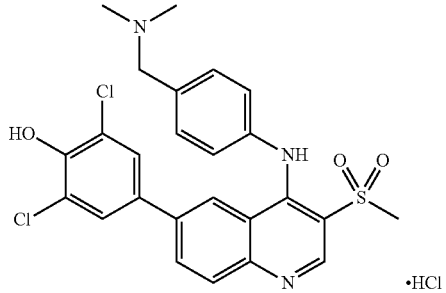 [SMILES: CN(C)Cc1ccc(Nc2c(S(C)(=O)=O)cnc3ccc(-c4cc(Cl)c(O)c(Cl)c4)cc23)cc1 ; Cl] | 2,6-dichloro-4-(4-(4-((dimethyl-amino)methyl)phenylamino)-3-(methylsulfonyl)quinolin-6-yl)phenol hydrochloride | 516 |
| 402 | 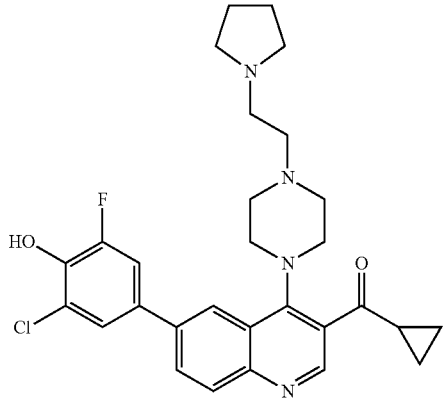 [SMILES: O=C(c1cnc2ccc(-c3cc(F)c(O)c(Cl)c3)cc2c1N1CCN(CCN2CCCC2)CC1)C1CC1] | (6-(3-chloro-5-fluoro-4-hydroxy-phenyl)-4-(4-(2-(pyrrolidin-1-yl)ethyl)piperazin-1-yl)quinolin-3-yl)(cyclopropyl)methanone | 523 |
| 403 | 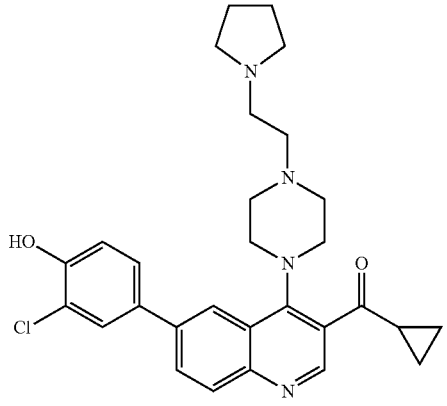 [SMILES: O=C(c1cnc2ccc(-c3ccc(O)c(Cl)c3)cc2c1N1CCN(CCN2CCCC2)CC1)C1CC1] | (6-(3-chloro-4-hydroxyphenyl)-4-(4-(2-(pyrrolidin-1-yl)ethyl)piperazin-1-yl)quinolin-3-yl)(cyclopropyl)methanone | 505 |
| 404 | 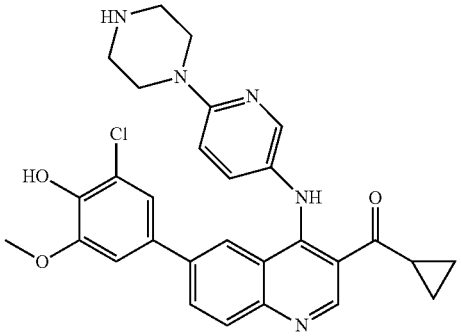 [SMILES: COc1cc(-c2ccc3ncc(C(=O)C4CC4)c(Nc4ccc(N5CCNCC5)nc4)c3c2)cc(Cl)c1O] | (6-(3-chloro-4-hydroxy-5-methoxy-phenyl)-4-(5-(piperazin-1-yl)pyridin-2-ylamino)quinolin-3-yl)(cyclo-propyl)methanone | 530 |

TABLE 1-continued

| No. | Structure | Compound Name | ESI MS (m/z) |
|---|---|---|---|
| 405 | 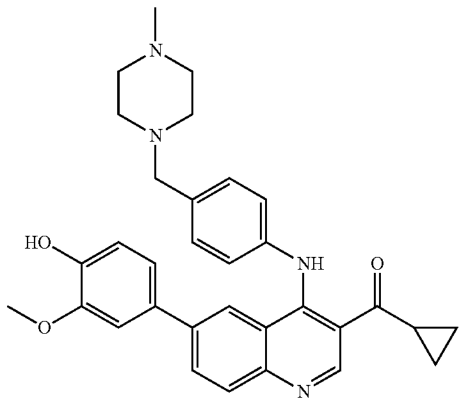 [SMILES: COc1cc(-c2ccc3ncc(C(=O)C4CC4)c(Nc4ccc(CN5CCN(C)CC5)cc4)c3c2)ccc1O] | cyclopropyl(6-(4-hydroxy-3-methoxy-phenyl)-4-(4-((4-methylpiperazin-1-yl)methyl)phenylamino)quinolin-3-yl)methanone | 523 |
| 406 | 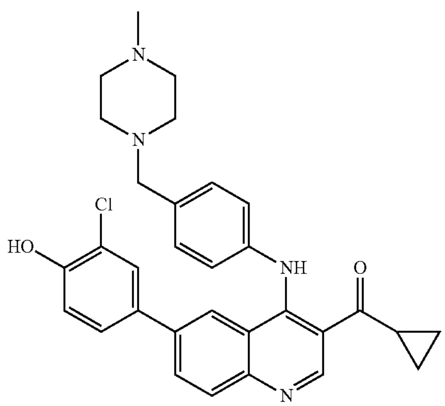 [SMILES: CN1CCN(Cc2ccc(Nc3c(C(=O)C4CC4)cnc4ccc(-c5ccc(O)c(Cl)c5)cc34)cc2)CC1] | (6-(3-chloro-4-hydroxyphenyl)-4-(4-((4-methylpiperazin-1-yl)methyl)phenylamino)quinolin-3-yl)(cyclopropyl)methanone | 527 |
| 407 | 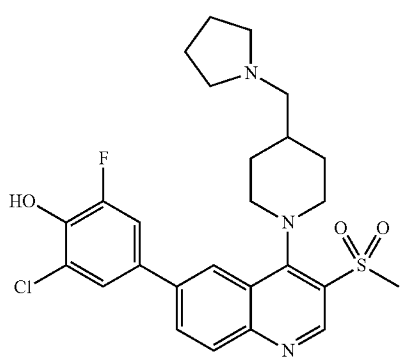 [SMILES: CS(=O)(=O)c1cnc2ccc(-c3cc(F)c(O)c(Cl)c3)cc2c1N1CCC(CN2CCCC2)CC1] | 2-chloro-6-fluoro-4-(3-(methylsulfonyl)-4-(4-(pyrrolidin-1-ylmethyl)piperidin-1-yl)quinolin-6-yl)phenol | 518 |
| 408 | 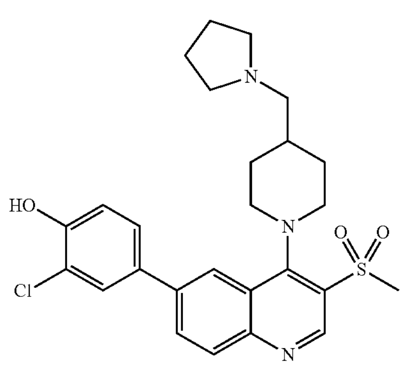 [SMILES: CS(=O)(=O)c1cnc2ccc(-c3ccc(O)c(Cl)c3)cc2c1N1CCC(CN2CCCC2)CC1] | 2-chloro-4-(3-(methylsulfonyl)-4-(4-(pyrrolidin-1-ylmethyl)piperidin-1-yl)quinolin-6-yl)phenol | 500 |

TABLE 1-continued

| No. | Structure | Compound Name | ESI MS (m/z) |
|---|---|---|---|
| 409 | 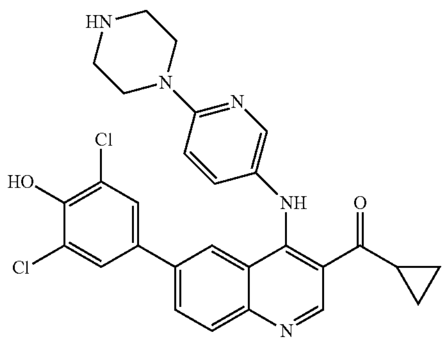 [SMILES: O=C(c1cnc2ccc(-c3cc(Cl)c(O)c(Cl)c3)cc2c1Nc1ccc(N2CCNCC2)nc1)C1CC1] | cyclopropyl(6-(3,5-dichloro-4-hydroxyphenyl)-4-(5-(piperazin-1-yl)pyridin-2-ylamino)quinolin-3-yl)methanone | 534 |
| 410 | 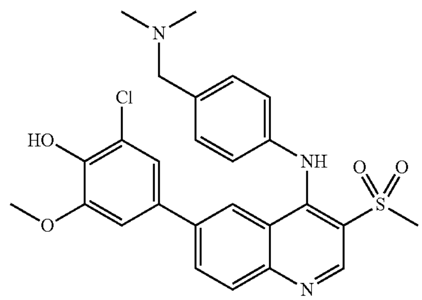 | 2-chloro-4-(4-(4-((dimethylamino)methyl)phenylamino)-3-(methyl-sulfonyl)quinolin-6-yl)-6-methoxyphenol | 512 |
| 411 | 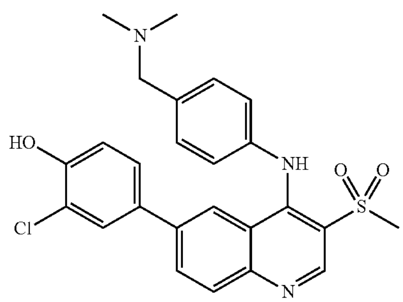 [SMILES: CN(C)Cc1ccc(Nc2c(S(C)(=O)=O)cnc3ccc(-c4ccc(O)c(Cl)c4)cc23)cc1] | 2-chloro-4-(4-(4-((dimethylamino)methyl)phenylamino)-3-(methyl-sulfonyl)quinolin-6-yl)phenol | 482 |
| 412 | 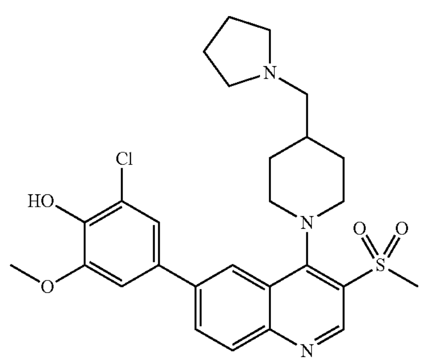 | 2-chloro-6-methoxy-4-(3-(methyl-sulfonyl)-4-(4-(pyrrolidin-1-ylmethyl)piperidin-1-yl)quinolin-6-yl)phenol | 530 |

TABLE 1-continued

| No. | Structure | Compound Name | ESI MS (m/z) |
|---|---|---|---|
| 413 | 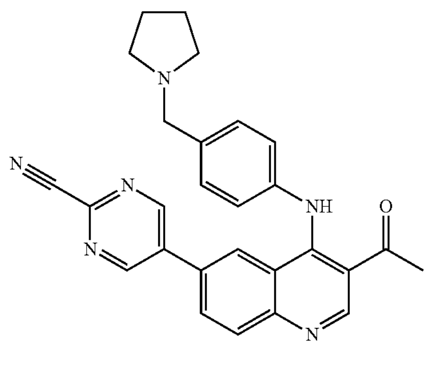 [SMILES: CC(=O)c1cnc2ccc(-c3cnc(C#N)nc3)cc2c1Nc1ccc(CN2CCCC2)cc1] | 5-(3-acetyl-4-(4-(pyrrolidin-1-ylmethyl)phenylamino)quinolin-6-yl)pyrimidine-2-carbonitrile | 449 |
| 414 | 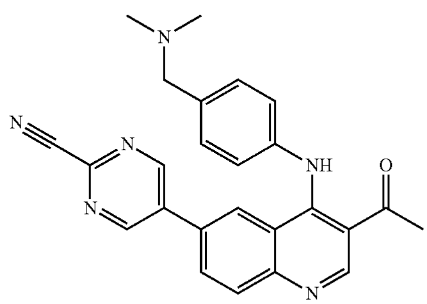 [SMILES: CC(=O)c1cnc2ccc(-c3cnc(C#N)nc3)cc2c1Nc1ccc(CN(C)C)cc1] | 5-(3-acetyl-4-(4-((dimethylamino)methyl)phenylamino)quinolin-6-yl)pyrimidine-2-carbonitrile | 422 |
| 415 | 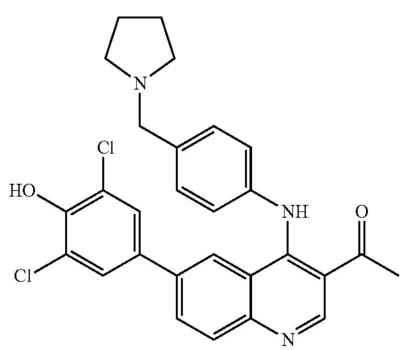 [SMILES: CC(=O)c1cnc2ccc(-c3cc(Cl)c(O)c(Cl)c3)cc2c1Nc1ccc(CN2CCCC2)cc1] | 1-(6-(3,5-dichloro-4-hydroxyphenyl)-4-(4-(pyrrolidin-1-ylmethyl)phenylamino)quinolin-3-yl)ethanone | 506 |
| 416 | 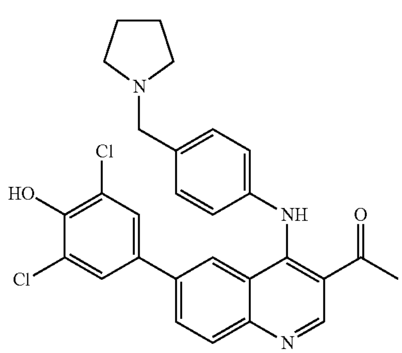 | 1-(6-(3,5-dichloro-4-hydroxyphenyl)-4-(4-(pyrrolidin-1-ylmethyl)phenylamino)quinolin-3-yl)ethanone dihydrobromide | 506 |

TABLE 1-continued

| No. | Structure | Compound Name | ESI MS (m/z) |
|---|---|---|---|
| 417 | 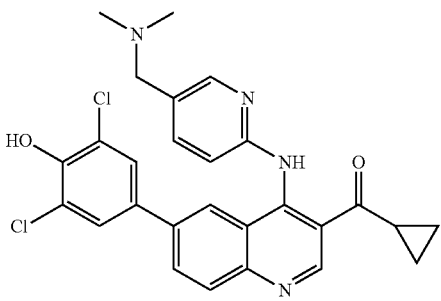 | cyclopropyl(6-(3,5-dichloro-4-hydroxyphenyl)-4-(5-((dimethylamino)methyl)pyridin-2-ylamino)quinolin-3-yl)methanone | 507 |
| 418 | 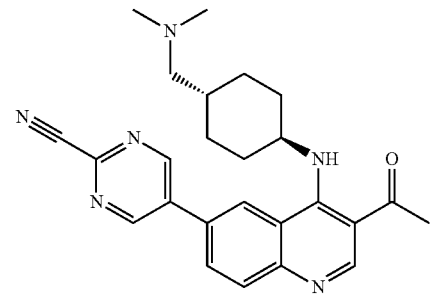 [SMILES: CC(=O)c1cnc2ccc(-c3cnc(C#N)nc3)cc2c1N[C@H]1CC[C@H](CN(C)C)CC1] | 5-(3-acetyl-4-(1R,4R)-4-((dimethylamino)methyl)cyclohexylamino)quinolin-6-yl)pyrimidine-2-carbonitrile | 429 |
| 419 | 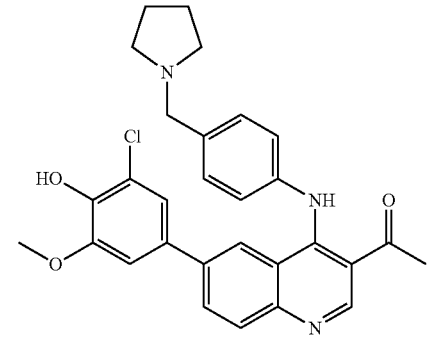 [SMILES: COc1cc(-c2ccc3ncc(C(C)=O)c(Nc4ccc(CN5CCCC5)cc4)c3c2)cc(Cl)c1O] | 1-(6-(3-chloro-4-hydroxy-5-methoxyphenyl)-4-(4-(pyrrolidin-1-ylmethyl)phenylamino)quinolin-3-yl)ethanone | 502 |
| 420 | 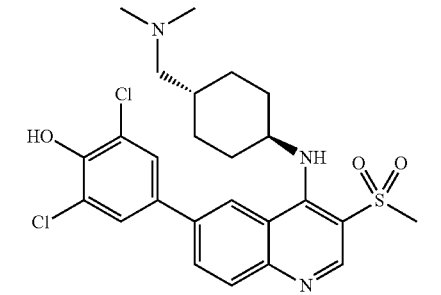 [SMILES: CN(C)C[C@H]1CC[C@H](Nc2c(S(C)(=O)=O)cnc3ccc(-c4cc(Cl)c(O)c(Cl)c4)cc23)CC1] | 2,6-dichloro-4-(4-(1R,4R)-4-((dimethylamino)methyl)cyclohexylamino)-3-(methylsulfonyl)quinolin-6-yl)phenol | 522 |
| 421 | 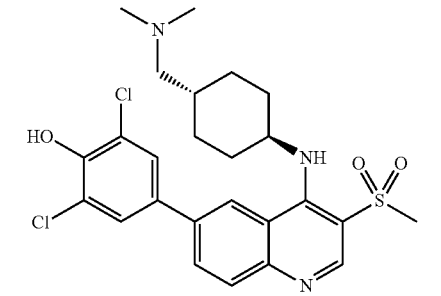 [SMILES: CN(C)C[C@H]1CC[C@H](Nc2c(S(C)(=O)=O)cnc3ccc(-c4cc(Cl)c(O)c(Cl)c4)cc23)CC1] | 2,6-dichloro-4-(4-(1R,4R)-4-((dimethylamino)methyl)cyclohexylamino)-3-(methylsulfonyl)quinolin-6-yl)phenol | 522 |

TABLE 1-continued

| No. | Structure | Compound Name | ESI MS (m/z) |
|---|---|---|---|
| 422 | 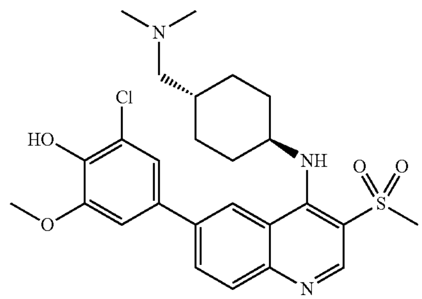 | 2-chloro-4-(4-(1R,4R)--4-((dimethyl-amino)methyl)cyclohexylamino)-3-(methylsulfonyl)quinolin-6-yl)-6-methoxyphenol | 518 |
| 423 | 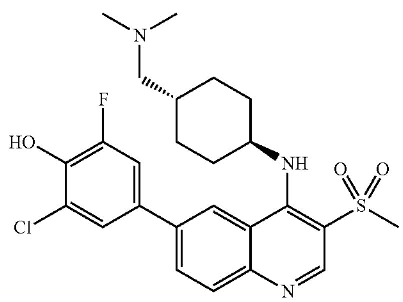 | 2-chloro-4-(4-(1R,4R)--4-((dimethyl-amino)methyl)cyclohexylamino)-3-(methylsulfonyl)quinolin-6-yl)-6-fluorophenol | 506 |
| 424 | 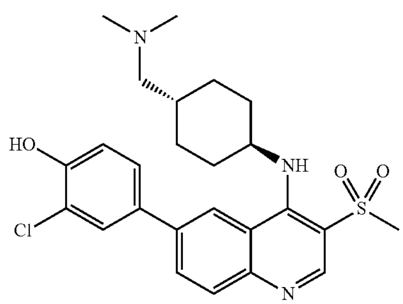 [SMILES: CN(C)C[C@H]1CC[C@H](Nc2c(S(C)(=O)=O)cnc3ccc(-c4ccc(O)c(Cl)c4)cc23)CC1] | 2-chloro-4-(4-(1R,4R)-4-((dimethyl-amino)methyl)cyclohexylamino)-3-(methylsulfonyl)quinolin-6-yl)phenol | 488 |
| 425 | 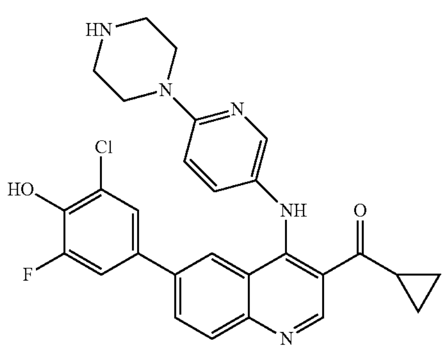 [SMILES: O=C(c1cnc2ccc(-c3cc(F)c(O)c(Cl)c3)cc2c1Nc1ccc(N2CCNCC2)nc1)C1CC1] | (6-(3-chloro-5-fluoro-4-hydroxy-phenyl)-4-(6-(piperazin-1-yl)pyridin-3-ylamino)quinolin-3-yl)(cyclo-propyl)methanone | 518 |
| 426 | 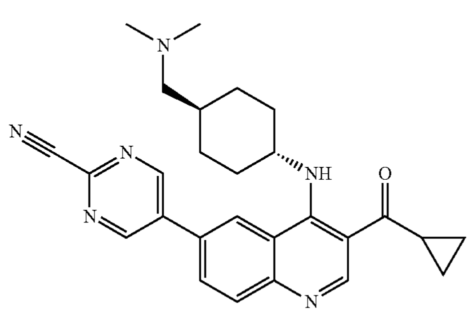 [SMILES: CN(C)C[C@H]1CC[C@H](Nc2c(C(=O)C3CC3)cnc3ccc(-c4cnc(C#N)nc4)cc23)CC1] | 5-(3-(cyclopropanecarbonyl)-4-(1R,4R)--4-((dimethylamino)methyl)cyclohexylamino)quinolin-6-yl)pyrimidine-2-carbonitrile | 455 |

TABLE 1-continued

| No. | Structure | Compound Name | ESI MS (m/z) |
|---|---|---|---|
| 427 | 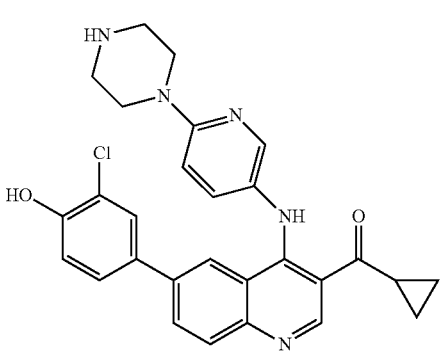 [SMILES: O=C(c1cnc2ccc(-c3ccc(O)c(Cl)c3)cc2c1Nc1ccc(N2CCNCC2)nc1)C1CC1] | (6-(3-chloro-4-hydroxyphenyl)-4-(5-(piperazin-1-yl)pyridin-2-ylamino)quinolin-3-yl)(cyclopropyl)methanone | 500 |
| 428 | 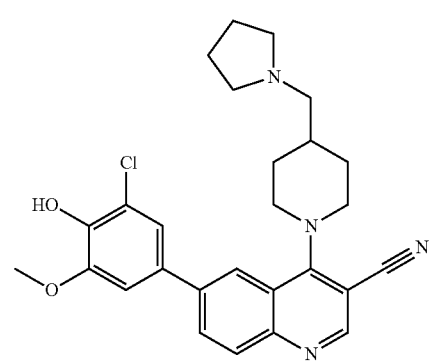 [SMILES: COc1cc(-c2ccc3ncc(C#N)c(N4CCC(CN5CCCC5)CC4)c3c2)cc(Cl)c1O] | 6-(3-chloro-4-hydroxy-5-methoxy-phenyl)-4-(4-(pyrrolidin-1-ylmethyl)piperidin-1-yl)quinoline-3-carbonitrile | 477 |
| 429 | 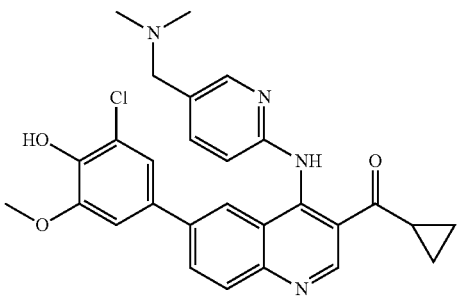 [SMILES: COc1cc(-c2ccc3ncc(C(=O)C4CC4)c(Nc4ccc(CN(C)C)cn4)c3c2)cc(Cl)c1O] | (6-(3-chloro-4-hydroxy-5-methoxy-phenyl)-4-(5-((dimethylamino)methyl)pyridin-2-ylamino)quinolin-3-yl)(cyclopropyl)methanone | 503 |
| 430 | 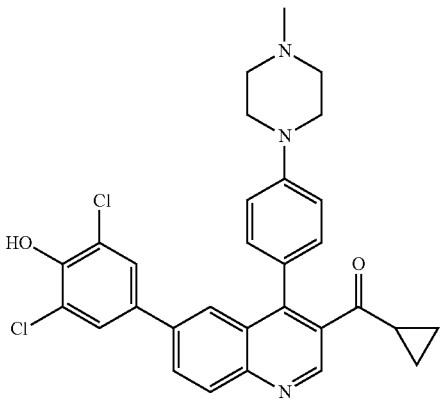 | cyclopropyl(6-(3,5-dichloro-4-hydroxyphenyl)-4-(4-(4-methyl-piperazin-1-yl)phenyl)quinolin-3-yl)methanone | 532 |

TABLE 1-continued

| No. | Structure | Compound Name | ESI MS (m/z) |
|---|---|---|---|
| 431 | 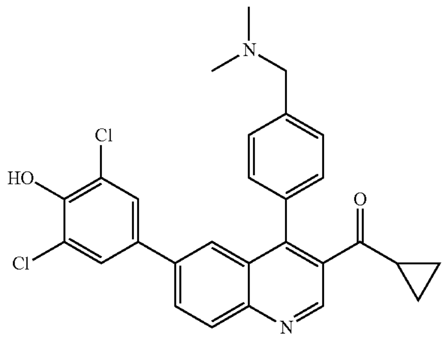 [SMILES: CN(C)Cc1ccc(-c2c(C(=O)C3CC3)cnc3ccc(-c4cc(Cl)c(O)c(Cl)c4)cc23)cc1] | cyclopropyl(6-(3,5-dichloro-4-hydroxyphenyl)-4-(4-((dimethylamino)methyl)phenyl)quinolin-3-yl)methanone | 491 |
| 432 | 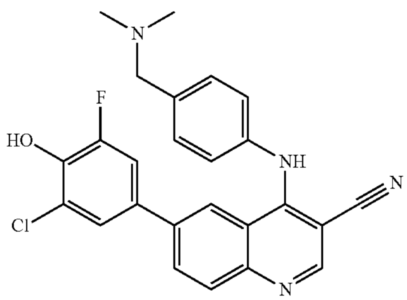 [SMILES: CN(C)Cc1ccc(Nc2c(C#N)cnc3ccc(-c4cc(F)c(O)c(Cl)c4)cc23)cc1] | 6-(3-chloro-5-fluoro-4-hydroxyphenyl)-4-(4-((dimethylamino)methyl)phenylamino)quinoline-3-carbonitrile | 447 |
| 433 | 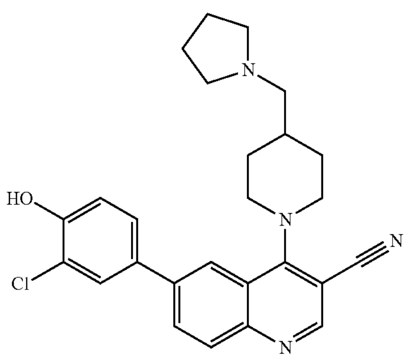 [SMILES: N#Cc1cnc2ccc(-c3ccc(O)c(Cl)c3)cc2c1N1CCC(CN2CCCC2)CC1] | 6-(3-chloro-4-hydroxyphenyl)-4-(4-(pyrrolidin-1-ylmethyl)piperidin-1-yl)quinoline-3-carbonitrile | 447 |
| 434 | 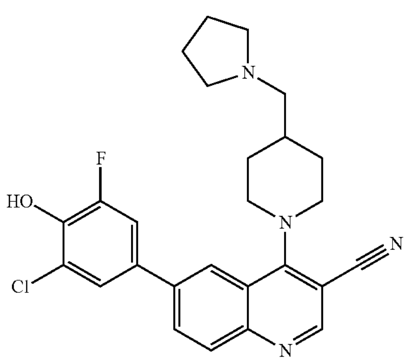 [SMILES: N#Cc1cnc2ccc(-c3cc(F)c(O)c(Cl)c3)cc2c1N1CCC(CN2CCCC2)CC1] | 6-(3-chloro-5-fluoro-4-hydroxyphenyl)-4-(4-(pyrrolidin-1-ylmethyl)piperidin-1-yl)quinoline-3-carbonitrile | 465 |

TABLE 1-continued

| No. | Structure | Compound Name | ESI MS (m/z) |
|---|---|---|---|
| 435 | 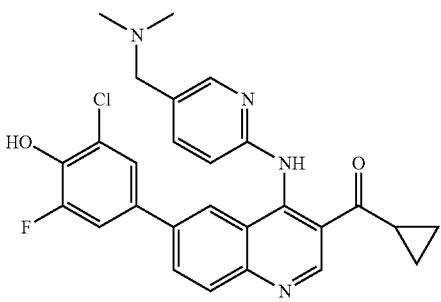 | (6-(3-chloro-5-fluoro-4-hydroxy-phenyl)-4-(5-((dimethylamino)methyl)pyridin-2-ylamino)quinolin-3-yl)(cyclopropyl)methanone | 491 |
| 436 | 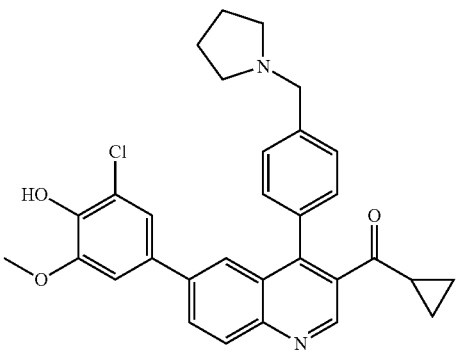 [SMILES: COc1cc(-c2ccc3ncc(C(=O)C4CC4)c(-c4ccc(CN5CCCC5)cc4)c3c2)cc(Cl)c1O] | (6-(3-chloro-4-hydroxy-5-methoxy-phenyl)-4-(4-(pyrrolidin-1-ylmethyl)phenyl)quinolin-3-yl)(cyclopropyl)methanone | 513 |
| 437 | 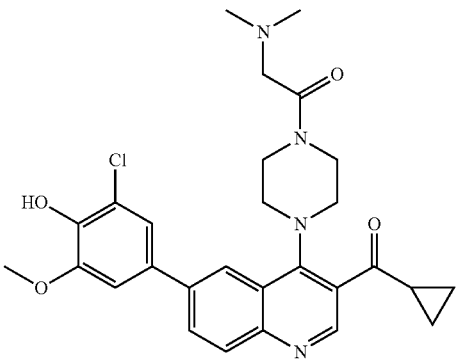 [SMILES: COc1cc(-c2ccc3ncc(C(=O)C4CC4)c(N4CCN(C(=O)CN(C)C)CC4)c3c2)cc(Cl)c1O] | 1-(4-(6-(3-chloro-4-hydroxy-5-methoxyphenyl)-3-(cyclopropane-carbonyl)quinolin-4-yl)piperazin-1-yl)-2-(dimethylamino)ethanone | 523 |
| 438 | 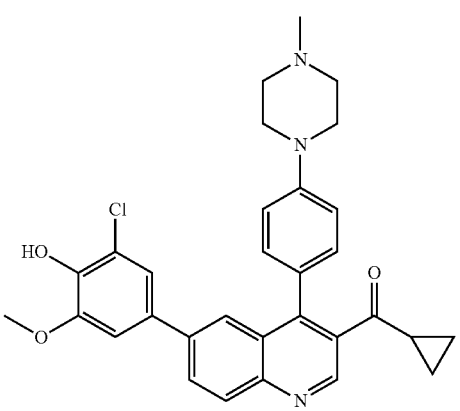 [SMILES: COc1cc(-c2ccc3ncc(C(=O)C4CC4)c(-c4ccc(N5CCN(C)CC5)cc4)c3c2)cc(Cl)c1O] | (6-(3-chloro-4-hydroxy-5-methoxy-phenyl)-4-(4-(4-methylpiperazin-1-yl)phenyl)quinolin-3-yl)(cyclopropyl)methanone | 528 |

TABLE 1-continued

| No. | Structure | Compound Name | ESI MS (m/z) |
|---|---|---|---|
| 439 | 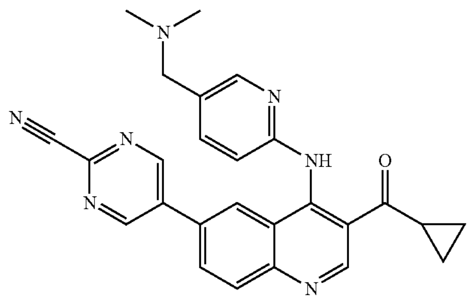 [SMILES: CN(C)Cc1ccc(Nc2c(C(=O)C3CC3)cnc3ccc(-c4cnc(C#N)nc4)cc23)nc1] | 5-(3-(cyclopropanecarbonyl)-4-(5-((dimethylamino)methyl)pyridin-2-ylamino)quinolin-6-yl)pyrimidine-2-carbonitrile | 450 |
| 440 | 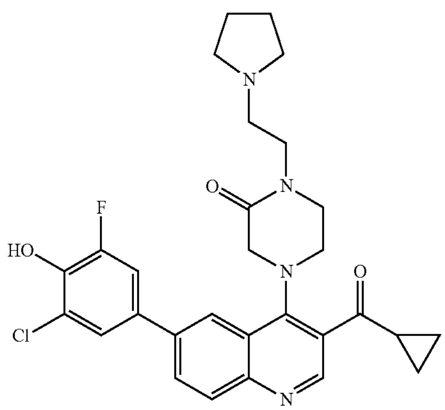 [SMILES: O=C(c1cnc2ccc(-c3cc(F)c(O)c(Cl)c3)cc2c1N1CCN(CCN2CCCC2)C(=O)C1)C1CC1] | 4-(6-(3-chloro-5-fluoro-4-hydroxyphenyl)-3-(cyclopropanecarbonyl)quinolin-4-yl)-1-(2-(pyrrolidin-1-yl)ethyl)piperazin-2-one | 537 |
| 441 | 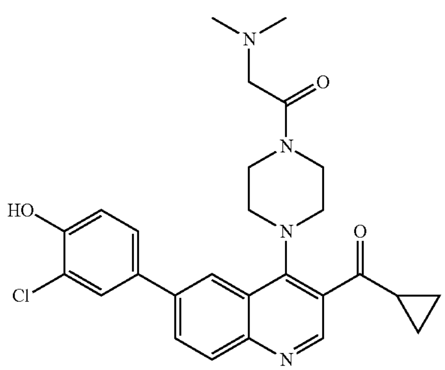 [SMILES: CN(C)CC(=O)N1CCN(c2c(C(=O)C3CC3)cnc3ccc(-c4ccc(O)c(Cl)c4)cc23)CC1] | 1-(4-(6-(3-chloro-4-hydroxyphenyl)-3-(cyclopropanecarbonyl)quinolin-4-yl)piperazin-1-yl)-2-(dimethylamino)ethanone | 493 |
| 442 | 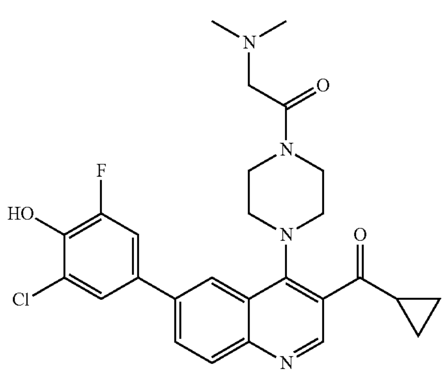 [SMILES: CN(C)CC(=O)N1CCN(c2c(C(=O)C3CC3)cnc3ccc(-c4cc(F)c(O)c(Cl)c4)cc23)CC1] | 1-(4-(6-(3-chloro-5-fluoro-4-hydroxyphenyl)-3-(cyclopropanecarbonyl)quinolin-4-yl)piperazin-1-yl)-2-(dimethylamino)ethanone | 511 |

| No. | Structure | Compound Name | ESI MS (m/z) |
|---|---|---|---|
| 443 | 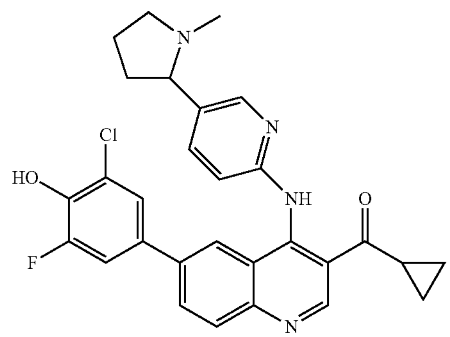 [SMILES: CN1CCCC1c1ccc(Nc2c(C(=O)C3CC3)cnc3ccc(-c4cc(F)c(O)c(Cl)c4)cc23)nc1] | (6-(3-chloro-5-fluoro-4-hydroxyphenyl)-4-(5-(1-methylpyrrolidin-2-yl)pyridin-2-ylamino)quinolin-3-yl)(cyclopropyl)methanone | 517 |
| 444 | 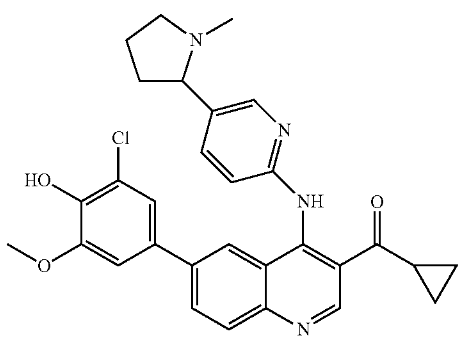 [SMILES: COc1cc(-c2ccc3ncc(C(=O)C4CC4)c(Nc4ccc(C5CCCN5C)cn4)c3c2)cc(Cl)c1O] | (6-(3-chloro-4-hydroxy-5-methoxyphenyl)-4-(5-(1-methylpyrrolidin-2-yl)pyridin-2-ylamino)quinolin-3-yl)(cyclopropyl)methanone | 529 |
| 445 | 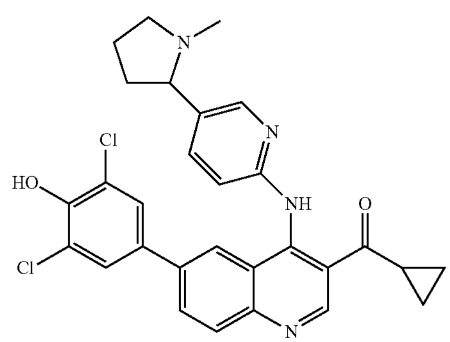 | cyclopropyl(6-(3,5-dichloro-4-hydroxyphenyl)-4-(5-(1-methylpyrrolidin-2-yl)pyridin-2-ylamino)quinolin-3-yl)methanone | 533 |
| 446 | 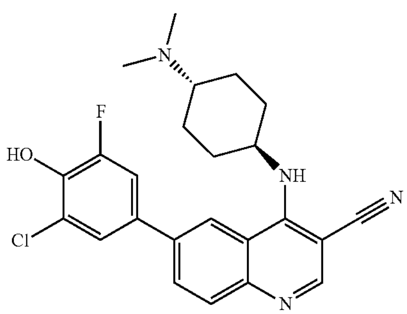 [SMILES: CN(C)[C@H]1CC[C@H](Nc2c(C#N)cnc3ccc(-c4cc(F)c(O)c(Cl)c4)cc23)CC1] | 6-(3-chloro-5-fluoro-4-hydroxyphenyl)-4-(1R,4R)--4-(dimethylamino)cyclohexylamino)quinoline-3-carbonitrile | 439 |

TABLE 1-continued

| No. | Structure | Compound Name | ESI MS (m/z) |
|---|---|---|---|
| 447 | 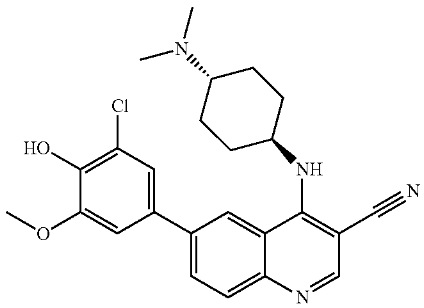 [SMILES: COc1cc(-c2ccc3ncc(C#N)c(N[C@H]4CC[C@H](N(C)C)CC4)c3c2)cc(Cl)c1O] | 6-(3-chloro-4-hydroxy-5-methoxy-phenyl)-4-(1R,4R)--4-(dimethylamino)cyclohexylamino)quinoline-3-carbonitrile | 451 |
| 448 | 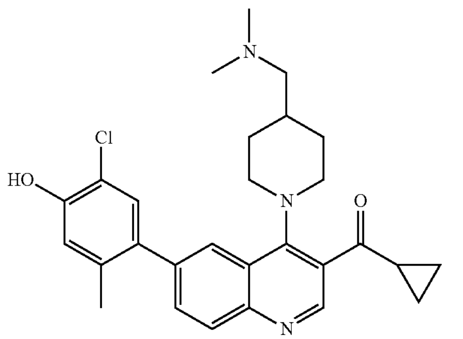 [SMILES: Cc1cc(O)c(Cl)cc1-c1ccc2ncc(C(=O)C3CC3)c(N3CCC(CN(C)C)CC3)c2c1] | (6-(5-chloro-4-hydroxy-2-methyl-phenyl)-4-(4-((dimethylamino)methyl)piperidin-1-yl)quinolin-3-yl)(cyclopropyl)methanone | 478 |
| 449 | 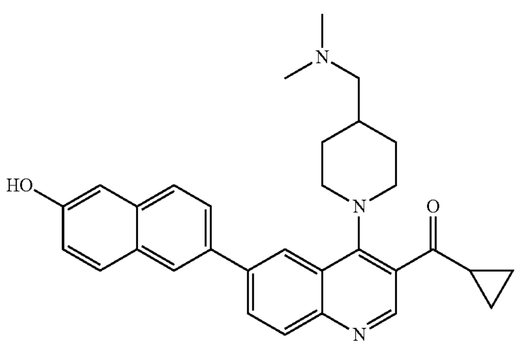 [SMILES: CN(C)CC1CCN(c2c(C(=O)C3CC3)cnc3ccc(-c4ccc5cc(O)ccc5c4)cc23)CC1] | cyclopropyl(4-(4-((dimethylamino)methyl)piperidin-1-yl)-6-(6-hydroxy-naphthalen-2-yl)quinolin-3-yl)methanone | 480 |
| 450 | 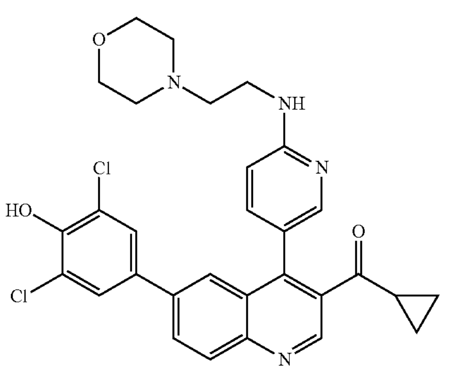 [SMILES: O=C(c1cnc2ccc(-c3cc(Cl)c(O)c(Cl)c3)cc2c1-c1ccc(NCCN2CCOCC2)nc1)C1CC1] | cyclopropyl(6-(3,5-dichloro-4-hydroxyphenyl)-4-(6-(2-morpholino-ethylamino)pyridin-3-yl)quinolin-3-yl)methanone | 563 |

TABLE 1-continued

| No. | Structure | Compound Name | ESI MS (m/z) |
|---|---|---|---|
| 451 | 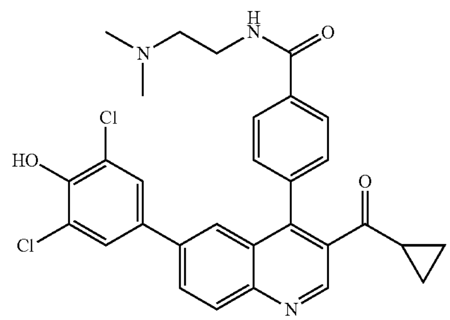 [SMILES: CN(C)CCNC(=O)c1ccc(-c2c(C(=O)C3CC3)cnc3ccc(-c4cc(Cl)c(O)c(Cl)c4)cc23)cc1] | 4-(3-(cyclopropanecarbonyl)-6-(3,5-dichloro-4-hydroxyphenyl)quinolin-4-yl)-N-(2-(dimethylamino)ethyl)benzamide | 548 |
| 452 | 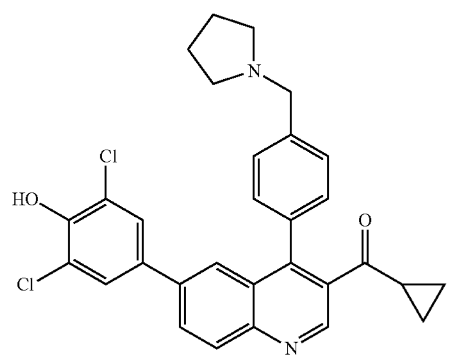 [SMILES: O=C(c1cnc2ccc(-c3cc(Cl)c(O)c(Cl)c3)cc2c1-c1ccc(CN2CCCC2)cc1)C1CC1] | cyclopropyl(6-(3,5-dichloro-4-hydroxyphenyl)-4-(4-(pyrrolidin-1-ylmethyl)phenyl)quinolin-3-yl)methanone | 517 |
| 453 | 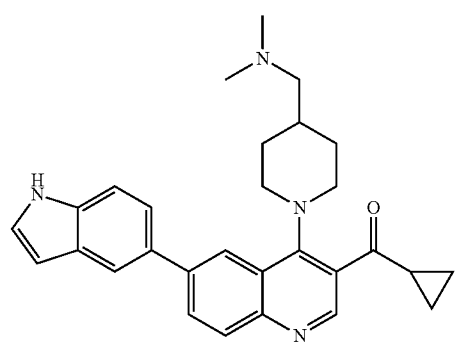 [SMILES: CN(C)CC1CCN(c2c(C(=O)C3CC3)cnc3ccc(-c4ccc5[nH]ccc5c4)cc23)CC1] | cyclopropyl(4-(4-((dimethylamino)methyl)piperidin-1-yl)-6-(1H-indol-5-yl)quinolin-3-yl)methanone | 453 |
| 454 | 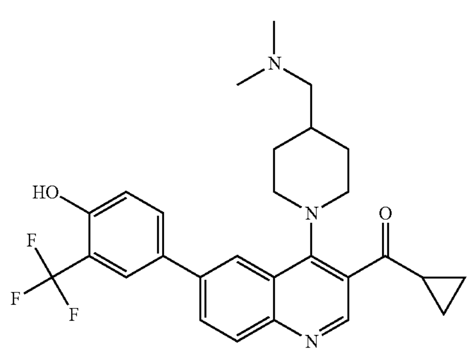 [SMILES: CN(C)CC1CCN(c2c(C(=O)C3CC3)cnc3ccc(-c4ccc(O)c(C(F)(F)F)c4)cc23)CC1] | cyclopropyl(4-(4-((dimethylamino)methyl)piperidin-1-yl)-6-(4-hydroxy-3-(trifluoromethyl)phenyl)quinolin-3-yl)methanone | 498 |

TABLE 1-continued

| No. | Structure | Compound Name | ESI MS (m/z) |
|---|---|---|---|
| 455 | 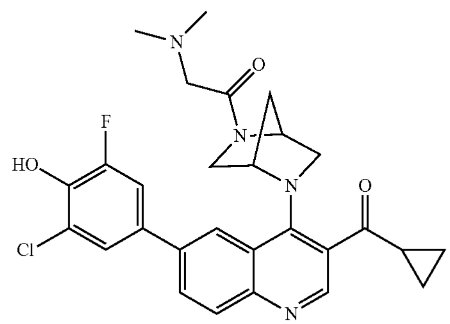 [SMILES: CN(C)CC(=O)N1CC2CC1CN2c1c(C(=O)C2CC2)cnc2ccc(-c3cc(F)c(O)c(Cl)c3)cc12] | 1-((1S,4S)-5-(6-(3-chloro-5-fluoro-4-hydroxyphenyl)-3-(cyclopropane-carbonyl)quinolin-4-yl)-2,5-diazabicyclo[2.2.1]heptan-2-yl)-2-(dimethylamino)ethanone | 523 |
| 456 | 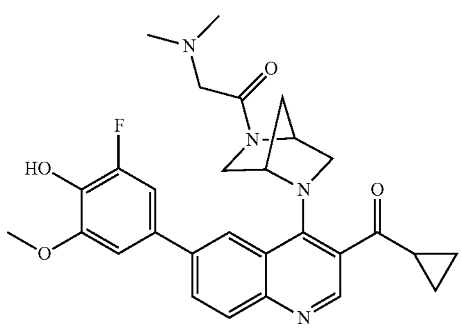 [SMILES: COc1cc(-c2ccc3ncc(C(=O)C4CC4)c(N4CC5CC4CN5C(=O)CN(C)C)c3c2)cc(F)c1O] | 1-((1S,4S)-5-(6-(3-chloro-4-hydroxy-5-methoxyphenyl)-3-(cyclopropane-carbonyl)quinolin-4-yl)-2,5-diazabicyclo[2.2.1]heptan-2-yl)-2-(dimethylamino)ethanone | 535 |
| 457 | 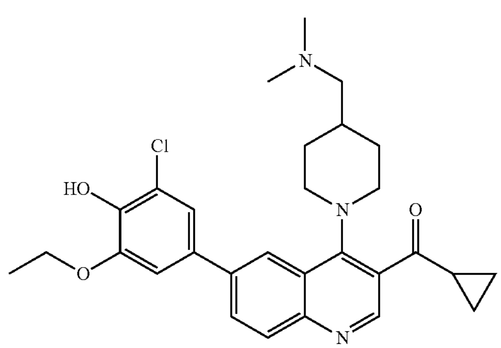 [SMILES: CCOc1cc(-c2ccc3ncc(C(=O)C4CC4)c(N4CCC(CN(C)C)CC4)c3c2)cc(Cl)c1O] | (6-(3-chloro-5-ethoxy-4-hydroxy-phenyl)-4-(4-((dimethylamino)methyl)piperidin-1-yl)quinolin-3-yl)(cyclopropyl)methanone | 508 |
| 458 | 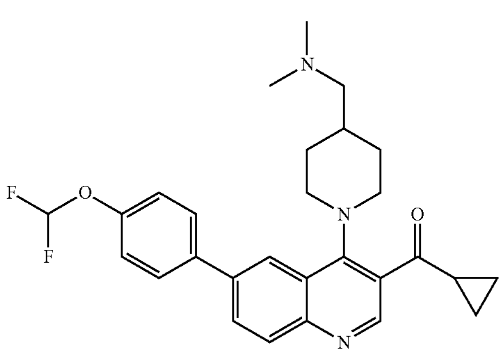 [SMILES: CN(C)CC1CCN(c2c(C(=O)C3CC3)cnc3ccc(-c4ccc(OC(F)F)cc4)cc23)CC1] | cyclopropyl(6-(4-(difluoromethoxy)phenyl)-4-(4-((dimethylamino)methyl)piperidin-1-yl)quinolin-3-yl)methanone | 480 |

TABLE 1-continued

| No. | Structure | Compound Name | ESI MS (m/z) |
|---|---|---|---|
| 459 | 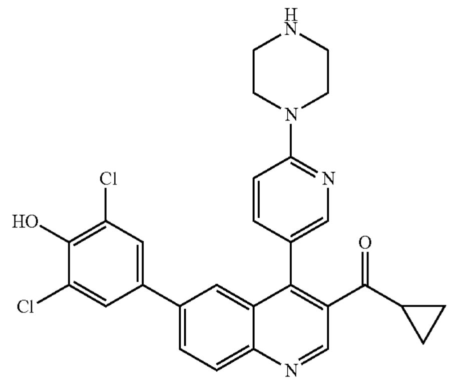 [SMILES: O=C(c1cnc2ccc(-c3cc(Cl)c(O)c(Cl)c3)cc2c1-c1ccc(N2CCNCC2)nc1)C1CC1] | cyclopropyl(6-(3,5-dichloro-4-hydroxyphenyl)-4-(6-(piperazin-1-yl)pyridin-3-yl)quinolin-3-yl)methanone | 519 |
| 460 | 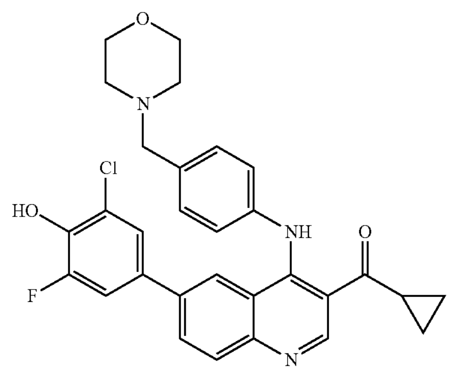 [SMILES: O=C(c1cnc2ccc(-c3cc(F)c(O)c(Cl)c3)cc2c1Nc1ccc(CN2CCOCC2)cc1)C1CC1] | (6-(3-chloro-5-fluoro-4-hydroxyphenyl)-4-(4-(morpholinomethyl)phenylamino)quinolin-3-yl)(cyclopropyl)methanone | 532 |
| 461 | 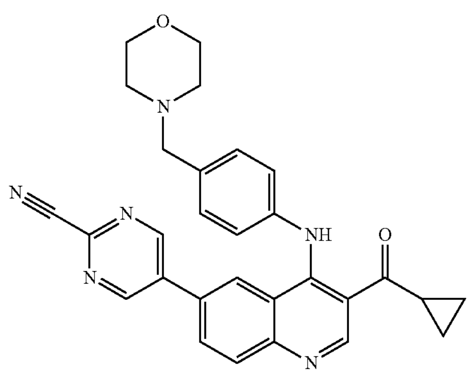 [SMILES: N#Cc1ncc(-c2ccc3ncc(C(=O)C4CC4)c(Nc4ccc(CN5CCOCC5)cc4)c3c2)cn1] | 5-(3-(cyclopropanecarbonyl)-4-(4-(morpholinomethyl)phenylamino)quinolin-6-yl)pyrimidine-2-carbonitrile | 491 |
| 462 | 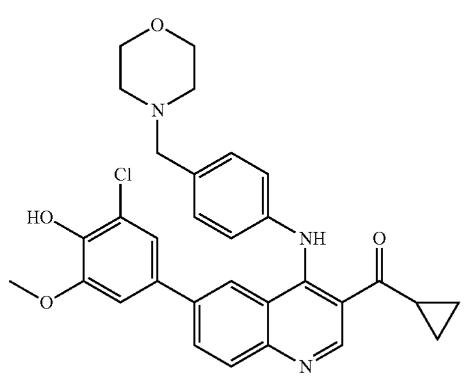 [SMILES: COc1cc(-c2ccc3ncc(C(=O)C4CC4)c(Nc4ccc(CN5CCOCC5)cc4)c3c2)cc(Cl)c1O] | (6-(3-chloro-4-hydroxy-5-methoxyphenyl)-4-(4-(morpholinomethyl)phenylamino)quinolin-3-yl)(cyclopropyl)methanone | 544 |

TABLE 1-continued

| No. | Structure | Compound Name | ESI MS (m/z) |
|---|---|---|---|
| 463 | 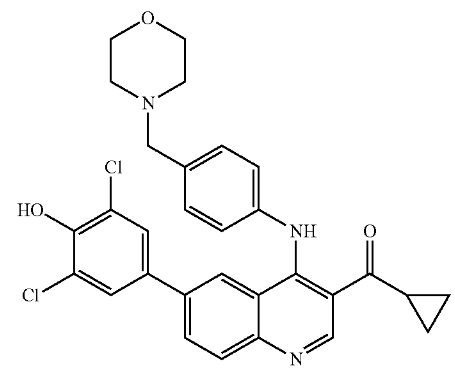 | cyclopropyl(6-(3,5-dichloro-4-hydroxyphenyl)-4-(4-(morpholinomethyl)phenylamino)quinolin-3-yl)methanone | 548 |
| 464 | 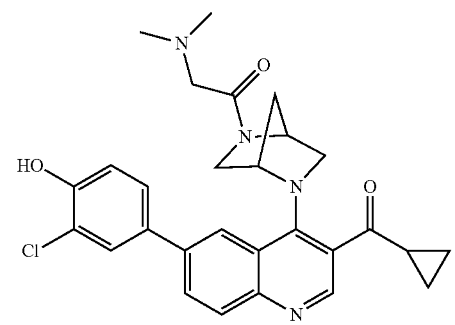 [SMILES: CN(C)CC(=O)N1CC2CC1CN2c1c(C(=O)C2CC2)cnc2ccc(-c3ccc(O)c(Cl)c3)cc12] | 1-((1S,4S)-5-(6-(3-chloro-4-hydroxyphenyl)-3-(cyclopropanecarbonyl)quinolin-4-yl)-2,5-diazabicyclo[2.2.1]heptan-2-yl)-2-(dimethylamino)ethanone | 505 |
| 465 | 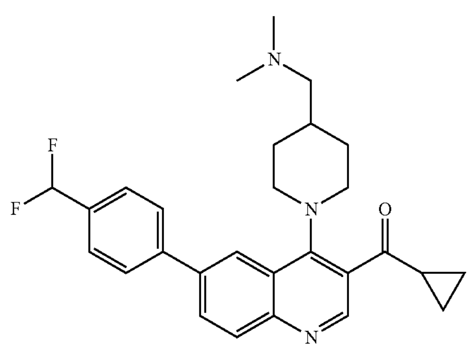 [SMILES: CN(C)CC1CCN(c2c(C(=O)C3CC3)cnc3ccc(-c4ccc(C(F)F)cc4)cc23)CC1] | cyclopropyl(6-(4-(difluoromethyl)phenyl)-4-(4-((dimethylamino)methyl)piperidin-1-yl)quinolin-3-yl)methanone | 464 |
| 466 | 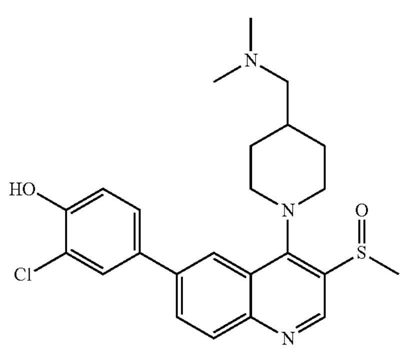 | 2-chloro-4-(4-(4-((dimethylamino)methyl)piperidin-1-yl)-3-(methylsulfinyl)quinolin-6-yl)phenol | 458 |

TABLE 1-continued

| No. | Structure | Compound Name | ESI MS (m/z) |
|---|---|---|---|
| 467 | 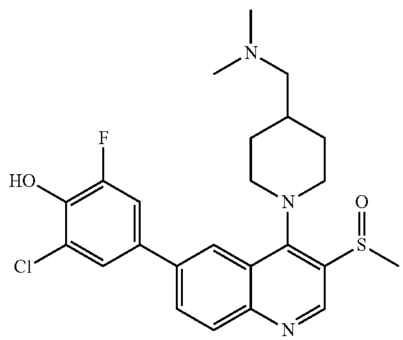 | 2-chloro-4-(4-(4-((dimethylamino)methyl)piperidin-1-yl)-3-(methylsulfinyl)quinolin-6-yl)-6-fluorophenol | 476 |
| 468 | 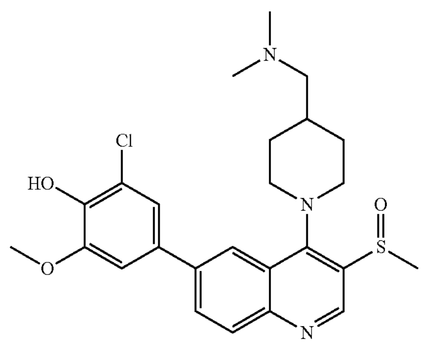 | 2-chloro-4-(4-(4-((dimethylamino)methyl)piperidin-1-yl)-3-(methylsulfinyl)quinolin-6-yl)-6-methoxyphenol | 488 |
| 469 | 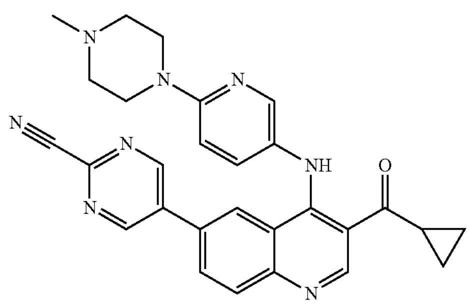 [SMILES: CN1CCN(c2ccc(Nc3c(C(=O)C4CC4)cnc4ccc(-c5cnc(C#N)nc5)cc34)cn2)CC1] | 5-(3-(cyclopropanecarbonyl)-4-(6-(4-methylpiperazin-1-yl)pyridin-3-ylamino)quinolin-6-yl)pyrimidine-2-carbonitrile | 491 |
| 470 | 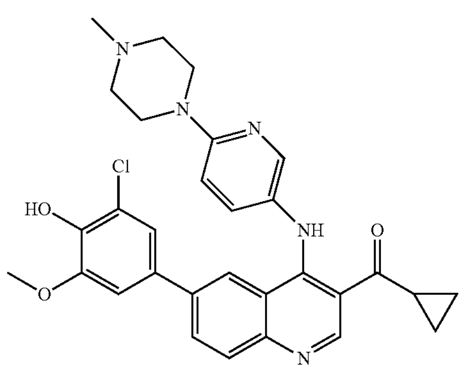 [SMILES: COc1cc(-c2ccc3ncc(C(=O)C4CC4)c(Nc4ccc(N5CCN(C)CC5)nc4)c3c2)cc(Cl)c1O] | (6-(3-chloro-4-hydroxy-5-methoxyphenyl)-4-(6-(4-methylpiperazin-1-yl)pyridin-3-ylamino)quinolin-3-yl)(cyclopropyl)methanone | 544 |

TABLE 1-continued

| No. | Structure | Compound Name | ESI MS (m/z) |
|---|---|---|---|
| 471 | 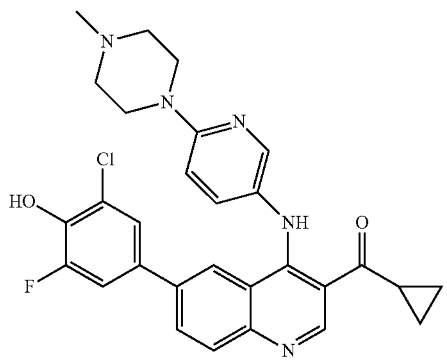 [SMILES: CN1CCN(c2ccc(Nc3c(C(=O)C4CC4)cnc4ccc(-c5cc(F)c(O)c(Cl)c5)cc34)cn2)CC1] | (6-(3-chloro-5-fluoro-4-hydroxy-phenyl)-4-(6-(4-methylpiperazin-1-yl)pyridin-3-ylamino)quinolin-3-yl)(cyclopropyl)methanone | 532 |
| 472 | 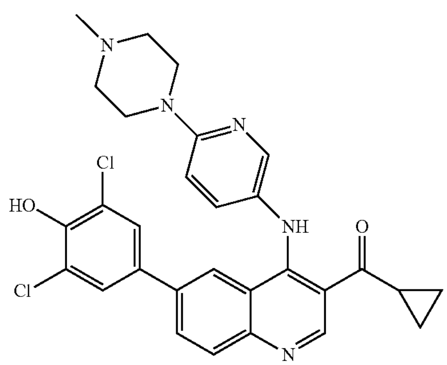 [SMILES: CN1CCN(c2ccc(Nc3c(C(=O)C4CC4)cnc4ccc(-c5cc(Cl)c(O)c(Cl)c5)cc34)cn2)CC1] | cyclopropyl(6-(3,5-dichloro-4-hydroxyphenyl)-4-(6-(4-methyl-piperazin-1-yl)pyridin-3-ylamino)quinolin-3-yl)methanone | 548 |
| 473 | 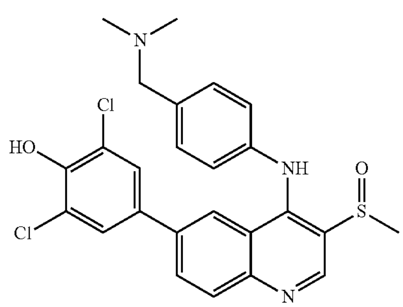 [SMILES: CN(C)Cc1ccc(Nc2c(S(C)=O)cnc3ccc(-c4cc(Cl)c(O)c(Cl)c4)cc23)cc1] | 2,6-dichloro-4-(4-(4-((dimethylamino)methyl)phenylamino)-3-(methylsulfinyl)quinolin-6-yl)phenol | 500 |
| 474 | 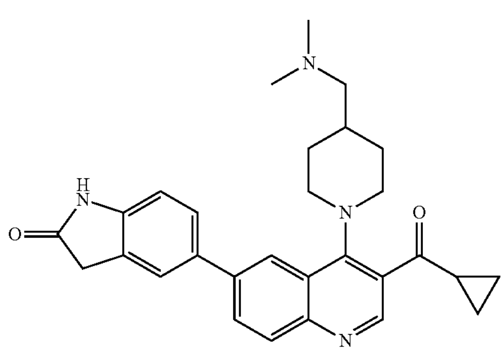 [SMILES: CN(C)CC1CCN(c2c(C(=O)C3CC3)cnc3ccc(-c4ccc5c(c4)CC(=O)N5)cc23)CC1] | 5-(3-(cyclopropanecarbonyl)-4-(4-((dimethylamino)methyl)piperidin-1-yl)quinolin-6-yl)indolin-2-one | 469 |

TABLE 1-continued

| No. | Structure | Compound Name | ESI MS (m/z) |
|---|---|---|---|
| 475 | 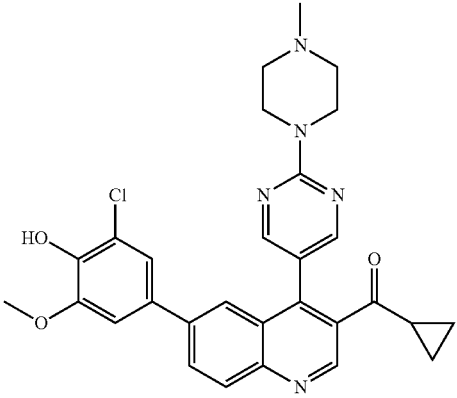 [SMILES: COc1cc(-c2ccc3ncc(C(=O)C4CC4)c(-c4cnc(N5CCN(C)CC5)nc4)c3c2)cc(Cl)c1O] | (6-(3-chloro-4-hydroxy-5-methoxy-phenyl)-4-(2-(4-methylpiperazin-1-yl)pyrimidin-5-yl)quinolin-3-yl)(cyclo-propyl)methanone | 530 |
| 476 | 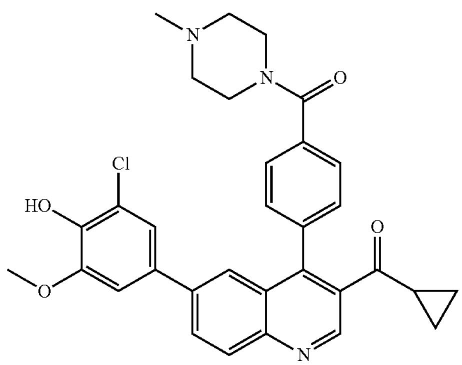 [SMILES: COc1cc(-c2ccc3ncc(C(=O)C4CC4)c(-c4ccc(C(=O)N5CCN(C)CC5)cc4)c3c2)cc(Cl)c1O] | (4-(6-(3-chloro-4-hydroxy-5-methoxy-phenyl)-3-(cyclopropanecarbonyl)quinolin-4-yl)phenyl)(4-methyl-piperazin-1-yl)methanone | 556 |
| 477 | 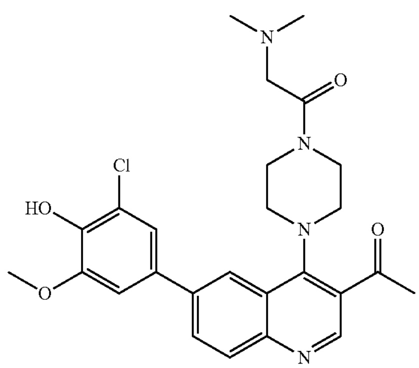 [SMILES: COc1cc(-c2ccc3ncc(C(C)=O)c(N4CCN(C(=O)CN(C)C)CC4)c3c2)cc(Cl)c1O] | 1-(4-(3-acetyl-6-(3-chloro-4-hydroxy-5-methoxyphenyl)quinolin-4-yl)piperazin-1-yl)-2-(dimethylamino)ethanone | 497 |
| 478 | 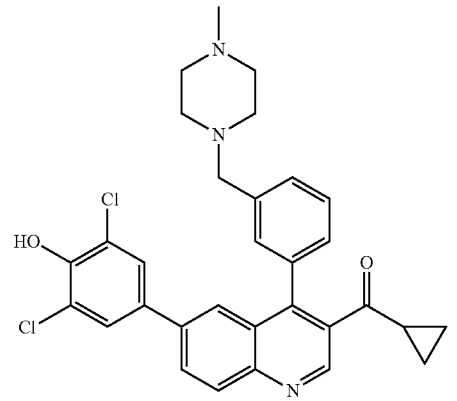 [SMILES: CN1CCN(Cc2cccc(-c3c(C(=O)C4CC4)cnc4ccc(-c5cc(Cl)c(O)c(Cl)c5)cc34)c2)CC1] | cyclopropyl(6-(3,5-dichloro-4-hydroxyphenyl)-4-(3-((4-methyl-piperazin-1-yl)methyl)phenyl)quinolin-3-yl)methanone | 546 |

TABLE 1-continued

| No. | Structure | Compound Name | ESI MS (m/z) |
|---|---|---|---|
| 479 | 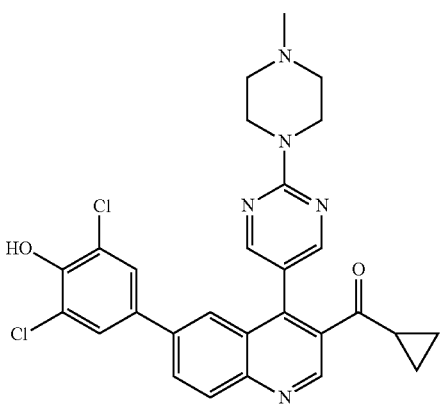 [SMILES: CN1CCN(c2ncc(-c3c(C(=O)C4CC4)cnc4ccc(-c5cc(Cl)c(O)c(Cl)c5)cc34)cn2)CC1] | cyclopropyl(6-(3,5-dichloro-4-hydroxyphenyl)-4-(2-(4-methyl-piperazin-1-yl)pyrimidin-5-yl)quinolin-3-yl)methanone | 534 |
| 480 | 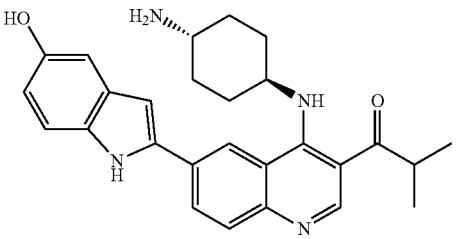 [SMILES: CC(C)C(=O)c1cnc2ccc(-c3cc4cc(O)ccc4[nH]3)cc2c1N[C@H]1CC[C@H](N)CC1] | 1-(4-(1R,4R)--4-aminocyclohexyl-amino)-6-(5-hydroxy-1H-indol-2-yl)quinolin-3-yl)-2-methylpropan-1-one | 443 |
| 481 | 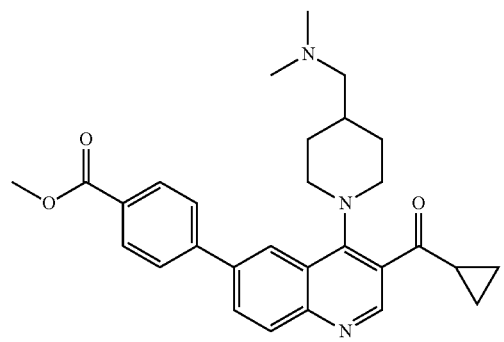 [SMILES: COC(=O)c1ccc(-c2ccc3ncc(C(=O)C4CC4)c(N4CCC(CN(C)C)CC4)c3c2)cc1] | methyl 4-(3-(cyclopropanecarbonyl)-4-(4-((dimethylamino)methyl)piperidin-1-yl)quinolin-6-yl)benzoate | 472 |
| 482 | 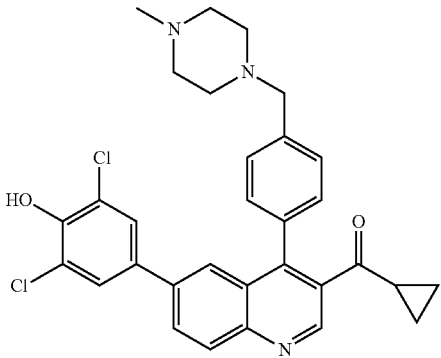 [SMILES: CN1CCN(Cc2ccc(-c3c(C(=O)C4CC4)cnc4ccc(-c5cc(Cl)c(O)c(Cl)c5)cc34)cc2)CC1] | cyclopropyl(6-(3,5-dichloro-4-hydroxy-phenyl)-4-(4-((4-methylpiperazin-1-yl)methyl)phenyl)quinolin-3-yl)methanone | 546 |

TABLE 1-continued

| No. | Structure | Compound Name | ESI MS (m/z) |
|---|---|---|---|
| 483 | 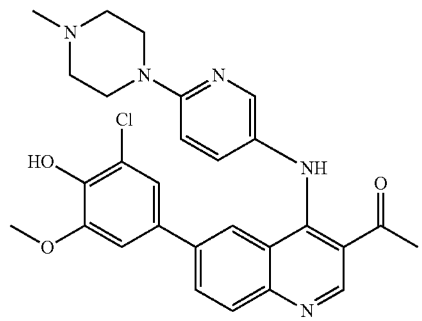 [SMILES: COc1cc(-c2ccc3ncc(C(C)=O)c(Nc4ccc(N5CCN(C)CC5)nc4)c3c2)cc(Cl)c1O] | 1-(6-(3-chloro-4-hydroxy-5-methoxy-phenyl)-4-(6-(4-methylpiperazin-1-yl)pyridin-3-ylamino)quinolin-3-yl)ethanone | 518 |
| 484 | 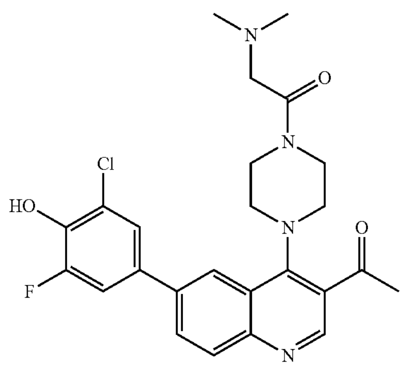 [SMILES: CC(=O)c1cnc2ccc(-c3cc(F)c(O)c(Cl)c3)cc2c1N1CCN(C(=O)CN(C)C)CC1] | 1-(4-(3-acetyl-6-(3-chloro-5-fluoro-4-hydroxyphenyl)quinolin-4-yl)piperazin-1-yl)-2-(dimethylamino)ethanone | 485 |
| 485 | 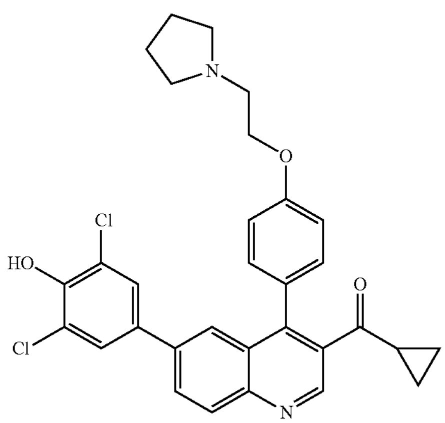 [SMILES: O=C(c1cnc2ccc(-c3cc(Cl)c(O)c(Cl)c3)cc2c1-c1ccc(OCCN2CCCC2)cc1)C1CC1] | cyclopropyl(6-(3,5-dichloro-4-hydroxy-phenyl)-4-(4-(2-(pyrrolidin-1-yl)ethoxy)phenyl)quinolin-3-yl)methanone | 547 |
| 486 | 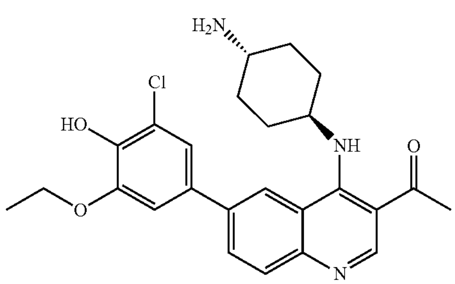 [SMILES: CCOc1cc(-c2ccc3ncc(C(C)=O)c(N[C@H]4CC[C@H](N)CC4)c3c2)cc(Cl)c1O] | 1-(4-((1R,4R)--4-aminocyclohexyl-amino)-6-(3-chloro-5-ethoxy-4-hydroxyphenyl)quinolin-3-yl)ethanone | 454 |

TABLE 1-continued

| No. | Structure | Compound Name | ESI MS (m/z) |
|---|---|---|---|
| 487 | 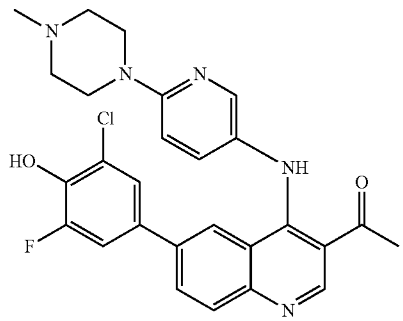 [SMILES: CC(=O)c1cnc2ccc(-c3cc(F)c(O)c(Cl)c3)cc2c1Nc1ccc(N2CCN(C)CC2)nc1] | 1-(6-(3-chloro-5-fluoro-4-hydroxyphenyl)-4-(6-(4-methylpiperazin-1-yl)pyridin-3-ylamino)quinolin-3-yl)ethanone | 506 |
| 488 | 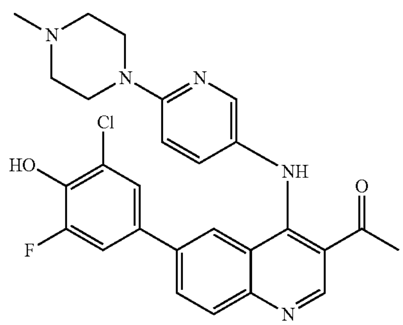 [SMILES: CC(=O)c1cnc2ccc(-c3cc(F)c(O)c(Cl)c3)cc2c1Nc1ccc(N2CCN(C)CC2)nc1] | 1-(6-(3-chloro-5-fluoro-4-hydroxyphenyl)-4-(6-(4-methylpiperazin-1-yl)pyridin-3-ylamino)quinolin-3-yl)ethanone | 506 |
| 489 | 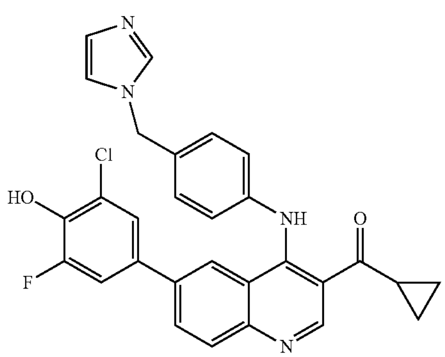 [SMILES: O=C(c1cnc2ccc(-c3cc(F)c(O)c(Cl)c3)cc2c1Nc1ccc(Cn2ccnc2)cc1)C1CC1] | (4-(4-((1H-imidazol-1-yl)methyl)phenylamino)-6-(3-chloro-5-fluoro-4-hydroxyphenyl)quinolin-3-yl)(cyclopropyl)methanone | 513 |
| 490 | 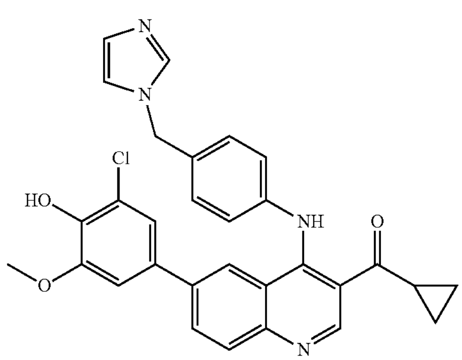 [SMILES: COc1cc(-c2ccc3ncc(C(=O)C4CC4)c(Nc4ccc(Cn5ccnc5)cc4)c3c2)cc(Cl)c1O] | (4-(4-((1H-imidazol-1-yl)methyl)phenylamino)-6-(3-chloro-4-hydroxy-5-methoxyphenyl)quinolin-3-yl)(cyclopropyl)methanone | 525 |

TABLE 1-continued

| No. | Structure | Compound Name | ESI MS (m/z) |
|---|---|---|---|
| 491 | 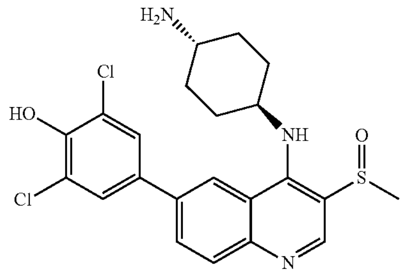 [SMILES: CS(=O)c1cnc2ccc(-c3cc(Cl)c(O)c(Cl)c3)cc2c1N[C@H]1CC[C@H](N)CC1] | 4-(4-(1R,4R)--4-aminocyclohexyl-amino)-3-(methylsulfinyl)quinolin-6-yl)-2,6-dichlorophenol | 464 |
| 492 | 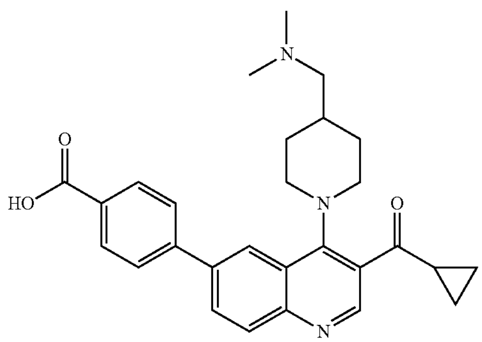 [SMILES: CN(C)CC1CCN(c2c(C(=O)C3CC3)cnc3ccc(-c4ccc(C(=O)O)cc4)cc23)CC1] | 4-(3-(cyclopropanecarbonyl)-4-(4-((dimethylamino)methyl)piperidin-1-yl)quinolin-6-yl)benzoic acid | 458 |
| 493 | 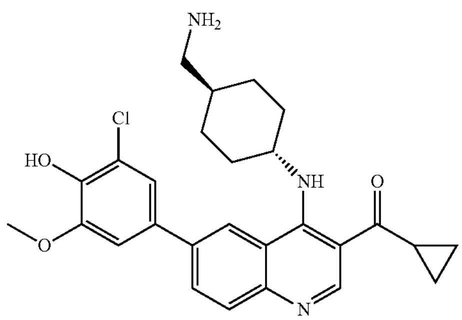 [SMILES: COc1cc(-c2ccc3ncc(C(=O)C4CC4)c(N[C@H]4CC[C@H](CN)CC4)c3c2)cc(Cl)c1O] | (4-(1R,4R)--4-(aminomethyl)cyclo-hexylamino)-6-(3-chloro-4-hydroxy-5-methoxyphenyl)quinolin-3-yl)(cyclopropyl)methanone | 480 |
| 494 | 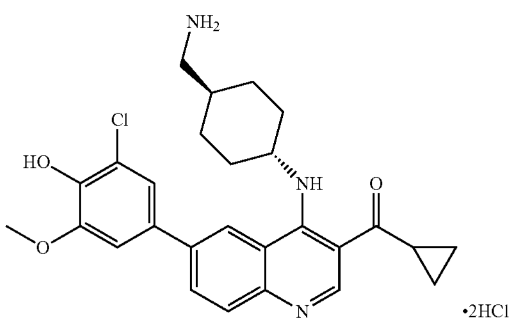 [SMILES: COc1cc(-c2ccc3ncc(C(=O)C4CC4)c(N[C@H]4CC[C@H](CN)CC4)c3c2)cc(Cl)c1O] | (4-(1R,4R)--4-(aminomethyl)cyclo-hexylamino)-6-(3-chloro-4-hydroxy-5-methoxyphenyl)quinolin-3-yl)(cyclopropyl)methanone hydrochloride | 480 |
| 495 | 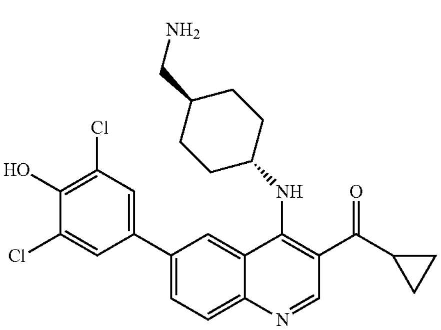 [SMILES: NC[C@H]1CC[C@H](Nc2c(C(=O)C3CC3)cnc3ccc(-c4cc(Cl)c(O)c(Cl)c4)cc23)CC1] | (4-(1R,4R)--4-(aminomethyl)cyclo-hexylamino)-6-(3,5-dichloro-4-hydroxyphenyl)quinolin-3-yl)(cyclo-propyl)methanone | 484 |

TABLE 1-continued

| No. | Structure | Compound Name | ESI MS (m/z) |
|---|---|---|---|
| 496 | 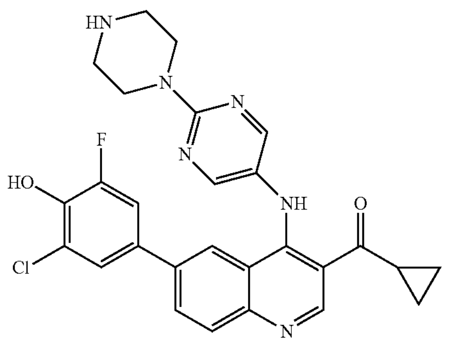 [SMILES: O=C(c1cnc2ccc(-c3cc(F)c(O)c(Cl)c3)cc2c1Nc1cnc(N2CCNCC2)nc1)C1CC1] | (6-(3-chloro-5-fluoro-4-hydroxyphenyl)-4-(2-(piperazin-1-yl)pyrimidin-5-ylamino)quinolin-3-yl)(cyclopropyl)methanone | 519 |
| 497 | 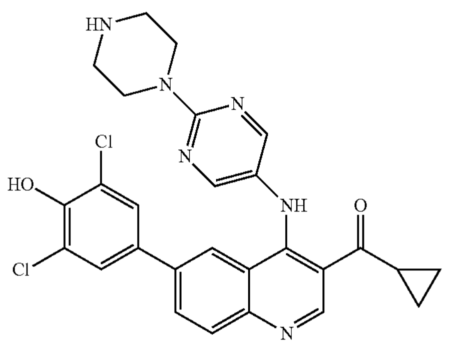 [SMILES: O=C(c1cnc2ccc(-c3cc(Cl)c(O)c(Cl)c3)cc2c1Nc1cnc(N2CCNCC2)nc1)C1CC1] | cyclopropyl(6-(3,5-dichloro-4-hydroxyphenyl)-4-(2-(piperazin-1-yl)pyrimidin-5-ylamino)quinolin-3-yl)methanone | 535 |
| 498 | 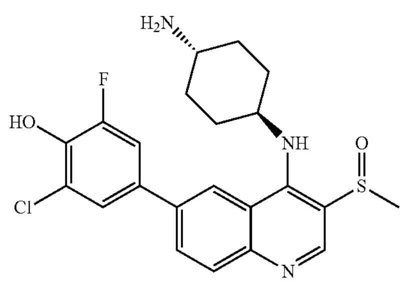 [SMILES: CS(=O)c1cnc2ccc(-c3cc(F)c(O)c(Cl)c3)cc2c1N[C@H]1CC[C@H](N)CC1] | 4-(4-(1R,4R)--4-aminocyclohexylamino)-3-(methylsulfinyl)quinolin-6-yl)-2-chloro-6-fluorophenol | 448 |
| 499 | 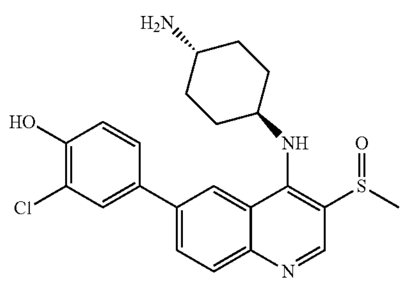 [SMILES: CS(=O)c1cnc2ccc(-c3ccc(O)c(Cl)c3)cc2c1N[C@H]1CC[C@H](N)CC1] | 4-(4-(1R,4R)--4-aminocyclohexylamino)-3-(methylsulfinyl)quinolin-6-yl)-2-chlorophenol | 430 |
| 500 | 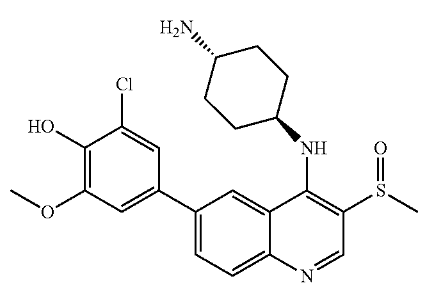 | 4-(4-(1R,4R)--4-aminocyclohexylamino)-3-(methylsulfinyl)quinolin-6-yl)-2-chloro-6-methoxyphenol | 460 |

TABLE 1-continued

| No. | Structure | Compound Name | ESI MS (m/z) |
|---|---|---|---|
| 501 | 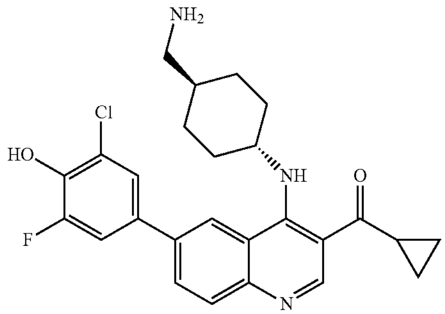 | (4-(1R,4R)--4-(aminomethyl)cyclo-hexylamino)-6-(3-chloro-5-fluoro-4-hydroxyphenyl)quinolin-3-yl)(cyclo-propyl)methanone | 468 |
| 502 | 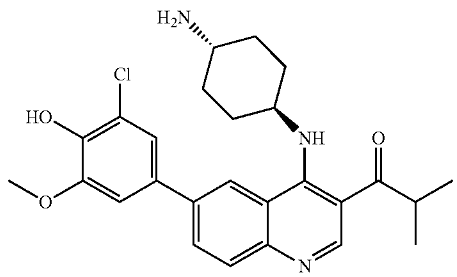 [SMILES: COc1cc(-c2ccc3ncc(C(=O)C(C)C)c(N[C@H]4CC[C@H](N)CC4)c3c2)cc(Cl)c1O] | 1-(4-(1R,4R)--4-aminocyclohexyl-amino)-6-(3-chloro-4-hydroxy-5-methoxyphenyl)quinolin-3-yl)-2-methylpropan-1-one | 468 |
| 503 | 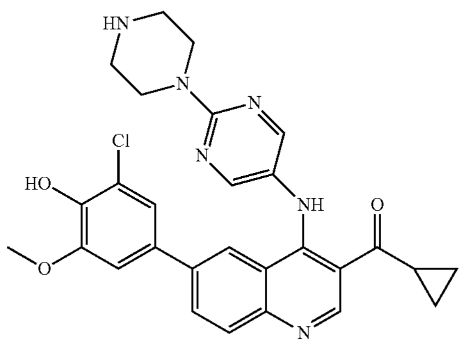 [SMILES: COc1cc(-c2ccc3ncc(C(=O)C4CC4)c(Nc4cnc(N5CCNCC5)nc4)c3c2)cc(Cl)c1O] | (6-(3-chloro-4-hydroxy-5-methoxy-phenyl)-4-(2-(piperazin-1-yl)pyrimidin-5-ylamino)quinolin-3-yl)(cyclopropyl)methanone | 531 |
| 504 | 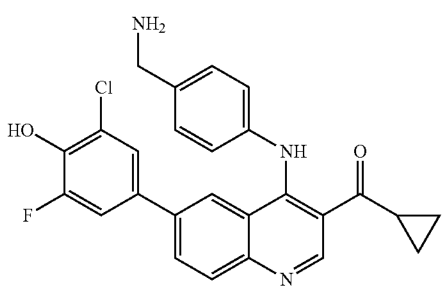 | (4-(4-(aminomethyl)phenylamino)-6-(3-chloro-5-fluoro-4-hydroxyphenyl)quinolin-3-yl)(cyclopropyl)methanone | 462 |
| 505 | 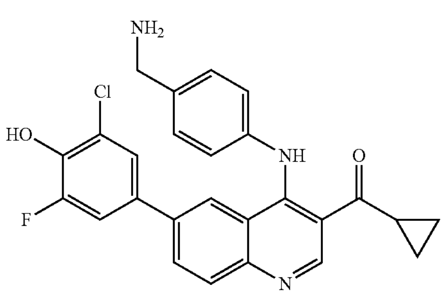 [SMILES: NCc1ccc(Nc2c(C(=O)C3CC3)cnc3ccc(-c4cc(F)c(O)c(Cl)c4)cc23)cc1] | (4-(4-(aminomethyl)phenylamino)-6-(3-chloro-5-fluoro-4-hydroxyphenyl)quinolin-3-yl)(cyclopropyl)methanone hydrochloride | 462 |

TABLE 1-continued

| No. | Structure | Compound Name | ESI MS (m/z) |
|---|---|---|---|
| 506 | 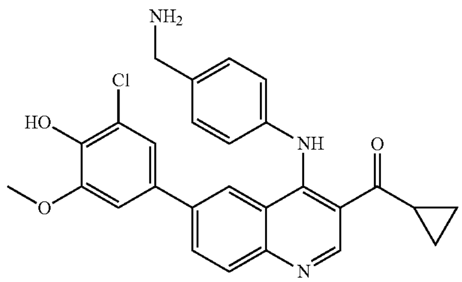 [SMILES: COc1cc(-c2ccc3ncc(C(=O)C4CC4)c(Nc4ccc(CN)cc4)c3c2)cc(Cl)c1O] | (4-(4-(aminomethyl)phenylamino)-6-(3-chloro-4-hydroxy-5-methoxy-phenyl)quinolin-3-yl)(cyclopropyl)methanone | 474 |
| 507 | 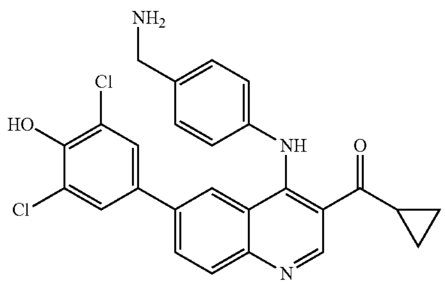 | (4-(4-(aminomethyl)phenylamino)-6-(3,5-dichloro-4-hydroxyphenyl)quinolin-3-yl)(cyclopropyl)methanone | 478 |
| 508 | 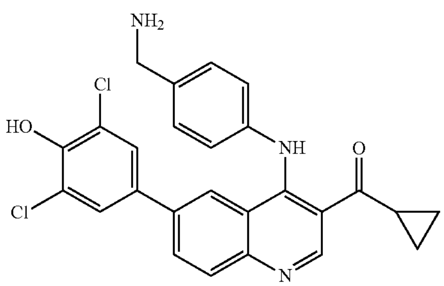 [SMILES: NCc1ccc(Nc2c(C(=O)C3CC3)cnc3ccc(-c4cc(Cl)c(O)c(Cl)c4)cc23)cc1] | (4-(4-(aminomethyl)phenylamino)-6-(3,5-dichloro-4-hydroxyphenyl)quinolin-3-yl)(cyclopropyl)methanone hydrochloride | 478 |
| 509 | 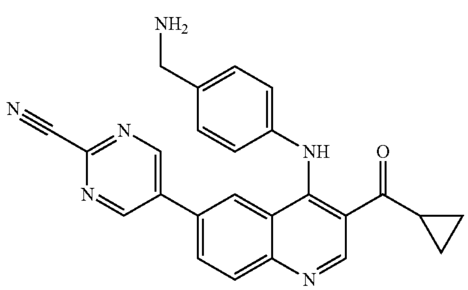 [SMILES: N#Cc1ncc(-c2ccc3ncc(C(=O)C4CC4)c(Nc4ccc(CN)cc4)c3c2)cn1] | 5-(4-(4-(aminomethyl)phenylamino)-3-(cyclopropanecarbonyl)quinolin-6-yl)pyrimidine-2-carbonitrile | 420 |
| 510 | 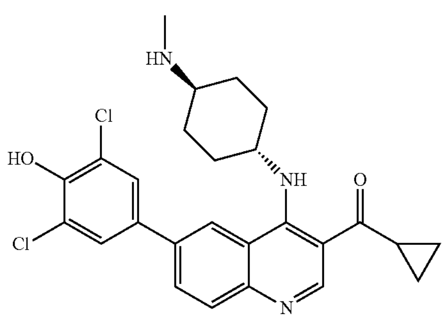 | cyclopropyl(6-(3,5-dichloro-4-hydroxy-phenyl)-4-4-(methylamino)cyclohexyl-amino)quinolin-3-yl)methanone | 484 |

TABLE 1-continued

| No. | Structure | Compound Name | ESI MS (m/z) |
|---|---|---|---|
| 511 | 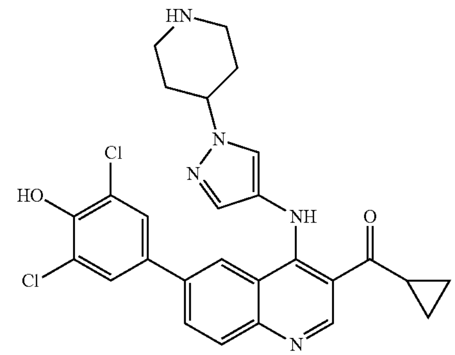 | cyclopropyl(6-(3,5-dichloro-4-hydroxyphenyl)-4-(1-(piperidin-4-yl)-1H-pyrazol-4-ylamino)quinolin-3-yl)methanone | 522 |
| 512 | 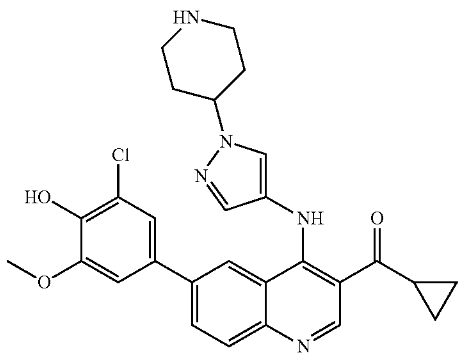 [SMILES: COc1cc(-c2ccc3ncc(C(=O)C4CC4)c(Nc4cnn(C5CCNCC5)c4)c3c2)cc(Cl)c1O] | (6-(3-chloro-4-hydroxy-5-methoxyphenyl)-4-(1-(piperidin-4-yl)-1H-pyrazol-4-ylamino)quinolin-3-yl)(cyclopropyl)methanone | 518 |
| 513 | 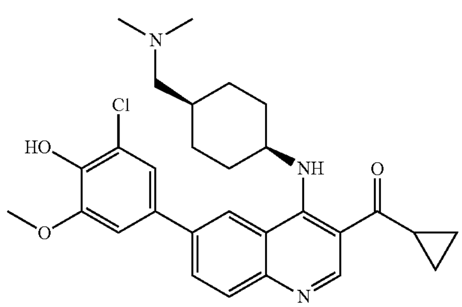 [SMILES: COc1cc(-c2ccc3ncc(C(=O)C4CC4)c(N[C@H]4CC[C@@H](CN(C)C)CC4)c3c2)cc(Cl)c1O] | (6-(3-chloro-4-hydroxy-5-methoxyphenyl)-4-((1s,4s)-4-((dimethylamino)methyl)cyclohexylamino)quinolin-3-yl)(cyclopropyl)methanone | 508 |
| 514 | 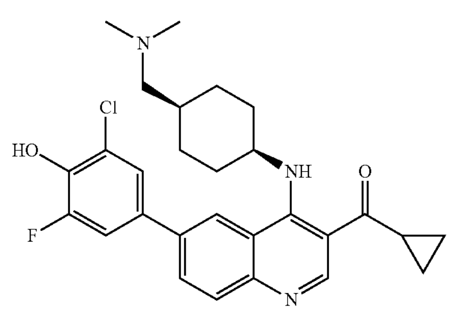 [SMILES: CN(C)C[C@H]1CC[C@@H](Nc2c(C(=O)C3CC3)cnc3ccc(-c4cc(F)c(O)c(Cl)c4)cc23)CC1] | (6-(3-chloro-5-fluoro-4-hydroxyphenyl)-4-((1s,4s)-4-((dimethylamino)methyl)cyclohexylamino)quinolin-3-yl)(cyclopropyl)methanone | 496 |

TABLE 1-continued

| No. | Structure | Compound Name | ESI MS (m/z) |
|---|---|---|---|
| 515 | 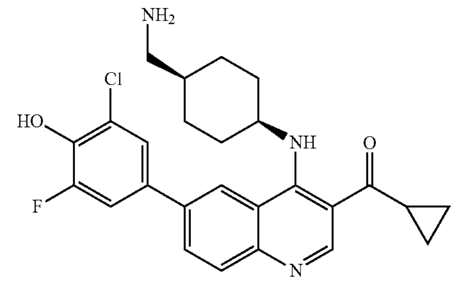 [SMILES: NC[C@H]1CC[C@@H](Nc2c(C(=O)C3CC3)cnc3ccc(-c4cc(F)c(O)c(Cl)c4)cc23)CC1] | (4-((1s,4s)-4-(aminomethyl)cyclo-hexylamino)-6-(3-chloro-5-fluoro-4-hydroxyphenyl)quinolin-3-yl)(cyclo-propyl)methanone | 468 |
| 516 | 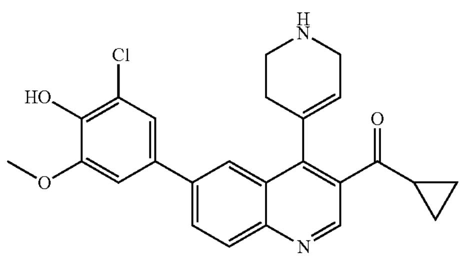 [SMILES: COc1cc(-c2ccc3ncc(C(=O)C4CC4)c(C4=CCNCC4)c3c2)cc(Cl)c1O] | (6-(3-chloro-4-hydroxy-5-methoxy-phenyl)-4-(1,2,3,6-tetrahydropyridin-4-yl)quinolin-3-yl)(cyclopropyl)methanone | 435 |
| 517 | 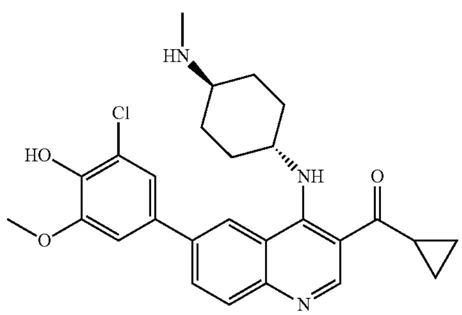 [SMILES: CN[C@H]1CC[C@H](Nc2c(C(=O)C3CC3)cnc3ccc(-c4cc(Cl)c(O)c(OC)c4)cc23)CC1] | (6-(3-chloro-4-hydroxy-5-methoxy-phenyl)-4-((1R,4R)-4-(methylamino)cyclohexyl)amino)quinolin-3-yl)(cyclopropyl)methanone | 480 |
| 518 | 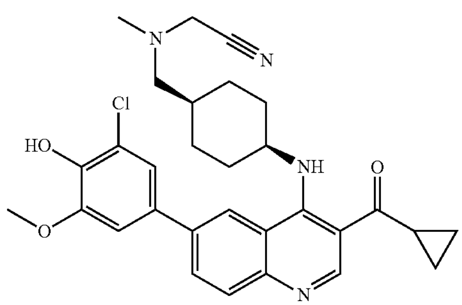 [SMILES: COc1cc(-c2ccc3ncc(C(=O)C4CC4)c(N[C@H]4CC[C@@H](CN(C)CC#N)CC4)c3c2)cc(Cl)c1O] | 2-((((1s,4s)-4-(6-(3-chloro-4-hydroxy-5-methoxyphenyl)-3-(cyclopropane-carbonyl)quinolin-4-ylamino)cyclo-hexyl)methyl)(methyl)amino)acetonitrile | 533 |
| 519 | 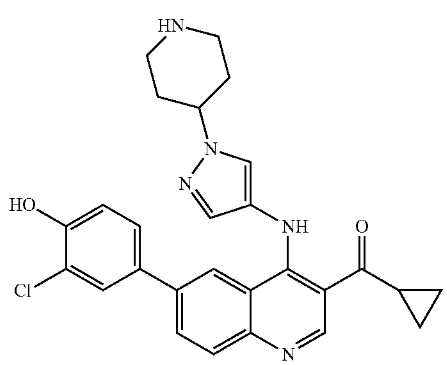 [SMILES: O=C(c1cnc2ccc(-c3ccc(O)c(Cl)c3)cc2c1Nc1cnn(C2CCNCC2)c1)C1CC1] | (6-(3-chloro-4-hydroxyphenyl)-4-(1-(piperidin-4-yl)-1H-pyrazol-4-ylamino)quinolin-3-yl)(cyclopropyl)methanone | 488 |

TABLE 1-continued

| No. | Structure | Compound Name | ESI MS (m/z) |
|---|---|---|---|
| 520 | 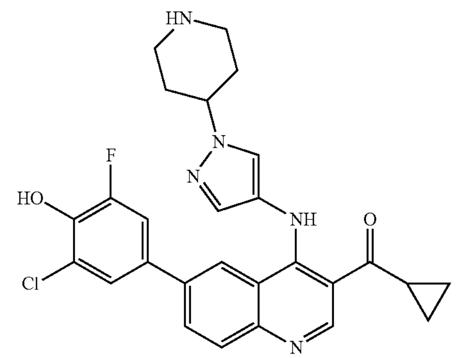 [SMILES: O=C(c1cnc2ccc(-c3cc(F)c(O)c(Cl)c3)cc2c1Nc1cnn(C2CCNCC2)c1)C1CC1] | (6-(3-chloro-5-fluoro-4-hydroxy-phenyl)-4-(1-(piperidin-4-yl)-1H-pyrazol-4-ylamino)quinolin-3-yl)(cyclopropyl)methanone | 506 |
| 521 | 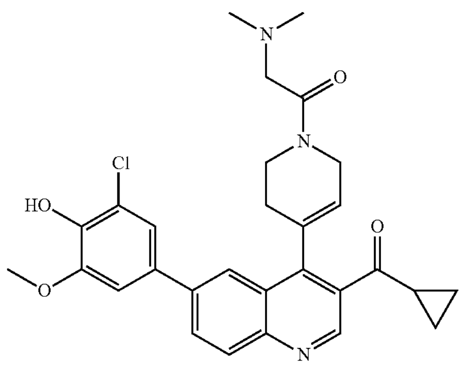 [SMILES: COc1cc(-c2ccc3ncc(C(=O)C4CC4)c(C4=CCN(C(=O)CN(C)C)CC4)c3c2)cc(Cl)c1O] | 1-(4-(6-(3-chloro-4-hydroxy-5-methoxyphenyl)-3-(cyclopropane-carbonyl)quinolin-4-yl)-5,6-dihydro-pyridin-1(2H)-yl)-2-(dimethyl-amino)ethanone | 520 |
| 522 | 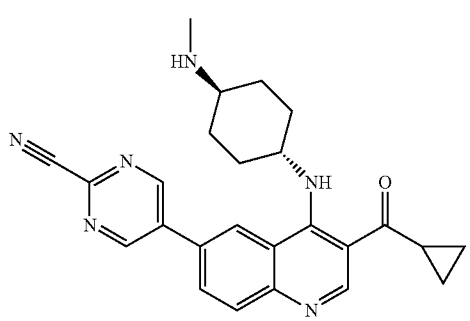 [SMILES: CN[C@H]1CC[C@H](Nc2c(C(=O)C3CC3)cnc3ccc(-c4cnc(C#N)nc4)cc23)CC1] | 5-(3-(cyclopropanecarbonyl)-4-(1R,4R)-4-(methylamino)cyclohexylamino)quinolin-6-yl)pyrimidine-2-carbonitrile | 427 |
| 523 | 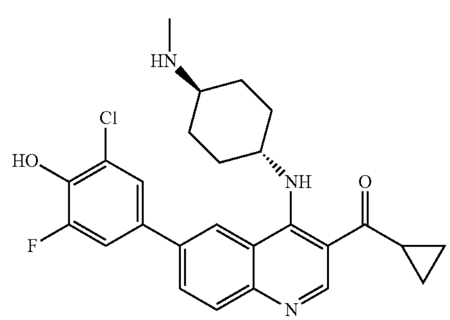 [SMILES: CN[C@H]1CC[C@H](Nc2c(C(=O)C3CC3)cnc3ccc(-c4cc(F)c(O)c(Cl)c4)cc23)CC1] | (6-(3-chloro-5-fluoro-4-hydroxy-phenyl)-4-(1R,4R)-4-(methylamino)cyclohexylamino)quinolin-3-yl)(cyclopropyl)methanone | 468 |

TABLE 1-continued

| No. | Structure | Compound Name | ESI MS (m/z) |
|---|---|---|---|
| 524 | 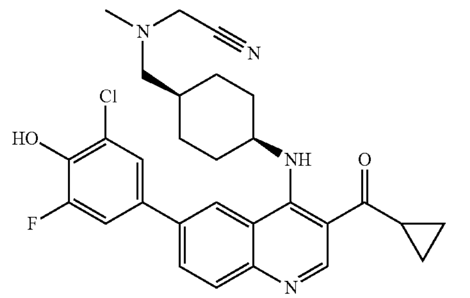 [SMILES: CN(CC#N)C[C@H]1CC[C@@H](Nc2c(C(=O)C3CC3)cnc3ccc(-c4cc(F)c(O)c(Cl)c4)cc23)CC1] | 2-((((1s,4s)-4-(6-(3-chloro-5-fluoro-4-hydroxyphenyl)-3-(cyclopropane-carbonyl)quinolin-4-ylamino)cyclo-hexyl)methyl)(methyl)amino) acetonitrile | 521 |
| 525 | •2HCl | (6-(3-chloro-5-fluoro-4-hydroxy-phenyl)-4-(5-(piperazin-1-yl)pyridin-2-ylamino)quinolin-3-yl)(cyclo-propyl)methanone | 518 |
| 526 | 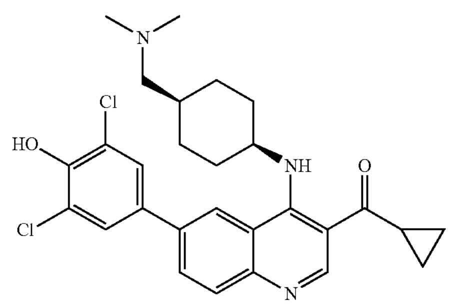 | cyclopropyl(6-(3,5-dichloro-4-hydroxy-phenyl)-4-((1s,4s)-4-((dimethyl-amino)methyl)cyclohexylamino) quinolin-3-yl)methanone | 512 |
| 527 | 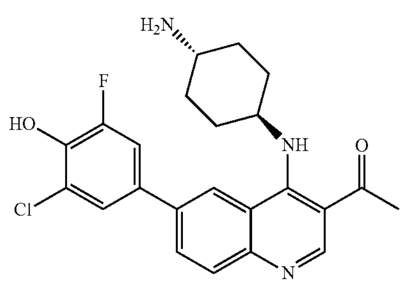 [SMILES: CC(=O)c1cnc2ccc(-c3cc(F)c(O)c(Cl)c3)cc2c1N[C@H]1CC[C@H](N)CC1] | 1-(4-(1R,4R)--4-aminocyclohexyl-amino)-6-(3-chloro-5-fluoro-4-hydroxyphenyl)quinolin-3-yl)ethanone | 428 |
| 528 | •HCl | (6-(3-chloro-4-hydroxy-5-methoxy-phenyl)-4-(5-(piperazin-1-yl)pyridin-2-ylamino)quinolin-3-yl)(cyclo-propyl)methanone hydrochloride | 530 |

TABLE 1-continued

| No. | Structure | Compound Name | ESI MS (m/z) |
|---|---|---|---|
| 529 | 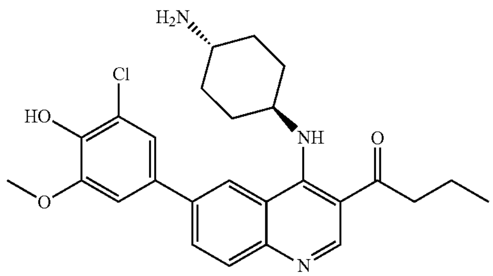 [SMILES: CCCC(=O)c1cnc2ccc(-c3cc(Cl)c(O)c(OC)c3)cc2c1N[C@H]1CC[C@H](N)CC1] | 1-(4-(1R,4R)-4-aminocyclohexyl-amino)-6-(3-chloro-4-hydroxy-5-methoxyphenyl)quinolin-3-yl)butan-1-one | 468 |
| 530 | 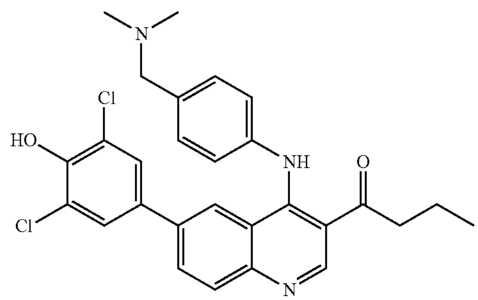 | 1-(6-(3,5-dichloro-4-hydroxyphenyl)-4-(4-((dimethylamino)methyl)phenyl-amino)quinolin-3-yl)butan-1-one | 508 |
| 531 | 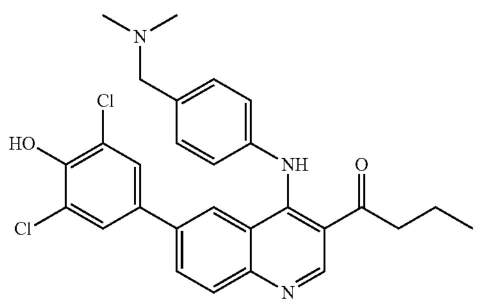 [SMILES: CCCC(=O)c1cnc2ccc(-c3cc(Cl)c(O)c(Cl)c3)cc2c1Nc1ccc(CN(C)C)cc1] | 1-(6-(3,5-dichloro-4-hydroxyphenyl)-4-(4-((dimethylamino)methyl)phenyl-amino)quinolin-3-yl)butan-1-one dihydrochloride | 508 |
| 532 | 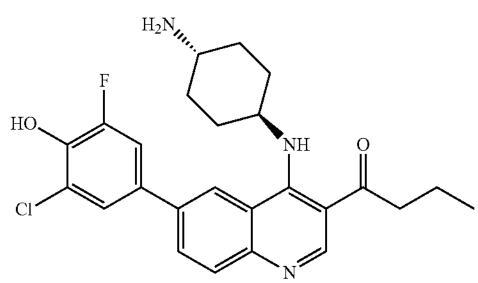 [SMILES: CCCC(=O)c1cnc2ccc(-c3cc(F)c(O)c(Cl)c3)cc2c1N[C@H]1CC[C@H](N)CC1] | 1-(4-(1R,4R)--4-aminocyclohexyl-amino)-6-(3-chloro-5-fluoro-4-hydroxy-phenyl)quinolin-3-yl)butan-1-one | 456 |
| 533 | 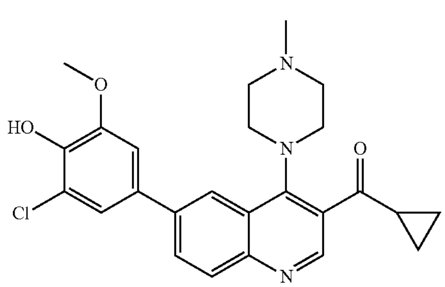 [SMILES: COc1cc(-c2ccc3ncc(C(=O)C4CC4)c(N4CCN(C)CC4)c3c2)cc(Cl)c1O] | (6-(3-chloro-4-hydroxy-5-methoxy-phenyl)-4-(4-methylpiperazin-1-yl)quinolin-3-yl)(cyclopropyl)methanone | 452 |

TABLE 1-continued

| No. | Structure | Compound Name | ESI MS (m/z) |
|---|---|---|---|
| 534 | 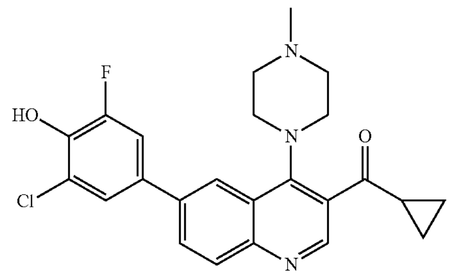 [SMILES: CN1CCN(c2c(C(=O)C3CC3)cnc3ccc(-c4cc(F)c(O)c(Cl)c4)cc23)CC1] | (6-(3-chloro-5-fluoro-4-hydroxyphenyl)-4-(4-methylpiperazin-1-yl)quinolin-3-yl)(cyclopropyl)methanone | 440 |
| 535 | 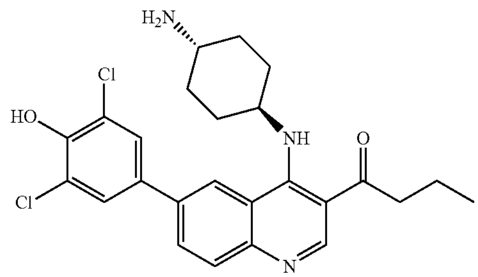 [SMILES: CCCC(=O)c1cnc2ccc(-c3cc(Cl)c(O)c(Cl)c3)cc2c1N[C@H]1CC[C@H](N)CC1] | 1-(4-(1R,4R)-4-aminocyclohexyl-amino)-6-(3,5-dichloro-4-hydroxy-phenyl)quinolin-3-yl)butan-1-one | 472 |
| 536 | 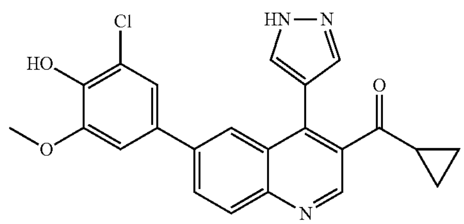 [SMILES: COc1cc(-c2ccc3ncc(C(=O)C4CC4)c(-c4cn[nH]c4)c3c2)cc(Cl)c1O] | (6-(3-chloro-4-hydroxy-5-methoxy-phenyl)-4-(1H-pyrazol-4-yl)quinolin-3-yl)(cyclopropyl)methanone | 420 |
| 537 | 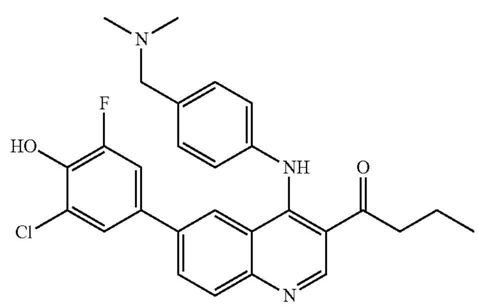 [SMILES: CCCC(=O)c1cnc2ccc(-c3cc(F)c(O)c(Cl)c3)cc2c1Nc1ccc(CN(C)C)cc1] | 1-(6-(3-chloro-5-fluoro-4-hydroxy-phenyl)-4-(4-((dimethylamino)methyl)phenylamino)quinolin-3-yl)butan-1-one | 492 |
| 538 | 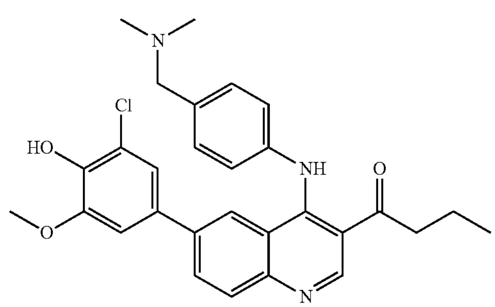 [SMILES: CCCC(=O)c1cnc2ccc(-c3cc(Cl)c(O)c(OC)c3)cc2c1Nc1ccc(CN(C)C)cc1] | 1-(6-(3-chloro-4-hydroxy-5-methoxy-phenyl)-4-(4-((dimethylamino)methyl)phenylamino)quinolin-3-yl)butan-1-one | 504 |

TABLE 1-continued

| No. | Structure | Compound Name | ESI MS (m/z) |
|---|---|---|---|
| 539 | 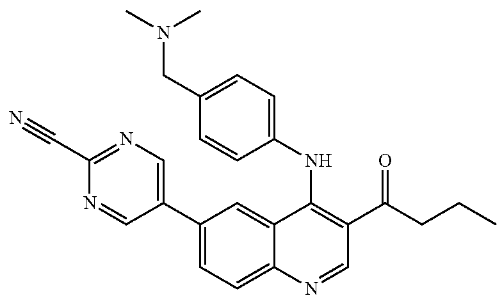 [SMILES: CCCC(=O)c1cnc2ccc(-c3cnc(C#N)nc3)cc2c1Nc1ccc(CN(C)C)cc1] | 5-(3-butyryl-4-(4-((dimethylamino) methyl)phenylamino)quinolin-6-yl) pyrimidine-2-carbonitrile | 451 |
| 540 | 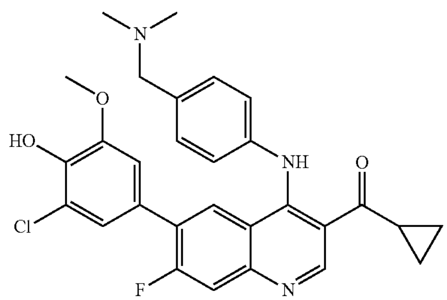 [SMILES: COc1cc(-c2cc3c(Nc4ccc(CN(C)C)cc4)c(C(=O)C4CC4)cnc3cc2F)cc(Cl)c1O] | (6-(3-chloro-4-hydroxy-5-methoxy-phenyl)-4-(4-((dimethylamino)methyl) phenylamino)-7-fluoroquinolin-3-yl) (cyclopropyl)methanone | 520 |
| 541 | 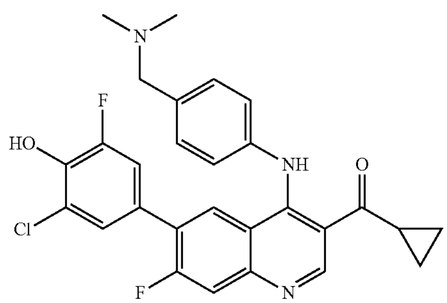 [SMILES: CN(C)Cc1ccc(Nc2c(C(=O)C3CC3)cnc3cc(F)c(-c4cc(F)c(O)c(Cl)c4)cc23)cc1] | (6-(3-chloro-5-fluoro-4-hydroxy-phenyl)-4-(4-((dimethylamino)methyl) phenylamino)-7-fluoroquinolin-3-yl)(cyclopropyl)methanone | 508 |
| 542 | 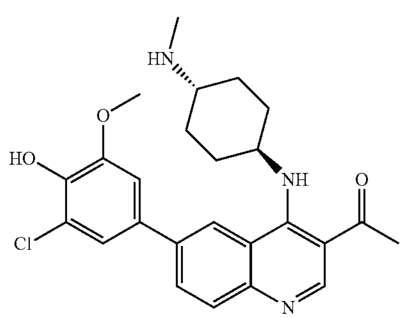 [SMILES: CN[C@H]1CC[C@H](Nc2c(C(C)=O)cnc3ccc(-c4cc(Cl)c(O)c(OC)c4)cc23)CC1] | 1-(6-(3-chloro-4-hydroxy-5-methoxy-phenyl)-4-(1R,4R)--4-(methylamino) cyclohexylamino)quinolin-3-yl) ethanone | 454 |
| 543 | 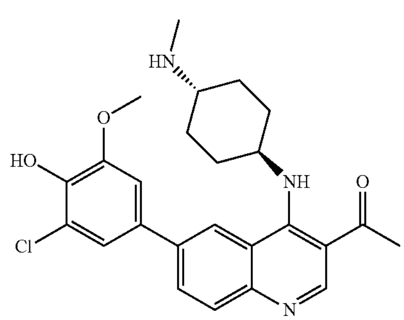 | 1-(6-(3-chloro-4-hydroxy-5-methoxy-phenyl)-4-(1R,4R)--4-(methylamino) cyclohexylamino)quinolin-3-yl) ethanone dihydrochloride | 454 |

TABLE 1-continued

| No. | Structure | Compound Name | ESI MS (m/z) |
|---|---|---|---|
| 544 | 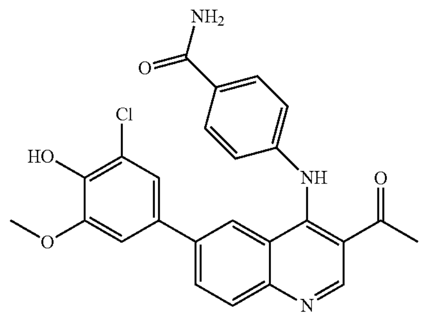 [SMILES: COc1cc(-c2ccc3ncc(C(C)=O)c(Nc4ccc(C(N)=O)cc4)c3c2)cc(Cl)c1O] | 4-(3-acetyl-6-(3-chloro-4-hydroxy-5-methoxyphenyl)quinolin-4-ylamino)benzamide | 462 |
| 545 | 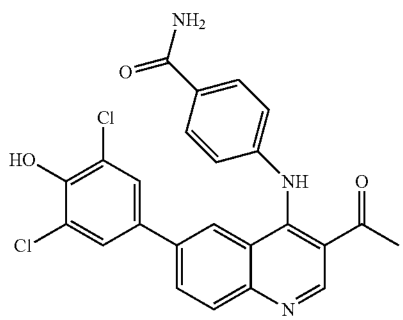 [SMILES: CC(=O)c1cnc2ccc(-c3cc(Cl)c(O)c(Cl)c3)cc2c1Nc1ccc(C(N)=O)cc1] | 4-(3-acetyl-6-(3,5-dichloro-4-hydroxyphenyl)quinolin-4-ylamino)benzamide | 466 |
| 546 | 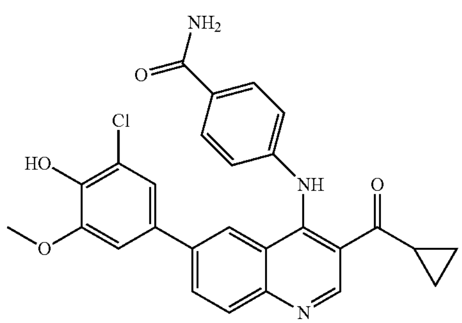 [SMILES: COc1cc(-c2ccc3ncc(C(=O)C4CC4)c(Nc4ccc(C(N)=O)cc4)c3c2)cc(Cl)c1O] | 4-(6-(3-chloro-4-hydroxy-5-methoxyphenyl)-3-(cyclopropanecarbonyl)quinolin-4-ylamino)benzamide | 488 |
| 547 | 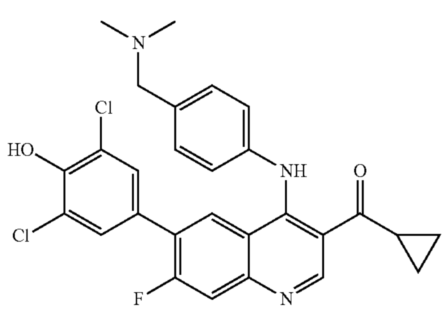 | cyclopropyl(6-(3,5-dichloro-4-hydroxyphenyl)-4-(4-((dimethylamino)methyl)phenylamino)-7-fluoroquinolin-3-yl)methanone | 524 |

TABLE 1-continued

| No. | Structure | Compound Name | ESI MS (m/z) |
|---|---|---|---|
| 548 | 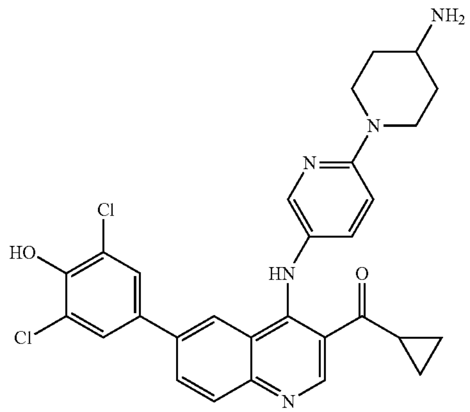 [SMILES: NC1CCN(c2ccc(Nc3c(C(=O)C4CC4)cnc4ccc(-c5cc(Cl)c(O)c(Cl)c5)cc34)cn2)CC1] | (4-(6-(4-aminopiperidin-1-yl)pyridin-3-ylamino)-6-(3,5-dichloro-4-hydroxyphenyl)quinolin-3-yl)(cyclopropyl)methanone | 548 |
| 549 | 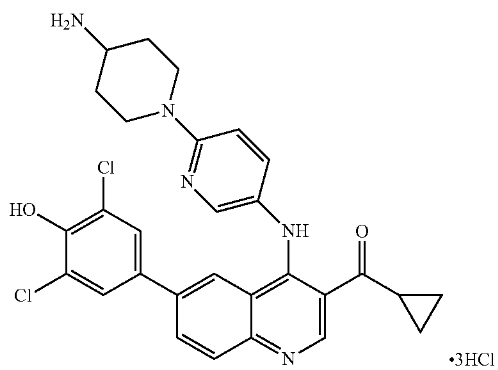 [SMILES: NC1CCN(c2ccc(Nc3c(C(=O)C4CC4)cnc4ccc(-c5cc(Cl)c(O)c(Cl)c5)cc34)cn2)CC1] | (4-(6-(4-aminopiperidin-1-yl)pyridin-3-ylamino)-6-(3,5-dichloro-4-hydroxyphenyl)quinolin-3-yl)(cyclopropyl)methanone hydrochloride | 548 |
| 550 | 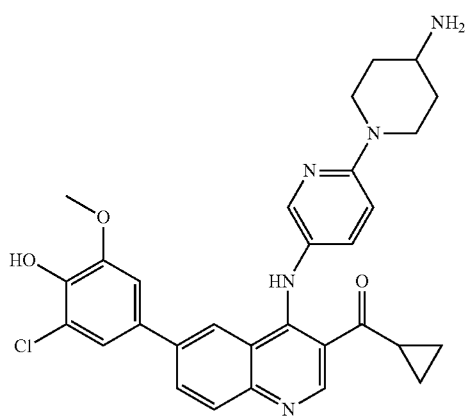 [SMILES: COc1cc(-c2ccc3ncc(C(=O)C4CC4)c(Nc4ccc(N5CCC(N)CC5)nc4)c3c2)cc(Cl)c1O] | (4-(6-(4-aminopiperidin-1-yl)pyridin-3-ylamino)-6-(3-chloro-4-hydroxy-5-methoxyphenyl)quinolin-3-yl)(cyclopropyl)methanone | 544 |
| 551 | 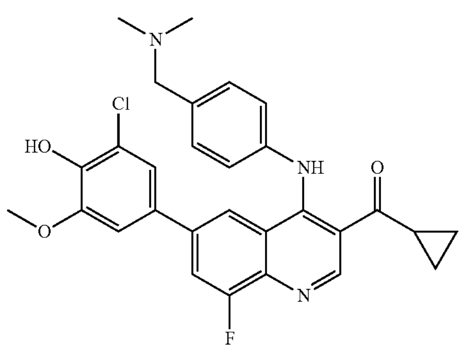 [SMILES: COc1cc(-c2cc(F)c3ncc(C(=O)C4CC4)c(Nc4ccc(CN(C)C)cc4)c3c2)cc(Cl)c1O] | (6-(3-chloro-4-hydroxy-5-methoxyphenyl)-4-(4-((dimethylamino)methyl)phenylamino)-8-fluoroquinolin-3-yl)(cyclopropyl)methanone | 520 |

TABLE 1-continued

| No. | Structure | Compound Name | ESI MS (m/z) |
|---|---|---|---|
| 552 | 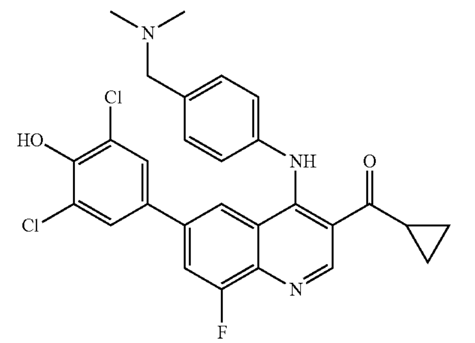 [SMILES: CN(C)Cc1ccc(Nc2c(C(=O)C3CC3)cnc3c(F)cc(-c4cc(Cl)c(O)c(Cl)c4)cc23)cc1] | cyclopropyl(6-(3,5-dichloro-4-hydroxyphenyl)-4-(4-((dimethylamino)methyl)phenylamino)-8-fluoro-quinolin-3-yl)methanone | 524 |
| 553 | 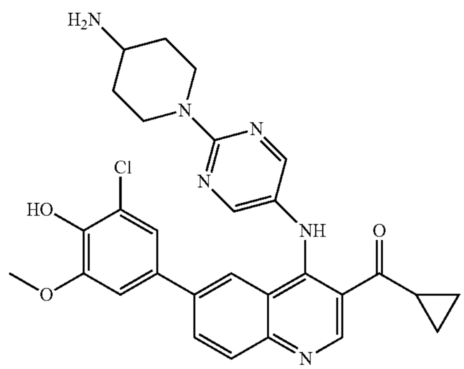 [SMILES: COc1cc(-c2ccc3ncc(C(=O)C4CC4)c(Nc4cnc(N5CCC(N)CC5)nc4)c3c2)cc(Cl)c1O] | (4-(2-(4-aminopiperidin-1-yl)pyrimidin-5-ylamino)-6-(3-chloro-4-hydroxy-5-methoxyphenyl)quinolin-3-yl)(cyclopropyl)methanone | 545 |
| 554 | 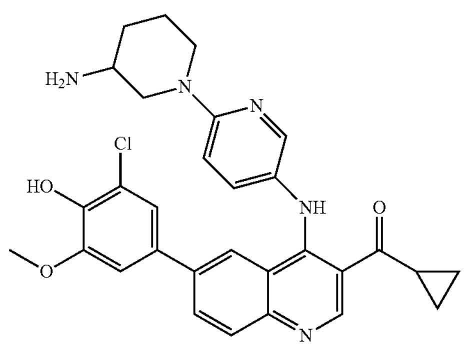 [SMILES: COc1cc(-c2ccc3ncc(C(=O)C4CC4)c(Nc4ccc(N5CCCC(N)C5)nc4)c3c2)cc(Cl)c1O] | (4-(6-(3-aminopiperidin-1-yl)pyridin-3-ylamino)-6-(3-chloro-4-hydroxy-5-methoxyphenyl)quinolin-3-yl)(cyclopropyl)methanone | 544 |
| 555 | 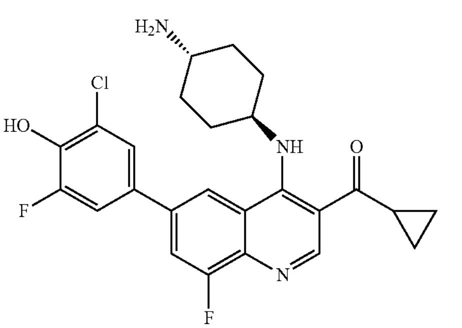 [SMILES: N[C@H]1CC[C@H](Nc2c(C(=O)C3CC3)cnc3c(F)cc(-c4cc(F)c(O)c(Cl)c4)cc23)CC1] | (4-(1R,4R)--4-aminocyclohexylamino)-6-(3-chloro-5-fluoro-4-hydroxy-phenyl)-8-fluoroquinolin-3-yl)(cyclo-propyl)methanone | 472 |

TABLE 1-continued

| No. | Structure | Compound Name | ESI MS (m/z) |
|---|---|---|---|
| 556 | 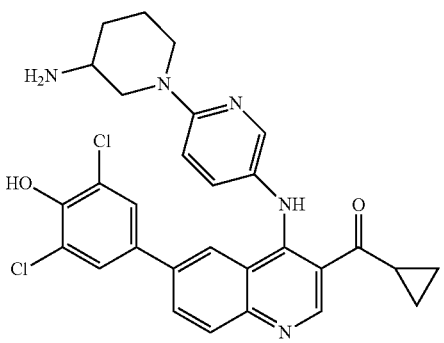 | (4-(6-(3-aminopiperidin-1-yl)pyridin-3-ylamino)-6-(3,5-dichloro-4-hydroxyphenyl)quinolin-3-yl)(cyclopropyl)methanone | 548 |
| 557 | 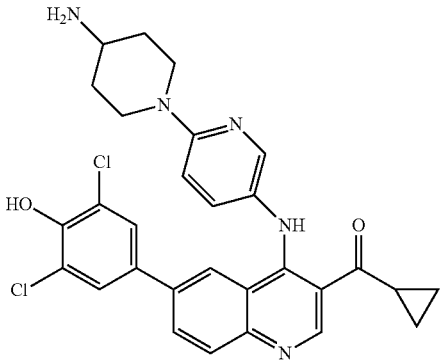 [SMILES: NC1CCN(c2ccc(Nc3c(C(=O)C4CC4)cnc4ccc(-c5cc(Cl)c(O)c(Cl)c5)cc34)cn2)CC1] | (4-(6-(4-aminopiperidin-1-yl)pyridin-3-ylamino)-6-(3-chloro-5-fluoro-4-hydroxyphenyl)quinolin-3-yl)(cyclopropyl)methanone | 532 |
| 558 | 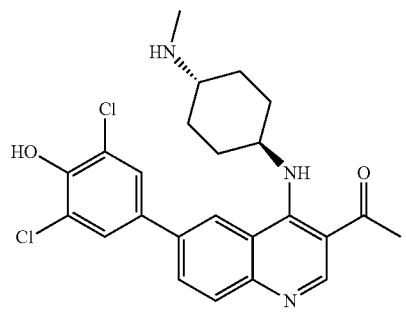 [SMILES: CN[C@H]1CC[C@H](Nc2c(C(C)=O)cnc3ccc(-c4cc(Cl)c(O)c(Cl)c4)cc23)CC1] | 1-(6-(3,5-dichloro-4-hydroxyphenyl)-4-(1R,4R)--4-(methylamino)cyclohexylamino)quinolin-3-yl)ethanone | 458 |
| 559 | 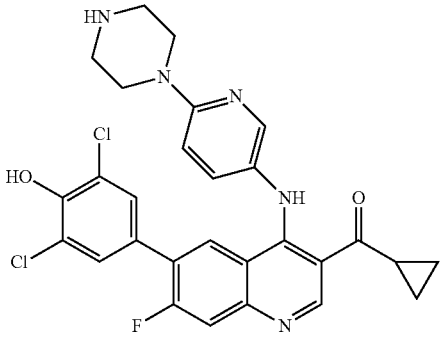 [SMILES: O=C(c1cnc2cc(F)c(-c3cc(Cl)c(O)c(Cl)c3)cc2c1Nc1ccc(N2CCNCC2)nc1)C1CC1] | cyclopropyl(6-(3,5-dichloro-4-hydroxyphenyl)-7-fluoro-4-(6-(piperazin-1-yl)pyridin-3-ylamino)quinolin-3-yl)methanone | 552 |

TABLE 1-continued

| No. | Structure | Compound Name | ESI MS (m/z) |
|---|---|---|---|
| 560 | 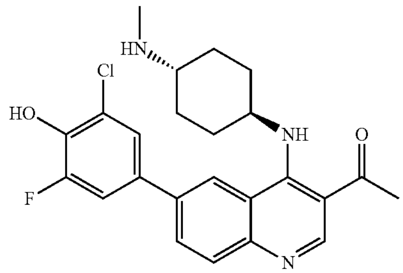 [SMILES: CN[C@H]1CC[C@H](Nc2c(C(C)=O)cnc3ccc(-c4cc(F)c(O)c(Cl)c4)cc23)CC1] | 1-(6-(3-chloro-5-fluoro-4-hydroxy-phenyl)-4-(1R,4R)--4-(methylamino)cyclohexylamino)quinolin-3-yl)ethanone | 442 |
| 561 | 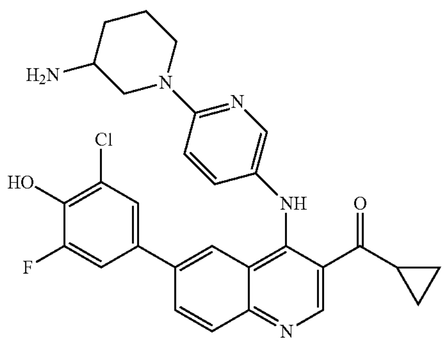 | (4-(6-(3-aminopiperidin-1-yl)pyridin-3-ylamino)-6-(3-chloro-5-fluoro-4-hydroxyphenyl)quinolin-3-yl)(cyclopropyl)methanone | 532 |
| 562 | 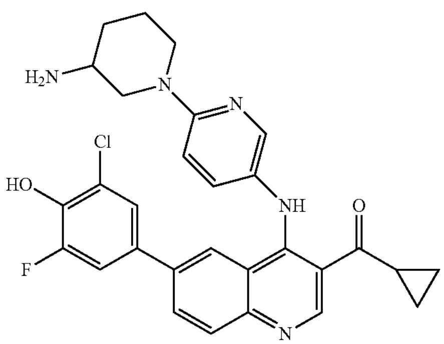 [SMILES: NC1CCCN(c2ccc(Nc3c(C(=O)C4CC4)cnc4ccc(-c5cc(F)c(O)c(Cl)c5)cc34)cn2)C1] | (4-(6-(3-aminopiperidin-1-yl)pyridin-3-ylamino)-6-(3-chloro-5-fluoro-4-hydroxyphenyl)quinolin-3-yl)(cyclopropyl)methanone hydrochloride | 532 |
| 563 | 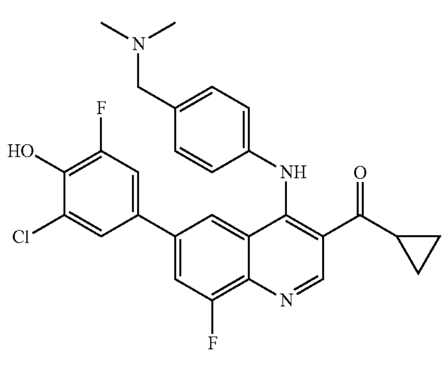 | (6-(3-chloro-5-fluoro-4-hydroxy-phenyl)-4-(4-((dimethylamnino)methyl)phenylamino)-8-fluoro-quinolin-3-yl)(cyclopropyl)methanone | 508 |

TABLE 1-continued

| No. | Structure | Compound Name | ESI MS (m/z) |
|---|---|---|---|
| 564 | 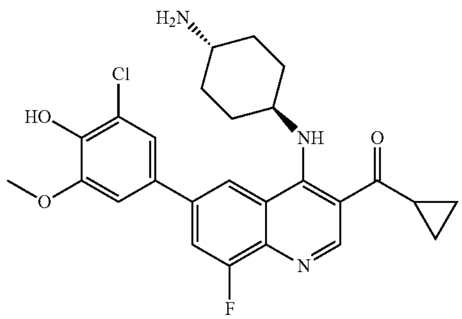 [SMILES: COc1cc(-c2cc(F)c3ncc(C(=O)C4CC4)c(N[C@H]4CC[C@H](N)CC4)c3c2)cc(Cl)c1O] | (4-(1R,4R)--4-aminocyclohexyl-amino)-6-(3-chloro-4-hydroxy-5-methoxyphenyl)-8-fluoroquinolin-3-yl)(cyclopropyl)methanone | 484 |
| 565 | 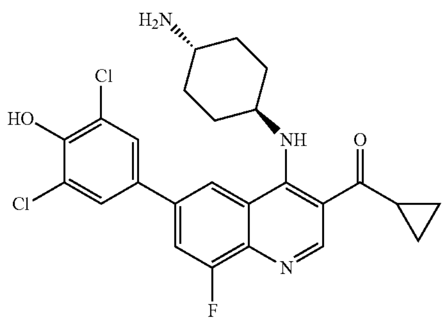 [SMILES: N[C@H]1CC[C@H](Nc2c(C(=O)C3CC3)cnc3c(F)cc(-c4cc(Cl)c(O)c(Cl)c4)cc23)CC1] | (4-(1R,4R)--4-aminocyclohexyl-amino)-6-(3,5-dichloro-4-hydroxy-phenyl)-8-fluoroquinolin-3-yl)(cyclopropyl)methanone | 488 |
| 566 | 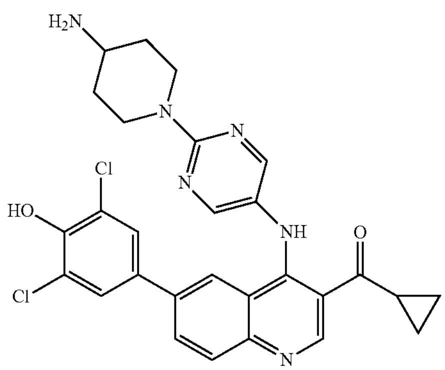 [SMILES: NC1CCN(c2ncc(Nc3c(C(=O)C4CC4)cnc4ccc(-c5cc(Cl)c(O)c(Cl)c5)cc34)cn2)CC1] | (4-(2-(4-aminopiperidin-1-yl)pyrimidin-5-ylamino)-6-(3,5-dichloro-4-hydroxyphenyl)quinolin-3-yl)(cyclopropyl)methanone | 549 |
| 567 | 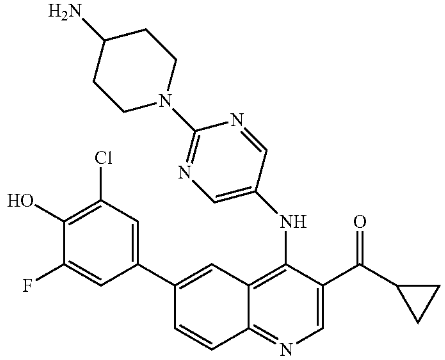 [SMILES: NC1CCN(c2ncc(Nc3c(C(=O)C4CC4)cnc4ccc(-c5cc(F)c(O)c(Cl)c5)cc34)cn2)CC1] | (4-(2-(4-aminopiperidin-1-yl)pyrimidin-5-ylamino)-6-(3-chloro-5-fluoro-4-hydroxyphenyl)quinolin-3-yl)(cyclopropyl)methanone | 533 |

TABLE 1-continued

| No. | Structure | Compound Name | ESI MS (m/z) |
|---|---|---|---|
| 568 | 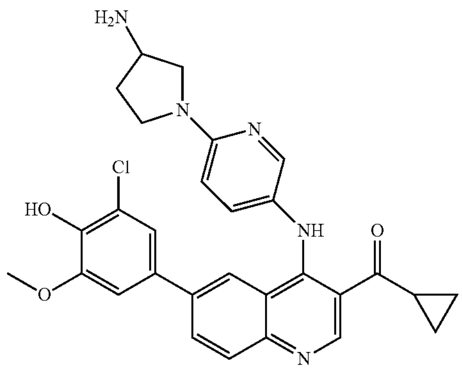 [SMILES: COc1cc(-c2ccc3ncc(C(=O)C4CC4)c(Nc4ccc(N5CCC(N)C5)nc4)c3c2)cc(Cl)c1O] | (4-(6-(3-aminopyrrolidin-1-yl)pyridin-3-ylamino)-6-(3-chloro-4-hydroxy-5-methoxyphenyl)quinolin-3-yl)(cyclopropyl)methanone | 530 |
| 569 | 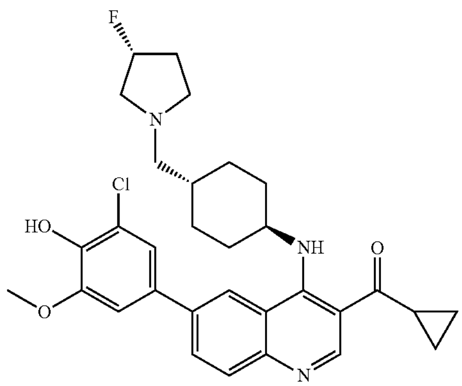 [SMILES: COc1cc(-c2ccc3ncc(C(=O)C4CC4)c(N[C@H]4CC[C@H](CN5CC[C@@H](F)C5)CC4)c3c2)cc(Cl)c1O] | (6-(3-chloro-4-hydroxy-5-methoxy-phenyl)-4-(1R,4R)--4-(((R)-3-fluoro-pyrrolidin-1-yl)methyl)cyclohexyl-amino)quinolin-3-yl)(cyclo-propyl)methanone | 552 |
| 570 | 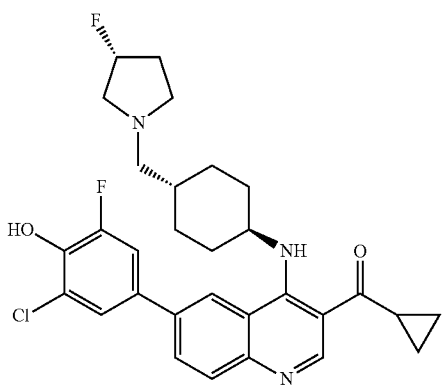 [SMILES: O=C(c1cnc2ccc(-c3cc(Cl)c(O)c(Cl)c3)cc2c1N[C@H]1CC[C@H](CN2CC[C@@H](F)C2)CC1)C1CC1] | (6-(3-chloro-5-fluoro-4-hydroxy-phenyl)-4-(1R,4R)--4-(((R)-3-fluoro-pyrrolidin-1-yl)methyl)cyclohexyl-amino)quinolin-3-yl)(cyclopropyl)methanone | 540 |
| 571 | 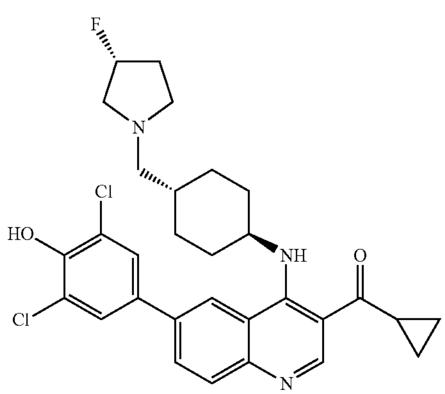 | cyclopropyl(6-(3,5-dichloro-4-hydroxy-phenyl)-4-(1R,4R)--4-(((R)-3-fluoro-pyrrolidin-1-yl)methyl)cyclohexyl-amino)quinolin-3-yl)methanone | 556 |

TABLE 1-continued

| No. | Structure | Compound Name | ESI MS (m/z) |
|---|---|---|---|
| 572 | 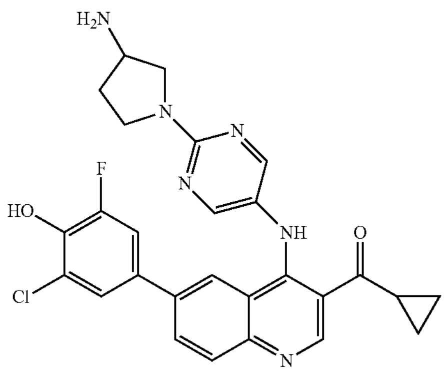 [SMILES: NC1CCN(c2ncc(Nc3c(C(=O)C4CC4)cnc4ccc(-c5cc(F)c(O)c(Cl)c5)cc34)cn2)C1] | (4-(2-(3-aminopyrrolidin-1-yl)pyrimidin-5-ylamino)-6-(3-chloro-5-fluoro-4-hydroxyphenyl)quinolin-3-yl)(cyclopropyl)methanone | 519 |
| 573 | 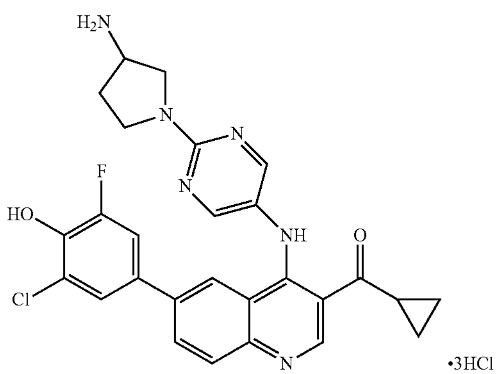 [SMILES: NC1CCN(c2ncc(Nc3c(C(=O)C4CC4)cnc4ccc(-c5cc(F)c(O)c(Cl)c5)cc34)cn2)C1] | (4-(2-(3-aminopyrrolidin-1-yl)pyrimidin-5-ylamino)-6-(3-chloro-5-fluoro-4-hydroxyphenyl)quinolin-3-yl)(cyclopropyl)methanone hydrochloride | 519 |
| 574 | 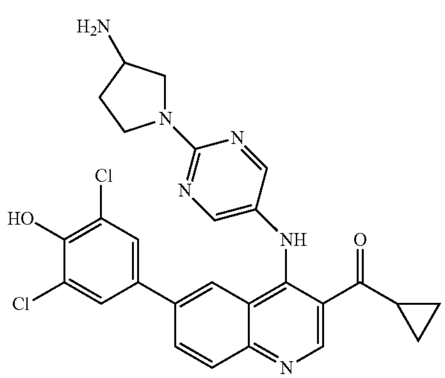 [SMILES: NC1CCN(c2ncc(Nc3c(C(=O)C4CC4)cnc4ccc(-c5cc(Cl)c(O)c(Cl)c5)cc34)cn2)C1] | (4-(2-(3-aminopyrrolidin-1-yl)pyrimidin-5-ylamino)-6-(3,5-dichloro-4-hydroxyphenyl)quinolin-3-yl)(cyclopropyl)methanone | 535 |
| 575 | 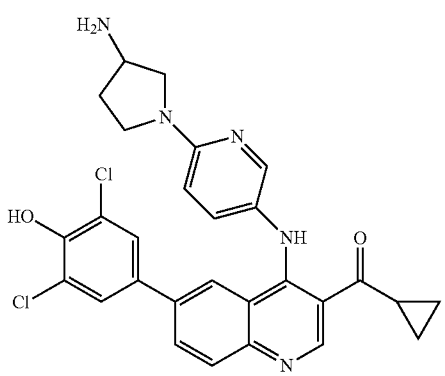 [SMILES: NC1CCN(c2ccc(Nc3c(C(=O)C4CC4)cnc4ccc(-c5cc(Cl)c(O)c(Cl)c5)cc34)cn2)C1] | (4-(6-(3-aminopyrrolidin-1-yl)pyridin-3-ylamino)-6-(3,5-dichloro-4-hydroxyphenyl)quinolin-3-yl)(cyclopropyl)methanone | 534 |

TABLE 1-continued

| No. | Structure | Compound Name | ESI MS (m/z) |
|---|---|---|---|
| 576 | 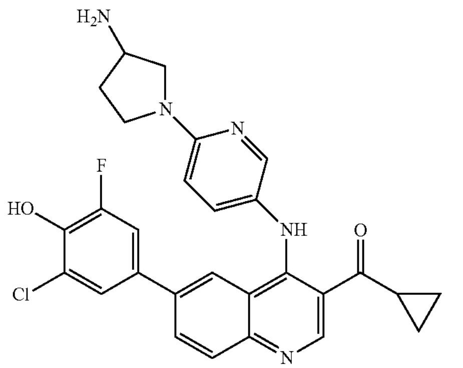 [SMILES: NC1CCN(c2ccc(Nc3c(C(=O)C4CC4)cnc4ccc(-c5cc(F)c(O)c(Cl)c5)cc34)cn2)C1] | (4-(6-(3-aminopyrrolidin-1-yl)pyridin-3-ylamino)-6-(3-chloro-5-fluoro-4-hydroxyphenyl)quinolin-3-yl)(cyclopropyl)methanone | 518 |
| 577 | 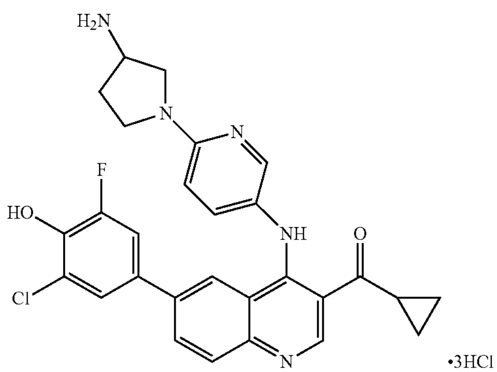 [SMILES: NC1CCN(c2ccc(Nc3c(C(=O)C4CC4)cnc4ccc(-c5cc(F)c(O)c(Cl)c5)cc34)cn2)C1] | (4-(6-(3-aminopyrrolidin-1-yl)pyridin-3-ylamino)-6-(3-chloro-5-fluoro-4-hydroxyphenyl)quinolin-3-yl)(cyclopropyl)methanone hydrochloride) | 518 |
| 578 | 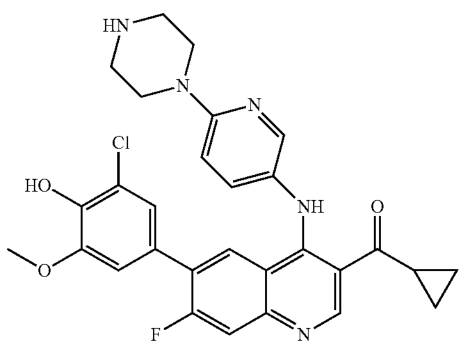 [SMILES: COc1cc(-c2cc3c(Nc4ccc(N5CCNCC5)nc4)c(C(=O)C4CC4)cnc3cc2F)cc(Cl)c1O] | (6-(3-chloro-4-hydroxy-5-methoxyphenyl)-7-fluoro-4-(6-(piperazin-1-yl)pyridin-3-ylamino)quinolin-3-yl)(cyclopropyl)methanone | 548 |
| 579 | 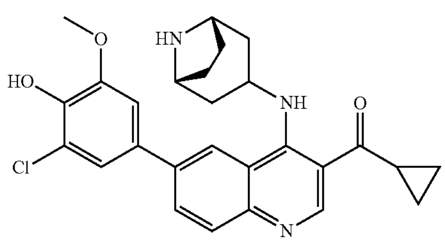 [SMILES: COc1cc(-c2ccc3ncc(C(=O)C4CC4)c(NC4C[C@H]5CC[C@@H](C4)N5)c3c2)cc(Cl)c1O] | (4-((1R,3r,5S)-8-azabicyclo[3.2.1]octan-3-ylamino)-6-(3-chloro-4-hydroxy-5-methoxyphenyl)quinolin-3-yl)(cyclopropyl)methanone | 478 |
| 580 | 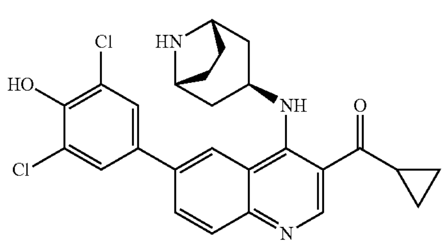 [SMILES: O=C(c1cnc2ccc(-c3cc(Cl)c(O)c(Cl)c3)cc2c1N[C@H]1C[C@H]2CC[C@@H](C1)N2)C1CC1] | (4-((1R,3r,5S)-8-azabicyclo[3.2.1]octan-3-ylamino)-6-(3,5-dichloro-4-hydroxyphenyl)quinolin-3-yl)(cyclopropyl)methanone | 482 |

TABLE 1-continued

| No. | Structure | Compound Name | ESI MS (m/z) |
|---|---|---|---|
| 581 | 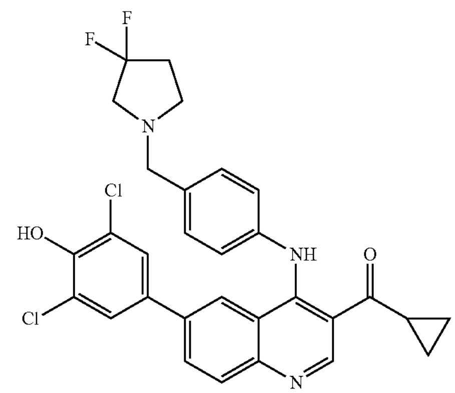 [SMILES: O=C(c1cnc2ccc(-c3cc(Cl)c(O)c(Cl)c3)cc2c1Nc1ccc(CN2CCC(F)(F)C2)cc1)C1CC1] | cyclopropyl(6-(3,5-dichloro-4-hydroxyphenyl)-4-(4-((3,3-difluoropyrrolidin-1-yl)methyl)phenylamino)quinolin-3-yl)methanone | 568 |
| 582 | 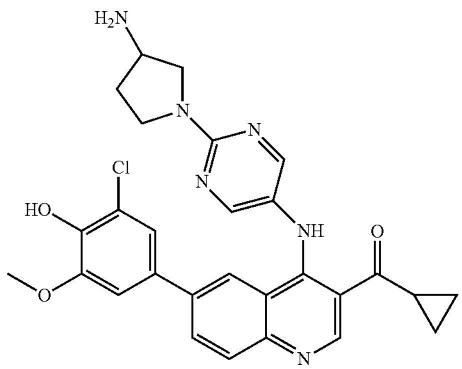 [SMILES: COc1cc(-c2ccc3ncc(C(=O)C4CC4)c(Nc4cnc(N5CCC(N)C5)nc4)c3c2)cc(Cl)c1O] | (4-(2-(3-aminopyrrolidin-1-yl)pyrimidin-5-ylamino)-6-(3-chloro-4-hydroxy-5-methoxyphenyl)quinolin-3-yl)(cyclopropyl)methanone | 531 |
| 583 | 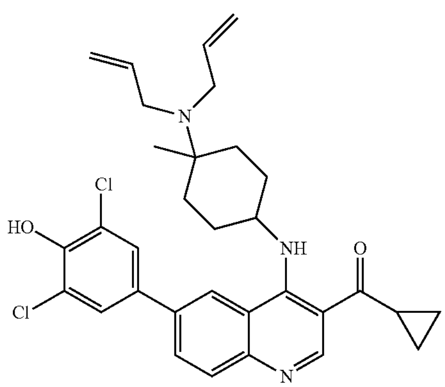 [SMILES: C=CCN(CC=C)C1(C)CCC(Nc2c(C(=O)C3CC3)cnc3ccc(-c4cc(Cl)c(O)c(Cl)c4)cc23)CC1] | cyclopropyl(4-(4-(diallylamino)-4-methylcyclohexylamino)-6-(3,5-dichloro-4-hydroxyphenyl)quinolin-3-yl)methanone | 565 |
| 584 | 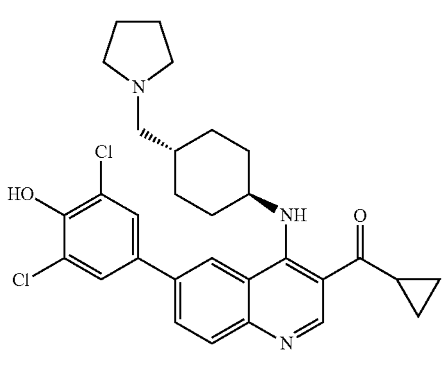 | cyclopropyl(6-(3,5-dichloro-4-hydroxyphenyl)-4-(1R,4R)--4-(pyrrolidin-1-ylmethyl)cyclohexylamino)quinolin-3-yl)methanone | 539 |

TABLE 1-continued

| No. | Structure | Compound Name | ESI MS (m/z) |
|---|---|---|---|
| 585 | 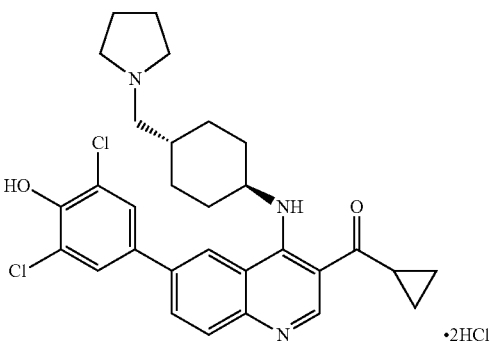 [SMILES: O=C(c1cnc2ccc(-c3cc(Cl)c(O)c(Cl)c3)cc2c1N[C@H]1CC[C@H](CN2CCCC2)CC1)C1CC1] | cyclopropyl(6-(3,5-dichloro-4-hydroxy-phenyl)-4-(1R,4R)--4-(pyrrolidin-1-ylmethyl)cyclohexylamino)quinolin-3-yl)methanone hydrochloride | 539 |
| 586 | 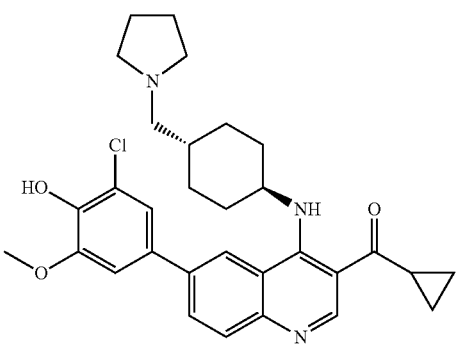 [SMILES: COc1cc(-c2ccc3ncc(C(=O)C4CC4)c(N[C@H]4CC[C@H](CN5CCCC5)CC4)c3c2)cc(Cl)c1O] | (6-(3-chloro-4-hydroxy-5-methoxy-phenyl)-4-(1R,4R)--4-(pyrrolidin-1-ylmethyl)cyclohexylamino)quinolin-3-yl)(cyclopropyl)methanone | 534 |
| 587 | 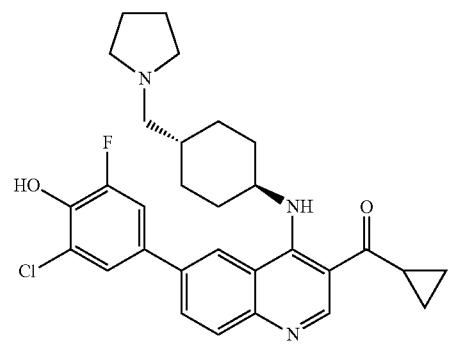 [SMILES: O=C(c1cnc2ccc(-c3cc(F)c(O)c(Cl)c3)cc2c1N[C@H]1CC[C@H](CN2CCCC2)CC1)C1CC1] | (6-(3-chloro-5-fluoro-4-hydroxy-phenyl)-4-(1R,4R)--4-(pyrrolidin-1-ylmethyl)cyclohexylamino)quinolin-3-yl)(cyclopropyl)methanone | 522 |
| 588 | 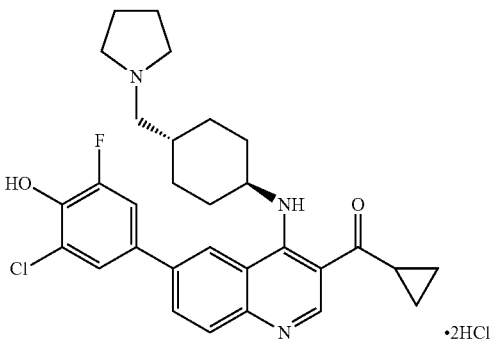 | (6-(3-chloro-5-fluoro-4-hydroxyphenyl)-4-(1R,4R)--4-(pyrrolidin-1-ylmethyl)cyclohexylamino)quinolin-3-yl)(cyclopropyl)methanone hydrochloride | 522 |

TABLE 1-continued

| No. | Structure | Compound Name | ESI MS (m/z) |
|---|---|---|---|
| 589 | 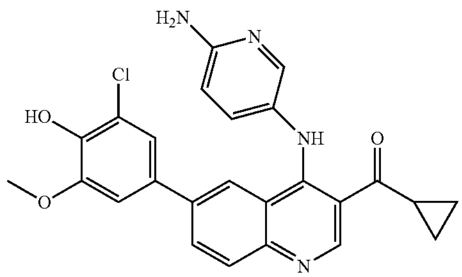 [SMILES: COc1cc(-c2ccc3ncc(C(=O)C4CC4)c(Nc4ccc(N)nc4)c3c2)cc(Cl)c1O] | (4-(6-aminopyridin-3-ylamino)-6-(3-chloro-4-hydroxy-5-methoxyphenyl)quinolin-3-yl)(cyclopropyl)methanone | 461 |
| 590 | 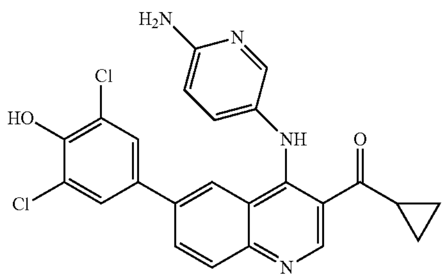 [SMILES: Nc1ccc(Nc2c(C(=O)C3CC3)cnc3ccc(-c4cc(Cl)c(O)c(Cl)c4)cc23)cn1] | (4-(6-aminopyridin-3-ylamino)-6-(3,5-dichloro-4-hydroxyphenyl)quinolin-3-yl)(cyclopropyl)methanone | 465 |
| 591 | 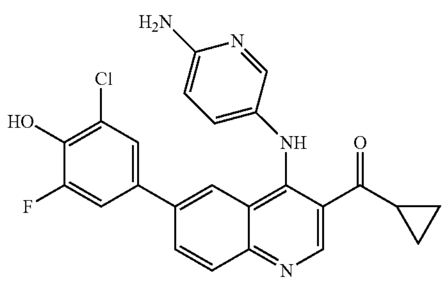 [SMILES: Nc1ccc(Nc2c(C(=O)C3CC3)cnc3ccc(-c4cc(F)c(O)c(Cl)c4)cc23)cn1] | (4-(6-aminopyridin-3-ylamino)-6-(3-chloro-5-fluoro-4-hydroxyphenyl)quinolin-3-yl)(cyclopropyl)methanone | 449 |
| 592 | 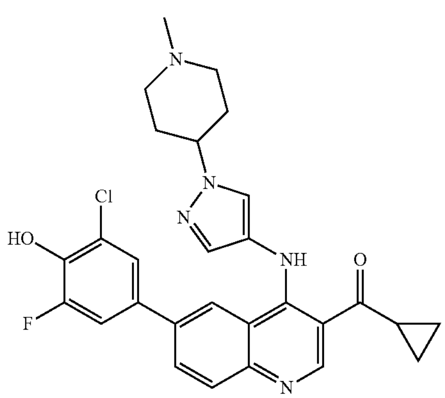 [SMILES: CN1CCC(n2cc(Nc3c(C(=O)C4CC4)cnc4ccc(-c5cc(F)c(O)c(Cl)c5)cc34)cn2)CC1] | (6-(3-chloro-5-fluoro-4-hydroxyphenyl)-4-(1-(1-methylpiperidin-4-yl)-1H-pyrazol-4-ylamino)quinolin-3-yl)(cyclopropyl)methanone | 520 |

US 9,120,749 B2

319                                                                                  320

TABLE 1-continued

| No. | Structure | Compound Name | ESI MS (m/z) |
|---|---|---|---|
| 593 | 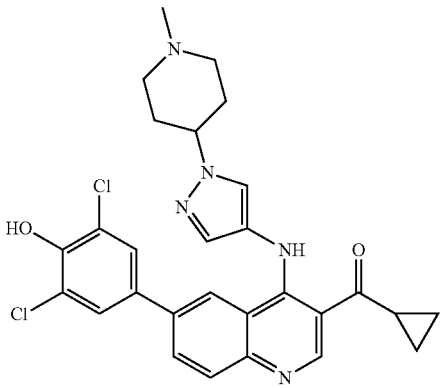 | cyclopropyl(6-(3,5-dichloro-4-hydroxy-phenyl)-4-(1-(1-methylpiperidin-4-yl)-1H-pyrazol-4-ylamino)quinolin-3-yl)methanone | 536 |
| 594 | 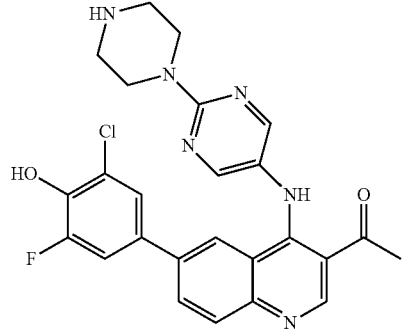 [SMILES: CC(=O)c1cnc2ccc(-c3cc(F)c(O)c(Cl)c3)cc2c1Nc1cnc(N2CCNCC2)nc1] | 1-(6-(3-chloro-5-fluoro-4-hydroxy-phenyl)-4-(2-(piperazin-1-yl)pyrimidin-5-ylamino)quinolin-3-yl)ethanone | 493 |
| 595 | 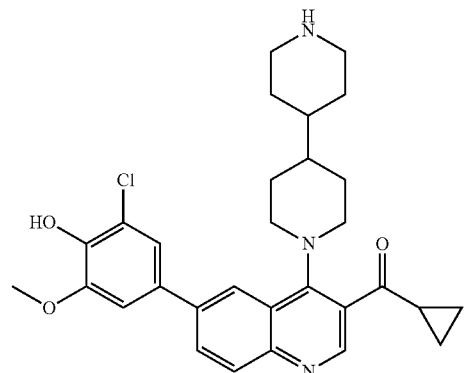 | (4-(4,4'-bipiperidin-1-yl)-6-(3-chloro-4-hydroxy-5-methoxyphenyl)quinolin-3-yl)(cyclopropyl)methanone | 520 |
| 596 | 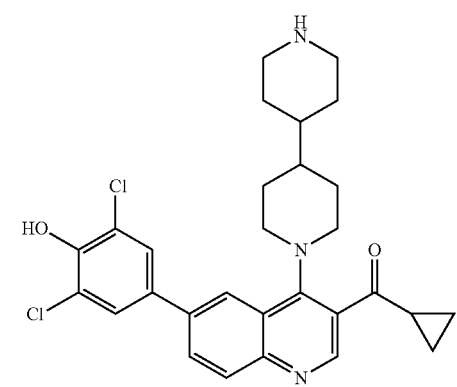 [SMILES: O=C(c1cnc2ccc(-c3cc(Cl)c(O)c(Cl)c3)cc2c1N1CCC(C2CCNCC2)CC1)C1CC1] | (4-(4,4'-bipiperidin-1-yl)-6-(3,5-dichloro-4-hydroxyphenyl)quinolin-3-yl)(cyclopropyl)methanone | 524 |

TABLE 1-continued

| No. | Structure | Compound Name | ESI MS (m/z) |
|---|---|---|---|
| 597 | 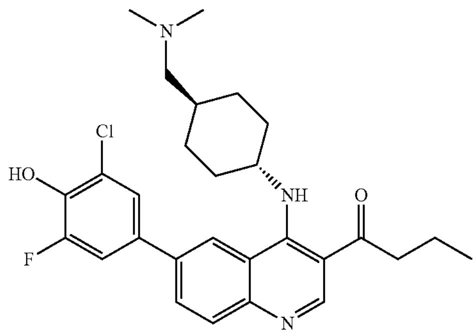 [SMILES: CCCC(=O)c1cnc2ccc(-c3cc(F)c(O)c(Cl)c3)cc2c1N[C@H]1CC[C@H](CN(C)C)CC1] | 1-(6-(3-chloro-5-fluoro-4-hydroxy-phenyl)-4-(1R,4R)--4-((dimethylamino)methyl)cyclohexylamino)quinolin-3-yl)butan-1-one | 498 |
| 598 | 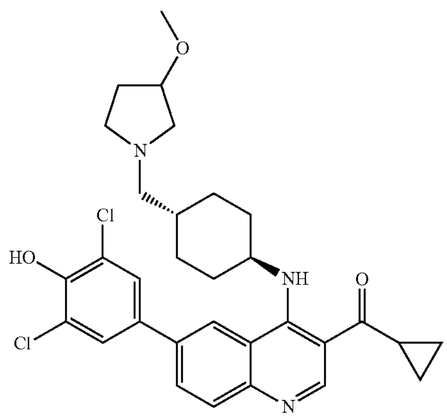 [SMILES: COC1CCN(C[C@H]2CC[C@H](Nc3c(C(=O)C4CC4)cnc4ccc(-c5cc(Cl)c(O)c(Cl)c5)cc34)CC2)C1] | cyclopropyl(6-(3,5-dichloro-4-hydroxy-phenyl)-4-(1R,4R)--4-((3-methoxy-pyrrolidin-1-yl)methyl)cyclohexyl-amino)quinolin-3-yl)methanone | 569 |
| 599 | 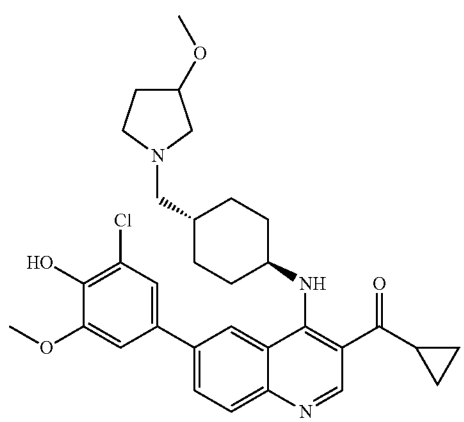 [SMILES: COc1cc(-c2ccc3ncc(C(=O)C4CC4)c(N[C@H]4CC[C@H](CN5CCC(OC)C5)CC4)c3c2)cc(Cl)c1O] | (6-(3-chloro-4-hydroxy-5-methoxy-phenyl)-4-(1R,4R)--4-((3-methoxy-pyrrolidin-1-yl)methyl)cyclohexyl-amino)quinolin-3-yl)(cyclopropyl)methanone | 564 |
| 600 | 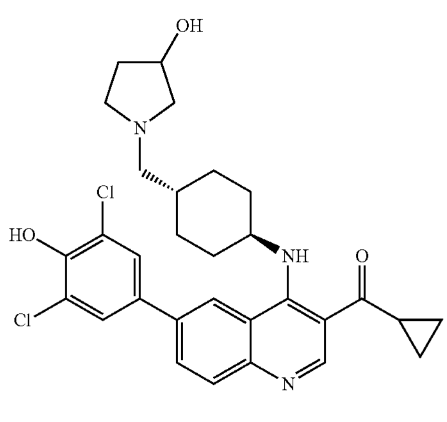 [SMILES: O=C(c1cnc2ccc(-c3cc(Cl)c(O)c(Cl)c3)cc2c1N[C@H]1CC[C@H](CN2CCC(O)C2)CC1)C1CC1] | cyclopropyl(6-(3,5-dichloro-4-hydroxy-phenyl)-4-(1R,4R)--4-((3-hydroxy-pyrrolidin-1-yl)methyl)cyclohexyl-amino)quinolin-3-yl)methanone | 555 |

| No. | Structure | Compound Name | ESI MS (m/z) |
|---|---|---|---|
| 601 | 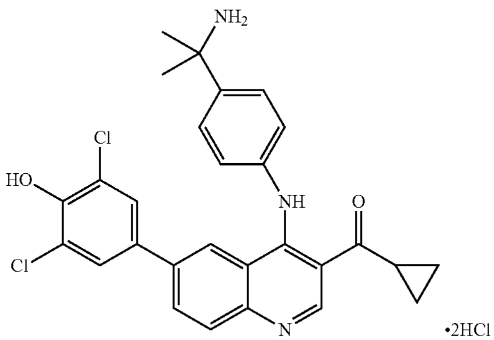 [SMILES: CC(C)(N)c1ccc(Nc2c(C(=O)C3CC3)cnc3ccc(-c4cc(Cl)c(O)c(Cl)c4)cc23)cc1] | (4-(4-(2-aminopropan-2-yl)phenyl-amino)-6-(3,5-dichloro-4-hydroxy-phenyl)quinolin-3-yl)(cyclopropyl)methanone hydrochloride | 506 |
| 602 | 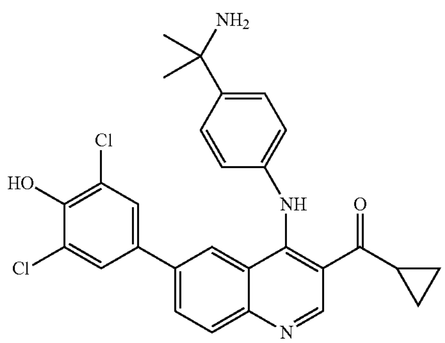 [SMILES: CC(C)(N)c1ccc(Nc2c(C(=O)C3CC3)cnc3ccc(-c4cc(Cl)c(O)c(Cl)c4)cc23)cc1] | (4-(4-(2-aminopropan-2-yl)phenyl-amino)-6-(3,5-dichloro-4-hydroxy-phenyl)quinolin-3-yl)(cyclopropyl)methanone | 506 |
| 603 | 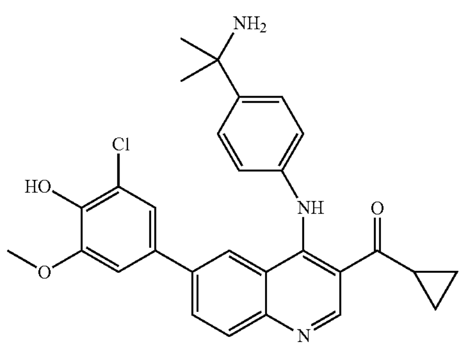 [SMILES: COc1cc(-c2ccc3ncc(C(=O)C4CC4)c(Nc4ccc(C(C)(C)N)cc4)c3c2)cc(Cl)c1O] | (4-(4-(2-aminopropan-2-yl)phenyl-amino)-6-(3-chloro-4-hydroxy-5-methoxyphenyl)quinolin-3-yl)(cyclopropyl)methanone | 502 |
| 604 | 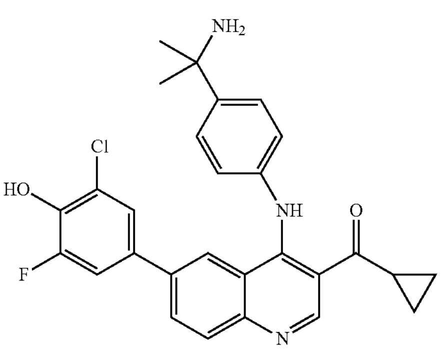 [SMILES: CC(C)(N)c1ccc(Nc2c(C(=O)C3CC3)cnc3ccc(-c4cc(F)c(O)c(Cl)c4)cc23)cc1] | (4-(4-(2-aminopropan-2-yl)phenyl-amino)-6-(3-chloro-5-fluoro-4-hydroxyphenyl)quinolin-3-yl)(cyclopropyl)methanone | 490 |

TABLE 1-continued

| No. | Structure | Compound Name | ESI MS (m/z) |
|---|---|---|---|
| 605 | 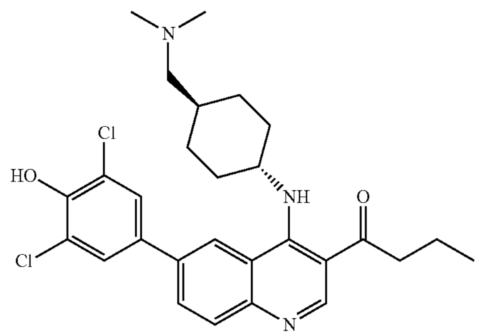 [SMILES: CCCC(=O)c1cnc2ccc(-c3cc(Cl)c(O)c(Cl)c3)cc2c1N[C@H]1CC[C@H](CN(C)C)CC1] | 1-(6-(3,5-dichloro-4-hydroxyphenyl)-4-(1R,4R)--4-((dimethylamino)methyl) cyclohexylamino)quinolin-3-yl) butan-1-one | 514 |
| 606 | 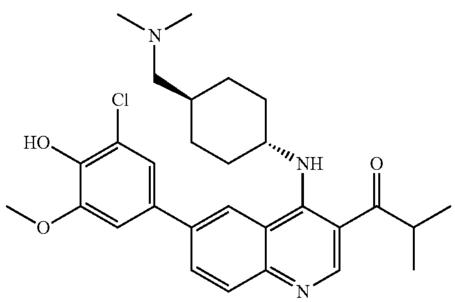 [SMILES: COc1cc(-c2ccc3ncc(C(=O)C(C)C)c(N[C@H]4CC[C@H](CN(C)C)CC4)c3c2)cc(Cl)c1O] | 1-(6-(3-chloro-4-hydroxy-5-methoxy-phenyl)-4-(1R,4R)--4-((dimethyl-amino)methyl)cyclohexylamino) quinolin-3-yl)-2-methylpropan-1-one | 510 |
| 607 | 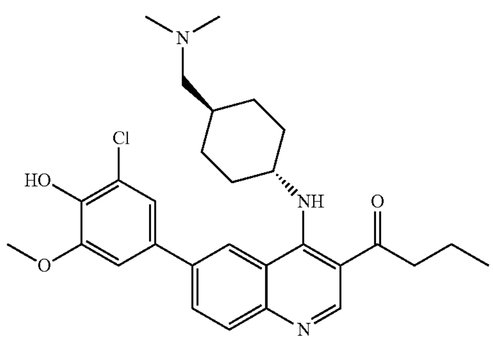 [SMILES: CCCC(=O)c1cnc2ccc(-c3cc(Cl)c(O)c(OC)c3)cc2c1N[C@H]1CC[C@H](CN(C)C)CC1] | 1-(6-(3-chloro-4-hydroxy-5-methoxy-phenyl)-4-(1R,4R)--4-((dimethyl-amino)methyl)cyclohexylamino) quinolin-3-yl)butan-1-one | 510 |
| 608 | 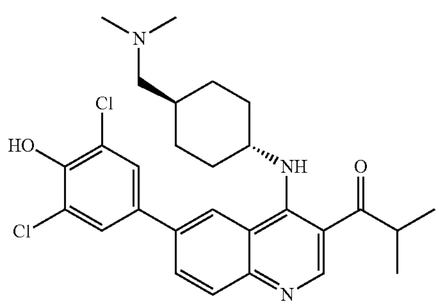 [SMILES: CC(C)C(=O)c1cnc2ccc(-c3cc(Cl)c(O)c(Cl)c3)cc2c1N[C@H]1CC[C@H](CN(C)C)CC1] | 1-(6-(3,5-dichloro-4-hydroxyphenyl)-4-(1R,4R)--4-((dimethylamino) methyl)cyclohexylamino)quinolin-3-yl)-2-methylpropan-1-one | 514 |

TABLE 1-continued

| No. | Structure | Compound Name | ESI MS (m/z) |
|---|---|---|---|
| 609 | 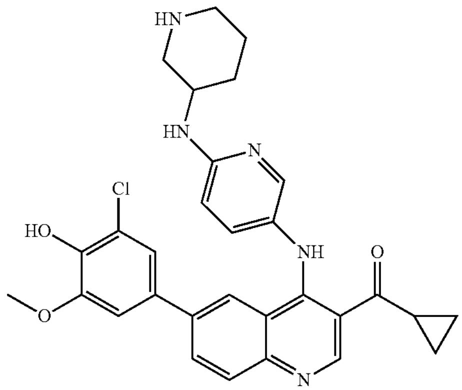 [SMILES: COc1cc(-c2ccc3ncc(C(=O)C4CC4)c(Nc4ccc(NC5CCCNC5)nc4)c3c2)cc(Cl)c1O] | (6-(3-chloro-4-hydroxy-5-methoxy-phenyl)-4-(6-(piperidin-3-ylamino)pyridin-3-ylamino)quinolin-3-yl)(cyclopropyl)methanone | 544 |
| 610 | 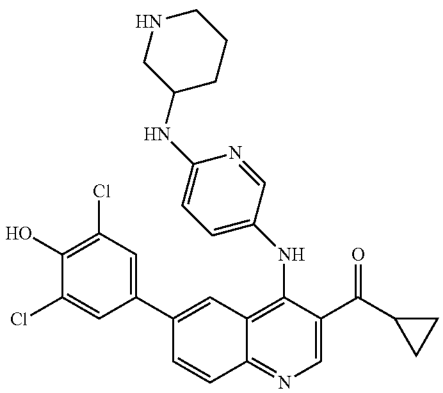 [SMILES: O=C(c1cnc2ccc(-c3cc(Cl)c(O)c(Cl)c3)cc2c1Nc1ccc(NC2CCCNC2)nc1)C1CC1] | cyclopropyl(6-(3,5-dichloro-4-hydroxy-phenyl)-4-(6-(piperidin-3-ylamino)pyridin-3-ylamino)quinolin-3-yl)methanone | 548 |
| 611 | 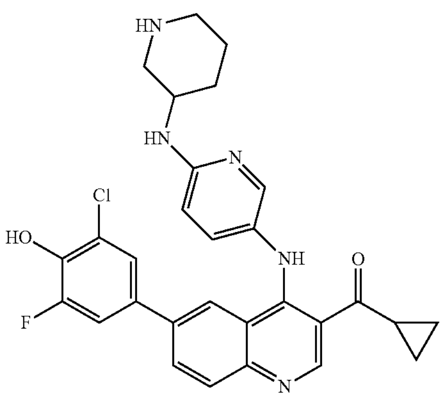 [SMILES: O=C(c1cnc2ccc(-c3cc(F)c(O)c(Cl)c3)cc2c1Nc1ccc(NC2CCCNC2)nc1)C1CC1] | (6-(3-chloro-5-fluoro-4-hydroxy-phenyl)-4-(6-(piperidin-3-ylamino)pyridin-3-ylamino)quinolin-3-yl)(cyclopropyl)methanone | 532 |
| 612 | 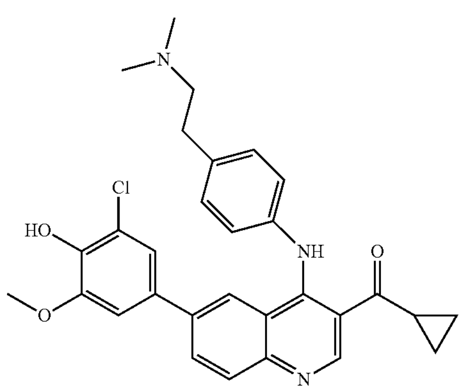 [SMILES: COc1cc(-c2ccc3ncc(C(=O)C4CC4)c(Nc4ccc(CCN(C)C)cc4)c3c2)cc(Cl)c1O] | (6-(3-chloro-4-hydroxy-5-methoxy-phenyl)-4-(4-(2-(dimethylamino)ethyl)phenylamino)quinolin-3-yl)(cyclopropyl)methanone | 516 |

TABLE 1-continued

| No. | Structure | Compound Name | ESI MS (m/z) |
|---|---|---|---|
| 613 | 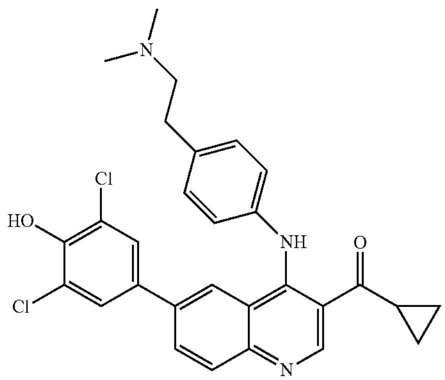 [SMILES: CN(C)CCc1ccc(Nc2c(C(=O)C3CC3)cnc3ccc(-c4cc(Cl)c(O)c(Cl)c4)cc23)cc1] | cyclopropyl(6-(3,5-dichloro-4-hydroxyphenyl)-4-(4-(2-(dimethylamino)ethyl)phenylamino)quinolin-3-yl)methanone | 520 |
| 614 | •2HCl | cyclopropyl(6-(3,5-dichloro-4-hydroxyphenyl)-4-(4-(2-(dimethylamino)ethyl)phenylamino)quinolin-3-yl)methanone hydrochloride | 520 |
| 615 | 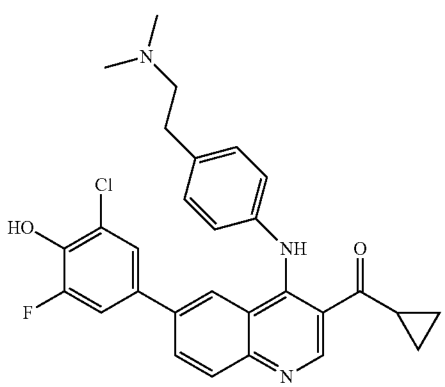 [SMILES: CN(C)CCc1ccc(Nc2c(C(=O)C3CC3)cnc3ccc(-c4cc(F)c(O)c(Cl)c4)cc23)cc1] | (6-(3-chloro-5-fluoro-4-hydroxyphenyl)-4-(4-(2-(dimethylamino)ethyl)phenylamino)quinolin-3-yl)(cyclopropyl)methanone | 504 |
| 616 | 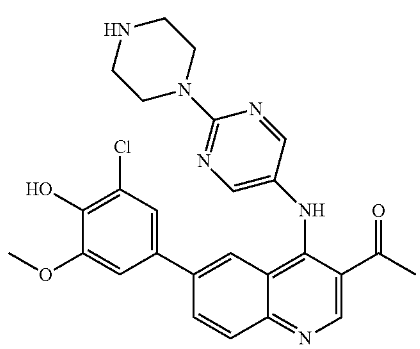 [SMILES: COc1cc(-c2ccc3ncc(C(C)=O)c(Nc4cnc(N5CCNCC5)nc4)c3c2)cc(Cl)c1O] | 1-(6-(3-chloro-4-hydroxy-5-methoxyphenyl)-4-(2-(piperazin-1-yl)pyrimidin-5-ylamino)quinolin-3-yl)ethanone | 505 |

TABLE 1-continued

| No. | Structure | Compound Name | ESI MS (m/z) |
|---|---|---|---|
| 617 | 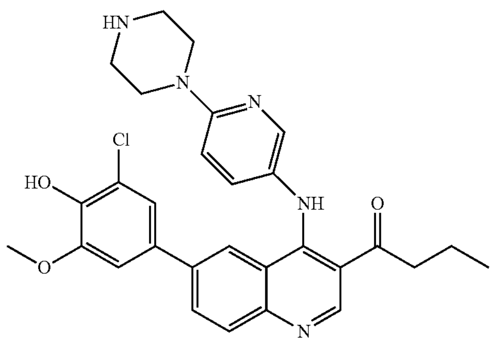 [SMILES: CCCC(=O)c1cnc2ccc(-c3cc(Cl)c(O)c(OC)c3)cc2c1Nc1ccc(N2CCNCC2)nc1] | 1-(6-(3-chloro-4-hydroxy-5-methoxy-phenyl)-4-(6-(piperazin-1-yl)pyridin-3-ylamino)quinolin-3-yl)butan-1-one | 532 |
| 618 | 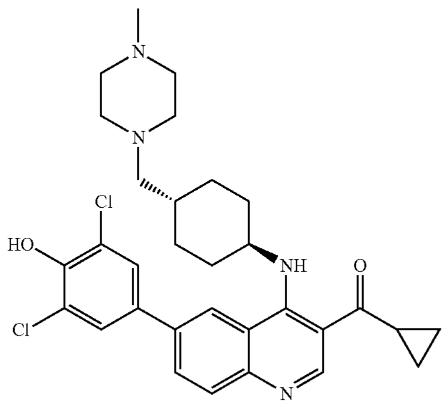 | cyclopropyl(6-(3,5-dichloro-4-hydroxy-phenyl)-4-(1R,4R)--4-((4-methyl-piperazin-1-yl)methyl)cyclohexyl-amino)quinolin-3-yl)methanone | 568 |
| 619 | 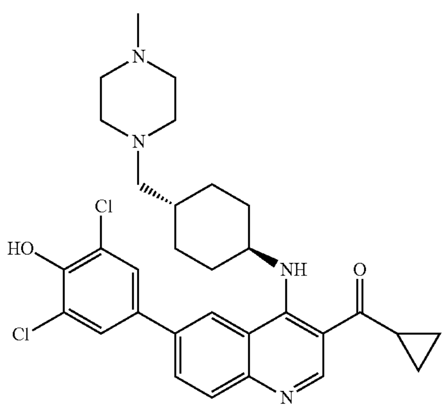 [SMILES: CN1CCN(C[C@H]2CC[C@H](Nc3c(C(=O)C4CC4)cnc4ccc(-c5cc(Cl)c(O)c(Cl)c5)cc34)CC2)CC1] | cyclopropyl(6-(3,5-dichloro-4-hydroxy-phenyl)-4-(1R,4R)--4-((4-methyl-piperazin-1-yl)methyl)cyclohexyl-amino)quinolin-3-yl)methanone hydrochloride | 568 |
| 620 | 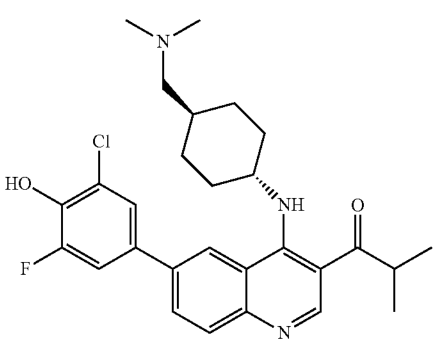 [SMILES: CC(C)C(=O)c1cnc2ccc(-c3cc(F)c(O)c(Cl)c3)cc2c1N[C@H]1CC[C@H](CN(C)C)CC1] | 1-(6-(3-chloro-5-fluoro-4-hydroxy-phenyl)-4-(1R,4R)--4-((dimethylamino)methyl)cyclohexylamino)quinolin-3-yl)-2-methylpropan-1-one | 498 |

TABLE 1-continued

| No. | Structure | Compound Name | ESI MS (m/z) |
|---|---|---|---|
| 621 | 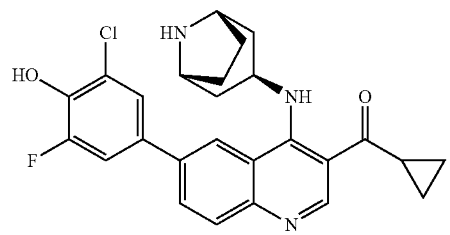 [SMILES: O=C(c1cnc2ccc(-c3cc(F)c(O)c(Cl)c3)cc2c1N[C@H]1C[C@H]2CC[C@@H](C1)N2)C1CC1] | (4-((1R,3r,5S)-8-azabicyclo[3.2.1]octan-3-ylamino)-6-(3-chloro-5-fluoro-4-hydroxyphenyl)quinolin-3-yl)(cyclopropyl)methanone | 466 |
| 622 | 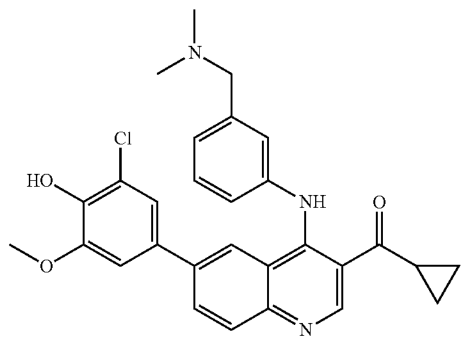 [SMILES: COc1cc(-c2ccc3ncc(C(=O)C4CC4)c(Nc4cccc(CN(C)C)c4)c3c2)cc(Cl)c1O] | (6-(3-chloro-4-hydroxy-5-methoxyphenyl)-4-(3-((dimethylamino)methyl)phenylamino)quinolin-3-yl)(cyclopropyl)methanone | 502 |
| 623 | 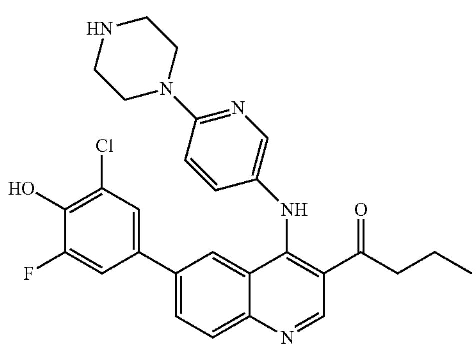 [SMILES: CCCC(=O)c1cnc2ccc(-c3cc(F)c(O)c(Cl)c3)cc2c1Nc1ccc(N2CCNCC2)nc1] | 1-(6-(3-chloro-5-fluoro-4-hydroxyphenyl)-4-(6-(piperazin-1-yl)pyridin-3-ylamino)quinolin-3-yl)butan-1-one | 520 |
| 624 | 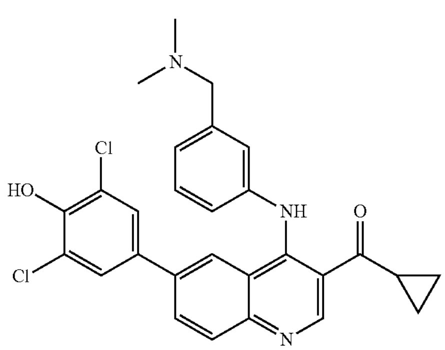 [SMILES: CN(C)Cc1cccc(Nc2c(C(=O)C3CC3)cnc3ccc(-c4cc(Cl)c(O)c(Cl)c4)cc23)c1] | cyclopropyl(6-(3,5-dichloro-4-hydroxyphenyl)-4-(3-((dimethylamino)methyl)phenylamino)quinolin-3-yl)methanone | 506 |

TABLE 1-continued

| No. | Structure | Compound Name | ESI MS (m/z) |
|---|---|---|---|
| 625 | 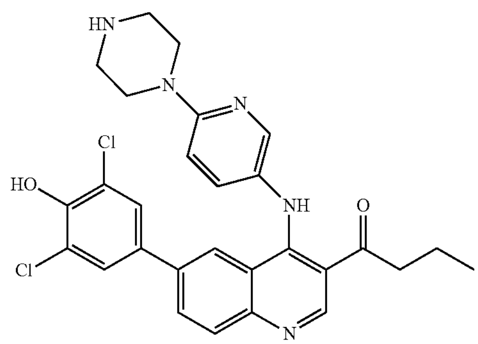 [SMILES: CCCC(=O)c1cnc2ccc(-c3cc(Cl)c(O)c(Cl)c3)cc2c1Nc1ccc(N2CCNCC2)nc1] | 1-(6-(3,5-dichloro-4-hydroxyphenyl)-4-(6-(piperazin-1-yl)pyridin-3-ylamino)quinolin-3-yl)butan-1-one | 536 |
| 626 | 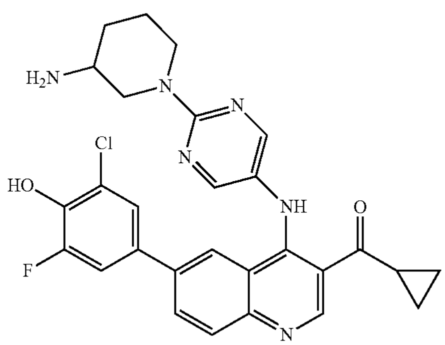 [SMILES: NC1CCCN(c2ncc(Nc3c(C(=O)C4CC4)cnc4ccc(-c5cc(F)c(O)c(Cl)c5)cc34)cn2)C1] | (4-(2-(3-aminopiperidin-1-yl)pyrimidin-5-ylamino)-6-(3-chloro-5-fluoro-4-hydroxyphenyl)quinolin-3-yl)(cyclopropyl)methanone | 533 |
| 627 | 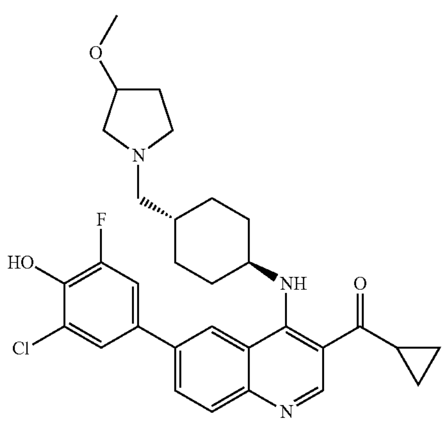 [SMILES: COC1CCN(C[C@H]2CC[C@H](Nc3c(C(=O)C4CC4)cnc4ccc(-c5cc(F)c(O)c(Cl)c5)cc34)CC2)C1] | (6-(3-chloro-5-fluoro-4-hydroxyphenyl)-4-(1R,4R)--4-((3-methoxypyrrolidin-1-yl)methyl)cyclohexylamino)quinolin-3-yl)(cyclopropyl)methanone | 552 |
| 628 | 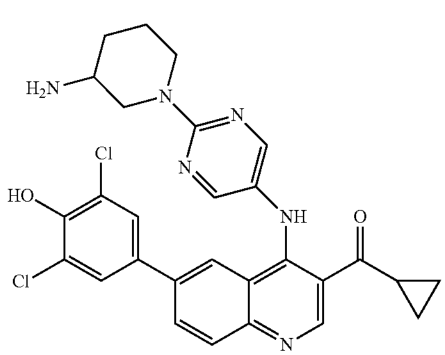 | (4-(2-(3-aminopiperidin-1-yl)pyrimidin-5-ylamino)-6-(3,5-dichloro-4-hydroxyphenyl)quinolin-3-yl)(cyclopropyl)methanone | 549 |

TABLE 1-continued

| No. | Structure | Compound Name | ESI MS (m/z) |
|---|---|---|---|
| 629 | 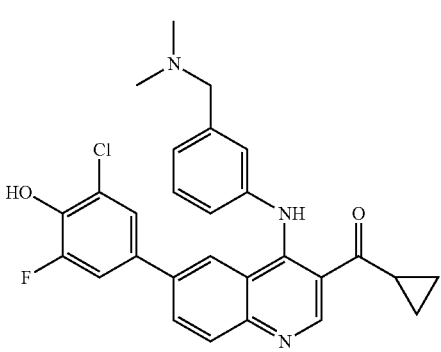 [SMILES: CN(C)Cc1cccc(Nc2c(C(=O)C3CC3)cnc3ccc(-c4cc(F)c(O)c(Cl)c4)cc23)c1] | (6-(3-chloro-5-fluoro-4-hydroxyphenyl)-4-(3-((dimethylamino)methyl)phenyl-amino)quinolin-3-yl)(cyclopropyl)methanone | 490 |
| 630 | 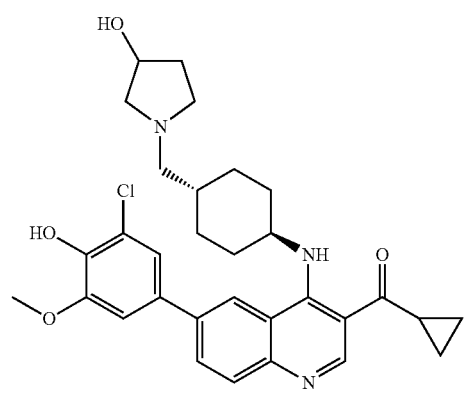 [SMILES: COc1cc(-c2ccc3ncc(C(=O)C4CC4)c(N[C@H]4CC[C@H](CN5CCC(O)C5)CC4)c3c2)cc(Cl)c1O] | (6-(3-chloro-4-hydroxy-5-methoxy-phenyl)-4-(1R,4R)--4-((3-hydroxy-pyrrolidin-1-yl)methyl)cyclohexyl-amino)quinolin-3-yl)(cyclopropyl)methanone | 550 |
| 631 | 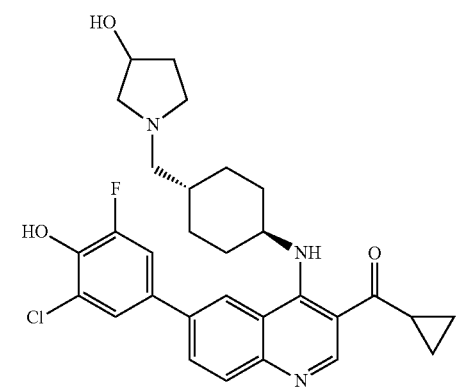 | (6-(3-chloro-5-fluoro-4-hydroxyphenyl)-4-(1R,4R)--4-((3-hydroxypyrrolidin-1-yl)methyl)cyclohexylamino)quinolin-3-yl)(cyclopropyl)methanone | 538 |
| 632 | 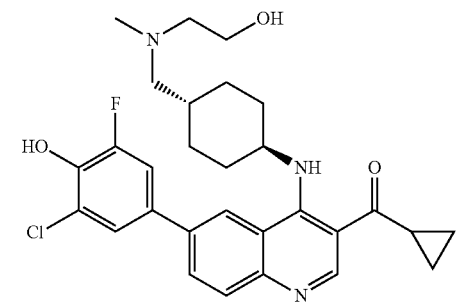 [SMILES: CN(CCO)C[C@H]1CC[C@H](Nc2c(C(=O)C3CC3)cnc3ccc(-c4cc(F)c(O)c(Cl)c4)cc23)CC1] | (6-(3-chloro-5-fluoro-4-hydroxy-phenyl)-4-(1R,4R)--4-(((2-hydroxy-ethyl)(methyl)amino)methyl)cyclo-hexylamino)quinolin-3-yl)(cyclo-propyl)methanone | 526 |

TABLE 1-continued

| No. | Structure | Compound Name | ESI MS (m/z) |
|---|---|---|---|
| 633 | 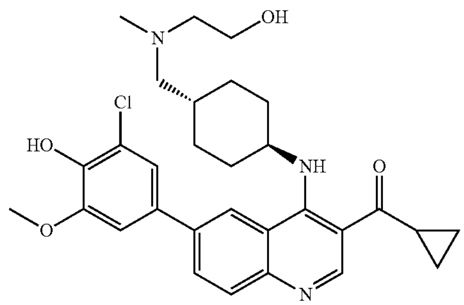 [SMILES: COc1cc(-c2ccc3ncc(C(=O)C4CC4)c(N[C@H]4CC[C@H](CN(C)CCO)CC4)c3c2)cc(Cl)c1O] | (6-(3-chloro-4-hydroxy-5-methoxy-phenyl)-4-(1R,4R)--4-(((2-hydroxy-ethyl)(methyl)amino)methyl)cyclo-hexylamino)quinolin-3-yl)(cyclo-propyl)methanone | 538 |
| 634 | 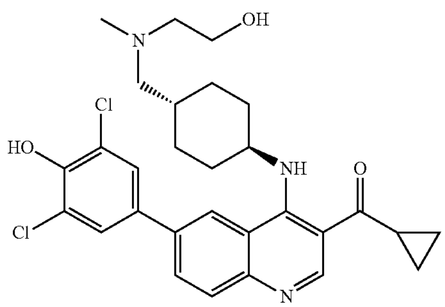 [SMILES: CN(CCO)C[C@H]1CC[C@H](Nc2c(C(=O)C3CC3)cnc3ccc(-c4cc(Cl)c(O)c(Cl)c4)cc23)CC1] | cyclopropyl(6-(3,5-dichloro-4-hydroxy-phenyl)-4-(1R,4R)--4-(((2-hydroxy-ethyl)(methyl)amino)methyl)cyclo-hexylamino)quinolin-3-yl)methanone | 542 |
| 635 | 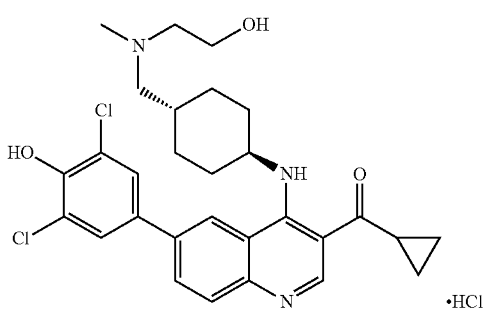 [SMILES: CN(CCO)C[C@H]1CC[C@H](Nc2c(C(=O)C3CC3)cnc3ccc(-c4cc(Cl)c(O)c(Cl)c4)cc23)CC1 ; Cl] | cyclopropyl(6-(3,5-dichloro-4-hydroxy-phenyl)-4-(1R,4R)--4-(((2-hydroxy-ethyl)(methyl)amino)methyl)cyclo-hexylamino)quinolin-3-yl)methanone hydrochloride | 542 |
| 636 | 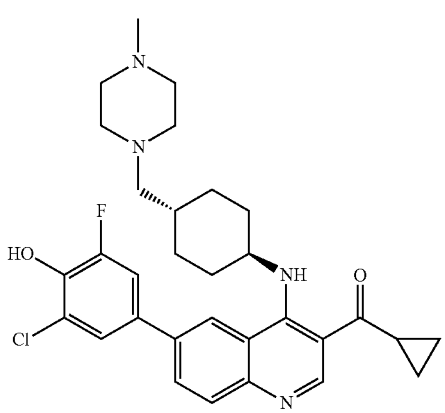 [SMILES: CN1CCN(C[C@H]2CC[C@H](Nc3c(C(=O)C4CC4)cnc4ccc(-c5cc(F)c(O)c(Cl)c5)cc34)CC2)CC1] | (6-(3-chloro-5-fluoro-4-hydroxy-phenyl)-4-(1R,4R)--4-((4-methyl-piperazin-1-yl)methyl)cyclohexyl-amino)quinolin-3-yl)(cyclopropyl)methanone | 551 |

TABLE 1-continued

| No. | Structure | Compound Name | ESI MS (m/z) |
|---|---|---|---|
| 637 | 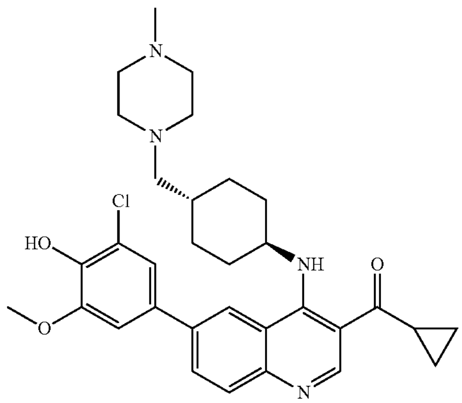 [SMILES: COc1cc(-c2ccc3ncc(C(=O)C4CC4)c(N[C@H]4CC[C@H](CN5CCN(C)CC5)CC4)c3c2)cc(Cl)c1O] | (6-(3-chloro-4-hydroxy-5-methoxy-phenyl)-4-(1R,4R)--4-((4-methyl-piperazin-1-yl)methyl)cyclo-hexylamino)quinolin-3-yl)(cyclo-propyl)methanone | 563 |
| 638 | 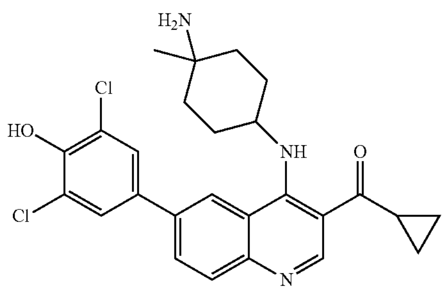 [SMILES: CC1(N)CCC(Nc2c(C(=O)C3CC3)cnc3ccc(-c4cc(Cl)c(O)c(Cl)c4)cc23)CC1] | (4-(4-amino-4-methylcyclohexylamino)-6-(3,5-dichloro-4-hydroxyphenyl)quinolin-3-yl)(cyclopropyl)methanone | 484 |
| 639 | 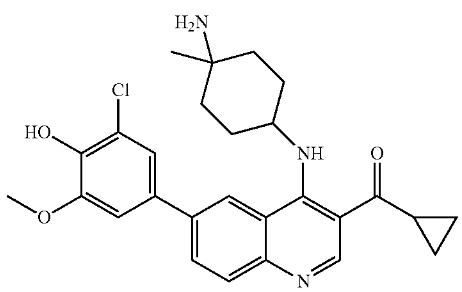 [SMILES: COc1cc(-c2ccc3ncc(C(=O)C4CC4)c(NC4CCC(C)(N)CC4)c3c2)cc(Cl)c1O] | (4-(4-amino-4-methylcyclohexylamino)-6-(3-chloro-4-hydroxy-5-methoxy-phenyl)quinolin-3-yl)(cyclopropyl)methanone | 480 |
| 640 | 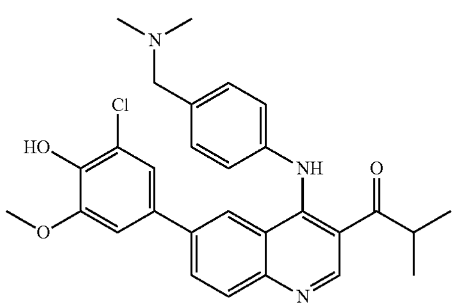 [SMILES: COc1cc(-c2ccc3ncc(C(=O)C(C)C)c(Nc4ccc(CN(C)C)cc4)c3c2)cc(Cl)c1O] | 1-(6-(3-chloro-4-hydroxy-5-methoxy-phenyl)-4-(4-((dimethylamino)methyl)phenylamino)quinolin-3-yl)-2-methylpropan-1-one | 504 |

TABLE 1-continued

| No. | Structure | Compound Name | ESI MS (m/z) |
|---|---|---|---|
| 641 | 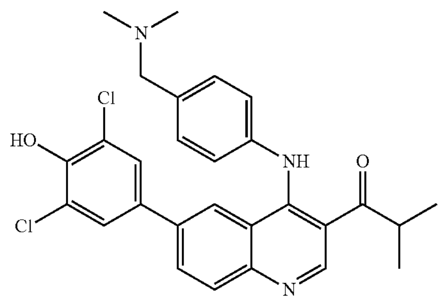 [SMILES: CC(C)C(=O)c1cnc2ccc(-c3cc(Cl)c(O)c(Cl)c3)cc2c1Nc1ccc(CN(C)C)cc1] | 1-(6-(3,5-dichloro-4-hydroxyphenyl)-4-(4-((dimethylamino)methyl)phenyl-amino)quinolin-3-yl)-2-methyl-propan-1-one | 508 |
| 642 | 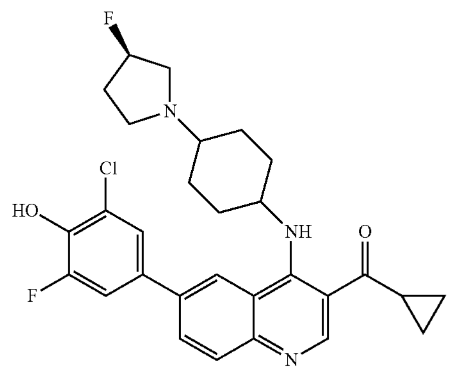 [SMILES: O=C(c1cnc2ccc(-c3cc(F)c(O)c(Cl)c3)cc2c1NC1CCC(N2CC[C@@H](F)C2)CC1)C1CC1] | (R)-(6-(3-chloro-5-fluoro-4-hydroxy-phenyl)-4-(4-(3-fluoropyrrolidin-1-yl)cyclohexylamino)quinolin-3-yl)(cyclopropyl)methanone | 526 |
| 643 | 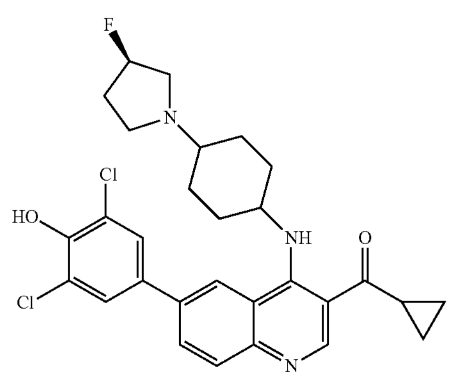 [SMILES: O=C(c1cnc2ccc(-c3cc(Cl)c(O)c(Cl)c3)cc2c1NC1CCC(N2CC[C@@H](F)C2)CC1)C1CC1] | (R)-cyclopropyl(6-(3,5-dichloro-4-hydroxyphenyl)-4-(4-(3-fluoro-pyrrolidin-1-yl)cyclohexylamino)quinolin-3-yl)methanone | 542 |
| 644 | 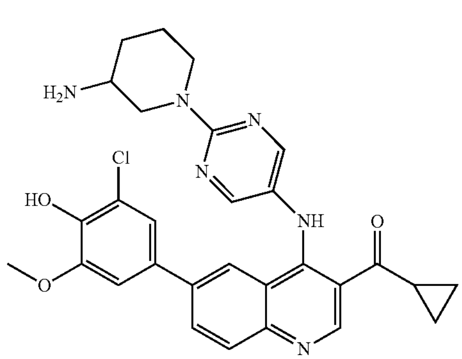 [SMILES: COc1cc(-c2ccc3ncc(C(=O)C4CC4)c(Nc4cnc(N5CCCC(N)C5)nc4)c3c2)cc(Cl)c1O] | (4-(2-(3-aminopiperidin-1-yl)pyrimidin-5-ylamino)-6-(3-chloro-4-hydroxy-5-methoxyphenyl)quinolin-3-yl)(cyclopropyl)methanone | 545 |

TABLE 1-continued

| No. | Structure | Compound Name | ESI MS (m/z) |
|---|---|---|---|
| 645 | 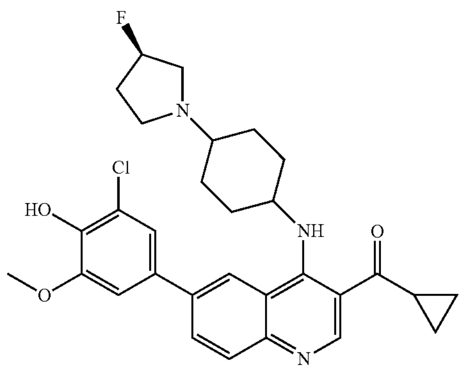 [SMILES: COc1cc(-c2ccc3ncc(C(=O)C4CC4)c(NC4CCC(N5CC[C@@H](F)C5)CC4)c3c2)cc(Cl)c1O] | (R)-(6-(3-chloro-4-hydroxy-5-methoxy-phenyl)-4-(4-(3-fluoropyrrolidin-1-yl)cyclohexylamino)quinolin-3-yl)(cyclopropyl)methanone | 538 |
| 646 | 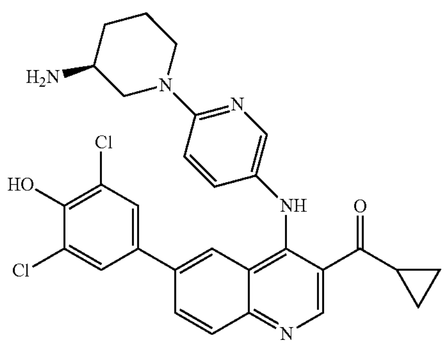 | (S)-(4-(6-(3-aminopiperidin-1-yl)pyridin-3-ylamino)-6-(3,5-dichloro-4-hydroxyphenyl)quinolin-3-yl)(cyclopropyl)methanone | 548 |
| 647 | 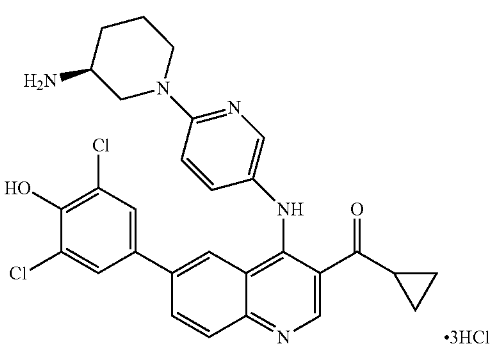 [SMILES: N[C@H]1CCCN(c2ccc(Nc3c(C(=O)C4CC4)cnc4ccc(-c5cc(Cl)c(O)c(Cl)c5)cc34)cn2)C1] | (S)-(4-(6-(3-aminopiperidin-1-yl)pyridin-3-ylamino)-6-(3,5-dichloro-4-hydroxyphenyl)quinolin-3-yl)(cyclopropyl)methanone hydrochloride | 548 |
| 648 | 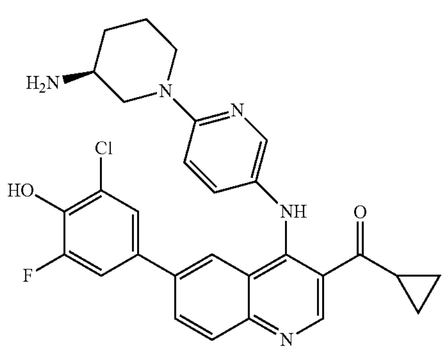 | (S)-(4-(6-(3-aminopiperidin-1-yl)pyridin-3-ylamino)-6-(3-chloro-5-fluoro-4-hydroxyphenyl)quinolin-3-yl)(cyclopropyl)methanone | 532 |

TABLE 1-continued

| No. | Structure | Compound Name | ESI MS (m/z) |
|---|---|---|---|
| 649 | 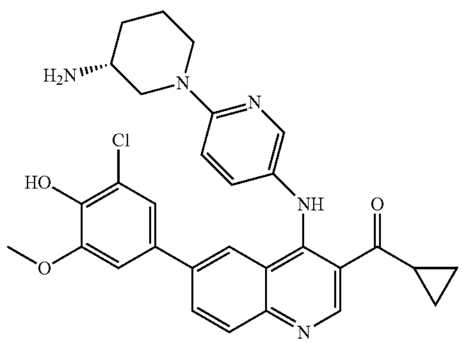 [SMILES: COc1cc(-c2ccc3ncc(C(=O)C4CC4)c(Nc4ccc(N5CCC[C@@H](N)C5)nc4)c3c2)cc(Cl)c1O] | (R)-(4-(6-(3-aminopiperidin-1-yl) pyridin-3-ylamino)-6-(3-chloro-4-hydroxy-5-methoxyphenyl)quinolin-3-yl)(cyclopropyl)methanone | 544 |
| 650 | 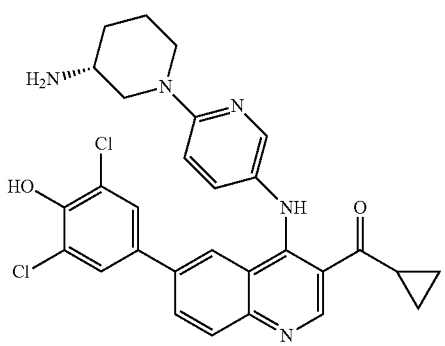 | (R)-(4-(6-(3-aminopiperidin-1-yl) pyridin-3-ylamino)-6-(3,5-dichloro-4-hydroxyphenyl)quinolin-3-yl)(cyclopropyl)methanone | 548 |
| 651 | 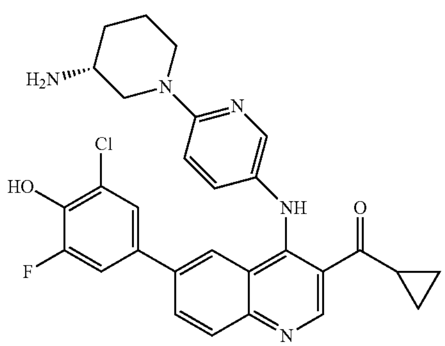 | (R)-(4-(6-(3-aminopiperidin-1-yl) pyridin-3-ylamino)-6-(3-chloro-5-fluoro-4-hydroxyphenyl)quinolin-3-yl)(cyclopropyl)methanone | 532 |
| 652 | 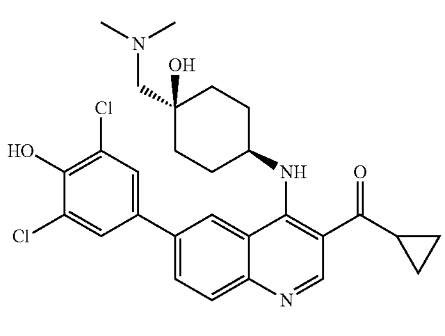 | cyclopropyl(6-(3,5-dichloro-4-hydroxyphenyl)-4-((1s,4s)-4-((dimethylamino)methyl)-4-hydroxycyclohexylamino)quinolin-3-yl)methanone | 528 |

TABLE 1-continued

| No. | Structure | Compound Name | ESI MS (m/z) |
|---|---|---|---|
| 653 | 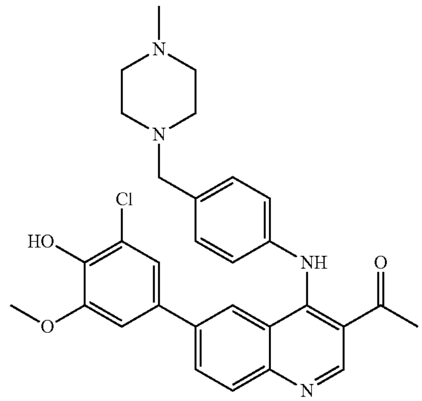 [SMILES: COc1cc(-c2ccc3ncc(C(C)=O)c(Nc4ccc(CN5CCN(C)CC5)cc4)c3c2)cc(Cl)c1O] | 1-(6-(3-chloro-4-hydroxy-5-methoxy-phenyl)-4-(4-((4-methylpiperazin-1-yl)methyl)phenylamino)quinolin-3-yl)ethanone | 531 |
| 654 | 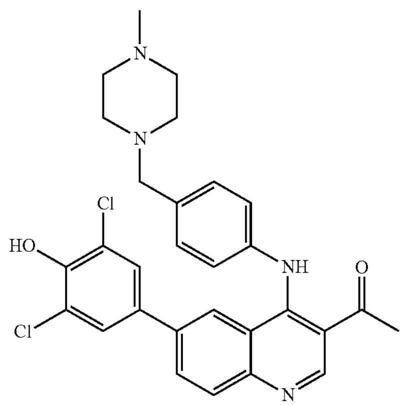 [SMILES: CC(=O)c1cnc2ccc(-c3cc(Cl)c(O)c(Cl)c3)cc2c1Nc1ccc(CN2CCN(C)CC2)cc1] | 1-(6-(3,5-dichloro-4-hydroxyphenyl)-4-(4-((4-methylpiperazin-1-yl)methyl)phenylamino)quinolin-3-yl)ethanone | 535 |
| 655 | 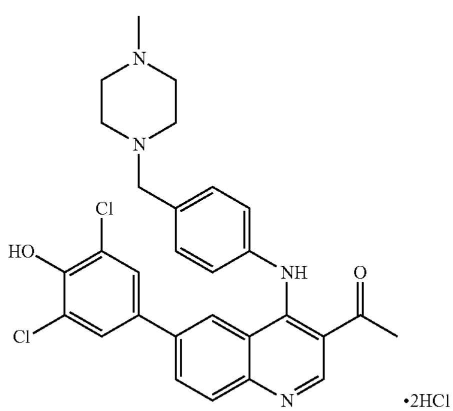 [SMILES: CC(=O)c1cnc2ccc(-c3cc(Cl)c(O)c(Cl)c3)cc2c1Nc1ccc(CN2CCN(C)CC2)cc1] | 1-(6-(3,5-dichloro-4-hydroxyphenyl)-4-((4-((4-methylpiperazin-1-yl)methyl)phenyl)amino)quinolin-3-yl)ethanone ·2HCl | 535 |

TABLE 1-continued

| No. | Structure | Compound Name | ESI MS (m/z) |
|---|---|---|---|
| 656 | 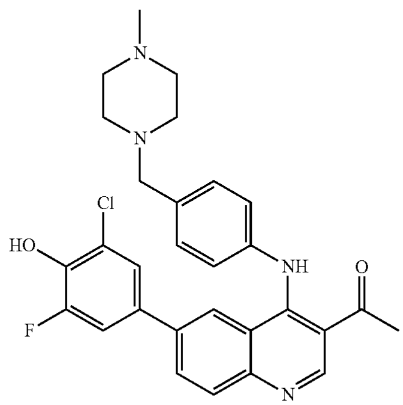 [SMILES: CC(=O)c1cnc2ccc(-c3cc(F)c(O)c(Cl)c3)cc2c1Nc1ccc(CN2CCN(C)CC2)cc1] | 1-(6-(3-chloro-5-fluoro-4-hydroxy-phenyl)-4-(4-((4-methylpiperazin-1-yl)methyl)phenylamino)quinolin-3-yl)ethanone | 519 |
| 657 | 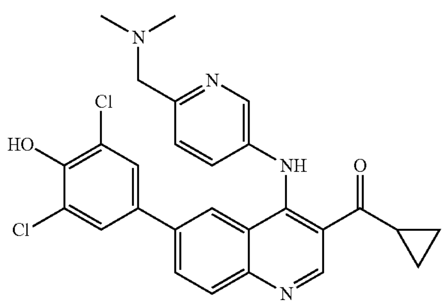 | cyclopropyl(6-(3,5-dichloro-4-hydroxy-phenyl)-4-(6-((dimethylamino)methyl)pyridin-3-ylamino)quinolin-3-yl)methanone | 507 |
| 658 | 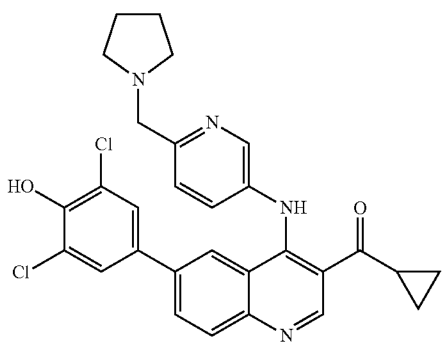 | cyclopropyl(6-(3,5-dichloro-4-hydroxy-phenyl)-4-(6-(pyrrolidin-1-ylmethyl)pyridin-3-ylamino)quinolin-3-yl)methanone | 533 |
| 659 | 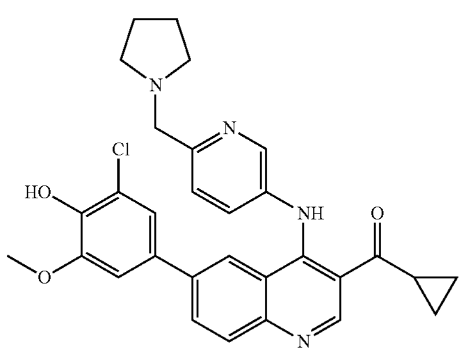 [SMILES: COc1cc(-c2ccc3ncc(C(=O)C4CC4)c(Nc4ccc(CN5CCCC5)nc4)c3c2)cc(Cl)c1O] | (6-(3-chloro-4-hydroxy-5-methoxy-phenyl)-4-(6-(pyrrolidin-1-ylmethyl)pyridin-3-ylamino)quinolin-3-yl)(cyclopropyl)methanone | 529 |

TABLE 1-continued

| No. | Structure | Compound Name | ESI MS (m/z) |
|---|---|---|---|
| 660 | 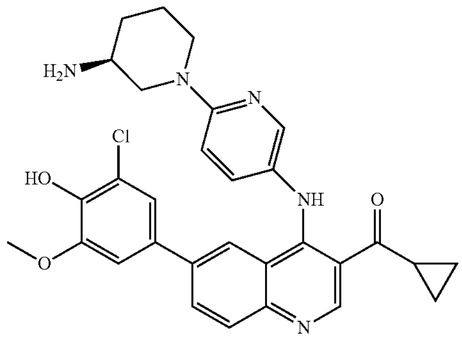 [SMILES: COc1cc(-c2ccc3ncc(C(=O)C4CC4)c(Nc4ccc(N5CCC[C@H](N)C5)nc4)c3c2)cc(Cl)c1O] | (S)-(4-(6-(3-aminopiperidin-1-yl)pyridin-3-ylamino)-6-(3-chloro-4-hydroxy-5-methoxyphenyl)quinolin-3-yl)(cyclopropyl)methanone | 544 |
| 661 | 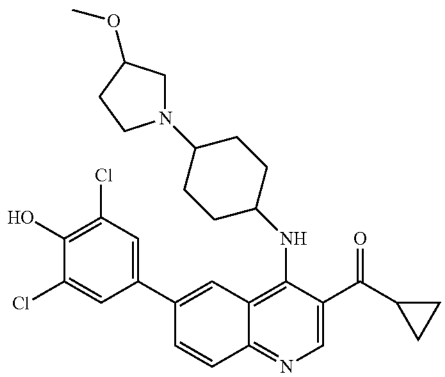 [SMILES: COC1CCN(C2CCC(Nc3c(C(=O)C4CC4)cnc4ccc(-c5cc(Cl)c(O)c(Cl)c5)cc34)CC2)C1] | cyclopropyl(6-(3,5-dichloro-4-hydroxyphenyl)-4-(4-(3-methoxypyrrolidin-1-yl)cyclohexylamino)quinolin-3-yl)methanone | 555 |
| 662 | 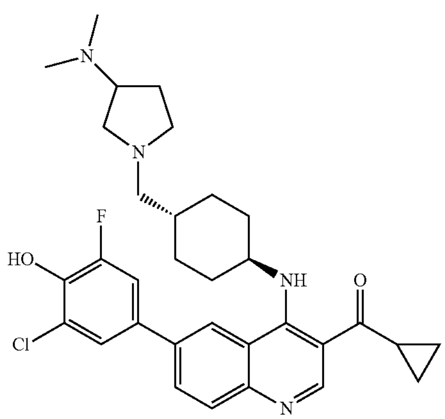 [SMILES: CN(C)C1CCN(C[C@H]2CC[C@H](Nc3c(C(=O)C4CC4)cnc4ccc(-c5cc(F)c(O)c(Cl)c5)cc34)CC2)C1] | (6-(3-chloro-5-fluoro-4-hydroxyphenyl)-4-(1R,4R)--4-((3-(dimethylamino)pyrrolidin-1-yl)methyl)cyclohexylamino)quinolin-3-yl)(cyclopropyl)methanone | 565 |
| 663 | 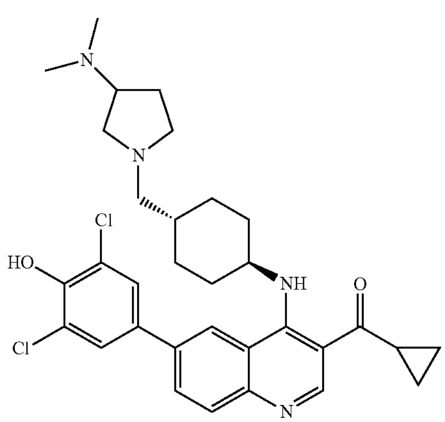 [SMILES: CN(C)C1CCN(C[C@H]2CC[C@H](Nc3c(C(=O)C4CC4)cnc4ccc(-c5cc(Cl)c(O)c(Cl)c5)cc34)CC2)C1] | cyclopropyl(6-(3,5-dichloro-4-hydroxyphenyl)-4-(1R,4R)-4-((3-(dimethylamino)pyrrolidin-1-yl)methyl)cyclohexylamino)quinolin-3-yl)methanone | 582 |

US 9,120,749 B2

355                                                                           356

TABLE 1-continued

| No. | Structure | Compound Name | ESI MS (m/z) |
|---|---|---|---|
| 664 | 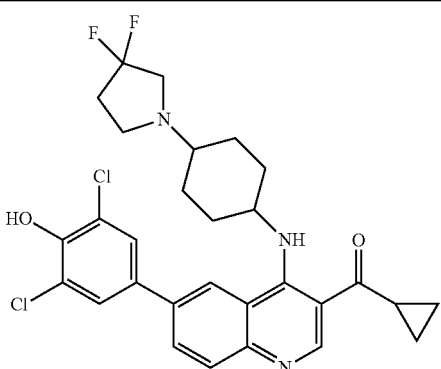 | cyclopropyl(6-(3,5-dichloro-4-hydroxy-phenyl)-4-(4-(3,3-difluoropyrrolidin-1-yl)cyclohexylamino)quinolin-3-yl)methanone | 560 |
| 665 | 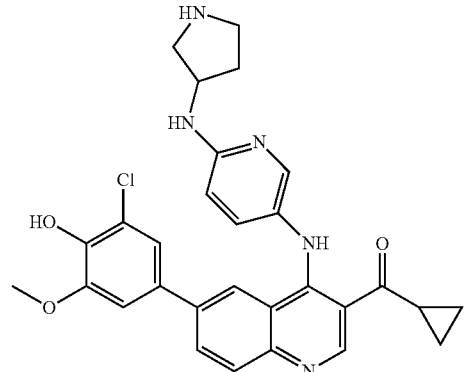 | (6-(3-chloro-4-hydroxy-5-methoxy-phenyl)-4-(6-(pyrrolidin-3-ylamino)pyridin-3-ylamino)quinolin-3-yl)(cyclopropyl)methanone | 530 |
| 666 | 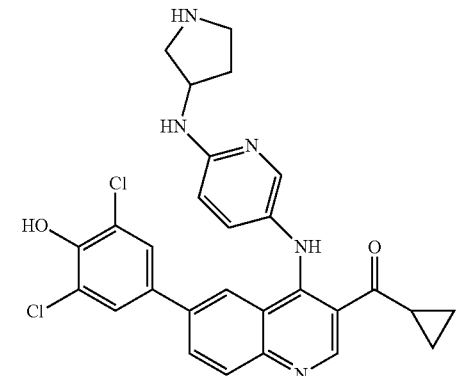 | cyclopropyl(6-(3,5-dichloro-4-hydroxy-phenyl)-4-(6-(pyrrolidin-3-ylamino)pyridin-3-ylamino)quinolin-3-yl)methanone | 534 |
| 667 | 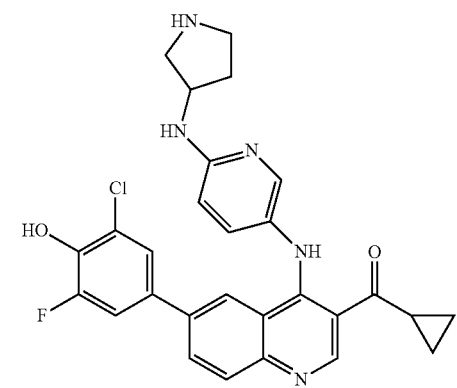 [SMILES: O=C(c1cnc2ccc(-c3cc(F)c(O)c(Cl)c3)cc2c1Nc1ccc(NC2CCNC2)nc1)C1CC1] | (6-(3-chloro-5-fluoro-4-hydroxyphenyl)-4-(6-(pyrrolidin-3-ylamino)pyridin-3-ylamino)quinolin-3-yl)(cyclopropyl)methanone | 518 |

TABLE 1-continued

| No. | Structure | Compound Name | ESI MS (m/z) |
|---|---|---|---|
| 668 | 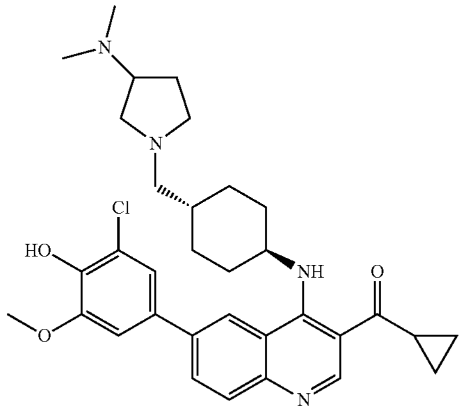 [SMILES: COc1cc(-c2ccc3ncc(C(=O)C4CC4)c(N[C@H]4CC[C@H](CN5CCC(N(C)C)C5)CC4)c3c2)cc(Cl)c1O] | (6-(3-chloro-4-hydroxy-5-methoxy-phenyl)-4-((1R,4R)-4-((3-(dimethyl-amino)pyrrolidin-1-yl)methyl)cyclo-hexylamino)quinolin-3-yl)(cyclo-propyl)methanone | 577 |
| 669 | 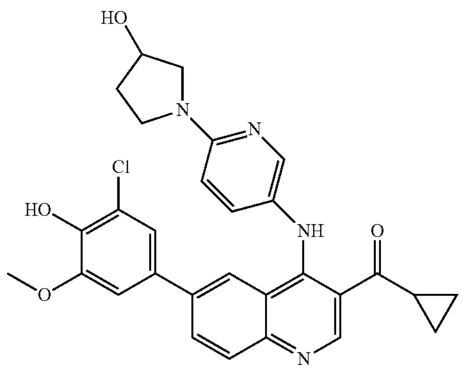 [SMILES: COc1cc(-c2ccc3ncc(C(=O)C4CC4)c(Nc4ccc(N5CCC(O)C5)nc4)c3c2)cc(Cl)c1O] | (6-(3-chloro-4-hydroxy-5-methoxy-phenyl)-4-(6-(3-hydroxypyrrolidin-1-yl)pyridin-3-ylamino)quinolin-3-yl)(cyclopropyl)methanone | 531 |
| 670 | 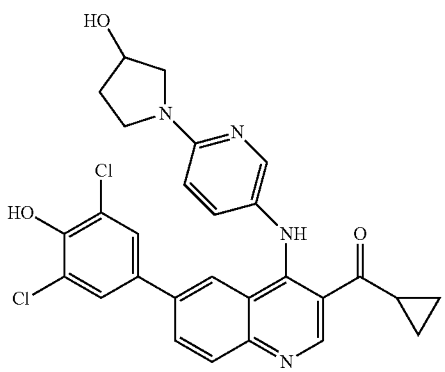 [SMILES: O=C(c1cnc2ccc(-c3cc(Cl)c(O)c(Cl)c3)cc2c1Nc1ccc(N2CCC(O)C2)nc1)C1CC1] | cyclopropyl(6-(3,5-dichloro-4-hydroxy-phenyl)-4-(6-(3-hydroxypyrrolidin-1-yl)pyridin-3-ylamino)quinolin-3-yl)methanone | 535 |
| 671 | 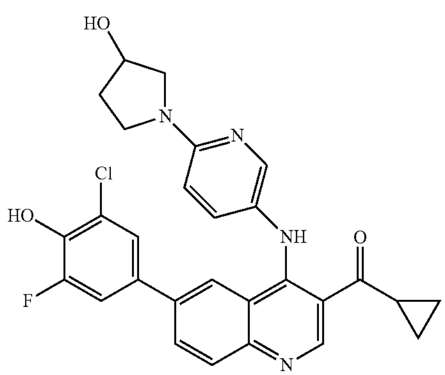 [SMILES: O=C(c1cnc2ccc(-c3cc(F)c(O)c(Cl)c3)cc2c1Nc1ccc(N2CCC(O)C2)nc1)C1CC1] | (6-(3-chloro-5-fluoro-4-hydroxyphenyl)-4-(6-(3-hydroxypyrrolidin-1-yl)pyridin-3-ylamino)quinolin-3-yl)(cyclopropyl)methanone | 519 |

TABLE 1-continued

| No. | Structure | Compound Name | ESI MS (m/z) |
|---|---|---|---|
| 672 | 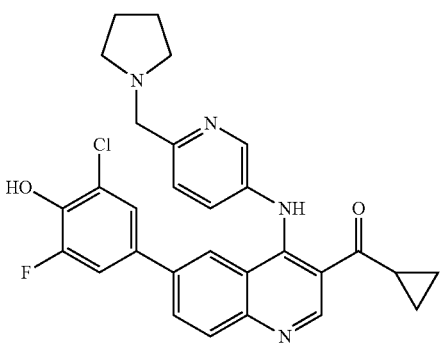 | (6-(3-chloro-5-fluoro-4-hydroxyphenyl)-4-(6-(pyrrolidin-1-ylmethyl)pyridin-3-ylamino)quinolin-3-yl)(cyclopropyl)methanone | 517 |
| 673 | 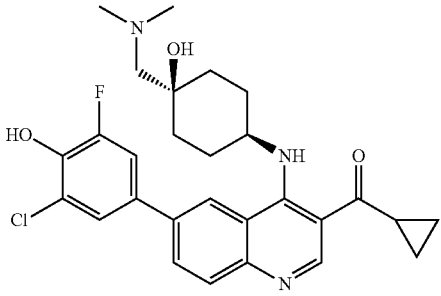 [SMILES: CN(C)C[C@]1(O)CC[C@@H](Nc2c(C(=O)C3CC3)cnc3ccc(-c4cc(F)c(O)c(Cl)c4)cc23)CC1] | (6-(3-chloro-5-fluoro-4-hydroxyphenyl)-4-((1s,4s)-4-((dimethylamino)methyl)-4-hydroxycyclohexylamino)quinolin-3-yl)(cyclopropyl)methanone | 512 |
| 674 | 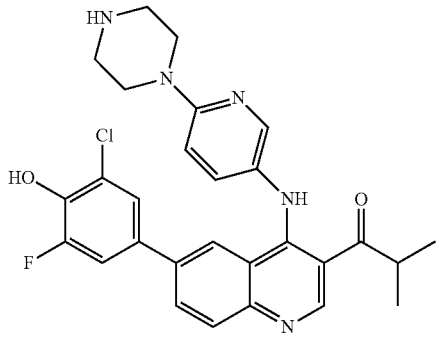 [SMILES: CC(C)C(=O)c1cnc2ccc(-c3cc(F)c(O)c(Cl)c3)cc2c1Nc1ccc(N2CCNCC2)nc1] | 1-(6-(3-chloro-5-fluoro-4-hydroxyphenyl)-4-(6-(piperazin-1-yl)pyridin-3-ylamino)quinolin-3-yl)-2-methylpropan-1-one | 520 |
| 675 | 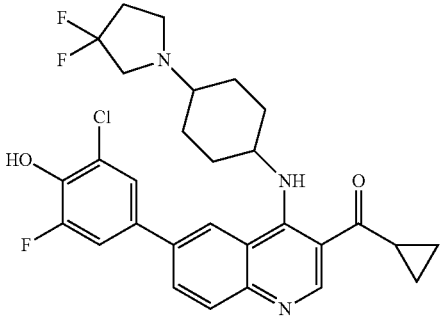 [SMILES: O=C(c1cnc2ccc(-c3cc(F)c(O)c(Cl)c3)cc2c1NC1CCC(N2CCC(F)(F)C2)CC1)C1CC1] | (6-(3-chloro-5-fluoro-4-hydroxyphenyl)-4-(4-(3,3-difluoropyrrolidin-1-yl)cyclohexylamino)quinolin-3-yl)(cyclopropyl)methanone | 544 |

TABLE 1-continued

| No. | Structure | Compound Name | ESI MS (m/z) |
|---|---|---|---|
| 676 | 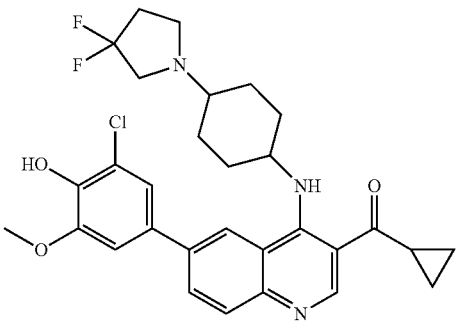 [SMILES: COc1cc(-c2ccc3ncc(C(=O)C4CC4)c(NC4CCC(N5CCC(F)(F)C5)CC4)c3c2)cc(Cl)c1O] | (6-(3-chloro-4-hydroxy-5-methoxy-phenyl)-4-(4-(3,3-difluoropyrrolidin-1-yl)cyclohexylamino)quinolin-3-yl)(cyclopropyl)methanone | 556 |
| 677 | 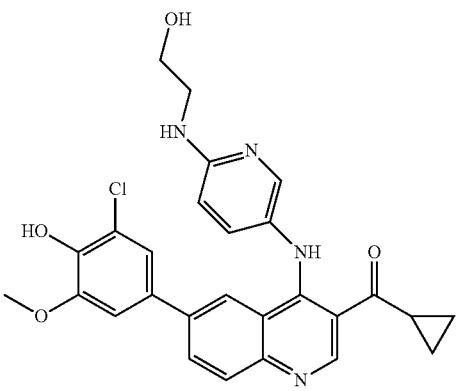 [SMILES: COc1cc(-c2ccc3ncc(C(=O)C4CC4)c(Nc4ccc(NCCO)nc4)c3c2)cc(Cl)c1O] | (6-(3-chloro-4-hydroxy-5-methoxy-phenyl)-4-(6-(2-hydroxyethylamino)pyridin-3-ylamino)quinolin-3-yl)(cyclopropyl)methanone | 505 |
| 678 | 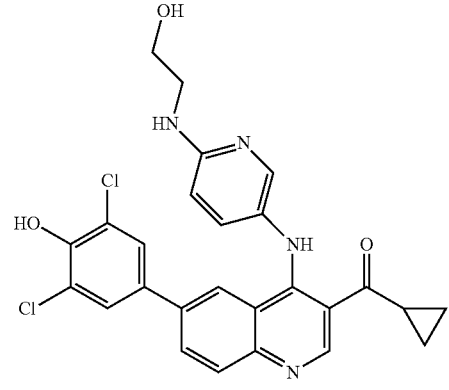 [SMILES: O=C(c1cnc2ccc(-c3cc(Cl)c(O)c(Cl)c3)cc2c1Nc1ccc(NCCO)nc1)C1CC1] | cyclopropyl(6-(3,5-dichloro-4-hydroxy-phenyl)-4-(6-(2-hydroxyethylamino)pyridin-3-ylamino)quinolin-3-yl)methanone | 509 |
| 679 | 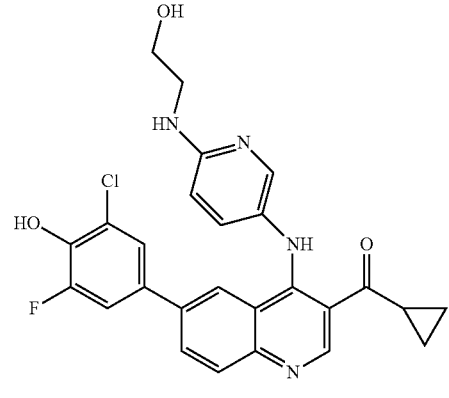 [SMILES: O=C(c1cnc2ccc(-c3cc(F)c(O)c(Cl)c3)cc2c1Nc1ccc(NCCO)nc1)C1CC1] | (6-(3-chloro-5-fluoro-4-hydroxyphenyl)-4-(6-(2-hydroxyethylamino)pyridin-3-ylamino)quinolin-3-yl)(cyclopropyl)methanone | 493 |

TABLE 1-continued

| No. | Structure | Compound Name | ESI MS (m/z) |
|---|---|---|---|
| 680 | 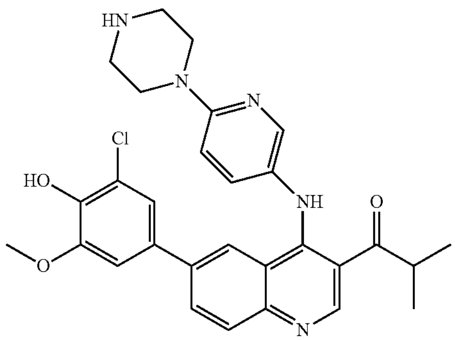 [SMILES: COc1cc(-c2ccc3ncc(C(=O)C(C)C)c(Nc4ccc(N5CCNCC5)nc4)c3c2)cc(Cl)c1O] | 1-(6-(3-chloro-4-hydroxy-5-methoxy-phenyl)-4-(6-(piperazin-1-yl)pyridin-3-ylamino)quinolin-3-yl)-2-methyl-propan-1-one | 532 |
| 681 | •3HCl | 1-(4-(6-(3-aminopiperidin-1-yl)pyridin-3-ylamino)-6-(3,5-dichloro-4-hydroxy-phenyl)quinolin-3-yl)ethanone | 522 |
| 682 | 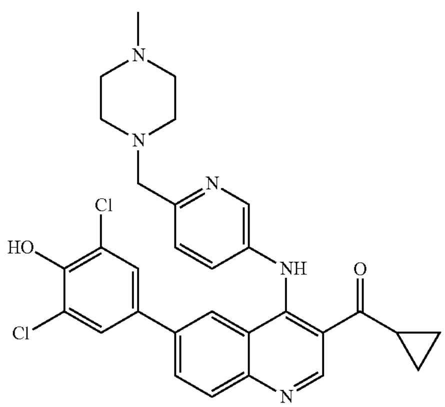 | cyclopropyl(6-(3,5-dichloro-4-hydroxy-phenyl)-4-(6-((4-methylpiperazin-1-yl)methyl)pyridin-3-ylamino)quinolin-3-yl)methanone | 562 |
| 683 | 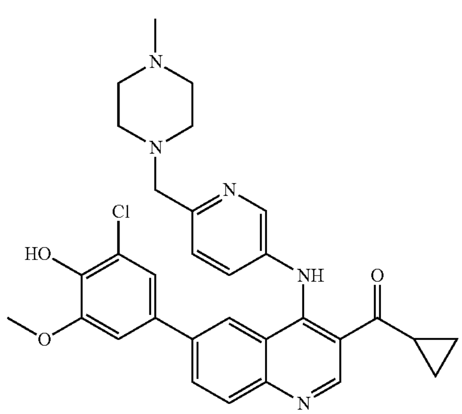 [SMILES: COc1cc(-c2ccc3ncc(C(=O)C4CC4)c(Nc4ccc(CN5CCN(C)CC5)nc4)c3c2)cc(Cl)c1O] | (6-(3-chloro-4-hydroxy-5-methoxy-phenyl)-4-(6-((4-methylpiperazin-1-yl)methyl)pyridin-3-ylamino)quinolin-3-yl)(cyclopropyl)methanone | 558 |

TABLE 1-continued

| No. | Structure | Compound Name | ESI MS (m/z) |
|---|---|---|---|
| 684 | 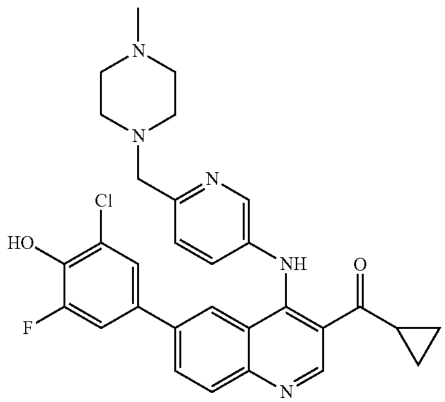 [SMILES: CN1CCN(Cc2ccc(Nc3c(C(=O)C4CC4)cnc4ccc(-c5cc(F)c(O)c(Cl)c5)cc34)cn2)CC1] | (6-(3-chloro-5-fluoro-4-hydroxyphenyl)-4-(6-((4-methylpiperazin-1-yl)methyl)pyridin-3-ylamino)quinolin-3-yl)(cyclopropyl)methanone | 546 |
| 685 | 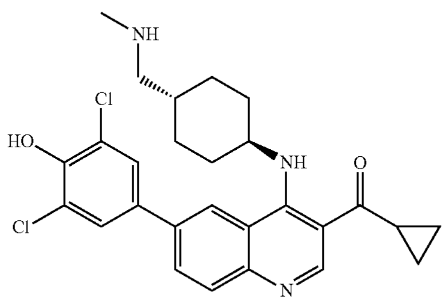 [SMILES: CNC[C@H]1CC[C@H](Nc2c(C(=O)C3CC3)cnc3ccc(-c4cc(Cl)c(O)c(Cl)c4)cc23)CC1] | cyclopropyl(6-(3,5-dichloro-4-hydroxyphenyl)-4-(1R,4R)-4-((methylamino)methyl)cyclohexylamino)quinolin-3-yl)methanone | 498 |
| 686 | 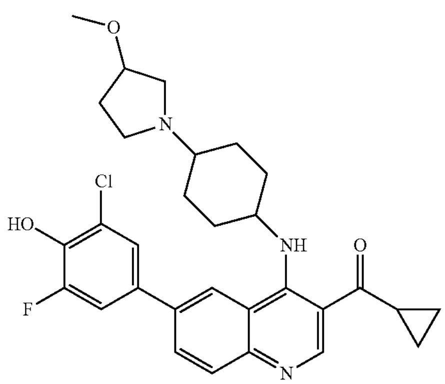 [SMILES: COC1CCN(C2CCC(Nc3c(C(=O)C4CC4)cnc4ccc(-c5cc(F)c(O)c(Cl)c5)cc34)CC2)C1] | (6-(3-chloro-5-fluoro-4-hydroxyphenyl)-4-(4-(3-methoxypyrrolidin-1-yl)cyclohexylamino)quinolin-3-yl)(cyclopropyl)methanone | 538 |
| 687 | 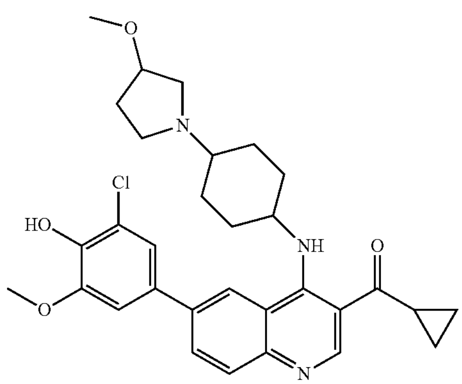 [SMILES: COc1cc(-c2ccc3ncc(C(=O)C4CC4)c(NC4CCC(N5CCC(OC)C5)CC4)c3c2)cc(Cl)c1O] | (6-(3-chloro-4-hydroxy-5-methoxyphenyl)-4-(4-(3-methoxypyrrolidin-1-yl)cyclohexylamino)quinolin-3-yl)(cyclopropyl)methanone | 550 |

TABLE 1-continued

| No. | Structure | Compound Name | ESI MS (m/z) |
|---|---|---|---|
| 688 | 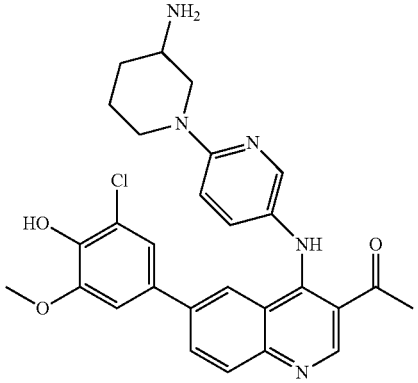 [SMILES: COc1cc(-c2ccc3ncc(C(C)=O)c(Nc4ccc(N5CCCC(N)C5)nc4)c3c2)cc(Cl)c1O] | 1-(4-(6-(3-aminopiperidin-1-yl)pyridin-3-ylamino)-6-(3-chloro-4-hydroxy-5-methoxyphenyl)quinolin-3-yl)ethanone | 518 |
| 689 | 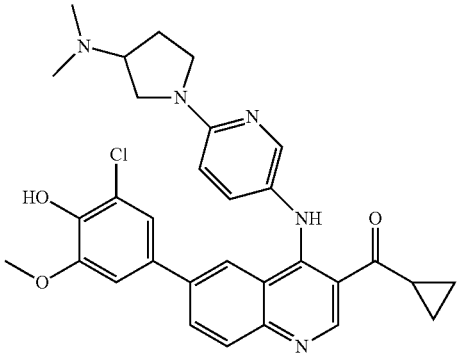 [SMILES: COc1cc(-c2ccc3ncc(C(=O)C4CC4)c(Nc4ccc(N5CCC(N(C)C)C5)nc4)c3c2)cc(Cl)c1O] | (6-(3-chloro-4-hydroxy-5-methoxyphenyl)-4-(6-(3-(dimethylamino)pyrrolidin-1-yl)pyridin-3-ylamino)quinolin-3-yl)(cyclopropyl)methanone | 558 |
| 690 | 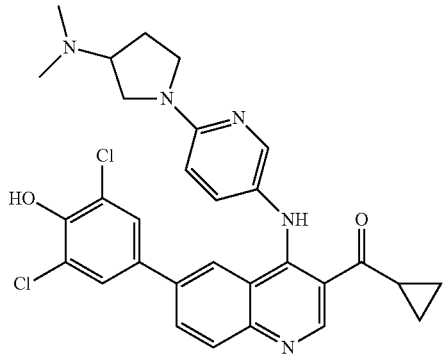 [SMILES: CN(C)C1CCN(c2ccc(Nc3c(C(=O)C4CC4)cnc4ccc(-c5cc(Cl)c(O)c(Cl)c5)cc34)cn2)C1] | cyclopropyl(6-(3,5-dichloro-4-hydroxyphenyl)-4-(6-(3-(dimethylamino)pyrrolidin-1-yl)pyridin-3-ylamino)quinolin-3-yl)methanone | 562 |
| 691 | 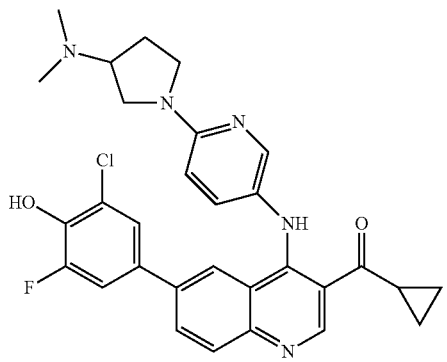 [SMILES: CN(C)C1CCN(c2ccc(Nc3c(C(=O)C4CC4)cnc4ccc(-c5cc(F)c(O)c(Cl)c5)cc34)cn2)C1] | (6-(3-chloro-5-fluoro-4-hydroxyphenyl)-4-(6-(3-(dimethylamino)pyrrolidin-1-yl)pyridin-3-ylamino)quinolin-3-yl)(cyclopropyl)methanone | 546 |

TABLE 1-continued

| No. | Structure | Compound Name | ESI MS (m/z) |
|---|---|---|---|
| 692 | 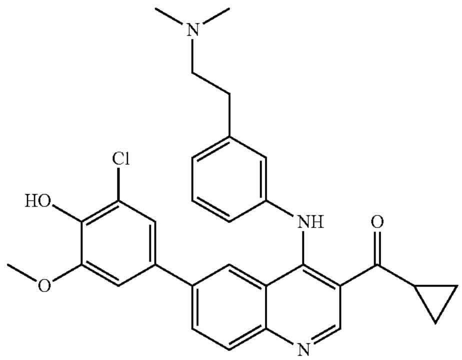 [SMILES: COc1cc(-c2ccc3ncc(C(=O)C4CC4)c(Nc4cccc(CCN(C)C)c4)c3c2)cc(Cl)c1O] | (6-(3-chloro-4-hydroxy-5-methoxyphenyl)-4-(3-(2-(dimethylamino)ethyl)phenylamino)quinolin-3-yl)(cyclopropyl)methanone | 516 |
| 693 | 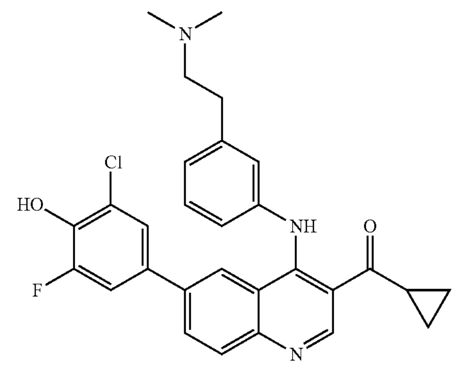 [SMILES: CN(C)CCc1cccc(Nc2c(C(=O)C3CC3)cnc3ccc(-c4cc(F)c(O)c(Cl)c4)cc23)c1] | (6-(3-chloro-5-fluoro-4-hydroxyphenyl)-4-(3-(2-(dimethylamino)ethyl)phenylamino)quinolin-3-yl)(cyclopropyl)methanone | 504 |
| 694 | 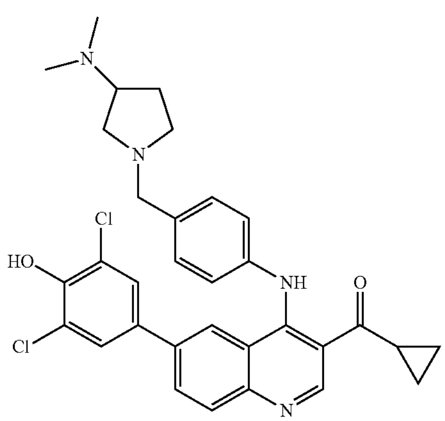 [SMILES: CN(C)C1CCN(Cc2ccc(Nc3c(C(=O)C4CC4)cnc4ccc(-c5cc(Cl)c(O)c(Cl)c5)cc34)cc2)C1] | cyclopropyl(6-(3,5-dichloro-4-hydroxyphenyl)-4-(4-((3-(dimethylamino)pyrrolidin-1-yl)methyl)phenylamino)quinolin-3-yl)methanone | 576 |
| 695 | 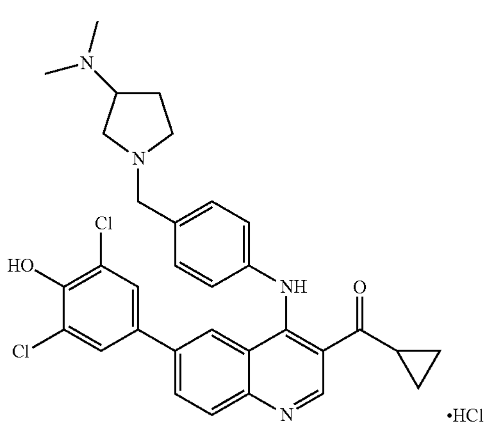 [SMILES: CN(C)C1CCN(Cc2ccc(Nc3c(C(=O)C4CC4)cnc4ccc(-c5cc(Cl)c(O)c(Cl)c5)cc34)cc2)C1 ; Cl] | cyclopropyl(6-(3,5-dichloro-4-hydroxyphenyl)-4-(4-((3-(dimethylamino)pyrrolidin-1-yl)methyl)phenylamino)quinolin-3-yl)methanone hydrochloride | 576 |

TABLE 1-continued

| No. | Structure | Compound Name | ESI MS (m/z) |
|---|---|---|---|
| 696 | 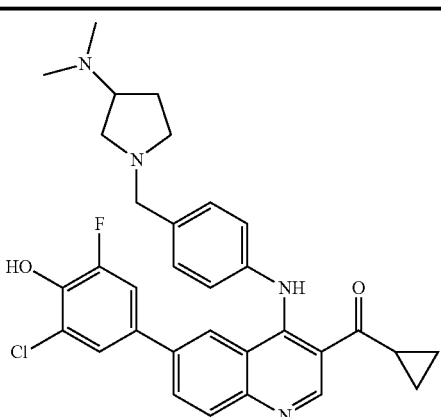 | (6-(3-chloro-5-fluoro-4-hydroxyphenyl)-4-(4-((3-(dimethylamino)pyrrolidin-1-yl)methyl)phenylamino)quinolin-3-yl)(cyclopropyl)methanone | 559 |
| 697 | 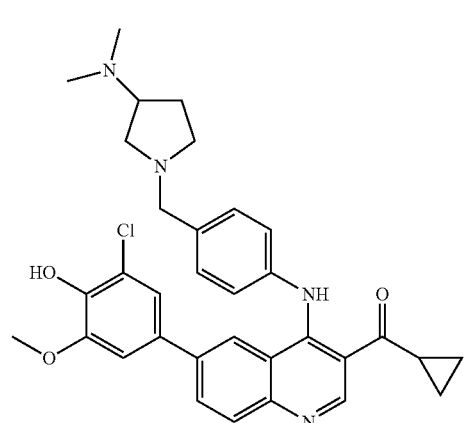 | (6-(3-chloro-4-hydroxy-5-methoxy-phenyl)-4-(4-((3-(dimethylamino)pyrrolidin-1-yl)methyl)phenylamino)quinolin-3-yl)(cyclopropyl)methanone | 571 |
| 698 | 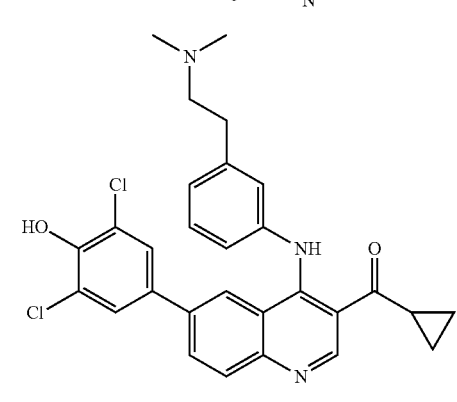 | cyclopropyl(6-(3,5-dichloro-4-hydroxy-phenyl)-4-(3-(2-(dimethylamino)ethyl)phenylamino)quinolin-3-yl)methanone | 520 |
| 699 | 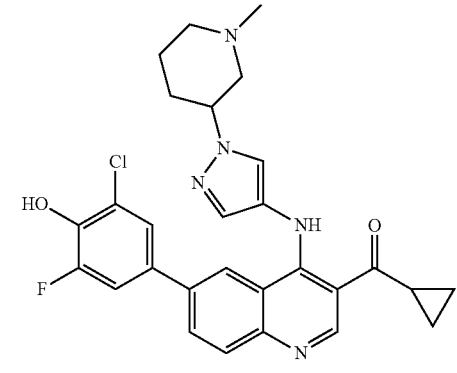 [SMILES: CN1CCCC(n2cc(Nc3c(C(=O)C4CC4)cnc4ccc(-c5cc(F)c(O)c(Cl)c5)cc34)cn2)C1] | (6-(3-chloro-5-fluoro-4-hydroxyphenyl)-4-(1-(1-methylpiperidin-3-yl)-1H-pyrazol-4-ylamino)quinolin-3-yl)(cyclopropyl)methanone | 520 |

TABLE 1-continued

| No. | Structure | Compound Name | ESI MS (m/z) |
|---|---|---|---|
| 700 | 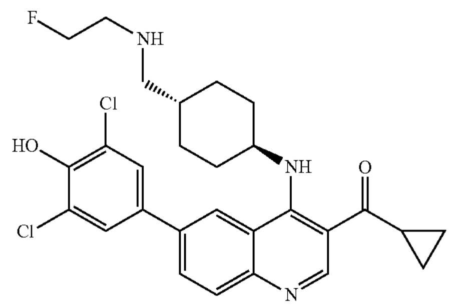 [SMILES: O=C(c1cnc2ccc(-c3cc(Cl)c(O)c(Cl)c3)cc2c1N[C@H]1CC[C@H](CNCCF)CC1)C1CC1] | cyclopropyl(6-(3,5-dichloro-4-hydroxy-phenyl)-4-(1R,4R)-4-((2-fluoroethyl-amino)methyl)cyclohexylamino)quinolin-3-yl)methanone | 530 |
| 701 | 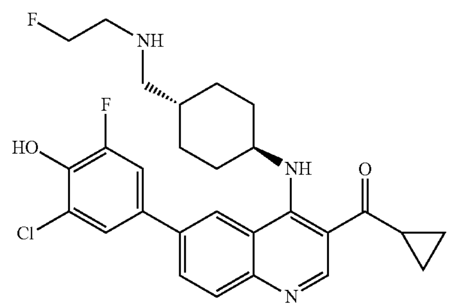 [SMILES: O=C(c1cnc2ccc(-c3cc(F)c(O)c(Cl)c3)cc2c1N[C@H]1CC[C@H](CNCCF)CC1)C1CC1] | (6-(3-chloro-5-fluoro-4-hydroxyphenyl)-4-(1R,4R)-4-((2-fluoroethylamino)methyl)cyclohexylamino)quinolin-3-yl)(cyclopropyl)methanone | 514 |
| 702 | 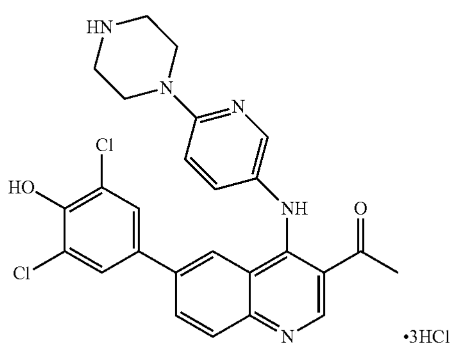 [SMILES: CC(=O)c1cnc2ccc(-c3cc(Cl)c(O)c(Cl)c3)cc2c1Nc1ccc(N2CCNCC2)nc1] | 1-(6-(3,5-dichloro-4-hydroxyphenyl)-4-(6-(piperazin-1-yl)pyridin-3-ylamino)quinolin-3-yl)ethanone hydrochloride | 508 |
| 703 | 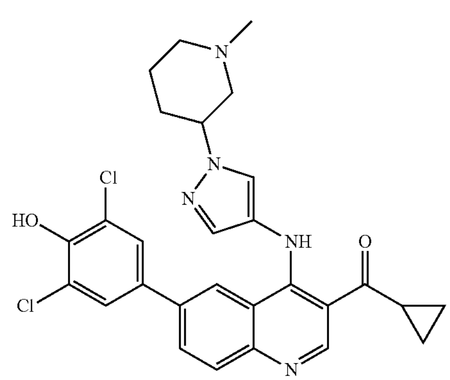 [SMILES: CN1CCCC(n2cc(Nc3c(C(=O)C4CC4)cnc4ccc(-c5cc(Cl)c(O)c(Cl)c5)cc34)cn2)C1] | cyclopropyl(6-(3,5-dichloro-4-hydroxy-phenyl)-4-(1-(1-methylpiperidin-3-yl)-1H-pyrazol-4-ylamino)quinolin-3-yl)methanone | 536 |

TABLE 1-continued

| No. | Structure | Compound Name | ESI MS (m/z) |
|---|---|---|---|
| 704 | 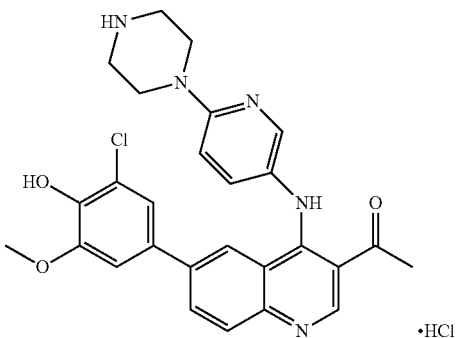 [SMILES: COc1cc(-c2ccc3ncc(C(C)=O)c(Nc4ccc(N5CCNCC5)nc4)c3c2)cc(Cl)c1O ; Cl] | 1-(6-(3-chloro-4-hydroxy-5-methoxy-phenyl)-4-(6-(piperazin-1-yl)pyridin-3-ylamino)quinolin-3-yl)ethanone hydrochloride | 504 |
| 705 | 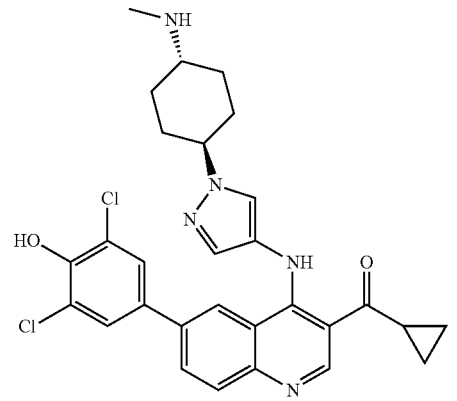 [SMILES: CN[C@H]1CC[C@H](n2cc(Nc3c(C(=O)C4CC4)cnc4ccc(-c5cc(Cl)c(O)c(Cl)c5)cc34)cn2)CC1] | cyclopropyl(6-(3,5-dichloro-4-hydroxy-phenyl)-4-(1-(1R,4R)-4-(methylamino)cyclohexyl)-1H-pyrazol-4-ylamino)quinolin-3-yl)methanone | 550 |
| 706 | 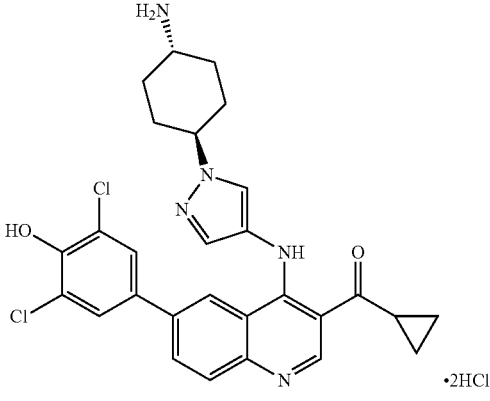 [SMILES: N[C@H]1CC[C@H](n2cc(Nc3c(C(=O)C4CC4)cnc4ccc(-c5cc(Cl)c(O)c(Cl)c5)cc34)cn2)CC1] | (4-(1-(1R,4R)-4-aminocyclohexyl)-1H-pyrazol-4-ylamino)-6-(3,5-dichloro-4-hydroxyphenyl)quinolin-3-yl)(cyclopropyl)methanone hydrochloride | 536 |
| 707 | 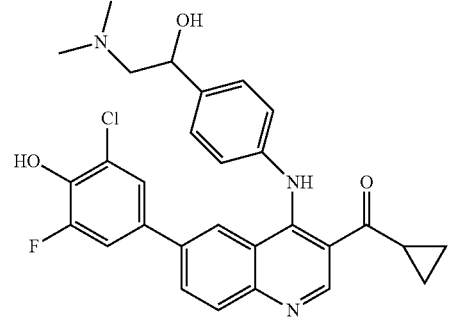 [SMILES: CN(C)CC(O)c1ccc(Nc2c(C(=O)C3CC3)cnc3ccc(-c4cc(F)c(O)c(Cl)c4)cc23)cc1] | (6-(3-chloro-5-fluoro-4-hydroxyphenyl)-4-(4-(2-(dimethylamino)-1-hydroxyethyl)phenylamino)quinolin-3-yl)(cyclopropyl)methanone | 520 |

TABLE 1-continued

| No. | Structure | Compound Name | ESI MS (m/z) |
|---|---|---|---|
| 708 | 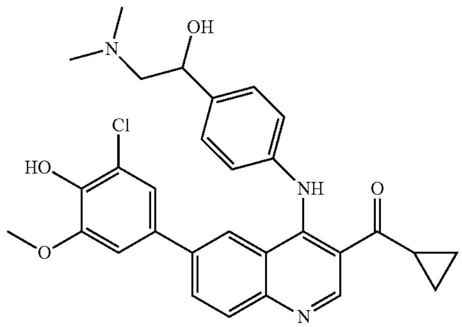 [SMILES: COc1cc(-c2ccc3ncc(C(=O)C4CC4)c(Nc4ccc(C(O)CN(C)C)cc4)c3c2)cc(Cl)c1O] | (6-(3-chloro-4-hydroxy-5-methoxy-phenyl)-4-(4-(2-(dimethylamino)-1-hydroxyethyl)phenylamino)quinolin-3-yl)(cyclopropyl)methanone | 532 |
| 709 | 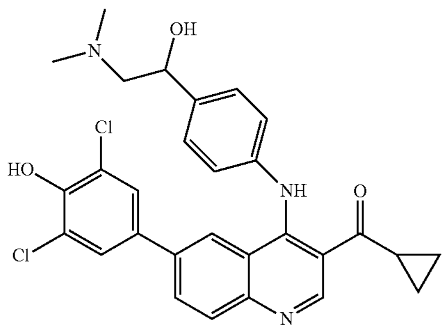 | cyclopropyl(6-(3,5-dichloro-4-hydroxy-phenyl)-4-(4-(2-(dimethylamino)-1-hydroxyethyl)phenylamino)quinolin-3-yl)methanone | 536 |
| 710 | 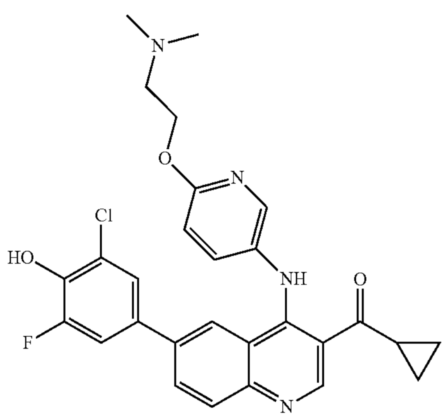 [SMILES: CN(C)CCOc1ccc(Nc2c(C(=O)C3CC3)cnc3ccc(-c4cc(F)c(O)c(Cl)c4)cc23)cn1] | (6-(3-chloro-5-fluoro-4-hydroxyphenyl)-4-(6-(2-(dimethylamino)ethoxy)pyridin-3-ylamino)quinolin-3-yl)(cyclopropyl)methanone | 521 |
| 711 | 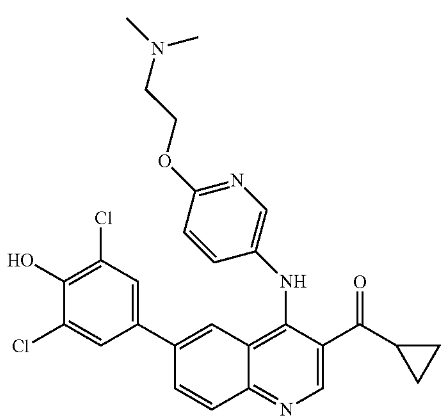 [SMILES: CN(C)CCOc1ccc(Nc2c(C(=O)C3CC3)cnc3ccc(-c4cc(Cl)c(O)c(Cl)c4)cc23)cn1] | cyclopropyl(6-(3,5-dichloro-4-hydroxy-phenyl)-4-(6-(2-(dimethylamino)ethoxy)pyridin-3-ylamino)quinolin-3-yl)methanone | 537 |

TABLE 1-continued

| No. | Structure | Compound Name | ESI MS (m/z) |
|---|---|---|---|
| 712 | 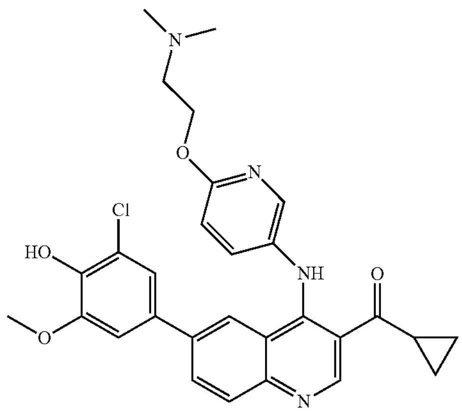 [SMILES: COc1cc(-c2ccc3ncc(C(=O)C4CC4)c(Nc4ccc(OCCN(C)C)nc4)c3c2)cc(Cl)c1O] | (6-(3-chloro-4-hydroxy-5-methoxy-phenyl)-4-(6-(2-(dimethylamino)ethoxy)pyridin-3-ylamino)quinolin-3-yl)(cyclopropyl)methanone | 533 |
| 713 | 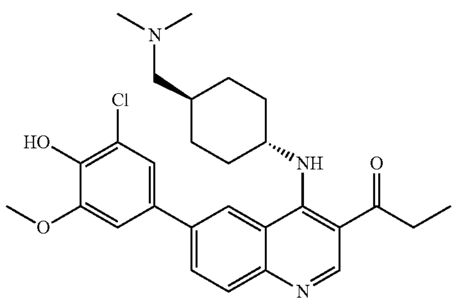 [SMILES: CCC(=O)c1cnc2ccc(-c3cc(Cl)c(O)c(OC)c3)cc2c1N[C@H]1CC[C@H](CN(C)C)CC1] | 1-(6-(3-chloro-4-hydroxy-5-methoxy-phenyl)-4-(1R,4R)-4-((dimethylamino)methyl)cyclohexylamino)quinolin-3-yl)propan-1-one | 496 |
| 714 | 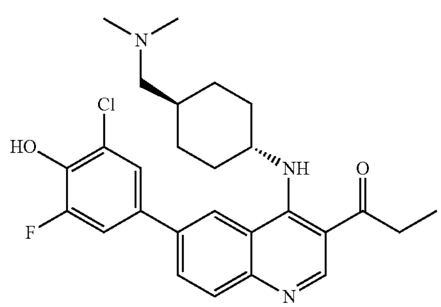 [SMILES: CCC(=O)c1cnc2ccc(-c3cc(F)c(O)c(Cl)c3)cc2c1N[C@H]1CC[C@H](CN(C)C)CC1] | 1-(6-(3-chloro-5-fluoro-4-hydroxy-phenyl)-4-(1R,4R)-4-((dimethylamino)methyl)cyclohexylamino)quinolin-3-yl)propan-1-one | 484 |
| 715 | 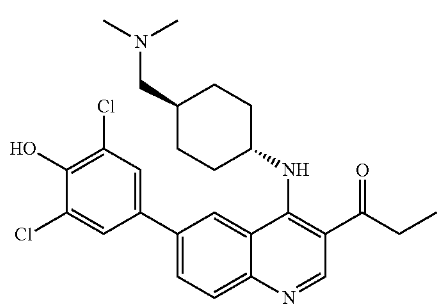 | 1-(6-(3,5-dichloro-4-hydroxyphenyl)-4-(1R,4R)-4-((dimethylamino)methyl)cyclohexylamino)quinolin-3-yl)propan-1-one | 500 |

TABLE 1-continued

| No. | Structure | Compound Name | ESI MS (m/z) |
|---|---|---|---|
| 716 | 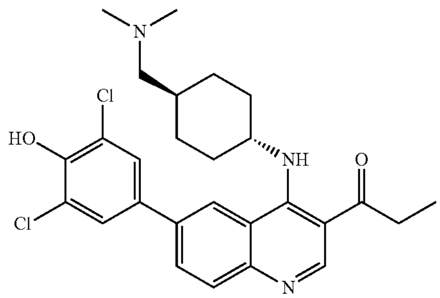 [SMILES: CCC(=O)c1cnc2ccc(-c3cc(Cl)c(O)c(Cl)c3)cc2c1N[C@H]1CC[C@H](CN(C)C)CC1] | 1-(6-(3,5-dichloro-4-hydroxyphenyl)-4-((1R,4R)-4-((dimethylamino)methyl)cyclohexyl)amino)quinolin-3-yl)propan-1-one dihydrochloride | 500 |
| 717 | 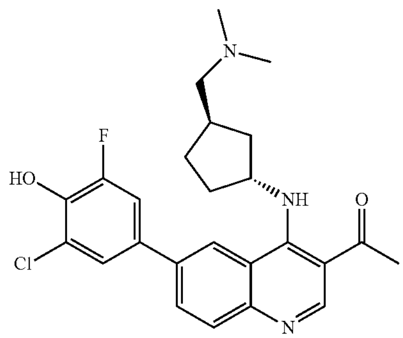 [SMILES: CC(=O)c1cnc2ccc(-c3cc(F)c(O)c(Cl)c3)cc2c1N[C@@H]1CC[C@@H](CN(C)C)C1] | 1-(6-(3-chloro-5-fluoro-4-hydroxyphenyl)-4-((1R,3R)-3-((dimethylamino)methyl)cyclopentylamino)quinolin-3-yl)ethanone | 456 |
| 718 | 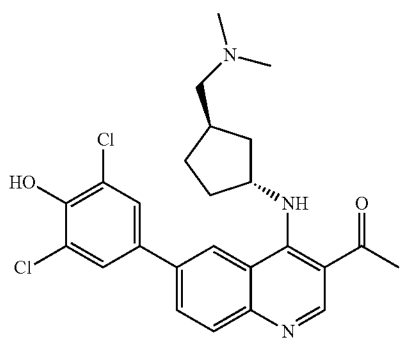 [SMILES: CC(=O)c1cnc2ccc(-c3cc(Cl)c(O)c(Cl)c3)cc2c1N[C@@H]1CC[C@@H](CN(C)C)C1] | 1-(6-(3,5-dichloro-4-hydroxyphenyl)-4-((1R,3R)-3-((dimethylamino)methyl)cyclopentylamino)quinolin-3-yl)ethanone | 472 |
| 719 | 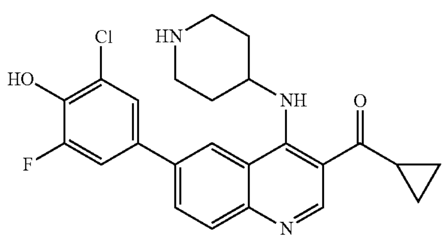 [SMILES: O=C(c1cnc2ccc(-c3cc(F)c(O)c(Cl)c3)cc2c1NC1CCNCC1)C1CC1] | (6-(3-chloro-5-fluoro-4-hydroxyphenyl)-4-(piperidin-4-ylamino)quinolin-3-yl)(cyclopropyl)methanone | 440 |
| 720 | 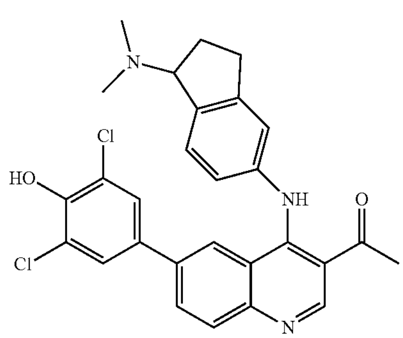 [SMILES: CC(=O)c1cnc2ccc(-c3cc(Cl)c(O)c(Cl)c3)cc2c1Nc1ccc2c(c1)CCC2N(C)C] | 1-(6-(3,5-dichloro-4-hydroxyphenyl)-4-(1-(dimethylamino)-2,3-dihydro-1H-inden-5-ylamino)quinolin-3-yl)ethanone | 506 |

TABLE 1-continued

| No. | Structure | Compound Name | ESI MS (m/z) |
|---|---|---|---|
| 721 | 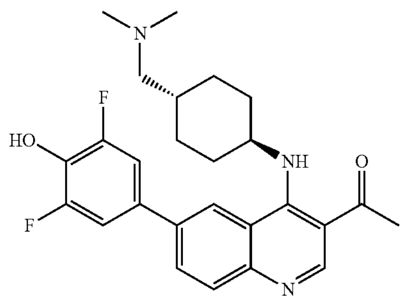 [SMILES: CC(=O)c1cnc2ccc(-c3cc(F)c(O)c(F)c3)cc2c1N[C@H]1CC[C@H](CN(C)C)CC1] | 1-(6-(3,5-difluoro-4-hydroxyphenyl)-4-(1R,4R)-4-((dimethylamino)methyl) cyclohexylamino)quinolin-3-yl) ethanone | 454 |
| 722 | 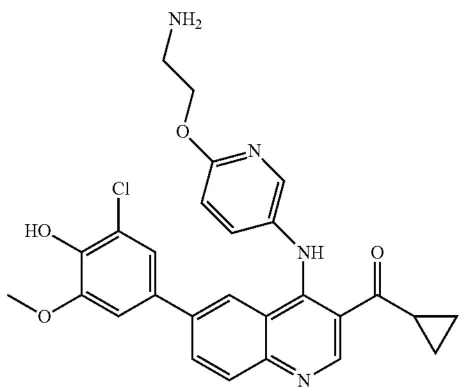 [SMILES: COc1cc(-c2ccc3ncc(C(=O)C4CC4)c(Nc4ccc(OCCN)nc4)c3c2)cc(Cl)c1O] | (4-(6-(2-aminoethoxy)pyridin-3-ylamino)-6-(3-chloro-4-hydroxy-5-methoxyphenyl)quinolin-3-yl) (cyclopropyl)methanone | 505 |
| 723 | 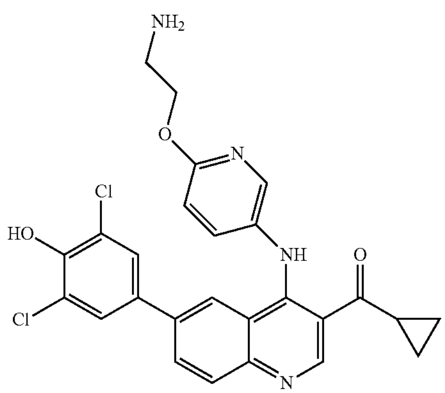 [SMILES: NCCOc1ccc(Nc2c(C(=O)C3CC3)cnc3ccc(-c4cc(Cl)c(O)c(Cl)c4)cc23)cn1] | (4-(6-(2-aminoethoxy)pyridin-3-ylamino)-6-(3,5-dichloro-4-hydroxy-phenyl)quinolin-3-yl)(cyclo-propyl)methanone | 509 |
| 724 | 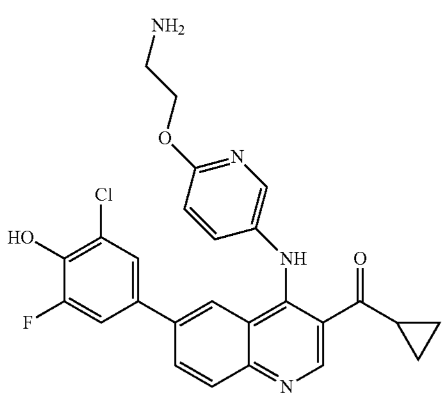 [SMILES: NCCOc1ccc(Nc2c(C(=O)C3CC3)cnc3ccc(-c4cc(F)c(O)c(Cl)c4)cc23)cn1] | (4-(6-(2-aminoethoxy)pyridin-3-ylamino)-6-(3-chloro-5-fluoro-4-hydroxyphenyl)quinolin-3-yl) (cyclopropyl)methanone | 493 |

TABLE 1-continued

| No. | Structure | Compound Name | ESI MS (m/z) |
|---|---|---|---|
| 725 | 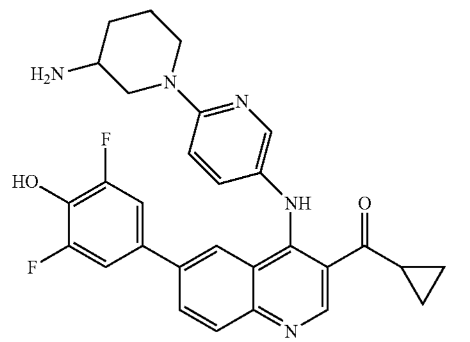 | (4-(6-(3-aminopiperidin-1-yl)pyridin-3-ylamino)-6-(3,5-difluoro-4-hydroxyphenyl)quinolin-3-yl)(cyclopropyl)methanone | 516 |
| 726 | 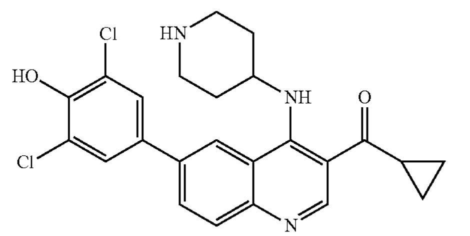 [SMILES: O=C(c1cnc2ccc(-c3cc(Cl)c(O)c(Cl)c3)cc2c1NC1CCNCC1)C1CC1] | cyclopropyl(6-(3,5-dichloro-4-hydroxyphenyl)-4-(piperidin-4-ylamino)quinolin-3-yl)methanone | 456 |
| 727 | 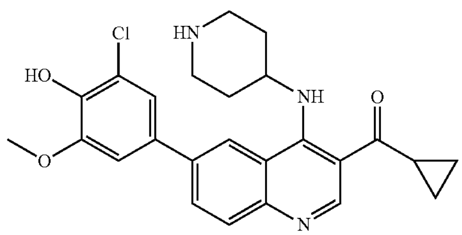 [SMILES: COc1cc(-c2ccc3ncc(C(=O)C4CC4)c(NC4CCNCC4)c3c2)cc(Cl)c1O] | (6-(3-chloro-4-hydroxy-5-methoxyphenyl)-4-(piperidin-4-ylamino)quinolin-3-yl)(cyclopropyl)methanone | 452 |
| 728 | 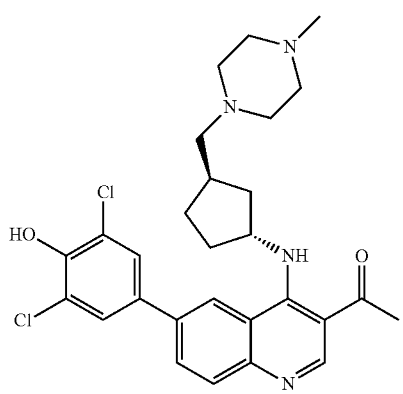 [SMILES: CC(=O)c1cnc2ccc(-c3cc(Cl)c(O)c(Cl)c3)cc2c1N[C@@H]1CC[C@@H](CN2CCN(C)CC2)C1] | 1-(6-(3,5-dichloro-4-hydroxyphenyl)-4-((1R,3R)-3-((4-methylpiperazin-1-yl)methyl)cyclopentylamino)quinolin-3-yl)ethanone | 527 |
| 729 | 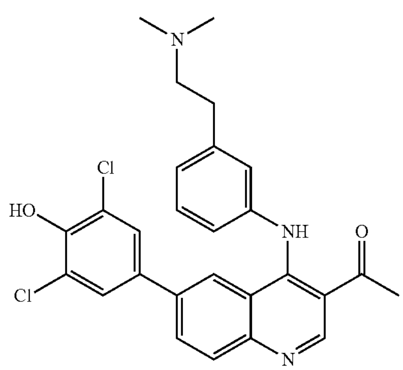 [SMILES: CC(=O)c1cnc2ccc(-c3cc(Cl)c(O)c(Cl)c3)cc2c1Nc1cccc(CCN(C)C)c1] | 1-(6-(3,5-dichloro-4-hydroxyphenyl)-4-(3-(2-(dimethylamino)ethyl)phenylamino)quinolin-3-yl)ethanone | 494 |

TABLE 1-continued

| No. | Structure | Compound Name | ESI MS (m/z) |
|---|---|---|---|
| 730 | 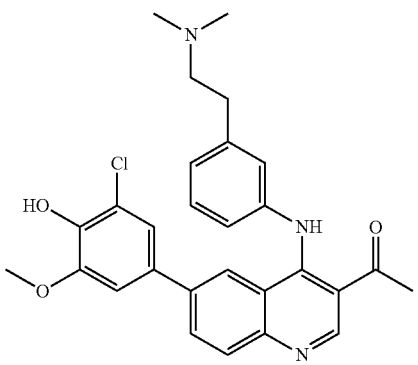 [SMILES: COc1cc(-c2ccc3ncc(C(C)=O)c(Nc4cccc(CCN(C)C)c4)c3c2)cc(Cl)c1O] | 1-(6-(3-chloro-4-hydroxy-5-methoxy-phenyl)-4-(3-(2-(dimethylamino)ethyl)phenylamino)quinolin-3-yl)ethanone | 490 |
| 731 | 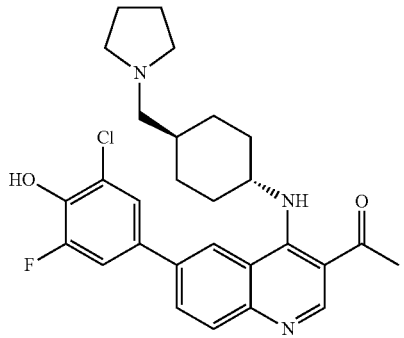 [SMILES: CC(=O)c1cnc2ccc(-c3cc(F)c(O)c(Cl)c3)cc2c1N[C@H]1CC[C@H](CN2CCCC2)CC1] | 1-(6-(3-chloro-5-fluoro-4-hydroxy-phenyl)-4-(1R,4R)-4-(pyrrolidin-1-ylmethyl)cyclohexylamino)quinolin-3-yl)ethanone | 496 |
| 732 | 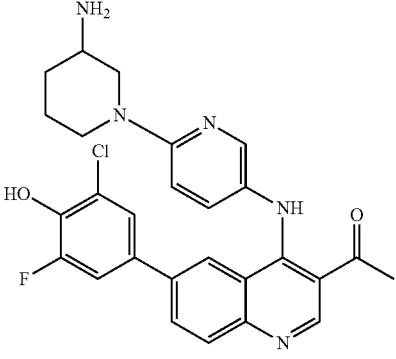 [SMILES: CC(=O)c1cnc2ccc(-c3cc(F)c(O)c(Cl)c3)cc2c1Nc1ccc(N2CCCC(N)C2)nc1] | 1-(4-(6-(3-aminopiperidin-1-yl)pyridin-3-ylamino)-6-(3-chloro-5-fluoro-4-hydroxyphenyl)quinolin-3-yl)ethanone | 506 |
| 733 | 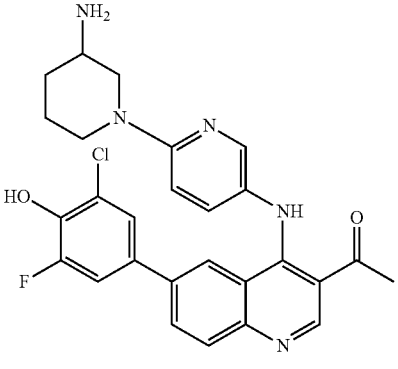 [SMILES: CC(=O)c1cnc2ccc(-c3cc(F)c(O)c(Cl)c3)cc2c1Nc1ccc(N2CCCC(N)C2)nc1] | 1-(4-((6-(3-aminopiperidin-1-yl)pyridin-3-yl)amino)-6-(3-chloro-5-fluoro-4-hydroxyphenyl)quinolin-3-yl)ethanone | 506 |

TABLE 1-continued

| No. | Structure | Compound Name | ESI MS (m/z) |
|---|---|---|---|
| 734 | 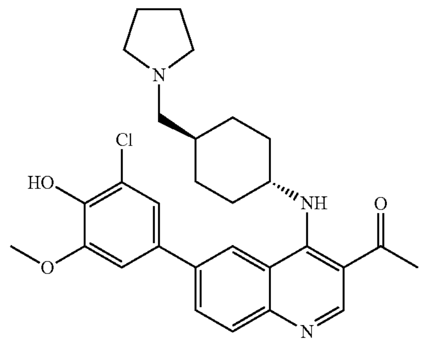 [SMILES: COc1cc(-c2ccc3ncc(C(C)=O)c(N[C@H]4CC[C@H](CN5CCCC5)CC4)c3c2)cc(Cl)c1O] | 1-(6-(3-chloro-4-hydroxy-5-methoxyphenyl)-4-(1R,4R)-4-(pyrrolidin-1-ylmethyl)cyclohexylamino)quinolin-3-yl)ethanone | 508 |
| 735 | 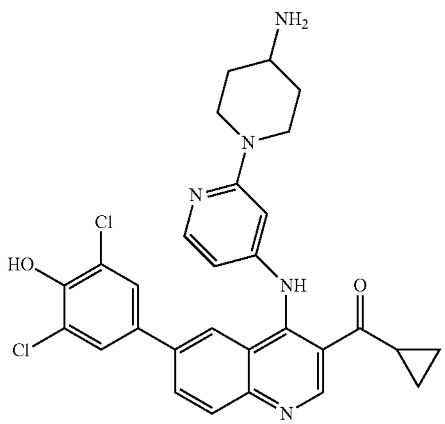 [SMILES: NC1CCN(c2cc(Nc3c(C(=O)C4CC4)cnc4ccc(-c5cc(Cl)c(O)c(Cl)c5)cc34)ccn2)CC1] | (4-(2-(4-aminopiperidin-1-yl)pyridin-4-ylamino)-6-(3,5-dichloro-4-hydroxyphenyl)quinolin-3-yl)(cyclopropyl)methanone | 548 |
| 736 | 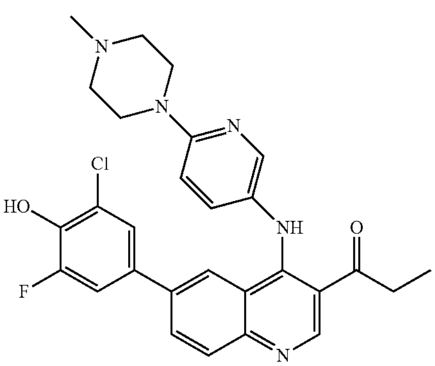 [SMILES: CCC(=O)c1cnc2ccc(-c3cc(F)c(O)c(Cl)c3)cc2c1Nc1ccc(N2CCN(C)CC2)nc1] | 1-(6-(3-chloro-5-fluoro-4-hydroxyphenyl)-4-(6-(4-methylpiperazin-1-yl)pyridin-3-ylamino)quinolin-3-yl)propan-1-one | 520 |
| 737 | 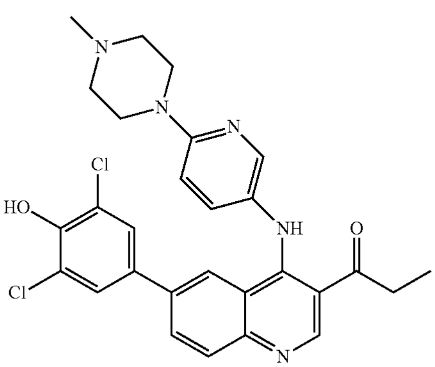 [SMILES: CCC(=O)c1cnc2ccc(-c3cc(Cl)c(O)c(Cl)c3)cc2c1Nc1ccc(N2CCN(C)CC2)nc1] | 1-(6-(3,5-dichloro-4-hydroxyphenyl)-4-(6-(4-methylpiperazin-1-yl)pyridin-3-ylamino)quinolin-3-yl)propan-1-one | 536 |

TABLE 1-continued

| No. | Structure | Compound Name | ESI MS (m/z) |
|---|---|---|---|
| 738 | 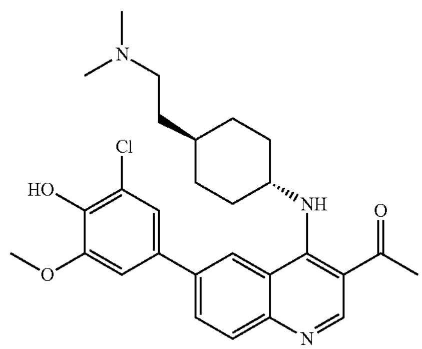 [SMILES: COc1cc(-c2ccc3ncc(C(C)=O)c(N[C@H]4CC[C@H](CCN(C)C)CC4)c3c2)cc(Cl)c1O] | 1-(6-(3-chloro-4-hydroxy-5-methoxy-phenyl)-4-(1R,4R)-4-(2-(dimethyl-amino)ethyl)cyclohexylamino)quinolin-3-yl)ethanone | 496 |
| 739 | 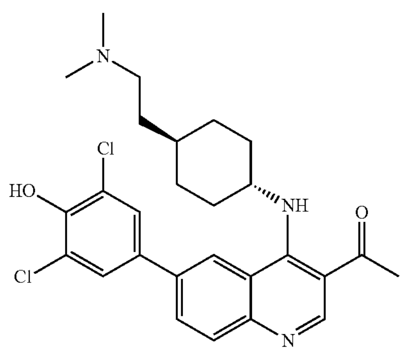 [SMILES: CC(=O)c1cnc2ccc(-c3cc(Cl)c(O)c(Cl)c3)cc2c1N[C@H]1CC[C@H](CCN(C)C)CC1] | 1-(6-(3,5-dichloro-4-hydroxyphenyl)-4-(1R,4R)-4-(2-(dimethylamino)ethyl)cyclohexylamino)quinolin-3-yl)ethanone | 500 |
| 740 | •2HCl | 1-(6-(3,5-dichloro-4-hydroxyphenyl)-4-((1R,4R)-4-(2-(dimethylamino)ethyl)cyclohexyl)amino)quinolin-3-yl)ethanone hydrochloride | 500 |
| 741 | 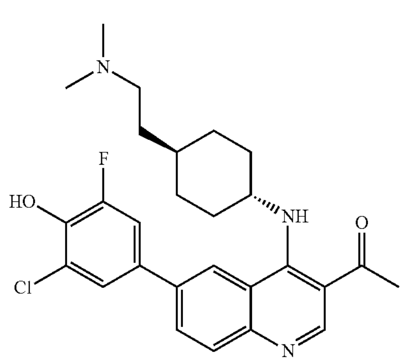 | 1-(6-(3-chloro-5-fluoro-4-hydroxy-phenyl)-4-(1R,4R)-4-(2-(dimethyl-amino)ethyl)cyclohexylamino)quinolin-3-yl)ethanone | 484 |

TABLE 1-continued

| No. | Structure | Compound Name | ESI MS (m/z) |
|---|---|---|---|
| 742 | 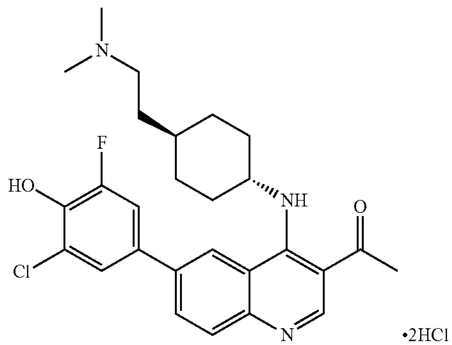 [SMILES: CC(=O)c1cnc2ccc(-c3cc(Cl)c(O)c(Cl)c3)cc2c1N[C@H]1CC[C@H](CCN(C)C)CC1] | 1-(6-(3-chloro-5-fluoro-4-hydroxy-phenyl)-4-(1R,4R)-4-(2-(dimethyl-amino)ethyl)cyclohexylamino)quinolin-3-yl)ethanone dihydrochloride | 484 |
| 743 | 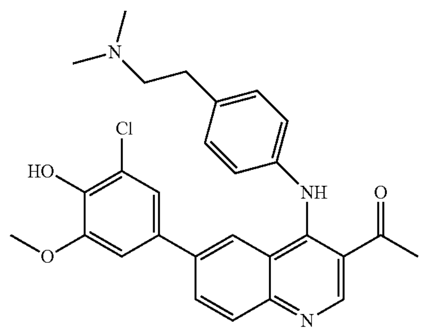 [SMILES: COc1cc(-c2ccc3ncc(C(C)=O)c(Nc4ccc(CCN(C)C)cc4)c3c2)cc(Cl)c1O] | 1-(6-(3-chloro-4-hydroxy-5-methoxy-phenyl)-4-(4-(2-(dimethylamino)ethyl)phenylamino)quinolin-3-yl)ethanone | 490 |
| 744 | 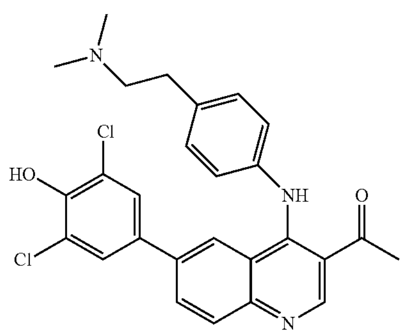 [SMILES: CC(=O)c1cnc2ccc(-c3cc(Cl)c(O)c(Cl)c3)cc2c1Nc1ccc(CCN(C)C)cc1] | 1-(6-(3,5-dichloro-4-hydroxyphenyl)-4-(4-(2-(dimethylamino)ethyl)phenyl-amino)quinolin-3-yl)ethanone | 494 |
| 745 | 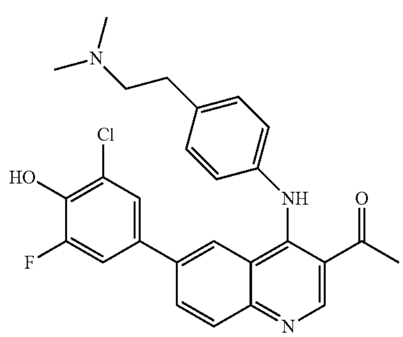 [SMILES: CC(=O)c1cnc2ccc(-c3cc(F)c(O)c(Cl)c3)cc2c1Nc1ccc(CCN(C)C)cc1] | 1-(6-(3-chloro-5-fluoro-4-hydroxy-phenyl)-4-(4-(2-(dimethylamino)ethyl)phenylamino)quinolin-3-yl)ethanone | 478 |

TABLE 1-continued

| No. | Structure | Compound Name | ESI MS (m/z) |
|---|---|---|---|
| 746 | 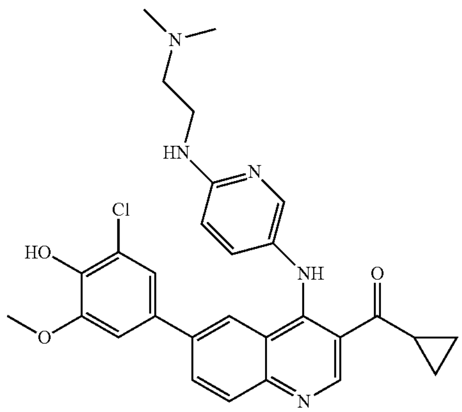 [SMILES: COc1cc(-c2ccc3ncc(C(=O)C4CC4)c(Nc4ccc(NCCN(C)C)nc4)c3c2)cc(Cl)c1O] | (6-(3-chloro-4-hydroxy-5-methoxy-phenyl)-4-(6-(2-(dimethylamino)ethyl-amino)pyridin-3-ylamino)quinolin-3-yl)(cyclopropyl)methanone | 532 |
| 747 | 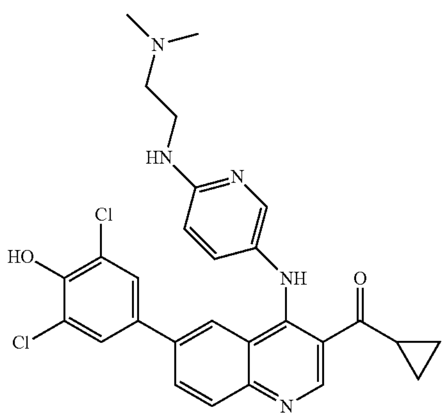 [SMILES: CN(C)CCNc1ccc(Nc2c(C(=O)C3CC3)cnc3ccc(-c4cc(Cl)c(O)c(Cl)c4)cc23)cn1] | cyclopropyl(6-(3,5-dichloro-4-hydroxy-phenyl)-4-(6-(2-(dimethylamino)ethyl-amino)pyridin-3-ylamino)quinolin-3-yl)methanone | 536 |
| 748 | 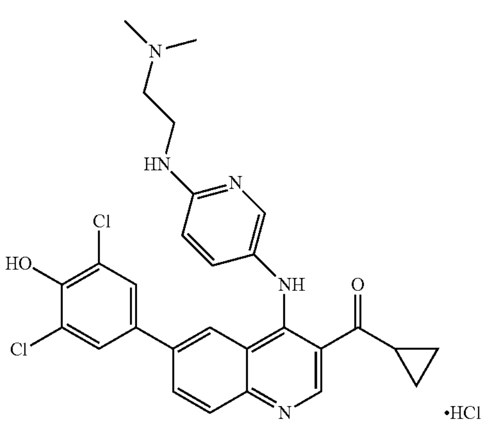 [SMILES: CN(C)CCNc1ccc(Nc2c(C(=O)C3CC3)cnc3ccc(-c4cc(Cl)c(O)c(Cl)c4)cc23)cn1 ; Cl] | cyclopropyl(6-(3,5-dichloro-4-hydroxy-phenyl)-4-(6-(2-(dimethylamino)ethylamino)pyridin-3-ylamino)quinolin-3-yl)methanone hydrochloride | 536 |

TABLE 1-continued

| No. | Structure | Compound Name | ESI MS (m/z) |
|---|---|---|---|
| 749 | 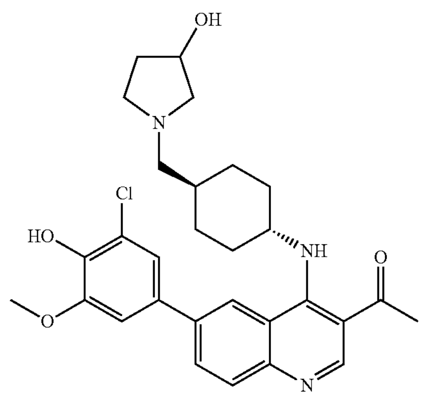 [SMILES: COc1cc(-c2ccc3ncc(C(C)=O)c(N[C@H]4CC[C@H](CN5CCC(O)C5)CC4)c3c2)cc(Cl)c1O] | 1-(6-(3-chloro-4-hydroxy-5-methoxy-phenyl)-4-(1R,4R)-4-((3-hydroxy-pyrrolidin-1-yl)methyl)cyclohexyl-amino)quinolin-3-yl)ethanone | 524 |
| 750 | 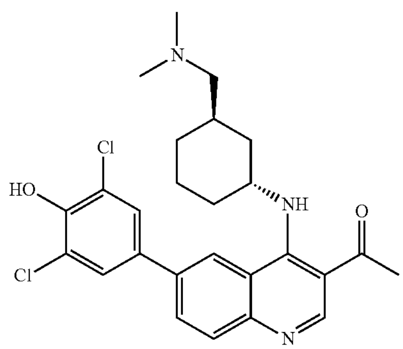 [SMILES: CC(=O)c1cnc2ccc(-c3cc(Cl)c(O)c(Cl)c3)cc2c1N[C@@H]1CCC[C@@H](CN(C)C)C1] | 1-(6-(3,5-dichloro-4-hydroxyphenyl)-4-((1R,3R)-3-((dimethylamino)methyl)cyclohexylamino)quinolin-3-yl)ethanone | 486 |
| 751 | 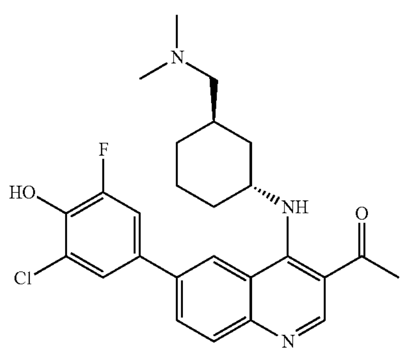 [SMILES: CC(=O)c1cnc2ccc(-c3cc(F)c(O)c(Cl)c3)cc2c1N[C@@H]1CCC[C@@H](CN(C)C)C1] | 1-(6-(3-chloro-5-fluoro-4-hydroxy-phenyl)-4-((1R,3R)-3-((dimethylamino)methyl)cyclohexylamino)quinolin-3-yl)ethanone | 470 |
| 752 | 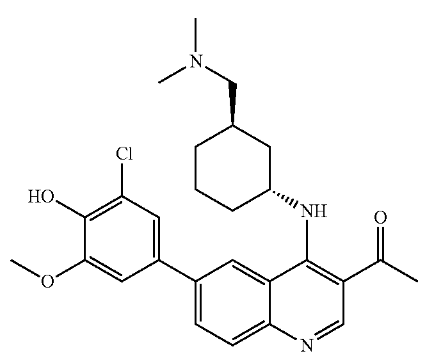 [SMILES: COc1cc(-c2ccc3ncc(C(C)=O)c(N[C@@H]4CCC[C@@H](CN(C)C)C4)c3c2)cc(Cl)c1O] | 1-(6-(3-chloro-4-hydroxy-5-methoxy-phenyl)-4-((1R,3R)-3-((dimethyl-amino)methyl)cyclohexylamino)quinolin-3-yl)ethanone | 482 |

TABLE 1-continued

| No. | Structure | Compound Name | ESI MS (m/z) |
|---|---|---|---|
| 753 | 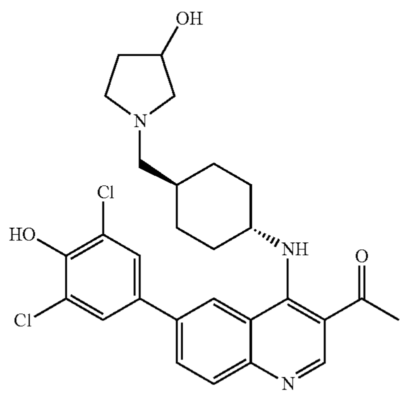 [SMILES: CC(=O)c1cnc2ccc(-c3cc(Cl)c(O)c(Cl)c3)cc2c1N[C@H]1CC[C@H](CN2CCC(O)C2)CC1] | 1-(6-(3,5-dichloro-4-hydroxyphenyl)-4-(1R,4R)-4-((3-hydroxypyrrolidin-1-yl)methyl)cyclohexylamino)quinolin-3-yl)ethanone | 528 |
| 754 | 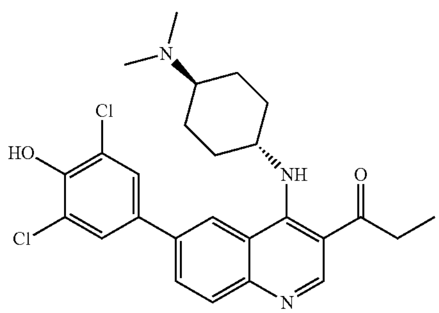 [SMILES: CCC(=O)c1cnc2ccc(-c3cc(Cl)c(O)c(Cl)c3)cc2c1N[C@H]1CC[C@H](N(C)C)CC1] | 1-(6-(3,5-dichloro-4-hydroxyphenyl)-4-(1R,4R)-4-(dimethylamino)cyclohexylamino)quinolin-3-yl)propan-1-one | 486 |
| 755 | 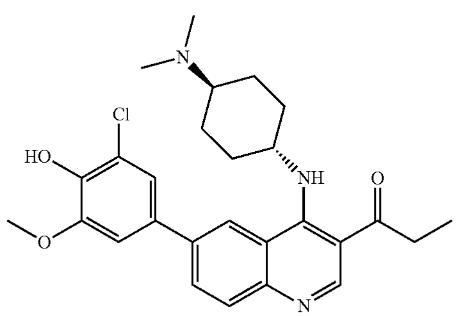 [SMILES: CCC(=O)c1cnc2ccc(-c3cc(Cl)c(O)c(OC)c3)cc2c1N[C@H]1CC[C@H](N(C)C)CC1] | 1-(6-(3-chloro-4-hydroxy-5-methoxyphenyl)-4-(1R,4R)-4-(dimethylamino)cyclohexylamino)quinolin-3-yl)propan-1-one | 482 |
| 756 | 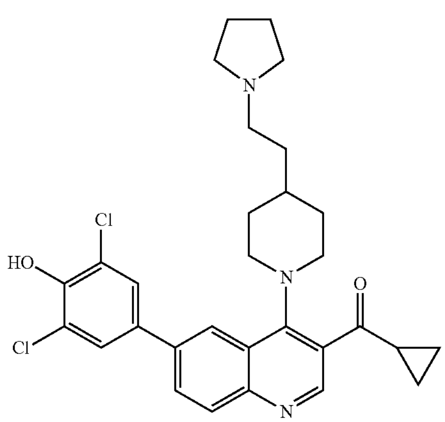 [SMILES: O=C(c1cnc2ccc(-c3cc(Cl)c(O)c(Cl)c3)cc2c1N1CCC(CCN2CCCC2)CC1)C1CC1] | cyclopropyl(6-(3,5-dichloro-4-hydroxyphenyl)-4-(4-(2-(pyrrolidin-1-yl)ethyl)piperidin-1-yl)quinolin-3-yl)methanone | 539 |

TABLE 1-continued

| No. | Structure | Compound Name | ESI MS (m/z) |
|---|---|---|---|
| 757 | 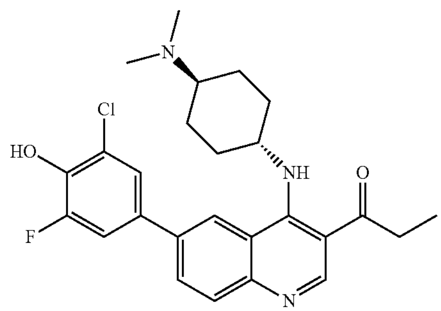 [SMILES: CCC(=O)c1cnc2ccc(-c3cc(F)c(O)c(Cl)c3)cc2c1N[C@H]1CC[C@H](N(C)C)CC1] | 1-(6-(3-chloro-5-fluoro-4-hydroxyphenyl)-4-(1R,4R)-4-(dimethylamino)cyclohexylamino)quinolin-3-yl)propan-1-one | 470 |
| 758 | 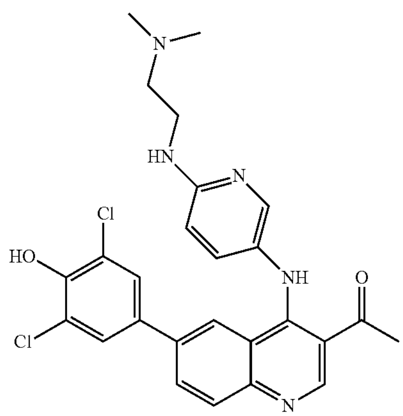 [SMILES: CC(=O)c1cnc2ccc(-c3cc(Cl)c(O)c(Cl)c3)cc2c1Nc1ccc(NCCN(C)C)nc1] | 1-(6-(3,5-dichloro-4-hydroxyphenyl)-4-(6-(2-(dimethylamino)ethylamino)pyridin-3-ylamino)quinolin-3-yl)ethanone | 510 |
| 759 | 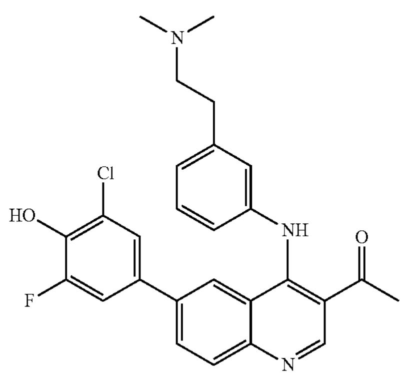 [SMILES: CC(=O)c1cnc2ccc(-c3cc(F)c(O)c(Cl)c3)cc2c1Nc1cccc(CCN(C)C)c1] | 1-(6-(3-chloro-5-fluoro-4-hydroxyphenyl)-4-(3-(2-(dimethylamino)ethyl)phenylamino)quinolin-3-yl)ethanone | 478 |
| 760 | 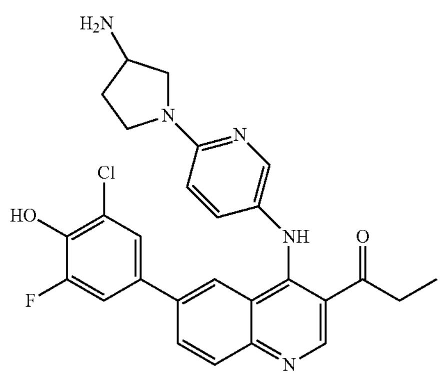 [SMILES: CCC(=O)c1cnc2ccc(-c3cc(F)c(O)c(Cl)c3)cc2c1Nc1ccc(N2CCC(N)C2)nc1] | 1-(4-(6-(3-aminopyrrolidin-1-yl)pyridin-3-ylamino)-6-(3-chloro-5-fluoro-4-hydroxyphenyl)quinolin-3-yl)propan-1-one | 506 |

TABLE 1-continued

| No. | Structure | Compound Name | ESI MS (m/z) |
|---|---|---|---|
| 761 | 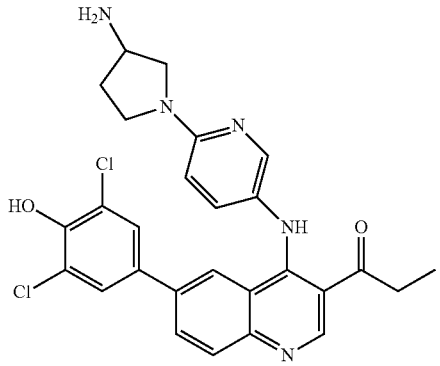 [SMILES: CCC(=O)c1cnc2ccc(-c3cc(Cl)c(O)c(Cl)c3)cc2c1Nc1ccc(N2CCC(N)C2)nc1] | 1-(4-(6-(3-aminopyrrolidin-1-yl)pyridin-3-ylamino)-6-(3,5-dichloro-4-hydroxyphenyl)quinolin-3-yl)propan-1-one | 522 |
| 762 | 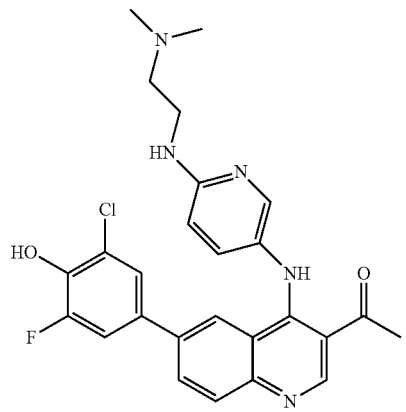 [SMILES: CC(=O)c1cnc2ccc(-c3cc(F)c(O)c(Cl)c3)cc2c1Nc1ccc(NCCN(C)C)nc1] | 1-(6-(3-chloro-5-fluoro-4-hydroxyphenyl)-4-(6-(2-(dimethylamino)ethylamino)pyridin-3-ylamino)quinolin-3-yl)ethanone | 494 |
| 763 | 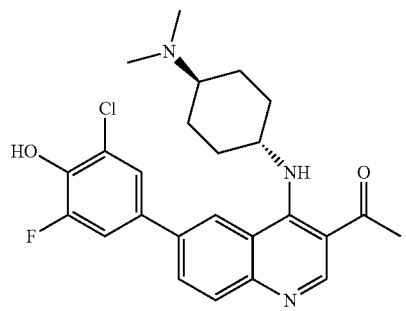 [SMILES: CC(=O)c1cnc2ccc(-c3cc(F)c(O)c(Cl)c3)cc2c1N[C@H]1CC[C@H](N(C)C)CC1] | 1-(6-(3-chloro-5-fluoro-4-hydroxyphenyl)-4-(1R,4R)-4-(dimethylamino)cyclohexylamino)quinolin-3-yl)ethanone | 456 |
| 764 | 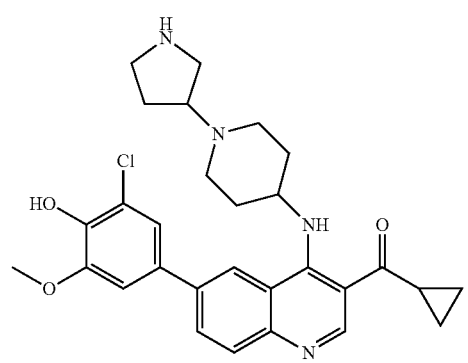 [SMILES: COc1cc(-c2ccc3ncc(C(=O)C4CC4)c(NC4CCN(C5CCNC5)CC4)c3c2)cc(Cl)c1O] | (6-(3-chloro-4-hydroxy-5-methoxyphenyl)-4-(1-(pyrrolidin-3-yl)piperidin-4-ylamino)quinolin-3-yl)(cyclopropyl)methanone | 521 |

TABLE 1-continued

| No. | Structure | Compound Name | ESI MS (m/z) |
|---|---|---|---|
| 765 | 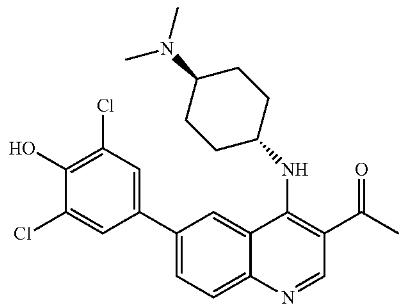 [SMILES: CC(=O)c1cnc2ccc(-c3cc(Cl)c(O)c(Cl)c3)cc2c1N[C@H]1CC[C@H](N(C)C)CC1] | 1-(6-(3,5-dichloro-4-hydroxyphenyl)-4-(1R,4R)-4-(dimethylamino)cyclohexylamino)quinolin-3-yl)ethanone | 472 |
| 766 | 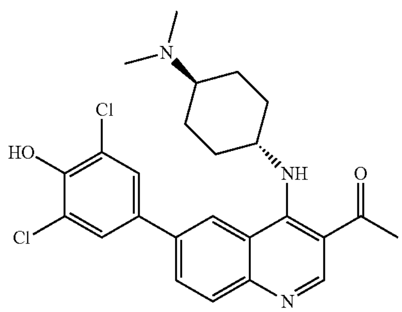 | 1-(6-(3,5-dichloro-4-hydroxyphenyl)-4-((1R,4R)-4-(dimethylamino)cyclohexyl)amino)quinolin-3-yl)ethanone hydrochloride | 472 |
| 767 | 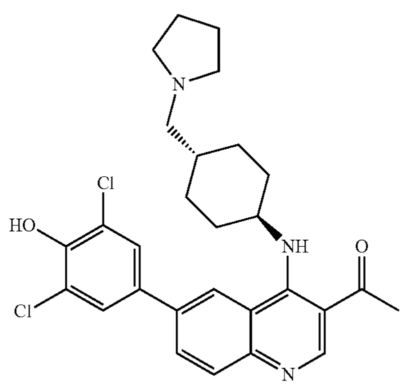 [SMILES: CC(=O)c1cnc2ccc(-c3cc(Cl)c(O)c(Cl)c3)cc2c1N[C@H]1CC[C@H](CN2CCCC2)CC1] | 1-(6-(3,5-dichloro-4-hydroxyphenyl)-4-(1R,4R)-4-(pyrrolidin-1-ylmethyl)cyclohexylamino)quinolin-3-yl)ethanone | 512 |
| 768 | 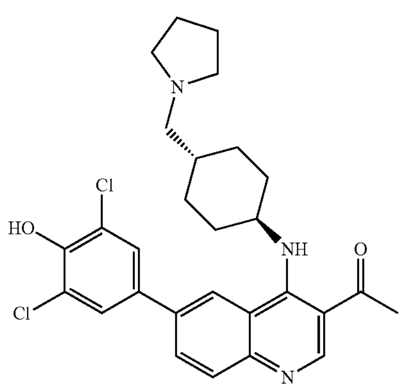 | 1-(6-(3,5-dichloro-4-hydroxyphenyl)-4-((1R,4R)-4-(pyrrolidin-1-ylmethyl)cyclohexyl)amino)quinolin-3-yl)ethanone hydrochloride | 512 |

TABLE 1-continued

| No. | Structure | Compound Name | ESI MS (m/z) |
|---|---|---|---|
| 769 | 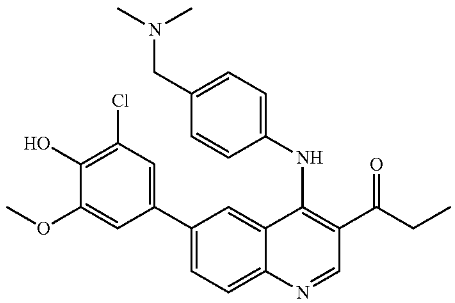 [SMILES: CCC(=O)c1cnc2ccc(-c3cc(Cl)c(O)c(OC)c3)cc2c1Nc1ccc(CN(C)C)cc1] | 1-(6-(3-chloro-4-hydroxy-5-methoxyphenyl)-4-(4-((dimethylamino)methyl)phenylamino)quinolin-3-yl)propan-1-one | 490 |
| 770 | 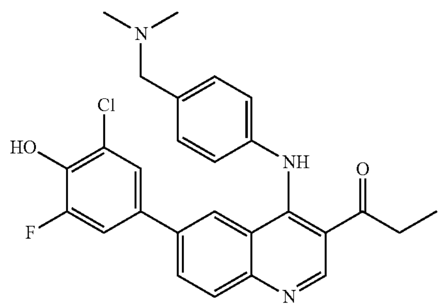 [SMILES: CCC(=O)c1cnc2ccc(-c3cc(F)c(O)c(Cl)c3)cc2c1Nc1ccc(CN(C)C)cc1] | 1-(6-(3-chloro-5-fluoro-4-hydroxyphenyl)-4-(4-((dimethylamino)methyl)phenylamino)quinolin-3-yl)propan-1-one | 478 |
| 771 | 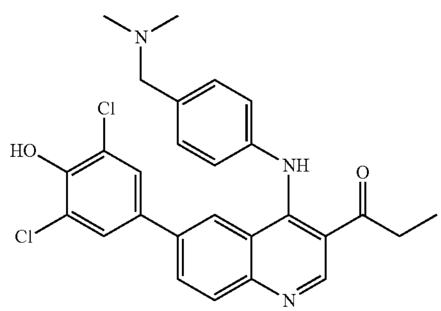 [SMILES: CCC(=O)c1cnc2ccc(-c3cc(Cl)c(O)c(Cl)c3)cc2c1Nc1ccc(CN(C)C)cc1] | 1-(6-(3,5-dichloro-4-hydroxyphenyl)-4-(4-((dimethylamino)methyl)phenylamino)quinolin-3-yl)propan-1-one | 494 |
| 772 | 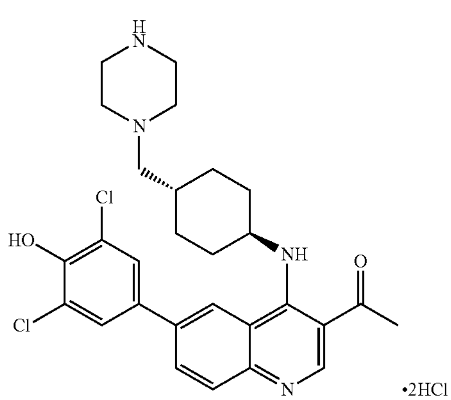 [SMILES: CC(=O)c1cnc2ccc(-c3cc(Cl)c(O)c(Cl)c3)cc2c1N[C@H]1CC[C@H](CN2CCNCC2)CC1] | 1-(6-(3,5-dichloro-4-hydroxyphenyl)-4-(1R,4R)-4-(piperazin-1-ylmethyl)cyclohexylamino)quinolin-3-yl)ethanone dihydrochloride | 527 |

TABLE 1-continued

| No. | Structure | Compound Name | ESI MS (m/z) |
|---|---|---|---|
| 773 | 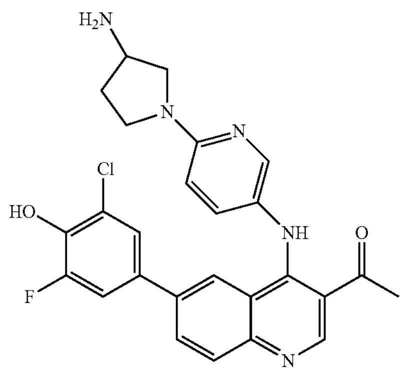 [SMILES: CC(=O)c1cnc2ccc(-c3cc(F)c(O)c(Cl)c3)cc2c1Nc1ccc(N2CCC(N)C2)nc1] | 1-(4-(6-(3-aminopyrrolidin-1-yl)pyridin-3-ylamino)-6-(3-chloro-5-fluoro-4-hydroxyphenyl)quinolin-3-yl)ethanone | 492 |
| 774 | 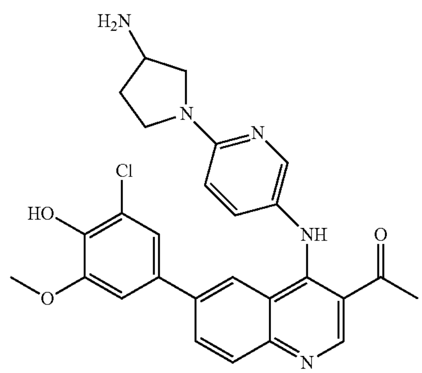 [SMILES: COc1cc(-c2ccc3ncc(C(C)=O)c(Nc4ccc(N5CCC(N)C5)nc4)c3c2)cc(Cl)c1O] | 1-(4-(6-(3-aminopyrrolidin-1-yl)pyridin-3-ylamino)-6-(3-chloro-4-hydroxy-5-methoxyphenyl)quinolin-3-yl)ethanone | 504 |
| 775 | 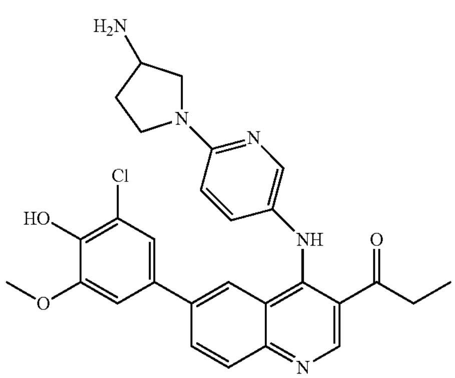 [SMILES: CCC(=O)c1cnc2ccc(-c3cc(Cl)c(O)c(OC)c3)cc2c1Nc1ccc(N2CCC(N)C2)nc1] | 1-(4-(6-(3-aminopyrrolidin-1-yl)pyridin-3-ylamino)-6-(3-chloro-4-hydroxy-5-methoxyphenyl)quinolin-3-yl)propan-1-one | 518 |
| 776 | 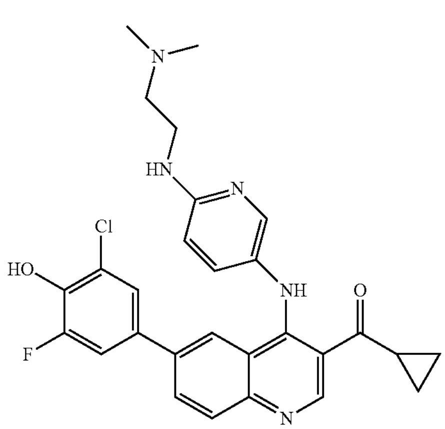 | (6-(3-chloro-5-fluoro-4-hydroxyphenyl)-4-(6-(2-(dimethylamino)ethylamino)pyridin-3-ylamino)quinolin-3-yl)(cyclopropyl)methanone | 520 |

TABLE 1-continued

| No. | Structure | Compound Name | ESI MS (m/z) |
|---|---|---|---|
| 777 | 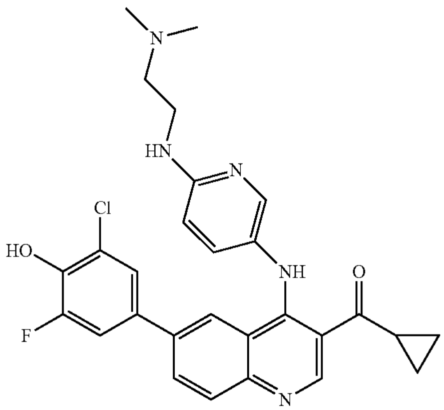 | (6-(3-chloro-5-fluoro-4-hydroxy-phenyl)-4-(6-(2-(dimethylamino)ethyl-amino)pyridin-3-ylamino)quinolin-3-yl)(cyclopropyl)methanone trihydrochloride | 520 |
| 778 | 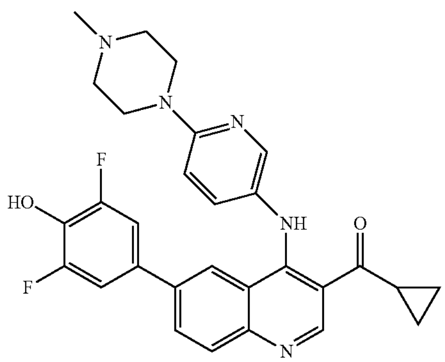 | cyclopropyl(6-(3,5-difluoro-4-hydroxy-phenyl)-4-(6-(4-methylpiperazin-1-yl)pyridin-3-ylamino)quinolin-3-yl)methanone | 516 |
| 779 | 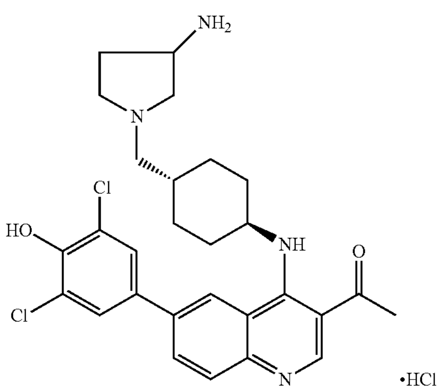 [SMILES: CC(=O)c1cnc2ccc(-c3cc(Cl)c(O)c(Cl)c3)cc2c1N[C@H]1CC[C@H](CN2CCC(N)C2)CC1 ; Cl] | 1-(4-(1R,4R)-4-((3-aminopyrrolidin-1-yl)methyl)cyclohexylamino)-6-(3,5-dichloro-4-hydroxyphenyl)quinolin-3-yl)ethanone hydrochloride | 527 |
| 780 | 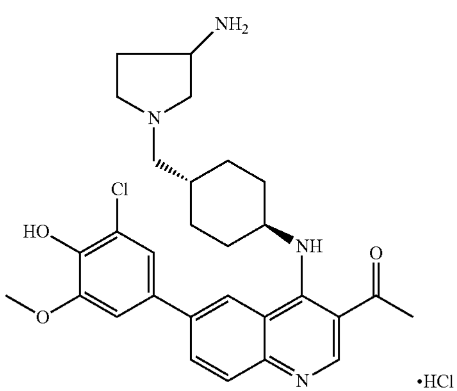 [SMILES: COc1cc(-c2ccc3ncc(C(C)=O)c(N[C@H]4CC[C@H](CN5CCC(N)C5)CC4)c3c2)cc(Cl)c1O ; Cl] | 1-(4-(1R,4R)-4-((3-aminopyrrolidin-1-yl)methyl)cyclohexylamino)-6-(3-chloro-4-hydroxy-5-methoxyphenyl)quinolin-3-yl)ethanone hydrochloride | 523 |

TABLE 1-continued

| No. | Structure | Compound Name | ESI MS (m/z) |
|---|---|---|---|
| 781 | 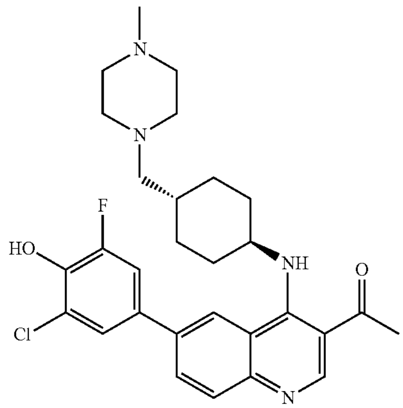 | 1-(6-(3-chloro-5-fluoro-4-hydroxyphenyl)-4-(1R,4R)-4-((4-methylpiperazin-1-yl)methyl)cyclohexylamino)quinolin-3-yl)ethanone hydrochloride | 525 |
| 782 | 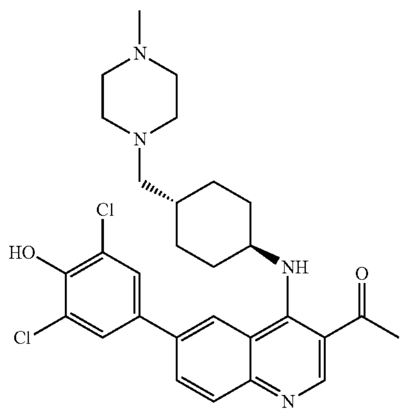 | 1-(6-(3,5-dichloro-4-hydroxyphenyl)-4-(1R,4R)-4-((4-methylpiperazin-1-yl)methyl)cyclohexylamino)quinolin-3-yl)ethanone hydrochloride | 542 |
| 783 | 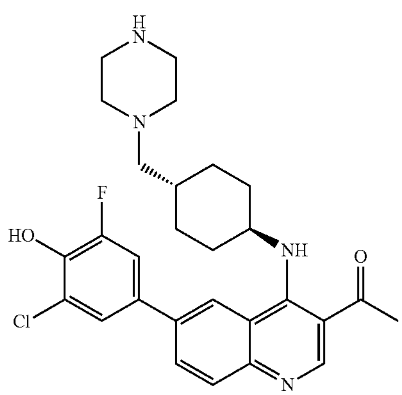 | 1-(6-(3-chloro-5-fluoro-4-hydroxyphenyl)-4-(1R,4R)-4-(piperazin-1-ylmethyl)cyclohexylamino)quinolin-3-yl)ethanone dihydrochloride | 511 |
| 784 | 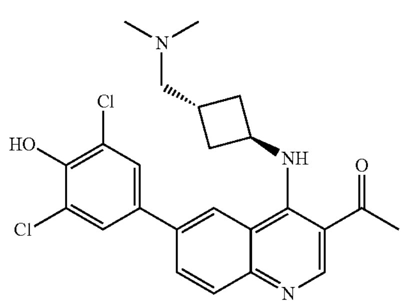 [SMILES: CC(=O)c1cnc2ccc(-c3cc(Cl)c(O)c(Cl)c3)cc2c1N[C@H]1C[C@H](CN(C)C)C1] | 1-(6-(3,5-dichloro-4-hydroxyphenyl)-4-((1r,3r)-3-((dimethylamino)methyl)cyclobutylamino)quinolin-3-yl)ethanone | 458 |

TABLE 1-continued

| No. | Structure | Compound Name | ESI MS (m/z) |
|---|---|---|---|
| 785 | 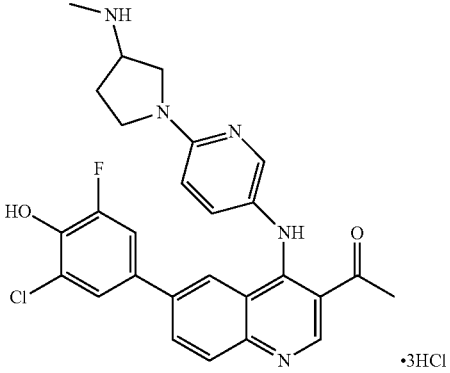 [SMILES: CNC1CCN(c2ccc(Nc3c(C(C)=O)cnc4ccc(-c5cc(F)c(O)c(Cl)c5)cc34)cn2)C1] | 1-(6-(3-chloro-5-fluoro-4-hydroxy-phenyl)-4-(6-(3-(methylamino)pyrrolidin-1-yl)pyridin-3-ylamino)quinolin-3-yl)ethanone trihydrochloride | 506 |
| 786 | 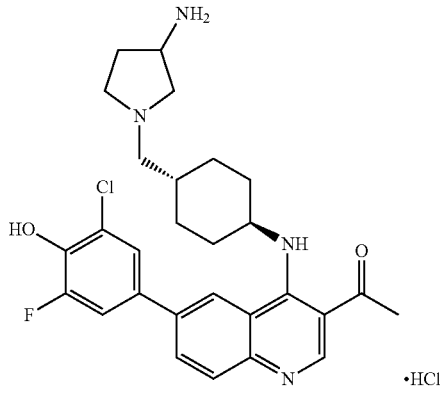 [SMILES: CC(=O)c1cnc2ccc(-c3cc(F)c(O)c(Cl)c3)cc2c1N[C@H]1CC[C@H](CN2CCC(N)C2)CC1 ; Cl] | 1-(4-(1R,4R)-4-((3-aminopyrrolidin-1-yl)methyl)cyclohexylamino)-6-(3-chloro-5-fluoro-4-hydroxyphenyl)quinolin-3-yl)ethanone hydrochloride | 511 |
| 787 | 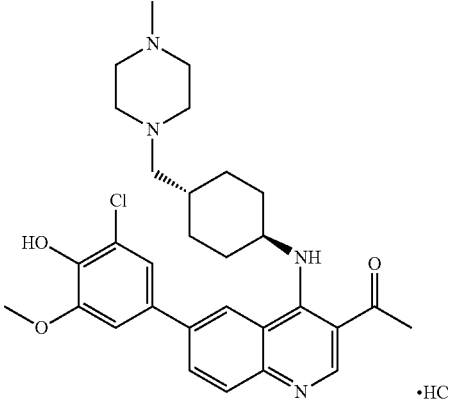 | 1-(6-(3-chloro-4-hydroxy-5-methoxy-phenyl)-4-(1R,4R)-4-((4-methyl-piperazin-1-yl)methyl)cyclohexyl-amino)quinolin-3-yl)ethanone hydrochloride | 537 |
| 788 | 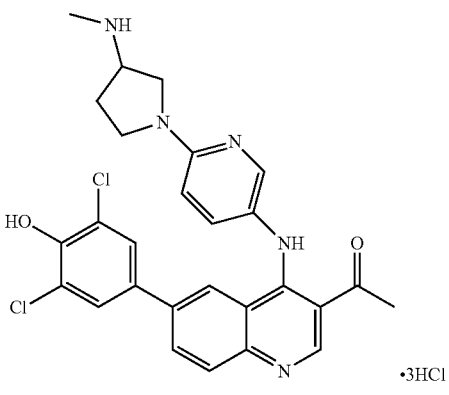 [SMILES: CNC1CCN(c2ccc(Nc3c(C(C)=O)cnc4ccc(-c5cc(Cl)c(O)c(Cl)c5)cc34)cn2)C1] | 1-(6-(3,5-dichloro-4-hydroxyphenyl)-4-(6-(3-(methylamino)pyrrolidin-1-yl)pyridin-3-ylamino)quinolin-3-yl)ethanone trihydrochloride | 522 |

TABLE 1-continued

| No. | Structure | Compound Name | ESI MS (m/z) |
|---|---|---|---|
| 789 | 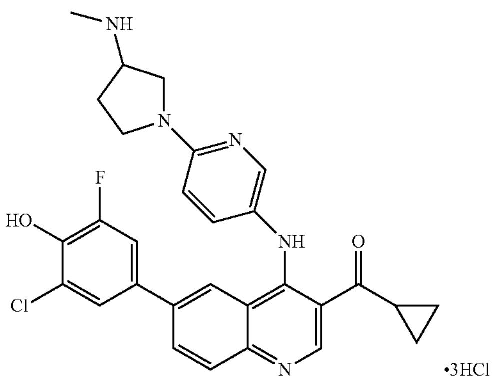 [SMILES: CNC1CCN(c2ccc(Nc3c(C(=O)C4CC4)cnc4ccc(-c5cc(F)c(O)c(Cl)c5)cc34)cn2)C1] | (6-(3-chloro-5-fluoro-4-hydroxy-phenyl)-4-(6-(3-(methylamino) pyrrolidin-1-yl)pyridin-3-ylamino) quinolin-3-yl)(cyclopropyl) methanone trihydrochloride | 532 |
| 790 | 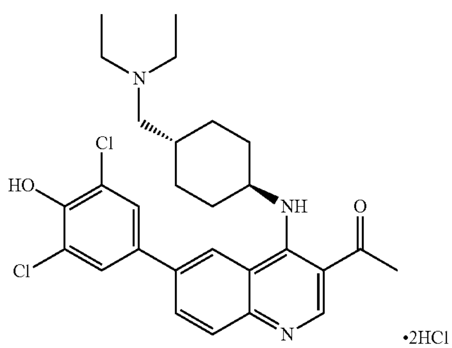 [SMILES: CCN(CC)C[C@H]1CC[C@H](Nc2c(C(C)=O)cnc3ccc(-c4cc(Cl)c(O)c(Cl)c4)cc23)CC1] | 1-(6-(3,5-dichloro-4-hydroxyphenyl)-4-(1R,4R)-4-((diethylamino)methyl) cyclohexylamino)quinolin-3-yl) ethanone dihydrochloride | 514 |
| 791 | 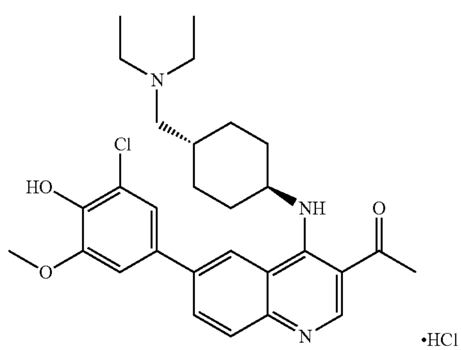 [SMILES: CCN(CC)C[C@H]1CC[C@H](Nc2c(C(C)=O)cnc3ccc(-c4cc(Cl)c(O)c(OC)c4)cc23)CC1 ; Cl] | 1-(6-(3-chloro-4-hydroxy-5-methoxy-phenyl)-4-(1R,4R)-4-((diethylamino) methyl)cyclohexylamino)quinolin-3-yl)ethanone hydrochloride | 510 |
| 792 | 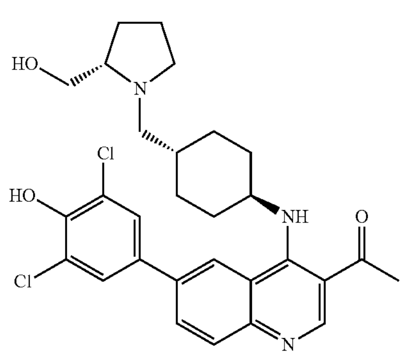 [SMILES: CC(=O)c1cnc2ccc(-c3cc(Cl)c(O)c(Cl)c3)cc2c1N[C@H]1CC[C@H](CN2CCC[C@H]2CO)CC1] | 1-(6-(3,5-dichloro-4-hydroxyphenyl)-4-((1S,4R)-4-(((S)-2-(hydroxymethyl) pyrrolidin-1-yl)methyl)cyclohexyl-amino)quinolin-3-yl)ethanone | 542 |

| No. | Structure | Compound Name | ESI MS (m/z) |
|---|---|---|---|
| 793 | 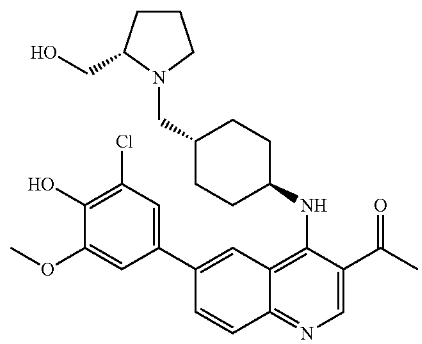 [SMILES: COc1cc(-c2ccc3ncc(C(C)=O)c(N[C@H]4CC[C@H](CN5CCC[C@H]5CO)CC4)c3c2)cc(Cl)c1O] | 1-(6-(3-chloro-4-hydroxy-5-methoxy-phenyl)-4-((1S,4R)-4-(((S)-2-(hydroxy-methyl)pyrrolidin-1-yl)methyl)cyclo-hexylamino)quinolin-3-yl)ethanone | 538 |
| 794 | 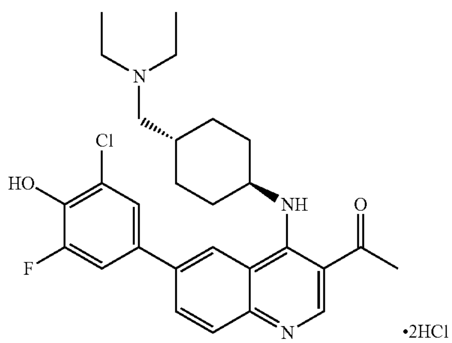 [SMILES: CCN(CC)C[C@H]1CC[C@H](Nc2c(C(C)=O)cnc3ccc(-c4cc(F)c(O)c(Cl)c4)cc23)CC1] | 1-(6-(3-chloro-5-fluoro-4-hydroxy-phenyl)-4-(1R,4R)-4-((diethylamino)methyl)cyclohexylamino)quinolin-3-yl)ethanone dihydrochloride | 498 |
| 795 | 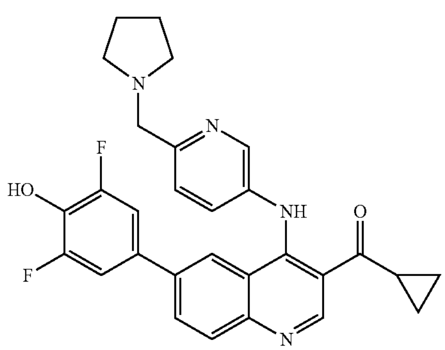 [SMILES: O=C(c1cnc2ccc(-c3cc(F)c(O)c(F)c3)cc2c1Nc1ccc(CN2CCCC2)nc1)C1CC1] | cyclopropyl(6-(3,5-difluoro-4-hydroxy-phenyl)-4-(6-(pyrrolidin-1-ylmethyl)pyridin-3-ylamino)quinolin-3-yl)methanone | 501 |
| 796 | 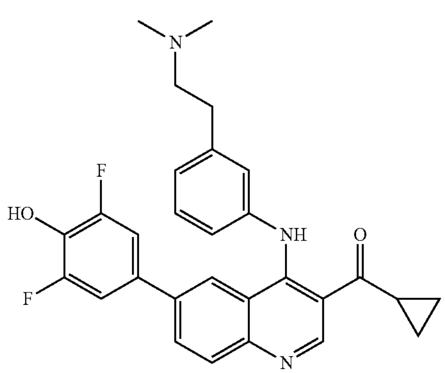 [SMILES: CN(C)CCc1cccc(Nc2c(C(=O)C3CC3)cnc3ccc(-c4cc(F)c(O)c(F)c4)cc23)c1] | cyclopropyl(6-(3,5-difluoro-4-hydroxy-phenyl)-4-(3-(2-(dimethylamino)ethyl)phenylamino)quinolin-3-yl)methanone | 488 |

TABLE 1-continued
| No. | Structure | Compound Name | ESI MS (m/z) |
|---|---|---|---|
| 797 | 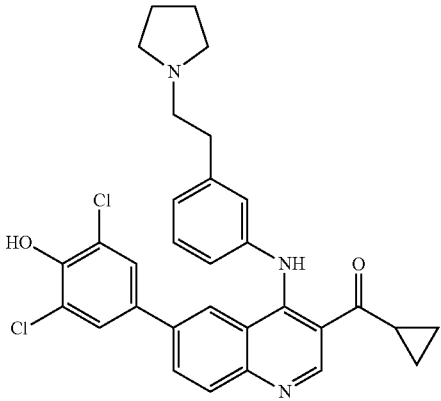 [SMILES: O=C(c1cnc2ccc(-c3cc(Cl)c(O)c(Cl)c3)cc2c1Nc1cccc(CCN2CCCC2)c1)C1CC1] | cyclopropyl(6-(3,5-dichloro-4-hydroxyphenyl)-4-(3-(2-(pyrrolidin-1-yl)ethyl)phenylamino)quinolin-3-yl)methanone | 546 |
| 798 | 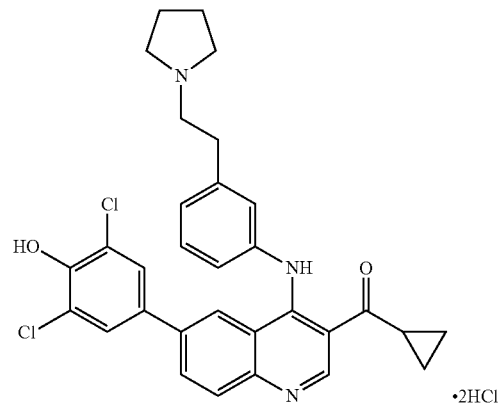 [SMILES: O=C(c1cnc2ccc(-c3cc(Cl)c(O)c(Cl)c3)cc2c1Nc1cccc(CCN2CCCC2)c1)C1CC1] | cyclopropyl(6-(3,5-dichloro-4-hydroxyphenyl)-4-(3-(2-(pyrrolidin-1-yl)ethyl)phenylamino)quinolin-3-yl)methanone hydrochloride | 546 |
| 799 | 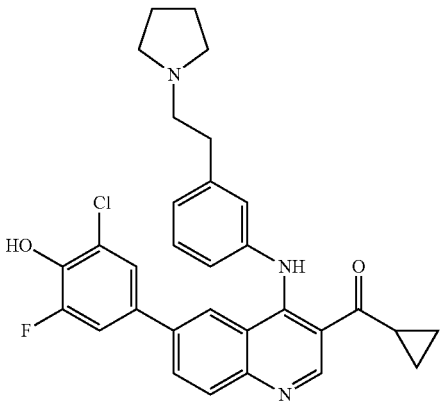 [SMILES: O=C(c1cnc2ccc(-c3cc(F)c(O)c(Cl)c3)cc2c1Nc1cccc(CCN2CCCC2)c1)C1CC1] | (6-(3-chloro-5-fluoro-4-hydroxyphenyl)-4-(3-(2-(pyrrolidin-1-yl)ethyl)phenylamino)quinolin-3-yl)(cyclopropyl)methanone | 530 |

TABLE 1-continued
| No. | Structure | Compound Name | ESI MS (m/z) |
|---|---|---|---|
| 800 | 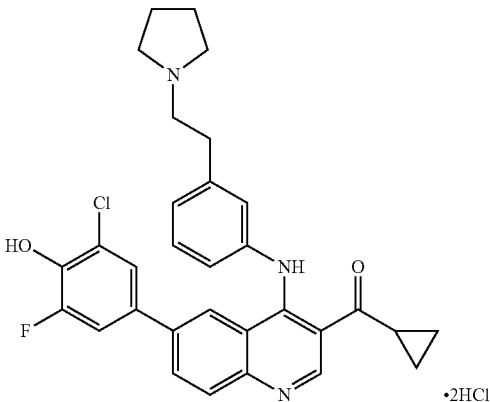 | (6-(3-chloro-5-fluoro-4-hydroxyphenyl)-4-(3-(2-(pyrrolidin-1-yl)ethyl)phenylamino)quinolin-3-yl)(cyclopropyl)methanone hydrochloride | 530 |
| 801 | 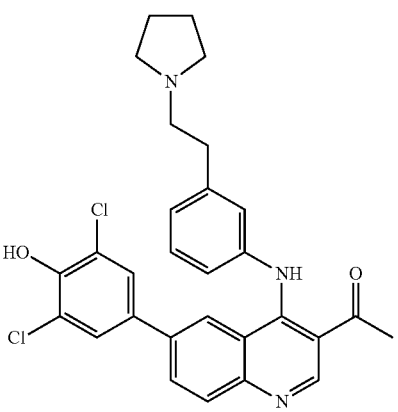 [SMILES: CC(=O)c1cnc2ccc(-c3cc(Cl)c(O)c(Cl)c3)cc2c1Nc1cccc(CCN2CCCC2)c1] | 1-(6-(3,5-dichloro-4-hydroxyphenyl)-4-(3-(2-(pyrrolidin-1-yl)ethyl)phenylamino)quinolin-3-yl)ethanone | 520 |
| 802 | 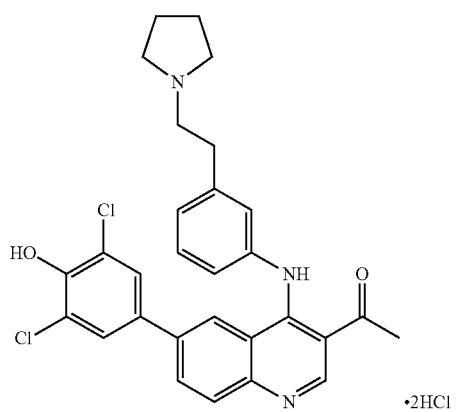 [SMILES: CC(=O)c1cnc2ccc(-c3cc(Cl)c(O)c(Cl)c3)cc2c1Nc1cccc(CCN2CCCC2)c1] | 1-(6-(3,5-dichloro-4-hydroxyphenyl)-4-((3-(2-(pyrrolidin-1-yl)ethyl)phenyl)amino)quinolin-3-yl)ethanone hydrochloride | 520 |

TABLE 1-continued

| No. | Structure | Compound Name | ESI MS (m/z) |
|---|---|---|---|
| 803 | 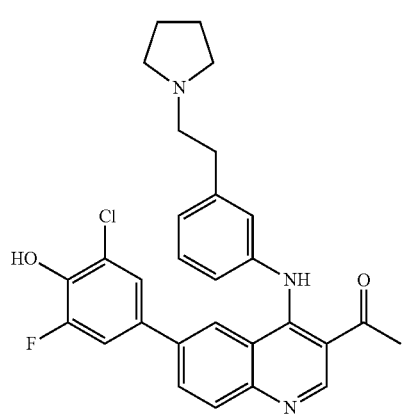 [SMILES: CC(=O)c1cnc2ccc(-c3cc(F)c(O)c(Cl)c3)cc2c1Nc1cccc(CCN2CCCC2)c1] | 1-(6-(3-chloro-5-fluoro-4-hydroxy-phenyl)-4-(3-(2-(pyrrolidin-1-yl)ethyl)phenylamino)quinolin-3-yl)ethanone | 504 |
| 804 | 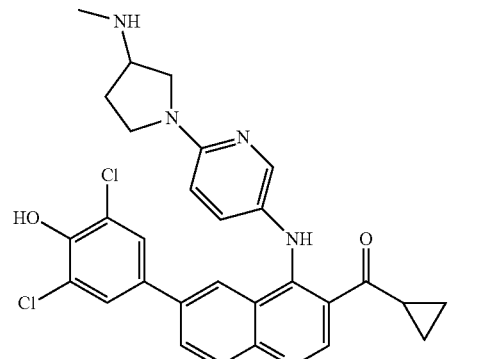 | cyclopropyl(6-(3,5-dichloro-4-hydroxy-phenyl)-4-(6-(3-(methylamino)pyrrolidin-1-yl)pyridin-3-ylamino)quinolin-3-yl)methanone trihydrochloride | 548 |
| 805 | 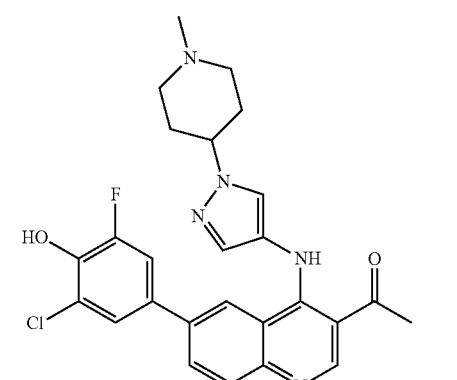 | 1-(6-(3-chloro-5-fluoro-4-hydroxy-phenyl)-4-(1-(1-methylpiperidin-4-yl)-1H-pyrazol-4-ylamino)quinolin-3-yl)ethanone hydrochloride | 494 |

TABLE 1-continued

| No. | Structure | Compound Name | ESI MS (m/z) |
|---|---|---|---|
| 806 | 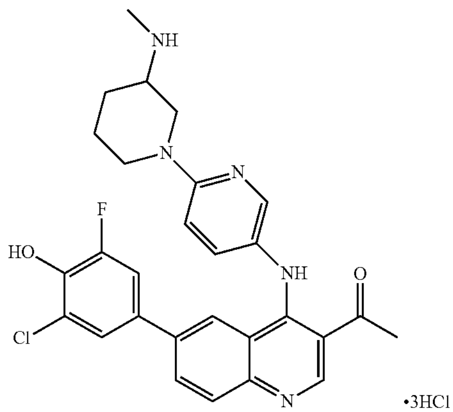 | 1-(6-(3,5-dichloro-4-hydroxyphenyl)-4-(6-(3-(methylamino)piperidin-1-yl)pyridin-3-ylamino)quinolin-3-yl)ethanone trihydrochloride | 536 |
| 807 | 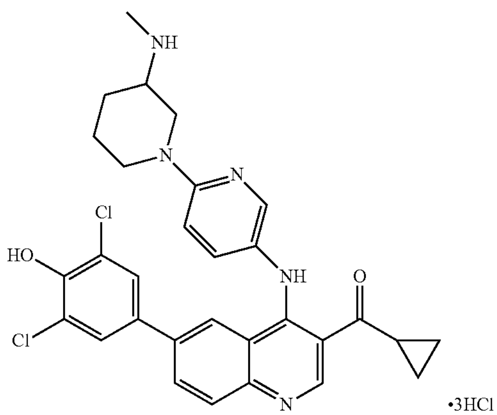 [SMILES: CNC1CCCN(c2ccc(Nc3c(C(=O)C4CC4)cnc4ccc(-c5cc(Cl)c(O)c(Cl)c5)cc34)cn2)C1 ; "·3HCl"] | cyclopropyl(6-(3,5-dichloro-4-hydroxyphenyl)-4-(6-(3-(methylamino)piperidin-1-yl)pyridin-3-ylamino)quinolin-3-yl)methanone trihydrochloride | 562 |
| 808 | 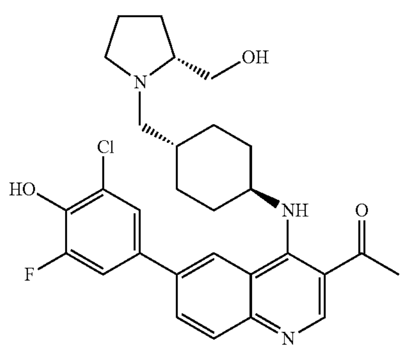 [SMILES: CC(=O)c1cnc2ccc(-c3cc(F)c(O)c(Cl)c3)cc2c1N[C@H]1CC[C@H](CN2CCC[C@@H]2CO)CC1] | 1-(6-(3-chloro-5-fluoro-4-hydroxyphenyl)-4-(1R,4R)-4-(((R)-2-(hydroxymethyl)pyrrolidin-1-yl)methyl)cyclohexylamino)quinolin-3-yl)ethanone hydrochloride | 526 |
| 809 | 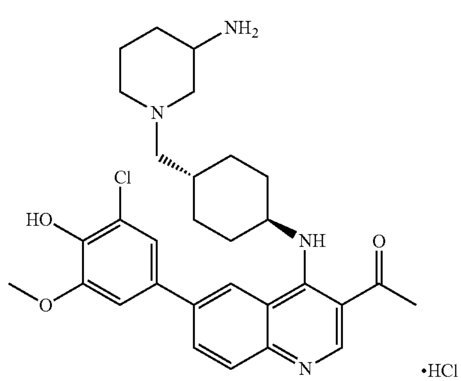 [SMILES: COc1cc(-c2ccc3ncc(C(C)=O)c(N[C@H]4CC[C@H](CN5CCCC(N)C5)CC4)c3c2)cc(Cl)c1O ; Cl] | 1-(4-(1R,4R)-4-((3-aminopiperidin-1-yl)methyl)cyclohexylamino)-6-(3-chloro-4-hydroxy-5-methoxyphenyl)quinolin-3-yl)ethanone hydrochloride | 537 |

TABLE 1-continued

| No. | Structure | Compound Name | ESI MS (m/z) |
|---|---|---|---|
| 810 | 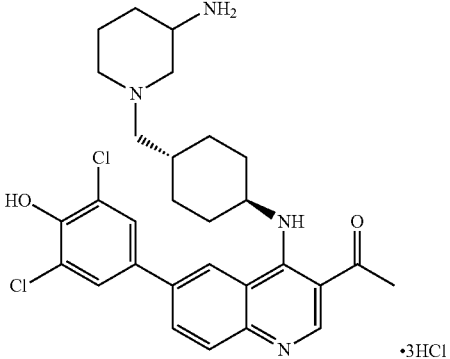 [SMILES: CC(=O)c1cnc2ccc(-c3cc(Cl)c(O)c(Cl)c3)cc2c1N[C@H]1CC[C@H](CN2CCCC(N)C2)CC1 ; "·3HCl"] | 1-(4-(1R,4R)-4-((3-aminopiperidin-1-yl)methyl)cyclohexylamino)-6-(3,5-dichloro-4-hydroxyphenyl)quinolin-3-yl)ethanone trihydrochloride | 542 |
| 811 | 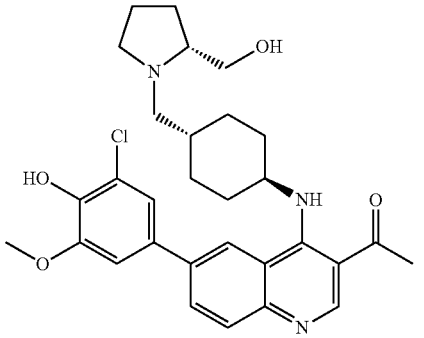 [SMILES: COc1cc(-c2ccc3ncc(C(C)=O)c(N[C@H]4CC[C@H](CN5CCC[C@@H]5CO)CC4)c3c2)cc(Cl)c1O] | 1-(6-(3-chloro-4-hydroxy-5-methoxyphenyl)-4-(1R,4R)-4-(((R)-2-(hydroxymethyl)pyrrolidin-1-yl)methyl)cyclohexylamino)quinolin-3-yl)ethanone | 538 |
| 812 | 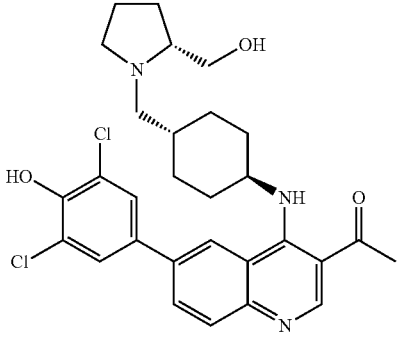 | 1-(6-(3,5-dichloro-4-hydroxyphenyl)-4-(1R,4R)-4-(((R)-2-(hydroxymethyl)pyrrolidin-1-yl)methyl)cyclohexylamino)quinolin-3-yl)ethanone | 542 |
| 813 | 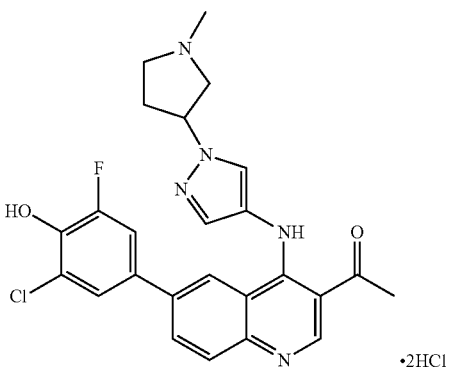 [SMILES: CC(=O)c1cnc2ccc(-c3cc(F)c(O)c(Cl)c3)cc2c1Nc1cnn(C2CCN(C)C2)c1] | 1-(6-(3-chloro-5-fluoro-4-hydroxyphenyl)-4-(1-(1-methylpyrrolidin-3-yl)-1H-pyrazol-4-ylamino)quinolin-3-yl)ethanone dihydrochloride | 480 |

TABLE 1-continued

| No. | Structure | Compound Name | ESI MS (m/z) |
|---|---|---|---|
| 814 | 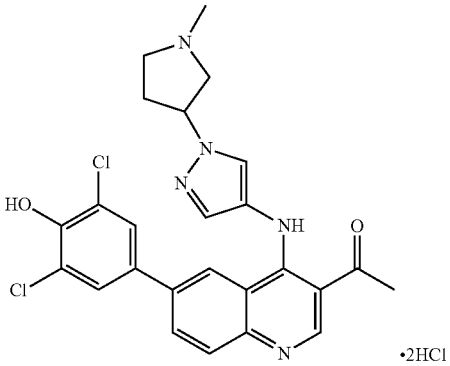 [SMILES: CC(=O)c1cnc2ccc(-c3cc(Cl)c(O)c(Cl)c3)cc2c1Nc1cnn(C2CCN(C)C2)c1] | 1-(6-(3,5-dichloro-4-hydroxyphenyl)-4-(1-(1-methylpyrrolidin-3-yl)-1H-pyrazol-4-ylamino)quinolin-3-yl)ethanone dihydrochloride | 496 |
| 815 | 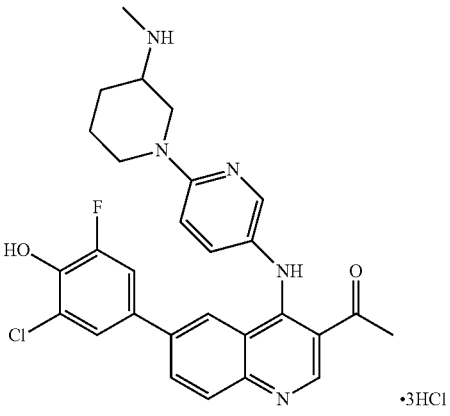 [SMILES: CNC1CCCN(c2ccc(Nc3c(C(C)=O)cnc4ccc(-c5cc(F)c(O)c(Cl)c5)cc34)cn2)C1] | 1-(6-(3-chloro-5-fluoro-4-hydroxyphenyl)-4-(6-(3-(methylamino)piperidin-1-yl)pyridin-3-ylamino)quinolin-3-yl)ethanone trihydrochloride | 520 |
| 816 | 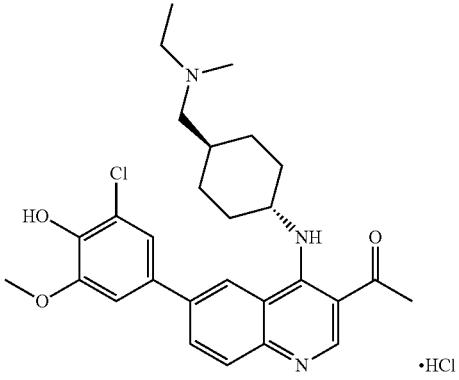 [SMILES: CCN(C)C[C@H]1CC[C@H](Nc2c(C(C)=O)cnc3ccc(-c4cc(Cl)c(O)c(OC)c4)cc23)CC1 ; Cl] | 1-(6-(3-chloro-4-hydroxy-5-methoxyphenyl)-4-(1R,4R)-4-((ethyl(methyl)amino)methyl)cyclohexylamino)quinolin-3-yl)ethanone hydrochloride | 496 |
| 817 | 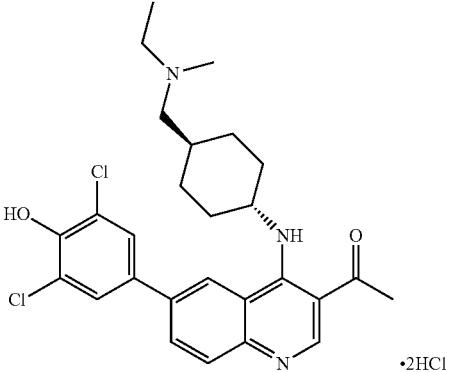 [SMILES: CCN(C)C[C@H]1CC[C@H](Nc2c(C(C)=O)cnc3ccc(-c4cc(Cl)c(O)c(Cl)c4)cc23)CC1 ; "·2HCl"] | 1-(6-(3,5-dichloro-4-hydroxyphenyl)-4-(1R,4R)-4-((ethyl(methyl)amino)methyl)cyclohexylamino)quinolin-3-yl)ethanone dihydrochloride | 500 |

TABLE 1-continued

| No. | Structure | Compound Name | ESI MS (m/z) |
|---|---|---|---|
| 818 | 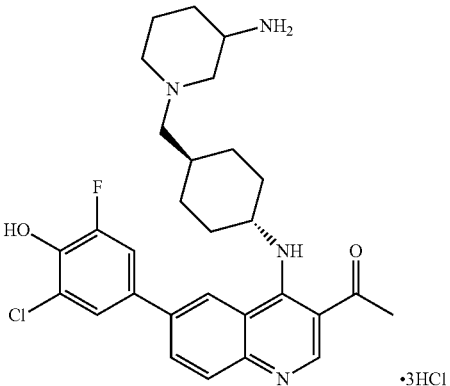 [SMILES: CC(=O)c1cnc2ccc(-c3cc(F)c(O)c(Cl)c3)cc2c1N[C@H]1CC[C@H](CN2CCCC(N)C2)CC1 ; "·3HCl"] | 1-(4-((1R,4R)-4-((3-aminopiperidin-1-yl)methyl)cyclohexylamino)-6-(3-chloro-5-fluoro-4-hydroxyphenyl)quinolin-3-yl)ethanone trihydrochloride | 525 |
| 819 | 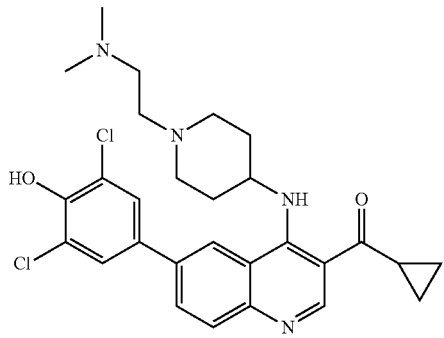 [SMILES: CN(C)CCN1CCC(Nc2c(C(=O)C3CC3)cnc3ccc(-c4cc(Cl)c(O)c(Cl)c4)cc23)CC1] | cyclopropyl(6-(3,5-dichloro-4-hydroxyphenyl)-4-(1-(2-(dimethylamino)ethyl)piperidin-4-ylamino)quinolin-3-yl)methanone | 527 |
| 820 | 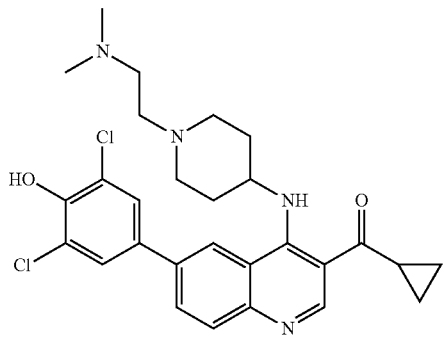 [SMILES: CN(C)CCN1CCC(Nc2c(C(=O)C3CC3)cnc3ccc(-c4cc(Cl)c(O)c(Cl)c4)cc23)CC1] | cyclopropyl(6-(3,5-dichloro-4-hydroxyphenyl)-4-(1-(2-(dimethylamino)ethyl)piperidin-4-ylamino)quinolin-3-yl)methanone | 527 |
| 821 | 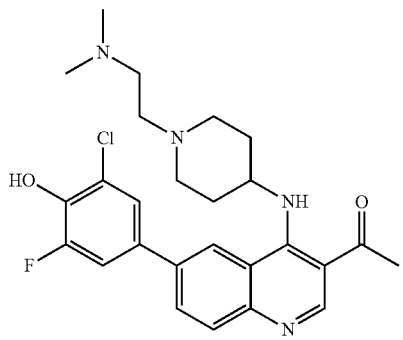 [SMILES: CC(=O)c1cnc2ccc(-c3cc(F)c(O)c(Cl)c3)cc2c1NC1CCN(CCN(C)C)CC1] | 1-(6-(3-chloro-5-fluoro-4-hydroxyphenyl)-4-(1-(2-(dimethylamino)ethyl)piperidin-4-ylamino)quinolin-3-yl)ethanone | 485 |

TABLE 1-continued

| No. | Structure | Compound Name | ESI MS (m/z) |
|---|---|---|---|
| 822 | 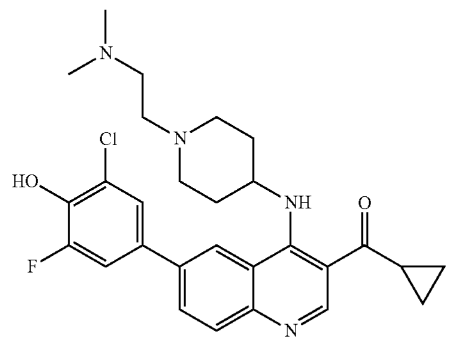 [SMILES: CN(C)CCN1CCC(Nc2c(C(=O)C3CC3)cnc3ccc(-c4cc(F)c(O)c(Cl)c4)cc23)CC1] | (6-(3-chloro-5-fluoro-4-hydroxyphenyl)-4-(1-(2-(dimethylamino)ethyl)piperidin-4-ylamino)quinolin-3-yl)(cyclopropyl)methanone | 511 |
| 823 | 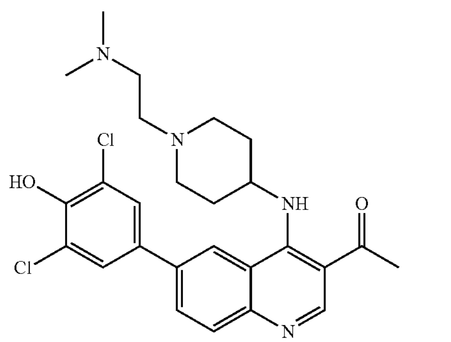 [SMILES: CC(=O)c1cnc2ccc(-c3cc(Cl)c(O)c(Cl)c3)cc2c1NC1CCN(CCN(C)C)CC1] | 1-(6-(3,5-dichloro-4-hydroxyphenyl)-4-(1-(2-(dimethylamino)ethyl)piperidin-4-ylamino)quinolin-3-yl)ethanone | 501 |
| 824 | 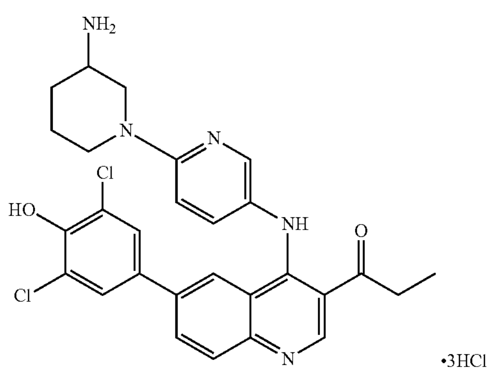 | 1-(4-(6-(3-aminopiperidin-1-yl)pyridin-3-ylamino)-6-(3,5-dichloro-4-hydroxyphenyl)quinolin-3-yl)propan-1-one trihydrochloride | 536 |
| 825 | 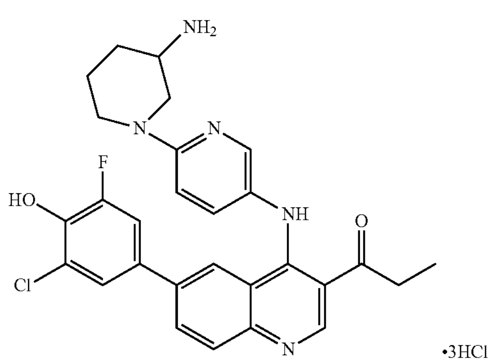 | 1-(4-(6-(3-aminopiperidin-1-yl)pyridin-3-ylamino)-6-(3-chloro-5-fluoro-4-hydroxyphenyl)quinolin-3-yl)propan-1-one trihydrochloride | 520 |

TABLE 1-continued

| No. | Structure | Compound Name | ESI MS (m/z) |
|---|---|---|---|
| 826 | 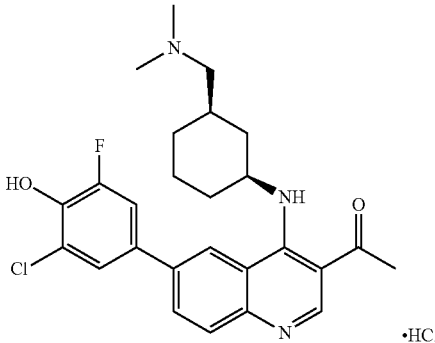 [SMILES: CC(=O)c1cnc2ccc(-c3cc(F)c(O)c(Cl)c3)cc2c1N[C@H]1CCC[C@@H](CN(C)C)C1 ; Cl] | 1-(6-(3-chloro-5-fluoro-4-hydroxyphenyl)-4-((1S,3R)-3-((dimethylamino)methyl)cyclohexylamino)quinolin-3-yl)ethanone hydrochloride | 470 |
| 827 | 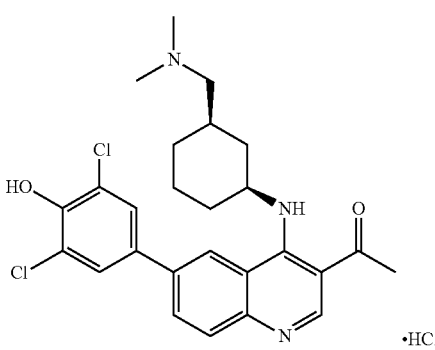 [SMILES: CC(=O)c1cnc2ccc(-c3cc(Cl)c(O)c(Cl)c3)cc2c1N[C@H]1CCC[C@@H](CN(C)C)C1 ; Cl] | 1-(6-(3,5-dichloro-4-hydroxyphenyl)-4-((1S,3R)-3-((dimethylamino)methyl)cyclohexylamino)quinolin-3-yl)ethanone hydrochloride | 486 |
| 828 | 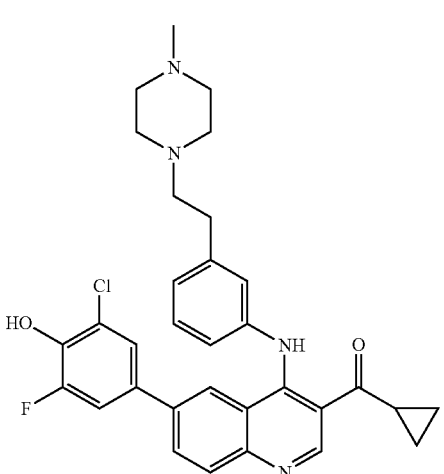 | (6-(3-chloro-5-fluoro-4-hydroxyphenyl)-4-(3-(2-(4-methylpiperazin-1-yl)ethyl)phenylamino)quinolin-3-yl)(cyclopropyl)methanone | 559 |

TABLE 1-continued
| No. | Structure | Compound Name | ESI MS (m/z) |
|---|---|---|---|
| 829 | 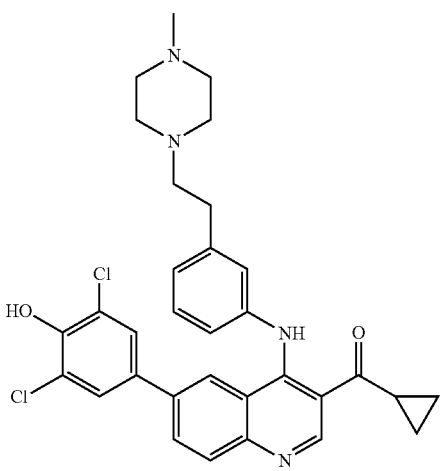 [SMILES: CN1CCN(CCc2cccc(Nc3c(C(=O)C4CC4)cnc4ccc(-c5cc(Cl)c(O)c(Cl)c5)cc34)c2)CC1] | cyclopropyl(6-(3,5-dichloro-4-hydroxy-phenyl)-4-(3-(2-(4-methylpiperazin-1-yl)ethyl)phenylamino)quinolin-3-yl)methanone | 576 |
| 830 | 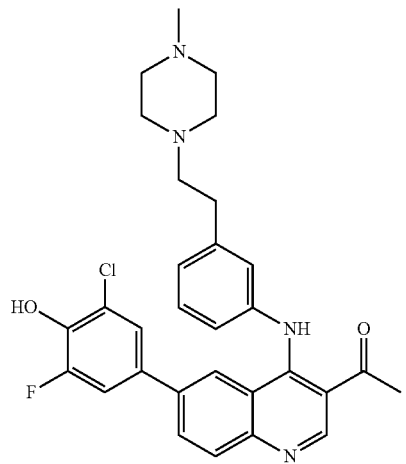 [SMILES: CC(=O)c1cnc2ccc(-c3cc(F)c(O)c(Cl)c3)cc2c1Nc1cccc(CCN2CCN(C)CC2)c1] | 1-(6-(3-chloro-5-fluoro-4-hydroxy-phenyl)-4-(3-(2-(4-methylpiperazin-1-yl)ethyl)phenylamino)quinolin-3-yl)ethanone | 533 |
| 831 | 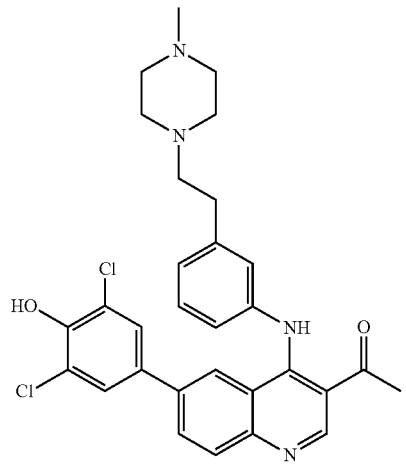 [SMILES: CC(=O)c1cnc2ccc(-c3cc(Cl)c(O)c(Cl)c3)cc2c1Nc1cccc(CCN2CCN(C)CC2)c1] | 1-(6-(3,5-dichloro-4-hydroxyphenyl)-4-(3-(2-(4-methylpiperazin-1-yl)ethyl)phenylamino)quinolin-3-yl)ethanone | 549 |

TABLE 1-continued

| No. | Structure | Compound Name | ESI MS (m/z) |
|---|---|---|---|
| 832 | 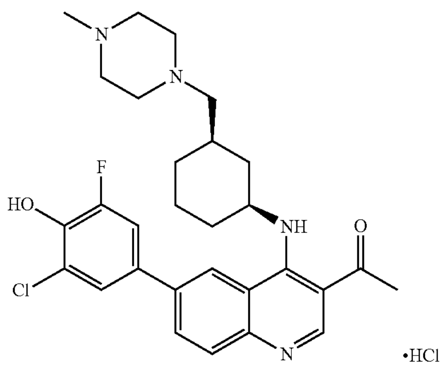 [SMILES: CC(=O)c1cnc2ccc(-c3cc(F)c(O)c(Cl)c3)cc2c1N[C@H]1CCC[C@@H](CN2CCN(C)CC2)C1 ; Cl] | 1-(6-(3-chloro-5-fluoro-4-hydroxyphenyl)-4-((1S,3R)-3-((4-methyl-piperazin-1-yl)methyl)cyclohexyl-amino)quinolin-3-yl)ethanone hydrochloride | 525 |
| 833 | 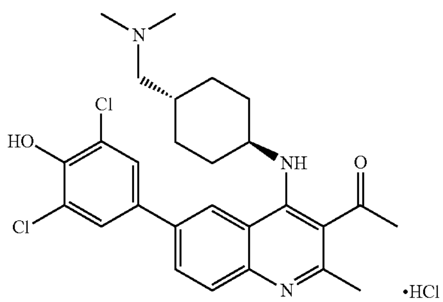 [SMILES: CC(=O)c1c(C)nc2ccc(-c3cc(Cl)c(O)c(Cl)c3)cc2c1N[C@H]1CC[C@H](CN(C)C)CC1 ; Cl] | 1-(6-(3,5-dichloro-4-hydroxyphenyl)-4-(1R,4R)-4-((dimethylamino)methyl)cyclohexylamino)-2-methylquinolin-3-yl)ethanone hydrochloride | 500 |
| 834 | 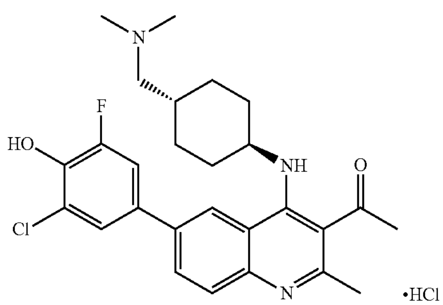 [SMILES: CC(=O)c1c(C)nc2ccc(-c3cc(F)c(O)c(Cl)c3)cc2c1N[C@H]1CC[C@H](CN(C)C)CC1 ; Cl] | 1-(6-(3-chloro-5-fluoro-4-hydroxy-phenyl)-4-(1R,4R)-4-((dimethylamino)methyl)cyclohexylamino)-2-methyl-quinolin-3-yl)ethanone hydrochloride | 484 |
| 835 | 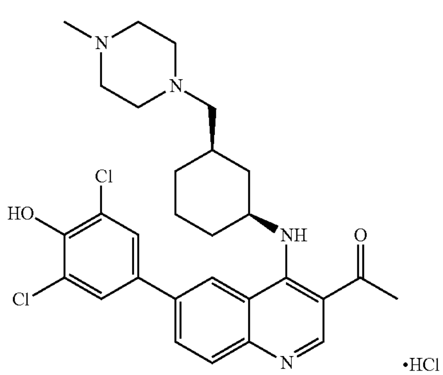 [SMILES: CC(=O)c1cnc2ccc(-c3cc(Cl)c(O)c(Cl)c3)cc2c1N[C@H]1CCC[C@@H](CN2CCN(C)CC2)C1 ; Cl] | 1-(6-(3,5-dichloro-4-hydroxyphenyl)-4-((1S,3R)-3-((4-methylpiperazin-1-yl)methyl)cyclohexylamino)quinolin-3-yl)ethanone hydrochloride | 542 |

TABLE 1-continued

| No. | Structure | Compound Name | ESI MS (m/z) |
|---|---|---|---|
| 836 | 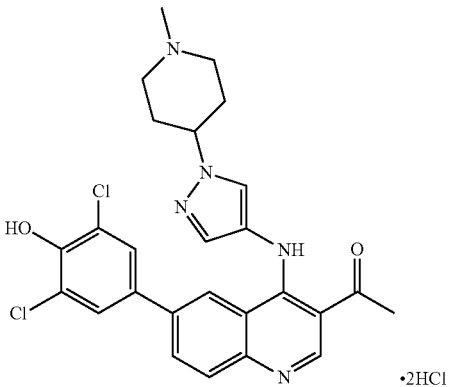 [SMILES: CC(=O)c1cnc2ccc(-c3cc(Cl)c(O)c(Cl)c3)cc2c1Nc1cnn(C2CCN(C)CC2)c1 ; "·2HCl"] | 1-(6-(3,5-dichloro-4-hydroxyphenyl)-4-(1-(1-methylpiperidin-4-yl)-1H-pyrazol-4-ylamino)quinolin-3-yl)ethanone dihydrochloride | 510 |
| 837 | 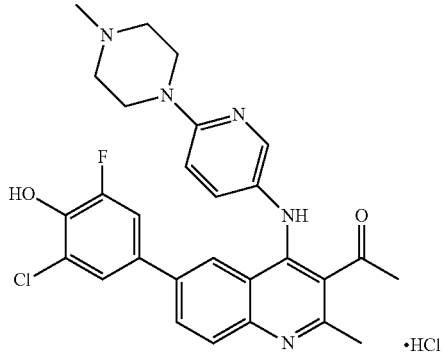 [SMILES: CC(=O)c1c(C)nc2ccc(-c3cc(F)c(O)c(Cl)c3)cc2c1Nc1ccc(N2CCN(C)CC2)nc1 ; Cl] | 1-(6-(3-chloro-5-fluoro-4-hydroxyphenyl)-2-methyl-4-(6-(4-methylpiperazin-1-yl)pyridin-3-ylamino)quinolin-3-yl)ethanone hydrochloride | 520 |
| 838 | 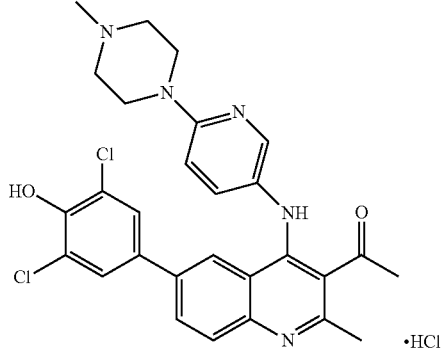 [SMILES: CC(=O)c1c(C)nc2ccc(-c3cc(Cl)c(O)c(Cl)c3)cc2c1Nc1ccc(N2CCN(C)CC2)nc1 ; Cl] | 1-(6-(3,5-dichloro-4-hydroxyphenyl)-2-methyl-4-(6-(4-methylpiperazin-1-yl)pyridin-3-ylamino)quinolin-3-yl)ethanone hydrochloride | 536 |
| 839 | 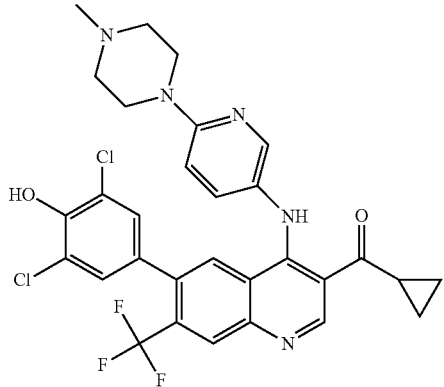 [SMILES: CN1CCN(c2ccc(Nc3c(C(=O)C4CC4)cnc4cc(C(F)(F)F)c(-c5cc(Cl)c(O)c(Cl)c5)cc34)cn2)CC1] | cyclopropyl(6-(3,5-dichloro-4-hydroxyphenyl)-4-(6-(4-methylpiperazin-1-yl)pyridin-3-ylamino)-7-(trifluoromethyl)quinolin-3-yl)methanone | 616 |

TABLE 1-continued

| No. | Structure | Compound Name | ESI MS (m/z) |
|---|---|---|---|
| 840 | 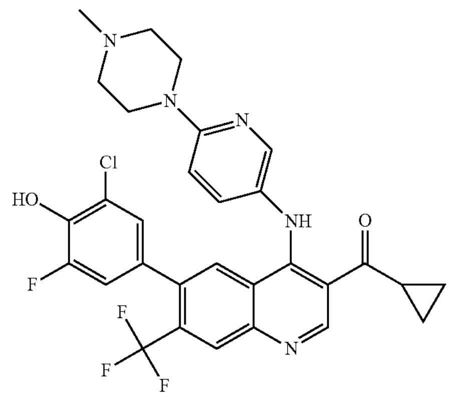 [SMILES: CN1CCN(c2ccc(Nc3c(C(=O)C4CC4)cnc4cc(C(F)(F)F)c(-c5cc(F)c(O)c(Cl)c5)cc34)cn2)CC1] | (6-(3-chloro-5-fluoro-4-hydroxyphenyl)-4-(6-(4-methylpiperazin-1-yl)pyridin-3-ylamino)-7-(trifluoromethyl)quinolin-3-yl)(cyclopropyl)methanone | 600 |
| 841 | 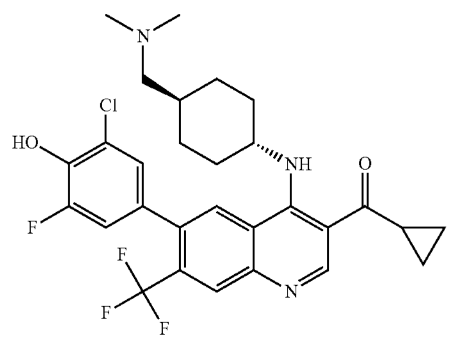 [SMILES: CN(C)C[C@H]1CC[C@H](Nc2c(C(=O)C3CC3)cnc3cc(C(F)(F)F)c(-c4cc(F)c(O)c(Cl)c4)cc23)CC1] | (6-(3-chloro-5-fluoro-4-hydroxyphenyl)-4-(1R,4R)-4-((dimethylamino)methyl)cyclohexylamino)-7-(trifluoromethyl)quinolin-3-yl)(cyclopropyl)methanone | 564 |
| 842 | 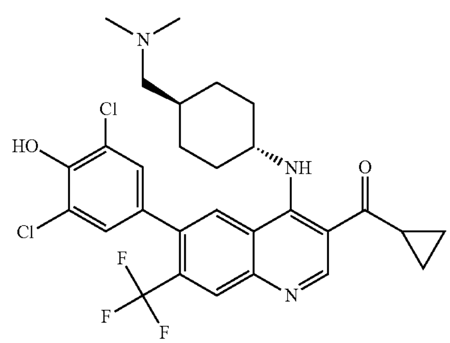 [SMILES: CN(C)C[C@H]1CC[C@H](Nc2c(C(=O)C3CC3)cnc3cc(C(F)(F)F)c(-c4cc(Cl)c(O)c(Cl)c4)cc23)CC1] | cyclopropyl(6-(3,5-dichloro-4-hydroxyphenyl)-4-(1R,4R)-4-((dimethylamino)methyl)cyclohexylamino)-7-(trifluoromethyl)quinolin-3-yl)methanone | 580 |
| 843 | 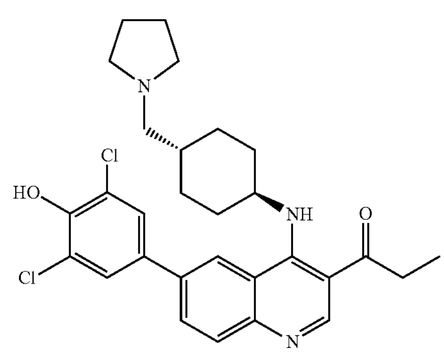 | 1-(6-(3,5-dichloro-4-hydroxyphenyl)-4-(1R,4R)-4-(pyrrolidin-1-ylmethyl)cyclohexylamino)quinolin-3-yl)propan-1-one dihydrochloride | 526 |

TABLE 1-continued

| No. | Structure | Compound Name | ESI MS (m/z) |
|---|---|---|---|
| 844 | 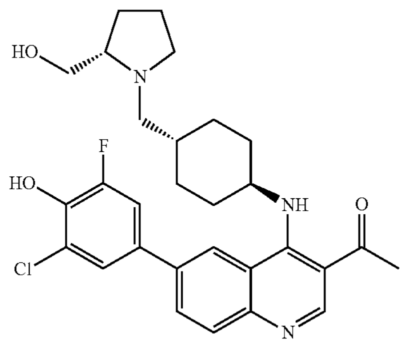 [SMILES: CC(=O)c1cnc2ccc(-c3cc(F)c(O)c(Cl)c3)cc2c1N[C@H]1CC[C@H](CN2CCC[C@H]2CO)CC1] | 1-(6-(3-chloro-5-fluoro-4-hydroxy-phenyl)-4-((1S,4r)-4-(((S)-2-(hydroxy-methyl)pyrrolidin-1-yl)methyl)cyclo-hexylamino)quinolin-3-yl)ethanone | 526 |
| 845 | 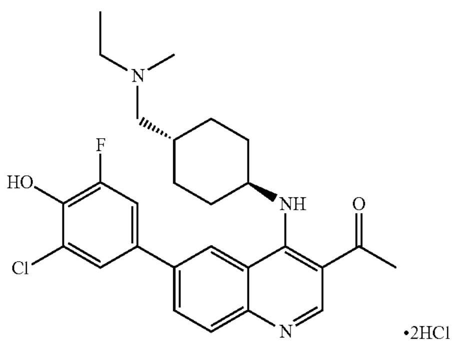 [SMILES: CCN(C)C[C@H]1CC[C@H](Nc2c(C(C)=O)cnc3ccc(-c4cc(F)c(O)c(Cl)c4)cc23)CC1] | 1-(6-(3-chloro-5-fluoro-4-hydroxy-phenyl)-4-(1R,4R)-4-((ethyl(methyl)amino)methyl)cyclohexylamino)quinolin-3-yl)ethanone dihydrochloride | 484 |
| 846 | 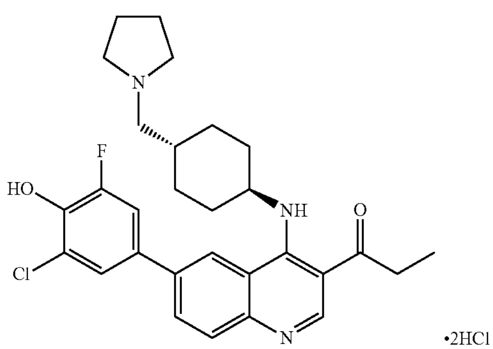 [SMILES: CCC(=O)c1cnc2ccc(-c3cc(F)c(O)c(Cl)c3)cc2c1N[C@H]1CC[C@H](CN2CCCC2)CC1] | 1-(6-(3-chloro-5-fluoro-4-hydroxy-phenyl)-4-(1R,4R)-4-(pyrrolidin-1-ylmethyl)cyclohexylamino)quinolin-3-yl)propan-1-one dihydrochloride | 510 |
| 847 | 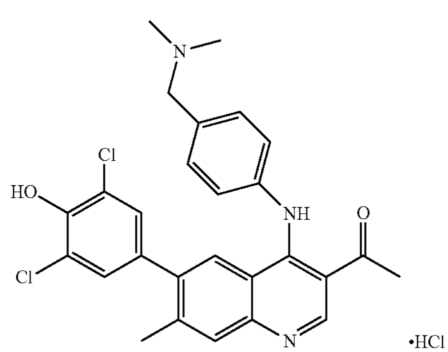 [SMILES: CC(=O)c1cnc2cc(C)c(-c3cc(Cl)c(O)c(Cl)c3)cc2c1Nc1ccc(CN(C)C)cc1 ; Cl] | 1-(6-(3,5-dichloro-4-hydroxyphenyl)-4-(4-((dimethylamino)methyl)phenyl-amino)-7-methylquinolin-3-yl)ethanone hydrochloride | 494 |

TABLE 1-continued

| No. | Structure | Compound Name | ESI MS (m/z) |
|---|---|---|---|
| 848 | 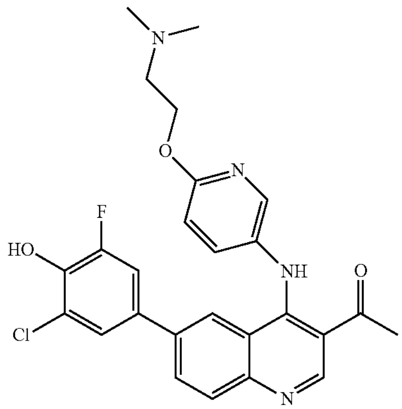 | 1-(6-(3-chloro-5-fluoro-4-hydroxyphenyl)-4-(6-(2-(dimethylamino)ethoxy)pyridin-3-ylamino)quinolin-3-yl)ethanone hydrochloride | 495 |
| 849 | 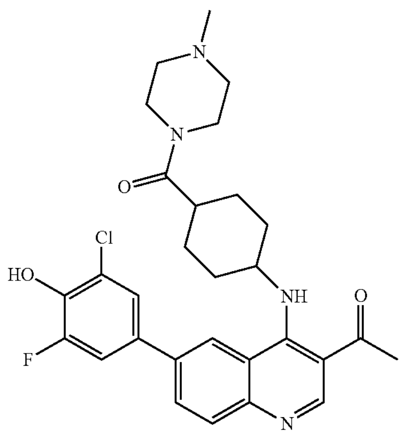 | 1-(6-(3-chloro-5-fluoro-4-hydroxyphenyl)-4-(4-(4-methylpiperazine-1-carbonyl)cyclohexylamino)quinolin-3-yl)ethanone hydrochloride | 539 |
| 850 | 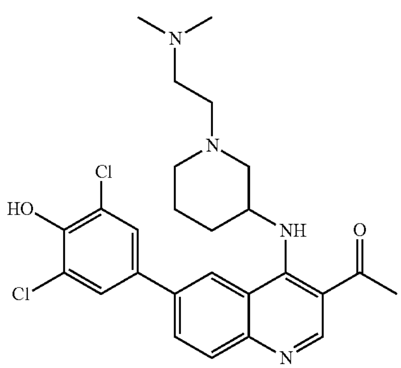 [SMILES: CC(=O)c1cnc2ccc(-c3cc(Cl)c(O)c(Cl)c3)cc2c1NC1CCCN(CCN(C)C)C1] | 1-(6-(3,5-dichloro-4-hydroxyphenyl)-4-(1-(2-(dimethylamino)ethyl)piperidin-3-ylamino)quinolin-3-yl)ethanone | 501 |
| 851 | 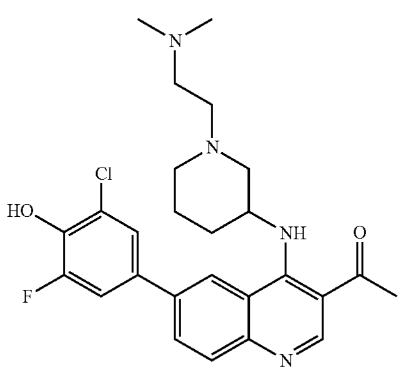 [SMILES: CC(=O)c1cnc2ccc(-c3cc(F)c(O)c(Cl)c3)cc2c1NC1CCCN(CCN(C)C)C1] | 1-(6-(3-chloro-5-fluoro-4-hydroxyphenyl)-4-(1-(2-(dimethylamino)ethyl)piperidin-3-ylamino)quinolin-3-yl)ethanone | 485 |

TABLE 1-continued

| No. | Structure | Compound Name | ESI MS (m/z) |
|---|---|---|---|
| 852 | 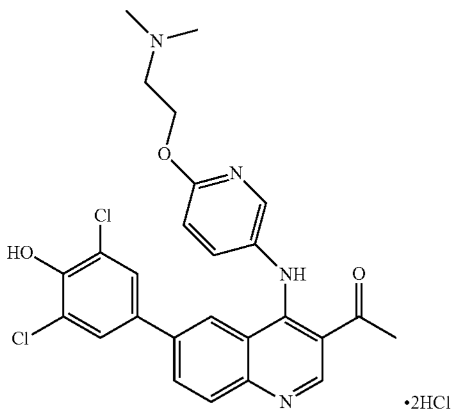 [SMILES: CC(=O)c1cnc2ccc(-c3cc(Cl)c(O)c(Cl)c3)cc2c1Nc1ccc(OCCN(C)C)nc1 ; "·2HCl"] | 1-(6-(3,5-dichloro-4-hydroxyphenyl)-4-(6-(2-(dimethylamino)ethoxy) pyridin-3-ylamino)quinolin-3-yl) ethanone dihydrochloride | 511 |
| 853 | 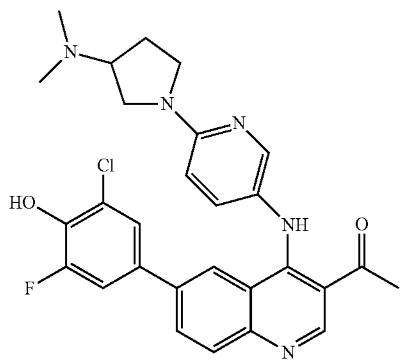 [SMILES: CC(=O)c1cnc2ccc(-c3cc(F)c(O)c(Cl)c3)cc2c1Nc1ccc(N2CCC(N(C)C)C2)nc1] | 1-(6-(3-chloro-5-fluoro-4-hydroxyphenyl)-4-((6-(3-(dimethylamino) pyrrolidin-1-yl)pyridin-3-yl)amino) quinolin-3-yl)ethanone | 520 |
| 854 | 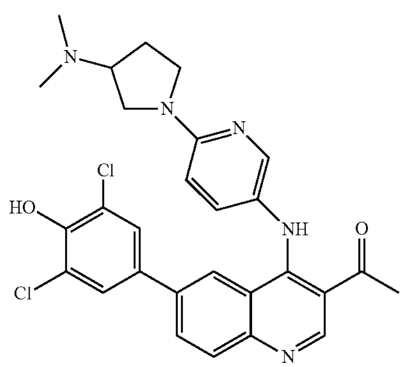 [SMILES: CC(=O)c1cnc2ccc(-c3cc(Cl)c(O)c(Cl)c3)cc2c1Nc1ccc(N2CCC(N(C)C)C2)nc1] | 1-(6-(3,5-dichloro-4-hydroxyphenyl)-4-((6-(3-(dimethylamino)pyrrolidin-1-yl)pyridin-3-yl)amino)quinolin-3-yl)ethanone | 536 |
| 855 | 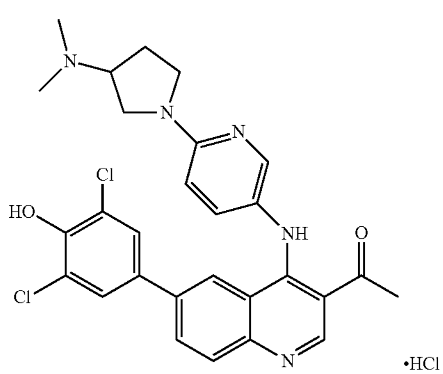 [SMILES: CC(=O)c1cnc2ccc(-c3cc(Cl)c(O)c(Cl)c3)cc2c1Nc1ccc(N2CCC(N(C)C)C2)nc1 ; Cl] | 1-(6-(3,5-dichloro-4-hydroxyphenyl)-4-((6-(3-(dimethylamino)pyrrolidin-1-yl)pyridin-3-yl)amino)quinolin-3-yl)ethanone hydrochloride | 536 |

TABLE 1-continued

| No. | Structure | Compound Name | ESI MS (m/z) |
|---|---|---|---|
| 856 | 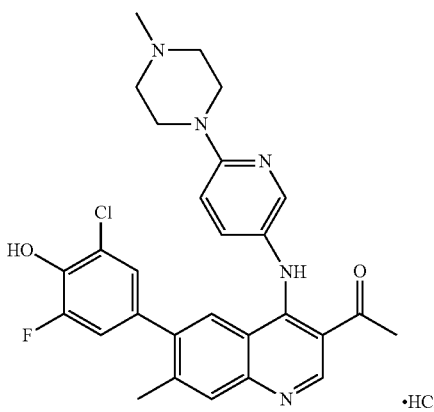 [SMILES: CC(=O)c1cnc2cc(C)c(-c3cc(F)c(O)c(Cl)c3)cc2c1Nc1ccc(N2CCN(C)CC2)nc1 ; Cl] | 1-(6-(3-chloro-5-fluoro-4-hydroxyphenyl)-7-methyl-4-((6-(4-methylpiperazin-1-yl)pyridin-3-yl)amino)quinolin-3-yl)ethanone hydrochloride | 520 |
| 857 | 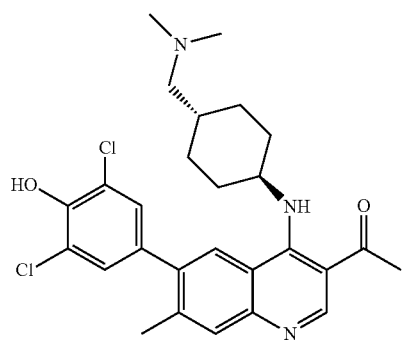 [SMILES: CC(=O)c1cnc2cc(C)c(-c3cc(Cl)c(O)c(Cl)c3)cc2c1N[C@H]1CC[C@H](CN(C)C)CC1] | 1-(6-(3,5-dichloro-4-hydroxyphenyl)-4-((1R,4R)-4-((dimethylamino)methyl)cyclohexyl)amino)-7-methyl-quinolin-3-yl)ethanone | 500 |
| 858 | 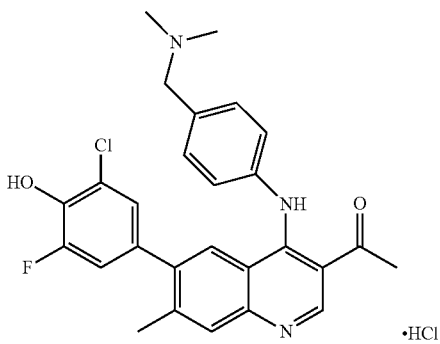 [SMILES: CC(=O)c1cnc2cc(C)c(-c3cc(F)c(O)c(Cl)c3)cc2c1Nc1ccc(CN(C)C)cc1 ; Cl] | 1-(6-(3-chloro-5-fluoro-4-hydroxyphenyl)-4-((4-((dimethylamino)methyl)phenyl)amino)-7-methylquinolin-3-yl)ethanone hydrochloride | 478 |
| 859 | 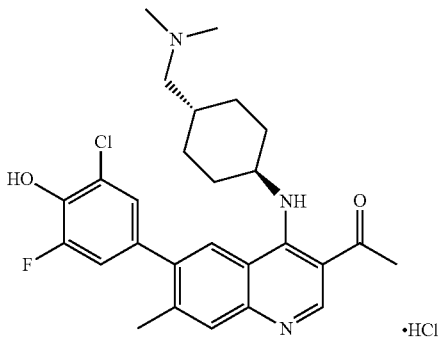 [SMILES: CC(=O)c1cnc2cc(C)c(-c3cc(F)c(O)c(Cl)c3)cc2c1N[C@H]1CC[C@H](CN(C)C)CC1 ; Cl] | 1-(6-(3-chloro-5-fluoro-4-hydroxyphenyl)-4-((1R,4R)-4-((dimethylamino)methyl)cyclohexyl)amino)-7-methyl-quinolin-3-yl)ethanone hydrochloride | 484 |

TABLE 1-continued

| No. | Structure | Compound Name | ESI MS (m/z) |
|---|---|---|---|
| 860 | 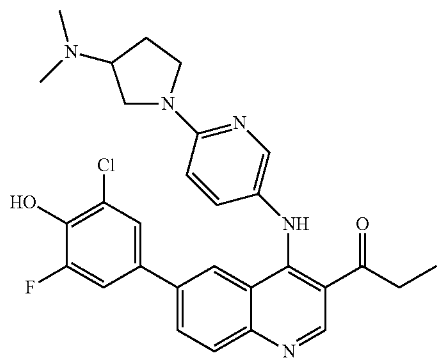 [SMILES: CCC(=O)c1cnc2ccc(-c3cc(F)c(O)c(Cl)c3)cc2c1Nc1ccc(N2CCC(N(C)C)C2)nc1] | 1-(6-(3-chloro-5-fluoro-4-hydroxy-phenyl)-4-((6-(3-(dimethylamino)pyrrolidin-1-yl)pyridin-3-yl)amino)quinolin-3-yl)propan-1-one | 534 |
| 861 | 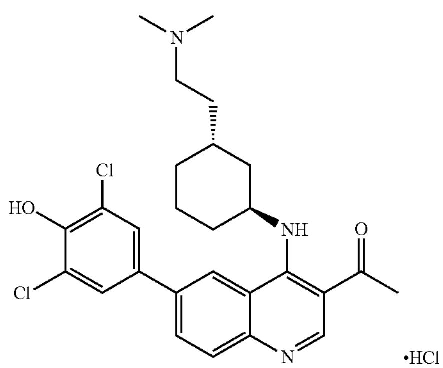 [SMILES: CC(=O)c1cnc2ccc(-c3cc(Cl)c(O)c(Cl)c3)cc2c1N[C@H]1CCC[C@H](CCN(C)C)C1 ; Cl] | 1-(6-(3,5-dichloro-4-hydroxyphenyl)-4-(((1S,3R)-3-(2-(dimethylamino)ethyl)cyclohexyl)amino)quinolin-3-yl)ethanone hydrochloride | 500 |
| 862 | 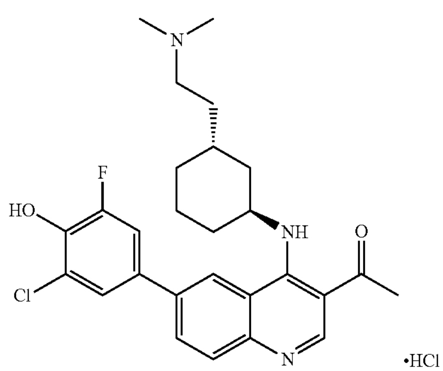 [SMILES: CC(=O)c1cnc2ccc(-c3cc(F)c(O)c(Cl)c3)cc2c1N[C@H]1CCC[C@H](CCN(C)C)C1 ; Cl] | 1-(6-(3-chloro-5-fluoro-4-hydroxy-phenyl)-4-(((1S,3R)-3-(2-(dimethyl-amino)ethyl)cyclohexyl)amino)quinolin-3-yl)ethanone hydrochloride | 484 |
| 863 | 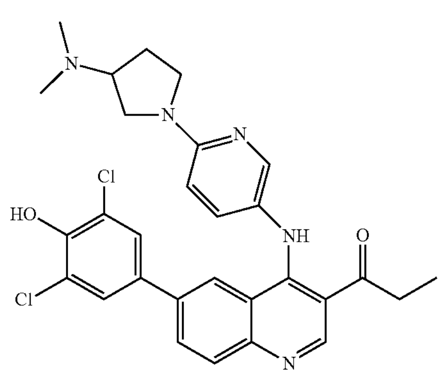 [SMILES: CCC(=O)c1cnc2ccc(-c3cc(Cl)c(O)c(Cl)c3)cc2c1Nc1ccc(N2CCC(N(C)C)C2)nc1] | 1-(6-(3,5-dichloro-4-hydroxyphenyl)-4-((6-(3-(dimethylamino)pyrrolidin-1-yl)pyridin-3-yl)amino)quinolin-3-yl)propan-1-one | 550 |

TABLE 1-continued

| No. | Structure | Compound Name | ESI MS (m/z) |
|---|---|---|---|
| 864 | 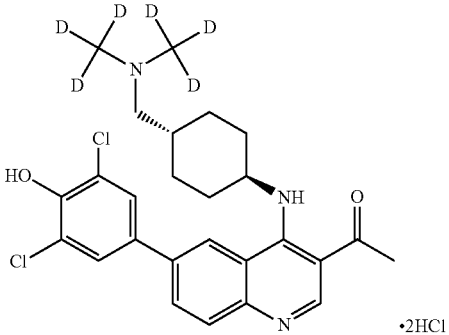 [SMILES: [2H]C([2H])([2H])N(C[C@H]1CC[C@H](Nc2c(C(C)=O)cnc3ccc(-c4cc(Cl)c(O)c(Cl)c4)cc23)CC1)C([2H])([2H])[2H] ; "·2HCl"] | 1-(6-(3,5-dichloro-4-hydroxyphenyl)-4-((1R,4R)-4-((bis-(trideuteromethyl)amino)methyl)cyclohexyl)amino)quinolin-3-yl)ethanone dihydrochloride | 492 |
| 865 | 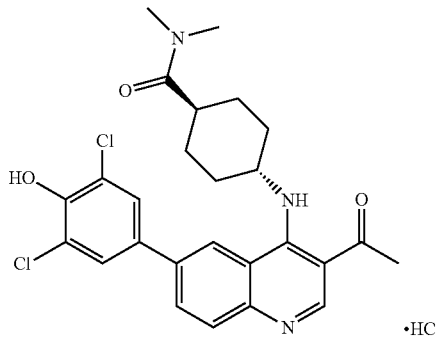 [SMILES: CC(=O)c1cnc2ccc(-c3cc(Cl)c(O)c(Cl)c3)cc2c1N[C@H]1CC[C@H](C(=O)N(C)C)CC1 ; Cl] | (1r,4r)-4-((3-acetyl-6-(3,5-dichloro-4-hydroxyphenyl)quinolin-4-yl)amino)-N,N-dimethylcyclohexane-carboxamide hydrochloride | 500 |
| 866 | 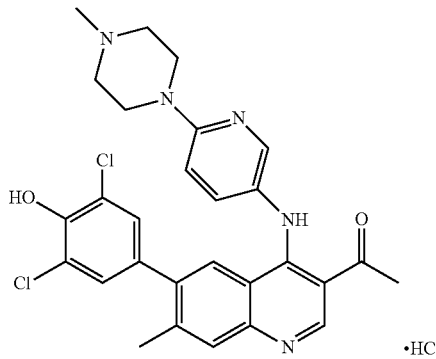 | 1-(6-(3,5-dichloro-4-hydroxyphenyl)-7-methyl-4-((6-(4-methylpiperazin-1-yl)pyridin-3-yl)amino)quinolin-3-yl)ethanone hydrochloride | 536 |
| 867 | 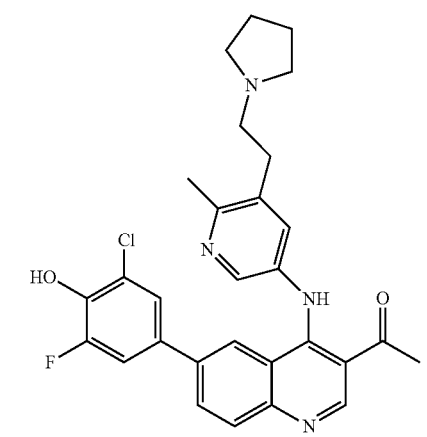 [SMILES: CC(=O)c1cnc2ccc(-c3cc(F)c(O)c(Cl)c3)cc2c1Nc1cnc(C)c(CCN2CCCC2)c1] | 1-(6-(3-chloro-5-fluoro-4-hydroxyphenyl)-4-((6-methyl-5-(2-(pyrrolidin-1-yl)ethyl)pyridin-3-yl)amino)quinolin-3-yl)ethanone | 519 |

TABLE 1-continued

| No. | Structure | Compound Name | ESI MS (m/z) |
|---|---|---|---|
| 868 | 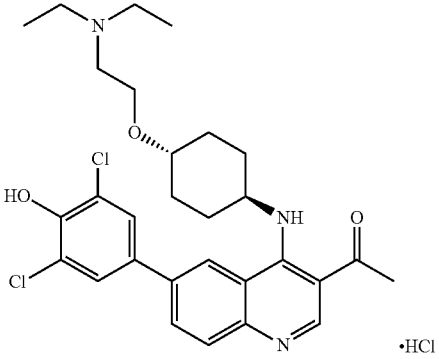 [SMILES: CCN(CC)CCO[C@H]1CC[C@H](Nc2c(C(C)=O)cnc3ccc(-c4cc(Cl)c(O)c(Cl)c4)cc23)CC1 ; Cl] | 1-(6-(3,5-dichloro-4-hydroxyphenyl)-4-((1R,4R)-4-(2-(diethylamino)ethoxy)cyclohexyl)amino)quinolin-3-yl)ethanone hydrochloride | 545 |
| 869 | 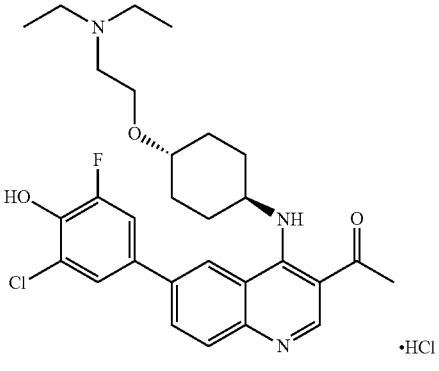 [SMILES: CCN(CC)CCO[C@H]1CC[C@H](Nc2c(C(C)=O)cnc3ccc(-c4cc(F)c(O)c(Cl)c4)cc23)CC1 ; Cl] | 1-(6-(3-chloro-5-fluoro-4-hydroxyphenyl)-4-((1R,4R)-4-(2-(diethylamino)ethoxy)cyclohexyl)amino)quinolin-3-yl)ethanone hydrochloride | 528 |
| 870 | 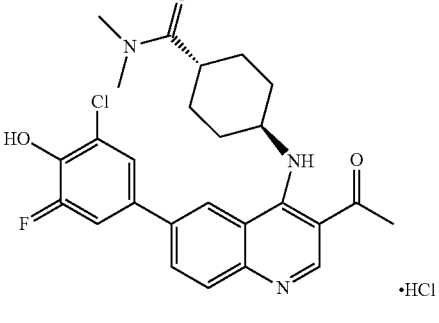 | (1r,4r)-4-((3-acetyl-6-(3-chloro-5-fluoro-4-hydroxyphenyl)quinolin-4-yl)amino)-N,N-dimethylcyclohexanecarboxamide hydrochloride | 484 |
| 871 | 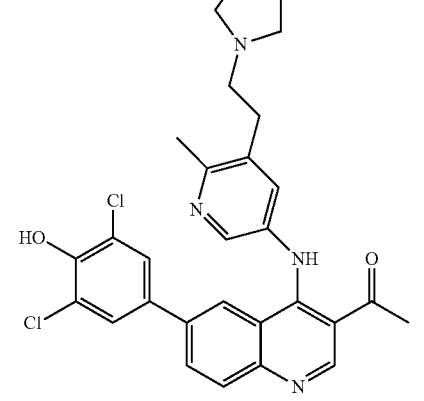 | 1-(6-(3,5-dichloro-4-hydroxyphenyl)-4-((6-methyl-5-(2-(pyrrolidin-1-yl)ethyl)pyridin-3-yl)amino)quinolin-3-yl)ethanone | 535 |

TABLE 1-continued

| No. | Structure | Compound Name | ESI MS (m/z) |
|---|---|---|---|
| 872 | 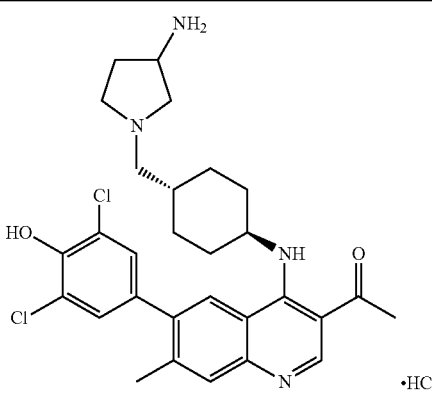 | 1-(4-((1R,4R)-4-((3-aminopyrrolidin-1-yl)methyl)cyclohexyl)amino)-6-(3,5-dichloro-4-hydroxyphenyl)-7-methylquinolin-3-yl)ethanone hydrochloride | 542 |
| 873 | 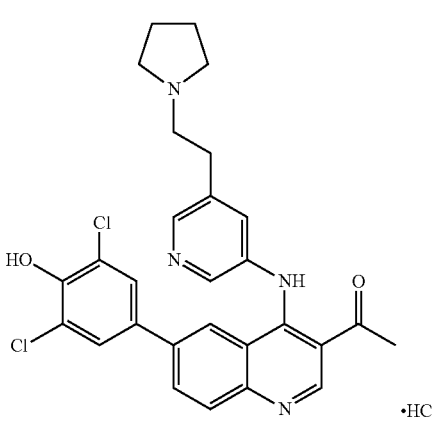 | 1-(6-(3,5-dichloro-4-hydroxyphenyl)-4-((5-(2-(pyrrolidin-1-yl)ethyl)pyridin-3-yl)amino)quinolin-3-yl)ethanone hydrochloride | 521 |
| 874 | 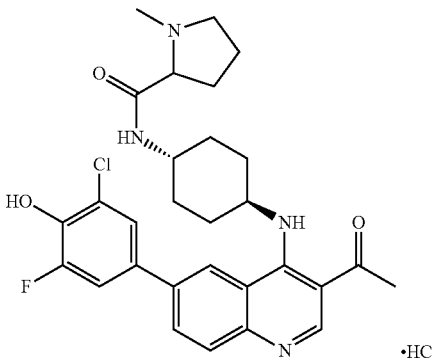 [SMILES: CC(=O)c1cnc2ccc(-c3cc(F)c(O)c(Cl)c3)cc2c1N[C@H]1CC[C@H](NC(=O)C2CCCN2C)CC1 ; Cl] | N-(1R,4R)-4-((3-acetyl-6-(3-chloro-5-fluoro-4-hydroxyphenyl)quinolin-4-yl)amino)cyclohexyl)-1-methyl-pyrrolidine-2-carboxamide hydrochloride | 539 |
| 875 | 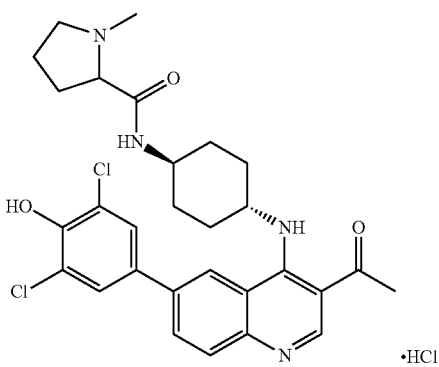 [SMILES: CC(=O)c1cnc2ccc(-c3cc(Cl)c(O)c(Cl)c3)cc2c1N[C@H]1CC[C@H](NC(=O)C2CCCN2C)CC1 ; Cl] | N-(1R,4R)-4-((3-acetyl-6-(3,5-dichloro-4-hydroxyphenyl)quinolin-4-yl)amino)cyclohexyl)-1-methyl-pyrrolidine-2-carboxamide hydrochloride | 555 |

TABLE 1-continued

| No. | Structure | Compound Name | ESI MS (m/z) |
|---|---|---|---|
| 876 | 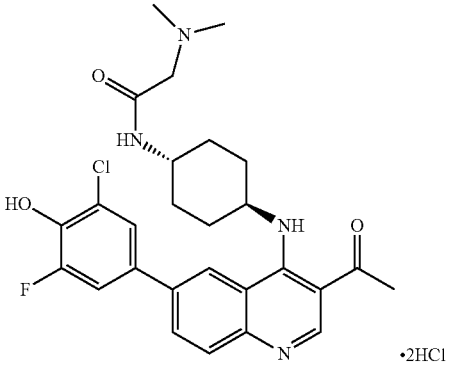 [SMILES: CC(=O)c1cnc2ccc(-c3cc(F)c(O)c(Cl)c3)cc2c1N[C@H]1CC[C@H](NC(=O)CN(C)C)CC1 ; "·2HCl"] | N-(1R,4R)-4-((3-acetyl-6-(3-chloro-5-fluoro-4-hydroxyphenyl)quinolin-4-yl)amino)cyclohexyl)-2-(dimethylamino)acetamide dihydrochloride | 513 |
| 877 | 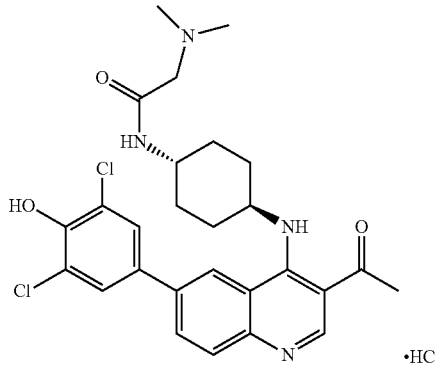 [SMILES: CC(=O)c1cnc2ccc(-c3cc(Cl)c(O)c(Cl)c3)cc2c1N[C@H]1CC[C@H](NC(=O)CN(C)C)CC1 ; Cl] | N-(1R,4R)-4-((3-acetyl-6-(3,5-dichloro-4-hydroxyphenyl)quinolin-4-yl)amino)cyclohexyl)-2-(dimethylamino)acetamide hydrochloride | 529 |
| 878 | 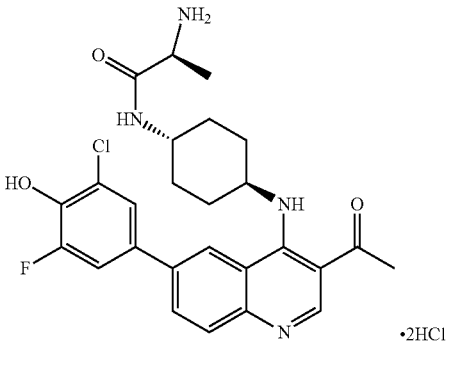 [SMILES: CC(=O)c1cnc2ccc(-c3cc(F)c(O)c(Cl)c3)cc2c1N[C@H]1CC[C@H](NC(=O)[C@H](C)N)CC1 ; "·2HCl"] | (S)-N-((1r,4S)-4-((3-acetyl-6-(3-chloro-5-fluoro-4-hydroxyphenyl)quinolin-4-yl)amino)cyclohexyl)-2-aminopropanamide dihydrochloride | 499 |
| 879 | 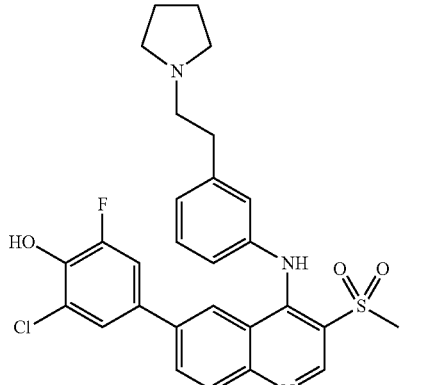 | 2-chloro-6-fluoro-4-(3-(methylsulfonyl)-4-((3-(2-(pyrrolidin-1-yl)ethyl)phenyl)amino)quinolin-6-yl)phenol hydrochloride | 540 |

TABLE 1-continued

| No. | Structure | Compound Name | ESI MS (m/z) |
|---|---|---|---|
| 880 | 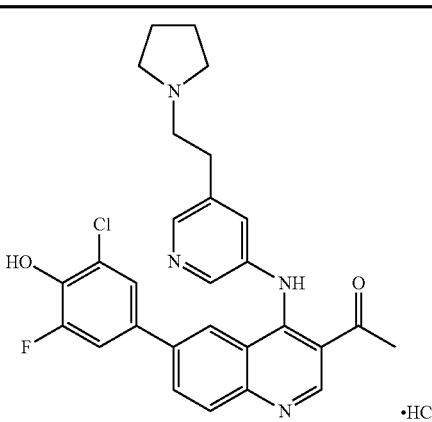 | 1-(6-(3-chloro-5-fluoro-4-hydroxy-phenyl)-4-((5-(2-(pyrrolidin-1-yl)ethyl) pyridin-3-yl)amino)quinolin-3-yl) ethanone hydrochloride | 505 |
| 881 | 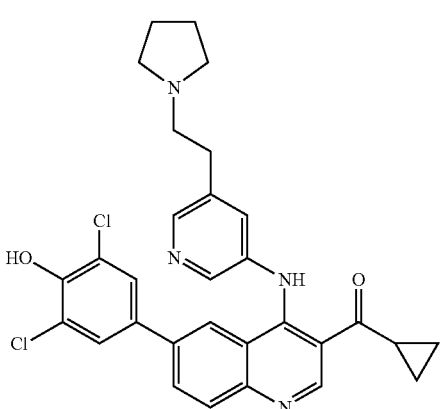 | cyclopropyl(6-(3,5-dichloro-4-hydroxy-phenyl)-4-((5-(2-(pyrrolidin-1-yl) ethyl)pyridin-3-yl)amino)quinolin-3-yl)methanone | 547 |
| 882 | 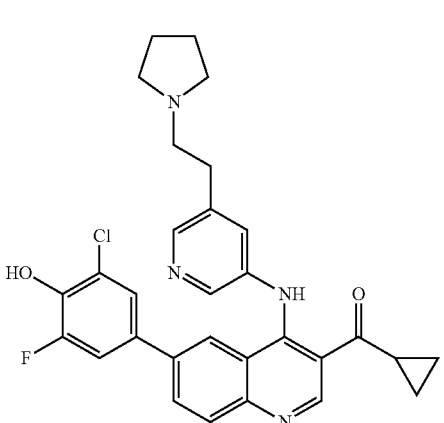 | (6-(3-chloro-5-fluoro-4-hydroxy-phenyl)-4-((5-(2-(pyrrolidin-1-yl)ethyl) pyridin-3-yl)amino)quinolin-3-yl) (cyclopropyl)methanone | 531 |

TABLE 1-continued

| No. | Structure | Compound Name | ESI MS (m/z) |
|---|---|---|---|
| 883 | 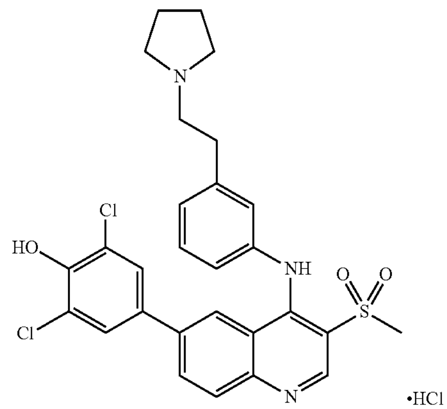 [SMILES: CS(=O)(=O)c1cnc2ccc(-c3cc(Cl)c(O)c(Cl)c3)cc2c1Nc1cccc(CCN2CCCC2)c1 ; Cl] | 2,6-dichloro-4-(3-(methylsulfonyl)-4-((3-(2-(pyrrolidin-1-yl)ethyl)phenyl)amino)quinolin-6-yl)phenol hydrochloride | 557 |
| 884 | 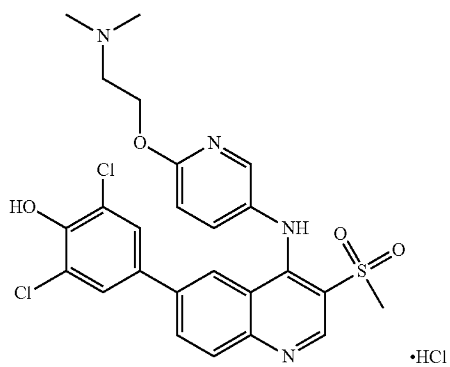 [SMILES: CN(C)CCOc1ccc(Nc2c(S(C)(=O)=O)cnc3ccc(-c4cc(Cl)c(O)c(Cl)c4)cc23)cn1 ; Cl] | 2,6-dichloro-4-(4-((6-(2-(dimethylamino)ethoxy)pyridin-3-yl)amino)-3-(methylsulfonyl)quinolin-6-yl)phenol hydrochloride | 547 |
| 885 | 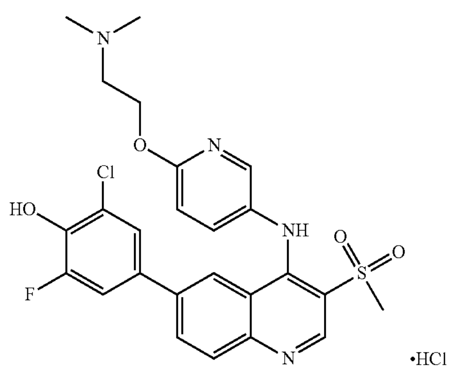 [SMILES: CN(C)CCOc1ccc(Nc2c(S(C)(=O)=O)cnc3ccc(-c4cc(F)c(O)c(Cl)c4)cc23)cn1 ; Cl] | 2-chloro-4-(4-((6-(2-(dimethylamino)ethoxy)pyridin-3-yl)amino)-3-(methylsulfonyl)quinolin-6-yl)-6-fluorophenol hydrochloride | 531 |
| 886 | 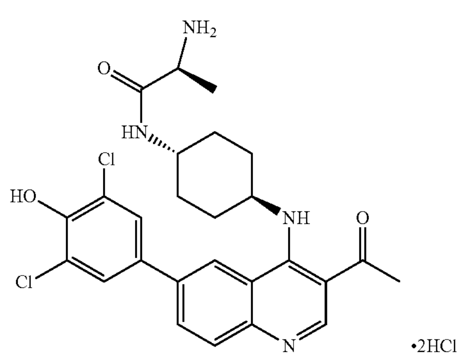 [SMILES: CC(=O)c1cnc2ccc(-c3cc(Cl)c(O)c(Cl)c3)cc2c1N[C@H]1CC[C@H](NC(=O)[C@H](C)N)CC1 ; "·2HCl"] | (S)-N-((1r,4S)-4-((3-acetyl-6-(3,5-dichloro-4-hydroxyphenyl)quinolin-4-yl)amino)cyclohexyl)-2-aminopropanamide dihydrochloride | 515 |

TABLE 1-continued

| No. | Structure | Compound Name | ESI MS (m/z) |
|---|---|---|---|
| 887 | 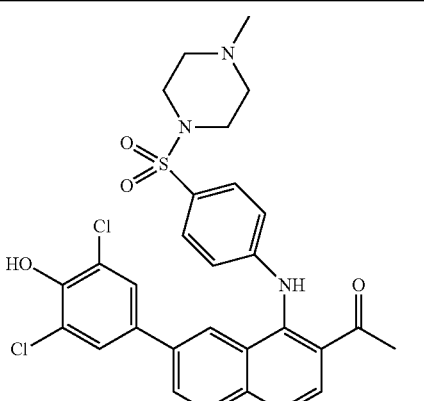 | 1-(6-(3,5-dichloro-4-hydroxyphenyl)-4-((4-((4-methylpiperazin-1-yl)sulfonyl)phenyl)amino)quinolin-3-yl)ethanone hydrochloride | 586 |
| 888 | 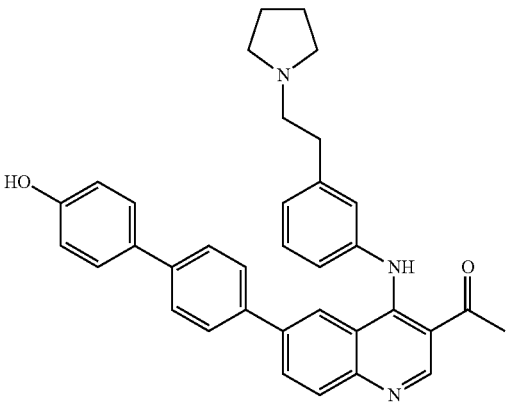 | 1-(6-(4'-hydroxy-[1,1'-biphenyl]-4-yl)-4-((3-(2-(pyrrolidin-1-yl)ethyl)phenyl)amino)quinolin-3-yl)ethanone hydrochloride | 528 |
| 889 | 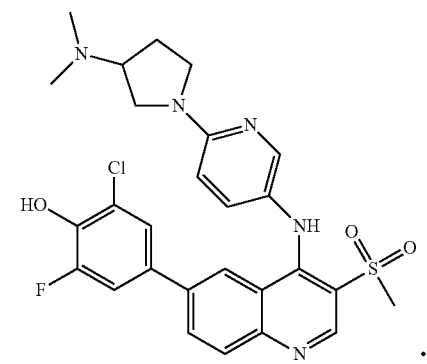 | 2-chloro-4-(4-((6-(3-(dimethylamino)pyrrolidin-1-yl)pyridin-3-yl)amino)-3-(methylsulfonyl)quinolin-6-yl)-6-fluorophenol hydrochloride | 556 |
| 890 | 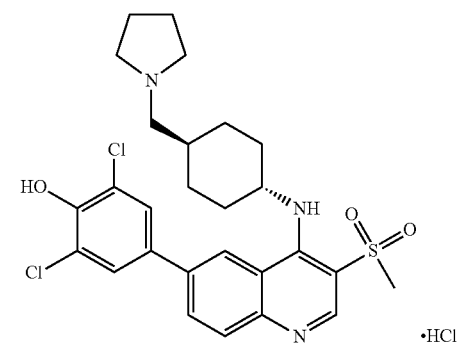 [SMILES: CS(=O)(=O)c1cnc2ccc(-c3cc(Cl)c(O)c(Cl)c3)cc2c1N[C@H]1CC[C@H](CN2CCCC2)CC1 ; Cl] | 2,6-dichloro-4-(3-(methylsulfonyl)-4-(((1R,4R)-4-(pyrrolidin-1-ylmethyl)cyclohexyl)amino)quinolin-6-yl)phenol hydrochloride | 549 |

TABLE 1-continued

| No. | Structure | Compound Name | ESI MS (m/z) |
|---|---|---|---|
| 891 | 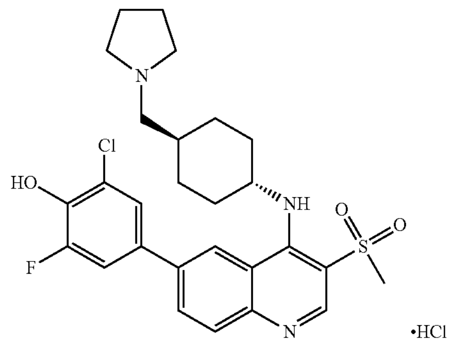 [SMILES: CS(=O)(=O)c1cnc2ccc(-c3cc(F)c(O)c(Cl)c3)cc2c1N[C@H]1CC[C@H](CN2CCCC2)CC1 ; Cl] | 2-chloro-6-fluoro-4-(3-(methylsulfonyl)-4-((1R,4R)-4-(pyrrolidin-1-ylmethyl)cyclohexyl)amino)quinolin-6-yl)phenol hydrochloride | 532 |
| 892 | 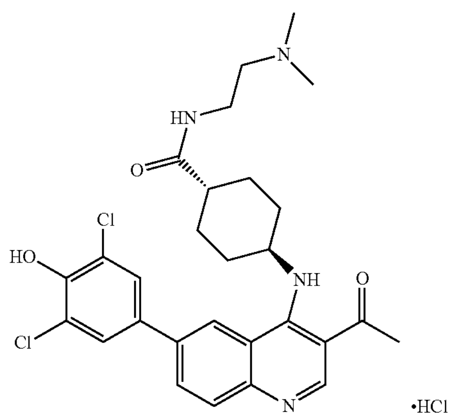 [SMILES: CC(=O)c1cnc2ccc(-c3cc(Cl)c(O)c(Cl)c3)cc2c1N[C@H]1CC[C@H](C(=O)NCCN(C)C)CC1 ; Cl] | (1r,4r)-4-((3-acetyl-6-(3,5-dichloro-4-hydroxyphenyl)quinolin-4-yl)amino)-N-(2-(dimethylamino)ethyl)cyclohexanecarboxamide hydrochloride | 543 |
| 893 | 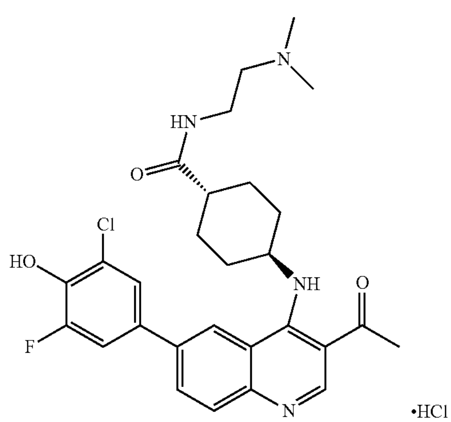 [SMILES: CC(=O)c1cnc2ccc(-c3cc(F)c(O)c(Cl)c3)cc2c1N[C@H]1CC[C@H](C(=O)NCCN(C)C)CC1 ; Cl] | (1r,4r)-4-((3-acetyl-6-(3-chloro-5-fluoro-4-hydroxyphenyl)quinolin-4-yl)amino)-N-(2-(dimethylamino)ethyl)cyclohexanecarboxamide hydrochloride | 527 |

TABLE 1-continued

| No. | Structure | Compound Name | ESI MS (m/z) |
|---|---|---|---|
| 894 | 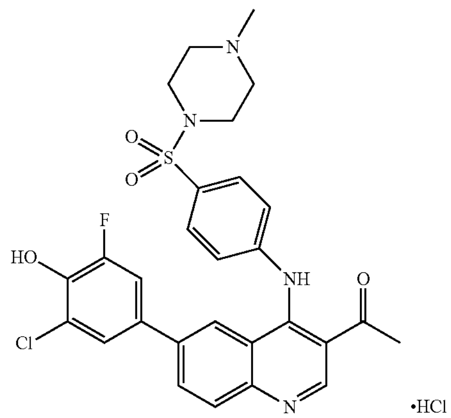 [SMILES: CC(=O)c1cnc2ccc(-c3cc(F)c(O)c(Cl)c3)cc2c1Nc1ccc(S(=O)(=O)N2CCN(C)CC2)cc1 ; Cl] | 1-(6-(3-chloro-5-fluoro-4-hydroxyphenyl)-4-((4-((4-methylpiperazin-1-yl)sulfonyl)phenyl)amino)quinolin-3-yl)ethanone hydrochloride | 569 |
| 895 | 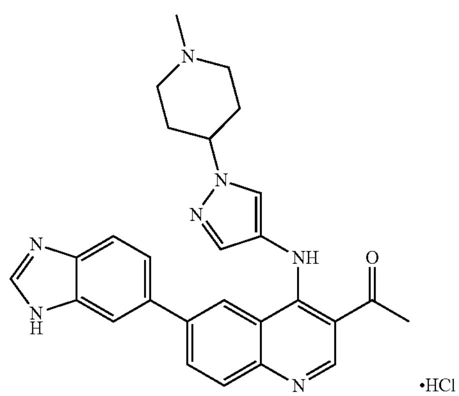 [SMILES: CC(=O)c1cnc2ccc(-c3ccc4nc[nH]c4c3)cc2c1Nc1cnn(C2CCN(C)CC2)c1 ; Cl] | 1-(6-(1H-benzo[d]imidazol-6-yl)-4-((1-(1-methylpiperidin-4-yl)-1H-pyrazol-4-yl)amino)quinolin-3-yl)ethanone hydrochloride | 466 |
| 896 | 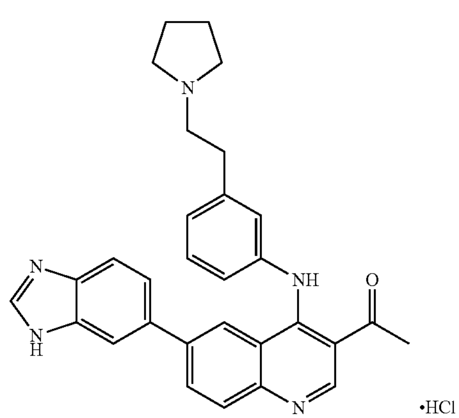 [SMILES: CC(=O)c1cnc2ccc(-c3ccc4nc[nH]c4c3)cc2c1Nc1cccc(CCN2CCCC2)c1 ; Cl] | 1-(6-(1H-benzo[d]imidazol-6-yl)-4-((3-(2-(pyrrolidin-1-yl)ethyl)phenyl)amino)quinolin-3-yl)ethanone hydrochloride | 476 |

TABLE 1-continued

| No. | Structure | Compound Name | ESI MS (m/z) |
|---|---|---|---|
| 897 | 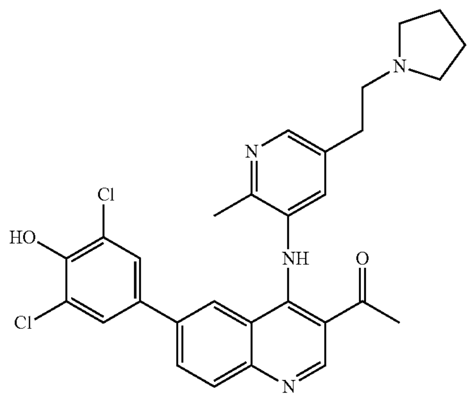 [SMILES: CC(=O)c1cnc2ccc(-c3cc(Cl)c(O)c(Cl)c3)cc2c1Nc1cc(CCN2CCCC2)cnc1C] | 1-(6-(3,5-dichloro-4-hydroxyphenyl)-4-((2-methyl-5-(2-(pyrrolidin-1-yl)ethyl)pyridin-3-yl)amino)quinolin-3-yl)ethanone | 535 |
| 898 | 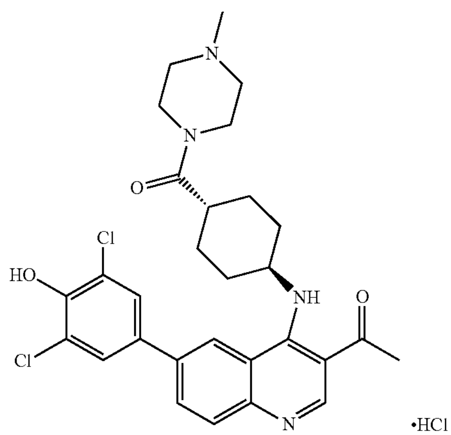 [SMILES: CC(=O)c1cnc2ccc(-c3cc(Cl)c(O)c(Cl)c3)cc2c1N[C@H]1CC[C@H](C(=O)N2CCN(C)CC2)CC1 ; Cl] | 1-(6-(3,5-dichloro-4-hydroxyphenyl)-4-(((1R,4R)-4-(4-methylpiperazine-1-carbonyl)cyclohexyl)amino)quinolin-3-yl)ethanone hydrochloride | 555 |
| 899 | 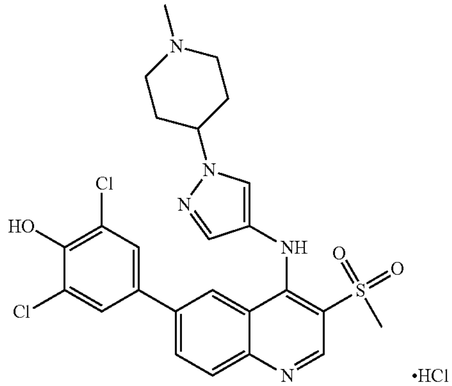 [SMILES: CN1CCC(n2cc(Nc3c(S(C)(=O)=O)cnc4ccc(-c5cc(Cl)c(O)c(Cl)c5)cc34)cn2)CC1 ; Cl] | 2,6-dichloro-4-(4-(((1-(1-methyl-piperidin-4-yl)-1H-pyrazol-4-yl)amino)-3-(methylsulfonyl)quinolin-6-yl)phenol hydrochloride | 546 |

TABLE 1-continued

| No. | Structure | Compound Name | ESI MS (m/z) |
|---|---|---|---|
| 900 | 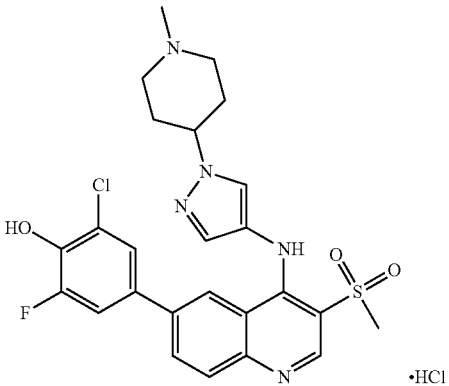 [SMILES: CN1CCC(n2cc(Nc3c(S(C)(=O)=O)cnc4ccc(-c5cc(F)c(O)c(Cl)c5)cc34)cn2)CC1 ; Cl] | 2-chloro-6-fluoro-4-(4-((1-(1-methyl-piperidin-4-yl)-1H-pyrazol-4-yl)amino)-3-(methylsulfonyl)quinolin-6-yl)phenol hydrochloride | 530 |
| 901 | 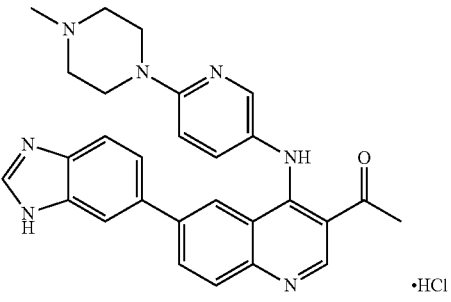 [SMILES: CC(=O)c1cnc2ccc(-c3ccc4nc[nH]c4c3)cc2c1Nc1ccc(N2CCN(C)CC2)nc1 ; Cl] | 1-(6-(1H-benzo[d]imidazol-6-yl)-4-((6-(4-methylpiperazin-1-yl)pyridin-3-yl)amino)quinolin-3-yl)ethanone hydrochloride | 478 |
| 902 | 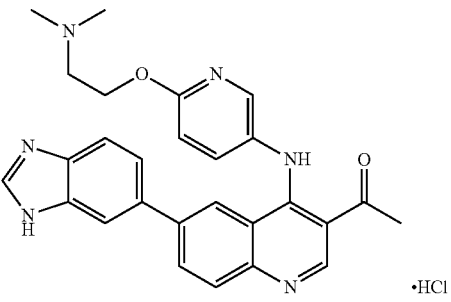 [SMILES: CC(=O)c1cnc2ccc(-c3ccc4nc[nH]c4c3)cc2c1Nc1ccc(OCCN(C)C)nc1 ; Cl] | 1-(6-(1H-benzo[d]imidazol-6-yl)-4-((6-(2-(dimethylamino)ethoxy)pyridin-3-yl)amino)quinolin-3-yl)ethanone hydrochloride | 467 |
| 903 | 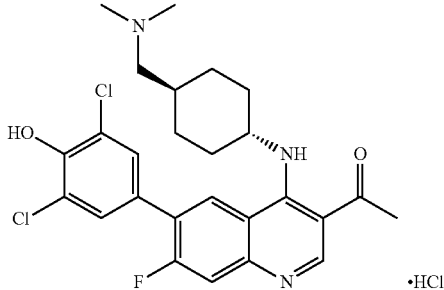 [SMILES: CC(=O)c1cnc2cc(F)c(-c3cc(Cl)c(O)c(Cl)c3)cc2c1N[C@H]1CC[C@H](CN(C)C)CC1 ; Cl] | 1-(6-(3,5-dichloro-4-hydroxyphenyl)-4-((1R,4R)-4-((dimethylamino)methyl)cyclohexyl)amino)-7-fluoroquinolin-3-yl)ethanone hydrochloride | 504 |

TABLE 1-continued

| No. | Structure | Compound Name | ESI MS (m/z) |
|---|---|---|---|
| 904 | 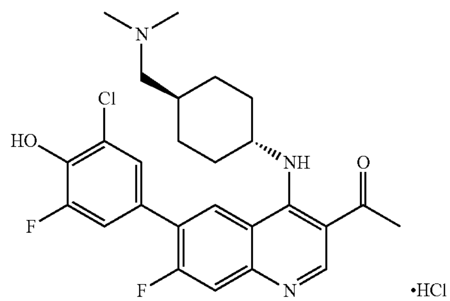 [SMILES: CC(=O)c1cnc2cc(F)c(-c3cc(F)c(O)c(Cl)c3)cc2c1N[C@H]1CC[C@H](CN(C)C)CC1 ; Cl] | 1-(6-(3-chloro-5-fluoro-4-hydroxyphenyl)-4-((1R,4R)-4-((dimethylamino)methyl)cyclohexyl)amino)-7-fluoroquinolin-3-yl)ethanone hydrochloride | 488 |
| 905 | 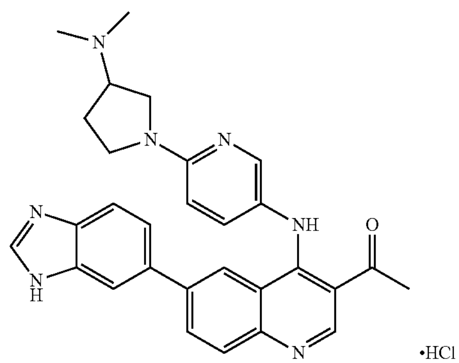 [SMILES: CC(=O)c1cnc2ccc(-c3ccc4nc[nH]c4c3)cc2c1Nc1ccc(N2CCC(N(C)C)C2)nc1 ; Cl] | 1-(6-(1H-benzo[d]imidazol-6-yl)-4-((6-(3-(dimethylamino)pyrrolidin-1-yl)pyridin-3-yl)amino)quinolin-3-yl)ethanone hydrochloride | 492 |
| 906 | 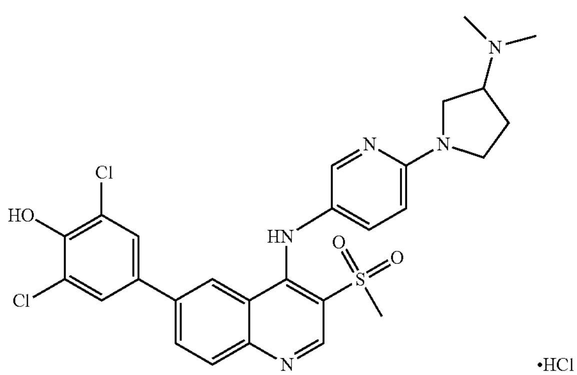 [SMILES: CN(C)C1CCN(c2ccc(Nc3c(S(C)(=O)=O)cnc4ccc(-c5cc(Cl)c(O)c(Cl)c5)cc34)cn2)C1 ; Cl] | 2,6-dichloro-4-(4-((6-(3-(dimethylamino)pyrrolidin-1-yl)pyridin-3-yl)amino)-3-(methylsulfonyl)quinolin-6-yl)phenol hydrochloride | 573 |
| 907 | 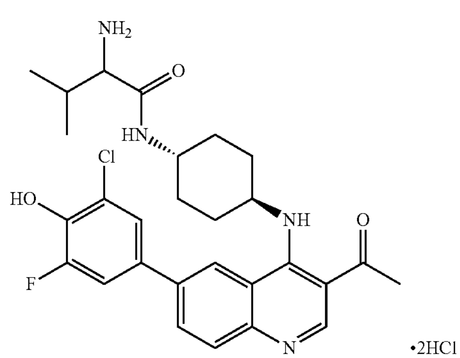 [SMILES: CC(=O)c1cnc2ccc(-c3cc(F)c(O)c(Cl)c3)cc2c1N[C@H]1CC[C@H](NC(=O)C(N)C(C)C)CC1 ; "·2HCl"] | N-(1R,4R)-4-((3-acetyl-6-(3-chloro-5-fluoro-4-hydroxyphenyl)quinolin-4-yl)amino)cyclohexyl)-2-amino-3-methylbutanamide dihydrochloride | 527 |

TABLE 1-continued

| No. | Structure | Compound Name | ESI MS (m/z) |
|---|---|---|---|
| 908 | 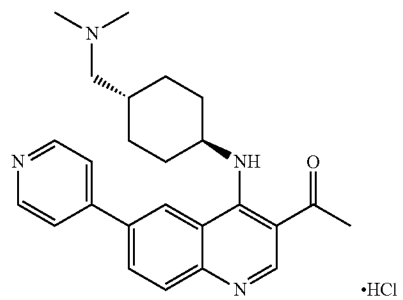 [SMILES: CC(=O)c1cnc2ccc(-c3ccncc3)cc2c1N[C@H]1CC[C@H](CN(C)C)CC1 ; Cl] | 1-(4-((1R,4R)-4-((dimethylamino)methyl)cyclohexyl)amino)-6-(pyridin-4-yl)quinolin-3-yl)ethanone hydrochloride | 403 |
| 909 | 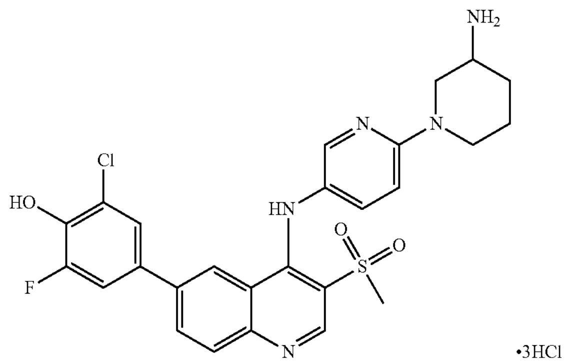 [SMILES: CS(=O)(=O)c1cnc2ccc(-c3cc(F)c(O)c(Cl)c3)cc2c1Nc1ccc(N2CCCC(N)C2)nc1 ; "·3HCl"] | 4-(4-((6-(3-aminopiperidin-1-yl)pyridin-3-yl)amino)-3-(methylsulfonyl)quinolin-6-yl)-2-chloro-6-fluorophenol trihydrochloride | 542 |
| 910 | 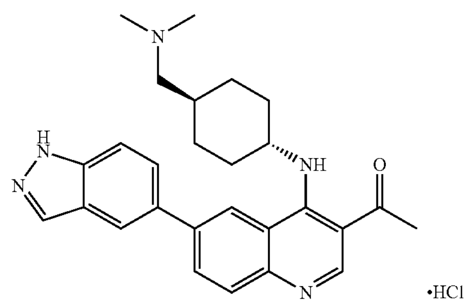 [SMILES: CC(=O)c1cnc2ccc(-c3ccc4[nH]ncc4c3)cc2c1N[C@H]1CC[C@H](CN(C)C)CC1 ; Cl] | 1-(4-((1R,4R)-4-((dimethylamino)methyl)cyclohexyl)amino)-6-(1H-indazol-5-yl)quinolin-3-yl)ethanone hydrochloride | 442 |
| 911 | 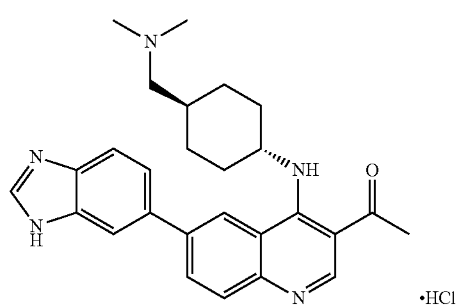 [SMILES: CC(=O)c1cnc2ccc(-c3ccc4nc[nH]c4c3)cc2c1N[C@H]1CC[C@H](CN(C)C)CC1 ; Cl] | 1-(6-(1H-benzo[d]imidazol-6-yl)-4-((1R,4R)-4-((dimethylamino)methyl)cyclohexyl)amino)quinolin-3-yl)ethanone hydrochloride | 442 |
| 912 | 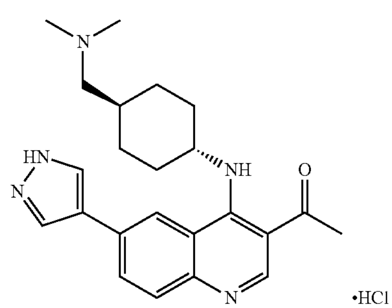 [SMILES: CC(=O)c1cnc2ccc(-c3cn[nH]c3)cc2c1N[C@H]1CC[C@H](CN(C)C)CC1 ; Cl] | 1-(4-((1R,4R)-4-((dimethylamino)methyl)cyclohexyl)amino)-6-(1H-pyrazol-4-yl)quinolin-3-yl)ethanone hydrochloride | 392 |

TABLE 1-continued

| No. | Structure | Compound Name | ESI MS (m/z) |
|---|---|---|---|
| 913 | 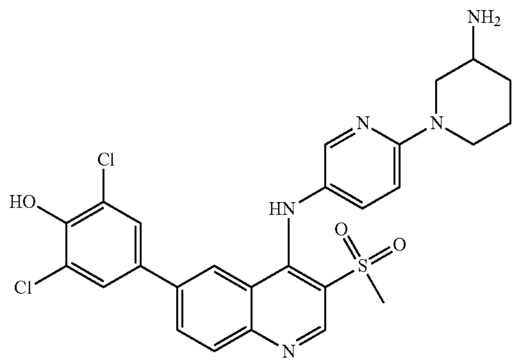 | 4-(4-((6-(3-aminopiperidin-1-yl)pyridin-3-yl)amino)-3-(methylsulfonyl)quinolin-6-yl)-2,6-dichlorophenol trihydrochloride | 558 |
| 914 | 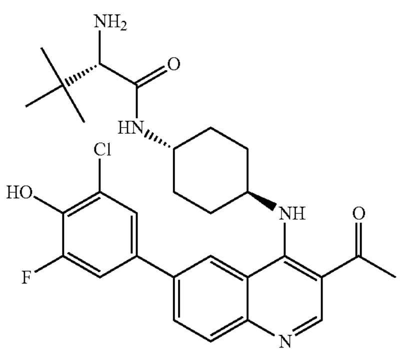 | (S)-N-((1r,4S)-4-((3-acetyl-6-(3-chloro-5-fluoro-4-hydroxyphenyl)quinolin-4-yl)amino)cyclohexyl)-2-amino-3,3-dimethylbutanamide hydrochloride | 541 |
| 915 | 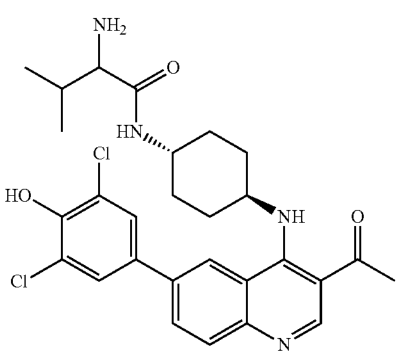 | N-(1R,4R)-4-((3-acetyl-6-(3,5-dichloro-4-hydroxyphenyl)quinolin-4-yl)amino)cyclohexyl)-2-amino-3-methylbutanamide dihydrochloride | 543 |
| 916 | 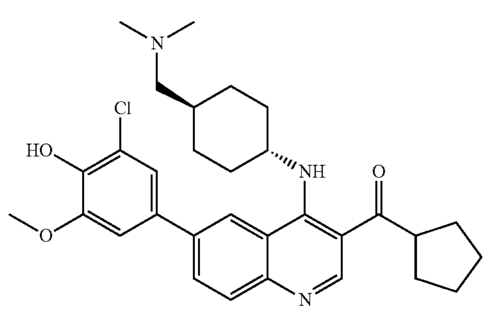 | (6-(3-chloro-4-hydroxy-5-methoxyphenyl)-4-((1R,4R)-4-((dimethylamino)methyl)cyclohexyl)amino)quinolin-3-yl)(cyclopentyl)methanone hydrochloride | 536 |

TABLE 1-continued

| No. | Structure | Compound Name | ESI MS (m/z) |
|---|---|---|---|
| 917 | 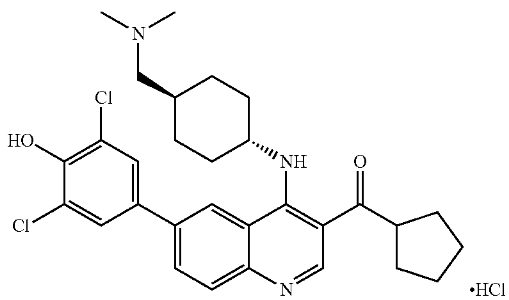 [SMILES: CN(C)C[C@H]1CC[C@H](Nc2c(C(=O)C3CCCC3)cnc3ccc(-c4cc(Cl)c(O)c(Cl)c4)cc23)CC1 ; Cl] | cyclopentyl(6-(3,5-dichloro-4-hydroxyphenyl)-4-((1R,4R)-4-((dimethylamino)methyl)cyclohexyl)amino)quinolin-3-yl)methanone hydrochloride | 541 |
| 918 | 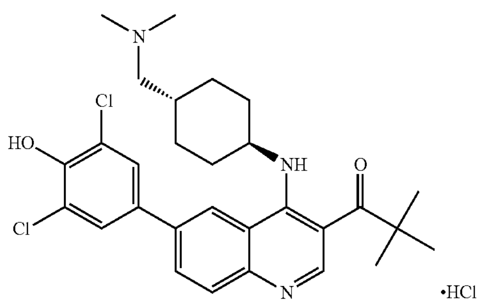 [SMILES: CN(C)C[C@H]1CC[C@H](Nc2c(C(=O)C(C)(C)C)cnc3ccc(-c4cc(Cl)c(O)c(Cl)c4)cc23)CC1 ; Cl] | 1-(6-(3,5-dichloro-4-hydroxyphenyl)-4-((1R,4R)-4-((dimethylamino)methyl)cyclohexyl)amino)quinolin-3-yl)-2,2-dimethylpropan-1-one hydrochloride | 529 |
| 919 | 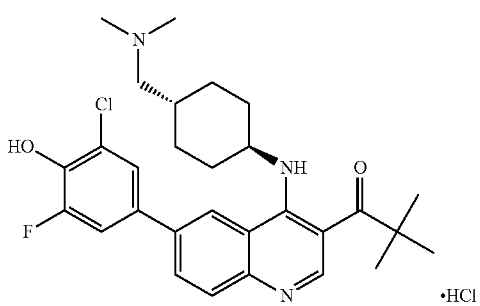 [SMILES: CN(C)C[C@H]1CC[C@H](Nc2c(C(=O)C(C)(C)C)cnc3ccc(-c4cc(F)c(O)c(Cl)c4)cc23)CC1 ; Cl] | 1-(6-(3-chloro-5-fluoro-4-hydroxyphenyl)-4-((1R,4R)-4-((dimethylamino)methyl)cyclohexyl)amino)quinolin-3-yl)-2,2-dimethylpropan-1-one hydrochloride | 512 |
| 920 | 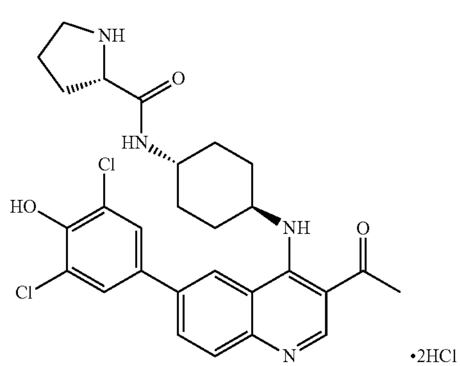 [SMILES: CC(=O)c1cnc2ccc(-c3cc(Cl)c(O)c(Cl)c3)cc2c1N[C@H]1CC[C@H](NC(=O)[C@@H]2CCCN2)CC1 ; "·2HCl"] | (S)-N-((1r,4S)-4-((3-acetyl-6-(3,5-dichloro-4-hydroxyphenyl)quinolin-4-yl)amino)cyclohexyl)pyrrolidine-2-carboxamide dihydrochloride | 541 |

488

TABLE 1-continued

| No. | Structure | Compound Name | ESI MS (m/z) |
|---|---|---|---|
| 921 | 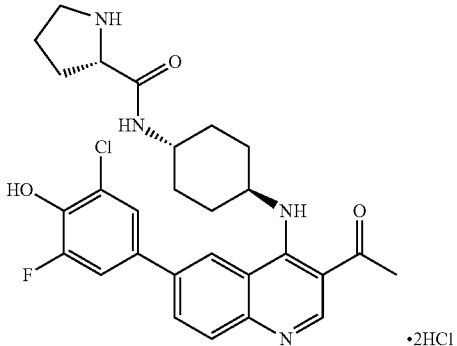 [SMILES: CC(=O)c1cnc2ccc(-c3cc(F)c(O)c(Cl)c3)cc2c1N[C@H]1CC[C@H](NC(=O)[C@@H]2CCCN2)CC1 ; "·2HCl"] | (S)-N-((1r,4S)-4-((3-acetyl-6-(3-chloro-5-fluoro-4-hydroxyphenyl)quinolin-4-yl)amino)cyclohexyl)pyrrolidine-2-carboxamide dihydrochloride | 525 |
| 922 | 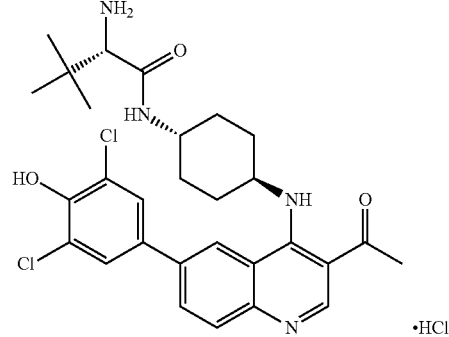 [SMILES: CC(=O)c1cnc2ccc(-c3cc(Cl)c(O)c(Cl)c3)cc2c1N[C@H]1CC[C@H](NC(=O)[C@@H](N)C(C)(C)C)CC1 ; Cl] | (S)-N-((1r,4S)-4-((3-acetyl-6-(3,5-dichloro-4-hydroxyphenyl)quinolin-4-yl)amino)cyclohexyl)-2-amino-3,3-dimethylbutanamide hydrochloride | 558 |
| 923 | 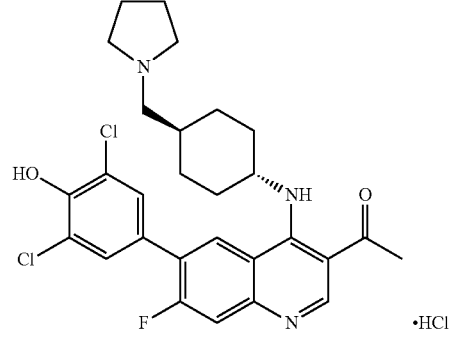 [SMILES: CC(=O)c1cnc2cc(F)c(-c3cc(Cl)c(O)c(Cl)c3)cc2c1N[C@H]1CC[C@H](CN2CCCC2)CC1 ; Cl] | 1-(6-(3,5-dichloro-4-hydroxyphenyl)-7-fluoro-4-((1R,4R)-4-(pyrrolidin-1-ylmethyl)cyclohexyl)amino)quinolin-3-yl)ethanone hydrochloride | 530 |
| 924 | 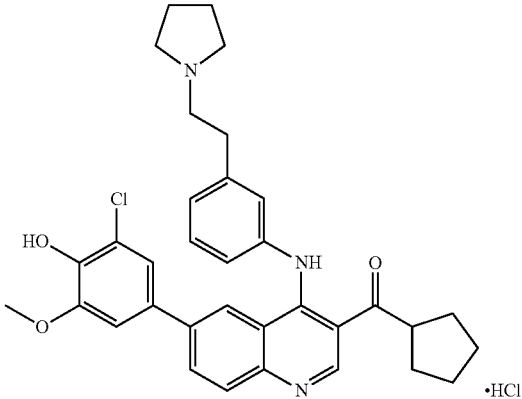 [SMILES: COc1cc(-c2ccc3ncc(C(=O)C4CCCC4)c(Nc4cccc(CCN5CCCC5)c4)c3c2)cc(Cl)c1O ; Cl] | (6-(3-chloro-4-hydroxy-5-methoxyphenyl)-4-((3-(2-(pyrrolidin-1-yl)ethyl)phenyl)amino)quinolin-3-yl)(cyclopentyl)methanone hydrochloride | 570 |

TABLE 1-continued

| No. | Structure | Compound Name | ESI MS (m/z) |
|---|---|---|---|
| 925 | 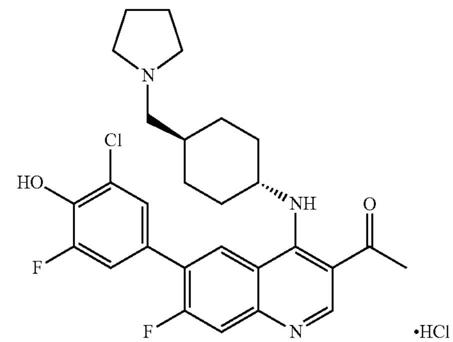 [SMILES: CC(=O)c1cnc2cc(F)c(-c3cc(F)c(O)c(Cl)c3)cc2c1N[C@H]1CC[C@H](CN2CCCC2)CC1 ; Cl] | 1-(6-(3-chloro-5-fluoro-4-hydroxy-phenyl)-7-fluoro-4-((1R,4R)-4-(pyrrolidin-1-ylmethyl)cyclohexyl)amino)quinolin-3-yl)ethanone hydrochloride | 514 |
| 926 | 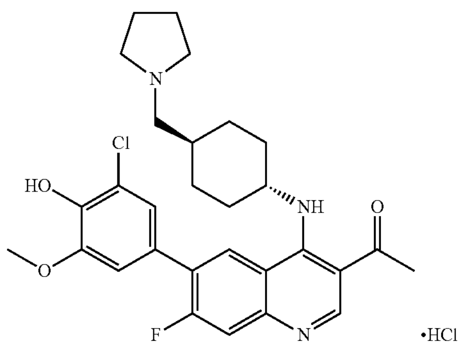 [SMILES: COc1cc(-c2cc3c(N[C@H]4CC[C@H](CN5CCCC5)CC4)c(C(C)=O)cnc3cc2F)cc(Cl)c1O ; Cl] | 1-(6-(3-chloro-4-hydroxy-5-methoxy-phenyl)-7-fluoro-4-((1R,4R)-4-(pyrrolidin-1-ylmethyl)cyclohexyl)amino)quinolin-3-yl)ethanone hydrochloride | 526 |
| 927 | 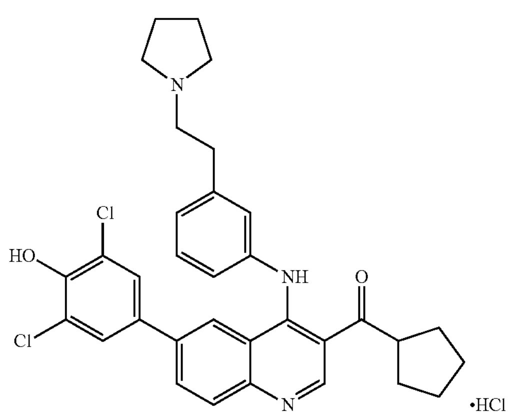 [SMILES: O=C(c1cnc2ccc(-c3cc(Cl)c(O)c(Cl)c3)cc2c1Nc1cccc(CCN2CCCC2)c1)C1CCCC1 ; Cl] | cyclopentyl(6-(3,5-dichloro-4-hydroxy-phenyl)-4-((3-(2-(pyrrolidin-1-yl)ethyl)phenyl)amino)quinolin-3-yl)methanone hydrochloride | 575 |
| 928 | 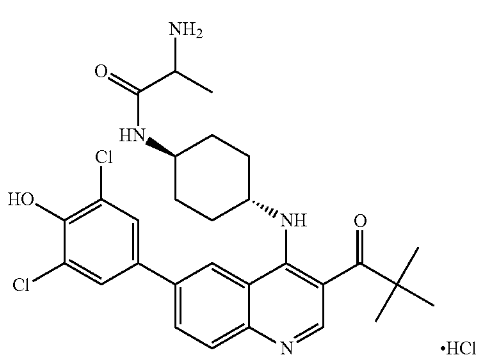 [SMILES: CC(N)C(=O)N[C@H]1CC[C@H](Nc2c(C(=O)C(C)(C)C)cnc3ccc(-c4cc(Cl)c(O)c(Cl)c4)cc23)CC1 ; Cl] | 2-amino-N-((1R,4R)-4-((6-(3,5-dichloro-4-hydroxyphenyl)-3-pivaloyl-quinolin-4-yl)amino)cyclohexyl)propanamide hydrochloride | 558 |

TABLE 1-continued

| No. | Structure | Compound Name | ESI MS (m/z) |
|---|---|---|---|
| 929 | 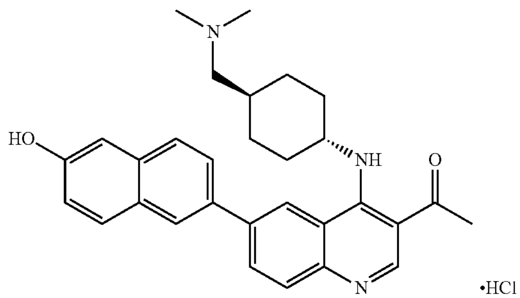 [SMILES: CC(=O)c1cnc2ccc(-c3ccc4cc(O)ccc4c3)cc2c1N[C@H]1CC[C@H](CN(C)C)CC1 ; Cl] | 1-(4-((1R,4R)-4-((dimethylamino)methyl)cyclohexyl)amino)-6-(6-hydroxynaphthalen-2-yl)quinolin-3-yl)ethanone hydrochloride | 468 |
| 930 | 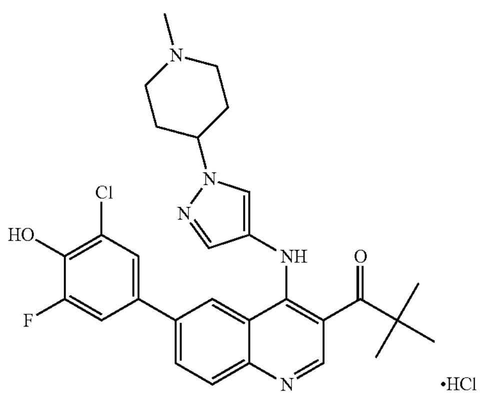 [SMILES: CN1CCC(n2cc(Nc3c(C(=O)C(C)(C)C)cnc4ccc(-c5cc(F)c(O)c(Cl)c5)cc34)cn2)CC1 ; Cl] | 1-(6-(3-chloro-5-fluoro-4-hydroxyphenyl)-4-((1-(1-methylpiperidin-4-yl)-1H-pyrazol-4-yl)amino)quinolin-3-yl)-2,2-dimethylpropan-1-one hydrochloride | 536 |
| 931 | 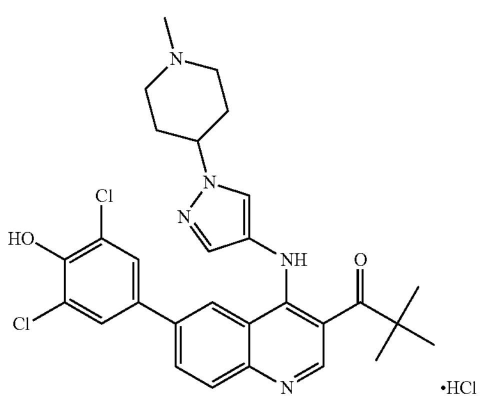 [SMILES: CN1CCC(n2cc(Nc3c(C(=O)C(C)(C)C)cnc4ccc(-c5cc(Cl)c(O)c(Cl)c5)cc34)cn2)CC1 ; Cl] | 1-(6-(3,5-dichloro-4-hydroxyphenyl)-4-((1-(1-methylpiperidin-4-yl)-1H-pyrazol-4-yl)amino)quinolin-3-yl)-2,2-dimethylpropan-1-one hydrochloride | 552 |
| 932 | 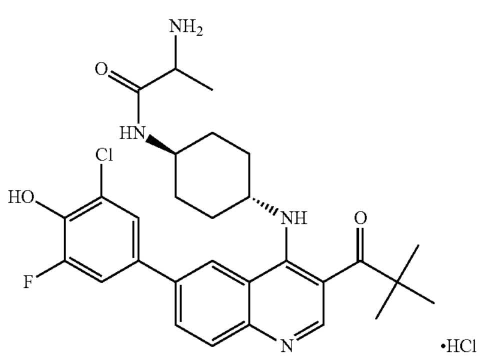 [SMILES: CC(N)C(=O)N[C@H]1CC[C@H](Nc2c(C(=O)C(C)(C)C)cnc3ccc(-c4cc(F)c(O)c(Cl)c4)cc23)CC1 ; Cl] | 2-amino-N-(1R,4R)-4-((6-(3-chloro-5-fluoro-4-hydroxyphenyl)-3-pivaloyl-quinolin-4-yl)amino)cyclohexyl)propanamide hydrochloride | 541 |

TABLE 1-continued

| No. | Structure | Compound Name | ESI MS (m/z) |
|---|---|---|---|
| 933 | 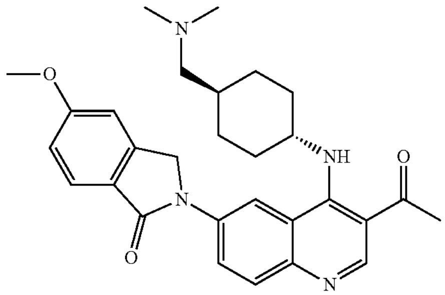 [SMILES: COc1ccc2c(c1)CN(c1ccc3ncc(C(C)=O)c(N[C@H]4CC[C@H](CN(C)C)CC4)c3c1)C2=O] | 2-(3-acetyl-4-(1R,4R)-4-((dimethyl-amino)methyl)cyclohexylamino)quinolin-6-yl)-5-methoxyiso indolin-1-one | 487 |
| 934 | 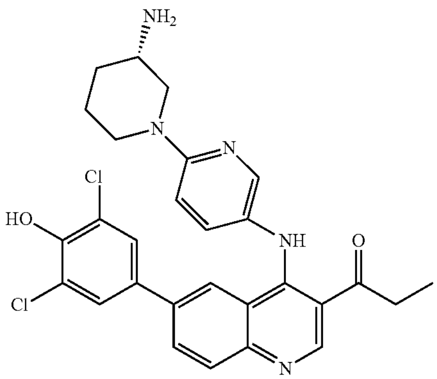 | (S)-1-(4-(6-(3-aminopiperidin-1-yl)pyridin-3-ylamino)-6-(3,5-dichloro-4-hydroxyphenyl)quinolin-3-yl)propan-1-one trihydrochloride | 536 |
| 935 | 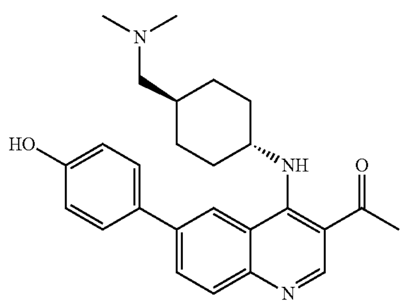 | 1-(4-(1R,4R)-4-((dimethylamino)methyl)cyclohexylamino)-6-(4-hydroxyphenyl)quinolin-3-yl)ethanone dihydrochloride | 418 |
| 936 | 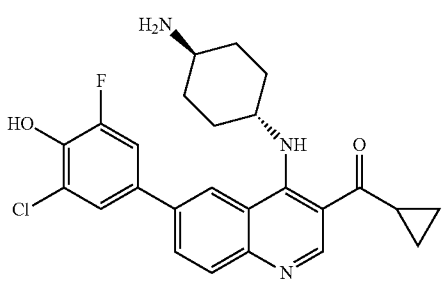 | (4-((trans)-4-aminocyclohexyl-amino)-6-(3-chloro-5-fluoro-4-hydroxyphenyl)quinolin-3-yl)(cyclopropyl)methanone hydrochloride | 454 |
| 937 | 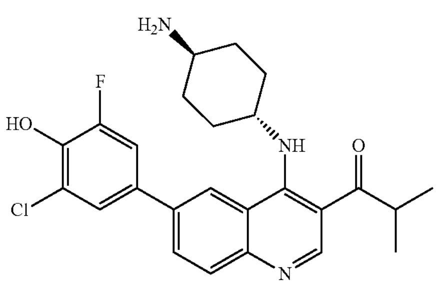 | 1-(4-((trans)-4-aminocyclohexyl-amino)-6-(3-chloro-5-fluoro-4-hydroxyphenyl)quinolin-3-yl)-2-methylpropan-1-one dihydrochloride | 456 |

TABLE 1-continued

| No. | Structure | Compound Name | ESI MS (m/z) |
|---|---|---|---|
| 938 | 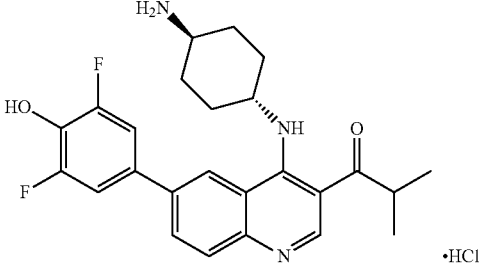 [SMILES: CC(C)C(=O)c1cnc2ccc(-c3cc(F)c(O)c(F)c3)cc2c1N[C@H]1CC[C@H](N)CC1 ; Cl] | 1-(4-((trans)-4-aminocyclohexyl-amino)-6-(3,5-difluoro-4-hydroxyphenyl)quinolin-3-yl)-2-methylpropan-1-one hydrochloride | 439 |
| 939 | 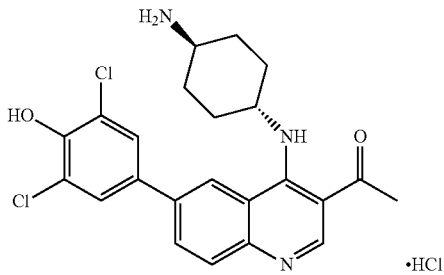 [SMILES: CC(=O)c1cnc2ccc(-c3cc(Cl)c(O)c(Cl)c3)cc2c1N[C@H]1CC[C@H](N)CC1 ; Cl] | 1-(4-((trans)-4-aminocyclohexyl-amino)-6-(3,5-dichloro-4-hydroxy-phenyl)quinolin-3-yl)ethanone hydrochloride | 444 |
| 940 | 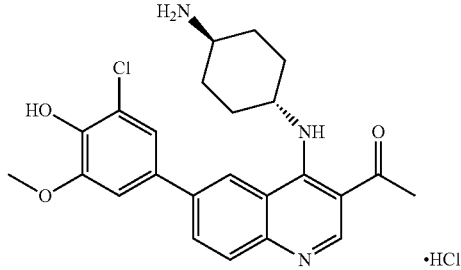 [SMILES: COc1cc(-c2ccc3ncc(C(C)=O)c(N[C@H]4CC[C@H](N)CC4)c3c2)cc(Cl)c1O ; Cl] | 1-(4-((trans)-4-aminocyclohexyl-amino)-6-(3-chloro-4-hydroxy-5-methoxyphenyl)quinolin-3-yl)ethanone hydrochloride | 440 |
| 941 | 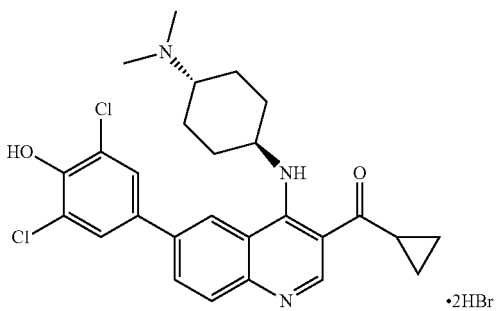 [SMILES: CN(C)[C@H]1CC[C@H](Nc2c(C(=O)C3CC3)cnc3ccc(-c4cc(Cl)c(O)c(Cl)c4)cc23)CC1 ; "·2HBr"] | cyclopropyl(6-(3,5-dichloro-4-hydroxyphenyl)-4-((trans)-4-(dimethylamino)cyclohexylamino)quinolin-3-yl)methanone dihydrobromide | 498 |
| 942 | 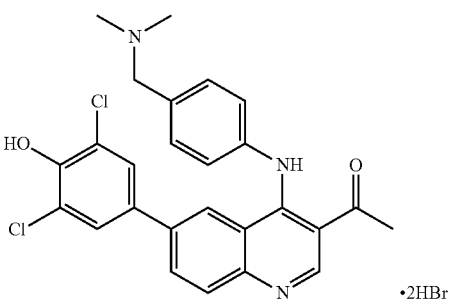 [SMILES: CC(=O)c1cnc2ccc(-c3cc(Cl)c(O)c(Cl)c3)cc2c1Nc1ccc(CN(C)C)cc1 ; "·2HBr"] | 1-(6-(3,5-dichloro-4-hydroxyphenyl)-4-(4-((dimethylamino)methyl)phenylamino)quinolin-3-yl)ethanone dihydrobromide | 480 |

TABLE 1-continued

| No. | Structure | Compound Name | ESI MS (m/z) |
|---|---|---|---|
| 943 | 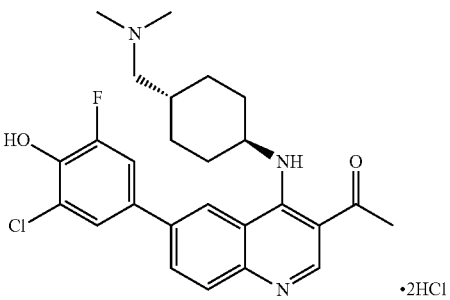 [SMILES: CC(=O)c1cnc2ccc(-c3cc(F)c(O)c(Cl)c3)cc2c1N[C@H]1CC[C@H](CN(C)C)CC1 ; "·2HCl"] | 1-(6-(3-chloro-5-fluoro-4-hydroxyphenyl)-4-((trans)-4-((dimethylamino)methyl)cyclohexylamino)quinolin-3-yl)ethanone dihydrochloride | 470 |
| 944 | 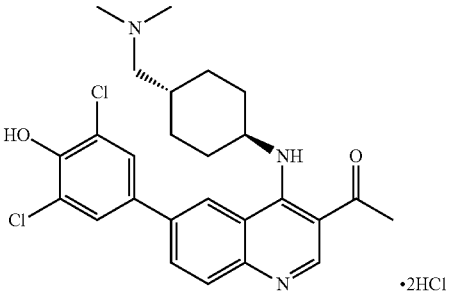 [SMILES: CC(=O)c1cnc2ccc(-c3cc(Cl)c(O)c(Cl)c3)cc2c1N[C@H]1CC[C@H](CN(C)C)CC1 ; "·2HCl"] | 1-(6-(3,5-dichloro-4-hydroxyphenyl)-4-((trans)-4-((dimethylamino)methyl)cyclohexylamino)quinolin-3-yl)ethanone dihydrochloride | 486 |
| 945 | 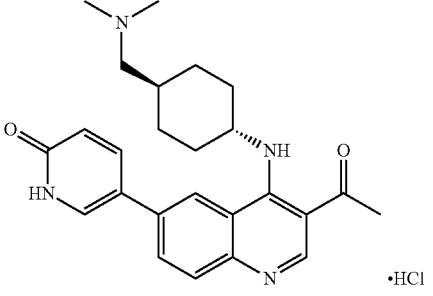 [SMILES: CC(=O)c1cnc2ccc(-c3ccc(=O)[nH]c3)cc2c1N[C@H]1CC[C@H](CN(C)C)CC1 ; Cl] | 5-(3-acetyl-4-((1R,4R)-4-((dimethylamino)methyl)cyclohexyl)amino)quinolin-6-yl)pyridin-2(1H)-one hydrochloride | 419 |

Compound (I) and pharmaceutically acceptable salts thereof may be administered singly as they are; however, ordinarily, they are desirably provided as various types of pharmaceutical formulations. Such pharmaceutical formulations are used for animals or humans.

Pharmaceutical formulations of the present invention may comprise as an active ingredient compound (I) or a pharmaceutically acceptable salt thereof alone, or a mixture with any other active ingredients for treatment. Furthermore, these pharmaceutical formulations are produced by any methods well known in the technical field of drug formulation by mixing the active ingredient together with one or more types of pharmaceutically acceptable carriers (for example, diluents, solvents, and excipients).

Desirably, the route of administration most effective for the treatment is used, and examples include oral route, or parenteral route such as intravenous route.

The form of administration is, for example, tablets and injections.

Tablets and such which are appropriate for oral administration can be produced using excipients such as lactose, disintegrants such as starch, lubricants such as magnesium stearate, and binders such as hydroxypropylcellulose.

Injections and such which are appropriate for parenteral administration can be produced using, for example, solvents or diluents such as salt solutions, glucose solutions, or a mixture of salt water and glucose solution.

The dose of compound (I) or a pharmaceutically acceptable salt thereof, and the number of doses differ depending on the form of administration, the age and body weight of the patient, the nature of the symptom to be treated or severity, and such, but ordinarily for oral administration, it is 0.01 mg to 1000 mg, preferably in the range of 0.05 mg to 100 mg for an adult, and it is administered once to several times a day. In the case of parenteral administration such as intravenous administration, 0.001 mg to 1000 mg, or preferably 0.01 mg to 100 mg is administered to an adult once to several times a day. However, these doses and the number of doses vary depending on the various conditions mentioned above.

Hereinbelow, the present invention will be specifically described with reference to the Examples, but the scope of the present invention is not to be construed as being limited thereto.

The intermediates and compounds of interest in the following Examples can be isolated and purified by subjecting them to separation and purification methods commonly used in synthetic organic chemistry unless otherwise specified, and examples include filtration, extraction, washing, drying, concentration, recrystallization, and various types of chromatographies. Alternatively, intermediates can be subjected to the next reaction without purification.

Furthermore, in the Examples shown below, unless otherwise specified, if a defined group becomes altered under the conditions of the production method or is unsuitable for carrying out the method, the compound of interest can be produced by using the methods for introducing and removing protecting groups commonly used in synthetic organic chemistry (for example, "Protective Groups in Organic Synthesis", T. W. Greene, John Wiley & Sons Inc., 1999). Furthermore, the order of the reaction processes such as substituent introduction can be changed as necessary.

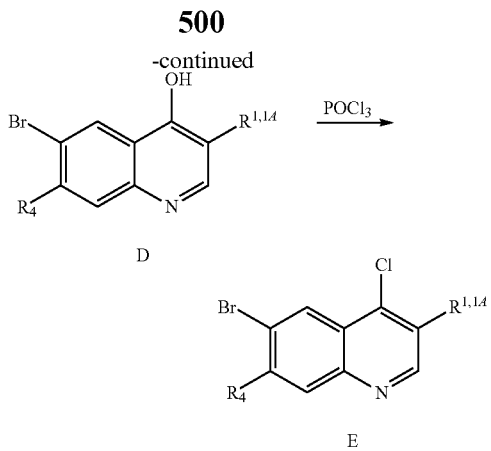

The requisite anilines A were heated in the presence of triethylorthoformate and the appropriately substituted esters B to afford the condensation products C (Scheme 1). Intermediates C were heated in Dowtherm A to facilitate the intramolecular cyclization and provide substituted quinolines D. Finally, the 4-position alcohol was converted to the chloride using phosphorus oxychloride to provide key intermediates E (Scheme 1).

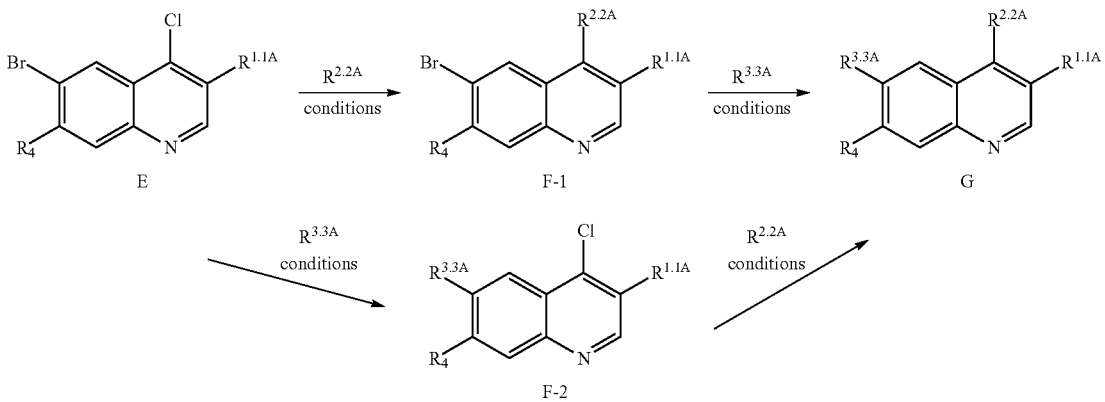

EXAMPLES

Specific methods for producing the above-mentioned compounds will be indicated below.

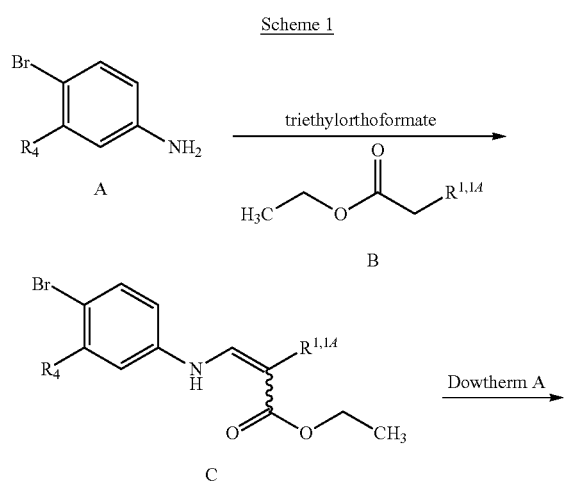

The chloride present in intermediates E was reacted under various reaction conditions (e.g. displacement with amines $R^6R^7N$ or metal mediated cross-couplings) to place the requisite substituents ($R^{2,2A}$) at the 4-position of the quinoline ring and afford compounds F-1. Optionally, intermediates E could be reacted under the appropriate conditions (e.g. metal mediated cross-couplings) to place the appropriate substituents ($R^{3,3A}$) at the 6-position of the quinoline ring and provide compounds F-2. Finally, the intermediates F-1 and F-2 could be elaborated with the requisite $R^3$ and $R^2$ substituent, respectively, to provide the quinoline compounds G (Scheme 2).

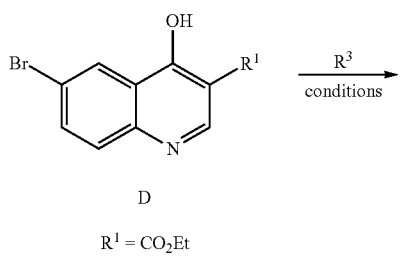

$R^1 = CO_2Et$

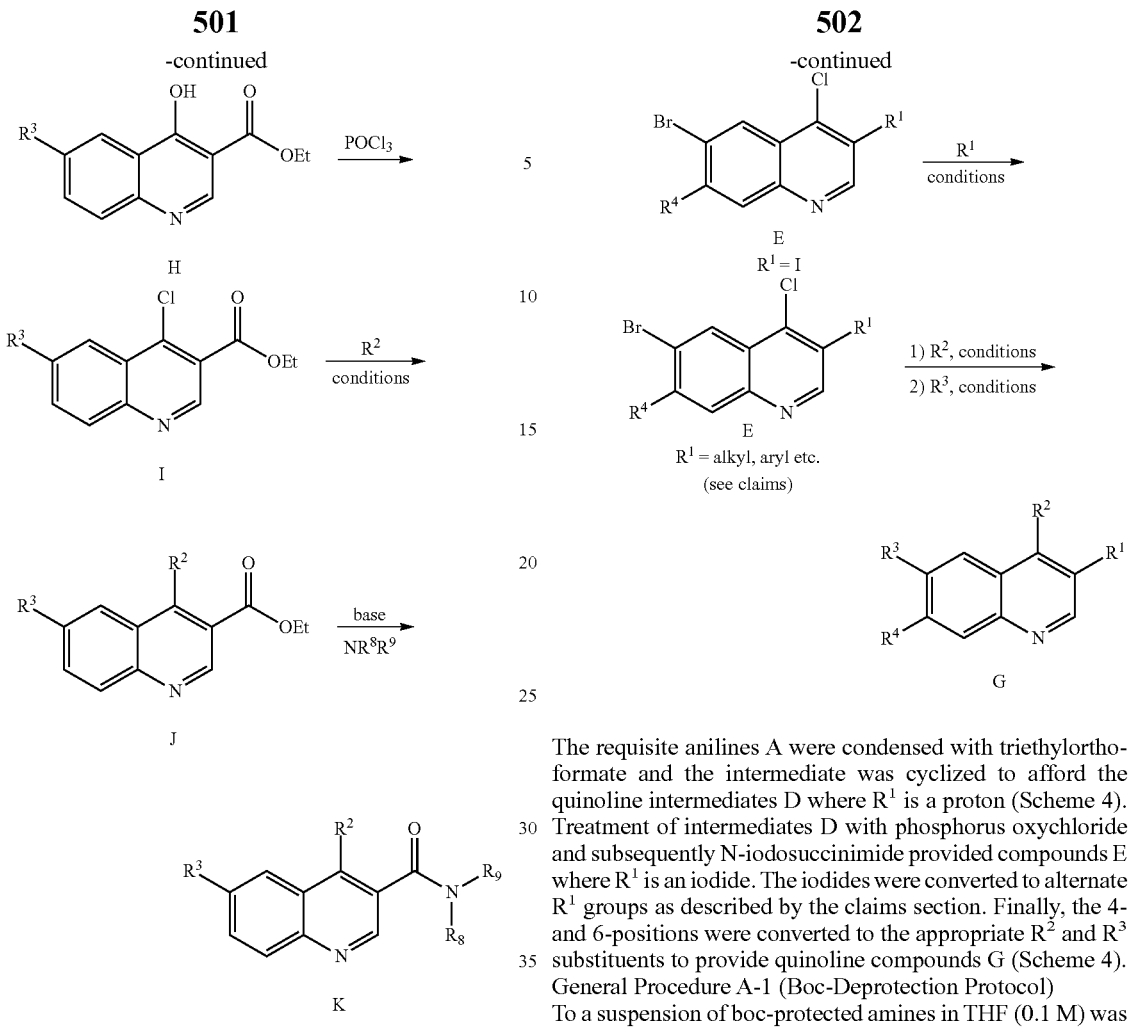

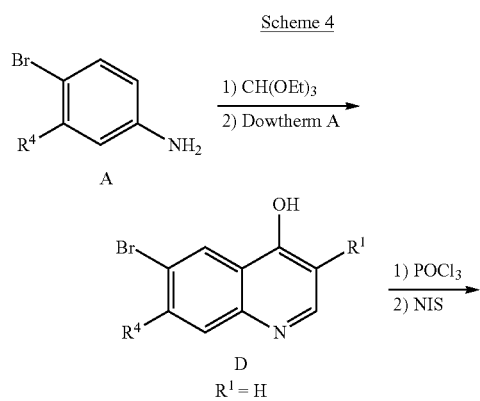

The intermediates D (where R¹=ethyl ester) were converted to intermediates H by replacing the bromide with the appropriate R³ group. A subsequent reaction with phosphorus oxychloride afforded the 4-chloro quinoline intermediates I (Scheme 3). These intermediates were reacted under various reaction conditions to install the requisite R² substituents and afford compounds J. Finally, the ethyl ester was saponified and the acid intermediate was reacted with the requisite amines ($R^8R^9N$) to afford quinoline compounds K (Scheme 3).

The requisite anilines A were condensed with triethylorthoformate and the intermediate was cyclized to afford the quinoline intermediates D where $R^1$ is a proton (Scheme 4). Treatment of intermediates D with phosphorus oxychloride and subsequently N-iodosuccinimide provided compounds E where $R^1$ is an iodide. The iodides were converted to alternate $R^1$ groups as described by the claims section. Finally, the 4- and 6-positions were converted to the appropriate $R^2$ and $R^3$ substituents to provide quinoline compounds G (Scheme 4).

General Procedure A-1 (Boc-Deprotection Protocol)

To a suspension of boc-protected amines in THF (0.1 M) was added excess aqueous HCl and the reaction mixture was heated at 65° C. until the reaction was complete, as observed by LCMS analysis. The reaction mixture was cooled and concentrated to obtain the desired compounds G as the HCl salt.

General Procedure A-2 (Boc-Deprotection Protocol)

To a suspension of boc-protected amines in THF (0.1 M) was added trifluoroacetic acid and the reaction mixture was heated at 65° C. until the reaction was complete, as observed by LCMS analysis. The reaction mixture was cooled, concentrated and the residue was purified by preparative HPLC (C18 silica, 10-90% methanol/water with 0.05% TFA). The desired fractions were combined, concentrated and eluted through an ion-exchange column (using methanol as the initial eluent and 7 N methanol in ammonia as the next eluent) to obtain products G as the free base.

General Procedure B (4-Position Chloro Displacement)

To a suspension of intermediate E (1.0 equiv) in dioxane was added the requisite amine (1.0-2.0 equiv) and N,N-diisopropylethylamine (2.0-5.0 equiv) and the reaction mixture was heated at 80° C. for 16 h. The reaction mixture was cooled to room temperature, diluted with satd. aq. sodium bicarbonate and extracted with ethyl acetate. The combined organic layers were dried over anhydrous sodium sulfate, concentrated and the residue was purified by column chromatography (silica, 0-20% methanol/dichloromethane) to afford the desired products F.

General Procedure C (4-Position Chloro Displacement)

To a suspension of intermediates E (1.0 equiv) in a 2:1 mixture of dioxane:DMF was added the requisite amine (1.0-2.0 equiv), N,N-diisopropylethylamine (2.0-5.0 equiv) and finely ground K$_2$CO$_3$ (2.0-3.0 equiv) and the reaction mixture was heated at 100° C. for 16 h. The reaction mixture was cooled, diluted with satd. aq. sodium bicarbonate and extracted with ethyl acetate. The combined organic layers were dried over anhydrous sodium sulfate, concentrated and the residue was purified by column chromatography (silica, 0-20% methanol/dichloromethane) to afford the desired products F.

General Procedure D (6-Position Substitution Using Microwave Conditions)

To a suspension of intermediates F (1.0 equiv), the requisite boronic ester (1.5-2.0 equiv) and Pd(dppf)Cl$_2$ (0.1-0.2 equiv) in dioxane was added Cs$_2$CO$_3$ (1.0 M in H$_2$O, 3.0-4.0 eq). The reaction mixture was degassed with nitrogen and placed in a microwave reactor at 120-140° C. for 30-60 min. The reaction mixture was cooled and purified by column chromatography (silica, 0-20% methanol/dichloromethane) to afford the desired products G.

General Procedure E (Synthesis of Boronic Esters)

To a suspension of the appropriate aryl bromide (1.0 equiv), bis(pinacolado)diboron (1.5-2.0 equiv) and K$_2$CO$_3$ (2.0-3.0 equiv) in dioxane was added Pd(dppf)Cl$_2$ (0.05-0.1 equiv). The reaction mixture was degassed with nitrogen followed by heating at 80° C. for 2-16 h. The reaction mixture was cooled, concentrated and the residue was purified by column chromatography (silica, ethyl acetate/hexanes gradient) to afford the desired product. In some instances the product was re-crystallized from hexanes or a hexanes/dichloromethane mixture.

General Procedure F (6-Position Substitution)

To a suspension of intermediates F (1.0 equiv), the requisite boronic ester (1.5-2.0 equiv) and Pd(dppf)Cl$_2$ (0.1-0.2 equiv) in dioxane was added Cs$_2$CO$_3$ (1.0 M in H$_2$O, 3.0 equiv). The reaction mixture was degassed with nitrogen followed by heating at 80° C. for 2-3 h. The reaction mixture was cooled, diluted with ethyl acetate, filtered and concentrated. The residue was purified by column chromatography (silica, 0-20% methanol/dichloromethane) to afford the desired product.

General Procedure A-2 (4-Position Substitution Under Acidic Conditions)

To a solution of the appropriate 6-bromo-4-chloroquinoline in a 2:1 mixture of dioxane:DMF was added the requisite amine and p-toluenesulfonic acid (0.8 equiv). The reaction mixture was heated at 80° C. for 2-16 h then cooled to room temperature, diluted with satd. aq. sodium bicarbonate and extracted with ethyl acetate or a CHCl$_3$/isopropanol 3:1 mixture. The combined organic layers were dried over anhydrous sodium sulfate and purified by column chromatography (silica, 0-20% methanol/dichloromethane) to afford the desired product.

General Procedure H (Substituted Pyridine and Pyrimidine Containing 4-Positions)

To a solution of 2-chloro-5-nitropyridine or 2-chloro-5-nitropyrimidine in THF (0.1 M) was added the requisite amine (1.1-1.6 equiv) and triethylamine (1.1-1.6 equiv) and the reaction mixture was stirred room temperature until completion, as observed by LCMS analysis. The reaction mixture was concentrated, the residue was dissolved in dichloromethane, washed with aqueous 1 N HCl and then water. The organic layer was dried over anhydrous sodium sulfate, filtered and concentrated. The residue was dissolved in tetrahydrofuran or ethanol (0.1-0.3 M), degassed and placed in a Parr shaker with Pd/C (10%, 0.1 equiv) and hydrogen gas at 40-50 psi. The reaction was allowed to proceed at room temperature until complete, as indicated by LCMS analysis. The reaction mixture was filtered over diatomaceous earth and the filtrate was concentrated to obtain the desired aniline.

General Procedure I (Substituted Pyridine and Pyrimidine Containing 4-Positions)

To a solution of 2-chloro-5-nitropyridine or 2-chloro-5-nitropyrimidine in dioxane (0.1 M) was added the requisite alcohol (1.1 equiv) and sodium hydride (60% dispersion in oil, 1.1 equiv) and the reaction mixture was stirred at room temperature until the reaction was complete, as observed by LCMS analysis. The reaction mixture was poured onto ice water and the product was extracted with dichloromethane. The combined organic layers were dried over anhydrous sodium sulfate, filtered, and concentrated. The residue was dissolved in tetrahydrofuran or ethanol (0.1-0.3 M), degassed and placed in a Parr shaker with Pd/C (10%, 0.1 equiv) and hydrogen gas at 40-50 psi. The reaction was allowed to proceed at room temperature until complete, as indicated by LCMS analysis. The reaction mixture was filtered over diatomaceous earth and the filtrate was concentrated to obtain the desired aniline.

General Procedure J (One-Pot Preparation of the 4 Position Amine Via Reductive Amination)

To a solution of the requisite amine (1.4 equiv) in dichloromethane (0.1 M), under nitrogen atmosphere, was added sodium acetate (1.4 equiv) and the mixture was stirred for 15 min followed by the addition of tert-butyl 4-oxocyclohexylcarbamate. The reaction mixture was stirred for an additional 15 min, then sodium triacetoxyborohydride (1.5 equiv) was added carefully and the reaction mixture was stirred until the reaction was complete, as observed by LCMS analysis. The reaction mixture was filtered and the filtrate was concentrated. The crude product was dissolved in a 1:1 mixture of tetrahydrofuran and aqueous HCl (3 N) and the mixture was stirred at room temperature for 12 h. The reaction mixture was concentrated and aqueous sodium hydroxide (6 N) was added until basic pH was achieved. The product was extracted with a 3:1 mixture of chloroform and isopropanol, the organic layer was dried and the solvent removed to obtain the desired amine.

Example 384

Methyl 3-(4-bromophenylamino)-2-(cyclopropanecarbonyl)acrylate

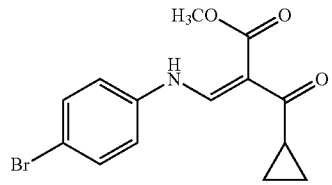 [SMILES: COC(=O)/C(=C\Nc1ccc(Br)cc1)C(=O)C1CC1]

A stirred mixture of methyl 3-cyclopropyl-3-oxopropanoate (20 g, 0.141 mol), triethyl orthoformate (28 mL, 0.169 mol), and 4-bromoaniline (24.2 g, 0.141 mol) were heated at 130° C. for 5 h with a Dean Stark trap. After this time the reaction was cooled to room temperature, diluted with methylene chloride and filtered through a pad of silica. The filtrate was concentrated to afford the desired product (26.5 g, 55%) as a yellow solid: ESI MS m/z 324 [C$_{14}$H$_{14}$BrNO$_2$+H]$^+$.

Example 385

(6-Bromo-4-hydroxyquinolin-3-yl)(cyclopropyl)methanone

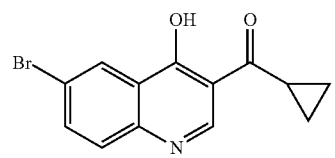 [SMILES: O=C(c1cnc2ccc(Br)cc2c1O)C1CC1]

Dowtherm was heated to 250° C., methyl 3-(4-bromophenylamino)-2-(cyclopropanecarbonyl)acrylate (24 g, 74.1 mmol) was added portionwise and upon complete addition the reaction mixture was stirred for 20 min. The reaction mixture was cooled to room temperature, diluted with 2:1 hexanes/diethyl ether and filtered to afford the desired product (9.71 g, 45%) as an off-white solid: $^1$H NMR (300 MHz, DMSO-$d_6$) δ 12.65 (s, 1H), 8.51 (s, 1H), 8.32 (d, J=2.3 Hz, 1H), 7.89 (dd, J=8.8, 2.3 Hz, 1H), 7.62 (d, J=8.8 Hz, 1H), 3.73-3.49 (m, J=7.5, 5.0 Hz, 1H), 1.15-0.76 (m, 4H).

Example 386

(6-Bromo-4-chloroquinolin-3-yl)(cyclopropyl)methanone

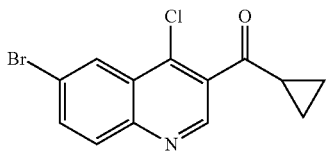

Phosphoryl chloride (50 mL, 0.547 mol) was cooled to 0° C. and (6-bromo-4-hydroxyquinolin-3-yl)(cyclopropyl)methanone (21 g, 67.7 mmol) was added. The reaction mixture was stirred at 0° C. for 2 h, at room temperature for 2 h and concentrated. The residue was dissolved in methylene chloride and poured into cold 30% aq. ammonium hydroxide. The aqueous layer was separated and extracted with methylene chloride. The combined organics were dried over anhydrous sodium sulfate, filtered, and concentrated. The residue was purified by a silica plug to afford the desired product (5.8 g, 22%) as a brown solid: $^1$H NMR (300 MHz, CDCl$_3$) δ 8.91 (s, J=6.4 Hz, 1H), 8.55-8.49 (m, 1H), 8.07-7.97 (m, 1H), 7.91 (dd, J=8.9, 2.1 Hz, 1H), 2.69-2.54 (m, 1H), 1.50-1.40 (m, 2H), 1.28-1.19 (m, 2H).

Example 387

Ethyl 2-[(4-bromophenylamino)methylene]-4-methyl-3-oxopentanoate

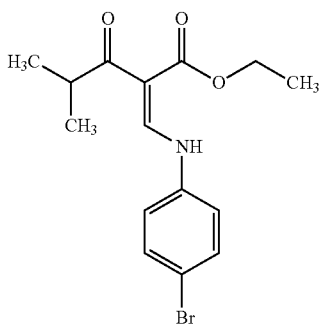 [SMILES: CCOC(=O)/C(=C\Nc1ccc(Br)cc1)C(=O)C(C)C]

A mixture of ethyl 4-methyl-3-oxopentanoate (31.6 g, 0.200 mol), triethyl orthoformate (41.6 mL, 0.250 mol), and 4-bromoaniline (36.1 g, 0.210 mol) was heated at 150° C. for 2 h with a Dean Stark trap. After this time triethyl orthoformate (20.8 mL) was added and the reaction mixture was stirred for 16 h. The reaction was cooled to room temperature, diluted with 1:1 methylene chloride/hexanes (200 mL), and filtered through a plug of silica. The filtrate was concentrated, triturated with hexanes and filtered to afford the desired product (33.2 g, 53%) as a pale yellow solid: $^1$H NMR (300 MHz, CDCl$_3$) δ 12.80 (d, J=11.9 Hz, 1H), 8.46 (d, J=13.0 Hz, 1H), 7.55-7.42 (m, 2H), 7.12-6.96 (m, 2H), 4.27 (q, J=7.1 Hz, 2H), 3.89-3.72 (m, 1H), 1.35 (t, J=7.1 Hz, 3H), 1.13 (d, J=6.8 Hz, 6H).

Example 388

1-(6-Bromo-4-hydroxyquinolin-3-yl)-2-methylpropan-1-one

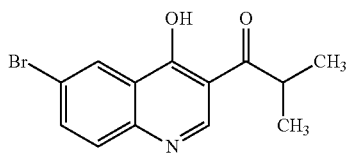 [SMILES: CC(C)C(=O)c1cnc2ccc(Br)cc2c1O]

To Dowtherm at 250° C. was added ethyl 2-[(4-bromophenylamino)methylene]-3-oxobutanoate (33.2 g, 97.6 mmol) portionwise and the reaction mixture was stirred for 1.5 h. The reaction mixture was cooled to room temperature, diluted with hexanes and the resulting precipitate was filtered to afford the desired product (17 g, 59%) as a yellow solid: $^1$H NMR (300 MHz, DMSO-$d_6$) δ 12.66 (s, 1H), 8.54 (s, 1H), 8.31 (s, 1H), 7.89 (d, J=8.7 Hz, 1H), 7.61 (d, J=8.7 Hz, 1H), 4.11-3.89 (m, 1H), 1.06 (dd, J=6.8, 1.6 Hz, 6H).

Example 389

1-(6-Bromo-4-chloroquinolin-3-yl)-2-methylpropan-1-one

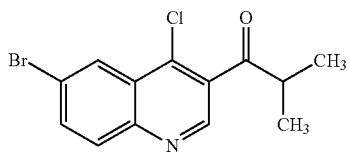 [SMILES: CC(C)C(=O)c1cnc2ccc(Br)cc2c1Cl]

1-(6-Bromo-4-hydroxyquinolin-3-yl)-2-methylpropan-1-one (16.0 g, 54.4 mmol) was added to phosphoryl chloride (160 mL) and the reaction was stirred at 85° C. for 1.5 h. The reaction mixture was cooled and slowly poured into a 2:1 solution of satd. aq. sodium bicarbonate/ethyl acetate at 0° C. The organic layer was separated and was washed with satd. aq. sodium bicarbonate and brine, dried over anhydrous sodium sulfate, filtered, and concentrated to afford the desired product (14.8 g, 89%) as a yellow solid: ESI MS m/z 312 [C$_{13}$H$_{11}$BrClNO+H]$^+$.

Example 390

Ethyl 3-(4-bromophenylamino)-2-(methylsulfonyl)acrylate

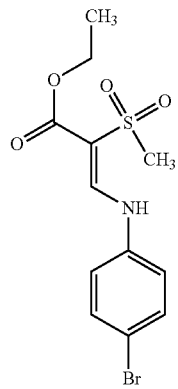 [SMILES: CCOC(=O)/C(=C/Nc1ccc(Br)cc1)S(C)(=O)=O]

A mixture of ethyl 2-(methylsulfonyl)acetate (1.9 g, 11.4 mmol), triethyl orthoformate (5.64 mL, 34.2 mmol), and acetic anhydride (5 mL) were heated at 130° C. for 5 h with a Dean Stark trap. The reaction was cooled, 4-bromoaniline (3.1 g, 18.0 mmol) was added and the reaction mixture was heated at 150° C. for 2 h. The reaction mixture was cooled, concentrated and the residue was purified by column chromatography to afford the desire product (1.08 g, 27% over 2 steps) as a tan solid: $^1$H NMR (300 MHz, CDCl$_3$) δ 10.58 (d, J=13.5 Hz, 1H), 8.39 (d, J=13.7 Hz, 1H), 7.59-7.48 (m, 2H), 7.15-7.02 (m, 2H), 4.41 (q, 1=7.1 Hz, 2H), 3.19 (s, 3H), 1.43 (t, J=7.1 Hz, 3H).

Example 391

6-Bromo-3-(methylsulfonyl)quinolin-4-ol

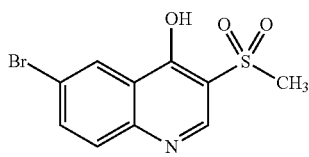 [SMILES: CS(=O)(=O)c1cnc2ccc(Br)cc2c1O]

To Dowtherm at 250° C. was added ethyl 3-(4-bromophenylamino)-2-(methylsulfonyl)acrylate (1.08 g, 3.10 mmol) portionwise and the reaction mixture was stirred for 2 h. The reaction mixture was cooled to room temperature, diluted with hexanes and the resulting precipitate was filtered to afford the desired product (573 mg, 61%) as a tan solid: ESI MS m/z 302 [C$_{10}$H$_8$BrNO$_3$S+H]$^+$.

Example 392

6-Bromo-4-chloro-3-(methylsulfonyl)quinoline

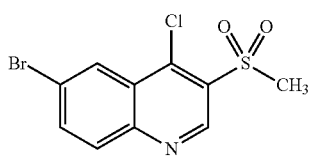 [SMILES: CS(=O)(=O)c1cnc2ccc(Br)cc2c1Cl]

6-Bromo-3-(methylsulfonyl)quinolin-4-ol (573 mg, 1.90 mmol) was added to phosphoryl chloride (19 mL) and the reaction was stirred at 100° C. 16 h. Additional THF (5 mL) was added and the reaction mixture was stirred at 100° C. for 4 h. The reaction mixture was cooled and slowly poured into a 2:1 solution of satd. aq sodium bicarbonate/ethyl acetate that was pre-cooled to 0° C. The layers were separated and the aqueous layer was extracted with ethyl acetate. The combined organic layers were washed with satd. aq.sodium bicarbonate, dried over anhydrous sodium sulfate, filtered, and concentrated to afford the desired product (360 mg, 59%) as a white solid: ESI MS m/z 321 [C$_{10}$H$_7$BrClNO$_2$S+H]$^+$.

Example 393

Ethyl 2-[(4-bromophenylamino)methylene]-3-oxobutanoate

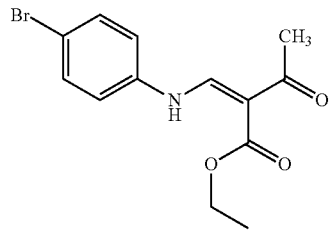 [SMILES: CCOC(=O)/C(=C\Nc1ccc(Br)cc1)C(C)=O]

A stirred mixture of ethyl 3-oxobutanoate (3.16 mL, 25.0 mmol), triethyl orthoformate (4.99 mL, 30.0 mmol), and bromoaniline (4.47 g, 26.0 mmol) were heated at 150° C. for 4 h with a Dean Stark trap. After this time the reaction was cooled to room temperature and the resulting precipitate was suspended in 1:1 ether/hexanes, and filtered to afford the desired product (3.4 g, 44%) as a brown solid: ESI MS m/z 312 [C$_{13}$H$_{14}$BrNO$_3$+H]$^+$.

Example 394

1-(6-Bromo-4-hydroxyquinolin-3-yl)ethanone

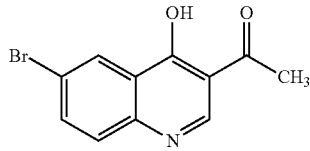

To Dowtherm at 250° C. was added Ethyl 2-[(4-bromophenylamino)methylene]-3-oxobutanoate (3.4 g, 10.9 mmol) portionwise and the reaction mixture was stirred for 1.5 h. The reaction mixture was cooled to room temperature, diluted with hexanes and the resulting precipitate was filtered to afford the desired product (2.2 g, 76%) as a brown solid: ESI MS m/z 266 [C$_{11}$H$_8$BrNO$_2$+H]$^+$.

Example 395

1-(6-Bromo-4-chloroquinolin-3-yl)ethanone

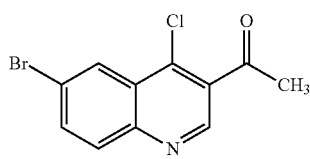

1-(6-Bromo-4-hydroxyquinolin-3-yl)ethanone (2.2 g, 8.27 mmol) was suspended in phosphoryl chloride (30 mL) and the reaction was heated to 85° C. and stirred for 3 h. After this time the reaction mixture was cooled to room temperature and slowly poured into a 2:1 solution of satd. aq. sodium bicarbonate/ethyl acetate that was cooled to 0° C. The organic layer was separated, washed with satd. aq. sodium bicarbonate, dried over anhydrous sodium sulfate, filtered, and concentrated under reduced pressure. The residue was purified by column chromatography to afford the desired product (710 mg, 72%) as a light brown solid: ESI MS m/z 280 $[C_{11}H_7BrClNO+H]^+$.

Example 396

Ethyl 2-[(4-Bromophenylamino)methylene]-5-methyl-3-oxohexanoate

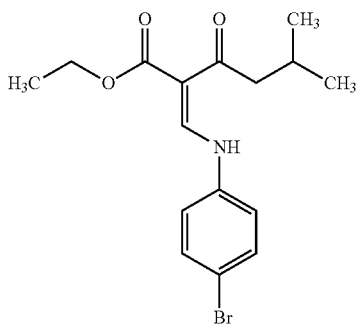 [SMILES: CCOC(=O)/C(=C/Nc1ccc(Br)cc1)C(=O)CC(C)C]

A stirred mixture of methyl 5-methyl-3-oxohexanoate (2.14 g, 13.5 mmol), triethyl orthoformate (2.64 mL, 16.2 mmol), and bromoaniline (2.32 g, 13.5 mmol) were heated at 150° C. for 3 h with a Dean Stark trap. After this time triethyl orthoformate (2.69 mL) was added and the mixture continued to stir for 2 h. After this time the reaction was cooled to room temperature, diluted with methylene chloride and filtered through a pad of silica. The plug was washed with 1:1 methylene chloride/hexanes, the filtrate was concentrated and the residue was purified by column chromatography to afford the desired product (2.37 g, 50%) as an off-white solid: ESI MS m/z 354 $[C_{16}H_{20}BrNO_3+H]^+$.

Example 397

1-(6-bromo-4-hydroxyquinolin-3-yl)-3-methylbutan-1-one

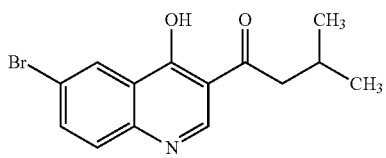 [SMILES: CC(C)CC(=O)c1cnc2ccc(Br)cc2c1O]

To Dowtherm at 250° C. was added a solution of ethyl 2-[(4-bromophenylamino)methylene]-5-methyl-3-oxohexanoate (700 mg, 6.75 mmol) in Dowtherm (5 mL) portionwise and the reaction mixture was stirred for 1.5 h. The reaction mixture was cooled to room temperature, diluted with hexanes and the resulting precipitate was filtered to afford the desired product (490 mg, 23%) as a white solid: $^1$H NMR (500 MHz, DMSO-d$_6$) δ 12.65 (s, 1H), 8.55 (d, J=6.4 Hz, 1H), 8.30 (d, J=2.3 Hz, 1H), 7.88 (dd, J=8.7, 2.3 Hz, 1H), 7.61 (d, J=8.8 Hz, 1H), 2.99 (d, J=6.8 Hz, 2H), 2.21-2.04 (m, 1H), 0.91 (d, J=6.7 Hz, 6H).

Example 398

1-(6-Bromo-4-chloroquinolin-3-yl)-3-methylbutan-1-one

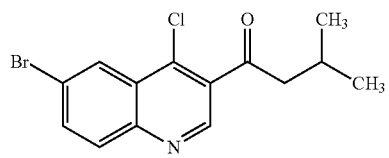 [SMILES: CC(C)CC(=O)c1cnc2ccc(Br)cc2c1Cl]

1-(6-Bromo-4-hydroxyquinolin-3-yl)-3-methylbutan-1-one (300 mg, 0.970 mmol) was added to phosphoryl chloride (9.7 mL) and the reaction was stirred at 85° C. for 1 h. After this time the reaction mixture was cooled to room temperature and slowly poured into a 2:1 solution of satd. aq. sodium bicarbonate/ethyl acetate that was cooled to 0° C. The organic layer was separated and was washed with satd. aq. sodium bicarbonate, dried over anhydrous sodium sulfate, filtered, and concentrated under reduced pressure to afford the desired product (309 mg, 98%) as a yellow oil: $^1$H NMR (500 MHz, CDCl$_3$) δ 8.86 (s, 1H), 8.51 (d, J=2.0 Hz, 1H), 8.01 (d, J=8.9 Hz, 1H), 7.91 (dd, J=8.9, 2.0 Hz, 1H), 2.96 (d, J=6.9 Hz, 2H), 2.39-2.23 (m, 1H), 1.03 (d, J=6.7 Hz, 6H).

Example 399

Methyl 3-(4-bromo-3-fluorophenylamino)-2-(cyclopropanecarbonyl)acrylate

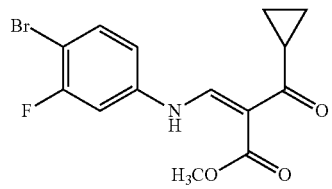 [SMILES: COC(=O)/C(=C\Nc1ccc(Br)c(F)c1)C(=O)C1CC1]

A stirred mixture of methyl 3-cyclopropyl-3-oxopropanoate (3.49 g, 26.3 mmol), triethyl orthoformate (5.2 mL, 31.6 mmol), and 4-bromo-3-fluoroaniline (4.47 g, 26.0 mmol) was heated at 140° C. overnight with a Dean Stark trap. After this time the reaction was cooled to room temperature, diluted with methylene chloride and filtered through a pad of silica. The filtrate was concentrated to afford the desired product (7.5 g, 85%) as a light yellow solid: ESI MS m/z 343 $[C_{14}H_{13}BrFNO_3+H]^+$.

Example 400

(6-Bromo-7-fluoro-4-hydroxyquinolin-3-yl)(cyclopropyl)methanone

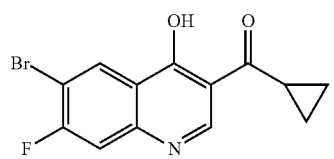 [SMILES: O=C(c1cnc2cc(F)c(Br)cc2c1O)C1CC1]

To Dowtherm at 250° C. was added methyl 3-(4-bromo-3-fluorophenylamino)-2-(cyclopropanecarbonyl)acrylate (7.5 g, 21.9 mmol) portionwise and the reaction mixture was stirred for 1.5 h. The reaction mixture was cooled to room temperature, diluted with hexanes and the resulting precipitate was filtered to afford the desired product (5.38 g, 79%) as a brown solid: ESI MS m/z 311 $[C_{13}H_9BrFNO_2+H]^+$.

Example 401

(6-Bromo-4-chloro-7-fluoroquinolin-3-yl)(cyclopropyl)methanone

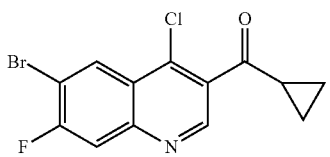 [SMILES: O=C(c1cnc2cc(F)c(Br)cc2c1Cl)C1CC1]

(6-Bromo-7-fluoro-4-hydroxyquinolin-3-yl)(cyclopropyl)methanone (3.35 g, 10.8 mmol) was suspended in phosphoryl chloride (10 mL) at 0° C. The reaction was warmed to room temperature and stirred overnight. After this time 2M ammonium hydroxide was added dropwise until a solid formed. Ethyl acetate was added and the layers were separated. The organic layer was dried over anhydrous sodium sulfate, filtered, and concentrated under reduced pressure. The residue was purified by column chromatography to afford the desired product (1.5 g, 42%) as an off-white solid: $^1$H NMR (300 MHz, CDCl$_3$) δ 8.92 (s, 1H), 8.63 (d, J=7.2 Hz, 1H), 7.84 (d, J=8.9 Hz, 1H), 2.70-2.45 (m, 1H), 1.55-1.35 (m, 2H), 1.35-1.05 (m, 2H).

Example 1001 ethyl 2-(((4-bromophenyl)amino)methylene)-3-oxopentanoate

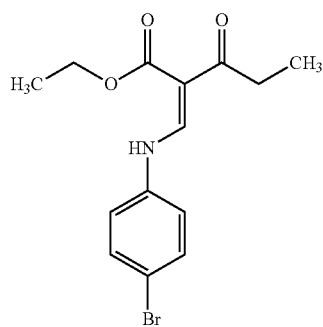 [SMILES: CCOC(=O)/C(=C\Nc1ccc(Br)cc1)C(=O)CC]

A stirred mixture of ethyl propionylacetate (33 g, 0.23 mol), triethyl orthoformate (46 mL, 0.28 mol), and 4-bromoaniline (42 g, 0.24 mol) were heated at 150° C. for 2 h with a Dean Stark trap. The reaction was cooled to room temperature. Trituration with 1:1 hexanes/diethyl ether afforded the desired product (25.1 g, 33%) as a tan solid: $^1$H NMR (300 MHz, DMSO-d$_6$) δ 12.44 (d, J=13.1 Hz, 1H), 8.42 (d, J=13.1 Hz 1H), 7.64-7.51 (m, 2H), 7.50-7.34 (m, 2H), 4.17 (q, J=7.1 Hz, 2H), 2.86 (q, J=7.3 Hz, 2H), 1.27 (t, J=7.1 Hz, 3H), 1.02 (t, J=7.3 Hz, 3H).

Example 1002

1-(6-bromo-4-hydroxyquinolin-3-yl)propan-1-one

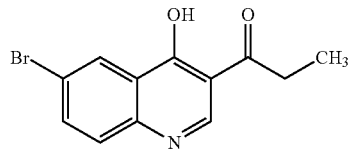 [SMILES: CCC(=O)c1cnc2ccc(Br)cc2c1O]

Dowtherm A (200 mL) was heated to 240° C. Ethyl 2-(((4-bromophenyl)amino) methylene)-3-oxopentanoate (25.1 g, 77 mmol) was added portionwise. The reaction was then heated to 250° C. and stirred for 1.25 h. The reaction mixture was slowly cooled to room temperature and a precipitate formed. The suspension was diluted with hexanes (500 mL) and filtered to afford the desired product (15.9 g, 73%) as a tan solid: $^1$H NMR (300 MHz, DMSO-d$_6$) δ 12.64 (br s, 1H), 8.56 (s, 1H), 8.30 (d, J=2.3 Hz, 1H), 7.88 (dd, J=8.8, 2.4 Hz, 1H), 7.61 (d, J=8.8 Hz, 1H), 3.10 (q, J=7.2 Hz, 2H), 1.05 (t, J=7.2 Hz, 3H).

Example 1003

1-(6-bromo-4-chloroquinolin-3-yl)propan-1-one

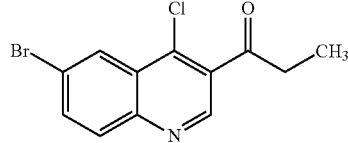 [SMILES: CCC(=O)c1cnc2ccc(Br)cc2c1Cl]

1-(6-Bromo-4-hydroxyquinolin-3-yl)propan-1-one (21 g, 67.7 mmol) was added to phosphoryl chloride (80 mL). The resultant suspension was then heated to 85° C. and stirred for 1.5 h. The reaction mixture was cooled to room temperature and poured carefully into a mixture of saturated sodium bicarbonate (250 mL) and 2N aqueous sodium hydroxide (250 mL). The solution was then extracted with ethyl acetate, the combined organics were washed with water and brine, dried over anhydrous sodium sulfate and concentrated under reduced pressure to afford the desired product (16 g, 96%) as a tan solid: APCI MS m/z 298 $[C_{12}H_9BrClNO+H]^+$.

Example 1004 ethyl 2-(((4-bromophenyl)amino)methylene)-3-oxohexanoate

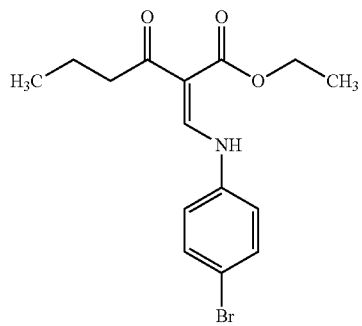 [SMILES: CCCC(=O)/C(=C/Nc1ccc(Br)cc1)C(=O)OCC]

A stirred mixture of ethyl 3-oxohexanoate (12.1 mL, 75 mmol), triethyl orthoformate (16.6 mL, 100 mmol), and 4-bromoaniline (12.9 g, 75 mmol) were heated at 120° C. for 4 h with a Dean Stark trap. After this time the reaction was cooled to room temperature. The resultant solid was triturated with diethyl ether to afford the desired product (8.17 g, 32%) as a white solid. ESI MS m/z 340 $[C_{15}H_{18}BrNO_3+H]^+$ Example 1005

1-(6-bromo-4-hydroxyquinolin-3-yl)butan-1-one

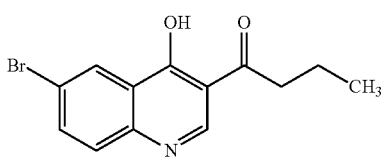 [SMILES: CCCC(=O)c1cnc2ccc(Br)cc2c1O]

To Dowtherm (82 mL) at 250° C. was added ethyl 2-(((4-bromophenyl)amino)methylene)-3-oxohexanoate (700 mg, 6.75 mmol) and the reaction mixture was stirred for 1.5 h. The reaction mixture was cooled to room temperature, and the precipitate was filtered and rinsed with hexanes to afford the desired product (3.73 g, 53%) as a light brown solid. ESI MS m/z 294 $[C_{13}H_{12}BrNO_2+H]^+$ Example 1006

1-(6-bromo-4-chloroquinolin-3-yl)butan-1-one

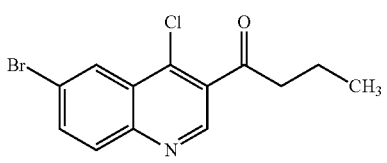 [SMILES: CCCC(=O)c1cnc2ccc(Br)cc2c1Cl]

1-(6-bromo-4-hydroxyquinolin-3-yl)butan-1-one (3.73 g, 12.7 mmol) was added to phosphoryl chloride (37 mL) and the reaction was stirred at 75° C. for 2 h. After this time the reaction mixture was cooled to room temperature and slowly poured into a solution of satd. aq. sodium carbonate that was cooled to 0° C. The resultant mixture was extracted with ethyl acetate, dried over anhydrous sodium sulfate, filtered, and concentrated. Purification by column chromatography (silica, ethyl acetate) afforded the desired product (3.90 g, 98%) as an off-white solid. ESI MS m/z 312 $[C_{13}H_{13}BrClNO+H]^+$ Example 1007

Benzyl 4-((dimethylamino)methyl)cyclohexylcarbamate

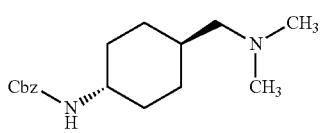 [SMILES: CN(C)C[C@H]1CC[C@H](NC(=O)OCc2ccccc2)CC1]

To a suspension of benzyl 4-(aminomethyl)cyclohexylcarbamate (15.0 g, 57 mmol) in water (150 mL) was added formaldehyde (14.0 mL, 0.17 mol, 37% solution) and formic acid (6.5 mL, 0.17 mol). The mixture was heated to reflux for 2 h, cooled to rt, neutralized with 2 N NaOH, and extracted with $CH_2Cl_2$. The organic extract was dried over anhydrous sodium sulfate, filtered, and concentrated to give desired product (15.87 g, 96%) as a tan, waxy solid. APCI MS m/z 291 $[C_{17}H_{26}N_2O_2+H]^+$.

Example 1008 trans-4-((Dimethylamino)methyl)cyclohexanamine diacetic acid

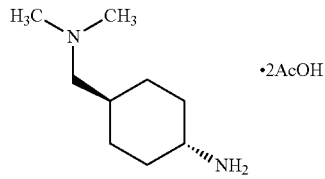

To a flask containing Pd/C (1.5 g, Degussa type E101) was added methanol/acetic acid (100 mL, 3:1). Benzyl 4-((dimethylamino)methyl)cyclohexylcarbamate (15.8 g, 54 mmol) in methanol/acetic acid (300 mL, 3:1) was added. A balloon of $H_2$ was added and the reaction stirred at rt for 6 h. The reaction was filtered through celite, the filtrate concentrated, and azeotroped with toluene. The thick oil was dried under vacuum to give desired product (17.9 g, crude) as a waxy solid. $^1$H NMR (300 MHz, MeOD) δ 3.11-2.98 (m, 1H), 2.78 (d, J=7.0 Hz, 2H), 2.69 (s, 6H), 2.07 (br d, J=13.9 Hz, 4H), 2.02-1.86 (m, 2H), 1.92 (s, 6H), 1.79-1.67 (m, 1H), 1.53-1.35 (m, 2H), 1.20-1.05 (m, 2H).

Example 1009

6-bromo-N-(1R,4R)-4-((dimethylamino)methyl)cyclohexyl)-3-(methylsulfonyl)quinolin-4-amine

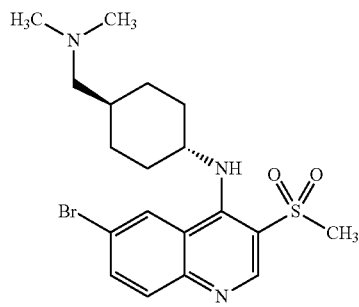

Following general procedure C, 6-bromo-4-chloro-3-(methylsulfonyl)quinoline (6.5 g, 20 mmol) was reacted with (1r,4r)-4-((dimethylamino)methyl)cyclohexanamine hydrochloride (6.0 g, 26 mmol) to obtain the desired product (5.7 g, 64%) as an off-white solid: ESI MS m/z 440 $[C_{19}H_{26}BrN_3O_2S+H]^+$.

Example 1010

1-(6-bromo-4-((trans-4-((dimethylamino)methyl)cyclohexyl)amino)quinolin-3-yl)propan-1-one

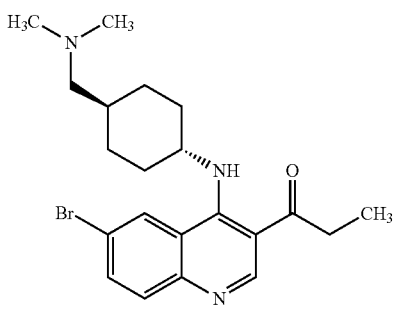 [SMILES: CCC(=O)c1cnc2ccc(Br)cc2c1N[C@H]1CC[C@H](CN(C)C)CC1]

To a suspension of 1-(6-bromo-4-chloroquinolin-3-yl)propan-1-one (500 mg, 1.67 mmol) in dioxane (10 mL) and DMF (4 mL) was added trans-4-((dimethylamino)methyl)cyclohexanamine diacetic acid salt (583 mg, 2.11 mmol) and $Cs_2CO_3$ (3.27 g, 10.0 mmol). The resultant suspension was then heated to 90° C. and stirred for 5.5 h. The reaction mixture was cooled to room temperature and diluted with ethyl acetate. The solution was then washed with saturated sodium bicarbonate, water and then brine, dried over anhydrous sodium sulfate and concentrated under reduced pressure. Purification by column chromatography (silica, 0-10% methanol/dichloromethane) afforded the desired product (403 mg, 58%) as a tan solid. $^1$H NMR (300 MHz, CDCl$_3$) δ 10.79 (d, J=8.4 Hz, 1H), 9.00 (s, 1H), 8.27 (d, J=2.0 Hz, 1H), 7.83-7.67 (m, 2H), 4.01-3.88 (m, 1H), 3.08 (q, J=7.2 Hz, 2H), 2.24 (s, 6H), 2.21-2.12 (m, 2H), 1.98 (d, J=13.4 Hz, 2H), 1.61-1.42 (m, 3H), 1.25 (t, J=7.3 Hz, 3H), 1.19-1.00 (m, 2H).

Example 1011

1-(6-bromo-4-((trans-4-(dimethylamino)cyclohexyl)amino)quinolin-3-yl)propan-1-one

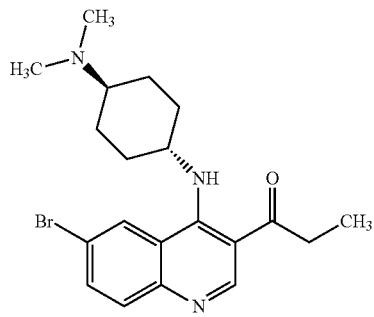 [SMILES: CCC(=O)c1cnc2ccc(Br)cc2c1N[C@H]1CC[C@H](N(C)C)CC1]

Following general procedure C, 1-(6-bromo-4-chloroquinolin-3-yl)propan-1-one (800 mg, 2.68 mmol) was reacted with trans-$N^1$,$N^1$-dimethylcyclohexane-1,4-diamine dihydrochloride (692 mg, 3.21 mmol) to afford the desired product (629 mg, 58%) as an off-white solid. $^1$H NMR (300 MHz, CDCl$_3$) δ 10.77 (br d, J=8.1 Hz, 1H), 9.01 (s, 1H), 8.27 (d, J=2.0 Hz, 1H), 7.84-7.68 (m, 2H), 4.05-3.89 (m, 1H), 3.08 (q, J=7.2 Hz, 2H), 2.33 (s, 6H), 2.33-2.23 (m, 2H), 2.12-1.99 (m, 2H), 1.63-1.31 (m, 4H), 1.25 (t, J=7.2 Hz, 3H).

Example 1012

1-(6-bromo-4-((4-((dimethylamino)methyl)phenyl)amino)quinolin-3-yl)propan-1-one

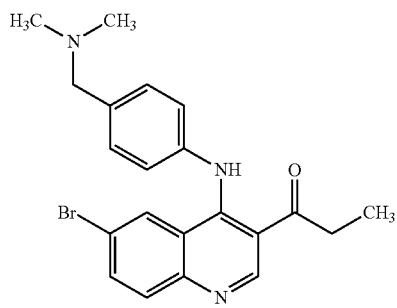 [SMILES: CCC(=O)c1cnc2ccc(Br)cc2c1Nc1ccc(CN(C)C)cc1]

Following general procedure C, 1-(6-bromo-4-chloroquinolin-3-yl)propan-1-one (750 mg, 2.51 mmol) was reacted with 4-(dimethylaminomethyl)aniline (377 mg, 2.51 mmol) to afford the desired product (889 mg, 86%) as a yellow solid. APCI MS m/z 412 $[C_{21}H_{22}BrN_3O+H]^+$.

Example 1013 trans-4-((tert-butoxycarbonyl)amino)cyclohexyl)methyl methanesulfonate

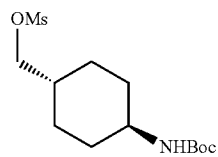 [SMILES: CC(C)(C)OC(=O)N[C@H]1CC[C@H](COS(C)(=O)=O)CC1]

To a suspension of tert-butyl (trans-4-(hydroxymethyl)cyclohexyl)carbamate (5.05 g, 22 mmol) in dichloromethane (70 mL) was added triethylamine (3.8 mL, 27.3 mmol). The resultant suspension was cooled to 0° C. and methanesulfonyl chloride (1.78 mL, 23 mmol) was added dropwise. The reaction mixture was allowed to warm to room temperature and stir for 2 h. The solution was then diluted with saturated sodium bicarbonate solution and extracted with dichloromethane. The combined organic layers were dried over anhydrous sodium sulfate and concentrated. Purification by column chromatography (silica, ethyl acetate/hexanes) afforded the desired product (6.65 g, 98%) as a white solid. $^1$H NMR (300 MHz, CDCl$_3$) δ 4.39 (br s, 1H), 4.03 (d, J=7.5 Hz, 1H), 3.39 (br s, 1H), 3.00 (s, 3H), 2.13-2.00 (m, 2H), 1.93-1.79 (m, 2H), 1.79-1.62 (m, 1H), 1.20-1.02 (m, 4H).

Example 1014 tert-butyl (trans-4-(pyrrolidin-1-ylmethyl)cyclohexyl)carbamate

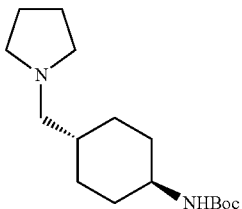 [SMILES: CC(C)(C)OC(=O)N[C@H]1CC[C@H](CN2CCCC2)CC1]

To a suspension of trans-4-((tert-butoxycarbonyl)amino)cyclohexyl)methyl methanesulfonate (1.84 g, 6.0 mmol) in acetonitrile (30 mL) was added $K_2CO_3$ (1.66 g, 12 mmol) and KI (600 mg, 3.6 mmol). Pyrrolidine (5.01 mL, 60 mmol) was added dropwise. The reaction mixture was heated at 85° C. for 16 h. The solution was cooled to room temperature, diluted with a saturated $NaHCO_3$ solution and extracted with a mixture of $CHCl_3$/isopropanol (3:1). The combined organic layers were dried over anhydrous sodium sulfate and concentrated. Purification by column chromatography (silica, 0-20% methanol/dichloromethane) afforded the desired product (1.28 g, 76%) as a white solid. ESI MS m/z 283 $[C_{16}H_{30}N_2O_2+H]^+$ Example 1015 tert-butyl (trans-4-(((R)-3-fluoropyrrolidin-1-yl)methyl)cyclohexyl)carbamate

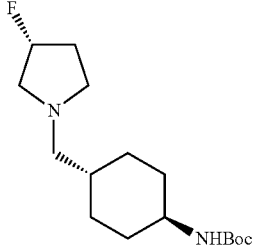 [SMILES: CC(C)(C)OC(=O)N[C@H]1CC[C@H](CN2CC[C@@H](F)C2)CC1]

To a suspension of trans-4-((tert-butoxycarbonyl)amino)cyclohexyl)methyl methanesulfonate (942 mg, 3.07 mmol) in acetonitrile (15 mL) was added $K_2CO_3$ (1.27 g, 9.21 mmol) and KI (100 mg, 0.60 mmol). (R)-3-fluoropyrrolidine hydrochloride (385 mg, 3.07 mmol) was added. The reaction mixture was heated at 50° C. for 72 h. The solution was cooled to room temperature, diluted with a saturated $NaHCO_3$ solution and extracted with dichloromethane. The combined organic layers were dried over anhydrous sodium sulfate and concentrated. Purification by column chromatography (silica, 0-20% methanol/dichloromethane) afforded the desired product (265 mg, 29%) as a white solid. ESI MS m/z 301 $[C_{16}H_{29}FN_2O_2+H]^+$ Example 1016 trans-4-(pyrrolidin-1-ylmethyl)cyclohexanamine dihydrochloride

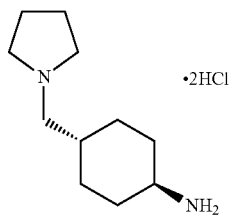 [SMILES: N[C@H]1CC[C@H](CN2CCCC2)CC1]

To a solution of tert-butyl (trans-4-(pyrrolidin-1-ylmethyl)cyclohexyl)carbamate (1.28 g, 4.53 mmol) in THF (15 mL) was added aqueous 6 N HCl (6 mL) and water (6 mL) and the reaction mixture was heated at 65° C. for 3 h. The reaction mixture was cooled to room temperature and concentrated to afford the desired product (1.2 g, >99%) as an off-white solid. ESI MS m/z 183 $[C_{11}H_{22}FN_2+H H]^+$ Example 1017 tert-butyl (cis-4-((dimethylamino)methyl)-4-hydroxycyclohexyl)carbamate

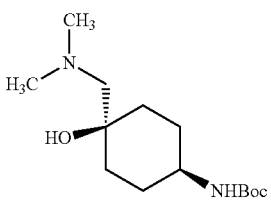 [SMILES: CN(C)C[C@]1(O)CC[C@@H](NC(=O)OC(C)(C)C)CC1]

To a solution of dimethylamine (33% in ethanol, 7 mL) was added tert-butyl cis-1-oxaspiro[2.5]octan-6-ylcarbamate (700 mg, 3.08 mmol). The resulting solution was stirred at room temperature for 4 h and concentrated to give the desired product (840 mg, 100%) as a white solid. ESI MS m/z 273 $[C_{14}H_{28}N_2O_3+H]^+$ Example 1018 cis-4-amino-1-((dimethylamino)methyl)cyclohexanol

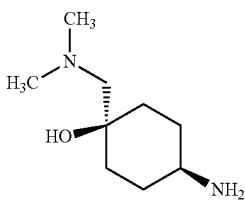

519

To a solution of HCl (2.0 M in diethyl ether, 10 mL, 20 mmol) was added tert-butyl (cis-4-((dimethylamino)methyl)-4-hydroxycyclohexyl)carbamate (840 mg, 3.08 mmol). The resulting solution was stirred at room temperature for 16 h and concentrated. Saturated sodium bicarbonate solution (100 mL) and 1 M aqueous sodium hydroxide solution (50 mL) were added, and the resultant solution extracted with a mixture of CHCl$_3$/isopropanol (3:1). The combined organic layers were dried over anhydrous sodium sulfate and concentrated to afford the desired product (90 mg, 12%) as a white semisolid. ESI MS m/z 173 [C$_9$H$_{20}$N$_2$O+H]$^+$ Example 1019 tert-butyl (1-(dimethylamino)-2,3-dihydro-1H-inden-5-yl)carbamate

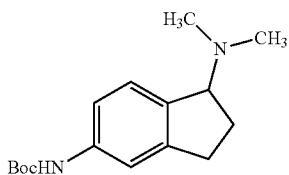 [SMILES: CN(C)C1CCc2cc(NC(=O)OC(C)(C)C)ccc21]

To a solution of tert-butyl (1-oxo-2,3-dihydro-1H-inden-5-yl)carbamate (371 mg, 1.5 mmol) in dimethylamine (2.0 M solution in THF, 5 mL, 10 mmol) was added sodium triacetoxyborohydride (636 mg, 3.0 mmol). The resultant suspension was stirred at room temperature for 16 h, diluted with a saturated NaHCO$_3$ solution and extracted with ethyl acetate. The combined organic layers were dried over anhydrous sodium sulfate and concentrated. Purification by column chromatography (silica, 0-20% methanol/dichloromethane) afforded the desired product (225 mg, 54%) as an off-white solid. ESI MS m/z 277 [C$_{16}$H$_{24}$N$_2$O$_2$+H]$^+$ Example 1020

N1,N1-dimethyl-2,3-dihydro-1H-indene-1,5-diamine dihydrochloride

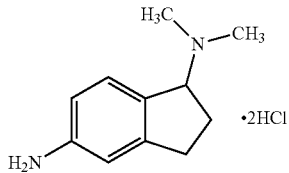

Following general procedure A-1, tert-butyl (1-(dimethylamino)-2,3-dihydro-1H-inden-5-yl) carbamate (225 mg, 0.814 mmol) was reacted with 6 N aqueous HCl (2 mL) to afford the desired product as a light brown solid that was used in the next step without further purification. ESI MS m/z 177 [C$_{11}$H$_{16}$N$_2$+H]$^+$

520

Example 1021 tert-butyl (trans-4-(2-(dimethylamino)ethyl)cyclohexyl)carbamate

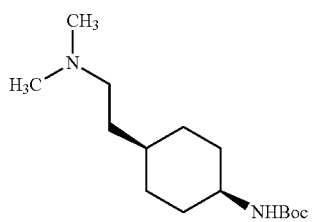 [SMILES: CN(C)CC[C@H]1CC[C@@H](NC(=O)OC(C)(C)C)CC1]

To a suspension of tert-butyl (trans-4-(2-aminoethyl)cyclohexyl)carbamate (970 mg, 4 mmol) and paraformaldehyde (360 mg, 12 mmol) in methanol (40 mL) was added sodium cyanoborohydride (754 mg, 12 mmol) and acetic acid (1 drop). The resultant suspension was stirred at room temperature for 16 h, diluted with a saturated NaHCO$_3$ solution and extracted with a mixture of CHCl$_3$/isopropanol (3:1). The combined organic layers were dried over anhydrous sodium sulfate and concentrated. Purification by column chromatography (silica, 0-20% methanol/dichloromethane) afforded the desired product (336 mg, 31%) as a white solid. ESI MS m/z 271 [C$_{15}$H$_{30}$N$_2$O$_2$+H]$^+$ Example 1022 tert-butyl methyl(1-(5-nitropyridin-2-yl)pyrrolidin-3-yl)carbamate

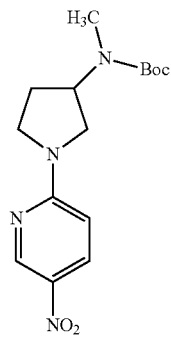

To a solution of tert-butyl methyl(pyrrolidin-3-yl)carbamate (1.00 g, 5.0 mmol) in THF (25 mL) was added triethylamine (0.70 mL, 5.0 mmol) and 2-chloro-5-nitropyridine (500 mg, 3.15 mmol). The reaction mixture was then stirred at room temperature for 16 h, diluted with a saturated NaHCO$_3$ solution and extracted with ethyl acetate. The combined organic layers were dried over anhydrous sodium sulfate and concentrated. Purification by column chromatography (silica, ethyl acetate/hexanes) afforded the desired product (1.02 g, 100%) as a yellow solid. ESI MS m/z 323 $[C_{15}H_{22}N_4O_4+H]^+$

Example 1023 tert-butyl (1-(5-aminopyridin-2-yl)pyrrolidin-3-yl)(methyl)carbamate

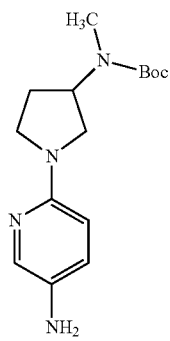

To a solution of tert-butyl methyl(1-(5-nitropyridin-2-yl)pyrrolidin-3-yl)carbamate (1.02 g, 3.2 mmol) in THF (50 mL) was added Pd/C (10 wt. %, 500 mg). The reaction mixture was stirred under 1 atm of hydrogen for 16 h, filtered through celite and concentrated to afford the desired product (940 mg, 100%) as a red oil. ESI MS m/z 293 $[C_{15}H_{24}N_4O_2+H]^+$

Example 1024 tert-butyl methyl(1-(5-nitropyridin-2-yl)piperidin-3-yl)carbamate

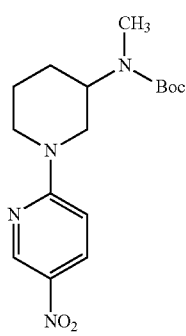

To a solution of tert-butyl methyl(piperidin-3-yl)carbamate (1.00 g, 4.67 mmol) in THF (25 mL) was added triethylamine (0.70 mL, 5.0 mmol) and 2-chloro-5-nitropyridine (500 mg, 3.1 mmol). The reaction mixture was then stirred at room temperature for 16 h, diluted with a saturated NaHCO₃ solution and extracted with ethyl acetate. The combined organic layers were dried over anhydrous sodium sulfate and concentrated. Purification by column chromatography (silica, ethyl acetate/hexanes) afforded the desired product (1.03 g, 99%) as a yellow solid. ESI MS m/z 337 $[C_{16}H_{24}N_4O_4+H]^+$

Example 1025 tert-butyl (1-(5-aminopyridin-2-yl)piperidin-3-yl)(methyl)carbamate

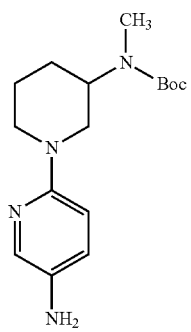 [SMILES: CN(C(=O)OC(C)(C)C)C1CCCN(c2ccc(N)cn2)C1]

To a solution of tert-butyl methyl(1-(5-nitropyridin-2-yl)piperidin-3-yl)carbamate (1.03 g, 3.1 mmol) in THF (50 mL) was added Pd/C (10 wt. %, 500 mg). The reaction mixture was stirred under 1 atm of hydrogen for 16 h, filtered through celite and concentrated to afford the desired product (902 mg, 96%) as a red oil. ESI MS m/z 307 $[C_{16}H_{26}N_4O_2+H]^+$

Example 1026 tert-butyl (trans-4-((dimethyl-d₆-amino)methyl)cyclohexyl)carbamate

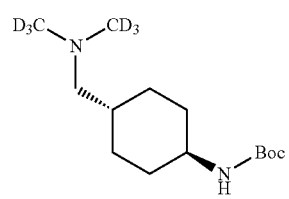 [SMILES: [2H]C([2H])([2H])N(C[C@H]1CC[C@H](NC(=O)OC(C)(C)C)CC1)C([2H])([2H])[2H]]

To a suspension of trans-4-((tert-butoxycarbonyl)amino)cyclohexyl)methyl methanesulfonate (307 mg, 1.0 mmol) in acetonitrile (4 mL) was added KI (332 mg, 2.0 mmol), N,N-diisopropylethylamine (1.78 mL, 10 mmol) and finally dimethyl-d₆-amine hydrochloride (350 mg, 4.0 mmol). The reaction mixture was heated in a microwave at 100° C. for 1 h. The reaction was cooled to room temperature, diluted with a satd. aq NaHCO₃ solution and extracted with ethyl acetate. The combined organic layers were dried over anhydrous sodium sulfate and concentrated to afford the desired product (236 mg, 90%) as a light brown solid. ESI MS m/z 263 $[C_{14}H_{22}D_6N_2O_2+H]^+$

Example 1027

1-(6-bromo-4-((trans-4-((dimethyl-$d_6$-amino)methyl)cyclohexyl)amino)quinolin-3-yl)ethanone

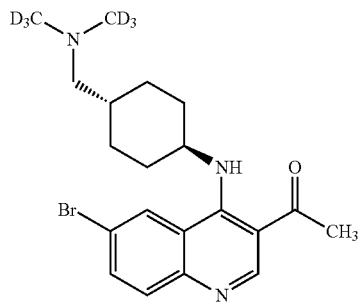 [SMILES: [2H]C([2H])([2H])N(C[C@H]1CC[C@H](Nc2c(C(C)=O)cnc3ccc(Br)cc23)CC1)C([2H])([2H])[2H]]

To a solution of tert-butyl (trans-4-((dimethyl-$d_6$-amino)methyl)cyclohexyl)carbamate (750 mg, 2.85 mmol) in THF (10 mL) was added water (5 mL) and HCl (6.0 M in H$_2$O, 5.0 mL, 30 mmol) and the reaction mixture heated at 65° C. for 2 h. After cooling to room temperature the reaction mixture was concentrated and the residue was dissolved in dioxane (40 mL) followed by the addition of N,N-diisopropylethylamine (5.0 mL, 28.7 mmol), K$_2$CO$_3$ (1.0 g, 7.24 mmol) and 1-(6-bromo-4-chloroquinolin-3-yl)ethanone (0.59 g, 2.0 mmol). The reaction mixture was heated at 100° C. for 16 h, cooled to room temperature, diluted with satd. aq NaHCO$_3$ and extracted with ethyl acetate. The combined organic layers were dried over anhydrous sodium sulfate and concentrated to afford the desired product (273 mg, 33%) as an off-white solid. ESI MS m/z 410 $[C_{20}H_{20}D_6BrN_3O+H]^+$

Example 1028

1-(6-bromo-4-((1-(1-methylpiperidin-4-yl)-1H-pyrazol-4-yl)amino)quinolin-3-yl)ethanone

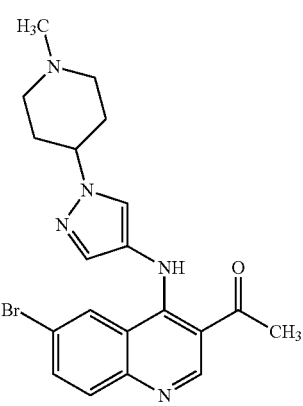 [SMILES: CC(=O)c1cnc2ccc(Br)cc2c1Nc1cnn(C2CCN(C)CC2)c1]

Following general procedure C, 1-(6-bromo-4-chloroquinolin-3-yl)ethanone (285 mg, 1.0 mmol) was reacted with 1-(1-methylpiperidin-4-yl)-1H-pyrazol-4-amine (0.30 g, 1.66 mmol) to afford the desired product (223 mg, 52%) as a light yellow solid. ESI MS m/z 428 $[C_{20}H_{22}BrN_5O+H]^+$

Example 1029 tert-butyl (1-(5-((3-acetyl-6-bromoquinolin-4-yl)amino)pyridin-2-yl)piperidin-3-yl)(methyl)carbamate

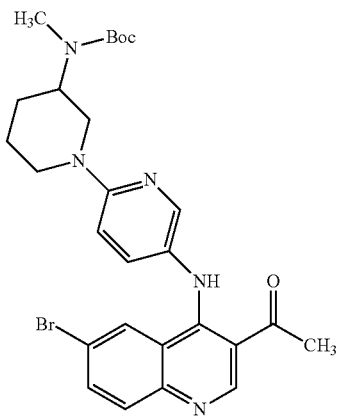 [SMILES: CC(=O)c1cnc2ccc(Br)cc2c1Nc1ccc(N2CCCC(N(C)C(=O)OC(C)(C)C)C2)nc1]

Following general procedure C, 1-(6-bromo-4-chloroquinolin-3-yl)ethanone (285 mg, 1.0 mmol) was reacted with tert-butyl (1-(5-aminopyridin-2-yl)piperidin-3-yl)(methyl)carbamate (442 mg, 1.45 mmol) to afford the desired product (446 mg, 80%) as an orange-red solid. ESI MS m/z 554 $[C_{27}H_{32}BrN_5O_3+H]^+$

Example 1030 tert-butyl (1-(5-((6-bromo-3-(cyclopropanecarbonyl)quinolin-4-yl)amino) pyridin-2-yl)piperidin-3-yl)(methyl)carbamate

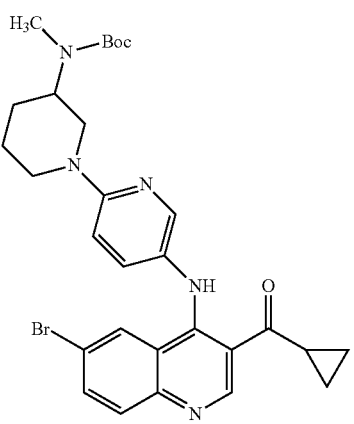 [SMILES: CN(C(=O)OC(C)(C)C)C1CCCN(c2ccc(Nc3c(C(=O)C4CC4)cnc4ccc(Br)cc34)cn2)C1]

Following general procedure C, (6-bromo-4-chloroquinolin-3-yl)(cyclopropyl)methanone (310 mg, 1.0 mmol) was reacted with tert-butyl (1-(5-aminopyridin-2-yl)piperidin-3-yl)(methyl) carbamate (460 mg, 1.51 mmol) to afford the

Example 1031

1-(6-bromo-4-((1-(1-methylpyrrolidin-3-yl)-1H-pyrazol-4-yl)amino)quinolin-3-yl)ethanone

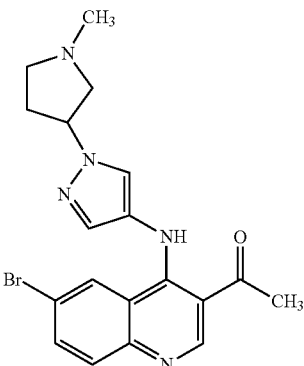

Following general procedure C, 1-(6-bromo-4-chloroquinolin-3-yl)ethanone (285 mg, 1.0 mmol) was reacted with 1-(1-methylpyrrolidin-3-yl)-1H-pyrazol-4-amine (0.28 g, 1.68 mmol) to afford the desired product (360 mg, 87%) as a light yellow solid. ESI MS m/z 414 $[C_{19}H_{20}BrN_5O+H]^+$

Example 1032 tert-butyl (1-(5-((3-acetyl-6-bromoquinolin-4-yl)amino)pyridin-2-yl)pyrrolidin-3-yl)(methyl)carbamate

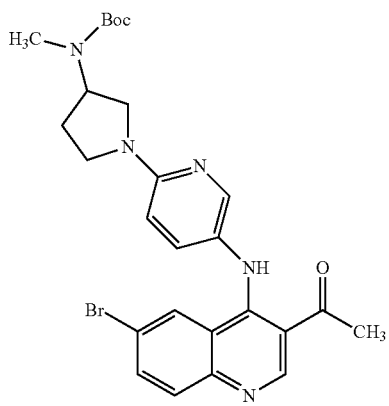 [SMILES: CC(=O)c1cnc2ccc(Br)cc2c1Nc1ccc(N2CCC(N(C)C(=O)OC(C)(C)C)C2)nc1]

Following general procedure C, 1-(6-bromo-4-chloroquinolin-3-yl)ethanone (285 mg, 1.0 mmol) was reacted with tert-butyl (1-(5-aminopyridin-2-yl)pyrrolidin-3-yl)(methyl)carbamate (440 mg, 1.50 mmol) to afford the desired product (273 mg, 51%) as an orange solid. ESI MS m/z 540 $[C_{26}H_{30}BrN_5O_3+H]^+$

Example 1033 tert-butyl (1-(5-((6-bromo-3-(cyclopropanecarbonyl)quinolin-4-yl)amino) pyridin-2-yl)pyrrolidin-3-yl)(methyl)carbamate

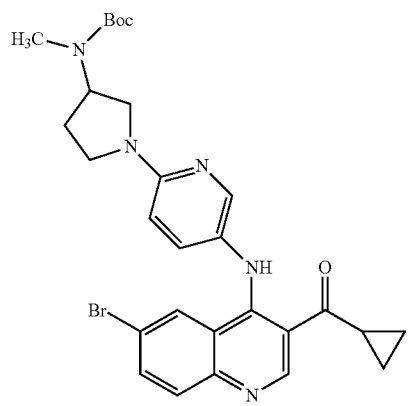 [SMILES: CN(C(=O)OC(C)(C)C)C1CCN(c2ccc(Nc3c(C(=O)C4CC4)cnc4ccc(Br)cc34)cn2)C1]

Following general procedure C, (6-bromo-4-chloroquinolin-3-yl)(cyclopropyl)methanone (310 mg, 1.0 mmol) was reacted with tert-butyl (1-(5-aminopyridin-2-yl)pyrrolidin-3-yl)(methyl) carbamate (500 mg, 1.71 mmol) to afford the desired product (350 mg, 62%) as an orange-red solid. ESI MS m/z 566 $[C_{28}H_{32}BrN_5O_3+H]^+$

Example 1034

1-(6-bromo-4-((trans-4-(2-(dimethylamino)ethyl)cyclohexyl)amino)quinolin-3-yl)ethanone

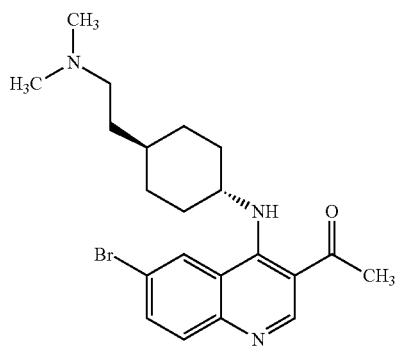 [SMILES: CC(=O)c1cnc2ccc(Br)cc2c1N[C@H]1CC[C@H](CCN(C)C)CC1]

Following general procedure A-1, tert-butyl (trans-4-(2-(dimethylamino)ethyl)cyclohexyl) carbamate (336 mg, 1.24 mmol) was reacted with 6 N aqueous HCl (2 mL) to afford a viscous colorless oil. The oil was dissolved in dioxane (10 mL) and DMF (5 mL) followed by the addition of 1-(6-bromo-4-chloroquinolin-3-yl)ethanone (285 mg, 1.0 mmol), $K_2CO_3$ (0.55 g, 4.0 mmol), and N,N-diisopropylethylamine (1.0 mL, 5.8 mmol) and the resultant suspension was heated at 100° C. for 16 h. The reaction mixture was cooled to room temperature, diluted with satd. aq. $NaHCO_3$ and extracted with ethyl acetate. The combined organic layers were dried over anhydrous sodium sulfate and concentrated. Purification by column chromatography (silica, 0-20% methanol/dichloromethane) afforded the desired product (227 mg, 54%) as a light yellow-brown solid. ESI MS m/z 418 $[C_{21}H_{28}BrN_3O+H]^+$ Example 1035 tert-butyl 4-(((trans-4-((3-acetyl-6-bromoquinolin-4-yl)amino)cyclohexyl)methyl)piperazine-1-carboxylate

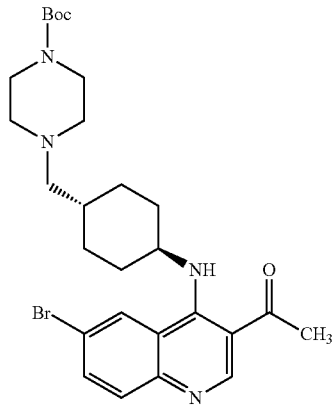 [SMILES: CC(=O)c1cnc2ccc(Br)cc2c1N[C@H]1CC[C@H](CN2CCN(C(=O)OC(C)(C)C)CC2)CC1]

To a solution of ((trans-4-((3-acetyl-6-bromoquinolin-4-yl)amino)cyclohexyl)methyl methanesulfonate (300 mg, 0.66 mmol) and tert-butyl piperazine-1-carboxylate (566 mg, 3.0 mmol) in acetonitrile (5 mL) and dioxane (5 mL) was added KI (500 mg, 3.0 mmol) and N,N-diisopropylethylamine (0.60 mL, 3.44 mmol) and the reaction mixture was heated at 70° C. for 16 h. The solution was cooled to room temperature, diluted with satd. aq. NaHCO₃ and extracted with ethyl acetate. The combined organic layers were dried over anhydrous sodium sulfate, concentrated and purified by column chromatography (silica, 0-20% methanol/dichloromethane) to afford the desired product (248 mg, 69%) as an off-white solid. ESI MS m/z 545 $[C_{27}H_{37}BrN_4O_3+H]^+$ Example 1036

1-(6-bromo-4-((1-(dimethylamino)-2,3-dihydro-1H-inden-5-yl)amino)quinolin-3-yl)ethanone

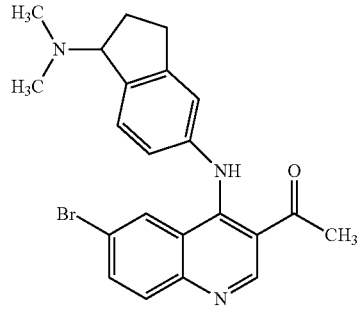 [SMILES: CC(=O)c1cnc2ccc(Br)cc2c1Nc1ccc2c(c1)CCC2N(C)C]

Following general procedure C, 1-(6-bromo-4-chloroquinolin-3-yl)ethanone (256 mg, 0.90 mmol) was reacted with N1,N1-dimethyl-2,3-dihydro-1H-indene-1,5-diamine dihydrochloride (0.814 mmol) to afford the desired product (19 mg, 5.5%) as a yellow-brown solid. ESI MS m/z 424 $[C_{22}H_{22}BrN_3O+H]^+$ Example 1037

(6-bromo-4-((cis-4-(((dimethylamino)methyl)-4-hydroxycyclohexyl)amino)quinolin-3-yl)(cyclopropyl)methanone

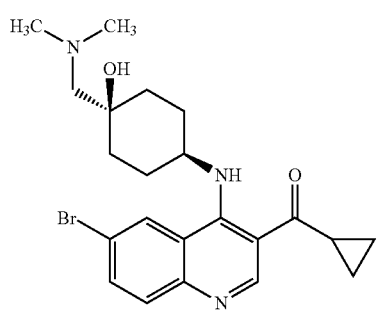 [SMILES: CN(C)C[C@]1(O)CC[C@@H](Nc2c(C(=O)C3CC3)cnc3ccc(Br)cc23)CC1]

Following general procedure C, (6-bromo-4-chloroquinolin-3-yl)(cyclopropyl)methanone (155 mg, 0.5 mmol) was reacted with cis-4-amino-1-((dimethylamino)methyl)cyclohexanol (90 mg, 0.37 mmol) to afford the desired product (72 mg, 44%) as an off-white solid. ESI MS m/z 446 $[C_{22}H_{28}BrN_3O_2+H]^+$ Example 1038 tert-butyl (trans-4-(4-((6-bromo-3-(cyclopropanecarbonyl)quinolin-4-yl)amino)-1H-pyrazol-1-yl)cyclohexyl)carbamate

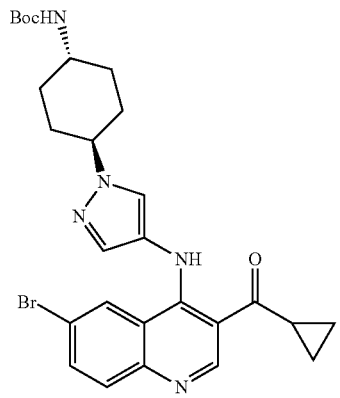 [SMILES: CC(C)(C)OC(=O)N[C@H]1CC[C@H](n2cc(Nc3c(C(=O)C4CC4)cnc4ccc(Br)cc34)cn2)CC1]

Following general procedure C, (6-bromo-4-chloroquinolin-3-yl)(cyclopropyl)methanone (310 mg, 1.0 mmol) was reacted with tert-butyl (cis-4-(4-amino-1H-pyrazol-1-yl)cyclohexyl) carbamate (610 mg, 2.18 mmol) to afford the desired product (90 mg, 16%) as a yellow solid. ESI MS m/z 554 $[C_{27}H_{32}BrN_5O_3+H]^+$

Example 1039

(6-bromo-4-((trans-4-(((R)-3-fluoropyrrolidin-1-yl)methyl)cyclohexyl)amino) quinolin-3-yl)(cyclopropyl)methanone

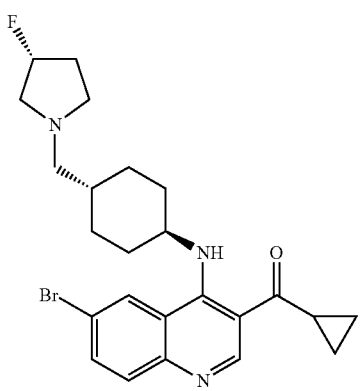 [SMILES: O=C(c1cnc2ccc(Br)cc2c1N[C@H]1CC[C@H](CN2CC[C@@H](F)C2)CC1)C1CC1]

To a solution of tert-butyl (trans-4-(((R)-3-fluoropyrrolidin-1-yl)methyl)cyclohexyl)carbamate (265 mg, 0.88 mmol) in THF (6 mL) was added aqueous 6N HCl (6 mL) and water (6 mL) and the reaction mixture was heated at 65° C. for 3 h. The reaction mixture was cooled to room temperature, diluted with satd. aq. sodium bicarbonate (50 mL) and 1 M aqueous sodium hydroxide (50 mL) and extracted with a mixture of $CHCl_3$/isopropanol (3:1). The combined organic layers were dried over anhydrous sodium sulfate and concentrated to afford a white semisolid. The residue was dissolved in dioxane followed by the addition of (6-bromo-4-chloroquinolin-3-yl)(cyclopropyl)methanone (225 mg, 0.724 mmol), $K_2CO_3$ (415 mg, 3.0 mmol), and N,N-diisopropylethylamine (0.39 mL, 3.0 mmol) and the resultant suspension was heated at 80° C. for 16 h. The reaction was cooled to room temperature, diluted with satd. aq. $NaHCO_3$ and extracted with ethyl acetate. The combined organic layers were dried over anhydrous sodium sulfate and concentrated. Purification by column chromatography (silica, 0-20% methanol/dichloromethane) afforded the desired product (180 mg, 52%) as an off-white solid. ESI MS m/z 474 $[C_{24}H_{29}BrFN_3O+H]^+$

Example 1040

(6-bromo-4-((trans-4-(pyrrolidin-1-ylmethyl)cyclohexyl)amino)quinolin-3-yl)(cyclopropyl)methanone

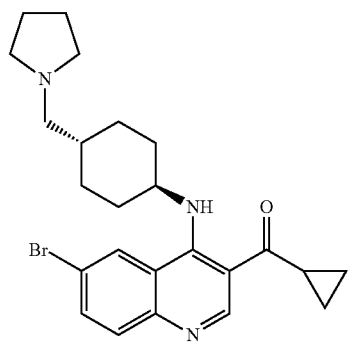 [SMILES: O=C(c1cnc2ccc(Br)cc2c1N[C@H]1CC[C@H](CN2CCCC2)CC1)C1CC1]

Following general procedure C, (6-bromo-4-chloroquinolin-3-yl)(cyclopropyl)methanone (466 mg, 1.5 mmol) was reacted with trans-4-(pyrrolidin-1-ylmethyl)cyclohexanamine dihydrochloride (847 mg, 3.0 mmol) to afford the desired product (180 mg, 52%) as an off-white solid. ESI MS m/z 456 $[C_{24}H_{30}BrN_3O+H]^+$

Example 1041

(6-bromo-4-((trans-4-(hydroxymethyl)cyclohexyl)amino)quinolin-3-yl)(cyclopropyl)methanone

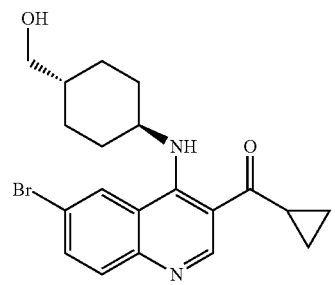 [SMILES: O=C(c1cnc2ccc(Br)cc2c1N[C@H]1CC[C@H](CO)CC1)C1CC1]

Following general procedure C, (6-bromo-4-chloroquinolin-3-yl)(cyclopropyl)methanone (1.16 g, 3.75 mmol) was reacted with (trans-4-aminocyclohexyl)methanol (726 mg, 5.61 mmol) to afford the desired product (1.23 g, 81%) as a white solid. ESI MS m/z 403 $[C_{20}H_{23}BrN_2O_2+H]^+$

Example 1042

(trans-4-((6-bromo-3-(cyclopropanecarbonyl)quinolin-4-yl)amino)cyclohexyl)methyl methanesulfonate

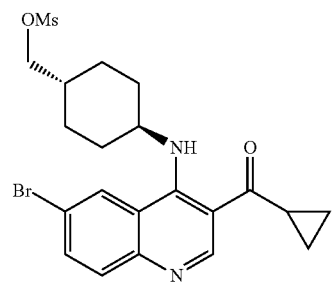 [SMILES: CS(=O)(=O)OC[C@H]1CC[C@H](Nc2c(C(=O)C3CC3)cnc3ccc(Br)cc23)CC1]

To a suspension of (6-bromo-4-((trans-4-(hydroxymethyl)cyclohexyl)amino)quinolin-3-yl) (cyclopropyl)methanone (1.23 g, 3.05 mmol) in dichloromethane (60 mL) was added triethylamine (2.09 mL, 15 mmol) and methanesulfonyl chloride (0.35 mL, 4.5 mmol) was added dropwise. The reaction mixture was stirred for 2 h. The solution was then diluted with saturated sodium bicarbonate solution and extracted with dichloromethane. The combined organic layers were dried over anhydrous sodium sulfate and concentrated. Purification by column chromatography (silica, ethyl acteate/hexanes)

afforded the desired product (0.98 g, 67%) as a white solid. ESI MS m/z 481 $[C_{21}H_{25}BrN_2O_4S+H]^+$

Example 1043

(6-bromo-4-((trans-4-((3-methoxypyrrolidin-1-yl)methyl)cyclohexyl)amino)quinolin-3-yl)(cyclopropyl)methanone

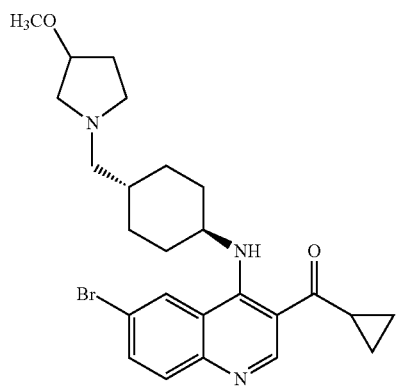 [SMILES: COC1CCN(C[C@H]2CC[C@H](Nc3c(C(=O)C4CC4)cnc4ccc(Br)cc34)CC2)C1]

To a solution of (trans-4-((6-bromo-3-(cyclopropanecarbonyl)quinolin-4-yl)amino)cyclohexyl)methyl methanesulfonate (362 mg, 0.75 mmol) and 3-methoxypyrrolidine hydrochloride (410 mg, 2.98 mmol) in acetonitrile (15 mL) was added $K_2CO_3$ (1.24 g, 9 mmol) and KI (300 mg, 1.81 mmol) and N,N-diisopropylethylamine (0.5 mL, 2.9 mmol) and the reaction mixture was heated at 50° C. for 16 h and 80° C. for 24 h. The solution was cooled to room temperature, diluted with satd. aq. $NaHCO_3$ and extracted with ethyl acetate. The combined organic layers were dried over anhydrous sodium sulfate, concentrated and purification by column chromatography (silica, 0-20% methanol/dichloromethane) to afford the desired product (155 mg, 42%) as an off-white solid. ESI MS m/z 486 $[C_{25}H_{32}BrN_3O_2+H]^+$

Example 1044

(6-bromo-4-((trans-4-((3-hydroxypyrrolidin-1-yl)methyl)cyclohexyl)amino)quinolin-3-yl)(cyclopropyl)methanone

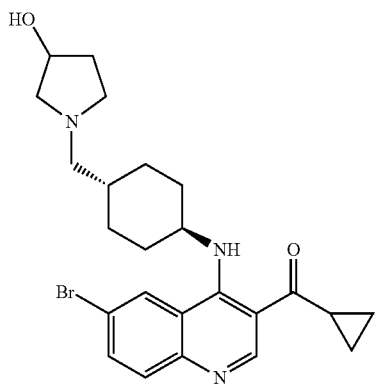 [SMILES: O=C(c1cnc2ccc(Br)cc2c1N[C@H]1CC[C@H](CN2CCC(O)C2)CC1)C1CC1]

To a solution of (trans-4-((6-bromo-3-(cyclopropanecarbonyl)quinolin-4-yl)amino)cyclohexyl)methyl methanesulfonate (362 mg, 0.75 mmol) and 3-hydroxypyrrolidine (262 mg, 3.0 mmol) in acetonitrile (15 mL) was added N,N-diisopropylethylamine (1.0 mL, 5.8 mmol) and the reaction mixture was heated at 80° C. for 16 h. The solution was cooled to room temperature, diluted satd. aq. $NaHCO_3$ and extracted with ethyl acetate. The combined organic layers were dried over anhydrous sodium sulfate, concentrated and purified by column chromatography (silica, 0-20% methanol/dichloromethane) to afford the desired product (174 mg, 49%) as an off-white solid. ESI MS m/z 472 $[C_{24}H_{30}BrN_3O_2+H]^+$

Example 1045

(6-bromo-4-((trans-4-(((2-hydroxyethyl)(methyl)amino)methyl)cyclohexyl)amino)quinolin-3-yl)(cyclopropyl)methanone

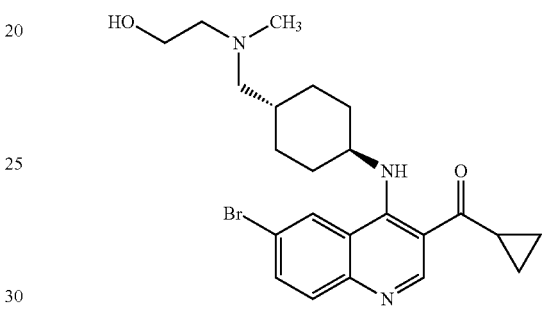

To a solution of (trans-4-((6-bromo-3-(cyclopropanecarbonyl)quinolin-4-yl)amino)cyclohexyl)methyl methanesulfonate (361 mg, 0.75 mmol) and 2-(methylamino)ethanol (0.30 mL, 3.75 mmol) in acetonitrile (15 mL) was added N,N-diisopropylethylamine (1.0 mL, 5.8 mmol) and the reaction mixture was heated at 70° C. for 16 h. The solution was cooled to room temperature, diluted with a saturated $NaHCO_3$ solution and extracted with ethyl acetate. The combined organic layers were dried over anhydrous sodium sulfate and concentrated. Purification by column chromatography (silica, 0-20% methanol/dichloromethane) afforded the desired product (150 mg, 43%) as an off-white solid. ESI MS m/z 460 $[C_{23}H_{30}BrN_3O_2+H]^+$

Example 1046

(6-bromo-4-((trans-4-((methylamino)methyl)cyclohexyl)amino)quinolin-3-yl)(cyclopropyl)methanone

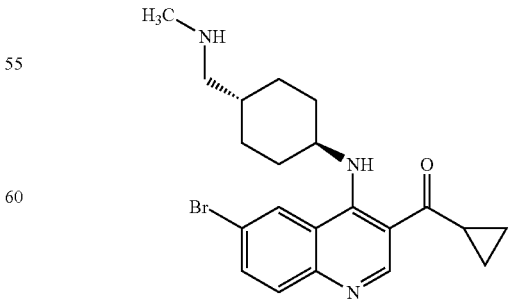

A suspension of (trans-4-((6-bromo-3-(cyclopropanecarbonyl)quinolin-4-yl)amino)cyclohexyl)methyl methanesulfonate (175 mg, 0.36 mmol) in methylamine (2.0 M solution in THF, 4.0 mL, 8.0 mmol) in a sealed vessel was heated under microwave irradiation conditions to 120° C. for 2 h. The solution was cooled to room temperature and concentrated. The resultant residue was purified by preparative HPLC (C18 silica, 10-90% methanol/water with 0.05% TFA). The residue was eluted through an ion-exchange column (using methanol and 7 N methanol in ammonia) to obtain the desired product (42 mg, 28%) a white solid. ESI MS m/z 416 $[C_{21}H_{26}BrN_3O+H]^+$ Example 1047 tert-butyl (trans-4-((6-bromo-3-butyrylquinolin-4-yl)amino)cyclohexyl)carbamate

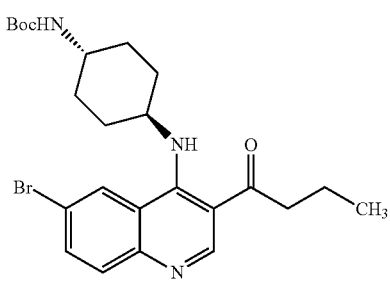 [SMILES: CCCC(=O)c1cnc2ccc(Br)cc2c1N[C@H]1CC[C@H](NC(=O)OC(C)(C)C)CC1]

Following general procedure B, 1-(6-bromo-4-chloroquinolin-3-yl)butan-1-one (470 mg, 1.50 mmol) was reacted with tert-butyl (trans-4-aminocyclohexyl)carbamate (643 mg, 3 mmol) to afford the desired product (498 mg, 68%) as a light orange solid. ESI MS m/z 490 $[C_{24}H_{32}BrN_3O_3+H]^+$ Example 1048

1-(6-bromo-4-((4-((dimethylamino)methyl)phenyl)amino)quinolin-3-yl)butan-1-one

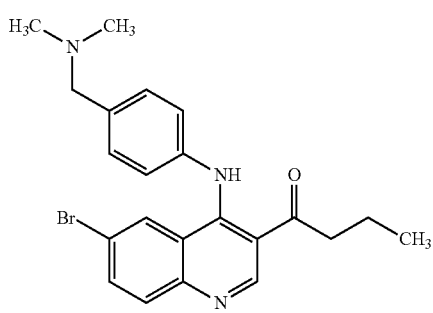 [SMILES: CCCC(=O)c1cnc2ccc(Br)cc2c1Nc1ccc(CN(C)C)cc1]

Following general procedure C, 1-(6-bromo-4-chloroquinolin-3-yl)butan-1-one (470 mg, 1.50 mmol) was reacted with 4-((dimethylamino)methyl)aniline (451 mg, 3 mmol) to afford the desired product (402 mg, 63%) as a yellow solid. ESI MS m/z 426 $[C_{22}H_{24}BrN_3O+H]^+$ Example 1049

1-(6-bromo-4-((4-((dimethylamino)methyl)phenyl)amino)quinolin-3-yl)ethanone

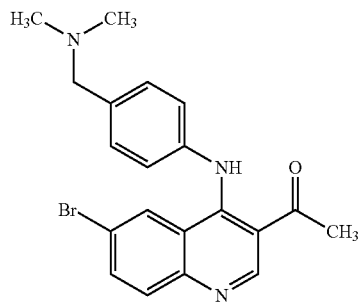 [SMILES: CC(=O)c1cnc2ccc(Br)cc2c1Nc1ccc(CN(C)C)cc1]

Following general procedure C, 1-(6-bromo-4-chloroquinolin-3-yl)ethanone (500 mg, 1.76 mmol) was reacted with 4-((dimethylamino)methyl)aniline hydrochloride (479 mg, 2.56 mmol) to afford the desired product (491 mg, 70%) as a yellow solid. ESI MS m/z 398 $[C_{20}H_{20}BrN_3O+H]^+$ Example 1050

1-(6-bromo-4-((trans-4-((dimethylamino)methyl)cyclohexyl)amino)quinolin-3-yl)ethanone

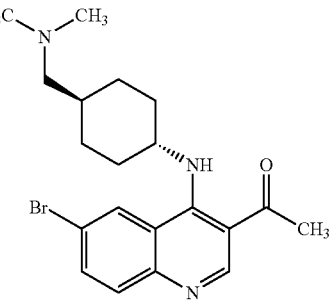

Following general procedure C, 1-(6-bromo-4-chloroquinolin-3-yl)ethanone (256 mg, 0.90 mmol) was reacted with trans-4-((dimethylamino)methyl)cyclohexanamine dihydrochloride (320 mg, 1.40 mmol) to afford the desired product (149 mg, 70%) as a light orange solid. ESI MS m/z 404 $[C_{20}H_{26}BrN_3O+H]^+$ Example 1051

6-bromo-N-(4-((dimethylamino)methyl)phenyl)-3-(methylsulfonyl)quinolin-4-amine

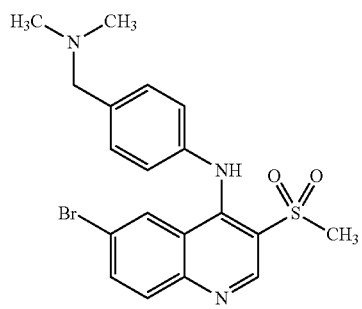

To a suspension of 6-bromo-4-chloro-3-(methylsulfonyl)quinoline (250 mg, 0.78 mmol) in dioxane (8 mL) was added 4-((dimethylamino)methyl)cyclohexanamine (233 mg, 1.55 mmol) and N,N-diisopropylethylamine (0.42 mL, 2.4 mmol). The reaction mixture was heated at 90° C. for 4 h. The reaction mixture was cooled to room temperature, diluted with saturated sodium bicarbonate solution and extracted with ethyl acetate. The combined organic layers were dried over anhydrous sodium sulfate and concentrated. Purification by column chromatography (silica, 0-20% methanol/dichloromethane) afforded the desired product (225 mg, 66%) as a yellow solid. ESI MS m/z 434 $[C_{29}H_{20}BrN_3O_2+H]^+$ Example 1052

1-(6-bromo-4-((4-(pyrrolidin-1-ylmethyl)phenyl)amino)quinolin-3-yl)ethanone

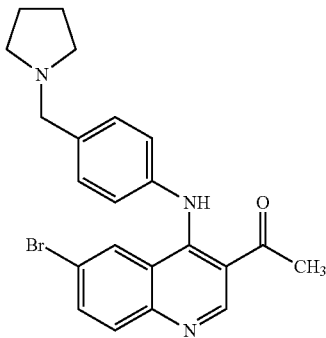 [SMILES: CC(=O)c1cnc2ccc(Br)cc2c1Nc1ccc(CN2CCCC2)cc1]

Following general procedure C, 1-(6-bromo-4-chloroquinolin-3-yl)ethanone (285 mg, 1.00 mmol) was reacted with 4-(pyrrolidin-1-ylmethyl)aniline (374 mg, 1.50 mmol) to afford the desired product (182 mg, 43%) as a light orange solid. ESI MS m/z 424 $[C_{22}H_{22}BrN_3O+H]^+$ Example 1053

6-bromo-4-((trans-4-(dimethylamino)cyclohexyl)amino)quinoline-3-carbonitrile

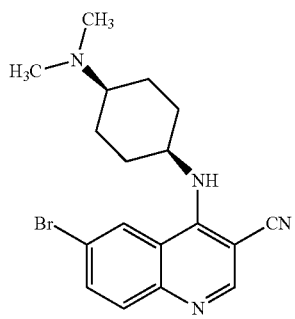 [SMILES: CN(C)[C@H]1CC[C@@H](Nc2c(C#N)cnc3ccc(Br)cc23)CC1]

Following general procedure C, 6-bromo-4-chloroquinoline-3-carbonitrile (262 mg, 0.98 mmol) was reacted with trans-$N^1,N^1$-dimethylcyclohexane-1,4-diamine dihydrochloride (422 mg, 1.96 mmol) to afford the desired product (56 mg, 15%) as a yellow solid. ESI MS m/z 373 $[C_{18}H_{21}BrN_4+H]^+$ Example 1054 tert-butyl 4-(5-(((6-bromo-3-(cyclopropanecarbonyl)quinolin-4-yl)amino)pyrimidin-2-yl)piperazine-1-carboxylate

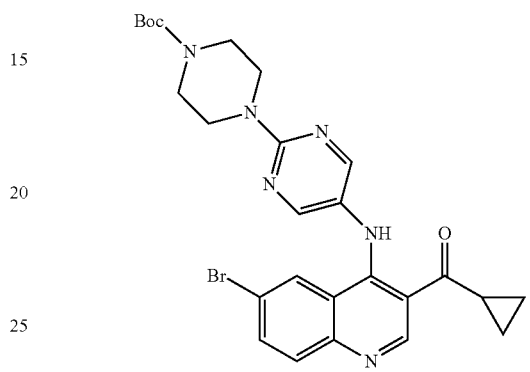

Following general procedure C, (6-bromo-4-chloroquinolin-3-yl)(cyclopropyl)methanone (311 mg, 1.0 mmol) was reacted with tert-butyl 4-(5-aminopyrimidin-2-yl)piperazine-1-carboxylate (419 mg, 1.5 mmol) to afford the desired product (215 mg, 39%) as a yellow solid. ESI MS m/z 553 $[C_{26}H_{29}BrN_6O_3+H]^+$ Example 1055 tert-butyl 4-(4-(((6-bromo-3-(cyclopropanecarbonyl)quinolin-4-yl)amino)-1H-pyrazol-1-yl)piperidine-1-carboxylate

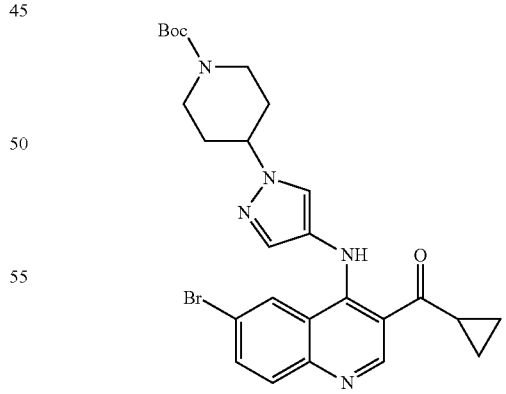

Following general procedure C, (6-bromo-4-chloroquinolin-3-yl)(cyclopropyl)methanone (311 mg, 1.0 mmol) was reacted with tert-butyl 4-(4-amino-1H-pyrazol-1-yl)piperidine-1'-carboxylate (400 mg, 1.5 mmol) to afford the desired product (441 mg, 82%) as a yellow solid. ESI MS m/z 540 $[C_{26}H_{30}BrN_5O_3+H]^+$

Example 402 tert-Butyl trans-4-(dimethylamino)cyclohexylcarbamate

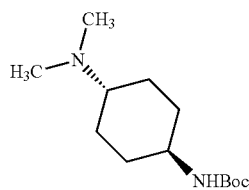 [SMILES: CN(C)[C@H]1CC[C@H](NC(=O)OC(C)(C)C)CC1]

To a solution of tert-butyl trans-4-aminocyclohexylcarbamate (750 mg, 3.50 mmol), paraformaldehyde (318 mg, 10.5 mmol), and sodium cyanoborohydride (660 mg, 13.5 mmol) in methanol (30 mL) was added acetic acid (catalytic) and the reaction stirred at room temperature for 18 h. The reaction mixture was quenched with water and the layers were separated. The pH of the aqueous layer was adjusted to 10 using 1 M sodium hydroxide followed by extraction with methylene chloride. The combined organic layers were dried over anhydrous sodium sulfate, filtered, and concentrated to afford the desired product (805 mg, 95%) as a white solid: ESI MS m/z 243 $[C_{13}H_{26}N_2O_2+H]^+$.

Example 403 trans-$N^1,N^1$-Dimethylcyclohexane-1,4-diamine

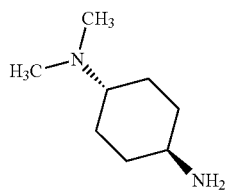

To a solution of tert-butyl trans-4-(dimethylamino)cyclohexylcarbamate (805 mg, 3.33 mmol) was added TFA (5 mL) and the reaction mixture was heated at 75° C. for 18 h. The reaction mixture was concentrated and the residue was eluted through an ion-exchange column (using methanol and 7 N methanol in ammonia) to obtain the desired product as the free base (400 mg, 85%) as an orange oil: ESI MS m/z 143 $[C_8H_{18}N_2+H]^+$.

Example 404 tert-Butyl 1-(3-aminoadamantane)carbamate

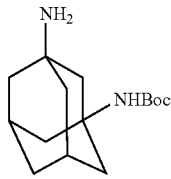 [SMILES: CC(C)(C)OC(=O)NC12CC3CC(CC(N)(C3)C1)C2]

To a mixture of 1,3-diaminoadamantane dihydrochloride (500 mg, 2.09 mmol) and sodium carbonate (1.10 g, 10.5 mmol) in 1,4 dioxane (20 mL) and water (10 mL) at 0° C. was added di-tert-butyl dicarbonate (450 mg, 2.09 mmol) in 1,4 dioxane (10 mL) portionwise over 10 min. The reaction mixture was warmed to room temperature, stirred for 18 h, diluted with methylene chloride and the layers were separated. The organic layer was dried over anhydrous sodium sulfate, filtered, and concentrated to afford the desired product (420 mg, 76%) as a white solid: ESI MS m/z 267 $[C_{15}H_{26}N_2O_2+H]^+$.

Example 405 tert-Butyl [trans-4-(dimethylamino)cyclohexyl]methylcarbamate

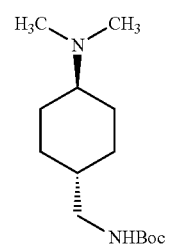

To a solution of tert-butyl [trans-4-aminocyclohexyl]methylcarbamate (1.15 g, 5.00 mmol), paraformaldehyde (454 mg, 15.0 mmol), and sodium cyanoborohydride (940 mg, 15.0 mmol) in methanol (40 mL) was added acetic acid (catalytic) and the reaction mixture stirred at room temperature for 18 h. The reaction mixture was quenched with water and concentrated to remove methanol. The pH of the aqueous layer was adjusted to 10 with 1 M aqueous sodium hydroxide followed by extraction with methylene chloride. The organic layers were dried over anhydrous sodium sulfate, filtered, and concentrated to afford the desired product (1.23 g, 96%) as a thick oil: ESI MS m/z 257 $[C_{14}H_{28}H_2O_2+H]^+$.

Example 406 trans-4-(Aminomethyl)-N,N-di methylcyclohexanamine

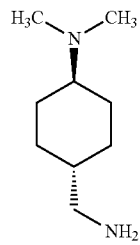

Following general procedure A-1, tert-butyl [trans-4-(dimethylamino)cyclohexyl]methyl carbamate (1.23 g, 4.80 mmol) was reacted with 3 M hydrochloric acid (10 mL) to afford the desired product (1.15 g, >99%) as white solid: ESI MS m/z 230 $[C_9H_{20}N_2+H]^+$.

Example 407 tert-Butyl trans-4-[(dimethylamino)methyl]cyclohexylcarbamate

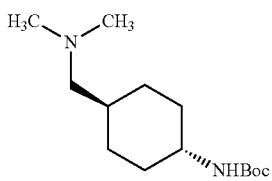 [SMILES: CN(C)C[C@H]1CC[C@H](NC(=O)OC(C)(C)C)CC1]

To a solution of tert-butyl trans-4-(aminomethyl)cyclohexylcarbamate (1.02 g, 4.47 mmol), paraformaldehyde (407 mg, 13.4 mmol), and sodium cyanoborohydride (842 mg, 13.4 mmol) in methanol (40 mL) was added acetic acid (catalytic) and the reaction mixture stirred at room temperature for 18 h. The reaction mixture was quenched with water and concentrated to remove methanol. The pH of the aqueous layer was adjusted to 10 with 1 M aqueous sodium hydroxide followed by extraction with methylene chloride. The organic layer was dried over anhydrous sodium sulfate, filtered, and concentrated to afford the desired product (1.1 g, 96%) as an oil: ESI MS m/z 257 $[C_{14}H_{28}N_2O_2+H]^+$.

Example 408 trans-4-[(Dimethylamino)methyl]cyclohexanamine

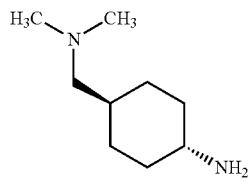

Following general procedure A-1, tert-butyl trans-4-[(dimethylamino)methyl]cyclohexylcarbamate (1.1 g, 4.30 mmol) was reacted with 3 M hydrochloric acid (10 mL) to afford the desired product (1.0 g, >99%) as a glass: ESI MS m/z 230 $[C_9H_{20}N_2+H]^+$.

Example 409 tert-Butyl trans-4-(pyrrolidin-1-yl)cyclohexylcarbamate

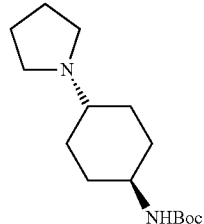

A stirred solution of tert-butyl trans-4-aminocyclohexylcarbamate (2.0 g, 9.33 mmol), 1,4-dibromobutane (1.33 mL, 11.2 mmol), and potassium hydrogen carbonate (4.67 g, 46.7 mmol) in DMF (90 mL) was stirred at room temperature overnight. After this time the reaction was diluted with aqueous lithium chloride and extracted with diethyl ether. The combined organics were dried over anhydrous sodium sulfate and concentrated under reduced pressure to afford the desired product (399 mg, 16%) as an off-white solid: ESI MS m/z 269 $[C_{15}H_{28}N_2O_2+H]^+$.

Example 410 trans-4-(Pyrrolidin-1-yl)cyclohexanamine hydrochloride

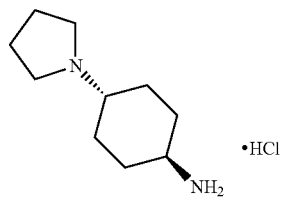 [SMILES: N[C@H]1CC[C@H](N2CCCC2)CC1 ; Cl]

To a solution of tert-butyl trans-4-(pyrrolidin-1-yl)cyclohexylcarbamate (399 mg, 1.44 mmol) in THF (12 mL) was added aqueous 6 N HCl (6 mL) and water (6 mL) and the reaction mixture was heated at 65° C. for 18 ht. The reaction mixture was cooled and concentrated to afford the desired product (350 mg, >99%) as an off-white solid: ESI MS m/z 169 $[C_{10}H_{20}N_2+H]^+$.

Example 411 tert-Butyl trans-4-[6-bromo-3-(cyclopropanecarbonyl)quinolin-4-ylamino]cyclohexylcarbamate

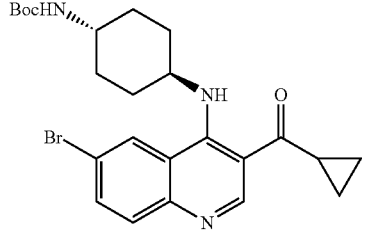 [SMILES: CC(C)(C)OC(=O)N[C@H]1CC[C@H](Nc2c(C(=O)C3CC3)cnc3ccc(Br)cc23)CC1]

Following general procedure B, (6-bromo-4-chloroquinolin-3-yl)(cyclopropyl)methanone (581 mg, 1.87 mmol) was reacted with tert-butyl trans-4-aminocyclohexylcarbamate (865 mg, 4.00 mmol) to afford the desired product (525 mg, 56%): ESI MS m/z 488 $[C_{24}H_{30}BrN_3O_3+H]^+$.

Example 412

(6-Bromo-4-{4-[(dimethylamino)methyl]piperidin-1-yl}quinolin-3-yl)(cyclopropyl)methanone

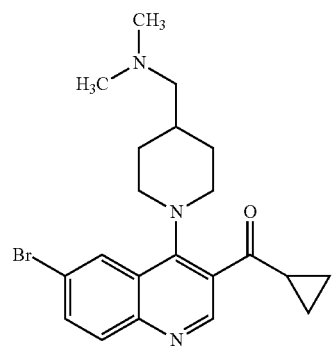 [SMILES: CN(C)CC1CCN(c2c(C(=O)C3CC3)cnc3ccc(Br)cc23)CC1]

Following general procedure B, (6-bromo-4-chloroquinolin-3-yl)(cyclopropyl)methanone (211 mg, 0.680 mmol) was reacted with N,N-dimethyl-1-(piperidin-4-yl)methanamine (97 mg, 0.680 mmol) to afford the desired product (160 mg, 46%) as a yellow glass: ESI MS m/z 417 [$C_{21}H_{26}BrN_3O$+ H]$^+$.

Example 413 tert-Butyl 8-[6-bromo-3-(cyclopropanecarbonyl)quinolin-4-yl]-2,8-diazaspiro[4,5]decane-2-carboxylate

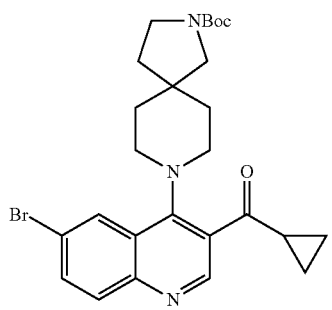 [SMILES: CC(C)(C)OC(=O)N1CCC2(CCN(c3c(C(=O)C4CC4)cnc4ccc(Br)cc34)CC2)C1]

Following general procedure B, (6-bromo-4-chloroquinolin-3-yl)(cyclopropyl)methanone (200 mg, 0.640 mmol) was reacted with tert-butyl 2,8-diazaspiro[4,5]decane-2-carboxylate (169 mg, 0.704 mmol) to afford the desired product (240 mg, 73%) as a yellow foam: ESI MS m/z 514 [$C_{26}H_{32}BrN_3O_3$+H]$^+$.

Example 414 tert-Butyl cis-4-[6-bromo-3-(cyclopropanecarbonyl)quinolin-4-ylamino]cyclohexylcarbamate

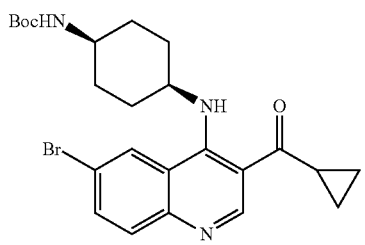 [SMILES: CC(C)(C)OC(=O)N[C@H]1CC[C@@H](Nc2c(C(=O)C3CC3)cnc3ccc(Br)cc23)CC1]

Following general procedure B, (6-bromo-4-chloroquinolin-3-yl)(cyclopropyl)methanone (200 mg, 0.640 mmol) was reacted with tert-butyl cis-4-aminocyclohexylcarbamate (164 mg, 0.767 mmol) to afford the desired product (259 mg, 83%) as a brown solid: ESI MS m/z 489 [$C_{24}H_{30}BrN_3O_3$+ H]$^+$.

Example 415

[6-Bromo-4-(1-methylpiperidin-4-ylamino)quinolin-3-yl](cyclopropyl)methanone

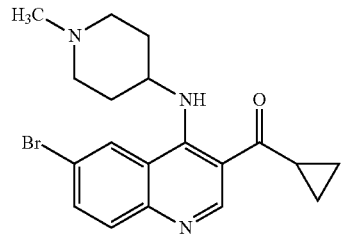 [SMILES: CN1CCC(Nc2c(C(=O)C3CC3)cnc3ccc(Br)cc23)CC1]

Following general procedure B, (6-bromo-4-chloroquinolin-3-yl)(cyclopropyl)methanone (510 mg, 1.64 mmol) was reacted with 1-methylpiperidin-4-amine (375 mg, 3.28 mmol) to afford the desired product (552 mg, 87%) as a brown solid: $^1$H NMR (300 MHz, CD$_3$OD) δ 9.12 (s, 1H), 8.38 (d, J=2.0 Hz, 1H), 7.84 (dd, J=8.9, 2.1 Hz, 1H), 7.79-7.71 (m, 1H), 4.20-3.97 (m, 1H), 2.93-2.69 (m, 3H), 2.47-2.19 (m, 5H), 2.19-2.03 (m, 2H), 1.86-1.60 (m, 2H), 1.32-1.16 (m, 2H), 1.16-1.00 (m, 2H).

Example 416

{6-Bromo-4-[4-(diethylamino)cyclohexylamino]quinolin-3-yl}(cyclopropyl)methanone

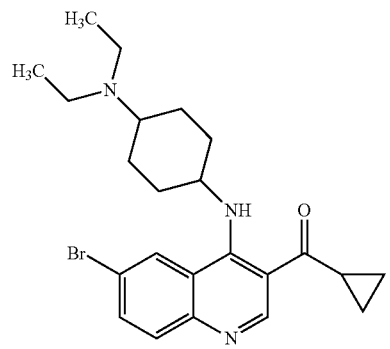 [SMILES: CCN(CC)C1CCC(Nc2c(C(=O)C3CC3)cnc3ccc(Br)cc23)CC1]

Following general procedure B, (6-bromo-4-chloroquinolin-3-yl)(cyclopropyl)methanone (1.01 g, 3.25 mmol) was reacted with N$^1$,N$^1$-diethylcyclohexane-1,4-diamine (660

Example 417

(6-Bromo-4-{4-[1-(dimethylamino)ethyl]piperidin-1-yl}quinolin-3-yl)(cyclopropyl)methanone

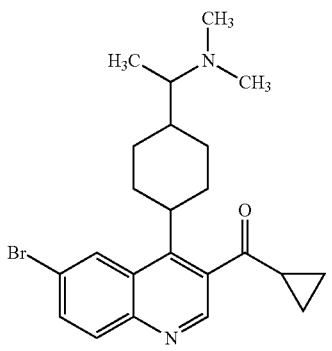 [SMILES: CC(C1CCC(c2c(C(=O)C3CC3)cnc3ccc(Br)cc23)CC1)N(C)C]

Following general procedure B, (6-bromo-4-chloroquinolin-3-yl)(cyclopropyl)methanone (300 mg, 0.965 mmol) was reacted with N,N-dimethyl-1-(piperidin-4-yl)ethanamine (332 mg, 1.45 mmol) to afford the desired product (264 mg, 63%) as a yellow solid: $^1$H NMR (300 MHz, CD$_3$OD) δ 8.78 (s, 1H), 8.32 (s, 1H), 7.95-7.80 (m, 2H), 3.57-3.39 (m, 2H), 3.21 3.05 (m, 2H), 2.59-2.42 (m, 2H), 2.31 (s, 6H), 2.11-1.97 (m, 1H), 1.89 (d, J=12.4 Hz, 1H), 1.80-1.67 (m, 1H), 1.68-1.49 (m, 2H), 1.36-1.16 (m, 4H), 1.06 (d, J=6.6 Hz, 3H).

Example 418

{6-Bromo-4-[(1-methylpiperidin-4-yl)methylamino]quinolin-3-yl}(cyclopropyl)methanone

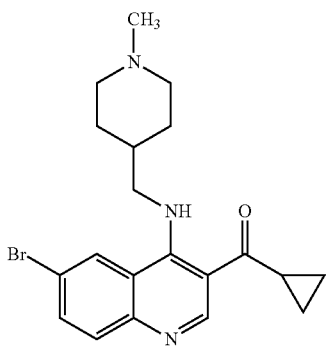 [SMILES: CN1CCC(CNc2c(C(=O)C3CC3)cnc3ccc(Br)cc23)CC1]

Following general procedure B, (6-bromo-4-chloroquinolin-3-yl)(cyclopropyl)methanone (0.880 g, 2.83 mmol) was reacted with (1-methylpiperidin-4-yl)methanamine (435 mg, 3.39 mmol) to afford the desired product (970 mg, 85%) as a light brown solid: $^1$H NMR (300 MHz, CDCl$_3$) δ 10.87 (s, 1H), 9.22 (s, 1H), 8.36 (d, J=1.9 Hz, 1H), 7.80 (d, J=8.9 Hz, 1H), 7.73 (dd, J=8.9, 2.0 Hz, 1H), 3.69 (dd, J=6.4, 5.2 Hz, 2H), 2.93 (d, J=11.4 Hz, 2H), 2.79-2.60 (m, 1H), 2.31 (s, J=9.0 Hz, 3H), 2.01 (t, J=11.7 Hz, 2H), 1.89 (d, J=12.7 Hz, 2H), 1.76-1.60 (m, 1H), 1.53-1.30 (m, 2H), 1.30-1.17 (m, 2H), 1.10-0.95 (m, 2H).

Example 419 tert-Butyl 4-{2-[6-bromo-3-(cyclopropanecarbonyl)quinolin-4-ylamino]ethyl}piperazine-1-carboxylate

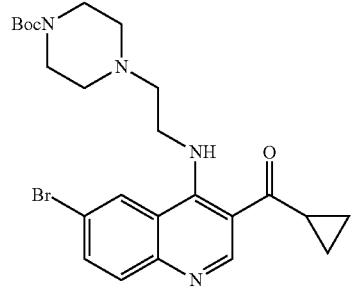 [SMILES: CC(C)(C)OC(=O)N1CCN(CCNc2c(C(=O)C3CC3)cnc3ccc(Br)cc23)CC1]

Following general procedure B, (6-bromo-4-chloroquinolin-3-yl)(cyclopropyl)methanone (940 mg, 3.03 mmol) was reacted with tert-butyl 4-(2-aminoethyl)piperazine-1-carboxylate (830 mg, 86%) to afford the desired product as an orange solid: $^1$H NMR (300 MHz, CDCl$_3$) δ 10.69 (s, 1H), 9.21 (s, 1H), 8.39 (d, J=2.0 Hz, 1H), 7.81 (d, J=8.9 Hz, 1H), 7.73 (dd, J=8.9, 2.0 Hz, 1H), 3.87 (dd, J=11.1, 5.5 Hz, 2H), 3.49 (t, J=4.9 Hz, 4H), 2.76-2.59 (m, 3H), 2.50 (t, J=4.9 Hz, 4H), 1.47 (s, J=11.3 Hz, 9H), 1.32-1.16 (m, 2H), 1.10-0.95 (m, 2H).

Example 420 tert-Butyl 4-{[6-bromo-3-(cyclopropanecarbonyl)quinolin-4-ylamino]methyl}piperidine-1-carboxylate

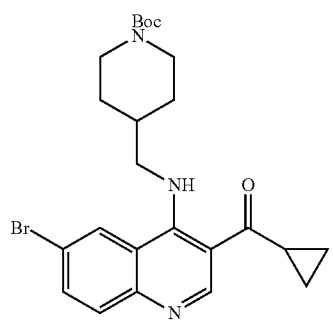 [SMILES: CC(C)(C)OC(=O)N1CCC(CNc2c(C(=O)C3CC3)cnc3ccc(Br)cc23)CC1]

Following general procedure B, (6-bromo-4-chloroquinolin-3-yl)(cyclopropyl)methanone (500 mg, 1.60 mmol) was reacted with tert-butyl 4-(aminomethyl)piperidine-1-carboxylate (516 mg, 2.41 mmol) to afford the desired product (80 mg, >99%) as an orange foam: ESI MS m/z 489 [C$_{24}$H$_{30}$BrN$_3$O$_3$+H]$^+$.

Example 421

{6-Bromo-4-[trans-4-(dimethylamino)cyclohexylamino]quinolin-3-yl}(cyclopropyl)methanone

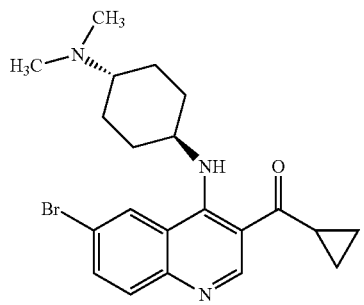 [SMILES: CN(C)[C@H]1CC[C@H](Nc2c(C(=O)C3CC3)cnc3ccc(Br)cc23)CC1]

Following general procedure B, (6-bromo-4-chloroquinolin-3-yl)(cyclopropyl)methanone (870 mg, 2.80 mmol) was reacted with trans-N$^1$,N$^1$-dimethylcyclohexane-1,4-diamine (400 mg, 2.80 mmol) to afford the desired product (398 mg, 36%) as a light yellow solid: $^1$H NMR (300 MHz, CD$_3$OD) δ 9.12 (s, 1H), 8.41 (d, J=2.0 Hz, 1H), 7.85 (dd, J=8.9, 2.0 Hz, 1H), 7.76 (d, J=8.9 Hz, 1H), 4.10-3.84 (m, 1H), 2.93-2.70 (m, 1H), 2.56-2.40 (m, 1H), 2.37 (s, 6H), 2.25 (d, J=12.0 Hz, 2H), 2.05 (d, J=11.4 Hz, 2H), 1.62-1.31 (m, 4H), 1.31-1.01 (m, 4H).

Example 422

{6-Bromo-4-[4-(pyrrolidin-1-ylmethyl)piperidin-1-yl]quinolin-3-yl}(cyclopropyl)methanone

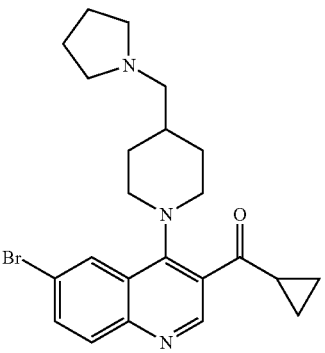 [SMILES: O=C(c1cnc2ccc(Br)cc2c1N1CCC(CN2CCCC2)CC1)C1CC1]

Following general procedure B, (6-bromo-4-chloroquinolin-3-yl)(cyclopropyl)methanone (210 mg, 0.680 mmol) was reacted with 4-(pyrrolidin-1-ylmethyl)piperidine (229 mg, 1.36 mmol) to afford the desired product (210 mg, 70%) as a yellow semisolid: ESI MS m/z 443 [C$_{23}$H$_{28}$BrN$_3$O+H]$^+$.

Example 423 tert-Butyl 4-[6-bromo-3-(cyclopropanecarbonyl)quinolin-4-ylamino]adamantylcarbamate

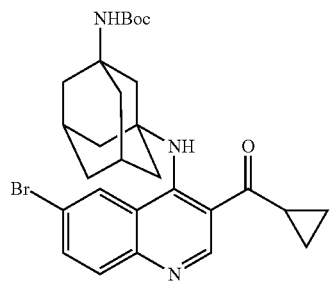 [SMILES: CC(C)(C)OC(=O)NC12CC3CC(C1)CC(Nc1c(C(=O)C4CC4)cnc4ccc(Br)cc14)(C3)C2]

Following general procedure B, (6-bromo-4-chloroquinolin-3-yl)(cyclopropyl)methanone (326 mg, 1.05 mmol) was reacted with tert-butyl 1-(3-aminoadamantane)carbamate (420 mg, 1.58 mmol) to afford the desired product (230 mg, 40%) as a yellow foam: ESI MS m/z 541 [C$_{23}$H$_{26}$BrN$_3$O+H]$^+$.

Example 424

(6-Bromo-4-{[trans-4-(dimethylamino)cyclohexyl]methylamino}quinolin-3-yl)(cyclopropyl)methanone

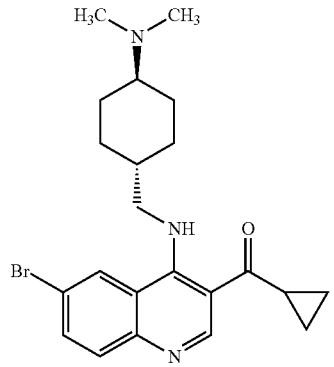 [SMILES: CN(C)[C@H]1CC[C@H](CNc2c(C(=O)C3CC3)cnc3ccc(Br)cc23)CC1]

Following general procedure C, (6-bromo-4-chloroquinolin-3-yl)(cyclopropyl)methanone (537 mg, 1.73 mmol) was reacted with trans-4-(aminomethyl)-N,N-dimethylcyclohexanamine (595 mg, 2.60 mmol) to afford the desired product (440 mg, 59%) as a white solid: $^1$H NMR (300 MHz, CH$_3$OD) δ 9.13 (s, 1H), 8.48 (d, J=2.0 Hz, 1H), 7.83 (dd, J=9.0, 2.0 Hz, 1H), 7.73 (d, J=8.9 Hz, 1H), 3.65 (d, J=6.4 Hz, 2H), 2.91-2.67

(m, 1H), 2.41-2.18 (m, 7H), 1.99 (d, J=10.1 Hz, 4H), 1.67 (d, J=3.3 Hz, 1H), 1.43-0.99 (m, 8H).

Example 425

{6-Bromo-4-[trans-4-{(dimethylamino)methyl}cyclohexylamino]quinolin-3-yl}(cyclopropyl)methanone

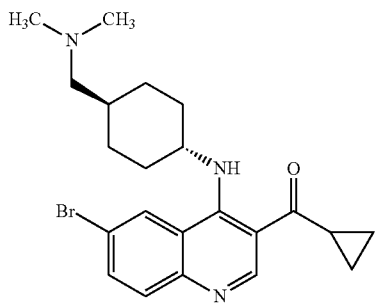

Following general procedure C, (6-bromo-4-chloroquinolin-3-yl)(cyclopropyl)methanone (560 mg, 1.80 mmol) was reacted with trans-4-[(dimethylamino)methyl]cyclohexanamine (620 mg, 2.70 mmol) to afford the desired product (335 mg, 43%) as a yellow solid: $^1$H NMR (300 MHz, CD$_3$OD) δ 9.12 (s, 1H), 8.41 (d, J=2.0 Hz, 1H), 7.84 (dd, J=8.9, 2.1 Hz, 1H), 7.75 (d, J=8.9 Hz, 1H), 4.12-3.84 (m, 1H), 2.91-2.72 (m, 1H), 2.42-2.26 (m, J=6.6 Hz, 8H), 2.21 (d, J=11.6 Hz, 2H), 1.94 (d, J=12.1 Hz, 2H), 1.75-1.59 (m, 1H), 1.59-1.35 (m, 2H), 1.25-0.98 (m, 6H).

Example 426

{6-Bromo-4-[4-(morpholinomethyl)piperidin-1-yl]quinolin-3-yl}(cyclopropyl)methanone

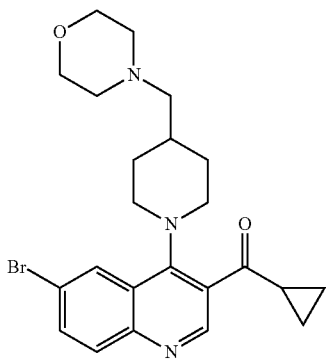 [SMILES: O=C(c1cnc2ccc(Br)cc2c1N1CCC(CN2CCOCC2)CC1)C1CC1]

Following general procedure B, (6-bromo-4-chloroquinolin-3-yl)(cyclopropyl)methanone (144 mg, 0.460 mmol) was reacted with 4-(piperidin-4-ylmethyl)morpholine (102 mg, 0.552 mmol) to afford the desired product (177 mg, 84%) as a yellow solid: ESI MS m/z 458 [C$_{23}$H$_{28}$BrN$_3$O$_2$+H]$^+$.

Example 427

(6-Bromo-4-{4-[(dimethylamino)methyl]phenylamino}quinolin-3-yl)(cyclopropyl)methanone

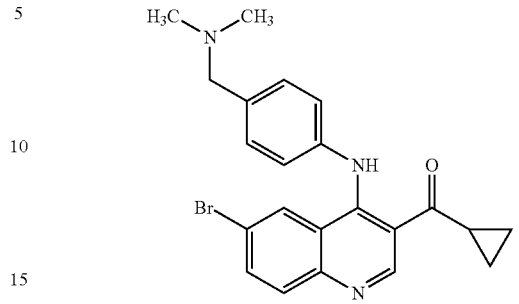

Following general procedure C, (6-bromo-4-chloroquinolin-3-yl)(cyclopropyl)methanone (320 mg, 1.03 mmol) was reacted with 4-[(dimethylamino)methyl]aniline (210 mg, 1.54 mmol) to afford the desired product (218 mg, 50%) as a yellow solid: ESI MS m/z 425 [C$_{22}$H$_{22}$BrN$_3$O+H]$^+$.

Example 428

{6-Bromo-4-[trans-4-(pyrrolidin-1-yl)cyclohexylamino]quinolin-3-yl}(cyclopropyl)methanone

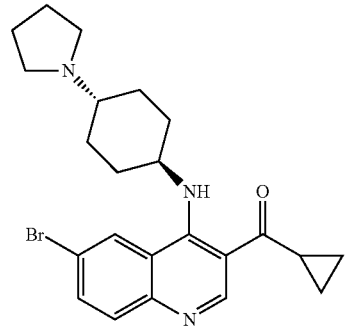 [SMILES: O=C(c1cnc2ccc(Br)cc2c1N[C@H]1CC[C@H](N2CCCC2)CC1)C1CC1]

Following general procedure C, (6-bromo-4-chloroquinolin-3-yl)(cyclopropyl)methanone (220 mg, 0.708 mmol) was reacted with trans-4-(pyrrolidin-1-yl)cyclohexanamine hydrochloride (350 mg, 2.08 mmol) to afford the desired product (75 mg, 24%) as an off-white solid: ESI MS m/z 442 [C$_{23}$H$_{28}$BrN$_3$O+H]$^+$.

Example 429

{6-Bromo-4-[4-(4-methylpiperazin-1-yl)piperidin-1-yl]quinolin-3-yl}(cyclopropyl)methanone

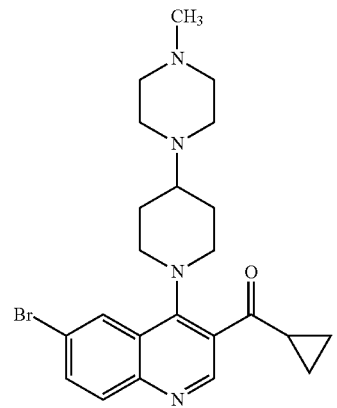 [SMILES: CN1CCN(C2CCN(c3c(C(=O)C4CC4)cnc4ccc(Br)cc34)CC2)CC1]

Following general procedure B, (6-bromo-4-chloroquinolin-3-yl)(cyclopropyl)methanone (155 mg, 0.500 mmol) was reacted with 3-(4-methylpiperazin-1-yl)butan-1-amine (183 mg, 1.00 mmol) to afford the desired product (102 mg, 45%) as a pale yellow solid: ESI MS m/z 457 $[C_{23}H_{29}BrN_4O+H]^+$.

Example 430 tert-Butyl trans-4-(6-bromo-3-isobutyrylquinolin-4-ylamino)cyclohexylcarbamate

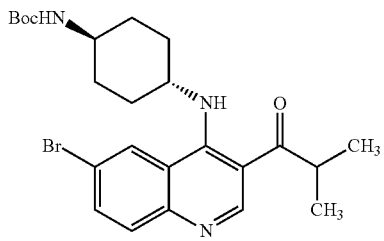 [SMILES: CC(C)C(=O)c1cnc2ccc(Br)cc2c1N[C@H]1CC[C@H](NC(=O)OC(C)(C)C)CC1]

Following general procedure B, 1-(6-bromo-4-chloroquinolin-3-yl)-2-methylpropan-1-one (10 g, 32.0 mmol) was reacted with tert-butyl trans-4-aminocyclohexylcarbamate (10.3 g, 48.0 mmol) to afford the desired product (12.8 g, 81%) as an off-white solid: ESI MS m/z 491 $[C_{24}H_{32}BrN_3O_3+H]^+$.

Example 431

1-{6-Bromo-4-[4-(pyrrolidin-1-ylmethyl)piperidin-1-yl]quinolin-3-yl}-2-methylpropan-1-one

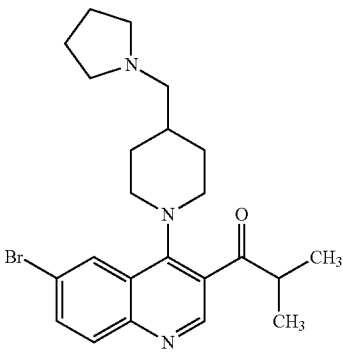 [SMILES: CC(C)C(=O)c1cnc2ccc(Br)cc2c1N1CCC(CN2CCCC2)CC1]

Following general procedure B, 1-(6-bromo-4-chloroquinolin-3-yl)-2-methylpropan-1-one (250 mg, 0.800 mmol) was reacted with 4-(pyrrolidin-1-ylmethyl)piperidine (168 mg, 1.00 mmol) to afford the desired product (243 mg, 68%) as a yellow solid: ESI MS m/z 444 $[C_{23}H_{30}BrN_3O+H]^+$.

Example 432

$N^1$-[6-Bromo-3-(methylsulfonyl)quinolin-4-yl]-$N^4$,$N^4$-diethylcyclohexane-1,4-diamine

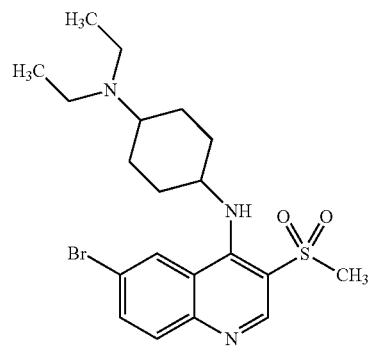 [SMILES: CCN(CC)C1CCC(Nc2c(S(C)(=O)=O)cnc3ccc(Br)cc23)CC1]

Following general procedure B, 6-bromo-4-chloro-3-(methylsulfonyl)quinoline (161 mg, 0.500 mmol) was reacted with $N^1$,$N^1$-diethylcyclohexane-1,4-diamine (170 mg, 1.00 mmol) to afford the desired product (197 mg, 87%) as a white solid: ESI MS m/z 454 $[C_{20}H_{28}BrN_3O_2S+H]^+$.

Example 433

1-{1-[6-Bromo-3-(methylsulfonyl)quinolin-4-yl]piperidin-4-yl}-N,N-dimethylethanamine

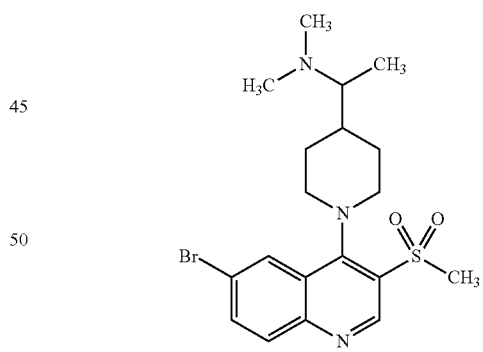

Following general procedure B, 6-bromo-4-chloro-3-(methylsulfonyl)quinoline (100 mg, 0.311 mmol) was reacted with N,N-dimethyl-1-(piperidin-4-yl)ethanamine (229 mg, 1.00 mmol) to afford the desired product (93 mg, 68%) as a white solid: $^1$H NMR (300 MHz, CDCl$_3$) δ 9.24 (s, 1H), 8.50 (d, J=1.5 Hz, 1H), 8.11-7.93 (m, 2H), 3.67-3.55 (m, 2H), 3.44 (s, 3H), 3.34 (s, 2H), 2.75-2.62 (m, 1H), 2.46 (s, 6H), 2.07-1.96 (m, 1H), 1.90 (d, J=12.3 Hz, 2H), 1.73-1.53 (m, 2H), 1.15 (d, J=6.6 Hz, 3H).

Example 434 tert-Butyl trans-4-(3-acetyl-6-bromoquinolin-4-ylamino)cyclohexylcarbamate

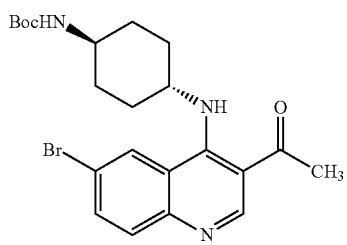 [SMILES: CC(=O)c1cnc2ccc(Br)cc2c1N[C@H]1CC[C@H](NC(=O)OC(C)(C)C)CC1]

Following general procedure B, 1-(6-bromo-4-chloroquinolin-3-yl)ethanone (420 mg, 1.48 mmol) was reacted with tert-butyl trans-4-aminocyclohexylcarbamate (642 mg, 3.00 mmol) to afford the desired product (550 mg, 80%) as an off-white solid: ESI MS m/z 462 $[C_{22}H_{28}BrN_3O_3+H]^+$.

Example 435

1-(6-Bromo-4-{4-[(dimethylamino)methyl]piperidin-1-yl}quinolin-3-yl)ethanone

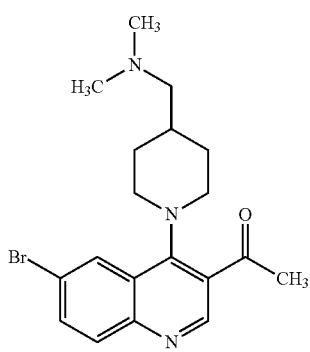 [SMILES: CC(=O)c1cnc2ccc(Br)cc2c1N1CCC(CN(C)C)CC1]

Following general procedure B, 1-(6-bromo-4-chloroquinolin-3-yl)ethanone (160 mg, 0.560 mmol) was reacted with N,N-dimethyl-1-(piperidin-4-yl)methanamine (172 mg, 0.800 mmol) to afford the desired product (17.7 mg, 8%) as an off-white solid: ESI MS m/z 390 $[C_{19}H_{24}BrN_3O+H]^+$.

Example 436

1-{6-Bromo-4-[4-(pyrrolidin-1-ylmethyl)piperidin-1-yl]quinolin-3-yl}ethanone

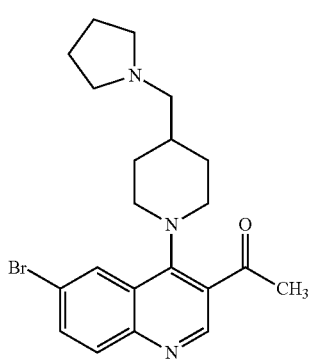 [SMILES: CC(=O)c1cnc2ccc(Br)cc2c1N1CCC(CN2CCCC2)CC1]

Following general procedure B, 1-(6-bromo-4-chloroquinolin-3-yl)ethanone (200 mg, 0.703 mmol) was reacted with 4-(pyrrolidin-1-ylmethyl)piperidine (168 mg, 1.00 mmol) to afford the desired product (233 mg, 80%) as a yellow solid: ESI MS m/z 416 $[C_{21}H_{26}BrN_3O+H]^+$.

Example 437

1-{6-Bromo-4-[4-(diethylamino)cyclohexylamino]quinolin-3-yl}ethanone

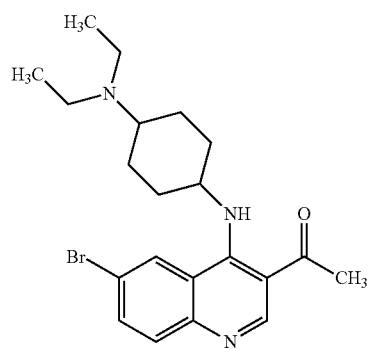 [SMILES: CCN(CC)C1CCC(Nc2c(C(C)=O)cnc3ccc(Br)cc23)CC1]

Following general procedure B, 1-(6-bromo-4-chloroquinolin-3-yl)ethanone (116 mg, 0.408 mmol) was reacted with $N^1,N^1$-diethylcyclohexane-1,4-diamine (138 mg, 0.812 mmol) to afford the desired product (157 mg, 51%) as an off-white solid: ESI MS m/z 418 $[C_{21}H_{28}BrN_3O+H]^+$.

Example 438 tert-Butyl trans-4-{6-bromo-3-(3-methylbutanoyl)quinolin-4-ylamino}cyclohexylcarbamate

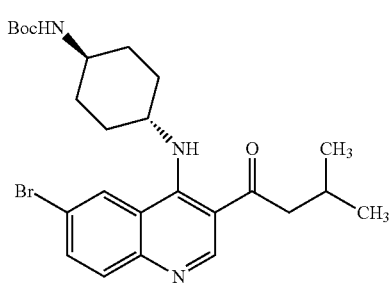 [SMILES: CC(C)CC(=O)c1cnc2ccc(Br)cc2c1N[C@H]1CC[C@H](NC(=O)OC(C)(C)C)CC1]

Following general procedure B, 1-(6-bromo-4-chloroquinolin-3-yl)-3-methylbutan-1-one (309 mg, 0.950 mmol) was reacted with tert-butyl trans-4-aminocyclohexylcarbamate (407 mg, 1.90 mmol) to afford the desired product (267 mg, 56%) as a yellow solid: ESI MS m/z 504 [$C_{20}H_{26}BrN_3O$+H]$^+$.

Example 439

1-{6-Bromo-4-[trans-4-(dimethylamino)cyclohexylamino]quinolin-3-yl}-3-methylbutan-1-one

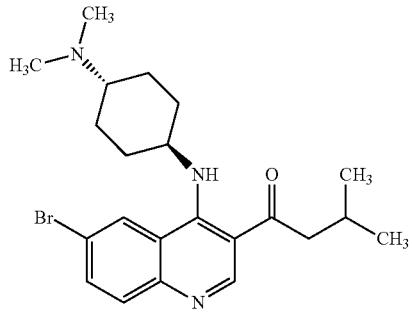 [SMILES: CC(C)CC(=O)c1cnc2ccc(Br)cc2c1N[C@H]1CC[C@H](N(C)C)CC1]

Following general procedure B, 1-(6-bromo-4-chloroquinolin-3-yl)-3-methylbutan-1-one (44 mg, 0.14 mmol) was reacted with trans-$N^1,N^1$-dimethylcyclohexane-1,4-diamine (92 mg, 0.43 mmol) to afford the desired product (13 mg, 21%) as an off-white solid: ESI MS m/z 433 [$C_{22}H_{30}BrN_3O$+H]$^+$.

Example 440 tert-Butyl trans-4-{6-bromo-3-(cyclopropanecarbonyl)-7-fluoroquinolin-4-ylamino}cyclohexylcarbamate

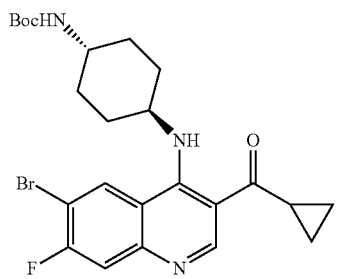 [SMILES: CC(C)(C)OC(=O)N[C@H]1CC[C@H](Nc2c(C(=O)C3CC3)cnc3cc(F)c(Br)cc23)CC1]

Following general procedure B, (6-bromo-4-chloro-7-fluoroquinolin-3-yl)(cyclopropyl)methanone (350 mg, 1.06 mmol) was reacted with tert-butyl trans-4-aminocyclohexylcarbamate (270 mg, 1.27 mmol) to afford the desired product (400 mg, 75%) as a light yellow solid: $^1$H NMR (300 MHz, CDCl$_3$) δ 10.67 (d, J=8.3 Hz, 1H), 9.22 (s, 1H), 8.32 (d, J=7.3 Hz, 1H), 7.62 (d, J=9.5 Hz, 1H), 4.42 (s, 1H), 3.91 (d, J=8.1 Hz, 1H), 3.52 (s, 1H), 2.75-2.56 (m, 1H), 2.18 (t, J=13.4 Hz, 4H), 1.72-1.62 (m, 1H), 1.59-1.50 (m, 2H), 1.45 (s, 9H), 1.30-1.18 (m, 3H), 1.13-1.01 (m, 2H).

Example 441

{6-Bromo-4-[trans-4-(dimethylamino)cyclohexylamino]-7-fluoroquinolin-3-yl}(cyclopropyl)methanone

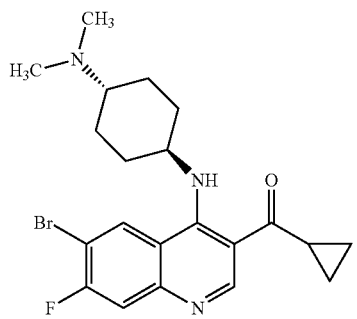

Following general procedure C, (6-bromo-4-chloro-7-fluoroquinolin-3-yl)(cyclopropyl)methanone (297 mg, 0.900 mmol) was reacted with trans-$N^1,N^1$-dimethylcyclohexane-1,4-diamine (290 mg, 1.35 mmol) to afford the desired product (212 mg, 54%) as an off-white solid: ESI MS m/z 435 [$C_{21}H_{25}BrFN_3O$+H]$^+$.

Example 442

[4-Chloro-6-(3-chloro-4-hydroxy-5-methoxyphenyl)quinolin-3-yl](cyclopropyl)methanone

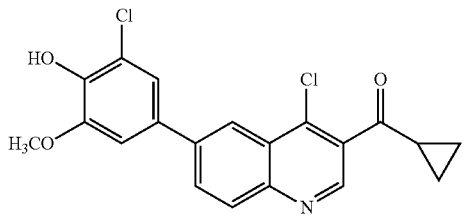 [SMILES: COc1cc(-c2ccc3ncc(C(=O)C4CC4)c(Cl)c3c2)cc(Cl)c1O]

To a suspension of (6-bromo-4-chloroquinolin-3-yl)(cyclopropyl)methanone (104 mg, 0.320 mmol), Pd(dppf)Cl$_2$ (23 mg, 0.03 mmol), and Cs$_2$CO$_3$ (0.95 mL, 1.0 M in H$_2$O) in dioxane (5 mL) was added 2-chloro-6-methoxy-4-(4,4,5,5-tetramethyl-1,3,2-dioxaborolan-2-yl)phenol (109 mg, 0.384 mmol). The reaction mixture was degassed with N$_2$ gas and the vessel was sealed and heated to 40° C. for 18 h. The reaction mixture was cooled, diluted with ethyl acetate, and filtered. The solution was concentrated and subjected to column chromatography (silica, hexanes/ethyl acetate) to afford the desired product (21 mg, 13%) as a light brown solid: $^1$H NMR (300 MHz, CDCl$_3$) δ 8.91 (s, 1H), 8.43 (d, J=1.9 Hz, 1H), 8.19 (t, J=7.5 Hz, 1H), 8.10-7.91 (m, 1H), 7.36 (d, J=1.9 Hz, 1H), 7.13 (d, J=1.8 Hz, 1H), 6.03 (s, 1H), 4.04 (s, 3H), 2.77-2.50 (m, 1H), 1.50-1.37 (m, 2H), 1.35-1.10 (m, 2H).

Example 1056

1-(6-Bromo-4-(6-(4-methylpiperazin-1-yl)pyridin-3-ylamino)quinolin-3-yl)ethanone

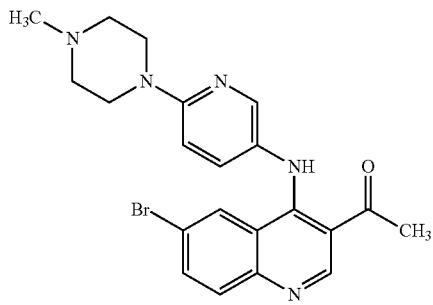 [SMILES: CC(=O)c1cnc2ccc(Br)cc2c1Nc1ccc(N2CCN(C)CC2)nc1]

Following general procedure B, 1-(6-bromo-4-chloroquinolin-3-yl)ethanone (200 mg, 0.704 mmol) was reacted with 6-(4-methylpiperazin-1-yl)pyridin-3-amine (163 mg, 0.845 mmol) to afford the desired product (90 mg, 29%) as a yellow solid: ESI MS m/z 440, $[C_{21}H_{22}BrN_5O+H]^+$

Example 1057

{6-Bromo-4-[(1r,4r)-4-[(dimethylamino)methyl]cyclohexylamino]quinolin-3-yl}(cyclopropyl)methanone

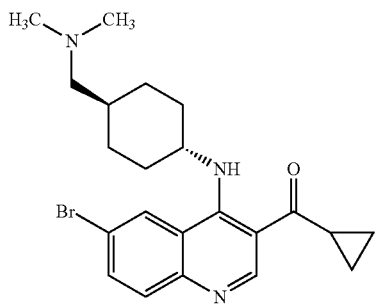 [SMILES: CN(C)C[C@H]1CC[C@H](Nc2c(C(=O)C3CC3)cnc3ccc(Br)cc23)CC1]

Following general procedure B, (6-bromo-4-chloroquinolin-3-yl)(cyclopropyl)methanone (300 mg, 0.967 mmol) was reacted with (1r,4r)-4-((dimethylamino)methyl)cyclohexanamine (153 mg, 1.16 mmol) to afford the desired product (220 mg, 53%) as a yellow solid: ESI MS m/z 431, $[C_{22}H_{28}BrN_3O+H]^+$

Example 1058

2-(((1R,4R)-4-(6-Bromo-3-(cyclopropanecarbonyl)quinolin-4-ylamino)cyclohexyl)methyl)(methyl)amino)acetonitrile

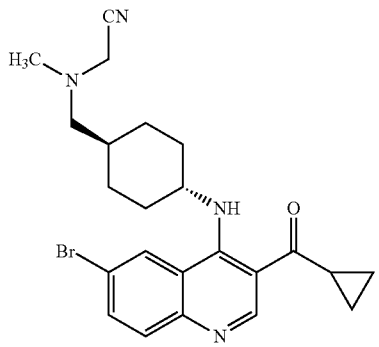 [SMILES: CN(CC#N)C[C@H]1CC[C@H](Nc2c(C(=O)C3CC3)cnc3ccc(Br)cc23)CC1]

Following general procedure B, (6-bromo-4-chloroquinolin-3-yl)(cyclopropyl)methanone (200 mg, 0.645 mmol) was reacted with 2-(((1R,4R)-4-aminocyclohexyl)methyl)(methyl)amino) acetonitrile (140 mg, 0.774 mmol) to afford the desired product (100 mg, 34%) as a yellow solid: ESI MS m/z 455, $[C_{23}H_{27}BrN_4O+H]^+$

Example 1059

(6-Bromo-4-(4-((dimethylamino)methyl)phenylamino)-7-fluoroquinolin-3-yl)(cyclopropyl)methanone

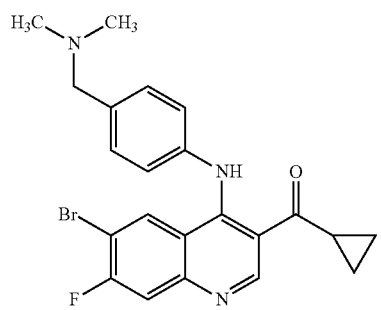 [SMILES: CN(C)Cc1ccc(Nc2c(C(=O)C3CC3)cnc3cc(F)c(Br)cc23)cc1]

Following general procedure B, (6-bromo-4-chloro-7-fluoroquinolin-3-yl)(cyclopropyl)methanone (328 mg, 1.00 mmol) was reacted with 2-(((1R,4R)-4-aminocyclohexyl)methyl)(methyl)amino)acetonitrile (180 mg, 1.2 mmol) to afford the desired product (150 mg, 34%) as a off-white solid: ESI MS m/z 442, $[C_{22}H_{21}BrFN_3O+H]^+$

Example 1060 tert-Butyl (1r,4r)-4-(3-acetyl-6-bromoquinolin-4-ylamino)cyclohexyl(methyl)carbamate

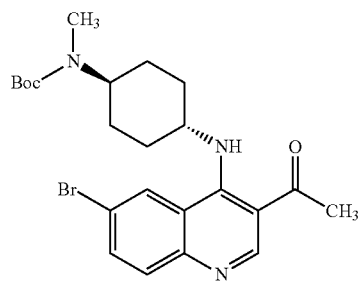

Following general procedure B, 1-(6-bromo-4-chloroquinolin-3-yl)ethanone (300 mg, 1.06 mmol) was reacted with tert-butyl (1r,4r)-4-aminocyclohexyl(methyl)carbamate (362

Example 1061 tert-butyl 4-(5-(3-acetyl-6-bromoquinolin-4-ylamino)pyrimidin-2-yl)piperazine-1-carboxylate

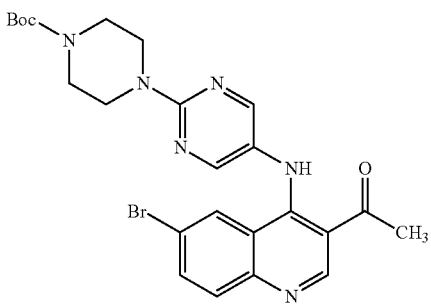 [SMILES: CC(=O)c1cnc2ccc(Br)cc2c1Nc1cnc(N2CCN(C(=O)OC(C)(C)C)CC2)nc1]

Following general procedure B, 1-(6-bromo-4-chloroquinolin-3-yl)ethanone (300 mg, 1.06 mmol) was reacted with tert-butyl 4-(5-aminopyrimidin-2-yl)piperazine-1-carboxylate (495 mg, 1.59 mmol) to afford the desired product (250 mg, 44%) as a yellow solid: ESI MS m/z 527, $[C_{24}H_{27}BrN_6O_3+H]^+$

Example 1062 tert-butyl 4-(5-(3-acetyl-6-(3-chloro-5-fluoro-4-hydroxyphenyl)quinolin-4-ylamino) pyrimidin-2-yl)piperazine-1-carboxylate

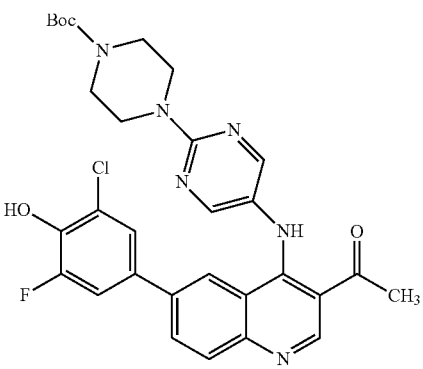 [SMILES: CC(=O)c1cnc2ccc(-c3cc(F)c(O)c(Cl)c3)cc2c1Nc1cnc(N2CCN(C(=O)OC(C)(C)C)CC2)nc1]

Following general procedure D, tert-butyl tert-butyl 4-(5-(3-acetyl-6-bromoquinolin-4-ylamino)pyrimidin-2-yl)piperazine-1-carboxylate (60 mg, 0.114 mmol) was reacted with 2-chloro-6-fluoro-4-(4,4,5,5-tetramethyl-1,3,2-dioxaborolan-2-yl)phenol (46 mg, 0.171 mmol) to afford the desired product (50 mg, 74%) as an orange solid: ESI MS m/z 593, $[C_{30}H_{30}ClFN_6O_4+H]^+$ mg, 1.59 mmol) to afford the desired product (250 mg, 47%) as a yellow solid: ESI MS m/z 501, $[C_{25}H_{32}BrN_3O_3+H]^+$

Example 1063

1-(6-bromo-4-(1R,4R)-4-((dimethylamino)methyl) cyclohexylamino)quinolin-3-yl)-2-methylpropan-1-one

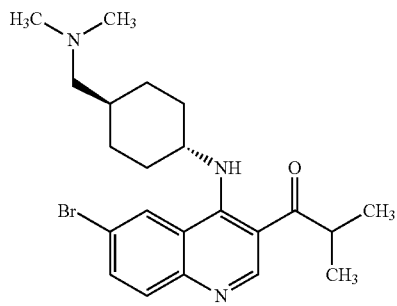 [SMILES: CC(C)C(=O)c1cnc2ccc(Br)cc2c1N[C@H]1CC[C@H](CN(C)C)CC1]

Following general procedure B, 1-(6-bromo-4-chloroquinolin-3-yl)-2-methylpropan-1-one (604 mg, 1.93 mmol) was reacted with (1r,4r)-4-((dimethylamino)methyl)cyclohexanamine (882 mg, 3.87 mmol) to afford the desired product (224 mg, 27%) as a yellow solid: ESI MS m/z 432, $[C_{22}H_{30}BrN_3O+H]^+$

Example 1064

1-(6-bromo-4-(4-((dimethylamino)methyl)phenylamino)quinolin-3-yl)-2-methylpropan-1-one

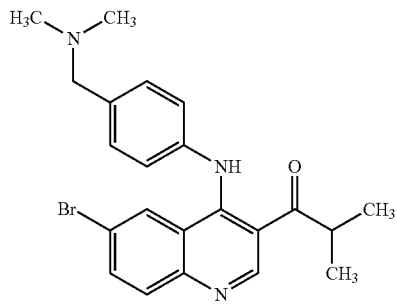 [SMILES: CC(C)C(=O)c1cnc2ccc(Br)cc2c1Nc1ccc(CN(C)C)cc1]

Following general procedure B, 1-(6-bromo-4-chloroquinolin-3-yl)-2-methylpropan-1-one (604 mg, 1.93 mmol) was reacted with 4-((dimethylamino)methyl)aniline (882 mg, 3.87 mmol) to afford the desired product (224 mg, 27%) as a yellow solid: ESI MS m/z 432, $[C_{22}H_{30}BrN_3O+H]^+$

Example 1065 tert-butyl 1-(5-(3-acetyl-6-bromoquinolin-4-ylamino)pyridin-2-yl)piperidin-3-ylcarbamate

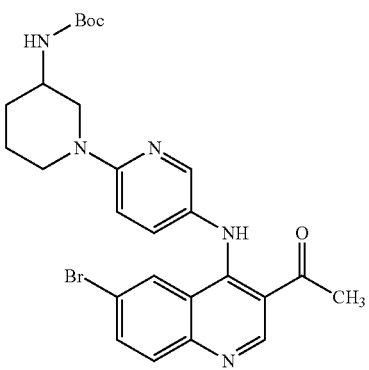 [SMILES: CC(=O)c1cnc2ccc(Br)cc2c1Nc1ccc(N2CCCC(NC(=O)OC(C)(C)C)C2)nc1]

Following general procedure B, 1-(6-bromo-4-chloroquinolin-3-yl)ethanone (194 mg, 0.681 mmol) was reacted with tert-butyl 1-(5-aminopyridin-2-yl)piperidin-3-ylcarbamate (210 mg, 0.821 mmol) to afford the desired product (205 mg, 55%) as a brown solid: ESI MS m/z 540, $[C_{26}H_{30}BrN_5O_3+H]^+$ Example 1066 tert-butyl 1-(5-(3-acetyl-6-(3,5-dichloro-4-hydroxyphenyl)quinolin-4-ylamino) pyridin-2-yl)piperidin-3-ylcarbamate

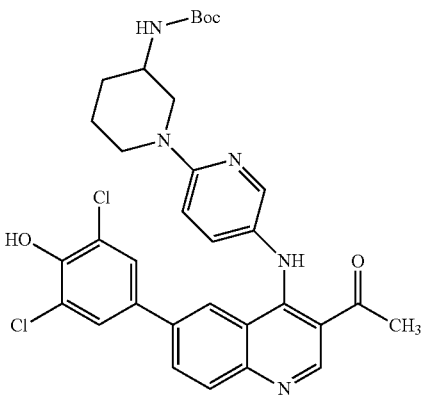 [SMILES: CC(=O)c1cnc2ccc(-c3cc(Cl)c(O)c(Cl)c3)cc2c1Nc1ccc(N2CCCC(NC(=O)OC(C)(C)C)C2)nc1]

Following general procedure D, tert-butyl 1-(5-(3-acetyl-6-bromoquinolin-4-ylamino)pyridin-2-yl)piperidin-3-ylcarbamate (60 mg, 0.110 mmol) was reacted with 2,6-dichloro-4-(4,4,5,5-tetramethyl-1,3,2-dioxaborolan-2-yl)phenol (48 mg, 0.166 mmol) to afford the desired product (52 mg, 76%) as an brown solid: ESI MS m/z 622, $[C_{32}H_{33}Cl_2N_5O_4+H]^+$ Example 1067 tert-butyl 4-(5-(3-acetyl-6-(3,5-dichloro-4-hydroxyphenyl)quinolin-4-ylamino) pyridin-2-yl)piperazine-1-carboxylate

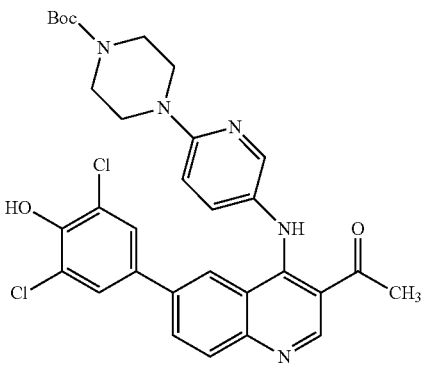 [SMILES: CC(=O)c1cnc2ccc(-c3cc(Cl)c(O)c(Cl)c3)cc2c1Nc1ccc(N2CCN(C(=O)OC(C)(C)C)CC2)nc1]

Following general procedure D, tert-butyl 4-(5-(3-acetyl-6-bromoquinolin-4-ylamino)pyridin-2-yl)piperazine-1-carboxylate (55 mg, 0.104 mmol) was reacted with 2,6-dichloro-4-(4,4,5,5-tetramethyl-1,3,2-dioxaborolan-2-yl)phenol (36 mg, 0.125 mmol) to afford the desired product (65 mg, 72%) as an green oil: ESI MS m/z 608, $[C_{31}H_{31}Cl_2N_5O_4+H]^+$ Example 1068

1-(6-bromo-4-(1R,4R)-4-(hydroxymethyl)cyclohexylamino)quinolin-3-yl)ethanone

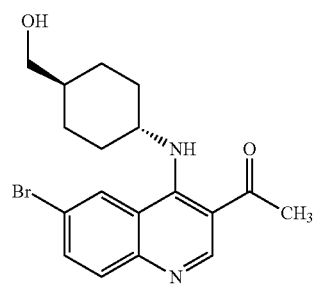 [SMILES: CC(=O)c1cnc2ccc(Br)cc2c1N[C@H]1CC[C@H](CO)CC1]

Following general procedure B, 1-(6-bromo-4-chloroquinolin-3-yl)ethanone (1.4 g, 4.89 mmol) was reacted with (1R,4R)-4-aminocyclohexyl)methanol (970 mg, 5.87 mmol) to afford the desired product (877 mg, 48%) as a brown solid: ESI MS m/z 377, $[C_{18}H_{21}BrN_2O_2+H]^+$ Example 1069

1-(6-bromo-4-(1R,4R)-4-((3-hydroxypyrrolidin-1-yl)methyl)cyclohexylamino)quinolin-3-yl)ethanone

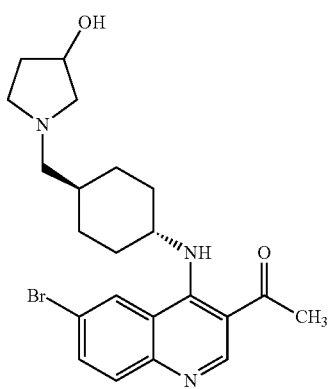 [SMILES: CC(=O)c1cnc2ccc(Br)cc2c1N[C@H]1CC[C@H](CN2CCC(O)C2)CC1]

To a solution of 1-(6-bromo-4-(1R,4R)-4-(hydroxymethyl)cyclohexylamino)quinolin-3-yl) ethanone (210 mg, 0.550 mmol) in dichloromethane (20 mL) was added triethylamine (229 μL, 1.65 mmol) and methanesulfonyl chloride (64 μL, 0.835 mmol) and the reaction was stirred at room temperature for 2 h. To the reaction mixture was added pyrrolidin-3-ol (222 μL, 2.75 mmol) and the reaction was stirred at 85° C. for 16 h. The reaction was concentrated and the residue was purified by flash chromatography to yield the expected product (150 mg, 61%) as a brown solid. ESI MS m/z 446, $[C_{22}H_{28}BrN_3O_2+H]^+$

Example 170

1-(6-bromo-4-(1R,4R)-4-(pyrrolidin-1-ylmethyl)cyclohexylamino)quinolin-3-yl)ethanone

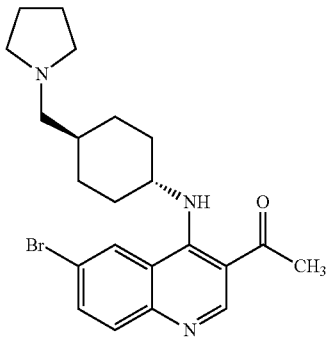 [SMILES: CC(=O)c1cnc2ccc(Br)cc2c1N[C@H]1CC[C@H](CN2CCCC2)CC1]

To a solution of 1-(6-bromo-4-(1R,4R)-4-(hydroxymethyl)cyclohexylamino)quinolin-3-yl) ethanone (200 mg, 0.530 mmol) in dichloromethane (20 mL) was added triethylamine (216 µL, 1.59 mmol) and methanesulfonyl chloride (60 µL, 0.795 mmol) and the reaction was stirred at room temperature for 2 h. To the reaction mixture was added pyrrolidine (213 pt, 2.65 mmol) and the reaction was stirred at 85° C. for 16 h. The reaction was concentrated and the residue was purified by flash chromatography to yield the expected product (127 mg, 56%) as a brown solid. ESI MS m/z 430, $[C_{22}H_{28}BrN_3O+H]^+$

Example 1071

(1R,4R)-4-(3-acetyl-6-bromoquinolin-4-ylamino)cyclohexyl)methyl methanesulfonate

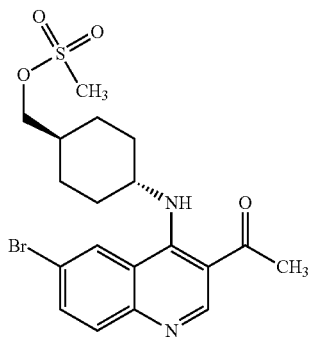 [SMILES: CC(=O)c1cnc2ccc(Br)cc2c1N[C@H]1CC[C@H](COS(C)(=O)=O)CC1]

To a solution of 1-(6-bromo-4-(1R,4R)-4-(hydroxymethyl)cyclohexylamino)quinolin-3-yl) ethanone (1.0 g, 2.65 mmol) in dichloromethane (70 mL) was added triethylamine (1.1 mL, 7.95 mmol) and methanesulfonyl chloride (306 µL, 3.97 mmol) and the reaction was stirred at room temperature for 16 h. The completed reaction was concentrated and purified by flash chromatography to yield the expected product (990 mg, 82%) as a off-white solid. ESI MS m/z 455, $[C_{19}H_{23}BrN_2O_4S+H]^+$

Example 1072

1-(6-bromo-4-(1R,4R)-4-((diethylamino)methyl)cyclohexylamino)quinolin-3-yl)ethanone

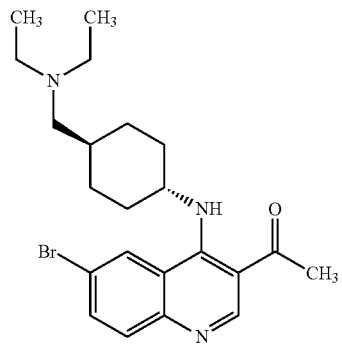 [SMILES: CCN(CC)C[C@H]1CC[C@H](Nc2c(C(C)=O)cnc3ccc(Br)cc23)CC1]

In 5 mL of DMF, (1R,4R)-4-(3-acetyl-6-bromoquinolin-4-ylamino)cyclohexyl)methyl methanesulfonate (200 mg, 0.437 mmol) was combined with diethylamine (95 mg, 1.31 mmol) in the presence of triethylamine (183 µL, 1.31 mmol). The reaction mixture was stirred at 80° C. for 20 hrs in a sealed tube. The completed reaction was diluted in 50 mL of ethyl acetate or a CHCl₃/isopropanol 3:1 mixture and washed with brine (2×50 mL) and water (50 mL). The organic layer was isolated and dried over anhydrous sodium sulfate and reduced to a orange residue. The material was purified by flash chromatography to afford the expected product (120 mg, 63%) as a yellow solid. ESI MS m/z 432, $[C_{22}H_{30}BrN_3O+H]^+$

Example 1073

1-(6-bromo-4-(1R,4R)-4-(((R)-2-(hydroxymethyl)pyrrolidin-1-yl)methyl)cyclohexylamino)quinolin-3-yl)ethanone

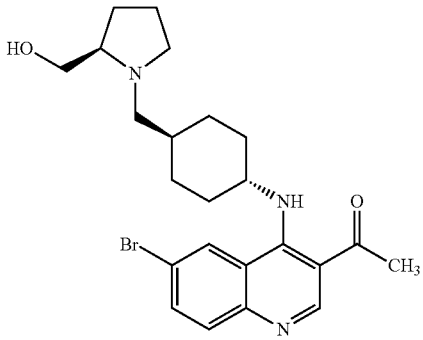 [SMILES: CC(=O)c1cnc2ccc(Br)cc2c1N[C@H]1CC[C@H](CN2CCC[C@@H]2CO)CC1]

To a solution of ((1R,4R)-4-(3-acetyl-6-bromoquinolin-4-ylamino)cyclohexyl)methyl methanesulfonate (350 mg, 0.765 mmol) and (R)-pyrrolidin-2-ylmethanol (400 mg, 3.82 mmol) in DMF (5 mL) was added triethylamine (531 µL, 3.82 mmol). The reaction mixture was stirred at 80° C. for 20 hrs in a sealed tube. The completed reaction was diluted in 50 mL of ethyl acetate or a CHCl₃/isopropanol 3:1 mixture and washed with brine (2×50 mL) and water (50 mL). The organic layer was isolated and dried over anhydrous sodium sulfate and reduced to a orange residue. The material was purified by flash chromatography to afford the expected product (314 mg, 89%) as a yellow solid. ESI MS m/z 460, $[C_{23}H_{30}BrN_3O_2+H]^+$ Example 1074 tert-butyl 1-((1R,4R)-4-(3-acetyl-6-bromoquinolin-4-ylamino)cyclohexyl)methyl)piperidin-3-ylcarbamate

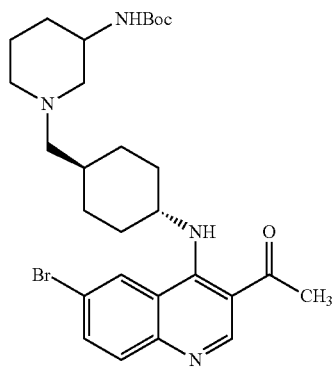 [SMILES: CC(=O)c1cnc2ccc(Br)cc2c1N[C@H]1CC[C@H](CN2CCCC(NC(=O)OC(C)(C)C)C2)CC1]

To a solution of (1R,4R)-4-(3-acetyl-6-bromoquinolin-4-ylamino)cyclohexyl)methyl methanesulfonate (350 mg, 0.765 mmol) in DMF (5 mL) was added (tert-butyl piperidin-3-ylcarbamate (460 mg, 2.29 mmol) and triethylamine (318 μL, 2.29 mmol). The reaction mixture was stirred at 80° C. for 20 h in a sealed tube. The completed reaction was diluted in 50 mL of ethyl acetate or a CHCl₃/isopropanol 3:1 mixture and washed with brine (2×50 mL) and water (50 mL). The organic layer was isolated and dried over anhydrous sodium sulfate and reduced to a orange residue. The material was purified by flash chromatography to afford the expected product (238 mg, 55%) as a yellow solid. ESI MS m/z 559, $[C_{28}H_{39}BrN_4O_3+H]^+$ Example 1075

1-(6-bromo-4-(1R,4R)-4-((ethyl(methyl)amino)methyl)cyclohexylamino)quinolin-3-yl)ethanone

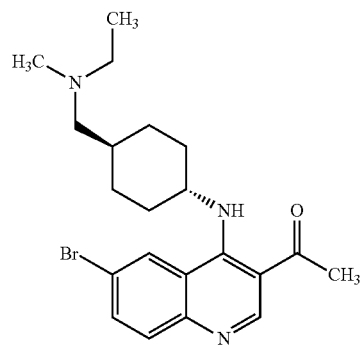 [SMILES: CCN(C)C[C@H]1CC[C@H](Nc2c(C(C)=O)cnc3ccc(Br)cc23)CC1]

To a solution of (1R,4R)-4-(3-acetyl-6-bromoquinolin-4-ylamino)cyclohexyl)methyl methanesulfonate (300 mg, 0.656 mmol) was added N-methylethanamine (190 mg, 3.28 mmol) and triethylamine (331 μL, 3.28 mmol). The reaction mixture was stirred at 80° C. for 20 hrs in a sealed tube. The completed reaction was diluted in 50 mL of ethyl acetate or a CHCl₃/isopropanol 3:1 mixture and washed with brine (2×50 mL) and water (50 mL). The organic layer was isolated and dried over anhydrous sodium sulfate and reduced to a orange residue. The material was purified by flash chromatography to afford the expected product (206 mg, 75%) as a yellow solid. ESI MS m/z 418, $[C_{21}H_{28}BrN_3O+H]^+$ Example 1076 tert-butyl 1-(5-(6-bromo-3-propionylquinolin-4-ylamino)pyridin-2-yl)piperidin-3-ylcarbamate

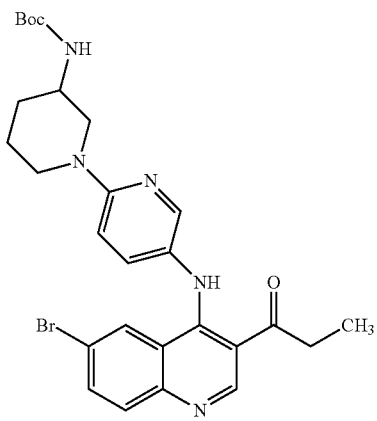 [SMILES: CCC(=O)c1cnc2ccc(Br)cc2c1Nc1ccc(N2CCCC(NC(=O)OC(C)(C)C)C2)nc1]

Following general procedure B, 1-(6-bromo-4-chloroquinolin-3-yl)propan-1-one (235 mg, 0.792 mmol) was reacted with tert-butyl 1-(5-aminopyridin-2-yl)piperidin-3-ylcarbamate (348 mg, 1.19 mmol) to afford the desired product (94 mg, 21%) as an orange solid: ESI MS m/z 554, $[C_{27}H_{32}BrN_5O_3+H]^+$ Example 1077

1-(6-bromo-4-(1R,4R)-4-(hydroxymethyl)cyclohexylamino)quinolin-3-yl)propan-1-one

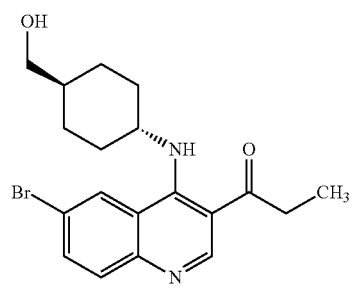

Following general procedure B, 1-(6-bromo-4-chloroquinolin-3-yl)propan-1-one (894 mg, 3.0 mmol) was reacted with (1R,4R)-4-aminocyclohexyl)methanol (633 mg, 4.89 mmol)

to afford the desired product (630 mg, 53%) as an yellow solid: ESI MS m/z 391, [C19H23BrN2O2+H]+

Example 1078

(1R,4R)-4-(6-bromo-3-propionylquinolin-4-ylamino)cyclohexyl)methyl methanesulfonate

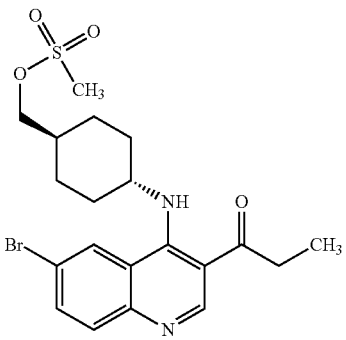 [SMILES: CCC(=O)c1cnc2ccc(Br)cc2c1N[C@H]1CC[C@H](COS(C)(=O)=O)CC1]

To a solution of 1-(6-bromo-4-(1R,4R)-4-(hydroxymethyl)cyclohexylamino)quinolin-3-yl) propan-1-one (630 mg, 1.6 mmol) and triethylamine (670 µL, 4.8 mmol) in 20 mL of dichloromethane was added dropwise methanesulfonyl chloride (186 µL, 2.4 mmol) and the reaction was stirred at room temperature for 16 h. The completed reaction was reduced to a yellow oil and purified by flash chromatography to yield the expected product (591 mg, 78%) as a white solid. ESI MS m/z 469, $[C_{20}H_{25}BrN_2O_4S+H]^+$

Example 1079

1-(6-bromo-4-(1R,4R)-4-(pyrrolidin-1-ylmethyl)cyclohexylamino)quinolin-3-yl)propan-1-one

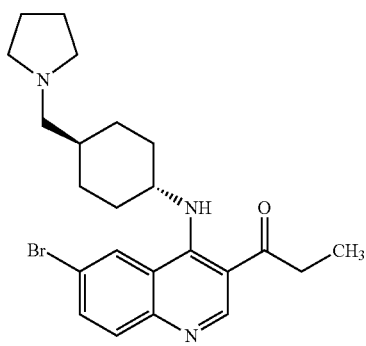 [SMILES: CCC(=O)c1cnc2ccc(Br)cc2c1N[C@H]1CC[C@H](CN2CCCC2)CC1]

To a solution of (1R,4R)-4-(6-bromo-3-propionylquinolin-4-ylamino)cyclohexyl)methyl methanesulfonate (295 mg, 0.629 mmol), N-methylethanamine (223 mg, 3.14 mmol) and triethylamine (436 µL, 3.14 mmol) in DMF (5 mL) and the reaction mixture was stirred at 80° C. for 20 h in a sealed tube. The completed reaction was diluted in 50 mL of ethyl acetate or a CHCl3/isopropanol 3:1 mixture and washed with brine (2×50 mL) and water (50 mL). The organic layer was isolated and dried over anhydrous sodium sulfate and reduced to a orange residue. The material was purified by flash chromatography to afford the expected product (210 mg, 75%) as a yellow solid. ESI MS m/z 444, $[C_{23}H_{30}BrN_3O+H]^+$

Example 1080 tert-butyl (1r,4r)-4-(3-acetyl-6-bromoquinolin-4-ylamino)cyclohexylcarbamate

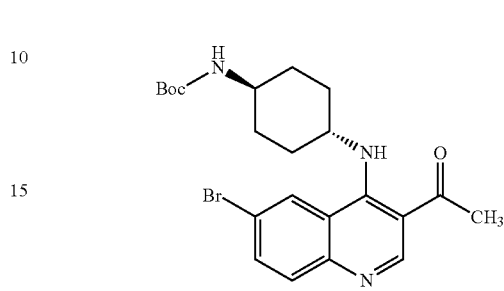

Following general procedure B, 1-(6-bromo-4-chloroquinolin-3-yl)ethanone (425 mg, 1.49 mmol) was reacted with tert-butyl (1r,4r)-4-aminocyclohexylcarbamate (400 mg, 1.87 mmol) to afford the desired product (501 mg, 73%) as an yellow solid: ESI MS m/z 462, $[C_{22}H_{28}BrN_3O_3+H]^+$

Example 1081

1-(4-(1R,4R)-4-aminocyclohexylamino)-6-bromoquinolin-3-yl)ethanone

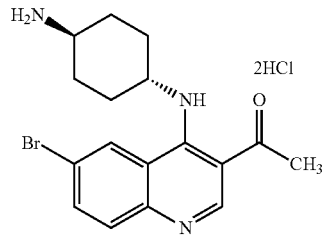 [SMILES: CC(=O)c1cnc2ccc(Br)cc2c1N[C@H]1CC[C@H](N)CC1]

Following general procedure A-1, tert-butyl (1r,4r)-4-(3-acetyl-6-bromoquinolin-4-ylamino)cyclohexylcarbamate (501 mg, 1.08 mmol) afforded the desired product (450 mg, 96%) as an white solid: ESI MS m/z 362, $[C_{17}H_{20}BrN_3O+H]^+$

Example 1081

N-(1R,4R)-4-(3-acetyl-6-bromoquinolin-4-ylamino)cyclohexyl)-2-(dimethylamino)acetamide

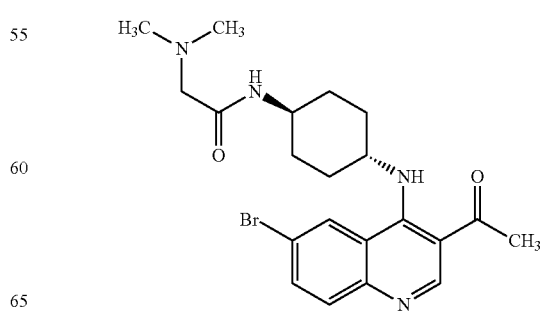

A solution of 2-(dimethylamino)acetic acid (58 mg, 0.568 mmol) and HATU (215 mg, 0.568 mmol) in DMF (5 mL) was stirred at rt for 10 min followed by the addition of N,N-diisopropylethylamine (443 μL, 2.73 mmol) and 1-(4-(1R,4R)-4-aminocyclohexylamino)-6-bromoquinolin-3-yl)ethanone (210 mg, 0.474 mmol) and the resulting solution was stirred at room temperature for 16 h. The completed reaction was diluted in 50 mL of CHCl$_3$/isopropanol 3:1 mixture and washed with 5% LiCl solution (2×50 mL) and water (50 mL). The organic layer was separated, dried over anhydrous sodium sulfate and concentrated to a orange residue. The material was purified by flash chromatography (MeOH/CH$_2$Cl$_2$) to afford the expected product (102 mg, 48%) as a yellow solid. ESI MS m/z 447, [C$_{21}$H$_{27}$BrN$_4$O$_2$+H]$^+$ Example 1082 tert-butyl 1-(1R,4R)-4-(3-acetyl-6-bromoquinolin-4-ylamino)cyclohexylamino)-1-oxopropan-2-ylcarbamate

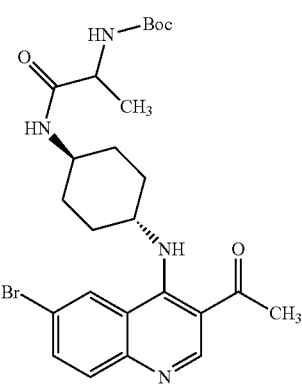 [SMILES: CC(=O)c1cnc2ccc(Br)cc2c1N[C@H]1CC[C@H](NC(=O)C(C)NC(=O)OC(C)(C)C)CC1]

A solution of 2-(tert-butoxycarbonylamino)propanoic acid (153 mg, 0.812 mmol) and HATU (308 mg, 0.812 mmol) in DMF (5 mL) was stirred at rt for 10 min followed by the addition of N,N-diisopropylethylamine (650 μL, 3.38 mmol) and 1-(4-(1R,4R)-4-aminocyclohexylamino)-6-bromoquinolin-3-yl)ethanone (300 mg, 0.677 mmol) and the resulting solution was stirred at room temperature for 16 h. The completed reaction was diluted in 50 mL of CHCl$_3$/isopropanol 3:1 mixture and washed with 5% LiCl solution (2×50 mL) and water (50 mL). The organic layer was dried over anhydrous sodium sulfate concentrated to an orange residue. The material was purified by flash chromatography (MeOH/CH$_2$Cl$_2$) to afford the expected product (140 mg, 38%) as a yellow solid. ESI MS m/z 533, [C$_{25}$H$_{33}$BrN$_4$O$_4$+H]$^+$ Example 1083

(S)-tert-butyl 2-(((1r,4S)-4-(3-acetyl-6-bromoquinolin-4-ylamino)cyclohexylcarbamoyl)pyrrolidine-1-carboxylate

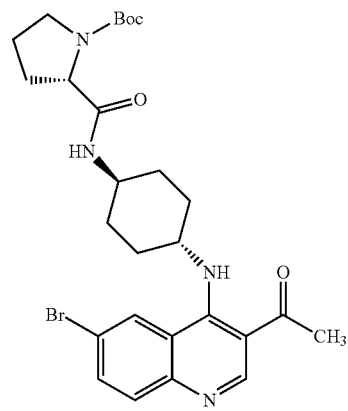 [SMILES: CC(=O)c1cnc2ccc(Br)cc2c1N[C@H]1CC[C@H](NC(=O)[C@@H]2CCCN2C(=O)OC(C)(C)C)CC1]

A solution of (S)-1-(tert-butoxycarbonyl)pyrrolidine-2-carboxylic acid (174 mg, 0.812 mmol) and HATU (308 mg, 0.812 mmol) was stirred at rt for 10 min followed by the addition of N,N-diisopropylethylamine (650 μL, 3.38 mmol) and 1-(4-(1R,4R)-4-aminocyclohexylamino)-6-bromoquinolin-3-yl)ethanone (300 mg, 0.677 mmol) and the resulting solution was stirred at room temperature for 16 h. The completed reaction was diluted in 50 mL of CHCl$_3$/isopropanol 3:1 mixture and washed with 5% LiCl solution (2×50 mL) and water (50 mL). The organic layer was isolated and dried over anhydrous sodium sulfate and reduced to a orange residue. The material was purified by flash chromatography (MeOH/CH$_2$Cl$_2$) to afford the expected product (273 mg, 72%) as a yellow solid. ESI MS m/z 559, [C$_{27}$H$_{35}$BrN$_4$O$_4$+H]$^+$ Example 1084

(S)-tert-butyl 2-(((1r,4S)-4-(3-acetyl-6-bromoquinolin-4-ylamino)cyclohexylcarbamoyl)pyrrolidine-1-carboxylate

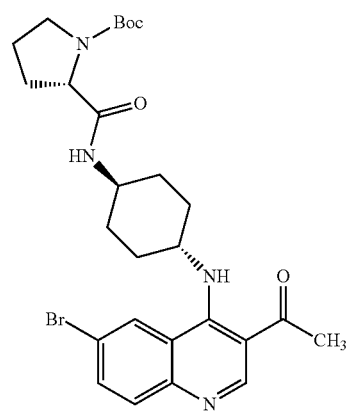 [SMILES: CC(=O)c1cnc2ccc(Br)cc2c1N[C@H]1CC[C@H](NC(=O)[C@@H]2CCCN2C(=O)OC(C)(C)C)CC1]

A solution of (S)-1-(tert-butoxycarbonyl)pyrrolidine-2-carboxylic acid (174 mg, 0.812 mmol) and HATU (308 mg, 0.812 mmol) in DMF (5 mL) was stirred at rt for 10 min followed by the addition of N,N-diisopropylethylamine (650 µL, 3.38 mmol) and 1-(4-(((1R,4R)-4-aminocyclohexylamino)-6-bromoquinolin-3-yl)ethanone (300 mg, 0.677 mmol) and the resulting solution was stirred at room temperature for 16 h. The completed reaction was diluted in 50 mL of $CHCl_3$/isopropanol 3:1 mixture and washed with 5% LiCl solution (2×50 mL) and water (50 mL). The organic layer was isolated and dried over anhydrous sodium sulfate and reduced to a orange residue. The material was purified by flash chromatography ($MeOH/CH_2Cl_2$) to afford the expected product (273 mg, 72%) as a yellow solid. ESI MS m/z 559, $[C_{27}H_{35}BrN_4O_4+H]^+$ Example 1085

(S)-tert-butyl 1-(5-(6-bromo-3-propionylquinolin-4-ylamino)pyridin-2-yl)piperidin-3-ylcarbamate

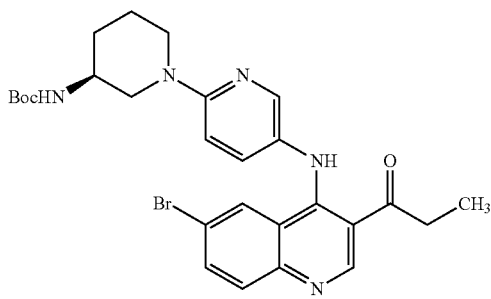 [SMILES: CCC(=O)c1cnc2ccc(Br)cc2c1Nc1ccc(N2CCC[C@H](NC(=O)OC(C)(C)C)C2)nc1]

Following general procedure C, 1-(6-bromo-4-chloroquinolin-3-yl)propan-1-one (301 mg, 1.02 mmol) was reacted with (S)-tert-butyl 1-(5-aminopyridin-2-yl)piperidin-3-ylcarbamate (600 mg, 2.05 mmol) to obtain the desired product (168 mg, 30%) as an purple semi-solid.: ESI MS m/z 554 $[C_{27}H_{32}BrN_5O_3+H]^+$.

Example 1086 tert-butyl 1-(5-aminopyridin-2-yl)piperidin-4-ylcarbamate

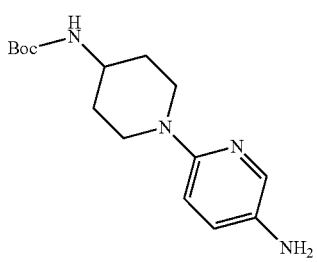 [SMILES: CC(C)(C)OC(=O)NC1CCN(c2ccc(N)cn2)CC1]

Following General procedure H, 2-chloro-5-nitropyridine (500 mg, 3.1 mmol) was reacted with tert-butyl piperidin-4-ylcarbamate (695 mg, 3.5 mmol) followed by reduction to afford the desired product (744 mg, 80%) as a purple solid: ESI MS m/z 293 $[C_{15}H_{24}N_4O_2+H]^+$.

Example 1087 tert-butyl 1-(5-aminopyrimidin-2-yl)piperidin-4-ylcarbamate

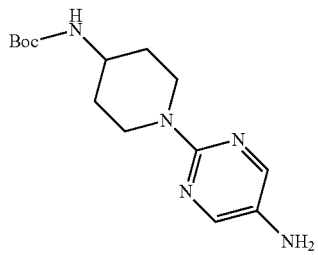 [SMILES: CC(C)(C)OC(=O)NC1CCN(c2ncc(N)cn2)CC1]

Following General procedure H, 2-chloro-5-nitropyrimidine (500 mg, 3.1 mmol) was reacted with tert-butyl piperidin-4-ylcarbamate (683 mg, 3.5 mmol) followed by reduction to afford the desired product (792 mg, 87%) as a purple solid: ESI MS m/z 294 $[C_{14}H_{23}N_5O_2+H]^+$.

Example 1088 tert-butyl 1-(5-aminopyridin-2-yl)piperidin-3-ylcarbamate

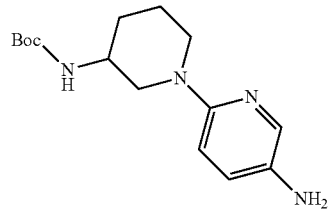 [SMILES: CC(C)(C)OC(=O)NC1CCCN(c2ccc(N)cn2)C1]

Following General procedure H, 2-chloro-5-nitropyridine (500 mg, 3.1 mmol) was reacted with tert-butyl piperidin-3-ylcarbamate (695 mg, 3.5 mmol) followed by reduction to afford the desired product (847 mg, 93%) as a purple solid: ESI MS m/z 293 $[C_{15}H_{24}N_4O_2+H]^+$.

Example 1089 tert-butyl 1-(5-aminopyrimidin-2-yl)piperidin-3-ylcarbamate

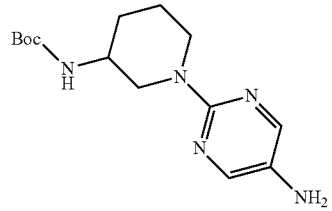

Following General procedure H, 2-chloro-5-nitropyrimidine (500 mg, 3.1 mmol) was reacted with tert-butyl piperidin-3- ylcarbamate (683 mg, 3.5 mmol) followed by reduction to afford the desired product (762 mg, 84%) as a purple solid: ESI MS m/z 294 $[C_{14}H_{23}N_5O_2+H]^+$.

Example 1090

(S)-tert-butyl 1-(5-aminopyridin-2-yl)piperidin-3-ylcarbamate

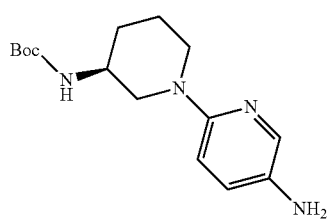 [SMILES: CC(C)(C)OC(=O)N[C@H]1CCCN(c2ccc(N)cn2)C1]

Following General procedure H, 2-chloro-5-nitropyridine (500 mg, 3.1 mmol) was reacted with (S)-tert-butyl piperidin-4-ylcarbamate (695 mg, 3.5 mmol) followed by reduction to afford the desired product (945 mg, quant.) as a purple solid: ESI MS m/z 293 $[C_{15}H_{24}N_4O_2+H]^+$.

Example 1091

(R)-tert-butyl 1-(5-aminopyridin-2-yl)piperidin-3-ylcarbamate

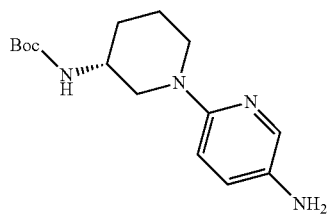 [SMILES: CC(C)(C)OC(=O)N[C@@H]1CCCN(c2ccc(N)cn2)C1]

Following General procedure H, 2-chloro-5-nitropyridine (500 mg, 3.1 mmol) was reacted with tert-butyl piperidin-4-ylcarbamate (695 mg, 3.5 mmol) followed by reduction to afford the desired product (872 mg, 96%) as a purple solid: ESI MS m/z 293 $[C_{15}H_{24}N_4O_2+H]^+$.

Example 1092 tert-butyl 1-(5-aminopyridin-2-yl)pyrrolidin-3-ylcarbamate

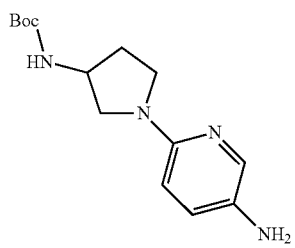 [SMILES: CC(C)(C)OC(=O)NC1CCN(c2ccc(N)cn2)C1]

Following General procedure H, 2-chloro-5-nitropyridine (500 mg, 3.1 mmol) was reacted with tert-butyl pyrrolidin-3-ylcarbamate (931 mg, 5 mmol) followed by reduction to afford the desired product (813 mg, 94%) as a purple solid: ESI MS m/z 279 $[C_{14}H_{22}N_4O_2+H]^+$.

Example 1093 tert-butyl 1-(5-aminopyrimidin-2-yl)pyrrolidin-3-ylcarbamate

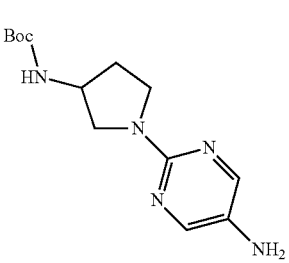 [SMILES: CC(C)(C)OC(=O)NC1CCN(c2ncc(N)cn2)C1]

Following General procedure H, 2-chloro-5-nitropyrimidine (500 mg, 3.1 mmol) was reacted with tert-butyl pyrrolidin-3-ylcarbamate (632 mg, 3.5 mmol) followed by reduction to afford the desired product (565 mg, 65%) as a purple solid: ESI MS m/z 280 $[C_{13}H_{21}N_5O_2+H]^+$.

Example 1094 tert-butyl 3-(5-aminopyridin-2-ylamino)piperidine-1-carboxylate

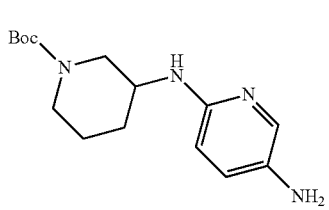 [SMILES: CC(C)(C)OC(=O)N1CCCC(Nc2ccc(N)cn2)C1]

Following General procedure H, 2-chloro-5-nitropyridine (500 mg, 3.1 mmol) was reacted with tert-butyl 3-aminopiperidine-1-carboxylate (695 mg, 3.5 mmol) followed by reduction to afford the desired product (337 mg, 35%) as a purple solid: ESI MS m/z 293 $[C_{15}H_{24}N_4O_2+H]^+$.

Example 1095 tert-butyl 3-(5-aminopyridin-2-ylamino)pyrrolidine-1-carboxylate

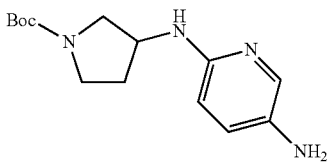

Following General procedure H, 2-chloro-5-nitropyridine (500 mg, 3.1 mmol) was reacted with tert-butyl 3-aminopyrrolidine-1-carboxylate (632 mg, 3.5 mmol) followed by reduction to afford the desired product (407 mg, 47%) as a purple solid: ESI MS m/z 279 $[C_{14}H_{22}N_4O_2+H]^+$.

Example 1096

1-(5-aminopyridin-2-yl)pyrrolidin-3-ol

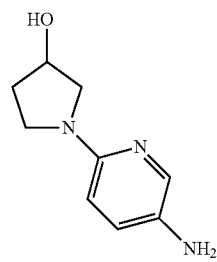 [SMILES: Nc1ccc(N2CCC(O)C2)nc1]

Following General procedure H, 2-chloro-5-nitropyridine (500 mg, 3.1 mmol) was reacted with pyrrolidin-3-ol (330 mg, 3.5 mmol) followed by reduction to afford the desired product (440 mg, 52%) as a purple solid: ESI MS m/z 180 $[C_9H_{13}N_3O+H]^+$.

Example 1097

6-(3-(dimethylamino)pyrrolidin-1-yl)pyridin-3-amine

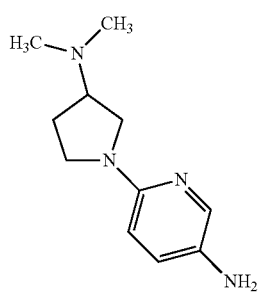

Following General procedure H, 2-chloro-5-nitropyridine (500 mg, 3.1 mmol) was reacted with N,N-dimethylpyrrolidin-3-amine (400 mg, 3.5 mmol) followed by reduction to afford the desired product (360 mg, 56%) as a purple solid: ESI MS m/z 207 $[C_{11}H_{18}N_4+H]^+$.

Example 1098

2-(5-aminopyridin-2-ylamino)ethanol

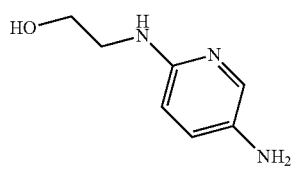 [SMILES: Nc1ccc(NCCO)nc1]

Following General procedure H, 2-chloro-5-nitropyridine (500 mg, 3.1 mmol) was reacted with 2-aminoethanol (213 mg, 3.5 mmol) followed by reduction to afford the desired product (306 mg, 65%) as a purple solid: ESI MS m/z 154 $[C_7H_{11}N_3O+H]^+$.

Example 1099

$N^2$-(2-(dimethylamino)ethyl)pyridine-2,5-diamine

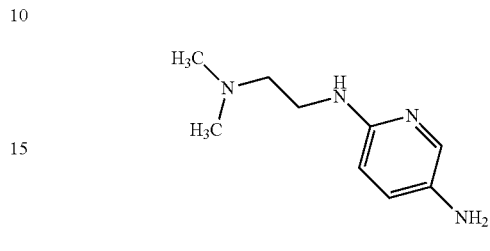

Following General procedure H, 2-chloro-5-nitropyridine (500 mg, 3.1 mmol) was reacted with $N^1,N^1$-dimethylethane-1,2-diamine (308 mg, 3.5 mmol) followed by reduction to afford the desired product (280 mg, 50%) as a purple solid: ESI MS m/z 181 $[C_9H_{16}N_4+H]^+$.

Example 1100

6-(2-(dimethylamino)ethoxy)pyridin-3-amine

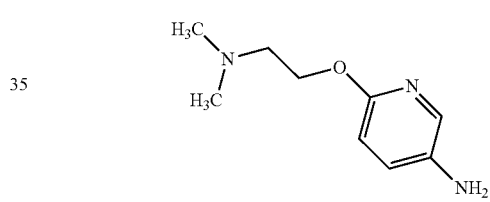

Following General procedure 1,2-chloro-5-nitropyridine (500 mg, 3.1 mmol) was reacted with 2-(dimethylamino)ethanol (309 mg, 3.5 mmol) followed by reduction to afford the desired product (340 mg, 61%) as a purple solid: ESI MS m/z 182 $[C_9H_{15}N_3O+H]^+$.

Example 1101 tert-butyl 2-(5-aminopyridin-2-yloxy)ethylcarbamate

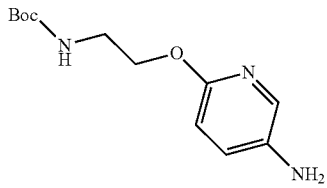 [SMILES: CC(C)(C)OC(=O)NCCOc1ccc(N)cn1]

Following General procedure 1,2-chloro-5-nitropyridine (500 mg, 3.1 mmol) was reacted with tert-butyl 2-hydroxyethylcarbamate (560 mg, 3.5 mmol) followed by reduction to afford the desired product (410 mg, 52%) as a purple solid: ESI MS m/z 254 $[C_{12}H_{19}N_3O_3+H]^+$.

Example 1102 tert-butyl 1-(4-aminopyridin-2-yl)piperidin-4-ylcarbamate

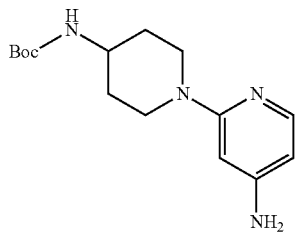 [SMILES: CC(C)(C)OC(=O)NC1CCN(c2cc(N)ccn2)CC1]

Following General procedure H, 2-chloro-4-nitropyridine (500 mg, 3.1 mmol) was reacted with tert-butyl piperidin-4-ylcarbamate (695 mg, 3.5 mmol) followed by reduction to afford the desired product (300 mg, 33%) as a purple solid: ESI MS m/z 293 $[C_{15}H_{24}N_4O_2+H]^+$.

Example 1103 tert-butyl 5-aminopyridin-2-ylcarbamate

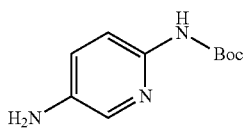

A solution of 5-nitropyridin-2-amine (500 mg, 3.5 mmol) in acetonitrile (10 mL), triethylamine (2.5 equiv) and dimethylaminopyridine (0.05 equiv) was stirred for 10 min followed by addition of di-tert-butyl dicarbonate (1 equiv). The reaction mixture was stirred at room temperature until the reaction was complete (by LCMS analysis). The reaction was concentrated and the residue was suspended in methanol and filtered. The n a glass clave, the crude product was dissolved in tertrahydrofuran (0.1 M), degassed with nitrogen and Pd/C (10%, 0.1 equiv) was added to the mixture. The clave was charged with hydrogen (40 Psi) and shaked at room temperature until the reduction was completed as indicated by LCMS analysis. The pressure was released and the reaction mixture was filtrated over a pad of celite. The filtrate was concentrated to obtain the desired product (437 mg, 60%) as a white solid: ESI MS m/z 210 [C10H15N3O2+H]$^+$.

Example 1104

4-(3-methoxypyrrolidin-1-yl)cyclohexanamine

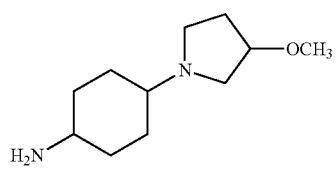

Following General procedure 1,3-methoxypyrrolidine hydrochloride (448 mg, 3.26 mmol) was reacted with tert-butyl 4-oxocyclohexylcarbamate (500 mg, 2.34 mmol) to afford the desired product (452 mg, 97%) as a yellow solid: ESI MS m/z 187 $[C_{11}H_{22}N_2O+H]^+$.

Example 1105

(R)-4-(3-fluoropyrrolidin-1-yl)cyclohexanamine

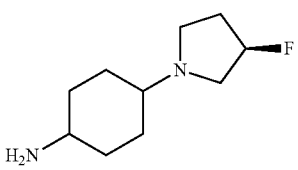

Following General procedure I, (R)-3-fluoropyrrolidine hydrochloride (407 mg, 3.26 mmol) was reacted with tert-butyl 4-oxocyclohexylcarbamate (500 mg, 2.34 mmol) to afford the desired product (200 mg, 51%) as a colorless oil: ESI MS m/z 187 $[C_{10}H_{19}FN_2+H]^+$.

Example 1106

4-(3,3-difluoropyrrolidin-1-yl)cyclohexanamine

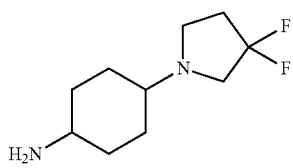

Following General procedure I, 3,3-difluoropyrrolidine hydrochloride (468 mg, 3.26 mmol) was reacted with tert-butyl 4-oxocyclohexylcarbamate (500 mg, 2.34 mmol) to afford the desired product (507 mg, quant.) as a colorless oil: ESI MS m/z 205 $[C_{10}H_{18}F_2N_2+H]^+$.

Example 1107 tert-butyl 1-(5-(6-bromo-3-(cyclopropanecarbonyl)quinoline-4-ylamino)pyridin-2-yl)piperidin-4-ylcarbamate

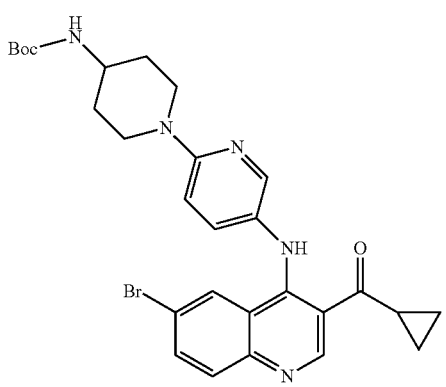 [SMILES: CC(C)(C)OC(=O)NC1CCN(c2ccc(Nc3c(C(=O)C4CC4)cnc4ccc(Br)cc34)cn2)CC1]

Following General procedure C, (6-bromo-4-chloroquinolin-3-yl)(cyclopropyl)methanone (311 mg, 1 mmol) was reacted with tert-butyl 1-(5-aminopyridin-2-yl)piperidin-4-ylcarbamate (439 mg, 1.5 mmol) to afford the desired product (423 mg, 75%) as a yellow solid: ESI MS m/z 566 $[C_{28}H_{32}BrN_5O_3+H]^+$.

Example 1108 tert-butyl 1-(5-(6-bromo-3-(cyclopropanecarbonyl)quinolin-4-ylamino) pyrimidin-2-yl)piperidin-4-ylcarbamate

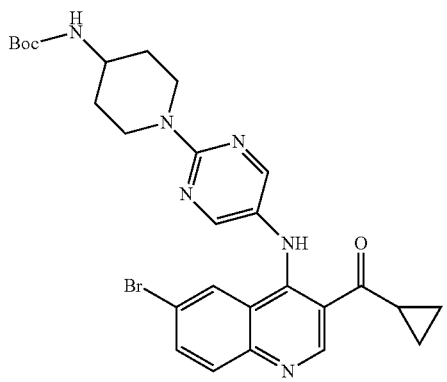 [SMILES: CC(C)(C)OC(=O)NC1CCN(c2ncc(Nc3c(C(=O)C4CC4)cnc4ccc(Br)cc34)cn2)CC1]

Following General procedure C, (6-bromo-4-chloroquinolin-3-yl)(cyclopropyl)methanone (311 mg, 1 mmol) was reacted with tert-butyl 1-(5-aminopyrimidin-2-yl)piperidin-4-ylcarbamate (440 mg, 1.5 mmol) to afford the desired product (374 mg, 66%) as a yellow solid: ESI MS m/z 567 $[C_{27}H_{31}BrN_6O_3+H]^+$.

Example 1109 tert-butyl 1-(5-(6-bromo-3-(cyclopropanecarbonyl)quinolin-4-ylamino) pyridin-2-ylpiperidin-3-ylcarbamate

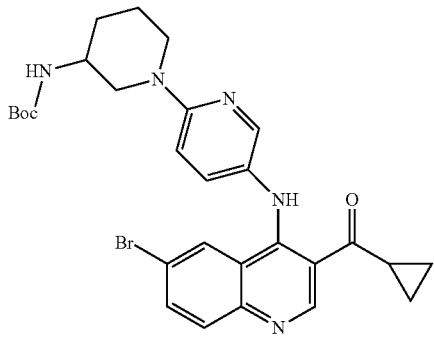

Following General procedure C, (6-bromo-4-chloroquinolin-3-yl)(cyclopropyl)methanone (311 mg, 1 mmol) was reacted with tert-butyl 1-(5-aminopyridin-2-yl)piperidin-3-ylcarbamate (439 mg, 1.5 mmol) to afford the desired product (523 mg, 92%) as a yellow solid: ESI MS m/z 566 $[C_{28}H_{32}BrN_5O_3+H]^+$.

Example 1110 tert-butyl 1-(5-(6-bromo-3-(cyclopropanecarbonyl)quinolin-4-ylamino)pyrimidin-2-yl)piperidin-3-ylcarbamate

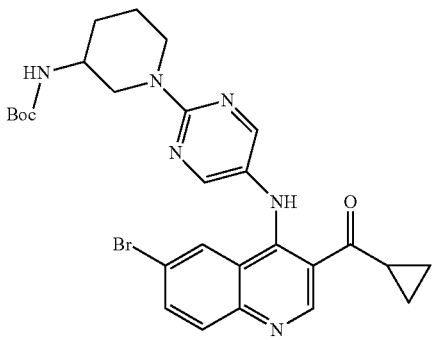

Following General procedure C, (6-bromo-4-chloroquinolin-3-yl)(cyclopropyl)methanone (311 mg, 1 mmol) was reacted with tert-butyl 1-(5-aminopyrimidin-2-yl)piperidin-3-ylcarbamate (440 mg, 1.5 mmol) to afford the desired product (462 mg, 80%) as a yellow solid: ESI MS m/z 567 $[C_{27}H_{31}BrN_6O_3+H]^+$.

Example 1111

(S)-tert-butyl 1-(5-(6-bromo-3-(cyclopropanecarbonyl)quinolin-4-ylamino)pyridin-2-yl)piperidin-3-ylcarbamate

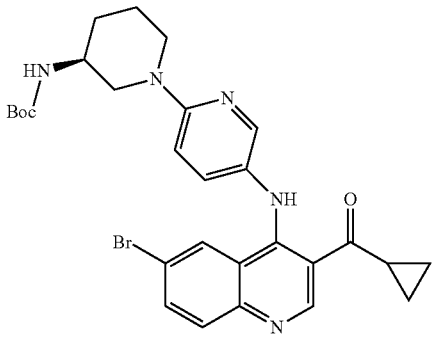 [SMILES: CC(C)(C)OC(=O)N[C@H]1CCCN(c2ccc(Nc3c(C(=O)C4CC4)cnc4ccc(Br)cc34)cn2)C1]

Following General procedure C, (6-bromo-4-chloroquinolin-3-yl)(cyclopropyl)methanone (311 mg, 1 mmol) was reacted with (S)-tert-butyl 1-(5-aminopyridin-2-yl)piperidin-3-ylcarbamate (439 mg, 1.5 mmol) to afford the desired product (527 mg, 93%) as a yellow solid: ESI MS m/z 566 $[C_{28}H_{32}BrN_5O_3+H]^+$.

Example 1112

(R)-tert-butyl 1-(5-(6-bromo-3-(cyclopropanecarbonyl)quinolin-4-ylamino)pyridin-2-yl)piperidin-3-ylcarbamate

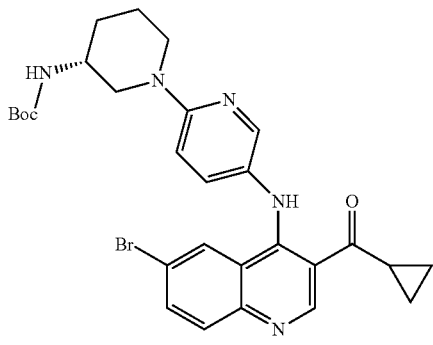 [SMILES: CC(C)(C)OC(=O)N[C@@H]1CCCN(c2ccc(Nc3c(C(=O)C4CC4)cnc4ccc(Br)cc34)cn2)C1]

Following General procedure C, (6-bromo-4-chloroquinolin-3-yl)(cyclopropyl)methanone (311 mg, 1 mmol) was reacted with (R)-tert-butyl 1-(5-aminopyridin-2-yl)piperidin-3-ylcarbamate (439 mg, 1.5 mmol) to afford the desired product (516 mg, 91%) as a yellow solid:: ESI MS m/z 566 $[C_{28}H_{32}BrN_5O_3+H]^+$.

Example 1113 tert-butyl 1-(5-(6-bromo-3-(cyclopropanecarbonyl)quinolin-4-ylamino)pyridin-2-yl)pyrrolidin-3-ylcarbamate

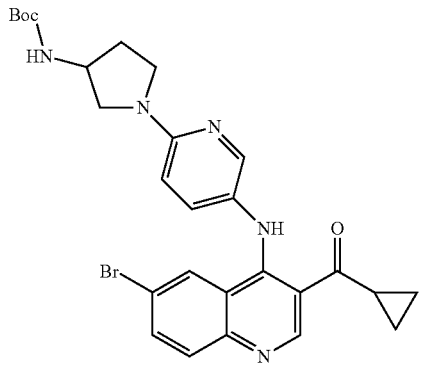 [SMILES: CC(C)(C)OC(=O)NC1CCN(c2ccc(Nc3c(C(=O)C4CC4)cnc4ccc(Br)cc34)cn2)C1]

Following General procedure C, (6-bromo-4-chloroquinolin-3-yl)(cyclopropyl)methanone (311 mg, 1 mmol) was reacted with tert-butyl 1-(5-aminopyridin-2-yl)pyrrolidin-3-ylcarbamate (417 mg, 1.5 mmol) to afford the desired product (488 mg, 88%) as a yellow solid: ESI MS m/z 552 $[C_{27}H_{30}BrN_5O_3+H]^+$.

Example 1114 tert-butyl 1-(5-(6-bromo-3-(cyclopropanecarbonyl)quinolin-4-ylamino)pyrimidin-2-yl)pyrrolidin-3-ylcarbamate

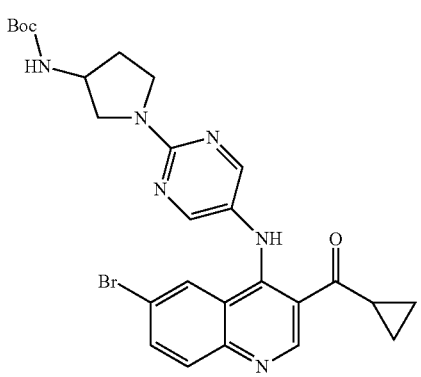 [SMILES: CC(C)(C)OC(=O)NC1CCN(c2ncc(Nc3c(C(=O)C4CC4)cnc4ccc(Br)cc34)cn2)C1]

Following General procedure C, (6-bromo-4-chloroquinolin-3-yl)(cyclopropyl)methanone (311 mg, 1 mmol) was reacted with tert-butyl 1-(5-aminopyrimidin-2-yl)pyrrolidin-3-ylcarbamate (418 mg, 1.5 mmol) to afford the desired product (336 mg, 61%) as a yellow solid: ESI MS m/z 553 $[C_{26}H_{29}BrN_6O_3+H]^+$.

Example 1115 tert-butyl 3-(5-(6-bromo-3-(cyclopropanecarbonyl)quinolin-4-ylamino)pyridin-2-ylamino)piperidine-1-carboxylate

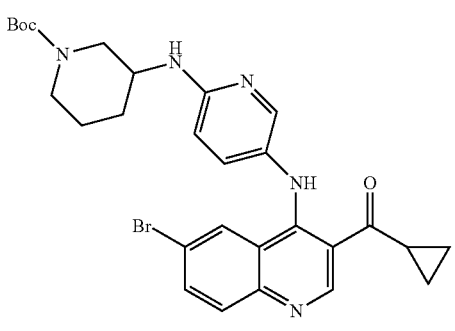 [SMILES: CC(C)(C)OC(=O)N1CCCC(Nc2ccc(Nc3c(C(=O)C4CC4)cnc4ccc(Br)cc34)cn2)C1]

Following General procedure C, (6-bromo-4-chloroquinolin-3-yl)(cyclopropyl)methanone (239 mg, 0.8 mmol) was reacted with tert-butyl 3-(5-aminopyridin-2-ylamino)piperidine-1-carboxylate (337 mg, 1.1 mmol) to afford the desired product (300 mg, 69%) as a yellow solid: ESI MS m/z 566 [$C_{28}H_{32}BrN_5O_3$+H]$^+$.

Example 1116 tert-butyl 3-(5-(6-bromo-3-(cyclopropanecarbonyl)quinolin-4-ylamino)pyridin-2-ylamino)pyrrolidine-1-carboxylate

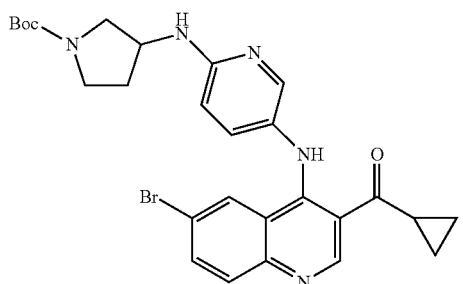

Following General procedure C, (6-bromo-4-chloroquinolin-3-yl)(cyclopropyl)methanone (311 mg, 1 mmol) was reacted with tert-butyl 3-(5-aminopyridin-2-ylamino)pyrrolidine-1-carboxylate (417 mg, 1.5 mmol) to afford the desired product (450 mg, 98%) as a yellow solid: ESI MS m/z 552 [$C_{27}H_{30}BrN_5O_3$+H]$^+$.

Example 1117

(6-bromo-4-(6-(3-hydroxypyrrolidin-1-yl)pyridin-3-ylamino)quinolin-3-yl)(cyclopropyl)methanone

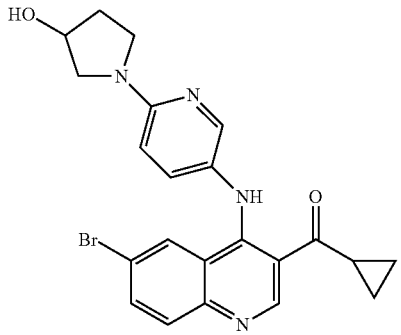 [SMILES: O=C(c1cnc2ccc(Br)cc2c1Nc1ccc(N2CCC(O)C2)nc1)C1CC1]

Following General procedure C, (6-bromo-4-chloroquinolin-3-yl)(cyclopropyl)methanone (311 mg, 1 mmol) was reacted with 1-(5-aminopyridin-2-yl)pyrrolidin-3-ol (269 mg, 1.5 mmol) to afford the desired product (234 mg, 51%) as a yellow solid: ESI MS m/z 453 [$C_{22}H_{21}BrN_4O_2$+H]$^+$.

Example 1118

(6-bromo-4-(6-(3-(dimethylamino)pyrrolidin-1-yl)pyridin-3-ylamino)quinolin-3-yl)(cyclopropyl)methanone

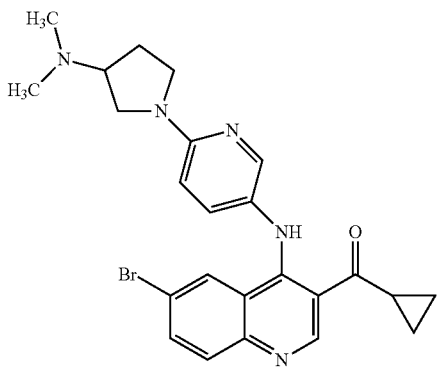 [SMILES: CN(C)C1CCN(c2ccc(Nc3c(C(=O)C4CC4)cnc4ccc(Br)cc34)cn2)C1]

Following General procedure C, (6-bromo-4-chloroquinolin-3-yl)(cyclopropyl)methanone (311 mg, 1 mmol) was reacted with 6-(3-(dimethylamino)pyrrolidin-1-yl)pyridin-3-amine (309 mg, 1.5 mmol) to afford the desired product (342 mg, 71%) as a yellow solid: ESI MS m/z 480 [$C_{24}H_{26}BrN_5O$+H]$^+$.

Example 1119

(6-bromo-4-(6-(2-hydroxyethylamino)pyridin-3-ylamino)quinolin-3-yl)(cyclopropyl)methanone

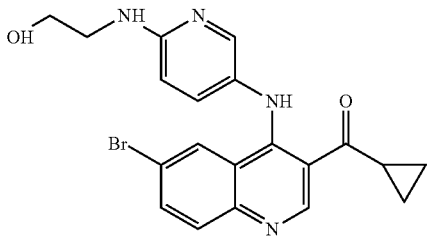 [SMILES: O=C(c1cnc2ccc(Br)cc2c1Nc1ccc(NCCO)nc1)C1CC1]

Following General procedure C, (6-bromo-4-chloroquinolin-3-yl)(cyclopropyl)methanone (311 mg, 1 mmol) was reacted with 2-(5-aminopyridin-2-ylamino)ethanol (230 mg, 1.5 mmol) to afford the desired product (287 mg, 67%) as a yellow solid: ESI MS m/z 427 [$C_{20}H_{19}BrN_4O_2$+H]$^+$.

Example 1120

(6-bromo-4-(6-(2-(dimethylamino)ethylamino)pyridin-3-ylamino)quinolin-3-yl)(cyclopropyl)methanone

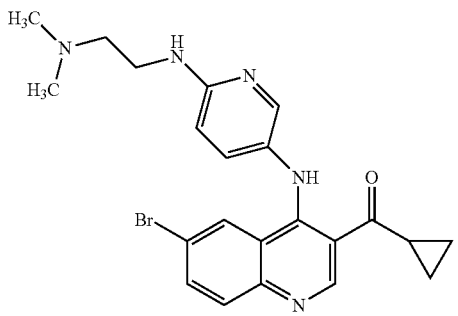 [SMILES: CN(C)CCNc1ccc(Nc2c(C(=O)C3CC3)cnc3ccc(Br)cc23)cn1]

Following General procedure C, (6-bromo-4-chloroquinolin-3-yl)(cyclopropyl)methanone (311 mg, 1 mmol) was reacted with $N^2$-(2-(dimethylamino)ethyl)pyridine-2,5-diamine (270 mg, 1.5 mmol) to afford the desired product (300 mg, 66%) as a yellow solid: ESI MS m/z 454 $[C_{22}H_{24}BrN_5O+H]^+$.

Example 1121

(6-bromo-4-(6-(2-(dimethylamino)ethoxy)pyridin-3-ylamino)quinolin-3-yl)(cyclopropyl)methanone

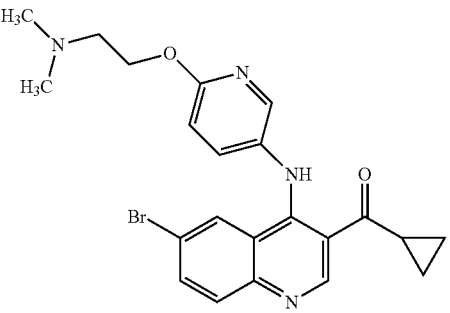 [SMILES: CN(C)CCOc1ccc(Nc2c(C(=O)C3CC3)cnc3ccc(Br)cc23)cn1]

Following General procedure C, (6-bromo-4-chloroquinolin-3-yl)(cyclopropyl)methanone (311 mg, 1 mmol) was reacted with 6-(2-(dimethylamino)ethoxy)pyridin-3-amine (340 mg, 1.8 mmol) to afford the desired product (340 mg, 75%) as a yellow solid: ESI MS m/z 455 $[C_{22}H_{23}BrN_4O_2+H]^+$.

Example 1122 tert-butyl 2-(5-(6-bromo-3-(cyclopropanecarbonyl)quinolin-4-ylamino) pyridin-2-yloxy)ethylcarbamate

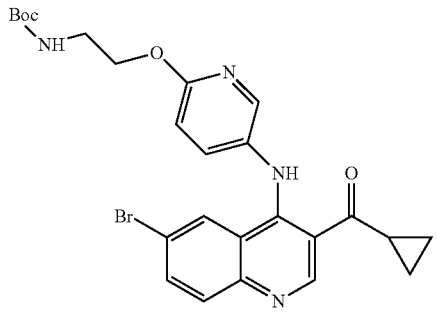 [SMILES: CC(C)(C)OC(=O)NCCOc1ccc(Nc2c(C(=O)C3CC3)cnc3ccc(Br)cc23)cn1]

Following General procedure C, (6-bromo-4-chloroquinolin-3-yl)(cyclopropyl)methanone (311 mg, 1 mmol) was reacted with tert-butyl 2-(5-aminopyridin-2-yloxy)ethylcarbamate (380 mg, 1.5 mmol) to afford the desired product (332 mg, 63%) as a yellow solid: ESI MS m/z 527 $[C_{25}H_{27}BrN_4O_4+H]^+$.

Example 1123 tert-butyl 1-(4-(6-bromo-3-(cyclopropanecarbonyl)quinolin-4-ylamino)pyridin-2-yl)piperidin-4-ylcarbamate

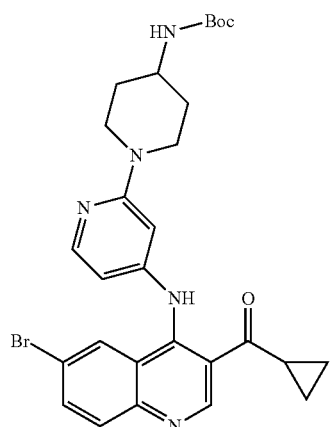

Following General procedure C, (6-bromo-4-chloroquinolin-3-yl)(cyclopropyl)methanone (211 mg, 0.7 mmol) was reacted with tert-butyl 1-(4-aminopyridin-2-yl)piperidin-4-ylcarbamate (300 mg, 1 mmol) to afford the desired product (120 mg, 30%) as a yellow solid: ESI MS m/z 566 $[C_{28}H_{32}BrN_5O_3+H]^+$.

Example 1124

(6-bromo-4-(4-(2-(dimethylamino)ethyl)phenylamino)quinolin-3-yl)(cyclopropyl)methanone

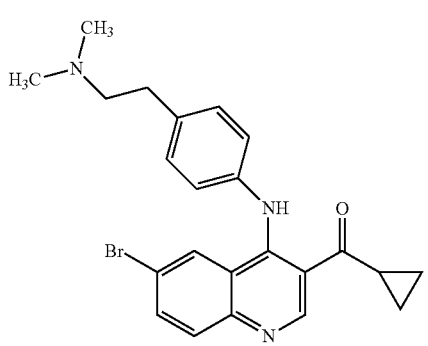 [SMILES: CN(C)CCc1ccc(Nc2c(C(=O)C3CC3)cnc3ccc(Br)cc23)cc1]

Following General procedure C, (6-bromo-4-chloroquinolin-3-yl)(cyclopropyl)methanone (311 mg, 1 mmol) was reacted with 4-(2-(dimethylamino)ethyl)aniline (247 mg, 1.5 mmol)

to afford the desired product (324 mg, 73%) as a yellow solid: ESI MS m/z 438 $[C_{23}H_{24}BrN_3O+H]^+$.

Example 1125

(6-bromo-4-(3-((dimethylamino)methyl)phenylamino)quinolin-3-yl)(cyclopropyl)methanone

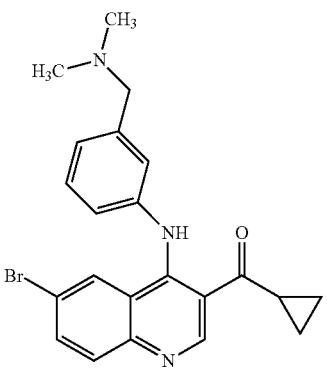 [SMILES: CN(C)Cc1cccc(Nc2c(C(=O)C3CC3)cnc3ccc(Br)cc23)c1]

Following General procedure C, (6-bromo-4-chloroquinolin-3-yl)(cyclopropyl)methanone (311 mg, 1 mmol) was reacted with 3-((dimethylamino)methyl)aniline (226 mg, 1.5 mmol) to afford the desired product (343 mg, 810%) as a yellow solid: ESI MS m/z 424 $[C_{22}H_{22}BrN_3O+H]^+$.

Example 1126 tert-butyl 1-(5-(3-acetyl-6-bromoquinolin-4-ylamino)pyridin-2-yl)pyrrolidin-3-ylcarbamate

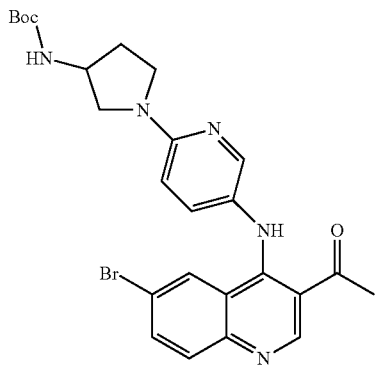 [SMILES: CC(=O)c1cnc2ccc(Br)cc2c1Nc1ccc(N2CCC(NC(=O)OC(C)(C)C)C2)nc1]

Following General procedure C, 1-(6-bromo-4-chloroquinolin-3-yl)ethanone (284 mg, 1 mmol) was reacted with tert-butyl 1-(5-aminopyridin-2-yl)pyrrolidin-3-ylcarbamate (439 mg, 1.5 mmol) to afford the desired product (240 mg, 46%) as a yellow solid: ESI MS ink 526 $[C_{25}H_{28}BrN_5O_3+H]^+$.

Example 1127 tert-butyl 1-(5-(6-bromo-3-propionylquinolin-4-ylamino)pyridin-2-yl)pyrrolidin-3-ylcarbamate

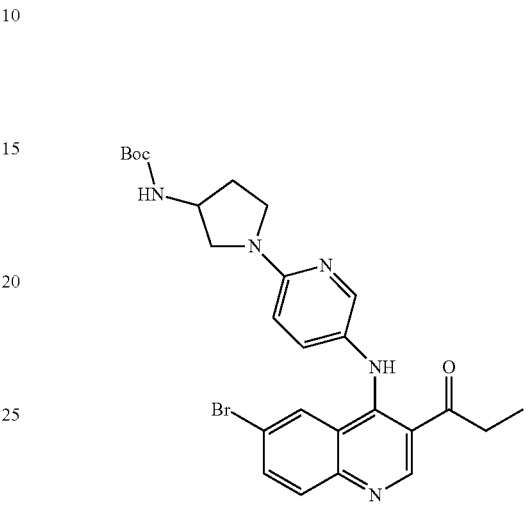

Following General procedure C, 1-(6-bromo-4-chloroquinolin-3-yl)propan-1-one (298 mg, 1 mmol) was reacted with tert-butyl 1-(5-aminopyridin-2-yl)pyrrolidin-3-ylcarbamate (439 mg, 1.5 mmol) to afford the desired product (332 mg, 61%) as a yellow solid: ESI MS m/z 540 $[C_{26}H_{30}BrN_5O_3+H]^+$.

Example 1128

1-(6-bromo-4-(4-(2-(dimethylamino)ethyl)phenylamino)quinolin-3-yl)ethanone

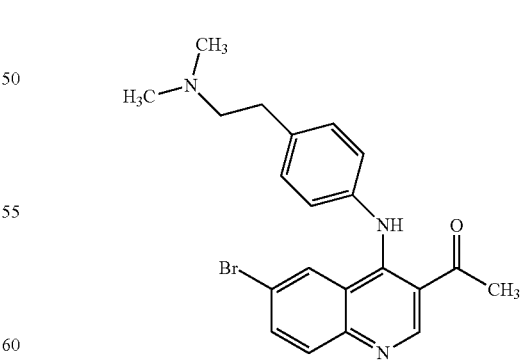

Following General procedure C, 1-(6-bromo-4-chloroquinolin-3-yl)ethanone (285 mg, 1 mmol) was reacted with 4-(2-

(dimethylamino)ethyl)aniline (247 mg, 1.5 mmol) to afford the desired product (2284 mg, 55%) as a yellow solid: ESI MS m/z 412 $[C_{21}H_{22}BrN_3O+H]^+$.

Example 1129

1-(6-bromo-4-(6-(2-(dimethylamino)ethylamino)pyridin-3-ylamino)quinolin-3-yl)ethanone

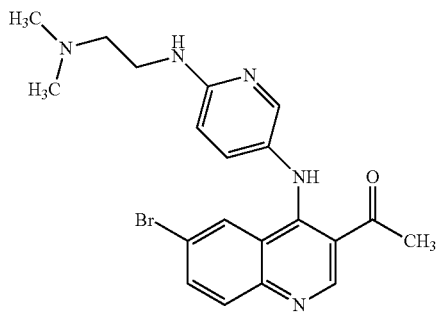 [SMILES: CC(=O)c1cnc2ccc(Br)cc2c1Nc1ccc(NCCN(C)C)nc1]

Following General procedure C, 1-(6-bromo-4-chloroquinolin-3-yl)ethanone (284 mg, 1 mmol) was reacted with $N^2$-(2-(dimethylamino)ethyl)pyridine-2,5-diamine (270 mg, 1.5 mmol) to afford the desired product (320 mg, 74%) as a yellow solid: ESI MS m/z 428 $[C_{20}H_{22}BrN_5O+H]^+$.

Example 1130

(R)-(6-bromo-4-(4-(3-fluoropyrrolidin-1-yl)cyclohexylamino)quinolin-3-yl)(cyclopropyl)methanone

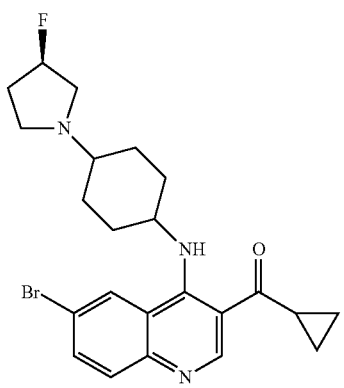 [SMILES: O=C(c1cnc2ccc(Br)cc2c1NC1CCC(N2CC[C@@H](F)C2)CC1)C1CC1]

Following General procedure C, (6-bromo-4-chloroquinolin-3-yl)(cyclopropyl)methanone (278 mg, 0.89 mmol) was reacted with (R)-4-(3-fluoropyrrolidin-1-yl)cyclohexanamine (200 mg, 1.1 mmol) to afford the desired product (307 mg, 75%) as a yellow solid: ESI MS m/z 460 $[C_{23}H_{27}BrFN_3O+H]^+$.

Example 1131

(6-bromo-4-(4-(3,3-difluoropyrrolidin-1-yl)cyclohexylamino)quinolin-3-yl)(cyclopropyl)methanone

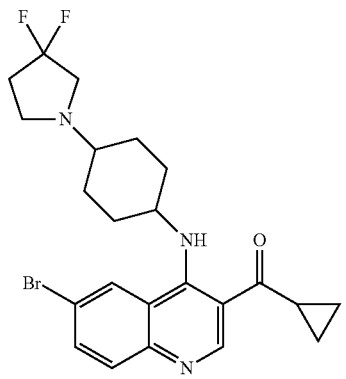 [SMILES: O=C(c1cnc2ccc(Br)cc2c1NC1CCC(N2CCC(F)(F)C2)CC1)C1CC1]

Following General procedure C, (6-bromo-4-chloroquinolin-3-yl)(cyclopropyl)methanone (311 mg, 1 mmol) was reacted with 4-(3,3-difluoropyrrolidin-1-yl)cyclohexanamine (306 mg, 1.5 mmol) to afford the desired product (218 mg, 46%) as a yellow solid: ESI MS m/z 478 $[C_{23}H_{26}BrF_2N_3O+H]^+$.

Example 1132

(6-bromo-4-(4-(3-methoxypyrrolidin-1-yl)cyclohexylamino)quinolin-3-yl)(cyclopropyl)methanone

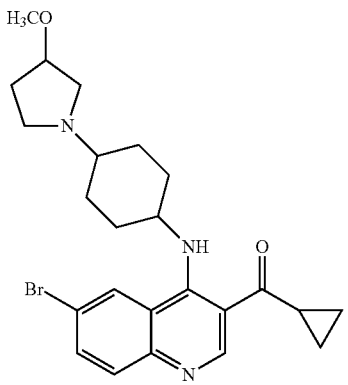 [SMILES: COC1CCN(C2CCC(Nc3c(C(=O)C4CC4)cnc4ccc(Br)cc34)CC2)C1]

Following General procedure C, (6-bromo-4-chloroquinolin-3-yl)(cyclopropyl)methanone (311 mg, 1 mmol) was reacted with 4-(3-methoxypyrrolidin-1-yl)cyclohexanamine (297 mg, 1.5 mmol) to afford the desired product (210 mg, 45%) as a yellow solid: ESI MS m/z 472 $[C_{24}H_{30}BrN_3O_2+H]^+$.

Example 1133 tert-butyl 5-(6-bromo-3-(cyclopropanecarbonyl) quinolin-4-ylamino)pyridin-2-ylcarbamate

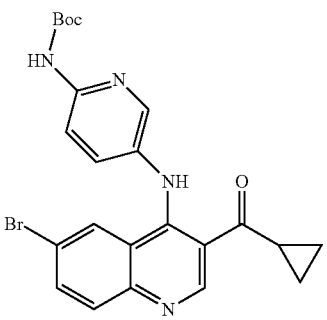 [SMILES: CC(C)(C)OC(=O)Nc1ccc(Nc2c(C(=O)C3CC3)cnc3ccc(Br)cc23)cn1]

Following General procedure C, (6-bromo-4-chloroquinolin-3-yl)(cyclopropyl)methanone (311 mg, 1 mmol) was reacted with tert-butyl 5-aminopyridin-2-ylcarbamate (313 mg, 1.5 mmol) to afford the desired product (352 mg, 72%) as a yellow solid: ESI MS m/z 483 $[C_{23}H_{23}BrN_4O_3+H]^+$.

Example 1134 tert-Butyl 2-(4-nitrophenyl)propan-2-ylcarbamate

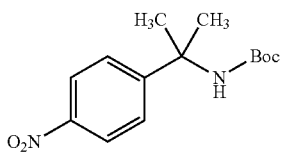 [SMILES: CC(C)(C)OC(=O)NC(C)(C)c1ccc([N+](=O)[O-])cc1]

To a solution of 2-(4-nitrophenyl)propan-2-amine (1.0 g, 4.62 mmol) in dioxane (30 mL) at 0° C. was added a saturated solution of $Na_2CO_3$ (10 mL) and di-tert-butyl dicarbonate (1.95 g, 6.93 mmol) in dioxane (5 mL) and the resultant mixture was stirred at rt overnight. The dioxane was removed under vacuum and the resultant slurry was diluted with water, extracted with $CH_2Cl_2$, dried with $Na_2SO_4$, and concentrated to give crude product (1.86 g) as an orange solid: $^1$H NMR (300 MHz, $CDCl_3$) δ 8.20-8.16 (m, 2H), 7.58-7.54 (m, 2H), 5.02 (s, 1H), 1.58 (s, 6H), 1.53 (s, 9H).

Example 1135 tert-Butyl 2-(4-aminophenyl)propan-2-ylcarbamate

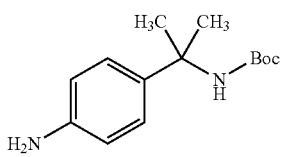

A pressure flask was charged with a suspension of tert-butyl 2-(4-nitrophenyl)propan-2-yl-carbamate (4.62 mmol) in ethanol (20 mL) and palladium on carbon (100 mg). The flask was placed on a Parr shaker, purged with $H_2$ (30 psi), and stirred overnight. The crude product was filtered through celite, concentrated, and chromatographed (hexane:ethyl acetate) to obtain the desired product (420 mg, 36% over two steps) as an orange-red oil: $^1$H NMR (300 MHz, $CDCl_3$) δ 7.26-7.17 (m, 2H), 6.67-6.62 (m, 2H), 4.82 (s, 1H), 1.60 (s, 3H), 1.57 (s, 3H), 1.37 (s, 9H).

Example 1136

2-(Dimethylamino)-1-(4-nitrophenyl)ethanol

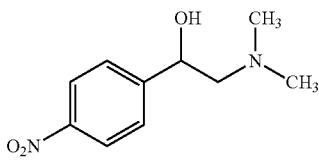

To a solution of 2-amino-1-(4-nitrophenyl)ethanone (500 mg, 2.30 mmol), paraformaldehyde (207 mg, 6.90 mmol), and sodium cyanoborohydride (433 mg, 6.90 mmol) in methanol (30 mL) was added acetic acid (catalytic) and the reaction stirred at room temperature for 18 h. The reaction mixture was quenched with water and the layers were separated. The combined organic layers were dried over anhydrous sodium sulfate, filtered, concentrated, and chromatographed ($CH_2Cl_2$/MeOH) to afford the desired product (164 mg, 34%) as an orange oil: ESI MS m/z 211 $[C_{10}H_{14}N_2O_3+H]^+$.

Example 1137

1-(4-Aminophenyl)-2-(dimethylamino)ethanol

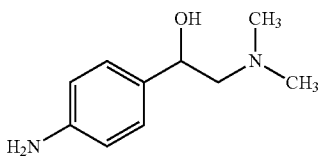

A pressure flask was charged with a suspension 2-(dimethylamino)-1-(4-nitrophenyl)ethanol (160 mg, 0.770 mmol) in ethanol (10 mL) and Raney nickel (0.5 mL). The flask was placed on a Parr shaker, purged with $H_2$ (30 psi), and stirred for 4 h. The crude product was filtered through celite, and concentrated to obtain the crude product (210 mg) as an off-white solid: $^1$H NMR (300 MHz, $CDCl_3$) δ 7.11-7.09 (m, 2H), 6.71-6.69 (m, 2H), 4.61-4.70 (m, 1H), 2.61-2.58 (m, 1H), 2.40-2.32 (m, 1H), 2.31 (s, 3H).

Example 1138

3-Nitro-5-((trimethylsilyl)ethynyl)pyridine

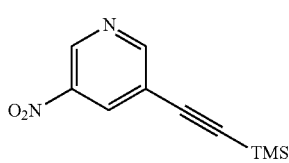 [SMILES: C[Si](C)(C)C#Cc1cncc([N+](=O)[O-])c1]

591

To a suspension of 3-bromo-5-nitropyridine (1.0 g, 4.90 mmol), Pd(Ph₃P)₄ (0.57 g, 0.49 mmol), and copper iodide (0.19 g, 0.98 mmol) in triethylamine (30 mL) was added ethynyltrimethylsilane (1.0 mL, 7.35 mmol) and the reaction was purged with $N_2$. The mixture was stirred at 80° C. for 2 h. The reaction mixture was filtered through celite and washed with ethyl acetate. The filtrate was washed with saturated solutions of $NaHCO_3$ and NaCl. The organic layer was concentrated to afford the crude product (1.72 g) as a light brown solid: ESI MS m/z 221 $[C_{10}H_{12}N_2O_2Si+H]^+$.

Example 1139

3-ethynyl-5-nitropyridine

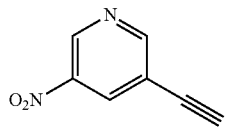

To a solution of 3-nitro-5-((trimethylsilyl)ethynyl)pyridine (4.90 mmol) in MeOH (15 mL) was added $K_2CO_3$ (67 mg, 0.49 mmol). The mixture was stirred at rt for 30 min. The reaction mixture was diluted with ethyl acetate, washed with water and brine, dried over sodium sulfate, and chromatographed (hexane/ethyl acetate) to afford the desired product (540 mg, 74% over two steps) as a light brown solid: ¹H NMR (300 MHz, CDCl₃) δ 9.39-9.38 (m, 1H), 8.99-8.98 (m, 1H), 8.56-8.54 (m, 1H), 3.40 (s, 1H).

Example 1140

5-(2-(Pyrrolidin-1-yl)ethyl)pyridin-3-amine

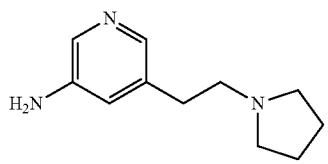 [SMILES: Nc1cncc(CCN2CCCC2)c1]

To a solution of 3-ethynyl-5-nitropyridine (250 mg, 1.69 mmol) in ethanol (5 mL) was added pyrrolidine (0.56 mL, 6.76 mmol) and the reaction mixture was stirred at 80° C. for 16 h. The reaction mixture was cooled and palladium hydroxide on carbon (20 mg) was added. The flask was charged with $H_2$ (ballon) and stirred at rt for 16 h. The mixture was filtered over celite and the filtrate was concentrated to afford crude product (380 mg) as a dark red oil: ESI MS m/z 192 $[C_{11}H_{17}N_3+H]^+$.

592

Example 1141

{6-Bromo-4-[4-(pyrrolidin-1-ylmethyl)phenylamino]quinolin-3-yl}(cyclopropyl)methanone

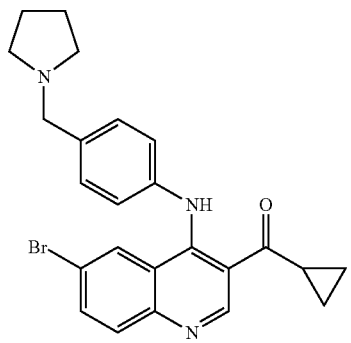 [SMILES: O=C(c1cnc2ccc(Br)cc2c1Nc1ccc(CN2CCCC2)cc1)C1CC1]

Following general procedure C, (6-bromo-4-chloroquinolin-3-yl)(cyclopropyl)methanone (320 mg, 1.03 mmol) was reacted 4-(pyrrolidin-1-ylmethyl)aniline (385 mg, 1.55 mmol) to afford the desired product (387 mg, 83%) as a yellow solid: ESI MS m/z 450 $[C_{24}H_{24}BrN_3O+H]^+$.

Example 1142

{6-Bromo-4-[4-((4-methylpiperazin-1-yl)methyl)phenylamino]quinolin-3-yl}(cyclopropyl)methanone

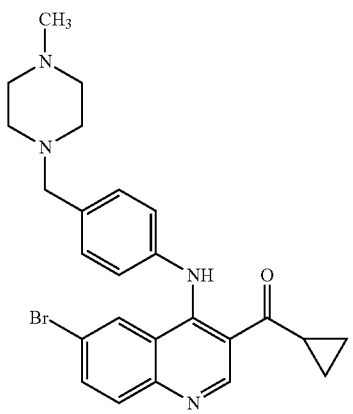 [SMILES: CN1CCN(Cc2ccc(Nc3c(C(=O)C4CC4)cnc4ccc(Br)cc34)cc2)CC1]

Following general procedure C, (6-bromo-4-chloroquinolin-3-yl)(cyclopropyl)methanone (200 mg, 0.644 mmol) was reacted with 4-[(4-methylpiperazin-1-yl)methyl]aniline (200 mg, 0.966 mmol) to afford the desired product (173 mg, 56%) as a yellow solid: ESI MS m/z 479 [$C_{25}H_{27}BrN_4O+H$]⁺.

Example 1143 tert-Butyl 4-{5-[6-bromo-3-(cyclopropanecarbonyl)quinolin-4-ylamino]pyridin-2-yl}piperazine-1-carboxylate

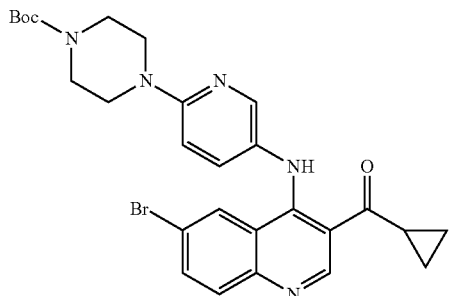

Following general procedure C, (6-bromo-4-chloroquinolin-3-yl)(cyclopropyl)methanone (225 mg, 0.724 mmol) was reacted with tert-butyl 4-(5-aminopyridin-2-yl)piperazine-1-carboxylate (300 mg, 1.09 mmol) to afford the desired product (320 mg, 80%) as an orange solid: ESI MS m/z 552 [$C_{27}H_{30}BrN_5O_3+H$]⁺.

Example 1144 tert-Butyl {trans-4-[6-bromo-3-(cyclopropanecarbonyl)quinolin-4-ylamino]cyclohexyl}methylcarbamate

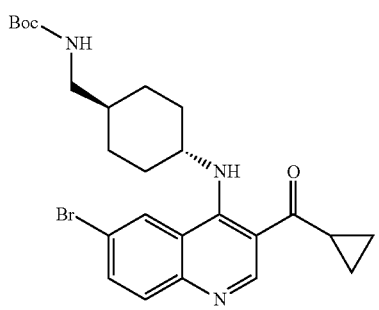 [SMILES: CC(C)(C)OC(=O)NC[C@H]1CC[C@H](Nc2c(C(=O)C3CC3)cnc3ccc(Br)cc23)CC1]

Following general procedure B, (6-bromo-4-chloroquinolin-3-yl)(cyclopropyl)methanone (260 mg, 0.840 mmol) was reacted with tert-trans-butyl (4-aminocyclohexyl)methylcarbamate (287 mg, 1.26 mmol) to afford the desired product (290 mg, 69%) as an off-white solid: ESI MS m/z 502 [$C_{25}H_{32}BrN_3O_3+H$]⁺.

Example 1145 tert-Butyl {trans-4-[6-bromo-3-(cyclopropanecarbonyl)quinolin-4-ylamino]cyclohexyl}(methyl)carbamate

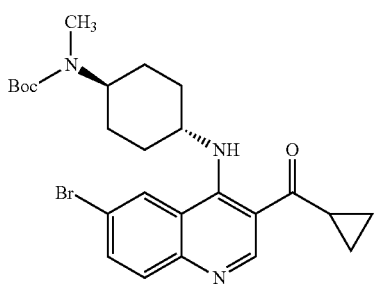 [SMILES: CN(C(=O)OC(C)(C)C)[C@H]1CC[C@H](Nc2c(C(=O)C3CC3)cnc3ccc(Br)cc23)CC1]

Following general procedure B, (6-bromo-4-chloroquinolin-3-yl)(cyclopropyl)methanone (335 mg, 1.07 mmol) was reacted with tert-butyl-(trans)-4-aminocyclohexyl(methyl)carbamate (366 mg, 1.61 mmol) to afford the desired product (470 mg, 87%) as an orange foam: ESI MS m/z 502 [$C_{25}H_{32}BrN_3O_3+H$]⁺.

Example 1146 tert-Butyl 4-[6-bromo-3-(cyclopropanecarbonyl)quinolin-4-ylamino]benzylcarbamate

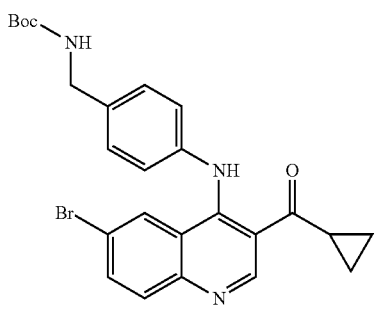 [SMILES: CC(C)(C)OC(=O)NCc1ccc(Nc2c(C(=O)C3CC3)cnc3ccc(Br)cc23)cc1]

Following general procedure C, (6-bromo-4-chloroquinolin-3-yl)(cyclopropyl)methanone (290 mg, 0.934 mmol) was reacted with tert-butyl 4-aminobenzylcarbamate (312 mg, 1.40 mmol) to afford the desired product (362 mg, 78%) as a yellow solid: ESI MS m/z 496 [$C_{25}H_{26}BrN_3O_3+H$]⁺.

Example 1147 tert-Butyl 2-{4-[6-bromo-3-(cyclopropanecarbonyl)quinolin-4-ylamino]phenyl}propan-2-ylcarbamate

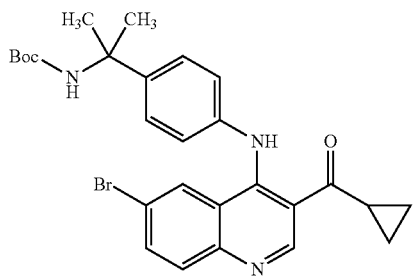 [SMILES: CC(C)(C)OC(=O)NC(C)(C)c1ccc(Nc2c(C(=O)C3CC3)cnc3ccc(Br)cc23)cc1]

Following general procedure C, (6-bromo-4-chloroquinolin-3-yl)(cyclopropyl)methanone (347 mg, 1.12 mmol) was reacted with tert-butyl 2-(4-aminophenyl)propan-2-ylcarbamate (420 mg, 1.68 mmol) to afford the desired product (422 mg, 63%) as a yellow solid: ESI MS m/z 524 $[C_{27}H_{30}BrN_3O_3+H]^+$.

Example 1148

1-{6-Bromo-4-[trans-4-((dimethylamino)methyl)cyclohexylamino]quinolin-3-yl}butan-1-one

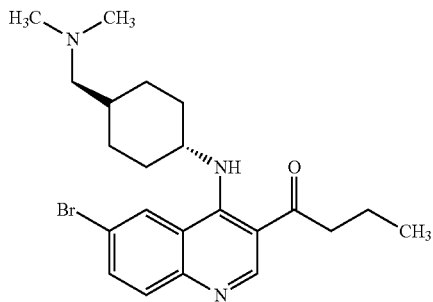

Following general procedure C, 1-(6-bromo-4-chloroquinolin-3-yl)butan-1-one (0.350 mg, 1.12 mmol) was reacted with trans-4-[(dimethylamino)methyl]cyclohexanamine.HCl (385 mg, 1.68 mmol) to afford the desired product (160 mg, 33%) as an off-white solid: ESI MS m/z 432 $[C_{22}H_{30}BrN_3O+H]^+$.

Example 1149 tert-Butyl 4-[5-(6-bromo-3-butyrylquinolin-4-ylamino)pyridin-2-yl]piperazine-1-carboxylate

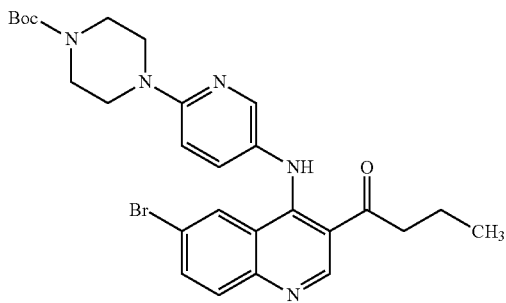 [SMILES: CCCC(=O)c1cnc2ccc(Br)cc2c1Nc1ccc(N2CCN(C(=O)OC(C)(C)C)CC2)nc1]

Following general procedure C, 1-(6-bromo-4-chloroquinolin-3-yl)butan-1-one (360 mg, 1.15 mmol) was reacted with tert-butyl 4-(5-aminopyridin-2-yl)piperazine-1-carboxylate (480 mg, 1.73 mmol) to afford the desired product (440 mg, 69%) as an orange solid: ESI MS m/z 554 $[C_{27}H_{32}BrN_5O_3+H]^+$.

Example 1150

{6-Bromo-4-[4-(diallylamino)-4-methylcyclohexylamino]quinolin-3-yl}(cyclopropyl)methanone

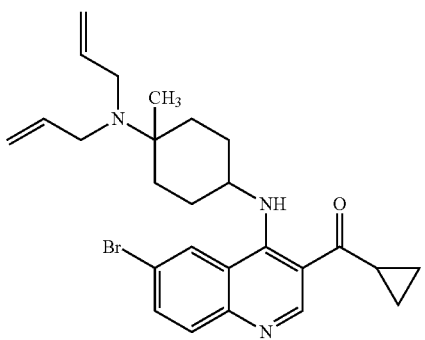 [SMILES: C=CCN(CC=C)C1(C)CCC(Nc2c(C(=O)C3CC3)cnc3ccc(Br)cc23)CC1]

Following general procedure B, (6-bromo-4-chloroquinolin-3-yl)(cyclopropyl)methanone (300 mg, 0.966 mmol) was reacted with $N^1,N^1$-diallyl-1-methylcyclohexane-1,4-diamine (400 mg, 1.93 mmol) to afford the desired product (220 mg, 47%) as a yellow solid: ESI MS m/z 482 $[C_{26}H_{32}BrN_3O+H]^+$.

Example 1151

{6-Bromo-4-[6-((dimethylamino)methyl)pyridin-3-ylamino]quinolin-3-yl}(cyclopropyl)methanone

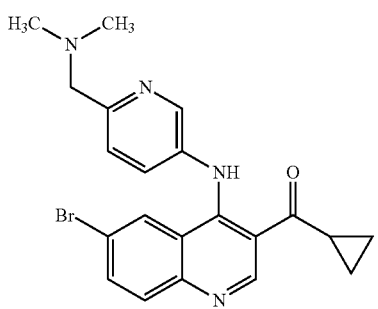 [SMILES: CN(C)Cc1ccc(Nc2c(C(=O)C3CC3)cnc3ccc(Br)cc23)cn1]

Following general procedure C, (6-bromo-4-chloroquinolin-3-yl)(cyclopropyl)methanone (330 mg, 1.06 mmol) was reacted with 6-[(dimethylamino)methyl]pyridin-3-amine (200 mg, 1.32 mmol) to afford the desired product (37 mg, 8%) as an orange oil: ESI MS m/z 425 $[C_{21}H_{21}BrN_4O+H]^+$.

Example 1152

{6-Bromo-4-[6-(pyrrolidin-1-ylmethyl)pyridin-3-ylamino]quinolin-3-yl}(cyclopropyl)methanone

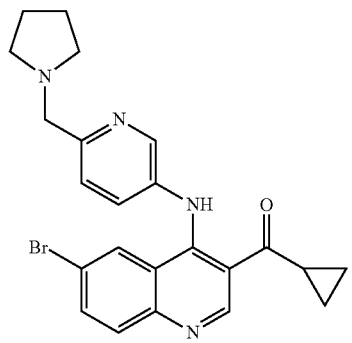 [SMILES: O=C(c1cnc2ccc(Br)cc2c1Nc1ccc(CN2CCCC2)nc1)C1CC1]

Following general procedure C, (6-bromo-4-chloroquinolin-3-yl)(cyclopropyl)methanone (310 mg, 1.00 mmol) was reacted with 6-(pyrrolidin-1-ylmethyl)pyridin-3-amine (280 mg, 1.50 mmol) to afford the desired product (352 mg, 78%) as a yellow foam: ESI MS m/z 451 $[C_{23}H_{23}BrN_4O+H]^+$.

Example 1153

{6-Bromo-4-[3-(2-(dimethylamino)ethyl)phenylamino]quinolin-3-yl}(cyclopropyl)methanone

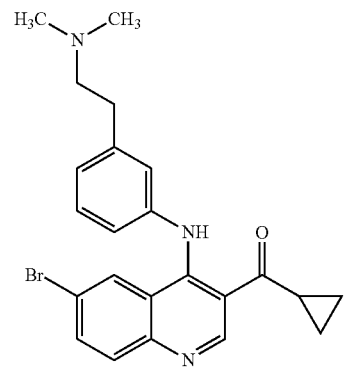 [SMILES: CN(C)CCc1cccc(Nc2c(C(=O)C3CC3)cnc3ccc(Br)cc23)c1]

Following general procedure C, (6-bromo-4-chloroquinolin-3-yl)(cyclopropyl)methanone (280 mg, 0.91 mmol) was reacted with 3-[2-(dimethylamino)ethyl]aniline (150 mg, 0.91 mmol) to afford the desired product (270 mg, 68%) as a yellow solid: ESI MS m/z 438 $[C_{23}H_{24}BrN_3O+H]^+$.

Example 1154

{6-Bromo-4-[1-(1-methylpiperidin-3-yl)-1H-pyrazol-4-ylamino]quinolin-3-yl}(cyclopropyl)methanone

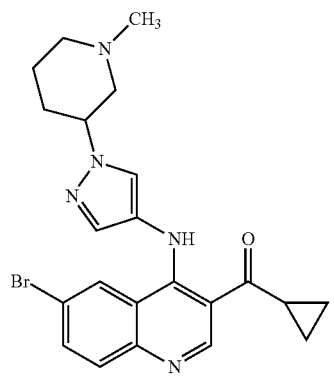 [SMILES: CN1CCCC(n2cc(Nc3c(C(=O)C4CC4)cnc4ccc(Br)cc34)cn2)C1]

Following general procedure C, (6-bromo-4-chloroquinolin-3-yl)(cyclopropyl)methanone (305 mg, 0.98 mmol) was reacted with 1-(1-methylpiperidin-3-yl)-1H-pyrazol-4-amine (265 mg, 1.47 mmol) to afford the desired product (100 mg, 22%) as a yellow solid: ESI MS m/z 454 $[C_{22}H_{24}BrN_5O+H]^+$.

Example 1155

{6-Bromo-4-[1-(trans-4-(methylamino)cyclohexyl)-1H-pyrazol-4-ylamino]quinolin-3-yl}(cyclopropyl)methanone

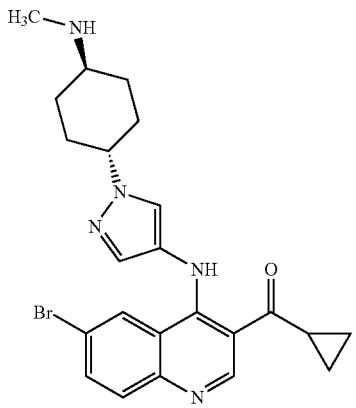 [SMILES: CN[C@H]1CC[C@H](n2cc(Nc3c(C(=O)C4CC4)cnc4ccc(Br)cc34)cn2)CC1]

Following general procedure C, (6-bromo-4-chloroquinolin-3-yl)(cyclopropyl)methanone (310 mg, 1.00 mmol) was reacted with 1-[trans-4-(methylamino)cyclohexyl]-1H-pyrazol-4-amine (388 mg, 2.00 mmol) to afford the desired product (65 mg, 14%) as an orange solid: ESI MS m/z 468 $[C_{23}H_{26}BrN_5O+H]^+$.

Example 1156

{6-Bromo-4-[4-(2-(dimethylamino)-1-hydroxyethyl)phenylamino]quinolin-3-yl}(cyclopropyl)methanone

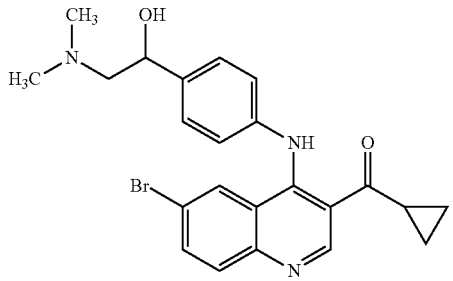 [SMILES: CN(C)CC(O)c1ccc(Nc2c(C(=O)C3CC3)cnc3ccc(Br)cc23)cc1]

Following general procedure C, (6-bromo-4-chloroquinolin-3-yl)(cyclopropyl)methanone (240 mg, 0.770 mmol) was reacted with 1-(4-aminophenyl)-2-(dimethylamino)ethanol (139 mg, 0.770 mmol) to afford the desired product (187 mg, 53%) as a yellow solid: ESI MS m/z 454 $[C_{23}H_{24}BrN_3O_2+H]^+$.

Example 1157

1-{6-Bromo-4-[3-(2-(dimethylamino)ethyl)phenylamino]quinolin-3-yl}ethanone

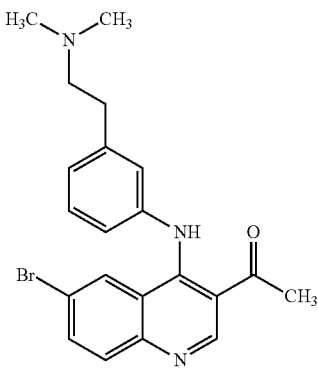 [SMILES: CC(=O)c1cnc2ccc(Br)cc2c1Nc1cccc(CCN(C)C)c1]

Following general procedure C, 1-(6-bromo-4-chloroquinolin-3-yl)ethanone (340 mg, 1.20 mmol) was reacted with 3-(2-(dimethylamino)ethyl)aniline (215 mg, 1.31 mmol) to afford the desired product (360 mg, 50%) as a yellow solid: ESI MS m/z 412 $[C_{21}H_{22}BrN_3O+H]^+$.

Example 1158

1-{6-Bromo-4-[trans-4-(dimethylamino)cyclohexylamino]quinolin-3-yl}ethanone

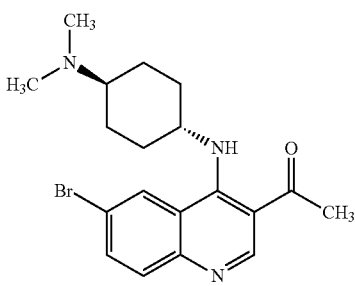 [SMILES: CC(=O)c1cnc2ccc(Br)cc2c1N[C@H]1CC[C@H](N(C)C)CC1]

Following general procedure C, 1-(6-bromo-4-chloroquinolin-3-yl)ethanone (250 mg, 0.880 mmol) was reacted with trans-$N^1,N^1$-dimethylcyclohexane-1,4-diamine hydrochloride (280 mg, 1.32 mmol) to afford the desired product (63 mg, 18%): ESI MS m/z 390 $[C_{19}H_{24}BrN_3O+H]^+$.

Example 1159

{6-bromo-4-[3-(2-(pyrrolidin-1-yl)ethyl)phenylamino]quinolin-3-yl}(cyclopropyl)methanone

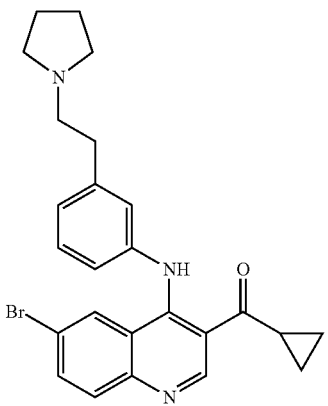 [SMILES: O=C(c1cnc2ccc(Br)cc2c1Nc1cccc(CCN2CCCC2)c1)C1CC1]

Following general procedure C, (6-bromo-4-chloroquinolin-3-yl)(cyclopropyl)methanone (197 mg, 0.635 mmol) was reacted with 3-[2-(pyrrolidin-1-yl)ethyl]aniline (120 mg, Example 1160

1-{6-bromo-4-[3-(2-(pyrrolidin-1-yl)ethyl)phenylamino]quinolin-3-yl}ethanone

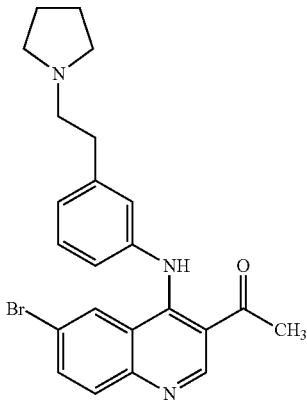 [SMILES: CC(=O)c1cnc2ccc(Br)cc2c1Nc1cccc(CCN2CCCC2)c1]

Following general procedure C, 1-(6-bromo-4-chloroquinolin-3-yl)ethanone (180 mg, 0.635 mmol) was reacted with 3-[2-(pyrrolidin-1-yl)ethyl]aniline (120 mg, 0.635 mmol) to afford the desired product (198 mg, 71%) as a yellow solid: ESI MS m/z 438 $[C_{23}H_{24}BrN_3O+H]^+$.

Example 1161

{6-Bromo-4-[3-(2-(4-methylpiperazin-1-yl)ethyl)phenylamino]quinolin-3-yl}(cyclopropyl)methanone

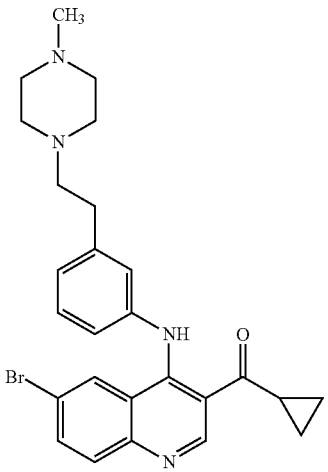 [SMILES: CN1CCN(CCc2cccc(Nc3c(C(=O)C4CC4)cnc4ccc(Br)cc34)c2)CC1]

Following general procedure C, (6-bromo-4-chloroquinolin-3-yl)(cyclopropyl)methanone (240 mg, 0.77 mmol) was reacted with 3-(2-(4-methylpiperazin-1-yl)ethyl)aniline (170 mg, 0.77 mmol) to afford the desired product (212 mg, 55%) as a yellow solid: ESI MS m/z 493 $[C_{26}H_{29}BrN_4O+H]^+$.

Example 1162

{6-Bromo-4-[5-(2-(pyrrolidin-1-yl)ethyl)pyridin-3-ylamino]quinolin-3-yl}(cyclopropyl)methanone

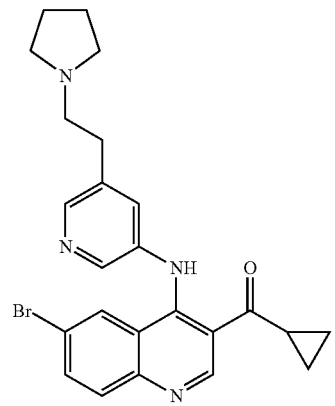 [SMILES: O=C(c1cnc2ccc(Br)cc2c1Nc1cncc(CCN2CCCC2)c1)C1CC1]

Following general procedure C, (6-bromo-4-chloroquinolin-3-yl)(cyclopropyl)methanone (262 mg, 0.845 mmol) was reacted with 5-[2-(pyrrolidin-1-yl)ethyl]pyridin-3-amine (161 mg, 0.845 mmol) to afford the desired product (178 mg, 45%) as a white solid: ESI MS m/z 465 $[C_{24}H_{25}BrN_4O+H]^+$.

Example 416

1-(6-(3,5-dichloro-4-hydroxyphenyl)-4-(4-(pyrrolidin-1-ylmethyl)phenylamino)quinolin-3-yl)ethanone hydrobromide

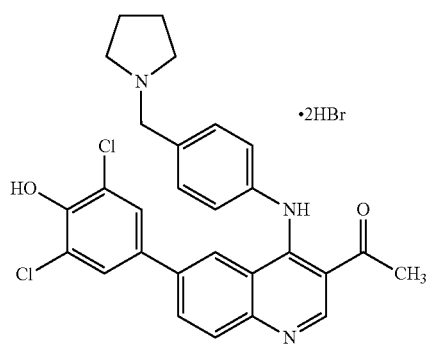 [SMILES: CC(=O)c1cnc2ccc(-c3cc(Cl)c(O)c(Cl)c3)cc2c1Nc1ccc(CN2CCCC2)cc1]

Following general procedure F, 1-(6-bromo-4-(4-(pyrrolidin-1-ylmethyl)phenylamino)quinoline-3-yl)ethanone (4.0 g, 9.42 mmol) was reacted with 2,6-dichloro-4-(4,4,5,5-tetramethyl-1,3,2-dioxaborolan-2-yl)phenol (4.0 g, 14.13 mmol) to obtain the free base. The purified product was suspended in dichloromethane/methanol (1:1, 40 mL) and HBr gas was bubbled through the suspension until a solution formed. The solution was concentrated to dryness and the resultant solid was triturated with diethyl ether. The mixture was filtered, washed with diethyl ether, and dried to obtain desired product (3.37 g, 52% over two steps) as a yellow solid: $^1$H NMR (300 MHz, DMSO-$d_6$) δ 12.03 (br s, 1H), 10.59 (br s, 1H), 10.08

(br s, 1H), 9.27 (s, 1H), 8.43-8.27 (m, 2H), 8.112 (d, J=8.8 Hz, 1H), 7.72 (d, J=8.1 Hz, 2H), 7.59-7.47 (m, 4H), 4.47 (d, J=5.3 Hz, 2H), 3.40-3.24 (m, 2H), 3.19-3.02 (m, 2H), 2.56 (s, 3H), 2.13-1.81 (m, 4H); APCI MS m/z 506 [$C_{28}H_{25}Cl_2N_3O_2$+H]$^+$; HPLC>99% (AUC), $t_R$=4.97 min.

Example 324 cyclopropyl(6-(3,5-dichloro-4-hydroxyphenyl)-4-(trans-4-((dimethylamino)methyl)cyclohexylamino)quinolin-3-yl)methanone

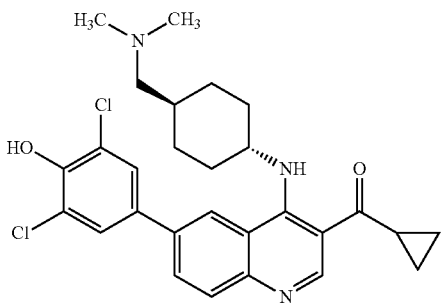 [SMILES: CN(C)C[C@H]1CC[C@H](Nc2c(C(=O)C3CC3)cnc3ccc(-c4cc(Cl)c(O)c(Cl)c4)cc23)CC1]

Following general procedure F except 2M $Na_2CO_3$ was used instead of 1M $Cs_2CO_3$, (6-bromo-4-(trans-4-((dimethylamino)methyl)cyclohexylamino)quinolin-3-yl)(cyclopropyl)methanone (4.29 g, 9.96 mmol) was reacted with 2,6-dichloro-4-(4,4,5,5-tetramethyl-1,3,2-dioxaborolan-2-yl)phenol (4.32 g, 14.95 mmol) to afford the desired product (3.0 g, 59%) as a yellow solid: $^1$H NMR (300 MHz, DMSO-$d_6$) δ 9.77 (br s, 1H), 9.05 (s, 1H), 8.36 (d, J=2.1 Hz, 1H), 8.03 (dd, J=8.7, 1.8 Hz, 1H), 7.85 (d, J=8.7 Hz, 1H), 7.73 (s, 2H), 3.96-3.86 (m, 1H), 2.97-2.82 (m, 1H), 2.19 (s, 6H), 2.17-2.06 (m, 4H), 1.86 (d, J=12.7 Hz, 2H), 1.60-1.36 (m, 3H), 1.15-0.91 (m, 6H); APCI MS m/z 512 [$C_{28}H_{31}Cl_2N_3O_2$+H]$^+$; HPLC>99% (AUC), $t_R$=5.15 min.

Example 768

1-(6-(3,5-dichloro-4-hydroxyphenyl)-4-(trans-4-(pyrrolidin-1-ylmethyl)cyclohexylamino)quinolin-3-yl)ethanone hydrochloride

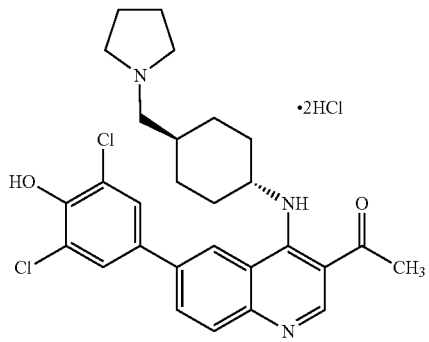 [SMILES: CC(=O)c1cnc2ccc(-c3cc(Cl)c(O)c(Cl)c3)cc2c1N[C@H]1CC[C@H](CN2CCCC2)CC1]

Following general procedure F, 1-(6-bromo-4-(trans-4-(pyrrolidin-1-ylmethyl)cyclohexylamino)quinolin-3-yl)ethanone (6.0 g, 14.0 mmol) was reacted with 2,6-dichloro-4-(4,4,5,5-tetramethyl-1,3,2-dioxaborolan-2-yl)phenol (4.4 g, 15.0 mmol) to obtain the free base. The purified product was suspended in dichloromethane/methanol (1:1, 200 mL) after which HCl (35 mL, 1.25 M in methanol) was added to form a solution. The solution was concentrated to dryness and the resultant solid was triturated with dichloromethane. The mixture was filtered, washed with dichloromethane, and dried to obtain desired product (4.9 g, 60% over two steps) as a yellow solid: $^1$H NMR (300 MHz, $CD_3OD$) δ 9.10 (s, 1H), 8.47 (d, J=2.1 Hz, 1H), 8.26 (dd, J=8.8, 1.8 Hz, 1H), 7.98 (d, J=8.8 Hz, 1H), 7.73 (s, 2H), 4.55-4.45 (m, 1H), 3.70 (br s, 2H), 3.20-3.04 (m, 4H), 2.74 (s, 3H), 2.45 (d, J=12.6 Hz, 2H), 2.17-1.94 (m, 7H), 1.89-1.70 (m, 2H), 1.46-1.27 (m, 2H); APCI MS m/z 512 [$C_{28}H_{31}Cl_2N_3O_2$+H]$^+$; HPLC>99% (AUC), $t_R$=8.69 min.

Example 802

1-(6-(3,5-dichloro-4-hydroxyphenyl)-4-(3-(2-(pyrrolidin-1-yl)ethyl)phenylamino)quinolin-3-yl)ethanone hydrochloride

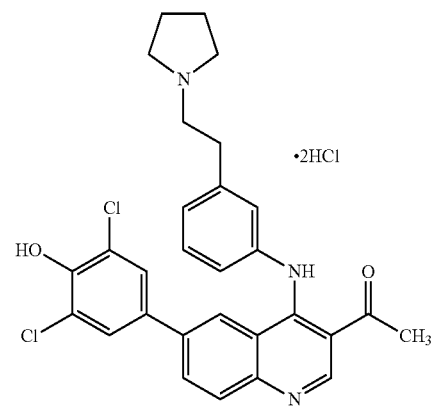 [SMILES: CC(=O)c1cnc2ccc(-c3cc(Cl)c(O)c(Cl)c3)cc2c1Nc1cccc(CCN2CCCC2)c1]

Following general procedure F, 1-(6-bromo-4-(3-(2-(pyrrolidin-1-yl)ethyl)phenylamino)quinolin-3-yl)ethanone (5.7 g, 13.0 mmol) was reacted with 2,6-dichloro-4-(4,4,5,5-tetramethyl-1,3,2-dioxaborolan-2-yl)phenol (4.1 g, 14.2 mmol) to obtain the free base. The purified product was suspended in dichloromethane/methanol (1:1, 100 mL) after which HCl (40 mL, 1.25 M in methanol) was added to form a solution. The solution was concentrated to dryness and the resultant solid was triturated with acetonitrile. The mixture was filtered, washed with acetonitrile, and dried to obtain desired product (5.6 g, 73% over two steps) as a yellow solid: $^1$H NMR (300 MHz, $CD_3OD$) δ 9.31 (s, 1H), 8.19 (dd, J=8.8, 2.0 Hz, 1H), 7.99 (d, J=8.8 Hz, 1H), 7.75-7.55 (m, 3H), 7.53 (s, 1H), 7.43-7.34 (m, 1H), 7.10 (s, 2H), 3.66 (br s, 2H), 3.48-

3.36 (m, 2H), 3.24-3.06 (m, 4H), 2.82 (s, 3H), 2.07 (br s, 4H); APCI MS m/z 520 [$C_{29}H_{27}Cl_2N_3O_2$+H]$^+$; HPLC>99% (AUC), $t_R$=9.17 min.

Example 1163

1-(6-bromo-4-(4-((4-methylpiperazin-1-yl)methyl) phenylamino)quinolin-3-yl)ethanone

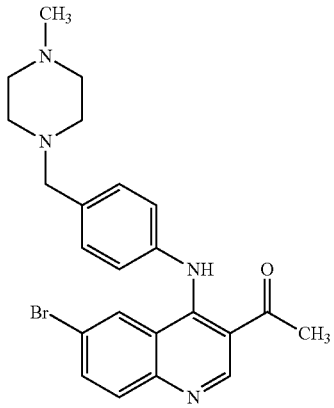 [SMILES: CC(=O)c1cnc2ccc(Br)cc2c1Nc1ccc(CN2CCN(C)CC2)cc1]

Following general procedure C, 1-(6-bromo-4-chloroquinolin-3-yl)ethanone (5.0 g, 18.0 mmol) was reacted with 4-((4-methylpiperazin-1-yl)methyl)aniline (4.0 g, 19.0 mmol) to afford the desired product (6.7 g, 82%) as a yellow foam: $^1$H NMR (300 MHz, CDCl$_3$) δ 11.96 (s, 1H), 9.11 (s, 1H), 7.85-7.72 (m, 1H), 7.71-7.57 (m, 2H), 7.40-7.29 (m, 2H), 7.14-7.02 (m, 2H), 3.53 (s, 2H), 2.77 (s, 3H), 2.58-2.44 (br s, 8H), 2.30 (s, 3H).

Example 655

1-(6-(3,5-dichloro-4-hydroxyphenyl)-4-(4-((4-methylpiperazin-1-yl)methyl)phenylamino)quinolin-3-yl) ethanone hydrochloride

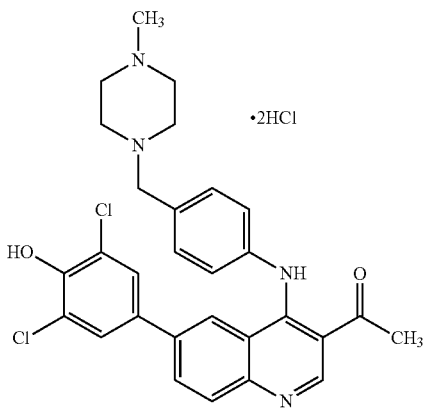 [SMILES: CC(=O)c1cnc2ccc(-c3cc(Cl)c(O)c(Cl)c3)cc2c1Nc1ccc(CN2CCN(C)CC2)cc1]

Following general procedure F, 1-(6-bromo-4-(4-((4-methylpiperazin-1-yl)methyl)phenylamino)quinolin-3-yl)ethanone (6.0 g, 13.0 mmol) was reacted with 2,6-dichloro-4-(4,4,5,5-tetramethyl-1,3,2-dioxaborolan-2-yl)phenol (4.2 g, 15.0 mmol) to obtain the free base. The purified product was suspended in dichloromethane/methanol (1:1, 200 mL) after which HCl (36 mL, 1.25 M in methanol) was added to form a solution. The solution was concentrated to dryness and the resultant solid was triturated with dichloromethane. The mixture was filtered, washed with dichloromethane, and dried to obtain desired product (5.2 g, 66% over two steps) as a yellow solid: $^1$H NMR (300 MHz, CD$_3$OD) δ 9.30 (s, 1H), 8.15 (dd, J=8.8, 1.9 Hz, 1H), 7.99 (d, J=8.8 Hz, 1H), 7.73 (d, J=2.0 Hz, 1H), 7.62 (d, J=8.0 Hz, 2H), 7.46 (d, J=8.0 Hz, 2H), 7.10 (s, 2H), 3.81 (s, 2H), 3.55-3.31 (m, 2H), 3.29-2.89 (m, 4H), 2.89 (s, 3H), 2.82 (s, 3H), 2.80-2.35 (m, 2H); APCI MS m/z 535 [$C_{29}H_{28}Cl_2N_4O_2$+H]$^+$; HPLC>99% (AUC), $t_R$=7.89 min.

Example 647

(S)-(4-(6-(3-aminopiperidin-1-yl)pyridin-3-ylamino)-6-(3,5-dichloro-4-hydroxyphenyl)quinolin-3-yl)(cyclopropyl)methanone hydrochloride

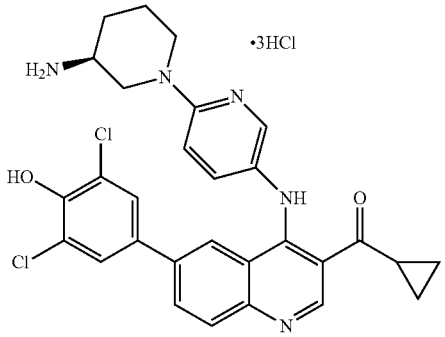 [SMILES: N[C@H]1CCCN(c2ccc(Nc3c(C(=O)C4CC4)cnc4ccc(-c5cc(Cl)c(O)c(Cl)c5)cc34)cn2)C1]

(S)-tert-Butyl 1-(5-(3-(cyclopropanecarbonyl)-6-(3,5-dichloro-4-hydroxyphenyl)quinolin-4-ylamino)pyridin-2-yl)piperidin-3-ylcarbamate (5.7 g, 8.8 mmol) was reacted HCl (100 mL, 1.25M in methanol). The mixture was heated to 40° C. for 16 h. The reaction was diluted with ethyl acetate (100 mL). The resultant solid was filtered and washed with ethyl acetate. The solids were dissolved in a mixture of water, methanol, and acetonitrile. The solution was concentrated by lyophilization to obtain desired product (4.7 g, 81%) as an orange solid: $^1$H NMR (500 MHz, CD$_3$OD) δ 9.36 (s, 1H), 8.32-8.22 (m, 3H), 8.08 (d, J=9.2 Hz, 1H), 7.90 (dd, J=9.5, 2.6 Hz, 1H), 7.48 (s, 2H), 7.36 (d, J=9.5 Hz, 1H), 4.51-4.45 (m, 1H), 4.11-4.03 (m, 1H), 3.53-3.36 (m, 3H), 2.87-2.78 (m, 1H), 2.27-2.20 (m, 1H), 2.06-1.97 (m, 1H), 1.85-1.72 (m, 2H), 1.25-1.10 (m, 4H); ESI MS m/z 548 [$C_{29}H_{27}Cl_2N_5O_2$+H]$^+$; HPLC 98.8% (AUC), $t_R$=9.51 min.

Example 766

1-(6-(3,5-dichloro-4-hydroxyphenyl)-4-(trans-4-(dimethylamino)cyclohexylamino)quinolin-3-yl) ethanone hydrochloride

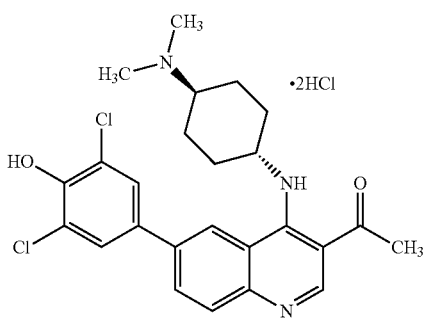 [SMILES: CC(=O)c1cnc2ccc(-c3cc(Cl)c(O)c(Cl)c3)cc2c1N[C@H]1CC[C@H](N(C)C)CC1]

Following general procedure F, 1-(6-bromo-4-(trans-4-(dimethylamino)cyclohexylamino)quinolin-3-yl)ethanone (4.48 g, 11.0 mmol) was reacted with 2,6-dichloro-4-(4,4,5,5-tetramethyl-1,3,2-dioxaborolan-2-yl)phenol (3.65 g, 13.0 mmol) to obtain the free base. The purified product was suspended in dichloromethane/methanol (2:1, 325 mL) after which HCl (115 mL, 1.25 M in methanol) was added to from a solution. The solution was concentrated to ~100 mL and the resultant solid was filtered, washed with dichloromethane, and dried to obtain desired product (4.2 g, 70% over two steps) as a yellow solid: $^1$H NMR (500 MHz, MeOD) δ 9.13 (s, 1H), 8.48 (br s, 1H), 8.30 (dd, J=8.8, 1.8 Hz, 1H), 8.01 (d, J=8.7 Hz, 1H), 7.77 (s, 2H), 4.62 (br s, 1H), 3.50-3.46 (m, 1H), 2.91 (s, 6H), 2.75 (s, 3H), 2.58-2.54 (m, 2H), 2.35-2.29 (m, 2H), 1.92-1.82 (m, 4H); ESI MS m/z 472 $[C_{25}H_{27}Cl_2N_3O_2+H]^+$; HPLC>99% (AUC), $t_R$=6.41 min.

Example 740

1-(6-(3,5-dichloro-4-hydroxyphenyl)-4-(trans-4-(2-(dimethylamino)ethyl)cyclohexylamino)quinolin-3-yl)ethanone hydrochloride

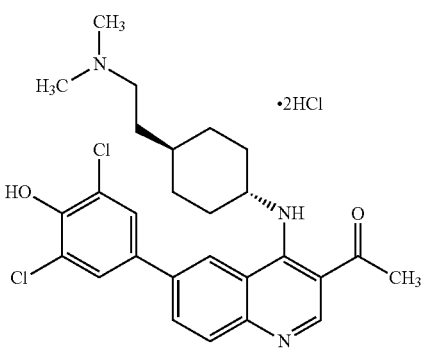 [SMILES: CC(=O)c1cnc2ccc(-c3cc(Cl)c(O)c(Cl)c3)cc2c1N[C@H]1CC[C@H](CCN(C)C)CC1]

Following general procedure F, 1-(6-bromo-4-(trans-4-(2-(dimethylamino)ethyl)cyclohexyl amino)quinolin-3-yl)ethanone (4.8 g, 11.5 mmol) was reacted with 2,6-dichloro-4-(4,4,5,5-tetramethyl-1,3,2-dioxaborolan-2-yl)phenol (3.8 g, 13.1 mmol) to obtain the free base. The purified product was suspended in methanol (100 mL) after which HCl (125 mL, 1.25 M in methanol) was added to form a solution. The solution was concentrated to ~50 mL and the resultant solid was filtered, washed with methanol, and dried to obtain desired product (3.8 g, 58% over two steps) as a yellow solid: $^1$H NMR (300 MHz, CD$_3$OD) δ 9.10 (s, 1H), 8.50 (s, 1H), 8.27 (dd, J=8.8, 1.8 Hz, 1H), 7.97 (d, J=8.8 Hz, 1H), 7.73 (s, 2H), 4.55-4.48 (m, 1H), 3.27-3.15 (m, 2H), 2.90 (s, 6H), 2.74 (s, 3H), 2.42 (br d, J=12.3 Hz, 2H), 2.04 (br d, J=12.9 Hz, 2H), 1.84-1.65 (m, 4H), 1.63-1.56 (m, 1H), 1.34 (q, J=12.3 Hz, 2H); ESI MS m/z 500 $[C_{27}H_{31}Cl_2N_3O_2+H]^+$; HPLC>99% (AUC), $t_R$=6.87 min.

Example 1164

1-(6-bromo-4-(6-(2-(dimethylamino)ethoxy)pyridin-3-ylamino)quinolin-3-yl)ethanone

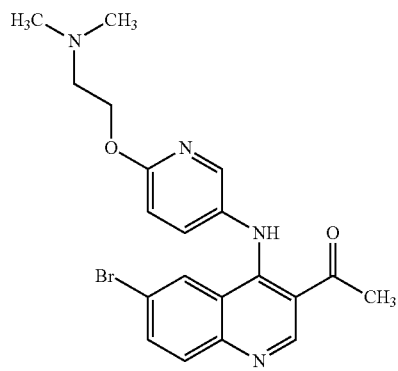 [SMILES: CC(=O)c1cnc2ccc(Br)cc2c1Nc1ccc(OCCN(C)C)nc1]

Following general procedure C, 1-(6-bromo-4-chloroquinolin-3-yl)ethanone (5.0 g, 18.0 mmol) was reacted with 6-(2-(dimethylamino)ethoxy)pyridin-3-amine (3.5 g, 19.0 mmol) to afford the desired product (5.7 g, 82%) as a yellow solid: $^1$H NMR (300 MHz, CDCl$_3$) δ 11.90 (s, 1H), 9.12 (s, 1H), 8.08-7.98 (m, 1H), 7.87-7.76 (m, 1H), 7.74-7.63 (m, 2H), 7.33 (dd, J=8.8, 2.8 Hz, 1H), 6.83 (d, J=8.8 Hz, 1H), 4.44 (t, J=5.5 Hz, 2H), 2.78 (s, 3H), 2.74 (t, J=8.8 Hz, 2H), 2.36 (s, 6H).

Example 852

1-(6-(3,5-dichloro-4-hydroxyphenyl)-4-(6-(2-(dimethylamino)ethoxy)pyridin-3-ylamino)quinolin-3-yl)ethanone hydrochloride

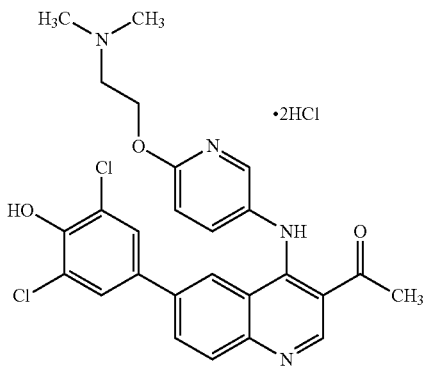 [SMILES: CC(=O)c1cnc2ccc(-c3cc(Cl)c(O)c(Cl)c3)cc2c1Nc1ccc(OCCN(C)C)nc1]

Following general procedure F, 1-(6-bromo-4-(6-(2-(dimethylamino)ethoxy)pyridin-3-ylamino)quinolin-3-yl)ethanone (5.0 g, 12.0 mmol) was reacted with 2,6-dichloro-4-(4,4,5,5-tetramethyl-1,3,2-dioxaborolan-2-yl)phenol (3.7 g, 13.0 mmol) to obtain the free base. The purified product was suspended in dichloromethane/methanol (1:1, 300 mL) after which HCl (30 mL, 1.25 M in methanol) was added to form a solution. The solution was concentrated to dryness to obtain desired product (5.2 g, 74% over two steps) as a yellow solid: $^1$H NMR (300 MHz, CD$_3$OD) δ 9.27 (s, 1H), 8.29 (d, J=2.9 Hz, 1H), 8.20-8.10 (m, 1H), 8.06-7.96 (m, 1H), 7.87-7.77 (m, 2H), 7.20 (s, 2H), 7.17-7.08 (m, 1H), 4.81-4.71 (m, 2H), 3.64 (t, J=5.1 Hz, 2H), 3.01 (s, 6H), 2.80 (s, 3H); ESI MS m/z 511 $[C_{26}H_{24}Cl_2N_4O_3+H]^+$; HPLC>99% (AUC), $t_R$=6.86 min.

Example 443

2,5-Dichloro-4-(4,4,5,5-tetramethyl-1,3,2-dioxaborolan-2-yl)phenol

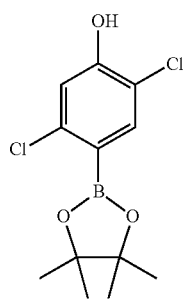 [SMILES: CC1(C)OB(c2cc(Cl)c(O)cc2Cl)OC1(C)C]

Following general procedure E, 4-bromo-2,5-dichlorophenol (290 mg, 1.2 mmol) was reacted with bis(pinacolato)diboron (305 mg, 1.2 mmol) to afford the desired product (83 mg, 25%) as a waxy solid: ESI MS m/z 289 $[C_{12}H_{15}BCl_2O_3+H]^+$.

Example 444

2-Chloro-6-fluoro-4-(4,4,5,5-tetramethyl-1,3,2-dioxaborolan-2-yl)phenol

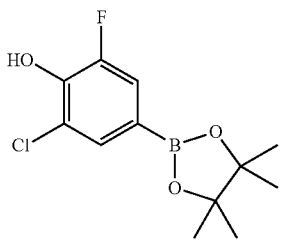 [SMILES: CC1(C)OB(c2cc(F)c(O)c(Cl)c2)OC1(C)C]

Following general procedure E, 4-bromo-2-chloro-6-fluorophenol (271 mg, 1.2 mmol) was reacted with bis(pinacolato)diboron (305 mg, 1.2 mmol) to afford the desired product (340 mg, >99%) as a colorless oil: $^1$H NMR (500 MHz, CDCl$_3$) δ 7.57 (t, J=1.3 Hz, 1H), 7.42 (dd, J=10.2, 1.3 Hz, 1H), 1.33 (s, 12H).

Example 445

2,6-Difluoro-4-(4,4,5,5-tetramethyl-1,3,2-dioxaborolan-2-yl)phenol

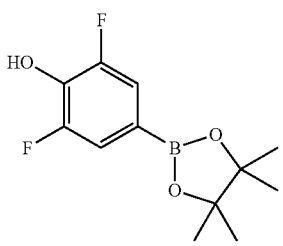 [SMILES: CC1(C)OB(c2cc(F)c(O)c(F)c2)OC1(C)C]

Following general procedure E, 4-bromo-2,6-difluorophenol (251 mg, 1.20 mmol) was reacted with bis(pinacolato)diboron (338 mg, 1.32 mmol) to afford the desired product (340 mg, >99%) as a white solid: ESI MS m/z 257 $[C_{12}H_{15}BF_2O_3+H]^+$.

Example 446

2,6-Dichloro-4-(4,4,5,5-tetramethyl-1,3,2-dioxaborolan-2-yl)phenol

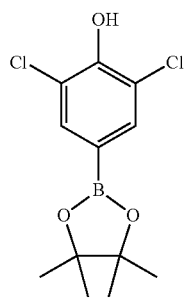 [SMILES: CC1(C)OB(c2cc(Cl)c(O)c(Cl)c2)OC1(C)C]

Following general procedure E, 4-bromo-2,6-dichlorophenol (290 mg, 1.20 mmol) was reacted with bis(pinacolato)diboron (305 mg, 1.20 mmol) to afford the desired product (298 mg, 86%): ESI MS m/z 289 $[C_{12}H_{15}BCl_2O_3+H]^+$.

Example 447

2-Ethoxy-4-(4,4,5,5-tetramethyl-1,3,2-dioxaborolan-2-yl)phenol

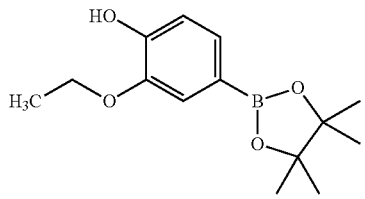 [SMILES: CCOc1cc(B2OC(C)(C)C(C)(C)O2)ccc1O]

Following general procedure E, 4-bromo-2-ethoxyphenol (1.26 g, 5.80 mmol) was reacted with bis(pinacolato)diboron (1.77 g, 6.96 mmol) to afford the desired product (580 mg, 38%) as a white solid: $^1$H NMR (500 MHz, CDCl$_3$) δ 7.36 (dd, J=7.8, 1.2 Hz, 1H), 6.92 (d, J=7.9 Hz, 1H), 5.91 (s, 1H), 4.16 (q, J=7.0 Hz, 2H), 1.44 (t, J=7.0 Hz, 3H), 1.33 (s, 12H).

Example 448 tert-Butyl trans-4-[3-(cyclopropanecarbonyl)-6-(4-hydroxyphenyl)quinolin-4-ylamino]cyclohexyl carbamate

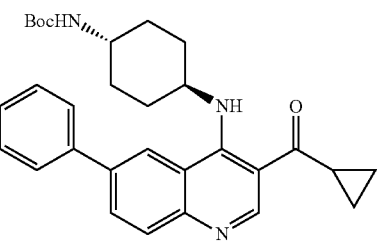

Following general procedure D, tert-butyl trans-4-[6-bromo-3-(cyclopropanecarbonyl)quinolin-4-ylamino]cyclohexylcarbamate (90 mg, 0.183 mmol) was reacted with 4-hydroxyphenyl boronic acid (38 mg, 0.275 mmol) to afford the desired product (48 mg, 52%) as an off-white solid: ESI MS m/z 502 $[C_{30}H_{35}N_3O_4+H]^+$.

Example 449 tert-Butyl trans-4-[3-(cyclopropanecarbonyl)-6-(4-hydroxy-3-methoxyphenyl)quinolin-4-ylamino]cyclohexylcarbamate

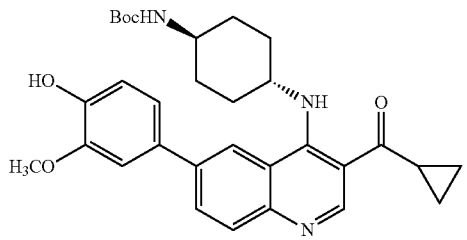 [SMILES: COc1cc(-c2ccc3ncc(C(=O)C4CC4)c(N[C@H]4CC[C@H](NC(=O)OC(C)(C)C)CC4)c3c2)ccc1O]

Following general procedure D, tert-butyl trans-4-[6-bromo-3-(cyclopropanecarbonyl)quinolin-4-ylamino]cyclohexylcarbamate (49 mg, 0.100 mmol) was reacted with 2-methoxy-4-(4,4,5,5-tetramethyl-1,3,2-dioxaborolan-2-yl)phenol (50 mg, 0.200 mmol) to afford the desired product (45 mg, 85%) as an off-white solid: ESI MS m/z 532 $[C_{31}H_{37}N_3O_5+H]^+$.

Example 450 tert-Butyl trans-4-[6-(2-cyanopyrimidin-5-yl)-3-(cyclopropanecarbonyl)quinolin-4-ylamino]cyclohexylcarbamate

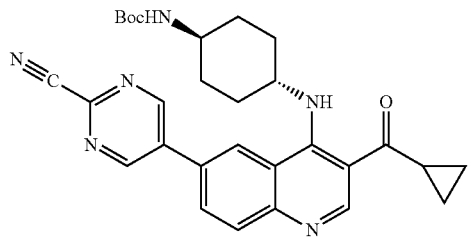 [SMILES: CC(C)(C)OC(=O)N[C@H]1CC[C@H](Nc2c(C(=O)C3CC3)cnc3ccc(-c4cnc(C#N)nc4)cc23)CC1]

Following general procedure D, tert-butyl trans-4-[6-bromo-3-(cyclopropanecarbonyl)quinolin-4-ylamino]cyclohexylcarbamate (49 mg, 0.100 mmol) was reacted with 5-(4,4,5,5-tetramethyl-1,3,2-dioxaborolan-2-yl)pyrimidine-2-carbonitrile (46 mg, 0.200 mmol) to afford the crude product (52 mg): ESI MS m/z 513 $[C_{29}H_{32}N_6O_3+H]^+$.

Example 451 tert-Butyl trans-4-[6-(1H-benzo[d]imidazol-5-yl)-3-(cyclopropanecarbonyl)quinolin-4-ylamino]cyclohexylcarbamate

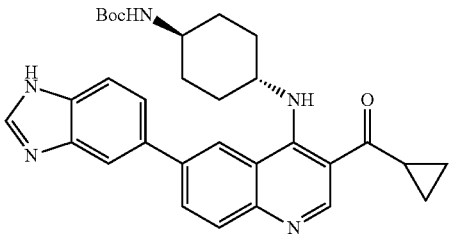 [SMILES: CC(C)(C)OC(=O)N[C@H]1CC[C@H](Nc2c(C(=O)C3CC3)cnc3ccc(-c4ccc5[nH]cnc5c4)cc23)CC1]

Following general procedure D, tert-butyl [trans-4-(6-bromo-3-(cyclopropanecarbonyl)quinolin-4-ylamino]cyclohexylcarbamate (49 mg, 0.100 mmol) was reacted with 6-(4,4,5,5-tetramethyl-1,3,2-dioxaborolan-2-yl)-1H-benzo[d]imidazole (49 mg, 0.200 mmol) to afford the desired product (45.3 mg, 86%) as an off-white solid: ESI MS m/z 526 $[C_{31}H_{35}N_5O_3+H]^+$.

Example 452 tert-Butyl trans-4-[6-(5-cyanothiophen-2-yl)-3-(cyclopropanecarbonyl)quinolin-4-ylamino]cyclohexylcarbamate

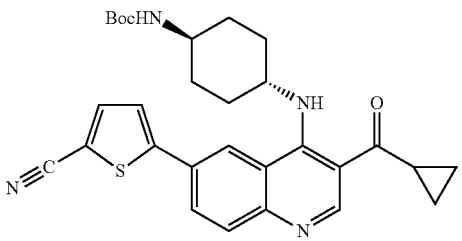 [SMILES: CC(C)(C)OC(=O)N[C@H]1CC[C@H](Nc2c(C(=O)C3CC3)cnc3ccc(-c4ccc(C#N)s4)cc23)CC1]

Following general procedure D, tert-butyl trans-4-[6-bromo-3-(cyclopropanecarbonyl)quinolin-4-ylamino]cyclohexylcarbamate (49 mg, 0.100 mmol) was reacted with 5-cyanothiophen-2-ylboronic acid (31 mg, 0.200 mmol) to afford the desired product (24 mg, 47%) as a brown solid: ESI MS m/z 517 $[C_{29}H_{32}N_4O_3S+H]^+$.

Example 453 tert-Butyl trans-4-[3-(Cyclopropanecarbonyl)-6-(3,5-difluoro-4-hydroxyphenyl)quinolin-4-ylamino]cyclohexylcarbamate

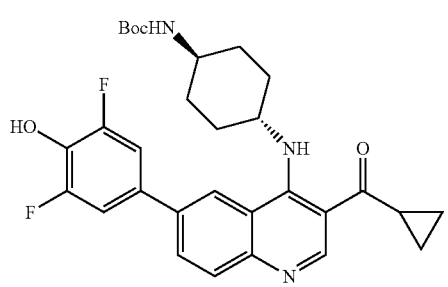 [SMILES: CC(C)(C)OC(=O)N[C@H]1CC[C@H](Nc2c(C(=O)C3CC3)cnc3ccc(-c4cc(F)c(O)c(F)c4)cc23)CC1]

Following general procedure D, tert-butyl trans-4-[6-bromo-3-(cyclopropanecarbonyl)quinolin-4-ylamino]cyclohexylcarbamate (49 mg, 0.100 mmol) was reacted with 2,6-difluoro-4-(4,4,5,5-tetramethyl-1,3,2-dioxaborolan-2-yl)phenol (50 mg, 0.196 mmol) to afford the desired product (26.2 mg, 49%) as an off-white solid: ESI MS m/z 538 $[C_{30}H_{33}F_2N_3O_4+H]^+$.

Example 454 tert-Butyl trans-4-[3-(cyclopropanecarbonyl)-6-(3,5-dichloro-4-hydroxyphenyl)quinolin-4-ylamino]cyclohexylcarbamate

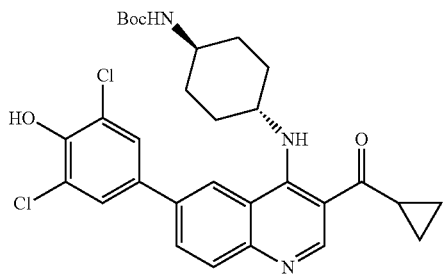

Following general procedure D, tert-butyl trans-4-[6-bromo-3-(cyclopropanecarbonyl)quinolin-4-ylamino]cyclohexylcarbamate (43 mg, 0.088 mmol) was reacted with 2,6-dichloro-4-(4,4,5,5-tetramethyl-1,3,2-dioxaborolan-2-yl)phenol (38 mg, 0.132 mmol) to afford the desired product (25 mg, 51%) as an off-white solid: ESI MS m/z 570 $[C_{30}H_{33}Cl_2N_3O_4+H]^+$.

Example 455 tert-Butyl trans-4-[3-(cyclopropanecarbonyl)-6-(2,5-dichloro-4-hydroxyphenyl)quinolin-4-ylamino]cyclohexylcarbamate

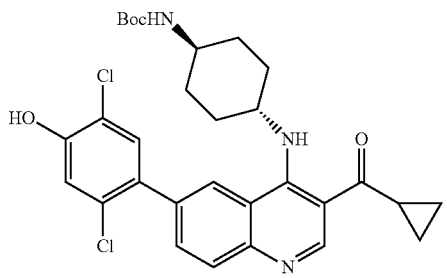 [SMILES: CC(C)(C)OC(=O)N[C@H]1CC[C@H](Nc2c(C(=O)C3CC3)cnc3ccc(-c4cc(Cl)c(O)cc4Cl)cc23)CC1]

Following general procedure D, tert-butyl trans-4-[6-bromo-3-(cyclopropanecarbonyl)quinolin-4-ylamino]cyclohexylcarbamate (49 mg, 0.100 mmol) was reacted with 2,5-dichloro-4-(4,4,5,5-tetramethyl-1,3,2-dioxaborolan-2-yl)phenol (85 mg, 0.300 mmol) to afford the crude product (57 mg) as a white solid: ESI MS m/z 570 $[C_{30}H_{33}Cl_2N_3O_4+H]^+$.

Example 456 tert-Butyl trans-4-[6-(3-chloro-5-fluoro-4-hydroxyphenyl)-3-(cyclopropanecarbonyl)quinolin-4-ylamino]cyclohexylcarbamate

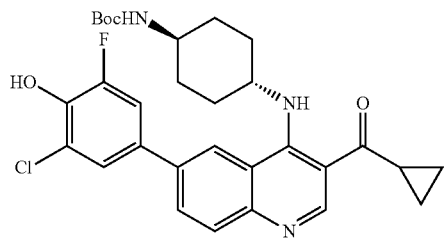 [SMILES: CC(C)(C)OC(=O)N[C@H]1CC[C@H](Nc2c(C(=O)C3CC3)cnc3ccc(-c4cc(F)c(O)c(Cl)c4)cc23)CC1]

Following general procedure D, tert-butyl trans-4-[6-bromo-3-(cyclopropanecarbonyl)quinoline-4-ylamino]cyclohexylcarbamate (49 mg, 0.100 mmol) was reacted with 2-chloro-6-fluoro-4-(4,4,5,5-tetramethyl-1,3,2-dioxaborolan-2-yl)phenol (130 mg, 0.478 mmol) to afford the desired product (20 mg, 36%) as an off white solid: ESI MS m/z 554 $[C_{30}H_{33}ClFN_3O_4+H]^+$.

Example 457 tert-Butyl trans-4-[3-(cyclopropanecarbonyl)-6-(pyridin-4-yl)quinolin-4-ylamino]cyclohexylcarbamate

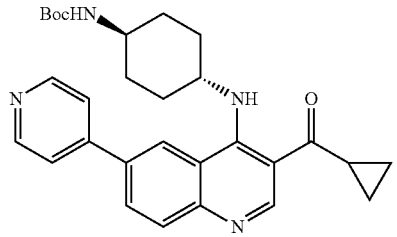 [SMILES: CC(C)(C)OC(=O)N[C@H]1CC[C@H](Nc2c(C(=O)C3CC3)cnc3ccc(-c4ccncc4)cc23)CC1]

Following general procedure D, tert-butyl trans-4-(6-bromo-3-isobutyrylquinolin-4-ylamino)cyclohexylcarbamate (49 mg, 0.100 mmol) was reacted with pyridin-4-ylboronic acid (25 mg, 0.200 mmol) to afford the crude product (50 mg) as an off-white solid: ESI MS m/z 487 $[C_{29}H_{34}N_4O_3+H]^+$.

Example 458 tert-Butyl trans-4-[3-(cyclopropanecarbonyl)-6-(1H-pyrazol-4-yl)quinolin-4-ylamino]cyclohexylcarbamate

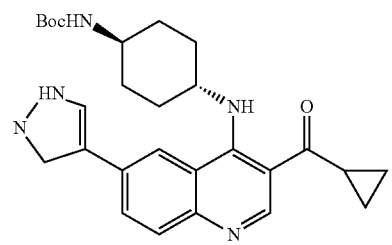 [SMILES: CC(C)(C)OC(=O)N[C@H]1CC[C@H](Nc2c(C(=O)C3CC3)cnc3ccc(C4=CNNC4)cc23)CC1]

Following general procedure D, tert-butyl trans-4-(6-bromo-3-isobutyrylquinolin-4-ylamino)cyclohexylcarbamate (49 mg, 0.100 mmol) was reacted with 4-(4,4,5,5-tetramethyl-1,3,2-dioxaborolan-2-yl)-1H-pyrazole (39 mg, 0.200 mmol) to afford the desired product (17 mg, 36%) as an off-white solid: ESI MS m/z 476 $[C_{27}H_{33}N_5O_3+H]^+$.

Example 459 tert-Butyl 8-[6-(3-chloro-4-hydroxy-5-methoxyphenyl)-3-(cyclopropanecarbonyl)quinolin-4-yl]-2,8-diazaspiro[4,5]decane-2-carboxylate

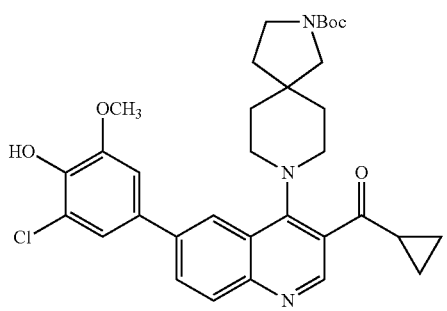 [SMILES: COc1cc(-c2ccc3ncc(C(=O)C4CC4)c(N4CCC5(CCN(C(=O)OC(C)(C)C)C5)CC4)c3c2)cc(Cl)c1O]

Following general procedure F, tert-butyl 8-[6-bromo-3-(cyclopropanecarbonyl)quinolin-4-yl]-2,8-diazaspiro[4,5]decane-2-carboxylate (50 mg, 0.097 mmol) was reacted with 3-chloro-4-hydroxy-5-methoxyphenylboronic acid (41 mg, 0.161 mmol) to afford the crude product (110 mg) as a brown oil: ESI MS m/z 593 $[C_{33}H_{38}ClN_3O_5+H]^+$.

Example 460 tert-Butyl cis-4-[3-(cyclopropanecarbonyl)-6-(4-hydroxy-3-methoxyphenyl)quinolin-4-ylamino]cyclohexylcarbamate

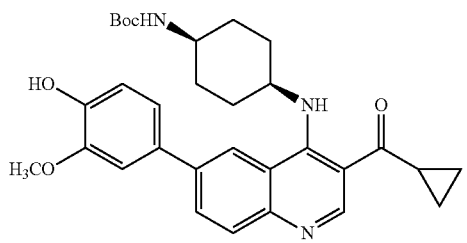 [SMILES: COc1cc(-c2ccc3ncc(C(=O)C4CC4)c(N[C@H]4CC[C@@H](NC(=O)OC(C)(C)C)CC4)c3c2)ccc1O]

Following general procedure F, tert-butyl cis-4-[6-bromo-3-(cyclopropanecarbonyl)quinolin-4-ylamino]cyclohexylcarbamate (40 mg, 0.082 mmol) was reacted with 2-methoxy-4-(4,4,5,5-tetramethyl-1,3,2-dioxaborolan-2-yl)phenol (31 mg, 0.124 mmol) to afford the crude product (43 mg) as a yellow solid: ESI MS m/z 532 $[C_{31}H_{37}N_3O_5+H]^+$.

Example 461 tert-Butyl cis-4-[3-(cyclopropanecarbonyl)-6-(3,5-difluoro-4-hydroxyphenyl)quinolin-4-ylamino]cyclohexylcarbamate

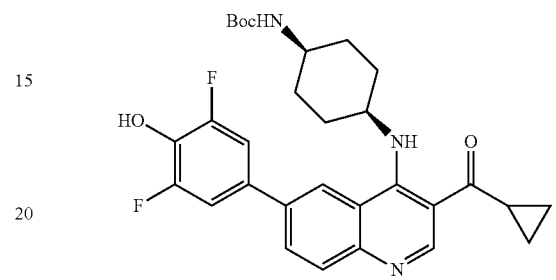

Following general procedure F, tert-butyl cis-4-[6-bromo-3-(cyclopropanecarbonyl)quinolin-4-ylamino]cyclohexylcarbamate (54 mg, 0.110 mmol) was reacted with 2,6-difluoro-4-(4,4,5,5-tetramethyl-1,3,2-dioxaborolan-2-yl)phenol (34 mg, 0.132 mmol) to afford the desired product (51 mg, 86%) as a light yellow solid: ESI MS m/z 538 $[C_{30}H_{33}F_2N_3O_4+H]^+$.

Example 462 tert-Butyl 4-{[6-(3-chloro-4-hydroxy-5-methoxyphenyl)-3-(cyclopropanecarbonyl)quinolin-4-ylamino]methyl}piperidine-1-carboxylate

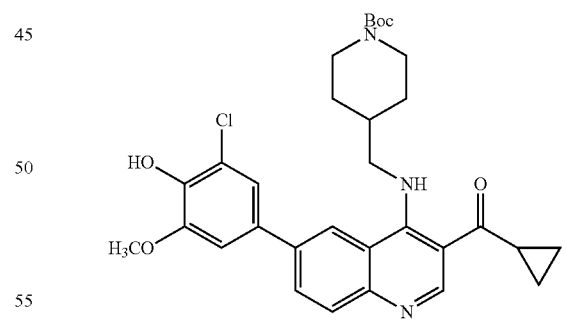

Following general procedure F, tert-butyl 4-{[6-bromo-3-(cyclopropanecarbonyl)quinolin-4-ylamino]methyl}piperidine-1-carboxylate (55 mg, 0.110 mmol) was reacted with 2-chloro-6-methoxy-4-(4,4,5,5-tetramethyl-1,3,2-dioxaborolan-2-yl)phenol (46 mg, 0.165 mmol) to afford the desired product (27 mg, 43%) as a yellow solid: ESI MS m/z 567 $[C_{31}H_{36}ClN_3O_5+H]^+$.

Example 463 tert-Butyl 4-[3-(cyclopropanecarbonyl)-6-(3-chloro-4-hydroxy-5-methoxyphenyl) quinolin-4-ylamino] adamantylcarbamate

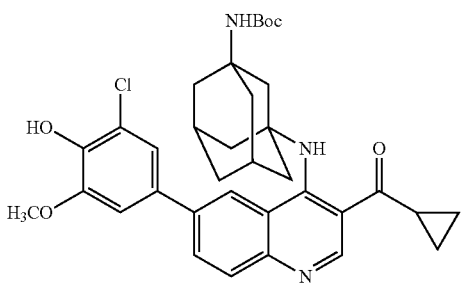 [SMILES: COc1cc(-c2ccc3ncc(C(=O)C4CC4)c(NC45CC6CC(CC(NC(=O)OC(C)(C)C)(C6)C4)C5)c3c2)cc(Cl)c1O]

Following general procedure F, tert-butyl 4-[6-bromo-3-(cyclopropanecarbonyl)quinolin-4-ylamino]adamantylcarbamate (57 mg, 0.100 mmol) was reacted with 2-chloro-6-methoxy-4-(4,4,5,5-tetramethyl-1,3,2-dioxaborolan-2-yl)phenol (43 mg, 0.150 mmol) to afford the crude product (84 mg) as a brown oil: ESI MS m/z 619 $[C_{35}H_{40}ClN_3O_5+H]^+$.

Example 464 tert-Butyl trans-4-[6-(6-cyanopyridin-3-yl)-3-isobutyrylquinolin-4-ylamino]cyclohexylcarbamate

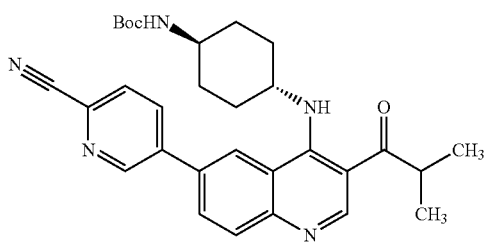 [SMILES: CC(C)C(=O)c1cnc2ccc(-c3ccc(C#N)nc3)cc2c1N[C@H]1CC[C@H](NC(=O)OC(C)(C)C)CC1]

Following general procedure D, tert-butyl trans-4-(6-bromo-3-isobutyrylquinolin-4-ylamino)cyclohexylcarbamate (47 mg, 0.093 mmol) was reacted with 5-(4,4,5,5-tetramethyl-1,3,2-dioxaborolan-2-yl)picolinonitrile (26 mg, 0.200 mmol) to afford the crude product (47 mg) as a yellow solid: ESI MS m/z 514 $[C_{30}H_{35}N_5O_3+H]^+$.

Example 465 tert-Butyl trans-4-[6-(3-chloro-5-fluoro-4-hydroxyphenyl)-3-isobutyrylquinolin-4-ylamino]cyclohexylcarbamate

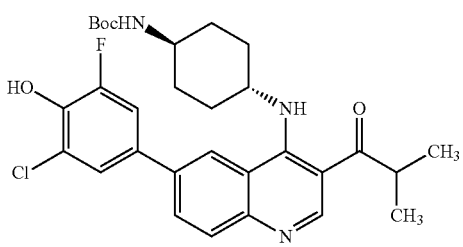

Following general procedure D, tert-butyl trans-4-(6-bromo-3-isobutyrylquinolin-4-ylamino)cyclohexylcarbamate (49 mg, 0.100 mmol) was reacted with 2-chloro-6-fluoro-4-(4,4,5,5-tetramethyl-1,3,2-dioxaborolan-2-yl)phenol (102 mg, 0.375 mmol) to afford the crude product (56 mg) as an off-white solid: ESI MS m/z 556 $[C_{30}H_{35}ClFN_3O_4+H]^+$.

Example 466 tert-Butyl trans-4-[6-(3,5-difluoro-4-hydroxyphenyl)-3-isobutyrylquinolin-4-ylamino]cyclohexylcarbamate

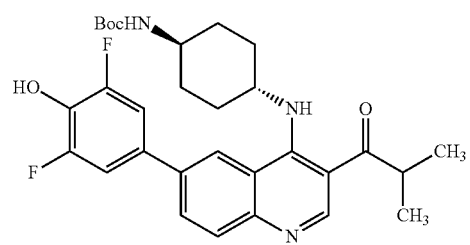 [SMILES: CC(C)C(=O)c1cnc2ccc(-c3cc(F)c(O)c(F)c3)cc2c1N[C@H]1CC[C@H](NC(=O)OC(C)(C)C)CC1]

Following general procedure D, tert-butyl trans-4-(6-bromo-3-isobutyrylquinolin-4-ylamino)cyclohexylcarbamate (49 mg, 0.100 mmol) was reacted with 2,6-difluoro-4-(4,4,5,5-tetramethyl-1,3,2-dioxaborolan-2-yl)phenol (58 mg, 0.227 mmol) to afford the crude product (64 mg) as an off-white solid: ESI MS m/z 540 $[C_{30}H_{35}F_2N_3O_4+H]^+$.

Example 467 tert-Butyl trans-4-[6-(3-chloro-4-hydroxyphenyl)-3-isobutyrylquinolin-4-ylamino]cyclohexylcarbamate

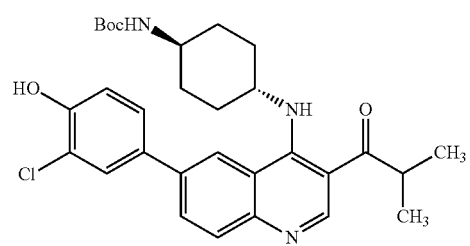 [SMILES: CC(C)C(=O)c1cnc2ccc(-c3ccc(O)c(Cl)c3)cc2c1N[C@H]1CC[C@H](NC(=O)OC(C)(C)C)CC1]

Following general procedure D, tert-butyl trans-4-(6-bromo-3-isobutyrylquinolin-4-ylamino)cyclohexylcarbamate (49 mg, 0.100 mmol) was reacted with 3-chloro-4-hydroxyphenylboronic acid (34 mg, 0.200 mmol) to afford the desired product (39 mg, 72%) as an off-white solid: ESI MS m/z 538 $[C_{30}H_{36}ClN_3O_4+H]^+$.

Example 468 tert-Butyl trans-4-[6-(3,5-dichloro-4-hydroxyphenyl)-3-isobutyrylquinolin-4-ylamino]cyclohexylcarbamate

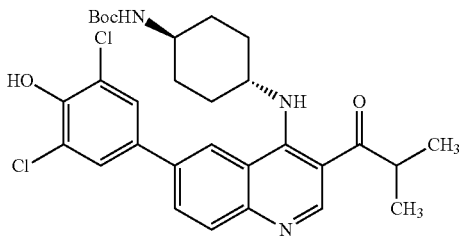 [SMILES: CC(C)C(=O)c1cnc2ccc(-c3cc(Cl)c(O)c(Cl)c3)cc2c1N[C@H]1CC[C@H](NC(=O)OC(C)(C)C)CC1]

Following general procedure D, tert-butyl trans-4-(6-bromo-3-isobutyrylquinolin-4-ylamino)cyclohexylcarbamate (49 mg, 0.100 mmol) was reacted with 2,6-dichloro-4-(4,4,5,5-tetramethyl-1,3,2-dioxaborolan-2-yl)phenol (73 mg, 0.253 mmol) to afford the crude product (60 mg) as an off-white solid: ESI MS m/z 572 $[C_{30}H_{35}Cl_2N_3O_4+H]^+$.

Example 469 tert-Butyl trans-4-[3-acetyl-6-(3,5-dichloro-4-hydroxyphenyl)quinolin-4-ylamino]cyclohexylcarbamate

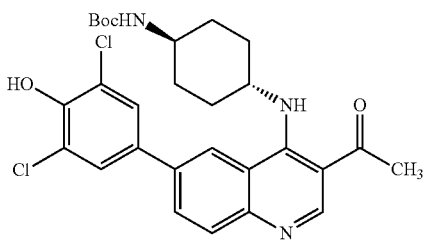 [SMILES: CC(=O)c1cnc2ccc(-c3cc(Cl)c(O)c(Cl)c3)cc2c1N[C@H]1CC[C@H](NC(=O)OC(C)(C)C)CC1]

Following general procedure D, tert-butyl trans-4-(3-acetyl-6-bromoquinolin-4-ylamino)cyclohexylcarbamate (40 mg, 0.087 mmol) was reacted with 2,6-dichloro-4-(4,4,5,5-tetramethyl-1,3,2-dioxaborolan-2-yl)phenol (50 mg, 0.195 mmol) to afford the crude product (46 mg) as a yellow solid: ESI MS m/z 544 $[C_{28}H_{31}Cl_2N_3O_4+H]^+$.

Example 470 tert-Butyl trans-4-[3-acetyl-6-(3,5-difluoro-4-hydroxyphenyl)quinolin-4-ylamino]cyclohexylcarbamate

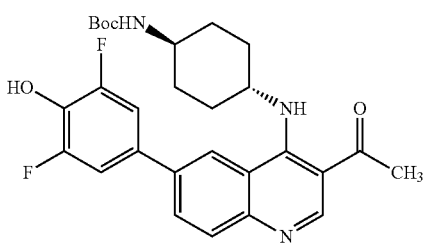 [SMILES: CC(=O)c1cnc2ccc(-c3cc(F)c(O)c(F)c3)cc2c1N[C@H]1CC[C@H](NC(=O)OC(C)(C)C)CC1]

Following general procedure D, tert-butyl trans-4-(3-acetyl-6-bromoquinolin-4-ylamino)cyclohexylcarbamate (47 mg, 0.100 mmol) was reacted with 2,6-difluoro-4-(3,3,4,4-tetramethylborolan-1-yl)phenol (97 mg, 0.382 mmol) to afford the desired product (30 mg, 59%) as a yellow solid: ESI MS m/z 512 $[C_{28}H_{31}F_2N_3O_4+H]^+$.

Example 471 tert-Butyl trans-4-[3-acetyl-6-(3-chloro-4-hydroxy-5-methoxyphenyl)quinolin-4-ylamino]cyclohexylcarbamate

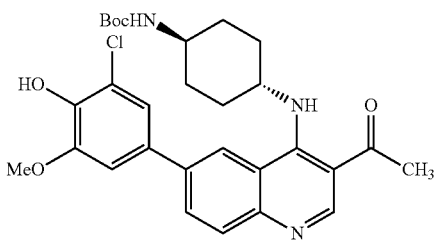 [SMILES: COc1cc(-c2ccc3ncc(C(C)=O)c(N[C@H]4CC[C@H](NC(=O)OC(C)(C)C)CC4)c3c2)cc(Cl)c1O]

Following general procedure D, tert-butyl trans-4-(3-acetyl-6-bromoquinolin-4-ylamino)cyclohexylcarbamate (56 mg, 0.200 mmol) was reacted with 2-chloro-6-methoxy-4-(3,3,4,4-tetramethylborolan-1-yl)phenol (47 mg, 0.100 mmol) to afford the desired product (35 mg, 65%) as a yellow solid: ESI MS m/z 541 $[C_{29}H_{34}ClN_3O_5+H]^+$.

Example 472 tert-Butyl trans-4-[6-(3,5-dichloro-4-hydroxyphenyl)-3-(3-methylbutanoyl)quinolin-4-ylamino]cyclohexylcarbamate

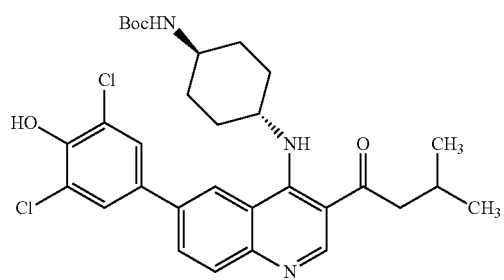 [SMILES: CC(C)CC(=O)c1cnc2ccc(-c3cc(Cl)c(O)c(Cl)c3)cc2c1N[C@H]1CC[C@H](NC(=O)OC(C)(C)C)CC1]

Following general procedure D, 1-{4-[trans-4-aminocyclohexylamino]-6-bromoquinolin-3-yl}-3-methylbutan-1-one (50 mg, 0.100 mmol) was reacted with 2,6-dichloro-4-(3,3,4,4-tetramethylborolan-1-yl)phenol (42 mg, 0.145 mmol) to afford the desired product (36 mg, 61%) as a yellow solid: ESI MS m/z 587 [$C_{31}H_{37}Cl_2N_3O_4$+H]$^+$.

Example 473 tert-Butyl trans-4-[6-(3-chloro-4-hydroxy-5-methoxyphenyl)-3-(3-methylbutanoyl)quinolin-4-ylamino]cyclohexylcarbamate

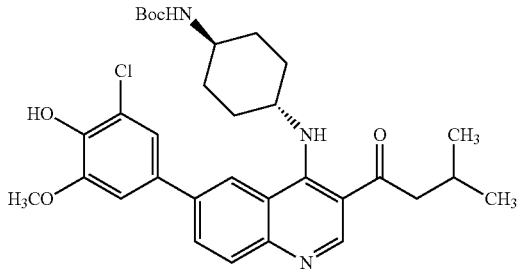 [SMILES: COc1cc(-c2ccc3ncc(C(=O)CC(C)C)c(N[C@H]4CC[C@H](NC(=O)OC(C)(C)C)CC4)c3c2)cc(Cl)c1O]

Following general procedure D, 1-{4-[trans-4-aminocyclohexylamino]-6-bromoquinolin-3-yl}-3-methylbutan-1-one (50 mg, 0.10 mmol) was reacted with 2-chloro-6-methoxy-4-(4,4,5,5-tetramethyl-1,3,2-dioxaborolan-2-yl)phenol (56 mg, 0.20 mmol) to afford the desired product (42 mg, 72%) as a yellow solid: $^1$H NMR (500 MHz, CDCl$_3$) 10.81 (d, J=7.9 Hz, 1H), 8.99 (s, 1H), 8.22 (s, 1H), 7.97 (d, J=8.3 Hz, 1H), 7.86 (d, J=8.3 Hz, 1H), 7.22 (d, J=1.9 Hz, 1H), 7.03 (d, J=1.9 Hz, 1H), 5.96-5.91 (m, 1H), 4.00 (s, 3H), 3.52-3.46 (m, 1H), 2.89 (d, J=6.9 Hz, 2H), 2.34-2.26 (m, 3H), 2.21-2.14 (m, 2H), 1.36-1.20 (m, 4H), 1.02 (d, J=6.6 Hz, 2H), 1.45 (s, 9H).

Example 474 tert-Butyl trans-4-[6-(3-chloro-4-hydroxy-5-methoxyphenyl)-3-(cyclopropanecarbonyl)-7-fluoroquinolin-4-ylamino]

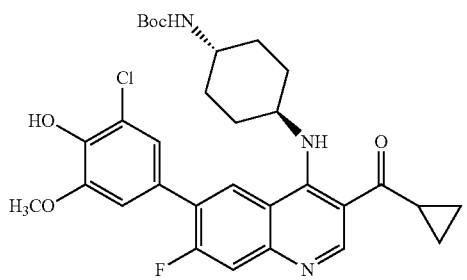 [SMILES: COc1cc(-c2cc3c(N[C@H]4CC[C@H](NC(=O)OC(C)(C)C)CC4)c(C(=O)C4CC4)cnc3cc2F)cc(Cl)c1O]

Following general procedure F, {4-[trans-4-aminocyclohexylamino]-6-bromo-7-fluoroquinolin-3-yl}(cyclopropyl)methanone (65 mg, 0.128 mmol) was reacted with 2-chloro-6-methoxy-4-(4,4,5,5-tetramethyl-1,3,2-dioxaborolan-2-yl)

phenol (54 mg, 0.192 mmol) to afford the desired product (53 mg, 71%) as a yellow solid: ESI MS m/z 585 [$C_{31}H_{35}ClFN_3O_5$+H]$^+$.

Example 55

{4-[trans-4-Aminocyclohexylamino]-6-(4-hydroxyphenyl)quinolin-3-yl}(cyclopropyl)methanone

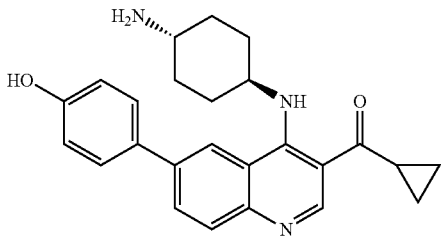 [SMILES: N[C@H]1CC[C@H](Nc2c(C(=O)C3CC3)cnc3ccc(-c4ccc(O)cc4)cc23)CC1]

Following general procedure A-2, tert-butyl trans-4-[3-(cyclopropanecarbonyl)-6-(4-hydroxyphenyl)quinolin-4-ylamino]cyclohexylcarbamate (48 mg, 0.096 mmol) was reacted with TFA (0.40 mL) to afford the desired product (17.8 mg, 46%) as an off-white solid: $^1$H NMR (500 MHz, CD$_3$OD) δ 9.16 (s, 1H), 8.37 (d, J=1.7 Hz, 1H), 8.07 (dd, J=8.7, 1.8 Hz, 1H), 7.92 (d, J=8.7 Hz, 1H), 7.60-7.56 (m, 2H), 6.96-6.92 (m, 2H), 4.29-4.19 (m, 1H), 3.29-3.20 (m, 1H), 2.89-2.80 (m, 1H), 2.37 (d, J=12.8 Hz, 2H), 2.18 (d, J=11.7 Hz, 2H), 1.75-1.64 (m, 2H), 1.64-1.53 (m, 2H), 1.23-1.18 (m, 2H), 1.15-1.09 (m, 2H); ESI MS m/z 402 [$C_{25}H_{27}N_3O_2$+H]$^+$; HPLC 98.5% (AUC), $t_R$=11.38 min.

Example 81

{4-[trans-4-Aminocyclohexylamino]-6-(4-hydroxy-3-methoxyphenyl)quinolin-3-yl}(cyclopropyl)methanone

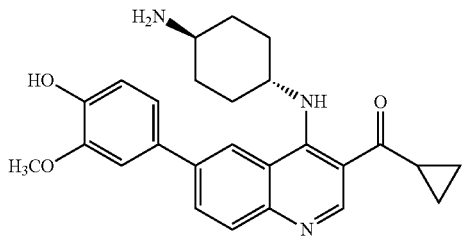

Following general procedure A-2, tert-butyl trans-4-[3-(cyclopropanecarbonyl)-6-(4-hydroxy-3-methoxyphenyl)quinolin-4-ylamino]cyclohexylcarbamate (45 mg, 0.085 mmol) was reacted with TFA (2 mL) to afford the desired product (11.3 mg, 31%) as a yellow solid: $^1$H NMR (500 MHz, CD$_3$OD) δ 9.12 (s, 1H), 8.36 (s, 1H), 8.04-7.98 (m, 1H), 7.89 (d, J=8.7 Hz, 1H), 7.26 (d, J=1.9 Hz, 1H), 7.17 (dd, J=8.2, 2.0 Hz, 1H), 6.93 (d, J=8.2 Hz, 1H), 4.14 (s, 1H), 3.97 (s, 3H), 3.20-3.07 (m, 2H), 2.87-2.75 (m, 2H), 2.28 (d, J=12.2 Hz, 2H), 2.01 (d, J=11.6 Hz, 2H), 1.64-1.53 (m, 2H), 1.40-

1.26 (m, 3H), 1.21-1.14 (m, 2H), 1.12-1.03 (m, 2H); ESI MS m/z 432 [$C_{26}H_{29}N_3O_3$+H]$^+$; HPLC 98.8% (AUC), $t_R$=7.95 min.

Example 96

5-{4-[trans-4-Aminocyclohexylamino]-3-(cyclopropanecarbonyl)quinolin-6-yl}pyrimidine-2-carbonitrile

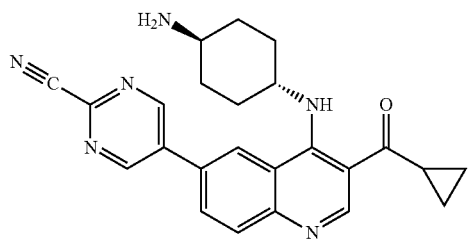 [SMILES: N#Cc1ncc(-c2ccc3ncc(C(=O)C4CC4)c(N[C@H]4CC[C@H](N)CC4)c3c2)cn1]

Following general procedure A-2, tert-butyl trans-4-[6-(2-cyanopyrimidin-5-yl)-3-(cyclopropane carbonyl)quinolin-4-ylamino]cyclohexylcarbamate (52 mg, 0.100 mmol) was reacted with TFA (1 mL) to afford the desired product (13.7 mg, 33%) as a yellow solid: $^1$H NMR (500 MHz, CD$_3$OD) δ 9.33 (s, 2H), 9.19 (s, 1H), 8.60 (d, J=1.9 Hz, 1H), 8.20 (dd, J=8.7, 2.0 Hz, 1H), 8.05 (d, J=8.7 Hz, 1H), 4.25-4.16 (m, 1H), 3.15-3.07 (m, 1H), 2.90-2.81 (m, 1H), 2.34 (d, J=13.1 Hz, 2H), 2.12 (d, J=11.8 Hz, 2H), 1.69-1.59 (m, 2H), 1.55-1.45 (m, 2H), 1.24-1.19 (m, 2H), 1.15-1.10 (m, 2H); ESI MS m/z 413 [$C_{24}H_{24}N_6O$+H]$^+$; HPLC 94.9% (AUC), $t_R$=9.67 min.

Example 116

{4-[trans-4-Aminocyclohexylamino]-6-(1H-benzo[d]imidazol-5-yl)quinolin-3-yl}(cyclopropyl)methanone

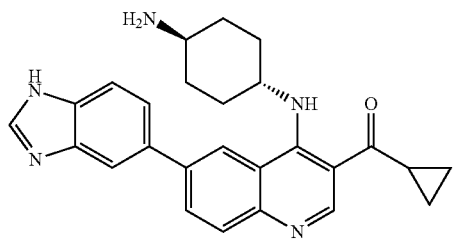 [SMILES: N[C@H]1CC[C@H](Nc2c(C(=O)C3CC3)cnc3ccc(-c4ccc5[nH]cnc5c4)cc23)CC1]

Following general procedure A-2, tert-butyl trans-4-[6-(1H-benzo[d]imidazol-5-yl)-3-(cyclopropanecarbonyl)quinolin-4-ylamino]cyclohexylcarbamate (45.3 mg, 0.086 mmol) was reacted with TFA (2 mL) to afford the desired product (21.3 mg, 58%) as an off-white solid: $^1$H NMR (500 MHz, CDCl$_3$) δ 9.16 (s, 1H), 8.48 (s, 1H), 8.27 (s, 1H), 8.12 (d, J=8.7 Hz, 1H), 7.99-7.93 (m, 2H), 7.74 (d, J=8.4 Hz, 1H), 7.67 (d, J=8.4 Hz, 1H), 4.29 (s, 1H), 3.17 (s, 1H), 2.93-2.78 (m, 1H), 2.36 (d, J=11.1 Hz, 2H), 2.15 (d, J=11.2 Hz, 2H), 1.72-1.53 (m, 4H), 1.23-1.17 (m, 2H), 1.14-1.05 (m, 2H); ESI MS m/z 426 [$C_{26}H_{27}N_5O$+H]$^+$; HPLC 96.0% (AUC), $t_R$=8.89 min.

Example 119

5-{4-[trans-4-Aminocyclohexylamino]-3-(cyclopropanecarbonyl)quinolin-6-yl}thiophene-2-carbonitrile

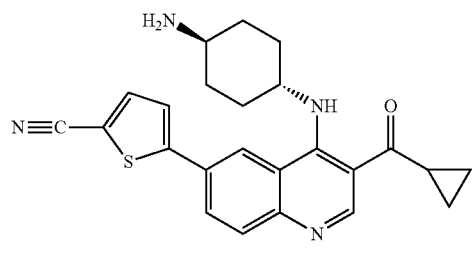 [SMILES: N#Cc1ccc(-c2ccc3ncc(C(=O)C4CC4)c(N[C@H]4CC[C@H](N)CC4)c3c2)s1]

Following general procedure A-2, tert-butyl trans-4-[6-(5-cyanothiophen-2-yl)-3-(cyclopropane carbonyl)quinolin-4-ylamino]cyclohexylcarbamate (24 mg, 0.047 mmol) was reacted with TFA (2 mL) to afford the desired product (13.2 mg, 32%) as a yellow solid: $^1$H NMR (500 MHz, CD$_3$OD) δ 9.25 (s, 1H), 8.54 (s, 1H), 8.27 (d, J=8.6 Hz, 1H), 7.98 (d, J=8.8 Hz, 1H), 7.85 (d, J=4.0 Hz, 1H), 7.70 (d, J=4.0 Hz, 1H), 4.28 (s, 1H), 3.28-3.25 (m, 1H), 2.89-2.83 (m, 1H), 2.42 (d, J=12.8 Hz, 2H), 2.23 (d, J=12.2 Hz, 2H), 1.80-1.63 (m, 4H), 1.27-1.21 (m, 2H), 1.19-1.13 (m, 2H); ESI MS m/z 417 [$C_{24}H_{24}N_4OS$+H]$^+$; HPLC 95.1% (AUC), $t_R$=10.32 min.

Example 156

{4-[trans-4-Aminocyclohexylamino]-6-(3,5-difluoro-4-hydroxyphenyl)quinolin-3-yl}(cyclopropyl)methanone

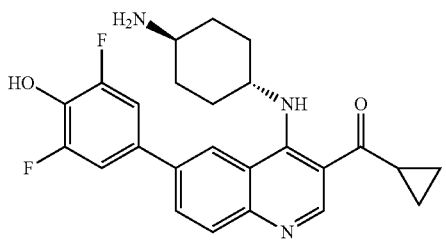 [SMILES: N[C@H]1CC[C@H](Nc2c(C(=O)C3CC3)cnc3ccc(-c4cc(F)c(O)c(F)c4)cc23)CC1]

Following general procedure A-2, tert-butyl trans-4-[3-(cyclopropanecarbonyl)-6-(3,5-difluoro-4-hydroxyphenyl)quinolin-4-ylamino]cyclohexylcarbamate (26.2 mg, 0.049 mmol) was reacted with TFA (2 mL) to afford the desired product (17 mg, 79%) as a yellow solid: $^1$H NMR (300 MHz, CD$_3$OD) δ 9.14 (s, 1H), 8.36 (s, 1H), 8.03 (d, J=9.5 Hz, 1H), 7.93 (d, J=8.7 Hz, 1H), 7.35 (d, J=9.6 Hz, 2H), 4.16 (s, 1H), 3.07 (s, 1H), 2.85 (s, 1H), 2.36 (d, J=10.7 Hz, 2H), 2.18 (d, J=14.1 Hz, 2H), 1.75-1.51 (m, 4H), 1.20 (s, 2H), 1.11 (s, 2H); ESI MS m/z 438 [C$_{25}$H$_{25}$F$_2$N$_3$O$_2$+H]$^+$; HPLC 98.5% (AUC), t$_R$=8.70 min.

Example 157(a)

{4-[trans-4-Aminocyclohexylamino]-6-(3,5-dichloro-4-hydroxyphenyl)quinolin-3-yl}(cyclopropyl)methanone

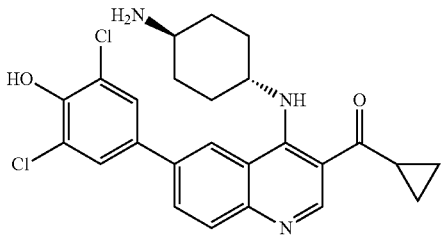 [SMILES: N[C@H]1CC[C@H](Nc2c(C(=O)C3CC3)cnc3ccc(-c4cc(Cl)c(O)c(Cl)c4)cc23)CC1]

Following general procedure A-2, tert-butyl trans-4-[3-(cyclopropanecarbonyl)-6-(3,5-dichloro-4-hydroxyphenyl)quinolin-4-ylamino]cyclohexylcarbamate (25.7 mg, 0.045 mmol) was reacted with TFA (2 mL) to afford the desired product (8.8 mg, 42%) as a yellow-orange solid: $^1$H NMR (500 MHz, CD$_3$OD) δ 9.14 (s, 1H), 8.35 (d, J=1.7 Hz, 1H), 8.04 (dd, J=8.7, 1.9 Hz, 1H), 7.94 (d, J=8.7 Hz, 1H), 7.69 (s, 2H), 4.14 (s, 1H), 3.29-3.20 (m, 1H), 2.88-2.79 (m, 1H), 2.37 (d, J=12.5 Hz, 2H), 2.19 (d, J=11.0 Hz, 2H), 1.76-1.64 (m, 2H), 1.64-1.52 (m, 2H), 1.23-1.18 (m, 2H), 1.15-1.10 (m, 2H); ESI MS m/z 470 [C$_{25}$H$_{25}$Cl$_2$N$_3$O$_2$+H]$^+$; HPLC 94.9% (AUC), t$_R$=10.74 min.

Example 157(b)

{4-[trans-4-Aminocyclohexylamino]-6-(3,5-dichloro-4-hydroxyphenyl)quinolin-3-yl}(cyclopropyl)methanone dihydrochloride

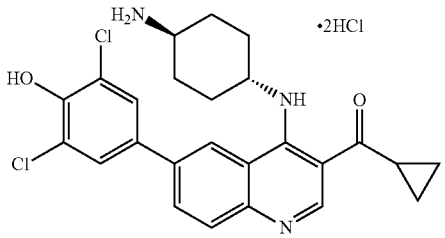 [SMILES: N[C@H]1CC[C@H](Nc2c(C(=O)C3CC3)cnc3ccc(-c4cc(Cl)c(O)c(Cl)c4)cc23)CC1]

A solution of {4-[trans-4-aminocyclohexylamino]-6-(3,5-dichloro-4-hydroxyphenyl)quinolin-3-yl}(cyclopropyl)methanone (9.1 mg, 0.019 mmol) in methanol (10 mL) was treated with 1 N HCl (2 mL) and the mixture was concentrated and dried to obtain the desired salt (7.7 mg, 77%) as an off-white solid: $^1$H NMR (500 MHz, CD$_3$OD) δ 9.38 (s, 1H), 8.46 (s, 1H), 8.28 (d, J=8.5 Hz, 1H), 7.99 (d, J=8.5 Hz, 1H), 7.75 (bs, 2H), 2.86 (bs, 1H), 2.54-2.48 (m, 2H), 2.25-2.19 (m, 2H), 1.87-1.79 (m, 2H), 1.72-1.50 (m, 2H), 1.40-1.18 (m, 4H); ESI MS m/z 470 [C$_{25}$H$_{25}$Cl$_2$N$_3$O$_2$+H]$^+$; HPLC 95.0% (AUC), t$_R$=10.79 min.

Example 160

{4-[trans-4-Aminocyclohexylamino]-6-(2,5-dichloro-4-hydroxyphenyl)quinolin-3-yl}(cyclopropyl)methanone

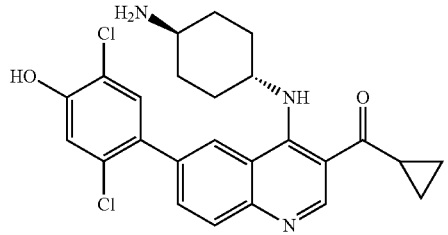 [SMILES: N[C@H]1CC[C@H](Nc2c(C(=O)C3CC3)cnc3ccc(-c4cc(Cl)c(O)cc4Cl)cc23)CC1]

Following general procedure A-2, tert-butyl trans-4-[3-(cyclopropanecarbonyl)-6-(2,5-dichloro-4-hydroxyphenyl)quinolin-4-ylamino]cyclohexylcarbamate (57 mg, 0.100 mmol) was reacted with TFA (2 mL) to afford the desired product (10.8 mg, 23%) as an off-white solid: $^1$H NMR (500 MHz, CD$_3$OD) δ 9.23 (s, 1H), 8.27 (d, J=1.6 Hz, 1H), 7.94 (d, J=8.6 Hz, 1H), 7.87 (dd, J=8.7, 1.7 Hz, 1H), 7.48 (s, 1H), 7.12 (s, 1H), 4.27-4.14 (m, 1H), 3.27-3.18 (m, 1H), 2.95-2.82 (m, 1H), 2.34 (d, J=11.5 Hz, 2H), 2.14 (d, J=10.7 Hz, 2H), 1.72-1.59 (m, 2H), 1.59-1.48 (m, 2H), 1.26-1.16 (m, 2H), 1.16-1.07 (m, 2H); ESI MS m/z 470 [C$_{25}$H$_{25}$Cl$_2$N$_3$O$_2$+H]$^+$; HPLC 96.4% (AUC), t$_R$=10.67 min.

Example 179

{4-[trans-4-Aminocyclohexylamino]-6-(3-chloro-5-fluoro-4-hydroxyphenyl)quinolin-3-yl}(cyclopropyl)methanone

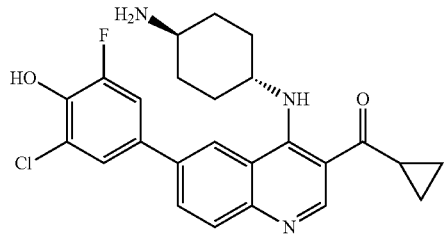 [SMILES: N[C@H]1CC[C@H](Nc2c(C(=O)C3CC3)cnc3ccc(-c4cc(F)c(O)c(Cl)c4)cc23)CC1]

Following general procedure A-2, tert-butyl trans-4-[6-(3-chloro-5-fluoro-4-hydroxyphenyl)-3-(cyclopropanecarbonyl)quinolin-4-ylamino]cyclohexylcarbamate (20 mg, 0.036 mmol) was reacted with TFA (2 mL) to afford the desired product (14.5 mg, 32%) as a yellow solid: $^1$H NMR (500 MHz, CD$_3$OD) δ 9.13 (s, 1H), 8.35 (d, J=1.8 Hz, 1H), 8.02 (dd, J=8.7, 1.9 Hz, 1H), 7.93 (d, J=8.7 Hz, 1H), 7.56-7.53 (m, 1H), 7.46 (dd, J=11.6, 2.2 Hz, 1H), 4.17-4.11 (m, 1H), 3.28-3.19 (m, 1H), 2.88-2.81 (m, 1H), 2.36 (d, J=12.8 Hz, 2H), 2.18 (d, J=12.2 Hz, 2H), 1.68 (q, J=10.6 Hz, 2H), 1.61-1.50

(m, 2H), 1.23-1.17 (m, 2H), 1.14-1.08 (m, 2H); ESI MS m/z 454 [$C_{25}H_{25}ClFN_3O_2$+H]$^+$; HPLC 99.0% (AUC), $t_R$=10.52 min.

Example 212

{4-[trans-4-Aminocyclohexylamino]-6-(pyridin-4-yl)quinolin-3-yl}(cyclopropyl)methanone

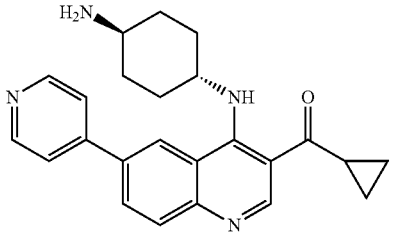

Following general procedure A-2, tert-butyl trans-4-[3-(cyclopropanecarbonyl)-6-(pyridin-4-yl)quinolin-4-ylamino]cyclohexylcarbamate (50 mg, 0.100 mmol) was reacted with TFA (2 mL) to afford the desired product (14.9 mg, 39%) as a yellow solid: NMR (500 MHz, CD$_3$OD) δ 9.26 (s, 1H), 8.70 (dd, J=4.6, 1.6 Hz, 2H), 8.65 (s, 1H), 8.30 (dd, J=8.7, 1.7 Hz, 1H), 8.05 (d, J=8.7 Hz, 1H), 7.87 (dd, J=4.6, 1.7 Hz, 2H), 4.31 (br s, 1H), 3.28-3.22 (m, 1H), 2.91-2.82 (m, 1H), 2.41 (d, J=13.2 Hz, 2H), 2.20 (d, J=11.3 Hz, 2H), 1.82-1.69 (m, 2H), 1.67-1.55 (m, 2H), 1.28-1.23 (m, 2H), 1.20-1.16 (m, 2H); ESI MS m/z 387 [$C_{24}H_{26}N_4O$+H]$^+$; HPLC 95.0% (AUC), $t_R$=8.34 min.

Example 213

{4-[trans-4-Aminocyclohexylamino]-6-(1H-pyrazol-4-yl)quinolin-3-yl}(cyclopropyl)methanone

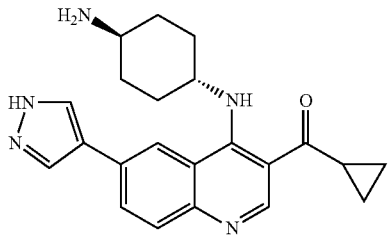 [SMILES: N[C@H]1CC[C@H](Nc2c(C(=O)C3CC3)cnc3ccc(-c4cn[nH]c4)cc23)CC1]

Following general procedure A-2, tert-butyl trans-4-[3-(cyclopropanecarbonyl)-6-(1H-pyrazol-4-yl)quinolin-4-ylamino]cyclohexylcarbamate (17 mg, 0.036 mmol) was reacted with TFA (2 mL) to afford the desired product (6.1 mg, 45%) as an off-white solid: $^1$H NMR (500 MHz, CD$_3$OD) δ 9.30 (br s, 1H), 8.54 (br s, 1H), 8.29 (dd, J=8.7, 1.7 Hz, 1H), 8.19 (s, 2H), 7.94 (d, J=8.8 Hz, 1H), 2.84 (s, 1H), 2.44 (s, 2H), 2.24 (d, J=11.1 Hz, 2H), 1.89-1.76 (m, 2H), 1.67 (br s, 2H), 1.35-1.19 (m, 6H); ESI MS m/z 376 [$C_{22}H_{25}N_5O$+H]$^+$; HPLC 97.6% (AUC), $t_R$=9.39 min.

Example 133

Cyclopropyl[4-{4-[(dimethylamino)methyl]piperidin-1-yl}-6-(4-hydroxy-3-methoxyphenyl)quinolin-3-yl]methanone

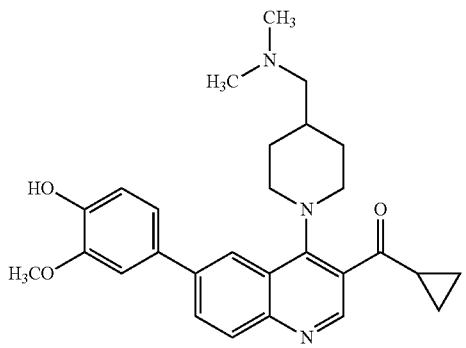 [SMILES: COc1cc(-c2ccc3ncc(C(=O)C4CC4)c(N4CCC(CN(C)C)CC4)c3c2)ccc1O]

Following general procedure D, (6-bromo-4-{4-[(dimethylamino)methyl]piperidin-1-yl}quinolin-3-yl)(cyclopropyl)methanone (47 mg, 0.113 mmol) was reacted with 2-methoxy-4-(4,4,5,5-tetramethyl-1,3,2-dioxaborolan-2-yl)phenol (55 mg, 0.220 mmol) to afford the desired product (23.5 mg, 45%) as a yellow solid: $^1$H NMR (500 MHz, CD$_3$OD) δ 8.81 (s, 1H), 8.29 (d, J=1.6 Hz, 1H), 8.10-8.00 (m, 2H), 7.30 (d, J=2.0 Hz, 1H), 7.22 (dd, J=8.2, 2.1 Hz, 1H), 6.94 (d, J=8.2 Hz, 1H), 3.97 (s, 3H), 3.56 (d, J=12.6 Hz, 2H), 3.27-3.15 (m, 4H), 2.95 (s, 6H), 2.65-2.55 (m, 1H), 2.15-2.25 (m, 1H), 1.95 (d, J=12.6 Hz, 2H), 1.78-1.67 (m, 2H), 1.38-1.28 (m, 2H), 1.28-1.19 (m, 2H); ESI MS m/z 460 [$C_{28}H_{33}N_3O_3$+H]$^+$; HPLC 95.9% (AUC), $t_R$=9.74 min.

Example 276

[6-(3-Chloro-4-hydroxy-5-methoxyphenyl)-4-{4-[(dimethylamino)methyl]piperidin-1-yl}quinolin-3-yl](cyclopropyl)methanone

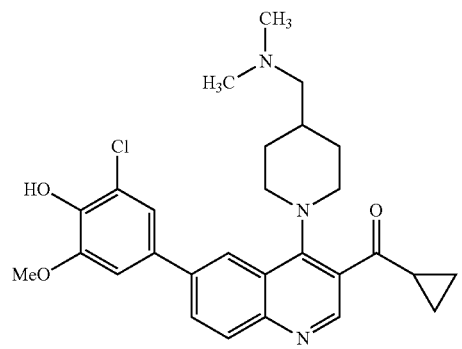 [SMILES: COc1cc(-c2ccc3ncc(C(=O)C4CC4)c(N4CCC(CN(C)C)CC4)c3c2)cc(Cl)c1O]

Following general procedure D, (6-bromo-4-{4-[(dimethylamino)methyl]piperidin-1-yl}quinolin-3-yl)(cyclopropyl)methanone (35 mg, 0.084 mmol) was reacted with 2-chloro-6-methoxy-4-(3,3,4,4-tetramethylborolan-1-yl)phenol (42 mg, 0.150 mmol) to afford the desired product (29.1 mg, 70%) as an off-white solid: $^1$H NMR (500 MHz, CDCl$_3$) δ

8.75 (s, 1H), 8.30 (s, 1H), 8.07-7.99 (m, 2H), 7.31 (d, J=2.0 Hz, 1H), 7.25 (d, J=1.9 Hz, 1H), 4.00 (s, 3H), 3.54 (d, J=12.4 Hz, 2H), 3.22 (t, J=12.2 Hz, 2H), 2.59-2.50 (m, 1H), 2.43 (d, J=6.2 Hz, 2H), 2.35 (s, 6H), 2.01-1.83 (m, 3H), 1.67-1.53 (m, 2H), 1.35-1.27 (m, 2H), 1.27-1.19 (m, 2H); ESI MS m/z 494 $[C_{28}H_{32}ClN_3O_3+H]^+$; HPLC 98.9% (AUC), $t_R$=10.51 min.

Example 279

[6-(3-Chloro-4-hydroxyphenyl)-4-{4-[(dimethylamino)methyl]piperidin-1-yl}quinolin-3-yl](cyclopropyl)methanone

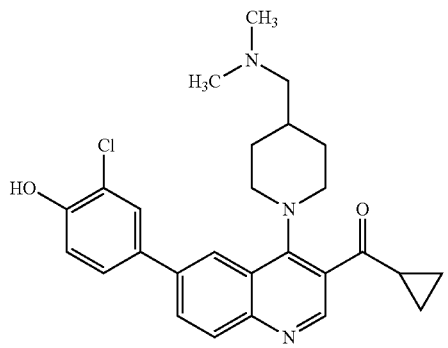 [SMILES: CN(C)CC1CCN(c2c(C(=O)C3CC3)cnc3ccc(-c4ccc(O)c(Cl)c4)cc23)CC1]

Following general procedure D, (6-bromo-4-{4-[(dimethylamino)methyl]piperidin-1-yl}quinolin-3-yl)(cyclopropyl)methanone (25 mg, 0.060 mmol) was reacted with 3-chloro-4-hydroxyphenylboronic acid (21 mg, 0.120 mmol) to afford the desired product (16.3 mg, 59%) as an off-white solid: $^1$H NMR (500 MHz, CD$_3$OD) δ 8.74 (s, 1H), 8.28 (s, 1H), 8.05-7.98 (m, 2H), 7.70 (d, J=2.3 Hz, 1H), 7.53 (dd, J=8.4, 2.3 Hz, 1H), 7.06 (d, J=8.4 Hz, 1H), 3.53 (d, J=12.7 Hz, 2H), 3.21 (t, J=11.5 Hz, 2H), 2.60-2.51 (m, 1H), 2.43 (d, J=6.8 Hz, 2H), 2.35 (s, 6H), 2.00-1.84 (m, 3H), 1.65-1.53 (m, 2H), 1.34-1.28 (m, 2H), 1.28-1.17 (m, 2H); ESI MS m/z 464 $[C_{27}H_{30}ClN_3O_2+H]^+$; HPLC>99% (AUC), $t_R$=10.38 min.

Example 347

[6-(3-Chloro-5-fluoro-4-hydroxyphenyl)-4-{4-[(dimethylamino)methyl]piperidin-1-yl}quinolin-3-yl](cyclopropyl)methanone

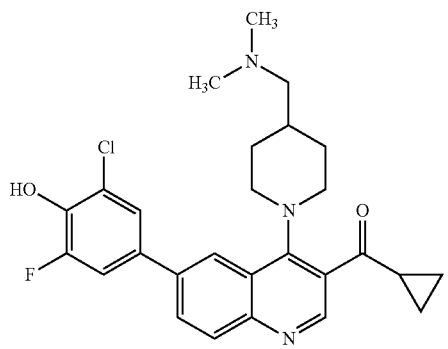 [SMILES: CN(C)CC1CCN(c2c(C(=O)C3CC3)cnc3ccc(-c4cc(F)c(O)c(Cl)c4)cc23)CC1]

Following general procedure D, (6-bromo-4-{4-[(dimethylamino)methyl]piperidin-1-yl}quinolin-3-yl)(cyclopropyl)methanone (30 mg, 0.072 mmol) was reacted with 2-chloro-6-fluoro-4-(4,4,5,5-tetramethyl-1,3,2-dioxaborolan-2-yl)phenol (41 mg, 0.150 mmol) to afford the desired product (22.3 mg, 64%) as a yellow solid: $^1$H NMR (500 MHz, CD$_3$OD) δ 8.76 (s, 1H), 8.25 (d, J=1.6 Hz, 1H), 8.10-7.95 (m, 2H), 7.55-7.46 (m, 1H), 7.42 (dd, J=11.7, 2.3 Hz, 1H); 3.53 (d, J=12.7 Hz, 2H), 3.22 (t, J=11.6 Hz, 2H), 2.61 (d, J=6.6 Hz, 2H), 2.59-2.51 (m, 1H), 2.48 (s, 6H), 1.96 (d, J=10.0 Hz, 3H), 1.69-1.56 (m, 2H), 1.35-1.28 (m, 2H), 1.28-1.16 (m, 2H); ESI MS m/z 482 $[C_{27}H_{29}ClFN_3O_2+H]^+$; HPLC 98.0% (AUC), $t_R$=10.47 min.

Example 353

Cyclopropyl[4-{4-[(dimethylamino)methyl]piperidin-1-yl}-6-(3-ethoxy-4-hydroxyphenyl)quinolin-3-yl]methanone

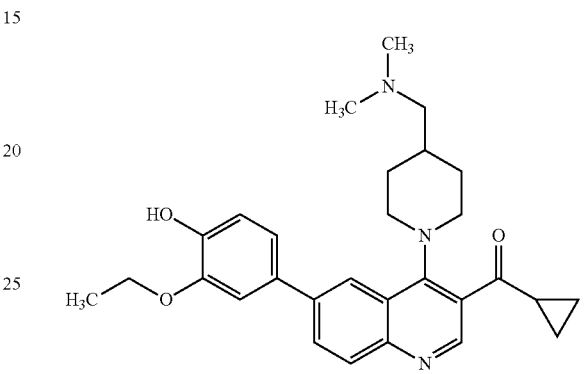

Following general procedure D, (6-bromo-4-{4-[(dimethylamino)methyl]piperidin-1-yl}quinolin-3-yl)(cyclopropyl)methanone (30 mg, 0.072 mmol) was reacted with 2-ethoxy-4-(4,4,5,5-tetramethyl-1,3,2-dioxaborolan-2-yl)phenol (40 mg, 0.150 mmol) to afford the desired product (14.3 mg, 42%) as a yellow solid: NMR (500 MHz, CD$_3$OD) δ 8.73 (s, 1H), 8.31 (d, J=1.7 Hz, 1H), 8.03 (m, 2H), 7.30 (d, J=2.1 Hz, 1H), 7.22 (dd, J=8.2, 2.1 Hz, 1H), 6.95 (d, J=8.2 Hz, 1H), 4.22 (q, J=7.0 Hz, 2H), 3.54 (d, J=12.6 Hz, 2H), 3.26-3.12 (m, 2H), 2.59-2.50 (m, 1H), 2.44 (s, 2H), 2.37 (s, 6H), 2.02-1.83 (m, 3H), 1.68-1.53 (m, 2H), 1.49 (t, J=7.0 Hz, 3H), 1.35-1.26 (m, 2H), 1.26-1.15 (m, 2H); ESI MS m/z 474 $[C_{29}H_{35}N_3O_3+H]^+$; HPLC 96.9% (AUC), $t_R$=10.59 min.

Example 181

Cyclopropyl[6-(3,5-difluoro-4-hydroxyphenyl)-4-{4-[1-(dimethylamino)ethyl]piperidin-1-yl}quinolin-3-yl]methanone

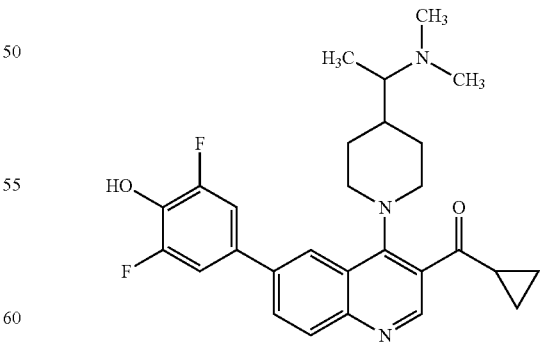

Following general procedure F, (6-bromo-4-{4-[1-(dimethylamino)ethyl]piperidin-1-yl}quinolin-3-yl)(cyclopropyl)methanone (60 mg, 0.139 mmol) was reacted with 2,6-difluoro-4-(4,4,5,5-tetramethyl-1,3,2-dioxaborolan-2-yl)phenol (39 mg, 0.153 mmol) to afford the desired product (30 mg, 44%) as a light yellow solid: $^1$H NMR (300 MHz, CD$_3$OD) δ 8.82 (s, 1H), 8.26 (s, 1H), 8.03 (p, J=8.8 Hz, 2H), 7.35 (dd, J=8.0, 1.7 Hz, 2H), 3.56 (t, J=10.3 Hz, 2H), 3.26-3.17 (m, 3H), 2.80 (s, 6H), 2.66-2.53 (m, 1H), 1.96 (d, J=11.2 Hz, 3H), 1.87-1.68 (m, 2H), 1.37-1.22 (m, 8H); ESI MS m/z 480 [C$_{28}$H$_{31}$F$_2$N$_3$O$_2$+H]$^+$; HPLC 98.6% (AUC), t$_R$=10.24 min.

Example 187

Cyclopropyl(4-{4-[1-(dimethylamino)ethyl]piperidin-1-yl}-6-(4-hydroxy-3-methoxyphenyl)quinolin-3-yl)methanone

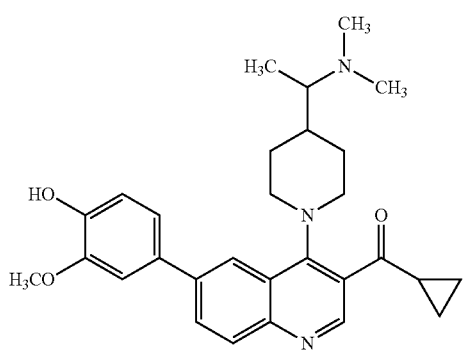 [SMILES: COc1cc(-c2ccc3ncc(C(=O)C4CC4)c(N4CCC(C(C)N(C)C)CC4)c3c2)ccc1O]

Following general procedure F, (6-bromo-4-{4-[1-(dimethylamino)ethyl]piperidin-1-yl}quinolin-3-yl)(cyclopropyl)methanone (42 mg, 0.097 mmol) was reacted with 2-methoxy-4-(4,4,5,5-tetramethyl-1,3,2-dioxaborolan-2-yl)phenol (36 mL, 0.146 mmol) to afford the desired product (26 mg, 56%) as a yellow solid: $^1$H NMR (300 MHz, CD$_3$OD) δ 8.82 (s, 1H), 8.29 (d, J=1.6 Hz, 1H), 8.19-7.97 (m, 2H), 7.31 (d, J=2.1 Hz, 1H), 7.23 (dd, J=8.2, 2.1 Hz, 1H), 6.95 (d, J=8.2 Hz, 1H), 3.98 (s, 3H), 3.61 (t, J=12.8 Hz, 2H), 3.48-3.36 (m, 1H), 3.27-3.17 (m, 2H), 2.98-2.84 (m, 5H), 2.67-2.56 (m, 1H), 2.11-1.73 (m, 5H), 1.40 (d, J=6.8 Hz, 3H), 1.34-1.23 (m, 6H); ESI MS m/z 474 [C$_{29}$H$_{35}$N$_3$O$_3$+H]$^+$; HPLC 98.6% (AUC), t$_R$=9.95 min.

Example 250

[6-(3-Chloro-4-hydroxy-5-methoxyphenyl)-4-{4-[1-(dimethylamino)ethyl]piperidin-1-yl}quinolin-3-yl](cyclopropyl)methanone

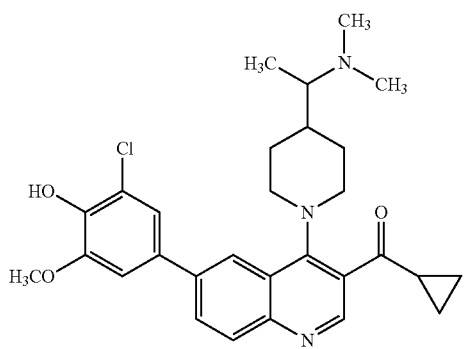 [SMILES: COc1cc(-c2ccc3ncc(C(=O)C4CC4)c(N4CCC(C(C)N(C)C)CC4)c3c2)cc(Cl)c1O]

Following general procedure F, (6-bromo-4-{4-[1-(dimethylamino)ethyl]piperidin-1-yl}quinolin-3-yl)(cyclopropyl)methanone (50 mg, 0.116 mmol) was reacted with 2-chloro-6-methoxy-4-(4,4,5,5-tetramethyl-1,3,2-dioxaborolan-2-yl)phenol (49 mg, 0.173 mmol) to afford the desired product (33 mg, 56%) as a yellow-green solid: $^1$H NMR (500 MHz, CD$_3$OD) δ 8.74 (s, 1H), 8.30 (d, J=1.6 Hz, 1H), 8.07-7.97 (m, 2H), 7.32 (d, J=2.1 Hz, 1H), 7.25 (d, J=2.1 Hz, 1H), 4.00 (s, 3H), 3.55 (d, J=12.2 Hz, 2H), 3.19 (dd, J=19.9, 7.2 Hz, 2H), 2.64-2.58 (m, 1H), 2.58-2.50 (m, 1H), 2.40 (s, 6H), 2.03 (d, J=12.7 Hz, 1H), 1.95-1.78 (m, 3H), 1.73-1.61 (m, 2H), 1.33-1.28 (m, 2H), 1.26-1.20 (m, 2H), 1.11 (d, J=6.6 Hz, 3H); ESI MS m/z 508 [C$_{29}$H$_{34}$ClN$_3$O$_3$+H]$^+$; HPLC 97.0% (AUC), t$_R$=10.04 min.

Example 269

[6-(3-Chloro-5-fluoro-4-hydroxyphenyl)-4-{4-[1-(dimethylamino)ethyl]piperidin-1-yl}quinolin-3-yl](cyclopropyl)methanone

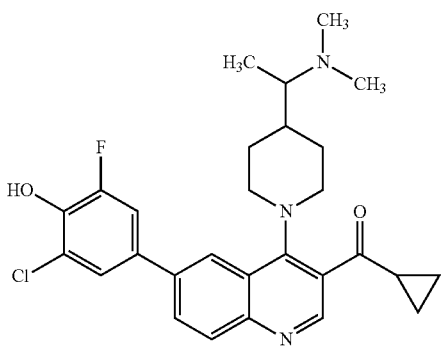 [SMILES: CC(C1CCN(c2c(C(=O)C3CC3)cnc3ccc(-c4cc(F)c(O)c(Cl)c4)cc23)CC1)N(C)C]

Following general procedure F, (6-bromo-4-{4-[1-(dimethylamino)ethyl]piperidin-1-yl}quinolin-3-yl)(cyclopropyl)methanone (39 mg, 0.090 mmol) was reacted with 2-chloro-6-fluoro-4-(4,4,5,5-tetramethyl-1,3,2-dioxaborolan-2-yl)phenol (30 mg, 0.108 mmol) to afford the desired product (27 mg, 60%) as a light brown solid: $^1$H NMR (500 MHz, CD$_3$OD) δ 8.81 (s, 1H), 8.26 (d, J=1.6 Hz, 1H), 8.08-7.99 (m, 2H), 7.57-7.51 (m, 1H), 7.46 (dd, J=11.6, 2.2 Hz, 1H), 3.55 (d, J=11.5 Hz, 2-H), 3.27-3.13 (m, 3H), 2.78 (s, 5H), 2.63-2.51 (m, 1H), 2.02 (s, 1H), 1.95 (d, J=12.8 Hz, 2H), 1.82-1.67 (m, 2H), 1.41-1.19 (m, 8H), 0.90 (s, 1H); ESI MS m/z 496 [C$_{28}$H$_{31}$ClFN$_3$O$_2$+H]$^+$; HPLC 98.4% (AUC), t$_R$=10.58 min.

Example 155

[6-(3-Chloro-4-hydroxy-5-methoxyphenyl)-4-(2,8-diazaspiro[4,5]decan-8-yl)quinolin-3-yl](cyclopropyl)methanone

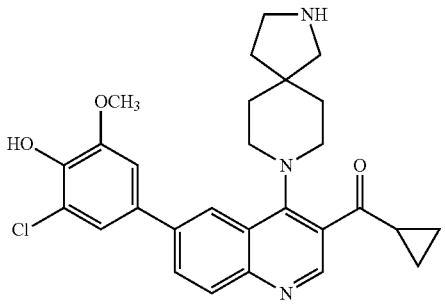 [SMILES: COc1cc(-c2ccc3ncc(C(=O)C4CC4)c(N4CCC5(CCNC5)CC4)c3c2)cc(Cl)c1O]

Following general procedure A-2, tert-butyl 8-[6-(3-chloro-4-hydroxy-5-methoxyphenyl)-3-(cyclopropanecarbonyl)quinolin-4-yl]-2,8-diazaspiro[4,5]decane-2-carboxylate (110 mg, 0.097 mmol) was reacted with TFA (2 mL) to afford the desired product (18 mg, 38%) as a green solid: $^1$H NMR (300 MHz, CD$_3$OD) δ 8.79 (s, 1H), 8.29 (s, 1H), 8.02 (s, 2H), 7.30 (d, J=2.1 Hz, 1H), 7.23 (d, J=2.1 Hz, 1H), 3.98 (s, 4H), 3.08 (s, 2H), 2.65-2.52 (m, 1H), 2.03-1.81 (m, 7H), 1.37-1.16 (m, 8H); ESI MS m/z 492 [C$_{28}$H$_{30}$ClN$_3$O$_3$+H]$^+$.

Example 165

{4-(cis-4-Aminocyclohexylamino)-6-(4-hydroxy-3-methoxyphenyl)quinolin-3-yl}(cyclopropyl)methanone

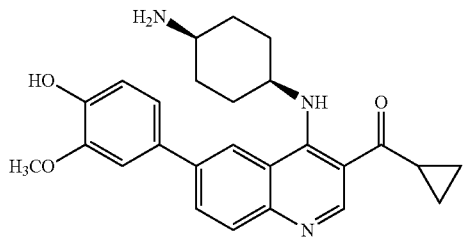 [SMILES: COc1cc(-c2ccc3ncc(C(=O)C4CC4)c(N[C@H]4CC[C@@H](N)CC4)c3c2)ccc1O]

Following general procedure A-2, tert-butyl cis-4-[3-(cyclopropanecarbonyl)-6-(4-hydroxy-3-methoxyphenyl)quinolin-4-ylamino]cyclohexylcarbamate (43 mg, 0.100 mmol) was reacted with TFA (2 mL) to afford the desired product (20 mg, 56%) as a light yellow solid: $^1$H NMR (300 MHz, CD$_3$OD) δ 9.26 (s, 1H), 8.39 (d, J=1.7 Hz, 1H), 8.10 (dd, J=8.8, 1.8 Hz, 1H), 7.93 (d, J=8.7 Hz, 1H), 7.27 (d, J=2.1 Hz, 1H), 7.18 (dd, J=8.2, 2.1 Hz, 1H), 6.93 (d, J=8.2 Hz, 1H), 4.74 (s, 1H), 3.96 (s, 3H), 3.12-3.02 (m, 1H), 2.98-2.84 (m, 1H), 2.17 (d, J=9.9 Hz, 2H), 2.10-1.93 (m, 4H), 1.93-1.73 (m, 2H), 1.31-1.20 (m, 2H), 1.16-1.08 (m, 2H); ESI MS m/z 432 [C$_{26}$H$_{29}$N$_3$O$_3$+H]$^+$; HPLC 98.4% (AUC), $t_R$=9.93 min.

Example 180

[4-(cis-4-Aminocyclohexylamino)-6-(3,5-difluoro-4-hydroxyphenyl)quinolin-3-yl](cyclopropyl)methanone

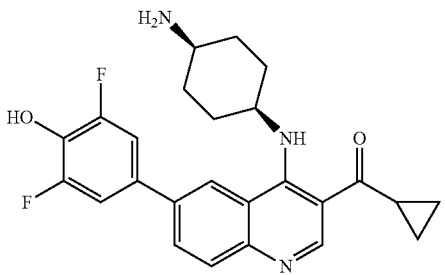 [SMILES: N[C@H]1CC[C@@H](Nc2c(C(=O)C3CC3)cnc3ccc(-c4cc(F)c(O)c(F)c4)cc23)CC1]

Following general procedure A-2, tert-butyl cis-4-[3-(cyclopropanecarbonyl)-6-(3,5-difluoro-4-hydroxyphenyl)quinolin-4-ylamino]cyclohexylcarbamate (51 mg, 0.095 mmol) was reacted with TFA (2 mL) to afford the desired product (25 mg, 52%) as a light yellow solid: $^1$H NMR (300 MHz, CD$_3$OD) δ 9.27 (s, 1H), 8.37 (d, J=1.7 Hz, 1H), 8.06 (dd, J=8.8, 1.9 Hz, 1H), 7.94 (d, J=8.7 Hz, 1H), 7.33 (dd, J=8.1, 1.6 Hz, 2H), 4.73 (s, 1H), 2.97-2.86 (m, 1H), 2.16 (d, J=9.1 Hz, 2H), 2.09-1.97 (m, 5H), 1.91-1.76 (m, 2H), 1.27-1.20 (m, 2H), 1.20-1.10 (m, 2H); ESI MS m/z 438 [C$_{25}$H$_{25}$F$_2$N$_3$O$_2$+H]$^+$; HPLC>99% (AUC), $t_R$=5.12 min.

Example 177

Cyclopropyl[6-(4-hydroxy-3-methoxyphenyl)-4-(1-methylpiperidin-4-ylamino)quinolin-3-yl]methanone

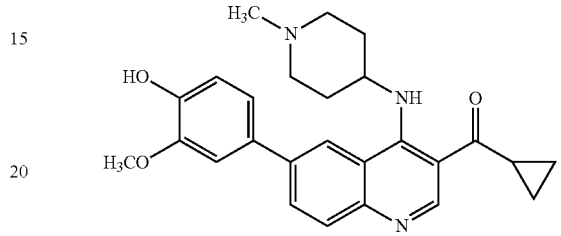

Following general procedure F, [6-bromo-4-(1-methylpiperidin-4-ylamino)quinolin-3-yl](cyclopropyl)methanone (47 mg, 0.121 mmol) was reacted with 2-methoxy-4-(4,4,5,5-tetramethyl-1,3,2-dioxaborolan-2-yl)phenol (45 mg, 0.182 mmol) to afford the desired product (33 mg, 63%) as a yellow solid: $^1$H NMR (300 MHz, CD$_3$OD) δ 9.17 (s, 1H), 8.33 (d, J=1.8 Hz, 1H), 8.05 (dd, J=8.7, 1.9 Hz, 1H), 7.92 (d, J=8.7 Hz, 1H), 7.27 (d, J=2.1 Hz, 1H), 7.19 (dd, J=8.2, 2.1 Hz, 1H), 6.94 (d, J=8.2 Hz, 1H), 4.36 (s, 1H), 3.97 (s, 3H), 3.34 (s, 1H), 3.08 (s, 2H), 2.94-2.82 (m, 1H), 2.65 (s, 2H), 2.53 (s, 3H), 2.28 (d, J=13.9 Hz, 2H), 1.89 (d, J=10.3 Hz, 2H), 1.26-1.17 (m, 2H), 1.17-1.08 (m, 2H); ESI MS m/z 432 [C$_{26}$H$_{29}$N$_3$O$_3$+H]$^+$; HPLC (AUC), $t_R$=9.78 min.

Example 249

6-(3-Chloro-4-hydroxy-5-methoxyphenyl)-4-(1-methylpiperidin-4-ylamino)quinolin-3-yl](cyclopropyl)methanone

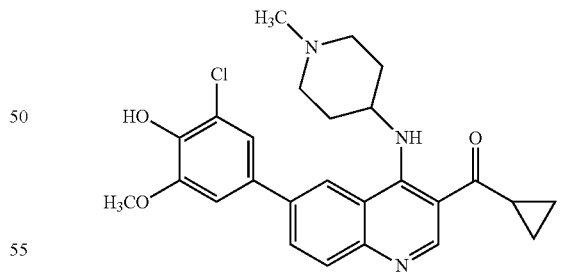

Following general procedure F, [6-bromo-4-(1-methylpiperidin-4-ylamino)quinolin-3-yl](cyclopropyl)methanone (63 mg, 0.160 mmol) was reacted with 2-chloro-6-methoxy-4-(4,4,5,5-tetramethyl-1,3,2-dioxaborolan-2-yl)phenol (68 mg, 0.240 mmol) to afford the desired product (30 mg, 40%) as a yellow-green solid: $^1$H NMR (300 MHz, CD$_3$OD) δ 9.17 (s, 1H), 8.31 (d, J=1.5 Hz, 1H), 8.04 (dd, J=8.7, 1.8 Hz, 1H), 7.93 (d, J=8.7 Hz, 1H), 7.29 (d, J=2.1 Hz, 1H), 7.21 (d, J=2.0 Hz, 1H), 4.36 (s, 1H), 3.99 (s, 3H), 3.20 (d, J=9.4 Hz, 2H), 2.93-2.68 (m, 3H), 2.61 (s, 3H), 2.31 (d, J=13.0 Hz, 2H), 2.00-1.81 (m, 2H), 1.28-1.18 (m, 2H), 1.17-1.05 (m, 2H); ESI MS m/z 466 [C$_{26}$H$_{28}$ClN$_3$O$_3$+H]$^+$; HPLC 96.4% (AUC), t$_R$=9.24 min.

Example 185(a)

{6-(3-Chloro-4-hydroxy-5-methoxyphenyl)-4-[4-(diethylamino)cyclohexylamino]quinolin-3-yl}(cyclopropyl)methanone

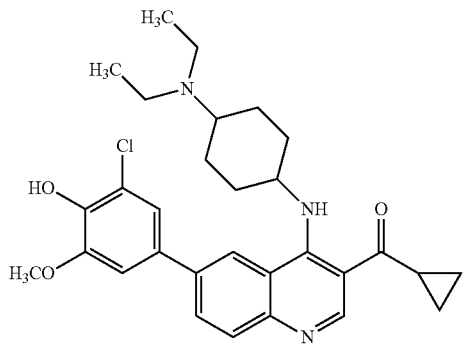 [SMILES: CCN(CC)C1CCC(Nc2c(C(=O)C3CC3)cnc3ccc(-c4cc(Cl)c(O)c(OC)c4)cc23)CC1]

Following general procedure F, {6-bromo-4-[4-(diethylamino)cyclohexylamino]quinolin-3-yl}(cyclopropyl)methanone (45 mg, 0.101 mmol) was reacted with 2-chloro-6-methoxy-4-(4,4,5,5-tetramethyl-1,3,2-dioxaborolan-2-yl)phenol (34 mg, 0.121 mmol) to afford the desired product (28 mg, 53%) as a yellow glass: $^1$H NMR (300 MHz, CD$_3$OD) δ 9.39 (s, 0.5H), 9.28 (s, 0.5H), 8.44 (d, J=2.2 Hz, 1H), 8.30-8.21 (m, 1H), 7.98 (d, J=8.8 Hz, 1H), 7.40-7.17 (m, 2H), 4.96 (s, 1H), 3.99 (d, J=2.5 Hz, 3H), 3.72-3.52 (m, 1H), 3.43-3.18 (m, 3H), 2.98-2.81 (m, 1H), 2.59-1.75 (m, 9H), 1.48-1.34 (m, 6H), 1.31-1.13 (m, 4H); ESI MS m/z 522 [C$_{30}$H$_{36}$ClN$_3$O$_3$+H]$^+$; HPLC>99% (AUC), t$_R$=7.67 min.

Example 185(b)

{6-(3-Chloro-4-hydroxy-5-methoxyphenyl)-4-[4-(diethylamino)cyclohexylamino]quinolin-3-yl}(cyclopropyl)methanone dihydrochloride

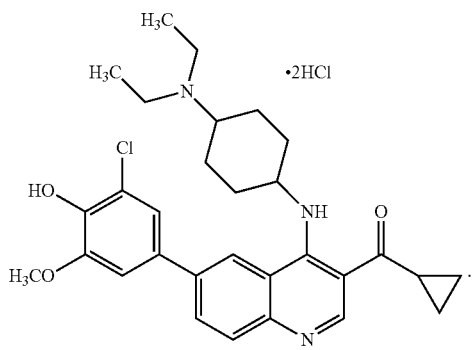 [SMILES: CCN(CC)C1CCC(Nc2c(C(=O)C3CC3)cnc3ccc(-c4cc(Cl)c(O)c(OC)c4)cc23)CC1]

To {6-(3-Chloro-4-hydroxy-5-methoxyphenyl)-4-[4-(diethylamino)cyclohexylamino]quinolin-3-yl}(cyclopropyl)methanone (18 mg, 0.34 mmol) was added 1 M HCl (5 mL) and the mixture was concentrated to afford the desired product (15 mg, 75%) as a yellow solid: $^1$H NMR (500 MHz, CD$_3$OD) δ 9.43-9.36 (m, 1H), 8.49 (d, J=2.2 Hz, 1H), 8.34-8.27 (m, 1H), 7.98-7.22 (m, 3H), 3.69-3.59 (m, 1H), 3.45-3.22 (m, 4H), 2.98-2.81 (m, 1H), 2.59-1.75 (m, 9H), 1.45-1.22 (m, 10H); ESI MS m/z 522 [C$_{30}$H$_{36}$ClN$_3$O$_3$+H]$^+$; HPLC 95.2% (AUC), t$_R$=10.26 min.

Example 192

{6-(3-Chloro-4-hydroxyphenyl)-4-[4-(diethylamino)cyclohexylamino]quinolin-3-yl}(cyclopropyl)methanone

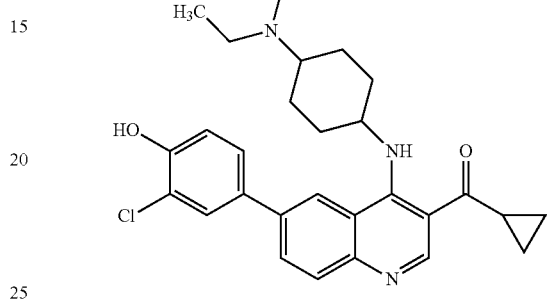

Following general procedure F, {6-bromo-4-[4-(diethylamino)cyclohexylamino]quinolin-3-yl}(cyclopropyl)methanone (65 mg, 0.146 mmol) was reacted with 3-chloro-4-hydroxyphenyl boronic acid (38 mg, 0.219 mmol) to afford the desired product (24 mg, 33%) as a light yellow-brown solid: $^1$H NMR (500 MHz, CD$_3$OD) δ 9.29 (s, 0.5H), 9.20 (s, 0.5H), 8.38 (s, 1H), 8.12-8.04 (m, 1H), 7.98-7.91 (m, 1H), 7.74 (d, J=2.3 Hz, 0.5H), 7.68 (d, J=2.3 Hz, 0.5H), 7.58-7.48 (m, 1H), 7.06 (dd, J=9.5, 8.5 Hz, 1H), 3.59-3.49 (m, 1H), 3.45-3.15 (m, 4H), 2.98-2.83 (m, 1H), 2.45 (d, J=11.9 Hz, 1H), 2.30-2.19 (m, 2H), 2.11-1.88 (m, 4H), 1.86-1.70 (m, 2H), 1.38 (q, J=7.4 Hz, 6H), 1.27-1.20 (m, 2H), 1.19-1.10 (m, 2H); ESI MS m/z 492 [C$_{29}$H$_{34}$ClN$_3$O$_2$+H]$^+$; HPLC 97.5% (AUC), t$_R$=4.53 min.

Example 193

Cyclopropyl{4-[4-(diethylamino)cyclohexylamino]-6-(4-hydroxy-3-methoxyphenyl)quinolin-3-yl}methanone

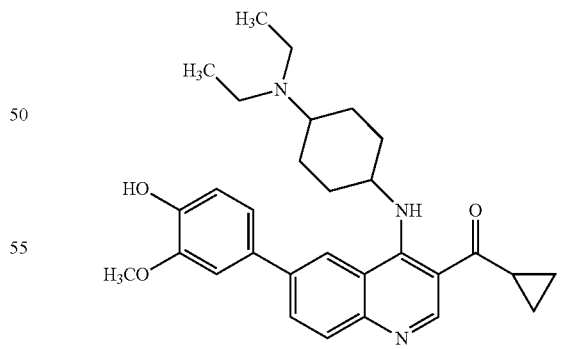

Following general procedure F, {6-bromo-4-[4-(diethylamino)cyclohexylamino]quinolin-3-yl}(cyclopropyl)methanone (58 mg, 0.130 mmol) was reacted with 2-methoxy-4-(4,4,5,5-tetramethyl-1,3,2-dioxaborolan-2-yl)phenol (34 mg, 0.136 mmol) to afford the desired product (40 mg, 60%) as a yellow glass: $^1$H NMR (300 MHz, CD$_3$OD) δ 9.26 (s, 0.5H), 9.17 (s, 0.5H), 8.33 (dd, J=8.2, 1.6 Hz, 1H), 8.09 (dt, J=8.8, 1.7 Hz, 1H), 7.90 (d, J=8.7 Hz, 1H), 7.25 (dd, J=12.8, 2.1 Hz, 1H), 7.21-7.08 (m, 1H), 6.99-6.87 (m, 1H), 4.81 (s, 1H), 3.96 (d, J=3.5 Hz, 3H), 3.64-3.44 (m, 1H), 3.40-3.12 (m, 3H), 2.96-2.76 (m, 1H), 2.41 (s, 1H), 2.24 (d, J=12.4 Hz, 2H), 2.14-1.83 (m, 4H), 1.73 (t, J=9.7 Hz, 2H), 1.46-1.30 (m, 6H), 1.26-1.07 (m, 4H); ESI MS m/z 488 $[C_{30}H_{37}N_3O_3+H]^+$; HPLC 98.9% (AUC), $t_R$=6.24 min.

Example 311

{6-(3-Chloro-4-hydroxy-5-methoxyphenyl)-4-[cis-4-(diethylamino)cyclohexylamino]quinolin-3-yl}(cyclopropyl)methanone

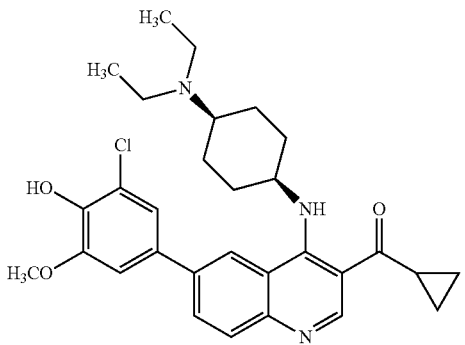 [SMILES: CCN(CC)[C@H]1CC[C@@H](Nc2c(C(=O)C3CC3)cnc3ccc(-c4cc(Cl)c(O)c(OC)c4)cc23)CC1]

Following general procedure F, {6-bromo-4-[cis-4-(diethylamino)cyclohexylamino]quinolin-3-yl}(cyclopropyl)methanone (31 mg, 0.070 mmol) was reacted with 2-chloro-6-methoxy-4-(4,4,5,5-tetramethyl-1,3,2-dioxaborolan-2-yl)phenol (43 mg, 0.150 mmol) to afford the desired product (14.1 mg, 39%) as a yellow-brown solid: $^1$H NMR (500 MHz, CD$_3$OD) δ 9.25 (s, 1H), 8.36 (d, J=1.8 Hz, 1H), 8.03 (dd, J=8.7, 1.9 Hz, 1H), 7.93 (d, J=8.7 Hz, 1H), 7.26 (d, J=2.1 Hz, 1H), 7.20 (d, J=2.1 Hz, 1H), 4.77 (s, J=12.7 Hz, 1H), 3.98 (s, 3H), 3.50-3.41 (m, 1H), 3.23 (q, J=7.2 Hz, 4H), 2.97-2.88 (m, 1H), 2.22 (d, J=12.9 Hz, 2H), 2.09-1.85 (m, 6H), 1.35 (t, J=7.3 Hz, 6H), 1.24-1.17 (m, 2H), 1.18-1.09 (m, 2H); ESI MS m/z 522 $[C_{30}H_{36}ClN_3O_3+H]^+$; HPLC 98.3% (AUC), $t_R$=11.07 min.

Example 314

{6-(3-Chloro-4-hydroxy-5-methoxyphenyl)-4-[trans-4-(diethylamino)cyclohexylamino]quinolin-3-yl}(cyclopropyl)methanone

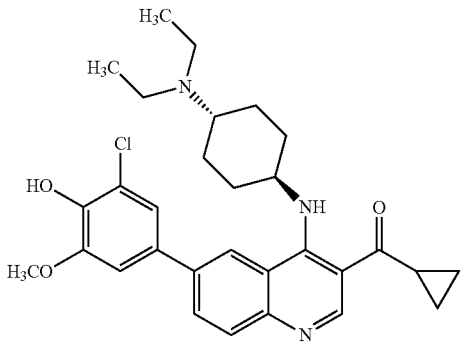 [SMILES: CCN(CC)[C@H]1CC[C@H](Nc2c(C(=O)C3CC3)cnc3ccc(-c4cc(Cl)c(O)c(OC)c4)cc23)CC1]

Following general procedure D, {6-bromo-4-[trans-4-(diethylamino)cyclohexylamino]quinolin-3-yl}(cyclopropyl)methanone (31 mg, 0.070 mmol) was reacted with 2-chloro-6-methoxy-4-(4,4,5,5-tetramethyl-1,3,2-dioxaborolan-2-yl)phenol (43 mg, 0.015 mmol) to afford the desired product (19.7 mg, 54%) as an orange-brown solid: $^1$H NMR (500 MHz, CD$_3$OD) δ 9.15 (s, 1H), 8.34 (d, J=1.8 Hz, 1H), 8.04 (dd, J=8.7, 1.9 Hz, 1H), 7.92 (d, J=8.7 Hz, 1H), 7.31 (d, J=2.1 Hz, 1H), 7.23 (d, J=2.0 Hz, 1H), 4.20 (s, 1H), 3.99 (s, 3H), 3.12 (q, J=7.2 Hz, 4H), 2.89-2.80 (m, 1H), 2.41 (d, J=10.4 Hz, 2H), 2.15 (d, J=9.8 Hz, 2H), 1.82-1.62 (m, 4H), 1.30 (t, J=7.3 Hz, 6H), 1.23-1.16 (m, 2H), 1.15-1.04 (m, 2H); ESI MS m/z 522 $[C_{30}H_{36}ClN_3O_3+H]^+$; HPLC 98.5% (AUC), $t_R$=11.05 min.

Example 201

{6-(3-Chloro-4-hydroxy-5-methoxyphenyl)-4-[(1-methylpiperidin-4-yl)methylamino]quinolin-3-yl}(cyclopropyl)methanone

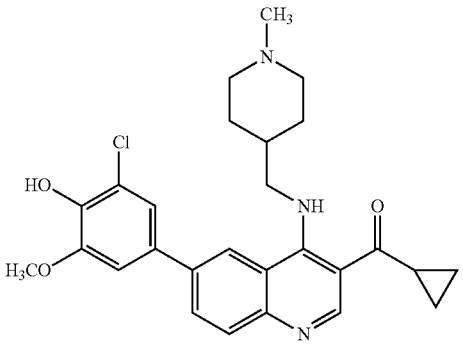 [SMILES: COc1cc(-c2ccc3ncc(C(=O)C4CC4)c(NCC4CCN(C)CC4)c3c2)cc(Cl)c1O]

Following general procedure F, {6-bromo-4-[(1-methylpiperidin-4-yl)methylamino]quinolin-3-yl}(cyclopropyl)methanone (63 mg, 0.156 mmol) was reacted with 2-chloro-6-methoxy-4-(4,4,5,5-tetramethyl-1,3,2-dioxaborolan-2-yl)phenol (53 mg, 0.187 mmol) to afford the desired product (33 mg, 44%) as a yellow solid: $^1$H NMR (500 MHz, CD$_3$OD) δ 9.12 (s, 1H), 8.41 (d, J=1.8 Hz, 1H), 7.99 (dd, J=8.7, 1.9 Hz, 1H), 7.88 (d, J=8.7 Hz, 1H), 7.26 (d, J=2.1 Hz, 1H), 7.19 (d, J=2.1 Hz, 1H), 3.98 (s, 3H), 3.84 (d, J=6.7 Hz, 2H), 3.20-3.13 (m, 2H), 2.87-2.80 (m, 1H), 2.51 (s, J=10.3 Hz, 3H), 2.46 (t, J=11.6 Hz, 2H), 1.97 (d, J=13.2 Hz, 2H), 1.90 (s, 1H), 1.53-1.40 (m, 2H), 1.24-1.17 (m, 2H), 1.14-1.07 (m, 2H); ESI MS m/z $[C_{27}H_{30}ClN_3O_3+H]^+$; HPLC>99% (AUC), $t_R$=8.32 min.

Example 270

{6-(3-Chloro-5-fluoro-4-hydroxyphenyl)-4-[(1-methylpiperidin-4-yl)methylamino]quinolin-3-yl}(cyclopropyl)methanone

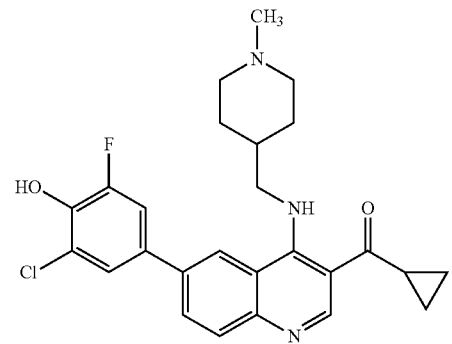 [SMILES: CN1CCC(CNc2c(C(=O)C3CC3)cnc3ccc(-c4cc(F)c(O)c(Cl)c4)cc23)CC1]

Following general procedure F, {6-bromo-4-[(1-methylpiperidin-4-yl)methylamino]quinolin-3-yl}(cyclopropyl)methanone (50 mg, 0.120 mmol) was reacted with 2-chloro-6-fluoro-4-(4,4,5,5-tetramethyl-1,3,2-dioxaborolan-2-yl)phenol (49 mg, 0.180 mmol) to afford the desired product (29 mg, 51%) as a yellow solid: $^1$H NMR (300 MHz, CD$_3$OD) δ 9.13 (s, 1H), 8.39 (d, J=1.5 Hz, 1H), 8.02-7.83 (m, 1H), 7.56-7.37 (m, 2H), 3.84 (d, J=5.9 Hz, 2H), 2.89-2.74 (m, 3H), 2.71 (s, 3H), 2.05 (d, J=13.4 Hz, 3H), 1.65-1.47 (m, 2H), 1.28 (s, 3H), 1.24-1.16 (m, 2H), 1.16-1.02 (m, 2H), 0.88 (d, J=6.9 Hz, 1H); ESI MS m/z [C$_{26}$H$_{27}$ClFN$_3$O$_2$+H]$^+$; HPLC>99% (AUC), $t_R$=9.14 min.

Example 215

{6-(3-Chloro-4-hydroxyphenyl)-4-[2-(piperazin-1-yl)ethylamino]quinolin-3-yl}(cyclopropyl)methanone

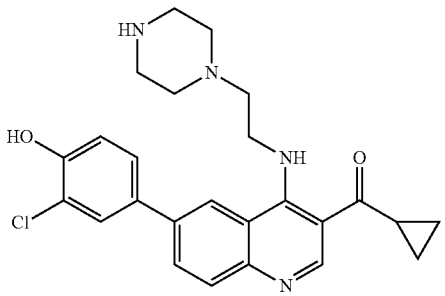 [SMILES: O=C(c1cnc2ccc(-c3ccc(O)c(Cl)c3)cc2c1NCCN1CCNCC1)C1CC1]

Following general procedure A-2, tert-butyl 4-{2-[6-(3-Chloro-4-hydroxyphenyl)-3-(cyclopropanecarbonyl)quinolin-4-ylamino]ethyl}piperazine-1-carboxylate (40 mg, 0.073 mmol) was reacted with TFA (2 mL) to afford the desired product (23 mg, 35%) as a yellow solid: $^1$H NMR (500 MHz, DMSO-d$_6$) δ 10.00 (s, 1H), 9.09 (s, 1H), 8.46 (d, J=1.8 Hz, 1H), 7.98 (dd, J=8.7, 1.9 Hz, 1H), 7.85 (d, J=8.7 Hz, 1H), 7.78 (d, J=2.3 Hz, 1H), 7.61 (dd, J=8.5, 2.3 Hz, 1H), 7.09 (d, J=8.4 Hz, 1H), 3.82 (d, J=5.2 Hz, 2H), 2.95-2.82 (m, 1H), 2.68 (t, J=4.7 Hz, 4H), 2.55 (t, J=6.0 Hz, 2H), 2.35 (s, 4H), 1.11-0.97 (m, 4H); ESI MS m/z 451 [C$_{25}$H$_{27}$ClN$_4$O$_2$+H]$^+$; HPLC>99% (AUC), $t_R$=9.32 min.

Example 243

6-(3-Chloro-4-hydroxy-5-methoxyphenyl)-4-(piperidin-4-ylmethylamino)quinolin-3-yl](cyclopropyl)methanone

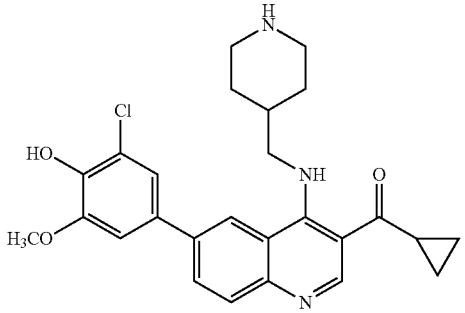 [SMILES: COc1cc(-c2ccc3ncc(C(=O)C4CC4)c(NCC4CCNCC4)c3c2)cc(Cl)c1O]

Following general procedure A-2, tert-butyl 4-{[6-(3-chloro-4-hydroxy-5-methoxyphenyl)-3-(cyclopropanecarbonyl)quinolin-4-ylamino]methyl}piperidine-1-carboxylate (27 mg, 0.047 mmol) was reacted with TFA (1 mL) to afford the desired product (11 mg, 21%) as a yellow-orange solid: $^1$H NMR (500 MHz, CD$_3$OD) δ 9.24 (s, 1H), 8.54 (d, J=1.6 Hz, 1H), 8.16 (dd, J=8.7, 1.7 Hz, 1H), 7.95 (d, J=8.7 Hz, 1H), 7.33 (d, J=2.1 Hz, 1H), 7.25 (d, J=2.1 Hz, 1H), 3.99 (s, J=23.2 Hz, 5H), 3.51-3.42 (m, 2H), 3.18-3.14 (m, 1H), 3.07 (td, J=13.0, 2.9 Hz, 2H), 2.90-2.81 (m, 1H), 2.22 (s, 1H), 2.13 (d, J=14.0 Hz, 2H), 1.67-1.53 (m, 2H), 1.29-1.21 (m, 2H), 1.21-1.13 (m, 2H); ESI MS m/z 466 [C$_{26}$H$_{28}$ClN$_3$O$_3$+H]$^+$; HPLC 97.7% (AUC), $t_R$=8.47 min.

Example 255

{6-(3-Chloro-4-hydroxy-5-methoxyphenyl)-4-[trans-4-(dimethylamino)cyclohexylamino]quinolin-3-yl}(cyclopropyl)methanone

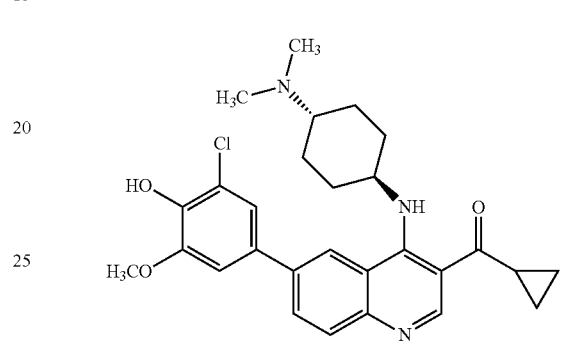

Following general procedure F, {6-bromo-4-[trans-4-(dimethylamino)cyclohexylamino]quinolin-3-yl}(cyclopropyl)methanone (50 mg, 0.120 mmol) was reacted with 2-chloro-6-methoxy-4-(4,4,5,5-tetramethyl-1,3,2-dioxaborolan-2-yl)phenol (51 mg, 0.180 mmol) to afford the desired product (22 mg, 37%) as a yellow-green solid: $^1$H NMR (300 MHz, CD$_3$OD) δ 9.18 (s, 1H), 8.36 (s, 1H), 8.09 (d, J=10.4 Hz, 1H), 7.94 (d, J=8.7 Hz, 1H), 7.33 (d, J=2.0 Hz, 1H), 7.25 (d, J=2.0 Hz, 1H), 4.24 (s, 1H), 3.99 (s, 3H), 3.35 (s, 1H), 2.86 (s, 7H), 2.46 (s, 2H), 2.21 (s, 2H), 1.73 (d, J=10.4 Hz, 4H), 1.28-1.06 (m, 4H); ESI MS m/z [C$_{28}$H$_{32}$ClN$_3$O$_3$+H]$^+$; HPLC 97.5% (AUC), $t_R$=10.92 min.

Example 262

1-{4-[trans-4-Aminocyclohexylamino]-6-(3-chloro-4-hydroxy-6-mothoxyphenyl)quinolin-3-yl}-3-methylbutan-1-one dihydrochloride

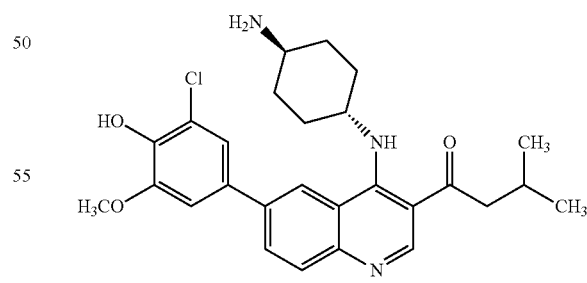

Following general procedure D, tert-butyl trans-4-[6-(3-chloro-4-hydroxy-5-methoxyphenyl)-3-(3-methylbutanoyl)quinolin-4-ylamino]cyclohexylcarbamate (42 mg, 0.072 mmol) was reacted with TFA (2 mL) to afford the desired product (15.4 mg, 44%) as a yellow solid: $^1$H NMR (500 MHz, CD$_3$OD) δ 8.96 (s, 1H), 8.32 (s, 1H), 8.04 (dd, J=8.7, 1.8 Hz, 1H), 7.91 (d, J=8.7 Hz, 1H), 7.28 (d, J=2.1 Hz, 1H), 7.22 (d, J=2.1 Hz, 1H), 4.26-4.17 (m, 1H), 3.99 (s, 3H), 3.26-3.18 (m, 1H), 2.95 (d, J=7.0 Hz, 2H), 2.41 (d, J=12.9 Hz, 2H), 2.31-2.22 (m, 1H), 2.17 (d, J=12.1 Hz, 2H), 1.78-1.66 (m, 2H), 1.62-1.50 (m, 2H) 1.03 (d, J=6.6 Hz, 2H); ESI MS m/z 482 [$C_{27}H_{32}ClN_3O_3$+H]$^+$; HPLC>99% (AUC), $t_R$=11.22 min.

Example 263

Cyclopropyl{6-(3,5-dichloro-4-hydroxyphenyl)-4-[trans-4-(dimethylamino)cyclohexylamino]quinolin-3-yl}methanone

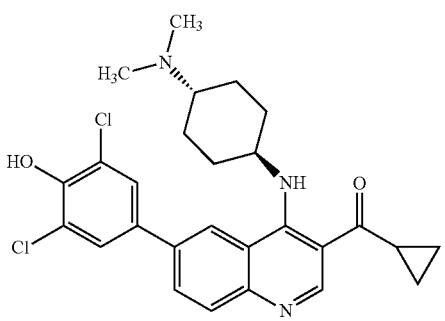 [SMILES: CN(C)[C@H]1CC[C@H](Nc2c(C(=O)C3CC3)cnc3ccc(-c4cc(Cl)c(O)c(Cl)c4)cc23)CC1]

Following general procedure F, {6-bromo-4-[trans-4-(dimethylamino)cyclohexylamino]quinolin-3-yl}(cyclopropyl) methanone (45 mg, 0.110 mmol) was reacted with 2,6-dichloro-4-(4,4,5,5-tetramethyl-1,3,2-dioxaborolan-2-yl)phenol (38 mg, 0.135 mmol) to afford the desired product (32 mg, 58%) as a light yellow solid: NMR (500 MHz, CD$_3$OD) δ 9.30 (s, 1H), 8.50 (s, 1H), 8.28 (d, J=8.8 Hz, 1H), 8.00 (d, J=8.8 Hz, 1H), 7.78 (s, 2H), 4.47 (s, 1H), 3.45 (s, 1H), 2.91 (s, 6H), 2.85 (s, 1H), 2.51 (s, 2H), 2.31 (s, 2H), 1.91-1.74 (m, 4H), 1.31-1.18 (m, 4H); ESI MS m/z 498 [$C_{27}H_{29}Cl_2N_3O_2$+H]$^+$; HPLC 96.9% (AUC), $t_R$=11.50 min.

Example 266

Cyclopropyl(4-((trans)-4-(dimethylamino)cyclohexylamino)-6-(4-hydroxy-3-methoxyphenyl)quinolin-3-yl)methanone

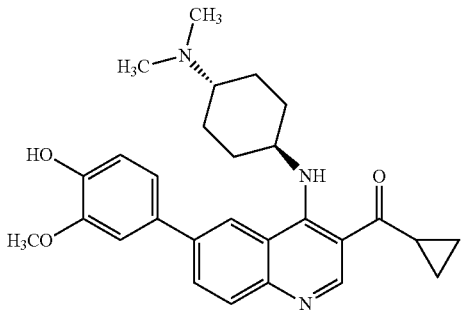 [SMILES: COc1cc(-c2ccc3ncc(C(=O)C4CC4)c(N[C@H]4CC[C@H](N(C)C)CC4)c3c2)ccc1O]

Following general procedure F, {6-bromo-4-[trans-4-(dimethylamino)cyclohexylamino]quinolin-3-yl}(cyclopropyl) methanone (52 mg, 0.120 mmol) was reacted with 2-methoxy-4-(4,4,5,5-tetramethyl-1,3,2-dioxaborolan-2-yl)phenol (45 mg, 0.180 mmol) to afford the desired product (17 mg, 31%) as a yellow-green solid: $^1$H NMR (300 MHz, CD$_3$OD)

δ 9.19 (s, 1H), 8.36 (s, 1H), 8.10 (dd, J=8.8, 1.9 Hz, 1H), 7.93 (d, J=8.8 Hz, 1H), 7.30 (d, J=2.1 Hz, 1H), 7.21 (dd, J=8.2, 2.1 Hz, 1H), 6.95 (d, J=8.2 Hz, 1H), 4.22 (s, 1H), 3.97 (s, 3H), 2.84 (s, 7H), 2.43 (s, 2H), 2.21 (s, 2H), 1.68 (s, 3H), 1.27-1.18 (m, 2H), 1.18-1.07 (m, 2H); ESI MS m/z 460 [$C_{28}H_{33}N_3O_3$+H]$^+$; HPLC>99% (AUC), $t_R$=10.86 min.

Example 280

{6-(3-Chloro-4-hydroxy-5-methoxyphenyl)-4-[4-(pyrrolidin-1-ylmethyl)piperidin-1-yl]quinolin-3-yl}(cyclopropyl)methanone

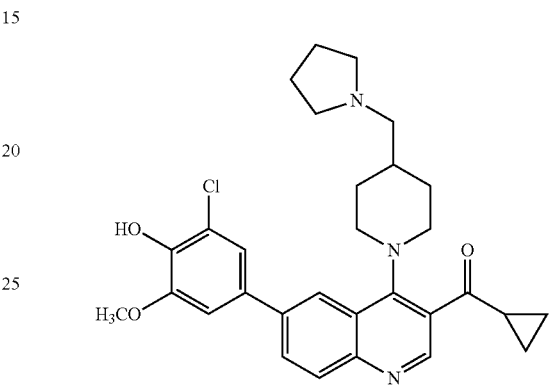

Following general procedure D, {6-bromo-4-[4-(pyrrolidin-1-ylmethyl)piperidin-1-yl]quinolin-3-yl}(cyclopropyl) methanone (30 mg, 0.068 mmol) was reacted with 2-chloro-6-methoxy-4-(4,4,5,5-tetramethyl-1,3,2-dioxaborolan-2-yl)phenol (30 mg, 0.106 mmol) to afford the desired product (21.5 mg, 61%) as a yellow solid: $^1$H NMR (500 MHz, CD$_3$OD) δ 8.76 (s, 1H), 8.29 (s, 1H), 8.07-7.99 (m, 2H), 7.31 (d, J=2.0 Hz, 1H), 7.24 (d, J=2.0 Hz, 1H), 3.99 (s, 3H), 3.54 (d, J=12.4 Hz, 2H), 3.22 (t, J=11.7 Hz, 2H), 2.82 (s, 4H), 2.71 (d, J=6.5 Hz, 2H), 2.60-2.51 (m, 1H), 2.06-1.81 (m, 7H), 1.71-1.59 (m, 2H), 1.36-1.27 (m, 2H), 1.27-1.19 (m, 2H); ESI MS m/z 520 [$C_{30}H_{34}ClN_3O_3$+H]$^+$; HPLC 98.6% (AUC), $t_R$=10.70 min.

Example 283

{6-(3-Chloro-5-fluoro-4-hydroxyphenyl)-4-[4-(pyrrolidin-1-ylmethyl)piperidin-1-yl]quinolin-3-yl}(cyclopropyl)methanone

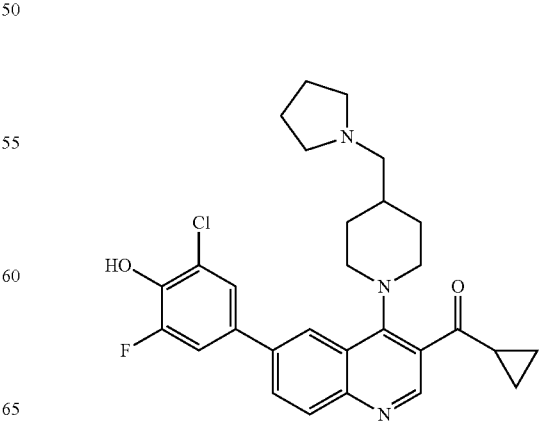

Following general procedure D, {6-bromo-4-[4-(pyrrolidin-1-ylmethyl)piperidin-1-yl]quinolin-3-yl}(cyclopropyl)methanone (30 mg, 0.068 mmol) was reacted with 2-chloro-6-fluoro-4-(4,4,5,5-tetramethyl-1,3,2-dioxaborolan-2-yl)phenol (27 mg, 0.099 mmol) to afford the desired product (24.3 mg, 71%) as a yellow solid: $^1$H NMR (500 MHz, CD$_3$OD) δ 8.79 (s, 1H), 8.24 (d, J=1.7 Hz, 1H), 8.06-7.96 (m, 2H), 7.53-7.49 (m, 1H), 7.42 (dd, J=11.7, 2.2 Hz, 1H), 3.53 (d, J=12.8 Hz, 2H), 3.28-3.15 (m, 6H), 3.09 (d, J=7.0 Hz, 2H), 2.62-2.54 (m, 1H), 2.14-2.02 (m, 5H), 1.99 (d, J=12.5 Hz, 2H), 1.77-1.63 (m, 2H), 1.36-1.28 (m, 2H), 1.28-1.17 (m, 2H); ESI MS m/z 508 [C$_{29}$H$_{31}$ClFN$_3$O$_2$+H]$^+$; HPLC 98.1% (AUC), t$_R$=10.69 min.

Example 307

Cyclopropyl{6-(3-fluoro-4-hydroxy-5-methoxyphenyl)-4-[4-(pyrrolidin-1-ylmethyl)piperidin-1-yl]quinolin-3-yl}methanone

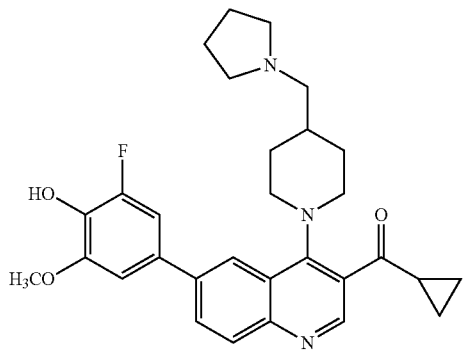 [SMILES: COc1cc(-c2ccc3ncc(C(=O)C4CC4)c(N4CCC(CN5CCCC5)CC4)c3c2)cc(F)c1O]

Following general procedure D, {6-bromo-4-[4-(pyrrolidin-1-ylmethyl)piperidin-1-yl]quinolin-3-yl}(cyclopropyl)methanone (26 mg, 0.059 mmol) was reacted with 2-fluoro-6-methoxy-4-(4,4,5,5-tetramethyl-1,3,2-dioxaborolan-2-yl)phenol (32 mg, 0.118 mmol) to afford the desired product (15.4 mg, 52%) as a gray solid: $^1$H NMR (500 MHz, CD$_3$OD) δ 8.78 (s, 1H), 8.27 (s, 1H), 8.03 (s, 2H), 7.23-7.04 (m, 2H), 3.99 (s, 3H), 3.54 (d, J=12.8 Hz, 2H), 3.28-3.11 (m, 6H), 3.05 (d, J=6.6 Hz, 2H), 2.63-2.51 (m, 1H), 2.20-1.89 (m, 7H), 1.80-1.58 (m, 2H), 1.41-1.16 (m, 4H).

Example 313

Cyclopropyl{6-[4-hydroxy-3-(trifluoromethoxy)phenyl]-4-[4-(pyrrolidin-1-ylmethyl]piperidin-1-yl}quinolin-3-yl)methanone

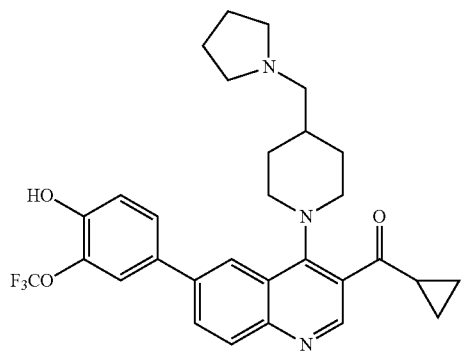 [SMILES: O=C(c1cnc2ccc(-c3ccc(O)c(OC(F)(F)F)c3)cc2c1N1CCC(CN2CCCC2)CC1)C1CC1]

Following general procedure D, {6-bromo-4-[4-(pyrrolidin-1-ylmethyl)piperidin-1-yl]quinolin-3-yl}(cyclopropyl)methanone (30 mg, 0.068 mmol) was reacted with 4-(4,4,5,5-tetramethyl-1,3,2-dioxaborolan-2-yl)-2-(trifluoromethoxy)phenol (36 mg, 0.140 mmol) as a yellow solid: $^1$H NMR (500 MHz, CD$_3$OD) δ 8.80 (s, 1H), 8.28 (d, J=1.6 Hz, 1H), 8.08-7.98 (m, 2H), 7.64-7.57 (m, 2H), 7.12 (d, J=9.0 Hz, 1H), 3.54 (d, J=12.8 Hz, 2H), 3.22 (t, J=11.5 Hz, 2H), 3.13 (s, 4H), 2.99 (s, 2H), 2.64-2.50 (m, 1H), 2.10-1.92 (m, 7H), 1.74-1.59 (m, 2H), 1.36-1.28 (m, 2H), 1.28-1.19 (m, 2H); ESI MS m/z 540 [C$_{30}$H$_{32}$F$_3$N$_3$O$_3$+H]$^+$; HPLC>99% (AUC), t$_R$=11.16 min.

Example 309

{6-(3-Chloro-4-hydroxy-5-methoxyphenyl)-4-[(3-amino)adamantylamino]quinolin-3-yl}(cyclopropyl)methanone

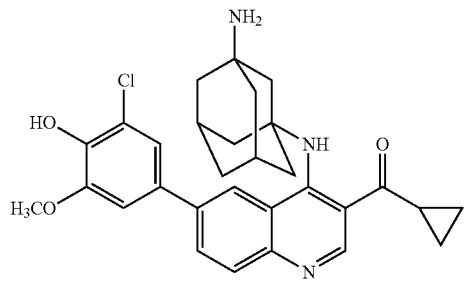 [SMILES: COc1cc(-c2ccc3ncc(C(=O)C4CC4)c(NC45CC6CC(CC(N)(C6)C4)C5)c3c2)cc(Cl)c1O]

Following general procedure F, tert-butyl 4-[3-(cyclopropanecarbonyl)-6-(3-chloro-4-hydroxy-5-methoxyphenyl)quinolin-4-ylamino]adamantylcarbamate (62 mg, 0.100 mmol) was reacted with TFA (2 mL) to afford the desired product (26 mg, 50%) as a yellow solid: $^1$H NMR (300 MHz, CD$_3$OD+Acetic Acid-d$_4$) δ 9.20 (s, 1H), 8.50 (d, J=1.9 Hz, 1H), 8.11 (dd, J=8.8, 2.0 Hz, 1H), 8.02 (d, J=8.8 Hz, 1H), 7.36 (d, J=2.0 Hz, 1H), 7.26 (d, J=2.1 Hz, 1H), 3.99 (s, 3H), 3.03-2.91 (m, 1H), 2.33 (s, 2H), 2.05 (d, J=12.5 Hz, 2H), 1.92-1.55 (m, 12H), 1.32-1.23 (m, 2H), 1.23-1.13 (m, 2H); ESI MS m/z 518 [C$_{30}$H$_{32}$ClN$_3$O$_3$+H]$^+$; HPLC 96.0% (AUC), t$_R$=9.59 min.

Example 315

6-(3-Chloro-4-hydroxy-5-methoxyphenyl)-4-{[trans-4-(dimethylamino)cyclohexyl]methylamino}quinolin-3-yl](cyclopropyl)methanone

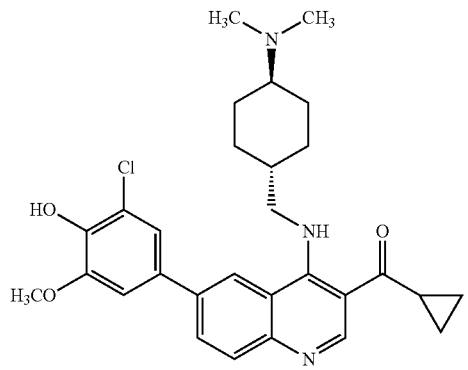 [SMILES: COc1cc(-c2ccc3ncc(C(=O)C4CC4)c(NC[C@H]4CC[C@H](N(C)C)CC4)c3c2)cc(Cl)c1O]

Following general procedure F, (6-bromo-4-{[trans-4-(dimethylamino)cyclohexyl]methylamino}quinolin-3-yl)(cyclopropyl)methanone (58 mg, 0.135 mmol) was reacted with 2-chloro-6-methoxy-4-(4,4,5,5-tetramethyl-1,3,2-dioxaborolan-2-yl)phenol (57 mg, 0.202 mmol) to afford the desired product (30 mg, 44%) as a yellow-green solid: $^1$H NMR (300 MHz, CD$_3$OD+Acetic Acid-d$_4$) δ 9.25 (s, 1H), 8.52 (s, 1H), 8.15 (d, J=8.7 Hz, 1H), 7.95 (d, J=8.8 Hz, 1H), 7.30 (d, J=2.0 Hz, 1H), 7.22 (d, J=1.9 Hz, 1H), 3.98 (s, 3H), 3.95 (d, J=6.5 Hz, 2H), 2.83 (s, J=13.2 Hz, 6H), 2.15 (s, 4H), 2.05-1.93 (m, 1H), 1.88 (s, 1H), 1.73-1.48 (m, 2H), 1.43-1.08 (m, 7H); ESI MS m/z 508 [C$_{29}$H$_{34}$ClN$_3$O$_3$+H]$^+$; HPLC 98.5% (AUC), t$_R$=10.37 min.

Example 325

Cyclopropyl[6-(3,5-dichloro-4-hydroxyphenyl)-4-{[trans-4-(dimethylamino)cyclohexyl]methylamino}quinolin-3-yl]methanone

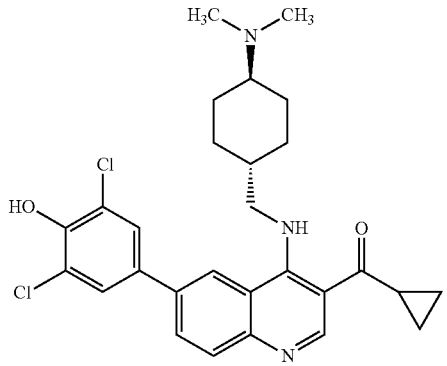 [SMILES: CN(C)[C@H]1CC[C@H](CNc2c(C(=O)C3CC3)cnc3ccc(-c4cc(Cl)c(O)c(Cl)c4)cc23)CC1]

Following general procedure F, (6-bromo-4-{[trans-4-(dimethylamino)cyclohexyl]methylamino}quinolin-3-yl)(cyclopropyl)methanone (66 mg, 0.153 mmol) was reacted with 2,6-dichloro-4-(4,4,5,5-tetramethyl-1,3,2-dioxaborolan-2-yl)phenol (65 mg, 0.230 mmol) to afford the desired product (38 mg, 50%) as a yellow solid: $^1$H NMR (300 MHz, CD$_3$OD+Acetic Acid-d$_4$) δ 9.24 (s, 1H), 8.49 (d, J=1.7 Hz, 1H), 8.10 (dd, J=8.8, 1.8 Hz, 1H), 7.95 (d, J=8.8 Hz, 1H), 7.68 (s, 2H), 3.90 (d, J=6.5 Hz, 2H), 2.85 (d, J=11.2 Hz, 6H), 2.15 (t, J=11.3 Hz, 4H), 2.01-1.74 (m, 2H), 1.61 (dd, J=21.6, 12.1 Hz, 2H), 1.46-1.07 (m, 7H); ESI MS m/z 512 [C$_{28}$H$_{31}$Cl$_2$N$_3$O$_2$+H]$^+$; HPLC 99.0% (AUC), t$_R$=10.65 min.

Example 327

6-(3-Chloro-5-fluoro-4-hydroxyphenyl)-4-{[trans-4-(dimethylamino)cyclohexyl]methylamino}quinolin-3-yl](cyclopropyl)methanone

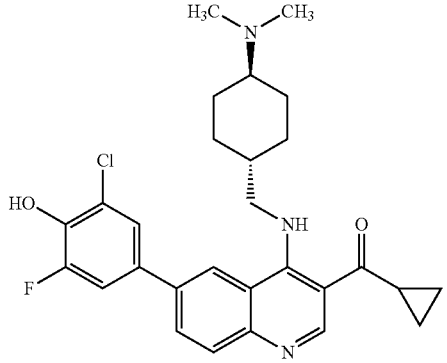 [SMILES: CN(C)[C@H]1CC[C@H](CNc2c(C(=O)C3CC3)cnc3ccc(-c4cc(F)c(O)c(Cl)c4)cc23)CC1]

Following general procedure F, (6-bromo-4-{[trans-4-(dimethylamino)cyclohexyl]methylamino}quinolin-3-yl)(cyclopropyl)methanone (58 mg, 0.134 mmol) was reacted with 2-chloro-6-fluoro-4-(4,4,5,5-tetramethyl-1,3,2-dioxaborolan-2-yl)phenol (55 mg, 0.201 mmol) to afford the desired product (19 mg, 29%) as a yellow solid: $^1$H NMR (300 MHz, CD$_3$OD+Acetic Acid-d$_4$) δ 9.24 (s, 1H), 8.52 (s, 1H), 8.11 (d, J=8.8 Hz, 1H), 7.95 (d, J=8.8 Hz, 1H), 7.56 (s, 1H), 7.49 (dd, J=11.5, 2.2 Hz, 1H), 3.92 (d, J=6.4 Hz, 2H), 2.84 (s, 6H), 2.15 (s, 4H), 2.02-1.93 (m, 1H), 1.88 (s, 1H), 1.72-1.51 (m, 2H), 1.43-1.10 (m, 7H); ESI MS m/z 496 [C$_{28}$H$_{31}$ClN$_3$O$_2$+H]$^+$; HPLC>99% (AUC), t$_R$=10.39 min.

Example 316

6-(3-Chloro-4-hydroxy-5-methoxyphenyl)-4-{trans-4-[(dimethylamino)methyl]cyclohexylamino}quinolin-3-yl](cyclopropyl)methanone

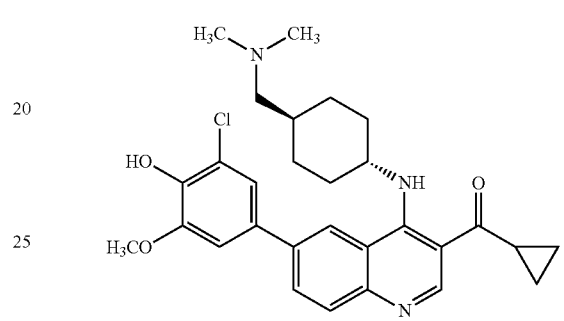

Following general procedure F, {6-bromo-4-[trans-4-{(dimethylamino)methyl}cyclohexylamino]quinolin-3-yl}(cyclopropyl)methanone (58 mg, 0.135 mmol) was reacted with 2-chloro-6-methoxy-4-(4,4,5,5-tetramethyl-1,3,2-dioxaborolan-2-yl)phenol (57 mg, 0.203 mmol) to afford the desired product (21 mg, 30%) as a yellow-green solid: $^1$H NMR (300 MHz, CD$_3$OD+Acetic Acid-d$_4$) δ 9.23 (s, 1H), 8.42 (s, 1H), 8.17 (dd, J=8.7, 1.7 Hz, 1H), 7.96 (d, J=8.8 Hz, 1H), 7.31 (d, J=2.1 Hz, 1H), 7.24 (d, J=2.0 Hz, 1H), 4.28 (s, 1H), 3.99 (s, 3H), 3.03 (d, J=6.7 Hz, 2H), 2.89 (s, 6H), 2.83 (d, J=4.7 Hz, 1H), 2.38 (d, J=12.1 Hz, 2H), 2.09-1.89 (m, 4H), 1.79-1.58 (m, J=24.6, 11.7 Hz, 2H), 1.38-1.09 (m, 7H); ESI MS m/z 508 [C$_{29}$H$_{34}$ClN$_3$O$_3$+H]$^+$; HPLC 98.8% (AUC), t$_R$=10.38 min.

Example 332

{6-(3-Chloro-4-hydroxyphenyl)-4-[4-(morpholinomethyl)piperidin-1-yl]quinolin-3-yl}(cyclopropyl)methanone

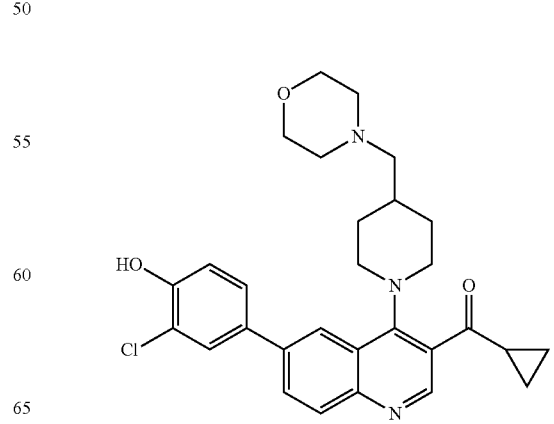

Following general procedure D, {6-bromo-4-[4-(morpholinomethyl)piperidin-1-yl]quinolin-3-yl}(cyclopropyl)methanone (30 mg, 0.065 mmol) was reacted with 3-chloro-4-hydroxyphenylboronic acid (34 mg, 0.200 mmol) to afford the desired product (20.3 mg, 62%) as an off-white solid: $^1$H NMR (500 MHz, CD$_3$OD) δ 8.73 (s, 1H), 8.29 (s, 1H), 8.04-7.98 (m, 2H), 7.71 (d, J=2.3 Hz, 1H), 7.54 (dd, J=8.4, 2.3 Hz, 1H), 7.07 (d, J=8.4 Hz, 1H), 3.74-3.71 (m, 3H), 3.53 (d, J=12.7 Hz, 2H), 3.34 (s, 3H), 3.26-3.15 (m, 2H), 2.59-2.46 (m, 4H), 2.38 (d, J=6.7 Hz, 2H), 1.98 (d, J=12.9 Hz, 3H), 1.66-1.52 (m, 2H), 1.36-1.27 (m, 2H), 1.27-1.20 (m, 2H); ESI MS m/z 506 [C$_{29}$H$_{32}$ClN$_3$O$_3$+H]$^+$; HPLC 98.0% (AUC), $t_R$=10.44 min.

Example 334

{6-(3-Chloro-4-hydroxy-5-methoxyphenyl)-4-[4-(morpholinomethyl)piperidin-1-yl]quinolin-3-yl}(cyclopropyl)methanone

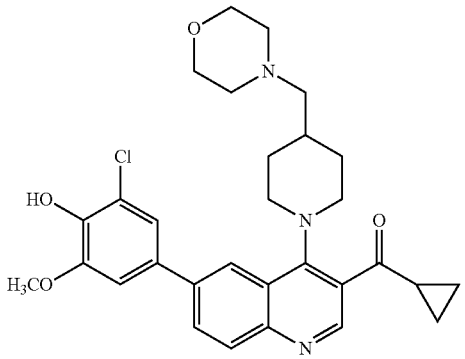 [SMILES: COc1cc(-c2ccc3ncc(C(=O)C4CC4)c(N4CCC(CN5CCOCC5)CC4)c3c2)cc(Cl)c1O]

Following general procedure D, {6-bromo-4-[4-(morpholinomethyl)piperidin-1-yl]quinolin-3-yl}(cyclopropyl)methanone (30 mg, 0.065 mmol) was reacted with 2-chloro-6-methoxy-4-(4,4,5,5-tetramethyl-1,3,2-dioxaborolan-2-yl)phenol (42 mg, 0.150 mmol) to afford the desired product (20 mg, 57%) as an off-white solid: $^1$H NMR (500 MHz, CD$_3$OD) δ 8.73 (s, 1H), 8.33 (d, J=1.7 Hz, 1H), 8.07-7.97 (m, 2H), 7.33 (d, J=2.1 Hz, 1H), 7.26 (d, J=2.1 Hz, 1H), 4.00 (s, 3H), 3.75-3.68 (m, 4H), 3.55 (d, J=12.7 Hz, 2H), 3.25-3.15 (m, 2H), 2.61-2.41 (m, 5H), 2.36 (d, J=6.9 Hz, 2H), 2.07-1.90 (m, 3H), 1.68-1.54 (m, 2H), 1.37-1.27 (m, 2H), 1.26-1.20 (m, 2H); ESI MS m/z 536 [C$_{30}$H$_{34}$ClN$_3$O$_4$+H]$^+$; HPLC>99% (AUC), $t_R$=10.57 min.

Example 339

-(3-Chloro-4-hydroxy-5-methoxyphenyl)-4-{4-[(dimethylamino)methyl]phenylamino}quinolin-3-yl)cyclopropyl)methanone

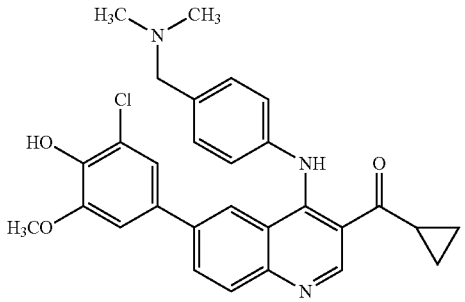 [SMILES: COc1cc(-c2ccc3ncc(C(=O)C4CC4)c(Nc4ccc(CN(C)C)cc4)c3c2)cc(Cl)c1O]

Following general procedure F, (6-bromo-4-{4-[(dimethylamino)methyl]phenylamino}quinolin-3-yl)(cyclopropyl)methanone (38 mg, 0.090 mmol) was reacted with 2-chloro-6-methoxy-4-(4,4,5,5-tetramethyl-1,3,2-dioxaborolan-2-yl)phenol (38 mg, 0.133 mmol) to afford the desired product (39 mg, 86%) as a yellow solid: $^1$H NMR (300 MHz, CD$_3$OD) δ 9.26 (s, 1H), 8.10-7.97 (m, 2H), 7.95 (s, 1H), 7.49 (d, J=8.4 Hz, 2H), 7.25 (d, J=8.3 Hz, 2H), 6.98 (d, J=1.9 Hz, 1H), 6.81 (d, J=2.0 Hz, 1H), 4.27 (s, 2H), 3.87 (s, 3H), 2.98-2.85 (m, 1H), 2.78 (s, 6H), 1.23-1.00 (m, 4H); ESI MS m/z 502 [C$_{29}$H$_{28}$ClN$_3$O$_3$+H]$^+$; HPLC>99% (AUC), $t_R$=10.69 min.

Example 345

Cyclopropyl[6-(3,5-dichloro-4-hydroxyphenyl)-4-{4-[(dimethylamino)methyl]phenylamino}quinolin-3-yl]methanone

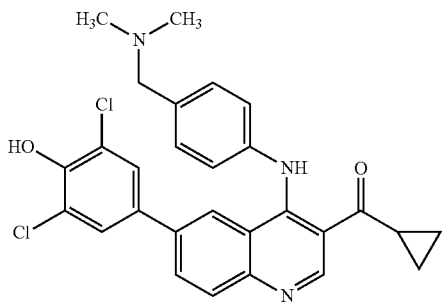 [SMILES: CN(C)Cc1ccc(Nc2c(C(=O)C3CC3)cnc3ccc(-c4cc(Cl)c(O)c(Cl)c4)cc23)cc1]

Following general procedure F, (6-bromo-4-{4-[(dimethylamino)methyl]phenylamino}quinolin-3-yl)(cyclopropyl)methanone (44 mg, 0.104 mmol) was reacted with 2,6-dichloro-4-(4,4,5,5-tetramethyl-1,3,2-dioxaborolan-2-yl)phenol (45 mg, 0.156 mmol) to afford the desired product (38 mg, 73%) as a yellow solid: $^1$H NMR (300 MHz, CD$_3$OD+ Acetic Acid-d$_4$) δ 9.26 (s, 1H), 7.99 (d, J=10.0 Hz, 2H), 7.94 (s, 1H), 7.51 (d, J=8.4 Hz, 2H), 7.29 (s, J=9.9 Hz, 3H), 7.25 (s, 1H), 4.32 (s, 2H), 2.94-2.85 (m, 1H), 2.82 (s, 6H), 1.17-1.01 (m, 4H); ESI MS m/z 506 [C$_{28}$H$_{25}$Cl$_2$N$_3$O$_2$+H]$^+$; HPLC 94.4% (AUC), $t_R$=11.19 min.

Example 342

{6-(3-Chloro-4-hydroxyphenyl)-4-[trans-4-(pyrrolidin-1-yl)cyclohexylamino]quinolin-3-yl}(cyclopropyl)methanone

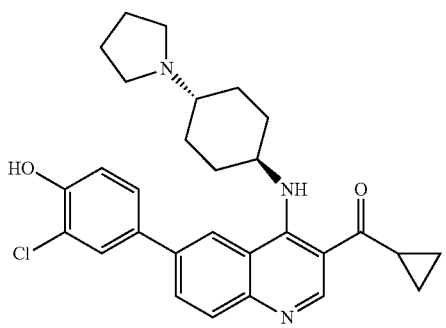

Following general procedure D, {6-bromo-4-[trans-4-(pyrrolidin-1-yl)cyclohexylamino]quinolin-3-yl}(cyclopropyl)methanone (24 mg, 0.054 mmol) was reacted with 3-chloro-4-hydroxyphenylboronic acid (26 mg, 0.150 mmol) to afford the desired product (22 mg, 83%) as a brown solid: $^1$H NMR (300 MHz, CD$_3$OD) δ 9.14 (s, 1H), 8.34 (s, 1H), 8.01 (dd, J=8.8, 1.8 Hz, 1H), 7.92 (d, J=8.7 Hz, 1H), 7.70 (d, J=2.2 Hz, 1H), 7.52 (dd, J=8.5, 2.3 Hz, 1H), 7.06 (d, J=8.5 Hz, 1H), 4.18 (s, 1H), 3.24 (s, 4H), 3.07 (s, 1H), 2.90-2.78 (m, 1H), 2.34 (d, J=14.5 Hz, 4H), 2.02 (s, 4H), 1.73-1.51 (m, 4H), 1.26-1.15 (m, 2H), 1.15-1.02 (m, 21-1); ESI MS m/z 490 $[C_{29}H_{32}ClN_3O_2+H]^+$; HPLC 98.9% (AUC), $t_R$=10.90 min.

Example 343

{6-(3-Chloro-4-hydroxy-5-methoxyphenyl)-4-[trans-4-(pyrrolidin-1-yl)cyclohexylamino]quinolin-3-yl}(cyclopropyl)methanone

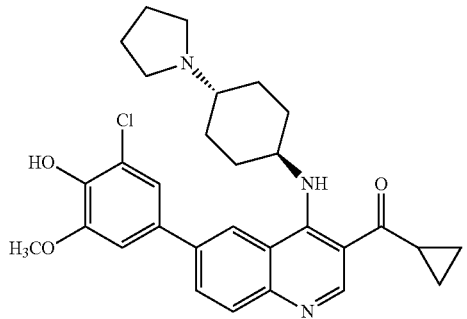 [SMILES: COc1cc(-c2ccc3ncc(C(=O)C4CC4)c(N[C@H]4CC[C@H](N5CCCC5)CC4)c3c2)cc(Cl)c1O]

Following general procedure D, {6-bromo-4-[trans-4-(pyrrolidin-1-yl)cyclohexylamino]quinolin-3-yl}(cyclopropyl)methanone (25 mg, 0.150 mmol) was reacted with 2-chloro-6-methoxy-4-(4,4,5,5-tetramethyl-1,3,2-dioxaborolan-2-yl)phenol (43 mg, 0.150 mmol) to afford the desired product (20 mg, 67%), as a yellow-brown solid: $^1$H NMR (500 MHz, CD$_3$OD) δ 9.14 (s, 1H), 8.34 (d, J=1.9 Hz, 1H), 8.03 (dd, J=8.7, 1.9 Hz, 1H), 7.92 (d, J=8.7 Hz, 1H), 7.29 (d, J=2.1 Hz, 1H), 7.22 (d, J=2.0 Hz, 1H), 4.15 (t, J=10.6 Hz, 1H), 3.99 (s, 3H), 3.16 (s, 4H), 2.94 (s, 1H), 2.89-2.79 (m, 1H), 2.38 (d, J=12.5 Hz, 2H), 2.28 (d, J=11.9 Hz, 2H), 1.99 (s, 4H), 1.70-1.50 (m, 4H), 1.23-1.17 (m, 2H), 1.13-1.06 (m, 2H); ESI MS m/z 520 $[C_{30}H_{34}ClN_3O_3+H]^+$; HPLC 98.7% (AUC), $t_R$=10.99 min.

Example 349

{6-(3-Chloro-5-fluoro-4-hydroxyphenyl)-4-[4-(4-methylpiperazin-1-yl)piperidin-1-yl]quinolin-3-yl}(cyclopropyl)methanone

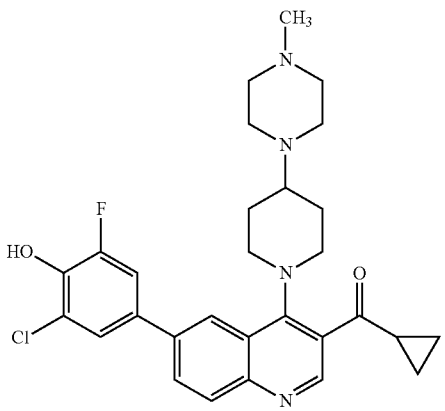 [SMILES: CN1CCN(C2CCN(c3c(C(=O)C4CC4)cnc4ccc(-c5cc(F)c(O)c(Cl)c5)cc34)CC2)CC1]

Following general procedure D, {6-bromo-4-[4-(4-methylpiperazin-1-yl)piperidin-1-yl]quinolin-3-yl}(cyclopropyl)methanone (30 mg, 0.066 mmol) was reacted with 2-chloro-6-fluoro-4-(4,4,5,5-tetramethyl-1,3,2-dioxaborolan-2-yl)phenol (41 mg, 0.150 mmol) to afford the desired product (23 mg, 67%) as a yellow solid: $^1$H NMR (500 MHz, CD$_3$OD) δ 8.77 (s, 1H), 8.28 (d, J=1.3 Hz, 1H), 8.05-7.99 (m, 2H), 7.58-7.53 (m, 1H), 7.46 (dd, J=11.6, 2.2 Hz, 1H), 3.55 (d, J=13.1 Hz, 2H), 3.25-3.15 (m, 2H), 2.93-2.47 (m, 10H), 2.39 (s, 3H), 2.12 (d, J=10.8 Hz, 2H), 1.96-1.82 (m, 2H), 1.34-1.28 (m, 2H), 1.27-1.20 (m, 2H); ESI MS m/z 523 $[C_{29}H_{32}ClFN_4O_2+H]^+$; HPLC>99% (AUC), $t_R$=10.14 min.

Example 350

{6-(3-Chloro-4-hydroxyphenyl)-4-[4-(4-methylpiperazin-1-yl)piperidin-1-yl]quinolin-3-yl}(cyclopropyl)methanone

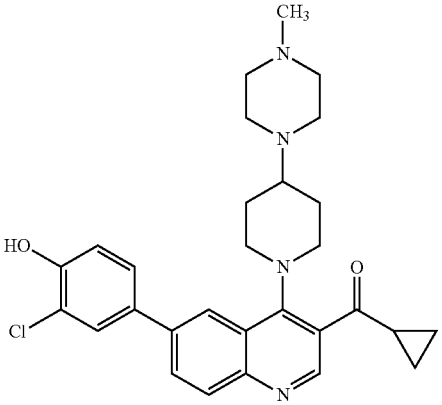 [SMILES: CN1CCN(C2CCN(c3c(C(=O)C4CC4)cnc4ccc(-c5ccc(O)c(Cl)c5)cc34)CC2)CC1]

Following general procedure D, {6-bromo-4-[4-(4-methylpiperazin-1-yl)piperidin-1-yl]quinolin-3-yl}(cyclopropyl)methanone (30 mg, 0.065 mmol) was reacted with 3-chloro-4-hydroxyphenylboronic acid (26 mg, 0.150 mmol) to afford the desired product (19 mg, 57%) as a yellow solid: $^1$H NMR (500 MHz, CD$_3$OD) δ 8.76 (s, 1H), 8.28 (s, 1H), 8.06-7.98 (m, 2H), 7.71 (d, J=2.3 Hz, 1H), 7.54 (dd, J=8.4, 2.3 Hz, 1H), 7.09-7.03 (m, 1H), 3.55 (d, J=12.8 Hz, 2H), 3.34 (s, 3H), 3.23-3.15 (m, 2H), 2.81-2.50 (m, 8H), 2.35 (s, 3H), 2.12 (d, J=10.6 Hz, 2H), 1.92-1.81 (m, 2H), 1.34-1.28 (m, 2H), 1.27-1.20 (m, 2H); ESI MS m/z 505 $[C_{29}H_{33}ClN_4O_4+H]^+$; HPLC>99% (AUC), $t_R$=10.01 min.

Example 351

{6-(3-Chloro-4-hydroxy-5-methoxyphenyl)-4-[4-(4-methylpiperazin-1-yl)piperidin-1-yl]quinolin-3-yl}(cyclopropyl)methanone

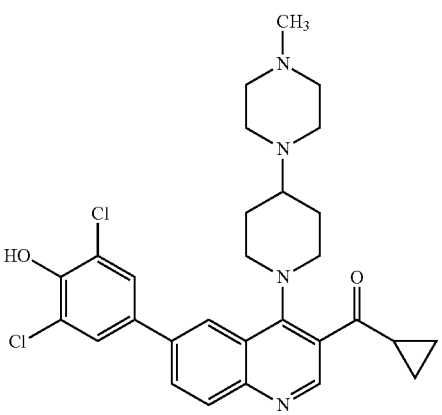 [SMILES: CN1CCN(C2CCN(c3c(C(=O)C4CC4)cnc4ccc(-c5cc(Cl)c(O)c(Cl)c5)cc34)CC2)CC1]

Following general procedure D, {6-bromo-4-[4-(4-methylpiperazin-1-yl)piperidin-1-yl]quinolin-3-yl}(cyclopropyl)methanone (102 mg, 0.225 mmol was reacted with 2-chloro-6-methoxy-4-(4,4,5,5-tetramethyl-1,3,2-dioxaborolan-2-yl)phenol (42 mg, 0.150 mmol) to afford the desired product (16.8 mg, 48%) as an orange-brown solid: $^1$H NMR (500 MHz, CD$_3$OD) δ 8.76 (2, 1H), 8.30 (d, J=1.4 Hz, 1H), 8.08-8.00 (m, 2H), 7.33 (d, 0.1=2.1 Hz, 1H), 7.26 (d, J=2.0 Hz, 1H), 4.00 (s, 3H), 3.57 (d, J=12.9 Hz, 2H), 3.34 (s, 3H), 3.24-3.16 (m, 2H), 2.79-2.52 (m, 7H), 2.36 (s, 3H), 2.11 (d, J=11.3 Hz, 2H), 1.96-1.83 (m, 2H), 1.34-1.28 (m, 2H), 126-1.19 (m, 2H); ESI MS m/z 535 [C$_{30}$H$_{35}$ClN$_4$O$_3$+H]$^+$; HPLC>99% (AUC), t$_R$=10.13 min.

Example 108

5-{4-[trans-4-Aminocyclohexylamino]-3-isobutyrylquinolin-6-yl}picolinonitrile

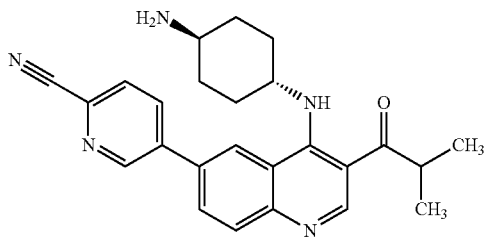 [SMILES: CC(C)C(=O)c1cnc2ccc(-c3ccc(C#N)nc3)cc2c1N[C@H]1CC[C@H](N)CC1]

Following general procedure A-1, tert-butyl trans-4-[6-(6-cyanopyridin-3-yl)-3-isobutyrylquinolin-4-ylamino]cyclohexylcarbamate (47.7 mg, 0.093 mmol) was reacted with 6 N hydrochloric acid (3 mL) to afford the desired product (20.8 mg, 54%) as a light yellow solid: $^1$H NMR (500 MHz, CD$_3$OD) δ 9.13-9.11 (m, 1H), 9.06 (s, 1H), 8.55 (d, J=1.8 Hz, 1H), 8.39 (dd, J=8.1, 2.3 Hz, 1H), 8.19 (dd, J=8.7, 1.9 Hz, 1H), 8.04 (d, J=3.8 Hz, 1H), 8.02 (d, J=4.4 Hz, 1H), 4.35-4.27 (m, 1H), 3.82-3.73 (m, 1H), 3.29-3.22 (m, 1H), 2.40 (d, J=12.7 Hz, 2H), 2.19 (d, J=12.1 Hz, 2H), 1.78-1.68 (m, 2H), 1.67-1.56 (m, 2H), 1.25 (d, J=6.8 Hz, 6H); ESI MS m/z 414 [C$_{25}$H$_{27}$N$_5$O+H]$^+$; HPLC 98.3% (AUC), t$_R$=7.96 min.

Example 205

1-{4-[trans-4-Aminocyclohexylamino]-6-(3-chloro-5-fluoro-4-hydroxyphenyl)quinolin-3-yl}-2-methylpropan-1-one

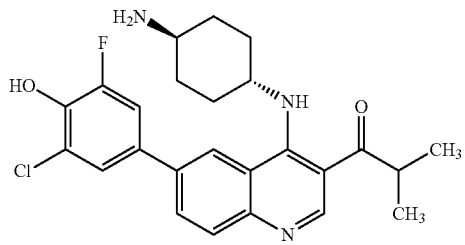 [SMILES: CC(C)C(=O)c1cnc2ccc(-c3cc(F)c(O)c(Cl)c3)cc2c1N[C@H]1CC[C@H](N)CC1]

Following general procedure A-2, tert-butyl trans-4-[6-(3-chloro-5-fluoro-4-hydroxyphenyl)-3-isobutyrylquinolin-4-ylamino]cyclohexylcarbamate (56 mg, 0.100 mmol) was reacted with TFA (2 mL) to afford the desired product (28 mg, 61%) as a yellow solid: $^1$H NMR (500 MHz, CD$_3$OD) δ 8.96 (s, 1H), 8.31 (d, J=1.8 Hz, 1H), 7.99 (dd, J=8.7, 1.9 Hz, 1H), 7.90 (d, J=8.7 Hz, 1H), 7.51-7.47 (m, 1H), 7.39 (dd, J=11.8, 2.3 Hz, 1H), 4.23-4.15 (m, 1H), 3.82-3.69 (m, 1H), 3.28-3.18 (m, 1H), 2.39 (d, J=12.7 Hz, 2H), 2.19 (d, J=12.0 Hz, 2H), 1.71 (q, J=10.5 Hz, 2H), 1.62-1.53 (m, 2H), 1.24 (d, J=6.8 Hz, 6H), ESI MS m/z 456[C$_{25}$H$_{27}$ClFN$_3$O$_2$+H]$^+$; HPLC 98.1% (AUC), t$_R$=10.69 min.

Example 214

1-{4-[trans-4-Aminocyclohexylamino]-6-(3,5-difluoro-4-hydroxyphenyl)quinolin-3-yl}-2-methylpropan-1-one

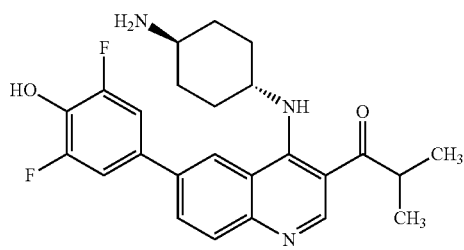 [SMILES: CC(C)C(=O)c1cnc2ccc(-c3cc(F)c(O)c(F)c3)cc2c1N[C@H]1CC[C@H](N)CC1]

Following general procedure A-2, tert-butyl trans-4-[6-(3,5-difluoro-4-hydroxyphenyl)-3-isobutyrylquinolin-4-ylamino]cyclohexylcarbamate (64 mg, 0.100 mmol) was reacted with TFA (2 mL) to afford the desired product (10.8 mg, 36%) as a yellow solid: $^1$H NMR (500 MHz, CD$_3$OD) δ 8.97 (s, 1H), 8.32 (d, J=1.8 Hz, 1H), 8.00 (dd, J=8.7, 2.0 Hz, 1H), 7.90 (d, J=8.7 Hz, 1H), 7.28 (dd, J=7.8, 1.9 Hz, 2H), 4.26-4.15 (m, 1H), 3.81-3.69 (m, 1H), 3.27-3.18 (m, 1H), 2.38 (d, J=12.6 Hz, 2H), 2.18 (d, J=11.7 Hz, 2H), 1.69 (q, J=10.4 Hz, 2H), 1.61-1.53 (m, 2H), 1.24 (d, J=6.8 Hz, 6H); ESI MS m/s 440 [C$_{25}$H$_{27}$F$_2$N$_3$O$_2$+H]$^+$; HPLC 95.0% (AUC), t$_R$=10.50 min.

Example 219

1-{4-[trans-4-Aminocyclohexylamino]-6-(3-chloro-4-hydroxyphenyl)quinolin-3-yl}-2-methylpropan-1-one

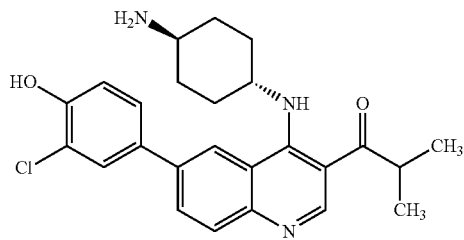 [SMILES: CC(C)C(=O)c1cnc2ccc(-c3ccc(O)c(Cl)c3)cc2c1N[C@H]1CC[C@H](N)CC1]

Following general procedure A-2, tert-butyl trans-4-[6-(3-chloro-4-hydroxyphenyl)-3-isobutyrylquinolin-4-ylamino]cyclohexylcarbamate (39 mg, 0.072 mmol) was reacted with TFA (2 mL) to afford the desired product (15.4 mg, 41%) as a yellow solid: $^1$H NMR (500 MHz, CD$_3$OD) δ 9.05 (s, 1H), 8.40 (s, 1H), 8.13 (d, J=8.8 Hz, 1H), 7.95 (d, J=8.7 Hz, 1H), 7.72 (d, J=2.3 Hz, 1H), 7.54 (dd, J=8.4, 2.3 Hz, 1H), 7.08 (d, J=8.4 Hz, 1H), 4.31 (s, 1H), 3.80-3.72 (m, 1H), 3.29-3.26 (m, 1H), 2.44 (d, J=12.7 Hz, 2H), 2.22 (d, J=10.6 Hz, 2H), 1.84-1.74 (m, 2H), 1.67-1.56 (m, 2H), 1.25 (d, J=6.8 Hz, 6H); ESI MS m/z 438 $[C_{25}H_{28}ClN_3O_2+H]^+$; HPLC 96.5% (AUC), $t_R$=9.19 min.

Example 225(a)

1-{4-[trans-4-Aminocyclohexylamino]-6-(3,5-dichloro-4-hydroxyphenyl)quinolin-3-yl}-2-methyl-propan-1-one

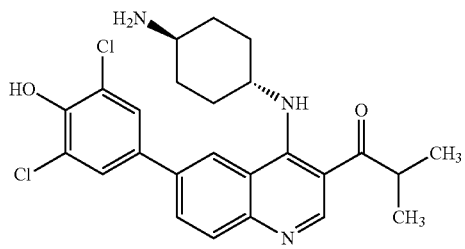 [SMILES: CC(C)C(=O)c1cnc2ccc(-c3cc(Cl)c(O)c(Cl)c3)cc2c1N[C@H]1CC[C@H](N)CC1]

Following general procedure A-2, tert-butyl trans-4-[6-(3,5-dichloro-4-hydroxyphenyl)-3-isobutyrylquinolin-4-ylamino]cyclohexylcarbamate (60 mg, 0.100 mmol) was reacted with TFA (2 mL) to afford the desired product (20.3 mg, 43%) as a yellow solid: $^1$H NMR (500 MHz, CD$_3$OD) δ 8.98 (s, 1H), 8.33 (s, 1H), 8.02 (d, J=8.8 Hz, 1H), 7.93 (d, J=8.7 Hz, 1H), 7.67 (s, 2H), 4.18 (s, 1H), 3.80-3.70 (m, 1H), 2.96 (s, 1H), 2.40 (d, J=11.4 Hz, 2H), 2.20 (d, J=12.2 Hz, 2H), 1.73 (q, J=11.1 Hz, 2H), 1.65-1.53 (m, 2H), 1.24 (d, J=6.8 Hz, 6H); ESI MS m/z 472 $[C_{25}H_{27}Cl_2N_3O_2+H]^+$; HPLC 98.7% (AUC), $t_R$=10.95 min.

Example 225(b)

1-{4-[trans-4-Aminocyclohexylamino]-6-(3,5-dichloro-4-hydroxyphenyl)quinolin-3-yl}-2-methyl-propan-1-one dihydrochloride

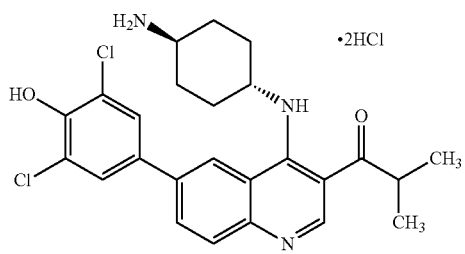 [SMILES: CC(C)C(=O)c1cnc2ccc(-c3cc(Cl)c(O)c(Cl)c3)cc2c1N[C@H]1CC[C@H](N)CC1]

To a suspension of 1-{4-[trans-4-Aminocyclohexylamino]-6-(3,5-dichloro-4-hydroxyphenyl)quinolin-3-yl}-2-methyl-propan-1-one (3.0 g, 6.4 mmol) in THF (50 mL) was added 3 M HCl (30 mL) and the reaction mixture was heated at 60° C. for 2 h. The reaction mixture was cooled and the precipitate was filtered to afford the desired product (4.7 g, 92%) as an off-white solid: $^1$H NMR (500 MHz, CD$_3$OD) δ 9.18 (bs, 1H), 8.49 (bs, 1H), 8.27 (d, J=8.8 Hz, 1H), 7.02 (d, J=8.8 Hz, 1H), 7.75 (bs, 2H), 4.54 (bs, 1H), 3.80-3.69 (m, 1H), 2.52 (bs, 2H), 2.29-2.22 (m, 2H), 1.94-1.81 (m, 2H), 1.75-1.62 (m, 2H), 1.24 (d, J=6.8 Hz, 6H); ESI MS m/z 472 $[C_{25}H_{27}C_{12}N_3O_2+H]^+$.

Example 318

1-{6-(3-Chloro-4-hydroxyphenyl)-4-[4-(pyrrolidin-1-ylmethyl)piperidin-1-yl]quinolin-3-yl}-2-methyl-propan-1-one

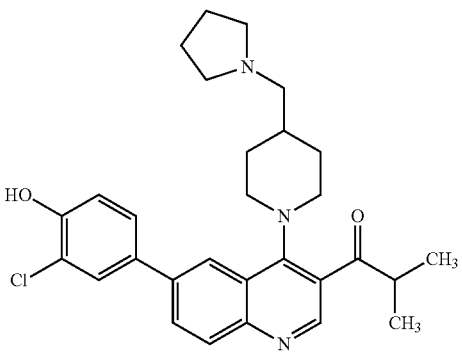 [SMILES: CC(C)C(=O)c1cnc2ccc(-c3ccc(O)c(Cl)c3)cc2c1N1CCC(CN2CCCC2)CC1]

Following general procedure D, 1-{6-bromo-4-[4-(pyrrolidin-1-ylmethyl)piperidin-1-yl]quinolin-3-yl}-2-methylpropan-1-one (30 mg, 0.068 mmol) was reacted with 3-chloro-4-hydroxyphenylboronic acid (17 mg, 0.100 mmol) to afford the desired product (18.9 mg, 56%) as an off-white solid: $^1$H NMR (500 MHz, CD$_3$OD) δ 8.75 (s, 1H), 8.28 (d, J=1.2 Hz, 1H), 8.06-7.99 (m, 2H), 7.70 (d, J=2.3 Hz, 1H), 7.54 (dd, J=8.4, 2.3 Hz, 1H), 7.06 (d, J=8.4 Hz, 1H), 3.54-3.41 (m, 3H), 3.23-3.11 (m, 6H), 3.03 (d, J=6.8 Hz, 2H), 2.11-1.93 (m, 7H), 1.74-1.62 (m, 2H), 1.26 (d, J=6.9 Hz, 6H); ESI MS m/z 492 $[C_{29}H_{34}ClN_3O_2+H]^+$; HPLC>99% (AUC), $t_R$=10.93 min.

Example 323

1-{6-(3-Chloro-5-fluoro-4-hydroxyphenyl)-4-[4-(pyrrolidin-1-ylmethyl)piperidin-1-yl]quinolin-3-yl}-2-methylpropan-1-one

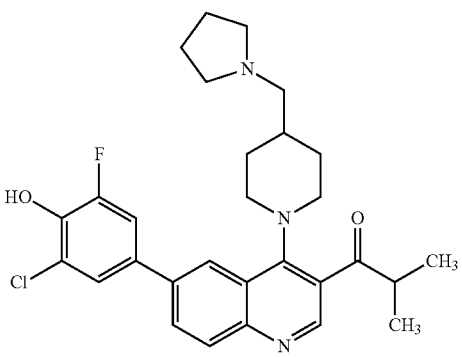 [SMILES: CC(C)C(=O)c1cnc2ccc(-c3cc(F)c(O)c(Cl)c3)cc2c1N1CCC(CN2CCCC2)CC1]

Following general procedure D, 1-{6-bromo-4-[4-(pyrrolidin-1-ylmethyl)piperidin-1-yl]quinolin-3-yl}-2-methylpropan-1-one (30 mg, 0.068 mmol) was reacted with 2-chloro-6-fluoro-4-(4,4,5,5-tetramethyl-1,3,2-dioxaborolan-2-yl)phenol (27 mg, 0.102 mmol) to afford the desired product (27.4 mg, 79%) as a yellow-brown solid: $^1$H NMR (500 MHz, CD$_3$OD) δ 8.77 (s, 1H), 8.27 (d, J=1.8 Hz, 1H), 8.07-7.99 (m, 2H), 7.55-7.51 (m, 1H), 7.44 (dd, J=11.6, 2.2 Hz, 1H), 3.54-3.42 (m, 3H), 3.38-3.33 (m, 4H), 3.21-3.11 (m, 4H), 2.15-2.06 (m, 5H), 1.99 (d, J=11.0 Hz, 2H), 1.75-1.64 (m, 2H), 1.26 (d, J=6.9 Hz, 6H); ESI MS m/z 510 [C$_{29}$H$_{33}$ClFN$_3$O$_2$+ H]$^+$; HPLC 97.7% (AUC), t$_R$=11.07 min.

Example 240

2-Chloro-4-{4-[4-(diethylamino)cyclohexylamino]-3-(methylsulfonyl)quinolin-6-yl}-6-methoxyphenol dihydrochloride

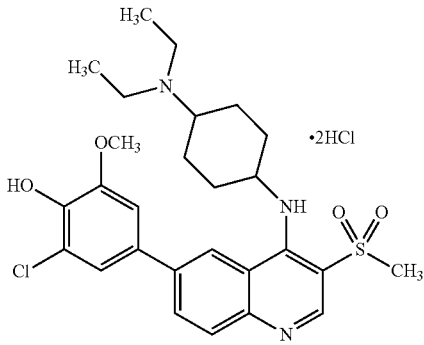 [SMILES: CCN(CC)C1CCC(Nc2c(S(C)(=O)=O)cnc3ccc(-c4cc(Cl)c(O)c(OC)c4)cc23)CC1]

Following general procedure D, N$^1$-[6-bromo-3-(methylsulfonyl)quinolin-4-yl]-N$^4$,N$^4$-diethylcyclohexane-1,4-diamine (40 mg, 0.088 mmol) was reacted with 2-chloro-6-methoxy-4-(4,4,5,5-tetramethyl-1,3,2-dioxaborolan-2-yl) phenol (50 mg, 0.176 mmol) to afford, after treatment with 1M HCl, the desired product (24.5 mg, 50%) as an orange-brown solid: $^1$H NMR (500 MHz, DMSO-d$_6$+D$_2$O) δ 8.91 (d, J=8.0 Hz, 1H), 8.44-8.32 (m, 2H), 8.08 (d, J=8.5 Hz, 1H), 7.48-7.27 (m, 2H), 3.98-3.95 (m, 3H), 3.46 (d, J=11.4 Hz, 5H), 3.28-3.03 (m, 5H), 2.38 (s, 2H), 2.27 (d, J=13.0 Hz, 1H), 2.15 (s, 1H), 2.10-1.96 (m, 2H), 1.90-1.69 (m, 3H), 1.33-1.23 (m, 6H); ESI MS m/z 532 [C$_{27}$H$_{34}$ClN$_3$O$_4$S+H]$^+$; HPLC 98.9% (AUC), t$_R$=10.49 min.

Example 245

2-Chloro-4-[4-{4-[1-(dimethylamino)ethyl]piperidin-1-yl}-3-(methylsulfonyl)quinolin-6-yl]-6-methoxyphenol

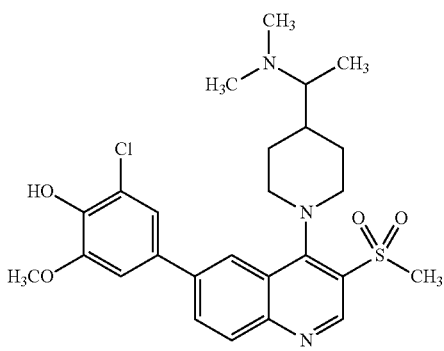 [SMILES: COc1cc(-c2ccc3ncc(S(C)(=O)=O)c(N4CCC(C(C)N(C)C)CC4)c3c2)cc(Cl)c1O]

Following general procedure D, 1-{1-[6-bromo-3-(methylsulfonyl)quinolin-4-yl]piperidin-4-yl}-N,N-dimethylethanamine (35 mg, 0.079 mmol) was reacted with 2-chloro-6-methoxy-4-(4,4,5,5-tetramethyl-1,3,2-dioxaborolan-2-yl) phenol (43 mg, 0.150 mmol) to afford the desired product (22.6 mg, 55%) as a yellow solid: $^1$H NMR (500 MHz, CD$_3$OD) δ 9.22 (s, 1H), 8.41 (s, 1H), 8.20-8.15 (m, 2H), 7.33 (d, J=2.1 Hz, 1H), 7.25 (d, J=2.1 Hz, 1H), 4.00 (s, 3H), 3.71 (t, J=11.8 Hz, 2H), 3.56 (d, J=11.9 Hz, 2H), 3.49-3.42 (m, 3H), 2.96 (s, 1H), 2.64 (s, 6H), 2.10-1.90 (m, 3H), 1.82-1.63 (m, 2H), 1.26 (d, J=6.7 Hz, 3H); ESI MS m/z 518 [C$_{26}$H$_{32}$ClN$_3$O$_4$S+H]$^+$; HPLC 98.8% (AUC), t$_R$=10.97 min.

Example 246

2-Chloro-4-[4-{4-[1-(dimethylamino)ethyl]piperidin-1-yl}-3-(methylsulfonyl)quinolin-6-yl]phenol

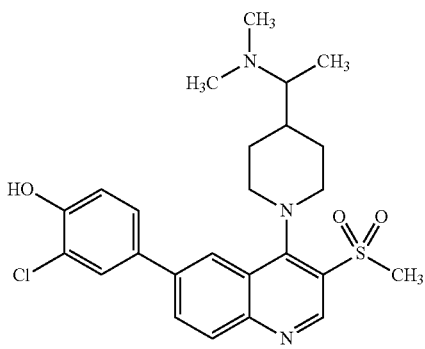 [SMILES: CC(C1CCN(c2c(S(C)(=O)=O)cnc3ccc(-c4ccc(O)c(Cl)c4)cc23)CC1)N(C)C]

Following general procedure D, 1-{1-[6-bromo-3-(methylsulfonyl)quinolin-4-yl]piperidin-4-yl}-N,N-dimethylethanamine (35 mg, 0.079 mmol) was reacted with 3-chloro-4-hydroxyphenylboronic acid (26 mg, 0.150 mmol) to afford the desired product (9.4 mg, 24%) as an off-white solid: $^1$H NMR (500 MHz, CD$_3$OD) δ 9.23 (s, 1H), 8.39 (d, J=1.5 Hz, 1H), 8.24-8.13 (m, 2H), 7.74 (d, J=2.2 Hz, 1H), 7.58 (dd, J=8.4, 2.3 Hz, 1H), 7.09 (d, J=8.4 Hz, 1H), 3.81-3.70 (m, 2H), 3.55 (s, 2H), 3.45 (s, 3H), 3.28-3.22 (m, 1H), 2.84 (s, 6H), 2.14 (d, J=7.9 Hz, 1H), 1.95 (d, J=11.0 Hz, 2H), 1.87-1.68 (m, 2H), 1.38 (d, J=6.7 Hz, 3H); ESI MS m/z 488 [C$_{25}$H$_{30}$ClN$_3$O$_3$S+H]$^+$; HPLC>99% (AUC), t$_R$=10.84 min.

Example 256

1-{4-[trans-4-Aminocyclohexylamino]-6-(3,5-dichloro-4-hydroxyphenyl)quinolin-3-yl}ethanone

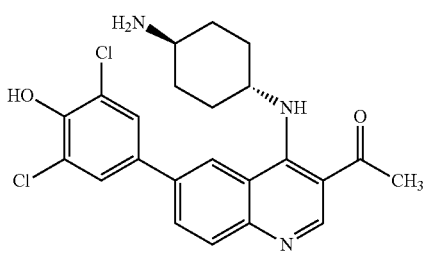

Following general procedure A-2, tert-butyl trans-4-[3-acetyl-6-(3,5-dichloro-4-hydroxyphenyl)quinolin-4-ylamino]cyclohexylcarbamate (46 mg, 0.085 mmol) was reacted with TFA (2 mL) to afford the desired product (19.4 mg, 51%) as an orange solid: $^1$H NMR (500 MHz, DMSO-$d_6$+$D_2O$) δ 8.92 (s, 1H), 8.20 (s, 1H), 8.04 (d, J=8.9 Hz, 1H), 7.89 (d, J=8.7 Hz, 1H), 7.63 (s, 2H), 4.09 (s, 1H), 3.20-3.11 (m, 1H), 2.68 (s, 3H), 2.26 (d, J=12.7 Hz, 2H), 2.08 (d, J=10.1 Hz, 2H), 1.69-1.58 (m, 2H), 1.57-1.46 (m, 2H); ESI MS m/z 444 $[C_{23}H_{23}Cl_2N_3O_2+H]^+$; HPLC>99% (AUC), $t_R$=8.70 min.

Example 258

1-{4-[trans-4-Aminocyclohexylamino]-6-(3,5-difluoro-4-hydroxyphenyl)quinolin-3-yl}ethanone

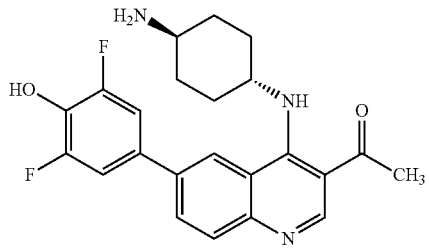 [SMILES: CC(=O)c1cnc2ccc(-c3cc(F)c(O)c(F)c3)cc2c1N[C@H]1CC[C@H](N)CC1]

Following general procedure A-2, tert-butyl trans-4-[3-acetyl-6-(3,5-difluoro-4-hydroxyphenyl)quinolin-4-ylamino]cyclohexylcarbamate (30 mg, 0.059 mmol) was reacted with TFA (2 mL) to afford the desired product (14.2 mg, 59%) as a yellow solid: $^1$H NMR (500 MHz, CD$_3$OD) δ 8.98 (s, 1H), 8.35 (d, J=1.9 Hz, 1H), 8.07-8.00 (m, 1H), 7.93 (d, J=8.7 Hz, 1H), 7.33 (dd, J=8.0, 1.6 Hz, 2H), 4.29 (s, 1H), 3.23 (s, 1H), 2.71 (s, 3H), 2.41 (d, J=12.2 Hz, 2H), 2.19 (d, J=12.1 Hz, 2H), 1.76-1.67 (m, 2H), 1.63-1.54 (m, 2H); ESI MS m/z 412 $[C_{23}H_{23}F_2N_3O_2+H]^+$; HPLC 98.7% (AUC), $t_R$=8.13 min.

Example 259

1-{4-[trans-4-Aminocyclohexylamino]-6-(3-chloro-4-hydroxy-5-methoxyphenyl)quinolin-3-yl}ethanone

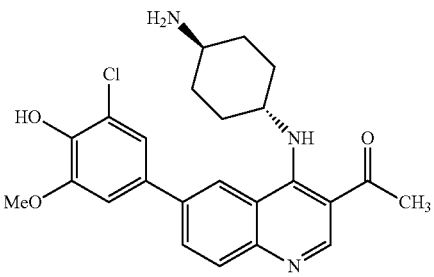 [SMILES: COc1cc(-c2ccc3ncc(C(C)=O)c(N[C@H]4CC[C@H](N)CC4)c3c2)cc(Cl)c1O]

Following general procedure A-2, tert-butyl trans-4-[3-acetyl-6-(3-chloro-4-hydroxy-5-methoxyphenyl)quinolin-4-ylamino]cyclohexylcarbamate (35 mg, 0.065 mmol) was reacted with TFA (2 mL) to afford the desired product (13.6 mg, 48%) as an orange solid: $^1$H NMR (500 MHz, CD$_3$OD) δ 8.95 (s, 1H), 8.32 (d, J=1.8 Hz, 1H), 8.04 (dd, J=8.7, 1.9 Hz, 1H), 7.92 (d, J=8.7 Hz, 1H), 7.27 (d, J=2.1 Hz, 1H), 7.22 (d, J=2.0 Hz, 1H), 4.23 (t, J=11.1 Hz, 1H), 3.99 (s, 3H), 3.24-3.16 (m, 1H), 2.70 (s, J=6.3 Hz, 3H), 2.41 (d, J=12.4 Hz, 2H), 2.18 (d, J=12.1 Hz, 2H), 1.80-1.66 (m, 2H), 1.61-1.50 (m, 2H); ESI MS m/z 440 $[C_{24}H_{26}ClN_3O_3+H]^+$; HPLC 97.6% (AUC), $t_R$=8.45 min.

Example 303

1-{6-(3-Chloro-4-hydroxy-5-methoxyphenyl)-4-[4-(diethylamino)cyclohexylamino]quinolin-3-yl}ethanone

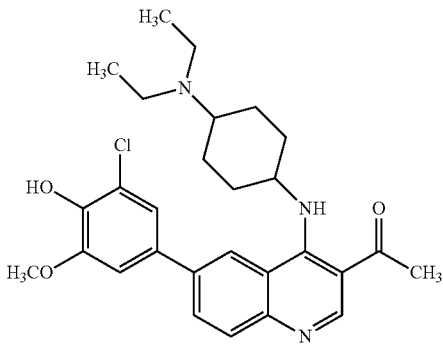 [SMILES: CCN(CC)C1CCC(Nc2c(C(C)=O)cnc3ccc(-c4cc(Cl)c(O)c(OC)c4)cc23)CC1]

Following general procedure D, 1-{6-bromo-4-[4-(diethylamino)cyclohexylamino]quinolin-3-yl}ethanone (42 mg, 0.100 mmol) was reacted with 2-chloro-6-methoxy-4-(4,4,5,5-tetramethyl-1,3,2-dioxaborolan-2-yl)phenol (57 mg, 0.200 mmol) to afford the desired product (21.5 mg, 43%) as an orange solid: $^1$H NMR (500 MHz, CD$_3$OD) δ 8.93 (s, 1H), 8.32 (d, J=1.8 Hz, 1H), 8.03 (dd, J=8.7, 1.9 Hz, 1H), 7.90 (d, J=8.7 Hz, 1H), 7.29 (d, J=2.1 Hz, 1H), 7.22 (d, J=2.1 Hz, 1H), 4.26 (s, 1H), 3.99 (s, 3H), 3.08 (q, J=7.2 Hz, 4H), 2.69 (s, 3H), 2.44 (s, 2H), 2.14 (s, 2H), 1.79-1.64 (m, 4H), 1.29 (t, J=7.2 Hz, 6H); ESI MS m/z 496 $[C_{28}H_{34}ClN_3O_3+H]^+$; HPLC>99% (AUC), $t_R$=10.50 min.

Example 335

1-{6-(3-Chloro-4-hydroxyphenyl)-4-[4-(diethylamino)cyclohexylamino]quinolin-3-yl}ethanone

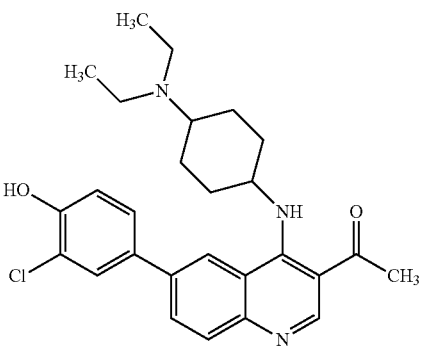 [SMILES: CCN(CC)C1CCC(Nc2c(C(C)=O)cnc3ccc(-c4ccc(O)c(Cl)c4)cc23)CC1]

Following general procedure D, 1-{6-bromo-4-[4-(diethylamino)cyclohexylamino]quinolin-3-yl}ethanone (30 mg, 0.072 mmol) was reacted with 3-chloro-4-hydroxyphenylboronic acid (34 mg, 0.200 mmol) to afford the desired product (19.7 mg, 59%) as a yellow-brown solid: $^1$H NMR (500 MHz, CD$_3$OD) δ 8.95 (s, 1H), 8.34 (d, J=1.8 Hz, 1H), 8.02 (dd, J=8.7, 1.9 Hz, 1H), 7.91 (d, J=8.7 Hz, 1H), 7.71 (d, J=2.3 Hz, 1H), 7.53 (dd, J=8.4, 2.3 Hz, 1H), 7.06 (d, J=8.4 Hz, 1H), 4.31 (s, 1H), 3.52-3.43 (m, 1H), 3.22 (q, J=7.2 Hz, 4H), 2.70 (s, 3H), 2.46 (d, J=12.3 Hz, 2H), 2.20 (d, J=11.9 Hz, 2H), 1.88-1.65 (m, 4H), 1.41-1.30 (m, 6H); ESI MS m/z 466 $[C_{27}H_{32}ClN_3O_2+H]^+$; HPLC 97.7% (AUC), $t_R$=10.44 min.

Example 305

1-[6-(3-chloro-4-hydroxy-5-methoxyphenyl)-4-{4-[(dimethylamino)methyl]piperidin-1-yl}quinolin-3-yl]ethanone

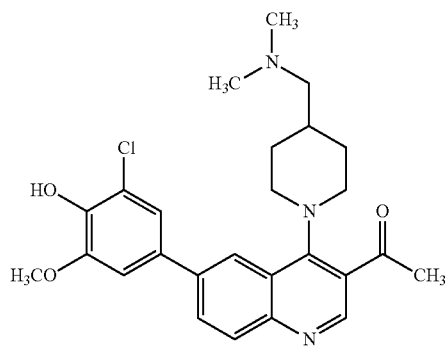 [SMILES: COc1cc(-c2ccc3ncc(C(C)=O)c(N4CCC(CN(C)C)CC4)c3c2)cc(Cl)c1O]

Following general procedure D, 1-(6-bromo-4-{4-[(dimethylamino)methyl]piperidin-1-yl}quinolin-3-yl)ethanone (17.7 mg, 0.045 mmol) was reacted with 2-chloro-6-methoxy-4-(4,4,5,5-tetramethyl-1,3,2-dioxaborolan-2-yl)phenol (28 mg, 0.100 mmol) to afford the desired product (10.4 mg, 49%) as an off-white solid: $^1$H NMR (500 MHz, CD$_3$OD) δ 8.76 (s, 1H), 8.32 (d, J=1.3 Hz, 1H), 8.07-7.97 (m, 2H), 7.31 (d, J=2.1 Hz, 1H), 7.25 (d, J=2.1 Hz, 1H), 4.00 (s, 3H), 3.48 (d, J=12.5 Hz, 2H), 3.16 (t, J=11.5 Hz, 2H), 2.68 (s, 3H), 2.43 (d, J=6.6 Hz, 2H), 2.36 (s, 6H), 2.01-1.85 (m, 3H), 1.67-1.54 (m, 2H); ESI MS m/z 468 $[C_{26}H_{30}ClN_3O_3+H]^+$; HPLC>99% (AUC), $t_R$=10.12 min.

Example 321

1-{6-(3-Chloro-4-hydroxy-5-methoxyphenyl)-4-[4-(pyrrolidin-1-ylmethyl)piperidin-1-yl]quinolin-3-yl}ethanone

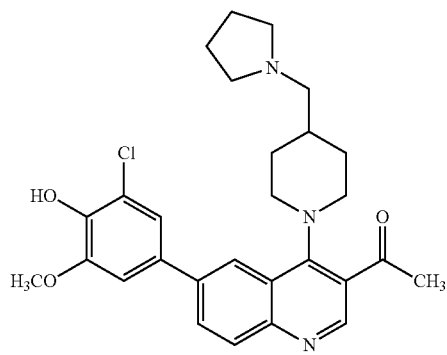 [SMILES: COc1cc(-c2ccc3ncc(C(C)=O)c(N4CCC(CN5CCCC5)CC4)c3c2)cc(Cl)c1O]

Following general procedure D, 1-{6-bromo-4-[4-(pyrrolidin-1-ylmethyl)piperidin-1-yl]quinolin-3-yl}ethanone (30 mg, 0.072 mmol) was reacted with 2-chloro-6-methoxy-4-(4,4,5,5-tetramethyl-1,3,2-dioxaborolan-2-yl)phenol (43 mg, 0.150 mmol) to afford the desired product (25.4 mg, 71%) as a yellow brown solid: $^1$H NMR (500 MHz, CD$_3$OD) δ 8.80 (s, 1H), 8.29 (s, 1H), 8.03 (s, 2H), 7.30 (d, J=2.1 Hz, 1H), 7.24 (d, J=2.0 Hz, 1H), 3.99 (s, 3H), 3.49 (d, J=12.9 Hz, 2H), 3.24-3.12 (m, 6H), 3.02 (d, J=5.5 Hz, 2H), 2.70 (s, 3H), 2.13-1.96 (m, 7H), 1.77-1.62 (m, 2H); ESI MS m/z 494 $[C_{28}H_{32}ClN_3O_3+H]^+$; HPLC>99% (AUC), $t_R$=10.45 min.

Example 336

1-{6-(3-Chloro-5-fluoro-4-hydroxyphenyl)-4-[4-(pyrrolidin-1-ylmethyl)piperidin-1-yl]quinolin-3-yl}ethanone

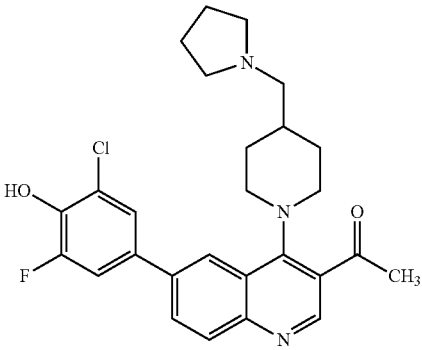 [SMILES: CC(=O)c1cnc2ccc(-c3cc(F)c(O)c(Cl)c3)cc2c1N1CCC(CN2CCCC2)CC1]

Following general procedure D, 1-{6-bromo-4-[4-(pyrrolidin-1-ylmethyl)piperidin-1-yl]quinolin-3-yl}ethanone (30 mg, 0.072 mmol) was reacted with 2-chloro-6-fluoro-4-(4,4,5,5-tetramethyl-1,3,2-dioxaborolan-2-yl)phenol (41 mg, 0.150 mmol) to afford the desired product (19.4 mg, 56%) as a yellow-brown solid: $^1$H NMR (500 MHz, CD$_3$OD) δ 8.81 (s, 1H), 8.26 (d, J=1.8 Hz, 1H), 8.07-7.96 (m, 2H), 7.56-7.48 (m, 1H), 7.44 (dd, J=11.6, 2.2 Hz, 1H), 3.48 (d, J=12.6 Hz, 2H), 3.38-3.33 (m, 4H), 3.23-3.13 (m, 4H), 2.71 (s, 3H), 2.16-2.06 (m, 5H), 2.00 (d, J=11.1 Hz, 2H), 1.78-1.65 (m, 2H); ESI MS m/z 482 $[C_{27}H_{29}ClN_3O_2+H]^+$; HPLC 98.9% (AUC), $t_R$=10.36 min.

Example 267

1-{4-[trans-4-Aminocyclohexylamino]-6-(3,5-dichloro-4-hydroxyphenyl)quinolin-3-yl}-3-methylbutan-1-one dihydrochloride

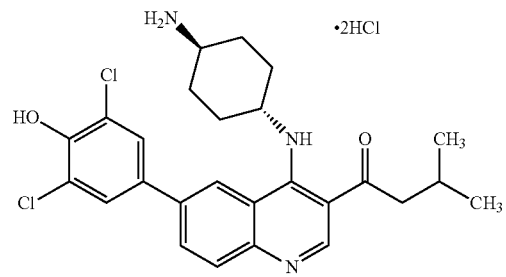 [SMILES: CC(C)CC(=O)c1cnc2ccc(-c3cc(Cl)c(O)c(Cl)c3)cc2c1N[C@H]1CC[C@H](N)CC1]

Following general procedure D, tert-butyl trans-4-[6-(3,5-dichloro-4-hydroxyphenyl)-3-(3-methylbutanoyl)quinolin- 4-ylamino]cyclohexyl carbamate (36 mg, 0.061 mmol) was reacted with TFA (2 mL) to afford the desired product (10.4 mg, 35%) as a white solid: $^1$H NMR (500 MHz, CD$_3$OD) δ 9.16 (s, 1H), 8.46 (s, 1H), 8.29 (d, J=8.7 Hz, 1H), 8.00 (d, J=8.8 Hz, 1H), 7.74 (s, 2H), 4.56 (s, 1H), 3.27 (s, 1H), 3.03 (d, J=6.8 Hz, 2H), 2.51 (s, 2H), 2.36-2.21 (m, 3H), 1.96-1.83 (m, 2H), 1.67 (d, J=12.5 Hz, 2H), 1.05 (d, J=6.6 Hz, 6H); ESI MS m/z 486 [C$_{26}$H$_{29}$Cl$_2$N$_3$O$_2$+H]$^+$; HPLC 98.2% (AUC), t$_R$=10.02 min.

Example 348

1-{6-(3-Chloro-4-hydroxy-5-methoxyphenyl)-4-[trans-4-(dimethylamino)cyclohexylamino]quinolin-3-yl}-3-methylbutan-1-one

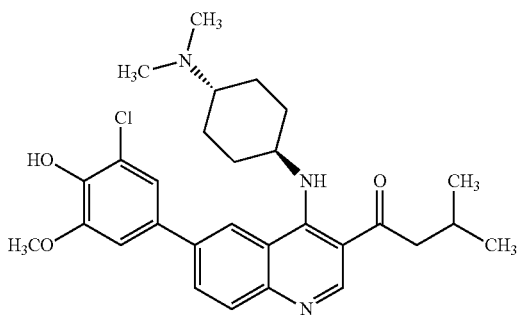 [SMILES: COc1cc(-c2ccc3ncc(C(=O)CC(C)C)c(N[C@H]4CC[C@H](N(C)C)CC4)c3c2)cc(Cl)c1O]

Following general procedure D, 1-{6-bromo-4-[trans-4-(dimethylamino)cyclohexylamino]quinolin-3-yl}-3-methylbutan-1-one (13 mg, 0.030 mmol) was reacted with 2-chloro-6-methoxy-4-(4,4,5,5-tetramethyl-1,3,2-dioxaborolan-2-yl)phenol (21 mg, 0.075 mmol) to afford the desired product (8.8 mg, 58%) as a yellow solid: NMR (500 MHz, CD$_3$OD) δ 8.94 (s, 1H), 8.35 (d, J=1.8 Hz, 1H), 8.03 (dd, J=8.7, 1.9 Hz, 1H), 7.90 (d, J=8.7 Hz, 1H), 7.29 (d, J=2.1 Hz, 1H), 7.22 (d, J=2.1 Hz, 1H), 4.24 (t, J=10.8 Hz, 1H), 3.99 (s, 3H), 2.94 (d, J=7.0 Hz, 2H), 2.82 (s, 1H), 2.53 (s, 6H), 2.42 (d, J=12.0 Hz, 2H), 2.33-2.21 (m, 1H), 2.14 (d, J=12.0 Hz, 2H), 1.72-1.53 (m, 4H), 1.03 (d, J=6.7 Hz, 6H); ESI MS m/z 510 [C$_{29}$H$_{36}$ClN$_3$O$_3$+H]$^+$; HPLC>99% (AUC), t$_R$=11.38 min.

Example 284

{4-[trans-4-aminocyclohexylamino]-6-(3-chloro-4-hydroxy-5-methoxyphenyl)-7-fluoroquinolin-3-yl}(cyclopropyl)methanone

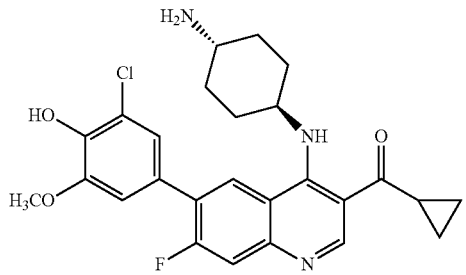 [SMILES: COc1cc(-c2cc3c(N[C@H]4CC[C@H](N)CC4)c(C(=O)C4CC4)cnc3cc2F)cc(Cl)c1O]

Following general procedure A-2, tert-butyl trans-4-[6-(3-chloro-4-hydroxy-5-methoxyphenyl)-3-(cyclopropanecarbonyl)-7-fluoroquinolin-4-ylamino]cyclohexylcarbamate (53 mg, 0.091 mmol) was reacted with TFA (2 mL) to afford the desired product (30 mg, 48%) as a light yellow solid: $^1$H NMR (300 MHz, CD$_3$OD) δ 9.23 (s, 1H), 8.35 (d, J=7.8 Hz, 1H), 7.65 (d, J=11.2 Hz, 1H), 7.21 (d, J=10.6 Hz, 2H), 4.20 (s, 1H), 3.95 (s, 3H), 2.84 (s, 1H), 2.39 (d, J=12.4 Hz, 2H), 2.18 (d, J=11.5 Hz, 2H), 1.83-1.64 (m, 2H), 1.62-1.43 (m, 2H), 1.31-1.09 (m, 4H); ESI MS m/z 484 [C$_{26}$H$_{27}$ClFN$_3$O$_3$+H]$^+$; HPLC 98.1% (AUC), t$_R$=8.84 min.

Example 294

Cyclopropyl{6-(3,5-difluoro-4-hydroxyphenyl)-4-[trans-4-(dimethylamino)cyclohexylamino]-7-fluoroquinolin-3-yl}methanone

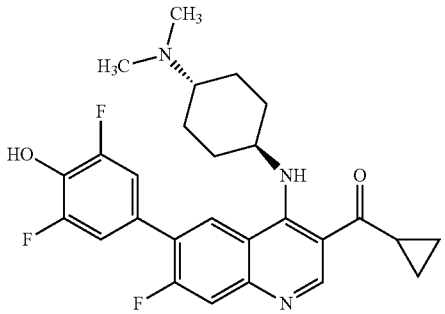 [SMILES: CN(C)[C@H]1CC[C@H](Nc2c(C(=O)C3CC3)cnc3cc(F)c(-c4cc(F)c(O)c(F)c4)cc23)CC1]

Following general procedure F, {6-bromo-4-[trans-4-(dimethylamino)cyclohexylamino]-7-fluoroquinolin-3-yl}(cyclopropyl)methanone (43 mg, 0.099 mmol) was reacted with 2,6-difluoro-4-(4,4,5,5-tetramethyl-1,3,2-dioxaborolan-2-yl)phenol (38 mg, 0.149 mmol) to afford the desired product (14 mg, 29%) as a light yellow solid: NMR (300 MHz, CD$_3$OD) δ 9.27 (s, 1H), 8.37 (d, J=7.8 Hz, 1H), 7.68 (d, J=11.1 Hz, 1H), 7.33 (d, J=7.8 Hz, 2H), 4.31 (s, 1H), 3.47-3.35 (m, 1H), 3.27 (s, J=6.8 Hz, 1H), 2.88 (s, 5H), 2.87-2.75 (m, 1H), 2.43 (s, 2H), 2.26 (s, 2H), 1.88-1.64 (m, 4H), 1.35-1.13 (m, 4H), ESI MS m/z 484 [C$_{27}$H$_{28}$F$_3$N$_3$O$_2$+H]$^+$; HPLC 98.3% (AUC), t$_R$=8.83 min.

Example 295

{6-(3-Chloro-5-fluoro-4-hydroxyphenyl)-4-[trans-4-(dimethylamino)cyclohexylamino]-7-fluoroquinolin-3-yl}(cyclopropyl)methanone

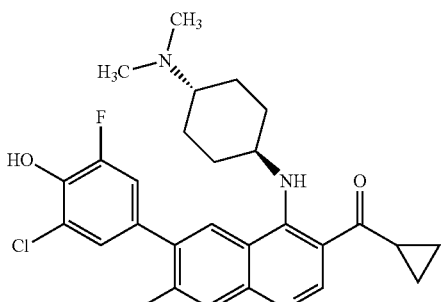

Following general procedure F, {6-bromo-4-[trans-4-(dimethylamino)cyclohexylamino]-7-fluoroquinolin-3-yl}(cyclopropyl)methanone (38 mg, 0.087 mmol) was reacted with 2-chloro-6-fluoro-4-(4,4,5,5-tetramethyl-1,3,2-dioxaborolan-2-yl)phenol (35 mg, 0.131 mmol) to afford the desired product (39 mg, 90%) as a green solid: $^1$H NMR (300 MHz, CD$_3$OD) δ 9.19 (s, 1H), 8.29 (d, J=8.1 Hz, 1H), 7.60 (d, J=11.8 Hz, 1H), 7.49 (s, 1H), 7.42 (dt, J=11.6, 2.0 Hz, 1H), 4.18 (s, 1H), 2.86 (s, 6H), 2.85-2.78 (m, 1H), 2.42 (s, 2H), 2.19 (s, 2H), 1.76-1.62 (m, 4H), 1.22-1.07 (m, 5H); ESI MS m/z 500 [C$_{27}$H$_{28}$ClF$_2$N$_3$O$_2$+H]$^+$; HPLC 97.4% (AUC), t$_R$=9.21 min.

Example 356

6-(3-Chloro-4-hydroxy-5-methoxyphenyl)-4-{4-[(dimethylamino)methyl]phenyl}quinolin-3-yl](cyclopropyl)methanone

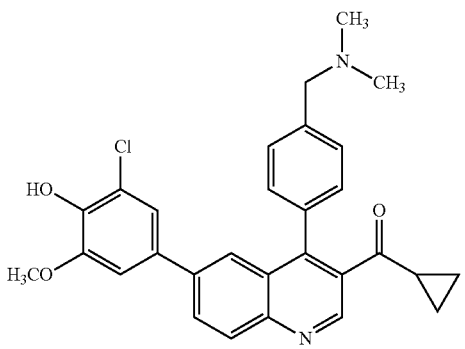 [SMILES: COc1cc(-c2ccc3ncc(C(=O)C4CC4)c(-c4ccc(CN(C)C)cc4)c3c2)cc(Cl)c1O]

Following general procedure F, [4-chloro-6-(3-chloro-4-hydroxy-5-methoxyphenyl)quinolin-3-yl](cyclopropyl)methanone (18 mg, 0.046 mmol) was reacted with 2-chloro-6-methoxy-4-(4,4,5,5-tetramethyl-1,3,2-dioxaborolan-2-yl)phenol (20 mg, 0.067 mmol) to afford the desired product (10 mg, 45%) as a light brown-yellow solid: $^1$H NMR (300 MHz, CD$_3$OD+Acetic Acid-d$_6$) δ 8.99 (s, 1H), 8.26-8.10 (m, 2H), 7.75 (d, J=7.6 Hz, 3H), 7.62 (d, J=8.1 Hz, 2H), 7.08 (dd, J=14.8, 2.0 Hz, 2H), 4.41 (s, 2H), 3.91 (s, J=10.1 Hz, 3H), 2.89 (s, 6H), 2.11-2.00 (m, 1H), 1.08-0.97 (m, 2H), 0.83-0.73 (m, 2H); ESI MS m/z 487 [C$_{29}$H$_{27}$ClN$_2$O$_3$+H]$^+$; HPLC 96.5% (AUC), t$_R$=12.01 min.

Example 715

1-(6-(3,5-dichloro-4-hydroxyphenyl)-4-((trans-4-((dimethylamino)methyl)cyclohexyl)amino)quinolin-3-yl)propan-1-one

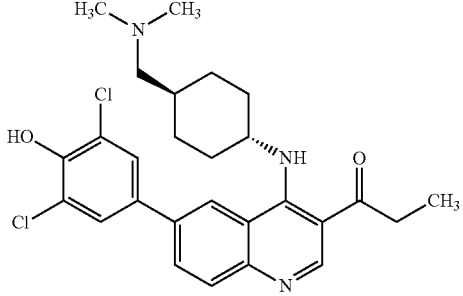 [SMILES: CCC(=O)c1cnc2ccc(-c3cc(Cl)c(O)c(Cl)c3)cc2c1N[C@H]1CC[C@H](CN(C)C)CC1]

Following general procedure M, 1-(6-bromo-4-((trans-4-((dimethylamino)methyl)cyclohexyl)amino)quinolin-3-yl)propan-1-one (125 mg, 0.30 mmol) was reacted with 2,6-dichloro-4-(4,4,5,5-tetramethyl-1,3,2-dioxaborolan-2-yl)phenol (95 mg, 0.33 mmol) to afford the desired product (53 mg, 35%) as a yellow solid. NMR (500 MHz, DMSO-d$_6$) δ 10.50 (d, J=8.0 Hz, 1H), 8.96 (s, 1H), 8.31 (d, J=2.1 Hz, 1H), 8.04 (dd, J=8.7, 1.9 Hz, 1H), 7.85 (d, J=8.7 Hz, 1H), 7.72 (s, 2H), 4.14-4.06 (m, 1H), 3.13 (q, J=7.2 Hz, 2H), 2.23-2.15 (m, 2H), 2.18 (s, 6H), 2.15-2.10 (m, 1H), 1.88 (d, J=12.9 Hz, 2H), 1.61-1.43 (m, 3H), 1.17-1.01 (m, 5H). ESI MS m/z 500 [C$_{27}$H$_{31}$Cl$_2$N$_3$O$_2$+H]$^+$; HPLC>99% (AUC), t$_R$=8.70 min.

Example 716

1-(6-(3,5-dichloro-4-hydroxyphenyl)-4-((trans-4-((dimethylamino)methyl)cyclohexyl)amino)quinolin-3-yl)propan-1-one dihydrochloride

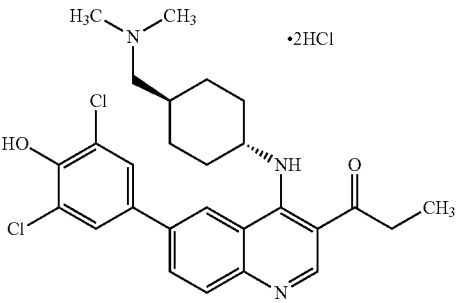 [SMILES: CCC(=O)c1cnc2ccc(-c3cc(Cl)c(O)c(Cl)c3)cc2c1N[C@H]1CC[C@H](CN(C)C)CC1]

To a solution of 1-(6-(3,5-dichloro-4-hydroxyphenyl)-4-((trans-4-((dimethylamino)methyl)cyclohexyl)amino)quinolin-3-yl)propan-1-one (3.75 g, 7.49 mmol) in methanol (150 mL) and dichloromethane (150 mL) was added HCl (1.25 M in methanol, 30 mL, 37.5 mmol). The solution was allowed to stir for 5 min, then concentrated under reduced pressure. The resultant solid was triturated with dichloromethane (25 mL), then dried under vacuum at 85° C. to afford the desired product (4.1 g, 95%) as a yellow solid. $^1$H NMR (500 MHz, MeOD) δ 9.12 (br s, 1H), 8.47 (br s, 1H), 8.26 (dd, J=8.7, 1.8 Hz, 1H), 7.99 (d, J=8.8 Hz, 1H), 7.73 (s, 2H), 4.51 (br s, 1H), 3.18 (q, J=7.2 Hz, 2H), 3.09 (d, J=6.5 Hz, 2H), 2.93 (s, 6H), 2.45 (d, J=12.3 Hz, 2H), 2.11-2.02 (m, 3H), 1.88-1.76 (m, 2H), 1.40-1.30 (m, 2H), 1.24 (t, J=7.1 Hz, 3H). APCI MS m/z 500 [C$_{27}$H$_{31}$C$_{12}$N$_3$O$_2$+H]$^+$; HPLC>99% (AUC), t$_R$=8.99 min.

Example 714

1-(6-(3-chloro-5-fluoro-4-hydroxyphenyl)-4-((trans-4-((dimethylamino)methyl)cyclohexyl)amino)quinolin-3-yl)propan-1-one

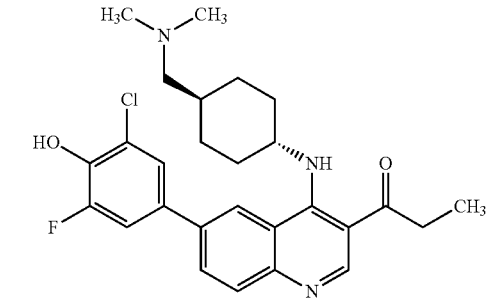 [SMILES: CCC(=O)c1cnc2ccc(-c3cc(F)c(O)c(Cl)c3)cc2c1N[C@H]1CC[C@H](CN(C)C)CC1]

Following general procedure M, 1-(6-bromo-4-((trans-4-((dimethylamino)methyl)cyclohexyl)amino)quinolin-3-yl)propan-1-one (125 mg, 0.30 mmol) was reacted with 2-chloro-6-fluoro-4-(4,4,5,5-tetramethyl-1,3,2-dioxaborolan-2-yl)phenol (90 mg, 0.33 mmol) to afford the desired product (41 mg, 28%) as a yellow solid. $^1$H NMR (500 MHz, DMSO-d$_6$) δ 10.46 (d, J=8.0 Hz, 1H), 8.96 (s, 1H), 8.33 (d, J=2.2 Hz, 1H), 8.04 (dd, J=8.7, 1.9 Hz, 1H), 7.86 (d, J=8.7 Hz, 1H), 7.64-7.57 (m, 2H), 4.13-4.07 (m, 1H), 3.13 (q, J=7.2 Hz, 2H), 2.22-2.15 (m, 2H), 2.13 (s, 6H), 1.87 (d, J=12.9 Hz, 2H), 1.57-1.42 (m, 3H), 1.16-0.99 (m, 5H). ESI MS m/z 484 [C$_{27}$H$_{31}$ClFN$_3$O$_2$+H]$^+$; HPLC 98.5% (AUC), t$_R$=8.36 min.

Example 754

1-(6-(3,5-dichloro-4-hydroxyphenyl)-4-((trans-4-(dimethylamino)cyclohexyl)amino)quinolin-3-yl)propan-1-one

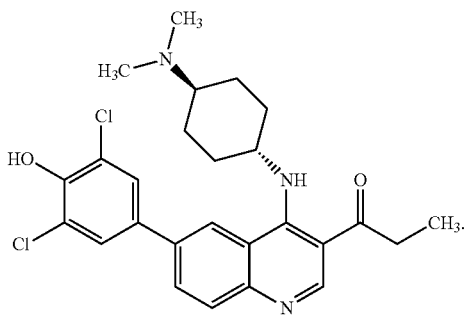 [SMILES: CCC(=O)c1cnc2ccc(-c3cc(Cl)c(O)c(Cl)c3)cc2c1N[C@H]1CC[C@H](N(C)C)CC1]

Following general procedure M, 1-(6-bromo-4-((trans-4-(dimethylamino)cyclohexyl)amino)quinolin-3-yl)propan-1-one (125 mg, 0.31 mmol) was reacted with 2,6-dichloro-4-(4,4,5,5-tetramethyl-1,3,2-dioxaborolan-2-yl)phenol (98 mg, 0.34 mmol) to afford the desired product (74 mg, 49%) as a yellow solid. $^1$H NMR (500 MHz, DMSO d6) δ 10.58 (d, J=7.9 Hz, 1H), 8.96 (s, 1H), 8.30 (d, J=2.1 Hz, 1H), 8.03 (dd, J=8.7, 1.9 Hz, 1H), 7.84 (d, J=8.7 Hz, 1H), 7.771 (s, 2H), 4.19-4.15 (br s, 1H), 3.13 (q, J=7.2 Hz, 2H), 2.56-2.51 (m, 1H), 2.32 (s, 6H), 2.26-2.22 (m, 2H), 1.96-1.89 (m, 2H), 1.56-1.47 (m, 4H), 1.14 (t, J=7.2 Hz, 3H). APCI MS m/z 486 [C$_{26}$H$_{29}$Cl$_2$N$_3$O$_2$+H]$^+$; HPLC>99% (AUC), t$_R$=8.28 min.

Example 757

1-(6-(3-chloro-5-fluoro-4-hydroxyphenyl)-4-((trans-4-(dimethylamino)cyclohexyl)amino)quinolin-3-yl)propan-1-one

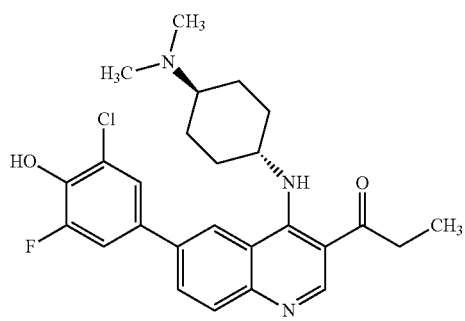 [SMILES: CCC(=O)c1cnc2ccc(-c3cc(F)c(O)c(Cl)c3)cc2c1N[C@H]1CC[C@H](N(C)C)CC1]

Following general procedure M, 1-(6-bromo-4-((trans-4-(dimethylamino)cyclohexyl)amino)quinolin-3-yl)propan-1-one (125 mg, 0.31 mmol) was reacted with 2-chloro-6-fluoro-4-(4,4,5,5-tetramethyl-1,3,2-dioxaborolan-2-yl)phenol (93 mg, 0.34 mmol) to afford the desired product (81 mg, 56%) as a yellow solid. $^1$H NMR (500 MHz, DMSO-d$_6$) δ 10.56 (d, J=8.0 Hz, 1H), 8.97 (s, 1H), 8.34 (d, J=2.1 Hz, 1H), 8.04 (dd, J=8.7, 1.9 Hz, 1H), 7.85 (d, J=8.7 Hz, 1H), 7.65-7.58 (m, 2H), 4.18-4.12 (m, 1H), 3.13 (q, J=7.2 Hz, 2H), 2.39-2.32 (m, 1H), 2.27-2.19 (m, 8H), 1.93-1.86 (m, 2H), 1.56-1.39 (m, 4H), 1.12 (t, J=7.2 Hz, 3H). ESI MS m/z 470 [C$_{26}$H$_{29}$ClFN$_3$O$_2$+H]$^+$; HPLC>99% (AUC), t$_R$=7.97 min.

Example 771

1-(6-(3,5-dichloro-4-hydroxyphenyl)-4-((4-((dimethylamino)methyl)phenyl)amino)quinolin-3-yl)propan-1-one

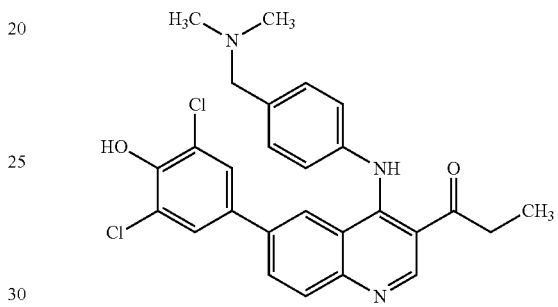

Following general procedure M, 1-(6-bromo-4-((4-((dimethylamino)methyl)phenyl)amino)quinolin-3-yl)propan-1-one (125 mg, 0.30 mmol) was reacted with 2,6-dichloro-4-(4,4,5,5-tetramethyl-1,3,2-dioxaborolan-2-yl)phenol (96 mg, 0.33 mmol) to afford the desired product (113 mg, 76%) as a yellow solid. $^1$H NMR (500 MHz, DMSO-d$_6$) δ 11.98 (s, 1H), 9.01 (s, 1H), 8.09-7.88 (m, 3H), 7.36 (s, 2H), 7.33-7.28 (m, 2H), 7.17-7.08 (m, 2H), 3.47 (s, 2H), 3.08 (q, J=7.1 Hz, 2H), 2.16 (s, 6H), 0.98 (t, J=7.1 Hz, 3H).

Example 770

1-(6-(3-chloro-5-fluoro-4-hydroxyphenyl)-4-((4-((dimethylamino)methyl)phenyl)amino)quinolin-3-yl)propan-1-one

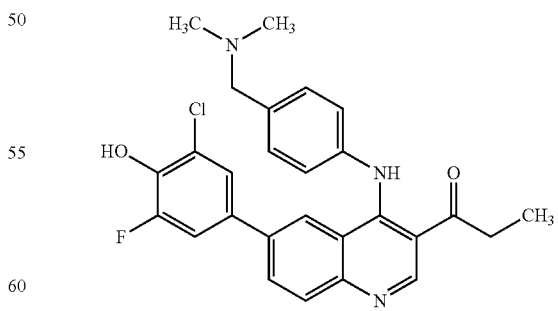

Following general procedure M, 1-(6-bromo-4-((4-((dimethylamino)methyl)phenyl)amino)quinolin-3-yl)propan-1-one (125 mg, 0.30 mmol) was reacted with 2-chloro-6-fluoro-4-(4,4,5,5-tetramethyl-1,3,2-dioxaborolan-2-yl)phenol (91 mg, 0.33 mmol) to afford the desired product (89 mg, 62%) as a yellow solid. $^1$H NMR (300 MHz, DMSO-d$_6$) δ 11.00 (s, 1H), 9.02 (s, 1H), 8.09-7.88 (m, 3H), 7.35-7.18 (m, 4H), 7.16-7.09 (m, 2H), 3.42 (s, 2H), 3.09 (q, J=7.1 Hz, 2H), 2.14 (s, 6H), 0.98 (t, J=7.1 Hz, 3H). APCI MS m/z 478 [C$_{27}$H$_{25}$ClFN$_3$O$_2$+H]$^+$; HPLC>99% (AUC), t$_R$=8.10 min.

Example 939

1-(4-((1R,4R)-4-aminocyclohexylamino)-6-(3,5-dichloro-4-hydroxyphenyl)quinolin-3-yl)ethanone

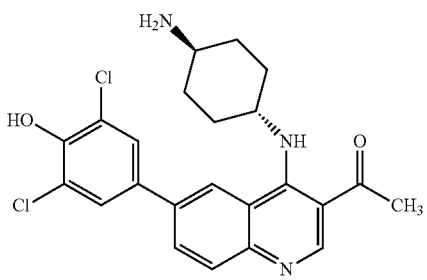 [SMILES: CC(=O)c1cnc2ccc(-c3cc(Cl)c(O)c(Cl)c3)cc2c1N[C@H]1CC[C@H](N)CC1]

Following general procedure A, 1 tert-butyl (1R,4R)-4-(3-acetyl-6-(3,5-dichloro-4-hydroxy phenyl)quinolin-4-ylamino)cyclohexylcarbamate (4.5 g, 8.3 mmol) was treated with a solution of 3N HCl to afford desired product (3.6 g, 99%) as a pale yellow solid: $^1$H NMR (500 MHz, D$_2$O) δ 8.93 (s, 1H), 7.89 (d, J=8.6 Hz, 1H), 7.76 (d, J=8.7 Hz, 1H), 7.64 (s, 1H), 7.06 (s, 2H), 4.08 (m, 1H), 3.31 (t, J=12.0 Hz, 1H), 2.18 (d, J=12.0 Hz, 4H), 1.80 (q, J=12.1 Hz, 2H), 1.50 (q, J=12.1 Hz, 2H); APCI MS m/z 444 [C$_{23}$H$_{23}$Cl$_2$N$_3$O$_2$+H]$^+$; HPLC 98.3% (AUC), t$_R$=6.93 min.

Example 264

(6-(3-chloro-5-fluoro-4-hydroxyphenyl)-4-((1R,4R)-4-(dimethylamino)cyclohexylamino)quinolin-3-yl)(cyclopropyl)methanone

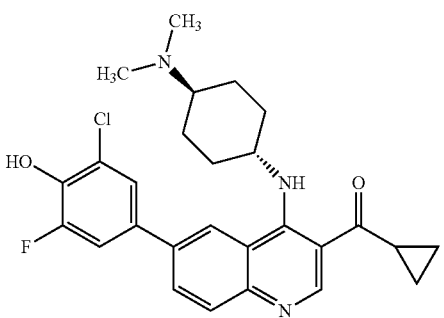 [SMILES: CN(C)[C@H]1CC[C@H](Nc2c(C(=O)C3CC3)cnc3ccc(-c4cc(F)c(O)c(Cl)c4)cc23)CC1]

Following general procedure F, (6-bromo-4-((1R,4R)-4-(dimethylamino)cyclohexylamino)quinolin-3-yl)(cyclopropyl)methanone (5.0 g, 12 mmol) was reacted with 2-chloro-6-fluoro-4-(4,4,5,5-tetramethyl-1,3,2-dioxaborolan-2-yl)phenol (3.9 g, 14.4 mmol) to afford the desired product (3.0 g, 52%) as a yellow solid: $^1$H NMR (300 MHz, DMSO) δ 9.84 (s, 1H), 9.06 (s, 1H), 8.38 (s, 1H), 8.04 (dd, J=8.8, 1.8 Hz, 1H), 7.86 (d, J=8.8 Hz, 1H), 7.61 (m, 2H), 3.99 (m, 1H), 2.90 (dt, J=8.0, 3.0 Hz, 1H), 2.35 (m, 1H), 2.23 (s, 5H), 2.16 (d, J=12.6 Hz, 4H), 1.89 (d, J=11.2 Hz, 2H), 1.43 (dt, J=22.4, 12.6 Hz, 4H), 1.06 (m, 4H); ESI MS m/z 482 [C$_{27}$H$_{29}$ClFN$_3$O$_2$+H]$^+$; HPLC>99.0% (AUC), t$_R$=4.85 min.

Example 936

(4-((1R,4R)-4-aminocyclohexylamino)-6-(3-chloro-5-fluoro-4-hydroxyphenyl)quinolin-3-yl)(cyclopropyl)methanone

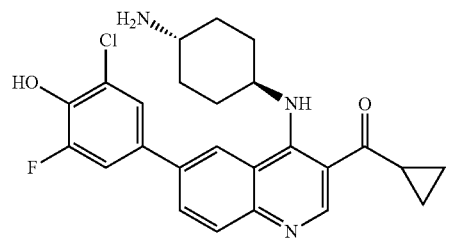 [SMILES: N[C@H]1CC[C@H](Nc2c(C(=O)C3CC3)cnc3ccc(-c4cc(F)c(O)c(Cl)c4)cc23)CC1]

(tert-butyl (1R,4R)-4-(6-(3-chloro-5-fluoro-4-hydroxyphenyl)-3-(cyclopropanecarbonyl)quinolin-4-ylamino)cyclohexylcarbamate (5.1 g, 9.2 mmol) was treated with a solution of HCl in dioxane (275 mL, 4N). The mixture was stirred for 8 h at ambient temperature, producing a off white precipitate. The precipitate was collected by vacuum filtration and purified by titration of dichloromethane in a solution of methanol to afford desired product (3.01 g, 62%) as an off-white solid: $^1$H NMR (300 MHz, D$_2$O) δ 9.03 (s, 1H), 7.90 (d, J=8.8 Hz, 1H), 7.78 (s, 1H), 7.71 (d, J=8.8 Hz, 1H), 7.12 (d, J=11.7 Hz, 1H), 7.05 (s, 1H), 4.04 (s, 1H), 3.27 (t, J=12.0 Hz, 1H), 2.62 (p, J=6.1 Hz, 1H), 2.14 (d, J=11.9 Hz, 4H), 1.71 (q, J=12.3 Hz, 2H), 1.47 (q, J=12.1 Hz, 2H), 1.20 (m, 4H); APCI MS m/z 454 [C$_{25}$H$_{25}$ClFN$_3$O$_2$+H]$^+$; HPLC 97.4% (AUC), t$_R$=10.64 min.

Example 942

1-(6-(3,5-dichloro-4-hydroxyphenyl)-4-(4-((dimethylamino)methyl)phenylamino)quinolin-3-yl)ethanone

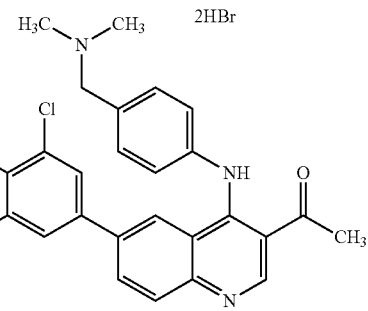

Following general procedure F, 1-(6-bromo-4-(4-((dimethylamino)methyl)phenylamino)quinolin-3-yl)ethanone (2.0 g, 5.09 mmol) was reacted with 2,6-dichloro-4-(4,4,5,5-tetramethyl-1,3,2-dioxaborolan-2-yl)phenol (2.2 g, 7.6 mmol) to obtain the free base. The purified product was suspended in dichloromethane/methanol (1:1, 40 mL) and HBr gas was bubbled through the suspension until a solution formed. The solution was concentrated to dryness and the resultant solid was triturated with diethyl ether. The mixture was filtered, washed with diethyl ether, and dried to obtain desired product (3.0 g, 94% over two steps) as a yellow solid: $^1$H NMR (300 MHz, DMSO) δ 11.93 (s, 1H), 10.59 (s, 1H), 9.81 (s, 1H), 9.24 (s, 1H), 8.37 (m, 2H), 8.11 (d, J=8.8 Hz, 1H), 7.66 (d, J=8.5 Hz, 2H), 7.56 (s, 2H), 7.51 (d, J=8.5 Hz, 2H), 4.39 (d, J=4.0 Hz, 2H), 2.74 (d, J=4.0 Hz, 6H), 2.54 (s, 3H). APCI MS m/z 480 [$C_{26}H_{23}Cl_2N_3O_2$+H]$^+$; HPLC>99% (AUC), $t_R$=4.79 min.

Example 941 cyclopropyl(6-(3,5-dichloro-4-hydroxyphenyl)-4-((1R,4R)-4-(dimethylamino)cyclohexylamino)quinolin-3-yl)methanone

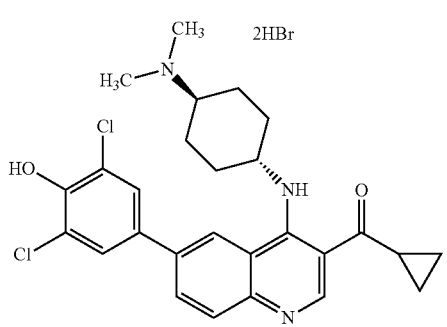 [SMILES: CN(C)[C@H]1CC[C@H](Nc2c(C(=O)C3CC3)cnc3ccc(-c4cc(Cl)c(O)c(Cl)c4)cc23)CC1]

Following general procedure F, (6-bromo-4-((1R,4R)-4-(dimethylamino)cyclohexylamino)quinolin-3-yl)(cyclopropyl)methanone (3.7 g, 8.9 mmol) was reacted with 2,6-dichloro-4-(4,4,5,5-tetramethyl-1,3,2-dioxaborolan-2-yl)phenol (3.8 g, 13.3 mmol) to obtain the free base. The purified product was suspended in dichloromethane/methanol (1:1, 40 mL) and HBr gas was bubbled through the suspension until a solution formed. The solution was concentrated to dryness and the resultant solid was triturated with diethyl ether. The mixture was filtered, washed with diethyl ether, and dried to obtain desired product (3.1 g, 53% over two steps) as a yellow solid: $^1$H NMR (300 MHz, MeOD) δ 9.34 (s, 1H), 8.48 (s, 1H), 8.27 (dd, J=8.8, 1.8 Hz, 1H), 8.01 (d, J=8.8 Hz, 1H), 7.76 (s, 2H), 4.60 (s, 1H), 3.52 (s, 1H), 2.93 (s, 6H), 2.86 (m, 1H), 2.52 (s, 2H), 2.34 (s, 2H), 1.89 (m, 4H), 1.26 (m, 3H); APCI MS m/z 498 [$C_{27}H_{29}Cl_2N_3O_2$+H]$^+$; HPLC 98.9% (AUC), $t_R$=5.08 min.

Example 420

2,6-dichloro-4-(4-((1R,4R)-4-((dimethylamino)methyl)cyclohexylamino)-3-(methylsulfonyl)quinolin-6-yl)phenol

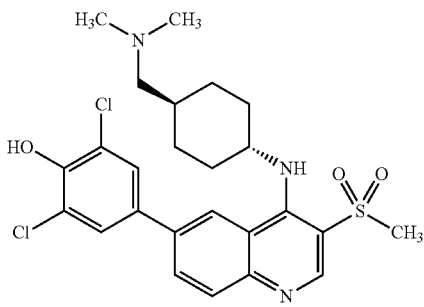 [SMILES: CN(C)C[C@H]1CC[C@H](Nc2c(S(C)(=O)=O)cnc3ccc(-c4cc(Cl)c(O)c(Cl)c4)cc23)CC1]

Following general procedure F, 6-bromo-N-((1R,4R)-4-((dimethylamino)methyl)cyclohexyl)-3-(methylsulfonyl)quinolin-4-amine (5.6 mg, 13 mmol) was reacted with 2,6-dichloro-4-(4,4,5,5-tetramethyl-1,3,2-dioxaborolan-2-yl)phenol (4.4 g, 15 mmol) to obtain the desired product (5.3 g, 77%) as a tan solid: $^1$H NMR (300 MHz, MeOD) δ 8.76 (s, 1H), 8.26 (d, J=1.8 Hz, 1H), 8.04 (dd, J=8.8, 1.8 Hz, 1H), 7.94 (d, J=8.8 Hz, 1H), 7.64 (s, 2H), 4.15 (tt, J=11.4, 3.9 Hz, 1H), 3.23 (s, 3H), 2.98 (d, J=6.6 Hz, 2H), 2.85 (s, 6H), 2.35 (d, J=12.6 Hz, 2H), 1.95 (m, 3H), 1.66 (q, J=12.5 Hz, 2H), 1.25 (q, J=12.5 Hz, 2H); ESI MS m/z 522 [$C_{25}H_{29}Cl_2N_3O_3S$+H]$^+$; HPLC 99.8% (AUC), $t_R$=5.61 min.

Example 937

1-(4-((1R,4R)-4-aminocyclohexylamino)-6-(3-chloro-5-fluoro-4-hydroxyphenyl)quinolin-3-yl)-2-methylpropan-1-one

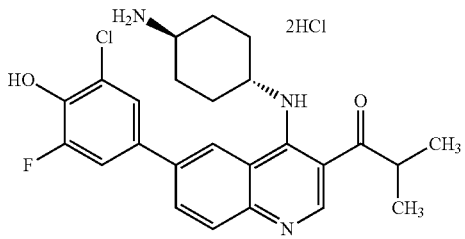 [SMILES: CC(C)C(=O)c1cnc2ccc(-c3cc(F)c(O)c(Cl)c3)cc2c1N[C@H]1CC[C@H](N)CC1]

tert-butyl (1r,4r)-4-(6-(3-chloro-5-fluoro-4-hydroxyphenyl)-3-isobutyrylquinolin-4-yl-amino)cyclohexylcarbamate (5.1 g, 9.2 mmol) was treated with a solution of HCl in dioxane (75 mL, 4 N). The mixture was stirred for 20 h at ambient temperature, producing a off white precipitate. The precipitate was collected by vacuum filtration and purified by titration of dichloromethane in a solution of methanol to afford desired product (4.7 g, %) as a yellow solid: $^1$H NMR (500 MHz, D$_2$O) δ 9.00 (s, 1H), 7.97 (dd, J=8.8, 1.8 Hz, 1H), 7.91 (s, 1H), 7.79 (d, J=8.8 Hz, 1H), 7.18 (dd, J=11.6, 2.3 Hz, 1H), 7.13 (s, 1H), 4.19 (s, 1H), 3.62 (dt, J=13.6, 6.8 Hz, 1H), 3.34 (tt, J=11.7, 3.9 Hz, 1H), 2.22 (m, 4H), 1.78 (q, J=12.4 Hz, 2H), 1.54 (q, J=12.4 Hz, 2H), 1.21 (d, J=6.7 Hz, 6H); APCI MS m/z 456 [$C_{25}H_{27}ClFN_3O_2$+H]$^+$; HPLC 99.3% (AUC), $t_R$=5.38 min.

Example 938

1-(4-((1R,4R)-4-aminocyclohexylamino)-6-(3,5-difluoro-4-hydroxyphenyl)quinolin-3-yl)-2-methylpropan-1-one

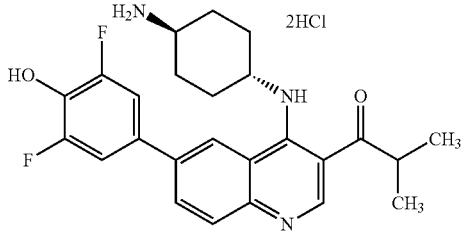 [SMILES: CC(C)C(=O)c1cnc2ccc(-c3cc(F)c(O)c(F)c3)cc2c1N[C@H]1CC[C@H](N)CC1]

tert-butyl (1R,4R)-4-(6-(3,5-difluoro-4-hydroxyphenyl)-3-isobutyrylquinolin-4-ylamino)cyclohexylcarbamate (8 g, 15 mmol) was treated with a solution of HCl in dioxane (125 mL, 4 N). The mixture was stirred for 16 h at ambient temperature, producing a off white precipitate. The precipitate was collected by vacuum filtration and purified by titration of dichloromethane in a solution of methanol to afford desired product (6.2 g, 81%) as a pale yellow solid: $^1$H NMR (500 MHz, D$_2$O) δ 8.96 (s, 1H), 7.90 (dd, J=8.8, 1.8 Hz, 1H), 7.86 (d, J=2.0 Hz, 1H), 7.74 (d, J=8.7 Hz, 1H), 6.96 (d, J=9.2 Hz, 2H), 4.14 (s, 1H), 3.58 (dt, J=13.6, 6.8 Hz, 1H), 3.33 (tt, J=11.6, 3.8 Hz, 1H), 2.20 (m, 4H), 1.76 (q, J=12.8, 2H), 1.52 (q, J=12.8, Hz, 2H), 1.20 (d, J=6.7 Hz, 6H); APCI MS m/z 440 [C$_{25}$H$_{27}$F$_2$N$_3$O$_2$+H]$^+$; HPLC 99.7% (AUC), t$_R$=7.52 min.

Example 940

1-(4-((1R,4R)-4-aminocyclohexylamino)-6-(3-chloro-4-hydroxy-5-methoxyphenyl)quinolin-3-yl)ethanone

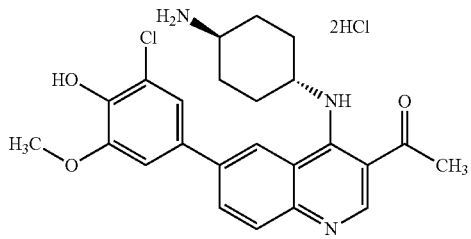 [SMILES: COc1cc(-c2ccc3ncc(C(C)=O)c(N[C@H]4CC[C@H](N)CC4)c3c2)cc(Cl)c1O]

Following general procedure A, tert-butyl (1R,4R)-4-(3-acetyl-6-(3-chloro-4-hydroxy-5-methoxyphenyl)quinolin-4-ylamino)cyclohexylcarbamate (6.2 g, 11.5 mmol) was treated with a solution of 3N HCl to afford desired product (5.6 g, 95%) as a yellow solid: $^1$H NMR (500 MHz, MeOD) δ 9.11 (s, 1H), 8.47 (s, 1H), 8.31 (dd, J=8.7, 1.8 Hz, 1H), 7.99 (d, J=8.7 Hz, 1H), 7.33 (d, 1=2.1 Hz, 1H), 7.27 (d, J=2.1 Hz, 1H), 4.52 (s, 1H), 4.00 (s, 3H), 2.75 (s, 3H), 2.52 (d, J=12.6 Hz, 2H), 2.25 (d, J=12.6 Hz, 2H), 1.88 (q, J=12.5 Hz, 2H), 1.64 (q, J=12.5 Hz, 2H); APCI MS m/z 440 [C$_{24}$H$_{26}$ClN$_3$O$_3$+H]$^+$; HPLC 98.8% (AUC), t$_R$=5.45 min.

Example 425

(6-(3-chloro-5-fluoro-4-hydroxyphenyl)-4-(6-(piperazin-1-yl)pyridin-3-ylamino)quinolin-3-yl)(cyclopropyl)methanone

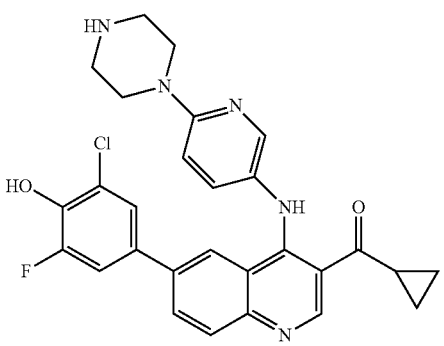 [SMILES: O=C(c1cnc2ccc(-c3cc(F)c(O)c(Cl)c3)cc2c1Nc1ccc(N2CCNCC2)nc1)C1CC1]

Following general procedure F, tert-butyl 4-(5-(6-bromo-3-(cyclopropanecarbonyl)quinolin-4-ylamino)pyridin-2-yl)piperazine-1-carboxylate (8.4 g, 15 mmol) was reacted with 2-chloro-6-fluoro-4-(4,4,5,5-tetramethyl-1,3,2-dioxaborolan-2-yl)phenol (5.0 g, 18 mmol) to obtain the protected intermediate which was subjected to general procedure A-2 to afford the desired product (3.9 g, 53% over 2 steps) as a yellow/orange solid: $^1$H NMR (300 MHz, MeOD) δ 9.26 (s, 1H), 8.07 (d, J=2.8 Hz, 1H), 7.89 (s, 2H), 7.75 (s, 1H), 7.47 (dd, J=9.0, 2.8 Hz, 1H), 7.02 (s, 1H), 6.96 (d, J=9.0 Hz, 1H), 6.84 (dd, J=12.2, 2.4 Hz, 1H), 3.72 (t, J=5.2 Hz, 5H), 3.12 (t, J=5.2 Hz, 5H), 2.92 (m, 1H), 1.22 (m, 2H), 1.12 (m, 2H); ESI MS m/z 518 [C$_{28}$H$_{25}$ClFN$_5$O$_2$+H]$^+$; HPLC 98.7% (AUC), t$_R$=8.67 min.

Example 374

1-(6-(3,5-dichloro-4-hydroxyphenyl)-4-(4-((dimethylamino)methyl)phenyl)amino)quinolin-3-yl)ethanone

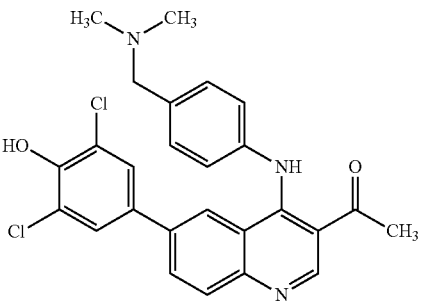 [SMILES: CC(=O)c1cnc2ccc(-c3cc(Cl)c(O)c(Cl)c3)cc2c1Nc1ccc(CN(C)C)cc1]

Following general procedure D, 1-(6-bromo-4-((4-((dimethylamino)methyl)phenyl)amino)quinolin-3-yl)ethanone (50 mg, 0.13 mmol) was reacted with 2,6-dichloro-4-(4,4,5,5-tetramethyl-1,3,2-dioxaborolan-2-yl)phenol (84 mg, 0.29 mmol) to afford the desired product (42.9 mg, 71%) as a yellow solid. $^1$H NMR (500 MHz, MeOD) δ 9.13 (s, 1H), 7.97-7.89 (m, 2H), 7.74 (d, J=1.6 Hz, 1H), 7.45 (d, J=8.1 Hz, 2H), 7.28-7.22 (m, 2H), 7.11 (s, 2H), 3.83 (s, 2H), 2.78 (s, 3H), 2.41 (s, 6H). ESI MS m/z 480 [C$_{26}$H$_{23}$Cl$_2$N$_3$O$_2$+H]$^+$; HPLC 98.3% (AUC), t$_R$=10.60 min.

Example 379

1-(6-(3,5-dichloro-4-hydroxyphenyl)-4-((trans-4-((dimethylamino)methyl)cyclohexyl)amino)quinolin-3-yl)ethanone

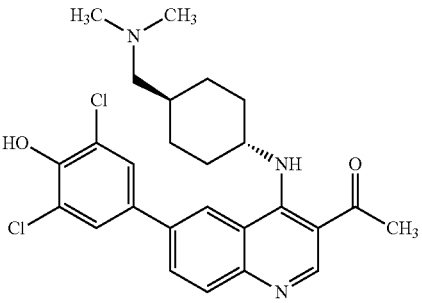 [SMILES: CC(=O)c1cnc2ccc(-c3cc(Cl)c(O)c(Cl)c3)cc2c1N[C@H]1CC[C@H](CN(C)C)CC1]

Following general procedure D, 1-(6-bromo-4-((trans-4-((dimethylamino)methyl)cyclohexyl)amino)quinolin-3-yl)ethanone (32 mg, 0.079 mmol) was reacted with 2,6- dichloro-4-(4,4,5,5-tetramethyl-1,3,2-dioxaborolan-2-yl)phenol (51 mg, 0.176 mmol) to afford the desired product (24.5 mg, 64%) as a yellow solid. $^1$H NMR (500 MHz, MeOD) δ 8.93 (s, 1H), 8.34 (d, J=2.0 Hz, 2H), 7.99 (dd, J=8.7, 2.0 Hz, 1H), 7.89 (d, J=8.7 Hz, 1H), 7.62 (s, 2H), 4.27-4.20 (m, 1H), 2.80-2.74 (d, J=6.9 Hz, 2H), 2.71-2.63 (m, 9H), 2.37 (d, J=12.8 Hz, 2H), 1.99 (d, J=13.2 Hz, 2H), 1.89-1.85 (m, 1H), 1.70-1.58 (m, 2H), 1.33-1.21 (m, 2H). ESI MS m/z 486 $[C_{26}H_{29}Cl_2N_3O_2+H]^+$; HPLC 97.9% (AUC), $t_R$=10.81 min.

Example 379 1-(6-(3-chloro-5-fluoro-4-hydroxyphenyl)-4-((trans-4-((dimethylamino)methyl)cyclohexyl)amino)quinolin-3-yl)ethanone

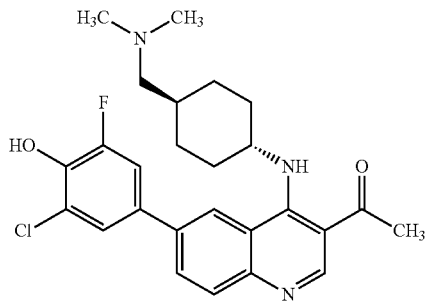 [SMILES: CC(=O)c1cnc2ccc(-c3cc(F)c(O)c(Cl)c3)cc2c1N[C@H]1CC[C@H](CN(C)C)CC1]

Following general procedure D, 1-(6-bromo-4-((trans-4-((dimethylamino)methyl)cyclohexyl)amino)quinolin-3-yl)ethanone (32 mg, 0.079 mmol) was reacted with 2-chloro-6-fluoro-4-(4,4,5,5-tetramethyl-1,3,2-dioxaborolan-2-yl)phenol (32 mg, 0.118 mmol) to afford the desired product (24.0 mg, 65%) as a yellow solid. $^1$H NMR (500 MHz, MeOD) δ 8.91 (s, 1H), 8.33 (d, J=1.9 Hz, 1H), 7.97 (dd, J=8.7, 1.9 Hz, 1H), 7.87 (d, J=8.7 Hz, 1H), 7.47 (s, 1H), 7.37 (d, J=11.8 Hz, 1H), 4.27-4.18 (m, H), 2.69 (s, 3H), 2.59-2.55 (m, 2H), 2.52 (s, 6H), 2.34 (d, J=12.7 Hz, 2H), 1.99 (d, J=13.2 Hz, 2H), 1.84-1.74 (m, 1H), 1.67-1.55 (m, 2H), 1.28-1.17 (m, 2H). ESI MS m/z 470 $[C_{26}H_{29}ClFN_3O_2+H]^+$; HPLC>99% (AUC), $t_R$=10.56 min.

Example 400

2,6-dichloro-4-(4-((4-((dimethylamino)methyl)phenyl)amino)-3-(methylsulfonyl)quinolin-6-yl)phenol

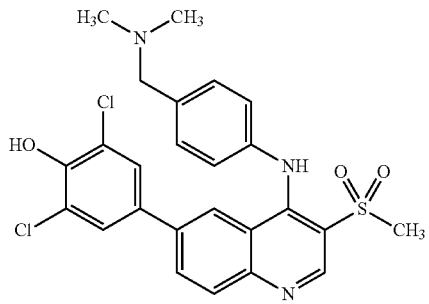 [SMILES: CN(C)Cc1ccc(Nc2c(S(C)(=O)=O)cnc3ccc(-c4cc(Cl)c(O)c(Cl)c4)cc23)cc1]

Following general procedure D, 6-bromo-N-(4-((dimethylamino)methyl)phenyl)-3-(methylsulfonyl)quinolin-4-amine (43 mg, 0.10 mmol) was reacted with 2,6-dichloro-4-(4,4,5,5-tetramethyl-1,3,2-dioxaborolan-2-yl)phenol (53 mg, 0.183 mmol) to afford the desired product (31.7 mg, 61%) as a yellow solid. $^1$H NMR (500 MHz, MeOD) δ 9.00 (s, 1H), 8.06-7.97 (m, 2H), 7.74 (s, 3H), 7.46-7.38 (m, 2H), 7.21 (d, J=8.0 Hz, 2H), 7.13 (s, 2H), 3.86 (s, 2H), 3.27 (s, 3H), 2.45 (s, 6H). ESI MS m/z 516 $[C_{25}H_{23}Cl_2N_3O_2S+H]^+$; HPLC 94.5% (AUC), $t_R$=11.57 min.

Example 415

1-(6-(3,5-dichloro-4-hydroxyphenyl)-4-((4-(pyrrolidin-1-ylmethyl)phenyl)amino)quinolin-3-yl)ethanone

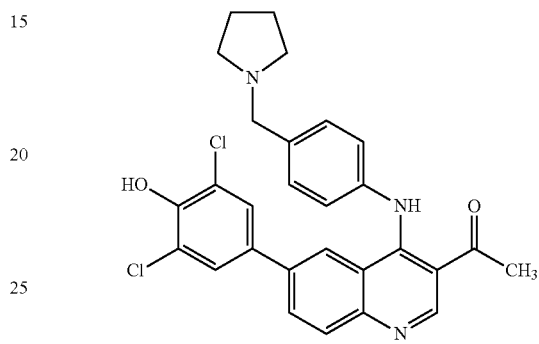

Following general procedure D, 1-(6-bromo-4-((4-(pyrrolidin-1-ylmethyl)phenyl)amino)quinolin-3-yl)ethanone (42.4 mg, 0.10 mmol) was reacted with 2,6-dichloro-4-(4,4,5,5-tetramethyl-1,3,2-dioxaborolan-2-yl)phenol (38.4 mg, 0.133 mmol) to afford the desired product (28.4 mg, 56%) as a yellow solid. $^1$H NMR (500 MHz, MeOD) δ 9.17 (s, 1H), 8.02-7.94 (m, 2H), 7.77 (s, 1H), 7.55 (d, J=8.4 Hz, 2H), 7.32 (d, J=8.4 Hz, 2H), 7.20 (s, 2H), 4.41 (s, 2H), 3.27 (br s, 4H), 2.78 (s, 3H), 2.07 (br s, 4H). ESI MS m/z 506 $[C_{28}H_{25}Cl_2N_3O_2+H]^+$; HPLC 95.1% (AUC), $t_R$=10.81 min.

Example 447

6-(3-chloro-4-hydroxy-5-methoxyphenyl)-4-((trans-4-(dimethylamino)cyclohexyl)amino)quinoline-3-carbonitrile

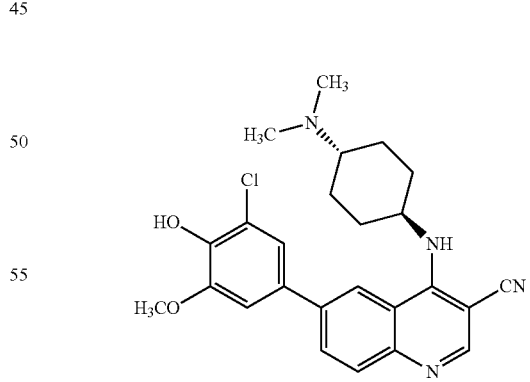

Following general procedure D, 6-bromo-4-((trans-4-(dimethylamino)cyclohexyl)amino)quinoline-3-carbonitrile (28 mg, 0.075 mmol) was reacted with 2-chloro-6-methoxy-4-(4,4,5,5-tetramethyl-1,3,2-dioxaborolan-2-yl)phenol (32 mg, 0.113 mmol) to afford the desired product (11.9 mg, 35%) as a yellow solid. $^1$H NMR (500 MHz, MeOD) δ 8.46-8.40 (m, 2H), 8.02 (dd, J=8.7, 1.9 Hz, 1H), 7.86 (d, J=8.7 Hz, 1H), 7.42

(d, J=2.0 Hz, 1H), 7.29 (d, J=2.0 Hz, 1H), 4.48-4.38 (m, 1H), 3.99 (s, 3H), 2.50-2.39 (m, 1H), 2.35 (s, 6H), 2.29 (d, J=11.8 Hz, 2H), 2.06 (d, J=12.0 Hz, 2H), 1.73-1.61 (m, 2H), 1.59-1.47 (m, 2H). ESI MS m/z 451 $[C_{25}H_{27}ClN_4O_2+H]^+$; HPLC 98.8% (AUC), $t_R$=10.61 min.

Example 1000 tert-buty 4-(5-((3-(cyclopropanecarbonyl)-6-(3,5-dichloro-4-hydroxyphenyl)quinolin-4-yl)amino)pyrimidin-2-yl)piperazine-1-carboxylate

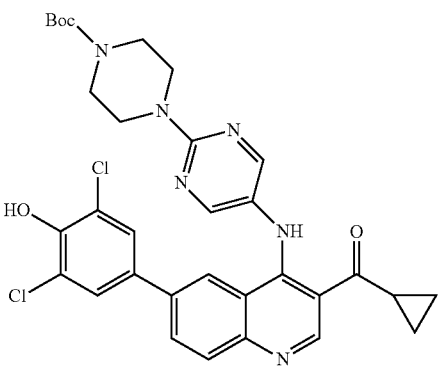 [SMILES: CC(C)(C)OC(=O)N1CCN(c2ncc(Nc3c(C(=O)C4CC4)cnc4ccc(-c5cc(Cl)c(O)c(Cl)c5)cc34)cn2)CC1]

Following general procedure D, tert-butyl 4-(5-((6-bromo-3-(cyclopropanecarbonyl)quinolin-4-yl)amino)pyrimidin-2-yl)piperazine-1-carboxylate (54 mg, 0.10 mmol) was reacted with 2,6-dichloro-4-(4,4,5,5-tetramethyl-1,3,2-dioxaborolan-2-yl)phenol (43 mg, 0.15 mmol) to afford the desired product (66 mg, >99%) as a yellow-brown solid. ESI MS m/z 635 $[C_{32}H_{32}Cl_2N_6O_4+H]^+$ Example 497 cyclopropyl(6-(3,5-dichloro-4-hydroxyphenyl)-4-((2-(piperazin-1-yl)pyrimidin-5-yl)amino)quinolin-3-yl)methanone

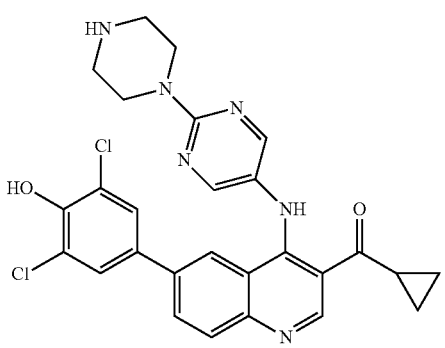

Following general procedure A-2, tert-butyl 4-(5-((3-(cyclopropanecarbonyl)-6-(3,5-dichloro-4-hydroxyphenyl)quinolin-4-yl)amino)pyrimidin-2-yl)piperazine-1-carboxylate (0.10 mmol) was reacted with TFA (2 mL) to afford the desired product (7.4 mg, 14% over two steps) as a yellow solid. $^1$H NMR (500 MHz, MeOD) δ 9.24 (s, 1H), 8.30 (s, 2H), 7.93 (d, J=1.3 Hz, 2H), 7.83 (d, J=1.3 Hz, 1H), 7.21 (s, 2H), 3.98 (t, J=5.2 Hz, 4H), 3.06 (t, J=5.2 Hz, 4H), 2.94-2.86 (m, 1H), 1.24-1.08 (m, 4H). ESI MS m/z 535 $[C_{27}H_{24}Cl_2N_6O_2+H]^+$; HPLC>99% (AUC), $t_R$=11.54 min.

Example 496

(6-(3-chloro-5-fluoro-4-hydroxyphenyl)-4-((2-(piperazin-1-yl)pyrimidin-5-yl)amino)quinolin-3-yl)(cyclopropyl)methanone

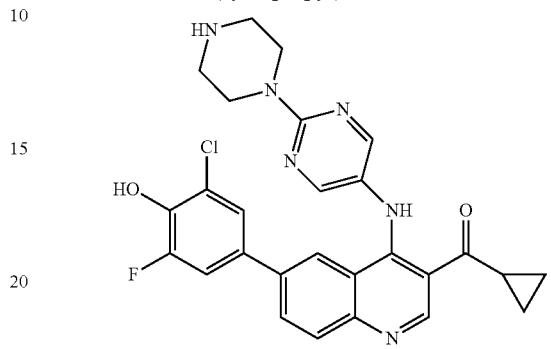

To a suspension of tert-butyl 4-(5-((6-bromo-3-(cyclopropanecarbonyl)quinolin-4-yl)amino)pyrimidin-2-yl)piperazine-1-carboxylate (54 mg, 0.10 mmol) and Pd(dppf)Cl$_2$ (11 mg, 0.015 mmol) in dioxane (4 mL) was added Cs$_2$CO$_3$ (1.0 M in H$_2$O, 400 μL, 0.4 mmol). N$_2$ gas was bubbled through the reaction mixture and the vessel was sealed. The mixture was then heated under microwave irradiation conditions at 140° C. for 30 min. The solution was allowed to cool to rt, then directly subjected to column chromatography (silica, 0-20% methanol/dichloromethane). The resultant residue was dissolved in THF (3 mL) and TFA (2 mL) and heated at 65° C. for 16 hours. The mixture was then cooled to room temperature and concentrated. The resultant residue was purified by preparative HPLC (C18 silica, 10-90% methanol/water with 0.05% TFA). The residue was eluted through an ion-exchange column (using methanol and 7 N methanol in ammonia) to obtain the desired product (13.0 mg, 25%) as a yellow solid. $^1$H NMR (500 MHz, MeOD) δ 9.24 (s, 1H), 8.30 (s, 2H), 7.98-7.90 (m, 2H), 7.84 (s, 1H), 7.14-7.09 (m, 1H), 6.93 (dd, J=12.0, 2.4 Hz, 1H), 3.96 (t, J=5.2 Hz, 4H), 3.05 (t, J=5.2 Hz, 4H), 2.94-2.85 (m, 1H), 1.24-1.08 (m, 4H). ESI MS m/z 519 $[C_{27}H_{24}ClFN_6O_2+H]^+$; HPLC>99% (AUC), $t_R$=11.34 min.

Example 1165 tert-butyl 4-(4-((3-(cyclopropanecarbonyl)-6-(3,5-dichloro-4-hydroxyphenyl)quinolin-4-yl)amino)-1H-pyrazol-1-yl)piperidine-1-carboxylate

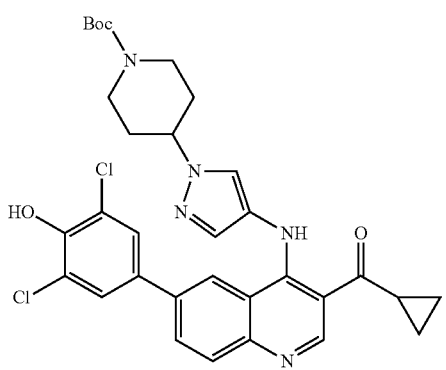 [SMILES: CC(C)(C)OC(=O)N1CCC(n2cc(Nc3c(C(=O)C4CC4)cnc4ccc(-c5cc(Cl)c(O)c(Cl)c5)cc34)cn2)CC1]

Following general procedure D, tert-butyl 4-(4-((6-bromo-3-(cyclopropanecarbonyl)quinolin-4-yl)amino)-1H-pyrazol-1-yl)piperidine-1-carboxylate (54 mg, 0.10 mmol) was reacted with 2,6-dichloro-4-(4,4,5,5-tetramethyl-1,3,2-dioxaborolan-2-yl)phenol (43 mg, 0.15 mmol) to afford the desired product (36 mg, 58%) as a yellow-brown solid. ESI MS m/z 622 [C$_{32}$H$_{33}$Cl$_2$N$_5$O$_4$+H]$^+$ Example 511 cyclopropyl(6-(3,5-dichloro-4-hydroxyphenyl)-4-((1-(piperidin-4-yl)-1H-pyrazol-4-yl)amino)quinolin-3-yl)methanone

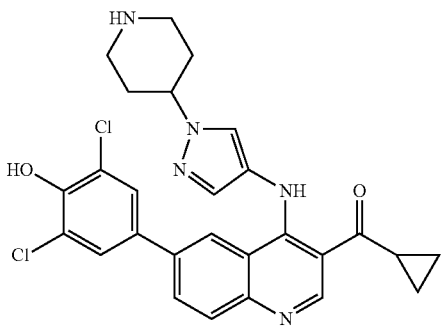 [SMILES: O=C(c1cnc2ccc(-c3cc(Cl)c(O)c(Cl)c3)cc2c1Nc1cnn(C2CCNCC2)c1)C1CC1]

Following general procedure A-2, tert-butyl 4-(4-((3-(cyclopropanecarbonyl)-6-(3,5-dichloro-4-hydroxyphenyl)quinolin-4-yl)amino)-1H-pyrazol-1-yl)piperidine-1-carboxylate (36 mg, 0.058 mmol) was reacted with TFA (2 mL) to afford the desired product (21.5 mg, 41%) as a yellow solid. $^1$H NMR (500 MHz, MeOD+TFA-d) δ 9.48 (br s, 1H), 8.22 (d, J=9.2 Hz, 1H), 8.01 (d, J=8.4 Hz, 2H), 7.69 (s, 1H), 7.39 (br s, 2H), 4.68-4.58 (m, 1H), 3.57 (dt, J=13.2, 3.8 Hz, 2H), 3.27-3.17 (m, 2H), 2.88 (br s, 1H), 2.36-2.25 (m, 4H), 1.41-1.10 (m, 4H). ESI MS m/z 522 [C$_{27}$H$_{25}$Cl$_2$N$_5$O$_2$+H]$^+$; HPLC>99% (AUC), t$_R$=9.75 min.

Example 1166 tert-butyl (trans-4-((6-(3-chloro-4-hydroxy-5-methoxyphenyl)-3-isobutyrylquinolin-4-yl)amino)cyclohexyl)carbamate

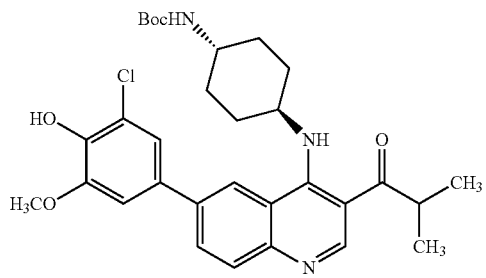 [SMILES: COc1cc(-c2ccc3ncc(C(=O)C(C)C)c(N[C@H]4CC[C@H](NC(=O)OC(C)(C)C)CC4)c3c2)cc(Cl)c1O]

Following general procedure D, tert-butyl (trans-4-((6-bromo-3-isobutyrylquinolin-4-yl)amino)cyclohexyl)carbamate (49 mg, 0.10 mmol) was reacted with 2-chloro-6-methoxy-4-(4,4,5,5-tetramethyl-1,3,2-dioxaborolan-2-yl)phenol (43 mg, 0.15 mmol) to afford the desired product (77 mg, >99%) as a viscous brown oil. ESI MS m/z 568 [C$_{31}$H$_{38}$ClN$_3$O$_5$+H]$^+$ Example 502

1-(4-((trans-4-aminocyclohexyl)amino)-6-(3-chloro-4-hydroxy-5-methoxyphenyl)quinolin-3-yl)-2-methylpropan-1-one

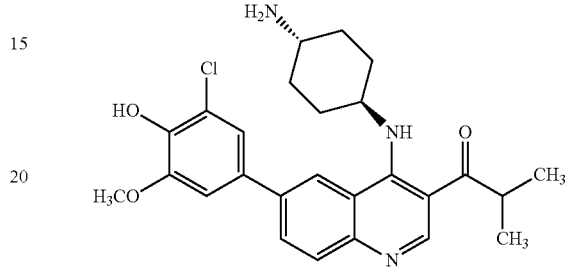

Following general procedure A-2, tert-butyl (trans-4-((6-(3-chloro-4-hydroxy-5-methoxyphenyl)-3-isobutyrylquinolin-4-yl)amino)cyclohexyl)carbamate (0.10 mmol) was reacted with TFA (2 mL) to afford the desired product (16.6 mg, 35% over 2 steps) as a yellow solid. $^1$H NMR (500 MHz, MeOD) δ 8.96 (s, 1H), 8.34 (d, J=2.1 Hz, 2H), 8.03 (dd, J=8.6, 2.1 Hz, 1H), 7.90 (d, J=8.6 Hz, 1H), 7.28 (d, J=2.2 Hz, 1H), 7.20 (d, J=2.2 Hz, 1H), 4.22-4.13 (m, 1H), 3.98 (s, 3H), 3.81-3.71 (m, 2H), 3.03-2.94 (m, 1H), 2.38-2.32 (d, J=12.6 Hz, 2H), 2.13-2.06 (m, 2H), 1.73-1.61 (q, J=12.5 Hz, 2H), 1.50-1.38 (m, 2H), 1.24 (d, J=6.7 Hz, 6H). ESI MS m/z 468 [C$_{26}$H$_{30}$ClN$_3$O$_3$+H]$^+$; HPLC>99% (AUC), t$_R$=11.34 min.

Example 1167 tert-butyl 4-(4-((6-(3-chloro-5-fluoro-4-hydroxyphenyl)-3-(cyclopropanecarbonyl)quinolin-4-yl)amino)-1H-pyrazol-1-yl)piperidine-1-carboxylate

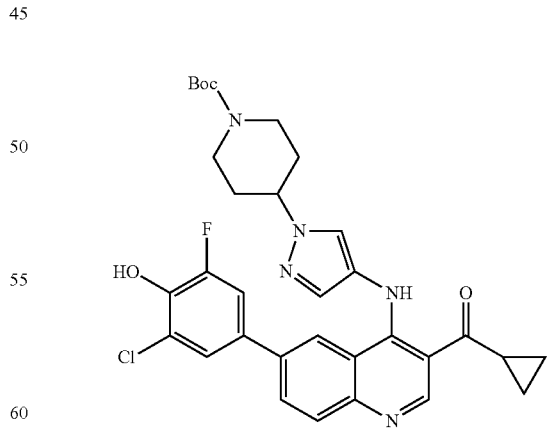

Following general procedure D, tert-butyl 4-(4-((6-bromo-3-(cyclopropanecarbonyl)quinolin-4-yl)amino)-1H-pyrazol-1-yl)piperidine-1-carboxylate (54 mg, 0.10 mmol) was reacted with 2-chloro-6-fluoro-4-(4,4,5,5-tetramethyl-1,3,2-dioxaborolan-2-yl)phenol (41 mg, 0.15 mmol) to afford the desired product (60 mg, 99%) as a yellow-brown solid. ESI MS m/z 606 [C$_{32}$H$_{33}$ClFN$_5$O$_4$+H]$^+$ Example 520 tert-butyl 4-(4-((6-(3-chloro-5-fluoro-4-hydroxyphenyl)-3-(cyclopropanecarbonyl)quinolin-4-yl)amino)-1H-pyrazol-1-yl)piperidine-1-carboxylate

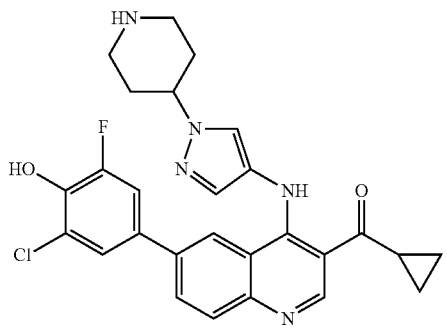 [SMILES: O=C(c1cnc2ccc(-c3cc(F)c(O)c(Cl)c3)cc2c1Nc1cnn(C2CCNCC2)c1)C1CC1]

Following general procedure A-2, tert-butyl 4-(4-((6-(3-chloro-5-fluoro-4-hydroxyphenyl)-3-(cyclopropanecarbonyl)quinolin-4-yl)amino)-1H-pyrazol-1-yl)piperidine-1-carboxylate (60 mg, 6.099 mmol) was reacted with TFA (2 mL) to afford the desired product (25.2 mg, 50%) as a yellow solid. $^1$H NMR (500 MHz, DMSO-d$_6$) δ 10.94 (s, 1H), 9.09 (s, 1H), 8.16 (d, J=2.1 Hz, 1H), 8.01 (dd, J=8.8, 2.1 Hz, 1H), 7.90-7.84 (m, 2H), 7.43 (s, 1H), 7.30 (s, 1H), 7.19 (d, J=12.1 Hz, 1H), 4.31-4.23 (m, 1H), 3.12 (d, J=12.6 Hz, 2H), 2.92-2.83 (m, 1H), 2.70 (t, J=12.3 Hz, 2H), 2.03-1.96 (m, 2H), 1.92-1.81 (m, 2H), 1.02-0.95 (m, 4H). ESI MS m/z 506 [C$_{27}$H$_{25}$ClFN$_5$O$_2$+H]$^+$; HPLC>99% (AUC), t$_R$=9.41 min.

Example 1168 tert-butyl 4-(4-((6-(3-chloro-4-hydroxyphenyl)-3-(cyclopropanecarbonyl)quinolin-4-yl)amino)-1H-pyrazol-1-yl)piperidine-1-carboxylate

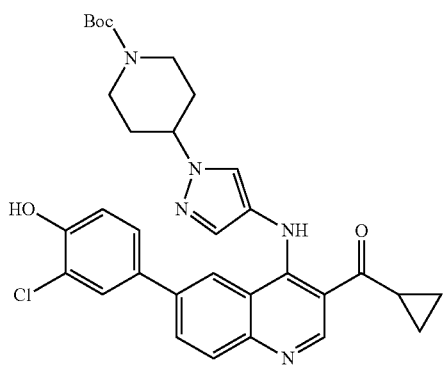 [SMILES: CC(C)(C)OC(=O)N1CCC(n2cc(Nc3c(C(=O)C4CC4)cnc4ccc(-c5ccc(O)c(Cl)c5)cc34)cn2)CC1]

Following general procedure D, tert-butyl 4-(4-((6-bromo-3-(cyclopropanecarbonyl)quinolin-4-yl)amino)-1H-pyrazol-1-yl)piperidine-1-carboxylate (54 mg, 0.10 mmol) was reacted with (3-chloro-4-hydroxyphenyl)boronic acid (34 mg, 0.20 mmol) to afford the desired product (62 mg, >99%) as a yellow-brown solid. ESI MS m/z 588 [C$_{32}$H$_{34}$ClN$_5$O$_4$+H]$^+$ Example 519

ALB 150143 (6-(3-chloro-4-hydroxyphenyl)-4-((1-(piperidin-4-yl)-1H-pyrazol-4-yl)amino)quinolin-3-yl)(cyclopropyl)methanone

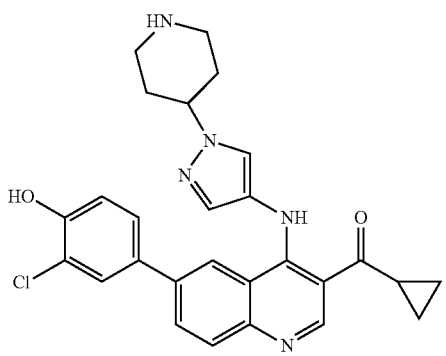 [SMILES: O=C(c1cnc2ccc(-c3ccc(O)c(Cl)c3)cc2c1Nc1cnn(C2CCNCC2)c1)C1CC1]

Following general procedure A-2, tert-butyl 4-(4-((6-(3-chloro-4-hydroxyphenyl)-3-(cyclopropanecarbonyl)quinolin-4-yl)amino)-1H-pyrazol-1-yl)piperidine-1-carboxylate (0.10 mmol) was reacted with TFA (2 mL) to afford the desired product (27 mg, 55% over 2 steps) as a yellow solid. $^1$H NMR (500 MHz, DMSO-d$_6$) δ 10.99 (s, 1H), 9.12 (s, 1H), 8.18 (d, J=2.2 Hz, 1H), 8.02-7.96 (m, 1H), 7.92-7.86 (m, 2H), 7.45 (d, J=2.3 Hz, 1H), 7.41 (s, 1H), 7.28-7.22 (m, 1H), 7.01 (d, J=8.5 Hz, 1H), 4.24-4.14 (m, 1H), 3.06-2.99 (m, 2H), 2.94-2.85 (m, 1H), 2.62-2.53 (m, 2H), 1.95-1.89 (m, 2H), 1.83-1.71 (m, 2H), 1.02-0.97 (m, 4H). ESI MS m/z 488 [C$_{27}$H$_{26}$ClN$_5$O$_2$+H]$^+$; HPLC>99% (AUC), t$_R$=9.30 min.

Example 1169 tert-butyl (trans-4-((3-acetyl-6-(3-chloro-5-fluoro-4-hydroxyphenyl)quinolin-4-yl)amino)cyclohexyl)carbamate

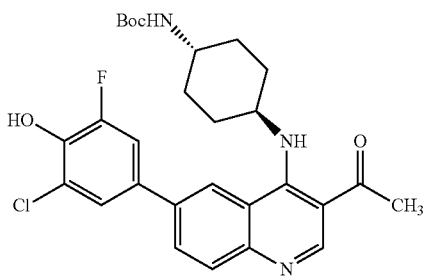 [SMILES: CC(=O)c1cnc2ccc(-c3cc(F)c(O)c(Cl)c3)cc2c1N[C@H]1CC[C@H](NC(=O)OC(C)(C)C)CC1]

Following general procedure D, tert-butyl (trans-4-((3-acetyl-6-bromoquinolin-4-yl)amino)cyclohexyl)carbamate (46 mg, 0.10 mmol) was reacted with 2-chloro-6-fluoro-4-(4,4,5,5-tetramethyl-1,3,2-dioxaborolan-2-yl)phenol (41 mg, 0.15 mmol) to afford the desired product (38 mg, 72%) as a light brown solid. ESI MS m/z 528 $[C_{28}H_{31}ClFN_3O_4+H]^+$ Example 527

1-(4-((trans-4-aminocyclohexyl)amino)-6-(3-chloro-5-fluoro-4-hydroxyphenyl)quinolin-3-yl)ethanone

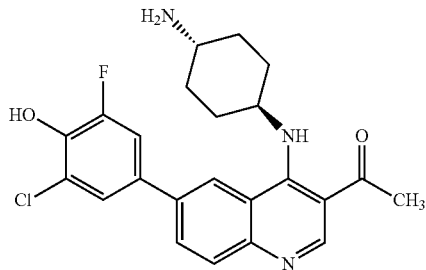 [SMILES: CC(=O)c1cnc2ccc(-c3cc(F)c(O)c(Cl)c3)cc2c1N[C@H]1CC[C@H](N)CC1]

To a suspension of tert-butyl (trans-4-((3-acetyl-6-(3-chloro-5-fluoro-4-hydroxyphenyl)quinolin-4-yl)amino)cyclohexyl) carbamate (38 mg, 0.072 mmol) in THF (3 mL) was added water (2 mL) and 6N aqueous HCl (2 mL). The resultant solution was heated at 65° C. for 4 h. The reaction mixture was cooled and concentrated. The resultant residue was purified by preparative HPLC (C18 silica, 10-90% methanol/water with 0.05% TFA). The residue was eluted through an ion-exchange column (using methanol and 7 N methanol in ammonia) to obtain the desired product (18.1 mg, 59%) as a yellow solid. $^1$H NMR (500 MHz, MeOD+TFA-d) δ 9.12 (s, 1H), 8.47 (s, 1H), 8.32-8.26 (m, 1H), 7.99 (d, J=8.7 Hz, 1H), 7.59 (s, 1H), 7.52 (d, J=11.5 Hz, 1H), 4.57-4.53 (m, 1H), 2.74 (s, 3H), 2.51 (d, J=12.3 Hz, 2H), 2.26 (d, J=12.3 Hz, 2H), 1.87 (q, J=12.5 Hz, 2H), 1.71-1.62 (m, 2H). ESI MS m/z 428 $[C_{23}H_{23}ClFN_3O_2+H]^+$; HPLC>99% (AUC), $t_R$=9.43 min.

Example 1170 tert-butyl (trans-4-((3-butyryl-6-(3,5-dichloro-4-hydroxyphenyl)quinolin-4-yl)amino)cyclohexyl) carbamate

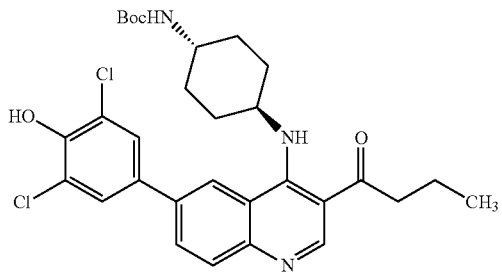 [SMILES: CCCC(=O)c1cnc2ccc(-c3cc(F)c(O)c(Cl)c3)cc2c1N[C@H]1CC[C@H](NC(=O)OC(C)(C)C)CC1]

Following general procedure D, tert-butyl (trans-4-((6-bromo-3-butyrylquinolin-4-yl)amino)cyclohexyl)carbamate (49 mg, 0.10 mmol) was reacted with 2,6-dichloro-4-(4,4,5,5-tetramethyl-1,3,2-dioxaborolan-2-yl)phenol (47 mg, 0.16 mmol) to afford the desired product (35.2 mg, 61%) as a yellow-brown solid. ESI MS m/z 572 $[C_{30}H_{35}Cl_2N_3O_4+H]^+$ Example 535

1-(4-((trans-4-aminocyclohexyl)amino)-6-(3,5-dichloro-4-hydroxyphenyl)quinolin-3-yl)butan-1-one

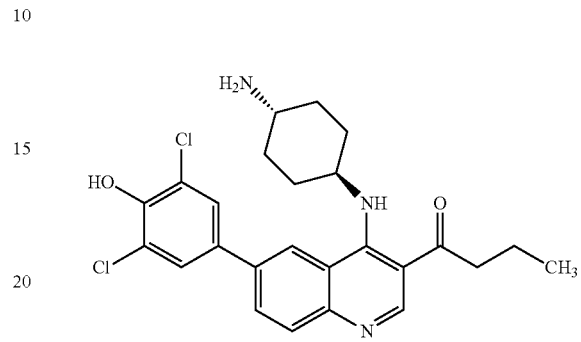

To a suspension of tert-butyl (trans-4-((3-butyryl-6-(3,5-dichloro-4-hydroxyphenyl)quinolin-4-yl)amino)cyclohexyl) carbamate (35.2 mg, 0.061 mmol) in THF (3 mL) was added water (2 mL) and 6N aqueous HCl (2 mL). The resultant solution was heated at 65° C. for 4 h. The reaction mixture was cooled and concentrated The resultant residue was purified by preparative HPLC (C18 silica, 10-90% acetonitrile/water with 0.05% TFA). The residue was eluted through an ion-exchange column (using methanol and 7 N methanol in ammonia) to obtain the desired product (3.7 mg, 13%) as a yellow solid. $^1$H NMR (500 MHz, MeOD+TFA-d) δ 9.15 (s, 1H), 8.46 (s, 1H), 8.27 (d, J=8.8 Hz, 1H), 8.00 (d, J=8.8 Hz, 1H), 7.72 (s, 2H), 4.53 (br s, 1H), 3.12 (t, J=7.2 Hz, 2H), 2.52 (s, 2H), 2.28 (d, J=12.3 Hz, 2H), 1.95-1.75 (m, 4H), 1.73-1.64 (m, 2H), 1.06 (t, J=7.4 Hz, 3H). ESI MS m/z 472 $[C_{25}H_{27}Cl_2N_3O_2+H]^+$; HPLC>99% (AUC), $t_R$=11.86 min.

Example 1171 tert-butyl (trans-4-((3-butyryl-6-(3-chloro-5-fluoro-4-hydroxyphenyl)quinolin-4-yl)amino)cyclohexyl) carbamate

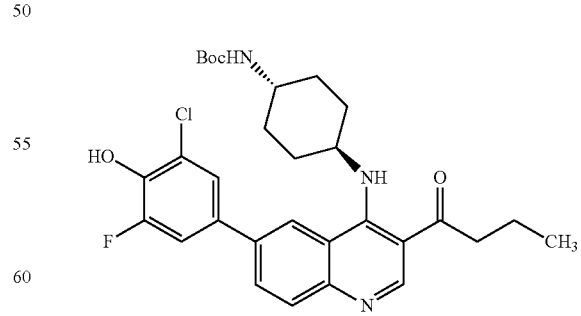

Following general procedure D, tert-butyl (trans-4-((6-bromo-3-butyrylquinolin-4-yl)amino)cyclohexyl)carbamate (49 mg, 0.10 mmol) was reacted with 2-chloro-6-fluoro-4-(4,4,5,5-tetramethyl-1,3,2-dioxaborolan-2-yl)phenol (41 mg, 0.15 mmol) to afford the desired product (36 mg, 64%) as a yellow-brown solid. ESI MS m/z 556 $[C_{30}H_{35}ClFN_3O_4+H]^+$

Example 532

1-(4-((trans-4-aminocyclohexyl)amino)-6-(3-chloro-5-fluoro-4-hydroxyphenyl)quinolin-3-yl)butan-1-one

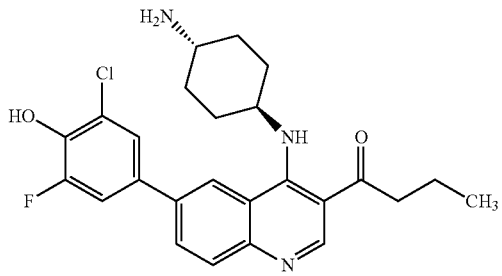 [SMILES: CCCC(=O)c1cnc2ccc(-c3cc(F)c(O)c(Cl)c3)cc2c1N[C@H]1CC[C@H](N)CC1]

To a suspension of tert-butyl (trans-4-((3-butyryl-6-(3-chloro-5-fluoro-4-hydroxyphenyl)quinolin-4-yl)amino)cyclohexyl)carbamate (36 mg, 0.065 mmol) in THF (3 mL) was added water (2 mL) and 6N aqueous HCl (2 mL). The resultant solution was heated at 65° C. for 4 h. The reaction mixture was cooled and concentrated. The resultant residue was triturated with diethyl ether. The residue was eluted through an ion-exchange column (using methanol and 7 N methanol in ammonia) to obtain the desired product (21.1 mg, 71%) as a yellow solid. $^1$H NMR (500 MHz, MeOD+TFA-d) δ 9.15 (s, 1H), 8.47 (s, 1H), 8.28 (dd, J=8.7, 1.8 Hz, 1H), 7.99 (d, J=8.7 Hz, 1H), 7.59 (s, 1H), 7.51 (d, J=11.4 Hz, 1H), 4.55 (br s, 1H), 3.13 (t, J=7.2 Hz, 2H), 2.53-2.49 (m, 2H), 2.26 (d, J=12.1 Hz, 2H), 1.94-1.74 (m, 4H), 1.68-1.62 (m, 2H), 1.06 (t, J=7.4 Hz, 3H). ESI MS m/z 456 $[C_{25}H_{27}ClFN_3O_2+H]^+$; HPLC>99% (AUC), $t_R$=10.83 min.

Example 1172 tert-butyl (trans-4-((3-butyryl-6-(3-chloro-4-hydroxy-5-methoxyphenyl)quinolin-4-yl)amino)cyclohexyl)carbamate

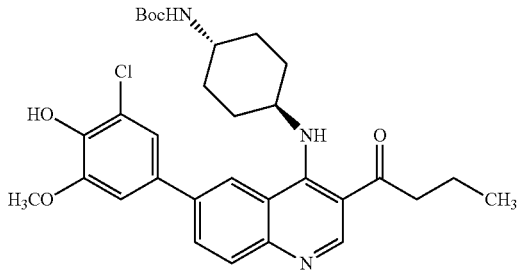 [SMILES: CCCC(=O)c1cnc2ccc(-c3cc(Cl)c(O)c(OC)c3)cc2c1N[C@H]1CC[C@H](NC(=O)OC(C)(C)C)CC1]

Following general procedure D, tert-butyl (trans-4-((6-bromo-3-butyrylquinolin-4-yl)amino)cyclohexyl)carbamate (49 mg, 0.10 mmol) was reacted with 2-chloro-6-methoxy-4-(4,4,5,5-tetramethyl-1,3,2-dioxaborolan-2-yl)phenol (43 mg, 0.15 mmol) to afford the desired product (36 mg, 63%) as a yellow solid. ESI MS m/z 568 $[C_{31}H_{38}ClN_3O_5+H]^+$

Example 529

1-(4-((trans-4-aminocyclohexyl)amino)-6-(3-chloro-4-hydroxy-5-methoxyphenyl)quinolin-3-yl)butan-1-one

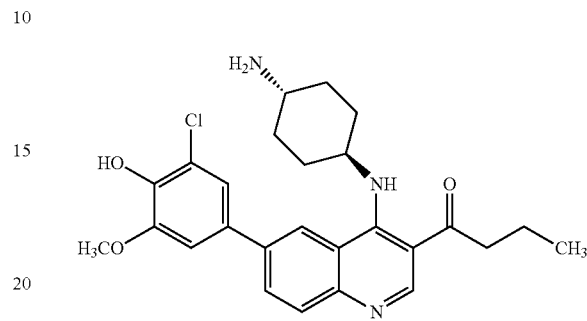

To a suspension of tert-butyl (trans-4-((3-butyryl-6-(3-chloro-4-hydroxy-5-methoxyphenyl)quinolin-4-yl)amino)cyclohexyl)carbamate (36 mg, 0.063 mmol) in THF (3 mL) was added water (2 mL) and 6N aqueous HCl (2 mL). The resultant solution was heated at 65° C. for 4 h. The reaction mixture was cooled and concentrated. The resultant residue was triturated with diethyl ether. The residue was eluted through an ion-exchange column (using methanol and 7 N methanol in ammonia) to obtain the desired product (22 mg, 75%) as a yellow solid. $^1$H NMR (500 MHz, MeOD) δ 8.96 (s, 1H), 8.34 (d, J=2.0 Hz, 1H), 8.02 (dd, J=8.7, 2.0 Hz, 1H), 7.90 (d, J=8.7 Hz, 1H), 7.28 (d, J=2.1 Hz, 1H), 7.20 (d, J=2.1 Hz, 2H), 4.24-4.18 (m, 1H), 3.98 (s, 3H), 3.11-3.00 (m, 3H), 2.37 (d, J=12.9 Hz, 2H), 2.10 (d, J=12.2 Hz, 2H), 1.84-1.74 (m, J=7.4 Hz, 2H), 1.71-1.65 (m, J=12.6 Hz, 2H), 1.49-1.43 (m, 2H), 1.04 (t, J=7.4 Hz, 3H). ESI MS m/z 468 $[C_{26}H_{30}ClN_3O_3+H]^+$; HPLC>99% (AUC), $t_R$=10.17 min.

Example 530

1-(6-(3,5-dichloro-4-hydroxyphenyl)-4-((4-((dimethylamino)methyl)phenyl)amino)quinolin-3-yl)butan-1-one

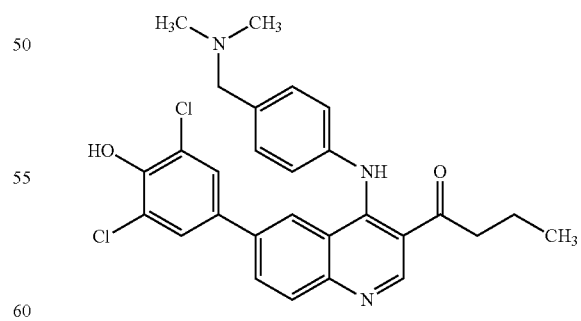

Following general procedure D, 1-(6-bromo-4-((4-((dimethylamino)methyl)phenyl)amino)quinolin-3-yl)butan-1-one (43 mg, 0.10 mmol) was reacted with 2,6-dichloro-4-(4,4,5,5-tetramethyl-1,3,2-dioxaborolan-2-yl)phenol (47 mg, 0.16 mmol) to afford the desired product (21.8 mg, 43%) as a yellow solid. $^1$H NMR (500 MHz, MeOD) δ 9.12 (s, 1H), 7.97-7.87 (m, 2H), 7.73 (d, J=1.8 Hz, 1H), 7.46-7.39 (m, 2H), 7.26-7.19 (m, 2H), 7.10 (s, 2H), 3.80 (s, 2H), 3.17 (t, J=7.3 Hz, 2H), 2.39 (s, 6H), 1.81 (h, J=7.4 Hz, 2H), 1.05 (t, J=7.4 Hz, 3H). ESI MS m/z 508 $[C_{28}H_{27}Cl_2N_3O_2+H]^+$; HPLC 99% (AUC), $t_R$=11.22 min.

Example 531

1-(6-(3,5-dichloro-4-hydroxyphenyl)-4-((4-((dimethylamino)methyl)phenyl)amino)quinolin-3-yl)butan-1-one dihydrochloride

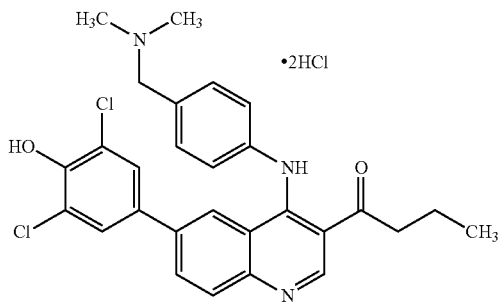 [SMILES: CCCC(=O)c1cnc2ccc(-c3cc(Cl)c(O)c(Cl)c3)cc2c1Nc1ccc(CN(C)C)cc1]

To a suspension of 1-(6-(3,5-dichloro-4-hydroxyphenyl)-4-((4-((dimethylamino)methyl)phenyl)amino)quinolin-3-yl)butan-1-one (6.5 mg, 0.0082 mmol) in methanol (4 mL) was added 2N HCl in ether (2.0 mL, 4 mmol). The resultant clear yellow solution was concentrated to afford the desired product as a yellow solid. $^1$H NMR (500 MHz, MeOD) δ 9.35 (s, 1H), 8.23 (dd, J=8.8, 1.9 Hz, 1H), 8.03 (d, J=8.8 Hz, 1H), 7.85 (d, J=1.9 Hz, 1H), 7.78-7.72 (m, 2H), 7.65-7.58 (m, 2H), 7.18 (s, 2H), 4.48 (s, 2H), 3.20 (t, J=7.2 Hz, 2H), 2.88 (s, 6H), 1.81 (h, J=7.3 Hz, 2H), 1.07 (t, J=7.4 Hz, 3H). ESI MS m/z 508 $[C_{28}H_{27}Cl_2N_3O_2+H]^+$; HPLC 93.5% (AUC), $t_R$=11.88 min.

Example 537

1-(6-(3-chloro-5-fluoro-4-hydroxyphenyl)-4-((4-((dimethylamino)methyl)phenyl)amino)quinolin-3-yl)butan-1-one

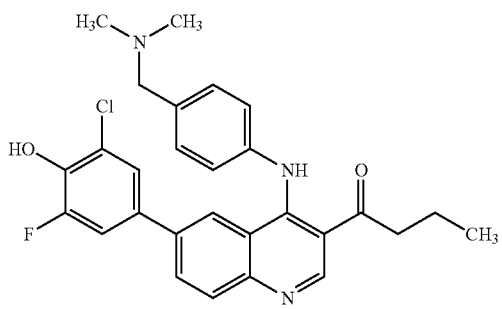 [SMILES: CCCC(=O)c1cnc2ccc(-c3cc(F)c(O)c(Cl)c3)cc2c1Nc1ccc(CN(C)C)cc1]

Following general procedure D, 1-(6-bromo-4-((4-((dimethylamino)methyl)phenyl)amino)quinolin-3-yl)butan-1-one (43 mg, 0.10 mmol) was reacted with 2-chloro-6-fluoro-4-(4,4,5,5-tetramethyl-1,3,2-dioxaborolan-2-yl)phenol (41 mg, 0.15 mmol) to afford the desired product (30.9 mg, 63%) as a yellow solid. $^1$H NMR (500 MHz, MeOD+TFA-d) δ 9.35 (s, 1H), 8.22 (dd, J=8.8, 1.9 Hz, 1H), 8.03 (d, J=8.8 Hz, 1H), 7.85 (d, J=1.9 Hz, 1H), 7.77-7.70 (m, 2H), 7.65-7.58 (m, 2H), 7.08 (dd, J=11.5, 2.1 Hz, 1H), 6.95 (s, J=2.1 Hz, 1H), 4.46 (s, 2H), 3.19 (t, J=7.2 Hz, 2H), 2.88 (s, 6H), 1.81 (h, J=7.4 Hz, 2H), 1.07 (t, J=7.4 Hz, 3H). ESI MS m/z 492 $[C_{28}H_{27}ClFN_3O_2+H]^+$; HPLC>99% (AUC), $t_R$=10.90 min.

Example 570

(6-(3-chloro-5-fluoro-4-hydroxyphenyl)-4-((trans-4-(((R)-3-fluoropyrrolidin-1-yl)methyl)cyclohexyl)amino)quinolin-3-yl)(cyclopropyl)methanone

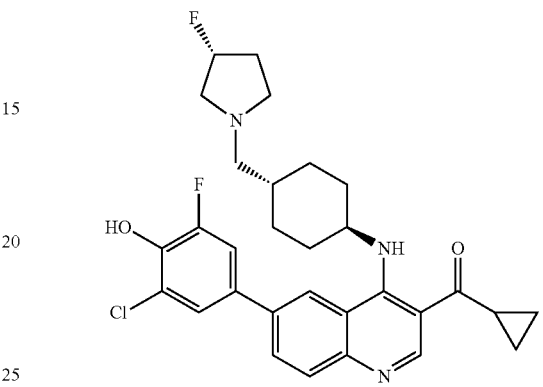

Following general procedure D, (6-bromo-4-((trans-4-(((R)-3-fluoropyrrolidin-1-yl)methyl)cyclohexyl)amino)quinolin-3-yl)(cyclopropyl)methanone (47 mg, 0.10 mmol) was reacted with 2-chloro-6-fluoro-4-(4,4,5,5-tetramethyl-1,3,2-dioxaborolan-2-yl)phenol (43 mg, 0.16 mmol) to afford the desired product (33.9 mg, 63%) as a yellow solid. $^1$H NMR (500 MHz, CDCl$_3$) $^1$H NMR (500 MHz, CDCl$_3$) δ 10.78 (br s, 1H), 9.24 (s, 1H), 8.24 (d, J=2.1 Hz, 1H), 8.03 (d, J=8.7 Hz, 1H), 7.84 (dd, J=8.7, 2.1 Hz, 1H), 7.44-7.39 (d, J=2.0 Hz, 1H), 7.29 (dd, J=11.1, 2.0 Hz, 1H), 5.25-5.10 (m, 1H), 4.10-4.04 (m, 1H), 2.91-2.65 (m, 4H), 2.51-2.27 (m, 5H), 2.24-2.01 (m, 5H), 1.65-1.50 (m, 3H), 1.31-1.21 (m, 1H), 1.13-1.04 (m, 4H). ESI MS m/z 540 $[C_{30}H_{32}ClF_2N_3O_2+H]^+$; HPLC>99% (AUC), $t_R$=10.95 min.

Example 571 cyclopropyl(6-(3,5-dichloro-4-hydroxyphenyl)-4-((trans-4-(((R)-3-fluoropyrrolidin)methyl)cyclohexyl)amino)quinolin-3-yl)methanon

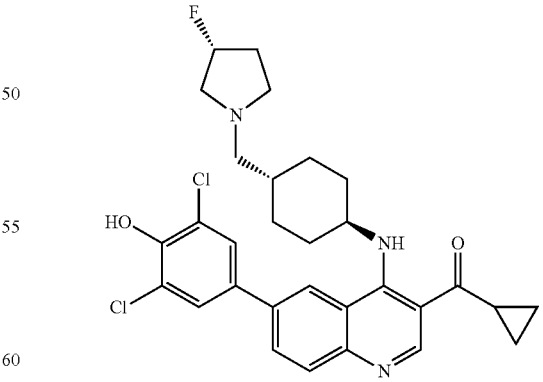

Following general procedure D, (6-bromo-4-((trans-4-(((R)-3-fluoropyrrolidin-1-yl)methyl)cyclohexyl)amino)quinolin-3-yl)(cyclopropyl)methanone (47 mg, 0.10 mmol) was reacted with 2,6-dichloro-4-(4,4,5,5-tetramethyl-1,3,2-dioxaborolan-2-yl)phenol (43 mg, 0.15 mmol) to afford the desired product (25.7 mg, 46%) as a yellow solid. $^1$H NMR (500 MHz, CDCl$_3$) δ 10.81 (br s, 1H), 9.24 (s, 1H), 8.24 (s, 1H), 8.04 (d, J=8.7 Hz, 1H), 7.85 (dd, J=8.7, 2.0 Hz, 2H), 7.54 (s, 2H), 5.25-5.10 (m, 1H), 4.10-4.04 (m, 1H), 2.85-2.65 (m, J=8.1, 4.6 Hz, 4H), 2.50-2.28 (m, 5H), 2.21-2.04 (m, 5H), 1.65-1.50 (m, 3H), 1.30-1.22 (m, 1H), 1.14-1.04 (m, 4H). ESI MS m/z 556 [C$_{30}$H$_{32}$Cl$_2$FN$_3$O$_2$+H]$^+$; HPLC>99% (AUC), t$_R$=11.19 min.

Example 587

(6-(3-chloro-5-fluoro-4-hydroxyphenyl)-4-((trans-4-(pyrrolidin-1-ylmethyl)cyclohexyl)amino)quinolin-3-yl)(cyclopropyl)methanone

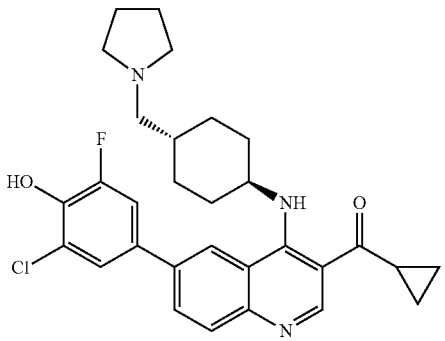 [SMILES: O=C(c1cnc2ccc(-c3cc(F)c(O)c(Cl)c3)cc2c1N[C@H]1CC[C@H](CN2CCCC2)CC1)C1CC1]

Following general procedure M, (6-bromo-4-((trans-4-(pyrrolidin-1-ylmethyl)cyclohexyl)amino)quinolin-3-yl)(cyclopropyl)methanone (46 mg, 0.10 mmol) was reacted with 2-chloro-6-fluoro-4-(4,4,5,5-tetramethyl-1,3,2-dioxaborolan-2-yl)phenol (43 mg, 0.16 mmol) to afford the desired product (32 mg, 61%) as a yellow solid. $^1$H NMR (500 MHz, MeOD) δ 9.10 (s, 1H), 8.28 (s, 1H), 7.94 (dd, J=8.7, 1.9 Hz, 1H), 7.85 (d, J=8.7 Hz, 1H), 7.47-7.43 (m, 1H), 7.35 (dd, J=11.9, 2.4 Hz, 1H), 4.15-4.07 (m, 1H), 3.23-3.15 (m, 4H), 2.92 (d, J=6.8 Hz, 2H), 2.87-2.78 (m, 1H), 2.30 (d, J=12.7 Hz, 2H), 2.06-1.97 (m, 6H), 1.87-1.78 (m, 1H), 1.56 (q, J=12.4 Hz, 2H), 1.30-1.14 (m, 4H), 1.13-1.05 (m, 2H). ESI MS m/z 522 [C$_{30}$H$_{33}$ClFN$_3$O$_2$+H]$^+$; HPLC>99% (AUC), t$_R$=11.04 min.

Example 584 cyclopropyl(6-(3,5-dichloro-4-hydroxyphenyl)-4-((trans-4-(pyrrolidin-1-ylmethyl)cyclohexyl)amino)quinolin-3-yl)methanone

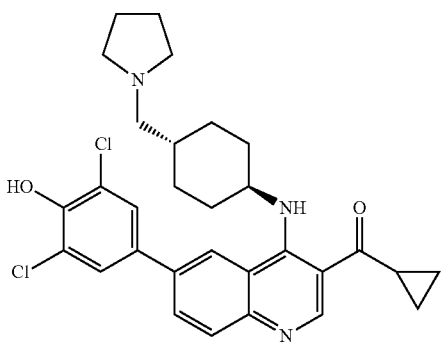 [SMILES: O=C(c1cnc2ccc(-c3cc(Cl)c(O)c(Cl)c3)cc2c1N[C@H]1CC[C@H](CN2CCCC2)CC1)C1CC1]

To a suspension of (6-bromo-4-((trans-4-(pyrrolidin-1-ylmethyl)cyclohexyl)amino)quinolin-3-yl)(cyclopropyl)methanone (46 mg, 0.10 mmol), 2,6-dichloro-4-(4,4,5,5-tetramethyl-1,3,2-dioxaborolan-2-yl)phenol (43 mg, 0.15 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, then directly subjected to column chromatography (silica, 0-20% methanol/dichloromethane). The resultant residue was dissolved in ethyl acetate and washed with saturated sodium bicarbonate solution. The organic layer was dried over anhydrous sodium sulfate and concentrated to afford the desired product (22.1 mg, 41%) as a yellow solid. $^1$H NMR (500 MHz, MeOD) δ 9.09 (s, 1H), 8.28 (d, J=2.1 Hz, 1H), 7.97-7.91 (m, 1H), 7.84 (d, J=8.7 Hz, 1H), 7.55 (s, 2H), 4.19-4.10 (m, 1H), 3.14-3.07 (m, 4H), 2.89-2.78 (m, 3H), 2.31 (d, J=12.6 Hz, 5H), 2.04-1.97 (m, 4H), 1.83-1.79 (m, 1H), 1.57 (q, J=12.3 Hz, 4H), 1.32-1.04 (m, 6H). ESI MS m/z 538 [C$_{30}$H$_{33}$Cl$_2$N$_3$O$_2$+H]$^+$; HPLC>99% (AUC), t$_R$=11.29 min.

Example 598 cyclopropyl(6-(3,5-dichloro-4-hydroxyphenyl)-4-((trans-4-((3-methoxypyrrolidin-1-yl)methyl)cyclohexyl)amino)quinolin-3-yl)methanone

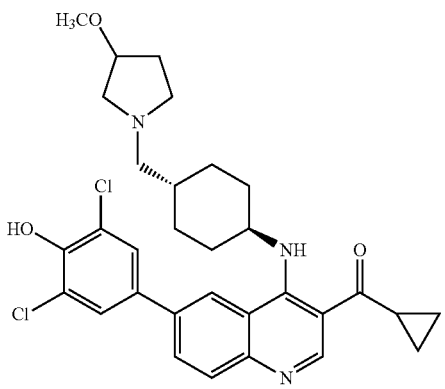

To a suspension of (6-bromo-4-((trans-4-((3-methoxypyrrolidin-1-yl)methyl)cyclohexyl)amino)quinolin-3-yl)(cyclopropyl)methanone (49 mg, 0.10 mmol), 2,6-dichloro-4-(4,4,5,5-tetramethyl-1,3,2-dioxaborolan-2-yl)phenol (43 mg, 0.15 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, then directly subjected to column chromatography (silica, 0-20% methanol/dichloromethane). The resultant residue was dissolved in ethyl acetate and washed with saturated sodium bicarbonate solution. The organic layer was dried over anhydrous sodium sulfate and concentrated to afford the desired product (30.6 mg, 54%) as a yellow solid. $^1$H NMR (500 MHz, MeOD+TFA-d) δ 9.36 (br s, 1H), 8.47 (br s, 1H), 8.27 (dd, J=8.7, 1.8 Hz, 1H), 7.98 (d, J=8.7 Hz, 1H), 7.75-7.71 (s, 2H), 4.53-4.49 (br s, 1H), 4.19 (d, J=18.9 Hz, 1H), 3.85-3.74 (m, 2H), 3.35 (s, 3H), 3.28-3.26 (m, 1H), 3.25-3.12 (m, 3H), 2.84 (br s, 1H), 2.45-2.29 (m, 3H), 2.20-1.97 (m, 4H), 1.80-1.73 (m, 2H), 1.37-1.18 (m, 6H). ESI MS m/z 568 [$C_{31}H_{35}Cl_2N_3O_3$+H]$^+$; HPLC>99% (AUC), $t_R$=11.42 min.

Example 627

(6-(3-chloro-5-fluoro-4-hydroxyphenyl)-4-((trans-4-((3-methoxypyrrolidin-1-yl)methyl)cyclohexyl)amino)quinolin-3-yl)(cyclopropyl)methanone

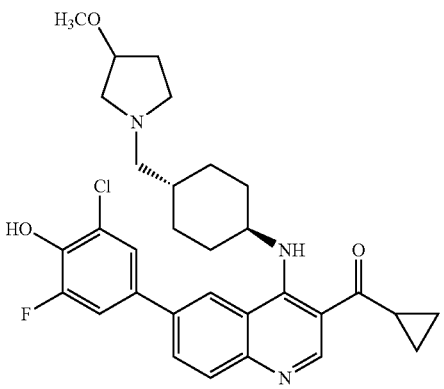

Following general procedure M, (6-bromo-4-((trans-4-((3-methoxypyrrolidin-1-yl)methyl)cyclohexyl)amino)quinolin-3-yl)(cyclopropyl)methanone (49 mg, 0.10 mmol) was reacted with 2-chloro-6-fluoro-4-(4,4,5,5-tetramethyl-1,3,2-dioxaborolan-2-yl)phenol (41 mg, 0.15 mmol) to afford the desired product (34 mg, 62%) as an off-white solid. $^1$H NMR (500 MHz, MeOD+TFA-d) δ 9.35 (br s, 1H), 8.47 (br s, 1H), 8.26 (dd, J=8.8, 1.8 Hz, 1H), 7.98 (d, J=8.7 Hz, 1H), 7.59 (br s, 1H), 7.51 (d, J=11.4 Hz, 1H), 4.50 (br s, 1H), 4.18 (d, J=19.4 Hz, 1H), 3.85-3.74 (m, 2H), 3.36 (s, 3H), 3.22-3.13 (m, 3H), 2.84 (s, 1H), 2.45-2.29 (m, 3H), 2.22-2.05 (m, 4H), 1.80-1.71 (m, 2H), 1.35-1.19 (m, 6H). ESI MS m/z 552 [$C_{31}H_{35}ClFN_3O_3$+H]$^+$; HPLC>99% (AUC), $t_R$=11.30 min.

Example 600 cyclopropyl(6-(3,5-dichloro-4-hydroxyphenyl)-4-((trans-4-((3-hydroxypyrrolidin-1-yl)methyl)cyclohexyl)amino)quinolin-3-yl)methanone

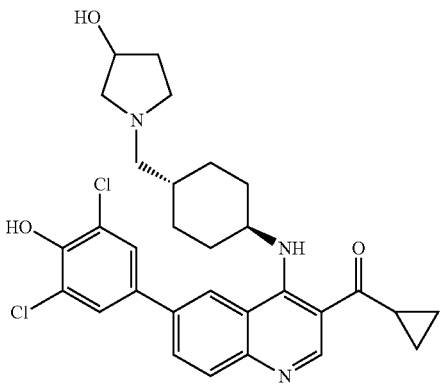

Following general procedure M, (6-bromo-4-((trans-4-((3-hydroxypyrrolidin-1-yl)methyl)cyclohexyl)amino)quinolin-3-yl)(cyclo propyl)methanone (47 mg, 0.10 mmol) was reacted with 2,6-dichloro-4-(4,4,5,5-tetramethyl-1,3,2-dioxaborolan-2-yl)phenol (43 mg, 0.15 mmol) to afford the desired product (34 mg, 61%) as an off-white solid. $^1$H NMR (500 MHz, MeOD) δ 9.13 (s, 1H), 8.34 (d, J=2.0 Hz, 1H), 7.98 (dd, J=8.7, 2.0 Hz, 1H), 7.92-7.87 (m, 1H), 7.63 (s, 2H), 4.59-4.54 (m, 1H), 4.53-4.47 (m, 1H), 4.17-4.11 (m, 1H), 3.16-3.10 (m, 2H), 2.94 (d, J=7.0 Hz, 2H), 2.88-2.79 (m, 1H), 2.33 (d, J=12.9 Hz, 2H), 2.28-2.17 (m, 1H), 2.06-1.96 (m, 3H), 1.84 (br s, 1H), 1.59 (q, J=12.2 Hz, 2H), 1.31-1.06 (m, 6H). ESI MS m/z 554 [$C_{30}H_{33}Cl_2N_3O_3$+H]$^+$; HPLC>99% (AUC), $t_R$=11.11 min.

Example 631

(6-(3-chloro-5-fluoro-4-hydroxyphenyl)-4-((trans-4-((3-hydroxypyrrolidin-1-yl)methyl)cyclohexyl)amino)quinolin-3-yl)(cyclopropyl)methanone

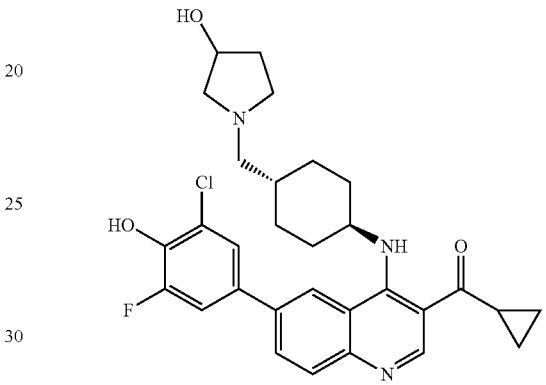

Following general procedure M, (6-bromo-4-((trans-4-((3-hydroxypyrrolidin-1-yl)methyl)cyclohexyl)amino)quinolin-3-yl)(cyclopropyl)methanone (25 mg, 0.053 mmol) was reacted with 2-chloro-6-fluoro-4-(4,4,5,5-tetramethyl-1,3,2-dioxaborolan-2-yl)phenol (27 mg, 0.10 mmol) to afford the desired product (17 mg, 60%) as a yellow solid. $^1$H NMR (500 MHz, MeOD) δ 9.11 (s, 1H), 8.34 (d, J=2.0 Hz, 1H), 7.97 (dd, J=8.7, 2.0 Hz, 1H), 7.88 (d, J=8.7 Hz, 1H), 7.48 (s, 1H), 7.38 (d, J=11.8, 1H), 4.46-4.38 (m, 1H), 4.18-4.10 (m, 1H), 3.08-3.01 (m, 2H), 2.93-2.78 (m, 3H), 2.70-2.64 (m, 2H), 2.331 (d, J=12.9 Hz, 2H), 2.23-2.12 (m, 1H), 2.01 (t, J=13.6 Hz, 2H), 1.87-1.80 (m, 1H), 1.75-1.71 (m, 1H), 1.56 (q, J=12.4 Hz, 2H), 1.27-1.05 (m, 6H). ESI MS m/z 538 [$C_{30}H_{33}ClFN_3O_3$+H]$^+$; HPLC>99% (AUC), $t_R$=10.78 min.

Example 634 cyclopropyl(6-(3,5-dichloro-4-hydroxyphenyl)-4-((trans-4-((2-hydroxyethyl)(methyl)amino)methyl)cyclohexyl)amino)quinolin-3-yl)methanone

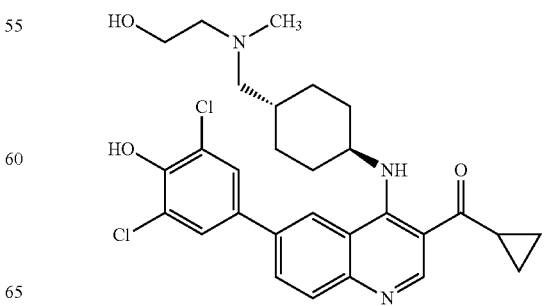

Following general procedure M, 6-bromo-4-(((trans-4-(((2-hydroxyethyl)(methyl)amino)methyl)cyclohexyl)amino)quinolin-3-yl)(cyclopropyl)methanone (46 mg, 0.10 mmol) was reacted with 2,6-dichloro-4-(4,4,5,5-tetramethyl-1,3,2-dioxaborolan-2-yl)phenol (43 mg, 0.15 mmol) to afford the desired product (30.7 mg, 57%) as a yellow solid. $^1$H NMR (500 MHz, MeOD) δ 9.10 (s, 1H), 8.32 (d, J=2.0 Hz, 1H), 7.96 (dd, J=8.7, 2.0 Hz, 1H), 7.87 (d, J=8.7 Hz, 1H), 7.58 (s, 2H), 4.18-4.10 (m, 1H), 3.73 (t, J=5.7 Hz, 2H), 2.87-2.78 (m, 3H), 2.63-2.56 (m, 2H), 2.53 (s, 3H), 2.30 (d, J=12.6 Hz, 2H), 2.02 (d, J=13.0 Hz, 2H), 1.79-1.75 (m, 1H), 1.56 (q, J=12.2 Hz, 2H), 1.30-1.15 (m, 4H), 1.12-1.05 (m, 2H). ESI MS m/z 542 $[C_{29}H_{33}Cl_2N_3O_3+H]^+$; HPLC>99% (AUC), $t_R$=11.14 min.

Example 632

(6-(3-chloro-5-fluoro-4-hydroxyphenyl)-4-((trans-4-(((2-hydroxyethyl)(methyl)amino)methyl)cyclohexyl)amino)quinolin-3-yl)(cyclopropyl)methanone

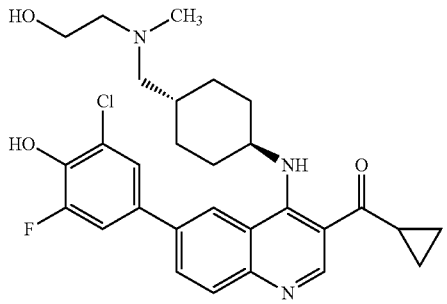 [SMILES: CN(CCO)C[C@H]1CC[C@H](Nc2c(C(=O)C3CC3)cnc3ccc(-c4cc(F)c(O)c(Cl)c4)cc23)CC1]

Following general procedure M, 6-bromo-4-(((trans-4-(((2-hydroxyethyl)(methyl)amino)methyl)cyclohexyl)amino)quinolin-3-yl)(cyclopropyl)methanone (40 mg, 0.087 mmol) was reacted with 2-chloro-6-fluoro-4-(4,4,5,5-tetramethyl-1,3,2-dioxaborolan-2-yl)phenol (35 mg, 0.13 mmol) to afford the desired product (27 mg, 59%) as a light yellow solid. $^1$H NMR (500 MHz, MeOD) δ 9.12 (s, 1H), 8.37 (d, J=2.0 Hz, 1H), 7.99 (dd, J=8.7, 2.0 Hz, 1H), 7.89 (d, J=8.8 Hz, 2H), 7.50 (d, J=2.1 Hz, 1H), 7.41 (dd, J=11.7, 2.1 Hz, 1H), 4.17-4.13 (m, 1H), 3.73 (t, J=5.8 Hz, 2H), 2.87-2.80 (m, 3H), 2.59 (d, J=6.8 Hz, 2H), 2.53 (s, 3H), 2.31 (d, J=13.1 Hz, 2H), 2.01 (d, J=13.1 Hz, 2H), 1.79-1.75 (m, 1H), 1.61-1.55 (m, 1H), 1.25-1.14 (m, 4H), 1.13-1.05 (m, 2H). ESI MS m/z 526 $[C_{29}H_{33}ClFN_3O_3+H]^+$; HPLC>99% (AUC), $t_R$=10.80 min.

Example 685 cyclopropyl(6-(3,5-dichloro-4-hydroxyphenyl)-4-((trans-4-((methylamino)methyl)cyclohexyl)amino)quinolin-3-yl)methanone

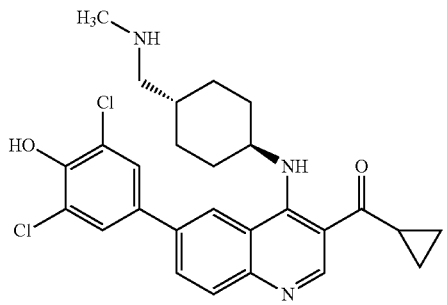 [SMILES: CNC[C@H]1CC[C@H](Nc2c(C(=O)C3CC3)cnc3ccc(-c4cc(Cl)c(O)c(Cl)c4)cc23)CC1]

To a suspension of (6-bromo-4-((trans-4-((methylamino)methyl)cyclohexyl)amino)quinolin-3-yl)(cyclopropyl)methanone (42 mg, 0.10 mmol), 2,6-dichloro-4-(4,4,5,5-tetramethyl-1,3,2-dioxaborolan-2-yl)phenol (43 mg, 0.15 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, diluted with saturated sodium bicarbonate solution and extracted with ethyl acetate. The combined organic layers were dried over anhydrous sodium sulfate and concentrated. The resultant residue was purified by preparative HPLC (C18 silica, 10-90% methanol/water with 0.05% TFA). The residue was eluted through an ion-exchange column (using methanol and 7 N methanol in ammonia) to obtain the desired product (14.7 mg, 29%) as a yellow solid. $^1$H NMR (500 MHz, MeOD+TFA-d) δ 9.35 (br s, 1H), 8.47 (br s, 1H), 8.27 (dd, J=8.8, 1.8 Hz, 1H), 7.98 (d, J=8.7 Hz, 1H), 7.74 (s, 2H), 4.52 (br s, 1H), 2.94 (d, J=6.9 Hz, 2H), 2.83 (br s, 2H), 2.73 (s, 3H), 2.46-2.42 (br s, 2H), 2.05 (d, J=13.0 Hz, 2H), 1.88 (br s, 1H), 1.77-1.68 (m, 2H), 1.36-1.19 (m, 6H). ESI MS m/z 498 $[C_{27}H_{29}Cl_2N_3O_2+H]^+$; HPLC>99% (AUC), $t_R$=11.08 min.

Example 652 cyclopropyl(6-(3,5-dichloro-4-hydroxyphenyl)-4-((cis-4-((dimethylamino)methyl)-4-hydroxycyclohexyl)amino)quinolin-3-yl)methanone

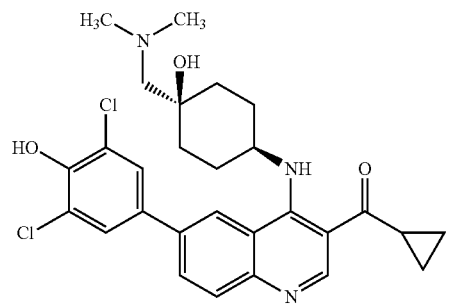 [SMILES: CN(C)C[C@]1(O)CC[C@@H](Nc2c(C(=O)C3CC3)cnc3ccc(-c4cc(Cl)c(O)c(Cl)c4)cc23)CC1]

Following general procedure M, (6-bromo-4-((cis-4-((dimethylamino)methyl)-4-hydroxycyclohexyl)amino)quinolin-3-yl)(cyclopropyl)methanone (35 mg, 0.078 mmol) was reacted with 2,6-dichloro-4-(4,4,5,5-tetramethyl-1,3,2-dioxaborolan-2-yl)phenol (35 mg, 0.12 mmol) to afford the desired product (28.8 mg, 70%) as an orange solid. NMR (500 MHz, MeOD) 9.12 (s, 1H), 8.31 (d, J=2.0 Hz, 1H), 7.96 (dd, J=8.7, 2.0 Hz, 1H), 7.91-7.84 (m, 1H), 7.60 (s, 2H), 4.20-4.12 (m, 1H), 2.88-2.80 (m, 2H), 2.77 (s, 2H), 2.66 (s, 3H), 2.09 (d, J=12.3 Hz, 2H), 2.00-1.84 (m, 4H), 1.68-1.58

(m, 2H), 1.23-1.13 (m, 2H), 1.14-1.05 (m, 2H). ESI MS m/z 528 [C$_{28}$H$_{31}$Cl$_2$N$_3$O$_3$+H]$^+$; HPLC>99% (AUC), t$_R$=10.70 min.

Example 673

(6-(3-chloro-5-fluoro-4-hydroxyphenyl)-4-((cis-4-((dimethylamino)methyl)-4-hydroxycyclohexyl)amino)quinolin-3-yl)(cyclopropyl)methanone

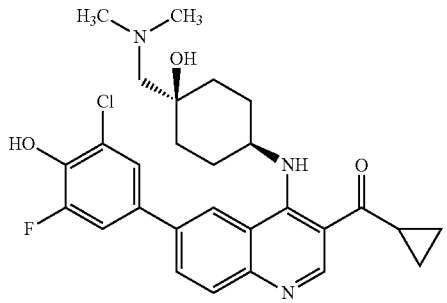

Following general procedure M, (6-bromo-4-((cis-4-((dimethylamino)methyl)-4-hydroxycyclohexyl)amino)quinolin-3-yl)(cyclopropyl)methanone (35 mg, 0.078 mmol) was reacted with 2-chloro-6-fluoro-4-(4,4,5,5-tetramethyl-1,3,2-dioxaborolan-2-yl)phenol (35 mg, 0.13 mmol) to afford the desired product (26.7 mg, 67%) as a yellow-brown solid. $^1$H NMR (500 MHz, MeOD) 9.14 (s, 1H), 8.35 (d, J=2.0 Hz, 1H), 7.97 (dd, J=8.7, 2.0 Hz, 1H), 7.92-7.84 (m, 1H), 7.51-7.46 (m, 1H), 7.39 (dd, J=11.8, 2.3 Hz, 1H), 4.20-4.12 (m, 1H), 2.90-2.78 (m, 1H), 2.74 (s, 2H), 2.64 (s, 3H), 2.12-2.06 (d, J=12.5 Hz, 2H), 2.00-1.82 (m, 4H), 1.72-1.56 (m, 2H), 1.23-1.12 (m, 2H), 1.14-1.05 (m, 2H). ESI MS m/z 512 [C$_{28}$H$_{31}$ClFN$_3$O$_3$+H]$^+$; HPLC>99% (AUC), t$_R$=10.47 min.

Example 1173 tert-butyl (trans-4-(4-((3-(cyclopropanecarbonyl)-6-(3,5-dichloro-4-hydroxyphenyl)quinolin-4-yl)amino)-1H-pyrazol-1-yl)cyclohexyl)carbamate

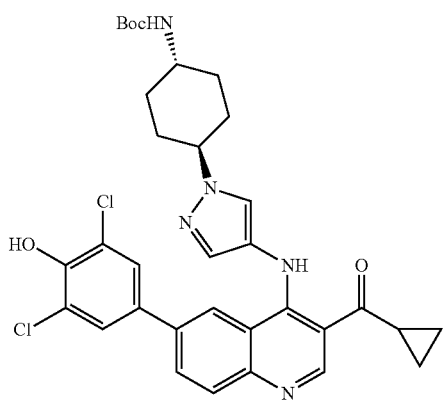 [SMILES: CC(C)(C)OC(=O)N[C@H]1CC[C@H](n2cc(Nc3c(C(=O)C4CC4)cnc4ccc(-c5cc(Cl)c(O)c(Cl)c5)cc34)cn2)CC1]

Following general procedure M, tert-butyl (trans-4-(4-((6-bromo-3-(cyclopropanecarbonyl)quinolin-4-yl)amino)-1H-pyrazol-1-yl)cyclohexyl)carbamate (45 mg, 0.081 mmol) was reacted with 2,6-dichloro-4-(4,4,5,5-tetramethyl-1,3,2-dioxaborolan-2-yl)phenol (43 mg, 0.15 mmol) to afford the desired product (23 mg, 45%) as a yellow-brown solid. ESI MS m/z 636 [C$_{33}$H$_{35}$Cl$_2$N$_5$O$_4$+H]$^+$ Example 706

(4-((1-(trans-4-aminocyclohexyl)-1H-pyrazol-4-yl)amino)-6-(3,5-dichloro-4-hydroxyphenyl)quinolin-3-yl)(cyclopropyl)methanone dihydrochloride

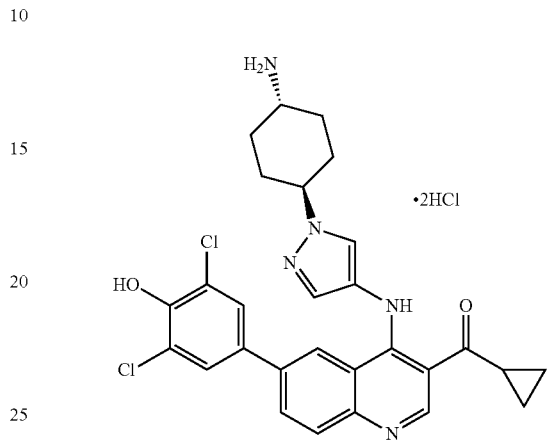

To a solution of tert-butyl (trans-4-(4-((3-(cyclopropanecarbonyl)-6-(3,5-dichloro-4-hydroxyphenyl)quinolin-4-yl)amino)-1H-pyrazol-1-yl)cyclohexyl)carbamate (23 mg, 0.036 mmol) in THF (3 mL) was added trifluoroacetic acid (2 mL). The resultant mixture was heated at 65° C. for 16 h. The mixture was then cooled to room temperature and concentrated. The resultant residue was purified by preparative HPLC (C18 silica, 10-90% acetonitrile/water with 0.05% TFA). The residue was dissolved in methanol (5 mL) and HCl (2 M in diethyl ether, 2.0 mL, 4 mmol) was added. The resultant solution was concentrated to give the desired product (11.1 mg, 50%) as a yellow solid. $^1$H NMR (500 MHz, MeOD) δ 9.50 (br s, 1H), 8.22 (d, J=8.7 Hz, 1H), 8.13 (br s, 1H), 8.00 (d, J=8.7 Hz, 2H), 7.63 (s, 2H), 7.36 (br s, 2H), 4.35-4.31 (m, 1H), 3.26-3.17 (m, 1H), 2.97-2.89 (br s, 1H), 2.28-2.16 (m, 4H), 2.04-1.91 (m, 2H), 1.70-1.58 (m, 2H), 1.33-1.20 (m, 4H). ESI MS m/z 536 [C$_{28}$H$_{27}$Cl$_2$N$_5$O$_2$+H]$^+$; HPLC 96.0% (AUC), t$_R$=11.44 min.

Example 720

1-(6-(3,5-dichloro-4-hydroxyphenyl)-4-((1-(dimethylamino)-2,3-dihydro-1H-inden-5-yl)amino)quinolin-3-yl)ethanone

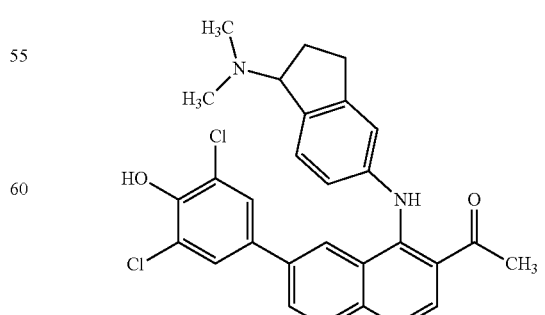

Following general procedure M, 1-(6-bromo-4-((1-(dimethylamino)-2,3-dihydro-1H-inden-5-yl)amino)quinolin-3-yl)ethanone (19 mg, 0.0448 mmol) was reacted with 2,6-dichloro-4-(4,4,5,5-tetramethyl-1,3,2-dioxaborolan-2-yl)phenol (35 mg, 0.12 mmol) to afford the desired product (13.9 mg, 61%) as an orange solid. $^1$H NMR (500 MHz, DMSO) δ 11.27 (s, 1H), 9.07 (s, 1H), 8.03 (dd, J=8.7, 2.1 Hz, 1H), 7.96-7.87 (m, 2H), 7.35-7.27 (m, 3H), 7.16 (d, J=2.1 Hz, 1H), 7.03-6.97 (m, 1H), 4.45 (br s, 1H), 2.95-2.84 (m, 1H), 2.84-2.73 (m, 1H), 2.65 (s, 3H), 2.21 (s, 6H), 2.14-2.06 (m, 2H). ESI MS m/z 505 $[C_{28}H_{25}Cl_2N_3O_2+H]^+$; HPLC 98.5% (AUC), $t_R$=11.22 min.

Example 739

1-(6-(3,5-dichloro-4-hydroxyphenyl)-4-((trans-4-(2-(dimethylamino)ethyl)cyclohexyl)amino)quinolin-3-yl)ethanone

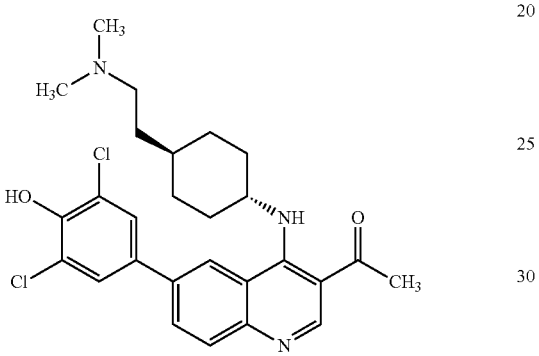

Following general procedure M, 1-(6-bromo-4-((trans-4-(2-(dimethylamino)ethyl)cyclohexyl)amino)quinolin-3-yl)ethanone (63 mg, 0.15 mmol) was reacted with 2,6-dichloro-4-(4,4,5,5-tetramethyl-1,3,2-dioxaborolan-2-yl)phenol (65 mg, 0.225 mmol) to afford the desired product (7.3 mg, 9.7%) as a yellow solid. NMR (500 MHz, DMSO) δ 10.69 (d, J=8.0 Hz, 1H), 8.92 (s, 1H), 8.27 (d, J=2.1 Hz, 1H), 8.01 (dd, J=8.6, 2.1 Hz, 1H), 7.82 (d, J=8.7 Hz, 1H), 7.66 (s, 2H), 4.21-4.12 (m, 1H), 2.65 (s, 3H), 2.48-2.41 (m, 2H), 2.28 (s, 3H), 2.23-2.16 (m, 2H), 1.88-1.81 (m, 2H), 1.51-1.38 (m, 5H), 1.23-1.12 (m, 2H). ESI MS m/z 500 $[C_{27}H_{31}Cl_2N_3O_2+H]^+$; HPLC>99% (AUC), $t_R$=11.40 min.

Example 741

1-(6-(3-chloro-5-fluoro-4-hydroxyphenyl)-4-((trans-4-(2-(dimethylamino)ethyl)cyclohexyl)amino)quinolin-3-yl)ethanone

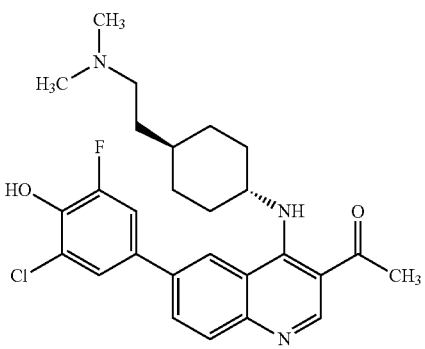 [SMILES: CC(=O)c1cnc2ccc(-c3cc(F)c(O)c(Cl)c3)cc2c1N[C@H]1CC[C@H](CCN(C)C)CC1]

Following general procedure M, 1-(6-bromo-4-((trans-4-(2-(dimethylamino)ethyl)cyclohexyl)amino)quinolin-3-yl)ethanone (63 mg, 0.15 mmol) was reacted with 2-chloro-6-fluoro-4-(4,4,5,5-tetramethyl-1,3,2-dioxaborolan-2-yl)phenol (61 mg, 0.225 mmol) to afford the desired product (37 mg, 51%) as a yellow solid. $^1$H NMR (500 MHz, DMSO) δ 10.65 (d, J=7.9 Hz, 1H), 8.93 (s, 1H), 8.31 (d, J=2.1 Hz, 1H), 8.03 (dd, J=8.7, 2.1 Hz, 1H), 7.85 (d, J=8.7 Hz, 1H), 7.61-7.54 (m, 2H), 4.20-4.11 (m, 1H), 2.66 (s, 3H), 2.28 (t, J=7.3 Hz, 2H), 2.22-2.15 (m, 2H), 2.15 (s, 6H), 1.84 (d, J=12.5 Hz, 2H), 1.51-1.31 (m, 5H), 1.21-1.09 (m, 2H). ESI MS m/z 484 $[C_{27}H_{31}ClFN_3O_2+H]^+$; HPLC>99% (AUC), $t_R$=11.13 min.

Example 1174 tert-butyl 4-((trans-4-((3-acetyl-6-(3,5-dichloro-4-hydroxyphenyl)quinolin-4-yl)amino)cyclohexyl)methyl)piperazine-1-carboxylate

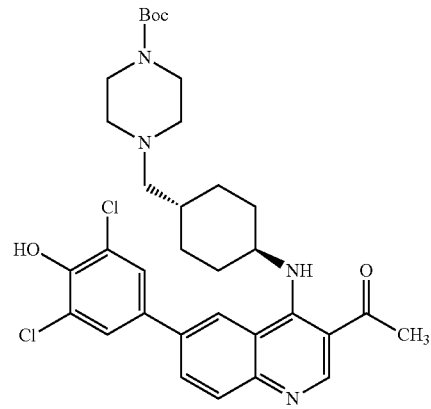 [SMILES: CC(=O)c1cnc2ccc(-c3cc(Cl)c(O)c(Cl)c3)cc2c1N[C@H]1CC[C@H](CN2CCN(C(=O)OC(C)(C)C)CC2)CC1]

To a suspension of tert-butyl 4-((trans-4-((3-acetyl-6-bromoquinolin-4-yl)amino)cyclohexyl)methyl)piperazine-1-carboxylate (55 mg, 0.10 mmol), 2,6-dichloro-4-(4,4,5,5-tetramethyl-1,3,2-dioxaborolan-2-yl)phenol (43 mg, 0.15 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, then directly subjected to column chromatography (silica, 0-20% methanol/dichloromethane) to afford the desired product (50 mg, 80%) as a brown solid. ESI MS m/z 627 $[C_{33}H_{40}Cl_2N_4O_4+H]^+$

Example 1175 tert-butyl 4-((trans-4-((3-acetyl-6-(3-chloro-5-fluoro-4-hydroxyphenyl)quinolin-4-yl)amino)cyclohexyl)methyl)piperazine-1-carboxylate

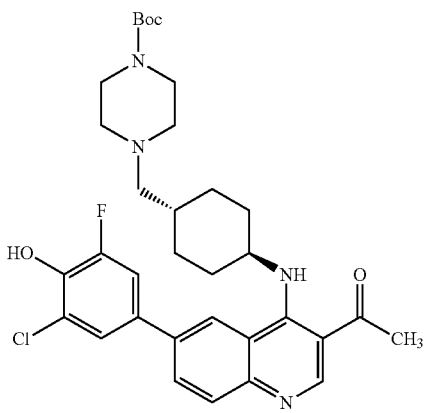 [SMILES: CC(=O)c1cnc2ccc(-c3cc(F)c(O)c(Cl)c3)cc2c1N[C@H]1CC[C@H](CN2CCN(C(=O)OC(C)(C)C)CC2)CC1]

Following general procedure M, tert-butyl 4-((trans-4-((3-acetyl-6-bromoquinolin-4-yl)amino)cyclohexyl)methyl)piperazine-1-carboxylate (55 mg, 0.10 mmol) was reacted with 2-chloro-6-fluoro-4-(4,4,5,5-tetramethyl-1,3,2-dioxaborolan-2-yl)phenol (41 mg, 0.15 mmol) to afford the desired product (66 mg, >99%) as an off-white solid. ESI MS m/z 611 [$C_{33}H_{40}ClFN_4O_4$+H]$^+$

Example 772

1-(6-(3,5-dichloro-4-hydroxyphenyl)-4-((trans-4-(piperazin-1-ylmethyl)cyclohexyl)amino)quinolin-3-yl)ethanone dihydrochloride

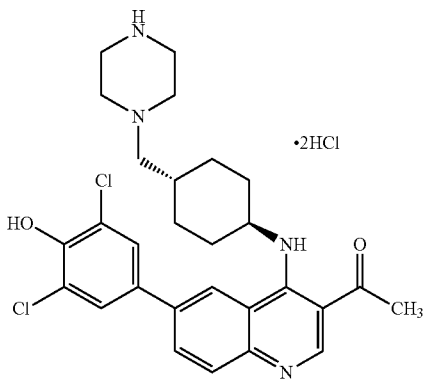 [SMILES: CC(=O)c1cnc2ccc(-c3cc(Cl)c(O)c(Cl)c3)cc2c1N[C@H]1CC[C@H](CN2CCNCC2)CC1]

To a solution of tert-butyl 4-((trans-4-((3-acetyl-6-(3,5-dichloro-4-hydroxyphenyl)quinolin-4-yl)amino)cyclohexyl)methyl)piperazine-1-carboxylate (50 mg, 0.80 mmol) in THF (5 mL) was added aqueous 1 N HCl (4 mL) and the reaction mixture was heated at 65° C. for 4 h. The reaction mixture was cooled to room temperature and concentrated. The resultant residue was purified by preparative HPLC (C18 silica, 10-90% acetonitrile/water with 0.05% TFA). The residue was dissolved in methanol (5 mL) and HCl (1 M in water, 2.0 mL, 2 mmol) was added. The resultant solution was concentrated to give the desired product (19.9 mg, 41%) as an off-white solid. $^1$H NMR (500 MHz, MeOD) δ 9.10 (s, 1H), 8.48 (s, 1H), 8.28 (dd, J=8.7, 1.8 Hz, 1H), 7.97 (d, J=8.7 Hz, 1H), 7.73 (s, 2H), 4.57-4.53 (m, 1H), 3.67-3.63 (br s, 4H), 3.63-3.31 (br s, 2H), 3.14-3.10 (br s, 2H), 2.74 (s, 3H), 2.46 (d, J=12.2 Hz, 2H), 2.18 (d, J=12.8 Hz, 2H), 2.08 (br s, 1H), 1.80 (q, J=12.4 Hz, 2H), 1.41-1.34 (m, 2H). ESI MS m/z 527 [$C_{28}H_{32}Cl_2N_4O_2$+H]$^+$; HPLC>99% (AUC), $t_R$=9.49 min.

Example 783

1-(6-(3-chloro-5-fluoro-4-hydroxyphenyl)-4-((trans-4-(piperazin-1-ylmethyl)cyclohexyl)amino)quinolin-3-yl)ethanone dihydrochloride

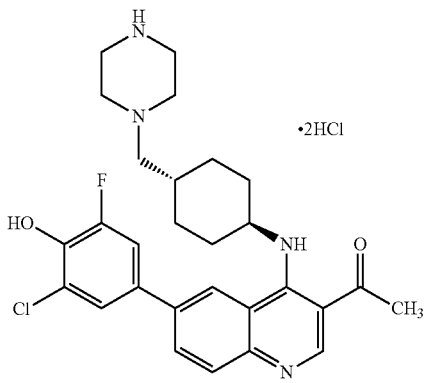 [SMILES: CC(=O)c1cnc2ccc(-c3cc(F)c(O)c(Cl)c3)cc2c1N[C@H]1CC[C@H](CN2CCNCC2)CC1]

To a solution of tert-butyl 4-((trans-4-((3-acetyl-6-(3-chloro-5-fluoro-4-hydroxyphenyl)quinolin-4-yl)amino)cyclohexyl)methyl)piperazine-1-carboxylate (66 mg, 0.10 mmol) in THF (5 mL) was added water (5 mL) and aqueous 6 N HCl (1.0 mL). The reaction mixture was heated at 65° C. for 2 h, cooled to room temperature and concentrated. The resultant residue was purified by preparative HPLC (C18 silica, 10-90% acetonitrile/water with 0.05% TFA). The residue was dissolved in methanol (5 mL) and HCl (6 M in water, 0.5 mL, 3 mmol) was added. The resultant solution was concentrated to give the desired product (24.2 mg, 41%) as an off-white solid. $^1$H NMR (500 MHz, MeOD) δ 9.10 (s, 1H), 8.48 (s, 1H), 8.27 (dd, J=8.7, 1.7 Hz, 1H), 7.98 (d, J=8.7 Hz, 1H), 7.59 (s, 1H), 7.52 (d, J=11.3 Hz, 1H), 4.57-4.53 (br s, 1H), 3.67 (br s, 4H), 3.50 (br s, 2H), 3.17 (br s, 2H), 2.74 (s, 3H), 2.46 (d, J=11.9 Hz, 2H), 2.18 (d, J=12.5 Hz, 2H), 2.10 (br s, 1H), 1.83-1.77 (m, 2H), 1.41-1.34 (m, 2H). ESI MS m/z 511 [$C_{28}H_{32}ClFN_4O_2$+H]$^+$; HPLC 98.3% (AUC), $t_R$=9.38 min.

Example 1176 tert-butyl (1-(5-((3-acetyl-6-(3,5-dichloro-4-hydroxyphenyl)quinolin-4-yl)amino)pyridin-2-yl)pyrrolidin-3-yl)(methyl)carbamate

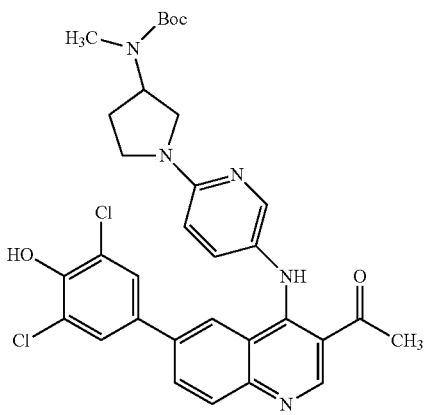

Following general procedure M, tert-butyl (1-(5-((3-acetyl-6-bromoquinolin-4-yl)amino)pyridin-2-yl)pyrrolidin-3-yl)(methyl)carbamate (80 mg, 0.15 mmol) was reacted with 2,6-dichloro-4-(4,4,5,5-tetramethyl-1,3,2-dioxaborolan-2-yl)phenol (72 mg, 0.25 mmol) to afford the desired product (94 mg, 100%) as a brown solid. ESI MS m/z 622 $[C_{32}H_{33}Cl_2N_5O_4+H]^+$

Example 1177 tert-butyl (1-(5-((3-acetyl-6-(3-chloro-5-fluoro-4-hydroxyphenyl)quinolin-4-yl)amino)pyridin-2-yl)pyrrolidin-3-yl)(methyl)carbamate

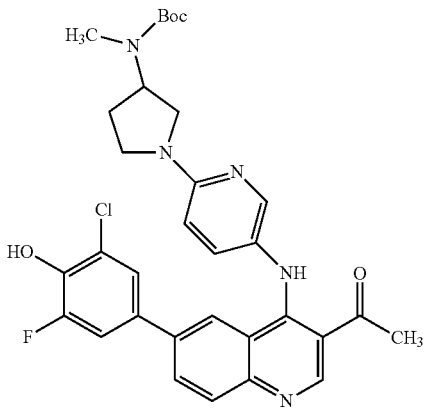 [SMILES: CC(=O)c1cnc2ccc(-c3cc(F)c(O)c(Cl)c3)cc2c1Nc1ccc(N2CCC(N(C)C(=O)OC(C)(C)C)C2)nc1]

Following general procedure M, tert-butyl (1-(5-((3-acetyl-6-bromoquinolin-4-yl)amino)pyridin-2-yl)pyrrolidin-3-yl)(methyl)carbamate (80 mg, 0.15 mmol) was reacted with 2-chloro-6-fluoro-4-(4,4,5,5-tetramethyl-1,3,2-dioxaborolan-2-yl)phenol (68 mg, 0.25 mmol) to afford the desired product (85 mg, 95%) as a brown solid. ESI MS m/z 606 $[C_{32}H_{33}ClFN_5O_4+H]^+$

Example 788

1-(6-(3,5-dichloro-4-hydroxyphenyl)-4-((6-(3-(methylamino)pyrrolidin-1-yl)pyridin-3-yl)amino)quinolin-3-yl)ethanone trihydrochloride

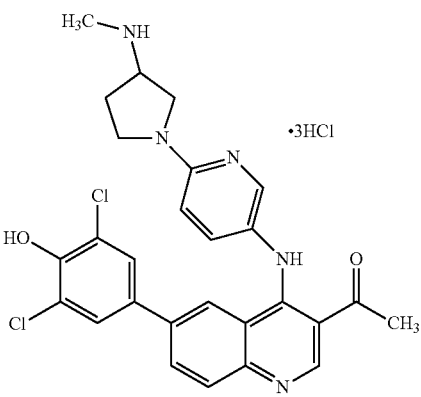 [SMILES: CNC1CCN(c2ccc(Nc3c(C(C)=O)cnc4ccc(-c5cc(Cl)c(O)c(Cl)c5)cc34)cn2)C1]

To a solution of tert-butyl (1-(5-((3-acetyl-6-(3,5-dichloro-4-hydroxyphenyl)quinolin-4-yl)amino)pyridin-2-yl)pyrrolidin-3-yl)(methyl)carbamate (94 mg, 0.15 mmol) in THF (5 mL) was added water (3 mL) and HCl (6 M in water, 2 mL, 12 mmol). The reaction mixture was heated at 65° C. for 4 h, cooled to room temperature and concentrated. The resultant residue was purified by preparative HPLC (C18 silica, 10-90% acetonitrile/water with 0.05% TEA). The residue was dissolved in methanol (5 mL) and HCl (6 M in water, 1.0 mL, 6 mmol) was added. The resultant solution was concentrated to give the desired product (81.2 mg, 85%) as an orange solid. $^1$H NMR (500 MHz, MeOD) δ 9.32 (s, 1H), 8.32-8.25 (m, 2H), 8.13-8.05 (m, 2H), 8.03-7.97 (m, 1H), 7.37 (s, 2H), 7.22 (d, J=9.1 Hz, 1H), 4.17-4.07 (m, 2H), 4.00-3.90 (m, 2H), 3.86-3.77 (m, 1H), 2.84 (s, 3H), 2.79 (s, 3H), 2.71-2.60 (m, 1H), 2.48-2.38 (m, 1H). ESI MS m/z 522 $[C_{27}H_{25}Cl_2N_5O_2+H]^+$; HPLC 97.5% (AUC), $t_R$=10.00 min.

Example 785

1-(6-(3-chloro-5-fluoro-4-hydroxyphenyl)-4-((6-(3-(methylamino)pyrrolidin-1-yl)pyridin-3-yl)amino)quinolin-3-yl)ethanone trihydrochloride

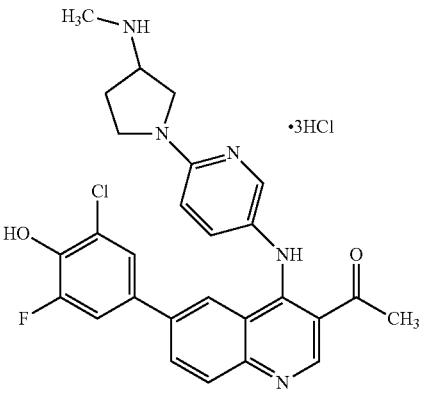 [SMILES: CNC1CCN(c2ccc(Nc3c(C(C)=O)cnc4ccc(-c5cc(F)c(O)c(Cl)c5)cc34)cn2)C1]

To a solution of tert-butyl (1-(5-((3-acetyl-6-(3-chloro-5-fluoro-4-hydroxyphenyl)quinolin-4-yl)amino)pyridin-2-yl)pyrrolidin-3-yl)(methyl)carbamate (85 mg, 0.14 mmol) in THF (5 mL) was added water (3 mL) and HCl (6 M in water, 2 mL, 12 mmol). The reaction mixture was heated at 65° C. for 3 h, cooled to room temperature and concentrated. The resultant residue was triturated with dichloromethane to give the desired product (55 mg, 64%) as an orange solid. $^1$H NMR (500 MHz, MeOD) δ 9.31 (s, 1H), 8.31-8.23 (m, 2H), 8.10-8.03 (m, 2H), 7.95 (dd, J=9.4, 2.4 Hz, 1H), 7.22 (dd, J=11.5, 2.3 Hz, 1H), 7.18-7.11 (m, 2H), 4.14-4.08 (m, 2H), 3.98-3.86 (m, 2H), 3.83-3.74 (m, 1H), 2.84 (s, 3H), 2.79 (s, 3H), 2.71-2.60 (m, 1H), 2.47-2.36 (m, 1H). ESI MS m/z 506 $[C_{27}H_{25}ClFN_5O_2+H]^+$; HPLC 97.4% (AUC), $t_R$=9.62 min.

Example 1178 tert-butyl (1-(5-((3-(cyclopropanecarbonyl)-6-(3,5-dichloro-4-hydroxyphenyl)quinolin-4-yl)amino)pyridin-2-yl)pyrrolidin-3-yl)(methyl)carbamate

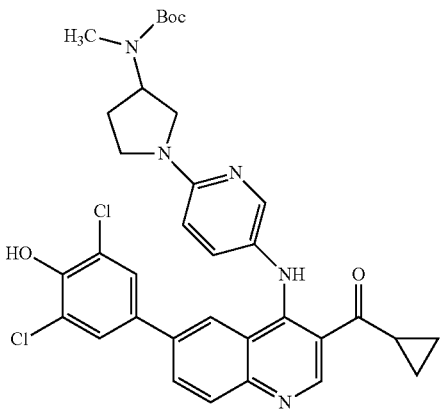 [SMILES: CN(C(=O)OC(C)(C)C)C1CCN(c2ccc(Nc3c(C(=O)C4CC4)cnc4ccc(-c5cc(Cl)c(O)c(Cl)c5)cc34)cn2)C1]

Following general procedure M, tert-butyl (1-(5-((6-bromo-3-(cyclopropanecarbonyl)quinolin-4-yl)amino)pyridin-2-yl)pyrrolidin-3-yl)(methyl)carbamate (98 mg, 0.173 mmol) was reacted with 2,6-dichloro-4-(4,4,5,5-tetramethyl-1,3,2-dioxaborolan-2-yl)phenol (80 mg, 0.275 mmol) to afford the desired product (90 mg, 80%) as a brown solid. ESI MS m/z 647 $[C_{34}H_{35}Cl_2N_5O_4+H]^+$ Example 804 cyclopropyl(6-(3,5-dichloro-4-hydroxyphenyl)-4-((6-(3-(methylamino)pyrrolidin-1-yl)pyridin-3-yl)amino)quinolin-3-yl)methanone trihydrochloride

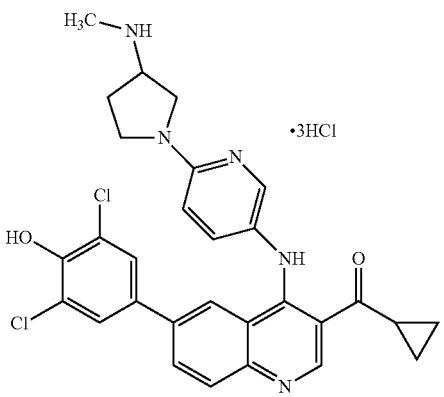 [SMILES: CNC1CCN(c2ccc(Nc3c(C(=O)C4CC4)cnc4ccc(-c5cc(Cl)c(O)c(Cl)c5)cc34)cn2)C1]

To a solution of tert-butyl (1-(5-((3-(cyclopropanecarbonyl)-6-(3,5-dichloro-4-hydroxyphenyl)quinolin-4-yl)amino)pyridin-2-yl)pyrrolidin-3-yl)(methyl)carbamate (90 mg, 0.14 mmol) in THF (3 mL) was added TFA (2 mL). The reaction mixture was heated at 65° C. for 16 h, cooled to room temperature and concentrated. The resultant residue was purified by preparative HPLC (C18 silica, 10-90% acetonitrile/water with 0.05% TFA). The residue was dissolved in methanol (8 mL) and HCl (6 M in water, 1.0 mL, 6 mmol) was added. The resultant solution was concentrated to give the desired product (12.3 mg, 13%) as an orange solid. $^1$H NMR (500 MHz, MeOD) δ 9.37 (s, 1H), 8.31-8.19 (m, 3H), 8.05 (d, J=8.8 Hz, 1H), 7.87 (dd, J=9.3, 2.7 Hz, 1H), 7.44 (s, 2H), 7.05 (d, J=9.3 Hz, 1H), 4.12-4.01 (m, 2H), 3.93-3.81 (m, 2H), 3.80-3.71 (m, 1H), 2.88-2.79 (m, 1H), 2.83 (s, 3H), 2.69-2.58 (m, 1H), 2.43-2.32 (m, 1H), 1.26-1.18 (m, 4H). ESI MS m/z 548 $[C_{29}H_{27}Cl_2N_5O_2+H]^+$; HPLC 95.9% (AUC), $t_R$=10.31 min.

Example 789

(6-(3-chloro-5-fluoro-4-hydroxyphenyl)-4-((6-(3-(methylamino)pyrrolidin-1-yl)pyridin-3-yl)amino)quinolin-3-yl)(cyclopropyl)methanone trihydrochloride

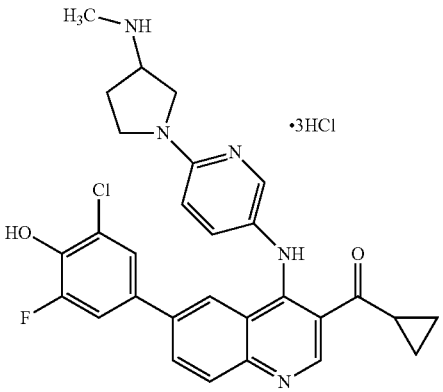 [SMILES: CNC1CCN(c2ccc(Nc3c(C(=O)C4CC4)cnc4ccc(-c5cc(F)c(O)c(Cl)c5)cc34)cn2)C1]

To a suspension of tert-butyl (1-(5-((6-bromo-3-(cyclopropanecarbonyl)quinolin-4-yl)amino)pyridin-2-yl)pyrrolidin-3-yl)(methyl)carbamate (88 mg, 0.155 mmol), 2,6-dichloro-4-(4,4,5,5-tetramethyl-1,3,2-dioxaborolan-2-yl)phenol (68 mg, 0.25 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, diluted with a saturated NaHCO$_3$ solution and extracted with ethyl acetate. The combined organic layers were dried over anhydrous sodium sulfate and concentrated. Purification by column chromatography (silica, 0-20% methanol/dichloromethane) afforded a brown solid. This solid was dissolved in TI-IF (3 mL) and TFA (2 mL). The reaction mixture was heated at 65° C. for 16 h, cooled to room temperature and concentrated. The resultant residue was purified by preparative HPLC (C18 silica, 10-90% acetonitrile/water with 0.05% TFA). The residue was dissolved in methanol (8 mL) and HCl (6 M in water, 1.0 mL, 6 mmol) was added. The resultant solution was concentrated to give the desired product (46.5 mg, 47%) as an orange solid. $^1$H NMR (500 MHz, MeOD) δ 9.34 (s, 1H), 8.36 (s, 1H), 8.31 (dd, J=8.8, 1.9 Hz, 1H), 8.24 (d, J=2.5 Hz, 1H), 8.08 (d, J=8.8 Hz, 1H), 8.02-7.95 (m, 1H), 7.41-7.33 (m, 2H), 7.20 (dd, J=9.6, 2.5 Hz, 1H), 4.17-4.07 (m, 2H), 3.99-3.88 (ddd, J=m, 2H), 3.85-3.76 (m, 1H), 2.84 (s, 3H), 2.83-2.75

(m, 1H), 2.72-2.61 (m, 1H), 2.49-2.38 (m, 1H), 1.24-1.12 (m, 4H). ESI MS m/z 532 [$C_{29}H_{27}ClFN_5O_2$+H]$^+$; HPLC 98.8% (AUC), $t_R$=10.10 min.

Example 806

1-(6-(3,5-dichloro-4-hydroxyphenyl)-4-((6-(3-(methylamino)piperidin-1-yl)pyridin-3-yl)amino)quinolin-3-yl)ethanone trihydrochloride

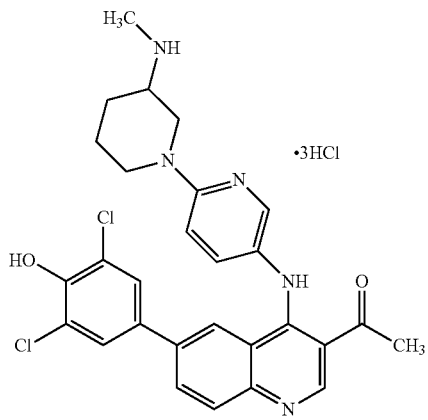 [SMILES: CNC1CCCN(c2ccc(Nc3c(C(C)=O)cnc4ccc(-c5cc(Cl)c(O)c(Cl)c5)cc34)cn2)C1]

To a suspension of tert-butyl (1-(5-((3-acetyl-6-bromoquinolin-4-yl)amino)pyridin-2-yl)piperidin-3-yl)(methyl)carbamate (80 mg, 0.144 mmol), 2,6-dichloro-4-(4,4,5,5-tetramethyl-1,3,2-dioxaborolan-2-yl)phenol (80 mg, 0.28 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, diluted with a saturated NaHCO$_3$ solution and extracted with ethyl acetate. The combined organic layers were dried over anhydrous sodium sulfate and concentrated. Purification by column chromatography (silica, 0-20% methanol/dichloromethane) afforded a brown solid. This solid was dissolved in THF (3 mL), water (2 mL) and HCl (6 M in water, 2 mL, 12 mmol). The reaction mixture was heated at 65° C. for 3 h, cooled to room temperature and concentrated. The resultant residue was purified by preparative HPLC (C18 silica, 10-90% acetonitrile/water with 0.05% TFA). The residue was dissolved in methanol (8 mL) and HCl (6 M in water, 1.0 mL, 6 mmol) was added. The resultant solution was concentrated to give the desired product (55.4 mg, 60%) as an orange solid. $^1$H NMR (500 MHz, MeOD) δ 9.30 (s, 1H), 8.29-8.21 (m, 2H), 8.06-8.00 (m, 2H), 7.83 (dd, J=9.1, 2.7 Hz, 1H), 7.30 (s, 2H), 7.30-7.26 (m, 1H), 4.47 (br s, 1H), 3.98 (d, J=13.4 Hz, 1H), 3.63 (br s, 1H), 3.50-3.40 (m, 1H), 3.37-3.32 (m, 1H), 2.80 (s, 3H), 2.80 (s, 3H), 2.30-2.23 (m, 1H), 2.03-1.95 (m, 1H), 1.88-1.69 (m, 2H). ESI MS m/z 536 [$C_{28}H_{27}Cl_2N_5O_2$+H]$^+$; HPLC>99% (AUC), $t_R$=10.17 min.

Example 815

1-(6-(3-chloro-5-fluoro-4-hydroxyphenyl)-4-((6-(3-(methylamino)piperidin-1-yl)pyridin-3-yl)amino)quinolin-3-yl)ethanone trihydrochloride

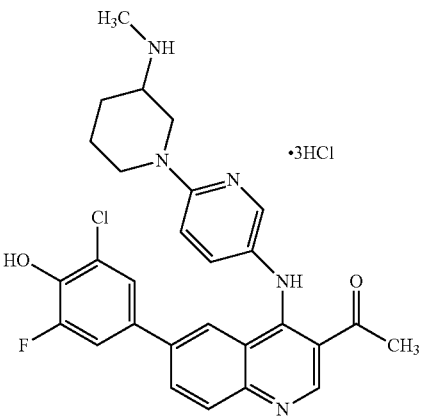

To a suspension of tert-butyl (1-(5-((3-acetyl-6-bromoquinolin-4-yl)amino)pyridin-2-yl)piperidin-3-yl)(methyl)carbamate (80 mg, 0.144 mmol), 2-chloro-6-fluoro-4-(4,4,5,5-tetramethyl-1,3,2-dioxaborolan-2-yl)phenol (68 mg, 0.28 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, diluted with a saturated NaHCO$_3$ solution and extracted with ethyl acetate. The combined organic layers were dried over anhydrous sodium sulfate and concentrated. Purification by column chromatography (silica, 0-20% methanol/dichloromethane) afforded a brown solid. This solid was dissolved in THF (3 mL), water (3 mL) and HCl (6 M in water, 2 mL, 12 mmol). The reaction mixture was heated at 65° C. for 4 h, cooled to room temperature and concentrated. The resultant residue was purified by preparative HPLC (C18 silica, 10-90% acetonitrile/water with 0.05% TFA). The residue was dissolved in methanol (8 mL) and HCl (6 M in water, 1.0 mL, 6 mmol) was added. The resultant solution was concentrated to give the desired product (63.2 mg, 70%) as an orange solid. $^1$H NMR (500 MHz, MeOD) δ 9.28 (s, 1H), 8.29-8.19 (m, 2H), 8.04-7.96 (m, 2H), 7.78 (d, J=9.5 Hz, 1H), 7.24 (d, J=9.3 Hz, 1H), 7.13-7.06 (m, 2H), 4.46 (br s, 1H), 3.96 (d, J=13.1 Hz, 1H), 3.61 (br s, 1H), 3.48-3.37 (m, 1H), 2.82 (s, 3H), 2.80 (s, 3H), 2.28-2.24 (m, 1H), 2.02-1.94 (m, 1H), 1.88-1.70 (m, 2H). ESI MS m/z 520 [C$_{32}$H$_{32}$Cl$_2$N$_4$O$_2$+H]$^+$; HPLC 98.8% (AUC), t$_R$=9.82 min.

Example 807 cyclopropyl(6-(3,5-dichloro-4-hydroxyphenyl)-4-((6-(3-(methylamino)piperidin-1-yl)pyridin-3-ylamino)quinolin-3-yl)methanone trihydrochloride

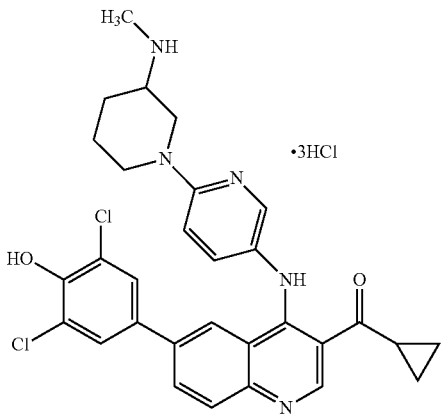 [SMILES: CNC1CCCN(c2ccc(Nc3c(C(=O)C4CC4)cnc4ccc(-c5cc(Cl)c(O)c(Cl)c5)cc34)cn2)C1]

To a suspension of tert-butyl (1-(5-((6-bromo-3-(cyclopropanecarbonyl)quinolin-4-yl)amino)pyridin-2-yl)piperidin-3-yl)(methyl)carbamate (80 mg, 0.137 mmol), 2,6-dichloro-4-(4,4,5,5-tetramethyl-1,3,2-dioxaborolan-2-yl)phenol (80 mg, 0.28 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, diluted with a saturated NaHCO$_3$ solution and extracted with ethyl acetate. The combined organic layers were dried over anhydrous sodium sulfate and concentrated. Purification by column chromatography (silica, 0-20% methanol/dichloromethane) afforded a brown solid. This solid was dissolved in THF (3 mL) and TFA (2 mL). The reaction mixture was heated at 65° C. for 16 h, cooled to room temperature and concentrated. The resultant residue was purified by preparative HPLC (C18 silica, 10-90% acetonitrile/water with 0.05% TFA). The residue was dissolved in methanol (8 mL) and HCl (6 M in water, 1.0 mL, 6 mmol) was added. The resultant solution was concentrated to give the desired product (39.6 mg, 43%) as an orange solid. $^1$H NMR (500 MHz, MeOD) δ 9.39 (s, 1H), 8.29-8.21 (m, 2H), 8.19 (s, 1H), 8.04 (d, J=8.8 Hz, 1H), 7.78 (dd, J=9.3, 2.7 Hz, 1H), 7.40 (s, 2H), 7.25 (d, J=9.3 Hz, 1H), 4.44 (br s, 1H), 4.00-3.92 (m, 1H), 3.61 (br s, 1H), 3.48-3.36 (m, 1H), 3.37-3.32 (m, 1H), 2.89-2.81 (s, 1H), 2.80 (s, 3H), 2.28-2.22 (m, 1H), 2.02-1.94 (m, 1H), 1.87-1.69 (m, 2H), 1.24-1.16 (m, 4H). ESI MS m/z 561 [C$_{30}$H$_{29}$Cl$_2$N$_5$O$_2$+H]$^+$; HPLC 97.8% (AUC), t$_R$=10.73 min.

Example 814

1-(6-(3,5-dichloro-4-hydroxyphenyl)-4-((1-(1-methylpyrrolidin-3-yl)-1H-pyrazol-4-yl)amino)quinolin-3-yl)ethanone dihydrochloride

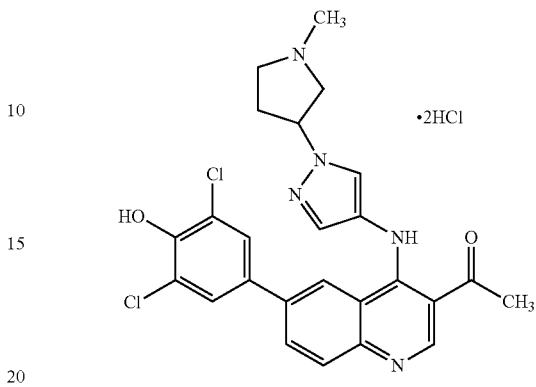

To a suspension of 1-(6-bromo-4-((1-(1-methylpyrrolidin-3-yl)-1H-pyrazol-4-yl)amino)quinolin-3-yl)ethanone (80 mg, 0.19 mmol), 2,6-dichloro-4-(4,4,5,5-tetramethyl-1,3,2-dioxaborolan-2-yl)phenol (80 mg, 0.28 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, diluted with a saturated NaHCO$_3$ solution and extracted with ethyl acetate. The combined organic layers were dried over anhydrous sodium sulfate and concentrated. Purification by column chromatography (silica, 0-20% methanol/dichloromethane) afforded a residue that was further purified by preparative HPLC (C18 silica, 10-90% acetonitrile/water with 0.05% TFA). The resultant residue was dissolved in methanol (8 mL) and HCl (6 M in water, 1.0 mL, 6 mmol) was added. The resultant solution was concentrated to give the desired product (66.2 mg, 60%) as a yellow solid. $^1$H NMR (500 MHz, MeOD) δ 9.27 (br s, 1H), 8.26-8.17 (m, 2H), 8.11 (s, 1H), 8.02 (d, J=8.8 Hz, 1H), 7.79 (s, 1H), 7.37 (s, 2H), 5.41 (br s, 1H), 4.25-3.93 (m, 2H), 3.84-3.32 (m, 2H), 3.21-3.03 (m, 3H), 2.82-2.78 (br s, 1H), 2.80 (3, 3H), 2.39 (br s, 1H). ESI MS m/z 496 [C$_{25}$H$_{23}$Cl$_2$N$_5$O$_2$+H]$^+$; HPLC>99% (AUC), t$_R$=9.56 min.

Example 813

1-(6-(3-chloro-5-fluoro-4-hydroxyphenyl)-4-((1-(1-methylpyrrolidin-3-yl)-1H-pyrazol-4-yl)amino)quinolin-3-yl)ethanone dihydrochloride

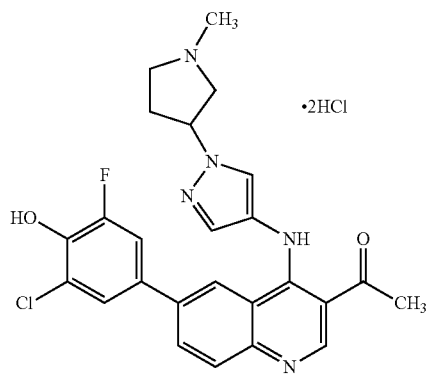 [SMILES: CC(=O)c1cnc2ccc(-c3cc(F)c(O)c(Cl)c3)cc2c1Nc1cnn(C2CCN(C)C2)c1]

To a suspension of 1-(6-bromo-4-((1-(1-methylpyrrolidin-3-yl)-1H-pyrazol-4-yl)amino)quinolin-3-yl)ethanone (80 mg, 0.19 mmol), 2-chloro-6-fluoro-4-(4,4,5,5-tetramethyl-1,3,2-dioxaborolan-2-yl)phenol (68 mg, 0.25 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, diluted with a saturated NaHCO$_3$ solution and extracted with ethyl acetate. The combined organic layers were dried over anhydrous sodium sulfate and concentrated. Purification by column chromatography (silica, 0-20% methanol/dichloromethane) afforded a residue that was dissolved in methanol (8 mL) and HCl (6 M in water, 1.0 mL, 6 mmol) was added. The resultant solution was concentrated to give the desired product (69.8 mg, 65%) as a yellow solid. $^1$H NMR (500 MHz, MeOD) δ 9.28 (s, 1H), 8.26-8.17 (m, 2H), 8.12 (s, 1H), 8.05-7.99 (d, J=8.8 Hz, 1H), 7.82-7.77 (m, 1H), 7.25 (s, 1H), 7.13 (d, J=11.3 Hz, 1H), 5.46-5.34 (m, 1H), 4.28-3.96 (m, 2H), 3.88-3.55 (m, 1H), 3.41-3.32 (m, 1H), 3.15 (s, 1H), 3.05 (s, 2H), 2.93-2.81 (m, 1H), 2.80 (s, 3H), 2.68-2.33 (m, 1H). ESI MS m/z 480 [C$_{25}$H$_{23}$ClFN$_5$O$_2$+H]$^+$; HPLC>99% (AUC), t$_R$=9.44 min.

Example 943

1-(6-(3-chloro-5-fluoro-4-hydroxyphenyl)-4-((trans-4-((dimethylamino)methyl)cyclohexyl)amino)quinolin-3-yl)ethanone dihydrochloride

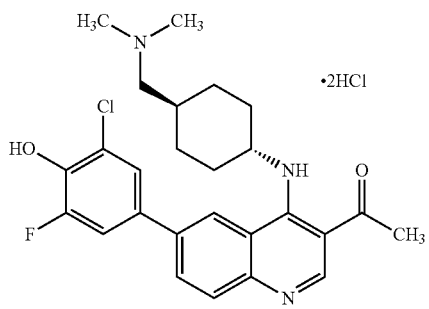 [SMILES: CC(=O)c1cnc2ccc(-c3cc(F)c(O)c(Cl)c3)cc2c1N[C@H]1CC[C@H](CN(C)C)CC1]

To a suspension of 1-(6-(3-chloro-5-fluoro-4-hydroxyphenyl)-4-((trans-4-((dimethylamino)methyl)cyclohexyl)amino)quinolin-3-yl)ethanone (3.06 g, 6.51 mmol) in methanol (250 mL) was added HCl (1.25 M in MeOH, 25 mL, 31.2 mmol). The resultant suspension was partially concentrated, filtered and rinsed with ethyl acetate to give the desired product (3.10 g, 88%) as a light yellow solid. $^1$H NMR (500 MHz, MeOD) δ 9.00 (s, 1H), 8.38 (d, J=2.0 Hz, 1H), 8.10 (dd, J=8.7, 2.0 Hz, 1H), 7.93 (d, J=8.7 Hz, 1H), 7.54 (dd, J=2.2, 1.5 Hz, 1H), 7.46 (dd, J=11.5, 2.3 Hz, 1H), 4.38-4.29 (m, 1H), 3.06 (d, J=6.6 Hz, 2H), 2.91 (s, 6H), 2.71 (s, 3H), 2.40 (d, J=12.7 Hz, 2H), 2.04-1.95 (m, 3H), 1.75-1.65 (m, 2H), 1.31 (q, J=12.8 Hz, 2H). ESI MS m/z 470 [C$_{26}$H$_{29}$ClFN$_3$O$_2$+H]$^+$; HPLC>99% (AUC), t$_R$=9.75 min.

Example 836

1-(6-(3,5-dichloro-4-hydroxyphenyl)-4-((1-(1-methylpiperidin-4-yl)-1H-pyrazol-4-yl)amino)quinolin-3-yl)ethanone dihydrochloride

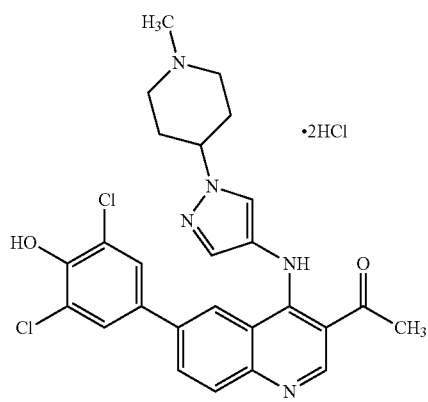 [SMILES: CC(=O)c1cnc2ccc(-c3cc(Cl)c(O)c(Cl)c3)cc2c1Nc1cnn(C2CCN(C)CC2)c1]

To a suspension of 1-(6-bromo-4-((1-(1-methylpiperidin-4-yl)-1H-pyrazol-4-yl)amino)quinolin-3-yl)ethanone (50 mg, 0.116 mmol), 2,6-dichloro-4-(4,4,5,5-tetramethyl-1,3,2-dioxaborolan-2-yl)phenol (43 mg, 0.15 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). N$_2$ gas was bubbled through the reaction mixture and the mixture was then heated at 80° C. for 2 h. The solution was allowed to cool to room temperature, diluted with a saturated NaHCO$_3$ solution and extracted with ethyl acetate. The combined organic layers were dried over anhydrous sodium sulfate and concentrated. Purification by column chromatography (silica, 0-20% methanol/dichloromethane) afforded a residue that was dissolved in methanol (4 mL) and HCl (1.25 M in methanol, 1.0 mL, 1.25 mmol) was added. The resultant solution was concentrated to give the desired product (18.6 mg, 27%) as a yellow solid. $^1$H NMR (500 MHz, MeOD) δ 9.26 (s, 1H), 8.25-8.18 (m, 1H), 8.18-8.07 (m, 2H), 8.00 (d, J=8.8 Hz, 1H), 7.71 (s, 1H), 7.36-7.32 (m, 2H), 4.70-4.61 (m, 1H), 3.68 (d, 2H), 3.53-3.45 (m, 1H), 3.41-3.22 (m, 1H), 2.94 (s, 3H), 2.80 (s, 3H), 2.53-2.33 (m, 4H). ESI MS m/z 510 [C$_{26}$H$_{25}$Cl$_2$N$_5$O$_2$+H]$^+$; HPLC 97.4% (AUC), t$_R$=9.46 min.

Example 864

1-(6-(3,5-dichloro-4-hydroxyphenyl)-4-((trans-4-((dimethyl-d$_6$-amino)methyl)cyclohexyl)amino)quinolin-3-yl)ethanone dihydrochloride

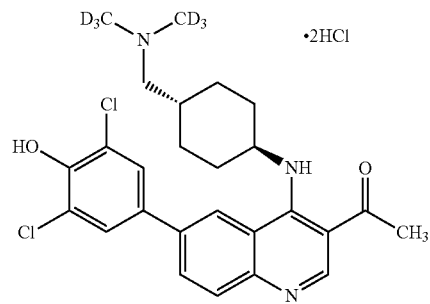 [SMILES: [2H]C([2H])([2H])N(C[C@H]1CC[C@H](Nc2c(C(C)=O)cnc3ccc(-c4cc(Cl)c(O)c(Cl)c4)cc23)CC1)C([2H])([2H])[2H]]

To a suspension of 1-(6-bromo-4-((trans-4-((dimethyl-$d_6$-amino)methyl)cyclohexyl)amino)quinolin-3-yl)ethanone (273 mg, 0.67 mmol), 2,6-dichloro-4-(4,4,5,5-tetramethyl-1,3,2-dioxaborolan-2-yl)phenol (289 mg, 1.0 mmol) and Pd(dppf)Cl$_2$ (49 mg, 0.067 mmol) in dioxane (20 mL) was added Cs$_2$CO$_3$ (1.0 M in H$_2$O, 2 mL, 2 mmol). N$_2$ gas was bubbled through the reaction mixture and the mixture was then heated at 80° C. for 2 h. The solution was allowed to cool to room temperature, diluted with a saturated NaHCO$_3$ solution and extracted with a mixture of CHCl$_3$/isopropanol (3:1). The combined organic layers were dried over anhydrous sodium sulfate. Purification by column chromatography (silica, 0-20% methanol/dichloromethane) afforded a residue that was dissolved in methanol (20 mL) and HCl (1.25 M in methanol, 8.0 mL, 12 mmol) was added. The resultant solution was concentrated to give the desired product (245 mg, 75%) as a light brown solid. $^1$H NMR (500 MHz, MeOD) δ 9.11 (s, 1H), 8.47 (s, 1H), 8.27 (dd, J=8.8, 1.8 Hz, 1H), 7.99 (d, J=8.8 Hz, 1H), 7.73 (s, 2H), 4.54 (br s, 1H), 3.08 (d, J=6.6 Hz, 2H), 2.74 (s, 3H), 2.46 (d, J=12.3 Hz, 2H), 2.10-2.00 (m, 3H), 1.87-1.75 (m, 2H), 1.36 (q, J=12.9 Hz, 2H). ESI MS m/z 492 [C$_{26}$H$_{23}$D$_6$Cl$_2$N$_3$O$_2$+H]$^+$; HPLC>99% (AUC), t$_R$=9.81 min.

Example 1179 tert-butyl 1-(5-(6-(3,5-dichloro-4-hydroxyphenyl)-3-propionylquinolin-4-ylamino)pyridin-2-yl)piperidin-3-ylcarbamate

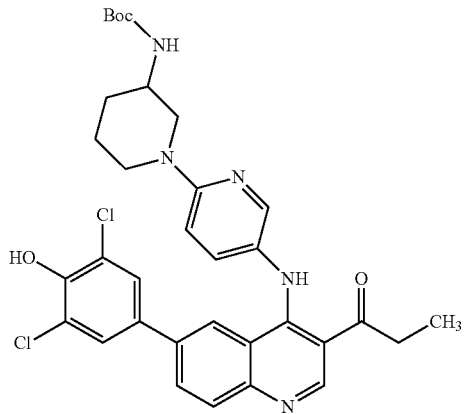 [SMILES: CCC(=O)c1cnc2ccc(-c3cc(Cl)c(O)c(Cl)c3)cc2c1Nc1ccc(N2CCCC(NC(=O)OC(C)(C)C)C2)nc1]

Following general procedure D, tert-butyl tert-butyl 1-(5-(6-bromo-3-propionyl quinolin-4-ylamino)pyridin-2-yl)piperidin-3-ylcarbamate (46 mg, 0.091 mmol) was reacted with 2,6-dichloro-4-(4,4,5,5-tetramethyl-1,3,2-dioxaborolan-2-yl)phenol (39 mg, 0.137 mmol) to afford the desired product (35 mg, 60%) as an yellow solid: ESI MS m/z 636, [C$_{33}$H$_{35}$Cl$_2$N$_5$O$_4$+H]$^+$

Example 1180 tert-butyl 1-(5-(6-(3-chloro-5-fluoro-4-hydroxyphenyl)-3-propionylquinolin-4-ylamino)pyridin-2-yl)piperidin-3-ylcarbamate

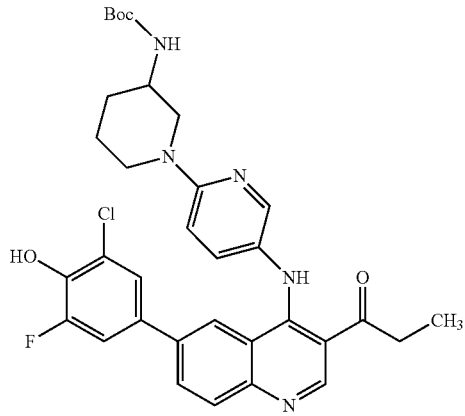 [SMILES: CCC(=O)c1cnc2ccc(-c3cc(F)c(O)c(Cl)c3)cc2c1Nc1ccc(N2CCCC(NC(=O)OC(C)(C)C)C2)nc1]

Following general procedure D, tert-butyl 1-(5-(6-bromo-3-propionylquinolin-4-ylamino)pyridin-2-yl)piperidin-3-ylcarbamate (46 mg, 0.091 mmol) was reacted with 2-chloro-6-fluoro-4-(4,4,5,5-tetramethyl-1,3,2-dioxaborolan-2-yl)phenol (37 mg, 0.137 mmol) to afford the desired product (32 mg, 60%) as an yellow solid: ESI MS m/z 619, [C$_{33}$H$_{35}$ClFN$_5$O$_4$+H]$^+$

Example 1181 tert-butyl 1-((1R,4R)-4-(3-acetyl-6-(3-chloro-5-fluoro-4-hydroxyphenyl)quinolin-4-ylamino)cyclohexylamino)-1-oxopropan-2-ylcarbamate

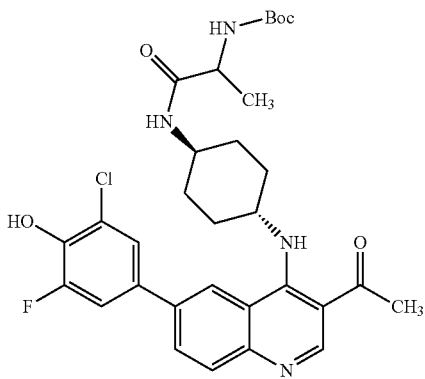 [SMILES: CC(=O)c1cnc2ccc(-c3cc(F)c(O)c(Cl)c3)cc2c1N[C@H]1CC[C@H](NC(=O)C(C)NC(=O)OC(C)(C)C)CC1]

Following general procedure D, tert-butyl 1-((1R,4R)-4-(3-acetyl-6-bromoquinolin-4-ylamino)cyclohexylamino)-1-oxopropan-2-ylcarbamate (70 mg, 0.131 mmol) was reacted with 2-chloro-6-fluoro-4-(4,4,5,5-tetramethyl-1,3,2-dioxaborolan-2-yl)phenol (42 mg, 0.157 mmol) to afford the desired product (42 mg, 53%) as an orange solid: ESI MS m/z 599, $[C_{31}H_{36}ClFN_4O_5+H]^+$ Example 1182 tert-butyl 1-((1R,4R)-4-(3-acetyl-6-(3-chloro-5-fluoro-4-hydroxyphenyl)quinolin-4-ylamino)cyclohexylamino)-3-methyl-1-oxobutan-2-ylcarbamate

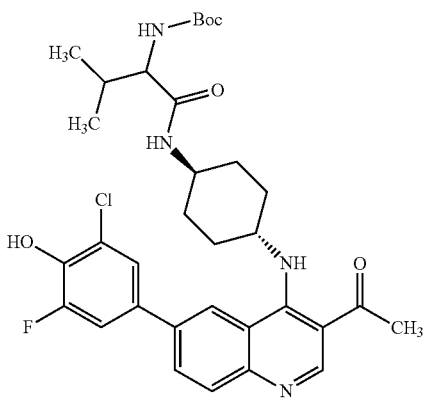 [SMILES: CC(=O)c1cnc2ccc(-c3cc(F)c(O)c(Cl)c3)cc2c1N[C@H]1CC[C@H](NC(=O)C(NC(=O)OC(C)(C)C)C(C)C)CC1]

Following general procedure D, tert-butyl 1-(1R,4R)-4-(3-acetyl-6-bromoquinolin-4-ylamino)cyclohexylamino)-3-methyl-1-oxobutan-2-ylcarbamate (70 mg, 0.131 mmol) was reacted with 2-chloro-6-fluoro-4-(4,4,5,5-tetramethyl-1,3,2-dioxaborolan-2-yl)phenol (40 mg, 0.150 mmol) to afford the desired product (24 mg, 31%) as an yellow solid: ESI MS m/z 627, $[C_{33}H_{40}ClFN_4O_5+H]^+$ Example 1183 tert-Butyl (1r,4r)-4-(3-acetyl-6-(3-chloro-4-hydroxy-5-methoxyphenyl)quinolin-4-ylamino)cyclohexyl(methyl)carbamate

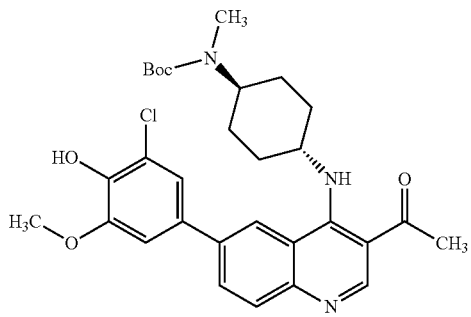 [SMILES: COc1cc(-c2ccc3ncc(C(C)=O)c(N[C@H]4CC[C@H](N(C)C(=O)OC(C)(C)C)CC4)c3c2)cc(Cl)c1O]

Following general procedure D, tert-butyl (1r,4r)-4-(3-acetyl-6-bromoquinolin-4-ylamino)cyclohexyl(methyl)carbamate (60 mg, 0.126 mmol) was reacted with 2-chloro-6-methoxy-4-(4,4,5,5-tetramethyl-1,3,2-dioxaborolan-2-yl) phenol (43 mg, 0.152 mmol) to afford the desired product (53 mg, 72%) as a yellow brown solid; ESI MS m/z 580, $[C_{32}H_{38}ClN_3O_5+H]^+$ Example 1184 tert-butyl (1r,4r)-4-(3-acetyl-6-(3,5-dichloro-4-hydroxyphenyl)quinolin-4-ylamino)cyclohexyl(methyl) carbamate

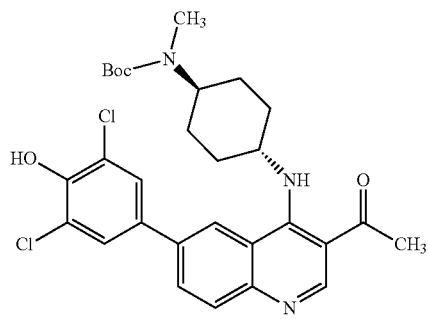 [SMILES: CC(=O)c1cnc2ccc(-c3cc(Cl)c(O)c(Cl)c3)cc2c1N[C@H]1CC[C@H](N(C)C(=O)OC(C)(C)C)CC1]

Following general procedure D, tert-butyl (1r,4r)-4-(3-acetyl-6-bromoquinolin-4-ylamino)cyclohexyl(methyl)carbamate (60 mg, 0.126 mmol) was reacted with 2,6-dichloro-4-(4,4,5,5-tetramethyl-1,3,2-dioxaborolan-2-yl)phenol (44 mg, 0.151 mmol) to afford the desired product (60 mg, 81%) as a yellow brown solid: ESI MS m/z 584, $[C_{31}H_{35}Cl_2N_3O_4+H]^+$ Example 487

1-(6-(3-Chloro-5-fluoro-4-hydroxyphenyl)-4-(6-(4-methylpiperazin-1-yl)pyridin-3-ylamino)quinolin-3-yl)ethanone

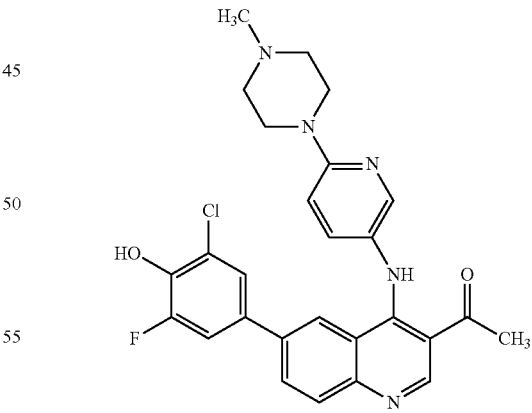

Following general procedure D, [1-(6-bromo-4-(6-(4-methylpiperazin-1-yl)pyridin-3-ylamino)quinolin-3-yl)ethanone (50 mg, 0.113 mmol) was reacted with 2-chloro-6-fluoro-4-(4,4,5,5-tetramethyl-1,3,2-dioxaborolan-2-yl)phenol (34 mg, 0.124 mmol) to afford the desired product (18 mg, 31%) as a yellow-orange solid: $^1$H NMR (500 MHz, CD$_3$OD) δ 9.08 (s, 1H), 8.07 (d, J=3 Hz, 1H), 7.91 (s, 2H), 7.82 (s, 1H), 7.49 (dd, J=12, 2.0 Hz, 1H), 7.00-6.92 (m, 3H), 3.66 (t, J=10

Hz, 4H), 2.77 (s, 3H), 2.62 (t, J=10 Hz, 4H), 2.39 (s, 3H); ESI MS m/z 506, $[C_{27}H_{25}ClFN_5O_2+H]^+$; HPLC 98.9% (AUC), $t_R$=14.39 min.

Example 513

(6-(3-Chloro-4-hydroxy-5-methoxyphenyl)-4-(1R,4R)-4-((dimethylamino)methyl)cyclohexylamino)quinolin-3-yl)(cyclopropyl)methanone

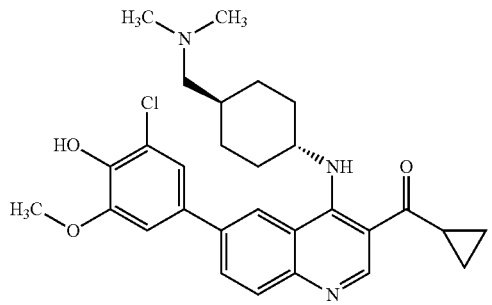 [SMILES: COc1cc(-c2ccc3ncc(C(=O)C4CC4)c(N[C@H]4CC[C@H](CN(C)C)CC4)c3c2)cc(Cl)c1O]

Following general procedure D, (6-bromo-4-(1R,4R)-4-((dimethylamino)methyl)cyclohexylamino)quinolin-3-yl)(cyclopropyl)methanone (60 mg, 0.139 mmol) was reacted with 2-chloro-6-methoxy-4-(4,4,5,5-tetramethyl-1,3,2-dioxaborolan-2-yl)phenol (48 mg, 0.167 mmol) to afford the desired product (25 mg, 35%) as a green-yellow solid: $^1$H NMR (500 MHz, CD$_3$OD) δ 9.16 (s, 1H), 8.34 (d, J=2 Hz, 1H), 7.99 (dd, J=11, 2 Hz, 1H), 7.89 (d, J=8.5 Hz, 1H), 7.24 (d, J=2.5 Hz, 1H), 7.1 (d, J=2 Hz, 1H), 4.61 (d, J=3.5 Hz, 1H), 3.97 (s, 3H), 2.85 (quint, J=15.5 Hz, 1H), 2.51 (d, J=7 Hz, 3H) 2.43 (s, 3H), 2.00 (m, 2H), 1.90 (m, 2H) 1.75 (m, 3H), 1.19 (q, J=10.5 Hz, 2H), 1.10 (quint, J=14.5, 2H); ESI MS m/z 508, $[C_{29}H_{34}ClN_3O_3+H]^+$; HPLC 99.0% (AUC), $t_R$=9.64 min.

Example 518

2-(((((1R,4R)-4-(6-(3-chloro-4-hydroxy-5-methoxyphenyl)-3-(cyclopropane carbonyl)quinolin-4-ylamino)cyclohexyl)methyl)(methyl)amino)acetonitrile

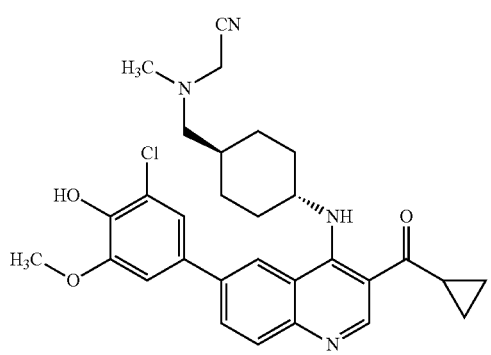 [SMILES: COc1cc(-c2ccc3ncc(C(=O)C4CC4)c(N[C@H]4CC[C@H](CN(C)CC#N)CC4)c3c2)cc(Cl)c1O]

Following general procedure D, 2-(((((1R,4R)-4-(6-bromo-3-(cyclopropanecarbonyl)quinolin-4-ylamino)cyclohexyl)methyl)(methyl)amino)acetonitrile (40 mg, 0.087 mmol) was reacted with 2-chloro-6-methoxy-4-(4,4,5,5-tetramethyl-1,3,2-dioxaborolan-2-yl)phenol (29 mg, 0.105 mmol) to afford the desired product (15 mg, 32%) as a yellow solid: $^1$H NMR (500 MHz, CD$_3$OD) δ 9.16 (s, 1H), 8.35 (s, 1H), 7.98 (dd, J=10.5, 1.5 Hz, 1H), 7.88 (d, J=8.5 Hz, 1H), 7.25 (d, J=2 Hz, 1H), 7.18 (d, J=1.5 Hz, 1H), 4.59 (s, 1H), 3.97 (s, 3H), 3.66 (s, 2H) 2.84 (quint, J=15.5 Hz, 1H), 2.39 (d, J=7 Hz, 2H) 2.35 (s, 3H) 1.98 (m, 2H), 1.87 (m, 2H), 1.73 (m, 3H), 1.45 (q, J=11 Hz, 2H) 1.21 (q, J=16.5 Hz, 2H), 1.10 (d, J=4 Hz, 2H); ESI MS m/z 533, $[C_{30}H_{33}ClN_4O_3+H]^+$; HPLC 96.4% (AUC), $t_R$=12.62 min.

Example 524

2-(((((1R,4R)-4-(6-(3-Chloro-5-fluoro-4-hydroxyphenyl)-3-(cyclopropanecarbonyl)quinolin-4-ylamino)cyclohexyl)methyl)(methyl)amino)acetonitrile

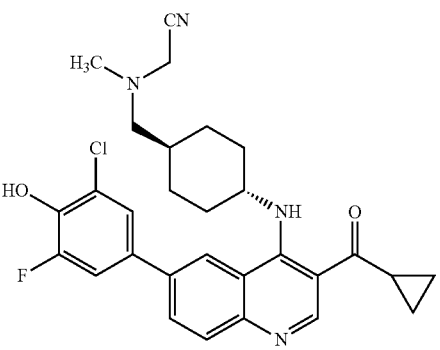 [SMILES: CN(CC#N)C[C@H]1CC[C@H](Nc2c(C(=O)C3CC3)cnc3ccc(-c4cc(F)c(O)c(Cl)c4)cc23)CC1]

Following general procedure D, 2-(((((1R,4R)-4-(6-bromo-3-(cyclopropanecarbonyl)quinolin-4-ylamino)cyclohexyl)methyl)(methyl)amino)acetonitrile (40 mg, 0.087 mmol) was reacted with 2-chloro-6-fluoro-4-(4,4,5,5-tetramethyl-1,3,2-dioxaborolan-2-yl)phenol (28 mg, 0.105 mmol) to afford the desired product (18 mg, 39%) as a yellow solid: $^1$H NMR (500 MHz, DMSO-d$_6$) δ 10.38 (s, 1H), 9.16 (s, 1H), 8.34 (s, 1H), 8.04 (dd, J=10.5, 1.5 Hz, 1H), 7.88 (d, J=8.5 Hz, 1H), 7.63 (m, 2H), 4.42 (s, 1H), 3.72 (s, 2H), 2.95 (quint, J=15.5 Hz, 1H), 2.28 (d, J=7.5 Hz, 2H) 2.24 (s, 3H) 1.79 (m, 4H), 1.64 (m, 3H), 1.34 (m, 2H), 1.10 (q, J=12 Hz, 2H), 1.04 (m, 2H); ESI MS m/z 521, $[C_{29}H_{30}ClFN_4O_2+H]^+$; HPLC 94.9% (AUC), $t_R$=12.59 min.

Example 541

(6-(3-Chloro-5-fluoro-4-hydroxyphenyl)-4-(4-((dimethylamino)methyl)phenylamino)-7-fluoroquinolin-3-yl)(cyclopropyl)methanone

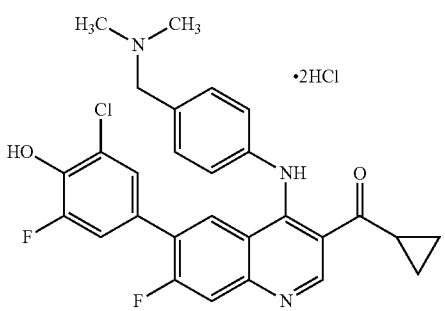 [SMILES: CN(C)Cc1ccc(Nc2c(C(=O)C3CC3)cnc3cc(F)c(-c4cc(F)c(O)c(Cl)c4)cc23)cc1]

Following general procedure D, ((6-bromo-4-(4-((dimethylamino)methyl)phenylamino)-7-fluoroquinolin-3-yl)(cyclopropyl)methanone (40 mg, 0.090 mmol) was reacted with 2-chloro-6-fluoro-4-(4,4,5,5-tetramethyl-1,3,2-dioxaborolan-2-yl)phenol (31 mg, 0.113 mmol) to afford the desired product (11 mg, 24%) as a yellow solid: $^1$H NMR (500 MHz, DMSO-$d_6$) δ 10.70 (s, 1H), 9.06 (s, 1H), 8.09 (d, J=8.5 Hz, 1H), 7.75 (d, J=12 Hz, 1H), 7.26 (d, J=8.5 Hz, 2H), 7.21 (d, J=6.5 Hz, 2H), 7.09 (d, J=8.5, 2H), 3.40 (s, 2H), 2.77 (quint, J=15 Hz, 1H), 2.13 (s, 6H), 0.86 (m, 4H); ESI MS m/z 508, $[C_{28}H_{24}ClF_2N_3O_2+H]^+$; HPLC 98.7% (AUC), $t_R$=10.83 min.

Example 542

1-(6-(3-chloro-4-hydroxy-5-methoxyphenyl)-4-(1R,4R)-4-(methylamino)cyclohexylamino)quinolin-3-yl)ethanone

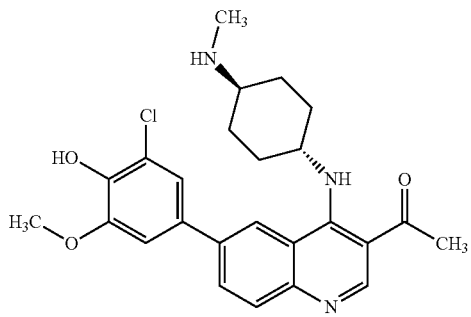 [SMILES: CN[C@H]1CC[C@H](Nc2c(C(C)=O)cnc3ccc(-c4cc(Cl)c(O)c(OC)c4)cc23)CC1]

tert-butyl(1r,4r)-4-(3-acetyl-6-(3-chloro-4-hydroxy-5-methoxyphenyl)quinolin-4-ylamino)cyclohexyl(methyl)carbamate (53 mg, 0.096 mmol) was dissolved in dichloromethane (5 mL). To this solution was added a 2.0 M HCl solution in diethyl ether (2 mL) the mixture was stirred for 16 h at room temperature where a precipitate formed. The precipitate was filtered off, washed with dichloromethane (10 mL), and eluted through an ion-exchange column (using methanol and 7 N ammonia in methanol) to obtain the desired product (11 mg, 25%) as a yellow solid: $^1$H NMR (500 MHz, DMSO-$d_6$) δ 10.56 (s, 1H), 8.94 (s, 1H), 8.28 (s, 1H), 8.05 (s, 1H), 7.87 (s, 1H), 7.29 (s, 2H), 4.17 (s, 1H), 3.95 (s, 3H), 2.66 (s, 3H), 2.38 (s, 4H), 2.23 (s, 2H), 2.03 (s, 2H), 1.67 (s, 1H), 1.51 (s, 2H), 1.30 (s, 3H), ESI MS m/z 454, $[C_{25}H_{28}ClN_3O_3+H]^+$; HPLC 99.5% (AUC), $t_R$=9.99 min.

Example 558

1-(6-(3,5-dichloro-4-hydroxyphenyl)-4-(1R,4R)-4-(methylamino)cyclohexylamino)quinolin-3-yl)ethanone

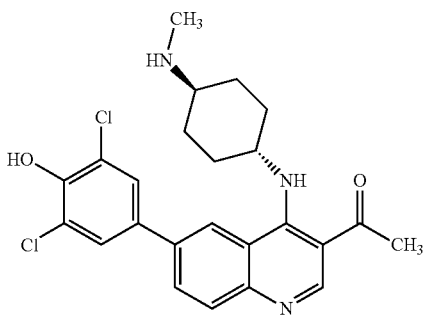 [SMILES: CN[C@H]1CC[C@H](Nc2c(C(C)=O)cnc3ccc(-c4cc(Cl)c(O)c(Cl)c4)cc23)CC1]

Following procedure A-2 tert-butyl(1r,4r)-4-(3-acetyl-6-(3,5-dichloro-4-hydroxyphenyl)quinolin-4-ylamino)cyclohexyl(methyl)carbamate (60 mg, 0.107 mmol) was treated with TFA (2 mL) to afford the desired product (8 mg, 16%) as a yellow-orange solid: $^1$H NMR (300 MHz, CD$_3$OD) δ 9.12 (s, 1H), 8.45 (s, 1H), 8.29 (d, J=8.7 Hz, 1H), 7.99 (d, J=8.7 Hz, 1H), 7.73 (s, 2H), 4.59 (s, 1H), 2.74 (s, 6H), 2.54 (t, J=13.5, 2H), 2.35 (d, J=11.4 Hz, 2H), 1.85 (m, 2H), 1.64 (m, 2H), 1.30 (m, 2H); ESI MS m/z 458, $[C_{24}H_{25}Cl_2N_3O_2+H]^+$; HPLC 99.2% (AUC), $t_R$=10.01 min.

Example 594

1-(6-(3-chloro-5-fluoro-4-hydroxyphenyl)-4-(2-(piperazin-1-yl)pyrimidin-5-ylamino)quinolin-3-yl)ethanone

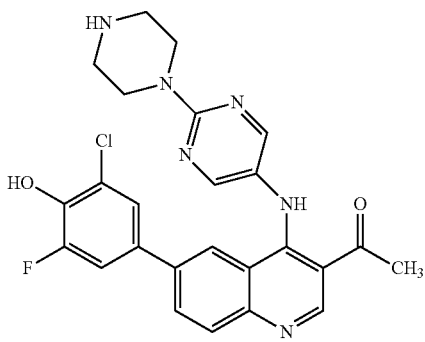 [SMILES: CC(=O)c1cnc2ccc(-c3cc(F)c(O)c(Cl)c3)cc2c1Nc1cnc(N2CCNCC2)nc1]

Following procedure A-2 tert-butyl 4-(5-(3-acetyl-6-(3-chloro-5-fluoro-4-hydroxyphenyl)quinolin-4-ylamino)pyrimidin-2-yl)piperazine-1-carboxylate (50 mg, 0.084 mmol) was treated with TFA (2 mL) to afford the desired product (11 mg, 26%) as a yellow solid: $^1$H NMR (500 MHz, CD$_3$OD) δ 9.29 (s, 1H), 8.55 (s, 2H), 8.23 (dd, J=11, 2 Hz, 1H), 8.02 (m, 2H), 7.12 (m, 2H), 4.21 (t, J=10 Hz, 4H), 3.35 (t, J=10.5 Hz, 4H) 2.80 (s, 3H); ESI MS m/z 493, $[C_{25}H_{22}ClFN_6O_2+H]^+$; HPLC 99.0% (AUC), $t_R$=9.90 min.

Example 608

1-(6-(3,5-dichloro-4-hydroxyphenyl)-4-((1R,4R)-4-((dimethylamino)methyl)cyclohexylamino)quinolin-3-yl)-2-methylpropan-1-one

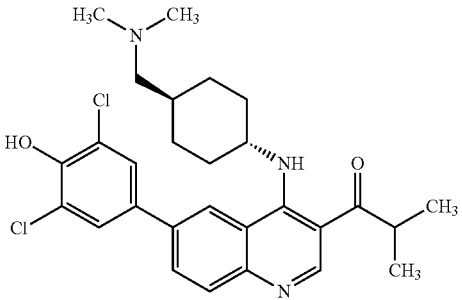 [SMILES: CC(C)C(=O)c1cnc2ccc(-c3cc(Cl)c(O)c(Cl)c3)cc2c1N[C@H]1CC[C@H](CN(C)C)CC1]

Following general procedure D, 1-(6-bromo-4-((1R,4R)-4-((dimethylamino)methyl)cyclohexylamino)quinolin-3-yl)-2-methylpropan-1-one (80 mg, 0.185 mmol) was reacted with 2,6-dichloro-4-(4,4,5,5-tetramethyl-1,3,2-dioxaborolan-2-yl)phenol (64 mg, 0.222 mmol) to afford the desired product (39 mg, 41%) as a yellow solid: $^1$H NMR (500 MHz, CD$_3$OD) δ 9.17 (s, 1H), 8.47 (s, 1H), 8.26 (dd, J=10, 1.5 Hz, 1H), 7.99 (d, J=8.5 Hz, 1H), 7.72 (s, 2H), 4.52 (s, 1H), 3.73 (t, J=11.5 Hz, 1H) 3.08 (d, J=6.5 Hz, 2H) 2.92 (s, 6H), 2.44 (s, 2H), 2.05 (d, J=11.5, 3H), 1.81 (q, J=35.5, 2H) 1.36 (m, 2H), 1.26 (d, J=6.5, 6H); ESI MS m/z 514, [C$_{28}$H$_{33}$Cl$_2$N$_3$O$_2$+H]$^+$; HPLC 98.9% (AUC), t$_R$=11.33 min.

Example 620

1-(6-(3-chloro-5-fluoro-4-hydroxyphenyl)-4-(1R, 4R)-4-((dimethylamino)methyl)cyclohexylamino) quinolin-3-yl)-2-methylpropan-1-one

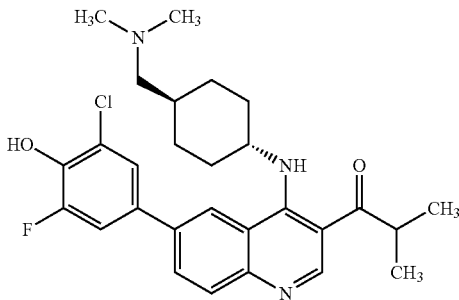 [SMILES: CC(C)C(=O)c1cnc2ccc(-c3cc(F)c(O)c(Cl)c3)cc2c1N[C@H]1CC[C@H](CN(C)C)CC1]

Following general procedure D, 1-(6-bromo-4-((1R,4R)-4-((dimethylamino)methyl)cyclohexyl amino)quinolin-3-yl)-2-methylpropan-1-one (64 mg, 0.148 mmol) was reacted with 2-chloro-6-fluoro-4-(4,4,5,5-tetramethyl-1,3,2-dioxaborolan-2-yl)phenol (60 mg, 0.222 mmol) to afford the desired product (18 mg, 24%) as a green-yellow solid: $^1$H NMR (300 MHz, CD$_3$OD) δ 8.92 (s, 1H), 8.29 (s, 1H), 7.95 (dd, J=10.5, 2 Hz, 1H), 7.84 (d, J=8.7 Hz, 1H), 7.45 (s, 1H), 7.35 (dd, J=14.1, 2.4 Hz, 1H) 4.16 (s, 1H), 3.74 (quint, J=13.5 Hz, 1H) 2.59 (d, J=7.2 Hz, 2H) 2.54 (s, 6H), 2.32 (d, J=12 Hz, 2H), 1.97 (d, J=12.9 Hz, 2H), 1.60 (q, J=35.5 Hz, 2H) 1.22 (m, 8H), ESI MS m/z 498, [C$_{28}$H$_{33}$ClFN$_3$O$_2$+H]$^+$; HPLC 98.7% (AUC), t$_R$=11.15 min.

Example 641

1-(6-(3,5-dichloro-4-hydroxyphenyl)-4-(4-((dimethylamino)methyl)phenylamino)quinolin-3-yl)-2-methylpropan-1-one

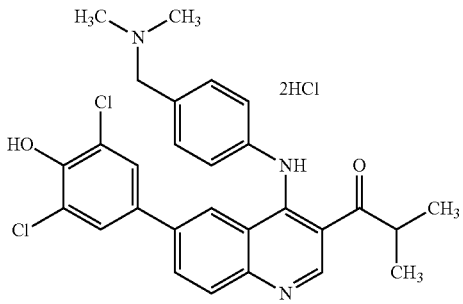 [SMILES: CC(C)C(=O)c1cnc2ccc(-c3cc(Cl)c(O)c(Cl)c3)cc2c1Nc1ccc(CN(C)C)cc1]

Following general procedure D, 1-(6-bromo-4-(4-((dimethylamino)methyl)phenylamino)quinolin-3-yl)-2-methylpropan-1-one (80 mg, 0.186 mmol) was reacted with 2,6-dichloro-4-(4,4,5,5-tetramethyl-1,3,2-dioxaborolan-2-yl)phenol (84 mg, 0.291 mmol) to afford the desired product (58 mg, 61%) as a yellow-green solid: $^1$H NMR (300 MHz, CD$_3$OD) δ 9.09 (s, 1H), 7.90 (s, 2H), 7.74 (s, 1H), 7.42 (d, J=8.4 Hz, 2H), 7.20 (d, J=8.1 Hz, 2H), 7.10 (s, 2H), 3.81 (m, 3H), 2.41 (s, 6H), 1.24 (d, J=6.6, 6H), ESI MS m/z 508, [C$_{28}$H$_{27}$Cl$_2$N$_3$O$_2$+H]$^+$; HPLC 99.7% (AUC), t$_R$=11.16 min.

Example 681

1-(4-(6-(3-aminopiperidin-1-yl)pyridin-3-ylamino)-6-(3,5-dichloro-4-hydroxyphenyl)quinolin-3-yl)ethanone

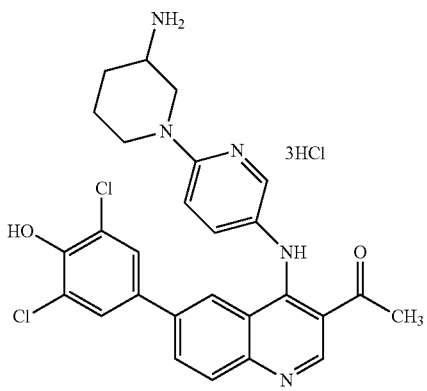 [SMILES: CC(=O)c1cnc2ccc(-c3cc(Cl)c(O)c(Cl)c3)cc2c1Nc1ccc(N2CCCC(N)C2)nc1]

tert-butyl 1-(5-(3-acetyl-6-(3,5-dichloro-4-hydroxyphenyl)quinolin-4-ylamino)pyridin-2-yl)piperidin-3-ylcarbamate (52 mg, 0.080 mmol) was dissolved in dichloromethane (5 mL). To this solution was added a 2.0 M HCl solution in diethyl ether (2 mL) the mixture was stirred for 16 h at room temperature where a precipitate formed. The precipitate was filtered off, washed with dichloromethane (10 mL), dried under vacuum to obtain the desired product as the HCl salt (40 mg, 79%) as a yellow-brown solid: $^1$H NMR (500 MHz, DMSO-d$_6$) δ 10.56 (s, 1H), 8.94 (s, 1H), 8.28 (s, 1H), 8.05 (s, 1H), 7.87 (s, 1H), 7.29 (s, 2H), 4.17 (s, 1H), 3.95 (s, 3H), 2.66 (s, 3H), 2.38 (s, 4H), 2.23 (s, 2H), 2.03 (s, 2H), 1.67 (s, 1H), 1.51 (s, 2H), 1.30 (s, 3H); ESI MS m/z 454, [C$_{25}$H$_{28}$ClN$_3$O$_3$+H]$^+$; HPLC 99.5% (AUC), t$_R$=9.99 min.

Example 733

1-(4-(6-(3-aminopiperidin-1-yl)pyridin-3-ylamino)-6-(3-chloro-5-fluoro-4-hydroxyphenyl)quinolin-3-yl)ethanone

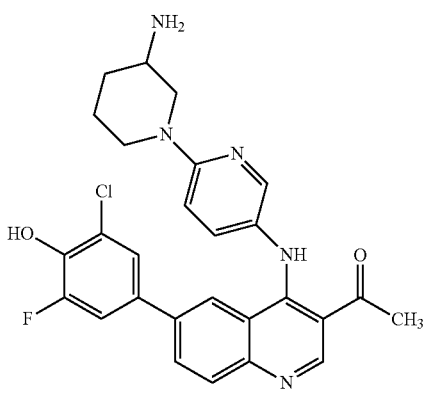 [SMILES: CC(=O)c1cnc2ccc(-c3cc(F)c(O)c(Cl)c3)cc2c1Nc1ccc(N2CCCC(N)C2)nc1]

719 tert-butyl 1-(5-(3-acetyl-6-(3-chloro-5-fluoro-4-hydroxyphenyl)quinolin-4-ylamino)pyridin-2-yl)piperidin-3-ylcarbamate (80 mg, 0.132 mmol) was dissolved in dichloromethane (5 mL). To this solution was added a 2.0 M HCl solution in diethyl ether (2 mL) the mixture was stirred for 16 h at room temperature where a precipitate formed. The precipitate was filtered off, washed with dichloromethane (10 mL), dried under vacuum to obtain the desired product as the HCl salt (30 mg, 45%) as a yellow-orange solid: $^1$H NMR (500 MHz, MeOD) δ 9.26 (s, 1H), 8.24 (d, J=2.9 Hz, 1H), 8.20 (dd, J=8.9, 1.9 Hz, 1H), 7.99 (d, J=8.9 Hz, 1H), 7.95 (d, J=2.0 Hz, 1H), 7.68 (dd, J=9.1, 2.8 Hz, 1H), 7.11 (d, J=9.1 Hz, 1H), 7.04 (m, 2H), 4.54 (s, 1H), 4.02 (d, J=12.7 Hz, 1H), 2.80 (s, 3H), 2.18 (m, 1H), 1.94 (m, 1H), 1.74 (m, 2H); ESI MS m/z 506, $[C_{27}H_{25}ClFN_5O_2+H]^+$; HPLC 95.2% (AUC), $t_R$=10.84 min.

Example 702

1-(6-(3,5-dichloro-4-hydroxyphenyl)-4-(2-(piperazin-1-yl)pyrimidin-5-ylamino)quinolin-3-yl)ethanone

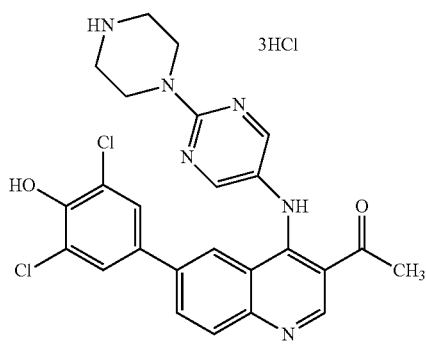 [SMILES: CC(=O)c1cnc2ccc(-c3cc(Cl)c(O)c(Cl)c3)cc2c1Nc1cnc(N2CCNCC2)nc1]

tert-butyl 4-(5-(3-acetyl-6-(3,5-dichloro-4-hydroxyphenyl)quinolin-4-ylamino)pyridin-2-yl)piperazine-1-carboxylate (65 mg, 0.106 mmol) was dissolved in dichloromethane (5 mL). To this solution was added a 2.0 M HCl solution in diethyl ether (2 mL) the mixture was stirred for 16 h at room temperature where a precipitate formed. The precipitate was filtered off, washed with dichloromethane (10 mL), dried under vacuum to obtain the desired product as the HCl salt (43 mg, 65%) as a yellow solid: $^1$H NMR (300 MHz, MeOD) δ 9.28 (s, 1H), 8.29 (d, J=2.7 Hz, 1H), 8.22 (dd, J=8.8, 2.0 Hz, 1H), 8.00 (m, 2H), 7.77 (dd, J=9.2, 2.7 Hz, 1H), 7.24 (s, 2H), 7.19 (d, J=9.2 Hz, 1H), 3.98 (t, J=5.3 Hz, 4H), 3.36 (t, J=5.3 Hz, 4H), 2.80 (s, 3H); ESI MS m/z 508, $[C_{25}H_{22}Cl_2N_6O_2+H]^+$; HPLC 97.4% (AUC), $t_R$=10.10 min.

720

Example 753

1-(6-(3,5-dichloro-4-hydroxyphenyl)-4-(1R,4R)-4-((3-hydroxypyrrolidin-1-yl)methyl)cyclohexylamino)quinolin-3-yl)ethanone

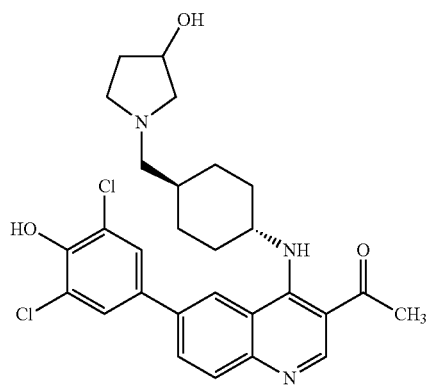 [SMILES: CC(=O)c1cnc2ccc(-c3cc(Cl)c(O)c(Cl)c3)cc2c1N[C@H]1CC[C@H](CN2CCC(O)C2)CC1]

Following general procedure D, 1-(6-bromo-4-(1R,4R)-4-((3-hydroxypyrrolidin-1-yl)methyl)cyclohexylamino)quinolin-3-yl)ethanone (75 mg, 0.168 mmol) was reacted with 2,6-dichloro-4-(4,4,5,5-tetramethyl-1,3,2-dioxaborolan-2-yl)phenol (60 mg, 0.201 mmol) to afford the desired product (9 mg, 10%) as an yellow solid: $^1$H NMR (500 MHz, MeOD+ TFA-d) δ 9.11 (s, 1H), 8.47 (s, 1H), 8.27 (dd, J=8.8, 1.8 Hz, 1H), 7.98 (d, J=8.8 Hz, 1H), 7.72 (s, 2H), 4.56 (m, 2H), 3.81 (m, 1H), 3.60 (d, J=11.8 Hz, 1H), 3.18 (m, 3H), 2.73 (s, 3H), 2.46 (d, J=11.8 Hz, 2H), 2.38 (d, J=7.2 Hz, 1H), 2.07 (m, 4H), 1.79 (q, J=12.3 Hz, 2H), 1.38 (q, J=12.3 Hz, 2H); ESI MS m/z 528, $[C_{28}H_{31}Cl_2N_3O_3+H]^+$; HPLC 96.4% (AUC), $t_R$=11.04 min.

Example 767

1-(6-(3,5-dichloro-4-hydroxyphenyl)-4-(1R,4R)-4-(pyrrolidin-1-ylmethyl)cyclohexylamino)quinolin-3-yl)ethanone

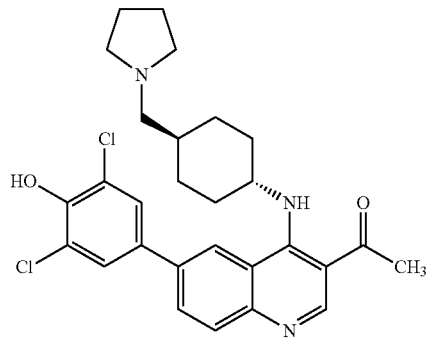 [SMILES: CC(=O)c1cnc2ccc(-c3cc(Cl)c(O)c(Cl)c3)cc2c1N[C@H]1CC[C@H](CN2CCCC2)CC1]

Following general procedure D, 1-(6-bromo-4-(1R,4R)-4-(pyrrolidin-1-ylmethyl)cyclohexylamino)quinolin-3-yl)ethanone (127 mg, 0.295 mmol) was reacted with 2,6- dichloro-4-(4,4,5,5-tetramethyl-1,3,2-dioxaborolan-2-yl)phenol (100 mg, 0.354 mmol) to afford the desired product (40 mg, 26%) as an light yellow solid: $^1$H NMR (500 MHz, MeOD+TFA-d) δ 9.11 (s, 1H), 8.47 (s, 1H), 8.27 (dd, J=8.7, 1.9 Hz, 1H), 7.97 (d, J=8.7 Hz, 1H), 7.72 (s, 2H), 4.53 (s, 1H), 3.70 (m, 2H), 3.14 (m, 4H), 2.73 (s, 3H), 2.46 (d, J=12.3 Hz, 2H), 2.18 (m, 1H), 2.06 (m, 5H), 1.80 (q, J=12.3 Hz, 2H), 1.37 (m, 2H); ESI MS m/z 512, $[C_{28}H_{31}Cl_2N_3O_2+H]^+$; HPLC 97.4% (AUC), $t_R$=10.49 min.

Example 790

1-(6-(3,5-dichloro-4-hydroxyphenyl)-4-(1R,4R)-4-((diethylamino)methyl)cyclohexylamino)quinolin-3-yl)ethanone

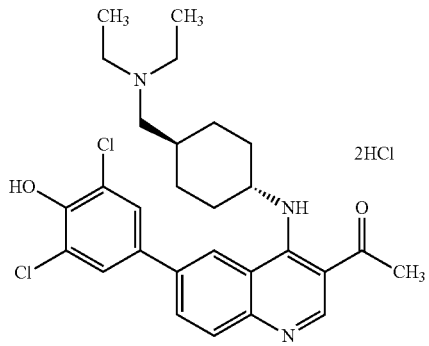 [SMILES: CCN(CC)C[C@H]1CC[C@H](Nc2c(C(C)=O)cnc3ccc(-c4cc(Cl)c(O)c(Cl)c4)cc23)CC1]

Following general procedure D, 1-(6-bromo-4-(1R,4R)-4-((diethylamino)methyl)cyclohexylamino)quinolin-3-yl)ethanone (60 mg, 0.139 mmol) was reacted with 2,6-dichloro-4-(4,4,5,5-tetramethyl-1,3,2-dioxaborolan-2-yl)phenol (50 mg, 0.167 mmol) to afford the desired product (38 mg, 46%) as an off-white solid: $^1$H NMR (500 MHz, MeOD) δ 9.11 (s, 1H), 8.47 (s, 1H), 8.28 (dd, J=8.7, 1.8 Hz, 1H), 7.98 (d, J=8.7 Hz, 1H), 7.73 (s, 2H), 4.54 (s, 1H), 3.27 (m, 2H), 3.07 (d, J=6.7 Hz, 2H), 2.74 (s, 3H), 2.46 (d, J=12.0 Hz, 2H), 2.11 (d, J=12.7 Hz, 2H), 2.03 (s, 1H), 1.83 (q, J=12.7 Hz, 2H), 1.38 (m, 8H); ESI MS m/z 514, $[C_{28}H_{33}Cl_2N_3O_2+H]^+$; HPLC 96.5% (AUC), $t_R$=10.38 min.

Example 794

1-(6-(3-chloro-5-fluoro-4-hydroxyphenyl)-4-(1R,4R)-4-((diethylamino)methyl)cyclohexylamino)quinolin-3-yl)ethanone

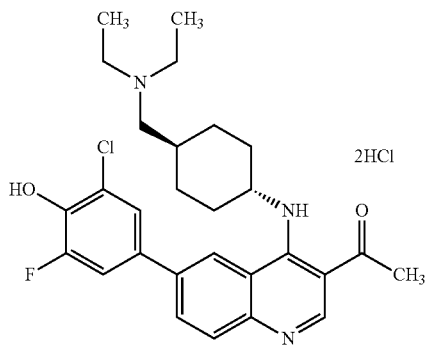 [SMILES: CCN(CC)C[C@H]1CC[C@H](Nc2c(C(C)=O)cnc3ccc(-c4cc(F)c(O)c(Cl)c4)cc23)CC1]

Following general procedure D, 1-(6-bromo-4-(1R,4R)-4-((diethylamino)methyl)cyclohexylamino)quinolin-3-yl)ethanone (113 mg, 0.261 mmol) was reacted with 2-chloro-6-fluoro-4-(4,4,5,5-tetramethyl-1,3,2-dioxaborolan-2-yl)phenol (100 mg, 0.392 mmol) to afford the desired product (80 mg, 53%) as an off-white solid: $^1$H NMR (500 MHz, MeOD) δ 9.11 (s, 1H), 8.48 (s, 1H), 8.27 (dd, J=8.8, 1.8 Hz, 1H), 7.98 (d, J=8.8 Hz, 1H), 7.59 (s, 1H), 7.52 (dd, J=11.5, 2.3 Hz, 1H), 4.54 (s, 1H), 3.28 (m, 2H), 3.08 (d, J=6.7 Hz, 2H), 2.74 (s, 3H), 2.46 (d, J=12.2 Hz, 2H), 2.10 (d, J=12.8 Hz, 2H), 2.02 (m, 1H), 1.81 (q, J=11.1 Hz, 2H), 1.35 (m, 8H); ESI MS m/z 498, $[C_{28}H_{33}ClFN_3O_2+H]^+$; HPLC 99.5% (AUC), $t_R$=10.23 min.

Example 792

1-(6-(3,5-dichloro-4-hydroxyphenyl)-4-((1S,4r)-4-(((S)-2-(hydroxymethyl)pyrrolidin-1-yl)methyl)cyclohexylamino)quinolin-3-yl)ethanone

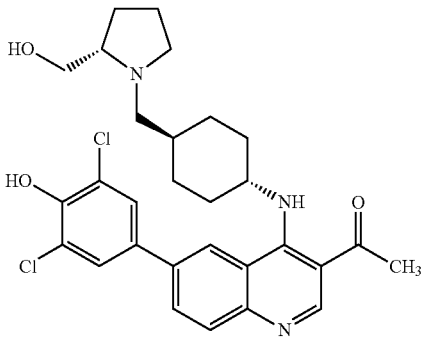 [SMILES: CC(=O)c1cnc2ccc(-c3cc(Cl)c(O)c(Cl)c3)cc2c1N[C@H]1CC[C@H](CN2CCC[C@H]2CO)CC1]

Following general procedure D, 1-(6-bromo-4-((1S,4r)-4-(((S)-2-(hydroxymethyl)pyrrolidin-1-yl)methyl)cyclohexylamino)quinolin-3-yl)ethanone (70 mg, 0.152 mmol) was reacted with 2,6-dichloro-4-(4,4,5,5-tetramethyl-1,3,2-dioxaborolan-2-yl)phenol (63 mg, 0.228 mmol) to afford the desired product (11 mg, 17%) as an yellow-brown solid: $^1$H NMR (300 MHz, MeOD) δ 9.11 (s, 1H), 8.49 (s, 1H), 8.28 (dd, J=8.8, 1.7 Hz, 1H), 7.98 (d, J=8.8 Hz, 1H), 7.73 (s, 2H), 4.56 (s, 1H), 3.90 (m, 1H), 3.70 (m, 3H), 3.32 (m, 2H), 3.23 (m, 2H), 3.08 (dd, J=12.8, 5.6 Hz, 1H), 2.74 (s, 3H), 2.46 (d, J=12.5 Hz, 2H), 2.17 (m, 7H), 1.83 (m, 3H), 1.38 (q, J=24.5, 11.3 Hz, 2H); ESI MS m/z 542, $[C_{29}H_{33}Cl_2N_3O_3+H]^+$; HPLC 99.2% (AUC), $t_R$=10.19 min.

Example 812

1-(6-(3,5-dichloro-4-hydroxyphenyl)-4-(1R,4R)-4-(((R)-2-(hydroxymethyl)pyrrolidin-1-yl)methyl)cyclohexylamino)quinolin-3-yl)ethanone

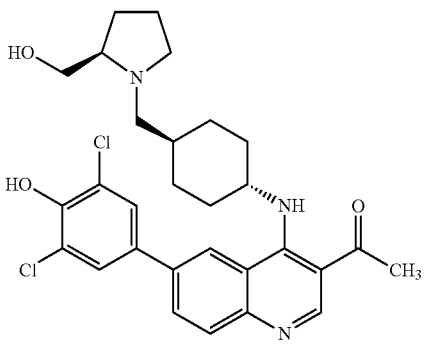 [SMILES: CC(=O)c1cnc2ccc(-c3cc(Cl)c(O)c(Cl)c3)cc2c1N[C@H]1CC[C@H](CN2CCC[C@@H]2CO)CC1]

Following general procedure D, 1-(6-bromo-4-(1R,4R)-4-(((R)-2-(hydroxymethyl)pyrrolidin-1-yl)methyl)cyclohexylamino)quinolin-3-yl)ethanone (94 mg, 0.204 mmol) was reacted with 2,6-dichloro-4-(4,4,5,5-tetramethyl-1,3,2-dioxaborolan-2-yl)phenol (86 mg, 0.306 mmol) to afford the desired product (42 mg, 38%) as a yellow solid: $^1$H NMR (300 MHz, MeOD) δ 9.05 (s, 1H), 8.44 (s, 1H), 8.20 (dd, J=8.7, 1.8 Hz, 1H), 7.95 (d, J=8.7 Hz, 1H), 7.71 (s, 2H), 4.44 (s, 1H), 3.89 (m, 1H), 3.70 (m, 3H), 3.09 (m, 1H), 2.72 (s, 3H), 2.43 (d, J=12.5 Hz, 2H), 2.12 (m, 5H), 1.85 (m, 3H), 1.36 (q, J=15.0, 13.8 Hz, 2H); ESI MS m/z 542, $[C_{29}H_{33}Cl_2N_3O_3+H]^+$; HPLC 99.8% (AUC), $t_R$=10.12 min.

Example 810

1-(4-(1R,4R)-4-((3-aminopiperidin-1-yl)methyl)cyclohexylamino)-6-(3,5-dichloro-4-hydroxy phenyl)quinolin-3-yl)ethanone

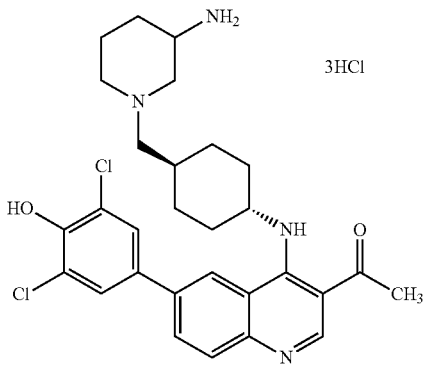 [SMILES: CC(=O)c1cnc2ccc(-c3cc(Cl)c(O)c(Cl)c3)cc2c1N[C@H]1CC[C@H](CN2CCCC(N)C2)CC1]

To a suspension of tert-butyl 1-((1R,4R)-4-(3-acetyl-6-bromoquinolin-4-ylamino)cyclohexyl)methyl)piperidin-3-yl-carbamate (80 mg, 0.173 mmol), 2,6-dichloro-4-(4,4,5,5-tetramethyl-1,3,2-dioxaborolan-2-yl)phenol (73 mg, 0.260 mmol) and Pd(dppf)Cl$_2$ (12 mg, 0.017 mmol) in dioxane (4 mL) was added Cs$_2$CO$_3$ (260 μL, 2.0 M solution in H$_2$O). N$_2$ gas was bubbled through the reaction mixture and the vessel was sealed. The mixture was then heated under microwave irradiation conditions to 140° C. for 30 min. The solution was allowed to cool to rt, then directly subjected to purification by preperatory HPLC. The crude mixture was then treated with TFA to deprotect the pendant amine and reduced to a red-orange residue. This residue was then dissolved in MeOH (2 mL) and treated with a 2.0 M HCl solution in diethyl ether to afford the product (26 mg, 23%) as an off-white solid: $^1$H NMR (500 MHz, MeOD) δ 9.01 (s, 1H), 8.37 (s, 1H), 8.17 (dd, J=8.7, 1.9 Hz, 1H), 7.89 (d, J=8.7 Hz, 1H), 7.62 (s, 2H), 4.45 (s, 1H), 3.73 (s, 2H), 3.61 (s, 1H), 3.11 (d, J=6.1 Hz, 2H), 2.97 (s, 1H), 2.65 (s, 3H), 2.36 (s, 2H), 2.08 (m, 6H), 1.72 (q, J=12.4 Hz, 2H), 1.62 (s, 1H), 1.31 (q, J=11.9 Hz, 2H); ESI MS m/z 541, $[C_{29}H_{34}Cl_2N_4O_2+H]^+$; HPLC 98.3% (AUC), $t_R$=9.34 min.

Example 818

1-(4-(1R,4R)-4-((3-aminopiperidin-1-yl)methyl)cyclohexylamino)-6-(3-chloro-5-fluoro-4-hydroxyphenyl)quinolin-3-yl)ethanone

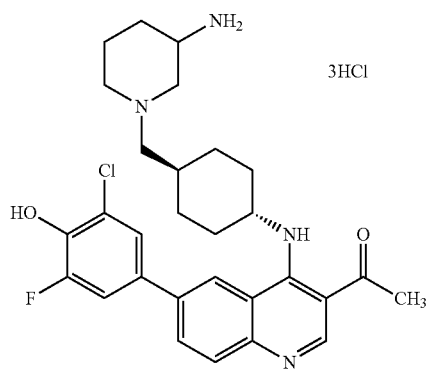 [SMILES: CC(=O)c1cnc2ccc(-c3cc(F)c(O)c(Cl)c3)cc2c1N[C@H]1CC[C@H](CN2CCCC(N)C2)CC1]

To a suspension of tert-butyl 1-((1R,4R)-4-(3-acetyl-6-bromoquinolin-4-ylamino)cyclohexyl)methyl)piperidin-3-yl-carbamate (100 mg, 0.217 mmol), 2-chloro-6-fluoro-4-(4,4,5,5-tetramethyl-1,3,2-dioxaborolan-2-yl)phenol (88 mg, 0.325 mmol) and Pd(dppf)Cl$_2$ (15 mg, 0.021 mmol) in dioxane (4 mL) was added Cs$_2$CO$_3$ (325 μL, 2.0 M solution in H$_2$O). N$_2$ gas was bubbled through the reaction mixture and the vessel was sealed. The mixture was then heated under microwave irradiation conditions to 140° C. for 30 min. The solution was allowed to cool to rt, then directly subjected to purification by preperatory HPLC. The crude fractions were then treated with TFA to deprotect the pendant amine and reduced to a red-orange residue. This residue was then dissolved in MeOH (2 mL) and treated with a 2.0 M HCl solution in diethyl ether to afford the product (28 mg, 20%) as a brown solid: $^1$H NMR (500 MHz, MeOD) δ 9.10 (s, 1H), 8.48 (s, 1H), 8.27 (dd, J=8.8, 1.8 Hz, 1H), 7.97 (d, J=8.8 Hz, 1H), 7.59 (s, 1H), 7.52 (dd, J=11.4, 2.3 Hz, 1H), 4.55 (s, 1H), 3.74 (m, 2H), 3.17 (m, 1H), 3.01 (m, 1H), 2.73 (s, 3H) 2.46 (d, J=6.3 Hz, 2H), 2.12 (m, 6H), 1.80 (q, J=12.5 Hz, 2H), 1.68 (m, 1H), 1.38 (m, 2H).; ESI MS m/z 525, $[C_{29}H_{34}ClFN_4O_2+H]^+$; HPLC 95.5% (AUC), $t_R$=9.07 min.

Example 817

1-(6-(3,5-dichloro-4-hydroxyphenyl)-4-((1R,4R)-4-((ethyl(methyl)amino)methyl)cyclohexylamino)quinolin-3-yl)ethanone

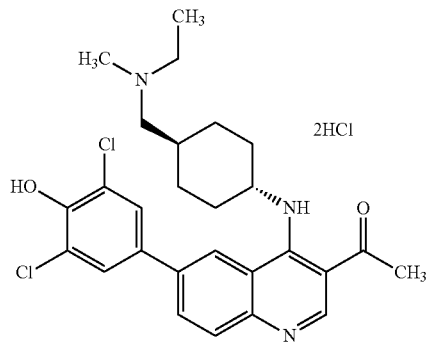 [SMILES: CCN(C)C[C@H]1CC[C@H](Nc2c(C(C)=O)cnc3ccc(-c4cc(Cl)c(O)c(Cl)c4)cc23)CC1]

Following general procedure D, 1-(6-bromo-4-((1R,4R)-4-((ethyl(methyl)amino)methyl)cyclo hexylamino)quinolin-3-yl)ethanone (68 mg, 0.162 mmol) was reacted with 2,6-dichloro-4-(4,4,5,5-tetramethyl-1,3,2-dioxaborolan-2-yl) phenol (69 mg, 0.244 mmol) to afford the desired product (34 mg, 59%) as an off-white solid: NMR (500 MHz, MeOD) δ 9.11 (s, 1H), 8.47 (s, 1H), 8.28 (dd, J=8.7, 1.8 Hz, 1H), 7.99 (d, J=8.8 Hz, 1H), 7.73 (s, 2H), 4.54 (s, 1H), 3.17 (ddd, J=31.2, 13.3, 7.4 Hz, 2H), 3.03 (m, 1H), 2.90 (s, 3H), 2.74 (s, 3H), 2.46 (d, J=12.0 Hz, 2H), 2.13 (d, J=13.6 Hz, 1H), 2.06 (d, J=12.0 Hz, 2H), 1.80 (m, 2H), 1.37 (m, 5H); ESI MS m/z 500, [C$_{27}$H$_{31}$Cl$_2$N$_3$O$_2$+H]$^+$; HPLC 96.5% (AUC), t$_R$=10.07 min.

Example 824

1-(4-(6-(3-aminopiperidin-1-yl)pyridin-3-ylamino)-6-(3,5-dichloro-4-hydroxyphenyl)quinolin-3-yl)propan-1-one

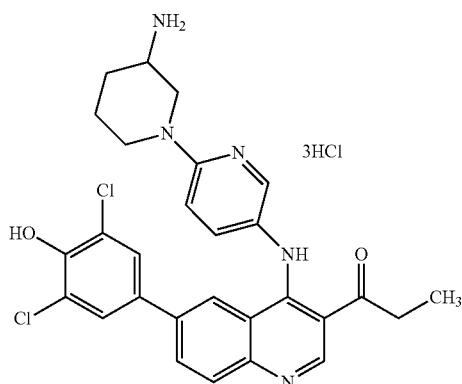

tert-butyl 1-(5-(6-(3,5-dichloro-4-hydroxyphenyl)-3-propionylquinolin-4-ylamino)pyridin-2-yl)piperidin-3-ylcarbamate (35 mg, 0.055 mmol) was dissolved in dichloromethane (5 mL). To this solution was added a 2.0 M HCl solution in diethyl ether (2 mL) the mixture was stirred for 16 h at room temperature where a precipitate formed. The precipitate was filtered off, washed with dichloromethane (10 mL), dried under vacuum to obtain the desired product as the HCl salt (12 mg, 33%) as a yellow solid: $^1$H NMR (500 MHz, MeOD) δ 9.29 (s, 1H), 8.24 (m, 2H), 8.04 (m, 2H), 7.81 (d, J=8.3 Hz, 1H), 7.31 (s, 2H), 7.25 (d, J=8.9 Hz, 1H), 4.53 (s, 1H), 4.06 (d, J=13.3 Hz, 1H), 3.39 (m, 2H), 3.24 (q, J=14.1, 7.0 Hz, 2H), 2.22 (m, 1H), 1.98 (m, 1H), 1.74 (m, 2H), 1.25 (t, J=6.9 Hz, 3H); ESI MS m/z 536, [C$_{28}$H$_{27}$Cl$_2$N$_5$O$_2$+H]$^+$; HPLC 98.9% (AUC), t$_R$=10.33 min.

Example 825

1-(4-(6-(3-aminopiperidin-1-yl)pyridin-3-ylamino)-6-(3-chloro-5-fluoro-4-hydroxyphenyl)quinolin-3-yl)propan-1-one

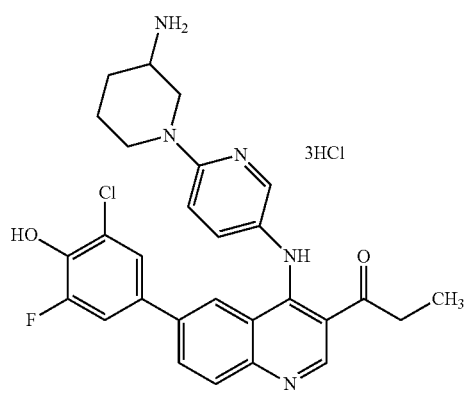 [SMILES: CCC(=O)c1cnc2ccc(-c3cc(F)c(O)c(Cl)c3)cc2c1Nc1ccc(N2CCCC(N)C2)nc1]

tert-butyl 1-(5-(6-(3-chloro-5-fluoro-4-hydroxyphenyl)-3-propionylquinolin-4-ylamino)pyridin-2-yl)piperidin-3-yl-carbamate (32 mg, 0.051 mmol) was dissolved in dichloromethane (5 mL). To this solution was added a 2.0 M HCl solution in diethyl ether (2 mL) the mixture was stirred for 16 h at room temperature where a precipitate formed. The precipitate was filtered off, washed with dichloromethane (10 mL), dried under vacuum to obtain the desired product as the HCl salt (16 mg, 49%) as an orange solid: $^1$H NMR (500 MHz, MeOD) δ 9.28 (s, 1H), 8.23 (m, 2H), 8.01 (m, 2H), 7.75 (d, J=8.5 Hz, 1H), 7.19 (d, J=8.4 Hz, 1H), 7.10 (t, J=4.9 Hz, 2H), 4.54 (s, 1H), 4.04 (d, J=13.0 Hz, 1H), 3.36 (m, 3H), 3.24 (q, J=13.3, 6.2 Hz, 1H), 2.20 (m, 1H), 1.97 (m, 1H), 1.74 (m, 2H), 1.26 (t, J=6.6 Hz, 3H); ESI MS m/z 520, [C$_{28}$H$_{27}$ClFN$_5$O$_2$+H]$^+$; HPLC 98.7% (AUC), t$_R$=10.05 min.

Example 844

1-(6-(3-chloro-5-fluoro-4-hydroxyphenyl)-4-((1S,4r)-4-(((S)-2-(hydroxymethyl)pyrrolidin-1-yl)methyl)cyclohexylamino)quinolin-3-yl)ethanone

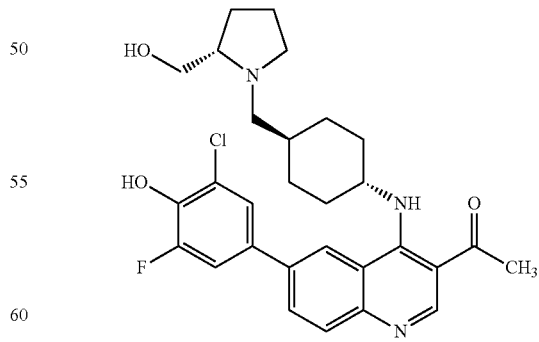

Following general procedure D, 1-(6-bromo-4-((1S,4r)-4-(((S)-2-(hydroxymethyl)pyrrolidin-1-yl)methyl)cyclohexylamino)quinolin-3-yl)ethanone (120 mg, 0.260 mmol) was reacted with 2-chloro-6-fluoro-4-(4,4,5,5-tetramethyl-1,3,2-dioxaborolan-2-yl)phenol (106 mg, 0.391 mmol) to afford the desired product (23 mg, 17%) as an off-white solid: $^1$H NMR (500 MHz, MeOD) δ 9.10 (s, 1H), 8.48 (s, 1H) 8.26 (dd, J=8.7, 1.8 Hz, 1H), 7.99 (d, J=8.7 Hz, 1H), 7.52 (dd, J=11.3, 2.3 Hz, 1H), 4.53 (s, 1H), 3.90 (dd, J=12.2, 3.8 Hz, 1H), 3.77 (m, 2H), 3.66 (m, 1H), 3.38 (m, 1H), 3.23 (m, 1H), 3.09 (dd, J=12.9, 5.5 Hz, 1H), 2.74 (s, 3H), 2.45 (d, J=12.3 Hz, 2H), 2.24 (m, 2H), 2.10 (m, 4H), 1.89 (m, 1H), 1.79 (q, J=12.2 Hz, 2H), 1.37 (dt, J=22.1, 12.6 Hz, 3H); ESI MS m/z 526, $[C_{29}H_{33}ClFN_3O_3+H]^+$; HPLC 97.4% (AUC), $t_R$=9.79 min.

Example 846

1-(6-(3-chloro-5-fluoro-4-hydroxyphenyl)-4-(1R,4R)-4-(pyrrolidin-1-ylmethyl)cyclohexylamino)quinolin-3-yl)propan-1-one

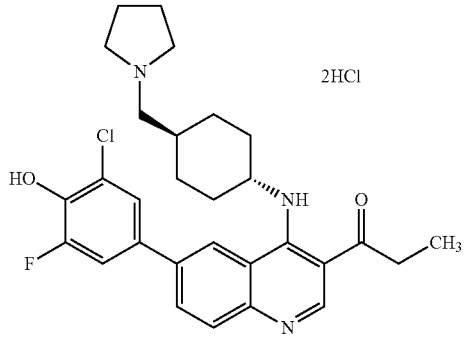 [SMILES: CCC(=O)c1cnc2ccc(-c3cc(F)c(O)c(Cl)c3)cc2c1N[C@H]1CC[C@H](CN2CCCC2)CC1]

Following general procedure D, 1-(6-bromo-4-((1R,4R)-4-(pyrrolidin-1-ylmethyl)cyclohexylamino)quinolin-3-yl)propan-1-one (90 mg, 0.209 mmol) was reacted with 2-chloro-6-fluoro-4-(4,4,5,5-tetramethyl-1,3,2-dioxaborolan-2-yl)phenol (85 mg, 0.313 mmol) to afford the desired product (43 mg, 35%) as an off-white solid: $^1$H NMR (500 MHz, MeOD) δ 9.12 (s, 1H), 8.48 (s, 1H), 8.26 (dd, J=8.7, 1.7 Hz, 1H), 7.98 (d, J=8.7 Hz, 1H), 7.59 (s, 1H), 7.52 (d, J=11.3 Hz, 1H), 4.54 (s, 1H), 3.71 (dt, J=11.1, 5.4 Hz, 2H), 3.17 (m, 6H), 2.47 (d, J=12.3 Hz, 2H), 2.17 (m, 2H), 2.07 (m, 2H), 1.81 (q, J=12.3 Hz, 2H), 1.36 (q, J=16.3, 15.2 Hz, 2H), 1.24 (t, J=7.1 Hz, 3H) ESI MS m/z 510, $[C_{29}H_{33}ClFN_3O_2+H]^+$; HPLC 98.8% (AUC), $t_R$=10.29 min.

Example 843

1-(6-(3,5-dichloro-4-hydroxyphenyl)-4-(1R,4R)-4-(pyrrolidin-1-ylmethyl)cyclohexylamino)quinolin-3-yl)propan-1-one

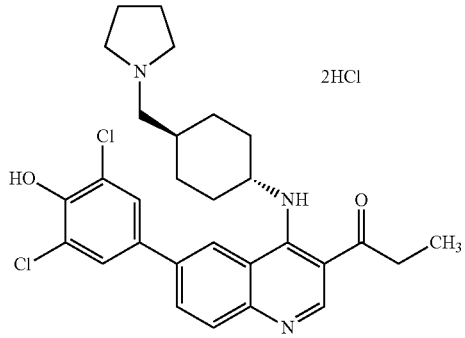 [SMILES: CCC(=O)c1cnc2ccc(-c3cc(Cl)c(O)c(Cl)c3)cc2c1N[C@H]1CC[C@H](CN2CCCC2)CC1]

Following general procedure D, 1-(6-bromo-4-(1R,4R)-4-(pyrrolidin-1-ylmethyl)cyclohexylamino)quinolin-3-yl)propan-1-one (90 mg, 0.209 mmol) was reacted with 2,6-dichloro-4-(4,4,5,5-tetramethyl-1,3,2-dioxaborolan-2-yl)phenol (80 mg, 0.314 mmol) to afford the desired product (38 mg, 30%) as an off-white solid: $^1$H NMR (500 MHz, MeOD) δ 9.13 (s, 1H), 8.48 (s, 1H), 8.27 (dd, J=8.7, 1.9 Hz, 1H), 7.98 (d, J=8.7 Hz, 1H), 7.73 (s, 2H), 4.54 (s, 1H), 3.71 (m, 2H), 3.15 (m, 7H), 2.47 (d, J=12.2 Hz, 2H), 2.17 (m, 2H), 2.07 (m, 4H), 1.81 (q, J=12.3 Hz, 2H), 1.37 (q, J=25.1, 12.0 Hz, 2H), 1.24 (t, J=7.1 Hz, 3H); ESI MS m/z 526, $[C_{29}H_{33}Cl_2N_3O_2+H]^+$; HPLC 99.0% (AUC), $t_R$=10.49 min.

Example 845

1-(6-(3-chloro-5-fluoro-4-hydroxyphenyl)-4-(1R,4R)-4-((ethyl(methyl)amino)methyl)cyclohexylamino)quinolin-3-yl)ethanone

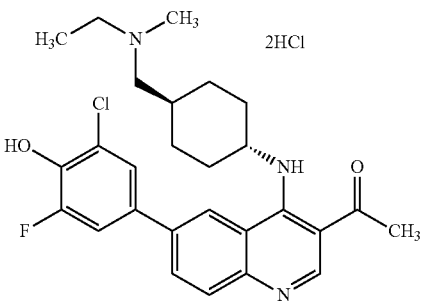 [SMILES: CCN(C)C[C@H]1CC[C@H](Nc2c(C(C)=O)cnc3ccc(-c4cc(F)c(O)c(Cl)c4)cc23)CC1]

Following general procedure D, 1-(6-bromo-4-(1R,4R)-4-((ethyl(methyl)amino)methyl)cyclohexylamino)quinolin-3-yl)ethanone (98 mg, 0.233 mmol) was reacted with 2,6-dichloro-4-(4,4,5,5-tetramethyl-1,3,2-dioxaborolan-2-yl)phenol (97 mg, 0.318 mmol) to afford the desired product (40 mg, 31%) as an off white solid: $^1$H NMR (500 MHz, MeOD) δ 9.10 (s, 1H), 8.48 (s, 1H), 8.27 (dd, J=8.7, 1.8 Hz, 1H), 7.98 (d, J=8.7 Hz, 1H), 7.59 (s, 1H), 7.52 (dd, J=11.4, 2.2 Hz, 1H), 4.53 (s, 1H), 3.12 (m, 2H), 2.89 (s, 3H), 2.74 (s, 3H), 2.46 (d, J=12.5 Hz, 2H), 2.08 (m, 3H), 1.81 (q, J=12.1 Hz, 2H), 1.37 (m, 5H); ESI MS m/z 484, $[C_{27}H_{31}ClFN_3O_2+H]^+$; HPLC 97.4% (AUC), $t_R$=9.90 min.

Example 876

N-(1R,4R)-4-(3-acetyl-6-(3-chloro-5-fluoro-4-hydroxyphenyl)quinolin-4-ylamino)cyclohexyl)-2-(dimethylamino)acetamide

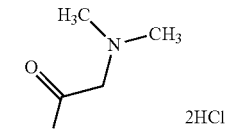
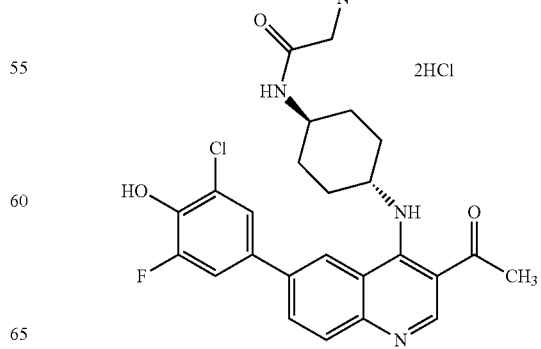

Following general procedure D, 1-(6-bromo-4-(1R,4R)-4-((ethyl(methyl)amino)methyl)cyclohexylamino)quinolin-3-yl)ethanone (50 mg, 0.112 mmol) was reacted with 2-chloro-6-fluoro-4-(4,4,5,5-tetramethyl-1,3,2-dioxaborolan-2-yl)phenol (37 mg, 0.134 mmol) to afford the desired product (40 mg, 61%) as a yellow solid: $^1$H NMR (500 MHz, MeOD) δ 9.10 (s, 1H), 8.49 (s, 1H), 8.27 (dd, J=8.7, 1.7 Hz, 1H), 7.98 (d, J=8.7 Hz, 1H), 7.59 (s, 1H), 7.52 (dd, J=11.5, 2.3 Hz, 1H), 4.55 (s, 1H), 3.93 (s, 3H), 2.94 (s, 6H), 2.74 (s, 3H), 2.44 (d, J=12.3 Hz, 2H), 2.17 (d, J=11.6 Hz, 2H), 1.85 (q, J=11.0 Hz, 2H), 1.55 (q, J=12.6 Hz, 2H); ESI MS m/z 513, $[C_{27}H_{30}ClFN_4O_3+H]^+$; HPLC 99.9% (AUC), $t_R$=9.49 min.

Example 878

N-(1R,4R)-4-(3-acetyl-6-(3-chloro-5-fluoro-4-hydroxyphenyl)quinolin-4-ylamino)cyclohexyl)-2-aminopropanamide

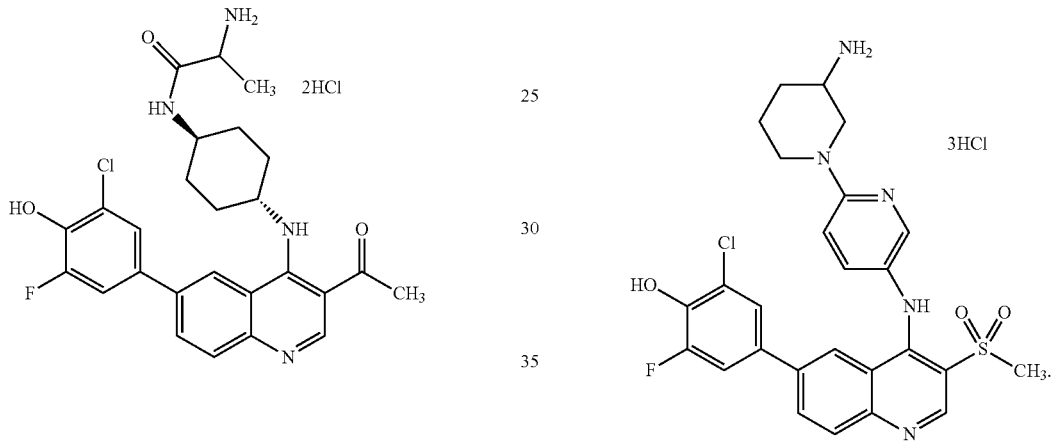

tert-butyl 1-(1R,4R)-4-(3-acetyl-6-(3-chloro-5-fluoro-4-hydroxyphenyl)quinolin-4-ylamino)cyclohexylamino)-1-oxopropan-2-ylcarbamate (42 mg, 0.070 mmol) was dissolved in dichloromethane (5 mL). To this solution was added a 2.0 M HCl solution in diethyl ether (2 mL) the mixture was stirred for 16 h at room temperature where a precipitate formed. The precipitate was filtered off, washed with dichloromethane (10 mL), dried under vacuum to obtain the desired product as the HCl salt (20 mg, 50%) as an off-white solid: $^1$H NMR (500 MHz, MeOD) δ 9.10 (s, 1H), 8.50 (s, 1H), 8.27 (dd, J=8.7, 1.7 Hz, 1H), 7.98 (d, J=8.7 Hz, 1H), 7.59 (s, 1H), 7.52 (dd, J=11.1, 2.3 Hz, 1H), 4.56 (s, 1H), 3.87 (dt, J=19.5, 7.0 Hz, 3H), 3.66 (m, 1H), 2.74 (s, 3H), 2.44 (d, J=12.2 Hz, 2H), 2.15 (m, 2H), 2.97 (m, 1H), 1.85 (q, J=12.7 Hz, 2H), 1.56 (m, 2H), 1.49 (m, 5H), 1.38 (t, J=10.1 Hz, 1H); ESI MS m/z 499, $[C_{26}H_{28}ClFN_4O_3+H]^+$; HPLC 98.7% (AUC), $t_R$=9.47 min.

Example 886

N-(1R,4R)-4-(3-acetyl-6-(3,5-dichloro-4-hydroxyphenyl)quinolin-4-ylamino)cyclohexyl)-2-aminopropanamide tert-butyl 1-((1R,4R)-4-(3-acetyl-6-(3,5-dichloro-4-hydroxyphenyl)quinolin-4-ylamino)cyclohexyl amino)-1-oxopropan-2-ylcarbamate (37 mg, 0.060 mmol) was dissolved in dichloromethane (5 mL). To this solution was added a 2.0 M HCl solution in diethyl ether (2 mL) the mixture was stirred for 16 h at room temperature where a precipitate formed. The precipitate was filtered off, washed with dichloromethane (10 mL), dried under vacuum to obtain the desired product as the HCl salt (18 mg, 58%) as a white solid: $^1$H NMR (300 MHz, MeOD) δ 9.09 (s, 1H), 8.48 (s, 1H), 8.27 (dd, J=8.8, 1.7 Hz, 1H), 7.97 (d, J=8.8 Hz, 1H), 7.72 (s, 2H), 4.52 (s, 1H), 3.87 (m, 2H), 2.73 (s, 3H), 2.43 (d, J=12.3 Hz, 2H), 2.15 (d, J=12.3 Hz, 2H), 1.84 (q, J=11.9 Hz, 2H), 1.51 (m, 5H); ESI MS m/z 515, $[C_{26}H_{28}Cl_2N_4O_3+H]^+$; HPLC 97.8% (AUC), $t_R$=9.75 min.

Example 909

4-(4-(6-(3-aminopiperidin-1-yl)pyridin-3-ylamino)-3-(methylsulfonyl)quinolin-6-yl)-2-chloro-6-fluorophenol To a suspension of tert-butyl 1-(5-(6-bromo-3-(methylsulfonyl)quinolin-4-ylamino)pyridin-2-yl)piperidin-3-ylcarbamate (70 mg, 0.121 mmol), 2-chloro-6-fluoro-4-(4,4,5,5-tetramethyl-1,3,2-dioxaborolan-2-yl)phenol (40 mg, 0.145 mmol) and Pd(dppf)Cl$_2$ (9 mg, 0.012 mmol) in dioxane (4 mL) was added Cs$_2$CO$_3$ (182 µL, 2.0 M solution in H$_2$O). The reaction mixture was degassed using N$_2$ and heated at 140° C. for 30 min. The reaction mixture was cooled to rt and to purification by preperatory HPLC. The crude mixture was then treated with TFA to deprotect the pendant amine and reduced to a red-orange residue. This residue was then dissolved in MeOH (2 mL) and treated with a 2.0 M HCl solution in diethyl ether to afford the product (15 mg, 19%) as a brown-yellow solid: $^1$H NMR (300 MHz, MeOD) δ 9.07 (s, 1H), 8.32 (d, J=2.7 Hz, 1H), 8.27 (dd, J=8.8, 1.9 Hz, 1H), 8.05 (d, J=8.8 Hz, 1H), 7.93 (d, J=1.8 Hz, 1H), 7.88 (dd, J=9.3, 2.7 Hz, 1H), 7.28 (m, 1H), 7.09 (m, 2H), 4.56 (q, J=10.4, 9.4 Hz, 1H), 4.09 (d, J=13.3 Hz, 1H), 3.47 (s, 3H), 3.39 (d, J=8.1 Hz, 2H), 2.21 (s, 1H), 2.01 (m, 1H), 1.75 (m, 2H); ESI MS m/z 542, $[C_{26}H_{25}ClFN_5O_3S+H]^+$; HPLC 99.6% (AUC), $t_R$=9.90 min.

Example 913

4-(4-(6-(3-aminopiperidin-1-yl)pyridin-3-ylamino)-3-(methylsulfonyl)quinolin-6-yl)-2,6-dichlorophenol

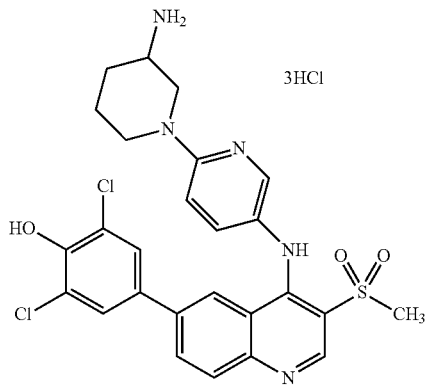 [SMILES: CS(=O)(=O)c1cnc2ccc(-c3cc(Cl)c(O)c(Cl)c3)cc2c1Nc1ccc(N2CCCC(N)C2)nc1]

To a suspension of tert-butyl 1-(5-(6-bromo-3-(methylsulfonyl)quinolin-4-ylamino)pyridin-2-yl)piperidin-3-ylcarbamate (70 mg, 0.121 mmol), 2,6-dichloro-4-(4,4,5,5-tetramethyl-1,3,2-dioxaborolan-2-yl)phenol (40 mg, 0.142 mmol) and Pd(dppf)Cl$_2$ (9 mg, 0.012 mmol) in dioxane (4 mL) was added Cs$_2$CO$_3$ (182 µL, 2.0 M solution in H$_2$O). N$_2$ gas was bubbled through the reaction mixture, the vessel was sealed and the mixture was then heated microwave irradiation conditions to 140° C. for 30 min. The solution was allowed to cool to rt, then directly subjected to purification by preparatory HPLC. The crude mixture was then treated with TFA to deprotect the pendant amine and reduced to a red-orange residue. This residue was then dissolved in MeOH (2 mL) and treated with a 2.0 M HCl solution in diethyl ether to afford the product (8.2 mg, 10%) as an orange solid: $^1$H NMR (500 MHz, MeOD) δ 9.03 (s, 1H), 8.27 (d, J=2.7 Hz, 1H), 8.24 (dd, J=8.8, 1.9 Hz, 1H), 8.01 (d, J=8.8 Hz, 1H), 7.93 (d, J=1.9 Hz, 1H), 7.74 (dd, J=9.2, 2.7 Hz, 1H), 7.22 (s, 2H), 7.11 (d, J=9.2 Hz, 1H), 4.60 (s, 1H), 4.05 (d, J=13.5 Hz, 1H), 3.45 (s, 3H), 3.26 (m, 3H), 2.19 (d, J=11.1 Hz, 1H), 1.94 (d, J=11.0 Hz, 1H), 1.71 (m, 2H); ESI MS m/z 558, [C$_{26}$H$_{25}$Cl$_2$N$_5$O$_3$S+H]$^+$; HPLC 98.9% (AUC), t$_R$=10.14 min.

Example 915

N-(1R,4R)-4-(3-acetyl-6-(3,5-dichloro-4-hydroxyphenyl)quinolin-4-ylamino)cyclohexyl)-2-amino-3-methylbutanamide

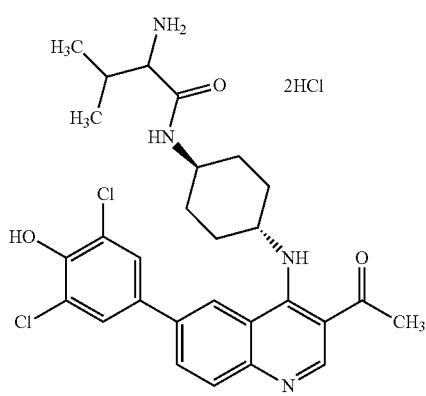 [SMILES: CC(=O)c1cnc2ccc(-c3cc(Cl)c(O)c(Cl)c3)cc2c1N[C@H]1CC[C@H](NC(=O)C(N)C(C)C)CC1]

To a solution of tert-butyl 1-(1R,4R)-4-(3-acetyl-6-(3,5-dichloro-4-hydroxyphenyl)quinoline-4-ylamino)cyclohexyl amino)-3-methyl-1-oxobutan-2-ylcarbamate (30 mg, 0.046 mmol) in dichloromethane (5 mL) was added a 2.0 M HCl solution in diethyl ether (2 mL) the mixture was stirred for 16 h at room temperature. The resulting precipitate was filtered off, washed with dichloromethane (10 mL) and dried under vacuum to obtain the desired product as the HCl salt (12 mg, 54%) as an orange-brown solid: $^1$H NMR (500 MHz, MeOD) δ 9.12-9.07 (s, 1H), 8.53-8.47 (s, 1H), 8.29-8.26 (dd, J=8.8, 1.7 Hz, 1H), 8.01-7.94 (d, J=8.7 Hz, 1H), 7.76-7.69 (s, 2H), 4.58-4.48 (s, 1H), 3.95-3.87 (m, 1H), 3.62-3.57 (d, J=6.0 Hz, 1H), 2.76-2.68 (m, 2H), 2.50-2.38 (t, J=13.9 Hz, 2H), 2.22-2.12 (td, J=13.8, 6.7 Hz, 3H), 1.90-1.78 (m, 1H), 1.65-1.51 (m, 2H), 1.11-0.98 (t, J=6.3 Hz, 6H); ESI MS m/z 545, [C$_{28}$H$_{32}$Cl$_2$N$_4$O$_3$+H]$^+$; HPLC 95.6% (AUC), t$_R$=10.13 min.

Example 907

N-(1R,4R)-4-(3-acetyl-6-(3-chloro-5-fluoro-4-hydroxyphenyl)quinolin-4-ylamino)cyclohexyl)-2-amino-3-methylbutanamide

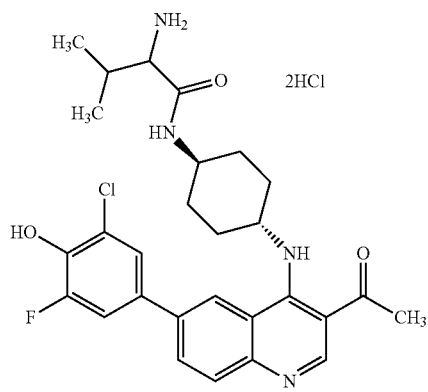

To a solution of tert-butyl 1-(1R,4R)-4-(3-acetyl-6-(3-chloro-5-fluoro-4-hydroxyphenyl)quinolin-4-ylamino)cyclohexylamino)-3-methyl-1-oxobutan-2-ylcarbamate (24 mg, 0.038 mmol) in dichloromethane (5 mL) was added a 2.0 M HCl solution in diethyl ether (2 mL) and the mixture was stirred for 16 h at room temperature. The resulting precipitate was filtered, washed with dichloromethane (10 mL) and dried under vacuum to obtain the desired product as the HCl salt (9 mg, 40%) as an off-white solid: $^1$H NMR (300 MHz, MeOD) δ 9.10 (s, 1H), 8.50 (s, 1H), 8.28 (dd, J=8.8, 1.7 Hz, 1H), 7.98 (d, J=8.8 Hz, 1H), 7.59 (s, 1H), 7.53 (dd, J=11.4, 2.2 Hz, 1H), 4.55 (s, 1H), 3.88 (m, 1H), 3.59 (d, J=6.1 Hz, 1H), 2.74 (s, 3H), 2.45 (d, J=12.2 Hz, 2H), 2.17 (q, J=6.8 Hz, 3H), 1.85 (q, J=12.5 Hz, 2H), 1.57 (p, J=12.9 Hz, 2H), 1.06 (dd, J=6.9, 3.5 Hz, 6H); ESI MS m/z 527, [C$_{28}$H$_{32}$ClFN$_4$O$_3$+H]$^+$; HPLC 99.0% (AUC), t$_R$=9.97 min.

Example 921

(S)-N-((1R,4S)-4-(3-acetyl-6-(3-chloro-5-fluoro-4-hydroxyphenyl)quinolin-4-ylamino)cyclohexyl)pyrrolidine-2-carboxamide

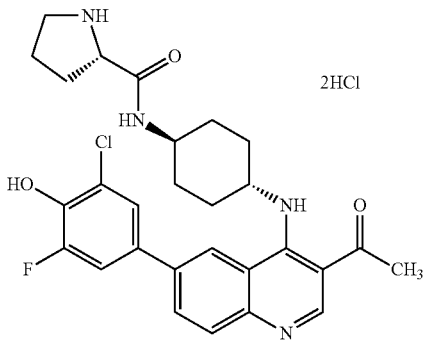 [SMILES: CC(=O)c1cnc2ccc(-c3cc(F)c(O)c(Cl)c3)cc2c1N[C@H]1CC[C@H](NC(=O)[C@@H]2CCCN2)CC1]

To a suspension of (S)-tert-butyl 2-((1r,4S)-4-(3-acetyl-6-bromoquinolin-4-ylamino)cyclohexylcarbamoyl)pyrrolidine-1-carboxylate (130 mg, 0.232 mmol), 2-chloro-6-fluoro-4-(4,4,5,5-tetramethyl-1,3,2-dioxaborolan-2-yl)phenol (76 mg, 0.279 mmol) and Pd(dppf)Cl$_2$ (16 mg, 0.023 mmol) in dioxane (4 mL) was added Cs$_2$CO$_3$ (348 µL, 2.0 M solution in H$_2$O). The crude mixture was then treated with TFA to deprotect the pendant amine and reduced to a red-orange residue. This residue was then dissolved in MeOH (2 mL) and treated with a 2.0 M HCl solution in diethyl ether to afford the product (14 mg, 11%) as a yellow solid: $^1$H NMR (500 MHz, MeOD) δ 9.10 (s, 1H), 8.50 (s, 1H), 8.27 (dd, J=8.8, 1.9 Hz, 1H), 7.98 (d, J=8.8 Hz, 1H), 7.59 (s, 1H), 7.52 (dd, J=11.4, 2.4 Hz, 1H), 4.55 (s, 1H), 4.21 (dd, J=8.5, 6.8 Hz, 1H), 3.88 (t, J=11.3 Hz, 1H), 3.42 (dt, J=11.4, 7.1 Hz, 1H), 2.74 (s, 3H), 2.44 (m, 3H), 2.17 (s, 2H), 2.03 (m, 3H), 1.84 (q, J=15.4, 14.6 Hz, 2H), 1.56 (dt, J=20.1, 9.9 Hz, 2H); ESI MS m/z 525, [C$_{28}$H$_{30}$ClFN$_4$O$_3$+H]$^+$; HPLC 98.5% (AUC), t$_R$=9.70 min.

Example 920

(S)-N-((1R,4S)-4-(3-acetyl-6-(3,5-dichloro-4-hydroxyphenyl)quinolin-4-ylamino)cyclohexyl)pyrrolidine-2-carboxamide

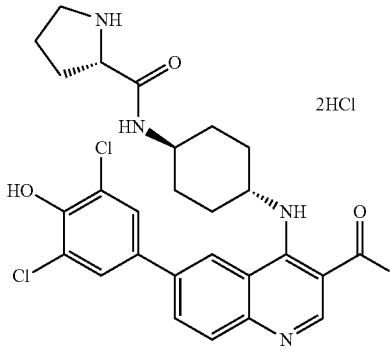

To a suspension of (S)-tert-butyl 2-((1r,4S)-4-(3-acetyl-6-bromoquinolin-4-ylamino)cyclohexylcarbamoyl)pyrrolidine-1-carboxylate (70 mg, 0.125 mmol), 2,6-dichloro-4-(4,4,5,5-tetramethyl-1,3,2-dioxaborolan-2-yl)phenol (42 mg, 0.150 mmol) and Pd(dppf)Cl$_2$ (9 mg, 0.013 mmol) in dioxane (4 mL) was added Cs$_2$CO$_3$ (187 µL, 2.0 M solution in H$_2$O). N$_2$ gas was bubbled through the reaction mixture and the vessel was sealed. The mixture was then heated under microwave irradiation conditions to 140° C. for 30 min. The solution was allowed to cool to rt, then directly subjected to purification by preperatory HPLC. The crude mixture was then treated with TFA to deprotect the pendant amine and reduced to a red-orange residue. This residue was then dissolved in MeOH (2 mL) and treated with a 2.0 M HCl solution in diethyl ether to afford the product (40 mg, 52%) as a yellow solid: $^1$H NMR (500 MHz, MeOD) δ 9.12 (s, 1H), 8.51 (s, 1H), 8.30 (dd, J=8.8, 1.8 Hz, 1H), 8.00 (d, J=8.8 Hz, 1H), 7.75 (s, 2H), 4.57 (s, 1H), 4.24 (m, 1H), 3.90 (t, J=11.8 Hz, 1H), 3.44 (dt, J=11.5, 6.9 Hz, 1H), 3.36 (m, 1H), 2.76 (s, 3H), 2.46 (m, 3H), 2.19 (d, J=12.2 Hz, 2H), 2.05 (m, 3H), 1.87 (q, J=13.5 Hz, 2H), 1.58 (p, J=13.7, 13.2 Hz, 2H); ESI MS m/z 541, [C$_{28}$H$_{30}$Cl$_2$N$_4$O$_3$+H]$^+$; HPLC 97.7% (AUC), t$_R$=9.94 min.

Example 1185

(S)-tert-butyl 1-(5-(6-(3,5-dichloro-4-hydroxyphenyl)-3-propionylquinolin-4-ylamino)pyridin-2-yl)piperidin-3-ylcarbamate

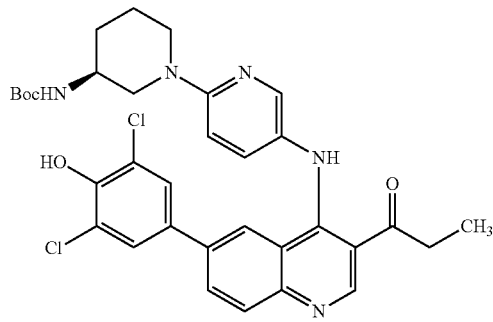 [SMILES: CCC(=O)c1cnc2ccc(-c3cc(Cl)c(O)c(Cl)c3)cc2c1Nc1ccc(N2CCC[C@H](NC(=O)OC(C)(C)C)C2)nc1]

Following general procedure F, (S)-tert-butyl 1-(5-(6-bromo-3-propionylquinolin-4-ylamino)pyridin-2-yl)piperidin-3-ylcarbamate (80 mg, 0.14 mmol) was reacted with 2,6-dichloro-4-(4,4,5,5-tetramethyl-1,3,2-dioxaborolan-2-yl)phenol (49 mg, 0.17 mmol) to afford the desired product (50 mg, 54%) as an orange solid: ESI MS m/z 636 [C$_{33}$H$_{35}$Cl$_2$H$_5$O$_4$+H]$^+$

Example 934

(S)-1-(4-(6-(3-aminopiperidin-1-yl)pyridin-3-ylamino)-6-(3,5-dichloro-4-hydroxyphenyl)quinolin-3-yl)propan-1-one

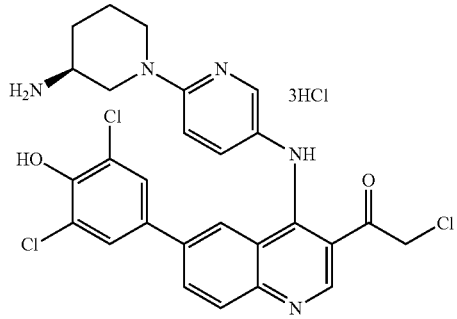 [SMILES: N[C@H]1CCCN(c2ccc(Nc3c(C(=O)CCl)cnc4ccc(-c5cc(Cl)c(O)c(Cl)c5)cc34)cn2)C1]

Following general procedure A, (S)-tert-butyl 1-(5-(6-(3,5-dichloro-4-hydroxyphenyl)-3-propionylquinolin-4-ylamino)pyridin-2-yl)piperidin-3-ylcarbamate (50 g, 0.078 mmol) was treated with a solution of 3N HCl to afford desired product (36.2 mg, 72%) as a yellow-orange solid: $^1$H NMR (500 MHz, MeOD) δ 9.29 (s, 1H), 8.25 (m, 2H), 8.05 (m, 2H), 7.85 (d, J=8.8 Hz, 1H), 7.31 (m, 3H), 4.52 (s, 1H), 4.06 (d, J=12.6 Hz, 1H), 3.81 (m, 3H); 2.16 (q, J=7.0 Hz, 2H), 2.22 (s, 1H), 1.98 (s, 1H), 1.24 (t, J=7.0 Hz, 3H); APCI MS m/z 536 $[C_{28}H_{27}Cl_2N_5O_2+H]^+$; HPLC 98.7% (AUC), $t_R$=10.30 min.

Example 548

(4-(6-(4-aminopiperidin-1-yl)pyridin-3-ylamino)-6-(3,5-dichloro-4-hydroxyphenyl)quinolin-3-yl)(cyclopropyl)methanone

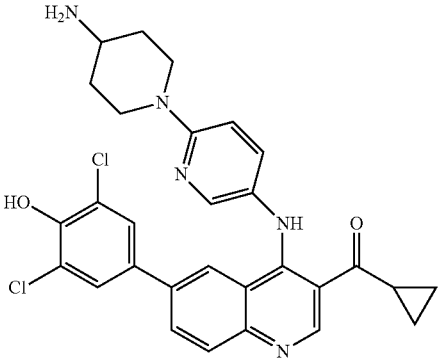

Following general procedure D, tert-butyl 1-(5-(6-bromo-3-(cyclopropanecarbonyl)quinoline-4-ylamino)pyridin-2-yl)piperidin-4-ylcarbamate (100 mg, 0.18 mmol) was reacted with 2,6-dichloro-4-(4,4,5,5-tetramethyl-1,3,2-dioxaborolan-2-yl)phenol (78 mg, 0.27 mmol) to obtain the protected intermediate which was subjected to general procedure A-2 to afford the desired product (52 mg, 53% over 2 steps) as a red solid: $^1$H NMR (500 MHz, CD$_3$OD+TFA-d) δ 9.37 (s, 1H), 8.21 (m, 3H), 8.02 (d, J=8.8 Hz, 1H), 7.72 (dd, J=9.3, 2.9 Hz, 1H), 7.36 (s, 2H), 7.18 (d, J=9.2 Hz, 1H), 4.52 (d, J=13.2 Hz, 2H), 3.44 (m, 1H), 3.14 (t, J=11.8 Hz, 2H), 2.83 (m, 1H), 2.15 (d, J=11.5 Hz, 2H), 1.69 (dd, J=24.5, 7.9 Hz, 2H), 1.21 (m, 4H); ESI MS m/z 548 $[C_{29}H_{27}Cl_2N_5O_2+H]^+$; HPLC 99.0% (AUC), $t_R$=10.73 min.

Example 554

(4-(6-(3-aminopiperidin-1-yl)pyridin-3-ylamino)-6-(3-chloro-4-hydroxy-5-methoxyphenyl)quinolin-3-yl)(cyclopropyl)methanone

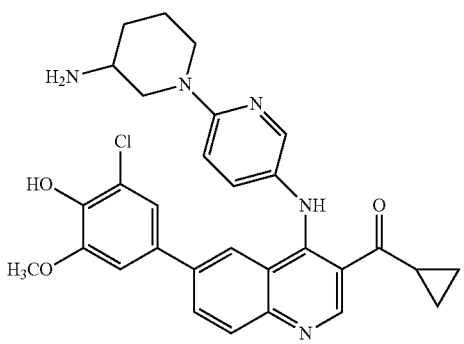 [SMILES: COc1cc(-c2ccc3ncc(C(=O)C4CC4)c(Nc4ccc(N5CCCC(N)C5)nc4)c3c2)cc(Cl)c1O]

Following general procedure D, tert-butyl 1-(5-(6-bromo-3-(cyclopropanecarbonyl)quinoline-4-ylamino)pyridin-2-yl)piperidin-3-ylcarbamate (100 mg, 0.18 mmol) was reacted with 2-chloro-6-methoxy-4-(4,4,5,5-tetramethyl-1,3,2-diox-aborolan-2-yl)phenol (77 mg, 0.27 mmol) to obtain the protected intermediate which was subjected to general procedure A-2 to afford the desired product (39 mg, 40% over 2 steps) as a yellow-orange solid: $^1$H NMR (500 MHz, CD$_3$OD+TFA-d) δ 9.39 (s, 1H), 8.25 (s, 1H), 8.14 (s, 1H), 8.05 (s, 1H), 7.77 (s, 1H), 7.21 (s, 1H), 7.02 (s, 1H), 6.87 (s, 1H), 4.49 (s, 1H), 4.02 (s, 1H), 3.93 (s, 3H), 2.84 (s, 1H), 2.22 (s, 1H), 1.97 (s, 1H), 1.75 (s, 2H), 1.23 (s, 4H); ESI MS m/z 544 $[C_{30}H_{30}ClN_5O_3+H]^+$; HPLC 99.7% (AUC), $t_R$=10.68 min.

Example 556

(4-(6-(3-aminopiperidin-1-yl)pyridin-3-ylamino)-6-(3,5-dichloro-4-hydroxyphenyl)quinolin-3-yl)(cyclopropyl)methanone

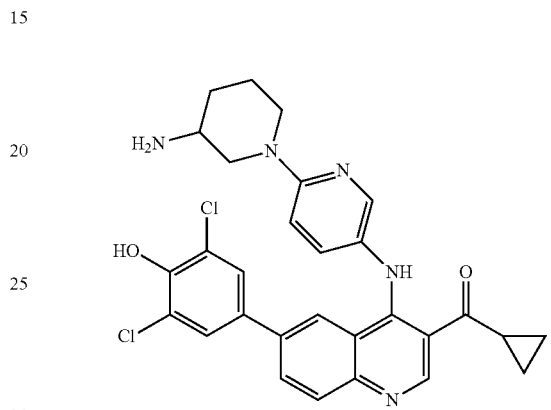

Following general procedure D, tert-butyl 1-(5-(6-bromo-3-(cyclopropanecarbonyl)quinolin-4-ylamino)pyridin-2-yl)piperidin-3-ylcarbamate (100 mg, 0.18 mmol) was reacted with 2,6-dichloro-4-(4,4,5,5-tetramethyl-1,3,2-dioxaborolan-2-yl)phenol (78 mg, 0.27 mmol) to obtain the protected intermediate which was subjected to general procedure A-2 to afford the desired product (49 mg, 50% over 2 steps) as a yellow solid: $^1$H NMR (500 MHz, CD$_3$OD+TFA-d) δ 9.40 (s, 1H), 8.22 (m, 2H), 8.12 (s, 1H), 8.02 (d, J=8.8 Hz, 1H), 7.70 (dd, J=9.2, 2.7 Hz, 1H), 7.34 (s, 2H), 7.13 (d, J=9.3 Hz, 1H), 4.52 (s, 1H), 4.02 (dt, J=13.0, 4.1 Hz, 1H), 3.35 (m, 2H), 2.85 (tt, J=7.8, 4.5 Hz, 1H), 2.20 (m, 1H), 1.95 (m, 1H), 1.73 (q, J=9.8 Hz, 2H), 1.22 (m, 4H); ESI MS m/z 548 $[C_{29}H_{27}Cl_2N_5O_2+H]^+$; HPLC 99.6% (AUC), $t_R$=10.95 min.

Example 561

(4-(6-(3-aminopiperidin-1-yl)pyridin-3-ylamino)-6-(3-chloro-5-fluoro-4-hydroxy phenyl)quinolin-3-yl)(cyclopropyl)methanone

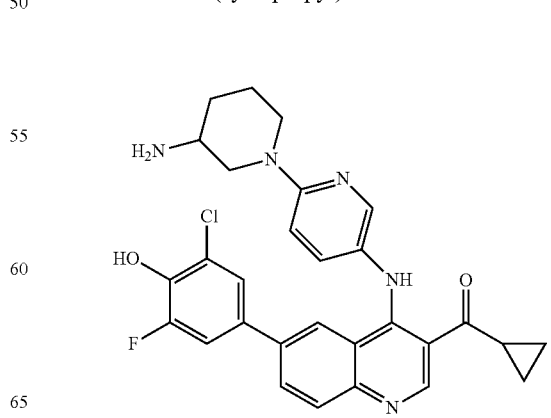

Following general procedure D, tert-butyl 1-(5-(6-bromo-3-(cyclopropanecarbonyl)quinolin-4-ylamino)pyridin-2-yl)piperidin-3-ylcarbamate (100 mg, 0.18 mmol) was reacted with 2-chloro-6-fluoro-4-(4,4,5,5-tetramethyl-1,3,2-dioxaborolan-2-yl)phenol (74 mg, 0.27 mmol) to obtain the protected intermediate which was subjected to general procedure A-2 to afford the desired product (39 mg, 41% over 2 steps) as a orange-red solid: $^1$H NMR (500 MHz, CD$_3$OD+TFA-d) δ 9.40 (s, 1H), 8.22 (m, 2H), 8.09 (s, 1H), 8.02 (d, J=8.8 Hz, 1H), 7.71 (dd, J=9.2, 2.8 Hz, 1H), 7.15 (m, 3H), 4.51 (d, J=10.3 Hz, 1H), 4.02 (m, 1H), 3.37 (m, 1H), 2.85 (tt, J=7.7, 4.6 Hz, 1H), 2.20 (m, 1H), 1.97 (m, 1H), 1.75 (m, 2H), 1.22 (m, 4H); ESI MS m/z 532 [C$_{29}$H$_{27}$ClFN$_5$O$_2$+H]$^+$; HPLC 99.0% (AUC), t$_R$=10.81 min.

Example 568

(4-(6-(3-aminopyrrolidin-1-yl)pyridin-3-ylamino)-6-(3-chloro-4-hydroxy-5-methoxyphenyl)quinolin-3-yl)(cyclopropyl)methanone

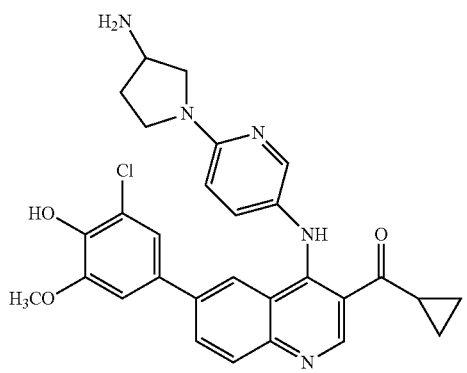 [SMILES: COc1cc(-c2ccc3ncc(C(=O)C4CC4)c(Nc4ccc(N5CCC(N)C5)nc4)c3c2)cc(Cl)c1O]

Following general procedure D, tert-butyl 1-(5-(6-bromo-3-(cyclopropanecarbonyl)quinolin-4-ylamino)pyridin-2-yl)pyrrolidin-3-ylcarbamate (100 mg, 0.18 mmol) was reacted with 2-chloro-6-methoxy-4-(4,4,5,5-tetramethyl-1,3,2-dioxaborolan-2-yl)phenol (77 mg, 0.27 mmol) to obtain the protected intermediate which was subjected to general procedure A-2 to afford the desired product (17 mg, 18% over 2 steps) as a orange-yellow solid: $^1$H NMR (500 MHz, CD$_3$OD+TFA-d) δ 9.38 (s, 1H), 8.31 (dd, J=8.8, 1.9 Hz, 1H), 8.25 (m, 2H), 8.05 (d, J=8.8 Hz, 1H), 7.89 (dd, J=9.3, 2.6 Hz, 1H), 7.13 (d, J=2.1 Hz, 1H), 7.06 (dd, J=9.3, 0.8 Hz, 1H), 6.90 (s, 1H), 4.15 (dt, J=11.2, 5.7 Hz, 1H), 4.04 (dd, J=11.9, 6.5 Hz, 1H), 3.94 (s, 3H), 3.86 (m, 1H), 3.76 (m, 2H), 2.83 (dt, J=12.1, 6.3 Hz, 1H), 2.60 (dt, J=21.4, 6.6 Hz, 1H), 2.31 (td, J=13.4, 5.7 Hz, 1H), 1.21 (m, 4H); ESI MS m/z 529 [C$_{29}$H$_{28}$ClN$_5$O$_3$+H]$^+$; HPLC 99.6% (AUC), t$_R$=9.97 min.

Example 572

(4-(2-(3-aminopyrrolidin-1-yl)pyrimidin-5-ylamino)-6-(3-chloro-5-fluoro-4-hydroxyphenyl)quinolin-3-yl)(cyclopropyl)methanone

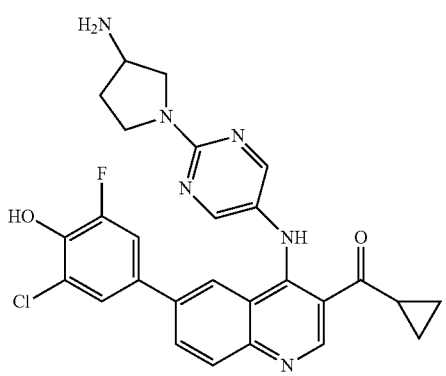

Following general procedure D, tert-butyl 1-(5-(6-bromo-3-(cyclopropanecarbonyl)quinolin-4-ylamino)pyrimidin-2-yl)pyrrolidin-3-ylcarbamate (100 mg, 0.18 mmol) was reacted with 2-chloro-6-fluoro-4-(4,4,5,5-tetramethyl-1,3,2-dioxaborolan-2-yl)phenol (74 mg, 0.27 mmol) to obtain the protected intermediate which was subjected to general procedure A-2 to afford the desired product (42 mg, 45% over 2 steps) as a yellow-orange solid: $^1$H NMR (500 MHz, CD$_3$OD+TFA-d) δ 9.35 (s, 1H), 8.48 (s, 2H), 8.25 (dd, J=8.8, 1.9 Hz, 1H), 8.19 (s, 1H), 8.04 (d, J=8.8 Hz, 1H), 7.22 (s, 2H), 4.06 (m, 2H), 3.91 (dt, J=11.7, 7.4 Hz, 1H), 3.82 (m, 2H), 2.82 (s, 1H), 2.54 (td, J=13.1, 6.8 Hz, 1H), 2.24 (td, J=13.2, 5.7 Hz, 1H), 1.21 (s, 4H); ESI MS m/z 519 [C$_{27}$H$_{24}$ClFN$_6$O$_2$+H]$^+$; HPLC 99.7% (AUC), t$_R$=10.05 min.

Example 574

(4-(2-(3-aminopyrrolidin-1-yl)pyrimidin-5-ylamino)-6-(3,5-dichloro-4-hydroxyphenyl)quinolin-3-yl)(cyclopropyl)methanone

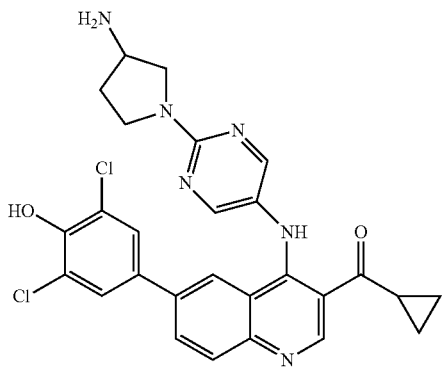

Following general procedure D, tert-butyl 1-(5-(6-bromo-3-(cyclopropanecarbonyl)quinoline-4-ylamino)pyrimidin-2-yl)pyrrolidin-3-ylcarbamate (100 mg, 0.18 mmol) was reacted with 2,6-dichloro-4-(4,4,5,5-tetramethyl-1,3,2-dioxaborolan-2-yl)phenol (78 mg, 0.27 mmol) to obtain the protected intermediate which was subjected to general procedure A-2 to afford the desired product (35 mg, 36% over 2 steps) as a yellow-orange solid: $^1$H NMR (500 MHz, CD$_3$OD+TFA-d) δ 9.34 (s, 1H), 8.47 (s, 2H), 8.26 (m, 2H), 8.04 (d, J=8.8 Hz, 1H), 7.41 (s, 2H), 4.07 (m, 1H), 3.91 (m, 1H), 3.81 (m, 2H), 2.81 (s, 1H), 2.52 (m, 1H), 2.23 (tt, J=13.0, 5.7 Hz, 1H), 1.20 (s, 4H); ESI MS m/z 535 [C$_{27}$H$_{24}$Cl$_2$N$_6$O$_2$+H]$^+$; HPLC 100.0% (AUC), t$_R$=10.30 min.

Example 575

(4-(6-(3-aminopyrrolidin-1-yl)pyridin-3-ylamino)-6-(3,5-dichloro-4-hydroxyphenyl)quinolin-3-yl)(cyclopropyl)methanone

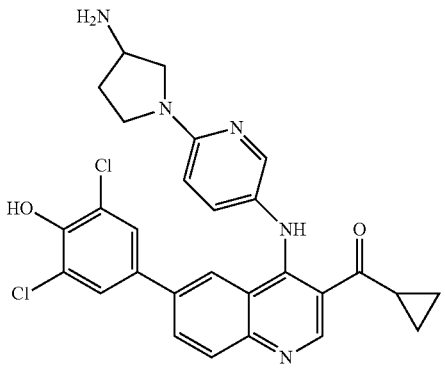

Following general procedure D, tert-butyl 1-(5-(6-bromo-3-(cyclopropanecarbonyl)quinoline-4-ylamino)pyridin-2-yl)pyrrolidin-3-ylcarbamate (100 mg, 0.18 mmol) was reacted with 2,6-dichloro-4-(4,4,5,5-tetramethyl-1,3,2-dioxaborolan-2-yl)phenol (78 mg, 0.27 mmol) to obtain the protected intermediate which was subjected to general procedure A-2 to afford the desired product (23 mg, 24% over 2 steps) as a orange solid: $^1$H NMR (500 MHz, CD$_3$OD+TFA-d) δ 9.35 (s, 1H), 8.33 (s, 1H), 8.30 (dd, J=8.8, 1.9 Hz, 1H), 8.28 (d, J=2.5 Hz, 1H), 8.11 (d, J=8.8 Hz, 1H), 8.04 (dd, J=9.6, 2.5 Hz, 1H), 7.49 (s, 2H), 7.26 (d, J=9.5 Hz, 1H), 4.22 (p, J=6.3 Hz, 1H), 4.12 (dd, J=12.0, 6.5 Hz, 1H), 3.96 (dt, J=10.9, 7.5 Hz, 1H), 3.86 (m, 2H), 2.78 (p, J=7.2 Hz, 1H), 2.65 (dq, J=15.3, 14.8, 6.8 Hz, 1H), 2.40 (td, J=13.3, 5.3 Hz, 1H), 1.20 (m, 4H); ESI MS m/z 534 [C$_{28}$H$_{25}$Cl$_2$N$_5$O$_2$+H]$^+$; HPLC 99.6% (AUC), t$_R$=10.29 min.

Example 576

(4-(6-(3-aminopyrrolidin-1-yl)pyridin-3-ylamino)-6-(3-chloro-5-fluoro-4-hydroxyphenyl)quinolin-3-yl)(cyclopropyl)methanone

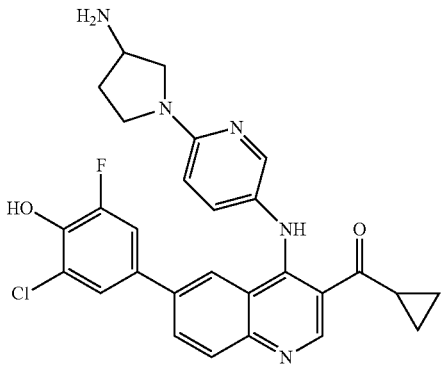

Following general procedure D, tert-butyl 1-(5-(6-bromo-3-(cyclopropanecarbonyl)quinoline-4-ylamino)pyridin-2-yl)pyrrolidin-3-ylcarbamate (100 mg, 0.18 mmol) was reacted with 2-chloro-6-fluoro-4-(4,4,5,5-tetramethyl-1,3,2-dioxaborolan-2-yl)phenol (74 mg, 0.27 mmol) to obtain the protected intermediate which was subjected to general procedure A-2 to afford the desired product (21 mg, 23% over 2 steps) as a yellow-brown solid: $^1$H NMR (500 MHz, CD$_3$OD+TFA-d) δ 9.36 (s, 1H), 8.27 (dd, J=8.8, 1.9 Hz, 1H), 8.24 (d, J=2.7 Hz, 2H), 8.06 (d, J=8.8 Hz, 1H), 7.90 (dd, J=9.4, 2.6 Hz, 1H), 7.27 (m, 2H), 7.08 (d, J=9.4 Hz, 1H), 4.16 (p, J=6.2 Hz, 1H), 4.05 (dd, J=11.9, 6.5 Hz, 1H), 3.88 (dt, J=10.8, 7.5 Hz, 1H), 3.79 (dt, J=10.5, 3.3 Hz, 2H), 2.81 (p, J=6.0 Hz, 1H), 2.61 (dq, J=13.3, 6.6 Hz, 1H), 2.33 (td, J=13.4, 5.3 Hz, 1H), 1.20 (m, 4H); ESI MS m/z 518 [C$_{28}$H$_{25}$ClFN$_5$O$_2$+H]$^+$; HPLC 99.4% (AUC), t$_R$=10.02 min.

Example 582

(4-(2-(3-aminopyrrolidin-1-yl)pyrimidin-5-ylamino)-6-(3-chloro-4-hydroxy-5-methoxyphenyl)quinolin-3-yl)(cyclopropyl)methanone

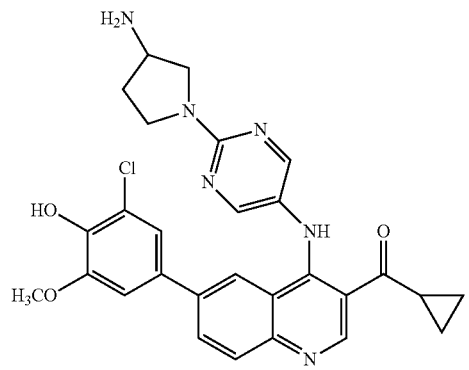 [SMILES: COc1cc(-c2ccc3ncc(C(=O)C4CC4)c(Nc4cnc(N5CCC(N)C5)nc4)c3c2)cc(Cl)c1O]

Following general procedure D, tert-butyl 1-(5-(6-bromo-3-(cyclopropanecarbonyl)quinolin-4-ylamino)pyrimidin-2-yl)pyrrolidin-3-ylcarbamate (100 mg, 0.18 mmol) was reacted with 2-chloro-6-methoxy-4-(4,4,5,5-tetramethyl-1,3,2-dioxaborolan-2-yl)phenol (77 mg, 0.27 mmol) to obtain the protected intermediate which was subjected to general procedure A-2 to afford the desired product (20 mg, 21% over 2 steps) as a yellow solid: $^1$H NMR (500 MHz, CD$_3$OD+TFA-d) δ 9.35 (s, 1H), 8.48 (s, 2H), 8.29 (dd, J=8.8, 1.9 Hz, 1H), 8.21 (s, 1H), 8.04 (d, J=8.8 Hz, 1H), 7.09 (s, 1H), 6.89 (s, 1H), 4.04 (m, 2H), 3.94 (s, 3H), 3.89 (m, 1H), 3.79 (m, 2H), 2.82 (s, 1H), 2.52 (ddd, J=14.8, 12.7, 6.4 Hz, 1H), 2.23 (dt, J=11.6, 6.2 Hz, 1H), 1.21 (s, 4H); ESI MS m/z 531 [C$_{28}$H$_{27}$ClN$_6$O$_3$+H]$^+$; HPLC 99.9% (AUC), t$_R$=10.11 min.

Example 592

(6-(3-Chloro-5-fluoro-4-hydroxyphenyl)-4-(1-(1-methylpiperidin-4-yl)-1H-pyrazol-4-ylamino)quinolin-3-yl)(cyclopropyl)methanone

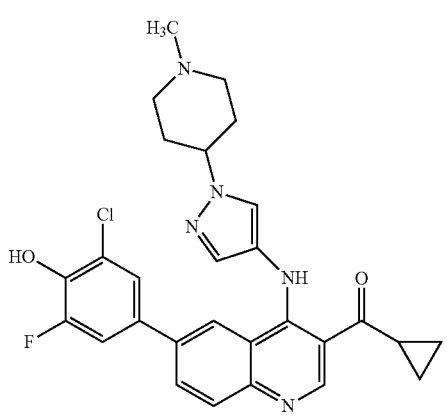 [SMILES: CN1CCC(n2cc(Nc3c(C(=O)C4CC4)cnc4ccc(-c5cc(F)c(O)c(Cl)c5)cc34)cn2)CC1]

Following general procedure D, (6-bromo-4-(1-(1-methylpiperidin-4-yl)-1H-pyrazol-4-ylamino)quinolin-3-yl)(cyclopropyl)methanone (50 mg, 0.11 mmol) was reacted with 2-chloro-6-fluoro-4-(4,4,5,5-tetramethyl-1,3,2-dioxaborolan-2-yl)phenol (47 mg, 0.17 mmol) to afford the desired product (35 mg, 59%) as a yellow-green solid: $^1$H NMR (500 MHz, CD$_3$OD+TFA-d) δ 9.94 (s, 1H), 8.24 (m, 1H), 8.02 (m, 2H), 7.68 (s, 1H), 7.22 (s, 2H), 4.62 (t, J=5.3 Hz, 1H), 3.69 (d, J=12.7 Hz, 2H), 3.50 (s, 1H), 3.25 (m, 2H), 2.95 (s, 3H), 2.39 (m, 4H), 1.24 (m, 4H); ESI MS m/z 520 [C$_{28}$H$_{27}$ClFN$_5$O$_2$+H]$^+$; HPLC 99.5% (AUC), $t_R$=10.37 min.

Example 593

Cyclopropyl(6-(3,5-dichloro-4-hydroxyphenyl)-4-(1-(1-methylpiperidin-4-yl)-1H-pyrazol-4-ylamino)quinolin-3-yl)methanone

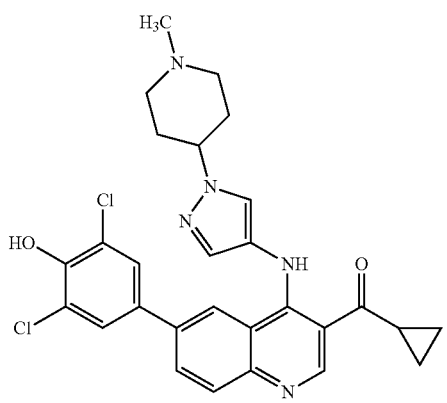 [SMILES: CN1CCC(n2cc(Nc3c(C(=O)C4CC4)cnc4ccc(-c5cc(Cl)c(O)c(Cl)c5)cc34)cn2)CC1]

Following general procedure D, (6-bromo-4-(1-(1-methylpiperidin-4-yl)-1H-pyrazol-4-ylamino) quinoline-3-yl)(cyclopropyl)methanone (50 mg, 0.11 mmol) was reacted with 2,6-dichloro-4-(4,4,5,5-tetramethyl-1,3,2-dioxaborolan-2-yl) phenol (49 mg, 0.17 mmol) to afford the desired product (36 mg, 63%) as a yellow solid: $^1$H NMR (500 MHz, CD$_3$OD+TFA-d) δ 9.45 (s, 1H), 8.23 (d, J=9.0 Hz, 1H), 8.01 (d, J=9.2 Hz, 2H), 7.68 (s, 1H), 7.40 (s, 1H), 4.62 (m, 1H), 3.68 (d, J=12.8 Hz, 2H), 3.41 (m, 1H), 3.25 (m, 2H), 2.94 (s, 3H), 2.37 (m, 3H), 1.22 (m, 3H); ESI MS m/z 536 [C$_{28}$H$_{27}$Cl$_2$N$_5$O$_2$+H]$^+$; HPLC 98.4% (AUC), $t_R$=10.57 min.

Example 610 cyclopropyl(6-(3,5-dichloro-4-hydroxyphenyl)-4-(6-(piperidin-3-ylamino)pyridine-3-ylamino)quinolin-3-yl)methanone

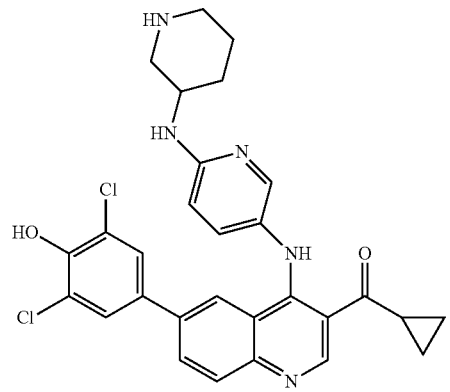

Following general procedure D, tert-butyl 3-(5-(6-bromo-3-(cyclopropanecarbonyl)quinolin-4-ylamino)pyridin-2-ylamino)piperidine-1-carboxylate (100 mg, 0.18 mmol) was reacted with 2,6-dichloro-4-(4,4,5,5-tetramethyl-1,3,2-dioxaborolan-2-yl)phenol (78 mg, 0.27 mmol) to obtain the protected intermediate which was subjected to general procedure A-2 to afford the desired product (11 mg, 11% over 2 steps) as a yellow-brown solid: $^1$H NMR (500 MHz, CD$_3$OD+TFA-d) δ 9.40 (s, 1H), 8.23 (dd, J=8.8, 1.9 Hz, 1H), 8.15 (s, 1H), 8.12 (d, J=2.6 Hz, 1H), 8.00 (d, J=8.7 Hz, 1H), 7.58 (dd, J=9.0, 2.7 Hz, 1H), 7.36 (s, 2H), 6.82 (d, J=9.2 Hz, 1H), 4.22 (ddd, J=14.0, 10.0, 3.8 Hz, 1H), 3.63 (dd, J=12.1, 3.5 Hz, 1H), 3.02 (td, J=11.9, 3.4 Hz, 2H), 2.89 (m, 2H), 2.12 (m, 1H), 1.86 (dtt, J=14.9, 11.2, 3.7 Hz, 1H), 1.71 (q, J=10.1 Hz, 1H), 1.21 (m, 4H); ESI MS m/z 548 [C$_{29}$H$_{27}$Cl$_2$N$_5$O$_2$+H]$^+$; HPLC 99.5% (AUC), $t_R$=10.58 min.

Example 613

Cyclopropyl(6-(3,5-dichloro-4-hydroxyphenyl)-4-(4-(2-(dimethylamino)ethyl)phenylamino)quinolin-3-yl)methanone

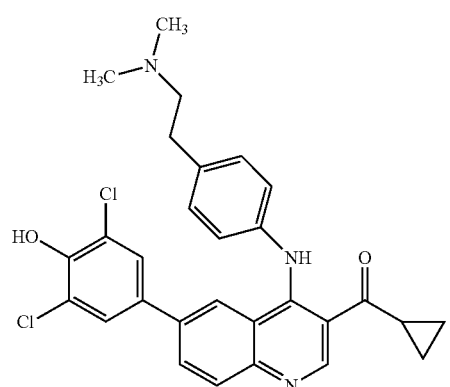

Following general procedure D, (6-bromo-4-(4-(2-(dimethylamino)ethyl)phenyl amino)quinolin-3-yl)(cyclopropyl)methanone (100 mg, 0.23 mmol) was reacted with 2,6-dichloro-4-(4,4,5,5-tetramethyl-1,3,2-dioxaborolan-2-yl)phenol (98 mg, 0.34 mmol) to afford the desired product (66 mg, 55%) as a yellow solid: $^1$H NMR (500 MHz, CD$_3$OD+TFA-d) δ 9.46 (s, 1H), 8.21 (dd, J=8.8, 1.9 Hz, 1H), 8.01 (d, J=8.8 Hz, 1H), 7.89 (s, 1H), 7.56 (d, J=8.4 Hz, 2H), 7.46 (d, J=8.4 Hz, 2H), 7.23 (s, 2H), 3.40 (m, 2H), 3.22 (m, 2H), 2.98 (s, 6H), 2.90 (m, 1H), 1.22 (m, 4H); ESI MS m/z 520 [C$_{29}$H$_{27}$Cl$_2$N$_3$O$_2$+H]$^+$; HPLC 97.6% (AUC), t$_R$=11.15 min.

Example 615

(6-(3-chloro-5-fluoro-4-hydroxyphenyl)-4-(4-(2-(dimethylamino)ethyl)phenylamino)quinolin-3-yl)(cyclopropyl)methanone

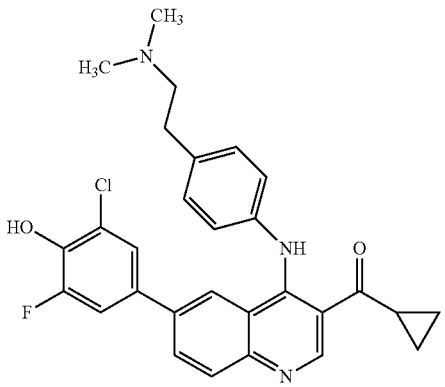 [SMILES: CN(C)CCc1ccc(Nc2c(C(=O)C3CC3)cnc3ccc(-c4cc(F)c(O)c(Cl)c4)cc23)cc1]

Following general procedure D, (6-bromo-4-(4-(2-(dimethylamino)ethyl)phenylamino)quinolin-3-yl)(cyclopropyl)methanone (100 mg, 0.23 mmol) was reacted with 2-chloro-6-fluoro-4-(4,4,5,5-tetramethyl-1,3,2-dioxaborolan-2-yl)phenol (93 mg, 0.34 mmol) to afford the desired product (83 mg, 72%) as a yellow-brown solid: $^1$H NMR (500 MHz, CD$_3$OD+TFA-d) δ 9.46 (s, 1H), 8.21 (dd, J=8.8, 1.9 Hz, 1H), 8.01 (d, J=8.8 Hz, 1H), 7.89 (s, 1H), 7.57 (d, J=8.4 Hz, 2H), 7.47 (d, J=8.4 Hz, 2H), 7.04 (m, 2H), 3.41 (m, 2H), 3.21 (m, 2H), 2.99 (s, 7H), 2.90 (m, 1H), 1.23 (m, 4H); ESI MS m/z 504 [C$_{29}$H$_{27}$ClFN$_3$O$_2$+H]$^+$; HPLC 97.0% (AUC), t$_R$=10.95 min.

Example 624 cyclopropyl(6-(3,5-dichloro-4-hydroxyphenyl)-4-(3-((dimethylamino)methyl)phenylamino)quinolin-3-yl)methanone

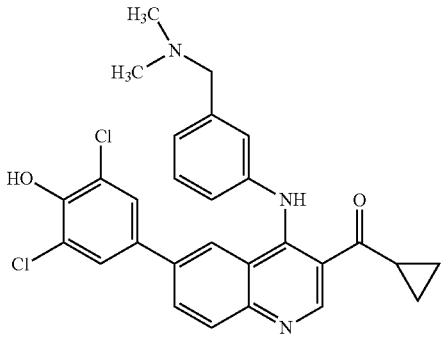

Following general procedure D, (6-bromo-4-(3-((dimethylamino)methyl)phenylamino)quinoline-3-yl)(cyclopropyl)methanone (100 mg, 0.23 mmol) was reacted with 2,6-dichloro-4-(4,4,5,5-tetramethyl-1,3,2-dioxaborolan-2-yl)phenol (98 mg, 0.34 mmol) to afford the desired product (87 mg, 75%) as a yellow-green solid: $^1$H NMR (500 MHz, CD$_3$OD+TFA-d) δ 9.45 (s, 1H), 8.25 (dd, J=8.8, 1.9 Hz, 1H), 8.05 (d, J=8.8 Hz, 1H), 7.97 (s, 1H), 7.74 (m, 1H), 7.63 (m, 3H), 7.28 (s, 2H), 4.39 (s, 2H), 2.84 (m, 7H), 1.19 (m, 4H); ESI MS m/z 506 [C$_{28}$H$_{25}$Cl$_2$N$_3$O$_2$+H]$^+$; HPLC 98.0% (AUC), t$_R$=11.15 min.

Example 626

(4-(2-(3-aminopiperidin-1-yl)pyrimidin-5-ylamino)-6-(3-chloro-5-fluoro-4-hydroxyphenyl)quinolin-3-yl)(cyclopropyl)methanone

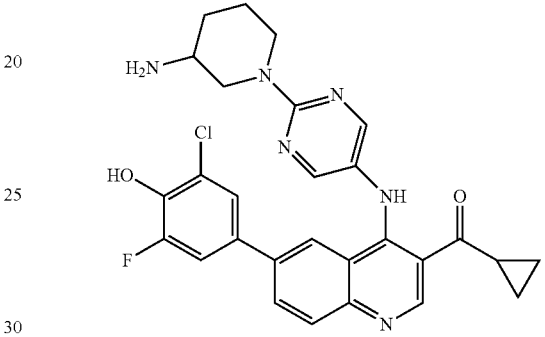

Following general procedure D, tert-butyl 1-(5-(6-bromo-3-(cyclopropanecarbonyl)quinoline-4-ylamino)pyrimidin-2-yl)piperidin-3-ylcarbamate (150 mg, 0.26 mmol) was reacted with 2-chloro-6-fluoro-4-(4,4,5,5-tetramethyl-1,3,2-dioxaborolan-2-yl)phenol (106 mg, 0.39 mmol) to obtain the protected intermediate which was subjected to general procedure A-2 to afford the desired product (28 mg, 23% over 2 steps) as a yellow solid. $^1$H NMR (500 MHz, MeOD+TFA-d) δ 9.34 (br s, 1H), 8.45 (s, 2H), 8.25 (dd, J=8.8, 1.9 Hz, 1H), 8.21 (br s, 1H), 8.04 (d, J=8.8 Hz, 1H), 7.25 (br s, 1H), 4.81-4.74 (m, 1H), 4.47 (d, J=12.8 Hz, 1H), 3.48-3.31 (m, 3H), 2.80 (br s, 1H), 2.24-2.16 (m, 1H), 1.97-1.87 (m, 1H), 1.81-1.62 (m, 2H), 1.21-1.16 (m, J=7.3 Hz, 4H); ESI MS m/z 533 [C$_{28}$H$_{26}$ClFN$_6$O$_2$+H]$^+$; HPLC>99.0% (AUC), t$_R$=10.89 min.

Example 628

(4-(2-(3-aminopiperidin-1-yl)pyrimidin-5-ylamino)-6-(3,5-dichloro-4-hydroxyphenyl) quinolin-3-yl)(cyclopropyl)methanone

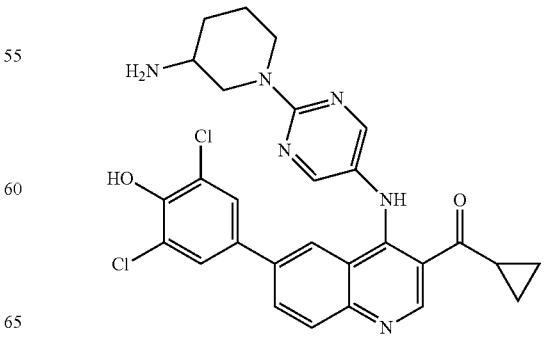

Following general procedure D, tert-butyl 1-(5-(6-bromo-3-(cyclopropanecarbonyl)quinoline-4-ylamino)pyrimidin-2-yl)piperidin-3-ylcarbamate (150 mg, 0.26 mmol) was reacted with 2,6-dichloro-4-(4,4,5,5-tetramethyl-1,3,2-dioxaborolan-2-yl)phenol (112 mg, 0.39 mmol) to obtain the protected intermediate which was subjected to general procedure A-2 to afford the desired product (8.0 mg, 8% over 2 steps) as a yellow solid. $^1$H NMR (500 MHz, MeOD+TFA-d) δ 9.33 (br s, 1H), 8.44 (s, 2H), 8.27 (dd, J=8.9, 1.8 Hz, 1H), 8.29-8.19 (m, 1H), 8.04 (d, J=8.9 Hz, 1H), 7.44 (br s, 2H), 4.81-4.71 (m, 1H), 4.48-4.44 (m, 1H), 3.46-3.31 (m, 3H), 2.84-2.77 (m, 1H), 2.23-2.16 (m, 1H), 1.96-1.87 (m, 1H), 1.80-1.60 (m, 2H), 1.21-1.15 (m, 4H); ESI MS m/z 549 [$C_{28}H_{26}Cl_2N_6O_2$+H]$^+$; HPLC>99% (AUC), $t_R$=11.00 min.

Example 629

(6-(3-chloro-5-fluoro-4-hydroxyphenyl)-4-(3-((dimethylamino)methyl)phenylamino)quinolin-3-yl)(cyclopropyl)methanone

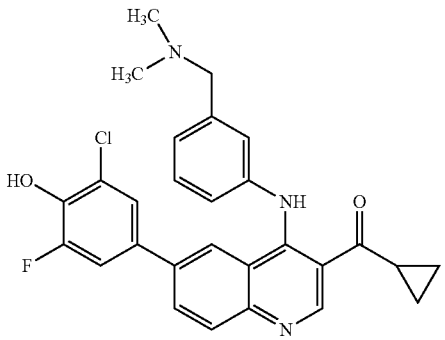 [SMILES: CN(C)Cc1cccc(Nc2c(C(=O)C3CC3)cnc3ccc(-c4cc(F)c(O)c(Cl)c4)cc23)c1]

Following general procedure D, (6-bromo-4-(3-((dimethylamino)methyl)phenylamino)quinoline-3-yl)(cyclopropyl)methanone (100 mg, 0.23 mmol) was reacted with 2-chloro-6-fluoro-4-(4,4,5,5-tetramethyl-1,3,2-dioxaborolan-2-yl)phenol (93 mg, 0.34 mmol) to afford the desired product (81 mg, 72%) as a yellow-green solid. $^1$H NMR (300 MHz, MeOD+TFA-d) δ 9.44 (s, 1H), 8.25 (dd, J=8.9, 1.9 Hz, 1H), 8.09-7.95 (m, 2H), 7.79-7.54 (m, 4H), 7.19 (dd, J=11.5, 2.3 Hz, 1H), 7.06 (s, 1H), 4.38 (s, 2H), 2.91-2.82 (m, 1H), 2.83 (s, 6H), 1.23-1.14 (m, 4H); ESI MS m/z 490 [$C_{29}H_{25}ClFN_3O_2$+H]$^+$; HPLC 97.3% (AUC), $t_R$=11.07 min.

Example 644

(4-(2-(3-aminopiperidin-1-yl)pyrimidin-5-ylamino)-6-(3-chloro-4-hydroxy-5-methoxyphenyl)quinolin-3-yl)(cyclopropyl)methanone

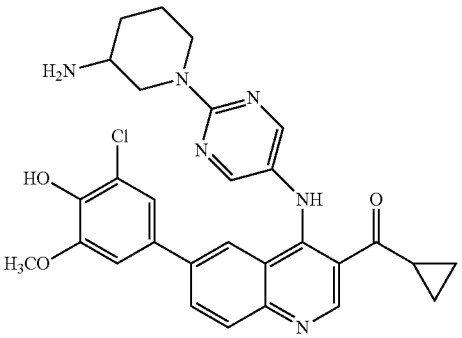

Following general procedure D, tert-butyl 1-(5-(6-bromo-3-(cyclopropanecarbonyl)quinolin-4-ylamino)pyrimidin-2-yl) piperidin-3-ylcarbamate (150 mg, 0.26 mmol) was reacted with 2-chloro-6-methoxy-4-(4,4,5,5-tetramethyl-1,3,2-dioxaborolan-2-yl)phenol (111 mg, 0.39 mmol) to obtain the protected intermediate which was subjected to general procedure A-2 to afford the desired product (16 mg, 11% over 2 steps) as an orange-yellow solid. $^1$H NMR (500 MHz, MeOD+TFA-d) δ 9.35 (br s, 1H), 8.45 (s, 2H), 8.29 (dd, J=8.8, 1.9 Hz, 1H), 8.26-8.15 (br s, 1H), 8.03 (d, J=8.8 Hz, 1H), 7.07 (br s, 1H), 6.96 (br s, 1H), 4.76 (d, J=12.9 Hz, 1H), 4.45 (br s, 1H), 3.37-3.31 (m, 1H), 2.82 (br s, 1H), 2.23-2.16 (m, 1H), 1.96-1.85 (m, 1H), 1.78-1.68 (m, 1H), 1.68-1.56 (m, 1H), 1.22-1.16 (m, 4H); ESI MS m/z 545 [$C_{29}H_{29}ClN_6O_3$+H]$^+$; HPLC 98.5% (AUC), $t_R$=10.69 min.

Example 646

(S)-(4-(6-(3-aminopiperidin-1-yl)pyridin-3-ylamino)-6-(3,5-dichloro-4-hydroxyphenyl)quinolin-3-yl)(cyclopropyl)methanone

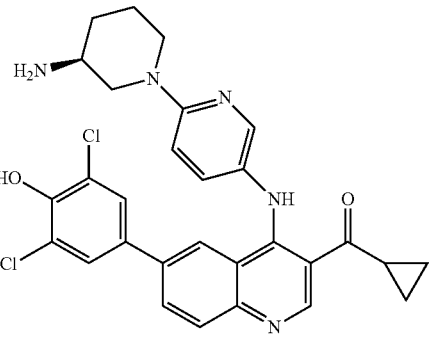

Following general procedure D, (S)-tert-butyl 1-(5-(6-bromo-3-(cyclopropanecarbonyl)quinoline-4-ylamino)pyridin-2-yl)piperidin-3-ylcarbamate (100 mg, 0.17 mmol) was reacted with 2,6-dichloro-4-(4,4,5,5-tetramethyl-1,3,2-dioxaborolan-2-yl)phenol (75 mg, 0.26 mmol) to obtain the protected intermediate which was subjected to general procedure A-2 to afford the desired product (29 mg, 31% over 2 steps) as a light orange solid. $^1$H NMR (500 MHz, MeOD+TFA-d) δ 9.40 (br s, 1H), 8.25-8.19 (m, 2H), 8.11 (br s, 1H), 8.01 (d, J=8.8 Hz, 1H), 7.65 (dd, J=9.1, 2.8 Hz, 1H), 7.32 (s, 2H), 7.7 (d, J=9.1 Hz, 1H), 4.53 (br s, 1H), 4.00 (dt, J=12.8, 4.0 Hz, 1H), 3.39-3.23 (m, 3H), 2.86 (br s, 1H), 2.22-2.12 (m, 1H), 1.98-1.88 (m, 1H), 1.78-1.64 (m, 2H), 1.26-1.16 (m, 4H). ESI MS m/z 548 [$C_{29}H_{27}Cl_2N_5O_2$+H]$^+$; HPLC>99.0% (AUC), $t_R$=10.97 min.

Example 648

(S)-(4-(6-(3-aminopiperidin-1-yl)pyridin-3-ylamino)-6-(3-chloro-5-fluoro-4-hydroxyphenyl)quinolin-3-yl)(cyclopropyl)methanone

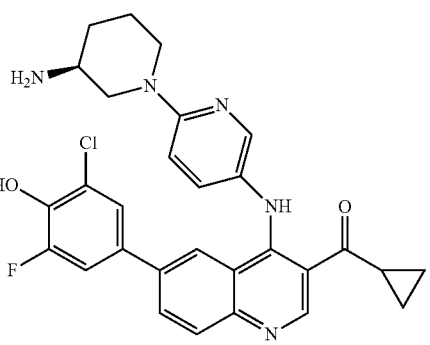

Following general procedure D, (S)-tert-butyl 1-(5-(6-bromo-3-(cyclopropanecarbonyl)quinoline-4-ylamino)pyridin-2-yl)piperidin-3-ylcarbamate (100 mg, 0.17 mmol) was reacted with 2-chloro-6-fluoro-4-(4,4,5,5-tetramethyl-1,3,2-dioxaborolan-2-yl)phenol (71 mg, 0.26 mmol) to obtain the protected intermediate which was subjected to general procedure A-2 to afford the desired product (27 mg, 30% over 2 steps) as an orange-yellow solid: $^1$H NMR (500 MHz, MeOD+TFA-d) δ 9.40 (br s, 1H), 8.28-8.15 (m, 2H), 8.06 (br s, 1H), 8.00 (d, J=8.8 Hz, 1H), 7.66 (dd, J=9.1, 2.8 Hz, 1H), 7.16-7.05 (m, 3H), 4.53 (d, J=11.0 Hz, 1H), 4.01 (dd, J=13.4, 4.6 Hz, 1H), 3.41-3.23 (m, 3H), 2.86 (br s, 1H), 2.23-2.15 (m, 1H), 1.99-1.88 (m, 1H), 1.79-1.66 (m, 2H), 1.27-1.16 (m, 4H). ESI MS m/z 532 $[C_{29}H_{27}ClFN_5O_2+H]^+$; HPLC>99.0% (AUC), $t_R$=10.78 min.

Example 649

(R)-(4-(6-(3-aminopiperidin-1-yl)pyridin-3-ylamino)-6-(3-chloro-4-hydroxy-5-methoxyphenyl)quinolin-3-yl)(cyclopropyl)methanone

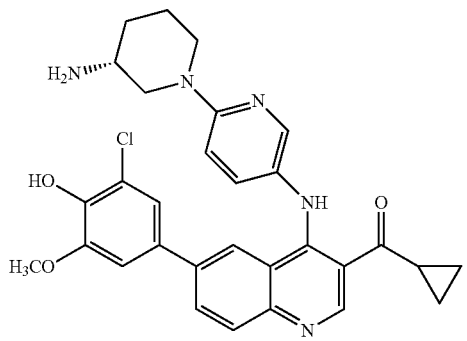

Following general procedure D, (R)-tert-butyl 1-(5-(6-bromo-3-(cyclopropanecarbonyl)quinoline-4-ylamino)pyridin-2-yl)piperidin-3-ylcarbamate (100 mg, 0.17 mmol) was reacted with 2-chloro-6-methoxy-4-(4,4,5,5-tetramethyl-1,3,2-dioxaborolan-2-yl)phenol (74 mg, 0.26 mmol) to obtain the protected intermediate which was subjected to general procedure A-2 to afford the desired product (30 mg, 32% over 2 steps) as an orange-yellow solid: $^1$H NMR (500 MHz, MeOD+TFA-d) δ 9.40 (br s, 1H), 8.28-8.20 (m, 2H), 8.10 (br s, 1H), 8.00 (d, J=8.8 Hz, 1H), 7.65 (dd, J=9.1, 2.8 Hz, 1H), 7.05 (d, J=9.1 Hz, 1H), 6.99 (s, 1H), 6.83 (br s, 1H), 4.55-4.49 (d, J=11.6 Hz, 1H), 4.04-3.95 (m, 1H), 3.91 (s, 3H), 3.28-3.18 (m, 3H), 2.87 (br s, 1H), 2.22-2.14 (m, 1H), 1.96-1.87 (m, 1H), 1.76-1.62 (m, 2H), 1.28-1.16 (m, 4H).; ESI MS m/z 544 $[C_{30}H_{30}ClN_5O_3+H]^+$; HPLC>99.0% (AUC), $t_R$=10.74 min.

Example 650

(R)-(4-(6-(3-aminopiperidin-1-yl)pyridin-3-ylamino)-6-(3,5-dichloro-4-hydroxyphenyl)quinolin-3-yl)(cyclopropyl)methanone

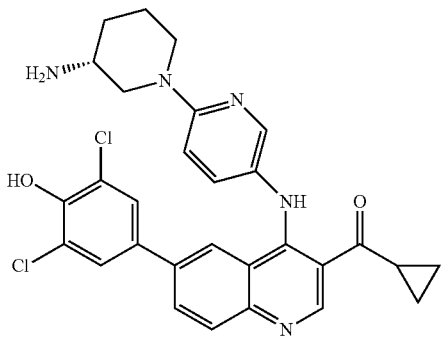

Following general procedure D, (R)-tert-butyl 1-(5-(6-bromo-3-(cyclopropanecarbonyl)quinolin-4-ylamino)pyridin-2-yl)piperidin-3-ylcarbamate (100 mg, 0.17 mmol) was reacted with 2,6-dichloro-4-(4,4,5,5-tetramethyl-1,3,2-dioxaborolan-2-yl)phenol (75 mg, 0.26 mmol) to obtain the protected intermediate which was subjected to general procedure A-2 to afford the desired product (18 mg, 19% over 2 steps) as a yellow-orange solid. NMR (500 MHz, MeOD+TFA-d) δ 9.40 (br s, 1H), 8.25-8.19 (m, 2H), 8.10 (br s, 1H), 8.01 (d, J=8.8 Hz, 1H), 7.65 (dd, J=9.1, 2.8 Hz, 1H), 7.32 (s, 2H), 7.07 (d, J=9.1 Hz, 1H), 4.53 (br s, 1H), 4.01 (dt, J=13.7, 4.0 Hz, 1H), 3.39-3.23 (m, 1H), 2.86 (br s, 1H), 2.22-2.12 (m, 1H), 1.97-1.88 (m, 1H), 1.78-1.64 (m, 2H), 1.26-1.16 (m, 4H). ESI MS m/z 548 $[C_{29}H_{27}Cl_2N_5O_2+H]^+$; HPLC>99.0% (AUC), $t_R$=10.96 min.

Example 651

(R)-(4-(6-(3-aminopiperidin-1-yl)pyridin-3-ylamino)-6-(3-chloro-5-fluoro-4-hydroxyphenyl)quinolin-3-yl)(cyclopropyl)methanone

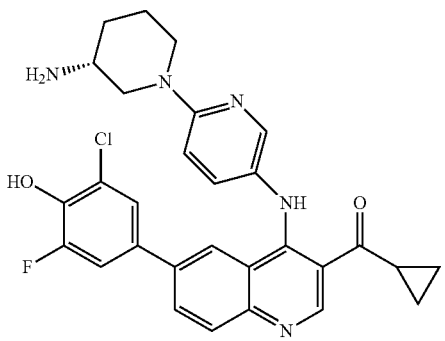

Following general procedure D, (R)-tert-butyl 1-(5-(6-bromo-3-(cyclopropanecarbonyl)quinoline-4-ylamino)pyridin-2-yl)piperidin-3-ylcarbamate (100 mg, 0.17 mmol) was reacted with 2-chloro-6-fluoro-4-(4,4,5,5-tetramethyl-1,3,2-dioxaborolan-2-yl)phenol (71 mg, 0.26 mmol) to obtain the protected intermediate which was subjected to general procedure A-2 to afford the desired product (33 mg, 37% over 2 steps) as an orange-yellow solid $^1$H NMR (500 MHz, MeOD+TFA-d) δ 9.41 (s, 1H), 8.28-8.14 (m, 2H), 8.05 (br s, 1H), 8.00 (d, J=8.8 Hz, 1H), 7.65 (dd, J=9.1, 2.8 Hz, 1H), 7.16-7.04 (m, 3H), 4.53 (d, J=11.6 Hz, 1H), 3.99 (dt, J=13.7, 4.0 Hz, 1H), 3.40-3.21 (m, 3H), 2.86 (br s, 3H), 2.23-2.15 (m, 1H), 1.98-1.89 (m, 1H), 1.79-1.65 (m, 2H), 1.27-1.16 (m, 4H). ESI MS m/z 532 [$C_{29}H_{27}Cl_{F}N_{5}O_{2}$+H]$^+$ HPLC>99.0% (AUC), $t_R$=10.77 min.

Example 660

(S)-(4-(6-(3-aminopiperidin-1-yl)pyridin-3-ylamino)-6-(3-chloro-4-hydroxy-5-methoxyphenyl)quinolin-3-yl)(cyclopropyl)methanone

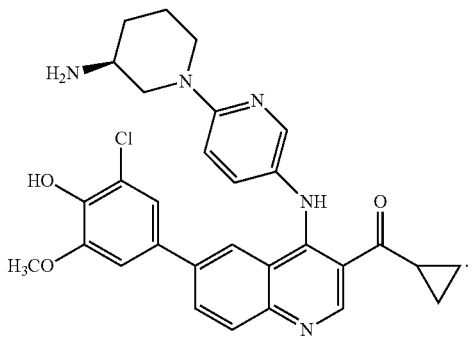 [SMILES: COc1cc(-c2ccc3ncc(C(=O)C4CC4)c(Nc4ccc(N5CCC[C@H](N)C5)nc4)c3c2)cc(Cl)c1O]

Following general procedure D, (S)-tert-butyl 1-(5-(6-bromo-3-(cyclopropanecarbonyl)quinoline-4-ylamino)pyridin-2-yl)piperidin-3-ylcarbamate (100 mg, 0.17 mmol) was reacted with 2-chloro-6-methoxy-4-(4,4,5,5-tetramethyl-1,3,2-dioxaborolan-2-yl)phenol (74 mg, 0.26 mmol) to obtain the protected intermediate which was subjected to general procedure A-2 to afford the desired product (42 mg, 45% over 2 steps) as an orange-yellow solid: $^1$H NMR (500 MHz, MeOD+TFA-d) δ 9.40 (br s, 1H), 8.28-8.20 (m, 2H), 8.10 (br s, 1H), 7.99 (d, J=8.8 Hz, 1H), 7.65 (dd, J=9.1, 2.8 Hz, 1H), 7.05 (d, J=9.1 Hz, 1H), 6.99 (s, 1H), 6.83 (br s, 1H), 4.52 (d, J=11.7 Hz, 1H), 4.04-3.96 (m, 1H), 3.91 (s, 3H), 3.37-3.18 (m, 3H), 2.87 (br s, 1H), 2.21-2.14 (m, 1H), 1.96-1.87 (m, 1H), 1.76-1.62 (m, 2H), 1.27-1.16 (m, 4H). ESI MS m/z 544 [$C_{30}H_{30}ClN_{5}O_{3}$+H]$^+$; HPLC>99.0% (AUC), $t_R$=10.76 min.

Example 661 cyclopropyl(6-(3,5-dichloro-4-hydroxyphenyl)-4-(4-(3-methoxypyrrolidin-1-yl)cyclohexylamino)quinolin-3-yl)methanone

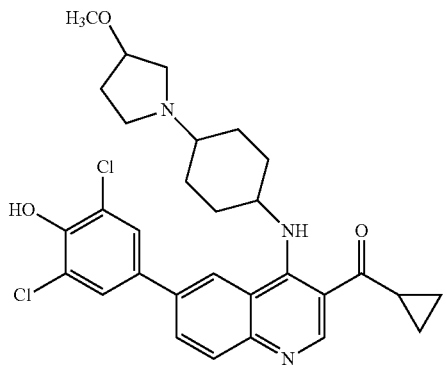 [SMILES: COC1CCN(C2CCC(Nc3c(C(=O)C4CC4)cnc4ccc(-c5cc(Cl)c(O)c(Cl)c5)cc34)CC2)C1]

Following general procedure D, (6-bromo-4-(4-(3-methoxypyrrolidin-1-yl)cyclohexylamino)quinolin-3-yl)(cyclopropyl)methanone (60 mg, 0.13 mmol) was reacted with 2,6-dichloro-4-(4,4,5,5-tetramethyl-1,3,2-dioxaborolan-2-yl)phenol (55 mg, 0.19 mmol) to afford the desired product (46 mg, 64%) as a brown solid: $^1$H NMR $^1$H NMR (500 MHz, MeOD+TFA-d) δ 9.42 (s, 1H), 8.46 (s, 1H), 8.31-8.23 (m, 1H), 8.04-7.97 (m, 1H), 7.75 (s, 1H), 7.71 (s, 1H), 4.99 (br s, 1H), 4.23-4.14 (m, 1H), 3.82-3.61 (m, 2H), 3.43-3.30 (m, 6H), 3.27-3.19 (m, 1H), 2.93-2.82 (m, 1H), 2.60-2.03 (m, 7H), 2.02-1.61 (m, 3H), 1.37-1.18 (m, 4H).; ESI MS m/z 554 [$C_{30}H_{33}Cl_2N_3O_3$+H]$^+$; HPLC>99.0% (AUC), $t_R$=10.97 min.

Example 666 cyclopropyl(6-(3,5-dichloro-4-hydroxyphenyl)-4-(6-(pyrrolidin-3-ylamino)pyridin-3-ylamino)quinolin-3-yl)methanone

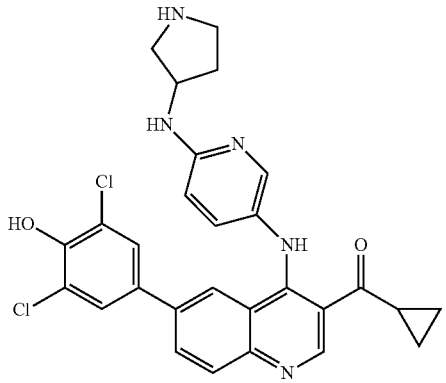 [SMILES: O=C(c1cnc2ccc(-c3cc(Cl)c(O)c(Cl)c3)cc2c1Nc1ccc(NC2CCNC2)nc1)C1CC1]

Following general procedure D, tert-butyl 3-(5-(6-bromo-3-(cyclopropanecarbonyl)quinoline-4-ylamino)pyridin-2-ylamino)pyrrolidine-1-carboxylate (100 mg, 0.18 mmol) was reacted with 2,6-dichloro-4-(4,4,5,5-tetramethyl-1,3,2-dioxaborolan-2-yl)phenol (78 mg, 0.27 mmol) to obtain the protected intermediate which was subjected to general procedure A-2 to afford the desired product (43 mg, 45% over 2 steps) as a yellow-orange solid: $^1$H NMR (500 MHz, MeOD+TFA-d) δ 9.40 (br s, 1H), 8.26-8.07 (m, 3H), 8.00 (d, J=8.9 Hz, 1H), 7.57 (dd, J=8.9, 2.7 Hz, 1H), 7.34 (s, 2H), 6.85-6.77 (m, 1H), 4.65-4.56 (m, 1H), 3.66-3.49 (m, 2H), 3.44-3.30 (m, 2H), 2.86 (br s, 1H), 2.47-2.36 (m, 1H), 2.18-2.07 (m, 1H), 1.27-1.15 (m, 4H). ESI MS m/z 534 [$C_{28}H_{25}Cl_2N_5O_2$+H]$^+$; HPLC>99.0% (AUC), $t_R$=10.64 min.

Example 667

(6-(3-chloro-5-fluoro-4-hydroxyphenyl)-4-(6-(pyrrolidin-3-ylamino)pyridin-3-ylamino)quinolin-3-yl)(cyclopropyl)methanone

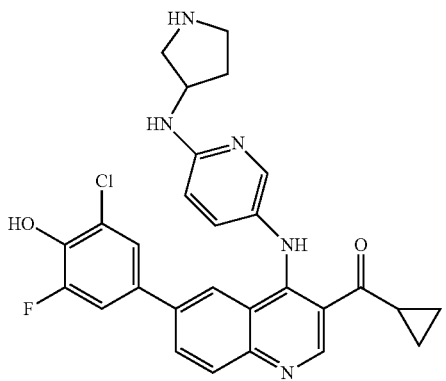 [SMILES: O=C(c1cnc2ccc(-c3cc(F)c(O)c(Cl)c3)cc2c1Nc1ccc(NC2CCNC2)nc1)C1CC1]

Following general procedure D, tert-butyl 3-(5-(6-bromo-3-(cyclopropanecarbonyl)quinolin-4-ylamino)pyridin-2-ylamino)pyrrolidine-1-carboxylate (100 mg, 0.18 mmol) was reacted with 2-chloro-6-fluoro-4-(4,4,5,5-tetramethyl-1,3,2-dioxaborolan-2-yl)phenol (73 mg, 0.27 mmol) to obtain the protected intermediate which was subjected to general procedure A-2 to afford the desired product (42 mg, 45% over 2 steps) as a yellow solid: NMR (500 MHz, MeOD+TFA-d) δ 9.40 (br s, 1H), 8.22 (dd, J=8.8, 2.0 Hz, 1H), 8.17-8.06 (m, 2H), 8.00 (d, J=8.8 Hz, 1H), 7.55 (dd, J=8.9, 2.7 Hz, 1H), 7.19-7.13 (m, 2H), 6.83-6.76 (m, 1H), 4.65-4.56 (m, 1H), 3.66-3.49 (m, 2H), 3.45-3.30 (m, 2H), 2.87 (br s, 1H), 2.48-2.37 (m, 1H), 2.19-2.08 (m, 1H), 1.28-1.16 (m, 4H). ESI MS m/z 518 $[C_{28}H_{25}ClFN_5O_2+H]^+$; HPLC>99.0% (AUC), $t_R$=10.43 min.

Example 562

(4-(6-(3-aminopiperidin-1-yl)pyridin-3-ylamino)-6-(3-chloro-5-fluoro-4-hydroxyphenyl)quinolin-3-yl)(cyclopropyl)methanone hydrochloride

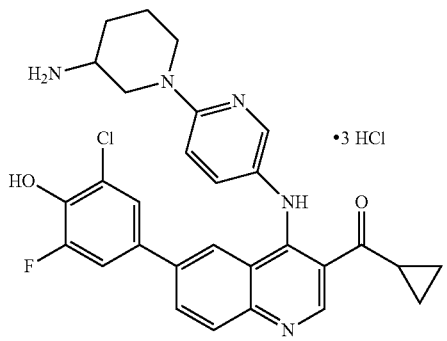 [SMILES: NC1CCCN(c2ccc(Nc3c(C(=O)C4CC4)cnc4ccc(-c5cc(F)c(O)c(Cl)c5)cc34)cn2)C1]

(4-(6-(3-aminopiperidin-1-yl)pyridin-3-ylamino)-6-(3-chloro-5-fluoro-4-hydroxyphenyl)quinolin-3-yl)(cyclopropyl)methanone (12 mg, 0.02 mmol) was suspended in methanol (1 mL) at 0° C. followed by dropwise addition of HCl in diethyl ether (2 M) until complete dissolution of the solid was observed. The solvent was removed under reduced pressure to afford the desired product (10 mg, 80%) as an orange-red solid: $^1$H NMR (500 MHz, MeOD) δ 9.39 (s, 1H), 8.27-8.19 (m, 2H), 8.13 (br s, 1H), 8.02 (d, J=8.8 Hz, 1H), 7.72 (dd, J=9.2, 2.7 Hz, 1H), 7.21-7.07 (m, 3H), 4.52 (d, J=10.8 Hz, 1H), 4.06-3.98 (m, 1H), 3.43-3.31 (m, 3H), 2.90-2.81 (m, 1H), 2.28-2.16 (m, 1H), 2.01-1.92 (m, 1H), 1.80-1.68 (m, 2H), 1.31-1.15 (m, 4H). ESI MS m/z 532 $[C_{29}H_{27}ClFN_5O_2+H]^+$; HPLC 98.7% (AUC), $t_R$=10.82 min.

Example 573

(4-(2-(3-aminopyrrolidin-1-yl)pyrimidin-5-ylamino)-6-(3-chloro-5-fluoro-4-hydroxyphenyl) quinolin-3-yl)(cyclopropyl)methanone hydrochloride

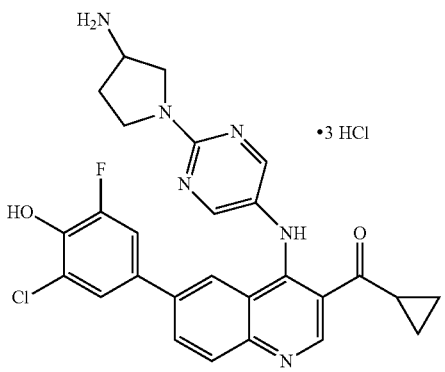

(4-(2-(3-aminopyrrolidin-1-yl)pyrimidin-5-ylamino)-6-(3-chloro-5-fluoro-4-hydroxyphenyl)quinolin-3-yl)(cyclopropyl)methanone (30 mg, 0.06 mmol) was suspended in methanol (1 mL) at 0° C. followed by dropwise addition of HCl in diethyl ether (2 M) until complete dissolution of the solid was observed. The solvent was removed under reduced pressure to afford the desired product (33 mg, 92%) as a yellow-orange solid: $^1$H NMR (500 MHz, MeOD) δ 9.31 (br s, 1H), 8.45 (s, 2H), 8.23-8.14 (m, 2H), 8.02 (d, J=8.8 Hz, 1H), 7.26-7.20 (m, 2H), 4.11-4.00 (m, 2H), 3.94-3.73 (m, 3H), 2.83 (br s, 1H), 2.58-2.48 (m, 1H), 2.28-2.17 (m, 1H), 1.22-1.14 (m, 4H), 0.92-0.88 (s, 0H). ESI MS m/z 519 $[C_{27}H_{24}ClFN_6O_2+H]^+$; HPLC>99.0% (AUC), $t_R$=5.18 min.

Example 577

(4-(6-(3-aminopyrrolidin-1-yl)pyridin-3-ylamino)-6-(3-chloro-5-fluoro-4-hydroxyphenyl)quinolin-3-yl)(cyclopropyl)methanone hydrochloride

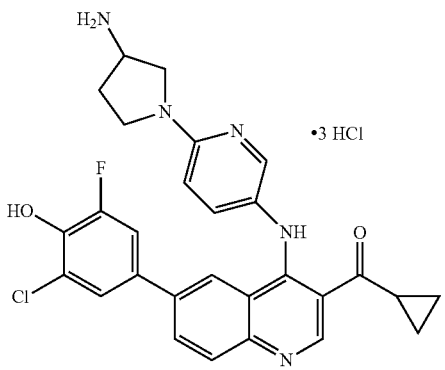 [SMILES: NC1CCN(c2ccc(Nc3c(C(=O)C4CC4)cnc4ccc(-c5cc(F)c(O)c(Cl)c5)cc34)cn2)C1]

(4-(6-(3-aminopyrrolidin-1-yl)pyridin-3-ylamino)-6-(3-chloro-5-fluoro-4-hydroxyphenyl)quinolin-3-yl)(cyclopropyl)methanone (15 mg, 0.03 mmol) was suspended in methanol (1 mL) at 0° C. followed by dropwise addition of HCl in diethyl ether (2 M) until complete dissolution of the solid was observed. The solvent was removed under reduced pressure to afford the desired product (23 mg, quant.) as a yellow-brown solid. $^1$H NMR (500 MHz, MeOD) δ 9.39 (s, 1H), 8.28-8.19 (m, 2H), 8.16 (br s, 1H), 8.02 (d, J=8.8 Hz, 1H), 7.79 (dd, J=9.1, 2.7 Hz, 1H), 7.26-7.16 (m, 2H), 6.94 (d, J=9.2 Hz, 1H), 4.16-4.08 (m, 1H), 4.05-3.97 (m, 1H), 3.88-3.79 (m, 1H), 3.78-3.69 (m, 2H), 2.85 (br s, 1H), 2.64-2.53 (m, 1H), 2.34-2.21 (m, 1H), 1.25-1.15 (m, 4H). ESI MS m/z 518 [$C_{28}H_{25}ClFN_5O_2$+H]$^+$; HPLC 98.1% (AUC), $t_R$=5.13 min.

Example 549

(4-(6-(4-Aminopiperidin-1-yl)pyridin-3-ylamino)-6-(3,5-dichloro-4-hydroxyphenyl)quinolin-3-1)(cyclopropyl)methanone hydrochloride

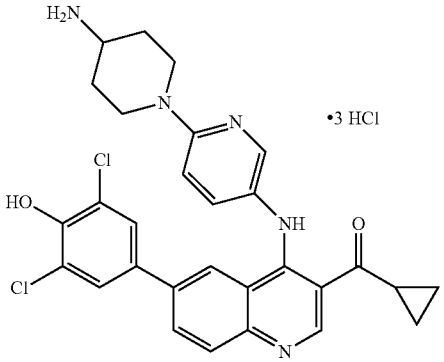 [SMILES: NC1CCN(c2ccc(Nc3c(C(=O)C4CC4)cnc4ccc(-c5cc(Cl)c(O)c(Cl)c5)cc34)cn2)CC1]

A suspension of {4-[6-(4-Aminopiperidin-1-yl)pyridin-3-ylamino]-6-(3,5-dichloro-4-hydroxy phenyl)quinolin-3-yl}(cyclopropyl)methanone (19 mg, 0.02 mmol) was suspended in methanol (1 mL) at 0° C. followed by dropwise addition of HCl in diethyl ether (2 M) until the suspension was clear. The solvent was removed under reduced pressure to afford the desired product (19 mg, 83%) as a red solid: $^1$H NMR (500 MHz, CD$_3$OD) δ 9.33 (s, 1H), 8.16-8.08 (m, 2H), 8.05 (s, 1H), 7.97 (d, J=8.8 Hz, 1H), 7.57 (dd, J=8.8, 2.9 Hz, 1H), 7.29 (s, 2H), 7.04 (d, J=9.1 Hz, 1H), 4.52 (d, J=13.4 Hz, 2H), 3.44-3.32 (m, 1H), 3.08-2.99 (m, 2H), 2.88 (s, 1H), 2.11 (d, J=12.2 Hz, 2H), 1.71-1.59 (m, 2H), 1.24-1.13 (m, 4H); ESI MS m/z 548 [$C_{29}H_{27}Cl_2N_5O_2$+H]$^+$; HPLC>99% (AUC), $t_R$=11.52 min.

Example 711

Cyclopropyl(6-(3,5-dichloro-4-hydroxyphenyl)-4-(6-(2-(dimethylamino)ethoxy)pyridin-3-ylamino)quinolin-3-yl)methanone

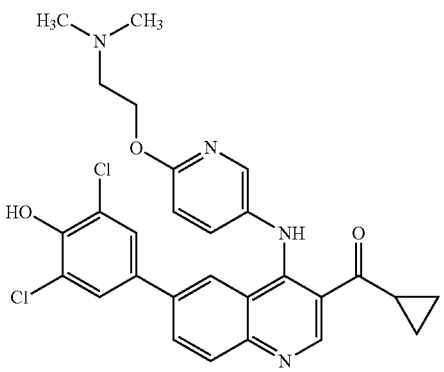 [SMILES: CN(C)CCOc1ccc(Nc2c(C(=O)C3CC3)cnc3ccc(-c4cc(F)c(O)c(Cl)c4)cc23)cn1]

Following general procedure D, (6-bromo-4-(6-(2-(dimethylamino)ethoxy)pyridin-3-ylamino)quinolin-3-yl) (cyclopropyl)methanone (100 mg, 0.22 mmol) was reacted with 2,6-dichloro-4-(4,4,5,5-tetramethyl-1,3,2-dioxaborolan-2-yl)phenol (95 mg, 0.33 mmol) to afford the desired product (24 mg, 20%) as a yellow solid: $^1$H NMR (500 MHz, CD$_3$OD+TFA-d) δ 9.25 (s, 1H), 8.07 (d, J=2.8 Hz, 1H), 7.94 (s, 2H), 7.80 (s, 1H), 7.56 (dd, J=8.5, 2.8 Hz, 1H), 7.18 (s, 2H), 6.93 (d, J=8.5 Hz, 1H), 4.54 (t, J=5.5 Hz, 2H), 3.04 (t, J=5.5 Hz, 2H), 2.95-2.86 (m, 1H), 2.54 (s, 6H), 1.23-1.14 (m, 2H), 1.17-1.08 (m, 2H); ESI MS m/z 537 [$C_{28}H_{26}Cl_2N_4O_3$+H]$^+$; HPLC>99% (AUC), $t_R$=11.42 min.

Example 710

(6-(3-Chloro-5-fluoro-4-hydroxyphenyl)-4-(6-(2-(dimethylamino)ethoxy)pyridin-3-ylamino) quinolin-3-yl)(cyclopropyl)methanone

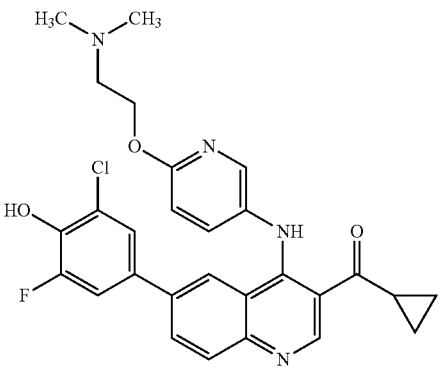

Following general procedure D, (6-bromo-4-(6-(2-(dimethylamino)ethoxy)pyridin-3-ylamino)quinolin-3-yl)(cyclopropyl)methanone (100 mg, 0.22 mmol) was reacted with 2-chloro-6-fluoro-4-(4,4,5,5-tetramethyl-1,3,2-dioxaborolan-2-yl)phenol (90 mg, 0.33 mmol) to afford the desired product (21 mg, 18%) as a yellow solid: $^1$H NMR (500 MHz, CD$_3$OD+TFA-d) δ 9.25 (s, 1H), 8.08 (d, J=2.7 Hz, 1H), 7.94 (m, 2H), 7.82 (s, 1H), 7.56 (dd, J=8.8, 2.7 Hz, 1H), 7.06-6.96 (m, 2H), 6.92 (d, J=8.8 Hz, 1H), 4.53 (t, J=5.5 Hz, 2H), 3.00 (t, J=5.5 Hz, 2H), 2.95-2.86 (m, 1H), 2.51 (s, 6H), 1.23-1.14 (m, 2H), 1.17-1.07 (m, 2H); ESI MS m/z 521 [$C_{28}H_{26}ClFN_4O_3$+H]$^+$; HPLC>99% (AUC), $t_R$=11.15 min.

Example 626

(4-(2-(3-aminopiperidin-1-yl)pyrimidin-5-ylamino)-6-(3-chloro-5-fluoro-4-hydroxyphenyl)quinolin-3-yl)(cyclopropyl)methanone

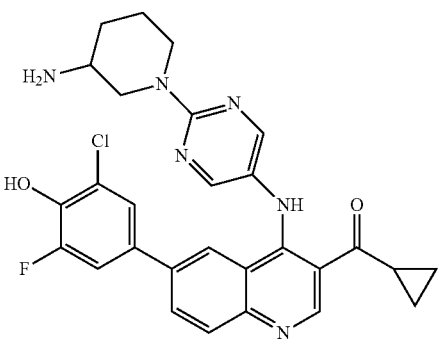 [SMILES: NC1CCCN(c2ncc(Nc3c(C(=O)C4CC4)cnc4ccc(-c5cc(F)c(O)c(Cl)c5)cc34)cn2)C1]

Following general procedure D, tert-butyl 1-(5-(6-bromo-3-(cyclopropanecarbonyl)quinolin-4-ylamino)pyrimidin-2-yl)piperidin-3-ylcarbamate (150 mg, 0.26 mmol) was reacted with 2-chloro-6-fluoro-4-(4,4,5,5-tetramethyl-1,3,2-dioxaborolan-2-yl)phenol (106 mg, 0.39 mmol) to obtain the protected intermediate which was subjected to general procedure A-2 to afford the desired product (28 mg, 23% over 2 steps) as a yellow solid. NMR (500 MHz, MeOD+TFA-d) δ 9.34 (br s, 1H), 8.45 (s, 2H), 8.25 (dd, J=8.8, 1.9 Hz, 1H), 8.21 (br s, 1H), 8.04 (d, J=8.8 Hz, 1H), 7.25 (br s, 1H), 4.81-4.74 (m, 1H), 4.47 (d, J=12.8 Hz, 1H), 3.48-3.31 (m, 3H), 2.80 (br s, 1H), 2.24-2.16 (m, 1H), 1.97-1.87 (m, 1H), 1.81-1.62 (m, 2H), 1.21-1.16 (m, J=7.3 Hz, 4H); ESI MS m/z 533 [$C_{28}H_{26}ClFN_6O_2$+H]$^+$; HPLC>99.0% (AUC), $t_R$=10.89 min.

Example 628

(4-(2-(3-aminopiperidin-1-yl)pyrimidin-5-ylamino)-6-(3,5-dichloro-4-hydroxyphenyl)quinolin-3-yl)(cyclopropyl)methanone

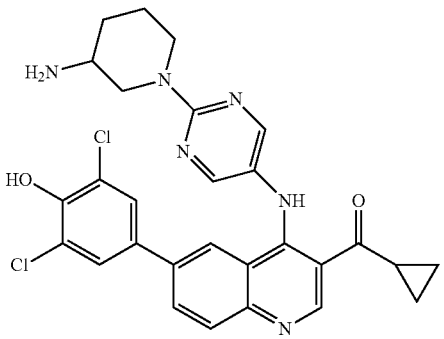

Following general procedure D, tert-butyl 1-(5-(6-bromo-3-(cyclopropanecarbonyl)quinoline-4-ylamino)pyrimidin-2-yl)piperidin-3-ylcarbamate (150 mg, 0.26 mmol) was reacted with 2,6-dichloro-4-(4,4,5,5-tetramethyl-1,3,2-dioxaborolan-2-yl)phenol (112 mg, 0.39 mmol) to obtain the protected intermediate which was subjected to general procedure A-2 to afford the desired product (8.0 mg, 8% over 2 steps) as a yellow solid. $^1$H NMR (500 MHz, MeOD+TFA-d) δ 9.33 (br s, 1H), 8.44 (s, 2H), 8.27 (dd, J=8.9, 1.8 Hz, 1H), 8.29-8.19 (m, 1H), 8.04 (d, J=8.9 Hz, 1H), 7.44 (br s, 2H), 4.81-4.71 (m, 1H), 4.48-4.44 (m, 1H), 3.46-3.31 (m, 3H), 2.84-2.77 (m, 1H), 2.23-2.16 (m, 1H), 1.96-1.87 (m, 1H), 1.80-1.60 (m, 2H), 1.21-1.15 (m, 4H); ESI MS m/z 549 [$C_{28}H_{26}Cl_2N_6O_2$+H]$^+$; HPLC>99% (AUC), $t_R$=11.00 min.

Example 629

(6-(3-chloro-5-fluoro-4-hydroxyphenyl)-4-(3-((dimethylamino)methyl)phenylamino)quinolin-3-yl)(cyclopropyl)methanone

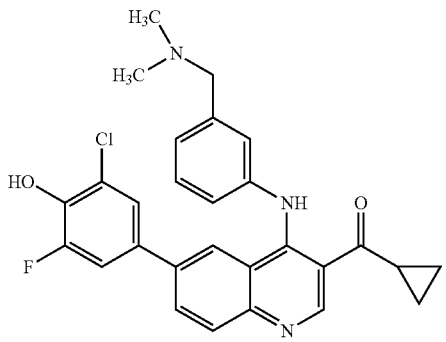 [SMILES: CN(C)Cc1cccc(Nc2c(C(=O)C3CC3)cnc3ccc(-c4cc(F)c(O)c(Cl)c4)cc23)c1]

Following general procedure D, (6-bromo-4-(3-((dimethylamino)methyl)phenylamino)quinoline-3-yl)(cyclopropyl)methanone (100 mg, 0.23 mmol) was reacted with 2-chloro-6-fluoro-4-(4,4,5,5-tetramethyl-1,3,2-dioxaborolan-2-yl)phenol (93 mg, 0.34 mmol) to afford the desired product (81 mg, 72%) as a yellow-green solid. NMR (300 MHz, MeOD+TFA-d) δ 9.44 (s, 1H), 8.25 (dd, J=8.9, 1.9 Hz, 1H), 8.09-7.95 (m, 2H), 7.79-7.54 (m, 4H), 7.19 (dd, J=11.5, 2.3 Hz, 1H), 7.06 (s, 1H), 4.38 (s, 2H), 2.91-2.82 (m, 1H), 2.83 (s, 6H), 1.23-1.14 (m, 4H); ESI MS m/z 490 [$C_{29}H_{25}ClFN_3O_2$+H]$^+$; HPLC 97.3% (AUC), $t_R$=11.07 min.

Example 644

(4-(2-(3-aminopiperidin-1-yl)pyrimidin-5-ylamino)-6-(3-chloro-4-hydroxy-5-methoxyphenyl)quinolin-3-yl)(cyclopropyl)methanone

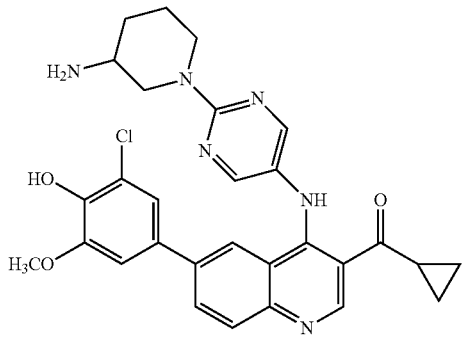

Following general procedure D, tert-butyl 1-(5-(6-bromo-3-(cyclopropanecarbonyl)quinolin-4-ylamino)pyrimidin-2-yl)piperidin-3-ylcarbamate (150 mg, 0.26 mmol) was reacted with 2-chloro-6-methoxy-4-(4,4,5,5-tetramethyl-1,3,2-dioxaborolan-2-yl)phenol (111 mg, 0.39 mmol) to obtain the protected intermediate which was subjected to general procedure A-2 to afford the desired product (16 mg, 11% over 2 steps) as an orange-yellow solid: $^1$H NMR (500 MHz, MeOD+TFA-d) δ 9.35 (br s, 1H), 8.45 (s, 2H), 8.29 (dd, J=8.8, 1.9 Hz, 1H), 8.26-8.15 (br s, 1H), 8.03 (d, J=8.8 Hz, 1H), 7.07 (br s, 1H), 6.96 (br s, 1H), 4.76 (d, J=12.9 Hz, 1H), 4.45 (br s, 1H), 3.37-3.31 (m, 1H), 2.82 (br s, 1H), 2.23-2.16 (m, 1H), 1.96-1.85 (m, 1H), 1.78-1.68 (m, 1H), 1.68-1.56 (m, 1H), 1.22-1.16 (m, 4H); ESI MS m/z 545 [C$_{29}$H$_{29}$ClN$_6$O$_3$+H]$^+$; HPLC 98.5% (AUC), t$_R$=10.69 min.

Example 646

(S)-(4-(6-(3-aminopiperidin-1-yl)pyridin-3-ylamino)-6-(3,5-dichloro-4-hydroxyphenyl)quinolin-3-yl)(cyclopropyl)methanone

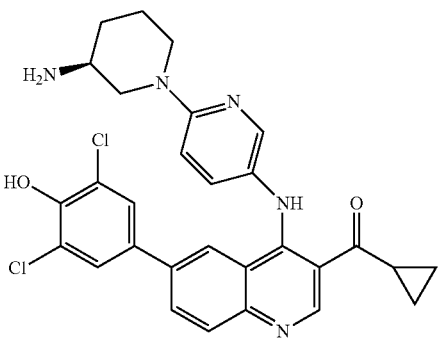 [SMILES: N[C@H]1CCCN(c2ccc(Nc3c(C(=O)C4CC4)cnc4ccc(-c5cc(Cl)c(O)c(Cl)c5)cc34)cn2)C1]

Following general procedure D, (S)-tert-butyl 1-(5-(6-bromo-3-(cyclopropanecarbonyl)quinolin-4-ylamino)pyridin-2-yl)piperidin-3-ylcarbamate (100 mg, 0.17 mmol) was reacted with 2,6-dichloro-4-(4,4,5,5-tetramethyl-1,3,2-dioxaborolan-2-yl)phenol (75 mg, 0.26 mmol) to obtain the protected intermediate which was subjected to general procedure A-2 to afford the desired product (29 mg, 31% over 2 steps) as a light orange solid: $^1$H NMR (500 MHz, MeOD+TFA-d) δ 9.40 (br s, 1H), 8.25-8.19 (m, 2H), 8.11 (br s, 1H), 8.01 (d, J=8.8 Hz, 1H), 7.65 (dd, J=9.1, 2.8 Hz, 1H), 7.32 (s, 2H), 7.7 (d, J=9.1 Hz, 1H), 4.53 (br s, 1H), 4.00 (dt, J=12.8, 4.0 Hz, 1H), 3.39-3.23 (m, 3H), 2.86 (br s, 1H), 2.22-2.12 (m, 1H), 1.98-1.88 (m, 1H), 1.78-1.64 (m, 2H), 1.26-1.16 (m, 4H). ESI MS m/z 548 [C$_{29}$H$_{27}$Cl$_2$N$_5$O$_2$+H]$^+$; HPLC>99.0% (AUC), t$_R$=10.97 min.

Example 648

(S)-(4-(6-(3-aminopiperidin-1-yl)pyridin-3-ylamino)-6-(3-chloro-5-fluoro-4-hydroxyphenyl)quinolin-3-yl)(cyclopropyl)methanone

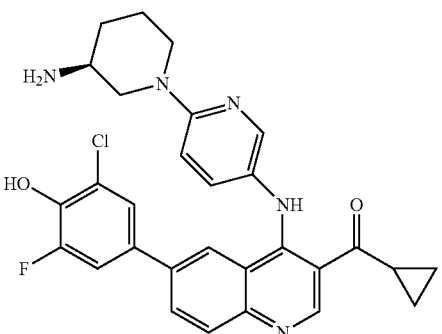

Following general procedure D, (S)-tert-butyl 1-(5-(6-bromo-3-(cyclopropanecarbonyl)quinolin-4-ylamino)pyridin-2-yl)piperidin-3-ylcarbamate (100 mg, 0.17 mmol) was reacted with 2-chloro-6-fluoro-4-(4,4,5,5-tetramethyl-1,3,2-dioxaborolan-2-yl)phenol (71 mg, 0.26 mmol) to obtain the protected intermediate which was subjected to general procedure A-2 to afford the desired product (27 mg, 30% over 2 steps) as an orange-yellow solid: $^1$H NMR (500 MHz, MeOD TFA-d) δ 9.40 (br s, 1H), 8.28-8.15 (m, 2H), 8.06 (br s, 1H), 8.00 (d, J=8.8 Hz, 1H), 7.66 (dd, J=9.1, 2.8 Hz, 1H), 7.16-7.05 (m, 3H), 4.53 (d, J=11.0 Hz, 1H), 4.01 (dd, J=13.4, 4.6 Hz, 1H), 3.41-3.23 (m, 3H), 2.86 (br s, 1H), 2.23-2.15 (m, 1H), 1.99-1.88 (m, 1H), 1.79-1.66 (m, 2H), 1.27-1.16 (m, 4H). ESI MS m/z 532 [C$_{29}$H$_{27}$ClFN$_5$O$_2$+H]$^+$; HPLC>99.0% (AUC), t$_R$=10.78 min.

Example 649

(R)-(4-(6-(3-aminopiperidin-1-yl)pyridin-3-ylamino)-6-(3-chloro-4-hydroxy-5-methoxyphenyl)quinolin-3-yl)(cyclopropyl)methanone

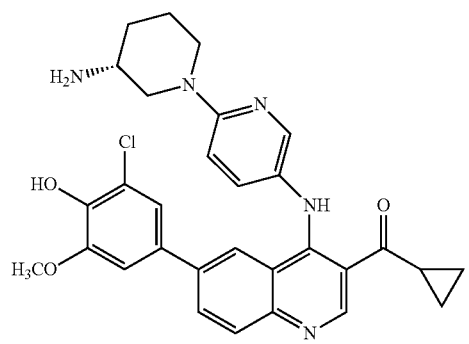

Following general procedure D, (R)-tert-butyl 1-(5-(6-bromo-3-(cyclopropanecarbonyl)quinolin-4-ylamino)pyridin-2-yl)piperidin-3-ylcarbamate (100 mg, 0.17 mmol) was reacted with 2-chloro-6-methoxy-4-(4,4,5,5-tetramethyl-1,3,2-dioxaborolan-2-yl)phenol (74 mg, 0.26 mmol) to obtain the protected intermediate which was subjected to general procedure A-2 to afford the desired product (30 mg, 32% over 2 steps) as an orange-yellow solid: $^1$H NMR (500 MHz, MeOD+TFA-d) δ 9.40 (br s, 1H), 8.28-8.20 (m, 2H), 8.10 (br s, 1H), 8.00 (d, J=8.8 Hz, 1H), 7.65 (dd, J=9.1, 2.8 Hz, 1H), 7.05 (d, J=9.1 Hz, 1H), 6.99 (s, 1H), 6.83 (br s, 1H), 4.55-4.49 (d, J=11.6 Hz, 1H), 4.04-3.95 (m, 1H), 3.91 (s, 3H), 3.28-3.18 (m, 3H), 2.87 (br s, 1H), 2.22-2.14 (m, 1H), 1.96-1.87 (m, 1H), 1.76-1.62 (m, 2H), 1.28-1.16 (m, 4H).; ESI MS m/z 544 [C$_{30}$H$_{30}$ClN$_5$O$_3$+H]$^+$; HPLC>99.0% (AUC), t$_R$=10.74 min.

Example 650

(R)-(4-(6-(3-aminopiperidin-1-yl)pyridin-3-ylamino)-6-(3,5-dichloro-4-hydroxyphenyl)quinolin-3-yl)(cyclopropyl)methanone

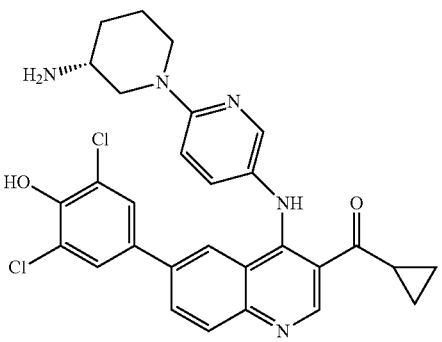

Following general procedure D, (R)-tert-butyl 1-(5-(6-bromo-3-(cyclopropanecarbonyl)quinolin-4-ylamino)pyridin-2-yl)piperidin-3-ylcarbamate (100 mg, 0.17 mmol) was reacted with 2,6-dichloro-4-(4,4,5,5-tetramethyl-1,3,2-dioxaborolan-2-yl)phenol (75 mg, 0.26 mmol) to obtain the protected intermediate which was subjected to general procedure A-2 to afford the desired product (18 mg, 19% over 2 steps) as a yellow-orange solid. NMR (500 MHz, MeOD+TFA-d) δ 9.40 (br s, 1H), 8.25-8.19 (m, 2H), 8.10 (br s, 1H), 8.01 (d, J=8.8 Hz, 1H), 7.65 (dd, J=9.1, 2.8 Hz, 1H), 7.32 (s, 2H), 7.07 (d, J=9.1 Hz, 1H), 4.53 (br s, 1H), 4.01 (dt, J=13.7, 4.0 Hz, 1H), 3.39-3.23 (m, 1H), 2.86 (br s, 1H), 2.22-2.12 (m, 1H), 1.97-1.88 (m, 1H), 1.78-1.64 (m, 2H), 1.26-1.16 (m, 4H). ESI MS m/z 548 $[C_{29}H_{27}Cl_2N_5O_2+H]^+$; HPLC>99.0% (AUC), $t_R$=10.96 min.

Example 651

(R)-(4-(6-(3-aminopiperidin-1-yl)pyridin-3-ylamino)-6-(3-chloro-5-fluoro-4-hydroxyphenyl)quinolin-3-yl)(cyclopropyl)methanone

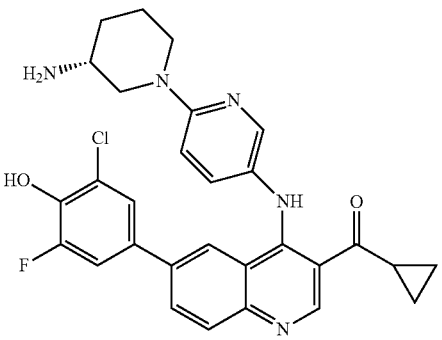

Following general procedure D, (R)-tert-butyl 1-(5-(6-bromo-3-(cyclopropanecarbonyl)quinolin-4-ylamino)pyridin-2-yl)piperidin-3-ylcarbamate (100 mg, 0.17 mmol) was reacted with 2-chloro-6-fluoro-4-(4,4,5,5-tetramethyl-1,3,2-dioxaborolan-2-yl)phenol (71 mg, 0.26 mmol) to obtain the protected intermediate which was subjected to general procedure A-2 to afford the desired product (33 mg, 37% over 2 steps) as an orange-yellow solid $^1$H NMR (500 MHz, MeOD+TFA-d) δ 9.41 (s, 1H), 8.28-8.14 (m, 2H), 8.05 (br s, 1H), 8.00 (d, J=8.8 Hz, 1H), 7.65 (dd, J=9.1, 2.8 Hz, 1H), 7.16-7.04 (m, 3H), 4.53 (d, J=11.6 Hz, 1H), 3.99 (dt, J=13.7, 4.0 Hz, 1H), 3.40-3.21 (m, 3H), 2.86 (br s, 3H), 2.23-2.15 (m, 1H), 1.98-1.89 (m, 1H), 1.79-1.65 (m, 2H), 1.27-1.16 (m, 4H). ESI MS m/z 532 $[C_{29}H_{27}Cl_FN_5O_2+H]^+$; HPLC>99.0% (AUC), $t_R$=10.77 min.

Example 660

(S)-(4-(6-(3-aminopiperidin-1-yl)pyridin-3-ylamino)-6-(3-chloro-4-hydroxy-5-methoxyphenyl)quinolin-3-yl)(cyclopropyl)methanone

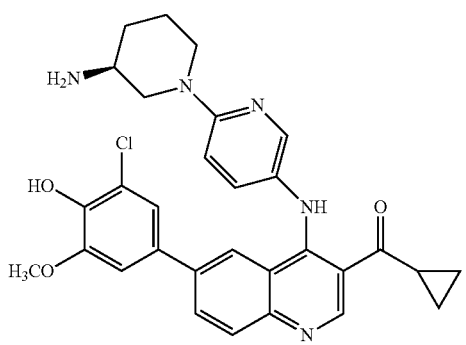 [SMILES: COc1cc(-c2ccc3ncc(C(=O)C4CC4)c(Nc4ccc(N5CCC[C@H](N)C5)nc4)c3c2)cc(Cl)c1O]

Following general procedure D, (S)-tert-butyl 1-(5-(6-bromo-3-(cyclopropanecarbonyl)quinolin-4-ylamino)pyridin-2-yl)piperidin-3-ylcarbamate (100 mg, 0.17 mmol) was reacted with 2-chloro-6-methoxy-4-(4,4,5,5-tetramethyl-1,3,2-dioxaborolan-2-yl)phenol (74 mg, 0.26 mmol) to obtain the protected intermediate which was subjected to general procedure A-2 to afford the desired product (42 mg, 45% over 2 steps) as an orange-yellow solid: $^1$H NMR (500 MHz, MeOD+TFA-d) δ 9.40 (br s, 1H), 8.28-8.20 (m, 2H), 8.10 (br s, 1H), 7.99 (d, J=8.8 Hz, 1H), 7.65 (dd, J=9.1, 2.8 Hz, 1H), 7.05 (d, J=9.1 Hz, 1H), 6.99 (s, 1H), 6.83 (br s, 1H), 4.52 (d, J=11.7 Hz, 1H), 4.04-3.96 (m, 1H), 3.91 (s, 3H), 3.37-3.18 (m, 3H), 2.87 (br s, 1H), 2.21-2.14 (m, 1H), 1.96-1.87 (m, 1H), 1.76-1.62 (m, 2H), 1.27-1.16 (m, 4H). ESI MS m/z 544 $[C_{30}H_{30}ClN_5O_3+H]^+$; HPLC>99.0% (AUC), $t_R$=10.76 min.

Example 661 cyclopropyl(6-(3,5-dichloro-4-hydroxyphenyl)-4-(4-(3-methoxypyrrolidin-1-yl)cyclohexylamino)quinolin-3-yl)methanone

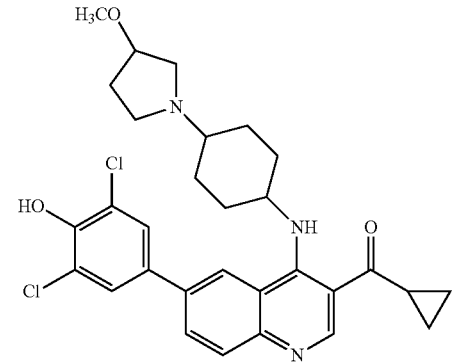 [SMILES: COC1CCN(C2CCC(Nc3c(C(=O)C4CC4)cnc4ccc(-c5cc(Cl)c(O)c(Cl)c5)cc34)CC2)C1]

Following general procedure D, (6-bromo-4-(4-(3-methoxypyrrolidin-1-yl)cyclohexylamino)quinolin-3-yl)(cyclopropyl)methanone (60 mg, 0.13 mmol) was reacted with 2,6-dichloro-4-(4,4,5,5-tetramethyl-1,3,2-dioxaborolan-2-yl)phenol (55 mg, 0.19 mmol) to afford the desired product (46 mg, 64%) as a brown solid: $^1$H NMR $^1$H NMR (500 MHz, MeOD+TFA-d) δ 9.42 (s, 1H), 8.46 (s, 1H), 8.31-8.23 (m, 1H), 8.04-7.97 (m, 1H), 7.75 (s, 1H), 7.71 (s, 1H), 4.99 (br s, 1H), 4.23-4.14 (m, 1H), 3.82-3.61 (m, 2H), 3.43-3.30 (m, 6H), 3.27-3.19 (m, 1H), 2.93-2.82 (m, 1H), 2.60-2.03 (m, 7H), 2.02-1.61 (m, 3H), 1.37-1.18 (m, 4H).; ESI MS m/z 554 [$C_{30}H_{33}Cl_2N_5O_3$+H]$^+$; HPLC>99.0% (AUC), $t_R$=10.97 min.

Example 666 cyclopropyl(6-(3,5-dichloro-4-hydroxyphenyl)-4-(6-(pyrrolidin-3-ylamino)pyridin-3-ylamino)quinolin-3-yl)methanone

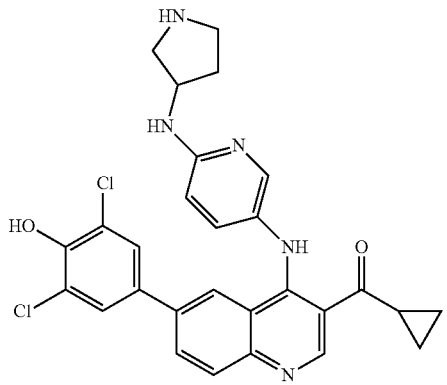

Following general procedure D, tert-butyl 3-(5-(6-bromo-3-(cyclopropanecarbonyl)quinolin-4-ylamino)pyridin-2-ylamino)pyrrolidine-1-carboxylate (100 mg, 0.18 mmol) was reacted with 2,6-dichloro-4-(4,4,5,5-tetramethyl-1,3,2-dioxaborolan-2-yl)phenol (78 mg, 0.27 mmol) to obtain the protected intermediate which was subjected to general procedure A-2 to afford the desired product (43 mg, 45% over 2 steps) as a yellow-orange solid: $^1$H NMR (500 MHz, MeOD+TFA-d) δ 9.40 (br s, 1H), 8.26-8.07 (m, 3H), 8.00 (d, J=8.9 Hz, 1H), 7.57 (dd, J=8.9, 2.7 Hz, 1H), 7.34 (s, 2H), 6.85-6.77 (m, 1H), 4.65-4.56 (m, 1H), 3.66-3.49 (m, 2H), 3.44-3.30 (m, 2H), 2.86 (br s, 1H), 2.47-2.36 (m, 1H), 2.18-2.07 (m, 1H), 1.27-1.15 (m, 4H). ESI MS m/z 534 [$C_{28}H_{25}Cl_2N_5O_2$+H]$^+$; HPLC>99.0% (AUC), $t_R$=10.64 min.

Example 667

(6-(3-chloro-5-fluoro-4-hydroxyphenyl)-4-(6-(pyrrolidin-3-ylamino)pyridin-3-ylamino)quinolin-3-yl)(cyclopropyl)methanone

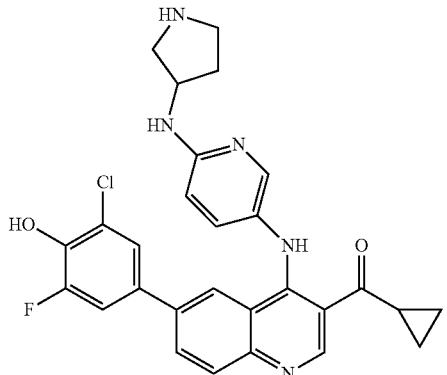

Following general procedure D, tert-butyl 3-(5-(6-bromo-3-(cyclopropanecarbonyl)quinolin-4-ylamino)pyridin-2-ylamino)pyrrolidine-1-carboxylate (100 mg, 0.18 mmol) was reacted with 2-chloro-6-fluoro-4-(4,4,5,5-tetramethyl-1,3,2-dioxaborolan-2-yl)phenol (73 mg, 0.27 mmol) to obtain the protected intermediate which was subjected to general procedure A-2 to afford the desired product (42 mg, 45% over 2 steps) as a yellow solid: $^1$H NMR (500 MHz, MeOD+TFA-d) δ 9.40 (br s, 1H), 8.22 (dd, J=8.8, 2.0 Hz, 1H), 8.17-8.06 (m, 2H), 8.00 (d, J=8.8 Hz, 1H), 7.55 (dd, J=8.9, 2.7 Hz, 1H), 7.19-7.13 (m, 2H), 6.83-6.76 (m, 1H), 4.65-4.56 (m, 1H), 3.66-3.49 (m, 2H), 3.45-3.30 (m, 2H), 2.87 (br s, 1H), 2.48-2.37 (m, 1H), 2.19-2.08 (m, 1H), 1.28-1.16 (m, 4H). ESI MS m/z 518 [$C_{28}H_{25}ClFN_5O_2$+H]$^+$; HPLC>99.0% (AUC), $t_R$=10.43 min.

Example 562

(4-(6-(3-aminopiperidin-1-yl)pyridin-3-ylamino)-6-(3-chloro-5-fluoro-4-hydroxyphenyl)quinolin-3-yl)(cyclopropyl)methanone hydrochloride

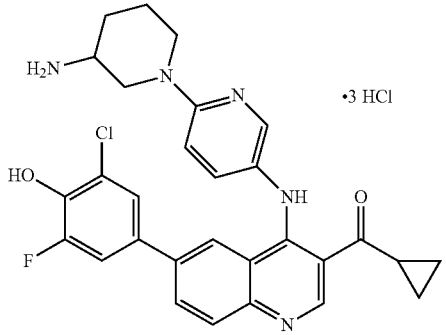

(4-(6-(3-aminopiperidin-1-yl)pyridin-3-ylamino)-6-(3-chloro-5-fluoro-4-hydroxyphenyl)quinolin-3-yl)(cyclopropyl)methanone (12 mg, 0.02 mmol) was suspended in methanol (1 mL) at 0° C. followed by dropwise addition of HCl in diethyl ether (2 M) until complete dissolution of the solid was observed. The solvent was removed under reduced pressure to afford the desired product (10 mg, 80%) as an orange-red solid: $^1$H NMR (500 MHz, MeOD) δ 9.39 (s, 1H), 8.27-8.19 (m, 2H), 8.13 (br s, 1H), 8.02 (d, J=8.8 Hz, 1H), 7.72 (dd, J=9.2, 2.7 Hz, 1H), 7.21-7.07 (m, 3H), 4.52 (d, J=10.8 Hz, 1H), 4.06-3.98 (m, 1H), 3.43-3.31 (m, 3H), 2.90-2.81 (m, 1H), 2.28-2.16 (m, 1H), 2.01-1.92 (m, 1H), 1.80-1.68 (m, 2H), 1.31-1.15 (m, 4H). ESI MS m/z 532 [$C_{29}H_{27}ClFN_5O_2$+H]$^+$; HPLC 98.7% (AUC), $t_R$=10.82 min.

Example 573

(4-(2-(3-aminopyrrolidin-1-yl)pyrimidin-5-ylamino)-6-(3-chloro-5-fluoro-4-hydroxyphenyl)quinolin-3-yl)(cyclopropyl)methanone hydrochloride

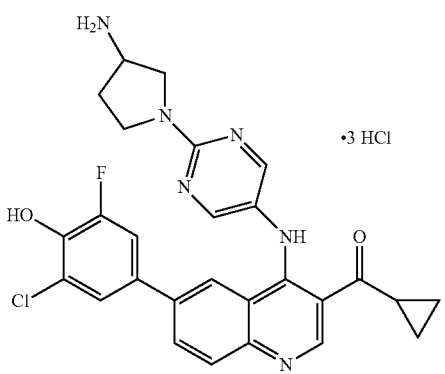 [SMILES: NC1CCN(c2ncc(Nc3c(C(=O)C4CC4)cnc4ccc(-c5cc(F)c(O)c(Cl)c5)cc34)cn2)C1]

(4-(2-(3-aminopyrrolidin-1-yl)pyrimidin-5-ylamino)-6-(3-chloro-5-fluoro-4-hydroxyphenyl)quinolin-3-yl)(cyclopropyl)methanone (30 mg, 0.06 mmol) was suspended in methanol (1 mL) at 0° C. followed by dropwise addition of HCl in diethyl ether (2 M) until complete dissolution of the solid was observed. The solvent was removed under reduced pressure to afford the desired product (33 mg, 92%) as a yellow-orange solid: $^1$H NMR (500 MHz, MeOD) δ 9.31 (br s, 1H), 8.45 (s, 2H), 8.23-8.14 (m, 2H), 8.02 (d, J=8.8 Hz, 1H), 7.26-7.20 (m, 2H), 4.11-4.00 (m, 2H), 3.94-3.73 (m, 3H), 2.83 (br s, 1H), 2.58-2.48 (m, 1H), 2.28-2.17 (m, 1H), 1.22-1.14 (m, 4H), 0.92-0.88 (s, OH). ESI MS m/z 519 $[C_{27}H_{24}ClFN_6O_2+H]^+$; HPLC>99.0% (AUC), $t_R$=5.18 min.

Example 577

(4-(6-(3-aminopyrrolidin-1-yl)pyridin-3-ylamino)-6-(3-chloro-5-fluoro-4-hydroxyphenyl)quinolin-3-yl)(cyclopropyl)methanone hydrochloride

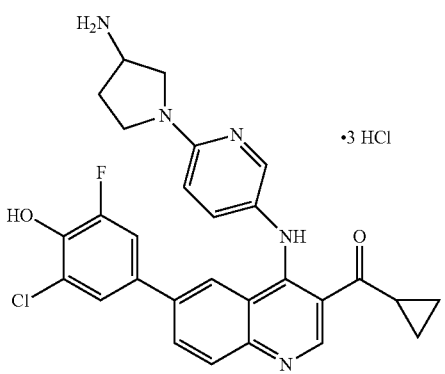 [SMILES: NC1CCN(c2ccc(Nc3c(C(=O)C4CC4)cnc4ccc(-c5cc(F)c(O)c(Cl)c5)cc34)cn2)C1]

(4-(6-(3-aminopyrrolidin-1-yl)pyridin-3-ylamino)-6-(3-chloro-5-fluoro-4-hydroxyphenyl)quinolin-3-yl)(cyclopropyl)methanone (15 mg, 0.03 mmol) was suspended in methanol (1 mL) at 0° C. followed by dropwise addition of HCl in diethyl ether (2 M) until complete dissolution of the solid was observed. The solvent was removed under reduced pressure to afford the desired product (23 mg, quant.) as a yellow-brown solid. $^1$H NMR (500 MHz, MeOD) δ 9.39 (s, 1H), 8.28-8.19 (m, 2H), 8.16 (br s, 1H), 8.02 (d, J=8.8 Hz, 1H), 7.79 (dd, J=9.1, 2.7 Hz, 1H), 7.26-7.16 (m, 2H), 6.94 (d, J=9.2 Hz, 1H), 4.16-4.08 (m, 1H), 4.05-3.97 (m, 1H), 3.88-3.79 (m, 1H), 3.78-3.69 (m, 2H), 2.85 (br s, 1H), 2.64-2.53 (m, 1H), 2.34-2.21 (m, 1H), 1.25-1.15 (m, 4H). ESI MS m/z 518 $[C_{28}H_{25}ClFN_5O_2+H]^+$; HPLC 98.1% (AUC), $t_R$=5.13 min.

Example 723

(4-(6-(2-Aminoethoxy)pyridin-3-ylamino)-6-(3,5-dichloro-4-hydroxyphenyl)quinolin-3-yl)(cyclopropyl)methanone

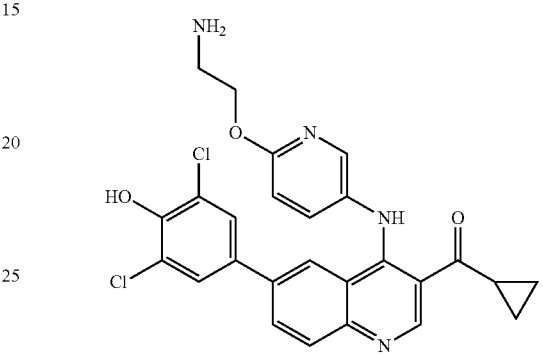

Following general procedure D, tert-butyl 2-(5-(6-bromo-3-(cyclopropanecarbonyl)quinolin-4-ylamino)pyridin-2-yloxy)ethylcarbamate (100 mg, 0.19 mmol) was reacted with 2,6-dichloro-4-(4,4,5,5-tetramethyl-1,3,2-dioxaborolan-2-yl)phenol (81 mg, 0.28 mmol) to obtain the protected intermediate which was subjected to general procedure A-2 to afford the desired product (21 mg, 22% over two steps) as a yellow solid: $^1$H NMR (500 MHz, CD$_3$OD+TFA-d) δ 9.40 (s, 1H), 8.33-8.24 (m, 2H), 8.13-8.04 (m, 2H), 7.83 (dd, J=8.8, 2.8 Hz, 1H), 7.37 (s, 2H), 7.14 (d, J=8.8 Hz, 1H), 4.66 (t, J=5.1 Hz, 2H), 3.43 (t, J=5.1 Hz, 2H), 2.87-2.80 (m, 1H), 1.22-1.15 (m, 4H); ESI MS m/z 509 $[C_{26}H_{22}Cl_2N_4O_3+H]^+$; HPLC 99.7% (AUC), $t_R$=11.26 min.

Example 724

(4-(6-(2-Aminoethoxy)pyridin-3-ylamino)-6-(3-chloro-5-fluoro-4-hydroxyphenyl)quinolin-3-yl)(cyclopropyl)methanone

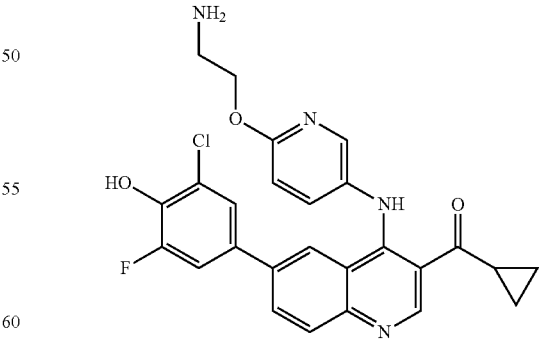

Following general procedure D, tert-butyl 2-(5-(6-bromo-3-(cyclopropanecarbonyl)quinolin-4-ylamino)pyridin-2-yloxy)ethylcarbamate (100 mg, 0.19 mmol) was reacted with 2-chloro-6-fluoro-4-(4,4,5,5-tetramethyl-1,3,2-dioxaborolan-2-yl)phenol (76 mg, 0.28 mmol) to obtain the protected intermediate which was subjected to general procedure A-2 to afford the desired product (24 mg, 26% over two steps) as a yellow solid: $^1$H NMR (500 MHz, CD$_3$OD+TFA-d) δ 9.40 (s, 1H), 8.34-8.24 (m, 2H), 8.13-8.03 (m, 2H), 7.82 (dd, J=8.8, 2.8 Hz, 1H), 7.24-7.10 (m, 3H), 4.65 (t, J 5.1=Hz, 2H), 3.43 (t, J=5.1 Hz, 2H), 2.87-2.81 (m, 1H), 1.23-1.15 (m, 4H); ESI MS m/z 493 [C$_{26}$H$_{22}$ClFN$_4$O$_3$+H]$^+$; HPLC>99% (AUC), t$_R$=11.00 min.

Example 725

(4-(6-(3-Aminopiperidin-1-yl)pyridin-3-ylamino)-6-(3,5-difluoro-4-hydroxyphenyl)quinolin-3-yl)(cyclopropyl)methanone

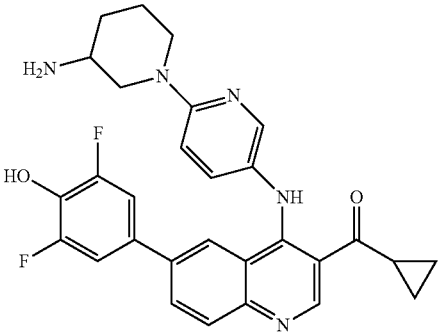

Following general procedure D, tert-butyl 1-(5-(6-bromo-3-(cyclopropanecarbonyl)quinolin-4-ylamino)pyridin-2-yl)piperidin-3-ylcarbamate (88 mg, 0.15 mmol) was reacted with 2,6-difluoro-4-(4,4,5,5-tetramethyl-1,3,2-dioxaborolan-2-yl)phenol (60 mg, 0.23 mmol) to obtain the protected intermediate which was subjected to general procedure A-2 to afford the desired product (72 mg, 93% over two steps) as a yellow-orange solid: $^1$H NMR (500 MHz, CD$_3$OD+TFA-d) δ 9.43 (s, 1H), 8.29-8.20 (m, 2H), 8.09-8.00 (m, 2H), 7.70 (dd, J=9.1, 2.7 Hz, 1H), 7.15 (d, J=9.1 Hz, 1H), 7.05-6.93 (m, 2H), 4.55 (d, J=12.5 Hz, 1H), 4.04 (d, J=12.5 Hz, 1H), 3.44-3.35 (m, 2H), 2.93-2.84 (m, 1H), 2.27-2.19 (m, 1H), 2.04-1.94 (m, 1H), 1.84-1.71 (m, 2H), 1.31-1.19 (m, 4H); ESI MS m/z 516 [C$_{29}$H$_{27}$F$_2$N$_5$O$_2$+H]$^+$; HPLC 99.0% (AUC), t$_R$=11.31 min.

Example 744

1-(6-(3,5-dichloro-4-hydroxyphenyl)-4-(4-(2-(dimethylamino)ethyl)phenylamino)quinolin-3-yl)ethanone

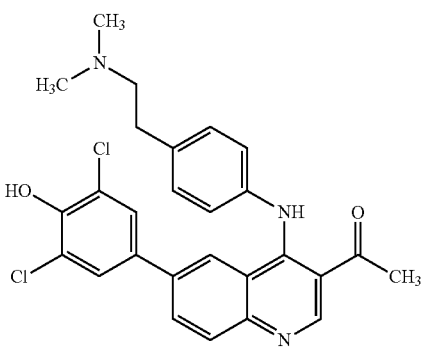 [SMILES: CC(=O)c1cnc2ccc(-c3cc(Cl)c(O)c(Cl)c3)cc2c1Nc1ccc(CCN(C)C)cc1]

Following general procedure D, 1-(6-bromo-4-(4-(2-(dimethylamino)ethyl)phenylamino)quinolin-3-yl)ethanone (76 mg, 0.18 mmol) was reacted with 2,6-dichloro-4-(4,4,5,5-tetramethyl-1,3,2-dioxaborolan-2-yl)phenol (81 mg, 0.28 mmol) to afford the desired product (49 mg, 55%) as a yellow solid: $^1$H NMR (500 MHz, CD$_3$OD+TFA-d) δ 9.30 (s, 1H), 8.19 (dd, J=8.8, 2.0 Hz, 1H), 8.01 (d, J=8.8 Hz, 1H), 7.76 (d, J=2.0 Hz, 1H), 7.60 (d, J=8.3 Hz, 2H), 7.49 (d, J=8.3 Hz, 2H), 7.13 (s, 2H), 3.45-3.37 (m, 2H), 3.29-3.20 (m, 2H), 3.00 (s, 6H), 2.82 (s, 3H); ESI MS m/z 494 [C$_{27}$H$_{25}$Cl$_2$N$_3$O$_2$+H]$^+$; HPLC 96.9% (AUC), t$_R$=12.01 min.

Example 745

1-(6-(3-chloro-5-fluoro-4-hydroxyphenyl)-4-(4-(2-(dimethylamino)ethyl)phenylamino)quinolin-3-yl)ethanone

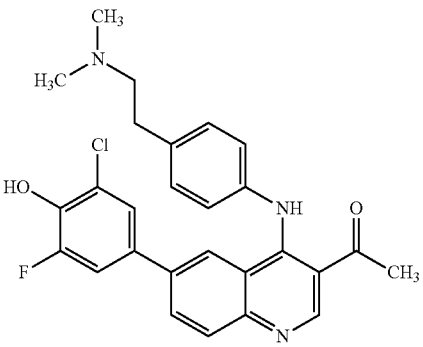

Following general procedure D, 1-(6-bromo-4-(4-(2-(dimethylamino)ethyl)phenyl amino)quinolin-3-yl)ethanone (76 mg, 0.18 mmol) was reacted with 2-chloro-6-fluoro-4-(4,4,5,5-tetramethyl-1,3,2-dioxaborolan-2-yl)phenol (76 mg, 0.28 mmol) to afford the desired product (23 mg, 27%) as a yellow-green solid: $^1$H NMR (500 MHz, CD$_3$OD+TFA-d) δ 9.30 (s, 1H), 8.19 (dd, J=8.8, 2.0 Hz, 1H), 8.00 (d, J=8.8 Hz, 1H), 7.76 (d, J=2.1 Hz, 1H), 7.60 (d, J=8.3 Hz, 2H), 7.50 (d, J=8.3 Hz, 2H), 6.99-6.92 (m, 2H), 3.46-3.39 (m, 2H), 3.27-3.19 (m, 2H), 3.00 (s, 6H), 2.82 (s, 3H); ESI MS m/z 478 [C$_{27}$H$_{25}$ClFN$_3$O$_2$+H]$^+$; HPLC 98.4% (AUC), t$_R$=10.91 min.

Example 747 cyclopropyl(6-(3,5-dichloro-4-hydroxyphenyl)-4-(6-(2-(dimethylamino)ethylamino)pyridin-3-ylamino)quinolin-3-yl)methanone

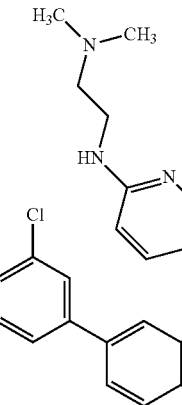

Following general procedure D, (6-bromo-4-(6-(2-(dimethylamino)ethylamino)pyridine-3-ylamino)quinolin-3-yl)(cyclopropyl)methanone (75 mg, 0.17 mmol) was reacted with 2,6-dichloro-4-(4,4,5,5-tetramethyl-1,3,2-dioxaborolan-2-yl)phenol (73 mg, 0.25 mmol) to afford the desired product (24 mg, 26%) as an orange solid: ¹H NMR (500 MHz, CD₃OD+TFA-d) δ 9.38 (s, 1H), 8.32-8.18 (m, 3H), 8.07 (d, J=9.3 Hz, 1H), 7.86 (dd, J=9.3, 2.6 Hz, 1H), 7.48 (s, 2H), 7.15 (d, J=9.3 Hz, 1H), 3.91 (t, J=6.1 Hz, 2H), 3.49 (t, J=6.1 Hz, 2H), 2.99 (s, 6H), 2.87-2.78 (m, 1H), 1.24-1.18 (m, 4H); ESI MS m/z 536 [C$_{28}$H$_{27}$Cl$_2$N$_5$O$_2$+H]⁺; HPLC 96.5% (AUC), t$_R$=11.28 min.

Example 758

1-(6-(3,5-dichloro-4-hydroxyphenyl)-4-(6-(2-(dimethylamino)ethylamino)pyridin-3-ylamino)quinolin-3-yl)ethanone

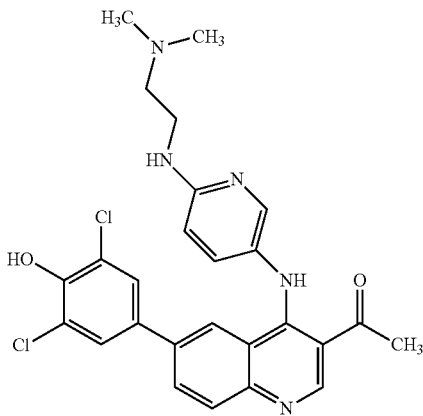 [SMILES: CC(=O)c1cnc2ccc(-c3cc(Cl)c(O)c(Cl)c3)cc2c1Nc1ccc(NCCN(C)C)nc1]

Following general procedure D, 1-(6-bromo-4-(6-(2-(dimethylamino)ethylamino)pyridine-3-ylamino)quinolin-3-yl)ethanone (100 mg, 0.23 mmol) was reacted with 2,6-dichloro-4-(4,4,5,5-tetramethyl-1,3,2-dioxaborolan-2-yl)phenol (101 mg, 0.35 mmol) to afford the desired product (39 mg, 33%) as a yellow solid: ¹H NMR (500 MHz, CD₃OD+TFA-d) δ 9.28 (s, 1H), 8.26-8.17 (m, 2H), 8.04-7.99 (m, 2H), 7.67 (dd, J=9.0, 2.7 Hz, 1H), 7.28 (s, 2H), 6.93 (d, J=9.0 Hz, 1H), 3.86-3.82 (m, 2H), 3.44-3.36 (m, 2H), 2.96 (s, 6H), 2.81 (s, 3H); ESI MS m/z 510 [C$_{26}$H$_{25}$Cl$_2$N$_5$O$_2$+H]⁺; HPLC 96.6% (AUC), t$_R$=10.74 min.

Example 762

1-(6-(3-chloro-5-fluoro-4-hydroxyphenyl)-4-(6-(2-(dimethylamino)ethylamino)pyridin-3-ylamino)quinolin-3-yl)ethanone

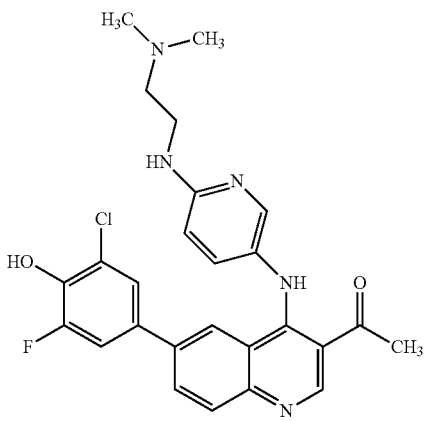 [SMILES: CC(=O)c1cnc2ccc(-c3cc(F)c(O)c(Cl)c3)cc2c1Nc1ccc(NCCN(C)C)nc1]

Following general procedure D, 1-(6-bromo-4-(6-(2-(dimethylamino)ethylamino)pyridine-3-ylamino)quinolin-3-yl)ethanone (100 mg, 0.23 mmol) was reacted with 2-chloro-6-fluoro-4-(4,4,5,5-tetramethyl-1,3,2-dioxaborolan-2-yl)phenol (82 mg, 0.35 mmol) to afford the desired product (18 mg, 16%) as a green-yellow solid: ¹H NMR (500 MHz, CD₃OD+TFA-d) δ 9.29 (s, 1H), 8.26-8.20 (m, 2H), 8.05-7.99 (m, 2H), 7.69 (dd, J=9.0, 2.7 Hz, 1H), 7.18-7.07 (m, 2H), 6.96 (d, J=9.0 Hz, 1H), 3.89-3.83 (m, 2H), 3.46-3.37 (m, 2H), 2.96 (s, 6H), 2.80 (s, 3H); ESI MS m/z 494 [C$_{26}$H$_{25}$ClFN$_5$O$_2$+H]⁺; HPLC 97.2% (AUC), t$_R$=10.46 min.

Example 761

1-(4-(6-(3-aminopyrrolidin-1-yl)pyridin-3-ylamino)-6-(3,5-dichloro-4-hydroxyphenyl)quinolin-3-yl)propan-1-one

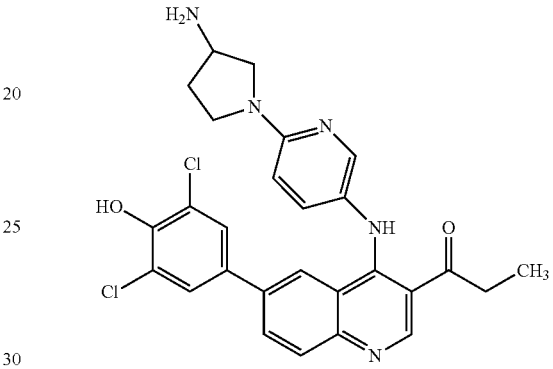

Following general procedure D, tert-butyl 1-(5-(6-bromo-3-propionylquinolin-4-ylamino)pyridin-2-yl)pyrrolidin-3-ylcarbamate (100 mg, 0.18 mmol) was reacted with 2,6-dichloro-4-(4,4,5,5-tetramethyl-1,3,2-dioxaborolan-2-yl)phenol (81 mg, 0.28 mmol) to obtain the protected intermediate which was subjected to general procedure A-2 to afford the desired product (8 mg, 9% over two steps) as an orange-brown solid: ¹H NMR (500 MHz, CD₃OD+TFA-d) δ 9.29 (s, 1H), 8.27-8.19 (m, 2H), 8.07-7.99 (m, 2H), 7.85-7.70 (m, 1H), 7.29 (s, 2H), 6.96 (d, J=9.2 Hz, 1H), 4.15-4.05 (m, 1H), 4.07-3.99 (m, 1H), 3.89-3.80 (m, 1H), 3.79-165 (m, 2H), 3.27-3.18 (m, 2H), 2.63-2.52 (m, 1H), 2.34-2.23 (m, 1H), 1.31-1.22 (m, 3H); ESI MS m/z 522 [C$_{27}$H$_{25}$Cl$_2$N$_5$O$_2$+H]⁺; HPLC 95.7% (AUC), t$_R$=10.98 min.

Example 760

1-(4-(6-(3-aminopyrrolidin-1-yl)pyridin-3-ylamino)-6-(3-chloro-5-fluoro-4-hydroxyphenyl)quinolin-3-yl)propan-1-one

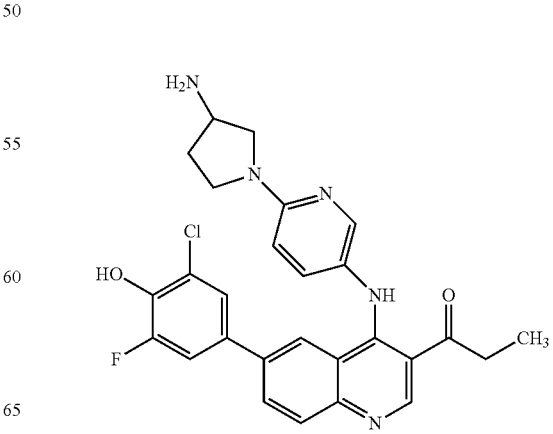

Following general procedure D, tert-butyl 1-(5-(6-bromo-3-propionylquinolin-4-ylamino) pyridin-2-yl)pyrrolidin-3-yl-carbamate (100 mg, 0.18 mmol) was reacted with 2-chloro-6-fluoro-4-(4,4,5,5-tetramethyl-1,3,2-dioxaborolan-2-yl) phenol (76 mg, 0.28 mmol) to obtain the protected intermediate which was subjected to general procedure A-2 to afford the desired product (34 mg, 37% over two steps) as a yellow solid: $^1$H NMR (500 MHz, CD$_3$OD+TFA-d) δ 9.29 (s, 1H), 8.29-8.18 (m, 2H), 8.06-7.99 (m, 2H), 7.82 (dd, J=9.1, 2.6 Hz, 1H), 7.16-7.10 (m, 1H), 7.07 (s, 1H), 6.97 (d, J=9.1 Hz, 1H), 4.17-4.08 (m, 1H), 4.06-3.98 (m, 1H), 3.90-3.81 (m, 1H), 3.79-3.70 (m, 2H), 3.27-3.19 (m, 2H), 2.64-2.53 (m, 1H), 2.35-2.25 (m, 1H), 1.26 (t, J=7.1 Hz, 3H); ESI MS m/z 506 [C$_{27}$H$_{25}$ClFN$_5$O$_2$+H]$^+$; HPLC>99% (AUC), t$_R$=10.75 min.

Example 776

(6-(3-chloro-5-fluoro-4-hydroxyphenyl)-4-(6-(2-(dimethylamino)ethylamino)pyridin-3-ylamino) quinolin-3-yl)(cyclopropyl)methanone

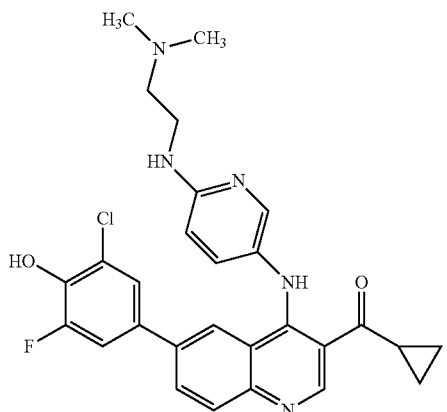

Following general procedure D, (6-bromo-4-(6-(2-(dimethylamino)ethylamino)pyridin-3-ylamino)quinolin-3-yl)(cyclopropyl)methanone (75 mg, 0.17 mmol) was reacted with 2-chloro-6-fluoro-4-(4,4,5,5-tetramethyl-1,3,2-dioxaborolan-2-yl)phenol (69 mg, 0.25 mmol) to afford the desired product (6 mg, 7%) as a yellow-orange solid: $^1$H NMR (500 MHz, CD$_3$OD+TFA-d) δ 9.40 (s, 1H), 8.25 (dd, J=8.8, 1.9 Hz, 1H), 8.22-8.15 (m, 2H), 8.03 (d, J=8.8 Hz, 1H), 7.69 (dd, J=9.1, 2.6 Hz, 1H), 7.27-7.18 (m, 2H), 6.95 (d, J=9.1 Hz, 1H), 3.87-3.81 (m, 2H), 3.46-3.39 (m, 2H), 2.97 (s, 6H), 2.89-2.78 (m, 1H), 1.28-1.17 (m, 4H); ESI MS m/z 520 [C$_{28}$H$_{27}$ClFN$_5$O$_2$+H]$^+$; HPLC>99% (AUC), t$_R$=10.34 min.

Example 775

1-(4-(6-(3-aminopyrrolidin-1-yl)pyridin-3-ylamino)-6-(3-chloro-4-hydroxy-5-methoxyphenyl)quinolin-3-yl)propan-1-one

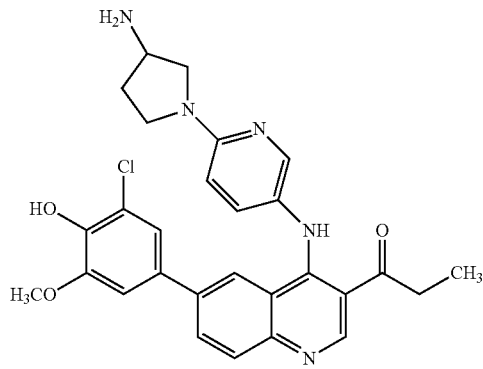 [SMILES: CCC(=O)c1cnc2ccc(-c3cc(Cl)c(O)c(OC)c3)cc2c1Nc1ccc(N2CCC(N)C2)nc1]

Following general procedure D, tert-butyl 1-(5-(6-bromo-3-propionylquinolin-4-ylamino) pyridin-2-yl)pyrrolidin-3-yl-carbamate (100 mg, 0.18 mmol) was reacted with 2-chloro-6-methoxy-4-(4,4,5,5-tetramethyl-1,3,2-dioxaborolan-2-yl) phenol (80 mg, 0.28 mmol) to obtain the protected intermediate which was subjected to general procedure A-2 to afford the desired product (24 mg, 27% over two steps) as a yellow solid: $^1$H NMR (500 MHz, CD$_3$OD+TFA-d) δ 9.28 (s, 1H), 8.29-8.23 (m, 2H), 8.06-7.98 (m, 2H), 7.78 (dd, J=9.1, 2.7 Hz, 1H), 7.02 (d, J=2.2 Hz, 1H), 6.92 (d, J=9.1 Hz, 1H), 6.70 (d, J=2.2 Hz, 1H), 4.14-4.06 (m, 1H), 4.04-3.96 (m, 1H), 3.91 (s, 3H), 3.87-3.77 (m, 1H), 3.75-3.66 (m, 2H), 3.23 (q, J=7.1 Hz, 2H), 2.62-2.51 (m, 1H), 2.32-2.22 (m, 1H), 1.27 (t, J=7.1 Hz, 3H); ESI MS m/z 518 [C$_{28}$H$_{28}$ClN$_5$O$_3$+H]$^+$; HPLC 98.5% (AUC), t$_R$=9.79 min.

Example 774

1-(4-(6-(3-aminopyrrolidin-1-yl)pyridin-3-ylamino)-6-(3-chloro-4-hydroxy-5-methoxyphenyl)quinolin-3-yl)ethanone

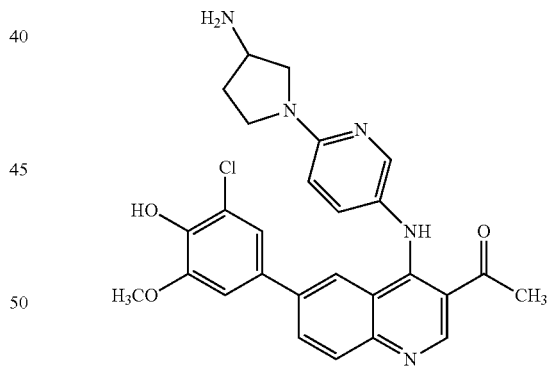

Following general procedure D, tert-butyl 1-(5-(3-acetyl-6-bromoquinolin-4-ylamino) pyridin-2-yl)pyrrolidin-3-ylcarbamate (80 mg, 0.15 mmol) was reacted with 2-chloro-6-methoxy-4-(4,4,5,5-tetramethyl-1,3,2-dioxaborolan-2-yl) phenol (65 mg, 0.23 mmol) to obtain the protected intermediate which was subjected to general procedure A-2 to afford the desired product (11 mg, 15% over two steps) as a yellow-brown: $^1$H NMR (500 MHz, CD$_3$OD+TFA-d) δ 9.28 (s, 1H), 8.31-8.25 (m, 2H), 8.06-7.99 (m, 2H), 7.83 (dd, J=9.2, 2.7 Hz, 1H), 7.04 (d, J=2.2 Hz, 1H), 7.98 (d, J=9.2 Hz, 1H), 6.71 (d, J=2.2 Hz, 1H), 4.16-4.07 (m, 1H), 4.07-3.96 (m, 2H), 3.91 (s, 3H), 3.88-3.79 (m, 1H), 3.79-3.69 (m, 2H), 2.80 (s, 3H), 2.63-2.53 (m, 1H), 2.34-2.23 (m, 1H); ESI MS m/z 504 [C$_{27}$H$_{26}$ClN$_5$O$_3$+H]$^+$; HPLC 95.4% (AUC), t$_R$=9.37 min.

Example 773

1-(4-(6-(3-aminopyrrolidin-1-yl)pyridin-3-ylamino)-6-(3-chloro-5-fluoro-4-hydroxyphenyl)quinolin-3-yl)ethanone

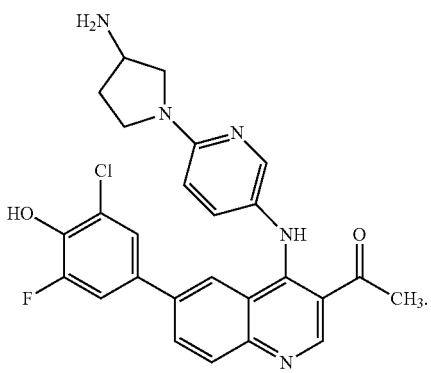 [SMILES: CC(=O)c1cnc2ccc(-c3cc(F)c(O)c(Cl)c3)cc2c1Nc1ccc(N2CCC(N)C2)nc1]

Following general procedure D, tert-butyl 1-(5-(3-acetyl-6-bromoquinolin-4-ylamino) pyridin-2-yl)pyrrolidin-3-ylcarbamate (100 mg, 0.19 mmol) was reacted with 2-chloro-6-fluoro-4-(4,4,5,5-tetramethyl-1,3,2-dioxaborolan-2-yl)phenol (76 mg, 0.28 mmol) to obtain the protected intermediate which was subjected to general procedure A-2 to afford the desired product (13 mg, 16% over two steps) as a yellow solid: $^1$H NMR (500 MHz, CD$_3$OD+TFA-d) δ 9.29 (s, 1H), 8.29-8.20 (m, 2H), 8.05-7.99 (m, 2H), 7.84 (dd, J=9.2, 2.6 Hz, 1H), 7.15 (d, J=11.6 Hz, 1H), 7.07 (s, 1H), 7.00 (d, J=9.2 Hz, 1H), 4.17-4.09 (m, 1H), 4.07-4.00 (m, 1H), 3.90-3.81 (m, 1H), 3.80-3.71 (m, 2H), 2.79 (s, 3H), 2.65-2.52 (m, 1H), 2.36-2.25 (m, 1H); ESI MS m/z 492 [C$_{26}$H$_{23}$ClFN$_5$O$_2$+H]$^+$; HPLC 97.6% (AUC), $t_R$=9.73 min.

Example 1186 tert-Butyl 4-{5-[3-(cyclopropanecarbonyl)-6-(3,5-dichloro-4-hydroxyphenyl)quinolin-4-ylamino]pyridin-2-yl}piperazine-1-carboxylate

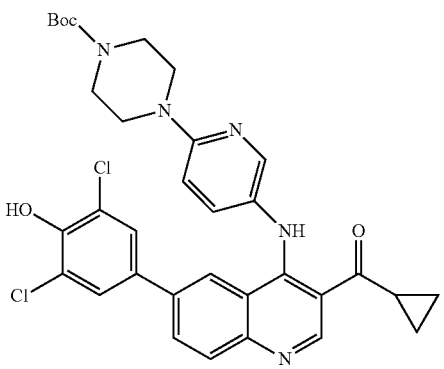 [SMILES: CC(C)(C)OC(=O)N1CCN(c2ccc(Nc3c(C(=O)C4CC4)cnc4ccc(-c5cc(Cl)c(O)c(Cl)c5)cc34)cn2)CC1]

Following general procedure F, tert-butyl 4-{5-[6-bromo-3-(cyclopropanecarbonyl)quinolin-4-ylamino]pyridin-2-yl}piperazine-1-carboxylate (65 mg, 0.118 mmol) was reacted with 2,6-dichloro-4-(4,4,5,5-tetramethyl-1,3,2-diox- aborolan-2-yl)phenol (51 mg, 0.177 mmol) to afford the crude product (75 mg) as an orange solid: ESI MS m/z 634 [C$_{33}$H$_{33}$C$_{12}$N$_5$O$_4$+H]$^+$.

Example 1187 tert-Butyl {trans-4-[3-(cyclopropanecarbonyl)-6-(3,5-dichloro-4-hydroxyphenyl)quinolin-4-ylamino]cyclohexyl}methylcarbamate

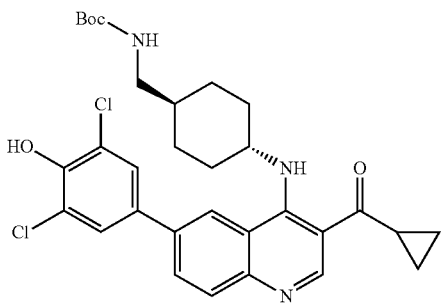 [SMILES: CC(C)(C)OC(=O)NC[C@H]1CC[C@H](Nc2c(C(=O)C3CC3)cnc3ccc(-c4cc(Cl)c(O)c(Cl)c4)cc23)CC1]

Following general procedure F, tert-butyl {trans-4-[6-bromo-3-(cyclopropanecarbonyl)quinolin-4-ylamino]cyclohexyl}methylcarbamate (62 mg, 0.123 mmol) was reacted with 2,6-dichloro-4-(4,4,5,5-tetramethyl-1,3,2-dioxaborolan-2-yl)phenol (53 mg, 0.185 mmol) to afford the crude product (58 mg) as a yellow solid: ESI MS m/z 584 [C$_{31}$H$_{35}$Cl$_2$N$_3$O$_4$+H]$^+$.

Example 1188 tert-Butyl {trans-4-[6-(3-chloro-4-hydroxy-5-methoxyphenyl)-3-(cyclopropanecarbonyl)quinolin-4-ylamino]cyclohexyl}methylcarbamate

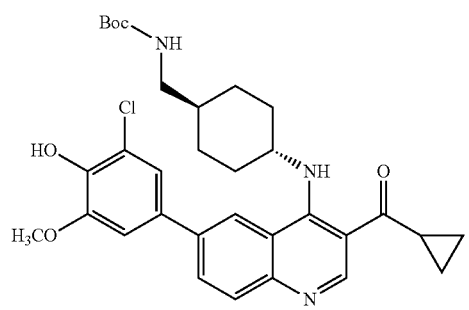 [SMILES: COc1cc(-c2ccc3ncc(C(=O)C4CC4)c(N[C@H]4CC[C@H](CNC(=O)OC(C)(C)C)CC4)c3c2)cc(Cl)c1O]

Following general procedure F, tert-butyl {trans-4-[6-bromo-3-(cyclopropanecarbonyl)quinolin-4-ylamino]cyclohexyl}methylcarbamate (65 mg, 0.123 mmol) was reacted with 2-chloro-6-methoxy-4-(4,4,5,5-tetramethyl-1,3,2-dioxaborolan-2-yl)phenol (55 mg, 0.185 mmol) to afford the crude product (90 mg) as a yellow-green solid: ESI MS m/z 580 $[C_{32}H_{38}ClN_3O_5+H]^+$.

Example 1189 tert-Butyl {trans-4-[6-(3-chloro-5-fluoro-4-hydroxyphenyl)-3-(cyclopropanecarbonyl)quinolin-4-ylamino]cyclohexyl}methylcarbamate

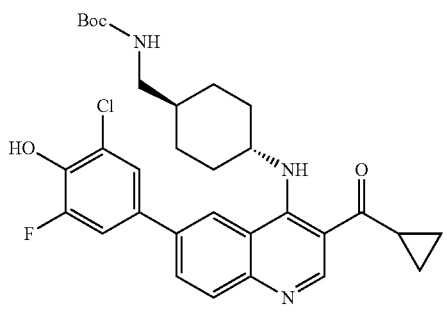 [SMILES: CC(C)(C)OC(=O)NC[C@H]1CC[C@H](Nc2c(C(=O)C3CC3)cnc3ccc(-c4cc(F)c(O)c(Cl)c4)cc23)CC1]

Following general procedure F, tert-butyl {trans-4-[6-bromo-3-(cyclopropanecarbonyl)quinolin-4-ylamino]cyclohexyl}methylcarbamate (62 mg, 0.123 mmol) was reacted with 2-chloro-6-fluoro-4-(4,4,5,5-tetramethyl-1,3,2-dioxaborolan-2-yl)phenol (50 mg, 0.185 mmol) to afford the crude product (69 mg) as a yellow-green solid.

Example 1190 tert-Butyl trans-4-[3-(cyclopropanecarbonyl)-6-(3,5-dichloro-4-hydroxyphenyl)quinolin-4-ylamino]cyclohexyl(methyl)carbamate

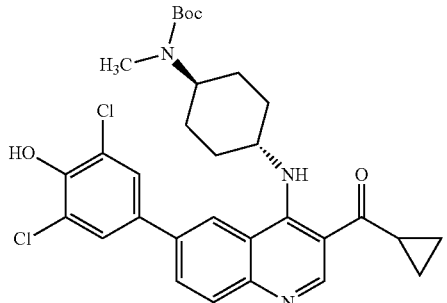

Following general procedure F, tert-butyl {trans-4-[6-bromo-3-(cyclopropanecarbonyl)quinolin-4-ylamino]cyclohexyl}(methyl)carbamate (61 mg, 0.120 mmol) was reacted with 2,6-dichloro-4-(4,4,5,5-tetramethyl-1,3,2-dioxaborolan-2-yl)phenol (52 mg, 0.180 mmol) to afford the crude product (65 mg) as a brown oil: ESI MS m/z 584 $[C_{31}H_{35}Cl_2N_3O_4+H]^+$.

Example 1191 tert-Butyl trans-4-[6-(3-chloro-4-hydroxy-5-methoxyphenyl)-3-(cyclopropanecarbonyl)quinolin-4-ylamino]cyclohexyl(methyl)carbamate

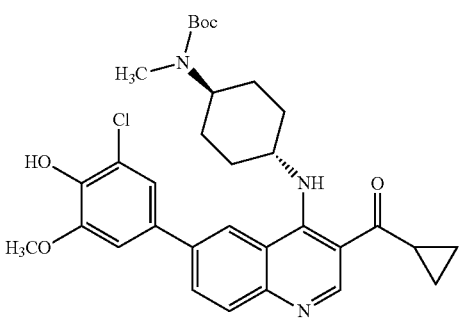 [SMILES: COc1cc(-c2ccc3ncc(C(=O)C4CC4)c(N[C@H]4CC[C@H](N(C)C(=O)OC(C)(C)C)CC4)c3c2)cc(Cl)c1O]

Following general procedure F, tert-butyl {trans-4-[6-bromo-3-(cyclopropanecarbonyl)quinolin-4-ylamino]cyclohexyl}(methyl)carbamate (68 mg, 0.135 mmol) was reacted with 2-chloro-6-methoxy-4-(4,4,5,5-tetramethyl-1,3,2-dioxaborolan-2-yl)phenol (58 mg, 0.203 mmol) to afford the crude product (90 mg) as a brown oil: ESI MS m/z 580 $[C_{32}H_{38}ClN_3O_5+H]^+$.

Example 1192 tert-Butyl 4-[6-(3-chloro-5-fluoro-4-hydroxyphenyl)-3-(cyclopropanecarbonyl)quinolin-4-ylamino]benzylcarbamate

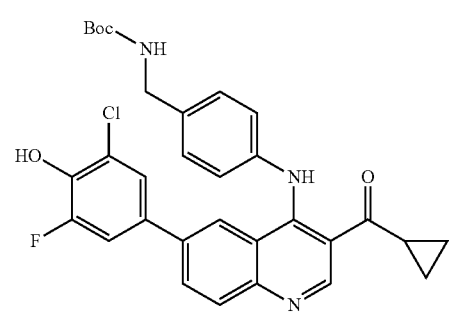 [SMILES: CC(C)(C)OC(=O)NCc1ccc(Nc2c(C(=O)C3CC3)cnc3ccc(-c4cc(F)c(O)c(Cl)c4)cc23)cc1]

Following general procedure F, tert-butyl 4-[6-bromo-3-(cyclopropanecarbonyl)quinolin-4-ylamino]benzylcarbamate (63 mg, 0.127 mmol) was reacted with 2-chloro-6-fluoro-4-(4,4,5,5-tetramethyl-1,3,2-dioxaborolan-2-yl)phenol (52 mg, 0.191 mmol) to afford the crude product (70 mg) as a yellow solid: ESI MS m/z 562 $[C_{31}H_{29}ClFN_3O_4+H]^+$.

Example 1193 tert-Butyl 4-[3-(cyclopropanecarbonyl)-6-(3,5-dichloro-4-hydroxyphenyl)quinolin-4-ylamino]benzylcarbamate

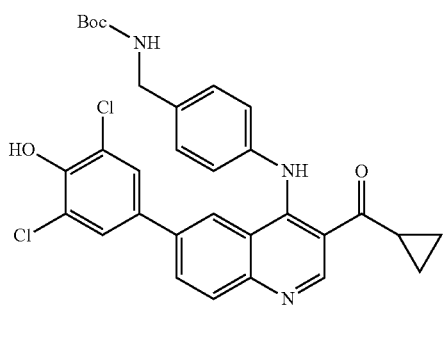 [SMILES: CC(C)(C)OC(=O)NCc1ccc(Nc2c(C(=O)C3CC3)cnc3ccc(-c4cc(Cl)c(O)c(Cl)c4)cc23)cc1]

Following general procedure F, tert-butyl 4-[6-bromo-3-(cyclopropanecarbonyl)quinolin-4-ylamino]benzylcarbamate (58 mg, 0.117 mmol) was reacted with 2,6-dichloro-4-(4,4,5,5-tetramethyl-1,3,2-dioxaborolan-2-yl)phenol (50 mg, 0.176 mmol) to afford the crude product (67 mg) as a yellow solid.

Example 1194 tert-Butyl trans-4-[6-(3-chloro-5-fluoro-4-hydroxyphenyl)-3-(cyclopropanecarbonyl)quinolin-4-ylamino]cyclohexyl(methyl)carbamate

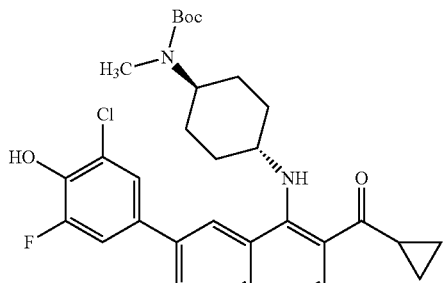

Following general procedure F, tert-butyl {trans-4-[6-bromo-3-(cyclopropanecarbonyl)quinolin-4-ylamino]cyclohexyl}(methyl)carbamate (63 mg, 0.125 mmol) was reacted with 2-chloro-6-fluoro-4-(4,4,5,5-tetramethyl-1,3,2- dioxaborolan-2-yl)phenol (51 mg, 0.188 mmol) to afford the crude product (75 mg) as a yellow-green solid: ESI MS m/z 568 $[C_{31}H_{35}ClFN_3O_4+H]^+$.

Example 1195 tert-Butyl 2-{4-[3-(cyclopropanecarbonyl)-6-(3,5-dichloro-4-hydroxyphenyl)quinolin-4-ylamino]phenyl}propan-2-ylcarbamate

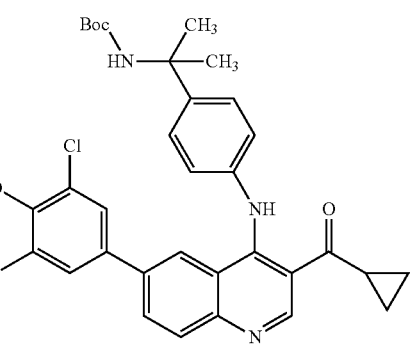

Following general procedure F, tert-butyl 2-{4-[6-bromo-3-(cyclopropanecarbonyl)quinolin-4-ylamino]phenyl}propan-2-ylcarbamate (76 mg, 0.145 mmol) was reacted with 2,6-dichloro-4-(4,4,5,5-tetramethyl-1,3,2-dioxaborolan-2-yl)phenol (63 mg, 0.212 mmol) to afford the crude product (75 mg) as a yellow solid: ESI MS m/z 606 $[C_{33}H_{33}Cl_2N_3O_4+H]^+$.

Example 1196 tert-Butyl 2-{4-[6-(3-chloro-5-fluoro-4-hydroxyphenyl)-3-(cyclopropanecarbonyl)quinolin-4-ylamino]phenyl}propan-2-ylcarbamate

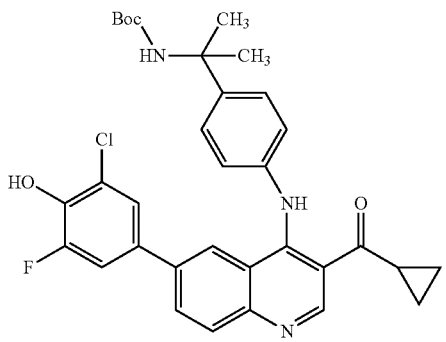 [SMILES: CC(C)(C)OC(=O)NC(C)(C)c1ccc(Nc2c(C(=O)C3CC3)cnc3ccc(-c4cc(F)c(O)c(Cl)c4)cc23)cc1]

Following general procedure F, tert-butyl 2-{4-[6-bromo-3-(cyclopropanecarbonyl)quinolin-4-ylamino]phenyl}propan-2-ylcarbamate (74 mg, 0.140 mmol) was reacted with 2-chloro-6-fluoro-4-(4,4,5,5-tetramethyl- 1,3,2-dioxaborolan-2-yl)phenol (57 mg, 0.210 mmol) to afford the crude product (68 mg) as a yellow solid: ESI MS m/z 590 $[C_{33}H_{33}ClFN_3O_4+H]^+$.

Example 1197 tert-Butyl 4-{5-[3-butyryl-6-(3-chloro-5-fluoro-4-hydroxyphenyl)quinolin-4-ylamino]pyridin-2-yl}piperazine-1-carboxylate

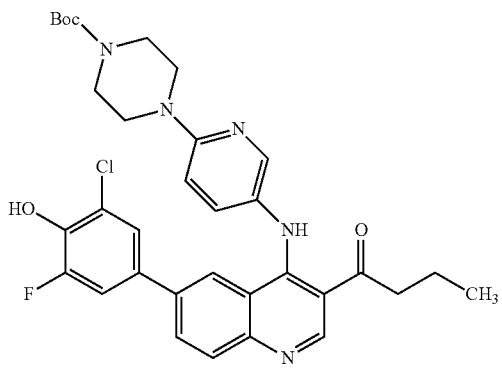 [SMILES: CCCC(=O)c1cnc2ccc(-c3cc(F)c(O)c(Cl)c3)cc2c1Nc1ccc(N2CCN(C(=O)OC(C)(C)C)CC2)nc1]

Following general procedure F, tert-butyl 4-[5-(6-bromo-3-butyrylquinolin-4-ylamino)pyridin-2-yl]piperazine-1-carboxylate (80 mg, 0.144 mmol) was reacted with 2-chloro-6-fluoro-4-(4,4,5,5-tetramethyl-1,3,2-dioxaborolan-2-yl)phenol (59 mg, 0.216 mmol) to afford the crude product (66 mg) as an orange solid: ESI MS m/z 620 $[C_{33}H_{35}ClFN_5O_4+H]^+$.

Example 583

Cyclopropyl{4-[4-(diallylamino)-4-methylcyclohexylamino]-6-(3,5-dichloro-4-hydroxyphenyl)quinolin-3-yl}methanone

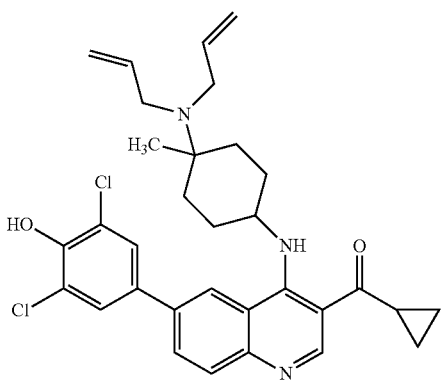 [SMILES: C=CCN(CC=C)C1(C)CCC(Nc2c(C(=O)C3CC3)cnc3ccc(-c4cc(Cl)c(O)c(Cl)c4)cc23)CC1]

Following general procedure F, {6-Bromo-4-[4-(diallylamino)-4-methylcyclohexylamino]quinolin-3-yl}(cyclopropyl)methanone (96 mg, 0.198 mmol) was reacted with 2,6-dichloro-4-(4,4,5,5-tetramethyl-1,3,2- dioxaborolan-2-yl)phenol (86 mg, 0.297 mmol) to afford the desired product (23 mg, 27%) as a yellow solid: ESI MS m/z 564 $[C_{32}H_{35}Cl_2N_3O_2+H]^+$.

Example 1198

{6-(3-Chloro-4-hydroxy-5-methoxyphenyl)-4-[4-(diallylamino)-4-methylcyclohexylamino]quinolin-3-yl}(cyclopropyl)methanone

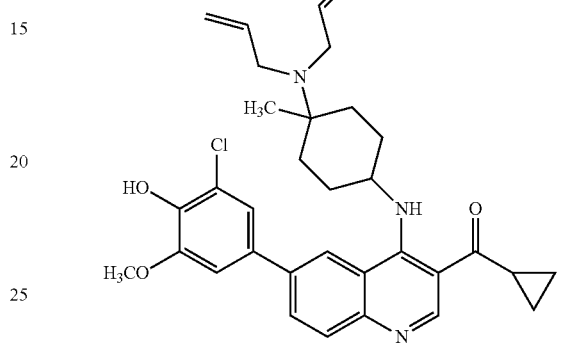

Following general procedure F, {6-Bromo-4-[4-(diallylamino)-4-methylcyclohexylamino]quinolin-3-yl}(cyclopropyl)methanone (120 mg, 0.248 mmol) was reacted with 2-chloro-6-methoxy-4-(4,4,5,5-tetramethyl-1,3,2-dioxaborolan-2-yl)phenol (105 mg, 0.372 mmol) to afford the crude product (49 mg) as a brown-green solid: ESI MS m/z 560 $[C_{33}H_{38}ClN_3O_3+H]^+$.

Example 366

Cyclopropyl{6-(3,5-dichloro-4-hydroxyphenyl)-4-[4-(pyrrolidin-1-ylmethyl)phenylamino]quinolin-3-yl}methanone

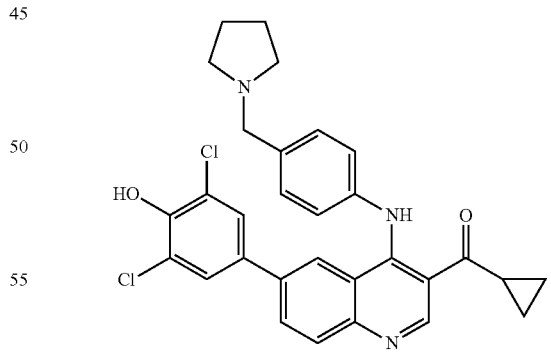

Following general procedure F, {6-bromo-4-[4-(pyrrolidin-1-ylmethyl)phenylamino]quinolin-3-yl}(cyclopropyl)methanone (49 mg, 0.108 mmol) was reacted with 2,6-dichloro-4-(4,4,5,5-tetramethyl-1,3,2-dioxaborolan-2-yl)phenol (46 mg, 0.162 mmol) to afford the desired product (31 mg, 54%) as a yellow solid: $^1$H NMR (300 MHz, CD$_3$OD+ acetic acid-d$_4$) δ 9.31 (s, 1H), 8.06-7.99 (m, 2H), 7.91 (s, 1H), 7.55 (d, J=8.4 Hz, 2H), 7.35-7.26 (m, 4H), 4.41 (s, 2H), 2.93-2.86 (m, 1H), 2.13-2.03 (m, 4H), 1.23-1.06 (m, 4H); ESI MS m/z 532 [C$_{30}$H$_{27}$Cl$_2$N$_3$O$_2$H]$^+$; HPLC 94.9% (AUC), t$_R$=11.43 min.

Example 397

Cyclopropyl{6-(3,5-dichloro-4-hydroxyphenyl)-4-[4-((4-methylpiperazin-1-yl)methyl)phenylamino]quinolin-3-yl}methanone

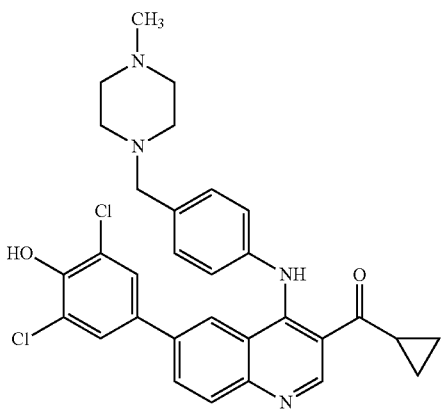

Following general procedure D, {6-bromo-4-[4-((4-methylpiperazin-1-yl)methyl)phenylamino]quinolin-3-yl}(cyclopropyl)methanone (42 mg, 0.088 mmol) was reacted with 2,6-dichloro-4-(4,4,5,5-tetramethyl-1,3,2-dioxaborolan-2-yl)phenol (38 mg, 0.132 mmol) to afford the desired product (41 mg, 83%) as a yellow solid: $^1$H NMR (300 MHz, CD$_3$OD) δ 9.27 (s, 1H), 7.93-7.85 (m, 2H), 7.74 (s, 1H), 7.37 (d, J=8.1 Hz, 2H), 7.19-7.10 (m, 4H), 3.61 (s, 2H), 2.95-2.88 (m, 1H), 2.74-2.68 (m, 4H), 2.57-2.46 (m, 7H), 1.23-1.10 (m, 4H); ESI MS m/z 561 [C$_{31}$H$_{30}$Cl$_2$N$_4$O$_2$+H]$^+$; HPLC 94.4% (AUC), t$_R$=8.57 min.

Example 396

{6-(3-chloro-5-fluoro-4-hydroxyphenyl)-4-[4-(pyrrolidin-1-ylmethyl)phenylamino]quinolin-3-yl}(cyclopropyl)methanone

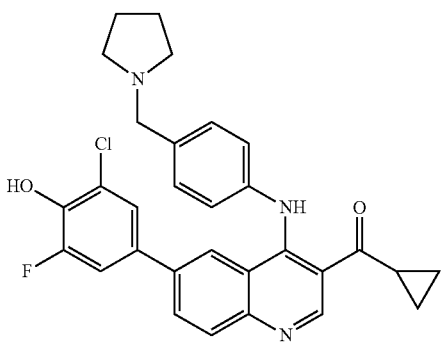

Following general procedure F, {6-bromo-4-[4-(pyrrolidin-1-ylmethyl)phenylamino]quinolin-3-yl}(cyclopropyl)methanone (45 mg, 0.100 mmol) was reacted with 2-chloro-6-fluoro-4-(4,4,5,5-tetramethyl-1,3,2-dioxaborolan-2-yl)phenol (41 mg, 0.150 mmol) to afford the desired product (37 mg, 72%) as a yellow solid: $^1$H NMR (300 MHz, CD$_3$OD+ acetic acid-d$_4$) δ 9.28 (s, 1H), 8.04-7.97 (m, 2H), 7.92 (s, 1H), 7.53 (d, J=8.4, 2H), 7.27 (d, J=8.4 Hz, 2H), 7.19-7.06 (m, 2H), 4.39 (s, 2H), 2.95-2.84 (m, 1H), 2.14-2.03 (m, 4H), 1.21-1.04 (m, 4H); ESI MS m/z 516 [C$_{30}$H$_{27}$ClFN$_3$O$_2$+H]$^+$; HPLC 95.7% (AUC), t$_R$=8.70 min.

Example 409

Cyclopropyl{6-(3,5-dichloro-4-hydroxyphenyl)-4-[6-(piperazin-1-yl)pyridin-3-ylamino]quinolin-3-yl}methanone

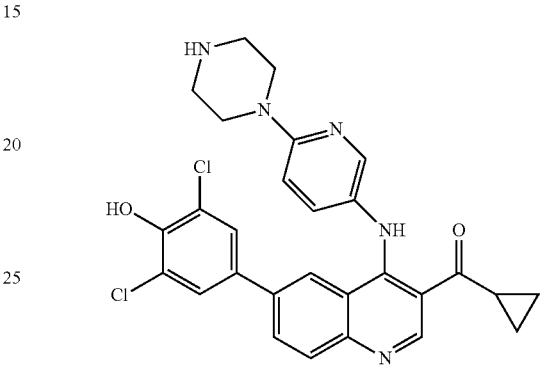

Following general procedure A-2, tert-butyl 4-{5-[3-(cyclopropanecarbonyl)-6-(3,5-dichloro-4-hydroxyphenyl)quinolin-4-ylamino]pyridin-2-yl}piperazine-1-carboxylate (0.118 mmol) was reacted with TFA (2 mL) to afford the desired product (26 mg, 41% over two steps) as an orange solid: $^1$H NMR (300 MHz, CDCl$_3$) δ 11.92 (s, 1H), 9.35 (s, 1H), 8.07-7.94 (m, 2H), 7.75-7.68 (m, 2H), 7.08-7.02 (m, 2H), 6.72-6.65 (m, 1H), 3.71-3.64 (m, 4H), 3.17-3.10 (m, 4H), 2.84-2.77 (m, 1H), 1.34-1.10 (m, 4H); ESI MS m/z 534 [C$_{28}$H$_{25}$Cl$_2$N$_5$O$_2$+H]$^+$; HPLC 97.3% (AUC), t$_R$=8.65 min.

Example 495

{4-[trans-4-(Aminomethyl)cyclohexylamino]-6-(3,5-dichloro-4-hydroxyphenyl)quinolin-3-yl}(cyclopropyl)methanone

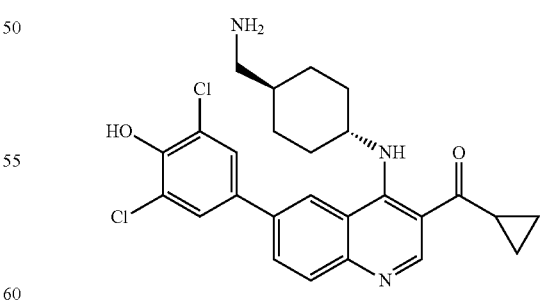

Following general procedure A-2, tert-butyl {trans-4-[3-(cyclopropanecarbonyl)-6-(3,5-dichloro-4-hydroxyphenyl)quinolin-4-ylamino]cyclohexyl}methylcarbamate (0.123 mmol) was reacted with TFA (2 mL) to afford the desired product (24 mg, 40% over two steps) as a yellow solid: $^1$H NMR (300 MHz, CD$_3$OD+TFA-d) δ 9.36 (s, 1H), 8.47 (s, 1H), 8.27 (d, J=8.4 Hz, 1H), 7.98 (d, J=8.4 Hz, 1H), 7.74 (s, 2H), 4.54-4.48 (m, 1H), 2.92-2.76 (m, 3H), 2.50-2.37 (m, 2H), 2.08-2.02 (m, 2H), 1.83-1.64 (m, 3H), 1.41-1.15 (m, 6H); ESI MS m/z 484 [$C_{26}H_{27}Cl_2N_3O_2$+H]$^+$; HPLC>99% (AUC), $t_R$=11.38 min.

Example 493

{4-[trans-4-(Aminomethyl)cyclohexylamino]-6-(3-chloro-4-hydroxy-5-methoxyphenyl)quinolin-3-yl}(cyclopropyl)methanone

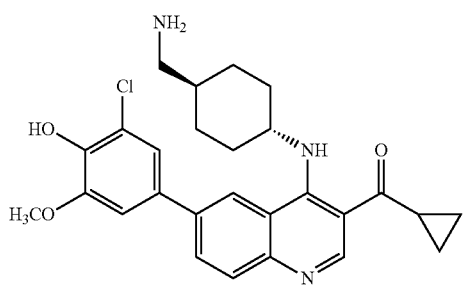 [SMILES: COc1cc(-c2ccc3ncc(C(=O)C4CC4)c(N[C@H]4CC[C@H](CN)CC4)c3c2)cc(Cl)c1O]

Following general procedure A-2, tert-butyl {trans-4-[6-(3-chloro-4-hydroxy-5-methoxyphenyl)-3-(cyclopropanecarbonyl)quinolin-4-ylamino]cyclohexyl}methylcarbamate (0.123 mmol) was reacted with TFA (2 mL) to afford the desired product (28 mg, 47% over two steps) as a yellow solid: $^1$H NMR (300 MHz, CD$_3$OD+TFA-d) δ 9.35 (s, 1H), 8.49 (s, 1H), 8.30 (d, J=8.7 Hz, 1H), 7.97 (d, J=8.7 Hz, 1H), 7.33 (s, 1H), 7.26 (s, 1H), 4.0 (s, 1H), 3.99 (s, 3H), 2.90-2.81 (m, 3H), 2.47-2.41 (m, 2H), 2.10-1.98 (m, 2H), 1.83-1.64 (m, 3H), 1.37-1.17 (m, 6H); ESI MS m/z 480 [$C_{27}H_{30}ClN_3O_3$+H]$^+$; HPLC>99% (AUC), $t_R$=11.15 min.

Example 501

{4-[trans-4-(Aminomethyl)cyclohexylamino]-6-(3-chloro-5-fluoro-4-hydroxyphenyl)quinolin-3-yl}(cyclopropyl)methanone

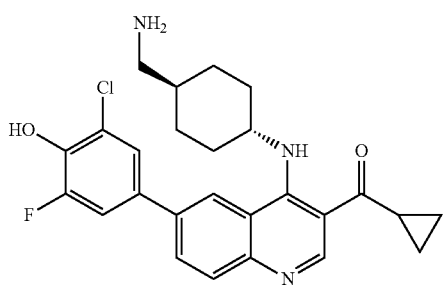 [SMILES: NC[C@H]1CC[C@H](Nc2c(C(=O)C3CC3)cnc3ccc(-c4cc(F)c(O)c(Cl)c4)cc23)CC1]

Following general procedure A-2, tert-butyl {trans-4-[6-(3-chloro-5-fluoro-4-hydroxyphenyl)-3-(cyclopropanecarbonyl)quinolin-4-ylamino]cyclohexyl}methylcarbamate (0.123 mmol) was reacted with TFA (2 mL) to afford the desired product (23 mg, 40% over two steps) as a yellow solid: $^1$H NMR (300 MHz, CD$_3$OD+TFA-d) δ 9.37 (s, 1H), 8.45 (s, 1H), 8.26 (d, J=8.7 Hz, 1H), 7.98 (d, J=8.7 Hz, 1H), 7.63-7.47 (m, 2H), 4.51 (s, 1H), 2.92-2.83 (m, 3H), 2.46-2.40 (m, 2H), 2.11-1.98 (m, 2H), 1.83-1.63 (m, 3H), 1.32-1.14 (m, 6H); ESI MS m/z 468 [$C_{26}H_{27}ClFN_3O_2$+H]$^+$; HPLC 98.6% (AUC), $t_R$=11.33 min.

Example 510

Cyclopropyl{6-(3,5-dichloro-4-hydroxyphenyl)-4-[trans-4-(methylamino)cyclohexylamino]quinolin-3-yl}methanone

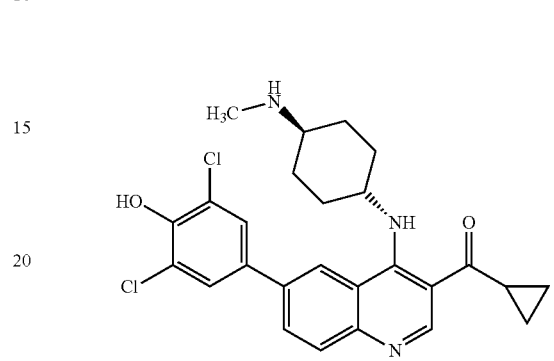

Following general procedure A-2, tert-butyl trans-4-[3-(cyclopropanecarbonyl)-6-(3,5-dichloro-4-hydroxyphenyl)quinolin-4-ylamino]cyclohexyl(methyl)carbamate (0.120 mmol) was reacted with TFA (2 mL) to afford the desired product (30 mg, 51% over two steps) as a yellow solid: $^1$H NMR (300 MHz, CD$_3$OD+TFA-d) δ 9.35 (s, 1H), 8.48 (s, 1H), 8.28 (d, J=8.7 Hz, 1H), 8.00 (d, J=8.7 Hz, 1H), 7.75 (s, 2H), 4.52 (s, 1H), 2.84 (s, 1H), 2.73 (s, 2H), 2.53-2.46 (m, 2H), 2.38-2.28 (m, 2H), 1.88-1.77 (m, 2H), 1.65-1.58 (m, 2H), 1.33-1.20 (m, 4H); ESI MS m/z 484 [$C_{26}H_{27}Cl_2N_3O_2$+H]$^+$; HPLC>99% (AUC), $t_R$=9.66 min.

Example 517

{6-(3-Chloro-4-hydroxy-5-methoxyphenyl)-4-[trans-4-(methylamino)cyclohexylamino]quinolin-3-yl}(cyclopropyl)methanone

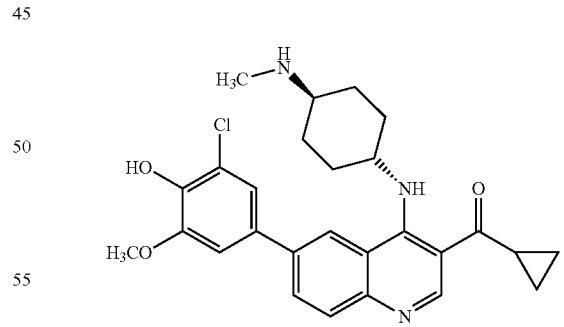

Following general procedure A-2, tert-butyl trans-4-[6-(3-chloro-4-hydroxy-5-methoxyphenyl)-3-(cyclopropanecarbonyl)quinolin-4-ylamino]cyclohexyl(methyl)carbamate (0.135 mmol) was reacted with TFA (2 mL) to afford the desired product (41 mg, 63% over two steps) as a yellow solid: $^1$H NMR (300 MHz, CD$_3$OD+TFA-d) δ 9.34 (s, 1H), 8.48 (s, 1H), 8.31 (d, J=8.7 Hz, 1H), 7.99 (d, J=8.7 Hz, 1H), 7.35 (s, 1H), 7.27 (s, 1H), 4.50 (s, 1H), 4.00 (s, 3H), 2.88-2.81 (m, 1H), 2.74 (s, 3H), 2.54-2.47 (m, 2H), 2.38-2.27 (m, 2H), 1.88-1.77 (m, 2H), 1.62-1.56 (m, 2H), 1.34-1.16 (m, 4H); ESI MS m/z 480 [C$_{27}$H$_{30}$ClN$_3$O$_3$+H]$^+$; HPLC>99% (AUC), t$_R$=9.45 min.

Example 504

{4-[4-(Aminomethyl)phenylamino]-6-(3-chloro-5-fluoro-4-hydroxyphenyl)quinolin-3-yl}(cyclopropyl)methanone

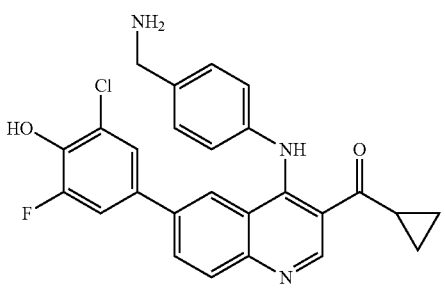

Following general procedure A-2, tert-butyl 4-[6-(3-chloro-5-fluoro-4-hydroxyphenyl)-3-(cyclopropanecarbonyl)quinolin-4-ylamino]benzylcarbamate (0.127 mmol) was reacted with TFA (2 mL) to afford the desired product (31 mg, 53% over two steps) as a yellow solid: $^1$H NMR (300 MHz, CD$_3$OD+TFA-d) δ 9.44 (s, 1H), 8.24 (dd, J=8.9, 1.9 Hz, 1H), 8.08-7.96 (m, 2H), 7.69 (d, J=8.4 Hz, 2H), 7.55 (d, J=8.4 Hz, 2H), 7.17-7.06 (m, 1H), 7.06-6.98 (m, 1H), 4.27 (s, 2H), 2.93-2.80 (m, 1H), 1.25-1.11 (m, 4H); ESI MS m/z 462 [C$_{26}$H$_{21}$ClFN$_3$O$_2$+H]$^+$; HPLC>99% (AUC), t$_R$=12.22 min.

Example 507

{4-[4-(Aminomethyl)phenylamino]-6-(3,5-dichloro-4-hydroxyphenyl)quinolin-3-yl}(cyclopropyl)methanone

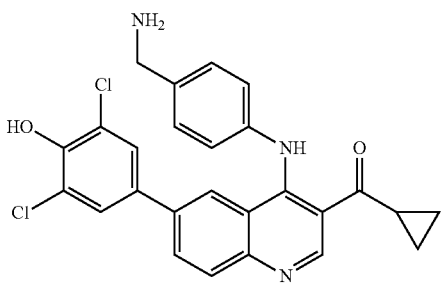

Following general procedure A-2, tert-butyl 4-[3-(cyclopropanecarbonyl)-6-(3,5-dichloro-4-hydroxyphenyl)quinolin-4-ylamino]benzylcarbamate (0.117 mmol) was reacted with TFA (2 mL) to afford the desired product (26 mg, 46% over two steps) a yellow solid: $^1$H NMR (300 MHz, CD$_3$OD+TFA-d) δ 9.44 (s, 1H), 8.25 (d, J=8.7 Hz, 1H), 8.09-7.95 (m, 2H), 7.70 (d, J=8.4 Hz, 2H), 7.55 (d, J=8.4 Hz, 2H), 7.24 (s, 2H), 4.28 (s, 2H), 2.88-2.83 (m, 1H), 1.26-1.13 (m, 4H); ESI MS m/z 478 [C$_{26}$H$_{21}$Cl$_2$N$_3$O$_2$+H]$^+$; HPLC>99% (AUC), t$_R$=11.99 min.

Example 523

{6-(3-Chloro-5-fluoro-4-hydroxyphenyl)-4-[trans-4-(methylamino)cyclohexylamino]quinolin-3-yl}(cyclopropyl)methanone

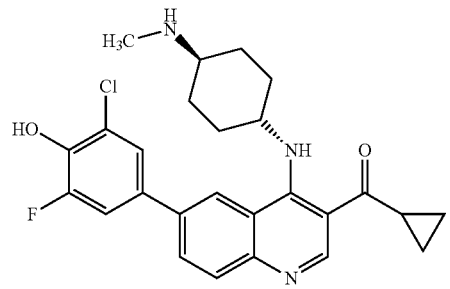

Following general procedure A-2, tert-butyl trans-4-[6-(3-chloro-5-fluoro-4-hydroxyphenyl)-3-(cyclopropanecarbonyl)quinolin-4-ylamino]cyclohexyl(methyl)carbamate (0.125 mmol) was reacted with TFA (2 mL) to afford the desired product (32 mg, 55% over two steps) as a yellow solid: $^1$H NMR (300 MHz, DMSO-d$_6$) δ 9.80 (s, 1H), 9.8 (s, 1H), 8.25 (s, 1H), 7.99 (d, J=8.7 Hz, 1H), 7.83 (d, J=8.7 Hz, 1H), 7.49-7.34 (m, 2H), 4.00-3.94 (s, 1H), 3.00-2.85 (m, 1H), 2.85-2.74 (m, 1H), 2.44 (s, 3H), 2.25-2.04 (m, 4H), 1.60-1.30 (m, 4H), 1.15-0.98 (m, 4H); ESI MS m/z 468 [C$_{26}$H$_{27}$ClFN$_3$O$_2$+H]$^+$; HPLC>99% (AUC), t$_R$=10.03 min.

Example 602

{4-[4-(2-Aminopropan-2-yl)phenylamino]-6-(3,5-dichloro-4-hydroxyphenyl)quinolin-3-yl}(cyclopropyl)methanone

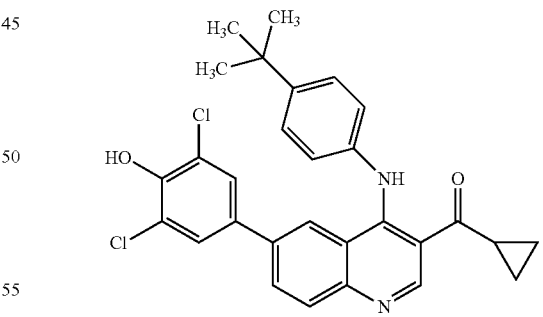

Following general procedure A-2, tert-butyl 2-{4-[3-(cyclopropanecarbonyl)-6-(3,5-dichloro-4-hydroxyphenyl)quinolin-4-ylamino]phenyl}propan-2-ylcarbamate (0.145 mmol) was TFA (2 mL) to afford the desired product (21 mg, 28% over two steps) as a yellow solid: $^1$H NMR (500 MHz, CD$_3$OD+TFA-d) δ 9.33 (s, 1H), 8.26 (dd, J=8.8, 1.9 Hz, 1H), 8.19 (s, 1H), 8.05 (d, J=8.8 Hz, 1H), 7.67 (d, J=8.6 Hz, 2H), 7.53 (d, J=8.6 Hz, 2H), 7.43 (s, 2H), 2.82-2.73 (m, 1H), 1.78 (s, 6H), 1.18-1.10 (m, 4H); ESI MS m/z 506 [C$_{28}$H$_{25}$Cl$_2$N$_3$O$_2$+H]$^+$; HPLC 98.7% (AUC), t$_R$=11.00 min.

Example 604

{4-[4-(2-Aminopropan-2-yl)phenylamino]-6-(3-chloro-5-fluoro-4-hydroxyphenyl)quinolin-3-yl}(cyclopropyl)methanone Following general procedure A-2, tert-butyl 2-{4-[6-(3-chloro-5-fluoro-4-hydroxyphenyl)-3-(cyclopropanecarbonyl)quinolin-4-ylamino]phenyl}propan-2-ylcarbamate (0.140 mmol) was reacted with TFA (2 mL) to afford the desired product (22 mg, 32% over two steps) as a yellow solid: $^1$H NMR (500 MHz, CD$_3$OD+TFA-l) δ 9.38 (s, 1H), 8.26 (dd, J=8.9, 1.9 Hz, 1H), 8.12 (s, 1H), 8.05 (d, J=8.8 Hz, 1H), 7.69 (d, J=8.0, 2H), 7.54 (d, J=8.0 Hz, 2H), 7.30 (t, J=1.9 Hz, 1H), 7.10-7.03 (m, 1H), 2.84-2.76 (m, 1H), 1.79 (s, 6H), 1.19-1.12 (m, 4H).; ESI MS m/z 490 [C$_{28}$H$_{25}$ClFN$_3$O$_2$+H]$^+$; HPLC>99% (AUC), t$_R$=10.80 min.

Example 605

1-{6-(3,5-Dichloro-4-hydroxyphenyl)-4-[trans-4-((dimethylamino)methyl)cylohexylamino]quinolin-3-yl}butan-1-one

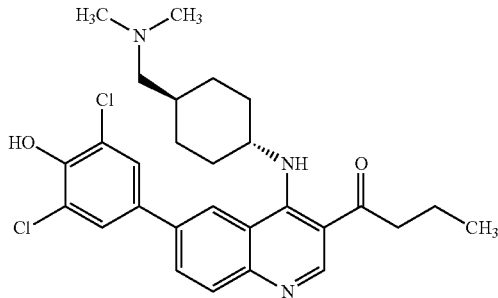 [SMILES: CCCC(=O)c1cnc2ccc(-c3cc(Cl)c(O)c(Cl)c3)cc2c1N[C@H]1CC[C@H](CN(C)C)CC1]

Following general procedure A-1, 1-{6-bromo-4-[trans-4-((dimethylamino)methyl)cyclohexylamino]quinolin-3-yl}butan-1-one (48 mg, 0.110 mmol) was reacted with 2,6-dichloro-4-(4,4,5,5-tetramethyl-1,3,2-dioxaborolan-2-yl)phenol (47 mg, 0.165 mmol) to afford the desired product (20 mg, 35%) as a yellow solid: $^1$H NMR (500 MHz, CD$_3$OD+TFA-d) δ 9.14 (s, 1H), 8.47 (s, 1H), 8.27 (dd, J=8.7, 1.8 Hz, 1H), 8.98 (d, J=8.7 Hz, 1H), 7.72 (s, 2H), 4.53 (s, 1H), 3.16-3.06 (m, 4H), 2.94 (s, 6H), 2.50-2.43 (m, 2H), 2.08-2.02 (m, 3H), 1.88-1.74 (m, 4H), 1.39-1.32 (m, 1H), 1.06 (t, J=7.4 Hz, 3H); ESI MS m/z 514 [C$_{28}$H$_{33}$Cl$_2$N$_3$O$_2$+H]$^+$; HPLC 98.7% (AUC), t$_R$=11.27 min.

Example 597

1-{6-(3-Chloro-5-fluoro-4-hydroxyphenyl)-4-[trans-4-((dimethylamino)methyl)cyclohexylamino]quinolin-3-yl}butan-1-one

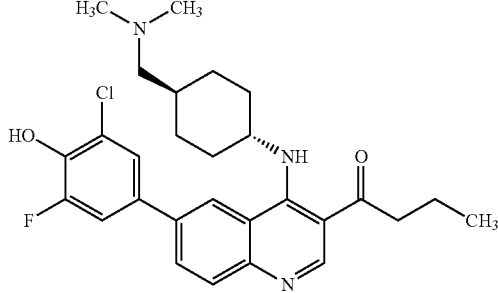 [SMILES: CCCC(=O)c1cnc2ccc(-c3cc(F)c(O)c(Cl)c3)cc2c1N[C@H]1CC[C@H](CN(C)C)CC1]

Following general procedure A-1, 1-{6-bromo-4-[trans-4-((dimethylamino)methyl)cyclohexylamino]quinolin-3-yl}butan-1-one (48 mg, 0.110 mmol) was reacted with 2-chloro-6-fluoro-4-(4,4,5,5-tetramethyl-1,3,2-dioxaborolan-2-yl)phenol (45 mg, 0.165 mmol) to afford the desired product (36 mg, 67%) as a yellow solid: $^1$H NMR (500 MHz, CD$_3$OD+TFA-d) δ 9.14 (s, 1H), 8.47 (s, 1H), 8.26 (dd, J=8.7, 1.8 Hz, 1H), 7.98 (d, J=8.7 Hz, 1H), 7.58 (s, 1H), 7.50 (d, J=11.3 Hz, 1H), 4.52 (s, 1H), 3.16-3.05 (m, 4H), 2.95 (s, 6H), 2.49-2.43 (m, 2H), 2.08-2.01 (m, 2H), 1.85-1.74 (m, 4H), 1.41-1.32 (m, 1H), 1.09-1.02 (t, J=7.4 Hz, 3H); ESI MS m/z 498 [C$_{28}$H$_{33}$ClFN$_3$O$_2$+H]$^+$; HPLC>99% (AUC), t$_R$=11.08 min.

Example 623

1-{6-(3-Chloro-5-fluoro-4-hydroxyphenyl)-4-[6-(piperazin-1-yl)pyridin-3-ylamino]quinolin-3-yl}butan-1-one

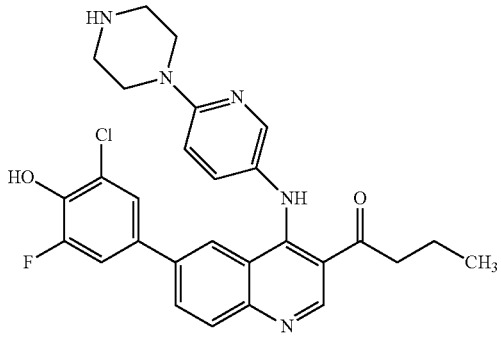 [SMILES: CCCC(=O)c1cnc2ccc(-c3cc(F)c(O)c(Cl)c3)cc2c1Nc1ccc(N2CCNCC2)nc1]

Following general procedure A-2, tert-butyl 4-{5-[3-butyryl-6-(3-chloro-5-fluoro-4-hydroxyphenyl)quinolin-4-ylamino]pyridin-2-yl}piperazine-1-carboxylate (0.144 mmol) was reacted with TFA (2 mL) to afford the desired product (39 mg, 51% over two steps) as a yellow solid: $^1$H NMR (500 MHz, CD$_3$OD+TFA-d) δ 9.29 (s, 1H), 8.29 (d, J=2.7 Hz, 1H), 8.20 (dd, J=8.8, 2.0 Hz, 1H), 8.03-7.95 (m, 2H), 7.74 (dd, J=8.8, 2.7 Hz, 1H), 7.16 (d, J=9.0 Hz, 1H), 7.11-7.02 (m, 2H), 3.94 (t, J=5.3 Hz, 4H), 3.37 (t, J=5.3 Hz, 4H), 3.19 (t, J=7.2 Hz, 2H), 1.87-1.76 (m, 2H), 1.11-1.04 (t, J=7.2 Hz, 3H); ESI MS m/z 520 [C$_{28}$H$_{27}$ClFN$_5$O$_2$+H]$^+$; HPLC>99% (AUC), t$_R$=10.99 min.

Example 638

[4-(4-Amino-4-methylcyclohexylamino)-6-(3,5-dichloro-4-hydroxyphenyl)quinolin-3-yl](cyclopropyl)methanone

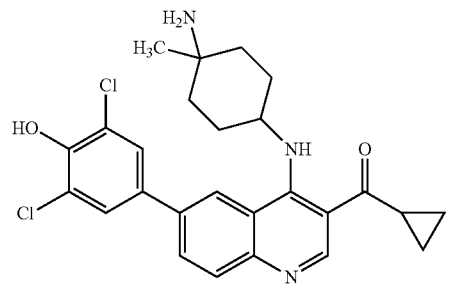 [SMILES: CC1(N)CCC(Nc2c(C(=O)C3CC3)cnc3ccc(-c4cc(Cl)c(O)c(Cl)c4)cc23)CC1]

To a solution of cyclopropyl{4-[4-(diallylamino)-4-methyl-cyclohexylamino]-6-(3,5-dichloro-4-hydroxyphenyl)quinolin-3-yl}methanone (23 mg, 0.041 mmol) in dioxane (3 mL) was added Pd(PPh$_3$)$_4$ (5 mg, 0.004 mmol) and N,N-dimethylbartituric acid (32 mg, 0.205 mmol). The resultant mixture purged with N$_2$ and heated to 80° C. for 16 h. The solution was allowed to cool to rt, diluted with ethyl acetate, filtered and concentrated. The resultant residue was purified by preparative HPLC (C18 silica, 10-90% acetonitrile/water with 0.05% TFA). The purified product was concentrated, diluted with a saturated NaHCO$_3$ solution, extracted with a mixture of CHCl$_3$/isopropanol (3:1), and dried with Na$_2$SO$_4$ to obtain the desired product as the free base (5 mg, 25%) as a yellow solid: $^1$H NMR (500 MHz, CD$_3$OD+TFA-d) δ 9.39 (s, 1H), 8.45 (s, 1H), 8.28 (dd, J=8.7, 1.9 Hz, 1H), 8.01 (d, J=8.7 Hz, 1H), 7.73 (s, 2H), 4.76-4.72 (m, 1H), 2.89-2.85 (m, 1H), 2.33-2.25 (m, 2H), 2.09-1.97 (m, 4H), 1.96-1.89 (m, 2H), 1.45 (s, 3H), 1.41-1.18 (m, 4H); ESI MS m/z 484 [C$_{26}$H$_{27}$Cl$_2$N$_3$O$_2$+H]$^+$; HPLC 98.6% (AUC), t$_R$=11.05 min.

Example 639

[4-(4-Amino-4-methylcyclohexylamino)-6-(3-chloro-4-hydroxy-5-methoxyphenyl)quinolin-3-yl](cyclopropyl)methanone

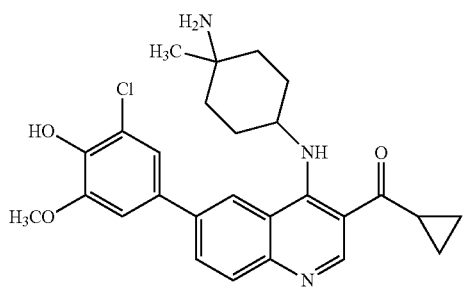 [SMILES: COc1cc(-c2ccc3ncc(C(=O)C4CC4)c(NC4CCC(C)(N)CC4)c3c2)cc(Cl)c1O]

To a solution of {6-(3-chloro-4-hydroxy-5-methoxyphenyl)-4-[4-(diallylamino)-4-methylcyclohexylamino]quinolin-3-yl}(cyclopropyl)methanone (49 mg, 0.088 mmol) in dioxane (3 mL) was added Pd(PPh$_3$)$_4$ (10 mg, 0.008 mmol) and N,N-dimethylbartituric acid (68 mg, 0.438 mmol). The resultant mixture purged with N$_2$ and heated to 80° C. for 16 h. The solution was allowed to cool to rt, diluted with ethyl acetate, filtered and concentrated. The resultant residue was purified by preparative HPLC (C18 silica, 10-90% acetonitrile/water with 0.05% TFA). The purified product was concentrated, diluted with a saturated NaHCO$_3$ solution, extracted with a mixture of CHCl$_3$/isopropanol (3:1), and dried with Na$_2$SO$_4$ to obtain the desired product as the free base (5 mg, 4%) as a yellow solid: $^1$H NMR (500 MHz, CD$_3$OD+TFA-d) δ 9.14 (s, 1H), 8.34 (s, 1H), 8.00 (dd, J=8.7, 2.0 Hz, 1H), 7.89 (d, J=8.7 Hz, 1H), 7.26 (d, J=2.2 Hz, 1H), 7.20 (d, J=2.2 Hz, 1H), 4.29-4.21 (m, 1H), 3.97 (s, 3H), 2.89-2.80 (m, 1H), 2.14-2.07 (m, 2H), 1.92-1.71 (m, 4H), 1.70-1.61 (m, 2H), 1.28 (s, 3H), 1.25-1.06 (m, 4H); ESI MS m/z 480 [C$_{27}$H$_{30}$ClN$_3$O$_3$+H]$^+$; HPLC>99% (AUC), t$_R$=10.46 min.

Example 657

Cyclopropyl{6-(3,5-dichloro-4-hydroxyphenyl)-4-[6-((dimethylamino)methyl)pyridin-3-ylamino]quinolin-3-yl}methanone

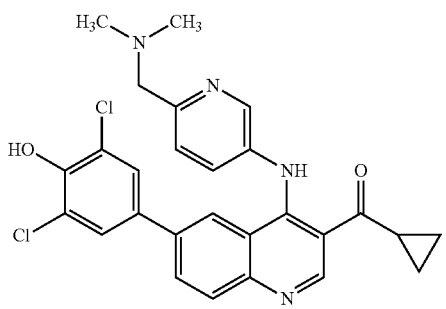 [SMILES: CN(C)Cc1ccc(Nc2c(C(=O)C3CC3)cnc3ccc(-c4cc(Cl)c(O)c(Cl)c4)cc23)cn1]

Following general procedure F, {6-bromo-4-[6-((dimethylamino)methyl)pyridin-3-ylamino]quinolin-3-yl}(cyclopropyl)methanone (37 mg, 0.087 mmol) was reacted with 2,6-dichloro-4-(4,4,5,5-tetramethyl-1,3,2-dioxaborolan-2-yl)phenol (38 mg, 0.131 mmol) to afford the desired product (25 mg, 57%) as a yellow solid: $^1$H NMR (500 MHz, CD$_3$OD+TFA-d) δ 9.37 (s, 1H), 8.75 (s, 1H), 8.32 (dd, J=8.8, 2.1 Hz, 1H), 8.22 (d, J=2.1 Hz, 1H), 8.10 (d, J=8.8 Hz, 1H), 7.96 (dd, J=8.4, 2.6 Hz, 1H), 7.65 (d, J=8.4 Hz, 1H), 7.47 (s, 2H), 4.58 (s, 2H), 2.95 (s, 6H), 2.83-2.74 (m, 1H), 1.19-1.07 (m, 4H); ESI MS m/z 507 [C$_{27}$H$_{24}$Cl$_2$N$_4$O$_2$+H]$^+$; HPLC 98.9% (AUC), t$_R$=10.66 min.

Example 658

Cyclopropyl{6-(3,5-dichloro-4-hydroxyphenyl)-4-[6-(pyrrolidin-1-ylmethyl)pyridin-3-ylamino]quinolin-3-yl}methanone

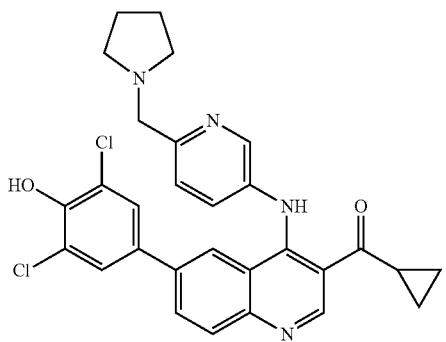

Following general procedure F, {6-Bromo-4-[6-(pyrrolidin-1-ylmethyl)pyridin-3-ylamino]quinolin-3-yl}(cyclopropyl)methanone (45 mg, 0.100 mmol) was reacted with 2,6-dichloro-4-(4,4,5,5-tetramethyl-1,3,2-dioxaborolan-2-yl)phenol (43 mg, 0.150 mmol) to afford the desired product (34 mg, 64%) as a yellow solid: $^1$H NMR (500 MHz, CD$_3$OD+TFA-d) δ 9.40 (s, 1H), 8.72 (d, J=2.5 Hz, 1H), 8.30 (dd, J=8.8, 2.0 Hz, 1H), 8.16-8.06 (m, 2H), 7.96 (dd, J=8.3, 2.5 Hz, 1H), 7.65 (d, J=8.3 Hz, 1H), 7.46 (s, 2H), 4.65 (s, 2H), 3.63-3.59 (m, 2H), 3.21-3.12 (m, 2H), 2.85-2.76 (m, 1H), 2.20-2.16 (m, 2H), 2.09-2.01 (m, 2H), 1.20-1.10 (m, 4H); ESI MS m/z 533 [C$_{29}$H$_{26}$Cl$_2$N$_4$O$_2$+H]$^+$; HPLC 98.8% (AUC), t$_R$=10.76 min.

Example 698

Cyclopropyl{6-(3,5-dichloro-4-hydroxyphenyl)-4-[3-(2-(dimethylamino)ethyl)phenylamino]quinolin-3-yl}methanone

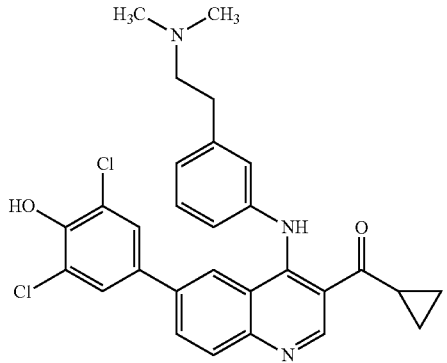 [SMILES: CN(C)CCc1cccc(Nc2c(C(=O)C3CC3)cnc3ccc(-c4cc(Cl)c(O)c(Cl)c4)cc23)c1]

Following general procedure F, {6-Bromo-4-[3-(2-(dimethylamino)ethyl)phenylamino]quinolin-3-yl}(cyclopropyl)methanone (58 mg, 0.132 mmol) was reacted with 2,6-dichloro-4-(4,4,5,5-tetramethyl-1,3,2-dioxaborolan-2-yl)phenol (57 mg, 0.198 mmol) to afford the desired product (49 mg, 71%) as a yellow solid: $^1$H NMR (500 MHz, CD$_3$OD+TFA-d) δ 9.46 (s, 1H), 8.22 (dd, J=8.7, 2.0 Hz, 1H), 8.02 (d, J=8.7 Hz, 1H), 7.89 (s, 1H), 7.67-7.59 (m, 1H), 7.56 (d, J=7.7 Hz, 1H), 7.8 (s, 1H), 7.39 (d, J=7.7 Hz, 1H), 7.20 (s, 2H), 3.40-3.34 (m, 2H), 3.19-3.12 (m, 2H), 2.98-2.85 (s, 8H), 1.27-1.16 (m, 4H); ESI MS m/z 520 [C$_{29}$H$_{27}$Cl$_2$N$_3$O$_2$+H]$^+$; HPLC 95.9% (AUC), t$_R$=11.40 min.

Example 693

{6-(3-Chloro-5-fluoro-4-hydroxyphenyl)-4-[3-(2-(dimethylamino)ethyl)phenylamino]quinolin-3-yl}(cyclopropyl)methanone

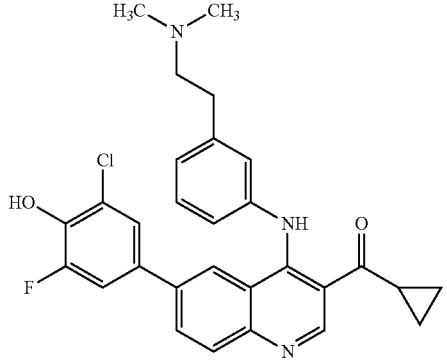 [SMILES: CN(C)CCc1cccc(Nc2c(C(=O)C3CC3)cnc3ccc(-c4cc(F)c(O)c(Cl)c4)cc23)c1]

Following general procedure F, {6-Bromo-4-[3-(2-(dimethylamino)ethyl)phenylamino]quinolin-3-yl}(cyclopropyl)methanone (54 mg, 0.123 mmol) was reacted with 2-chloro-6-fluoro-4-(4,4,5,5-tetramethyl-1,3,2-dioxaborolan-2-yl)phenol (50 mg, 0.185 mmol) to afford the desired product (57 mg, 92%) as a yellow solid: $^1$H NMR (500 MHz, CD$_3$OD+TFA-d) δ 9.44 (s, 1H), 8.21 (dd, J=8.8, 1.9 Hz, 1H), 8.02 (d, J=8.8 Hz, 1H), 7.92 (s, 1H), 7.66-7.57 (m, 1H), 7.54 (d, J=7.7 Hz, 1H), 7.50 (s, 1H), 7.39 (dd, J=7.8, 2.2 Hz, 1H), 7.12 (d, J=11.5 Hz, 1H), 6.96 (s, 1H), 3.40-3.32 (m, 2H), 3.18-3.11 (m, 2H), 2.97-2.86 (m, 8H), 1.26-1.15 (m, 4H); ESI MS m/z 504 [C$_{29}$H$_{27}$ClFN$_3$O$_2$+H]$^+$; HPLC 96.4% (AUC), t$_R$=11.15 min.

Example 703

Cyclopropyl{6-(3,5-dichloro-4-hydroxyphenyl)-4-[1-(1-methylpiperidin-3-yl)-1H-pyrazol-4-ylamino]quinolin-3-yl}methanone

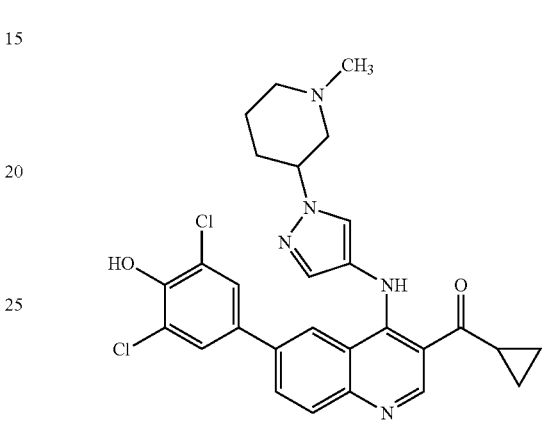

Following general procedure F, {6-Bromo-4-[1-(1-methylpiperidin-3-yl)-1H-pyrazol-4-ylamino]quinolin-3-yl}(cyclopropyl)methanone (53 mg, 0.110 mmol) was reacted with 2,6-dichloro-4-(4,4,5,5-tetramethyl-1,3,2-dioxaborolan-2-yl)phenol (47 mg, 0.165 mmol) to afford the desired product (50 mg, 84%) as a green-yellow solid: $^1$H NMR (500 MHz, DMSO-d$_6$) δ 10.83 (s, 1H), 9.06 (s, 1H), 8.23 (d, J=2.1 Hz, 1H), 8.04 (dd, J=8.7, 2.1 Hz, 1H), 7.93-7.85 (m, 2H), 7.50 (s, 2H), 7.43 (s, 1H), 4.22-4.12 (m, 1H), 2.94 (d, J=11.4 Hz, 2H), 2.88-2.79 (m, 1H), 2.39 (s, 3H), 2.27-2.20 (m, 2H), 2.02-1.89 (m, 4H), 1.02-0.91 (m, 4H); ESI MS m/z 536 [C$_{28}$H$_{27}$Cl$_2$N$_5$O$_2$+H]$^+$; HPLC 98.6% (AUC), t$_R$=10.40 min.

Example 699

{6-(3-Chloro-5-fluoro-4-hydroxyphenyl)-4-[1-(1-methylpiperidin-3-yl)-1H-pyrazol-4-ylamino]quinolin-3-yl}(cyclopropyl)methanone

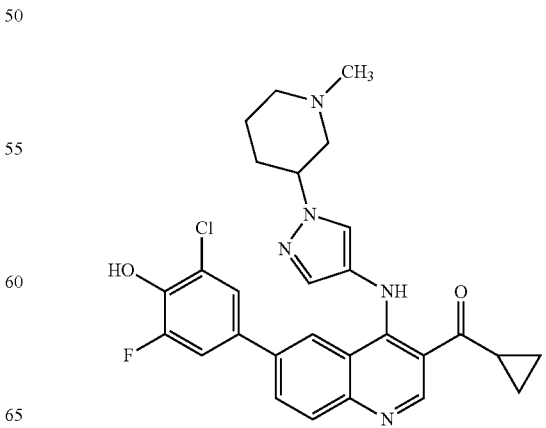

Following general procedure F, {6-Bromo-4-[1-(1-methylpiperidin-3-yl)-1H-pyrazol-4-ylamino]quinolin-3-yl}(cyclopropyl)methanone (58 mg, 0.120 mmol) was reacted with 2-chloro-6-fluoro-4-(4,4,5,5-tetramethyl-1,3,2-dioxaborolan-2-yl)phenol (49 mg, 0.180 mmol) to afford the desired product (46 mg, 74%) as a yellow-green solid: $^1$H NMR (500 MHz, DMSO-$d_6$) δ 10.86 (s, 1H), 9.08 (s, 1H), 8.24 (d, J=2.1 Hz, 1H), 8.04 (dd, J=8.8, 2.1 Hz, 1H), 7.93-7.83 (m, 2H), 7.43 (s, 1H), 7.39-7.30 (m, 2H), 4.19-4.12 (m, 1H), 2.95-2.81 (m, 3H), 2.29-2.15 (s, 5H), 2.01-1.89 (m, 4H), 1.02-0.92 (m, 4H).; ESI MS m/z 520 $[C_{28}H_{27}ClFN_5O_2+H]^+$; HPLC 98.6% (AUC), $t_R$=10.16 min.

Example 601

{4-[4-(2-Aminopropan-2-yl)phenylamino]-6-(3,5-dichloro-4-hydroxyphenyl)quinolin-3-yl}(cyclopropyl)methanone hydrochloride

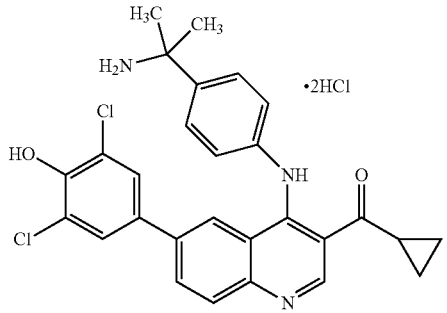 [SMILES: CC(C)(N)c1ccc(Nc2c(C(=O)C3CC3)cnc3ccc(-c4cc(Cl)c(O)c(Cl)c4)cc23)cc1]

To a suspension of {4-[4-(2-aminopropan-2-yl)phenylamino]-6-(3,5-dichloro-4-hydroxyphenyl)quinolin-3-yl}(cyclopropyl)methanone (14 mg, 0.028 mmol) in methanol (5 mL) was added HCl in ether (3 drops, 2 M). The resultant solution was concentrated to obtain the desired product as the hydrochloride salt (13 mg) as a yellow solid: $^1$H NMR (500 MHz, CD$_3$OD) δ 9.31 (s, 1H), 8.24-8.22 (m, 1H), 8.18 (s, 1H), 8.04 (d, J=8.8 Hz, 1H), 7.65 (d, J=9.0 Hz, 2H), 7.49 (d, J=9.0 Hz, 2H), 7.42 (s, 2H), 2.84-2.75 (m, 1H), 1.78 (s, 6H), 1.18-1.09 (m, 4H); ESI MS m/z 506 $[C_{28}H_{25}Cl_2N_3O_2+H]^+$; HPLC 98.5% (AUC), $t_R$=10.80 min.

Example 705

Cyclopropyl{6-(3,5-dichloro-4-hydroxyphenyl)-4-[1-(trans-4-(methylamino)cyclohexyl)-1H-pyrazol-4-ylamino]quinolin-3-yl}methanone

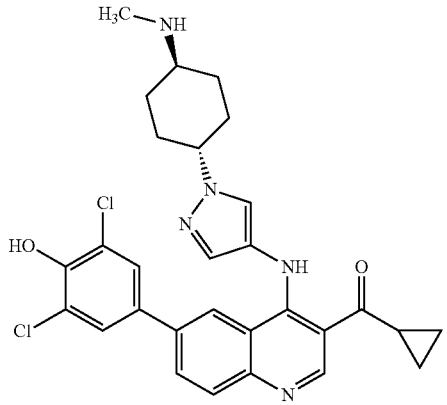 [SMILES: CN[C@H]1CC[C@H](n2cc(Nc3c(C(=O)C4CC4)cnc4ccc(-c5cc(Cl)c(O)c(Cl)c5)cc34)cn2)CC1]

Following general procedure F, {6-bromo-4-[1-(trans-4-(methylamino)cyclohexyl)-1H-pyrazol-4-ylamino]quinolin-3-yl}(cyclopropyl)methanone (60 mg, 0.128 mmol) was reacted with 2,6-dichloro-4-(4,4,5,5-tetramethyl-1,3,2-dioxaborolan-2-yl)phenol (55 mg, 0.192 mmol) to afford the desired product (17 mg, 24%) as a light yellow solid: $^1$H NMR (500 MHz, DMSO-$d_6$+TFA-d) δ 8.95-8.65 (br s, 1H), 8.63-8.51 (m, 1H), 8.40 (d, J=8.8 Hz, 1H), 8.06 (d, J=8.8 Hz, 1H), 8.02-7.97 (m, 1H), 7.54 (s, 1H), 4.26 (m, 1H), 3.11-3.02 (m, 1H), 2.60 (s, 3H), 2.20-2.08 (m, 4H), 1.88-1.76 (m, 2H), 1.58-1.46 (m, 2H), 1.00-0.76 (m, 4H); ESI MS m/z 550 $[C_{29}H_{29}Cl_2N_5O_2+H]^+$; HPLC 98.4% (AUC), $t_R$=11.56 min.

Example 709

Cyclopropyl{6-(3,5-dichloro-4-hydroxyphenyl)-4-[4-(2-(dimethylamino)-1-hydroxyethyl)phenylamino]quinolin-3-yl}methanone

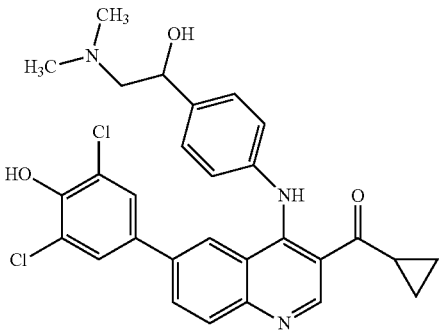

Following general procedure F, {6-bromo-4-[4-(2-(dimethylamino)-1-hydroxyethyl)phenylamino]quinolin-3-yl}(cyclopropyl)methanone (50 mg, 0.110 mmol) was reacted with 2,6-dichloro-4-(4,4,5,5-tetramethyl-1,3,2-dioxaborolan-2-yl)phenol (48 mg, 0.165 mmol) to afford the desired product (41 mg, 69%) as a yellow solid: $^1$H NMR (300 MHz, CD$_3$OD+TFA-d) δ 9.38 (s, 1H), 8.22 (dd, J=8.8, 2.0 Hz, 1H), 8.07-7.98 (m, 2H), 7.65 (d, J=8.4 Hz, 2H), 7.48 (d, J=8.4 Hz, 2H), 7.38 (s, 2H), 5.18 (dd, J=9.8, 4.3 Hz, 1H), 3.25-3.14 (m, 2H), 3.02 (s, 3H), 2.95 (s, 3H), 2.86-2.79 (m, 1H), 1.22-1.11 (m, 4H); ESI MS m/z 536 $[C_{29}H_{27}Cl_2N_3O_3+H]^+$; HPLC 95.1% (AUC), $t_R$=11.42 min.

Example 707

{6-(3-Chloro-5-fluoro-4-hydroxyphenyl)-4-[4-(2-(dimethylamino)-1-hydroxyethyl)phenylamino]quinolin-3-yl}(cyclopropyl)methanone

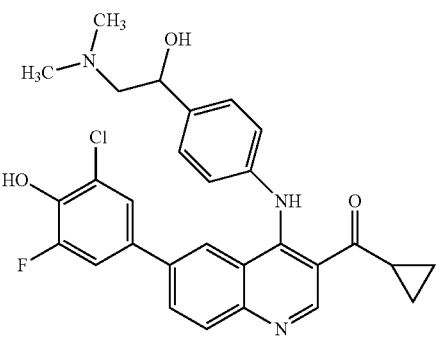 [SMILES: CN(C)CC(O)c1ccc(Nc2c(C(=O)C3CC3)cnc3ccc(-c4cc(F)c(O)c(Cl)c4)cc23)cc1]

Following general procedure A-1, {6-bromo-4-[4-(2-(dimethylamino)-1-hydroxyethyl)phenylamino]quinolin-3-yl}(cyclopropyl)methanone (50 mg, 0.110 mmol) was reacted with 2-chloro-6-fluoro-4-(4,4,5,5-tetramethyl-1,3,2-dioxaborolan-2-yl)phenol (30 mg, 0.165 mmol) to afford the desired product (23 mg, 40%) as a yellow solid: $^1$H NMR (500 MHz, CD$_3$OD+TFA-d) 9.41 (s, 1H), 8.22 (dd, J=8.8, 2.0 Hz, 1H), 8.02 (d, J=8.8 Hz, 2H), 7.66 (d, J=8.0 Hz, 2H), 7.49 (d, J=8.0 Hz, 2H), 7.23 (s, 1H), 7.09-7.02 (m, 1H), 5.20 (dd, J=10.6, 3.8 Hz, 1H), 3.31-3.20 (m, 2H), 3.03 (s, 3H), 2.97 (s, 3H), 2.89-2.80 (m, 1H), 1.25-1.14 (m, 4H); ESI MS m/z 520 [C$_{29}$H$_{27}$ClFN$_3$O$_3$+H]$^+$; HPLC 94.8% (AUC), t$_R$=11.31 min.

Example 729

1-{6-(3,5-Dichloro-4-hydroxyphenyl)-4-[3-(2-(dimethylamino)ethyl)phenylamino]quinolin-3-yl}ethanone

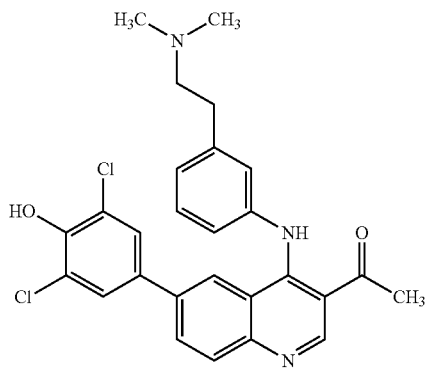 [SMILES: CC(=O)c1cnc2ccc(-c3cc(Cl)c(O)c(Cl)c3)cc2c1Nc1cccc(CCN(C)C)c1]

Following general procedure F, 1-{6-bromo-4-[3-(2-(dimethylamino)ethyl)phenylamino]quinolin-3-yl}ethanone (50 mg, 0.120 mmol) was reacted with 2,6-dichloro-4-(4,4,5,5-tetramethyl-1,3,2-dioxaborolan-2-yl)phenol (52 mg, 0.180 mmol) to afford the desired product (46 mg, 77%) as a yellow solid: $^1$H NMR (500 MHz, CD$_3$OD+TFA-d) δ 9.31 (s, 1H), 8.20 (dd, J=8.8, 2.0 Hz, 1H), 8.00 (d, J=8.8 Hz, 1H), 7.72 (s, 1H), 7.70-7.56 (m, 2H), 7.51 (s, 1H), 7.40 (d, J=7.8 Hz, 1H), 7.10 (s, 2H), 3.40-3.30 (m, 2H), 3.21-3.11 (m, 2H), 2.94 (s, 6H), 2.82 (s, 3H); ESI MS m/z 494 [C$_{27}$H$_{25}$Cl$_2$N$_3$O$_2$+H]$^+$; HPLC 96.8% (AUC), t$_R$=8.94 min.

Example 765

1-{6-(3,5-Dichloro-4-hydroxyphenyl)-4-[trans-4-(dimethylamino)cyclohexylamino]quinolin-3-yl}ethanone

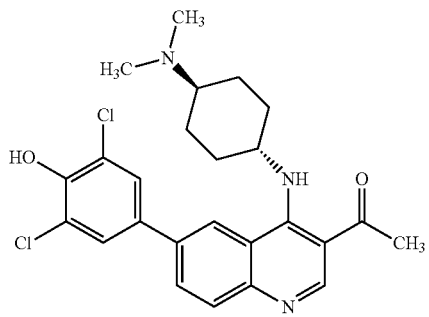 [SMILES: CC(=O)c1cnc2ccc(-c3cc(Cl)c(O)c(Cl)c3)cc2c1N[C@H]1CC[C@H](N(C)C)CC1]

Following general procedure F, 1-{6-bromo-4-[trans-4-(dimethylamino)cyclohexylamino]quinolin-3-yl}ethanone (30 mg, 0.0.77 mmol) was reacted with 2,6-dichloro-4-(4,4,5,5-tetramethyl-1,3,2-dioxaborolan-2-yl)phenol (44 mg, 0.154 mmol) to afford the desired product (29 mg, 80%) as a yellow solid: $^1$H NMR (500 MHz, CD$_3$OD TFA-d) δ 9.13 (s, 1H), 8.48 (s, 1H), 8.30 (dd, J=8.7, 1.8 Hz, 1H), 8.00 (d, J=8.7 Hz, 1H), 7.77 (s, 2H), 4.66-4.62 (m, 1H), 3.50-3.46 (m, 1H), 2.91 (s, 6H), 2.75 (s, 3H), 2.59-2.55 (m, 2H), 2.34-2.30 (m, 2H), 1.92-1.84 (m, 4H); ESI MS m/z 472 [C$_{25}$H$_{27}$Cl$_2$N$_3$O$_2$+H]$^+$; HPLC 98.0% (AUC), t$_R$=9.78 min.

Example 763

1-{6-(3-Chloro-5-fluoro-4-hydroxyphenyl)-4-[trans-4-(dimethylamino)cyclohexylamino]quinolin-3-yl}ethanone

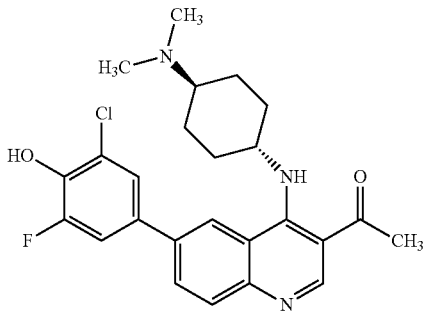 [SMILES: CC(=O)c1cnc2ccc(-c3cc(F)c(O)c(Cl)c3)cc2c1N[C@H]1CC[C@H](N(C)C)CC1]

Following general procedure F, 1-{6-bromo-4-[trans-4-(dimethylamino)cyclohexylamino]quinolin-3-yl}ethanone (30 mg, 0.077 mmol) was reacted with 2-chloro-6-fluoro-4-(4,4,5,5-tetramethyl-1,3,2-dioxaborolan-2-yl)phenol (42 mg, 0.154 mmol) to afford the desired product (24 mg, 68%) as a yellow-orange solid: $^1$H NMR (500 MHz, CD$_3$OD+TFA-d) δ 9.13 (s, 1H), 8.48 (s, 1H), 8.29 (dd, J=8.8, 1.8 Hz, 1H), 8.00 (d, J=8.8 Hz, 1H), 7.63 (s, 1H), 7.56 (dd, J=11.4, 2.3 Hz, 1H), 4.65-4.61 (m, 1H), 3.50-3.46 (m, 1H), 2.91 (s, 6H), 2.75 (s, 3H), 2.58-2.54 (m, 2H), 2.34-2.28 (m, 2H), 1.91-1.81 (m, 4H); ESI MS m/z 456 [C$_{25}$H$_{27}$ClFN$_3$O$_2$+H]$^+$; HPLC 97.1% (AUC), t$_R$=9.52 min.

Example 797

Cyclopropyl{6-(3,5-dichloro-4-hydroxyphenyl)-4-[3-(2-(pyrrolidin-1-yl)ethyl)phenylamino]quinolin-3-yl}methanone

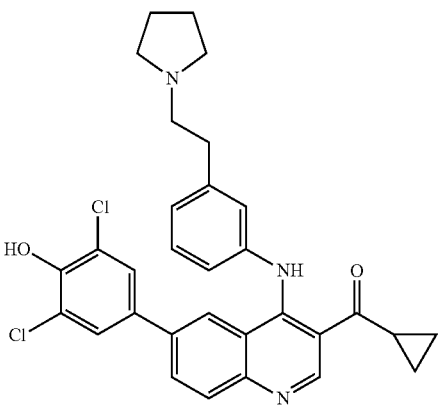

Following general procedure A-1, {6-bromo-4-[3-(2-(pyrrolidin-1-yl)ethyl)phenylamino]quinolin-3-yl}(cyclopropyl)methanone (56 mg, 0.120 mmol) was reacted with 2,6-dichloro-4-(4,4,5,5-tetramethyl-1,3,2-dioxaborolan-2-yl)phenol (52 mg, 0.180 mmol) to afford the desired product (10 mg, 15%) as a yellow solid: $^1$H NMR (500 MHz, CD$_3$OD+TFA-d) δ 9.46 (s, 1H), 8.22 (dd, J=8.8, 1.9 Hz, 2H), 8.02 (d, J=8.8 Hz, 2H), 7.90-7.85 (m, 1H), 7.66-7.59 (m, 1H), 7.58-7.53 (m, 1H), 7.47 (s, 1H), 7.42-7.36 (m, 1H), 7.19 (s, 2H), 3.72-3.63 (m, 2H), 3.45-3.37 (m, 2H), 3.18-3.04 (m, 4H), 2.92-2.84 (m, 1H), 2.20-2.08 (m, 2H), 2.08-1.97 (m, 2H), 1.31-1.13 (m, 4H); ESI MS m/z 546 [C$_{31}$H$_{29}$Cl$_2$N$_3$O$_2$+H]$^+$; HPLC 97.3% (AUC), t$_R$=11.04 min.

Example 799

{6-(3-Chloro-5-fluoro-4-hydroxyphenyl)-4-[3-(2-(pyrrolidin-1-yl)ethyl)phenylamino]quinolin-3-yl}(cyclopropyl)methanone

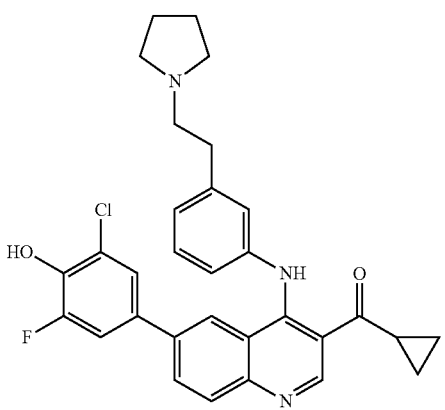

Following general procedure A-1, {6-bromo-4-[3-(2-(pyrrolidin-1-yl)ethyl)phenylamino]quinolin-3-yl}(cyclopropyl)methanone (56 mg, 0.120 mmol) was reacted with 2-chloro-6-fluoro-4-(4,4,5,5-tetramethyl-1,3,2-dioxaborolan-2-yl)phenol (49 mg, 0.180 mmol) to afford the desired product (20 mg, 32%) as a yellow solid: $^1$H NMR (500 MHz, CD$_3$OD+TFA-d) δ 9.45 (s, 1H), 8.22 (dd, J=8.8, 1.9 Hz, 1H), 8.02 (d, J=8.8 Hz, 1H), 7.91 (s, 1H), 7.65-7.58 (m, 1H), 7.54 (d, J=7.8, 1H), 7.46 (s, 1H), 7.38 (d, J=7.8 Hz, 1H), 7.12 (dd, 11.5, 2.3 Hz, 1H), 6.95 (s, 1H), 3.72-3.64 (m, 2H), 3.45-3.36 (m, 2H), 3.17-3.05 (m, 4H), 2.92-2.83 (m, 1H), 2.20-2.09 (m, 2H), 2.08-1.99 (m, 2H), 1.31-1.16 (m, 4H); ESI MS m/z 530 [C$_{31}$H$_{29}$ClFN$_3$O$_2$+H]$^+$; HPLC>99% (AUC), t$_R$=10.82 min.

Example 801

1-{6-(3,5-Dichloro-4-hydroxyphenyl)-4-[3-(2-(pyrrolidin-1-yl)ethyl)phenylamino]quinolin-3-yl}ethanone

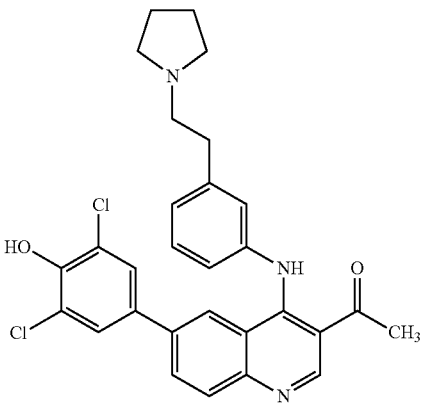 [SMILES: CC(=O)c1cnc2ccc(-c3cc(Cl)c(O)c(Cl)c3)cc2c1Nc1cccc(CCN2CCCC2)c1]

Following general procedure F, {6-bromo-4-[3-(2-(pyrrolidin-1-yl)ethyl)phenylamino]quinolin-3-yl}ethanone (53 mg, 0.120 mmol) was reacted with 2,6-dichloro-4-(4,4,5,5-tetramethyl-1,3,2-dioxaborolan-2-yl)phenol (52 mg, 0.180 mmol) to afford the desired product (31 mg, 50%) as a yellow solid: $^1$H NMR (300 MHz, CD$_3$OD+TFA-d) δ 9.31 (s, 1H), 8.21 (dd; J=8.8, 2.0 Hz, 1H), 8.00 (d, J=8.8 Hz, 1H), 7.73 (s, 1H), 7.69-7.58 (m, 2H), 7.53 (s, 1H), 7.44-7.38 (m, 1H), 7.10 (s, 2H), 3.72-3.63 (m, 2H), 3.46-3.39 (m, 2H), 3.25-3.14 (m, 2H), 3.14-3.04 (m, 2H), 2.82 (s, 3H), 2.19-2.08 (m, 2H), 2.08-1.97 (m, 2H); ESI MS m/z 520[C$_{29}$H$_{27}$Cl$_2$N$_3$O$_2$+H]$^+$; HPLC 97.5% (AUC), t$_R$=10.62 min.

Example 944

1-{6-(3,5-Dichloro-4-hydroxyphenyl)-4-[trans-4-((dimethylamino)methyl)cyclohexylamino]quinolin-3-yl}ethanone hydrochloride

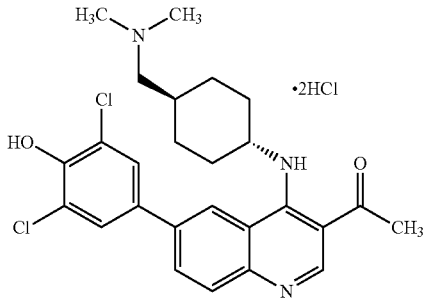 [SMILES: CC(=O)c1cnc2ccc(-c3cc(Cl)c(O)c(Cl)c3)cc2c1N[C@H]1CC[C@H](CN(C)C)CC1]

To a suspension of 1-{6-(3,5-dichloro-4-hydroxyphenyl)-4-[trans-4-((dimethylamino)methyl)cyclohexylamino]quinolin-3-yl}ethanone (200 mg, 0.410 mmol) in methanol (20 mL) was added 1M HCl in water (1.03 mL, 1.03 mmol). The resultant solution was concentrated to an approximate volume of 5 mL. The precipitate was washed with acetonitrile to obtain the desired product as the hydrochloride salt (200 mg) as a yellow solid: $^1$H NMR (500 MHz, CD$_3$OD) δ 9.05 (s, 1H), 8.43 (d, J=1.9 Hz, 1H), 8.18 (dd, J=8.7, 1.9 Hz, 1H), 7.96 (d, J=8.7 Hz, 1H), 7.70 (s, 2H), 4.46-4.38 (m, 1H), 3.07 (d, J=6.6 Hz, 2H), 2.92 (s, 6H), 2.73 (s, 3H), 2.44 (d, J=12.2 Hz, 2H), 2.08-1.98 (m, 3H), 1.82-1.70 (m, 2H), 1.40-1.28 (m, 2H); ESI MS m/z 486 [C$_{26}$H$_{29}$Cl$_2$N$_3$O$_2$+H]$^+$; HPLC>99% (AUC), $t_R$=9.94 min.

Example 585

Cyclopropyl{6-(3,5-dichloro-4-hydroxyphenyl)-4-[trans-4-(pyrrolidin-1-ylmethyl)cyclohexylamino]quinolin-3-yl}methanone hydrochloride

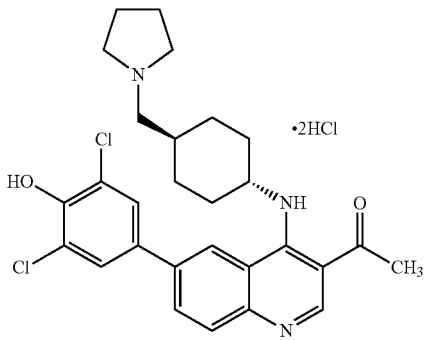 [SMILES: CC(=O)c1cnc2ccc(-c3cc(Cl)c(O)c(Cl)c3)cc2c1N[C@H]1CC[C@H](CN2CCCC2)CC1]

To a suspension of cyclopropyl{6-(3,5-dichloro-4-hydroxyphenyl)-4-[trans-4-(pyrrolidin-1-ylmethyl)cyclohexylamino]quinolin-3-yl}methanone (3.69 g, 6.85 mmol) in methanol (70 mL) was added 1M HCl in water (17 mL, 17 mmol) at 0° C. The resultant solution was concentrated to an approximate volume of 30 mL. The precipitate was washed with acetonitrile to obtain the desired product as the hydrochloride salt (3.58 g) as a yellow solid: $^1$H NMR (500 MHz, CD$_3$OD) δ 9.34 (s, 1H), 8.49 (s, 1H), 8.27 (dd, J=8.8, 1.8 Hz, 1H), 7.99 (d, J=8.8 Hz, 1H), 7.74 (s, 2H), 4.51-4.47 (m, 1H), 3.73-3.69 (m, 2H), 3.18-3.09 (m, 4H), 2.84 (br s, 1H), 2.44-2.40 (br s, 2H), 2.19-1.97 (m, 7H), 1.84-1.71 (m, 2H), 1.36-1.18 (m, 6H); ESI MS m/z 538 [C$_{30}$H$_{33}$Cl$_2$N$_3$O$_2$+H]$^+$; HPLC>99% (AUC), $t_R$=10.65 min.

Example 829

Cyclopropyl{6-(3,5-dichloro-4-hydroxyphenyl)-4-[3-(2-(4-methylpiperazin-1-yl)ethyl)phenylamino]quinolin-3-yl}methanone

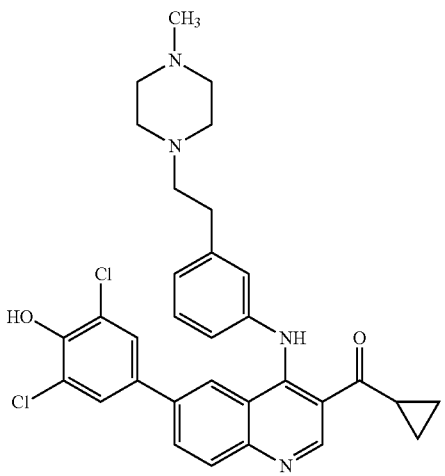 [SMILES: CN1CCN(CCc2cccc(Nc3c(C(=O)C4CC4)cnc4ccc(-c5cc(Cl)c(O)c(Cl)c5)cc34)c2)CC1]

Following general procedure F, {6-bromo-4-[3-(2-(4-methylpiperazin-1-yl)ethyl)phenylamino]quinolin-3-yl}(cyclopropyl)methanone (56 mg, 0.110 mmol) was reacted with 2,6-dichloro-4-(4,4,5,5-tetramethyl-1,3,2-dioxaborolan-2-yl)phenol (48 mg, 0.165 mmol) to afford the desired product (47 mg, 74%) as a yellow solid: $^1$H NMR (500 MHz, CD$_3$OD) δ 9.25 (s, 1H), 7.89 (s, 2H), 7.69 (s, 1H), 7.41 (t, J=7.7 Hz, 1H), 7.24 (d, J=7.7 Hz, 1H), 7.13-6.94 (m, 4H), 2.97-2.84 (m, 1H), 2.82-2.72 (m, 2H), 2.66-2.51 (m, 10H), 2.43 (s, 3H), 1.32-1.06 (m, 4H). ESI MS m/z 575 [C$_{32}$H$_{32}$C$_{12}$N$_4$O$_2$+H]$^+$; HPLC 95.1% (AUC), $t_R$=10.37 min.

Example 881

Cyclopropyl{6-(3,5-dichloro-4-hydroxyphenyl)-4-[5-(2-(pyrrolidin-1-yl)ethyl)pyridin-3-ylamino]quinolin-3-yl}methanone

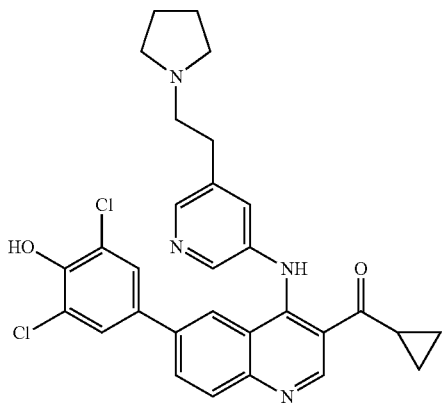

Following general procedure A-1, {6-bromo-4-[5-(2-(pyrrolidin-1-yl)ethyl)pyridin-3-ylamino]quinolin-3-yl}(cyclopropyl)methanone (54 mg, 0.116 mmol) was reacted with 2,6-dichloro-4-(4,4,5,5-tetramethyl-1,3,2-dioxaborolan-2-yl)phenol (50 mg, 0.174 mmol) to afford the desired product (29 mg, 46%) as a yellow solid: $^1$H NMR (500 MHz, CD$_3$OD+ TFA-d) δ 9.36 (s, 1H), 8.64 (dd, J=16.9, 2.1 Hz, 2H), 8.32 (dd, J=8.8, 2.0 Hz, 1H), 8.17 (d, J=2.0 Hz, 1H), 8.11 (d, J=8.8 Hz, 1H), 7.99 (t, J=2.0 Hz, 1H), 7.43 (s, 2H), 3.74-3.70 (m, 2H), 3.50-3.43 (m, 2H), 3.24-3.17 (m, 2H), 3.16-3.12 (m, 2H), 2.79-2.76 (m, 1H), 2.19-2.15 (m, 2H), 2.07-2.03 (m, 2H), 1.18-1.07 (m, 4H); ESI MS m/z 547 [C$_{30}$H$_{28}$Cl$_2$N$_4$O$_2$+H]$^+$; HPLC>99% (AUC), $t_R$=9.93 min.

Example 614

Cyclopropyl(6-(3,5-dichloro-4-hydroxyphenyl)-4-(4-(2-(dimethylamino)ethyl)phenylamino)quinolin-3-yl)methanone dihydrochloride

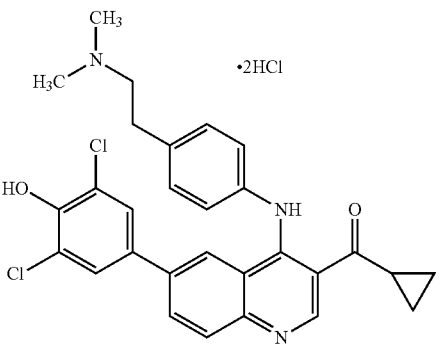 [SMILES: CN(C)CCc1ccc(Nc2c(C(=O)C3CC3)cnc3ccc(-c4cc(Cl)c(O)c(Cl)c4)cc23)cc1]

Following general procedure D, (6-bromo-4-(4-(2-(dimethylamino)ethyl)phenylamino)quinolin-3-yl)(cyclopropyl)methanone (7.3 g, 16.7 mmol) was reacted with 2,6-dichloro-4-(4,4,5,5-tetramethyl-1,3,2-dioxaborolan-2-yl)phenol (5.6 g, 20 mol) to obtain the desired product which was dissolved methanol and treated with excess 1 N aq. HCl. During removal of the methanol via rotary evaporation a precipitate appeared which was filtered to obtain the desired product (5.6 g, 64% over 2 steps) as a yellow solid: $^1$H NMR (300 MHz, MeOD) δ 9.46 (s, 1H), 8.21 (dd, J=8.8, 1.9 Hz, 1H), 8.01 (d, J=8.8 Hz, 1H), 7.89 (s, 1H), 7.57 (d, J=9 Hz, 2H), 7.46 (d, J=9 Hz, 2H), 7.23 (s, 2H), 3.40 (m, 2H), 3.22 (m, 2H), 2.98 (s, 7H), 2.90 (t, J=4.8 Hz, 1H), 1.22 (m, 4H); ESI MS m/z 520 $[C_{29}H_{27}Cl_2N_3O_2+H]^+$; HPLC 99.1% (AUC), $t_R$=10.54 min.

Example 543

1-(6-(3-chloro-4-hydroxy-5-methoxyphenyl)-4-(1R, 4R)-4-(methylamino)cyclohexylamino)quinolin-3-yl)ethanone dihydrochloride

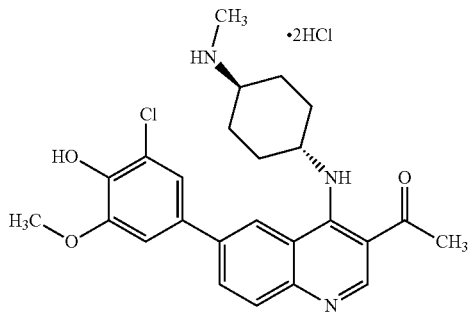 [SMILES: CN[C@H]1CC[C@H](Nc2c(C(C)=O)cnc3ccc(-c4cc(Cl)c(O)c(OC)c4)cc23)CC1]

To a solution of tert-butyl(1r,4r)-4-(3-acetyl-6-(3-chloro-4-hydroxy-5-methoxyphenyl)quinolin-4-ylamino)cyclohexyl (methyl)carbamate (100 mg, 0.180 mmol) in dichloromethane (5 mL) was added HCl (2 mL, 2 M in diethylether) and the mixture was stirred for 16 h at room temperature. The resulting precipitate was filtered, washed with dichloromethane (10 mL), and dried under vacuum to obtain the desired product (40 mg, 42%) as a yellow solid: NMR (500 MHz, MeOD) δ 9.12 (s, 1H), 8.47 (s, 1H), 8.31 (dd, J=8.7, 1.8 Hz, 1H), 8.00 (d, J=8.7 Hz, 1H), 7.33 (s, 1H), 7.27 (s, 1H), 4.56 (s, 1H), 4.00 (s, 3H), 3.26 (t, J=12.6 Hz, 1H), 2.75 (s, 3H), 2.73 (s, 3H), 2.54 (d, J=12.6 Hz, 2H), 2.35 (d, J=11.7 Hz, 2H), 1.86 (q, J=12.6 Hz, 2H), 1.63 (q, J=12.6 Hz, 2H); ESI MS m/z 454, $[C_{25}H_{28}ClN_3O_3+H]^+$; HPLC 97.6% (AUC), $t_R$=9.49 min.

Example 588

(6-(3-chloro-5-fluoro-4-hydroxyphenyl)-4-((trans-4-(pyrrolidin-1-ylmethyl)cyclohexyl)amino)quinolin-3-yl)(cyclopropyl)methanone dihydrochloride

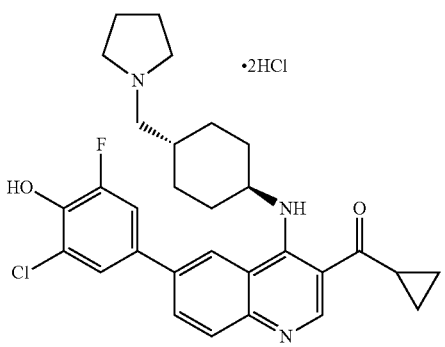 [SMILES: O=C(c1cnc2ccc(-c3cc(F)c(O)c(Cl)c3)cc2c1N[C@H]1CC[C@H](CN2CCCC2)CC1)C1CC1]

To a suspension of (6-bromo-4-((trans-4-(pyrrolidin-1-ylmethyl)cyclohexyl)amino) quinoline-3-yl)(cyclopropyl)methanone (60 mg, 0.13 mmol), 2-chloro-6-fluoro-4-(4,4,5,5-tetramethyl-1,3,2-dioxaborolan-2-yl)phenol (54 mg, 0.20 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). The reaction mixture was degassed with nitrogen and heated at 80° C. for 2 h. The reaction mixture was cooled to room temperature, diluted with a satd. aq. NaHCO$_3$ (20 mL) and extracted with ethyl acetate. The combined organic layers were dried over anhydrous sodium sulfate, concentrated and purified by preparative HPLC (C18 silica, 10-90% acetonitrile/water with 0.05% TFA). The desired fractions were combined and concentrated and the residue was dissolved in methanol (4 mL) and HCl (1.25 M in methanol, 1.5 mL, 1.9 mmol). The mixture was concentrated to obtain the desired product (42.9 mg, 55%) as an off-white solid. $^1$H NMR (500 MHz, MeOD) δ 9.35 (br s, 1H), 8.47 (br s, 1H), 8.27 (dd, J=8.8, 1.8 Hz, 1H), 7.98 (d, J=8.8 Hz, 1H), 7.60 (br s, 1H), 7.53 (d, J=11.1 Hz, 1H), 4.51 (br s, 1H), 3.74-3.66 (m, 2H), 3.18-3.07 (m, 4H), 2.85 (br s, 1H), 2.44 (br s, 2H), 2.24-1.96 (m, 5H), 1.83-1.71 (m, 2H), 1.36-1.18 (m, 6H). ESI MS m/z 522 $[C_{30}H_{33}ClFN_3O_2+H]^+$; HPLC 98.9% (AUC), $t_R$=10.35 min.

Example 742

1-(6-(3-chloro-5-fluoro-4-hydroxyphenyl)-4-((trans-4-(2-(dimethylamino)ethyl)cyclohexyl)amino)quinolin-3-yl)ethanone dihydrochloride

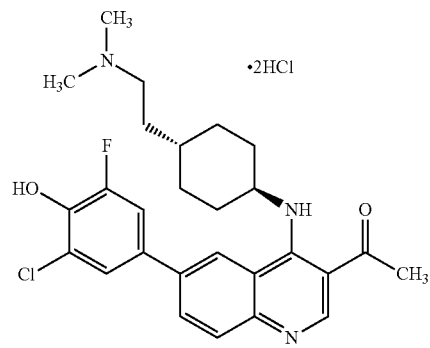 [SMILES: CC(=O)c1cnc2ccc(-c3cc(F)c(O)c(Cl)c3)cc2c1N[C@H]1CC[C@H](CCN(C)C)CC1]

To a suspension of 1-(6-bromo-4-((trans-4-(2-(dimethylamino)ethyl)cyclohexyl)amino)quinolin-3-yl)ethanone (63 mg, 0.15 mmol), 2-chloro-6-fluoro-4-(4,4,5,5-tetramethyl-1,3,2-dioxaborolan-2-yl)phenol (61 mg, 0.22 mmol) and Pd(dppf)Cl$_2$ (11 mg, 0.015 mmol) in dioxane (4 mL) was added Cs$_2$CO$_3$ (1.0 M in H$_2$O, 0.4 mL, 0.4 mmol). The reaction mixture was degassed with nitrogen and heated at 80° C. for 2 h. The reaction mixture was cooled to room temperature, diluted with a satd. aq. NaHCO$_3$ (20 mL) and extracted with ethyl acetate. The combined organic layers were dried over anhydrous sodium sulfate, concentrated and purified by preparative HPLC (C18 silica, 10-90% acetonitrile/water with a mixture of CHCl$_3$/isopropanol (3:1). The desired fractions were concentrated and dissolved in methanol and resultant

Example 777

(6-(3-chloro-5-fluoro-4-hydroxyphenyl)-4-((6-((2-(dimethylamino)ethyl)amino)pyridin-3-yl)amino)quinolin-3-yl)(cyclopropyl)methanone trihydrochloride

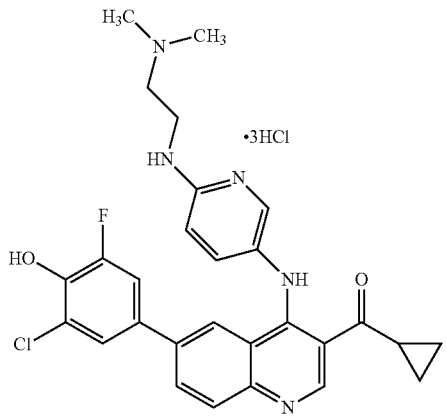 [SMILES: CN(C)CCNc1ccc(Nc2c(C(=O)C3CC3)cnc3ccc(-c4cc(F)c(O)c(Cl)c4)cc23)cn1]

To a suspension of (6-bromo-4-((6-((2-(dimethylamino)ethyl)amino)pyridin-3-yl)amino)quinolin-3-yl)(cyclopropyl)methanone (91 mg, 0.20 mmol), 2-chloro-6-fluoro-4-(4,4,5,5-tetramethyl-1,3,2-dioxaborolan-2-yl)phenol (82 mg, 0.30 mmol) and Pd(dppf)Cl$_2$ (14.6 mg, 0.02 mmol) in dioxane (6 mL) was added Cs$_2$CO$_3$ (1.0 M in H$_2$O, 0.6 mL, 0.6 mmol). The reaction mixture was degassed with nitrogen and heated at 80° C. for 2 h. The solution was cooled to room temperature, diluted with a satd. aq. NaHCO$_3$ solution and extracted with CHCl$_3$/isopropanol (3:1). The combined organic layers were dried over anhydrous sodium sulfate, concentrated and purified by preparative HPLC (C18 silica, 10-90% acetonitrile/water with 0.05% TFA). The desired fractions were combined and concentrated. The residue was dissolved in methanol (4 mL) and HCl (1.25 M in methanol, 1.5 mL, 1.9 mmol) and the mixture was concentrated to give the desired product (97.7 mg, 78%) as an off-white solid. $^1$H NMR (500 MHz, MeOD) δ 9.38 (s, 1H), 8.32-8.17 (m, 3H), 8.04 (d, J=8.8 Hz, 1H), 7.73 (d, J=9.0 Hz, 1H), 7.31-7.23 (m, 2H), 7.01 (d, J=9.2 Hz, 1H), 3.87 (t, J=6.1 Hz, 2H), 3.44 (t, J=6.1 Hz, 2H), 2.98 (s, 6H), 2.89-2.80 (m, 1H), 1.24-1.18 (m, 4H). ESI MS m/z 520 [C$_{28}$H$_{27}$ClFN$_5$O$_2$+H]$^+$; HPLC 97.9% (AUC), t$_R$=9.99 min.

Example 748 cyclopropyl(6-(3,5-dichloro-4-hydroxyphenyl)-4-((6-((2-(dimethylamino)ethyl)amino)pyridin-3-yl)amino)quinolin-3-yl)methanone trihydrochloride

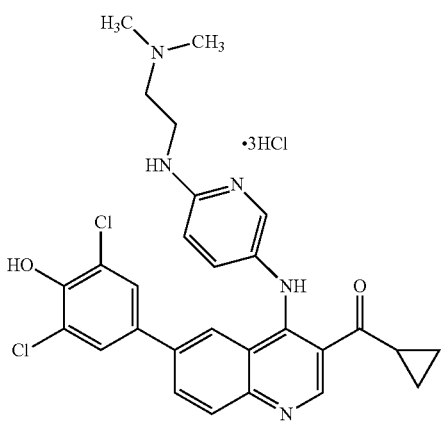 [SMILES: CN(C)CCNc1ccc(Nc2c(C(=O)C3CC3)cnc3ccc(-c4cc(Cl)c(O)c(Cl)c4)cc23)cn1]

To a suspension of (6-bromo-4-((6-((2-(dimethylamino)ethyl)amino)pyridin-3-yl)amino)quinolin-3-yl)(cyclopropyl)methanone (91 mg, 0.20 mmol), 2,6-dichloro-4-(4,4,5,5-tetramethyl-1,3,2-dioxaborolan-2-yl)phenol (87 mg, 0.30 mmol) and Pd(dppf)Cl$_2$ (14.6 mg, 0.02 mmol) in dioxane (6 mL) was added Cs$_2$CO$_3$ (1.0 M in H$_2$O, 0.6 mL, 0.6 mmol). The reaction mixture was degassed with nitrogen and heated at 80° C. for 2 h. The reaction mixture was cooled to room temperature, diluted with a satd. aq. NaHCO$_3$ (20 mL) and extracted with CHCl$_3$/isopropanol (3:1). The combined organic layers were dried over anhydrous sodium sulfate, concentrated and purified by preparative HPLC (C18 silica, 10-90% acetonitrile/water with a mixture of CHCl$_3$/isopropanol (3:1). The desired fractions were concentrated and dissolved in methanol (4 mL) and HCl (1.25 M in methanol, 1.5 mL, 1.9 mmol). The resulting solution was concentrated to give the desired product (95.6 mg, 74%) as an off-white solid. NMR (500 MHz, MeOD) δ 9.38 (s, 1H), 8.33-8.23 (m, 2H), 8.19 (d, J=2.5 Hz, 1H), 8.05 (d, J=8.8 Hz, 1H), 7.77 (dd, J=9.2, 2.6 Hz, 1H), 7.45 (s, 2H), 7.06 (d, J=9.2 Hz, 1H), 3.88 (t, J=6.1 Hz, 2H), 3.45 (t, J=6.1 Hz, 2H), 2.98 (s, 6H), 2.88-2.79 (m, 1H), 1.24-1.18 (m, 4H). ESI MS m/z 536 [C$_{28}$H$_{27}$Cl$_2$N$_5$O$_2$+H]$^+$; HPLC 98.4% (AUC), t$_R$=10.24 min.

Example 508

(4-(4-(aminomethyl)phenylamino)-6-(3,5-dichloro-4-hydroxyphenyl)quinolin-3-yl)(cyclopropyl)methanone hydrochloride

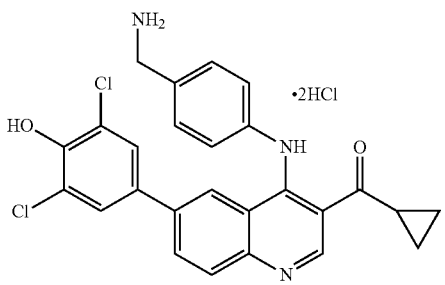 [SMILES: NCc1ccc(Nc2c(C(=O)C3CC3)cnc3ccc(-c4cc(Cl)c(O)c(Cl)c4)cc23)cc1]

--- residue was dissolved in methanol (4 mL) and HCl (1.25 M in methanol, 1.5 mL, 1.9 mmol) was added. The resulting solution was concentrated to give the desired product (55.9 mg, 67%) as an off-white solid NMR (500 MHz, MeOD) δ 9.10 (s, 1H), 8.50 (s, 1H), 8.27 (dd, J=8.7, 1.7 Hz, 1H), 7.97 (d, J=8.7 Hz, 1H), 7.59 (s, 1H), 7.52 (dd, J=11.4, 2.3 Hz, 1H), 4.54-4.50 (m, 1H), 3.25-3.17 (m, 2H), 2.90 (s, 6H), 2.73 (s, 3H), 2.42 (d, J=12.2 Hz, 2H), 2.04 (d, J=12.9 Hz, 2H), 1.80-1.68 (m, 4H), 1.59 (br s, 1H), 1.39-1.27 (m, 2H). ESI MS m/z 484 [C$_{27}$H$_{31}$ClFN$_3$O$_2$+H]$^+$; HPLC>99% (AUC), t$_R$=10.01 min.

Following general procedure F, tert-butyl 4-(6-bromo-3-(cyclopropanecarbonyl)quinolin-4-ylamino)benzylcarbamate (20 mg, 0.04 mmol) was reacted with 2,6-dichloro-4-(4,4,5,5-tetramethyl-1,3,2-dioxaborolan-2-yl)phenol (17 mg, 0.06 mmol) to obtain the boc-intermediate, which was deprotected using general procedure A-2. The desired fractions from the preparative HPLC were combined and concentrated. The residue was dissolved in methanol and HCl (2 mL, 1.25 M in methanol) and concentrated to obtain the desired product (15 mg, 68% over two steps) as a yellow solid: $^1$H NMR (500 MHz, MeOD) δ 9.43 (s, 1H), 8.24 (dd, J=8.8, 1.9 Hz, 1H), 8.04 (d, J=8.8 Hz, 1H), 7.99 (s, 1H), 7.70 (d, J=8.2 Hz, 2H), 7.55 (d, J=8.2 Hz, 2H), 7.25 (s, 2H), 4.28 (s, 2H), 2.91-2.82 (m, 1H), 1.25-1.14 (m, 4H); ESI MS m/z 478 $[C_{26}H_{21}Cl_2N_3O_2+H]^+$; HPLC 98.7% (AUC), $t_R$=10.00 min.

Example 505

(4-(4-(aminomethyl)phenylamino)-6-(3-chloro-5-fluoro-4-hydroxyphenyl)quinolin-3-yl)(cyclopropyl)methanone hydrochloride

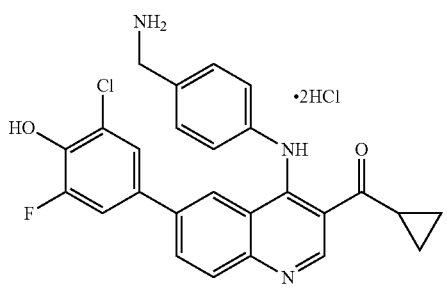

Following general procedure F, tert-butyl 4-(6-bromo-3-(cyclopropanecarbonyl)quinolin-4-ylamino)benzylcarbamate (20 mg, 0.04 mmol) was reacted with 2-chloro-6-fluoro-4-(4,4,5,5-tetramethyl-1,3,2-dioxaborolan-2-yl)phenol (16 mg, 0.06 mmol) to obtain the Boc-intermediate, which was deprotected using general procedure A-2. The desired fractions from the preparative HPLC were combined and concentrated. The residue was dissolved in methanol and HCl (2 mL, 1.25 M in methanol) and concentrated to obtain the desired product (17 mg, 81% over two steps) as a yellow solid: $^1$H NMR (500 MHz, MeOD) δ 9.43 (s, 1H), 8.24 (dd, J=8.8, 2.0 Hz, 1H), 8.04 (d, J=8.8 Hz, 1H), 8.00 (s, 1H), 7.70 (d, J=8.3 Hz, 2H), 7.55 (d, J=8.3 Hz, 2H), 7.13 (dd, J=11.5, 2.3 Hz, 1H), 7.03 (s, 1H), 4.27 (s, 2H), 2.91-2.82 (m, 1H), 1.25-1.14 (m, 4H); ESI MS m/z 462 $[C_{26}H_{21}ClFN_3O_2+H]^+$; HPLC>99% (AUC), $t_R$=9.77 min.

Example 798 cyclopropyl(6-(3,5-dichloro-4-hydroxyphenyl)-4-(3-(2-(pyrrolidin-1-yl)ethyl)phenylamino)quinolin-3-yl)methanone hydrochloride

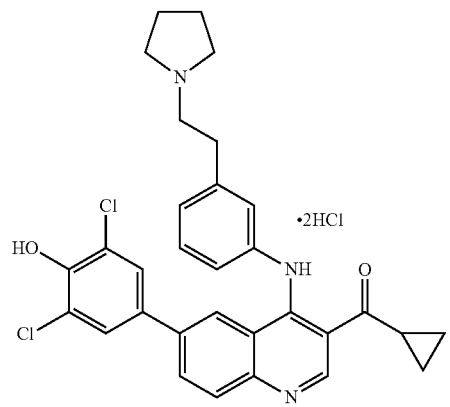 [SMILES: O=C(c1cnc2ccc(-c3cc(Cl)c(O)c(Cl)c3)cc2c1Nc1cccc(CCN2CCCC2)c1)C1CC1]

Following general procedure F, (6-bromo-4-(3-(2-(pyrrolidin-1-yl)ethyl)phenylamino)quinolin-3-yl)(cyclopropyl)methanone (41 mg, 0.088 mmol) was reacted with 2,6-dichloro-4-(4,4,5,5-tetramethyl-1,3,2-dioxaborolan-2-yl)phenol (38 mg, 0.13 mmol) and the desired compound was dissolved in methanol (4 mL) and HCl (2 mL, 1.25 M in methanol). The mixture was concentrated to obtain the desired product (47 mg, 86% over two steps) as a yellow solid: $^1$H NMR (500 MHz, CD$_3$OD) δ 9.45 (s, 1H), 8.22 (dd, J=8.8, 1.9 Hz, 1H), 8.02 (d, J=8.8 Hz, 1H), 7.88 (s, 1H), 7.65-7.58 (m, 1H), 7.57-7.54 (m, 1H), 7.48 (s, 1H), 7.41-7.31 (m, 1H), 7.20 (s, 2H), 3.69-3.65 (m, 2H), 3.45-3.38 (m, 2H), 3.19-3.12 (m, 2H), 3.11-3.07 (m, 2H), 2.93-2.86 (m, 1H), 2.15-2.11 (s, 2H), 2.05-2.01 (s, 2H), 1.24-1.16 (m, 4H); ESI MS m/z 546 $[C_{31}H_{29}Cl_2N_3O_2+H]^+$; HPLC 97.8% (AUC), $t_R$=10.83 min.

Example 800

(6-(3-chloro-5-fluoro-4-hydroxyphenyl)-4-(3-(2-(pyrrolidin-1-yl)ethyl)phenylamino)quinolin-3-yl)(cyclopropyl)methanone hydrochloride

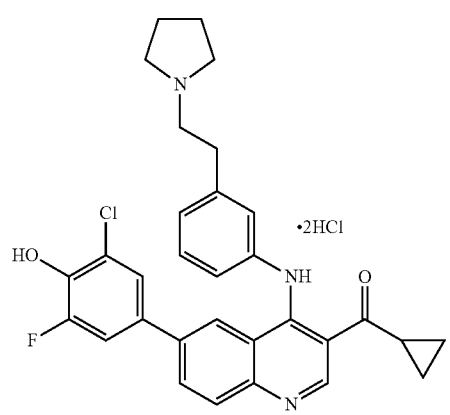

Following general procedure F, (6-bromo-4-(3-(2-(pyrrolidin-1-yl)ethyl)phenylamino)quinolin-3-yl)(cyclopropyl)methanone (45 mg, 0.097 mmol) was reacted with 2-chloro-6-fluoro-4-(4,4,5,5-tetramethyl-1,3,2-dioxaborolan-2-yl)phenol (40 mg, 0.15 mmol) to obtain the desired product which was dissolved in methanol and HCl (2 mL, 1.25 M in methanol). The mixture was concentrated to obtain the desired product (46 mg, 79% over two steps) as a yellow solid: $^1$H NMR (500 MHz, CD$_3$OD) δ 9.44 (s, 1H), 8.23 (dd, J=8.8, 1.9 Hz, 1H), 8.02 (d, J=8.8 Hz, 1H), 7.92 (s, 1H), 7.65-7.57 (m, 1H), 7.56-7.47 (m, 2H), 7.41-7.35 (m, 1H), 7.16-7.10 (m, 1H), 6.97 (s, 1H), 3.71-3.65 (m, 2H), 3.46-3.39 (m, 2H), 3.19-3.06 (m, 4H), 2.91-2.87 (m, 1H), 2.19-2.09 (m, 2H), 2.06-2.00 (m, 2H), 1.26-1.15 (m, 4H); ESI MS m/z 530 [C$_{31}$H$_{29}$ClFN$_3$O$_2$+H]$^+$; HPLC 98.4% (AUC), t$_R$=10.81 min.

Example 494

(4-(4-(aminomethyl)cyclohexylamino)-6-(3-chloro-4-hydroxy-5-methoxyphenyl)quinolin-3-yl)(cyclopropyl)methanone hydrochloride

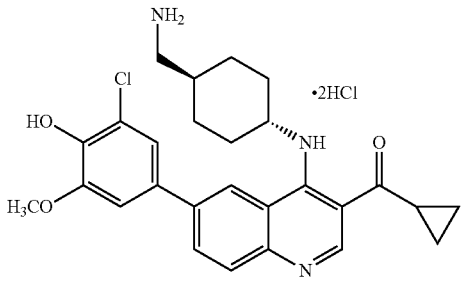 [SMILES: COc1cc(-c2ccc3ncc(C(=O)C4CC4)c(N[C@H]4CC[C@H](CN)CC4)c3c2)cc(Cl)c1O]

Following general procedure F, tert-butyl (4-(6-bromo-3-(cyclopropanecarbonyl)quinolin-4-ylamino)cyclohexyl)methylcarbamate (25 mg, 0.05 mmol) was reacted with 2-chloro-6-methoxy-4-(4,4,5,5-tetramethyl-1,3,2-dioxaborolan-2-yl)phenol (21 mg, 0.08 mmol) to obtain the Boc-intermediate, which was deprotected using general procedure A-2. The desired fractions from the preparative HPLC were combined and concentrated and the residue was dissolved in methanol and HCl (2 mL, 1.25 M in methanol). The mixture was concentrated to obtain desired product (18 mg, 66% over two steps) as a yellow solid: $^1$H NMR (500 MHz, MeOD) δ 9.34 (s, 1H), 8.50 (s, 1H), 8.30 (dd, J=8.7, 1.8 Hz, 1H), 7.98 (d, J=8.7 Hz, 1H), 7.35 (s, 1H), 7.27 (s, 1H), 4.53-4.49 (m, 1H), 4.00 (s, 3H), 2.89-2.81 (m, 3H), 2.46-2.42 (m, 2H), 2.08-2.02 (m, 2H), 1.83-1.68 (m, 3H), 1.35-1.18 (m, 6H).; ESI MS m/z 480 [C$_{27}$H$_{30}$ClN$_3$O$_3$+H]$^+$; HPLC 98.2% (AUC), t$_R$=10.03 min.

Example 1199

1-(1-methylpyrrolidin-3-yl)-1H-pyrazol-4-amine

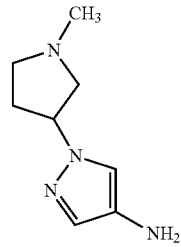

A solution of tert-butyl 3-(4-nitro-1H-pyrazol-1-yl)pyrrolidine-1-carboxylate (1.0 g, 3.5 mmol) in THF and slowly added to a round bottomed flask with LAH (0.54 g, 14 mmol) in THF at 0° C. Upon complete addition the reaction mixture was heated at reflux for 2 h. The reaction mixture was cooled to 0° C. and quenched by the stepwise addition of 0.5 mL ethanol, 0.5 mL water and 1.5 mL of 3 N NaOH. The resulting solids were filtered and the residue was concentrated to obtain the desired amino pyrazole as a dark foam. ESI MS m/z 167 [C$_8$H$_{14}$N$_4$+H]$^+$ Example 1200 tert-butyl (1r,4r)-4-(4-amino-1H-pyrazol-1-yl)cyclohexylcarbamate

BocHN

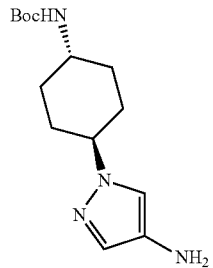 [SMILES: CC(C)(C)OC(=O)N[C@H]1CC[C@H](n2cc(N)cn2)CC1]

To a solution of nitro pyrazole (1.0 g, 8.8 mmol), tert-butyl (1r,4r)-4-hydroxycyclohexyl carbamate (1.9 g, 8.8 mmol) and triphenyl phosphine (2.1 g, 11 mmol) in THF (50 mL) was added DIAD (2.9 g, 11 mmol) and the reaction mixture was stirred for 18 h. The reaction mixture was concentrated and purified by flash chromatography to obtain tert-butyl (1r,4r)-4-(4-nitro-1H-pyrazol-1-yl)cyclohexylcarbamate (1.1 g) as an off-white foam. The foam was dissolved in tertrahydrofuran (0.1 M), degassed with nitrogen and placed in a Parr shaker with Pd/C (10%, 0.1 equiv). The Parr shaker was charged with hydrogen (40 Psi) and the reaction was allowed to proceed at room temperature until complete, as indicated by LCMS analysis. The reaction mixture was filtered over diatomaceous earth and the filtrate was concentrated to obtain the desired amino pyrazole.

Compounds of the invention not particularly described in the Examples above were also be synthesized by similar or analogous methods by referring to the above-mentioned Examples and such.

Next, the pharmacological activities of a representative example, compound (I), will be described using Test Examples.

Examples

Kinase Assay

MELK activity was determined in the presence or absence of compounds using fluorescein isothiocyanate-labeled (FITC-labeled) histone H3 peptide as a substrate. The extent of FITC-labeled histone H3 peptide phosphorylation was measured by immobilized metal ion affinity-based fluorescence polarization (IMAP) technology (Sportsman J R, et al., Assay Drug Dev. Technol. 2: 205-14, 2004) using IMAP FP Progressive Binding System (Molecular Devices Corporation). Test compounds were dissolved in DMSO at 12.5 mM and then serially diluted as the DMSO concentration in the assays to be 1%. The serially diluted compounds, 0.8 ng/micro-L PBK (Carna Biosciences) and 100 nM FITC-labeled histone H3 peptide were reacted in a reaction buffer (20 mM HEPES, 0.01% Tween-20, 0.3 mM $MgCl_2$, 2 mM dithiothreitol, 50 micro-M ATP, pH 7.4) at room temperature for 1 hour. The reaction was stopped by the addition of three fold assay volume of progressive binding solution. Following 0.5 hour incubation at room temperature, fluorescence polarization was measured by Wallac EnVision 2103 multilabel reader (PerkinElmer). IC50 values were calculated by nonlinear four parameter fit using SigmaPlot, version 10.0 (Systat Software, Inc.).

$IC_{50}$ values of the typical compounds of the present invention are shown in following table 2:

TABLE 2

| Example | Compound Name | $IC_{50}$ (μM) (kinase assay) |
|---|---|---|
| 55 | {4-[trans-4-Aminocyclohexylamino]-6-(4-hydroxyphenyl)quinolin-3-yl}(cyclopropyl)methanone | 0.021 |
| 81 | {4-[trans-4-Aminocyclohexylamino]-6-(4-hydroxy-3-methoxyphenyl)quinolin-3-yl}(cyclopropyl)methanone | 0.007 |
| 96 | 5-{4-[trans-4-Aminocyclohexylamino]-3-(cyclopropanecarbonyl)quinolin-6-yl}pyrimidine-2-carbonitrile | 0.0024 |
| 108 | 5-{4-[trans-4-Aminocyclohexylamino]-3-isobutyrylquinolin-6-yl}picolinonitrile | 0.03 |
| 116 | {4-[trans-4-Aminocyclohexylamino]-6-(1H-benzo[d]imidazol-5-yl)quinolin-3-yl}(cyclopropyl)methanone | 0.018 |
| 119 | 5-{4-[trans-4-Aminocyclohexylamino]-3-(cyclopropanecarbonyl)quinolin-6-yl}thiophene-2-carbonitrile | 0.046 |
| 133 | Cyclopropyl[4-{4-[(dimethylamino)methyl]piperidin-1-yl}-6-(4-hydroxy-3-methoxyphenyl)quinolin-3-yl]methanone | 0.0036 |
| 155 | [6-(3-Chloro-4-hydroxy-5-methoxyphenyl)-4-(2,8-diazaspiro[4,5]decan-8-yl)quinolin-3-yl](cyclopropyl)methanone | 0.004 |
| 156 | {4-[trans-4-Aminocyclohexylamino]-6-(3,5-difluoro-4-hydroxyphenyl)quinolin-3-yl}(cyclopropyl)methanone | 0.023 |
| 157(a) | {4-[trans-4-Aminocyclohexylamino]-6-(3,5-dichloro-4-hydroxyphenyl)quinolin-3-yl}(cyclopropyl)methanone | 0.0076 |
| 157(b) | {4-[trans-4-Aminocyclohexylamino]-6-(3,5-dichloro-4-hydroxyphenyl)quinolin-3-yl}(cyclopropyl) methanone dihydrochloride | 0.003 |
| 160 | {4-[trans-4-Aminocyclohexylamino]-6-(2,5-dichloro-4-hydroxyphenyl)quinolin-3-yl}(cyclopropyl)methanone | 0.072 |
| 165 | {4-(cis-4-Aminocyclohexylamino)-6-(4-hydroxy-3-methoxyphenyl)quinolin-3-yl}(cyclopropyl)methanone | 0.0019 |
| 177 | Cyclopropyl[6-(4-hydroxy-3-methoxyphenyl)-4-(1-methylpiperidin-4-ylamino)quinolin-3-yl]methanone | 0.026 |
| 179 | {4-[trans-4-Aminocyclohexylamino]-6-(3-chloro-5-fluoro-4-hydroxyphenyl)quinolin-3-yl}(cyclopropyl)methanone | 0.0065 |
| 180 | [4-(cis-4-Aminocyclohexylamino)-6-(3,5-difluoro-4-hydroxyphenyl)quinolin-3-yl](cyclopropyl)methanone | 0.0026 |
| 181 | Cyclopropyl[6-(3,5-difluoro-4-hydroxyphenyl)-4-{4-[1-(dimethylamino)ethyl]piperidin-1-yl}quinolin-3-yl]methanone | 0.011 |
| 185(a) | {6-(3-Chloro-4-hydroxy-5-methoxyphenyl)-4-[4-(diethylamino)cyclohexylamino]quinolin-3-yl}(cyclopropyl)methanone | 0.0026 |
| 185(b) | {6-(3-Chloro-4-hydroxy-5-methoxyphenyl)-4-[4-(diethylamino)cyclohexylamino]quinolin-3-yl}(cyclopropyl)methanone dihydrochloride | 0.0026 |
| 187 | Cyclopropyl(4-{4-[1-(dimethylamino)ethyl]piperidin-1-yl}-6-(4-hydroxy-3-methoxyphenyl)quinolin-3-yl)methanone | 0.0034 |
| 192 | {6-(3-Chloro-4-hydroxyphenyl)-4-[4-(diethylamino)cyclohexylamino]quinolin-3-yl}(cyclopropyl)methanone | 0.011 |
| 193 | Cyclopropyl{4-[4-(diethylamino)cyclohexylamino]-6-(4-hydroxy-3-methoxyphenyl)quinolin-3-yl}methanone | 0.007 |
| 201 | {6-(3-Chloro-4-hydroxy-5-methoxyphenyl)-4-[(1-methylpiperidin-4-yl)methylamino]quinolin-3-yl}(cyclopropyl)methanone | 0.0034 |
| 205 | 1-{4-[trans-4-Aminocyclohexylamino]-6-(3-chloro-5-fluoro-4-hydroxyphenyl)quinolin-3-yl}-2-methylpropan-1-one | 0.01 |
| 212 | {4-[trans-4-Aminocyclohexylamino]-6-(pyridin-4-yl)quinolin-3-yl}(cyclopropyl)methanone | 0.054 |
| 213 | {4-[trans-4-Aminocyclohexylamino]-6-(1H-pyrazol-4-yl)quinolin-3-yl}(cyclopropyl)methanone | 0.067 |
| 214 | 1-{4-[trans-4-Aminocyclohexylamino]-6-(3,5-difluoro-4-hydroxyphenyl)quinolin-3-yl}-2-methylpropan-1-one | 0.043 |

TABLE 2-continued

| Example | Compound Name | IC$_{50}$ (μM) (kinase assay) |
|---|---|---|
| 215 | {6-(3-Chloro-4-hydroxyphenyl)-4-[2-(piperazin-1-yl)ethylamino]quinolin-3-yl}(cyclopropyl)methanone | 0.017 |
| 219 | 1-{4-[trans-4-Aminocyclohexylamino]-6-(3-chloro-4-hydroxyphenyl)quinolin-3-yl}-2-methylpropan-1-one | 0.023 |
| 225(a) | 1-{4-[trans-4-Aminocyclohexylamino]-6-(3,5-dichloro-4-hydroxyphenyl)quinolin-3-yl}-2-methylpropan-1-one | 0.0025 |
| 225(b) | 1-{4-[trans-4-Aminocyclohexylamino]-6-(3,5-dichloro-4-hydroxyphenyl)quinolin-3-yl}-2-methylpropan-1-one dihydrochloride | 0.0028 |
| 240 | 2-Chloro-4-{4-[4-(diethylamino)cyclohexylamino]-3-(methylsulfonyl)quinolin-6-yl}-6-methoxyphenol dihydrochloride | 0.0053 |
| 243 | [6-(3-Chloro-4-hydroxy-5-methoxyphenyl)-4-(piperidin-4-ylmethylamino)quinolin-3-yl](cyclopropyl)methanone | 0.0044 |
| 245 | 2-Chloro-4-[4-{4-[1-(dimethylamino)ethyl]piperidin-1-yl}-3-(methylsulfonyl)quinolin-6-yl]-6-methoxyphenol | 0.0016 |
| 246 | 2-Chloro-4-[4-{4-[1-(dimethylamino)ethyl]piperidin-1-yl}-3-(methylsulfonyl)quinolin-6-yl]phenol | 0.01 |
| 249 | [6-(3-Chloro-4-hydroxy-5-methoxyphenyl)-4-(1-methylpiperidin-4-ylamino)quinolin-3-yl](cyclopropyl)methanone | 0.0079 |
| 250 | [6-(3-Chloro-4-hydroxy-5-methoxyphenyl)-4-{4-[1-(dimethylamino)ethyl]piperidin-1-yl}quinolin-3-yl](cyclopropyl)methanone | 0.0013 |
| 255 | {6-(3-Chloro-4-hydroxy-5-methoxyphenyl)-4-[trans-4-(dimethylamino)cyclohexylamino]quinolin-3-yl}(cyclopropyl)methanone | 0.0019 |
| 256 | 1-{4-[trans-4-Aminocyclohexylamino]-6-(3,5-dichloro-4-hydroxyphenyl)quinolin-3-yl}ethanone | 0.0041 |
| 258 | 1-{4-[trans-4-Aminocyclohexylamino]-6-(3,5-difluoro-4-hydroxyphenyl)quinolin-3-yl}ethanone | 0.04 |
| 259 | 1-{4-[trans-4-Aminocyclohexylamino]-6-(3-chloro-4-hydroxy-5-methoxyphenyl)quinolin-3-yl}ethanone | 0.0024 |
| 262 | 1-(4-((trans)-4-aminocyclohexylamino)-6-(3-chloro-4-hydroxy-5-methoxyphenyl)quinolin-3-yl)-3-methylbutan-1-one | 0.005 |
| 263 | Cyclopropyl{6-(3,5-dichloro-4-hydroxyphenyl)-4-[trans-4-(dimethylamino)cyclohexylamino]quinolin-3-yl}methanone | 0.0017 |
| 266 | Cyclopropyl(4-((trans)-4-(dimethylamino)cyclohexylamino)-6-(4-hydroxy-3-methoxyphenyl)quinolin-3-yl)methanone | 0.0016 |
| 267 | 1-{4-[trans-4-Aminocyclohexylamino]-6-(3,5-dichloro-4-hydroxyphenyl)quinolin-3-yl}-3-methylbutan-1-one dihydrochloride | 0.0022 |
| 269 | [6-(3-Chloro-5-fluoro-4-hydroxyphenyl)-4-{4-[1-(dimethylamino)ethyl]piperidin-1-yl}quinolin-3-yl](cyclopropyl)methanone | 0.0037 |
| 270 | {6-(3-Chloro-5-fluoro-4-hydroxyphenyl)-4-[(1-methylpiperidin-4-yl)methylamino]quinolin-3-yl}(cyclopropyl)methanone | 0.021 |
| 276 | [6-(3-Chloro-4-hydroxy-5-methoxyphenyl)-4-{4-[(dimethylamino)methyl]piperidin-1-yl}quinolin-3-yl](cyclopropyl)methanone | 0.0008 |
| 279 | [6-(3-Chloro-4-hydroxyphenyl)-4-{4-[(dimethylamino)methyl]piperidin-1-yl}quinolin-3-yl](cyclopropyl)methanone | 0.0046 |
| 280 | {6-(3-Chloro-4-hydroxy-5-methoxyphenyl)-4-[4-(pyrrolidin-1-ylmethyl)piperidin-1-yl]quinolin-3-yl}(cyclopropyl)methanone | 0.0017 |
| 283 | {6-(3-Chloro-5-fluoro-4-hydroxyphenyl)-4-[4-(pyrrolidin-1-ylmethyl)piperidin-1-yl]quinolin-3-yl}(cyclopropyl)methanone | 0.0029 |
| 284 | {4-[trans-4-aminocyclohexylamino]-6-(3-chloro-4-hydroxy-5-methoxyphenyl)-7-fluoroquinolin-3-yl}(cyclopropyl)methanone | 0.013 |
| 294 | Cyclopropyl{6-(3,5-difluoro-4-hydroxyphenyl)-4-[trans-4-(dimethylamino)cyclohexylamino]-7-fluoroquinolin-3-yl}methanone | 0.042 |
| 295 | {6-(3-Chloro-5-fluoro-4-hydroxyphenyl)-4-[trans-4-(dimethylamino)cyclohexylamino]-7-fluoroquinolin-3-yl}(cyclopropyl)methanone | 0.027 |
| 303 | 1-{6-(3-Chloro-4-hydroxy-5-methoxyphenyl)-4-[4-(diethylamino)cyclohexylamino]quinolin-3-yl}ethanone | 0.0061 |
| 305 | 1-[6-(3-chloro-4-hydroxy-5-methoxyphenyl)-4-{4-[(dimethylamino)methyl]piperidin-1-yl}quinolin-3-yl]ethanone | 0.0022 |

TABLE 2-continued

| Example | Compound Name | IC$_{50}$ (μM) (kinase assay) |
|---|---|---|
| 307 | Cyclopropyl{6-(3-fluoro-4-hydroxy-5-methoxyphenyl)-4-[4-(pyrrolidin-1-ylmethyl)piperidin-1-yl]quinolin-3-yl}methanone | 0.0041 |
| 309 | {6-(3-Chloro-4-hydroxy-5-methoxyphenyl)-4-[(3-amino)adamantylamino]quinolin-3-yl}(cyclopropyl)methanone | 0.0087 |
| 311 | {6-(3-Chloro-4-hydroxy-5-methoxyphenyl)-4-[cis-4-(diethylamino)cyclohexylamino]quinolin-3-yl}(cyclopropyl)methanone | 0.0032 |
| 313 | Cyclopropyl{6-[4-hydroxy-3-(trifluoromethoxy)phenyl]-4-[4-(pyrrolidin-1-ylmethyl]piperidin-1-yl}quinolin-3-yl)methanone | 0.012 |
| 314 | {6-(3-Chloro-4-hydroxy-5-methoxyphenyl)-4-[trans-4-(diethylamino)cyclohexylamino]quinolin-3-yl}(cyclopropyl)methanone | 0.0031 |
| 315 | [6-(3-Chloro-4-hydroxy-5-methoxyphenyl)-4-{[trans-4-(dimethylamino)cyclohexyl]methylamino}quinolin-3-yl](cyclopropyl)methanone | 0.0043 |
| 316 | [6-(3-Chloro-4-hydroxy-5-methoxyphenyl)-4-{trans-4-[(dimethylamino)methyl]cyclohexylamino}quinolin-3-yl](cyclopropyl)methanone | 0.011 |
| 318 | 1-{6-(3-Chloro-4-hydroxyphenyl)-4-[4-(pyrrolidin-1-ylmethyl)piperidin-1-yl]quinolin-3-yl}-2-methylpropan-1-one | 0.02 |
| 321 | 1-{6-(3-Chloro-4-hydroxy-5-methoxyphenyl)-4-[4-(pyrrolidin-1-ylmethyl)piperidin-1-yl]quinolin-3-yl}ethanone | 0.0027 |
| 323 | 1-{6-(3-Chloro-5-fluoro-4-hydroxyphenyl)-4-[4-(pyrrolidin-1-ylmethyl)piperidin-1-yl]quinolin-3-yl}-2-methylpropan-1-one | 0.013 |
| 325 | Cyclopropyl[6-(3,5-dichloro-4-hydroxyphenyl)-4-{[trans-4-(dimethylamino)cyclohexyl]methylamino}quinolin-3-yl]methanone | 0.011 |
| 327 | [6-(3-Chloro-5-fluoro-4-hydroxyphenyl)-4-{[trans-4-(dimethylamino)cyclohexyl]methylamino}quinolin-3-yl](cyclopropyl)methanone | 0.0055 |
| 332 | {6-(3-Chloro-4-hydroxyphenyl)-4-[4-(morpholinomethyl)piperidin-1-yl]quinolin-3-yl}(cyclopropyl)methanone | 0.035 |
| 334 | {6-(3-Chloro-4-hydroxy-5-methoxyphenyl)-4-[4-(morpholinomethyl)piperidin-1-yl]quinolin-3-yl}(cyclopropyl)methanone | 0.0081 |
| 335 | 1-{6-(3-Chloro-4-hydroxyphenyl)-4-[4-(diethylamino)cyclohexylamino]quinolin-3-yl}ethanone | 0.021 |
| 336 | 1-{6-(3-Chloro-5-fluoro-4-hydroxyphenyl)-4-[4-(pyrrolidin-1-ylmethyl)piperidin-1-yl]quinolin-3-yl}ethanone | 0.0069 |
| 339 | [-(3-Chloro-4-hydroxy-5-methoxyphenyl)-4-{4-[(dimethylamino)methyl]phenylamino}quinolin-3-yl]cyclopropyl)methanone | 0.004 |
| 342 | {6-(3-Chloro-4-hydroxyphenyl)-4-[trans-4-(pyrrolidin-1-yl)cyclohexylamino]quinolin-3-yl}(cyclopropyl)methanone | 0.0046 |
| 343 | {6-(3-Chloro-4-hydroxy-5-methoxyphenyl)-4-[trans-4-(pyrrolidin-1-yl)cyclohexylamino]quinolin-3-yl}(cyclopropyl)methanone | 0.0021 |
| 345 | Cyclopropyl[6-(3,5-dichloro-4-hydroxyphenyl)-4-{4-[(dimethylamino)methyl]phenylamino}quinolin-3-yl]methanone | 0.0032 |
| 347 | [6-(3-Chloro-5-fluoro-4-hydroxyphenyl)-4-{4-[(dimethylamino)methyl]piperidin-1-yl}quinolin-3-yl](cyclopropyl)methanone | 0.0024 |
| 348 | 1-{6-(3-Chloro-4-hydroxy-5-methoxyphenyl)-4-[trans-4-(dimethylamino)cyclohexylamino]quinolin-3-yl}-3-methylbutan-1-one | 0.0043 |
| 349 | {6-(3-Chloro-5-fluoro-4-hydroxyphenyl)-4-[4-(4-methylpiperazin-1-yl)piperidin-1-yl]quinolin-3-yl}(cyclopropyl)methanone | 0.0046 |
| 350 | {6-(3-Chloro-4-hydroxyphenyl)-4-[4-(4-methylpiperazin-1-yl)piperidin-1-yl]quinolin-3-yl}(cyclopropyl)methanone | 0.005 |
| 351 | {6-(3-Chloro-4-hydroxy-5-methoxyphenyl)-4-[4-(4-methylpiperazin-1-yl)piperidin-1-yl]quinolin-3-yl}(cyclopropyl)methanone | 0.0022 |
| 353 | Cyclopropyl[4-{4-[(dimethylamino)methyl]piperidin-1-yl}-6-(3-ethoxy-4-hydroxyphenyl)quinolin-3-yl]methanone | 0.0017 |

TABLE 2-continued

| Example | Compound Name | IC$_{50}$ (μM) (kinase assay) |
|---|---|---|
| 356 | [6-(3-Chloro-4-hydroxy-5-methoxyphenyl)-4-{4-[(dimethylamino)methyl]phenyl}quinolin-3-yl](cyclopropyl)methanone | 0.0042 |
| 384 | (6-(3-chloro-5-fluoro-4-hydroxyphenyl)-4-(4-((dimethylamino)methyl)piperidin-1-yl)quinolin-3-yl)(cyclopentyl)methanone | 0.0046 |
| 385 | (6-(3-chloro-4-hydroxyphenyl)-4-(4-(diethylamino)cyclohexylamino)quinolin-3-yl)(cyclopentyl)methanone | 0.019 |
| 386 | (6-(3-chloro-5-fluoro-4-hydroxyphenyl)-4-(4-(diethylamino)cyclohexylamino)quinolin-3-yl)(cyclopentyl)methanone | 0.0092 |
| 387 | (6-(3-chloro-4-hydroxyphenyl)-4-(4-((dimethylamino)methyl)phenylamino)quinolin-3-yl)(cyclopentyl)methanone | 0.089 |
| 388 | (6-(3-chloro-5-fluoro-4-hydroxyphenyl)-4-(4-((dimethylamino)methyl)phenylamino)quinolin-3-yl)(cyclopentyl)methanone | 0.014 |
| 389 | (6-(3-chloro-4-hydroxyphenyl)-4-(4-((dimethylamino)methyl)piperidin-1-yl)quinolin-3-yl)(cyclopentyl)methanone | 0.031 |
| 390 | 2-(6-(3-chloro-5-fluoro-4-hydroxyphenyl)-3-(cyclopropanecarbonyl)quinolin-4-ylamino)-1-(4-methylpiperazin-1-yl)ethanone | 0.025 |
| 391 | 1-(6-(3-chloro-4-hydroxy-5-methoxyphenyl)-4-(4-((dimethylamino)methyl)phenylamino)quinolin-3-yl)ethanone | 0.0037 |
| 392 | 1-(6-(3-chloro-4-hydroxy-5-methoxyphenyl)-4-(1R,4R)-4-((dimethylamino)methyl)cyclohexylamino)quinolin-3-yl)ethanone | 0.0034 |
| 393 | 2-(6-chloro-4-hydroxyphenyl)-3-(cyclopropanecarbonyl)quinolin-4-ylamino)-1-(4-methylpiperazin-1-yl)ethanone | 0.095 |
| 394 | (6-(3-chloro-4-hydroxy-5-methoxyphenyl)-4-(4-(2-(pyrrolidin-1-yl)ethyl)piperazin-1-yl)quinolin-3-yl)(cyclopropyl)methanone | 0.0018 |
| 395 | 2-(6-(3-chloro-4-hydroxy-5-methoxyphenyl)-3-(cyclopropanecarbonyl)quinolin-4-ylamino)-1-(4-methylpiperazin-1-yl)ethanone | 1 |
| 396 | (6-(3-chloro-5-fluoro-4-hydroxyphenyl)-4-(4-(pyrrolidin-1-ylmethyl)phenylamino)quinolin-3-yl)(cyclopropyl)methanone | 0.0088 |
| 397 | cyclopropyl(6-(3,5-dichloro-4-hydroxyphenyl)-4-(4-((4-methylpiperazin-1-yl)methyl)phenylamino)quinolin-3-yl)methanone | 0.0076 |
| 398 | (6-(3-chloro-4-hydroxy-5-methoxyphenyl)-4-(4-((4-methylpiperazin-1-yl)methyl)phenylamino)quinolin-3-yl)(cyclopropyl)methanone | 0.0084 |
| 399 | 2-chloro-4-(4-(4-((dimethylamino)methyl)phenylamino)-3-(methylsulfonyl)quinolin-6-yl)-6-fluorophenol | 0.016 |
| 400 | 2,6-dichloro-4-(4-(4-((dimethylamino)methyl)phenylamino)-3-(methylsulfonyl)quinolin-6-yl)phenol | 0.0034 |
| 401 | 2,6-dichloro-4-(4-(4-((dimethylamino)methyl)phenylamino)-3-(methylsulfonyl)quinolin-6-yl)phenol hydrochloride | 0.0055 |
| 402 | (6-(3-chloro-5-fluoro-4-hydroxyphenyl)-4-(4-(2-(pyrrolidin-1-yl)ethyl)piperazin-1-yl)quinolin-3-yl)(cyclopropyl)methanone | 0.0058 |
| 403 | (6-(3-chloro-4-hydroxyphenyl)-4-(4-(2-(pyrrolidin-1-yl)ethyl)piperazin-1-yl)quinolin-3-yl)(cyclopropyl)methanone | 0.011 |
| 404 | (6-(3-chloro-4-hydroxy-5-methoxyphenyl)-4-(5-(piperazin-1-yl)pyridin-2-ylamino)quinolin-3-yl)(cyclopropyl)methanone | 0.0038 |
| 405 | cyclopropyl(6-(4-hydroxy-3-methoxyphenyl)-4-(4-((4-methylpiperazin-1-yl)methyl)phenylamino)quinolin-3-yl)methanone | 0.017 |
| 406 | (6-(3-chloro-4-hydroxyphenyl)-4-((4-methylpiperazin-1-yl)methyl)phenylamino)quinolin-3-yl)(cyclopropyl)methanone | 0.019 |
| 407 | 2-chloro-6-fluoro-4-(3-(methylsulfonyl)-4-(4-(pyrrolidin-1-ylmethyl)piperidin-1-yl)quinolin-6-yl)phenol | 0.0051 |
| 408 | 2-chloro-4-(3-(methylsulfonyl)-4-(4-(pyrrolidin-1-ylmethyl)piperidin-1-yl)quinolin-6-yl)phenol | 0.009 |
| 409 | cyclopropyl(6-(3,5-dichloro-4-hydroxyphenyl)-4-(5-(piperazin-1-yl)pyridin-2-ylamino)quinolin-3-yl)methanone | 0.0017 |
| 410 | 2-chloro-4-(4-(4-((dimethylamino)methyl)phenylamino)-3-(methylsulfonyl)quinolin-6-yl)-6-methoxyphenol | 0.0068 |
| 411 | 2-chloro-4-(4-(4-((dimethylamino)methyl)phenylamino)-3-(methylsulfonyl)quinolin-6-yl)phenol | 0.0091 |
| 412 | 2-chloro-6-methoxy-4-(3-(methylsulfonyl)-4-(4-(pyrrolidin-1-ylmethyl)piperidin-1-yl)quinolin-6-yl)phenol | 0.002 |
| 413 | 5-(3-acetyl-4-(4-(pyrrolidin-1-ylmethyl)phenylamino)quinolin-6-yl)pyrimidine-2-carbonitrile | 0.0029 |
| 414 | 5-(3-acetyl-4-(4-((dimethylamino)methyl)phenylamino)quinolin-6-yl)pyrimidine-2-carbonitrile | 0.0022 |
| 415 | 1-(6-(3,5-dichloro-4-hydroxyphenyl)-4-(4-(pyrrolidin-1-ylmethyl)phenylamino)quinolin-3-yl)ethanone | 0.035 |
| 416 | 1-(6-(3,5-dichloro-4-hydroxyphenyl)-4-(4-(pyrrolidin-1-ylmethyl)phenylamino)quinolin-3-yl)ethanone dihydrobromide | 0.0032 |
| 417 | cyclopropyl(6-(3,5-dichloro-4-hydroxyphenyl)-4-(5-((dimethylamino)methyl)pyridin-2-ylamino)quinolin-3-yl)methanone | 0.0099 |
| 418 | 5-(3-acetyl-4-(1R,4R)-4-((dimethylamino)methyl)cyclohexylamino)quinolin-6-yl)pyrimidine-2-carbonitrile | 0.0073 |
| 419 | 1-(6-(3-chloro-4-hydroxy-5-methoxyphenyl)-4-(4-(pyrrolidin-1-ylmethyl)phenylamino)quinolin-3-yl)ethanone | 0.0059 |

TABLE 2-continued

| Example | Compound Name | IC$_{50}$ (μM) (kinase assay) |
|---|---|---|
| 420 | 2,6-dichloro-4-(4-(1R,4R)-4-((dimethylamino)methyl)cyclohexylamino)-3-(methylsulfonyl)quinolin-6-yl)phenol | 0.0023 |
| 421 | 2,6-dichloro-4-(4-(1R,4R)-4-((dimethylamino)methyl)cyclohexylamino)-3-(methylsulfonyl)quinolin-6-yl)phenol | 0.0017 |
| 422 | 2-chloro-4-(4-(1R,4R)-4-((dimethylamino)methyl)cyclohexylamino)-3-(methylsulfonyl)quinolin-6-yl)-6-methoxyphenol | 0.0041 |
| 423 | 2-chloro-4-(4-(1R,4R)-4-((dimethylamino)methyl)cyclohexylamino)-3-(methylsulfonyl)quinolin-6-yl)-6-fluorophenol | 0.0063 |
| 424 | 2-chloro-4-(4-(1R,4R)-4-((dimethylamino)methyl)cyclohexylamino)-3-(methylsulfonyl)quinolin-6-yl)phenol | 0.013 |
| 425 | (6-(3-chloro-5-fluoro-4-hydroxyphenyl)-4-(6-(piperazin-1-yl)pyridin-3-ylamino)quinolin-3-yl)(cyclopropyl)methanone | 0.0027 |
| 426 | 5-(3-(cyclopropanecarbonyl)-4-(1R,4R)-4-((dimethylamino)methyl)cyclohexylamino)quinolin-6-yl)pyrimidine-2-carbonitrile | 0.0025 |
| 427 | (6-(3-chloro-4-hydroxyphenyl)-4-(5-(piperazin-1-yl)pyridin-2-ylamino)quinolin-3-yl)(cyclopropyl)methanone | 0.0062 |
| 428 | 6-(3-chloro-4-hydroxy-5-methoxyphenyl)-4-(4-(pyrrolidin-1-ylmethyl)piperidin-1-yl)quinoline-3-carbonitrile | 0.0037 |
| 429 | (6-(3-chloro-4-hydroxy-5-methoxyphenyl)-4-(5-((dimethylamino)methyl)pyridin-2-ylamino)quinolin-3-yl)(cyclopropyl)methanone | 0.019 |
| 430 | cyclopropyl(6-(3,5-dichloro-4-hydroxyphenyl)-4-(4-methylpiperazin-1-yl)phenyl)quinolin-3-yl)methanone | 0.033 |
| 431 | cyclopropyl(6-(3,5-dichloro-4-hydroxyphenyl)-4-(4-((dimethylamino)methyl)phenyl)quinolin-3-yl)methanone | 0.0039 |
| 432 | 6-(3-chloro-5-fluoro-4-hydroxyphenyl)-4-(4-((dimethylamino)methyl)phenylamino)quinoline-3-carbonitrile | 0.056 |
| 433 | 6-(3-chloro-4-hydroxyphenyl)-4-(4-(pyrrolidin-1-ylmethyl)piperidin-1-yl)quinoline-3-carbonitrile | 0.043 |
| 434 | 6-(3-chloro-5-fluoro-4-hydroxyphenyl)-4-(4-(pyrrolidin-1-ylmethyl)piperidin-1-yl)quinoline-3-carbonitrile | 0.035 |
| 435 | (6-(3-chloro-5-fluoro-4-hydroxyphenyl)-4-(5-((dimethylamino)methyl)pyridin-2-ylamino)quinolin-3-yl)(cyclopropyl)methanone | 0.049 |
| 436 | (6-(3-chloro-4-hydroxy-5-methoxyphenyl)-4-(4-(pyrrolidin-1-ylmethyl)phenyl)quinolin-3-yl)(cyclopropyl)methanone | 0.014 |
| 437 | 1-(4-(6-(3-chloro-4-hydroxy-5-methoxyphenyl)-3-(cyclopropanecarbonyl)quinolin-4-yl)piperazin-1-yl)-2-(dimethylamino)ethanone | 0.0011 |
| 438 | (6-(3-chloro-4-hydroxy-5-methoxyphenyl)-4-(4-(4-methylpiperazin-1-yl)phenyl)quinolin-3-yl)(cyclopropyl)methanone | 0.018 |
| 439 | 5-(3-(cyclopropanecarbonyl)-4-(5-((dimethylamino)methyl)pyridin-2-ylamino)quinolin-6-yl)pyrimidine-2-carbonitrile | 0.058 |
| 440 | 4-(6-(3-chloro-5-fluoro-4-hydroxyphenyl)-3-(cyclopropanecarbonyl)quinolin-4-yl)-1-(2-(pyrrolidin-1-yl)ethyl)piperazin-2-one | 0.0044 |
| 441 | 1-(4-(6-(3-chloro-4-hydroxyphenyl)-3-(cyclopropanecarbonyl)quinolin-4-yl)piperazin-1-yl)-2-(dimethylamino)ethanone | 0.004 |
| 442 | 1-(4-(6-(3-chloro-5-fluoro-4-hydroxyphenyl)-3-(cyclopropanecarbonyl)quinolin-4-yl)piperazin-1-yl)-2-(dimethylamino)ethanone | 0.0035 |
| 443 | (6-(3-chloro-5-fluoro-4-hydroxyphenyl)-4-(5-(1-methylpyrrolidin-2-yl)pyridin-2-ylamino)quinolin-3-yl)(cyclopropyl)methanone | 0.043 |
| 444 | (6-(3-chloro-4-hydroxy-5-methoxyphenyl)-4-(5-(1-methylpyrrolidin-2-yl)pyridin-2-ylamino)quinolin-3-yl)(cyclopropyl)methanone | 0.036 |
| 445 | cyclopropyl(6-(3,5-dichloro-4-hydroxyphenyl)-4-(5-(1-methylpyrrolidin-2-yl)pyridin-2-ylamino)quinolin-3-yl)methanone | 0.022 |
| 446 | 6-(3-chloro-5-fluoro-4-hydroxyphenyl)-4-(1R,4R)-4-(dimethylamino)cyclohexylamino)quinoline-3-carbonitrile | 0.0027 |
| 447 | 6-(3-chloro-4-hydroxy-5-methoxyphenyl)-4-(1R,4R)-4-(dimethylamino)cyclohexylamino)quinoline-3-carbonitrile | 0.0018 |
| 448 | (6-(5-chloro-4-hydroxy-2-methylphenyl)-4-(4-((dimethylamino)methyl)piperidin-1-yl)quinolin-3-yl)(cyclopropyl)methanone | 0.06 |
| 449 | cyclopropyl(4-(4-((dimethylamino)methyl)piperidin-1-yl)-6-(6-hydroxynaphthalen-2-yl)quinolin-3-yl)methanone | 0.014 |
| 450 | cyclopropyl(6-(3,5-dichloro-4-hydroxyphenyl)-4-(6-(2-morpholinoethylamino)pyridin-3-yl)quinolin-3-yl)methanone | 0.018 |
| 451 | 4-(3-(cyclopropanecarbonyl)-6-(3,5-dichloro-4-hydroxyphenyl)quinolin-4-yl)-N-(2-(dimethylamino)ethyl)benzamide | 0.0025 |
| 452 | cyclopropyl(6-(3,5-dichloro-4-hydroxyphenyl)-4-(4-(pyrrolidin-1-ylmethyl)phenyl)quinolin-3-yl)methanone | 0.0026 |
| 453 | cyclopropyl(4-(4-((dimethylamino)methyl)piperidin-1-yl)-6-(1H-indol-5-yl)quinolin-3-yl)methanone | 0.094 |
| 454 | cyclopropyl(4-(4-((dimethylamino)methyl)piperidin-1-yl)-6-(4-hydroxy-3-(trifluoromethyl)phenyl)quinolin-3-yl)methanone | 0.014 |
| 455 | 1-((1S,4S)-5-(6-(3-chloro-5-fluoro-4-hydroxyphenyl)-3-(cyclopropanecarbonyl)quinolin-4-yl)-2,5-diazabicyclo[2.2.1]heptan-2-yl)-2-(dimethylamino)ethanone | 0.069 |

TABLE 2-continued

| Example | Compound Name | IC$_{50}$ (μM) (kinase assay) |
|---|---|---|
| 456 | 1-((1S,4S)-5-(6-(3-chloro-4-hydroxy-5-methoxyphenyl)-3-(cyclopropanecarbonyl)quinolin-4-yl)-2,5-diazabicyclo[2.2.1]heptan-2-yl)-2-(dimethylamino)ethanone | 0.0078 |
| 457 | (6-(3-chloro-5-ethoxy-4-hydroxyphenyl)-4-(4-((dimethylamino)methyl)piperidin-1-yl)quinolin-3-yl)(cyclopropyl)methanone | 0.0024 |
| 458 | cyclopropyl(6-(4-(difluoromethoxy)phenyl)-4-(4-((dimethylamino)methyl)piperidin-1-yl)quinolin-3-yl)methanone | 0.63 |
| 459 | cyclopropyl(6-(3,5-dichloro-4-hydroxyphenyl)-4-(6-(piperazin-1-yl)pyridin-3-yl)quinolin-3-yl)methanone | 0.0091 |
| 460 | (6-(3-chloro-5-fluoro-4-hydroxyphenyl)-4-(4-(morpholinomethyl)phenylamino)quinolin-3-yl)(cyclopropyl)methanone | 0.083 |
| 461 | 5-(3-(cyclopropanecarbonyl)-4-(4-(morpholinomethyl)phenylamino)quinolin-6-yl)pyrimidine-2-carbonitrile | 0.015 |
| 462 | (6-(3-chloro-4-hydroxy-5-methoxyphenyl)-4-(4-(morpholinomethyl)phenylamino)quinolin-3-yl)(cyclopropyl)methanone | 0.066 |
| 463 | cyclopropyl(6-(3,5-dichloro-4-hydroxyphenyl)-4-(4-(morpholinomethyl)phenylamino)quinolin-3-yl)methanone | 0.02 |
| 464 | 1-((1S,4S)-5-(6-(3-chloro-4-hydroxyphenyl)-3-cyclopropanecarbonyl)quinolin-4-yl)-2,5-diazabicyclo[2.2.1]heptan-2-yl)-2-(dimethylamino)ethanone | 0.051 |
| 465 | cyclopropyl(6-(4-(difluoromethyl)phenyl)-4-(4-((dimethylamino)methyl)piperidin-1-yl)quinolin-3-yl)methanone | 0.91 |
| 466 | 2-chloro-4-(4-(4-((dimethylamino)methyl)piperidin-1-yl)-3-(methylsulfinyl)quinolin-6-yl)phenol | 0.016 |
| 467 | 2-chloro-4-(4-(4-((dimethylamino)methyl)piperidin-1-yl)-3-(methylsulfinyl)quinolin-6-yl)-6-fluorophenol | 0.011 |
| 468 | 2-chloro-4-(4-(4-((dimethylamino)methyl)piperidin-1-yl)-3-(methylsulfinyl)quinolin-6-yl)-6-methoxyphenol | 0.0051 |
| 469 | 5-(3-(cyclopropanecarbonyl)-4-(6-(4-methylpiperazin-1-yl)pyridin-3-ylamino)quinolin-6-yl)pyrimidine-2-carbonitrile | 0.0015 |
| 470 | (6-(3-chloro-4-hydroxy-5-methoxyphenyl)-4-(6-(4-methylpiperazin-1-yl)pyridin-3-ylamino)quinolin-3-yl)(cyclopropyl)methanone | 0.015 |
| 471 | (6-(3-chloro-5-fluoro-4-hydroxyphenyl)-4-(6-(4-methylpiperazin-1-yl)pyridin-3-ylamino)quinolin-3-yl)(cyclopropyl)methanone | 0.011 |
| 472 | cyclopropyl(6-(3,5-dichloro-4-hydroxyphenyl)-4-(6-(4-methylpiperazin-1-yl)pyridin-3-ylamino)quinolin-3-yl)methanone | 0.023 |
| 473 | 2,6-dichloro-4-(4-(4-((dimethylamino)methyl)phenylamino)-3-(methylsulfinyl)quinolin-6-yl)phenol | 0.0082 |
| 474 | 5-(3-(cyclopropanecarbonyl)-4-(4-((dimethylamino)methyl)piperidin-1-yl)quinolin-6-yl)indolin-2-one | 0.66 |
| 475 | (6-(3-chloro-4-hydroxy-5-methoxyphenyl)-4-(2-(4-methylpiperazin-1-yl)pyrimidin-5-yl)quinolin-3-yl)(cyclopropyl)methanone | 0.072 |
| 476 | (4-(6-(3-chloro-4-hydroxy-5-methoxyphenyl)-3-(cyclopropanecarbonyl)quinolin-4-yl)phenyl)(4-methylpiperazin-1-yl)methanone | 0.0081 |
| 477 | 1-(4-(3-acetyl-6-(3-chloro-hydroxy-5-methoxyphenyl)quinolin-4-yl)piperazin-1-yl)-2-(dimethylamino)ethanone | 0.0016 |
| 478 | cyclopropyl(6-(3,5-dichloro-4-hydroxyphenyl)-4-(3-((4-methylpiperazin-1-yl)methyl)phenyl)quinolin-3-yl)methanone | 0.0078 |
| 479 | cyclopropyl(6-(3,5-dichloro-4-hydroxyphenyl)-4-(2-(4-methylpiperazin-1-yl)pyrimidin-5-yl)quinolin-3-yl)methanone | 0.04 |
| 480 | 1-(4-(1R,4R)-4-aminocyclohexylamino)-6-(5-hydroxy-1H-indol-2-yl)quinolin-3-yl)-2-methylpropan-1-one | 0.054 |
| 481 | methyl 4-(3-(cyclopropanecarbonyl)-4-(4-((dimethylamino)methyl)piperidin-1-yl)quinolin-6-yl)benzoate | 1.4 |
| 482 | cyclopropyl(6-(3,5-dichloro-4-hydroxyphenyl)-4-(4-((4-methylpiperazin-1-yl)methyl)phenyl)quinolin-3-yl)methanone | 0.0061 |
| 483 | 1-(6-(3-chloro-4-hydroxy-5-methoxyphenyl)-4-(6-(4-methylpiperazin-1-yl)pyridin-3-ylamino)quinolin-3-yl)ethanone | 0.016 |
| 484 | 1-(4-(3-acetyl-6-(3-chloro-5-fluoro-4-hydroxyphenyl)quinolin-4-yl)piperazin-1-yl)-2-(dimethylamino)ethanone | 0.0069 |
| 485 | cyclopropyl(6-(3,5-dichloro-4-hydroxyphenyl)-4-(4-(2-(pyrrolidin-1-yl)ethoxy)phenyl)quinolin-3-yl)methanone | 0.0056 |
| 486 | 1-(4-((1R,4R)-4-aminocyclohexylamino)-6-(3-chloro-5-ethoxy-4-hydroxyphenyl)quinolin-3-yl)ethanone | 0.0021 |
| 487 | 1-(6-(3-chloro-5-fluoro-4-hydroxyphenyl)-4-(6-(4-methylpiperazin-1-yl)pyridin-3-ylamino)quinolin-3-yl)ethanone | 0.01 |
| 488 | 1-(6-(3-chloro-5-fluoro-4-hydroxyphenyl)-4-(6-(4-methylpiperazin-1-yl)pyridin-3-ylamino)quinolin-3-yl)ethanone | 0.0041 |
| 489 | (4-(4-((1H-imidazol-1-yl)methyl)phenylamino)-6-(3-chloro-5-fluoro-4-hydroxyphenyl)quinolin-3-yl)(cyclopropyl)methanone | 0.019 |
| 490 | (4-(4-((1H-imidazol-1-yl)methyl)phenylamino)-6-(3-chloro-4-hydroxy-5-methoxyphenyl)quinolin-3-yl)(cyclopropyl)methanone | 0.014 |

TABLE 2-continued

| Example | Compound Name | IC$_{50}$ (μM) (kinase assay) |
|---|---|---|
| 491 | 4-(4-(1R,4R)-4-aminocyclohexylamino)-3-(methylsulfinyl)quinolin-6-yl)-2,6-dichlorophenol | 0.0075 |
| 492 | 4-(3-(cyclopropanecarbonyl)-4-(4-((dimethylamino)methyl)piperidin-1-yl)quinolin-6-yl)benzoic acid | 1.4 |
| 493 | (4-(1R,4R)-4-(aminomethyl)cyclohexylamino)-6-(3-chloro-4-hydroxy-5-methoxyphenyl)quinolin-3-yl)(cyclopropyl)methanone | 0.003 |
| 494 | (4-(1R,4R)-4-(aminomethyl)cyclohexylamino)-6-(3-chloro-4-hydroxy-5-methoxyphenyl)quinolin-3-yl)(cyclopropyl)methanone hydrochloride | 0.0016 |
| 495 | (4-(1R,4R)-4-(aminomethyl)cyclohexylamino)-6-(3,5-dichloro-4-hydroxyphenyl)quinolin-3-yl)(cyclopropyl)methanone | 0.0029 |
| 496 | (6-(3-chloro-5-fluoro-4-hydroxyphenyl)-4-(2-(piperazin-1-yl)pyrimidin-5-ylamino)quinolin-3-yl)(cyclopropyl)methanone | 0.0048 |
| 497 | cyclopropyl(6-(3,5-dichloro-4-hydroxyphenyl)-4-(2-(piperazin-1-yl)pyrimidin-5-ylamino)quinolin-3-yl)methanone | 0.0021 |
| 498 | 4-(4-(1R,4R)-4-aminocyclohexylamino)-3-(methylsulfinyl)quinolin-6-yl)-2-chloro-6-fluorophenol | 0.046 |
| 499 | 4-(4-(1R,4R)-4-aminocyclohexylamino)-3-(methylsulfinyl)quinolin-6-yl)-2-chlorophenol | 0.036 |
| 500 | 4-(4-(1R,4R)-4-aminocyclohexylamino)-3-(methylsulfinyl)quinolin-6-yl)-2-chloro-6-methoxyphenol | 0.0049 |
| 501 | (4-(1R,4R)-4-(aminomethyl)cyclohexylamino)-6-(3-chloro-5-fluoro-4-hydroxyphenyl)quinolin-3-yl)(cyclopropyl)methanone | 0.046 |
| 502 | 1-(4-(1R,4R)-4-aminocyclohexylamino)-6-(3-chloro-4-hydroxy-5-methoxyphenyl)quinolin-3-yl)-2-methylpropan-1-one | 0.007 |
| 503 | (6-(3-chloro-4-hydroxy-5-methoxyphenyl)-4-(2-(piperazin-1-yl)pyrimidin-5-ylamino)quinolin-3-yl)(cyclopropyl)methanone | 0.0047 |
| 504 | (4-(4-(aminomethyl)phenylamino)-6-(3-chloro-5-fluoro-4-hydroxyphenyl)quinolin-3-yl)(cyclopropyl)methanone | 0.0089 |
| 505 | (4-(4-(aminomethyl)phenylamino)-6-(3-chloro-5-fluoro-4-hydroxyphenyl)quinolin-3-yl)(cyclopropyl)methanone hydrochloride | 0.0027 |
| 506 | (4-(4-(aminomethyl)phenylamino)-6-(3-chloro-4-hydroxy-5-methoxyphenyl)quinolin-3-yl)(cyclopropyl)methanone | 0.0032 |
| 507 | (4-(4-(aminomethyl)phenylamino)-6-(3,5-dichloro-4-hydroxyphenyl)quinolin-3-yl)(cyclopropyl)methanone | 0.0038 |
| 508 | (4-(4-(aminomethyl)phenylamino)-6-(3,5-dichloro-4-hydroxyphenyl)quinolin-3-yl)(cyclopropyl)methanone hydrochloride | 0.0017 |
| 509 | 5-(4-(4-(aminomethyl)phenylamino)-3-(cyclopropanecarbonyl)quinolin-6-yl)pyrimidine-2-carbonitrile | 0.0013 |
| 510 | cyclopropyl(6-(3,5-dichloro-4-hydroxyphenyl)-4-(1R,4R)-4-(methylamino)cyclohexylamino)quinolin-3-yl)methanone | 0.0019 |
| 511 | cyclopropyl(6-(3,5-dichloro-4-hydroxyphenyl)-4-(1-(piperidin-4-yl)-1H-pyrazol-4-ylamino)quinolin-3-yl)methanone | 0.017 |
| 512 | (6-(3-chloro-4-hydroxy-5-methoxyphenyl)-4-(1-(piperidin-4-yl)-1H-pyrazol-4-ylamino)quinolin-3-yl)(cyclopropyl)methanone | 0.0022 |
| 513 | (6-(3-chloro-4-hydroxy-5-methoxyphenyl)-4-((1s,4s)-4-((dimethylamino)methyl)cyclohexylamino)quinolin-3-yl)(cyclopropyl)methanone | 0.002 |
| 514 | (6-(3-chloro-5-fluoro-4-hydroxyphenyl)-4-((1s,4s)-4-((dimethylamino)methyl)cyclohexylamino)quinolin-3-yl)(cyclopropyl)methanone | 0.0028 |
| 515 | (4-((1s,4s)-4-(aminomethyl)cyclohexylamino)-6-(3-chloro-5-fluoro-4-hydroxyphenyl)quinolin-3-yl)(cyclopropyl)methanone | 0.0034 |
| 516 | (6-(3-chloro-4-hydroxy-5-methoxyphenyl)-4-(1,2,3,6-tetrahydropyridin-4-yl)quinolin-3-yl)(cyclopropyl)methanone | 0.0044 |
| 517 | (6-(3-chloro-4-hydroxy-5-methoxyphenyl)-4-((1R,4R)-4-(methylamino)cyclohexyl)amino)quinolin-3-yl)(cyclopropyl)methanone | 0.0014 |
| 518 | 2-(((((1s,4s)-4-(6-(3-chloro-4-hydroxy-5-methoxyphenyl)-3-(cyclopropanecarbonyl)quinolin-4-ylamino)cyclohexyl)methyl)(methyl)amino)acetonitrile | 0.013 |
| 519 | (6-(3-chloro-4-hydroxyphenyl)-4-(1-(piperidin-4-yl)-1H-pyrazol-4-ylamino)quinolin-3-yl)(cyclopropyl)methanone | 0.003 |
| 520 | (6-(3-chloro-5-fluoro-4-hydroxyphenyl)-4-(1-(piperidin-4-yl)-1H-pyrazol-4-ylamino)quinolin-3-yl)(cyclopropyl)methanone | 0.0016 |
| 521 | 1-(4-(6-(3-chloro-4-hydroxy-5-methoxyphenyl)-3-(cyclopropanecarbonyl)quinolin-4-yl)-5,6-dihydropyridin-1(2H)-yl)-2-(dimethylamino)ethanone | 0.0024 |
| 522 | 5-(3-(cyclopropanecarbonyl)-4-(1R,4R)-4-(methylamino)cyclohexylamino)quinolin-6-yl)pyrimidine-2-carbonitrile | 0.0014 |
| 523 | (6-(3-chloro-5-fluoro-4-hydroxyphenyl)-4-(1R,4R)-4-(methylamino)cyclohexylamino)quinolin-3-yl)(cyclopropyl)methanone | 0.0024 |
| 524 | 2-(((((1s,4s)-4-(6-(3-chloro-5-fluoro-4-hydroxyphenyl)-3-(cyclopropanecarbonyl)quinolin-4-ylamino)cyclohexyl)methyl)(methyl)amino)acetonitrile | 0.01 |
| 525 | (6-(3-chloro-5-fluoro-4-hydroxyphenyl)-4-(5-(piperazin-1-yl)pyridin-2-ylamino)quinolin-3-yl)(cyclopropyl)methanone | 0.0048 |

TABLE 2-continued

| Example | Compound Name | IC$_{50}$ (μM) (kinase assay) |
|---|---|---|
| 526 | cyclopropyl(6-(3,5-dichloro-4-hydroxyphenyl)-4-((1s,4s)-4-((dimethylamino)methyl)cyclohexylamino)quinolin-3-yl)methanone | 0.0021 |
| 527 | 1-(4-(1R,4R)-4-aminocyclohexylamino)-6-(3-chloro-5-fluoro-4-hydroxyphenyl)quinolin-3-yl)ethanone | 0.015 |
| 528 | (6-(3-chloro-4-hydroxy-5-methoxyphenyl)-4-(5-(piperazin-1-yl)pyridin-2-ylamino)quinolin-3-yl)(cyclopropyl)methanone hydrochloride | 0.0044 |
| 529 | 1-(4-(1R,4R)-4-aminocyclohexylamino)-6-(3-chloro-4-hydroxy-5-methoxyphenyl)quinolin-3-yl)butan-1-one | 0.0038 |
| 530 | 1-(6-(3,5-dichloro-4-hydroxyphenyl)-4-(4-((dimethylamino)methyl)phenylamino)quinolin-3-yl)butan-1-one | 0.0045 |
| 531 | 1-(6-(3,5-dichloro-4-hydroxyphenyl)-4-(4-((dimethylamino)methyl)phenylamino)quinolin-3-yl)butan-1-one dihydrochloride | 0.0052 |
| 532 | 1-(4-(1R,4R)-4-aminocyclohexylamino)-6-(3-chloro-5-fluoro-4-hydroxyphenyl)quinolin-3-yl)butan-1-one | 0.017 |
| 533 | (6-(3-chloro-4-hydroxy-5-methoxyphenyl)-4-(4-methylpiperazin-1-yl)quinolin-3-yl)(cyclopropyl)methanone | 0.0088 |
| 534 | (6-(3-chloro-5-fluoro-4-hydroxyphenyl)-4-(4-methylpiperazin-1-yl)quinolin-3-yl)(cyclopropyl)methanone | 0.025 |
| 535 | 1-(4-(1R,4R)-4-aminocyclohexylamino)-6-(3,5-dichloro-4-hydroxyphenyl)quinolin-3-yl)butan-1-one | 0.0024 |
| 536 | (6-(3-chloro-4-hydroxy-5-methoxyphenyl)-4-(1H-pyrazol-4-yl)quinolin-3-yl)(cyclopropyl)methanone | 0.11 |
| 537 | 1-(6-(3-chloro-5-fluoro-4-hydroxyphenyl)-4-(4-((dimethylamino)methyl)phenylamino)quinolin-3-yl)butan-1-one | 0.016 |
| 538 | 1-(6-(3-chloro-4-hydroxy-5-methoxyphenyl)-4-(4-((dimethylamino)methyl)phenylamino)quinolin-3-yl)butan-1-one | 0.02 |
| 539 | 5-(3-butyryl-4-(4-((dimethylamino)methyl)phenylamino)quinolin-6-yl)pyrimidine-2-carbonitrile | 0.0038 |
| 540 | (6-(3-chloro-4-hydroxy-5-methoxyphenyl)-4-(4-((dimethylamino)methyl)phenylamino)-7-fluoroquinolin-3-yl)(cyclopropyl)methanone | 0.064 |
| 541 | (6-(3-chloro-5-fluoro-4-hydroxyphenyl)-4-(4-((dimethylamino)methyl)phenylamino)-7-fluoroquinolin-3-yl)(cyclopropyl)methanone | 0.077 |
| 542 | 1-(6-(3-chloro-4-hydroxy-5-methoxyphenyl)-4-(1R,4R)-4-(methylamino)cyclohexylamino)quinolin-3-yl)ethanone | 0.0043 |
| 543 | 1-(6-(3-chloro-4-hydroxy-5-methoxyphenyl)-4-(1R,4R)-4-(methylamino)cyclohexylamino)quinolin-3-yl)ethanone dihydrochloride | 0.0018 |
| 544 | 4-(3-acetyl-6-(3-chloro-4-hydroxy-5-methoxyphenyl)quinolin-4-ylamino)benzamide | 0.018 |
| 545 | 4-(3-acetyl-6-(3,5-dichloro-4-hydroxyphenyl)quinolin-4-ylamino)benzamide | 0.019 |
| 546 | 4-(6-(3-chloro-4-hydroxy-5-methoxyphenyl)-3-(cyclopropanecarbonyl)quinolin-4-ylamino)benzamide | 0.04 |
| 547 | cyclopropyl(6-(3,5-dichloro-4-hydroxyphenyl)-4-(4-((dimethylamino)methyl)phenylamino)-7-fluoroquinolin-3-yl)methanone | 0.02 |
| 548 | (4-(6-(4-aminopiperidin-1-yl)pyridin-3-ylamino)-6-(3,5-dichloro-4-hydroxyphenyl)quinolin-3-yl)(cyclopropyl)methanone | 0.002 |
| 549 | (4-(6-(4-aminopiperidin-1-yl)pyridin-3-ylamino)-6-(3,5-dichloro-4-hydroxyphenyl)quinolin-3-yl)(cyclopropyl)methanone hydrochloride | 0.0027 |
| 550 | (4-(6-(4-aminopiperidin-1-yl)pyridin-3-ylamino)-6-(3-chloro-4-hydroxy-5-methoxyphenyl)quinolin-3-yl)(cyclopropyl)methanone | 0.0057 |
| 551 | (6-(3-chloro-4-hydroxy-5-methoxyphenyl)-4-(4-((dimethylamino)methyl)phenylamino)-8-fluoroquinolin-3-yl)(cyclopropyl)methanone | 1.1 |
| 552 | cyclopropyl(6-(3,5-dichloro-4-hydroxyphenyl)-4-(4-((dimethylamino)methyl)phenylamino)-8-fluoroquinolin-3-yl)methanone | 0.58 |
| 553 | (4-(2-(4-aminopiperidin-1-yl)pyrimidin-5-ylamino)-6-(3-chloro-4-hydroxy-5-methoxyphenyl)quinolin-3-yl)(cyclopropyl)methanone | 0.0056 |
| 554 | (4-(6-(3-aminopiperidin-1-yl)pyridin-3-ylamino)-6-(3-chloro-4-hydroxy-5-methoxyphenyl)quinolin-3-yl)(cyclopropyl)methanone | 0.0031 |
| 555 | (4-(1R,4R)-4-aminocyclohexylamino)-6-(3-chloro-5-fluoro-4-hydroxyphenyl)-8-fluoroquinolin-3-yl)(cyclopropyl)methanone | 5.1 |
| 556 | (4-(6-(3-aminopiperidin-1-yl)pyridin-3-ylamino)-6-(3,5-dichloro-4-hydroxyphenyl)quinolin-3-yl)(cyclopropyl)methanone | 0.0044 |
| 557 | (4-(6-(4-aminopiperidin-1-yl)pyridin-3-ylamino)-6-(3-chloro-5-fluoro-4-hydroxyphenyl)quinolin-3-yl)(cyclopropyl)methanone | 0.0056 |
| 558 | 1-(6-(3,5-dichloro-4-hydroxyphenyl)-4-(1R,4R)-4-(methylamino)cyclohexylamino)quinolin-3-yl)ethanone | 0.0025 |
| 559 | cyclopropyl(6-(3,5-dichloro-4-hydroxyphenyl)-7-fluoro-4-(6-(piperazin-1-yl)pyridin-3-ylamino)quinolin-3-yl)methanone | 0.01 |
| 560 | 1-(6-(3-chloro-5-fluoro-4-hydroxyphenyl)-4-(1R,4R)-4-(methylamino)cyclohexylamino)quinolin-3-yl)ethanone | 0.11 |
| 561 | (4-(6-(3-aminopiperidin-1-yl)pyridin-3-ylamino)-6-(3-chloro-5-fluoro-4-hydroxyphenyl)quinolin-3-yl)(cyclopropyl)methanone | 0.0027 |

TABLE 2-continued

| Example | Compound Name | IC$_{50}$ (μM) (kinase assay) |
|---|---|---|
| 562 | (4-(6-(3-aminopiperidin-1-yl)pyridin-3-ylamino)-6-(3-chloro-5-fluoro-4-hydroxyphenyl)quinolin-3-yl)(cyclopropyl)methanone hydrochloride | 0.0017 |
| 563 | (6-(3-chloro-5-fluoro-4-hydroxyphenyl)-4-(4-((dimethylamino)methyl)phenylamino)-8-fluoroquinolin-3-yl)(cyclopropyl)methanone | 1.8 |
| 564 | (4-(1R,4R)-4-aminocyclohexylamino)-6-(3-chloro-4-hydroxy-5-methoxyphenyl)-8-fluoroquinolin-3-yl)(cyclopropyl)methanone | 0.26 |
| 565 | (4-(1R,4R)-4-aminocyclohexylamino)-6-(3,5-dichloro-4-hydroxyphenyl)-8-fluoroquinolin-3-yl)(cyclopropyl)methanone | 2.1 |
| 566 | (4-(2-(4-aminopiperidin-1-yl)pyrimidin-5-ylamino)-6-(3,5-dichloro-4-hydroxyphenyl)quinolin-3-yl)(cyclopropyl)methanone | 0.003 |
| 567 | (4-(2-(4-aminopiperidin-1-yl)pyrimidin-5-ylamino)-6-(3-chloro-5-fluoro-4-hydroxyphenyl)quinolin-3-yl)(cyclopropyl)methanone | 0.0083 |
| 568 | (4-(6-(3-aminopyrrolidin-1-yl)pyridin-3-ylamino)-6-(3-chloro-4-hydroxy-5-methoxyphenyl)quinolin-3-yl)(cyclopropyl)methanone | 0.0027 |
| 569 | (6-(3-chloro-4-hydroxy-5-methoxyphenyl)-4-(1R,4R)-4-(((R)-3-fluoropyrrolidin-1-yl)methyl)cyclohexylamino)quinolin-3-yl)(cyclopropyl)methanone | 0.011 |
| 570 | (6-(3-chloro-5-fluoro-4-hydroxyphenyl)-4-(1R,4R)-4-(((R)-3-fluoropyrrolidin-1-yl)methyl)cyclohexylamino)quinolin-3-yl)(cyclopropyl)methanone | 0.016 |
| 571 | cyclopropyl(6-(3,5-dichloro-4-hydroxyphenyl)-4-(1R,4R)-4-(((R)-3-fluoropyrrolidin-1-yl)methyl)cyclohexylamino)quinolin-3-yl)methanone | 0.0043 |
| 572 | (4-(2-(3-aminopyrrolidin-1-yl)pyrimidin-5-ylamino)-6-(3-chloro-5-fluoro-4-hydroxyphenyl)quinolin-3-yl)(cyclopropyl)methanone | 0.003 |
| 573 | (4-(2-(3-aminopyrrolidin-1-yl)pyrimidin-5-ylamino)-6-(3-chloro-5-fluoro-4-hydroxyphenyl)quinolin-3-yl)(cyclopropyl)methanone hydrochloride | 0.004 |
| 574 | (4-(2-(3-aminopyrrolidin-1-yl)pyrimidin-5-ylamino)-6-(3,5-dichloro-4-hydroxyphenyl)quinolin-3-yl)(cyclopropyl)methanone | 0.0018 |
| 575 | (4-(6-(3-aminopyrrolidin-1-yl)pyridin-3-ylamino)-6-(3,5-dichloro-4-hydroxyphenyl)quinolin-3-yl)(cyclopropyl)methanone | 0.0031 |
| 576 | (4-(6-(3-aminopyrrolidin-1-yl)pyridin-3-ylamino)-6-(3-chloro-5-fluoro-4-hydroxyphenyl)quinolin-3-yl)(cyclopropyl)methanone | 0.0019 |
| 577 | (4-(6-(3-aminopyrrolidin-1-yl)pyridin-3-ylamino)-6-(3-chloro-5-fluoro-4-hydroxyphenyl)quinolin-3-yl)(cyclopropyl)methanone hydrochloride) | 0.0037 |
| 578 | (6-(3-chloro-4-hydroxy-5-methoxyphenyl)-7-fluoro-4-(6-(piperazin-1-yl)pyridin-3-ylamino)quinolin-3-yl)(cyclopropyl)methanone | 0.021 |
| 579 | (4-((1R,3r,5S)-8-azabicyclo[3.2.1]octan-3-ylamino)-6-(3-chloro-4-hydroxy-5-methoxyphenyl)quinolin-3-yl)(cyclopropyl)methanone | 0.0042 |
| 580 | (4-((1R,3r,5S)-8-azabicyclo[3.2.1]octan-3-ylamino)-6-(3,5-dichloro-4-hydroxyphenyl)quinolin-3-yl)(cyclopropyl)methanone | 0.0045 |
| 581 | cyclopropyl(6-(3,5-dichloro-4-hydroxyphenyl)-4-(4-((3,3-difluoropyrrolidin-1-yl)methyl)phenylamino)quinolin-3-yl)methanone | 0.63 |
| 582 | (4-(2-(3-aminopyrrolidin-1-yl)pyrimidin-5-ylamino)-6-(3-chloro-4-hydroxy-5-methoxyphenyl)quinolin-3-yl)(cyclopropyl)methanone | 0.0031 |
| 583 | cyclopropyl(4-(4-(diallylamino)-4-methylcyclohexylamino)-6-(3,5-dichloro-4-hydroxyphenyl)quinolin-3-yl)methanone | 0.089 |
| 584 | cyclopropyl(6-(3,5-dichloro-4-hydroxyphenyl)-4-(1R,4R)-4-(pyrrolidin-1-ylmethyl)cyclohexylamino)quinolin-3-yl)methanone | 0.0016 |
| 585 | cyclopropyl(6-(3,5-dichloro-4-hydroxyphenyl)-4-(1R,4R)-4-(pyrrolidin-1-ylmethyl)cyclohexylamino)quinolin-3-yl)methanone hydrochloride | 0.0014 |
| 586 | (6-(3-chloro-4-hydroxy-5-methoxyphenyl)-4-(1R,4R)-4-(pyrrolidin-1-ylmethyl)cyclohexylamino)quinolin-3-yl)(cyclopropyl)methanone | 0.0028 |
| 587 | (6-(3-chloro-5-fluoro-4-hydroxyphenyl)-4-(1R,4R)-4-(pyrrolidin-1-ylmethyl)cyclohexylamino)quinolin-3-yl)(cyclopropyl)methanone | 0.0032 |
| 588 | (6-(3-chloro-5-fluoro-4-hydroxyphenyl)-4-(1R,4R)-4-(pyrrolidin-1-ylmethyl)cyclohexylamino)quinolin-3-yl)(cyclopropyl)methanone hydrochloride | 0.0037 |
| 589 | (4-(6-aminopyridin-3-ylamino)-6-(3-chloro-4-hydroxy-5-methoxyphenyl)quinolin-3-yl)(cyclopropyl)methanone | 0.011 |
| 590 | (4-(6-aminopyridin-3-ylamino)-6-(3,5-dichloro-4-hydroxyphenyl)quinolin-3-yl)(cyclopropyl)methanone | 0.014 |
| 591 | (4-(6-aminopyridin-3-ylamino)-6-(3-chloro-5-fluoro-4-hydroxyphenyl)quinolin-3-yl)(cyclopropyl)methanone | 0.032 |
| 592 | (6-(3-chloro-5-fluoro-4-hydroxyphenyl)-4-(1-(1-methylpiperidin-4-yl)-1H-pyrazol-4-ylamino)quinolin-3-yl)(cyclopropyl)methanone | 0.0015 |
| 593 | cyclopropyl(6-(3,5-dichloro-4-hydroxyphenyl)-4-(1-(1-methylpiperidin-4-yl)-1H-pyrazol-4-ylamino)quinolin-3-yl)methanone | 0.0013 |

TABLE 2-continued

| Example | Compound Name | IC$_{50}$ (μM) (kinase assay) |
|---|---|---|
| 594 | 1-(6-(3-chloro-5-fluoro-4-hydroxyphenyl)-4-(2-(piperazin-1-yl)pyrimidin-5-ylamino)quinolin-3-yl)ethanone | 0.0048 |
| 595 | (4-(4,4'-bipiperidin-1-yl)-6-(3-chloro-4-hydroxy-5-methoxyphenyl)quinolin-3-yl)(cyclopropyl)methanone | 0.0042 |
| 596 | (4-(4,4'-bipiperidin-1-yl)-6-(3,5-dichloro-4-hydroxyphenyl)quinolin-3-yl)(cyclopropyl)methanone | 0.0016 |
| 597 | 1-(6-(3-chloro-5-fluoro-4-hydroxyphenyl)-4-(1R,4R)-4-((dimethylamino)methylcyclohexylamino)quinolin-3-yl)butan-1-one | 0.0073 |
| 598 | cyclopropyl(6-(3,5-dichloro-4-hydroxyphenyl)-4-(1R,4R)-4-((3-methoxypyrrolidin-1-yl)methyl)cyclohexylamino)quinolin-3-yl)methanone | 0.0023 |
| 599 | (6-(3-chloro-4-hydroxy-5-methoxyphenyl)-4-(1R,4R)-4-((3-methoxypyrrolidin-1-yl)methyl)cyclohexylamino)quinolin-3-yl)(cyclopropyl)methanone | 0.005 |
| 600 | cyclopropyl(6-(3,5-dichloro-4-hydroxyphenyl)-4-(1R,4R)-4-((3-hydroxypyrrolidin-1-yl)methyl)cyclohexylamino)quinolin-3-yl)methanone | 0.00073 |
| 601 | (4-(4-(2-aminopropan-2-yl)phenylamino)-6-(3,5-dichloro-4-hydroxyphenyl)quinolin-3-yl)(cyclopropyl)methanone hydrochloride | 0.0014 |
| 602 | (4-(4-(2-aminopropan-2-yl)phenylamino)-6-(3,5-dichloro-4-hydroxyphenyl)quinolin-3-yl)(cyclopropyl)methanone | 0.0011 |
| 603 | (4-(4-(2-aminopropan-2-yl)phenylamino)-6-(3-chloro-4-hydroxy-5-methoxyphenyl)quinolin-3-yl)(cyclopropyl)methanone | 0.0036 |
| 604 | (4-(4-(2-aminopropan-2-yl)phenylamino)-6-(3-chloro-5-fluoro-4-hydroxyphenyl)quinolin-3-yl)(cyclopropyl)methanone | 0.0028 |
| 605 | 1-(6-(3,5-dichloro-4-hydroxyphenyl)-4-(1R,4R)-4-((dimethylamino)methylcyclohexylamino)quinolin-3-yl)butan-1-one | 0.002 |
| 606 | 1-(6-(3-chloro-4-hydroxy-5-methoxyphenyl)-4-(1R,4R)-4-((dimethylamino)methylcyclohexylamino)quinolin-3-yl)-2-methylpropan-1-one | 0.0063 |
| 607 | 1-(6-(3-chloro-4-hydroxy-5-methoxyphenyl)-4-(1R,4R)-4-((dimethylamino)methylcyclohexylamino)quinolin-3-yl)butan-1-one | 0.0051 |
| 608 | 1-(6-(3,5-dichloro-4-hydroxyphenyl)-4-(1R,4R)-4-((dimethylamino)methylcyclohexylamino)quinolin-3-yl)-2-methyl propan-1-one | 0.0022 |
| 609 | (6-(3-chloro-4-hydroxy-5-methoxyphenyl)-4-(6-(piperidin-3-ylamino)pyridin-3-ylamino)quinolin-3-yl)(cyclopropyl)methanone | 0.0025 |
| 610 | cyclopropyl(6-(3,5-dichloro-4-hydroxyphenyl)-4-(6-(piperidin-3-ylamino)pyridin-3-ylamino)quinolin-3-yl)methanone | 0.0017 |
| 611 | (6-(3-chloro-5-fluoro-4-hydroxyphenyl)-4-(6-(piperidin-3-ylamino)pyridin-3-ylamino)quinolin-3-yl)(cyclopropyl)methanone | 0.0023 |
| 612 | (6-(3-chloro-4-hydroxy-5-methoxyphenyl)-4-(4-(2-(dimethylamino)ethyl)phenylamino)quinolin-3-yl)(cyclopropyl)methanone | 0.0055 |
| 613 | cyclopropyl(6-(3,5-dichloro-4-hydroxyphenyl)-4-(4-(2-(dimethylamino)ethyl)phenylamino)quinolin-3-yl)methanone | 0.0022 |
| 614 | cyclopropyl(6-(3,5-dichloro-4-hydroxyphenyl)-4-(4-(2-(dimethylamino)ethyl)phenylamino)quinolin-3-yl)methanone hydrochloride | 0.0016 |
| 615 | (6-(3-chloro-5-fluoro-4-hydroxyphenyl)-4-(4-(2-(dimethylamino)ethyl)phenylamino)quinolin-3-yl)(cyclopropyl)methanone | 0.0082 |
| 616 | 1-(6-(3-chloro-4-hydroxy-5-methoxyphenyl)-4-(2-(piperazin-1-yl)pyrimidin-5-ylamino)quinolin-3-yl)ethanone | 0.0044 |
| 617 | 1-(6-(3-chloro-4-hydroxy-5-methoxyphenyl)-4-(6-(piperazin-1-yl)pyridin-3-ylamino)quinolin-3-yl)butan-1-one | 0.0042 |
| 618 | cyclopropyl(6-(3,5-dichloro-4-hydroxyphenyl)-4-(1R,4R)-4-((4-methylpiperazin-1-yl)methyl)cyclohexylamino)quinolin-3-yl)methanone | 0.0042 |
| 619 | cyclopropyl(6-(3,5-dichloro-4-hydroxyphenyl)-4-(1R,4R)-4-((4-methylpiperazin-1-yl)methyl)cyclohexylamino)quinolin-3-yl)methanone hydrochloride | 0.0028 |
| 620 | 1-(6-(3-chloro-5-fluoro-4-hydroxyphenyl)-4-(1R,4R)-4-((dimethylamino)methylcyclohexylamino)quinolin-3-yl)-2-methylpropan-1-one | 0.0066 |
| 621 | (4-((1R,3r,5S)-8-azabicyclo[3.2.1]octan-3-ylamino)-6-(3-chloro-5-fluoro-4-hydroxyphenyl)quinolin-3-yl)(cyclopropyl)methanone | 0.01 |
| 622 | (6-(3-chloro-4-hydroxy-5-methoxyphenyl)-4-(3-((dimethylamino)methyl)phenylamino)quinolin-3-yl)(cyclopropyl)methanone | 0.0037 |
| 623 | 1-(6-(3-chloro-5-fluoro-4-hydroxyphenyl)-4-(6-(piperazin-1-yl)pyridin-3-ylamino)quinolin-3-yl)butan-1-one | 0.011 |
| 624 | cyclopropyl(6-(3,5-dichloro-4-hydroxyphenyl)-4-(3-((dimethylamino)methyl)phenylamino)quinolin-3-yl)methanone | 0.0016 |
| 625 | 1-(6-(3,5-dichloro-4-hydroxyphenyl)-4-(6-(piperazin-1-yl)pyridin-3-ylamino)quinolin-3-yl)butan-1-one | 0.15 |

TABLE 2-continued

| Example | Compound Name | IC$_{50}$ (μM) (kinase assay) |
|---|---|---|
| 626 | (4-(2-(3-aminopiperidin-1-yl)pyrimidin-5-ylamino)-6-(3-chloro-5-fluoro-4-hydroxyphenyl)quinolin-3-yl)(cyclopropyl)methanone | 0.0011 |
| 627 | (6-(3-chloro-5-fluoro-4-hydroxyphenyl)-4-(1R,4R)-4-((3-methoxypyrrolidin-1-yl)methyl)cyclohexylamino)quinolin-3-yl)(cyclopropyl)methanone | 0.024 |
| 628 | (4-(2-(3-aminopiperidin-1-yl)pyrimidin-5-ylamino)-6-(3,5-dichloro-4-hydroxyphenyl)quinolin-3-yl)(cyclopropyl)methanone | 0.0015 |
| 629 | (6-(3-chloro-5-fluoro-4-hydroxyphenyl)-4-(3-((dimethylamino)methyl)phenylamino)quinolin-3-yl)(cyclopropyl)methanone | 0.0051 |
| 630 | (6-(3-chloro-4-hydroxy-5-methoxyphenyl)-4-(1R,4R)-4-((3-hydroxypyrrolidin-1-yl)methyl)cyclohexylamino)quinolin-3-yl)(cyclopropyl)methanone | 0.0023 |
| 631 | (6-(3-chloro-5-fluoro-4-hydroxyphenyl)-4-(1R,4R)-4-((3-hydroxypyrrolidin-1-yl)methyl)cyclohexylamino)quinolin-3-yl)(cyclopropyl)methanone | 0.0021 |
| 632 | (6-(3-chloro-5-fluoro-4-hydroxyphenyl)-4-(1R,4R)-4-(((2-hydroxyethyl)(methyl)amino)methyl)cyclohexylamino)quinolin-3-yl)(cyclopropyl)methanone | 0.0031 |
| 633 | (6-(3-chloro-4-hydroxy-5-methoxyphenyl)-4-(1R,4R)-4-(((2-hydroxyethyl)(methyl)amino)methyl)cyclohexylamino)quinolin-3-yl)(cyclopropyl)methanone | 0.0016 |
| 634 | cyclopropyl(6-(3,5-dichloro-4-hydroxyphenyl)-4-(1R,4R)-4-(((2-hydroxyethyl)(methyl)amino)methyl)cyclohexylamino)quinolin-3-yl)methanone | 0.0008 |
| 635 | cyclopropyl(6-(3,5-dichloro-4-hydroxyphenyl)-4-(1R,4R)-4-(((2-hydroxyethyl)(methyl)amino)methyl)cyclohexylamino)quinolin-3-yl)methanone hydrochloride | 0.00074 |
| 636 | (6-(3-chloro-5-fluoro-4-hydroxyphenyl)-4-(1R,4R)-4-((4-methylpiperazin-1-yl)methyl)cyclohexylamino)quinolin-3-yl)(cyclopropyl)methanone | 0.0098 |
| 637 | (6-(3-chloro-4-hydroxy-5-methoxyphenyl)-4-(1R,4R)-4-((4-methylpiperazin-1-yl)methyl)cyclohexylamino)quinolin-3-yl)(cyclopropyl)methanone | 0.0035 |
| 638 | (4-(4-amino-4-methylcyclohexylamino)-6-(3,5-dichloro-4-hydroxyphenyl)quinolin-3-yl)(cyclopropyl)methanone | 0.0034 |
| 639 | (4-(4-amino-4-methylcyclohexylamino)-6-(3-chloro-4-hydroxy-5-methoxyphenyl)quinolin-3-yl)(cyclopropyl)methanone | 0.0012 |
| 640 | 1-(6-(3-chloro-4-hydroxy-5-methoxyphenyl)-4-(4-((dimethylamino)methyl)phenylamino)quinolin-3-yl)-2-methylpropan-1-one | 0.027 |
| 641 | 1-(6-(3,5-dichloro-4-hydroxyphenyl)-4-(4-((dimethylamino)methyl)phenylamino)quinolin-3-yl)-2-methylpropan-1-one | 0.0076 |
| 642 | (R)-(6-(3-chloro-5-fluoro-4-hydroxyphenyl)-4-(4-(3-fluoropyrrolidin-1-yl)cyclohexylamino)quinolin-3-yl)(cyclopropyl)methanone | 0.0075 |
| 643 | (R)-cyclopropyl(6-(3,5-dichloro-4-hydroxyphenyl)-4-(4-(3-fluoropyrrolidin-1-yl)cyclohexylamino)quinolin-3-yl)methanone | 0.004 |
| 644 | (4-(2-(3-aminopiperidin-1-yl)pyrimidin-5-ylamino)-6-(3-chloro-4-hydroxy-5-methoxyphenyl)quinolin-3-yl)(cyclopropyl)methanone | 0.0028 |
| 645 | (R)-(6-(3-chloro-4-hydroxy-5-methoxyphenyl)-4-(4-(3-fluoropyrrolidin-1-yl)cyclohexylamino)quinolin-3-yl)(cyclopropyl)methanone | 0.0062 |
| 646 | (S)-(4-(6-(3-aminopiperidin-1-yl)pyridin-3-ylamino)-6-(3,5-dichloro-4-hydroxyphenyl)quinolin-3-yl)(cyclopropyl)methanone | 0.0011 |
| 647 | (S)-(4-(6-(3-aminopiperidin-1-yl)pyridin-3-ylamino)-6-(3,5-dichloro-4-hydroxyphenyl)quinolin-3-yl)(cyclopropyl)methanone hydrochloride | 0.0015 |
| 648 | (S)-(4-(6-(3-aminopiperidin-1-yl)pyridin-3-ylamino)-6-(3-chloro-5-fluoro-4-hydroxyphenyl)quinolin-3-yl)(cyclopropyl)methanone | 0.0019 |
| 649 | (R)-(4-(6-(3-aminopiperidin-1-yl)pyridin-3-ylamino)-6-(3-chloro-4-hydroxy-5-methoxyphenyl)quinolin-3-yl)(cyclopropyl)methanone | 0.0021 |
| 650 | (R)-(4-(6-(3-aminopiperidin-1-yl)pyridin-3-ylamino)-6-(3,5-dichloro-4-hydroxyphenyl)quinolin-3-yl)(cyclopropyl)methanone | 0.001 |
| 651 | (R)-(4-(6-(3-aminopiperidin-1-yl)pyridin-3-ylamino)-6-(3-chloro-5-fluoro-4-hydroxyphenyl)quinolin-3-yl)(cyclopropyl)methanone | 0.00076 |
| 652 | cyclopropyl(6-(3,5-dichloro-4-hydroxyphenyl)-4-((1s,4s)-4-((dimethylamino)methyl)-4-hydroxycyclohexylamino)quinolin-3-yl)methanone | 0.0011 |
| 653 | 1-(6-(3-chloro-4-hydroxy-5-methoxyphenyl)-4-(4-((4-methylpiperazin-1-yl)methyl)phenylamino)quinolin-3-yl)ethanone | 0.0098 |
| 654 | 1-(6-(3,5-dichloro-4-hydroxyphenyl)-4-(4-((4-methylpiperazin-1-yl)methyl)phenylamino)quinolin-3-yl)ethanone | 0.0082 |
| 655 | 1-(6-(3,5-dichloro-4-hydroxyphenyl)-4-(4-((4-methylpiperazin-1-yl)methyl)phenyl)amino)quinolin-3-yl)ethanone | 0.0029 |
| 656 | 1-(6-(3-chloro-5-fluoro-4-hydroxyphenyl)-4-(4-((4-methylpiperazin-1-yl)methyl)phenylamino)quinolin-3-yl)ethanone | 0.033 |
| 657 | cyclopropyl(6-(3,5-dichloro-4-hydroxyphenyl)-4-(6-((dimethylamino)methyl)pyridin-3-ylamino)quinolin-3-yl)methanone | 0.0089 |

TABLE 2-continued

| Example | Compound Name | IC$_{50}$ (μM) (kinase assay) |
|---|---|---|
| 658 | cyclopropyl(6-(3,5-dichloro-4-hydroxyphenyl)-4-(6-(pyrrolidin-1-ylmethyl)pyridin-3-ylamino)quinolin-3-yl)methanone | 0.0078 |
| 659 | (6-(3-chloro-4-hydroxy-5-methoxyphenyl)-4-(6-(pyrrolidin-1-ylmethyl)pyridin-3-ylamino)quinolin-3-yl)(cyclopropyl)methanone | 0.013 |
| 660 | (S)-(4-(6-(3-aminopiperidin-1-yl)pyridin-3-ylamino)-6-(3-chloro-4-hydroxy-5-methoxyphenyl)quinolin-3-yl)(cyclopropyl)methanone | 0.0024 |
| 661 | cyclopropyl(6-(3,5-dichloro-4-hydroxyphenyl)-4-(4-(3-methoxypyrrolidin-1-yl)cyclohexylamino)quinolin-3-yl)methanone | 0.0018 |
| 662 | (6-(3-chloro-5-fluoro-4-hydroxyphenyl)-4-(1R,4R)-4-((3-(dimethylamino)pyrrolidin-1-yl)methyl)cyclohexylamino)quinolin-3-yl)(cyclopropyl)methanone | 0.004 |
| 663 | cyclopropyl(6-(3,5-dichloro-4-hydroxyphenyl)-4-(1R,4R)-4-((3-(dimethylamino)pyrrolidin-1-yl)methyl)cyclohexylamino)quinolin-3-yl)methanone | 0.003 |
| 664 | cyclopropyl(6-(3,5-dichloro-4-hydroxyphenyl)-4-(4-(3,3-difluoropyrrolidin-1-yl)cyclohexylamino)quinolin-3-yl)methanone | 0.14 |
| 665 | (6-(3-chloro-4-hydroxy-5-methoxyphenyl)-4-(6-(pyrrolidin-3-ylamino)pyridin-3-ylamino)quinolin-3-yl)(cyclopropyl)methanone | 0.0033 |
| 666 | cyclopropyl(6-(3,5-dichloro-4-hydroxyphenyl)-4-(6-(pyrrolidin-3-ylamino)pyridin-3-ylamino)quinolin-3-yl)methanone | 0.024 |
| 667 | (6-(3-chloro-5-fluoro-4-hydroxyphenyl)-4-(6-(pyrrolidin-3-ylamino)pyridin-3-ylamino)quinolin-3-yl)(cyclopropyl)methanone | 0.01 |
| 668 | (6-(3-chloro-4-hydroxy-5-methoxyphenyl)-4-(1R,4R)-4-((3-(dimethylamino)pyrrolidin-1-yl)methyl)cyclohexylamino)quinolin-3-yl)(cyclopropyl)methanone | 0.0039 |
| 669 | (6-(3-chloro-4-hydroxy-5-methoxyphenyl)-4-(6-(3-hydroxypyrrolidin-1-yl)pyridin-3-ylamino)quinolin-3-yl)(cyclopropyl)methanone | 0.012 |
| 670 | cyclopropyl(6-(3,5-dichloro-4-hydroxyphenyl)-4-(6-(3-hydroxypyrrolidin-1-yl)pyridin-3-ylamino)quinolin-3-yl)methanone | 0.0069 |
| 671 | (6-(3-chloro-5-fluoro-4-hydroxyphenyl)-4-(6-(3-hydroxypyrrolidin-1-yl)pyridin-3-ylamino)quinolin-3-yl)(cyclopropyl)methanone | 0.025 |
| 672 | (6-(3-chloro-5-fluoro-4-hydroxyphenyl)-4-(6-(pyrrolidin-1-ylmethyl)pyridin-3-ylamino)quinolin-3-yl)(cyclopropyl)methanone | 0.014 |
| 673 | (6-(3-chloro-4-hydroxy-5-methoxyphenyl)-4-((1s,4s)-4-((dimethylamino)methyl)-4-hydroxycyclohexylamino)quinolin-3-yl)(cyclopropyl)methanone | 0.0042 |
| 674 | 1-(6-(3-chloro-5-fluoro-4-hydroxyphenyl)-4-(6-(piperazin-1-yl)pyridin-3-ylamino)quinolin-3-yl)-2-methylpropan-1-one | 0.0069 |
| 675 | (6-(3-chloro-5-fluoro-4-hydroxyphenyl)-4-(4-(3,3-difluoropyrrolidin-1-yl)cyclohexylamino)quinolin-3-yl)(cyclopropyl)methanone | 0.83 |
| 676 | (6-(3-chloro-4-hydroxy-5-methoxyphenyl)-4-(4-(3,3-difluoropyrrolidin-1-yl)cyclohexylamino)quinolin-3-yl)(cyclopropyl)methanone | 0.29 |
| 677 | (6-(3-chloro-4-hydroxy-5-methoxyphenyl)-4-(6-(2-hydroxyethylamino)pyridin-3-ylamino)quinolin-3-yl)(cyclopropyl)methanone | 0.014 |
| 678 | cyclopropyl(6-(3,5-dichloro-4-hydroxyphenyl)-4-(6-(2-hydroxyethylamino)pyridin-3-ylamino)quinolin-3-yl)methanone | 0.011 |
| 679 | (6-(3-chloro-5-fluoro-4-hydroxyphenyl)-4-(6-(2-hydroxyethylamino)pyridin-3-ylamino)quinolin-3-yl)(cyclopropyl)methanone | 0.03 |
| 680 | 1-(6-(3-chloro-4-hydroxy-5-methoxyphenyl)-4-(6-(piperazin-1-yl)pyridin-3-ylamino)quinolin-3-yl)-2-methylpropan-1-one | 0.011 |
| 681 | 1-(4-(6-(3-aminopiperidin-1-yl)pyridin-3-ylamino)-6-(3,5-dichloro-4-hydroxyphenyl)quinolin-3-yl)ethanone | 0.00086 |
| 682 | cyclopropyl(6-(3,5-dichloro-4-hydroxyphenyl)-4-(6-((4-methylpiperazin-1-yl)methyl)pyridin-3-ylamino)quinolin-3-yl)methanone | 0.018 |
| 683 | (6-(3-chloro-4-hydroxy-5-methoxyphenyl)-4-(6-((4-methylpiperazin-1-yl)methyl)pyridin-3-ylamino)quinolin-3-yl)(cyclopropyl)methanone | 0.016 |
| 684 | (6-(3-chloro-5-fluoro-4-hydroxyphenyl)-4-(6-((4-methylpiperazin-1-yl)methyl)pyridin-3-ylamino)quinolin-3-yl)(cyclopropyl)methanone | 0.05 |
| 685 | cyclopropyl(6-(3,5-dichloro-4-hydroxyphenyl)-4-(1R,4R)-4-((methylamino)methyl)cyclohexylamino)quinolin-3-yl)methanone | 0.0016 |
| 686 | (6-(3-chloro-5-fluoro-4-hydroxyphenyl)-4-(4-(3-methoxypyrrolidin-1-yl)cyclohexylamino)quinolin-3-yl)(cyclopropyl)methanone | 0.0035 |
| 687 | (6-(3-chloro-4-hydroxy-5-methoxyphenyl)-4-(4-(3-methoxypyrrolidin-1-yl)cyclohexylamino)quinolin-3-yl)(cyclopropyl)methanone | 0.0033 |
| 688 | 1-(4-(6-(3-aminopiperidin-1-yl)pyridin-3-ylamino)-6-(3-chloro-4-hydroxy-5-methoxyphenyl)quinolin-3-yl)ethanone | 0.0032 |
| 689 | (6-(3-chloro-4-hydroxy-5-methoxyphenyl)-4-(6-(3-(dimethylamino)pyrrolidin-1-yl)pyridin-3-ylamino)quinolin-3-yl)(cyclopropyl)methanone | 0.013 |
| 690 | cyclopropyl(6-(3,5-dichloro-4-hydroxyphenyl)-4-(6-(3-(dimethylamino)pyrrolidin-1-yl)pyridin-3-ylamino)quinolin-3-yl)methanone | 0.0047 |
| 691 | (6-(3-chloro-5-fluoro-4-hydroxyphenyl)-4-(6-(3-(dimethylamino)pyrrolidin-1-yl)pyridin-3-ylamino)quinolin-3-yl)(cyclopropyl)methanone | 0.012 |
| 692 | (6-(3-chloro-4-hydroxy-5-methoxyphenyl)-4-(3-(2-(dimethylamino)ethyl)phenylamino)quinolin-3-yl)(cyclopropyl)methanone | 0.0056 |

TABLE 2-continued

| Example | Compound Name | IC$_{50}$ (μM) (kinase assay) |
|---|---|---|
| 693 | (6-(3-chloro-5-fluoro-4-hydroxyphenyl)-4-(3-(2-(dimethylamino)ethyl)phenylamino)quinolin-3-yl)(cyclopropyl)methanone | 0.0083 |
| 694 | cyclopropyl(6-(3,5-dichloro-4-hydroxyphenyl)-4-(4-((3-(dimethylamino)pyrrolidin-1-yl)methyl)phenylamino)quinolin-3-yl)methanone | 0.0072 |
| 695 | cyclopropyl(6-(3,5-dichloro-4-hydroxyphenyl)-4-(4-((3-(dimethylamino)pyrrolidin-1-yl)methyl)phenylamino)quinolin-3-yl)methanone hydrochloride | 0.0056 |
| 696 | (6-(3-chloro-5-fluoro-4-hydroxyphenyl)-4-(4-((3-(dimethylamino)pyrrolidin-1-yl)methyl)phenylamino)quinolin-3-yl)(cyclopropyl)methanone | 0.012 |
| 697 | (6-(3-chloro-4-hydroxy-5-methoxyphenyl)-4-(4-((3-(dimethylamino)pyrrolidin-1-yl)methyl)phenylamino)quinolin-3-yl)(cyclopropyl)methanone | 0.0084 |
| 698 | cyclopropyl(6-(3,5-dichloro-4-hydroxyphenyl)-4-(3-(2-(dimethylamino)ethyl)phenylamino)quinolin-3-yl)methanone | 0.0024 |
| 699 | (6-(3-chloro-5-fluoro-4-hydroxyphenyl)-4-(1-(1-methylpiperidin-3-yl)-1H-pyrazol-4-ylamino)quinolin-3-yl)(cyclopropyl)methanone | 0.0026 |
| 700 | cyclopropyl(6-(3,5-dichloro-4-hydroxyphenyl)-4-(1R,4R)-4-((2-fluoroethylamino)methyl)cyclohexylamino)quinolin-3-yl)methanone | 0.0015 |
| 701 | (6-(3-chloro-5-fluoro-4-hydroxyphenyl)-4-(1R,4R)-4-((2-fluoroethylamino)methyl)cyclohexylamino)quinolin-3-yl)(cyclopropyl)methanone | 0.003 |
| 702 | 1-(6-(3,5-dichloro-4-hydroxyphenyl)-4-(6-(piperazin-1-yl)pyridin-3-ylamino)quinolin-3-yl)ethanone hydrochloride | 0.0014 |
| 703 | cyclopropyl(6-(3,5-dichloro-4-hydroxyphenyl)-4-(1-(1-methylpiperidin-3-yl)-1H-pyrazol-4-ylamino)quinolin-3-yl)methanone | 0.0013 |
| 704 | 1-(6-(3-chloro-4-hydroxy-5-methoxyphenyl)-4-(6-(piperazin-1-yl)pyridin-3-ylamino)quinolin-3-yl)ethanone hydrochloride | 0.0023 |
| 705 | cyclopropyl(6-(3,5-dichloro-4-hydroxyphenyl)-4-(1-(1R,4R)-4-(methylamino)cyclohexyl)-1H-pyrazol-4-ylamino)quinolin-3-yl)methanone | 0.0017 |
| 706 | (4-(1-(1R,4R)-4-aminocyclohexyl)-1H-pyrazol-4-ylamino)-6-(3,5-dichloro-4-hydroxyphenyl)quinolin-3-yl)(cyclopropyl)methanone hydrochloride | 0.0011 |
| 707 | (6-(3-chloro-5-fluoro-4-hydroxyphenyl)-4-(4-(2-(dimethylamino)-1-hydroxyethyl)phenylamino)quinolin-3-yl)(cyclopropyl)methanone | 0.0059 |
| 708 | (6-(3-chloro-4-hydroxy-5-methoxyphenyl)-4-(4-(2-(dimethylamino)-1-hydroxyethyl)phenylamino)quinolin-3-yl)(cyclopropyl)methanone | 0.0065 |
| 709 | cyclopropyl(6-(3,5-dichloro-4-hydroxyphenyl)-4-(4-(2-(dimethylamino)-1-hydroxyethyl)phenylamino)quinolin-3-yl)methanone | 0.0035 |
| 710 | (6-(3-chloro-5-fluoro-4-hydroxyphenyl)-4-(6-(2-(dimethylamino)ethoxy)pyridin-3-ylamino)quinolin-3-yl)(cyclopropyl)methanone | 0.0069 |
| 711 | cyclopropyl(6-(3,5-dichloro-4-hydroxyphenyl)-4-(6-(2-(dimethylamino)ethoxy)pyridin-3-ylamino)quinolin-3-yl)methanone | 0.0032 |
| 712 | (6-(3-chloro-4-hydroxy-5-methoxyphenyl)-4-(6-(2-(dimethylamino)ethoxy)pyridin-3-ylamino)quinolin-3-yl)(cyclopropyl)methanone | 0.0036 |
| 713 | 1-(6-(3-chloro-4-hydroxy-5-methoxyphenyl)-4-(1R,4R)-4-((dimethylamino)methyl)cyclohexylamino)quinolin-3-yl)propan-1-one | 0.0024 |
| 714 | 1-(6-(3-chloro-5-fluoro-4-hydroxyphenyl)-4-(1R,4R)-4-((dimethylamino)methyl)cyclohexylamino)quinolin-3-yl)propan-1-one | 0.004 |
| 715 | 1-(6-(3,5-dichloro-4-hydroxyphenyl)-4-(1R,4R)-4-((dimethylamino)methyl)cyclohexylamino)quinolin-3-yl)propan-1-one | 0.0015 |
| 716 | 1-(6-(3,5-dichloro-4-hydroxyphenyl)-4-((1R,4R)-4-((dimethylamino)methyl)cyclohexyl)amino)quinolin-3-yl)propan-1-one dihydrochloride | 0.0016 |
| 717 | 1-(6-(3-chloro-5-fluoro-4-hydroxyphenyl)-4-((1R,3R)-3-((dimethylamino)methyl)cyclopentylamino)quinolin-3-yl)ethanone | 0.011 |
| 718 | 1-(6-(3,5-dichloro-4-hydroxyphenyl)-4-((1R,3R)-3-((dimethylamino)methyl)cyclopentylamino)quinolin-3-yl)ethanone | 0.0055 |
| 719 | (6-(3-chloro-5-fluoro-4-hydroxyphenyl)-4-(piperidin-4-ylamino)quinolin-3-yl)(cyclopropyl)methanone | 0.0092 |
| 720 | 1-(6-(3,5-dichloro-4-hydroxyphenyl)-4-(1-(dimethylamino)-2,3-dihydro-1H-inden-5-ylamino)quinolin-3-yl)ethanone | 0.0033 |
| 721 | 1-(6-(3,5-difluoro-4-hydroxyphenyl)-4-(1R,4R)-4-((dimethylamino)methyl)cyclohexylamino)quinolin-3-yl)ethanone | 0.035 |
| 722 | (4-(6-(2-aminoethoxy)pyridin-3-ylamino)-6-(3-chloro-4-hydroxy-5-methoxyphenyl)quinolin-3-yl)(cyclopropyl)methanone | 0.0043 |
| 723 | (4-(6-(2-aminoethoxy)pyridin-3-ylamino)-6-(3,5-dichloro-4-hydroxyphenyl)quinolin-3-yl)(cyclopropyl)methanone | 0.0019 |
| 724 | (4-(6-(2-aminoethoxy)pyridin-3-ylamino)-6-(3-chloro-5-fluoro-4-hydroxyphenyl)quinolin-3-yl)(cyclopropyl)methanone | 0.0055 |

TABLE 2-continued

| Example | Compound Name | IC$_{50}$ (μM) (kinase assay) |
|---|---|---|
| 725 | (4-(6-(3-aminopiperidin-1-yl)pyridin-3-ylamino)-6-(3,5-difluoro-4-hydroxyphenyl)quinolin-3-yl)(cyclopropyl)methanone | 0.003 |
| 726 | cyclopropyl(6-(3,5-dichloro-4-hydroxyphenyl)-4-(piperidin-4-ylamino)quinolin-3-yl)methanone | 0.0057 |
| 727 | (6-(3-chloro-4-hydroxy-5-methoxyphenyl)-4-(piperidin-4-ylamino)quinolin-3-yl)(cyclopropyl)methanone | 0.0034 |
| 728 | 1-(6-(3,5-dichloro-4-hydroxyphenyl)-4-((1R,3R)-3-((4-methylpiperazin-1-yl)methyl)cyclopentylamino)quinolin-3-yl)ethanone | 0.0057 |
| 729 | 1-(6-(3,5-dichloro-4-hydroxyphenyl)-4-(3-(2-(dimethylamino)ethyl)phenylamino)quinolin-3-yl)ethanone | 0.0022 |
| 730 | 1-(6-(3-chloro-4-hydroxy-5-methoxyphenyl)-4-(3-(2-(dimethylamino)ethyl)phenylamino)quinolin-3-yl)ethanone | 0.0026 |
| 731 | 1-(6-(3-chloro-5-fluoro-4-hydroxyphenyl)-4-(1R,4R)-4-(pyrrolidin-1-ylmethyl)cyclohexylamino)quinolin-3-yl)ethanone | 0.0047 |
| 732 | 1-(4-(6-(3-aminopiperidin-1-yl)pyridin-3-ylamino)-6-(3-chloro-5-fluoro-4-hydroxyphenyl)quinolin-3-yl)ethanone | 0.0017 |
| 733 | 1-(4-((6-(3-aminopiperidin-1-yl)pyridin-3-yl)amino)-6-(3-chloro-5-fluoro-4-hydroxyphenyl)quinolin-3-yl)ethanone | 0.00099 |
| 734 | 1-(6-(3-chloro-4-hydroxy-5-methoxyphenyl)-4-(1R,4R)-4-(pyrrolidin-1-ylmethyl)cyclohexylamino)quinolin-3-yl)ethanone | 0.0016 |
| 735 | (4-(2-(4-aminopiperidin-1-yl)pyridin-4-ylamino)-6-(3,5-dichloro-4-hydroxyphenyl)quinolin-3-yl)(cyclopropyl)methanone | 0.0041 |
| 736 | 1-(6-(3-chloro-5-fluoro-4-hydroxyphenyl)-4-(6-(4-methylpiperazin-1-yl)pyridin-3-ylamino)quinolin-3-yl)propan-1-one | 0.036 |
| 737 | 1-(6-(3,5-dichloro-4-hydroxyphenyl)-4-(6-(4-methylpiperazin-1-yl)pyridin-3-ylamino)quinolin-3-yl)propan-1-one | 0.055 |
| 738 | 1-(6-(3-chloro-4-hydroxy-5-methoxyphenyl)-4-(1R,4R)-4-(2-(dimethylamino)ethyl)cyclohexylamino)quinolin-3-yl)ethanone | 0.0026 |
| 739 | 1-(6-(3,5-dichloro-4-hydroxyphenyl)-4-(1R,4R)-4-(2-(dimethylamino)ethyl)cyclohexylamino)quinolin-3-yl)ethanone | 0.0032 |
| 740 | 1-(6-(3,5-dichloro-4-hydroxyphenyl)-4-((1R,4R)-4-(2-(dimethylamino)ethyl)cyclohexyl)amino)quinolin-3-yl)ethanone hydrochloride | 0.0013 |
| 741 | 1-(6-(3-chloro-5-fluoro-4-hydroxyphenyl)-4-(1R,4R)-4-(2-(dimethylamino)ethyl)cyclohexylamino)quinolin-3-yl)ethanone | 0.0048 |
| 742 | 1-(6-(3-chloro-5-fluoro-4-hydroxyphenyl)-4-(1R,4R)-4-(2-(dimethylamino)ethyl)cyclohexylamino)quinolin-3-yl)ethanone dihydrochloride | 0.0044 |
| 743 | 1-(6-(3-chloro-4-hydroxy-5-methoxyphenyl)-4-(4-(2-(dimethylamino)ethyl)phenylamino)quinolin-3-yl)ethanone | 0.0042 |
| 744 | 1-(6-(3,5-dichloro-4-hydroxyphenyl)-4-(4-(2-(dimethylamino)ethyl)phenylamino)quinolin-3-yl)ethanone | 0.0017 |
| 745 | 1-(6-(3-chloro-5-fluoro-4-hydroxyphenyl)-4-(4-(2-(dimethylamino)ethyl)phenylamino)quinolin-3-yl)ethanone | 0.0083 |
| 746 | (6-(3-chloro-4-hydroxy-5-methoxyphenyl)-4-(6-(2-(dimethylamino)ethylamino)pyridin-3-ylamino)quinolin-3-yl)(cyclopropyl)methanone | 0.0029 |
| 747 | cyclopropyl(6-(3,5-dichloro-4-hydroxyphenyl)-4-(6-(2-(dimethylamino)ethylamino)pyridin-3-ylamino)quinolin-3-yl)methanone | 0.0043 |
| 748 | cyclopropyl(6-(3,5-dichloro-4-hydroxyphenyl)-4-(6-(2-(dimethylamino)ethylamino)pyridin-3-ylamino)quinolin-3-yl)methanone hydrochloride | 0.0026 |
| 749 | 1-(6-(3-chloro-4-hydroxy-5-methoxyphenyl)-4-(1R,4R)-4-((3-hydroxypyrrolidin-1-yl)methyl)cyclohexylamino)quinolin-3-yl)ethanone | 0.0017 |
| 750 | 1-(6-(3,5-dichloro-4-hydroxyphenyl)-4-((1R,3R)-3-((dimethylamino)methyl)cyclohexylamino)quinolin-3-yl)ethanone | 0.0023 |
| 751 | 1-(6-(3-chloro-5-fluoro-4-hydroxyphenyl)-4-((1R,3R)-3-((dimethylamino)methyl)cyclohexylamino)quinolin-3-yl)ethanone | 0.0067 |
| 752 | 1-(6-(3-chloro-4-hydroxy-5-methoxyphenyl)-4-((1R,3R)-3-((dimethylamino)methyl)cyclohexylamino)quinolin-3-yl)ethanone | 0.001 |
| 753 | 1-(6-(3,5-dichloro-4-hydroxyphenyl)-4-(1R,4R)-4-((3-hydroxypyrrolidin-1-yl)methyl)cyclohexylamino)quinolin-3-yl)ethanone | 0.0015 |
| 754 | 1-(6-(3,5-dichloro-4-hydroxyphenyl)-4-(1R,4R)-4-(dimethylamino)cyclohexylamino)quinolin-3-yl)propan-1-one | 0.02 |
| 755 | 1-(6-(3-chloro-4-hydroxy-5-methoxyphenyl)-4-(1R,4R)-4-(dimethylamino)cyclohexylamino)quinolin-3-yl)propan-1-one | 0.0018 |
| 756 | cyclopropyl(6-(3,5-dichloro-4-hydroxyphenyl)-4-(4-(2-(pyrrolidin-1-yl)ethyl)piperidin-1-yl)quinolin-3-yl)methanone | 0.0023 |
| 757 | 1-(6-(3-chloro-5-fluoro-4-hydroxyphenyl)-4-(1R,4R)-4-(dimethylamino)cyclohexylamino)quinolin-3-yl)propan-1-one | 0.0062 |
| 758 | 1-(6-(3,5-dichloro-4-hydroxyphenyl)-4-(6-(2-(dimethylamino)ethylamino)pyridin-3-ylamino)quinolin-3-yl)ethanone | 0.0053 |
| 759 | 1-(6-(3-chloro-5-fluoro-4-hydroxyphenyl)-4-(3-(2-(dimethylamino)ethyl)phenylamino)quinolin-3-yl)ethanone | 0.013 |

TABLE 2-continued

| Example | Compound Name | IC$_{50}$ (μM) (kinase assay) |
|---|---|---|
| 760 | 1-(4-(6-(3-aminopyrrolidin-1-yl)pyridin-3-ylamino)-6-(3-chloro-5-fluoro-4-hydroxyphenyl)quinolin-3-yl)propan-1-one | 0.0034 |
| 761 | 1-(4-(6-(3-aminopyrrolidin-1-yl)pyridin-3-ylamino)-6-(3,5-dichloro-4-hydroxyphenyl)quinolin-3-yl)propan-1-one | 0.0026 |
| 762 | 1-(6-(3-chloro-5-fluoro-4-hydroxyphenyl)-4-(6-(2-(dimethylamino)ethylamino)pyridin-3-ylamino)quinolin-3-yl)ethanone | 0.014 |
| 763 | 1-(6-(3-chloro-5-fluoro-4-hydroxyphenyl)-4-(1R,4R)-4-(dimethylamino)cyclohexylamino)quinolin-3-yl)ethanone | 0.0087 |
| 764 | (6-(3-chloro-4-hydroxy-5-methoxyphenyl)-4-(1-(pyrrolidin-3-yl)piperidin-4-ylamino)quinolin-3-yl)(cyclopropyl)methanone | 0.0029 |
| 765 | 1-(6-(3,5-dichloro-4-hydroxyphenyl)-4-(1R,4R)-4-(dimethylamino)cyclohexylamino)quinolin-3-yl)ethanone | 0.0022 |
| 766 | 1-(6-(3,5-dichloro-4-hydroxyphenyl)-4-((1R,4R)-4-(dimethylamino)cyclohexyl)amino)quinolin-3-yl)ethanone hydrochloride | 0.0017 |
| 767 | 1-(6-(3,5-dichloro-4-hydroxyphenyl)-4-(1R,4R)-4-(pyrrolidin-1-ylmethyl)cyclohexylamino)quinolin-3-yl)ethanone | 0.0018 |
| 768 | 1-(6-(3,5-dichloro-4-hydroxyphenyl)-4-((1R,4R)-4-(pyrrolidin-1-ylmethyl)cyclohexyl)amino)quinolin-3-yl)ethanone hydrochloride | 0.0015 |
| 769 | 1-(6-(3-chloro-4-hydroxy-5-methoxyphenyl)-4-(4-((dimethylamino)methyl)phenylamino)quinolin-3-yl)propan-1-one | 0.0049 |
| 770 | 1-(6-(3-chloro-5-fluoro-4-hydroxyphenyl)-4-(4-((dimethylamino)methyl)phenylamino)quinolin-3-yl)propan-1-one | 0.015 |
| 771 | 1-(6-(3,5-dichloro-4-hydroxyphenyl)-4-(4-((dimethylamino)methyl)phenylamino)quinolin-3-yl)propan-1-one | 0.0054 |
| 772 | 1-(6-(3,5-dichloro-4-hydroxyphenyl)-4-(1R,4R)-4-(piperazin-1-ylmethyl)cyclohexylamino)quinolin-3-yl)ethanone dihydrochloride | 0.0021 |
| 773 | 1-(4-(6-(3-aminopyrrolidin-1-yl)pyridin-3-ylamino)-6-(3-chloro-5-fluoro-4-hydroxyphenyl)quinolin-3-yl)ethanone | 0.006 |
| 774 | 1-(4-(6-(3-aminopyrrolidin-1-yl)pyridin-3-ylamino)-6-(3-chloro-4-hydroxy-5-methoxyphenyl)quinolin-3-yl)ethanone | 0.0019 |
| 775 | 1-(4-(6-(3-aminopyrrolidin-1-yl)pyridin-3-ylamino)-6-(3-chloro-4-hydroxy-5-methoxyphenyl)quinolin-3-yl)propan-1-one | 0.0034 |
| 776 | (6-(3-chloro-5-fluoro-4-hydroxyphenyl)-4-(6-(2-(dimethylamino)ethylamino)pyridin-3-ylamino)quinolin-3-yl)(cyclopropyl)methanone | 0.0027 |
| 777 | (6-(3-chloro-5-fluoro-4-hydroxyphenyl)-4-(6-(2-(dimethylamino)ethylamino)pyridin-3-ylamino)quinolin-3-yl)(cyclopropyl)methanone trihydrochloride | 0.0034 |
| 778 | cyclopropyl(6-(3,5-difluoro-4-hydroxyphenyl)-4-(6-(4-methylpiperazin-1-yl)pyridin-3-ylamino)quinolin-3-yl)methanone | 0.021 |
| 779 | 1-(4-(1R,4R)-4-((3-aminopyrrolidin-1-yl)methyl)cyclohexylamino)-6-(3,5-dichloro-4-hydroxyphenyl)quinolin-3-yl)ethanone hydrochloride | 0.0017 |
| 780 | 1-(4-(1R,4R)-4-((3-aminopyrrolidin-1-yl)methyl)cyclohexylamino)-6-(3-chloro-4-hydroxy-5-methoxyphenyl)quinolin-3-yl)ethanone hydrochloride | 0.002 |
| 781 | 1-(6-(3-chloro-5-fluoro-4-hydroxyphenyl)-4-(1R,4R)-4-((4-methylpiperazin-1-yl)methyl)cyclohexylamino)quinolin-3-yl)ethanone hydrochloride | 0.013 |
| 782 | 1-(6-(3,5-dichloro-4-hydroxyphenyl)-4-(1R,4R)-4-((4-methylpiperazin-1-yl)methyl)cyclohexylamino)quinolin-3-yl)ethanone hydrochloride | 0.0055 |
| 783 | 1-(6-(3-chloro-5-fluoro-4-hydroxyphenyl)-4-(1R,4R)-4-(piperazin-1-ylmethyl)cyclohexylamino)quinolin-3-yl)ethanone dihydrochloride | 0.0088 |
| 784 | 1-(6-(3,5-dichloro-4-hydroxyphenyl)-4-((1r,3r)-3-((dimethylamino)methyl)cyclobutylamino)quinolin-3-yl)ethanone | 0.0031 |
| 785 | 1-(6-(3-chloro-5-fluoro-4-hydroxyphenyl)-4-(6-(3-(methylamino)pyrrolidin-1-yl)pyridin-3-ylamino)quinolin-3-yl)ethanone trihydrochloride | 0.0056 |
| 786 | 1-(4-(1R,4R)-4-((3-aminopyrrolidin-1-yl)methyl)cyclohexylamino)-6-(3-chloro-5-fluoro-4-hydroxyphenyl)quinolin-3-yl)ethanone hydrochloride | 0.0031 |
| 787 | 1-(6-(3-chloro-4-hydroxy-5-methoxyphenyl)-4-(1R,4R)-4-((4-methylpiperazin-1-yl)methyl)cyclohexylamino)quinolin-3-yl)ethanone hydrochloride | 0.0058 |
| 788 | 1-(6-(3,5-dichloro-4-hydroxyphenyl)-4-(6-(3-(methylamino)pyrrolidin-1-yl)pyridin-3-ylamino)quinolin-3-yl)ethanone trihydrochloride | 0.0017 |
| 789 | (6-(3-chloro-5-fluoro-4-hydroxyphenyl)-4-(6-(3-(methylamino)pyrrolidin-1-yl)pyridin-3-ylamino)quinolin-3-yl)(cyclopropyl)methanone trihydrochloride | 0.0028 |

TABLE 2-continued

| Example | Compound Name | IC$_{50}$ (μM) (kinase assay) |
|---|---|---|
| 790 | 1-(6-(3,5-dichloro-4-hydroxyphenyl)-4-(1R,4R)-4-((diethylamino)methyl)cyclohexylamino)quinolin-3-yl)ethanone dihydrochloride | 0.0018 |
| 791 | 1-(6-(3-chloro-4-hydroxy-5-methoxyphenyl)-4-(1R,4R)-4-((diethylamino)methyl)cyclohexylamino)quinolin-3-yl)ethanone hydrochloride | 0.0031 |
| 792 | 1-(6-(3,5-dichloro-4-hydroxyphenyl)-4-((1S,4r)-4-(((S)-2-(hydroxymethyl)pyrrolidin-1-yl)methyl)cyclohexylamino)quinolin-3-yl)ethanone | 0.0011 |
| 793 | 1-(6-(3-chloro-4-hydroxy-5-methoxyphenyl)-4-((1S,4r)-4-(((S)-2-(hydroxymethyl)pyrrolidin-1-yl)methyl)cyclohexylamino)quinolin-3-yl)ethanone | 0.0018 |
| 794 | 1-(6-(3-chloro-5-fluoro-4-hydroxyphenyl)-4-(1R,4R)-4-((diethylamino)methyl)cyclohexylamino)quinolin-3-yl)ethanone dihydrochloride | 0.0056 |
| 795 | cyclopropyl(6-(3,5-difluoro-4-hydroxyphenyl)-4-(6-(pyrrolidin-1-ylmethyl)pyridin-3-ylamino)quinolin-3-yl)methanone | 0.035 |
| 796 | cyclopropyl(6-(3,5-difluoro-4-hydroxyphenyl)-4-(3-(2-(dimethylamino)ethyl)phenylamino)quinolin-3-yl)methanone | 0.026 |
| 797 | cyclopropyl(6-(3,5-dichloro-4-hydroxyphenyl)-4-(3-(2-(pyrrolidin-1-yl)ethyl)phenylamino)quinolin-3-yl)methanone | 0.0056 |
| 798 | cyclopropyl(6-(3,5-dichloro-4-hydroxyphenyl)-4-(3-(2-(pyrrolidin-1-yl)ethyl)phenylamino)quinolin-3-yl)methanone hydrochloride | 0.0029 |
| 799 | (6-(3-chloro-5-fluoro-4-hydroxyphenyl)-4-(3-(2-(pyrrolidin-1-yl)ethyl)phenylamino)quinolin-3-yl)(cyclopropyl)methanone | 0.0047 |
| 800 | (6-(3-chloro-5-fluoro-4-hydroxyphenyl)-4-(3-(2-(pyrrolidin-1-yl)ethyl)phenylamino)quinolin-3-yl)(cyclopropyl)methanone hydrochloride | 0.012 |
| 801 | 1-(6-(3,5-dichloro-4-hydroxyphenyl)-4-(3-(2-(pyrrolidin-1-yl)ethyl)phenylamino)quinolin-3-yl)ethanone | 0.004 |
| 802 | 1-(6-(3,5-dichloro-4-hydroxyphenyl)-4-((3-(2-(pyrrolidin-1-yl)ethyl)phenyl)amino)quinolin-3-yl)ethanone hydrochloride | 0.0021 |
| 803 | 1-(6-(3-chloro-5-fluoro-4-hydroxyphenyl)-4-(3-(2-(pyrrolidin-1-yl)ethyl)phenylamino)quinolin-3-yl)ethanone | 0.016 |
| 804 | cyclopropyl(6-(3,5-dichloro-4-hydroxyphenyl)-4-(6-(3-(methylamino)pyrrolidin-1-yl)pyridin-3-ylamino)quinolin-3-yl)methanone trihydrochloride | 0.002 |
| 805 | 1-(6-(3-chloro-5-fluoro-4-hydroxyphenyl)-4-(1-(1-methylpiperidin-4-yl)-1H-pyrazol-4-ylamino)quinolin-3-yl)ethanone hydrochloride | 0.0028 |
| 806 | 1-(6-(3,5-dichloro-4-hydroxyphenyl)-4-(6-(3-(methylamino)piperidin-1-yl)pyridin-3-ylamino)quinolin-3-yl)ethanone trihydrochloride | 0.0012 |
| 807 | cyclopropyl(6-(3,5-dichloro-4-hydroxyphenyl)-4-(6-(3-(methylamino)piperidin-1-yl)pyridin-3-ylamino)quinolin-3-yl)methanone trihydrochloride | 0.0015 |
| 808 | 1-(6-(3-chloro-5-fluoro-4-hydroxyphenyl)-4-(1R,4R)-4-(((R)-2-(hydroxymethyl)pyrrolidin-1-yl)methyl)cyclohexylamino)quinolin-3-yl)ethanone hydrochloride | 0.0065 |
| 809 | 1-(4-(1R,4R)-4-((3-aminopiperidin-1-yl)methyl)cyclohexylamino)-6-(3-chloro-4-hydroxy-5-methoxyphenyl)quinolin-3-yl)ethanone hydrochloride | 0.016 |
| 810 | 1-(4-(1R,4R)-4-((3-aminopiperidin-1-yl)methyl)cyclohexylamino)-6-(3,5-dichloro-4-hydroxyphenyl)quinolin-3-yl)ethanone trihydrochloride | 0.0018 |
| 811 | 1-(6-(3-chloro-4-hydroxy-5-methoxyphenyl)-4-(1R,4R)-4-(((R)-2-(hydroxymethyl)pyrrolidin-1-yl)methyl)cyclohexylamino)quinolin-3-yl)ethanone | 0.0027 |
| 812 | 1-(6-(3,5-dichloro-4-hydroxyphenyl)-4-(1R,4R)-4-(((R)-2-(hydroxymethyl)pyrrolidin-1-yl)methyl)cyclohexylamino)quinolin-3-yl)ethanone | 0.0017 |
| 813 | 1-(6-(3-chloro-5-fluoro-4-hydroxyphenyl)-4-(1-(1-methylpyrrolidin-3-yl)-1H-pyrazol-4-ylamino)quinolin-3-yl)ethanone dihydrochloride | 0.0021 |
| 814 | 1-(6-(3,5-dichloro-4-hydroxyphenyl)-4-(1-(1-methylpyrrolidin-3-yl)-1H-pyrazol-4-ylamino)quinolin-3-yl)ethanone dihydrochloride | 0.0009 |
| 815 | 1-(6-(3-chloro-5-fluoro-4-hydroxyphenyl)-4-(6-(3-(methylamino)piperidin-1-yl)pyridin-3-ylamino)quinolin-3-yl)ethanone trihydrochloride | 0.0018 |
| 816 | 1-(6-(3-chloro-4-hydroxy-5-methoxyphenyl)-4-(1R,4R)-4-((ethyl(methyl)amino)methyl)cyclohexylamino)quinolin-3-yl)ethanone hydrochloride | 0.0027 |

TABLE 2-continued

| Example | Compound Name | IC$_{50}$ (μM) (kinase assay) |
|---|---|---|
| 817 | 1-(6-(3,5-dichloro-4-hydroxyphenyl)-4-(1R,4R)-4-((ethyl(methyl)amino)methyl)cyclohexylamino)quinolin-3-yl)ethanone dihydrochloride | 0.0014 |
| 818 | 1-(4-(1R,4R)-4-((3-aminopiperidin-1-yl)methyl)cyclohexylamino)-6-(3-chloro-5-fluoro-4-hydroxyphenyl)quinolin-3-yl)ethanone trihydrochloride | 0.0043 |
| 819 | cyclopropyl(6-(3,5-dichloro-4-hydroxyphenyl)-4-(1-(2-(dimethylamino)ethyl)piperidin-4-ylamino)quinolin-3-yl)methanone | 0.0024 |
| 820 | cyclopropyl(6-(3,5-dichloro-4-hydroxyphenyl)-4-(1-(2-(dimethylamino)ethyl)piperidin-4-ylamino)quinolin-3-yl)methanone | 0.0018 |
| 821 | 1-(6-(3-chloro-5-fluoro-4-hydroxyphenyl)-4-(1-(2-(dimethylamino)ethyl)piperidin-4-ylamino)quinolin-3-yl)ethanone | 0.0053 |
| 822 | (6-(3-chloro-5-fluoro-4-hydroxyphenyl)-4-(1-(2-(dimethylamino)ethyl)piperidin-4-ylamino)quinolin-3-yl)(cyclopropyl)methanone | 0.0031 |
| 823 | 1-(6-(3,5-dichloro-4-hydroxyphenyl)-4-(1-(2-(dimethylamino)ethyl)piperidin-4-ylamino)quinolin-3-yl)ethanone | 0.0027 |
| 824 | 1-(4-(6-(3-aminopiperidin-1-yl)pyridin-3-ylamino)-6-(3,5-dichloro-4-hydroxyphenyl)quinolin-3-yl)propan-1-one trihydrochloride | 0.0016 |
| 825 | 1-(4-(6-(3-aminopiperidin-1-yl)pyridin-3-ylamino)-6-(3-chloro-5-fluoro-4-hydroxyphenyl)quinolin-3-yl)propan-1-one trihydrochloride | 0.0018 |
| 826 | 1-(6-(3-chloro-5-fluoro-4-hydroxyphenyl)-4-((1S,3R)-3-((dimethylamino)methyl)cyclohexylamino)quinolin-3-yl)ethanone hydrochloride | 0.0083 |
| 827 | 1-(6-(3,5-dichloro-4-hydroxyphenyl)-4-((1S,3R)-3-((dimethylamino)methyl)cyclohexylamino)quinolin-3-yl)ethanone hydrochloride | 0.0033 |
| 828 | (6-(3-chloro-5-fluoro-4-hydroxyphenyl)-4-(3-(2-(4-methylpiperazin-1-yl)ethyl)phenylamino)quinolin-3-yl)(cyclopropyl)methanone | 0.017 |
| 829 | cyclopropyl(6-(3,5-dichloro-4-hydroxyphenyl)-4-(3-(2-(4-methylpiperazin-1-yl)ethyl)phenylamino)quinolin-3-yl)methanone | 0.0051 |
| 830 | 1-(6-(3-chloro-5-fluoro-4-hydroxyphenyl)-4-(3-(2-(4-methylpiperazin-1-yl)ethyl)phenylamino)quinolin-3-yl)ethanone | 0.019 |
| 831 | 1-(6-(3,5-dichloro-4-hydroxyphenyl)-4-(3-(2-(4-methylpiperazin-1-yl)ethyl)phenylamino)quinolin-3-yl)ethanone | 0.0054 |
| 832 | 1-(6-(3-chloro-5-fluoro-4-hydroxyphenyl)-4-((1S,3R)-3-((4-methylpiperazin-1-yl)methyl)cyclohexylamino)quinolin-3-yl)ethanone hydrochloride | 0.009 |
| 833 | 1-(6-(3,5-dichloro-4-hydroxyphenyl)-4-(1R,4R)-4-((dimethylamino)methyl)cyclohexylamino)-2-methylquinolin-3-yl)ethanone hydrochloride | 0.17 |
| 834 | 1-(6-(3-chloro-5-fluoro-4-hydroxyphenyl)-4-(1R,4R)-4-((dimethylamino)methyl)cyclohexylamino)-2-methylquinolin-3-yl)ethanone hydrochloride | 0.82 |
| 835 | 1-(6-(3,5-dichloro-4-hydroxyphenyl)-4-((1S,3R)-3-((4-methylpiperazin-1-yl)methyl)cyclohexylamino)quinolin-3-yl)ethanone hydrochloride | 0.0027 |
| 836 | 1-(6-(3,5-dichloro-4-hydroxyphenyl)-4-(1-(1-methylpiperidin-4-yl)-1H-pyrazol-4-ylamino)quinolin-3-yl)ethanone dihydrochloride | 0.0014 |
| 837 | 1-(6-(3-chloro-5-fluoro-4-hydroxyphenyl)-2-methyl-4-(6-(4-methylpiperazin-1-yl)pyridin-3-ylamino)quinolin-3-yl)ethanone hydrochloride | 0.54 |
| 838 | 1-(6-(3,5-dichloro-4-hydroxyphenyl)-2-methyl-4-(6-(4-methylpiperazin-1-yl)pyridin-3-ylamino)quinolin-3-yl)ethanone hydrochloride | 0.097 |
| 839 | cyclopropyl(6-(3,5-dichloro-4-hydroxyphenyl)-4-(6-(4-methylpiperazin-1-yl)pyridin-3-ylamino)-7-(trifluoromethyl)quinolin-3-yl)methanone | 4.2 |
| 840 | (6-(3-chloro-5-fluoro-4-hydroxyphenyl)-4-(6-(4-methylpiperazin-1-yl)pyridin-3-ylamino)-7-(trifluoromethyl)quinolin-3-yl)(cyclopropyl)methanone | 3.1 |
| 841 | (6-(3-chloro-5-fluoro-4-hydroxyphenyl)-4-(1R,4R)-4-((dimethylamino)methyl)cyclohexylamino)-7-(trifluoromethyl)quinolin-3-yl)(cyclopropyl)methanone | 0.77 |
| 842 | cyclopropyl(6-(3,5-dichloro-4-hydroxyphenyl)-4-(1R,4R)-4-((dimethylamino)methyl)cyclohexylamino)-7-(trifluoromethyl)quinolin-3-yl)methanone | 0.93 |
| 843 | 1-(6-(3,5-dichloro-4-hydroxyphenyl)-4-(1R,4R)-4-(pyrrolidin-1-ylmethyl)cyclohexylamino)quinolin-3-yl)propan-1-one dihydrochloride | 0.0016 |
| 844 | 1-(6-(3-chloro-5-fluoro-4-hydroxyphenyl)-4-((1S,4r)-4-(((S)-2-(hydroxymethyl)pyrrolidin-1-yl)methyl)cyclohexylamino)quinolin-3-yl)ethanone | 0.0046 |

TABLE 2-continued

| Example | Compound Name | IC$_{50}$ (μM) (kinase assay) |
|---|---|---|
| 845 | 1-(6-(3-chloro-5-fluoro-4-hydroxyphenyl)-4-(1R,4R)-4-((ethyl(methyl)amino)methyl)cyclohexylamino)quinolin-3-yl) ethanone dihydrochloride | 0.002045 |
| 846 | 1-(6-(3-chloro-5-fluoro-4-hydroxyphenyl)-4-(1R,4R)-4-(pyrrolidin-1-ylmethyl)cyclohexylamino)quinolin-3-yl)propan-1-one dihydrochloride | 0.0023 |
| 847 | 1-(6-(3,5-dichloro-4-hydroxyphenyl)-4-(4-((dimethylamino)methyl)phenylamino)-7-methylquinolin-3-yl)ethanone hydrochloride | 0.55 |
| 848 | 1-(6-(3-chloro-5-fluoro-4-hydroxyphenyl)-4-(6-(2-(dimethylamino)ethoxy)pyridin-3-ylamino)quinolin-3-yl)ethanone hydrochloride | 0.011 |
| 849 | 1-(6-(3-chloro-5-fluoro-4-hydroxyphenyl)-4-(4-(4-methylpiperazine-1-carbonyl)cyclohexylamino)quinolin-3-yl)ethanone hydrochloride | 0.018 |
| 850 | 1-(6-(3,5-dichloro-4-hydroxyphenyl)-4-(1-(2-(dimethylamino)ethyl)piperidin-3-ylamino)quinolin-3-yl)ethanone | 0.0019 |
| 851 | 1-(6-(3-chloro-5-fluoro-4-hydroxyphenyl)-4-(1-(2-(dimethylamino)ethyl)piperidin-3-ylamino)quinolin-3-yl)ethanone | 0.04 |
| 852 | 1-(6-(3,5-dichloro-4-hydroxyphenyl)-4-(6-(2-(dimethylamino)ethoxy)pyridin-3-ylamino)quinolin-3-yl)ethanone dihydrochloride | 0.0028 |
| 853 | 1-(6-(3-chloro-5-fluoro-4-hydroxyphenyl)-4-((6-(3-(dimethylamino)pyrrolidin-1-yl)pyridin-3-yl)amino)quinolin-3-yl) ethanone | 0.018 |
| 854 | 1-(6-(3,5-dichloro-4-hydroxyphenyl)-4-((6-(3-(dimethylamino)pyrrolidin-1-yl)pyridin-3-yl)amino)quinolin-3-yl)ethanone | 0.0032 |
| 855 | 1-(6-(3,5-dichloro-4-hydroxyphenyl)-4-((6-(3-(dimethylamino)pyrrolidin-1-yl)pyridin-3-yl)amino)quinolin-3-yl)ethanone hydrochloride | 0.0021 |
| 856 | 1-(6-(3-chloro-5-fluoro-4-hydroxyphenyl)-7-methyl-4-((6-(4-methylpiperazin-1-yl)pyridin-3-yl)amino)quinolin-3-yl)ethanone hydrochloride | 0.46 |
| 857 | 1-(6-(3,5-dichloro-4-hydroxyphenyl)-4-((1R,4R)-4-((dimethylamino)methyl)cyclohexyl)amino)-7-methylquinolin-3-yl)ethanone | 3.4 |
| 858 | 1-(6-(3-chloro-5-fluoro-4-hydroxyphenyl)-4-((4-((dimethylamino)methyl)phenyl)amino)-7-methylquinolin-3-yl)ethanone hydrochloride | 0.2 |
| 859 | 1-(6-(3-chloro-5-fluoro-4-hydroxyphenyl)-4-((1R,4R)-4-((dimethylamino)methyl)cyclohexyl)amino)-7-methylquinolin-3-yl)ethanone hydrochloride | 0.84 |
| 860 | 1-(6-(3-chloro-5-fluoro-4-hydroxyphenyl)-4-((6-(3-(dimethylamino)pyrrolidin-1-yl)pyridin-3-yl)amino)quinolin-3-yl) propan-1-one | 0.0062 |
| 861 | 1-(6-(3,5-dichloro-4-hydroxyphenyl)-4-(((1S,3R)-3-(2-(dimethylamino)ethyl)cyclohexyl)amino)quinolin-3-yl)ethanone hydrochloride | 0.0032 |
| 862 | 1-(6-(3-chloro-5-fluoro-4-hydroxyphenyl)-4-(((1S,3R)-3-(2-(dimethylamino)ethyl)cyclohexyl)amino)quinolin-3-yl)ethanone hydrochloride | 0.0067 |
| 863 | 1-(6-(3,5-dichloro-4-hydroxyphenyl)-4-((6-(3-(dimethylamino)pyrrolidin-1-yl)pyridin-3-yl)amino)quinolin-3-yl)propan-1-one | 0.0039 |
| 864 | 1-(6-(3,5-dichloro-4-hydroxyphenyl)-4-((1R,4R)-4-((bis-(trideuteromethyl)amino)methyl)cyclohexyl)amino)quinolin-3-yl)ethanone dihydrochloride | 0.0011 |
| 865 | (1r,4r)-4-((3-acetyl-6-(3,5-dichloro-4-hydroxyphenyl)quinolin-4-yl)amino)-N,N-dimethylcyclohexanecarboxamide hydrochloride | 0.0093 |
| 866 | 1-(6-(3,5-dichloro-4-hydroxyphenyl)-7-methyl-4-((6-(4-methylpiperazin-1-yl)pyridin-3-yl)amino)quinolin-3-yl)ethanone hydrochloride | 0.34 |
| 867 | 1-(6-(3-chloro-5-fluoro-4-hydroxyphenyl)-4-((6-methyl-5-(2-(pyrrolidin-1-yl)ethyl)pyridin-3-yl)amino)quinolin-3-yl)ethanone | 0.014 |
| 868 | 1-(6-(3,5-dichloro-4-hydroxyphenyl)-4-((1R,4R)-4-(2-(diethylamino)ethoxy)cyclohexyl)amino)quinolin-3-yl)ethanone hydrochloride | 0.0029 |
| 869 | 1-(6-(3-chloro-5-fluoro-4-hydroxyphenyl)-4-((1R,4R)-4-(2-(diethylamino)ethoxy)cyclohexyl)amino)quinolin-3-yl)ethanone hydrochloride | 0.01 |
| 870 | (1r,4r)-4-((3-acetyl-6-(3-chloro-5-fluoro-4-hydroxyphenyl)quinolin-4-yl)amino)-N,N-dimethylcyclohexanecarboxamide hydrochloride | 0.035 |
| 871 | 1-(6-(3,5-dichloro-4-hydroxyphenyl)-4-((6-methyl-5-(2-(pyrrolidin-1-yl)ethyl)pyridin-3-yl)amino)quinolin-3-yl)ethanone | 0.0028 |
| 872 | 1-(4-((1R,4R)-4-((3-aminopyrrolidin-1-yl)methyl)cyclohexyl)amino)-6-(3,5-dichloro-4-hydroxyphenyl)-7-methylquinolin-3-yl)ethanone hydrochloride | 0.055 |

TABLE 2-continued

| Example | Compound Name | IC$_{50}$ (μM) (kinase assay) |
|---|---|---|
| 873 | 1-(6-(3,5-dichloro-4-hydroxyphenyl)-4-((5-(2-(pyrrolidin-1-yl)ethyl)pyridin-3-yl)amino)quinolin-3-yl)ethanone hydrochloride | 0.0067 |
| 874 | N-(1R,4R)-4-((3-acetyl-6-(3-chloro-5-fluoro-4-hydroxyphenyl)quinolin-4-yl)amino)cyclohexyl)-1-methylpyrrolidine-2-carboxamide hydrochloride | 0.016 |
| 875 | N-(1R,4R)-4-((3-acetyl-6-(3,5-dichloro-4-hydroxyphenyl)quinolin-4-yl)amino)cyclohexyl)-1-methylpyrrolidine-2-carboxamide hydrochloride | 0.0035 |
| 876 | N-(1R,4R)-4-((3-acetyl-6-(3-chloro-5-fluoro-4-hydroxyphenyl)quinolin-4-yl)amino)cyclohexyl)-2-(dimethylamino)acetamide dihydrochloride | 0.0088 |
| 877 | N-(1R,4R)-4-((3-acetyl-6-(3,5-dichloro-4-hydroxyphenyl)quinolin-4-yl)amino)cyclohexyl)-2-(dimethylamino)acetamide hydrochloride | 0.0027 |
| 878 | (S)-N-((1r,4S)-4-((3-acetyl-6-(3-chloro-5-fluoro-4-hydroxyphenyl)quinolin-4-yl)amino)cyclohexyl)-2-aminopropanamide dihydrochloride | 0.0079 |
| 879 | 2-chloro-6-fluoro-4-(3-(methylsulfonyl)-4-((3-(2-(pyrrolidin-1-yl)ethyl)phenyl)amino)quinolin-6-yl)phenol hydrochloride | 0.011 |
| 880 | 1-(6-(3-chloro-5-fluoro-4-hydroxyphenyl)-4-((5-(2-(pyrrolidin-1-yl)ethyl)pyridin-3-yl)amino)quinolin-3-yl)ethanone hydrochloride | 0.04 |
| 881 | cyclopropyl(6-(3,5-dichloro-4-hydroxyphenyl)-4-((5-(2-(pyrrolidin-1-yl)ethyl)pyridin-3-yl)amino)quinolin-3-yl)methanone hydrochloride | 0.0064 |
| 882 | (6-(3-chloro-5-fluoro-4-hydroxyphenyl)-4-((5-(2-(pyrrolidin-1-yl)ethyl)pyridin-3-yl)amino)quinolin-3-yl)(cyclopropyl)methanone | 0.019 |
| 883 | 2,6-dichloro-4-(3-(methylsulfonyl)-4-((3-(2-(pyrrolidin-1-yl)ethyl)phenyl)amino)quinolin-6-yl)phenol hydrochloride | 0.002 |
| 884 | 2,6-dichloro-4-(4-((6-(2-(dimethylamino)ethoxy)pyridin-3-yl)amino)-3-(methylsulfonyl)quinolin-6-yl)phenol hydrochloride | 0.0035 |
| 885 | 2-chloro-4-(4-((6-(2-(dimethylamino)ethoxy)pyridin-3-yl)amino)-3-(methylsulfonyl)quinolin-6-yl)-6-fluorophenol hydrochloride | 0.0083 |
| 886 | (S)-N-((1r,4S)-4-((3-acetyl-6-(3,5-dichloro-4-hydroxyphenyl)quinolin-4-yl)amino)cyclohexyl)-2-aminopropanamide dihydrochloride | 0.00066 |
| 887 | 1-(6-(3,5-dichloro-4-hydroxyphenyl)-4-((4-((4-methylpiperazin-1-yl)sulfonyl)phenyl)amino)quinolin-3-yl)ethanone hydrochloride | 0.036 |
| 888 | 1-(6-(4'-hydroxy-[1,1'-biphenyl]-4-yl)-4-((3-(2-(pyrrolidin-1-yl)ethyl)phenyl)amino)quinolin-3-yl)ethanone hydrochloride | 3.4 |
| 889 | 2-chloro-4-(4-((6-(3-(dimethylamino)pyrrolidin-1-yl)pyridin-3-yl)amino)-3-(methylsulfonyl)quinolin-6-yl)-6-fluorophenol hydrochloride | 0.0092 |
| 890 | 2,6-dichloro-4-(3-(methylsulfonyl)-4-(((1R,4R)-4-(pyrrolidin-1-ylmethyl)cyclohexyl)amino)quinolin-6-yl)phenol hydrochloride | 0.0027 |
| 891 | 2-chloro-6-fluoro-4-(3-(methylsulfonyl)-4-(((1R,4R)-4-(pyrrolidin-1-ylmethyl)cyclohexyl)amino)quinolin-6-yl)phenol hydrochloride | 0.0095 |
| 892 | (1r,4r)-4-((3-acetyl-6-(3,5-dichloro-4-hydroxyphenyl)quinolin-4-yl)amino)-N-(2-(dimethylamino)ethyl)cyclohexanecarboxamide hydrochloride | 0.0023 |
| 893 | (1r,4r)-4-((3-acetyl-6-(3-chloro-5-fluoro-4-hydroxyphenyl)quinolin-4-yl)amino)-N-(2-(dimethylamino)ethyl)cyclohexanecarboxamide hydrochloride | 0.0052 |
| 894 | 1-(6-(3-chloro-5-fluoro-4-hydroxyphenyl)-4-((4-((4-methylpiperazin-1-yl)sulfonyl)phenyl)amino)quinolin-3-yl)ethanone hydrochloride | 0.039 |
| 895 | 1-(6-(1H-benzo[d]imidazol-6-yl)-4-((1-(1-methylpiperidin-4-yl)-1H-pyrazol-4-yl)amino)quinolin-3-yl)ethanone hydrochloride | 0.065 |
| 896 | 1-(6-(1H-benzo[d]imidazol-6-yl)-4-((3-(2-(pyrrolidin-1-yl)ethyl)phenyl)amino)quinolin-3-yl)ethanone hydrochloride | 0.22 |
| 897 | 1-(6-(3,5-dichloro-4-hydroxyphenyl)-4-((2-methyl-5-(2-(pyrrolidin-1-yl)ethyl)pyridin-3-yl)amino)quinolin-3-yl)ethanone | 0.021 |
| 898 | 1-(6-(3,5-dichloro-4-hydroxyphenyl)-4-(((1R,4R)-4-(4-methylpiperazine-1-carbonyl)cyclohexyl)amino)quinolin-3-yl)ethanone hydrochloride | 0.0044 |
| 899 | 2,6-dichloro-4-(4-((1-(1-methylpiperidin-4-yl)-1H-pyrazol-4-yl)amino)-3-(methylsulfonyl)quinolin-6-yl)phenol hydrochloride | 0.0017 |

TABLE 2-continued

| Example | Compound Name | IC$_{50}$ (μM) (kinase assay) |
|---|---|---|
| 900 | 2-chloro-6-fluoro-4-(4-((1-(1-methylpiperidin-4-yl)-1H-pyrazol-4-yl)amino)-3-(methylsulfonyl)quinolin-6-yl)phenol hydrochloride | 0.0032 |
| 901 | 1-(6-(1H-benzo[d]imidazol-6-yl)-4-((6-(4-methylpiperazin-1-yl)pyridin-3-yl)amino)quinolin-3-yl)ethanone hydrochloride | 0.1 |
| 902 | 1-(6-(1H-benzo[d]imidazol-6-yl)-4-((6-(2-(dimethylamino)ethoxy)pyridin-3-yl)amino)quinolin-3-yl)ethanone hydrochloride | 0.042 |
| 903 | 1-(6-(3,5-dichloro-4-hydroxyphenyl)-4-((1R,4R)-4-((dimethylamino)methyl)cyclohexyl)amino)-7-fluoroquinolin-3-yl)ethanone hydrochloride | 0.0017 |
| 904 | 1-(6-(3-chloro-5-fluoro-4-hydroxyphenyl)-4-((1R,4R)-4-((dimethylamino)methyl)cyclohexyl)amino)-7-fluoroquinolin-3-yl)ethanone hydrochloride | 0.017 |
| 905 | 1-(6-(1H-benzo[d]imidazol-6-yl)-4-((6-(3-(dimethylamino)pyrrolidin-1-yl)pyridin-3-yl)amino)quinolin-3-yl)ethanone hydrochloride | 0.11 |
| 906 | 2,6-dichloro-4-(4-((6-(3-(dimethylamino)pyrrolidin-1-yl)pyridin-3-yl)amino)-3-(methylsulfonyl)quinolin-6-yl)phenol hydrochloride | 0.0024 |
| 907 | N-((1R,4R)-4-((3-acetyl-6-(3-chloro-5-fluoro-4-hydroxyphenyl)quinolin-4-yl)amino)cyclohexyl)-2-amino-3-methylbutanamide dihydrochloride | 0.0047 |
| 908 | 1-(4-((1R,4R)-4-((dimethylamino)methyl)cyclohexyl)amino)-6-(pyridin-4-yl)quinolin-3-yl)ethanone hydrochloride | 0.23 |
| 909 | 4-(4-((6-(3-aminopiperidin-1-yl)pyridin-3-yl)amino)-3-(methylsulfonyl)quinolin-6-yl)-2-chloro-6-fluorophenol trihydrochloride | 0.0016 |
| 910 | 1-(4-((1R,4R)-4-((dimethylamino)methyl)cyclohexyl)amino)-6-(1H-indazol-5-yl)quinolin-3-yl)ethanone hydrochloride | 0.1 |
| 911 | 1-(6-(1H-benzo[d]imidazol-6-yl)-4-((1R,4R)-4-((dimethylamino)methyl)cyclohexyl)amino)quinolin-3-yl)ethanone hydrochloride | 0.13 |
| 912 | 1-(4-((1R,4R)-4-((dimethylamino)methyl)cyclohexyl)amino)-6-(1H-pyrazol-4-yl)quinolin-3-yl)ethanone hydrochloride | 0.074 |
| 913 | 4-(4-((6-(3-aminopiperidin-1-yl)pyridin-3-yl)amino)-3-(methylsulfonyl)quinolin-6-yl)-2,6-dichlorophenol trihydrochloride | 0.00094 |
| 914 | (S)-N-((1r,4S)-4-((3-acetyl-6-(3-chloro-5-fluoro-4-hydroxyphenyl)quinolin-4-yl)amino)cyclohexyl)-2-amino-3,3-dimethylbutanamide hydrochloride | 0.028 |
| 915 | N-((1R,4R)-4-((3-acetyl-6-(3,5-dichloro-4-hydroxyphenyl)quinolin-4-yl)amino)cyclohexyl)-2-amino-3-methylbutanamide dihydrochloride | 0.0031 |
| 916 | (6-(3-chloro-4-hydroxy-5-methoxyphenyl)-4-((1R,4R)-4-((dimethylamino)methyl)cyclohexyl)amino)quinolin-3-yl)(cyclopentyl)methanone hydrochloride | 0.0048 |
| 917 | cyclopentyl(6-(3,5-dichloro-4-hydroxyphenyl)-4-((1R,4R)-4-((dimethylamino)methyl)cyclohexyl)amino)quinolin-3-yl)methanone hydrochloride | 0.003 |
| 918 | 1-(6-(3,5-dichloro-4-hydroxyphenyl)-4-((1R,4R)-4-((dimethylamino)methyl)cyclohexyl)amino)quinolin-3-yl)-2,2-dimethylpropan-1-one hydrochloride | 0.022 |
| 919 | 1-(6-(3-chloro-5-fluoro-4-hydroxyphenyl)-4-((1R,4R)-4-((dimethylamino)methyl)cyclohexyl)amino)quinolin-3-yl)-2,2-dimethylpropan-1-one hydrochloride | 0.034 |
| 920 | (S)-N-((1r,4S)-4-((3-acetyl-6-(3,5-dichloro-4-hydroxyphenyl)quinolin-4-yl)amino)cyclohexyl)pyrrolidine-2-carboxamide dihydrochloride | 0.0019 |
| 921 | (S)-N-((1r,4S)-4-((3-acetyl-6-(3-chloro-5-fluoro-4-hydroxyphenyl)quinolin-4-yl)amino)cyclohexyl)pyrrolidine-2-carboxamide dihydrochloride | 0.012 |
| 922 | (S)-N-((1r,4S)-4-((3-acetyl-6-(3,5-dichloro-4-hydroxyphenyl)quinolin-4-yl)amino)cyclohexyl)-2-amino-3,3-dimethylbutanamide hydrochloride | 0.0042 |
| 923 | 1-(6-(3,5-dichloro-4-hydroxyphenyl)-7-fluoro-4-((1R,4R)-4-(pyrrolidin-1-ylmethyl)cyclohexyl)amino)quinolin-3-yl)ethanone hydrochloride | 0.007 |
| 924 | (6-(3-chloro-4-hydroxy-5-methoxyphenyl)-4-((3-(2-(pyrrolidin-1-yl)ethyl)phenyl)amino)quinolin-3-yl)(cyclopentyl)methanone hydrochloride | 0.018 |
| 925 | 1-(6-(3-chloro-5-fluoro-4-hydroxyphenyl)-7-fluoro-4-((1R,4R)-4-(pyrrolidin-1-ylmethyl)cyclohexyl)amino)quinolin-3-yl)ethanone hydrochloride | 0.019 |

TABLE 2-continued

| Example | Compound Name | IC$_{50}$ (μM) (kinase assay) |
|---|---|---|
| 926 | 1-(6-(3-chloro-4-hydroxy-5-methoxyphenyl)-7-fluoro-4-((1R,4R)-4-(pyrrolidin-1-ylmethyl)cyclohexyl)amino)quinolin-3-yl)ethanone hydrochloride | 0.0079 |
| 927 | cyclopentyl(6-(3,5-dichloro-4-hydroxyphenyl)-4-((3-(2-(pyrrolidin-1-yl)ethyl)phenyl)amino)quinolin-3-yl)methanone hydrochloride | 0.0096 |
| 928 | 2-amino-N-(1R,4R)-4-((6-(3,5-dichloro-4-hydroxyphenyl)-3-pivaloylquinolin-4-yl)amino)cyclohexyl)propanamide hydrochloride | 0.015 |
| 929 | 1-(4-((1R,4R)-4-((dimethylamino)methyl)cyclohexyl)amino)-6-(6-hydroxynaphthalen-2-yl)quinolin-3-yl)ethanone hydrochloride | 0.064 |
| 930 | 1-(6-(3-chloro-5-fluoro-4-hydroxyphenyl)-4-((1-(1-methylpiperidin-4-yl)-1H-pyrazol-4-yl)amino)quinolin-3-yl)-2,2-dimethylpropan-1-one hydrochloride | 0.017 |
| 931 | 1-(6-(3,5-dichloro-4-hydroxyphenyl)-4-((1-(1-methylpiperidin-4-yl)-1H-pyrazol-4-yl)amino)quinolin-3-yl)-2,2-dimethylpropan-1-one hydrochloride | 0.0062 |
| 932 | 2-amino-N-(1R,4R)-4-((6-(3-chloro-5-fluoro-4-hydroxyphenyl)-3-pivaloylquinolin-4-yl)amino)cyclohexyl)propanamide hydrochloride | 0.047 |
| 933 | 2-(3-acetyl-4-(1R,4R)-4-((dimethylamino)methyl)cyclohexylamino)quinolin-6-yl)-5-methoxyisoindolin-1-one | 1.2 |
| 934 | (S)-1-(4-(6-(3-aminopiperidin-1-yl)pyridin-3-ylamino)-6-(3,5-dichloro-4-hydroxy phenyl)quinolin-3-yl)propan-1-one trihydrochloride | 0.0012 |
| 935 | 1-(4-(1R,4R)-4-((dimethylamino)methyl)cyclohexylamino)-6-(4-hydroxyphenyl)quinolin-3-yl)ethanone dihydrochloride | 0.08 |
| 936 | (4-((trans)-4-aminocyclohexylamino)-6-(3-chloro-5-fluoro-4-hydroxyphenyl)quinolin-3-yl)(cyclopropyl)methanone hydrochloride | 0.0019 |
| 937 | 1-(4-((trans)-4-aminocyclohexylamino)-6-(3-chloro-5-fluoro-4-hydroxyphenyl)quinolin-3-yl)-2-methylpropan-1-one dihydrochloride | 0.0054 |
| 938 | 1-(4-((trans)-4-aminocyclohexylamino)-6-(3,5-difluoro-4-hydroxyphenyl) quinolin-3-yl)-2-methylpropan-1-one dihydrochloride | 0.017 |
| 939 | 1-(4-((trans)-4-aminocyclohexylamino)-6-(3,5-dichloro-4-hydroxyphenyl) quinolin-3-yl)ethanone hydrochloride | 0.0034 |
| 940 | 1-(4-((trans)-4-aminocyclohexylamino)-6-(3-chloro-4-hydroxy-5-methoxyphenyl)quinolin-3-yl) ethanone dihydrochloride | 0.0012 |
| 941 | cyclopropyl(6-(3,5-dichloro-4-hydroxyphenyl)-4-((trans)-4-(dimethylamino)cyclohexylamino) quinolin-3-yl)methanone dihydrobromide | 0.0016 |
| 264 | (6-(3-chloro-5-fluoro-4-hydroxyphenyl)-4-((trans)-4-(dimethylamino)cyclohexylamino) quinolin-3-yl)(cyclopropyl) methanone | 0.0029 |
| 324 | cyclopropyl(6-(3,5-dichloro-4-hydroxyphenyl)-4-((trans)-4-((dimethylamino)methyl) cyclohexylamino)quinolin-3-yl) methanone | 0.00085 |
| 366 | Cyclopropyl{6-(3,5-dichloro-4-hydroxyphenyl)-4-[4-(pyrrolidin-1-ylmethyl)phenylamino]quinolin-3-yl}methanone | 0.15 |
| 374 | 1-(6-(3,5-dichloro-4-hydroxyphenyl)-4-((4-((dimethylamino)methyl)phenyl)amino)quinolin-3-yl)ethanone | 0.0066 |
| 942 | 1-(6-(3,5-dichloro-4-hydroxyphenyl)-4-(4-((dimethylamino)methyl) phenylamino)quinolin-3-yl) ethanone dihydrobromide | 0.0022 |
| 378 | 1-(6-(3-chloro-5-fluoro-4-hydroxyphenyl)-4-((trans-4-((dimethylamino)methyl)cyclohexyl)amino)quinolin-3-yl)ethanone | 0.0061 |
| 943 | 1-(6-(3-chloro-5-fluoro-4-hydroxyphenyl)-4-((trans)-4-((dimethylamino)methyl) cyclohexylamino)quinolin-3-yl) ethanone dihydrochloride | 0.004 |
| 379 | 1-(6-(3,5-dichloro-4-hydroxyphenyl)-4-((trans-4-((dimethylamino)methyl)cyclohexyl)amino)quinolin-3-yl)ethanone | 0.0031 |
| 944 | 1-(6-(3,5-dichloro-4-hydroxyphenyl)-4-((trans)-4-((dimethylamino)methyl) cyclohexylamino)quinolin-3-yl) ethanone dihydrochloride | 0.00094 |

EXAMPLES

Western Blot Analysis

To evaluate the expression status of MELK in several cell lines, western blot analysis was performed using crude cell lysate collected from those cells. Anti-MELK antibody (clone 31, BD Biosciences) was used to visualize the expression. Breast cancer cell lines, BT-549, T47D and A549 expressed MELK significantly although Bladder cancer cell line and HT-1197 showed no expression of MELK.

EXAMPLES

Cell-Based Assay

Active candidate inhibitors against MELK were evaluated for their target-specific cytotoxicity using T47D, A549, BT-549, and HT-1197 cells was used for negative control. 100 micro-L of cell suspension was seeded onto 96-well microtiter plate (ViewPlate-96FTC, PerkinElmer). The initial cell concentration of T47D, A549, BT-549, and HT-1197 were 3,000 cells/well, 2,000 cells/well and 2,500 cells/well, respectively. Cellular growth was determined using Cell Counting Kit-8 (DOJINDO) at 72 hours after the exposure of the candidate inhibitors. IC50 was used as an indicator of the anti-proliferative activity of the inhibitors, and calculated by serial dilution method (0, 1.5625, 3.125, 6.25, 12.5, 25, 50, and 100 micro-M). Accurate IC50 values were calculated as described previously.

$IC_{50}$ values of the typical compounds of the present invention are shown in following table 3:

TABLE 3

| Example | Compound Name | IC50 (μM) (BT549) | $IC_{50}$ (μM) (T47D) | $IC_{50}$ (μM) (A549) | $IC_{50}$ (μM) (HT1197) |
|---|---|---|---|---|---|
| 55 | {4-[trans-4-aminocyclohexylamino]-6-(4-hydroxyphenyl)quinolin-3-yl}(cyclopropyl)methanone | 0.43 | 0.2 | 0.48 | 2 |
| 81 | {4-[trans-4-aminocyclohexylamino]-6-(4-hydroxy-3-methoxyphenyl)quinolin-3-yl}(cyclopropyl)methanone | 0.55 | 0.13 | 0.23 | 1.2 |
| 96 | 5-{4-[trans-4-aminocyclohexylamino]-3-(cyclopropanecarbonyl)quinolin-6-yl}pyrimidine-2-carbonitrile | 0.93 | 0.29 | 1.3 | 1.5 |
| 108 | 5-{4-[trans-4-aminocyclohexylamino]-3-isobutyrylquinolin-6-yl}picolinonitrile | 14 | 6.1 | 13 | 15 |
| 116 | {4-[trans-4-aminocyclohexylamino]-6-(1H-benzo[d]imidazol-5-yl)quinolin-3-yl}(cyclopropyl)methanone | 5.7 | 1.8 | 13 | 15 |
| 119 | 5-{4-[trans-4-aminocyclohexylamino]-3-(cyclopropanecarbonyl)quinolin-6-yl}thiophene-2-carbonitrile | 14 | 8.8 | 5.4 | 8 |
| 133 | Cyclopropyl[4-{4-[(dimethylamino)methyl]piperidin-1-yl}-6-(4-hydroxy-3-methoxyphenyl)quinolin-3-yl]methanone | 1.7 | 0.7 | 0.79 | 1.9 |
| 155 | [6-(3-Chloro-4-hydroxy-5-methoxyphenyl)-4-(2,8-diazaspiro[4,5]decan-8-yl)quinolin-3-yl](cyclopropyl)methanone | 0.79 | 0.43 | 0.68 | 2.4 |
| 156 | {4-[trans-4-aminocyclohexylamino]-6-(3,5-difluoro-4-hydroxyphenyl)quinolin-3-yl}(cyclopropyl)methanone | 0.16 | 0.095 | 0.88 | 3.1 |
| 157(a) | {4-[trans-4-aminocyclohexylamino]-6-(3,5-dichloro-4-hydroxyphenyl)quinolin-3-yl}(cyclopropyl)methanone | 0.33 | 0.15 | 0.57 | 3.7 |
| 157(b) | {4-[trans-4-aminocyclohexylamino]-6-(3,5-dichloro-4-hydroxyphenyl)quinolin-3-yl}(cyclopropyl)methanone dihydrochloride | 0.31 | 0.096 | 0.3 | 4.7 |
| 160 | {4-[trans-4-aminocyclohexylamino]-6-(2,5-dichloro-4-hydroxyphenyl)quinolin-3-yl}(cyclopropyl)methanone | 0.39 | 0.28 | 0.68 | 1.2 |
| 165 | {4-(cis-4-aminocyclohexylamino)-6-(4-hydroxy-3-methoxyphenyl)quinolin-3-yl}(cyclopropyl)methanone | 0.93 | 0.57 | 0.45 | 2.1 |

TABLE 3-continued

| Example | Compound Name | IC50 (μM) (BT549) | IC$_{50}$ (μM) (T47D) | IC$_{50}$ (μM) (A549) | IC$_{50}$ (μM) (HT1197) |
|---|---|---|---|---|---|
| 177 | Cyclopropyl[6-(4-hydroxy-3-methoxyphenyl)-4-(1-methylpiperidin-4-ylamino)quinolin-3-yl]methanone | 2.6 | 0.88 | 0.83 | 2.3 |
| 179 | {4-[trans-4-aminocyclohexylamino]-6-(3-chloro-5-fluoro-4-hydroxyphenyl)quinolin-3-yl}(cyclopropyl)methanone | 0.22 | 0.11 | 0.85 | 5.2 |
| 180 | [4-(cis-4-aminocyclohexylamino)-6-(3,5-difluoro-4-hydroxyphenyl)quinolin-3-yl](cyclopropyl)methanone | 0.3 | 0.17 | 0.9 | 4.5 |
| 181 | Cyclopropyl[6-(3,5-difluoro-4-hydroxyphenyl)-4-{4-[1-(dimethylamino)ethyl]piperidin-1-yl}quinolin-3-yl]methanone | 0.73 | 0.47 | 0.7 | 1.1 |
| 185(a) | {6-(3-Chloro-4-hydroxy-5-methoxyphenyl)-4-[4-(diethylamino)cyclohexylamino]quinolin-3-yl}(cyclopropyl)methanone | 2 | 0.59 | 0.42 | 6.9 |
| 185(b) | {6-(3-Chloro-4-hydroxy-5-methoxyphenyl)-4-[4-(diethylamino)cyclohexylamino]quinolin-3-yl}(cyclopropyl)methanone dihydrochloride | 1 | 0.49 | 0.18 | 4.7 |
| 187 | Cyclopropyl(4-{4-[1-(dimethylamino)ethyl]piperidin-1-yl}-6-(4-hydroxy-3-methoxyphenyl)quinolin-3-yl)methanone | 2 | 0.44 | 0.65 | 2.2 |
| 192 | {6-(3-Chloro-4-hydroxyphenyl)-4-[4-(diethylamino)cyclohexylamino]quinolin-3-yl}(cyclopropyl)methanone | 1.3 | 0.57 | 0.42 | 2.2 |
| 193 | Cyclopropyl{4-[4-(diethylamino)cyclohexylamino]-6-(4-hydroxy-3-methoxyphenyl)quinolin-3-yl}methanone | 2 | 0.52 | 0.59 | 4.2 |
| 201 | {6-(3-Chloro-4-hydroxy-5-methoxyphenyl)-4-[(1-methylpiperidin-4-yl)methylamino]quinolin-3-yl}(cyclopropyl)methanone | 1.8 | 0.76 | 0.73 | 7.4 |
| 205 | 1-{4-[trans-4-aminocyclohexylamino]-6-(3-chloro-5-fluoro-4-hydroxyphenyl)quinolin-3-yl}-2-methylpropan-1-one | 0.15 | 0.066 | 0.6 | 2.4 |
| 212 | {4-[trans-4-aminocyclohexylamino]-6-(pyridin-4-yl)quinolin-3-yl}(cyclopropyl)methanone | 2.5 | 2.7 | 0.99 | 7.2 |
| 213 | {4-[trans-4-aminocyclohexylamino]-6-(1H-pyrazol-4-yl)quinolin-3-yl}(cyclopropyl)methanone | 1.7 | 0.89 | 5.1 | 14 |
| 214 | 1-{4-[trans-4-aminocyclohexylamino]-6-(3,5-difluoro-4-hydroxyphenyl)quinolin-3-yl}-2-methylpropan-1-one | 0.084 | 0.048 | 0.65 | 1.4 |
| 215 | {6-(3-Chloro-4-hydroxyphenyl)-4-[2-(piperazin-1-yl)ethylamino]quinolin-3-yl}(cyclopropyl)methanone | 1.5 | 0.92 | 1.2 | 3.9 |
| 219 | 1-{4-[trans-4-aminocyclohexylamino]-6-(3-chloro-4-hydroxyphenyl)quinolin-3-yl}-2-methylpropan-1-one | 0.25 | 0.11 | 0.32 | 1.2 |
| 225(a) | 1-{4-[trans-4-aminocyclohexylamino]-6-(3,5-dichloro-4-hydroxyphenyl)quinolin-3-yl}-2-methylpropan-1-one | 0.18 | 0.073 | 0.43 | 2 |
| 225(b) | 1-{4-[trans-4-aminocyclohexylamino]-6-(3,5-dichloro-4-hydroxyphenyl)quinolin-3-yl}-2-methylpropan-1-one dihydrochloride | 0.17 | 0.048 | 0.22 | 1.6 |

TABLE 3-continued

| Example | Compound Name | IC50 (μM) (BT549) | IC$_{50}$ (μM) (T47D) | IC$_{50}$ (μM) (A549) | IC$_{50}$ (μM) (HT1197) |
|---|---|---|---|---|---|
| 240 | 2-Chloro-4-{4-[4-(diethylamino) cyclohexylamino]-3-(methylsulfonyl)quinolin-6-yl}-6-methoxyphenol dihydrochloride | 1.5 | 0.97 | 0.78 | 3.8 |
| 243 | [6-(3-Chloro-4-hydroxy-5-methoxyphenyl)-4-(piperidin-4-ylmethylamino)quinolin-3-yl](cyclopropyl)methanone | 1.8 | 0.33 | 0.62 | 7.3 |
| 245 | 2-Chloro-4-[4-{4-[1-(dimethylamino)ethyl]piperidin-1-yl}-3-(methylsulfonyl)quinolin-6-yl]-6-methoxyphenol | 0.74 | 0.35 | 0.25 | 2.3 |
| 246 | 2-Chloro-4-[4-{4-[1-(dimethylamino)ethyl]piperidin-1-yl}-3-(methylsulfonyl)quinolin-6-yl] phenol | 0.72 | 0.18 | 0.35 | 1.2 |
| 249 | [6-(3-Chloro-4-hydroxy-5-methoxyphenyl)-4-(1-methylpiperidin-4-ylamino)quinolin-3-yl](cyclopropyl)methanone | 1.3 | 0.83 | 0.3 | 4.4 |
| 250 | [6-(3-Chloro-4-hydroxy-5-methoxyphenyl)-4-{4-[1-(dimethylamino)ethyl]piperidin-1-yl}quinolin-3-yl](cyclopropyl)methanone | 0.61 | 0.16 | 0.11 | 1.7 |
| 255 | {6-(3-Chloro-4-hydroxy-5-methoxyphenyl)-4-[trans-4-(dimethylamino)cyclohexylamino]quinolin-3-yl}(cyclopropyl)methanone | 0.64 | 0.28 | 0.18 | 1.9 |
| 256 | 1-{4-[trans-4-aminocyclohexylamino]-6-(3,5-dichloro-4-hydroxyphenyl)quinolin-3-yl}ethanone | 0.31 | 0.064 | 0.44 | 100 |
| 258 | 1-{4-[trans-4-aminocyclohexylamino]-6-(3,5-difluoro-4-hydroxyphenyl)quinolin-3-yl}ethanone | 0.16 | 0.071 | 0.85 | 100 |
| 259 | 1-{4-[trans-4-aminocyclohexylamino]-6-(3-chloro-4-hydroxy-5-methoxyphenyl)quinolin-3-yl}ethanone | 0.43 | 0.057 | 0.099 | 2.5 |
| 262 | 1-(4-((trans)-4-aminocyclohexylamino)-6-(3-chloro-4-hydroxy-5-methoxyphenyl)quinolin-3-yl)-3-methylbutan-1-one | 0.91 | 0.13 | 0.36 | 2.2 |
| 263 | Cyclopropyl{6-(3,5-dichloro-4-hydroxyphenyl)-4-[trans-4-(dimethylamino)cyclohexylamino]quinolin-3-yl}methanone | 0.41 | 0.13 | 0.2 | 1.2 |
| 266 | Cyclopropyl(4-((trans)-4-(dimethylamino)cyclohexylamino)-6-(4-hydroxy-3-methoxyphenyl)quinolin-3-yl)methanone | 0.94 | 0.29 | 0.37 | 3 |
| 267 | 1-{4-[trans-4-aminocyclohexylamino]-6-(3,5-dichloro-4-hydroxyphenyl)quinolin-3-yl}-3-methylbutan-1-one dihydrochloride | 0.72 | 0.14 | 0.38 | 3 |
| 269 | [6-(3-Chloro-5-fluoro-4-hydroxyphenyl)-4-{4-[1-(dimethylamino)ethyl]piperidin-1-yl}quinolin-3-yl](cyclopropyl)methanone | 0.5 | 0.22 | 0.44 | 1.3 |
| 270 | {6-(3-Chloro-5-fluoro-4-hydroxyphenyl)-4-[(1-methylpiperidin-4-yl)methylamino]quinolin-3-yl}(cyclopropyl)methanone | 1.1 | 0.51 | 0.69 | 2.9 |
| 276 | [6-(3-Chloro-4-hydroxy-5-methoxyphenyl)-4-{4-[(dimethylamino)methyl]piperidin-1-yl}quinolin-3-yl](cyclopropyl)methanone | 0.58 | 0.16 | 0.21 | 1.8 |
| 279 | [6-(3-Chloro-4-hydroxyphenyl)-4-{4-[(dimethylamino)methyl]piperidin-1-yl}quinolin-3-yl](cyclopropyl)methanone | 0.86 | 0.21 | 0.3 | 6.7 |

TABLE 3-continued

| Example | Compound Name | IC50 (μM) (BT549) | IC$_{50}$ (μM) (T47D) | IC$_{50}$ (μM) (A549) | IC$_{50}$ (μM) (HT1197) |
| --- | --- | --- | --- | --- | --- |
| 280 | {6-(3-Chloro-4-hydroxy-5-methoxyphenyl)-4-[4-(pyrrolidin-1-ylmethyl) piperidin-1-yl]quinolin-3-yl} (cyclopropyl)methanone | 0.71 | 0.25 | 0.2 | 2.9 |
| 283 | {6-(3-Chloro-5-fluoro-4-hydroxyphenyl)-4-[4-(pyrrolidin-1-ylmethyl) piperidin-1-yl]quinolin-3-yl} (cyclopropyl)methanone | 0.72 | 0.35 | 0.54 | 3 |
| 284 | {4-[trans-4-aminocyclohexylamino]-6-(3-chloro-4-hydroxy-5-methoxyphenyl)-7-fluoroquinolin-3-yl} (cyclopropyl)methanone | 1.7 | 0.62 | 0.49 | 2.2 |
| 294 | Cyclopropyl{6-(3,5-difluoro-4-hydroxyphenyl)-4-[trans-4-(dimethylamino) cyclohexylamino]-7-fluoroquinolin-3-yl} methanone | 0.55 | 0.68 | 0.43 | 1.5 |
| 295 | {6-(3-Chloro-5-fluoro-4-hydroxyphenyl)-4-[trans-4-(dimethylamino) cyclohexylamino]-7-fluoroquinolin-3-yl} (cyclopropyl)methanone | 0.39 | 0.42 | 0.31 | 1.2 |
| 303 | 1-{6-(3-Chloro-4-hydroxy-5-methoxyphenyl)-4-[4-(diethylamino) cyclohexylamino]quinolin-3-yl}ethanone | 1.7 | 0.39 | 0.35 | 7.4 |
| 305 | 1-[6-(3-chloro-4-hydroxy-5-methoxyphenyl)-4-{4-[(dimethylamino)methyl] piperidin-1-yl}quinolin-3-yl] ethanone | 0.33 | 0.21 | 0.14 | 3.6 |
| 307 | Cyclopropyl{6-(3-fluoro-4-hydroxy-5-methoxyphenyl)-4-[4-(pyrrolidin-1-ylmethyl) piperidin-1-yl]quinolin-3-yl} methanone | 1.2 | 0.79 | 0.53 | 3 |
| 309 | {6-(3-Chloro-4-hydroxy-5-methoxyphenyl)-4-[(3-amino) adamantylamino]quinolin-3-yl}(cyclopropyl)methanone | 0.49 | 0.32 | 0.28 | 0.5 |
| 311 | {6-(3-Chloro-4-hydroxy-5-methoxyphenyl)-4-[cis-4-(diethylamino) cyclohexylamino]quinolin-3-yl}(cyclopropyl)methanone | 1.5 | 0.51 | 0.21 | 7.6 |
| 313 | Cyclopropyl{6-[4-hydroxy-3-(trifluoromethoxy)phenyl]-4-[4-(pyrrolidin-1-ylmethyl] piperidin-1-yl}quinolin-3-yl) methanone | 1.3 | 0.67 | 0.8 | 3.2 |
| 314 | {6-(3-Chloro-4-hydroxy-5-methoxyphenyl)-4-[trans-4-(diethylamino) cyclohexylamino]quinolin-3-yl}(cyclopropyl)methanone | 0.73 | 0.16 | 0.22 | 4.3 |
| 315 | [6-(3-Chloro-4-hydroxy-5-methoxyphenyl)-4-{[trans-4-(dimethylamino)cyclohexyl] methylamino}quinolin-3-yl] (cyclopropyl)methanone | 1.4 | 0.64 | 0.3 | 3 |
| 316 | [6-(3-Chloro-4-hydroxy-5-methoxyphenyl)-4-{trans-4-[(dimethylamino)methyl] cyclohexylamino}quinolin-3-yl](cyclopropyl)methanone | 1.3 | 0.5 | 0.32 | 6.3 |
| 318 | 1-{6-(3-Chloro-4-hydroxyphenyl)-4-[4-(pyrrolidin-1-ylmethyl) piperidin-1-yl]quinolin-3-yl}-2-methylpropan-1-one | 1.8 | 0.92 | 0.87 | 1.4 |
| 321 | 1-{6-(3-Chloro-4-hydroxy-5-methoxyphenyl)-4-[4-(pyrrolidin-1-ylmethyl) piperidin-1-yl]quinolin-3-yl}ethanone | 0.29 | 0.19 | 0.18 | 5.1 |

TABLE 3-continued

| Example | Compound Name | IC50 (μM) (BT549) | IC$_{50}$ (μM) (T47D) | IC$_{50}$ (μM) (A549) | IC$_{50}$ (μM) (HT1197) |
|---|---|---|---|---|---|
| 323 | 1-{6-(3-Chloro-5-fluoro-4-hydroxyphenyl)-4-[4-(pyrrolidin-1-ylmethyl)piperidin-1-yl]quinolin-3-yl}-2-methylpropan-1-one | 1.5 | 0.63 | 0.87 | 1.2 |
| 325 | Cyclopropyl[6-(3,5-dichloro-4-hydroxyphenyl)-4-{[trans-4-(dimethylamino)cyclohexyl]methylamino}quinolin-3-yl]methanone | 1.9 | 0.78 | 0.62 | 10 |
| 327 | [6-(3-Chloro-5-fluoro-4-hydroxyphenyl)-4-{[trans-4-(dimethylamino)cyclohexyl]methylamino}quinolin-3-yl](cyclopropyl)methanone | 1 | 0.48 | 0.42 | 3 |
| 332 | {6-(3-Chloro-4-hydroxyphenyl)-4-[4-(morpholinomethyl)piperidin-1-yl]quinolin-3-yl}(cyclopropyl)methanone | 1.5 | 0.67 | 0.55 | 10 |
| 334 | {6-(3-Chloro-4-hydroxy-5-methoxyphenyl)-4-[4-(morpholinomethyl)piperidin-1-yl]quinolin-3-yl}(cyclopropyl)methanone | 0.77 | 0.55 | 0.41 | 4.8 |
| 335 | 1-{6-(3-Chloro-4-hydroxyphenyl)-4-[4-(diethylamino)cyclohexylamino]quinolin-3-yl}ethanone | 0.65 | 0.1 | 0.29 | 1.2 |
| 336 | 1-{6-(3-Chloro-5-fluoro-4-hydroxyphenyl)-4-[4-(pyrrolidin-1-ylmethyl)piperidin-1-yl]quinolin-3-yl}ethanone | 0.85 | 0.33 | 0.8 | 5 |
| 339 | [-(3-Chloro-4-hydroxy-5-methoxyphenyl)-4-{4-[(dimethylamino)methyl]phenylamino}quinolin-3-yl]cyclopropyl)methanone | 0.49 | 0.15 | 0.19 | 1.9 |
| 342 | {6-(3-Chloro-4-hydroxyphenyl)-4-[trans-4-(pyrrolidin-1-yl)cyclohexylamino]quinolin-3-yl}(cyclopropyl)methanone | 0.68 | 0.25 | 0.27 | 1.8 |
| 343 | {6-(3-Chloro-4-hydroxy-5-methoxyphenyl)-4-[trans-4-(pyrrolidin-1-yl)cyclohexylamino]quinolin-3-yl}(cyclopropyl)methanone | 0.68 | 0.33 | 0.2 | 3.4 |
| 345 | Cyclopropyl[6-(3,5-dichloro-4-hydroxyphenyl)-4-{4-[(dimethylamino)methyl]phenylamino}quinolin-3-yl]methanone | 0.1 | 0.054 | 0.051 | 0.67 |
| 347 | [6-(3-Chloro-5-fluoro-4-hydroxyphenyl)-4-{4-[(dimethylamino)methyl]piperidin-1-yl}quinolin-3-yl](cyclopropyl)methanone | 0.62 | 0.42 | 0.48 | 1.8 |
| 348 | 1-{6-(3-Chloro-4-hydroxy-5-methoxyphenyl)-4-[trans-4-(dimethylamino)cyclohexylamino]quinolin-3-yl}-3-methylbutan-1-one | 0.93 | 0.41 | 0.47 | 3 |
| 349 | {6-(3-Chloro-5-fluoro-4-hydroxyphenyl)-4-[4-(4-methylpiperazin-1-yl)piperidin-1-yl]quinolin-3-yl}(cyclopropyl)methanone | 0.91 | 0.49 | 0.98 | 5.8 |
| 350 | {6-(3-Chloro-4-hydroxyphenyl)-4-[4-(4-methylpiperazin-1-yl)piperidin-1-yl]quinolin-3-yl}(cyclopropyl)methanone | 0.98 | 0.26 | 0.44 | 2.5 |
| 351 | {6-(3-Chloro-4-hydroxy-5-methoxyphenyl)-4-[4-(4-methylpiperazin-1-yl)piperidin-1-yl]quinolin-3-yl}(cyclopropyl)methanone | 0.67 | 0.34 | 0.33 | 3 |

TABLE 3-continued

| Example | Compound Name | IC50 (μM) (BT549) | IC$_{50}$ (μM) (T47D) | IC$_{50}$ (μM) (A549) | IC$_{50}$ (μM) (HT1197) |
|---|---|---|---|---|---|
| 353 | Cyclopropyl[4-{4-[(dimethylamino)methyl]piperidin-1-yl}-6-(3-ethoxy-4-hydroxyphenyl)quinolin-3-yl]methanone | 1.5 | 0.61 | 0.68 | 2.5 |
| 356 | [6-(3-Chloro-4-hydroxy-5-methoxyphenyl)-4-{4-[(dimethylamino)methyl]phenyl}quinolin-3-yl](cyclopropyl)methanone | 0.87 | 0.46 | 0.45 | 3.5 |

">100" in the table means over 100 microM.

IC$_{50}$ values of the typical compounds of the present invention are shown in following table 4:

TABLE 4

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 384 | (6-(3-chloro-5-fluoro-4-hydroxyphenyl)-4-(4-((dimethylamino)methyl)piperidin-1-yl)quinolin-3-yl)(cyclopentyl)methanone | NT | 2 | 4 | 1.9 | NT |
| 385 | (6-(3-chloro-4-hydroxyphenyl)-4-(4-(diethylamino)cyclohexylamino)quinolin-3-yl)(cyclopentyl)methanone | NT | 1.7 | 1.9 | 0.94 | NT |
| 386 | (6-(3-chloro-5-fluoro-4-hydroxyphenyl)-4-(4-(diethylamino)cyclohexylamino)quinolin-3-yl)(cyclopentyl)methanone | NT | 0.41 | 0.78 | 0.4 | 0.29 |
| 387 | (6-(3-chloro-4-hydroxyphenyl)-4-(4-((dimethylamino)methyl)phenylamino)quinolin-3-yl)(cyclopentyl)methanone | NT | 1.6 | 1.9 | 1 | NT |
| 388 | (6-(3-chloro-5-fluoro-4-hydroxyphenyl)-4-(4-((dimethylamino)methyl)phenylamino)quinolin-3-yl)(cyclopentyl)methanone | NT | 0.52 | 1.5 | 0.52 | 0.21 |
| 389 | (6-(3-chloro-4-hydroxyphenyl)-4-(4-((dimethylamino)methyl)piperidin-1-yl)quinolin-3-yl)(cyclopentyl)methanone | NT | 2.9 | 6.9 | 1.7 | NT |
| 390 | 2-(6-(3-chloro-5-fluoro-4-hydroxyphenyl)-3-(cyclopropanecarbonyl)quinolin-4-ylamino)-1-(4-methylpiperazin-1-yl)ethanone | NT | 2 | 10 | 2.7 | NT |
| 391 | 1-(6-(3-chloro-4-hydroxy-5-methoxyphenyl)-4-(4-((dimethylamino)methyl)phenylamino)quinolin-3-yl)ethanone | NT | 0.12 | 4.2 | 1 | NT |
| 392 | 1-(6-(3-chloro-4-hydroxy-5-methoxyphenyl)-4-(1R,4R)-4-((dimethylamino)methyl)cyclohexylamino)quinolin-3-yl)ethanone | NT | 0.25 | 10 | 0.27 | 0.44 |
| 393 | 2-(6-(3-chloro-4-hydroxyphenyl)-3-(cyclopropanecarbonyl)quinolin-4-ylamino)-1-(4-methylpiperazin-1-yl)ethanone | NT | 2.6 | 100 | 2.2 | NT |
| 394 | (6-(3-chloro-4-hydroxy-5-methoxyphenyl)-4-(4-(2-(pyrrolidin-1-yl)ethyl)piperazin-1-yl)quinolin-3-yl)(cyclopropyl)methanone | NT | 0.4 | 5.3 | 0.25 | 0.24 |
| 395 | 2-(6-(3-chloro-4-hydroxy-5-methoxyphenyl)-3-(cyclopropanecarbonyl)quinolin-4-ylamino)-1-(4-methylpiperazin-1-yl)ethanone | NT | 10 | 10 | NT | NT |
| 396 | (6-(3-chloro-5-fluoro-4-hydroxyphenyl)-4-(4-(pyrrolidin-1-ylmethyl)phenylamino)quinolin-3-yl)(cyclopropyl)methanone | 0.38 | 0.21 | 1.6 | 0.087 | 0.084 |
| 397 | cyclopropyl(6-(3,5-dichloro-4-hydroxyphenyl)-4-(4-((4-methylpiperazin-1-yl)methyl)phenylamino)quinolin-3-yl)methanone | NT | 0.33 | 5.2 | 0.15 | 0.088 |
| 398 | (6-(3-chloro-4-hydroxy-5-methoxyphenyl)-4-(4-((4-methylpiperazin-1-yl)methyl)phenylamino)quinolin-3-yl)(cyclopropyl)methanone | NT | 0.78 | 4.7 | 0.38 | 0.73 |
| 399 | 2-chloro-4-(4-((dimethylamino)methyl)phenylamino)-3-(methylsulfonyl)quinolin-6-yl)-6-fluorophenol | NT | 0.27 | 1.9 | 0.47 | 0.16 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 400 | 2,6-dichloro-4-(4-(4-((dimethylamino)methyl)phenylamino)-3-(methylsulfonyl)quinolin-6-yl)phenol | NT | 0.23 | 1.8 | 0.3 | 0.07 |
| 401 | 2,6-dichloro-4-(4-(4-((dimethylamino)methyl)phenylamino)-3-(methylsulfonyl)quinolin-6-yl)phenol hydrochloride | 0.52 | 0.19 | 2.2 | 0.44 | 0.11 |
| 402 | (6-(3-chloro-5-fluoro-4-hydroxyphenyl)-4-(4-(2-(pyrrolidin-1-yl)ethyl)piperazin-1-yl)quinolin-3-yl)(cyclopropyl)methanone | NT | 0.88 | 5.1 | 1.2 | 0.48 |
| 403 | (6-(3-chloro-4-hydroxyphenyl)-4-(4-(2-(pyrrolidin-1-yl)ethyl)piperazin-1-yl)quinolin-3-yl)(cyclopropyl)methanone | NT | 4.5 | 10 | 1.3 | NT |
| 404 | (6-(3-chloro-4-hydroxy-5-methoxyphenyl)-4-(5-(piperazin-1-yl)pyridin-2-ylamino)quinolin-3-yl)(cyclopropyl)methanone | NT | 0.31 | 2.2 | 0.42 | NT |
| 405 | cyclopropyl(6-(4-hydroxy-3-methoxyphenyl)-4-(4-((4-methylpiperazin-1-yl)methyl)phenylamino)quinolin-3-yl)methanone | NT | 0.76 | 3.5 | 0.8 | NT |
| 406 | (6-(3-chloro-4-hydroxyphenyl)-4-(4-((4-methylpiperazin-1-yl)methyl)phenylamino)quinolin-3-yl)(cyclopropyl)methanone | NT | 1.3 | 3.4 | 0.49 | NT |
| 407 | 2-chloro-6-fluoro-4-(3-(methylsulfonyl)-4-(4-(pyrrolidin-1-ylmethyl)piperidin-1-yl)quinolin-6-yl)phenol | NT | 0.75 | 6.5 | 3.8 | NT |
| 408 | 2-chloro-4-(3-(methylsulfonyl)-4-(4-(pyrrolidin-1-ylmethyl)piperidin-1-yl)quinolin-6-yl)phenol | NT | 8.2 | 9.5 | 3.2 | NT |
| 409 | cyclopropyl(6-(3,5-dichloro-4-hydroxyphenyl)-4-(5-(piperazin-1-yl)pyridin-2-ylamino)quinolin-3-yl)methanone | NT | 0.074 | 1.6 | 0.26 | 0.098 |
| 410 | 2-chloro-4-(4-(4-((dimethylamino)methyl)phenylamino)-3-(methylsulfonyl)quinolin-6-yl)-6-methoxyphenol | NT | 0.58 | 6.2 | 1.2 | NT |
| 411 | 2-chloro-4-(4-(4-((dimethylamino)methyl)phenylamino)-3-(methylsulfonyl)quinolin-6-yl)phenol | NT | 0.29 | 0.63 | 0.37 | NT |
| 412 | 2-chloro-6-methoxy-4-(3-(methylsulfonyl)-4-(4-(pyrrolidin-1-ylmethyl)piperidin-1-yl)quinolin-6-yl)phenol | NT | 1.4 | 2.5 | 0.58 | NT |
| 413 | 5-(3-acetyl-4-(4-(pyrrolidin-1-ylmethyl)phenylamino)quinolin-6-yl)pyrimidine-2-carbonitrile | NT | 0.35 | 1.2 | 1.7 | NT |
| 414 | 5-(3-acetyl-4-(4-((dimethylamino)methyl)phenylamino)quinolin-6-yl)pyrimidine-2-carbonitrile | NT | 0.24 | 0.8 | 1.5 | NT |
| 415 | 1-(6-(3,5-dichloro-4-hydroxyphenyl)-4-(4-(pyrrolidin-1-ylmethyl)phenylamino)quinolin-3-yl)ethanone | NT | 0.12 | 10 | 0.15 | 0.067 |
| 416 | 1-(6-(3,5-dichloro-4-hydroxyphenyl)-4-(4-(pyrrolidin-1-ylmethyl)phenylamino)quinolin-3-yl)ethanone dihydrobromide | 0.19 | 0.066 | 6.1 | 0.11 | 0.053 |
| 417 | cyclopropyl(6-(3,5-dichloro-4-hydroxyphenyl)-4-(5-((dimethylamino)methyl)pyridin-2-ylamino)quinolin-3-yl)methanone | NT | 1.7 | 22 | 1.8 | NT |
| 418 | 5-(3-acetyl-4-(1R,4R)-4-((dimethylamino)methyl)cyclohexylamino)quinolin-6-yl)pyrimidine-2-carbonitrile | NT | 0.23 | 1.4 | 0.95 | 0.5 |
| 419 | 1-(6-(3-chloro-4-hydroxy-5-methoxyphenyl)-4-(4-(pyrrolidin-1-ylmethyl)phenylamino)quinolin-3-yl)ethanone | NT | 0.99 | 5.1 | 0.84 | NT |
| 420 | 2,6-dichloro-4-(4-(1R,4R)-4-((dimethylamino)methyl)cyclohexylamino)-3-(methylsulfonyl)quinolin-6-yl)phenol | NT | 0.47 | 2.5 | 0.69 | 0.14 |
| 421 | 2,6-dichloro-4-(4-(1R,4R)-4-((dimethylamino)methyl)cyclohexylamino)-3-(methylsulfonyl)quinolin-6-yl)phenol | 0.64 | 0.47 | 2.1 | 0.68 | 0.086 |
| 422 | 2-chloro-4-(4-(1R,4R)-4-((dimethylamino)methyl)cyclohexylamino)-3-(methylsulfonyl)quinolin-6-yl)-6-methoxyphenol | NT | 0.7 | 4.4 | 0.65 | NT |
| 423 | 2-chloro-4-(4-(1R,4R)-4-((dimethylamino)methyl)cyclohexylamino)-3-(methylsulfonyl)quinolin-6-yl)-6-fluorophenol | NT | 0.42 | 2.4 | 0.93 | 0.31 |
| 424 | 2-chloro-4-(4-(1R,4R)-4-((dimethylamino)methyl)cyclohexylamino)-3-(methylsulfonyl)quinolin-6-yl)phenol | NT | 0.43 | 1.1 | 0.79 | NT |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 425 | (6-(3-chloro-5-fluoro-4-hydroxyphenyl)-4-(6-(piperazin-1-yl)pyridin-3-ylamino)quinolin-3-yl)(cyclopropyl)methanone | 0.082 | 0.042 | 1.4 | 0.16 | 0.044 |
| 426 | 5-(3-(cyclopropanecarbonyl)-4-(1R,4R)-4-((dimethylamino)methyl)cyclohexylamino)quinolin-6-yl)pyrimidine-2-carbonitrile | NT | 0.43 | 3.7 | 1.5 | NT |
| 427 | (6-(3-chloro-4-hydroxyphenyl)-4-(5-(piperazin-1-yl)pyridin-2-ylamino)quinolin-3-yl)(cyclopropyl)methanone | NT | 0.2 | 1.4 | 0.24 | 0.24 |
| 428 | 6-(3-chloro-4-hydroxy-5-methoxyphenyl)-4-(4-(pyrrolidin-1-ylmethyl)piperidin-1-yl)quinoline-3-carbonitrile | NT | 7.6 | 13 | 2.6 | NT |
| 429 | (6-(3-chloro-4-hydroxy-5-methoxyphenyl)-4-(5-((dimethylamino)methyl)pyridin-2-ylamino)quinolin-3-yl)(cyclopropyl)methanone | NT | 3.8 | 19 | 5.1 | NT |
| 430 | cyclopropyl(6-(3,5-dichloro-4-hydroxyphenyl)-4-(4-(4-methylpiperazin-1-yl)phenyl)quinolin-3-yl)methanone | NT | 1.3 | 9.2 | 2.7 | NT |
| 431 | cyclopropyl(6-(3,5-dichloro-4-hydroxyphenyl)-4-(4-((dimethylamino)methyl)phenyl)quinolin-3-yl)methanone | NT | 0.97 | 7.5 | 0.59 | NT |
| 432 | 6-(3-chloro-5-fluoro-4-hydroxyphenyl)-4-(4-((dimethylamino)methyl)phenylamino)quinoline-3-carbonitrile | NT | 0.98 | 4.9 | 1.1 | NT |
| 433 | 6-(3-chloro-4-hydroxyphenyl)-4-(4-(pyrrolidin-1-ylmethyl)piperidin-1-yl)quinoline-3-carbonitrile | NT | 0.54 | 3.7 | 0.7 | NT |
| 434 | 6-(3-chloro-5-fluoro-4-hydroxyphenyl)-4-(4-(pyrrolidin-1-ylmethyl)piperidin-1-yl)quinoline-3-carbonitrile | NT | 0.45 | 10 | 1.1 | NT |
| 435 | (6-(3-chloro-5-fluoro-4-hydroxyphenyl)-4-(5-((dimethylamino)methyl)pyridin-2-ylamino)quinolin-3-yl)(cyclopropyl)methanone | NT | 2.7 | 12 | 2.8 | NT |
| 436 | (6-(3-chloro-4-hydroxy-5-methoxyphenyl)-4-(4-(pyrrolidin-1-ylmethyl)phenyl)quinolin-3-yl)(cyclopropyl)methanone | NT | 0.63 | 4.9 | 0.63 | NT |
| 437 | 1-(4-(6-(3-chloro-4-hydroxy-5-methoxyphenyl)-3-(cyclopropanecarbonyl)quinolin-4-yl)piperazin-1-yl)-2-(dimethylamino)ethanone | NT | 0.28 | 1.7 | 0.19 | 0.22 |
| 438 | (6-(3-chloro-4-hydroxy-5-methoxyphenyl)-4-(4-(4-methylpiperazin-1-yl)phenyl)quinolin-3-yl)(cyclopropyl)methanone | NT | 0.39 | 6.5 | 0.25 | 0.49 |
| 439 | 5-(3-(cyclopropanecarbonyl)-4-(5-((dimethylamino)methyl)pyridin-2-ylamino)quinolin-6-yl)pyrimidine-2-carbonitrile | NT | 0.61 | 3.6 | 4 | NT |
| 440 | 4-(6-(3-chloro-5-fluoro-4-hydroxyphenyl)-3-(cyclopropanecarbonyl)quinolin-4-yl)-1-(2-(pyrrolidin-1-yl)ethyl)piperazin-2-one | NT | 1.1 | 10 | 5.1 | NT |
| 441 | 1-(4-(6-(3-chloro-4-hydroxyphenyl)-3-(cyclopropanecarbonyl)quinolin-4-yl)piperazin-1-yl)-2-(dimethylamino)ethanone | NT | 0.63 | 46 | 0.54 | NT |
| 442 | 1-(4-(6-(3-chloro-5-fluoro-4-hydroxyphenyl)-3-(cyclopropanecarbonyl)quinolin-4-yl)piperazin-1-yl)-2-(dimethylamino)ethanone | NT | 0.74 | 5.5 | 1.5 | NT |
| 443 | (6-(3-chloro-5-fluoro-4-hydroxyphenyl)-4-(5-(1-methylpyrrolidin-2-yl)pyridin-2-ylamino)quinolin-3-yl)(cyclopropyl)methanone | NT | 7.1 | 10 | 6.6 | NT |
| 444 | (6-(3-chloro-4-hydroxy-5-methoxyphenyl)-4-(5-(1-methylpyrrolidin-2-yl)pyridin-2-ylamino)quinolin-3-yl)(cyclopropyl)methanone | NT | 6.8 | 10 | 7.6 | NT |
| 445 | cyclopropyl(6-(3,5-dichloro-4-hydroxyphenyl)-4-(5-(1-methylpyrrolidin-2-yl)pyridin-2-ylamino)quinolin-3-yl)methanone | NT | 7.5 | 10 | 4.1 | NT |
| 446 | 6-(3-chloro-5-fluoro-4-hydroxyphenyl)-4-(1R,4R)-4-(dimethylamino)cyclohexylamino)quinoline-3-carbonitrile | NT | 0.61 | 10 | 8.4 | NT |
| 447 | 6-(3-chloro-4-hydroxy-5-methoxyphenyl)-4-(1R,4R)-4-(dimethylamino)cyclohexylamino)quinoline-3-carbonitrile | NT | 0.15 | 2 | 0.4 | 0.076 |

TABLE 4-continued

| Example | Compound Name | IC50 (µM) (22Rv1) | IC50 (µM) (T47D) | IC50 (µM) (HT1197) | IC50 (µM) (A549) | IC50 (µM) (DU4475) |
|---|---|---|---|---|---|---|
| 448 | (6-(5-chloro-4-hydroxy-2-methylphenyl)-4-(4-((dimethylamino)methyl)piperidin-1-yl)quinolin-3-yl)(cyclopropyl)methanone | NT | 2 | 7.9 | 1.7 | NT |
| 449 | cyclopropyl(4-(4-((dimethylamino)methyl)piperidin-1-yl)-6-(6-hydroxynaphthalen-2-yl)quinolin-3-yl)methanone | NT | 1.8 | 3.3 | 0.64 | NT |
| 450 | cyclopropyl(6-(3,5-dichloro-4-hydroxyphenyl)-4-(6-(2-morpholinoethylamino)pyridin-3-yl)quinolin-3-yl)methanone | NT | 1.8 | 12 | 4.6 | NT |
| 451 | 4-(3-(cyclopropanecarbonyl)-6-(3,5-dichloro-4-hydroxyphenyl)quinolin-4-yl)-N-(2-(dimethylamino)ethyl)benzamide | NT | 0.68 | 17 | 3.8 | NT |
| 452 | cyclopropyl(6-(3,5-dichloro-4-hydroxyphenyl)-4-(4-(pyrrolidin-1-ylmethyl)phenyl)quinolin-3-yl)methanone | NT | 0.55 | 10 | 1.6 | NT |
| 453 | cyclopropyl(4-(4-((dimethylamino)methyl)piperidin-1-yl)-6-(1H-indol-5-yl)quinolin-3-yl)methanone | NT | 1.2 | 2.3 | 0.48 | NT |
| 454 | cyclopropyl(4-(4-((dimethylamino)methyl)piperidin-1-yl)-6-(4-hydroxy-3-(trifluoromethyl)phenyl)quinolin-3-yl)methanone | NT | 4 | 5.3 | 1.3 | NT |
| 455 | 1-((1S,4S)-5-(6-(3-chloro-5-fluoro-4-hydroxyphenyl)-3-(cyclopropanecarbonyl)quinolin-4-yl)-2,5-diazabicyclo[2.2.1]heptan-2-yl)-2-(dimethylamino)ethanone | NT | 12 | 60 | 37 | NT |
| 456 | 1-((1S,4S)-5-(6-(3-chloro-4-hydroxy-5-methoxyphenyl)-3-(cyclopropanecarbonyl)quinolin-4-yl)-2,5-diazabicyclo[2.2.1]heptan-2-yl)-2-(dimethylamino)ethanone | NT | 3.8 | 29 | 4.2 | NT |
| 457 | (6-(3-chloro-5-ethoxy-4-hydroxyphenyl)-4-(4-((dimethylamino)methyl)piperidin-1-yl)quinolin-3-yl)(cyclopropyl)methanone | NT | 0.22 | 2.4 | 0.14 | 0.21 |
| 458 | cyclopropyl(6-(4-(difluoromethoxy)phenyl)-4-(4-((dimethylamino)methyl)piperidin-1-yl)quinolin-3-yl)methanone | NT | 7.2 | 8.4 | NT | NT |
| 459 | cyclopropyl(6-(3,5-dichloro-4-hydroxyphenyl)-4-(6-(piperazin-1-yl)pyridin-3-yl)quinolin-3-yl)methanone | NT | 0.83 | 10 | 1.9 | NT |
| 460 | (6-(3-chloro-5-fluoro-4-hydroxyphenyl)-4-(4-(morpholinomethyl)phenylamino)quinolin-3-yl)(cyclopropyl)methanone | NT | 0.65 | 4.2 | 0.59 | 0.42 |
| 461 | 5-(3-(cyclopropanecarbonyl)-4-(4-(morpholinomethyl)phenylamino)quinolin-6-yl)pyrimidine-2-carbonitrile | NT | 0.17 | 2 | 1.6 | 0.41 |
| 462 | (6-(3-chloro-4-hydroxy-5-methoxyphenyl)-4-(4-(morpholinomethyl)phenylamino)quinolin-3-yl)(cyclopropyl)methanone | NT | 0.44 | 6 | 0.7 | 1.1 |
| 463 | cyclopropyl(6-(3,5-dichloro-4-hydroxyphenyl)-4-(4-(morpholinomethyl)phenylamino)quinolin-3-yl)methanone | NT | 0.52 | 3.6 | 0.43 | 0.26 |
| 464 | 1-((1S,4S)-5-(6-(3-chloro-4-hydroxyphenyl)-3-(cyclopropanecarbonyl)quinolin-4-yl)-2,5-diazabicyclo[2.2.1]heptan-2-yl)-2-(dimethylamino)ethanone | NT | 6.6 | 17 | 5.5 | 3.4 |
| 465 | cyclopropyl(6-(4-(difluoromethyl)phenyl)-4-(4-((dimethylamino)methyl)piperidin-1-yl)quinolin-3-yl)methanone | NT | 8.6 | 5.6 | NT | NT |
| 466 | 2-chloro-4-(4-(4-((dimethylamino)methyl)piperidin-1-yl)-3-(methylsulfinyl)quinolin-6-yl)phenol | NT | 0.67 | 6.7 | 1.9 | 1.1 |
| 467 | 2-chloro-4-(4-(4-((dimethylamino)methyl)piperidin-1-yl)-3-(methylsulfinyl)quinolin-6-yl)-6-fluorophenol | NT | 1.5 | 35 | 13 | 1.2 |
| 468 | 2-chloro-4-(4-(4-((dimethylamino)methyl)piperidin-1-yl)-3-(methylsulfinyl)quinolin-6-yl)-6-methoxyphenol | NT | 0.93 | 9.2 | 1.4 | 0.93 |
| 469 | 5-(3-(cyclopropanecarbonyl)-4-(6-(4-methylpiperazin-1-yl)pyridin-3-ylamino)quinolin-6-yl)pyrimidine-2-carbonitrile | NT | 0.18 | 1.4 | 0.99 | 0.43 |
| 470 | (6-(3-chloro-4-hydroxy-5-methoxyphenyl)-4-(6-(4-methylpiperazin-1-yl)pyridin-3-ylamino)quinolin-3-yl)(cyclopropyl)methanone | NT | 0.26 | 2.2 | 0.56 | 0.68 |
| 471 | (6-(3-chloro-5-fluoro-4-hydroxyphenyl)-4-(6-(4-methylpiperazin-1-yl)pyridin-3-ylamino)quinolin-3-yl)(cyclopropyl)methanone | NT | 0.14 | 2.8 | 0.21 | 0.14 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 472 | cyclopropyl(6-(3,5-dichloro-4-hydroxyphenyl)-4-(6-(4-methylpiperazin-1-yl)pyridin-3-ylamino)quinolin-3-yl)methanone | NT | 0.3 | 5.7 | 0.18 | 0.11 |
| 473 | 2,6-dichloro-4-(4-(4-((dimethylamino)methyl)phenylamino)-3-(methylsulfinyl)quinolin-6-yl)phenol | NT | 0.43 | 2.4 | 1.2 | 0.6 |
| 474 | 5-(3-(cyclopropanecarbonyl)-4-(4-((dimethylamino)methyl)piperidin-1-yl)quinolin-6-yl)indolin-2-one | NT | 10 | 10 | NT | NT |
| 475 | (6-(3-chloro-4-hydroxy-5-methoxyphenyl)-4-(2-(4-methylpiperazin-1-yl)pyrimidin-5-yl)quinolin-3-yl)(cyclopropyl)methanone | NT | 0.53 | 4.7 | 0.79 | 1.9 |
| 476 | (4-(6-(3-chloro-4-hydroxy-5-methoxyphenyl)-3-(cyclopropanecarbonyl)quinolin-4-yl)phenyl)(4-methylpiperazin-1-yl)methanone | NT | 0.23 | 2.1 | 0.31 | 0.5 |
| 477 | 1-(4-(3-acetyl-6-(3-chloro-4-hydroxy-5-methoxyphenyl)quinolin-4-yl)piperazin-1-yl)-2-(dimethylamino)ethanone | NT | 0.87 | 4.7 | 0.36 | 0.3 |
| 478 | cyclopropyl(6-(3,5-dichloro-4-hydroxyphenyl)-4-(3-((4-methylpiperazin-1-yl)methyl)phenyl)quinolin-3-yl)methanone | NT | 0.53 | 2.9 | 0.87 | 0.75 |
| 479 | cyclopropyl(6-(3,5-dichloro-4-hydroxyphenyl)-4-(2-(4-methylpiperazin-1-yl)pyrimidin-5-yl)quinolin-3-yl)methanone | NT | 0.92 | 7.9 | 1.7 | 1.7 |
| 480 | 1-(4-(1R,4R)-4-aminocyclohexylamino)-6-(5-hydroxy-1H-indol-2-yl)quinolin-3-yl)-2-methylpropan-1-one | NT | 0.59 | 4.6 | 2.7 | 0.93 |
| 481 | methyl4-(3-(cyclopropanecarbonyl)-4-(4-((dimethylamino)methyl)piperidin-1-yl)quinolin-6-yl)benzoate | NT | 10 | 10 | NT | NT |
| 482 | cyclopropyl(6-(3,5-dichloro-4-hydroxyphenyl)-4-(4-((4-methylpiperazin-1-yl)methyl)phenyl)quinolin-3-yl)methanone | NT | 0.54 | 3.1 | 0.96 | 0.9 |
| 483 | 1-(6-(3-chloro-4-hydroxy-5-methoxyphenyl)-4-(6-(4-methylpiperazin-1-yl)pyridin-3-ylamino)quinolin-3-yl)ethanone | NT | 0.64 | 0.89 | 0.64 | 0.69 |
| 484 | 1-(4-(3-acetyl-6-(3-chloro-5-fluoro-4-hydroxyphenyl)quinolin-4-yl)piperazin-1-yl)-2-(dimethylamino)ethanone | NT | 1.1 | 17 | 3.4 | 0.58 |
| 485 | cyclopropyl(6-(3,5-dichloro-4-hydroxyphenyl)-4-(4-(2-(pyrrolidin-1-yl)ethoxy)phenyl)quinolin-3-yl)methanone | NT | 0.77 | 10 | 1.2 | 1.2 |
| 486 | 1-(4-((1R,4R)-4-aminocyclohexylamino)-6-(3-chloro-5-ethoxy-4-hydroxyphenyl)quinolin-3-yl)ethanone | NT | 0.15 | 2.2 | 0.11 | 0.13 |
| 487 | 1-(6-(3-chloro-5-fluoro-4-hydroxyphenyl)-4-(6-(4-methylpiperazin-1-yl)pyridin-3-ylamino)quinolin-3-yl)ethanone | NT | 0.041 | 1.4 | 0.088 | 0.1 |
| 488 | 1-(6-(3-chloro-5-fluoro-4-hydroxyphenyl)-4-(6-(4-methylpiperazin-1-yl)pyridin-3-ylamino)quinolin-3-yl)ethanone | 0.38 | 0.084 | 2.1 | 0.2 | 0.14 |
| 489 | (4-(4-((1H-imidazol-1-yl)methyl)phenylamino)-6-(3-chloro-5-fluoro-4-hydroxyphenyl)quinolin-3-yl)(cyclopropyl)methanone | NT | 1.1 | 5.1 | 1.4 | 0.97 |
| 490 | (4-(4-((1H-imidazol-1-yl)methyl)phenylamino)-6-(3-chloro-4-hydroxy-5-methoxyphenyl)quinolin-3-yl)(cyclopropyl)methanone | NT | 0.78 | 5.8 | 0.68 | 0.86 |
| 491 | 4-(4-(1R,4R)-4-aminocyclohexylamino)-3-(methylsulfinyl)quinolin-6-yl)-2,6-dichlorophenol | NT | 7 | 10 | 10 | 2.9 |
| 492 | 4-(3-(cyclopropanecarbonyl)-4-(4-((dimethylamino)methyl)piperidin-1-yl)quinolin-6-yl)benzoic acid | NT | 10 | 10 | NT | NT |
| 493 | (4-((1R,4R)-4-(aminomethyl)cyclohexylamino)-6-(3-chloro-4-hydroxy-5-methoxyphenyl)quinolin-3-yl)(cyclopropyl)methanone | NT | 0.078 | 0.82 | 0.095 | 0.068 |
| 494 | (4-((1R,4R)-4-(aminomethyl)cyclohexylamino)-6-(3-chloro-4-hydroxy-5-methoxyphenyl)quinolin-3-yl)(cyclopropyl)methanone hydrochloride | 0.13 | 0.081 | 0.48 | 0.085 | 0.055 |
| 495 | (4-((1R,4R)-4-(aminomethyl)cyclohexylamino)-6-(3,5-dichloro-4-hydroxyphenyl)quinolin-3-yl)(cyclopropyl)methanone | NT | 0.045 | 3.9 | 0.35 | 0.018 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 496 | (6-(3-chloro-5-fluoro-4-hydroxyphenyl)-4-(2-(piperazin-1-yl)pyrimidin-5-ylamino)quinolin-3-yl)(cyclopropyl)methanone | NT | 0.036 | 0.64 | 0.079 | 0.068 |
| 497 | cyclopropyl(6-(3,5-dichloro-4-hydroxyphenyl)-4-(2-(piperazin-1-yl)pyrimidin-5-ylamino)quinolin-3-yl)methanone | NT | 0.052 | 0.97 | 0.12 | 0.056 |
| 498 | 4-(4-(1R,4R)-4-aminocyclohexylamino)-3-(methylsulfinyl)quinolin-6-yl)-2-chloro-6-fluorophenol | NT | 10 | 10 | 10 | 2.8 |
| 499 | 4-(4-(1R,4R)-4-aminocyclohexylamino)-3-(methylsulfinyl)quinolin-6-yl)-2-chlorophenol | NT | 2.7 | 18 | 9.7 | 2.5 |
| 500 | 4-(4-(1R,4R)-4-aminocyclohexylamino)-3-(methylsulfinyl)quinolin-6-yl)-2-chloro-6-methoxyphenol | NT | 1.6 | 13 | 4.5 | 1.8 |
| 501 | (4-(1R,4R)-4-(aminomethyl)cyclohexylamino)-6-(3-chloro-5-fluoro-4-hydroxyphenyl)quinolin-3-yl)(cyclopropyl)methanone | NT | 0.061 | 1.2 | 0.57 | 0.031 |
| 502 | 1-(4-(1R,4R)-4-aminocyclohexylamino)-6-(3-chloro-4-hydroxy-5-methoxyphenyl)quinolin-3-yl)-2-methylpropan-1-one | NT | 0.045 | 0.31 | 0.1 | 0.041 |
| 503 | (6-(3-chloro-4-hydroxy-5-methoxyphenyl)-4-(2-(piperazin-1-yl)pyrimidin-5-ylamino)quinolin-3-yl)(cyclopropyl)methanone | NT | 0.24 | 1.1 | 0.37 | 0.46 |
| 504 | (4-(4-(aminomethyl)phenylamino)-6-(3-chloro-5-fluoro-4-hydroxyphenyl)quinolin-3-yl)(cyclopropyl)methanone | NT | 0.084 | 0.71 | 0.081 | 0.019 |
| 505 | (4-(4-(aminomethyl)phenylamino)-6-(3-chloro-5-fluoro-4-hydroxyphenyl)quinolin-3-yl)(cyclopropyl)methanone hydrochloride | 0.088 | 0.063 | 0.4 | 0.067 | 0.026 |
| 506 | (4-(4-(aminomethyl)phenylamino)-6-(3-chloro-4-hydroxy-5-methoxyphenyl)quinolin-3-yl)(cyclopropyl)methanone | NT | 0.15 | 0.74 | 0.18 | 0.13 |
| 507 | (4-(4-(aminomethyl)phenylamino)-6-(3,5-dichloro-4-hydroxyphenyl)quinolin-3-yl)(cyclopropyl)methanone | NT | 0.094 | 0.58 | 0.059 | 0.018 |
| 508 | (4-(4-(aminomethyl)phenylamino)-6-(3,5-dichloro-4-hydroxyphenyl)quinolin-3-yl)(cyclopropyl)methanone hydrochloride | 0.099 | 0.078 | 0.49 | 0.067 | 0.02 |
| 509 | 5-(4-(4-(aminomethyl)phenylamino)-3-(cyclopropanecarbonyl)quinolin-6-yl)pyrimidine-2-carbonitrile | NT | 0.19 | 0.95 | 0.79 | 0.6 |
| 510 | cyclopropyl(6-(3,5-dichloro-4-hydroxyphenyl)-4-(1R,4R)-4-(methylamino)cyclohexylamino)quinolin-3-yl)methanone | NT | 0.054 | 1 | 0.12 | 0.018 |
| 511 | cyclopropyl(6-(3,5-dichloro-4-hydroxyphenyl)-4-(1-(piperidin-4-yl)-1H-pyrazol-4-ylamino)quinolin-3-yl)methanone | NT | 0.18 | 10 | 0.31 | 0.019 |
| 512 | (6-(3-chloro-4-hydroxy-5-methoxyphenyl)-4-(1-(piperidin-4-yl)-1H-pyrazol-4-ylamino)quinolin-3-yl)(cyclopropyl)methanone | NT | 0.41 | 2.9 | 0.3 | 0.31 |
| 513 | (6-(3-chloro-4-hydroxy-5-methoxyphenyl)-4-((1s,4s)-4-((dimethylamino)methyl)cyclohexylamino)quinolin-3-yl)(cyclopropyl)methanone | NT | 0.19 | 3.8 | 0.099 | 0.086 |
| 514 | (6-(3-chloro-5-fluoro-4-hydroxyphenyl)-4-((1s,4s)-4-((dimethylamino)methyl)cyclohexylamino)quinolin-3-yl)(cyclopropyl)methanone | NT | 0.44 | 0.77 | 0.26 | 0.21 |
| 515 | (4-((1s,4s)-4-(aminomethyl)cyclohexylamino)-6-(3-chloro-5-fluoro-4-hydroxyphenyl)quinolin-3-yl)(cyclopropyl)methanone | NT | 0.23 | 3.9 | 0.83 | 0.12 |
| 516 | (6-(3-chloro-4-hydroxy-5-methoxyphenyl)-4-(1,2,3,6-tetrahydropyridin-4-yl)quinolin-3-yl)(cyclopropyl)methanone | NT | 0.52 | 3 | 0.36 | 0.66 |
| 517 | (6-(3-chloro-4-hydroxy-5-methoxyphenyl)-4-((1R,4R)-4-(methylamino)cyclohexyl)amino)quinolin-3-yl)(cyclopropyl)methanone | 0.18 | 0.067 | 0.38 | 0.072 | 0.048 |
| 518 | 2-((((1s,4s)-4-(6-(3-chloro-4-hydroxy-5-methoxyphenyl)-3-(cyclopropanecarbonyl)quinolin-4-ylamino)cyclohexyl)methyl)(methyl)amino)acetonitrile | NT | 0.16 | 3.4 | 0.17 | 0.078 |
| 519 | (6-(3-chloro-4-hydroxyphenyl)-4-(1-(piperidin-4-yl)-1H-pyrazol-4-ylamino)quinolin-3-yl)(cyclopropyl)methanone | NT | 0.12 | 1.6 | 0.14 | 0.1 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 520 | (6-(3-chloro-5-fluoro-4-hydroxyphenyl)-4-(1-(piperidin-4-yl)-1H-pyrazol-4-ylamino)quinolin-3-yl)(cyclopropyl)methanone | NT | 0.081 | 10 | 0.52 | 0.042 |
| 521 | 1-(4-(6-(3-chloro-4-hydroxy-5-methoxyphenyl)-3-(cyclopropanecarbonyl)quinolin-4-yl)-5,6-dihydropyridin-1(2H)-yl)-2-(dimethylamino)ethanone | NT | 0.22 | 1.5 | 0.18 | 0.27 |
| 522 | 5-(3-(cyclopropanecarbonyl)-4-(1R,4R)-4-(methylamino)cyclohexylamino)quinolin-6-yl)pyrimidine-2-carbonitrile | NT | 0.23 | 1.1 | 0.95 | 0.91 |
| 523 | (6-(3-chloro-5-fluoro-4-hydroxyphenyl)-4-(1R,4R)-4-(methylamino)cyclohexylamino)quinolin-3-yl)(cyclopropyl)methanone | NT | 0.033 | 1.3 | 0.19 | 0.024 |
| 524 | 2-((((1s,4s)-4-(6-(3-chloro-5-fluoro-4-hydroxyphenyl)-3-(cyclopropanecarbonyl)quinolin-4-ylamino)cyclohexyl)methyl)(methyl)amino)acetonitrile | NT | 0.2 | 1.7 | 0.39 | 0.1 |
| 525 | (6-(3-chloro-5-fluoro-4-hydroxyphenyl)-4-(5-(piperazin-1-yl)pyridin-2-ylamino)quinolin-3-yl)(cyclopropyl)methanone | NT | 0.48 | 11 | 1.7 | 0.46 |
| 526 | cyclopropyl(6-(3,5-dichloro-4-hydroxyphenyl)-4-((1s,4s)-4-((dimethylamino)methyl)cyclohexylamino)quinolin-3-yl)methanone | NT | 0.29 | 1.2 | 0.25 | 0.15 |
| 527 | 1-(4-(1R,4R)-4-aminocyclohexylamino)-6-(3-chloro-5-fluoro-4-hydroxyphenyl)quinolin-3-yl)ethanone | NT | 0.034 | 10 | 0.42 | 0.02 |
| 528 | (6-(3-chloro-4-hydroxy-5-methoxyphenyl)-4-(5-(piperazin-1-yl)pyridin-2-ylamino)quinolin-3-yl)(cyclopropyl)methanone hydrochloride | NT | 1.8 | 4.2 | 1.3 | 1.7 |
| 529 | 1-(4-(1R,4R)-4-aminocyclohexylamino)-6-(3-chloro-4-hydroxy-5-methoxyphenyl)quinolin-3-yl)butan-1-one | NT | 0.081 | 1.5 | 0.15 | 0.076 |
| 530 | 1-(6-(3,5-dichloro-4-hydroxyphenyl)-4-(4-((dimethylamino)methyl)phenylamino)quinolin-3-yl)butan-1-one | NT | 0.07 | 1.2 | 0.15 | 0.086 |
| 531 | 1-(6-(3,5-dichloro-4-hydroxyphenyl)-4-(4-((dimethylamino)methyl)phenylamino)quinolin-3-yl)butan-1-one dihydrochloride | NT | 0.11 | 1.3 | 0.18 | 0.072 |
| 532 | 1-(4-(1R,4R)-4-aminocyclohexylamino)-6-(3-chloro-5-fluoro-4-hydroxyphenyl)quinolin-3-yl)butan-1-one | NT | 0.046 | 2.9 | 0.49 | 0.03 |
| 533 | (6-(3-chloro-4-hydroxy-5-methoxyphenyl)-4-(4-methylpiperazin-1-yl)quinolin-3-yl)(cyclopropyl)methanone | NT | 0.48 | 2.6 | 0.26 | 0.4 |
| 534 | (6-(3-chloro-5-fluoro-4-hydroxyphenyl)-4-(4-methylpiperazin-1-yl)quinolin-3-yl)(cyclopropyl)methanone | NT | 1.1 | 2.8 | 1.4 | 0.96 |
| 535 | 1-(4-(1R,4R)-4-aminocyclohexylamino)-6-(3,5-dichloro-4-hydroxyphenyl)quinolin-3-yl)butan-1-one | NT | 0.077 | 3.3 | 0.24 | 0.025 |
| 536 | (6-(3-chloro-4-hydroxy-5-methoxyphenyl)-4-(1H-pyrazol-4-yl)quinolin-3-yl)(cyclopropyl)methanone | NT | 1.3 | 14 | NT | NT |
| 537 | 1-(6-(3-chloro-5-fluoro-4-hydroxyphenyl)-4-(4-((dimethylamino)methyl)phenylamino)quinolin-3-yl)butan-1-one | NT | 0.11 | 0.94 | 0.15 | 0.098 |
| 538 | 1-(6-(3-chloro-4-hydroxy-5-methoxyphenyl)-4-(4-((dimethylamino)methyl)phenylamino)quinolin-3-yl)butan-1-one | NT | 0.28 | 3.1 | 0.45 | 0.27 |
| 539 | 5-(3-butyryl-4-(4-((dimethylamino)methyl)phenylamino)quinolin-6-yl)pyrimidine-2-carbonitrile | NT | 0.37 | 1.6 | 1.6 | 1.5 |
| 540 | (6-(3-chloro-4-hydroxy-5-methoxyphenyl)-4-(4-((dimethylamino)methyl)phenylamino)-7-fluoroquinolin-3-yl)(cyclopropyl)methanone | NT | 0.89 | 3.7 | 0.25 | 0.35 |
| 541 | (6-(3-chloro-5-fluoro-4-hydroxyphenyl)-4-(4-((dimethylamino)methyl)phenylamino)-7-fluoroquinolin-3-yl)(cyclopropyl)methanone | NT | 0.42 | 1.1 | 0.076 | 0.087 |
| 542 | 1-(6-(3-chloro-4-hydroxy-5-methoxyphenyl)-4-(1R,4R)-4-(methylamino)cyclohexylamino)quinolin-3-yl)ethanone | NT | 0.078 | 1.7 | 0.1 | 0.069 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 543 | 1-(6-(3-chloro-4-hydroxy-5-methoxyphenyl)-4-(1R,4R)-4-(methylamino)cyclohexylamino)quinolin-3-yl)ethanone dihydrochloride | 0.14 | 0.047 | 1.1 | 0.076 | 0.051 |
| 544 | 4-(3-acetyl-6-(3-chloro-4-hydroxy-5-methoxyphenyl)quinolin-4-ylamino)benzamide | NT | 0.17 | 2.2 | 0.47 | 0.2 |
| 545 | 4-(3-acetyl-6-(3,5-dichloro-4-hydroxyphenyl)quinolin-4-ylamino)benzamide | NT | 0.62 | 16 | 3.9 | 0.56 |
| 546 | 4-(6-(3-chloro-4-hydroxy-5-methoxyphenyl)-3-(cyclopropanecarbonyl)quinolin-4-ylamino)benzamide | NT | 1.1 | 12 | 1 | 1 |
| 547 | cyclopropyl(6-(3,5-dichloro-4-hydroxyphenyl)-4-(4-((dimethylamino)methyl)phenylamino)-7-fluoroquinolin-3-yl)methanone | NT | 0.41 | 1.9 | 0.13 | 0.14 |
| 548 | (4-(6-(4-aminopiperidin-1-yl)pyridin-3-ylamino)-6-(3,5-dichloro-4-hydroxyphenyl)quinolin-3-yl)(cyclopropyl)methanone | NT | 0.097 | 3.4 | 0.45 | 0.099 |
| 549 | (4-(6-(4-aminopiperidin-1-yl)pyridin-3-ylamino)-6-(3,5-dichloro-4-hydroxyphenyl)quinolin-3-yl)(cyclopropyl)methanone hydrochloride | NT | 0.15 | 3.2 | 0.48 | 0.078 |
| 550 | (4-(6-(4-aminopiperidin-1-yl)pyridin-3-ylamino)-6-(3-chloro-4-hydroxy-5-methoxyphenyl)quinolin-3-yl)(cyclopropyl)methanone | NT | 0.1 | 2.7 | 0.58 | 1 |
| 551 | (6-(3-chloro-4-hydroxy-5-methoxyphenyl)-4-(4-((dimethylamino)methyl)phenylamino)-8-fluoroquinolin-3-yl)(cyclopropyl)methanone | NT | 2 | 6.9 | NT | NT |
| 552 | cyclopropyl(6-(3,5-dichloro-4-hydroxyphenyl)-4-(4-((dimethylamino)methyl)phenylamino)-8-fluoroquinolin-3-yl)methanone | NT | 1.1 | 9 | NT | NT |
| 553 | (4-(2-(4-aminopiperidin-1-yl)pyrimidin-5-ylamino)-6-(3-chloro-4-hydroxy-5-methoxyphenyl)quinolin-3-yl)(cyclopropyl)methanone | NT | 0.12 | 2.1 | 0.39 | 0.95 |
| 554 | (4-(6-(3-aminopiperidin-1-yl)pyridin-3-ylamino)-6-(3-chloro-4-hydroxy-5-methoxyphenyl)quinolin-3-yl)(cyclopropyl)methanone | NT | 0.068 | 1.9 | 0.08 | 0.025 |
| 555 | (4-(1R,4R)-4-aminocyclohexylamino)-6-(3-chloro-5-fluoro-4-hydroxyphenyl)-8-fluoroquinolin-3-yl)(cyclopropyl)methanone | NT | 0.44 | 10 | NT | NT |
| 556 | (4-(6-(3-aminopiperidin-1-yl)pyridin-3-ylamino)-6-(3,5-dichloro-4-hydroxyphenyl)quinolin-3-yl)(cyclopropyl)methanone | NT | 0.03 | 0.96 | 0.023 | 0.016 |
| 557 | (4-(6-(4-aminopiperidin-1-yl)pyridin-3-ylamino)-6-(3-chloro-5-fluoro-4-hydroxyphenyl)quinolin-3-yl)(cyclopropyl)methanone | NT | 0.11 | 3.1 | 0.52 | 0.18 |
| 558 | 1-(6-(3,5-dichloro-4-hydroxyphenyl)-4-(1R,4R)-4-(methylamino)cyclohexylamino)quinolin-3-yl)ethanone | NT | 0.094 | 10 | 0.32 | 0.043 |
| 559 | cyclopropyl(6-(3,5-dichloro-4-hydroxyphenyl)-7-fluoro-4-(6-(piperazin-1-yl)pyridin-3-ylamino)quinolin-3-yl)methanone | NT | 0.46 | 3.2 | 0.59 | 0.35 |
| 560 | 1-(6-(3-chloro-5-fluoro-4-hydroxyphenyl)-4-(1R,4R)-4-(methylamino)cyclohexylamino)quinolin-3-yl)ethanone | NT | 0.041 | 10 | NT | NT |
| 561 | (4-(6-(3-aminopiperidin-1-yl)pyridin-3-ylamino)-6-(3-chloro-5-fluoro-4-hydroxyphenyl)quinolin-3-yl)(cyclopropyl)methanone | NT | 0.0055 | 0.3 | 0.008 | 0.0066 |
| 562 | (4-(6-(3-aminopiperidin-1-yl)pyridin-3-ylamino)-6-(3-chloro-5-fluoro-4-hydroxyphenyl)quinolin-3-yl)(cyclopropyl)methanone hydrochloride | NT | 0.0064 | 0.19 | 0.012 | 0.0089 |
| 563 | (6-(3-chloro-5-fluoro-4-hydroxyphenyl)-4-(4-((dimethylamino)methyl)phenylamino)-8-fluoroquinolin-3-yl)(cyclopropyl)methanone | NT | 1.3 | 3.3 | NT | NT |
| 564 | (4-(1R,4R)-4-aminocyclohexylamino)-6-(3-chloro-4-hydroxy-5-methoxyphenyl)-8-fluoroquinolin-3-yl)(cyclopropyl)methanone | NT | 0.43 | 1.8 | NT | NT |
| 565 | (4-(1R,4R)-4-aminocyclohexylamino)-6-(3,5-dichloro-4-hydroxyphenyl)-8-fluoroquinolin-3-yl)(cyclopropyl)methanone | NT | 0.3 | 10 | NT | NT |

TABLE 4-continued

| Example | Compound Name | IC50 (µM) (22Rv1) | IC50 (µM) (T47D) | IC50 (µM) (HT1197) | IC50 (µM) (A549) | IC50 (µM) (DU4475) |
|---------|---------------|-------------------|------------------|--------------------|------------------|--------------------|
| 566 | (4-(2-(4-aminopiperidin-1-yl)pyrimidin-5-ylamino)-6-(3,5-dichloro-4-hydroxyphenyl)quinolin-3-yl)(cyclopropyl)methanone | NT | 0.11 | 2.6 | 0.4 | 0.13 |
| 567 | (4-(2-(4-aminopiperidin-1-yl)pyrimidin-5-ylamino)-6-(3-chloro-5-fluoro-4-hydroxyphenyl)quinolin-3-yl)(cyclopropyl)methanone | NT | 0.076 | 1.9 | 0.34 | 0.18 |
| 568 | (4-(6-(3-aminopyrrolidin-1-yl)pyridin-3-ylamino)-6-(3-chloro-4-hydroxy-5-methoxyphenyl)quinolin-3-yl)(cyclopropyl)methanone | NT | 0.057 | 0.62 | 0.082 | 0.045 |
| 569 | (6-(3-chloro-4-hydroxy-5-methoxyphenyl)-4-(1R,4R)-4-(((R)-3-fluoropyrrolidin-1-yl)methyl)cyclohexylamino)quinolin-3-yl)(cyclopropyl)methanone | NT | 0.62 | 1.8 | 0.4 | 0.41 |
| 570 | (6-(3-chloro-5-fluoro-4-hydroxyphenyl)-4-(1R,4R)-4-(((R)-3-fluoropyrrolidin-1-yl)methyl)cyclohexylamino)quinolin-3-yl)(cyclopropyl)methanone | NT | 0.14 | 0.16 | 0.13 | 0.089 |
| 571 | cyclopropyl(6-(3,5-dichloro-4-hydroxyphenyl)-4-(1R,4R)-4-(((R)-3-fluoropyrrolidin-1-yl)methyl)cyclohexylamino)quinolin-3-yl)methanone | NT | 0.18 | 0.39 | 0.16 | 0.08 |
| 572 | (4-(2-(3-aminopyrrolidin-1-yl)pyrimidin-5-ylamino)-6-(3-chloro-5-fluoro-4-hydroxyphenyl)quinolin-3-yl)(cyclopropyl)methanone | NT | 0.0076 | 0.37 | 0.03 | 0.011 |
| 573 | (4-(2-(3-aminopyrrolidin-1-yl)pyrimidin-5-ylamino)-6-(3-chloro-5-fluoro-4-hydroxyphenyl)quinolin-3-yl)(cyclopropyl)methanone hydrochloride | NT | 0.0072 | 0.57 | 0.032 | 0.013 |
| 574 | (4-(2-(3-aminopyrrolidin-1-yl)pyrimidin-5-ylamino)-6-(3,5-dichloro-4-hydroxyphenyl)quinolin-3-yl)(cyclopropyl)methanone | NT | 0.031 | 1.4 | 0.087 | 0.021 |
| 575 | (4-(6-(3-aminopyrrolidin-1-yl)pyridin-3-ylamino)-6-(3,5-dichloro-4-hydroxyphenyl)quinolin-3-yl)(cyclopropyl)methanone | NT | 0.028 | 1.2 | 0.068 | 0.029 |
| 576 | (4-(6-(3-aminopyrrolidin-1-yl)pyridin-3-ylamino)-6-(3-chloro-5-fluoro-4-hydroxyphenyl)quinolin-3-yl)(cyclopropyl)methanone | NT | 0.0094 | 0.53 | 0.026 | 0.012 |
| 577 | (4-(6-(3-aminopyrrolidin-1-yl)pyridin-3-ylamino)-6-(3-chloro-5-fluoro-4-hydroxyphenyl)quinolin-3-yl)(cyclopropyl)methanone hydrochloride) | NT | 0.0065 | 0.52 | 0.029 | 0.014 |
| 578 | (6-(3-chloro-4-hydroxy-5-methoxyphenyl)-7-fluoro-4-(6-(piperazin-1-yl)pyridin-3-ylamino)quinolin-3-yl)(cyclopropyl)methanone | NT | 3 | 8 | 1.9 | 2.8 |
| 579 | (4-((1R,3r,5S)-8-azabicyclo[3.2.1]octan-3-ylamino)-6-(3-chloro-4-hydroxy-5-methoxyphenyl)quinolin-3-yl)(cyclopropyl)methanone | NT | 0.17 | 7.8 | 0.27 | 0.14 |
| 580 | (4-((1R,3r,5S)-8-azabicyclo[3.2.1]octan-3-ylamino)-6-(3,5-dichloro-4-hydroxyphenyl)quinolin-3-yl)(cyclopropyl)methanone | NT | 0.25 | 4.1 | 0.69 | 0.12 |
| 581 | cyclopropyl(6-(3,5-dichloro-4-hydroxyphenyl)-4-(4-((3,3-difluoropyrrolidin-1-yl)methyl)phenylamino)quinolin-3-yl)methanone | NT | 1.4 | 5.3 | NT | NT |
| 582 | (4-(2-(3-aminopyrrolidin-1-yl)pyrimidin-5-ylamino)-6-(3-chloro-4-hydroxy-5-methoxyphenyl)quinolin-3-yl)(cyclopropyl)methanone | NT | 0.052 | 1.1 | 0.097 | 0.064 |
| 583 | cyclopropyl(4-(4-(diallylamino)-4-methylcyclohexylamino)-6-(3,5-dichloro-4-hydroxyphenyl)quinolin-3-yl)methanone | NT | 2.6 | 10 | 3.1 | 2.3 |
| 584 | cyclopropyl(6-(3,5-dichloro-4-hydroxyphenyl)-4-(1R,4R)-4-(pyrrolidin-1-ylmethyl)cyclohexylamino)quinolin-3-yl)methanone | NT | 0.13 | 0.86 | 0.071 | 0.053 |
| 585 | cyclopropyl(6-(3,5-dichloro-4-hydroxyphenyl)-4-(1R,4R)-4-(pyrrolidin-1-ylmethyl)cyclohexylamino)quinolin-3-yl)methanone hydrochloride | 0.1 | 0.12 | 0.78 | 0.073 | 0.043 |
| 586 | (6-(3-chloro-4-hydroxy-5-methoxyphenyl)-4-(1R,4R)-4-(pyrrolidin-1-ylmethyl)cyclohexylamino)quinolin-3-yl)(cyclopropyl)methanone | NT | 0.38 | 3 | 0.2 | 0.19 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 587 | (6-(3-chloro-5-fluoro-4-hydroxyphenyl)-4-(1R,4R)-4-(pyrrolidin-1-ylmethyl)cyclohexylamino)quinolin-3-yl)(cyclopropyl)methanone | NT | 0.11 | 0.55 | 0.084 | 0.065 |
| 588 | (6-(3-chloro-5-fluoro-4-hydroxyphenyl)-4-(1R,4R)-4-(pyrrolidin-1-ylmethyl)cyclohexylamino)quinolin-3-yl)(cyclopropyl)methanone hydrochloride | 0.16 | 0.091 | 0.46 | 0.096 | 0.063 |
| 589 | (4-(6-aminopyridin-3-ylamino)-6-(3-chloro-4-hydroxy-5-methoxyphenyl)quinolin-3-yl)(cyclopropyl)methanone | NT | 0.61 | 1.4 | 0.18 | 0.21 |
| 590 | (4-(6-aminopyridin-3-ylamino)-6-(3,5-dichloro-4-hydroxyphenyl)quinolin-3-yl)(cyclopropyl)methanone | NT | 0.48 | 2.2 | 0.48 | 0.19 |
| 591 | (4-(6-aminopyridin-3-ylamino)-6-(3-chloro-5-fluoro-4-hydroxyphenyl)quinolin-3-yl)(cyclopropyl)methanone | NT | 0.26 | 1.4 | 0.36 | 0.12 |
| 592 | (6-(3-chloro-5-fluoro-4-hydroxyphenyl)-4-(1-(1-methylpiperidin-4-yl)-1H-pyrazol-4-ylamino)quinolin-3-yl)(cyclopropyl)methanone | NT | 0.24 | 2.8 | 0.13 | 0.068 |
| 593 | cyclopropyl(6-(3,5-dichloro-4-hydroxyphenyl)-4-(1-(1-methylpiperidin-4-yl)-1H-pyrazol-4-ylamino)quinolin-3-yl)methanone | NT | 0.32 | 4.3 | 0.094 | 0.044 |
| 594 | 1-(6-(3-chloro-5-fluoro-4-hydroxyphenyl)-4-(2-(piperazin-1-yl)pyrimidin-5-ylamino)quinolin-3-yl)ethanone | NT | 0.025 | 0.66 | 0.063 | 0.048 |
| 595 | (4-(4,4'-bipiperidin-1-yl)-6-(3-chloro-4-hydroxy-5-methoxyphenyl)quinolin-3-yl)(cyclopropyl)methanone | NT | 0.41 | 3.4 | 0.57 | 0.64 |
| 596 | (4-(4,4'-bipiperidin-1-yl)-6-(3,5-dichloro-4-hydroxyphenyl)quinolin-3-yl)(cyclopropyl)methanone | NT | 0.18 | 5.1 | 1.5 | 0.14 |
| 597 | 1-(6-(3-chloro-5-fluoro-4-hydroxyphenyl)-4-(1R,4R)-4-((dimethylamino)methyl)cyclohexylamino)quinolin-3-yl)butan-1-one | NT | 0.11 | 1.1 | 0.16 | 0.083 |
| 598 | cyclopropyl(6-(3,5-dichloro-4-hydroxyphenyl)-4-(1R,4R)-4-((3-methoxypyrrolidin-1-yl)methyl)cyclohexylamino)quinolin-3-yl)methanone | NT | 0.18 | 1 | 0.13 | 0.066 |
| 599 | (6-(3-chloro-4-hydroxy-5-methoxyphenyl)-4-(1R,4R)-4-((3-methoxypyrrolidin-1-yl)methyl)cyclohexylamino)quinolin-3-yl)(cyclopropyl)methanone | NT | 0.51 | 2.8 | 0.54 | 0.37 |
| 600 | cyclopropyl(6-(3,5-dichloro-4-hydroxyphenyl)-4-(1R,4R)-4-((3-hydroxypyrrolidin-1-yl)methyl)cyclohexylamino)quinolin-3-yl)methanone | NT | 0.078 | 0.76 | 0.12 | 0.029 |
| 601 | (4-(4-(2-aminopropan-2-yl)phenylamino)-6-(3,5-dichloro-4-hydroxyphenyl)quinolin-3-yl)(cyclopropyl)methanone hydrochloride | NT | 0.09 | 0.42 | 0.047 | 0.023 |
| 602 | (4-(4-(2-aminopropan-2-yl)phenylamino)-6-(3,5-dichloro-4-hydroxyphenyl)quinolin-3-yl)(cyclopropyl)methanone | 0.082 | 0.13 | 0.73 | 0.074 | 0.038 |
| 603 | (4-(4-(2-aminopropan-2-yl)phenylamino)-6-(3-chloro-4-hydroxy-5-methoxyphenyl)quinolin-3-yl)(cyclopropyl)methanone | NT | 0.52 | 1.7 | 0.64 | 0.37 |
| 604 | (4-(4-(2-aminopropan-2-yl)phenylamino)-6-(3-chloro-5-fluoro-4-hydroxyphenyl)quinolin-3-yl)(cyclopropyl)methanone | 0.087 | 0.094 | 0.79 | 0.097 | 0.039 |
| 605 | 1-(6-(3,5-dichloro-4-hydroxyphenyl)-4-(1R,4R)-4-((dimethylamino)methyl)cyclohexylamino)quinolin-3-yl)butan-1-one | NT | 0.095 | 1.1 | 0.13 | 0.051 |
| 606 | 1-(6-(3-chloro-4-hydroxy-5-methoxyphenyl)-4-(1R,4R)-4-((dimethylamino)methyl)cyclohexylamino)quinolin-3-yl)-2-methylpropan-1-one | NT | 0.65 | 1.1 | 0.65 | 0.34 |
| 607 | 1-(6-(3-chloro-4-hydroxy-5-methoxyphenyl)-4-(1R,4R)-4-((dimethylamino)methyl)cyclohexylamino)quinolin-3-yl)butan-1-one | NT | 0.24 | 3.4 | 0.48 | 0.24 |
| 608 | 1-(6-(3,5-dichloro-4-hydroxyphenyl)-4-(1R,4R)-4-((dimethylamino)methyl)cyclohexylamino)quinolin-3-yl)-2-methylpropan-1-one | NT | 0.15 | 0.46 | 0.25 | 0.072 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 609 | (6-(3-chloro-4-hydroxy-5-methoxyphenyl)-4-(6-(piperidin-3-ylamino)pyridin-3-ylamino)quinolin-3-yl)(cyclopropyl)methanone | NT | 0.22 | 3.9 | 0.68 | 0.34 |
| 610 | cyclopropyl(6-(3,5-dichloro-4-hydroxyphenyl)-4-(6-(piperidin-3-ylamino)pyridin-3-ylamino)quinolin-3-yl)methanone | NT | 0.22 | 10 | 0.39 | 0.073 |
| 611 | (6-(3-chloro-5-fluoro-4-hydroxyphenyl)-4-(6-(piperidin-3-ylamino)pyridin-3-ylamino)quinolin-3-yl)(cyclopropyl)methanone | NT | 0.13 | 10 | 0.57 | 0.39 |
| 612 | (6-(3-chloro-4-hydroxy-5-methoxyphenyl)-4-(4-(2-(dimethylamino)ethyl)phenylamino)quinolin-3-yl)(cyclopropyl)methanone | NT | 0.84 | 4.7 | 0.72 | 0.4 |
| 613 | cyclopropyl(6-(3,5-dichloro-4-hydroxyphenyl)-4-(4-(2-(dimethylamino)ethyl)phenylamino)quinolin-3-yl)methanone | NT | 0.13 | 1 | 0.075 | 0.028 |
| 614 | cyclopropyl(6-(3,5-dichloro-4-hydroxyphenyl)-4-(4-(2-(dimethylamino)ethyl)phenylamino)quinolin-3-yl)methanone hydrochloride | 0.12 | 0.12 | 1.6 | 0.075 | 0.024 |
| 615 | (6-(3-chloro-5-fluoro-4-hydroxyphenyl)-4-(4-(2-(dimethylamino)ethyl)phenylamino)quinolin-3-yl)(cyclopropyl)methanone | NT | 0.17 | 1.4 | 0.086 | 0.042 |
| 616 | 1-(6-(3-chloro-4-hydroxy-5-methoxyphenyl)-4-(2-(piperazin-1-yl)pyrimidin-5-ylamino)quinolin-3-yl)ethanone | NT | 0.22 | 1.8 | 0.66 | 0.5 |
| 617 | 1-(6-(3-chloro-4-hydroxy-5-methoxyphenyl)-4-(6-(piperazin-1-yl)pyridin-3-ylamino)quinolin-3-yl)butan-1-one | NT | 0.33 | 1.7 | 0.19 | 0.32 |
| 618 | cyclopropyl(6-(3,5-dichloro-4-hydroxyphenyl)-4-(1R,4R)-4-((4-methylpiperazin-1-yl)methyl)cyclohexylamino)quinolin-3-yl)methanone | NT | 0.23 | 2.3 | 0.21 | 0.12 |
| 619 | cyclopropyl(6-(3,5-dichloro-4-hydroxyphenyl)-4-(1R,4R)-4-((4-methylpiperazin-1-yl)methyl)cyclohexylamino)quinolin-3-yl)methanone hydrochloride | 0.51 | 0.32 | 2.6 | 0.28 | 0.15 |
| 620 | 1-(6-(3-chloro-5-fluoro-4-hydroxyphenyl)-4-(1R,4R)-4-((dimethylamino)methyl)cyclohexylamino)quinolin-3-yl)-2-methylpropan-1-one | NT | 0.16 | 0.17 | 0.18 | 0.095 |
| 621 | (4-((1R,3r,5S)-8-azabicyclo[3.2.1]octan-3-ylamino)-6-(3-chloro-5-fluoro-4-hydroxyphenyl)quinolin-3-yl)(cyclopropyl)methanone | NT | 0.24 | 3.9 | 0.91 | 0.11 |
| 622 | (6-(3-chloro-4-hydroxy-5-methoxyphenyl)-4-(3-((dimethylamino)methyl)phenylamino)quinolin-3-yl)(cyclopropyl)methanone | NT | 1.1 | 5.5 | 0.43 | 0.32 |
| 623 | 1-(6-(3-chloro-5-fluoro-4-hydroxyphenyl)-4-(6-(piperazin-1-yl)pyridin-3-ylamino)quinolin-3-yl)butan-1-one | NT | 0.085 | 2 | 0.2 | 0.1 |
| 624 | cyclopropyl(6-(3,5-dichloro-4-hydroxyphenyl)-4-(3-((dimethylamino)methyl)phenylamino)quinolin-3-yl)methanone | NT | 0.55 | 3 | 0.089 | 0.043 |
| 625 | 1-(6-(3,5-dichloro-4-hydroxyphenyl)-4-(6-(piperazin-1-yl)pyridin-3-ylamino)quinolin-3-yl)butan-1-one | NT | 1.5 | 10 | NT | NT |
| 626 | (4-(2-(3-aminopiperidin-1-yl)pyrimidin-5-ylamino)-6-(3-chloro-5-fluoro-4-hydroxyphenyl)quinolin-3-yl)(cyclopropyl)methanone | NT | 0.0051 | 0.05 | 0.0073 | 0.0048 |
| 627 | (6-(3-chloro-5-fluoro-4-hydroxyphenyl)-4-(1R,4R)-4-((3-methoxypyrrolidin-1-yl)methyl)cyclohexylamino)quinolin-3-yl)(cyclopropyl)methanone | NT | 0.15 | 0.55 | 0.11 | 0.083 |
| 628 | (4-(2-(3-aminopiperidin-1-yl)pyrimidin-5-ylamino)-6-(3,5-dichloro-4-hydroxyphenyl)quinolin-3-yl)(cyclopropyl)methanone | NT | 0.0069 | 0.33 | 0.019 | 0.0056 |
| 629 | (6-(3-chloro-5-fluoro-4-hydroxyphenyl)-4-(3-((dimethylamino)methyl)phenylamino)quinolin-3-yl)(cyclopropyl)methanone | NT | 0.58 | 3.3 | 0.12 | 0.069 |
| 630 | (6-(3-chloro-4-hydroxy-5-methoxyphenyl)-4-(1R,4R)-4-((3-hydroxypyrrolidin-1-yl)methyl)cyclohexylamino)quinolin-3-yl)(cyclopropyl)methanone | NT | 0.41 | 3.6 | 0.19 | 0.17 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 631 | (6-(3-chloro-5-fluoro-4-hydroxyphenyl)-4-(1R,4R)-4-((3-hydroxypyrrolidin-1-yl)methyl)cyclohexylamino)quinolin-3-yl)(cyclopropyl)methanone | NT | 0.074 | 0.85 | 0.17 | 0.055 |
| 632 | (6-(3-chloro-5-fluoro-4-hydroxyphenyl)-4-(1R,4R)-4-(((2-hydroxyethyl)(methyl)amino)methyl)cyclohexylamino)quinolin-3-yl)(cyclopropyl)methanone | NT | 0.069 | 0.72 | 0.1 | 0.069 |
| 633 | (6-(3-chloro-4-hydroxy-5-methoxyphenyl)-4-(1R,4R)-4-(((2-hydroxyethyl)(methyl)amino)methyl)cyclohexylamino)quinolin-3-yl)(cyclopropyl)methanone | NT | 0.21 | 2.3 | 0.12 | 0.15 |
| 634 | cyclopropyl(6-(3,5-dichloro-4-hydroxyphenyl)-4-(1R,4R)-4-(((2-hydroxyethyl)(methyl)amino)methyl)cyclohexylamino)quinolin-3-yl)methanone | NT | 0.099 | 0.75 | 0.095 | 0.042 |
| 636 | (6-(3-chloro-5-fluoro-4-hydroxyphenyl)-4-(1R,4R)-4-((4-methylpiperazin-1-yl)methyl)cyclohexylamino)quinolin-3-yl)(cyclopropyl)methanone | NT | 0.16 | 0.94 | 0.2 | 0.18 |
| 637 | (6-(3-chloro-4-hydroxy-5-methoxyphenyl)-4-(1R,4R)-4-((4-methylpiperazin-1-yl)methyl)cyclohexylamino)quinolin-3-yl)(cyclopropyl)methanone | NT | 0.68 | 2.9 | 0.32 | 0.67 |
| 638 | (4-(4-amino-4-methylcyclohexylamino)-6-(3,5-dichloro-4-hydroxyphenyl)quinolin-3-yl)(cyclopropyl)methanone | NT | 0.1 | 0.67 | 0.12 | 0.022 |
| 639 | (4-(4-amino-4-methylcyclohexylamino)-6-(3-chloro-4-hydroxy-5-methoxyphenyl)quinolin-3-yl)(cyclopropyl)methanone | NT | 0.1 | 0.46 | 0.09 | 0.062 |
| 640 | 1-(6-(3-chloro-4-hydroxy-5-methoxyphenyl)-4-(4-((dimethylamino)methyl)phenylamino)quinolin-3-yl)-2-methylpropan-1-one | NT | 0.54 | 0.82 | 0.61 | 0.52 |
| 641 | 1-(6-(3,5-dichloro-4-hydroxyphenyl)-4-(4-((dimethylamino)methyl)phenylamino)quinolin-3-yl)-2-methylpropan-1-one | NT | 0.22 | 0.74 | 0.23 | 0.097 |
| 642 | (R)-(6-(3-chloro-5-fluoro-4-hydroxyphenyl)-4-(4-(3-fluoropyrrolidin-1-yl)cyclohexylamino)quinolin-3-yl)(cyclopropyl)methanone | NT | 0.17 | 0.76 | 0.2 | 0.11 |
| 643 | (R)-cyclopropyl(6-(3,5-dichloro-4-hydroxyphenyl)-4-(4-(3-fluoropyrrolidin-1-yl)cyclohexylamino)quinolin-3-yl)methanone | NT | 0.37 | 2.4 | 0.34 | 0.14 |
| 644 | (4-(2-(3-aminopiperidin-1-yl)pyrimidin-5-ylamino)-6-(3-chloro-4-hydroxy-5-methoxyphenyl)quinolin-3-yl)(cyclopropyl)methanone | NT | 0.047 | 2.4 | 0.23 | 0.068 |
| 645 | (R)-(6-(3-chloro-4-hydroxy-5-methoxyphenyl)-4-(4-(3-fluoropyrrolidin-1-yl)cyclohexylamino)quinolin-3-yl)(cyclopropyl)methanone | NT | 0.45 | 2.2 | 0.33 | 0.29 |
| 646 | (S)-(4-(6-(3-aminopiperidin-1-yl)pyridin-3-ylamino)-6-(3,5-dichloro-4-hydroxyphenyl)quinolin-3-yl)(cyclopropyl)methanone | NT | 0.02 | 0.56 | 0.022 | 0.0035 |
| 647 | (S)-(4-(6-(3-aminopiperidin-1-yl)pyridin-3-ylamino)-6-(3,5-dichloro-4-hydroxyphenyl)quinolin-3-yl)(cyclopropyl)methanone hydrochloride | 0.03 | 0.03 | 0.75 | 0.08 | 0.015 |
| 648 | (S)-(4-(6-(3-aminopiperidin-1-yl)pyridin-3-ylamino)-6-(3-chloro-5-fluoro-4-hydroxyphenyl)quinolin-3-yl)(cyclopropyl)methanone | NT | 0.0095 | 0.28 | 0.013 | 0.0046 |
| 649 | (R)-(4-(6-(3-aminopiperidin-1-yl)pyridin-3-ylamino)-6-(3-chloro-4-hydroxy-5-methoxyphenyl)quinolin-3-yl)(cyclopropyl)methanone | NT | 0.087 | 1.4 | 0.15 | 0.077 |
| 650 | (R)-(4-(6-(3-aminopiperidin-1-yl)pyridin-3-ylamino)-6-(3,5-dichloro-4-hydroxyphenyl)quinolin-3-yl)(cyclopropyl)methanone | NT | 0.0099 | 0.32 | 0.015 | 0.0072 |
| 651 | (R)-(4-(6-(3-aminopiperidin-1-yl)pyridin-3-ylamino)-6-(3-chloro-5-fluoro-4-hydroxyphenyl)quinolin-3-yl)(cyclopropyl)methanone | NT | 0.0054 | 0.12 | 0.0075 | 0.0071 |
| 652 | cyclopropyl(6-(3,5-dichloro-4-hydroxyphenyl)-4-((1s,4s)-4-((dimethylamino)methyl)-4-hydroxycyclohexylamino)quinolin-3-yl)methanone | NT | 0.15 | 1.4 | 0.15 | 0.051 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 653 | 1-(6-(3-chloro-4-hydroxy-5-methoxyphenyl)-4-(4-((4-methylpiperazin-1-yl)methyl)phenylamino)quinolin-3-yl)ethanone | NT | 1.3 | 1.9 | 0.5 | 0.32 |
| 654 | 1-(6-(3,5-dichloro-4-hydroxyphenyl)-4-(4-((4-methylpiperazin-1-yl)methyl)phenylamino)quinolin-3-yl)ethanone | NT | 0.091 | 8.7 | 0.19 | 0.11 |
| 655 | 1-(6-(3,5-dichloro-4-hydroxyphenyl)-4-((4-((4-methylpiperazin-1-yl)methyl)phenyl)amino)quinolin-3-yl)ethanone | 0.18 | 0.072 | 7.8 | 0.23 | 0.097 |
| 656 | 1-(6-(3-chloro-5-fluoro-4-hydroxyphenyl)-4-(4-((4-methylpiperazin-1-yl)methyl)phenylamino)quinolin-3-yl)ethanone | NT | 0.19 | 6.1 | 0.41 | 0.27 |
| 657 | cyclopropyl(6-(3,5-dichloro-4-hydroxyphenyl)-4-(6-((dimethylamino)methyl)pyridin-3-ylamino)quinolin-3-yl)methanone | NT | 0.31 | 2.8 | 0.18 | 0.098 |
| 658 | cyclopropyl(6-(3,5-dichloro-4-hydroxyphenyl)-4-(6-(pyrrolidin-1-ylmethyl)pyridin-3-ylamino)quinolin-3-yl)methanone | NT | 0.3 | 4.5 | 0.072 | 0.07 |
| 659 | (6-(3-chloro-4-hydroxy-5-methoxyphenyl)-4-(6-(pyrrolidin-1-ylmethyl)pyridin-3-ylamino)quinolin-3-yl)(cyclopropyl)methanone | NT | 0.6 | 7.3 | 0.32 | 0.28 |
| 660 | (S)-(4-(6-(3-aminopiperidin-1-yl)pyridin-3-ylamino)-6-(3-chloro-4-hydroxy-5-methoxyphenyl)quinolin-3-yl)(cyclopropyl)methanone | NT | 0.1 | 2.9 | 0.22 | 0.046 |
| 661 | cyclopropyl(6-(3,5-dichloro-4-hydroxyphenyl)-4-(4-(3-methoxypyrrolidin-1-yl)cyclohexylamino)quinolin-3-yl)methanone | NT | 0.25 | 1.4 | 0.17 | 0.1 |
| 662 | (6-(3-chloro-5-fluoro-4-hydroxyphenyl)-4-(1R,4R)-4-((3-(dimethylamino)pyrrolidin-1-yl)methyl)cyclohexylamino)quinolin-3-yl)(cyclopropyl)methanone | NT | 0.19 | 0.95 | 0.15 | 0.14 |
| 663 | cyclopropyl(6-(3,5-dichloro-4-hydroxyphenyl)-4-(1R,4R)-4-((3-(dimethylamino)pyrrolidin-1-yl)methyl)cyclohexylamino)quinolin-3-yl)methanone | NT | 0.32 | 4.6 | 0.22 | 0.17 |
| 664 | cyclopropyl(6-(3,5-dichloro-4-hydroxyphenyl)-4-(4-(3,3-difluoropyrrolidin-1-yl)cyclohexylamino)quinolin-3-yl)methanone | NT | 1.7 | 10 | NT | NT |
| 665 | (6-(3-chloro-4-hydroxy-5-methoxyphenyl)-4-(6-(pyrrolidin-3-ylamino)pyridin-3-ylamino)quinolin-3-yl)(cyclopropyl)methanone | NT | 0.16 | 3.7 | 0.53 | 0.22 |
| 666 | cyclopropyl(6-(3,5-dichloro-4-hydroxyphenyl)-4-(6-(pyrrolidin-3-ylamino)pyridin-3-ylamino)quinolin-3-yl)methanone | NT | 0.34 | 10 | 10 | 0.071 |
| 667 | (6-(3-chloro-5-fluoro-4-hydroxyphenyl)-4-(6-(pyrrolidin-3-ylamino)pyridin-3-ylamino)quinolin-3-yl)(cyclopropyl)methanone | NT | 0.17 | 10 | 7.7 | 0.077 |
| 668 | (6-(3-chloro-4-hydroxy-5-methoxyphenyl)-4-(1R,4R)-4-((3-(dimethylamino)pyrrolidin-1-yl)methyl)cyclohexylamino)quinolin-3-yl)(cyclopropyl)methanone | NT | 1 | 2.6 | 0.56 | 1.4 |
| 669 | (6-(3-chloro-4-hydroxy-5-methoxyphenyl)-4-(6-(3-hydroxypyrrolidin-1-yl)pyridin-3-ylamino)quinolin-3-yl)(cyclopropyl)methanone | NT | 0.24 | 4.4 | 0.46 | 0.75 |
| 670 | cyclopropyl(6-(3,5-dichloro-4-hydroxyphenyl)-4-(6-(3-hydroxypyrrolidin-1-yl)pyridin-3-ylamino)quinolin-3-yl)methanone | NT | 0.43 | 5.3 | 0.72 | 0.59 |
| 671 | (6-(3-chloro-5-fluoro-4-hydroxyphenyl)-4-(6-(3-hydroxypyrrolidin-1-yl)pyridin-3-ylamino)quinolin-3-yl)(cyclopropyl)methanone | NT | 0.3 | 4.9 | 0.85 | 0.52 |
| 672 | (6-(3-chloro-5-fluoro-4-hydroxyphenyl)-4-(6-(pyrrolidin-1-ylmethyl)pyridin-3-ylamino)quinolin-3-yl)(cyclopropyl)methanone | NT | 0.39 | 3.2 | 0.17 | 0.16 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 673 | (6-(3-chloro-5-fluoro-4-hydroxyphenyl)-4-((1s,4s)-4-((dimethylamino)methyl)-4-hydroxycyclohexylamino)quinolin-3-yl)(cyclopropyl)methanone | NT | 0.16 | 1.4 | 0.16 | 0.089 |
| 674 | 1-(6-(3-chloro-5-fluoro-4-hydroxyphenyl)-4-(6-(piperazin-1-yl)pyridin-3-ylamino)quinolin-3-yl)-2-methyl propan-1-one | NT | 0.11 | 2.4 | 0.46 | 0.15 |
| 675 | (6-(3-chloro-5-fluoro-4-hydroxyphenyl)-4-(4-(3,3-difluoropyrrolidin-1-yl)cyclohexylamino)quinolin-3-yl)(cyclopropyl)methanone | NT | 0.8 | 4.4 | NT | NT |
| 676 | (6-(3-chloro-4-hydroxy-5-methoxyphenyl)-4-(4-(3,3-difluoropyrrolidin-1-yl)cyclohexylamino)quinolin-3-yl)(cyclopropyl)methanone | NT | 1 | 11 | NT | NT |
| 677 | (6-(3-chloro-4-hydroxy-5-methoxyphenyl)-4-(6-(2-hydroxyethylamino)pyridin-3-ylamino)quinolin-3-yl)(cyclopropyl)methanone | NT | 0.33 | 1.5 | 0.36 | 0.38 |
| 678 | cyclopropyl(6-(3,5-dichloro-4-hydroxyphenyl)-4-(6-(2-hydroxyethylamino)pyridin-3-ylamino)quinolin-3-yl)methanone | NT | 0.41 | 5.1 | 1.2 | 0.11 |
| 679 | (6-(3-chloro-5-fluoro-4-hydroxyphenyl)-4-(6-(2-hydroxyethylamino)pyridin-3-ylamino)quinolin-3-yl)(cyclopropyl)methanone | NT | 0.23 | 3.7 | 1.3 | 0.12 |
| 680 | 1-(6-(3-chloro-4-hydroxy-5-methoxyphenyl)-4-(6-(piperazin-1-yl)pyridin-3-ylamino)quinolin-3-yl)-2-methylpropan-1-one | NT | 0.59 | 2.4 | 1.3 | 1 |
| 681 | 1-(4-(6-(3-aminopiperidin-1-yl)pyridin-3-ylamino)-6-(3,5-dichloro-4-hydroxyphenyl)quinolin-3-yl)ethanone | NT | 0.0046 | 0.25 | 0.017 | 0.0085 |
| 682 | cyclopropyl(6-(3,5-dichloro-4-hydroxyphenyl)-4-(6-((4-methylpiperazin-1-yl)methyl)pyridin-3-ylamino)quinolin-3-yl)methanone | NT | 0.55 | 14 | 0.7 | 0.32 |
| 683 | (6-(3-chloro-4-hydroxy-5-methoxyphenyl)-4-(6-((4-methylpiperazin-1-yl)methyl)pyridin-3-ylamino)quinolin-3-yl)(cyclopropyl)methanone | NT | 0.69 | 9.8 | 1.2 | 1.3 |
| 684 | (6-(3-chloro-5-fluoro-4-hydroxyphenyl)-4-(6-((4-methylpiperazin-1-yl)methyl)pyridin-3-ylamino)quinolin-3-yl)(cyclopropyl)methanone | NT | 0.88 | 15 | 1.5 | 0.82 |
| 685 | cyclopropyl(6-(3,5-dichloro-4-hydroxyphenyl)-4-(1R,4R)-4-((methylamino)methyl)cyclohexylamino)quinolin-3-yl)methanone | NT | 0.054 | 0.73 | 0.14 | 0.018 |
| 686 | (6-(3-chloro-5-fluoro-4-hydroxyphenyl)-4-(4-(3-methoxypyrrolidin-1-yl)cyclohexylamino)quinolin-3-yl)(cyclopropyl)methanone | NT | 0.19 | 1.1 | 0.17 | 0.16 |
| 687 | (6-(3-chloro-4-hydroxy-5-methoxyphenyl)-4-(4-(3-methoxypyrrolidin-1-yl)cyclohexylamino)quinolin-3-yl)(cyclopropyl)methanone | NT | 0.63 | 3.3 | 0.45 | 0.33 |
| 688 | 1-(4-(6-(3-aminopiperidin-1-yl)pyridin-3-ylamino)-6-(3-chloro-4-hydroxy-5-methoxyphenyl)quinolin-3-yl)ethanone | NT | 0.056 | 1.7 | 0.23 | 0.11 |
| 689 | (6-(3-chloro-4-hydroxy-5-methoxyphenyl)-4-(6-(3-(dimethylamino)pyrrolidin-1-yl)pyridin-3-ylamino)quinolin-3-yl)(cyclopropyl)methanone | NT | 0.28 | 9.4 | 1.5 | 3.2 |
| 690 | cyclopropyl(6-(3,5-dichloro-4-hydroxyphenyl)-4-(6-(3-(dimethylamino)pyrrolidin-1-yl)pyridin-3-ylamino)quinolin-3-yl)methanone | NT | 0.25 | 4 | 0.3 | 0.19 |
| 691 | (6-(3-chloro-5-fluoro-4-hydroxyphenyl)-4-(6-(3-(dimethylamino)pyrrolidin-1-yl)pyridin-3-ylamino)quinolin-3-yl)(cyclopropyl)methanone | NT | 0.18 | 5.9 | 0.32 | 0.22 |
| 692 | (6-(3-chloro-4-hydroxy-5-methoxy phenyl)-4-(3-(2-(dimethylamino)ethyl)phenylamino)quinolin-3-yl)(cyclopropyl)methanone | NT | 1 | 5.9 | 0.37 | 0.3 |
| 693 | (6-(3-chloro-5-fluoro-4-hydroxyphenyl)-4-(3-(2-(dimethylamino)ethyl)phenylamino)quinolin-3-yl)(cyclopropyl)methanone | NT | 0.37 | 10 | 0.09 | 0.085 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 694 | cyclopropyl(6-(3,5-dichloro-4-hydroxyphenyl)-4-(4-((3-(dimethylamino)pyrrolidin-1-yl)methyl)phenylamino)quinolin-3-yl)methanone | NT | 0.41 | 7.5 | 0.15 | 0.12 |
| 695 | cyclopropyl(6-(3,5-dichloro-4-hydroxyphenyl)-4-(4-((3-(dimethylamino)pyrrolidin-1-yl)methyl)phenylamino)quinolin-3-yl)methanone hydrochloride | 0.23 | 0.26 | 5.8 | 0.13 | 0.1 |
| 696 | (6-(3-chloro-5-fluoro-4-hydroxyphenyl)-4-(4-((3-(dimethylamino)pyrrolidin-1-yl)methyl)phenylamino)quinolin-3-yl)(cyclopropyl)methanone | NT | 0.46 | 5.4 | 0.18 | 0.17 |
| 697 | (6-(3-chloro-4-hydroxy-5-methoxyphenyl)-4-(4-((3-(dimethylamino)pyrrolidin-1-yl)methyl)phenylamino)quinolin-3-yl)(cyclopropyl)methanone | NT | 0.81 | 1.8 | 0.44 | 0.64 |
| 698 | cyclopropyl(6-(3,5-dichloro-4-hydroxyphenyl)-4-(3-(2-(dimethylamino)ethyl)phenylamino)quinolin-3-yl)methanone | NT | 0.3 | 10 | 0.05 | 0.04 |
| 699 | (6-(3-chloro-5-fluoro-4-hydroxyphenyl)-4-(1-(1-methylpiperidin-3-yl)-1H-pyrazol-4-ylamino)quinolin-3-yl)(cyclopropyl)methanone | NT | 0.24 | 2.7 | 0.18 | 0.072 |
| 700 | cyclopropyl(6-(3,5-dichloro-4-hydroxyphenyl)-4-(1R,4R)-4-((2-fluoroethylamino)methyl)cyclohexylamino)quinolin-3-yl)methanone | NT | 0.47 | 2.2 | 0.47 | 0.25 |
| 701 | (6-(3-chloro-5-fluoro-4-hydroxyphenyl)-4-(1R,4R)-4-((2-fluoroethylamino)methyl)cyclohexylamino)quinolin-3-yl)(cyclopropyl)methanone | NT | 0.29 | 0.98 | 0.41 | 0.38 |
| 702 | 1-(6-(3,5-dichloro-4-hydroxyphenyl)-4-(6-(piperazin-1-yl)pyridin-3-ylamino)quinolin-3-yl)ethanone hydrochloride | NT | 0.046 | 2.4 | 0.14 | 0.044 |
| 703 | cyclopropyl(6-(3,5-dichloro-4-hydroxyphenyl)-4-(1-(1-methylpiperidin-3-yl)-1H-pyrazol-4-ylamino)quinolin-3-yl)methanone | NT | 0.33 | 5.5 | 0.11 | 0.052 |
| 704 | 1-(6-(3-chloro-4-hydroxy-5-methoxyphenyl)-4-(6-(piperazin-1-yl)pyridin-3-ylamino)quinolin-3-yl)ethanone hydrochloride | NT | 0.17 | 2.1 | 0.2 | 0.12 |
| 705 | cyclopropyl(6-(3,5-dichloro-4-hydroxyphenyl)-4-(1-(1R,4R)-4-(methylamino)cyclohexyl)-1H-pyrazol-4-ylamino)quinolin-3-yl)methanone | NT | 0.24 | 10 | 1.7 | 0.072 |
| 706 | (4-(1-(1R,4R)-4-aminocyclohexyl)-1H-pyrazol-4-ylamino)-6-(3,5-dichloro-4-hydroxyphenyl)quinolin-3-yl)(cyclopropyl)methanone hydrochloride | NT | 0.042 | 7.9 | 0.59 | 0.02 |
| 707 | (6-(3-chloro-5-fluoro-4-hydroxyphenyl)-4-(4-(2-(dimethylamino)-1-hydroxyethyl)phenylamino)quinolin-3-yl)(cyclopropyl)methanone | NT | 0.21 | 3.4 | 0.13 | 0.081 |
| 708 | (6-(3-chloro-4-hydroxy-5-methoxyphenyl)-4-(4-(2-(dimethylamino)-1-hydroxyethyl)phenylamino)quinolin-3-yl)(cyclopropyl)methanone | NT | 0.41 | 4.6 | 0.3 | 0.25 |
| 709 | cyclopropyl(6-(3,5-dichloro-4-hydroxyphenyl)-4-(4-(2-(dimethylamino)-1-hydroxyethyl)phenylamino)quinolin-3-yl)methanone | NT | 0.2 | 3.8 | 0.14 | 0.077 |
| 710 | (6-(3-chloro-5-fluoro-4-hydroxyphenyl)-4-(6-(2-(dimethylamino)ethoxy)pyridin-3-ylamino)quinolin-3-yl)(cyclopropyl)methanone | NT | 0.15 | 2 | 0.09 | 0.083 |
| 711 | cyclopropyl(6-(3,5-dichloro-4-hydroxyphenyl)-4-(6-(2-(dimethylamino)ethoxy)pyridin-3-ylamino)quinolin-3-yl)methanone | NT | 0.22 | 5.7 | 0.11 | 0.073 |
| 712 | (6-(3-chloro-4-hydroxy-5-methoxyphenyl)-4-(6-(2-(dimethylamino)ethoxy)pyridin-3-ylamino)quinolin-3-yl)(cyclopropyl)methanone | NT | 0.31 | 5.4 | 0.31 | 0.34 |
| 713 | 1-(6-(3-chloro-4-hydroxy-5-methoxyphenyl)-4-(1R,4R)-4-((dimethylamino)methyl)cyclohexylamino)quinolin-3-yl)propan-1-one | NT | 0.2 | 4.9 | 0.18 | 0.15 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 714 | 1-(6-(3-chloro-5-fluoro-4-hydroxyphenyl)-4-(1R,4R)-4-((dimethylamino)methyl cyclohexylamino)quinolin-3-yl)propan-1-one | NT | 0.054 | 0.55 | 0.11 | 0.067 |
| 715 | 1-(6-(3,5-dichloro-4-hydroxyphenyl)-4-(1R,4R)-4-((dimethylamino)methyl cyclohexylamino)quinolin-3-yl)propan-1-one | NT | 0.087 | 0.84 | 0.11 | 0.046 |
| 716 | 1-(6-(3,5-dichloro-4-hydroxyphenyl)-4-((1R,4R)-4-((dimethylamino)methyl cyclohexyl)amino)quinolin-3-yl)propan-1-one dihydrochloride | 0.14 | 0.14 | 0.82 | 0.12 | 0.055 |
| 717 | 1-(6-(3-chloro-5-fluoro-4-hydroxyphenyl)-4-((1R,3R)-3-((dimethylamino)methyl cyclopentylamino)quinolin-3-yl)ethanone | NT | 0.42 | 2 | 0.65 | 0.34 |
| 718 | 1-(6-(3,5-dichloro-4-hydroxyphenyl)-4-((1R,3R)-3-((dimethylamino)methyl cyclopentylamino)quinolin-3-yl)ethanone | NT | 0.36 | 2 | 0.44 | 0.19 |
| 719 | (6-(3-chloro-5-fluoro-4-hydroxyphenyl)-4-(piperidin-4-ylamino)quinolin-3-yl)(cyclopropyl)methanone | NT | 0.32 | 10 | 0.69 | 0.17 |
| 720 | 1-(6-(3,5-dichloro-4-hydroxyphenyl)-4-(1-(dimethylamino)-2,3-dihydro-1H-inden-5-ylamino)quinolin-3-yl)ethanone | NT | 0.059 | 0.38 | 0.063 | 0.032 |
| 721 | 1-(6-(3,5-difluoro-4-hydroxyphenyl)-4-(1R,4R)-4-((dimethylamino)methyl cyclohexylamino)quinolin-3-yl)ethanone | NT | 0.15 | 3.4 | 0.32 | 0.22 |
| 722 | (4-(6-(2-aminoethoxy)pyridin-3-ylamino)-6-(3-chloro-4-hydroxy-5-methoxyphenyl)quinolin-3-yl)(cyclopropyl)methanone | NT | 0.19 | 2.3 | 0.32 | 0.19 |
| 723 | (4-(6-(2-aminoethoxy)pyridin-3-ylamino)-6-(3,5-dichloro-4-hydroxyphenyl)quinolin-3-yl)(cyclopropyl)methanone | NT | 0.099 | 2.1 | 0.23 | 0.028 |
| 724 | (4-(6-(2-aminoethoxy)pyridin-3-ylamino)-6-(3-chloro-5-fluoro-4-hydroxyphenyl)quinolin-3-yl)(cyclopropyl)methanone | NT | 0.07 | 2.8 | 0.23 | 0.035 |
| 725 | (4-(6-(3-aminopiperidin-1-yl)pyridin-3-ylamino)-6-(3,5-difluoro-4-hydroxyphenyl)quinolin-3-yl)(cyclopropyl)methanone | NT | 0.0078 | 0.11 | 0.012 | 0.01 |
| 726 | cyclopropyl(6-(3,5-dichloro-4-hydroxypheny)-4-(piperidin-4-ylamino)quinolin-3-yl)methanone | NT | 0.56 | 2.4 | 0.52 | 0.14 |
| 727 | (6-(3-chloro-4-hydroxy-5-methoxyphenyl)-4-(piperidin-4-ylamino)quinolin-3-yl)(cyclopropyl)methanone | NT | 0.37 | 1.1 | 0.19 | 0.14 |
| 728 | 1-(6-(3,5-dichloro-4-hydroxyphenyl)-4-((1R,3R)-3-((4-methylpiperazin-1-yl)methyl cyclopentylamino)quinolin-3-yl)ethanone | NT | 0.83 | 5.7 | 0.85 | 0.48 |
| 729 | 1-(6-(3,5-dichloro-4-hydroxyphenyl)-4-(3-(2-(dimethylamino)ethyl)phenylamino)quinolin-3-yl)ethanone | NT | 0.52 | 10 | 0.2 | 0.1 |
| 730 | 1-(6-(3-chloro-4-hydroxy-5-methoxyphenyl)-4-(3-(2-(dimethylamino)ethyl)phenylamino)quinolin-3-yl)ethanone | NT | 2.1 | 8 | 0.82 | 0.69 |
| 731 | 1-(6-(3-chloro-5-fluoro-4-hydroxyphenyl)-4-(1R,4R)-4-(pyrrolidin-1-ylmethyl)cyclohexylamino)quinolin-3-yl)ethanone | NT | 0.11 | 1.3 | 0.17 | 0.13 |
| 732 | 1-(4-(6-(3-aminopiperidin-1-yl)pyridin-3-ylamino)-6-(3-chloro-5-fluoro-4-hydroxyphenyl)quinolin-3-yl)ethanone | NT | 0.0056 | 0.18 | 0.0094 | 0.0099 |
| 733 | 1-(4-((6-(3-aminopiperidin-1-yl)pyridin-3-yl)amino)-6-(3-chloro-5-fluoro-4-hydroxyphenyl)quinolin-3-yl)ethanone | 0.0064 | 0.0035 | 0.064 | 0.0086 | 0.01 |
| 734 | 1-(6-(3-chloro-4-hydroxy-5-methoxyphenyl)-4-((1R,4R)-4-(pyrrolidin-1-ylmethyl)cyclohexylamino)quinolin-3-yl)ethanone | NT | 0.51 | 6.4 | 0.25 | 0.36 |
| 735 | (4-(2-(4-aminopiperidin-1-yl)pyridin-4-ylamino)-6-(3,5-dichloro-4-hydroxyphenyl)quinolin-3-yl)(cyclopropyl)methanone | NT | 1 | 20 | 3.5 | 0.5 |
| 736 | 1-(6-(3-chloro-5-fluoro-4-hydroxyphenyl)-4-(6-(4-methylpiperazin-1-yl)pyridin-3-ylamino)quinolin-3-yl)propan-1-one | NT | 0.14 | 10 | 0.22 | 0.19 |
| 737 | 1-(6-(3,5-dichloro-4-hydroxyphenyl)-4-(6-(4-methylpiperazin-1-yl)pyridin-3-ylamino)quinolin-3-yl)propan-1-one | NT | 0.31 | 10 | 0.29 | 0.27 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 738 | 1-(6-(3-chloro-4-hydroxy-5-methoxyphenyl)-4-(1R,4R)-4-(2-(dimethylamino)ethyl)cyclohexylamino)quinolin-3-yl)ethanone | NT | 0.51 | 7.8 | 0.34 | 2.1 |
| 739 | 1-(6-(3,5-dichloro-4-hydroxyphenyl)-4-(1R,4R)-4-(2-(dimethylamino)ethyl)cyclohexylamino)quinolin-3-yl)ethanone | NT | 0.14 | 4 | 0.14 | 0.099 |
| 740 | 1-(6-(3,5-dichloro-4-hydroxyphenyl)-4-((1R,4R)-4-(2-(dimethylamino)ethyl)cyclohexyl)amino)quinolin-3-yl)ethanone hydrochloride | 0.17 | 0.099 | 3.5 | 0.13 | 0.087 |
| 741 | 1-(6-(3-chloro-5-fluoro-4-hydroxyphenyl)-4-(1R,4R)-4-(2-(dimethylamino)ethyl)cyclohexylamino)quinolin-3-yl)ethanone | NT | 0.037 | 2 | 0.085 | 0.062 |
| 742 | 1-(6-(3-chloro-5-fluoro-4-hydroxyphenyl)-4-(1R,4R)-4-(2-(dimethylamino)ethyl)cyclohexylamino)quinolin-3-yl)ethanone dihydrochloride | 0.094 | 0.034 | 1.7 | 0.078 | 0.063 |
| 743 | 1-(6-(3-chloro-4-hydroxy-5-methoxyphenyl)-4-(4-(2-(dimethylamino)ethyl)phenylamino)quinolin-3-yl)ethanone | NT | 0.66 | 4.8 | 0.53 | 0.36 |
| 744 | 1-(6-(3,5-dichloro-4-hydroxyphenyl)-4-(4-(2-(dimethylamino)ethyl)phenylamino)quinolin-3-yl)ethanone | NT | 0.11 | 0.43 | 0.082 | 0.031 |
| 745 | 1-(6-(3-chloro-5-fluoro-4-hydroxyphenyl)-4-(4-(2-(dimethylamino)ethyl)phenylamino)quinolin-3-yl)ethanone | NT | 0.12 | 0.99 | 0.16 | 0.063 |
| 746 | (6-(3-chloro-4-hydroxy-5-methoxyphenyl)-4-(6-(2-(dimethylamino)ethylamino)pyridin-3-ylamino)quinolin-3-yl)(cyclopropyl)methanone | NT | 0.23 | 6.2 | 0.18 | 0.11 |
| 747 | cyclopropyl(6-(3,5-dichloro-4-hydroxyphenyl)-4-(6-(2-(dimethylamino)ethylamino)pyridin-3-ylamino)quinolin-3-yl)methanone | NT | 0.16 | 2.6 | 0.091 | 0.043 |
| 748 | cyclopropyl(6-(3,5-dichloro-4-hydroxyphenyl)-4-(6-(2-(dimethylamino)ethylamino)pyridin-3-ylamino)quinolin-3-yl)methanone hydrochloride | 0.1 | 0.088 | 1.6 | 0.069 | 0.032 |
| 749 | 1-(6-(3-chloro-4-hydroxy-5-methoxyphenyl)-4-(1R,4R)-4-((3-hydroxypyrrolidin-1-yl)methyl)cyclohexylamino)quinolin-3-yl)ethanone | NT | 0.12 | 6.4 | 0.22 | 0.21 |
| 750 | 1-(6-(3,5-dichloro-4-hydroxyphenyl)-4-((1R,3R)-3-((dimethylamino)methyl)cyclohexylamino)quinolin-3-yl)ethanone | NT | 0.2 | 1.7 | 0.39 | 0.19 |
| 751 | 1-(6-(3-chloro-5-fluoro-4-hydroxyphenyl)-4-((1R,3R)-3-((dimethylamino)methyl)cyclohexylamino)quinolin-3-yl)ethanone | NT | 0.32 | 1.7 | 0.58 | 0.29 |
| 752 | 1-(6-(3-chloro-4-hydroxy-5-methoxyphenyl)-4-((1R,3R)-3-((dimethylamino)methyl)cyclohexylamino)quinolin-3-yl)ethanone | NT | 0.18 | 3.4 | 0.2 | 0.17 |
| 753 | 1-(6-(3,5-dichloro-4-hydroxyphenyl)-4-(1R,4R)-4-((3-hydroxypyrrolidin-1-yl)methyl)cyclohexylamino)quinolin-3-yl)ethanone | NT | 0.13 | 71 | 0.37 | 0.057 |
| 754 | 1-(6-(3,5-dichloro-4-hydroxyphenyl)-4-(1R,4R)-4-(dimethylamino)cyclohexylamino)quinolin-3-yl)propan-1-one | NT | 0.19 | 10 | 0.22 | 0.072 |
| 755 | 1-(6-(3-chloro-4-hydroxy-5-methoxyphenyl)-4-(1R,4R)-4-(dimethylamino)cyclohexylamino)quinolin-3-yl)propan-1-one | NT | 0.35 | 3.4 | 0.34 | 0.21 |
| 756 | cyclopropyl(6-(3,5-dichloro-4-hydroxyphenyl)-4-(4-(2-(pyrrolidin-1-yl)ethyl)piperidin-1-yl)quinolin-3-yl)methanone | NT | 0.5 | 10 | 0.54 | 0.27 |
| 757 | 1-(6-(3-chloro-5-fluoro-4-hydroxyphenyl)-4-(1R,4R)-4-(dimethylamino)cyclohexylamino)quinolin-3-yl)propan-1-one | NT | 0.064 | 0.76 | 0.15 | 0.069 |
| 758 | 1-(6-(3,5-dichloro-4-hydroxyphenyl)-4-(6-(2-(dimethylamino)ethylamino)pyridin-3-ylamino)quinolin-3-yl)ethanone | NT | 0.15 | 24 | 0.22 | 0.055 |
| 759 | 1-(6-(3-chloro-5-fluoro-4-hydroxyphenyl)-4-(3-(2-(dimethylamino)ethyl)phenylamino)quinolin-3-yl)ethanone | NT | 0.67 | 10 | 0.42 | 0.2 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 760 | 1-(4-(6-(3-aminopyrrolidin-1-yl)pyridin-3-ylamino)-6-(3-chloro-5-fluoro-4-hydroxyphenyl)quinolin-3-yl)propan-1-one | NT | 0.0087 | 0.77 | 0.031 | 0.016 |
| 761 | 1-(4-(6-(3-aminopyrrolidin-1-yl)pyridin-3-ylamino)-6-(3,5-dichloro-4-hydroxyphenyl)quinolin-3-yl)propan-1-one | NT | 0.031 | 1.5 | 0.053 | 0.022 |
| 762 | 1-(6-(3-chloro-5-fluoro-4-hydroxyphenyl)-4-(6-(2-(dimethylamino)ethylamino)pyridin-3-ylamino)quinolin-3-yl)ethanone | NT | 0.12 | 5.2 | 0.25 | 0.089 |
| 763 | 1-(6-(3-chloro-5-fluoro-4-hydroxyphenyl)-4-(1R,4R)-4-(dimethylamino)cyclohexylamino)quinolin-3-yl)ethanone | 0.14 | 0.05 | 1.8 | 0.27 | 0.093 |
| 764 | (6-(3-chloro-4-hydroxy-5-methoxyphenyl)-4-(1-(pyrrolidin-3-yl)piperidin-4-ylamino)quinolin-3-yl)(cyclopropyl)methanone | 0.95 | 0.18 | 5.3 | 1.3 | 0.18 |
| 765 | 1-(6-(3,5-dichloro-4-hydroxyphenyl)-4-(1R,4R)-4-(dimethylamino)cyclohexylamino)quinolin-3-yl)ethanone | 0.14 | 0.081 | 1.7 | 0.17 | 0.047 |
| 766 | 1-(6-(3,5-dichloro-4-hydroxyphenyl)-4-((1R,4R)-4-(dimethylamino)cyclohexyl)amino)quinolin-3-yl)ethanone hydrochloride | 0.1 | 0.074 | 1 | 0.14 | 0.06 |
| 767 | 1-(6-(3,5-dichloro-4-hydroxyphenyl)-4-(1R,4R)-4-(pyrrolidin-1-ylmethyl)cyclohexylamino)quinolin-3-yl)ethanone | 0.15 | 0.12 | 24 | 0.16 | 0.083 |
| 768 | 1-(6-(3,5-dichloro-4-hydroxyphenyl)-4-((1R,4R)-4-(pyrrolidin-1-ylmethyl)cyclohexyl)amino)quinolin-3-yl)ethanone hydrochloride | 0.11 | 0.11 | 28 | 0.13 | 0.07 |
| 769 | 1-(6-(3-chloro-4-hydroxy-5-methoxyphenyl)-4-(4-((dimethylamino)methyl)phenylamino)quinolin-3-yl)propan-1-one | 0.79 | 0.12 | 2.8 | 0.48 | 0.14 |
| 770 | 1-(6-(3-chloro-5-fluoro-4-hydroxyphenyl)-4-(4-((dimethylamino)methyl)phenylamino)quinolin-3-yl)propan-1-one | 0.17 | 0.074 | 0.84 | 0.11 | 0.062 |
| 771 | 1-(6-(3,5-dichloro-4-hydroxyphenyl)-4-(4-((dimethylamino)methyl)phenylamino)quinolin-3-yl)propan-1-one | 0.16 | 0.072 | 0.72 | 0.095 | 0.045 |
| 772 | 1-(6-(3,5-dichloro-4-hydroxyphenyl)-4-(1R,4R)-4-(piperazin-1-ylmethyl)cyclohexylamino)quinolin-3-yl)ethanone dihydrochloride | 0.14 | 0.058 | 3.2 | 0.26 | 0.076 |
| 773 | 1-(4-(6-(3-aminopyrrolidin-1-yl)pyridin-3-ylamino)-6-(3-chloro-5-fluoro-4-hydroxyphenyl)quinolin-3-yl)ethanone | 0.0094 | 0.0042 | 0.7 | 0.028 | 0.017 |
| 774 | 1-(4-(6-(3-aminopyrrolidin-1-yl)pyridin-3-ylamino)-6-(3-chloro-4-hydroxy-5-methoxyphenyl)quinolin-3-yl)ethanone | 0.082 | 0.034 | 0.71 | 0.045 | 0.056 |
| 775 | 1-(4-(6-(3-aminopyrrolidin-1-yl)pyridin-3-ylamino)-6-(3-chloro-4-hydroxy-5-methoxyphenyl)quinolin-3-yl)propan-1-one | 0.12 | 0.049 | 0.75 | 0.049 | 0.065 |
| 776 | (6-(3-chloro-5-fluoro-4-hydroxyphenyl)-4-(6-(2-(dimethylamino)ethylamino)pyridin-3-ylamino)quinolin-3-yl)(cyclopropyl)methanone | 0.15 | 0.073 | 1.2 | 0.08 | 0.038 |
| 777 | (6-(3-chloro-5-fluoro-4-hydroxyphenyl)-4-(6-(2-(dimethylamino)ethylamino)pyridin-3-ylamino)quinolin-3-yl)(cyclopropyl)methanone trihydrochloride | 0.17 | 0.12 | 1.6 | 0.12 | 0.047 |
| 778 | cyclopropyl(6-(3,5-difluoro-4-hydroxyphenyl)-4-(6-(4-methylpiperazin-1-yl)pyridin-3-ylamino)quinolin-3-yl)methanone | 0.48 | 0.1 | 2.6 | 0.17 | 0.22 |
| 779 | 1-(4-(1R,4R)-4-((3-aminopyrrolidin-1-yl)methyl)cyclohexylamino)-6-(3,5-dichloro-4-hydroxyphenyl)quinolin-3-yl)ethanone hydrochloride | 0.23 | 0.14 | 10 | 1 | 0.13 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 780 | 1-(4-(1R,4R)-4-((3-aminopyrrolidin-1-yl)methyl)cyclohexylamino)-6-(3-chloro-4-hydroxy-5-methoxyphenyl)quinolin-3-yl)ethanone hydrochloride | 0.67 | 0.41 | 3.2 | 0.62 | 1.5 |
| 781 | 1-(6-(3-chloro-5-fluoro-4-hydroxyphenyl)-4-(1R,4R)-4-((4-methylpiperazin-1-yl)methyl)cyclohexylamino)quinolin-3-yl)ethanone hydrochloride | 0.34 | 0.1 | 3.3 | 0.2 | 0.19 |
| 782 | 1-(6-(3,5-dichloro-4-hydroxyphenyl)-4-(1R,4R)-4-((4-methylpiperazin-1-yl)methyl)cyclohexylamino)quinolin-3-yl)ethanone hydrochloride | 0.41 | 0.15 | 5.9 | 0.23 | 0.16 |
| 783 | 1-(6-(3-chloro-5-fluoro-4-hydroxyphenyl)-4-(1R,4R)-4-(piperazin-1-ylmethyl)cyclohexylamino)quinolin-3-yl)ethanone dihydrochloride | 0.087 | 0.027 | 4.2 | 0.2 | 0.057 |
| 784 | 1-(6-(3,5-dichloro-4-hydroxyphenyl)-4-((1r,3r)-3-((dimethylamino)methyl)cyclobutylamino)quinolin-3-yl)ethanone | 0.95 | 0.6 | 3.2 | 0.74 | 0.2 |
| 785 | 1-(6-(3-chloro-5-fluoro-4-hydroxyphenyl)-4-(6-(3-(methylamino)pyrrolidin-1-yl)pyridin-3-ylamino)quinolin-3-yl)ethanone trihydrochloride | 0.076 | 0.035 | 1.3 | 0.094 | 0.074 |
| 786 | 1-(4-(1R,4R)-4-((3-aminopyrrolidin-1-yl)methyl)cyclohexylamino)-6-(3-chloro-5-fluoro-4-hydroxyphenyl)quinolin-3-yl)ethanone hydrochloride | 0.17 | 0.07 | 10 | 0.96 | 0.23 |
| 787 | 1-(6-(3-chloro-4-hydroxy-5-methoxyphenyl)-4-(1R,4R)-4-((4-methylpiperazin-1-yl)methyl)cyclohexylamino)quinolin-3-yl)ethanone hydrochloride | 0.72 | 0.48 | 5.2 | 0.44 | 2.7 |
| 788 | 1-(6-(3,5-dichloro-4-hydroxyphenyl)-4-(6-(3-(methylamino)pyrrolidin-1-yl)pyridin-3-ylamino)quinolin-3-yl)ethanone trihydrochloride | 0.1 | 0.071 | 8.6 | 0.16 | 0.07 |
| 789 | (6-(3-chloro-5-fluoro-4-hydroxyphenyl)-4-(6-(3-(methylamino)pyrrolidin-1-yl)pyridin-3-ylamino)quinolin-3-yl)(cyclopropyl)methanone trihydrochloride | 0.077 | 0.039 | 0.8 | 0.076 | 0.053 |
| 790 | 1-(6-(3,5-dichloro-4-hydroxyphenyl)-4-(1R,4R)-4-((diethylamino)methyl)cyclohexylamino)quinolin-3-yl)ethanone dihydrochloride | 0.14 | 0.1 | 4.2 | 0.14 | 0.098 |
| 791 | 1-(6-(3-chloro-4-hydroxy-5-methoxyphenyl)-4-(1R,4R)-4-((diethylamino)methyl)cyclohexylamino)quinolin-3-yl)ethanone hydrochloride | 0.49 | 0.58 | 9.3 | 0.27 | 0.43 |
| 792 | 1-(6-(3,5-dichloro-4-hydroxyphenyl)-4-((1S,4r)-4-(((S)-2-(hydroxymethyl)pyrrolidin-1-yl)methyl)cyclohexylamino)quinolin-3-yl)ethanone | 0.12 | 0.079 | 100 | 0.1 | 0.073 |
| 793 | 1-(6-(3-chloro-4-hydroxy-5-methoxyphenyl)-4-((1S,4r)-4-(((S)-2-(hydroxymethyl)pyrrolidin-1-yl)methyl)cyclohexylamino)quinolin-3-yl)ethanone | 0.34 | 0.15 | 7.1 | 0.17 | 0.33 |
| 794 | 1-(6-(3-chloro-5-fluoro-4-hydroxyphenyl)-4-(1R,4R)-4-((diethylamino)methyl)cyclohexylamino)quinolin-3-yl)ethanone dihydrochloride | 0.094 | 0.031 | 0.75 | 0.077 | 0.074 |
| 795 | cyclopropyl(6-(3,5-difluoro-4-hydroxyphenyl)-4-(6-(pyrrolidin-1-ylmethyl)pyridin-3-ylamino)quinolin-3-yl)methanone | 0.83 | 0.51 | 3.5 | 0.34 | 0.31 |
| 796 | cyclopropyl(6-(3,5-difluoro-4-hydroxyphenyl)-4-(3-(2-(dimethylamino)ethyl)phenylamino)quinolin-3-yl)methanone | 0.52 | 0.43 | 0.67 | 0.14 | 0.14 |
| 797 | cyclopropyl(6-(3,5-dichloro-4-hydroxyphenyl)-4-(3-(2-(pyrrolidin-1-yl)ethyl)phenylamino)quinolin-3-yl)methanone | 0.12 | 0.31 | 100 | 0.022 | 0.03 |
| 798 | cyclopropyl(6-(3,5-dichloro-4-hydroxyphenyl)-4-(3-(2-(pyrrolidin-1-yl)ethyl)phenylamino)quinolin-3-yl)methanone hydrochloride | 0.092 | 0.16 | NT | 0.019 | 0.02 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 799 | (6-(3-chloro-5-fluoro-4-hydroxyphenyl)-4-(3-(2-(pyrrolidin-1-yl)ethyl)phenylamino)quinolin-3-yl)(cyclopropyl)methanone | 0.25 | 0.52 | 10 | 0.081 | 0.079 |
| 800 | (6-(3-chloro-5-fluoro-4-hydroxyphenyl)-4-(3-(2-(pyrrolidin-1-yl)ethyl)phenylamino)quinolin-3-yl)(cyclopropyl)methanone hydrochloride | 0.17 | 0.26 | NT | 0.041 | 0.046 |
| 801 | 1-(6-(3,5-dichloro-4-hydroxyphenyl)-4-(3-(2-(pyrrolidin-1-yl)ethyl)phenylamino)quinolin-3-yl)ethanone | 0.15 | 0.37 | 100 | 0.081 | 0.06 |
| 802 | 1-(6-(3,5-dichloro-4-hydroxyphenyl)-4-((3-(2-(pyrrolidin-1-yl)ethyl)phenyl)amino)quinolin-3-yl)ethanone hydrochloride | 0.16 | 0.45 | 100 | 0.08 | 0.072 |
| 803 | 1-(6-(3-chloro-5-fluoro-4-hydroxyphenyl)-4-(3-(2-(pyrrolidin-1-yl)ethyl)phenylamino)quinolin-3-yl)ethanone | 0.44 | 0.65 | 100 | 0.17 | 0.12 |
| 804 | cyclopropyl(6-(3,5-dichloro-4-hydroxyphenyl)-4-(6-(3-(methylamino)pyrrolidin-1-yl)pyridin-3-ylamino)quinolin-3-yl)methanone trihydrochloride | 0.1 | 0.088 | 1.4 | 0.17 | 0.042 |
| 805 | 1-(6-(3-chloro-5-fluoro-4-hydroxyphenyl)-4-(1-(1-methylpiperidin-4-yl)-1H-pyrazol-4-ylamino)quinolin-3-yl)ethanone hydrochloride | 0.32 | 0.17 | 2.4 | 0.34 | 0.11 |
| 806 | 1-(6-(3,5-dichloro-4-hydroxyphenyl)-4-(6-(3-(methylamino)piperidin-1-yl)pyridin-3-ylamino)quinolin-3-yl)ethanone trihydrochloride | 0.039 | 0.027 | 0.33 | 0.054 | 0.032 |
| 807 | cyclopropyl(6-(3,5-dichloro-4-hydroxyphenyl)-4-(6-(3-(methylamino)piperidin-1-yl)pyridin-3-ylamino)quinolin-3-yl)methanone trihydrochloride | 0.055 | 0.058 | 1.1 | 0.056 | 0.032 |
| 808 | 1-(6-(3-chloro-5-fluoro-4-hydroxyphenyl)-4-(1R,4R)-4-(((R)-2-(hydroxymethyl)pyrrolidin-1-yl)methyl)cyclohexylamino)quinolin-3-yl)ethanone hydrochloride | 0.22 | 0.12 | 8.2 | 0.22 | 0.11 |
| 809 | 1-(4-(1R,4R)-4-((3-aminopiperidin-1-yl)methyl)cyclohexylamino)-6-(3-chloro-4-hydroxy-5-methoxyphenyl)quinolin-3-yl)ethanone hydrochloride | 2.6 | 4.6 | 10 | 3.1 | 10 |
| 810 | 1-(4-(1R,4R)-4-((3-aminopiperidin-1-yl)methyl)cyclohexylamino)-6-(3,5-dichloro-4-hydroxyphenyl)quinolin-3-yl)ethanone trihydrochloride | 0.056 | 0.034 | 2.3 | 0.12 | 0.044 |
| 811 | 1-(6-(3-chloro-4-hydroxy-5-methoxyphenyl)-4-(1R,4R)-4-(((R)-2-(hydroxymethyl)pyrrolidin-1-yl)methyl)cyclohexylamino)quinolin-3-yl)ethanone | 0.45 | 0.49 | 5.4 | 0.28 | 0.38 |
| 812 | 1-(6-(3,5-dichloro-4-hydroxyphenyl)-4-(1R,4R)-4-(((R)-2-(hydroxymethyl)pyrrolidin-1-yl)methyl)cyclohexylamino)quinolin-3-yl)ethanone | 0.2 | 0.15 | 100 | 0.18 | 0.086 |
| 813 | 1-(6-(3-chloro-5-fluoro-4-hydroxyphenyl)-4-(1-(1-methylpyrrolidin-3-yl)-1H-pyrazol-4-ylamino)quinolin-3-yl)ethanone dihydrochloride | 0.11 | 0.07 | 0.75 | 0.25 | 0.054 |
| 814 | 1-(6-(3,5-dichloro-4-hydroxyphenyl)-4-(1-(1-methylpyrrolidin-3-yl)-1H-pyrazol-4-ylamino)quinolin-3-yl)ethanone dihydrochloride | 0.13 | 0.14 | 0.78 | 0.29 | 0.057 |
| 815 | 1-(6-(3-chloro-5-fluoro-4-hydroxyphenyl)-4-(6-(3-(methylamino)piperidin-1-yl)pyridin-3-ylamino)quinolin-3-yl)ethanone trihydrochloride | 0.034 | 0.016 | 0.052 | 0.041 | 0.041 |
| 816 | 1-(6-(3-chloro-4-hydroxy-5-methoxyphenyl)-4-(1R,4R)-4-((ethyl(methyl)amino)methyl)cyclohexylamino)quinolin-3-yl)ethanone hydrochloride | 0.44 | 0.28 | 7.3 | 0.25 | 0.36 |
| 817 | 1-(6-(3,5-dichloro-4-hydroxyphenyl)-4-(1R,4R)-4-((ethyl(methyl)amino)methyl)cyclohexylamino)quinolin-3-yl)ethanone dihydrochloride | 0.12 | 0.097 | 11 | 0.15 | 0.074 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 818 | 1-(4-(1R,4R)-4-((3-aminopiperidin-1-yl)methyl)cyclohexylamino)-6-(3-chloro-5-fluoro-4-hydroxyphenyl)quinolin-3-yl)ethanone trihydrochloride | 0.064 | 0.022 | 2.7 | 0.14 | 0.071 |
| 819 | cyclopropyl(6-(3,5-dichloro-4-hydroxyphenyl)-4-(1-(2-(dimethylamino)ethyl)piperidin-4-ylamino)quinolin-3-yl)methanone | 0.64 | 0.38 | 3.3 | 0.44 | 0.17 |
| 820 | cyclopropyl(6-(3,5-dichloro-4-hydroxyphenyl)-4-(1-(2-(dimethylamino)ethyl)piperidin-4-ylamino)quinolin-3-yl)methanone | 0.82 | 0.32 | 2.9 | 0.46 | 0.15 |
| 821 | 1-(6-(3-chloro-5-fluoro-4-hydroxyphenyl)-4-(1-(2-(dimethylamino)ethyl)piperidin-4-ylamino)quinolin-3-yl)ethanone | 0.25 | 0.23 | 3.3 | 0.59 | 0.17 |
| 822 | (6-(3-chloro-5-fluoro-4-hydroxyphenyl)-4-(1-(2-(dimethylamino)ethyl)piperidin-4-ylamino)quinolin-3-yl)(cyclopropyl)methanone | 0.43 | 0.29 | 2.5 | 0.48 | 0.16 |
| 823 | 1-(6-(3,5-dichloro-4-hydroxyphenyl)-4-(1-(2-(dimethylamino)ethyl)piperidin-4-ylamino)quinolin-3-yl)ethanone | 0.32 | 0.21 | 2.6 | 0.45 | 0.16 |
| 824 | 1-(4-(6-(3-aminopiperidin-1-yl)pyridin-3-ylamino)-6-(3,5-dichloro-4-hydroxyphenyl)quinolin-3-yl)propan-1-one trihydrochloride | 0.026 | 0.021 | 0.28 | 0.036 | 0.026 |
| 825 | 1-(4-(6-(3-aminopiperidin-1-yl)pyridin-3-ylamino)-6-(3-chloro-5-fluoro-4-hydroxyphenyl)quinolin-3-yl)propan-1-one trihydrochloride | 0.016 | 0.01 | 0.069 | 0.017 | 0.018 |
| 826 | 1-(6-(3-chloro-5-fluoro-4-hydroxyphenyl)-4-((1S,3R)-3-((dimethylamino)methyl)cyclohexylamino)quinolin-3-yl)ethanone hydrochloride | 0.48 | 0.25 | 1.9 | 0.54 | 0.22 |
| 827 | 1-(6-(3,5-dichloro-4-hydroxyphenyl)-4-((1S,3R)-3-((dimethylamino)methyl)cyclohexylamino)quinolin-3-yl)ethanone hydrochloride | 0.43 | 0.49 | 5.9 | 0.51 | 0.2 |
| 828 | (6-(3-chloro-5-fluoro-4-hydroxyphenyl)-4-(3-(2-(4-methylpiperazin-1-yl)ethyl)phenylamino)quinolin-3-yl)(cyclopropyl)methanone | 0.72 | 5.7 | 9.5 | 0.23 | 0.16 |
| 829 | cyclopropyl(6-(3,5-dichloro-4-hydroxyphenyl)-4-(3-(2-(4-methylpiperazin-1-yl)ethyl)phenylamino)quinolin-3-yl)methanone | 0.23 | 0.7 | 5.7 | 0.087 | 0.057 |
| 830 | 1-(6-(3-chloro-5-fluoro-4-hydroxyphenyl)-4-(3-(2-(4-methylpiperazin-1-yl)ethyl)phenylamino)quinolin-3-yl)ethanone | 1.3 | 1.5 | 15 | 0.73 | 0.26 |
| 831 | 1-(6-(3,5-dichloro-4-hydroxyphenyl)-4-(3-(2-(4-methylpiperazin-1-yl)ethyl)phenylamino)quinolin-3-yl)ethanone | 0.83 | 1.1 | 11 | 0.32 | 0.12 |
| 832 | 1-(6-(3-chloro-5-fluoro-4-hydroxyphenyl)-4-((1S,3R)-3-((4-methylpiperazin-1-yl)methyl)cyclohexylamino)quinolin-3-yl)ethanone hydrochloride | 0.44 | 0.17 | 0.79 | 0.26 | 0.24 |
| 835 | 1-(6-(3,5-dichloro-4-hydroxyphenyl)-4-((1S,3R)-3-((4-methylpiperazin-1-yl)methyl)cyclohexylamino)quinolin-3-yl)ethanone hydrochloride | 0.81 | 0.58 | 2.7 | 0.79 | 0.6 |
| 836 | 1-(6-(3,5-dichloro-4-hydroxyphenyl)-4-(1-(1-methylpiperidin-4-yl)-1H-pyrazol-4-ylamino)quinolin-3-yl)ethanone dihydrochloride | 0.27 | 0.35 | 100 | 0.45 | 0.082 |
| 838 | 1-(6-(3,5-dichloro-4-hydroxyphenyl)-2-methyl-4-(6-(4-methylpiperazin-1-yl)pyridin-3-ylamino)quinolin-3-yl)ethanone hydrochloride | 7.2 | 17 | 25 | 11 | 14 |
| 843 | 1-(6-(3,5-dichloro-4-hydroxyphenyl)-4-(1R,4R)-4-(pyrrolidin-1-ylmethyl)cyclohexylamino)quinolin-3-yl)propan-1-one dihydrochloride | 0.19 | 0.15 | 4.2 | 0.15 | 0.057 |

TABLE 4-continued

| Example | Compound Name | IC50 (µM) (22Rv1) | IC50 (µM) (T47D) | IC50 (µM) (HT1197) | IC50 (µM) (A549) | IC50 (µM) (DU4475) |
|---|---|---|---|---|---|---|
| 844 | 1-(6-(3-chloro-5-fluoro-4-hydroxyphenyl)-4-((1S,4r)-4-(((S)-2-(hydroxymethyl)pyrrolidin-1-yl)methyl)cyclohexylamino)quinolin-3-yl)ethanone | 0.18 | 0.067 | 3.3 | 0.18 | 0.092 |
| 845 | 1-(6-(3-chloro-5-fluoro-4-hydroxyphenyl)-4-(1R,4R)-4-((ethyl(methyl)amino)methyl)cyclohexylamino)quinolin-3-yl)ethanone dihydrochloride | 0.11 | 0.063 | 1.4 | 0.14 | 0.069 |
| 846 | 1-(6-(3-chloro-5-fluoro-4-hydroxyphenyl)-4-(1R,4R)-4-(pyrrolidin-1-ylmethyl)cyclohexylamino)quinolin-3-yl)propan-1-one dihydrochloride | 0.16 | 0.096 | 0.71 | 0.13 | 0.071 |
| 848 | 1-(6-(3-chloro-5-fluoro-4-hydroxyphenyl)-4-(6-(2-(dimethylamino)ethoxy)pyridin-3-ylamino)quinolin-3-yl)ethanone hydrochloride | 0.44 | 0.14 | 5.3 | 0.29 | 0.16 |
| 849 | 1-(6-(3-chloro-5-fluoro-4-hydroxyphenyl)-4-(4-(4-methylpiperazine-1-carbonyl)cyclohexylamino)quinolin-3-yl)ethanone hydrochloride | 1 | 0.47 | 4.5 | 1.3 | 1 |
| 850 | 1-(6-(3,5-dichloro-4-hydroxyphenyl)-4-(1-(2-(dimethylamino)ethyl)piperidin-3-ylamino)quinolin-3-yl)ethanone | 1.2 | 1.1 | 4 | 0.89 | 0.32 |
| 851 | 1-(6-(3-chloro-5-fluoro-4-hydroxyphenyl)-4-(1-(2-(dimethylamino)ethyl)piperidin-3-ylamino)quinolin-3-yl)ethanone | 1.5 | 1.6 | 6 | 1.6 | 0.65 |
| 852 | 1-(6-(3,5-dichloro-4-hydroxyphenyl)-4-(6-(2-(dimethylamino)ethoxy)pyridin-3-ylamino)quinolin-3-yl)ethanone dihydrochloride | 0.55 | 0.16 | 22 | 0.29 | 0.088 |
| 853 | 1-(6-(3-chloro-5-fluoro-4-hydroxyphenyl)-4-((6-(3-(dimethylamino)pyrrolidin-1-yl)pyridin-3-yl)amino)quinolin-3-yl)ethanone | 0.65 | 0.2 | 10 | 0.45 | 0.38 |
| 854 | 1-(6-(3,5-dichloro-4-hydroxyphenyl)-4-((6-(3-(dimethylamino)pyrrolidin-1-yl)pyridin-3-yl)amino)quinolin-3-yl)ethanone | 0.51 | 0.25 | 10 | 0.39 | 0.28 |
| 855 | 1-(6-(3,5-dichloro-4-hydroxyphenyl)-4-((6-(3-(dimethylamino)pyrrolidin-1-yl)pyridin-3-yl)amino)quinolin-3-yl)ethanone hydrochloride | 0.64 | 0.26 | 73 | 0.38 | 0.23 |
| 860 | 1-(6-(3-chloro-5-fluoro-4-hydroxyphenyl)-4-((6-(3-(dimethylamino)pyrrolidin-1-yl)pyridin-3-yl)amino)quinolin-3-yl)propan-1-one | 0.45 | 0.14 | 3.6 | 0.29 | 0.24 |
| 861 | 1-(6-(3,5-dichloro-4-hydroxyphenyl)-4-(((1S,3R)-3-(2-(dimethylamino)ethyl)cyclohexyl)amino)quinolin-3-yl)ethanone hydrochloride | 0.24 | 0.22 | 1 | 0.25 | 0.19 |
| 862 | 1-(6-(3-chloro-5-fluoro-4-hydroxyphenyl)-4-(((1S,3R)-3-(2-(dimethylamino)ethyl)cyclohexyl)amino)quinolin-3-yl)ethanone hydrochloride | 0.2 | 0.26 | 1.1 | 0.29 | 0.2 |
| 863 | 1-(6-(3,5-dichloro-4-hydroxyphenyl)-4-((6-(3-(dimethylamino)pyrrolidin-1-yl)pyridin-3-yl)amino)quinolin-3-yl)propan-1-one | 0.59 | 0.44 | 14 | 0.5 | 0.31 |
| 864 | 1-(6-(3,5-dichloro-4-hydroxyphenyl)-4-(((1R,4R)-4-((bis-(trideuteromethyl)amino)methyl)cyclohexyl)amino)quinolin-3-yl)ethanone dihydrochloride | 0.081 | 0.067 | 1.3 | 0.11 | 0.043 |
| 865 | (1r,4r)-4-((3-acetyl-6-(3,5-dichloro-4-hydroxyphenyl)quinolin-4-yl)amino)-N,N-dimethylcyclohexanecarboxamide hydrochloride | 1.5 | 0.38 | 3.9 | 0.86 | 0.94 |
| 866 | 1-(6-(3,5-dichloro-4-hydroxyphenyl)-7-methyl-4-((6-(4-methylpiperazin-1-yl)pyridin-3-yl)amino)quinolin-3-yl)ethanone hydrochloride | 4.1 | 2.4 | 4.5 | 2.3 | 2.9 |
| 867 | 1-(6-(3-chloro-5-fluoro-4-hydroxyphenyl)-4-((6-methyl-5-(2-(pyrrolidin-1-yl)ethyl)pyridin-3-yl)amino)quinolin-3-yl)ethanone | 4.6 | 2.9 | 53 | 1.6 | 1.3 |
| 868 | 1-(6-(3,5-dichloro-4-hydroxyphenyl)-4-(((1R,4R)-4-(2-(diethylamino)ethoxy)cyclohexyl)amino)quinolin-3-yl)ethanone hydrochloride | 0.3 | 0.14 | 2.8 | 0.28 | 0.29 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 869 | 1-(6-(3-chloro-5-fluoro-4-hydroxyphenyl)-4-((1R,4R)-4-(2-(diethylamino)ethoxy)cyclohexyl)amino)quinolin-3-yl)ethanone hydrochloride | 0.32 | 0.084 | 0.7 | 0.23 | 0.26 |
| 870 | (1r,4r)-4-((3-acetyl-6-(3-chloro-5-fluoro-4-hydroxyphenyl)quinolin-4-yl)amino)-N,N-dimethylcyclohexanecarboxamide hydrochloride | 2.3 | 0.53 | 3.5 | 1.6 | 2.1 |
| 871 | 1-(6-(3,5-dichloro-4-hydroxyphenyl)-4-((6-methyl-5-(2-(pyrrolidin-1-yl)ethyl)pyridin-3-yl)amino)quinolin-3-yl)ethanone | 0.82 | 1.8 | 25 | 0.4 | 0.33 |
| 872 | 1-(4-((1R,4R)-4-((3-aminopyrrolidin-1-yl)methyl)cyclohexyl)amino)-6-(3,5-dichloro-4-hydroxyphenyl)-7-methylquinolin-3-yl)ethanone hydrochloride | 14 | 17 | 100 | 100 | 0.26 |
| 873 | 1-(6-(3,5-dichloro-4-hydroxyphenyl)-4-((5-(2-(pyrrolidin-1-yl)ethyl)pyridin-3-yl)amino)quinolin-3-yl)ethanone hydrochloride | 100 | 100 | 100 | 0.35 | 0.17 |
| 874 | N-(1R,4R)-4-((3-acetyl-6-(3-chloro-5-fluoro-4-hydroxyphenyl)quinolin-4-yl)amino)cyclohexyl)-1-methylpyrrolidine-2-carboxamide hydrochloride | 0.18 | 0.04 | 1 | 0.14 | 0.12 |
| 875 | N-(1R,4R)-4-((3-acetyl-6-(3,5-dichloro-4-hydroxyphenyl)quinolin-4-yl)amino)cyclohexyl)-1-methylpyrrolidine-2-carboxamide hydrochloride | 0.29 | 0.14 | 4.4 | 0.24 | 0.21 |
| 876 | N-(1R,4R)-4-((3-acetyl-6-(3-chloro-5-fluoro-4-hydroxyphenyl)quinolin-4-yl)amino)cyclohexyl)-2-(dimethylamino)acetamide dihydrochloride | 0.14 | 0.033 | 1.5 | 0.16 | 0.092 |
| 877 | N-(1R,4R)-4-((3-acetyl-6-(3,5-dichloro-4-hydroxyphenyl)quinolin-4-yl)amino)cyclohexyl)-2-(dimethylamino)acetamide hydrochloride | 0.18 | 0.11 | 2 | 0.2 | 0.11 |
| 878 | (S)-N-((1r,4S)-4-((3-acetyl-6-(3-chloro-5-fluoro-4-hydroxyphenyl)quinolin-4-yl)amino)cyclohexyl)-2-aminopropanamide dihydrochloride | 0.096 | 0.027 | 21 | 0.83 | 0.03 |
| 879 | 2-chloro-6-fluoro-4-(3-(methylsulfonyl)-4-((3-(2-(pyrrolidin-1-yl)ethyl)phenyl)amino)quinolin-6-yl)phenol hydrochloride | 3 | 1.1 | 9 | 3.8 | 0.9 |
| 880 | 1-(6-(3-chloro-5-fluoro-4-hydroxyphenyl)-4-((5-(2-(pyrrolidin-1-yl)ethyl)pyridin-3-yl)amino)quinolin-3-yl)ethanone hydrochloride | 7.4 | 3.1 | 46 | 1.8 | 0.96 |
| 881 | cyclopropyl(6-(3,5-dichloro-4-hydroxyphenyl)-4-((5-(2-(pyrrolidin-1-yl)ethyl)pyridin-3-yl)amino)quinolin-3-yl)methanone | 100 | 100 | 100 | 0.15 | 0.078 |
| 882 | (6-(3-chloro-5-fluoro-4-hydroxyphenyl)-4-((5-(2-(pyrrolidin-1-yl)ethyl)pyridin-3-yl)amino)quinolin-3-yl)(cyclopropyl)methanone | 3.1 | 100 | 100 | 0.27 | 0.15 |
| 883 | 2,6-dichloro-4-(3-(methylsulfonyl)-4-((3-(2-(pyrrolidin-1-yl)ethyl)phenyl)amino)quinolin-6-yl)phenol hydrochloride | 1.5 | 1.4 | 100 | 1.9 | 0.53 |
| 884 | 2,6-dichloro-4-(4-((6-(2-(dimethylamino)ethoxy)pyridin-3-yl)amino)-3-(methylsulfonyl)quinolin-6-yl)phenol hydrochloride | 4.1 | 0.91 | 13 | 2.1 | 0.51 |
| 885 | 2-chloro-4-(4-((6-(2-(dimethylamino)ethoxy)pyridin-3-yl)amino)-3-(methylsulfonyl)quinolin-6-yl)-6-fluorophenol hydrochloride | 2.5 | 0.7 | 10 | 3 | 0.62 |
| 886 | (S)-N-((1r,4S)-4-((3-acetyl-6-(3,5-dichloro-4-hydroxyphenyl)quinolin-4-yl)amino)cyclohexyl)-2-aminopropanamide dihydrochloride | 0.088 | 0.045 | 11 | 0.64 | 0.016 |
| 887 | 1-(6-(3,5-dichloro-4-hydroxyphenyl)-4-((4-((4-methylpiperazin-1-yl)sulfonyl)phenyl)amino)quinolin-3-yl)ethanone hydrochloride | 100 | 1.3 | 100 | 100 | 100 |
| 889 | 2-chloro-4-(4-((6-(3-(dimethylamino)pyrrolidin-1-yl)pyridin-3-yl)amino)-3-(methylsulfonyl)quinolin-6-yl)-6-fluorophenol hydrochloride | 1.8 | 1.5 | 12 | 2.5 | 1.2 |
| 890 | 2,6-dichloro-4-(3-(methylsulfonyl)-4-((1R,4R)-4-(pyrrolidin-1-ylmethyl)cyclohexyl)amino)quinolin-6-yl)phenol hydrochloride | 0.94 | 1.3 | 3 | 1.1 | 0.35 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 891 | 2-chloro-6-fluoro-4-(3-(methylsulfonyl)-4-((1R,4R)-4-(pyrrolidin-1-ylmethyl)cyclohexyl)amino)quinolin-6-yl)phenol hydrochloride | 0.92 | 0.73 | 2.4 | 1.3 | 0.46 |
| 892 | (1r,4r)-4-((3-acetyl-6-(3,5-dichloro-4-hydroxyphenyl)quinolin-4-yl)amino)-N-(2-(dimethylamino)ethyl)cyclohexanecarboxamide hydrochloride | 1.1 | 0.59 | 100 | 6.3 | 0.4 |
| 893 | (1r,4r)-4-((3-acetyl-6-(3-chloro-5-fluoro-4-hydroxyphenyl)quinolin-4-yl)amino)-N-(2-(dimethylamino)ethyl)cyclohexanecarboxamide hydrochloride | 1.6 | 0.59 | 100 | 100 | 0.67 |
| 894 | 1-(6-(3-chloro-5-fluoro-4-hydroxyphenyl)-4-((4-((4-methylpiperazin-1-yl)sulfonyl)phenl)amino)quinolin-3-yl)ethanone hydrochloride | 100 | 1.5 | 63 | 100 | 100 |
| 895 | 1-(6-(1H-benzo[d]imidazol-6-yl)-4-((1-(1-methylpiperidin-4-yl)-1H-pyrazol-4-yl)amino)quinolin-3-yl)ethanone hydrochloride | 2.2 | 0.94 | 9.3 | 4 | 9.1 |
| 897 | 1-(6-(3,5-dichloro-4-hydroxyphenyl)-4((2-methyl-5-(2-(pyrrolidin-1-yl)ethyl)pyridin-3-yl)amino)quinolin-3-yl)ethanone | 11 | 4.5 | 71 | 8.5 | 8.8 |
| 898 | 1-(6-(3,5-dichloro-4-hydroxyphenyl)-4-((1R,4R)-4-(4-methylpiperazine-1-carbonyl)cyclohexyl)amino)quinolin-3-yl)ethanone hydrochloride | 0.78 | 0.44 | 3 | 0.87 | 0.96 |
| 899 | 2,6-dichloro-4-(4-((1-(1-methylpiperidin-4-yl)-1H-pyrazol-4-yl)amino)-3-(methylsulfonyl)quinolin-6-yl)phenol hydrochloride | 1.5 | 1.6 | 10 | 4 | 0.26 |
| 900 | 2-chloro-6-fluoro-4-(4-((1-(1-methylpiperidin-4-yl)-1H-pyrazol-4-yl)amino)-3-(methylsulfonyl)quinolin-6-yl)phenol hydrochloride | 3.1 | 1.6 | 10 | 10 | 0.54 |
| 901 | 1-(6-(1H-benzo[d]imidazol-6-yl)-4-((6-(4-methylpiperazin-1-yl)pyridin-3-yl)amino)quinolin-3-yl)ethanone hydrochloride | 2.1 | 1.2 | 9.1 | 2.3 | 9.5 |
| 902 | 1-(6-(1H-benzo[d]imidazol-6-yl)-4-((6-(2-(dimethylamino)ethoxy)pyridin-3-yl)amino)quinolin-3-yl)ethanone hydrochloride | 3.1 | 3.3 | 12 | 2.9 | 14 |
| 903 | 1-(6-(3,5-dichloro-4-hydroxyphenyl)-4-((1R,4R)-4-((dimethylamino)methyl)cyclohexyl)amino)-7-fluoroquinolin-3-yl)ethanone hydrochloride | 0.27 | 0.55 | 1.5 | 0.36 | 0.16 |
| 904 | 1-(6-(3-chloro-5-fluoro-4-hydroxyphenyl)-4-((1R,4R)-4-((dimethylamino)methyl)cyclohexyl)amino)-7-fluoroquinolin-3-yl)ethanone hydrochloride | 0.33 | 0.51 | 1.6 | 0.43 | 0.26 |
| 906 | 2,6-dichloro-4-(4-((6-(3-(dimethylamino)pyrrolidin-1-yl)pyridin-3-yl)amino)-3-(methylsulfonyl)quinolin-6-yl)phenol hydrochloride | 2 | 1.3 | 9.3 | 2 | 0.66 |
| 907 | N-(1R,4R)-4-((3-acetyl-6-(3-chloro-5-fluoro-4-hydroxyphenyl)quinolin-4-yl)amino)cyclohexyl)-2-amino-3-methylbutanamide dihydrochloride | 0.059 | 0.016 | 3.7 | 0.18 | 0.033 |
| 909 | 4-(4-((6-(3-aminopiperidin-1-yl)pyridin-3-yl)amino)-3-(methylsulfonyl)quinolin-6-yl)-2-chloro-6-fluorophenol trihydrochloride | 0.44 | 0.19 | 10 | 2.8 | 0.042 |
| 910 | 1-(4-((1R,4R)-4-((dimethylamino)methyl)cyclohexyl)amino)-6-(1H-indazol-5-yl)quinolin-3-yl)ethanone hydrochloride | 3.4 | 6 | 9.8 | 2.6 | 5.4 |
| 911 | 1-(6-(1H-benzo[d]imidazol-6-yl)-4-((1R,4R)-4-((dimethylamino)methyl)cyclohexyl)amino)quinolin-3-yl)ethanone hydrochloride | 5.4 | 10 | 13 | 3.2 | 10 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 912 | 1-(4-((1R,4R)-4-((dimethylamino)methyl)cyclohexyl)amino)-6-(1H-pyrazol-4-yl)quinolin-3-yl)ethanone hydrochloride | 1.7 | 4.2 | 3 | 1.3 | 1.4 |
| 913 | 4-(4-((6-(3-aminopiperidin-1-yl)pyridin-3-yl)amino)-3-(methylsulfonyl)quinolin-6-yl)-2,6-dichlorophenol trihydrochloride | 0.58 | 0.27 | 100 | 2.6 | 0.025 |
| 914 | (S)-N-((1r,4S)-4-((3-acetyl-6-(3-chloro-5-fluoro-4-hydroxyphenyl)quinolin-4-yl)amino)cyclohexyl)-2-amino-3,3-dimethylbutanamide hydrochloride | 0.28 | 0.075 | 3.6 | 0.65 | 0.19 |
| 915 | N-(1R,4R)-4-((3-acetyl-6-(3,5-dichloro-4-hydroxyphenyl)quinolin-4-yl)amino)cyclohexyl)-2-amino-3-methylbutanamide dihydrochloride | 0.099 | 0.053 | 3.5 | 0.29 | 0.062 |
| 916 | (6-(3-chloro-4-hydroxy-5-methoxyphenyl)-4-((1R,4R)-4-((dimethylamino)methyl)cyclohexyl)amino)quinolin-3-yl)(cyclopentyl)methanone hydrochloride | 1.5 | 1.2 | 3.1 | 1.1 | 1 |
| 917 | cyclopentyl(6-(3,5-dichloro-4-hydroxyphenyl)-4-((1R,4R)-4-((dimethylamino)methyl)cyclohexyl)amino)quinolin-3-yl)methanone hydrochloride | 0.91 | 0.7 | 3.3 | 0.68 | 0.19 |
| 918 | 1-(6-(3,5-dichloro-4-hydroxyphenyl)-4-((1R,4R)-4-((dimethylamino)methyl)cyclohexyl)amino)quinolin-3-yl)-2,2-dimethylpropan-1-one hydrochloride | 6.6 | 3 | 10 | 5.5 | 3.2 |
| 919 | 1-(6-(3-chloro-5-fluoro-4-hydroxyphenyl)-4-((1R,4R)-4-((dimethylamino)methyl)cyclohexyl)amino)quinolin-3-yl)-2,2-dimethylpropan-1-one hydrochloride | 3.5 | 1.9 | 6.4 | 4.3 | 2.5 |
| 920 | (S)-N-((1r,4S)-4-((3-acetyl-6-(3,5-dichloro-4-hydroxyphenyl)quinolin-4-yl)amino)cyclohexyl)pyrrolidine-2-carboxamide dihydrochloride | 0.34 | 0.1 | 6.5 | 0.86 | 0.073 |
| 921 | (S)-N-((1r,4S)-4-((3-acetyl-6-(3-chloro-5-fluoro-4-hydroxyphenyl)quinolin-4-yl)amino)cyclohexyl)pyrrolidine-2-carboxamide dihydrochloride | 0.21 | 0.048 | 10 | 1.2 | 0.068 |
| 922 | (S)-N-((1r,4S)-4-((3-acetyl-6-(3,5-dichloro-4-hydroxyphenyl)quinolin-4-yl)amino)cyclohexyl)-2-amino-3,3-dimethylbutanamide hydrochloride | 0.65 | 0.2 | 4.5 | 0.62 | 0.21 |
| 923 | 1-(6-(3,5-dichloro-4-hydroxyphenyl)-7-fluoro-4-((1R,4R)-4-(pyrrolidin-1-ylmethyl)cyclohexyl)amino)quinolin-3-yl)ethanone hydrochloride | 0.29 | 0.63 | 2.5 | 0.39 | 0.2 |
| 924 | (6-(3-chloro-4-hydroxy-5-methoxyphenyl)-4-((3-(2-(pyrrolidin-1-yl)ethyl)phenyl)amino)quinolin-3-yl)(cyclopentyl)methanone hydrochloride | 3 | 3.2 | 3.3 | 3.7 | 1.8 |
| 925 | 1-(6-(3-chloro-5-fluoro-4-hydroxyphenyl)-7-fluoro-4-((1R,4R)-4-(pyrrolidin-1-ylmethyl)cyclohexyl)amino)quinolin-3-yl)ethanone hydrochloride | 0.27 | 0.52 | 1.5 | 0.38 | 0.27 |
| 926 | 1-(6-(3-chloro-4-hydroxy-5-methoxyphenyl)-7-fluoro-4-((1R,4R)-4-(pyrrolidin-1-ylmethyl)cyclohexyl)amino)quinolin-3-yl)ethanone hydrochloride | 0.69 | 2.7 | 5 | 0.61 | 0.55 |
| 927 | cyclopentyl(6-(3,5-dichloro-4-hydroxyphenyl)-4-((3-(2-(pyrrolidin-1-yl)ethyl)phenyl)amino)quinolin-3-yl)methanone hydrochloride | 0.78 | 1.3 | 12 | 0.71 | 0.48 |
| 928 | 2-amino-N-(1R,4R)-4-((6-(3,5-dichloro-4-hydroxyphenyl)-3-pivaloylquinolin-4-yl)amino)cyclohexyl)propanamide hydrochloride | 2 | 1.4 | 8.1 | 4.1 | 1.1 |
| 929 | 1-(4-((1R,4R)-4-((dimethylamino)methyl)cyclohexyl)amino)-6-(6-hydroxynaphthalen-2-yl)quinolin-3-yl)ethanone hydrochloride | 0.71 | 3.3 | 3.9 | 0.87 | 2.8 |

TABLE 4-continued

| Example | Compound Name | IC50 (μM) (22Rv1) | IC50 (μM) (T47D) | IC50 (μM) (HT1197) | IC50 (μM) (A549) | IC50 (μM) (DU4475) |
|---|---|---|---|---|---|---|
| 930 | 1-(6-(3-chloro-5-fluoro-4-hydroxyphenyl)-4-((1-(1-methylpiperidin-4-yl)-1H-pyrazol-4-yl)amino)quinolin-3-yl)-2,2-dimethylpropan-1-one hydrochloride | 2.5 | 1.7 | 14 | 4.4 | 1.3 |
| 931 | 1-(6-(3,5-dichloro-4-hydroxyphenyl)-4-((1-(1-methylpiperidin-4-yl)-1H-pyrazol-4-yl)amino)quinolin-3-yl)-2,2-dimethylpropan-1-one hydrochloride | 2.1 | 1.4 | 100 | 1.8 | 1.5 |
| 932 | 2-amino-N-(1R,4R)-4-((6-(3-chloro-5-fluoro-4-hydroxyphenyl)-3-pivaloylquinolin-4-yl)amino)cyclohexyl)propanamide hydrochloride | 1.6 | 0.71 | 7.6 | 4.7 | 1 |
| 934 | (S)-1-(4-(6-(3-aminopiperidin-1-yl)pyridin-3-ylamino)-6-(3,5-dichloro-4-hydroxyphenyl)quinolin-3-yl)propan-1-one trihydrochloride | 0.02 | 0.014 | 0.6 | 0.034 | 0.016 |
| 935 | 1-(4-(1R,4R)-4-((dimethylamino)methyl)cyclohexylamino)-6-(4-hydroxyphenyl)quinolin-3-yl)ethanone dihydrochloride | 0.53 | 1.6 | 4.3 | 0.86 | 1.5 |

NT: Not tested

INDUSTRIAL APPLICABILITY

The present invention provides a novel quinoline derivative having MELK inhibitory effect. The compounds of the present invention may be used for pharmaceutical composition for inhibiting MELK. Such pharmaceutical compositions are suitable for treating or preventing cancer.

The invention claimed is:

1. A compound represented by the following formula or a pharmaceutically acceptable salt thereof:

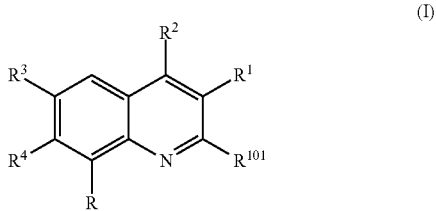

(I)

wherein,
$R^1$ represents
  a $C_1$-$C_6$ alkylsulfonyl, or
  —CO—$R^5$ wherein,
    $R^5$ is
      a $C_1$-$C_6$ alkyl, or
      a $C_3$-$C_{10}$ cycloalkyl,
$R^2$ represents
  an aryl which may have a substituent group selected from Substituent Group C, an aromatic heterocyclic group which may have a substituent group selected from Substituent Group H, or
  —$NR^{6A}R^{7A}$;
    wherein $R^{6A}$ represents a hydrogen atom, and $R^{7A}$ represents —$(CH_2)_n$—$R^{10A}$ (wherein n represents an integer of 0 to 6, and $R^{10A}$ represents a $C_3$-$C_{10}$ cycloalkyl which may have a substituent group selected from Substituent Group D, an aryl which may have a substituent group selected from Substituent Group E, an aliphatic heterocyclic group which may be substituted with a $C_1$-$C_6$ alkyl, an aromatic heterocyclic group which may have a substituent group selected from Substituent Group I), or $R^{6A}$ and $R^{7A}$ form with an adjacent nitrogen atom a heterocyclic group which may have a substituent group selected from Substituent Group F,
$R^3$ represents
  an aryl which may have a substituent group selected from Substituent Group G, or an aromatic heterocyclic group which may have a substituent group selected from Substituent Group H;
$R^4$ represents
  a hydrogen atom, or
  a halogen
R represents
  a hydrogen atom, or
  a halogen, and
$R^{101}$ represents
  a hydrogen atom
wherein Substituent Groups C to I are one to three substituents each independently selected from the following Substituent Groups:
Substituent Group C: a halogen, a hydroxy, a $C_1$-$C_6$ alkoxy, and a di($C_1$-$C_6$ alkyl) amino;
Substituent Group D: a hydroxy, a $C_1$-$C_6$ alkyl, a $C_1$-$C_6$ aminoalkyl, an aliphatic heterocyclic-($C_1$-$C_6$ alkylenyl) (wherein, the aliphatic heterocyclic may have an amino, a hydroxy, a $C_1$-$C_6$ hydroxyalkyl, a $C_1$-$C_6$ alkoxy, or a halogen as a substituent), a $C_1$-$C_6$ alkylamino-($C_1$-$C_6$ alkylenyl), a di($C_1$-$C_6$ alkyl)amino-($C_1$-$C_6$ alkylenyl) (wherein, either one of $C_1$-$C_6$ alkyl may have a hydroxy or a cyano as a substituent, and wherein hydrogen atom of $C_1$-$C_6$ alkyl may be substituted with deuterium atom), an amino, a $C_1$-$C_6$ alkylamino, a di($C_1$-$C_6$ alkyl)amino, a $C_1$-$C_6$ aminoalkylcarbonylamino, a di($C_1$-$C_6$ alkyl)amino($C_1$-$C_6$ alkylenyl)carbonylamino, an aliphatic heterocyclic group (wherein, the aliphatic heterocyclic group may have a $C_1$-$C_6$ alkoxy as a substituent), and an aliphatic heterocyclic-carbonylamino;
Substituent Group E: a halogen, a di($C_1$-$C_6$ alkyl)amino-($C_1$-$C_6$ alkylenyl) (wherein, the $C_1$-$C_6$ alkylenyl may have a hydroxy as a substituent), an amino, a $C_2$-$C_7$ alkanoylamino, a di($C_1$-$C_6$ alkyl)amino, a $C_1$-$C_6$ aminoalkyl, and an aliphatic heterocyclic-($C_1$-$C_6$ alkylenyl) (wherein, the aliphatic heterocyclic may have a $C_1$-$C_6$ alkyl as a substituent);

Substituent Group F: a carbamoyl, an amino, a $C_1$-$C_6$ aminoalkyl, a di($C_1$-$C_6$ alkyl)amino-($C_1$-$C_6$ alkylenyl), a $C_1$-$C_6$ alkylamino-($C_1$-$C_6$ alkylenyl), an aliphatic heterocyclic-($C_1$-$C_6$ alkylenyl), and an aliphatic heterocyclic group which may be substituted with a $C_1$-$C_6$ alkyl;

Substituent Group G: a halogen, a hydroxy, a cyano, a $C_1$-$C_6$ alkyl, a $C_1$-$C_6$ alkoxy, a trifluoromethoxy, a $C_1$-$C_6$ aminoalkyl, a $C_1$-$C_6$ alkylamino-($C_1$-$C_6$ alkylenyl), a di($C_1$-$C_6$ alkyl)amino-($C_1$-$C_6$ alkylenyl), an amino, a $C_1$-$C_6$ alkylsulfonylamino, a carbamoyl, a sulfamoyl, a ($C_1$-$C_6$ alkyl)ureide, a benzylureide, and an aliphatic heterocyclic group;

Substituent Group H: a halogen, a cyano, a $C_1$-$C_6$ alkyl, a $C_1$-$C_6$ alkoxy, an amino, a carbamoyl, a dimethylaminopropylaminocarbonyl, and an aminocyclohexylaminocarbonyl;

Substituent Group I: an aliphatic heterocyclic group (wherein, the aliphatic heterocyclic group may have a $C_1$-$C_6$ alkyl, an amino group or a $C_1$-$C_6$ alkylamino as a substituent); an aliphatic heterocyclic-($C_1$-$C_6$ alkylenyl); an aliphatic heterocyclic-amino (wherein, the aliphatic heterocyclic may have a $C_1$-$C_6$ alkyl or an amino as a substituent); a di($C_1$-$C_6$ alkyl)amino-($C_1$-$C_6$ alkylenyl); a $C_1$-$C_6$ aminoalkyloxy; a di($C_1$-$C_6$ alkyl)amino-($C_1$-$C_6$ alkylenyl)oxy; a di($C_1$-$C_6$ alkyl) amino-($C_1$-$C_6$ alkylenyl)amino; a cyclohexyl (wherein, the cyclohexyl may have an amino or a $C_1$-$C_6$ aminoalkyl as a substituent).

2. The compound or a pharmaceutically acceptable salt thereof of claim 1, wherein $R^1$ is —CO—$R^5$.

3. The compound or a pharmaceutically acceptable salt thereof of claim 1, wherein $R^1$ is a methylsulfonyl.

4. The compound or a pharmaceutically acceptable salt thereof of claim 1, wherein $R^2$ is —$NR^{6A}R^{7A}$ (wherein, $R^{6A}$ and $R^{7A}$ have the same meaning as described in claim 1).

5. The compound or a pharmaceutically acceptable salt thereof of claim 2, wherein $R^{6A}$ is a hydrogen atom, and $R^{7A}$ is —$(CH_2)_n$—$R^{10A}$ (wherein, n and $R^{10A}$ each have the same meaning as described in claim 1).

6. The compound or a pharmaceutically acceptable salt thereof of claim 2, wherein $R^{6A}$ and $R^{7A}$ form with an adjacent nitrogen atom a heterocyclic group which may have a substituent group selected from Substituent Group F described in claim 1.

7. The compound or a pharmaceutically acceptable salt thereof of claim 1, wherein $R^2$ is a piperidin-4-spiro-3'-pyrrolidin-1-yl, a piperidyl which may have a substituent group selected from Substituent Group F described in claim 1, or a 1-piperazinyl which may have a substituent group selected from Substituent Group F described in claim 1.

8. The compound or a pharmaceutically acceptable salt thereof of claim 1, wherein $R^2$ is an aryl which may have a substituent group selected from Substituent Group C described in claim 1.

9. The compound or a pharmaceutically acceptable salt thereof of claim 1, wherein $R^2$ is a phenyl which may have a substituent group selected from Substituent Group C described in claim 1.

10. The compound or a pharmaceutically acceptable salt thereof of claim 1, wherein $R^3$ is an aryl which may have a substituent group selected from Substituent Group G described in claim 1, or an optionally substituted aromatic heterocyclic group which may have a substituent group selected from Substituent Group H described in claim 1.

11. A pharmaceutical composition comprising as an active ingredient a compound or a pharmaceutically acceptable salt thereof claim 1.

12. An MELK inhibitor comprising as an active ingredient a compound or a pharmaceutically acceptable salt thereof of claim 1.

13. An MELK-expression modulating agent comprising as an active ingredient a compound or a pharmaceutically acceptable salt thereof of claim 1.

14. An antitumor agent comprising as an active ingredient a compound or a pharmaceutically acceptable salt thereof of claim 1.

15. A method for treating cancer that involves overexpression of MELK, wherein an effective amount of a compound or a pharmaceutically acceptable salt thereof of claim 1 is administered to a subject in need thereof.

16. The method of claim 15, wherein the cancer is selected from the group consisting of breast cancer, lung cancer, bladder cancer, lymphoma, and uterine cancer.

17. The compound or a pharmaceutically acceptable salt thereof of claim 1, which is selected from 1-(6-(3-chloro-4-hydroxy-5-methoxyphenyl)-4-(1R,4R)-4-((dimethylamino)methyl)-cyclo-hexylamino)quinolin-3-yl)ethanone;

2,6-dichloro-4-(4-(1R,4R)-4-((dimethylamino)methyl) cyclohexylamino)-3-(methylsulfonyl)-quinolin-6-yl) phenol;

cyclopropyl(6-(3,5-dichloro-4-hydroxyphenyl)-4-((1s,4s)-4-((dimethylamino)-methyl)cyclo-hexylamino) quinolin-3-yl)methanone;

1-(6-(3-chloro-4-hydroxy-5-methoxyphenyl)-4-(1R,4R)-4-((dimethylamino)-methyl)cyclo-hexylamino)quinolin-3-yl)propan-1-one;

1-(6-(3,5-dichloro-4-hydroxyphenyl)-4-((1R,4R)-4-((dimethylamino)methyl)-cyclohexyl)-amino)quinolin-3-yl)propan-1-one;

1-(6-(3-chloro-5-fluoro-4-hydroxyphenyl)-4-((trans)-4-((dimethylamino)methyl)-cyclo-hexylamino)quinolin-3-yl)ethanone;

1-(6-(3,5-dichloro-4-hydroxyphenyl)-4-((trans)-4-((dimethylamino)methyl)-cyclohexylamino)-quinolin-3-yl) ethanone;

cyclopropyl(6-(3,5-dichloro-4-hydroxyphenyl)-4-((trans)-4-((dimethylamino)-methyl)cyclo-hexylamino)quinolin-3-yl)methanone;

(4-(6-(3-aminopiperidin-1-yl)pyridin-3-ylamino)-6-(3,5-dichloro-4-hydroxyphenyl)-quinolin-3-yl)(cyclopropyl)methanone;

(S)-(4-(6-(3-aminopiperidin-1-yl)pyridin-3-ylamino)-6-(3,5-dichloro-4-hydroxyphenyl)-quinolin-3-yl)(cyclopropyl)methanone;

(R)-(4-(6-(3-aminopiperidin-1-yl)pyridin-3-ylamino)-6-(3,5-dichloro-4-hydroxyphenyl)-quinolin-3-yl)(cyclopropyl)methanone;

1-(4-(6-(3-aminopiperidin-1-yl)pyridin-3-ylamino)-6-(3,5-dichloro-4-hydroxyphenyl)-quinolin-3-yl)ethanone;

1-(4-(6-(3-aminopiperidin-1-yl)pyridin-3-ylamino)-6-(3,5-dichloro-4-hydroxyphenyl)-quinolin-3-yl)propan-1-one; and (S)-1-(4-(6-(3-aminopiperidin-1-yl)pyridin-3-ylamino)-6-(3,5-dichloro-4-hydroxyphenyl)quinolin-3-yl) propan-1-one;

and a pharmaceutically acceptable salt thereof.

* * * * *